US011174252B2

(12) United States Patent
Pham et al.

(10) Patent No.: US 11,174,252 B2
(45) Date of Patent: Nov. 16, 2021

(54) HETEROCYCLIC COMPOUNDS AS KINASE INHIBITORS

(71) Applicant: NUVATION BIO INC., New York, NY (US)

(72) Inventors: Son Minh Pham, San Francisco, CA (US); Sarvajit Chakravarty, Edmond, OK (US); Jayakanth Kankanala, St. Paul, MN (US); Brahmam Pujala, Greater Noida (IN); Amit Shete, Noida (IN); Bhawana Bhatt, Greater Noida (IN); Anil Kumar Agarwal, Noida (IN); Sanjeev Soni, Noida (IN); Jiyun Chen, Moraga, CA (US)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 16/277,355

(22) Filed: Feb. 15, 2019

(65) Prior Publication Data
US 2019/0248774 A1 Aug. 15, 2019

Related U.S. Application Data

(60) Provisional application No. 62/631,437, filed on Feb. 15, 2018.

(51) Int. Cl.
C07D 413/14 (2006.01)
A61P 35/00 (2006.01)

(52) U.S. Cl.
CPC ............ C07D 413/14 (2013.01); A61P 35/00 (2018.01)

(58) Field of Classification Search
CPC .................................................. C07D 413/14
See application file for complete search history.

(56) References Cited

U.S. PATENT DOCUMENTS

| 6,949,544 | B2 | 9/2005 | Bethiel |
| 7,259,161 | B2 | 8/2007 | Bethiel |
| 9,309,252 | B2 | 4/2016 | Brain |
| 9,908,884 | B2 | 3/2018 | Gray et al. |
| 10,189,849 | B2 | 1/2019 | Tavares |
| 10,189,850 | B2 | 1/2019 | Tavares |
| 10,189,851 | B2 | 1/2019 | Tavares |
| 10,618,905 | B2 | 4/2020 | Strum |
| 2004/0097504 | A1 | 5/2004 | Bethiel |
| 2006/0142312 | A1 | 6/2006 | Flamme et al. |
| 2010/0160340 | A1 | 6/2010 | Coates et al. |
| 2010/0173823 | A1 | 7/2010 | Mccormick et al. |
| 2012/0814572 | | 7/2012 | Song et al. |
| 2013/0231348 | A1 | 9/2013 | Campbell |
| 2013/0252967 | A1 | 9/2013 | Campbell |
| 2014/0271466 | A1 | 9/2014 | Sharpless |
| 2014/0275067 | A1 | 9/2014 | Sharpless |
| 2017/0182043 | A1 | 6/2017 | Strum |
| 2017/0355712 | A1 | 12/2017 | Campbell et al. |
| 2018/0289718 | A1 | 10/2018 | Saito |
| 2018/0305363 | A1 | 10/2018 | Liu et al. |
| 2019/0135784 | A1 | 5/2019 | Strum |
| 2019/0135811 | A1 | 5/2019 | Strum |
| 2019/0135820 | A1 | 5/2019 | Smith |
| 2020/0022983 | A1 | 1/2020 | Strum |
| 2020/0039983 | A1 | 2/2020 | Liu |
| 2020/0115378 | A1 | 4/2020 | Sokolsky |
| 2020/0165239 | A1 | 5/2020 | Yin et al. |

FOREIGN PATENT DOCUMENTS

| CN | 107382974 A | 11/2017 |
| CN | 110835334 A | 2/2020 |
| EP | 2598483 A1 | 6/2013 |
| EP | 2440559 B1 | 1/2018 |
| EP | 2877174 B1 | 1/2020 |
| WO | WO2001070741 A1 | 9/2001 |
| WO | 2006015124 A2 | 2/2006 |
| WO | 2006015124 A3 | 10/2006 |
| WO | 2010008739 A2 | 1/2010 |
| WO | 2010020675 A1 | 2/2010 |
| WO | 2010008739 A3 | 4/2010 |
| WO | WO2010071846 A2 | 6/2010 |

(Continued)

OTHER PUBLICATIONS

Alves, C.L. (Nov. 15, 2016, e-pub. Jun. 1, 2016). "High CDK6 Protects Cells from Fulvestrant-Mediated Apoptosis and is a Predictor of Resistance to Fulvesrant in Estrogen Receptor-Positive Metastatic Breast Cancer," Clinical Cancer Research 22(22):5514-5526.

(Continued)

Primary Examiner — Susanna Moore
(74) Attorney, Agent, or Firm — Morrison & Foerster LLP

(57) ABSTRACT

Heterocyclic compounds of Formula (J) as CDK4 or CDK6 or other CDK inhibitors are provided. The compounds may find use as therapeutic agents for the treatment of diseases and may find particular use in oncology.

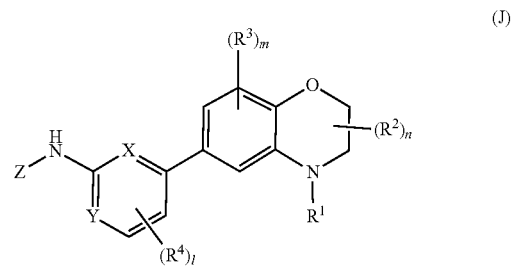

106 Claims, 7 Drawing Sheets

(56) References Cited

FOREIGN PATENT DOCUMENTS

| | | | |
|---|---|---|---|
| WO | WO2010071846 A3 | 11/2010 |
| WO | WO2011101409 A1 | 8/2011 |
| WO | WO2011101417 A1 | 8/2011 |
| WO | WO2011156775 A2 | 12/2011 |
| WO | 2012016217 A1 | 2/2012 |
| WO | 2012018540 A1 | 2/2012 |
| WO | WO2011156775 A3 | 4/2012 |
| WO | WO2013175415 A1 | 11/2013 |
| WO | 2014144596 A2 | 9/2014 |
| WO | 2014144596 A3 | 12/2014 |
| WO | 2015048547 A2 | 4/2015 |
| WO | 2015048547 A3 | 6/2015 |
| WO | 2015180642 A1 | 12/2015 |
| WO | 2016015597 A1 | 2/2016 |
| WO | 2016015598 A1 | 2/2016 |
| WO | 2016015604 A1 | 2/2016 |
| WO | 2016141881 A1 | 9/2016 |
| WO | WO2017101763 A1 | 6/2017 |
| WO | 2017114351 A1 | 7/2017 |
| WO | 2017133701 A1 | 8/2017 |
| WO | 2017177836 A1 | 10/2017 |
| WO | 2017177837 A1 | 10/2017 |
| WO | WO2017181177 A1 | 10/2017 |
| WO | WO2017185031 A1 | 10/2017 |
| WO | 2017193872 A1 | 11/2017 |
| WO | WO2018113771 A1 | 6/2018 |
| WO | WO2019148161 A1 | 8/2019 |
| WO | WO2019165204 A1 | 8/2019 |
| WO | WO2020006210 A1 | 1/2020 |
| WO | WO2020023480 A1 | 1/2020 |
| WO | WO2020023917 A1 | 1/2020 |
| WO | 2020108661 A1 | 6/2020 |
| WO | 2020119739 A1 | 6/2020 |
| WO | WO2010129053 A2 | 11/2020 |
| WO | WO2010129053 A3 | 11/2020 |

OTHER PUBLICATIONS

Anscombe, E. et al. (2015). "Identification and Characterization of an Irreversibel Inhibitor of CDK2," Chemistry & Biology 22:1159-1164.

Ardelt, M.A. et al. (2019). "Inhibition of Cyclin-Dependent Kinase 5—A Novel Strategy to Improve Sorafenib Response in HCC Therapy," 33 pages.

Arif, A. (Oct. 2012, e-pub. Jul. 4, 2012). "Extraneuronal Activities and Regulatory Mechanisms of the Atypical Cyclin-Dependent Kinase Cdk5," Biochem Pharmacol 84(8):985-993.

Asghar, U. (Feb. 2015). "The History and Future of Targeting Cyclin-Dependent Kinases in Cancer Therapy," Nature Reviews Drug Discovery 14:130-146.

Asghar, U.S. (2017, e-pub. Jun. 12, 2017). "Single-Cell Dynamics Determines Response to CDK4/6 Inhibition in Triple-Negative Breast Cancer," Clinical Cancer Research 23:5561-5572.

Athuluri-Divakar, S. et al. (2016). "Abstract # 3029: Dual Targeting of ARK5 and CDK4 Pathways with ON123300 as a Therapeutic Strategy for Colorectal Carcinoma," Onconova Therapeutics, 1 page.

Baker, A. et al. (Mar. 1, 2016, e-pub. Dec. 1, 2015). "The CD9 Inhibitor Dinaciclib Exerts Potent Apoptotic and Antitumor Effects in Preclinical Models of MLL-Rearranged Acute Myeloid Leukemia," Cancer Research 76(5):1158-1169.

Beale, G. et al. (2016). "Combined PI3K and CDK2 Inhibition Induces Cell Death and Enhances in vivo Antitumour Activity in Colorectal Cancer," British Journal of Cancer 115:682-690.

Beck, H. et al. (Oct. 2012). "Cyclin-Dependent Kinase Suppression by WEE1 Kinase Protects the Genome Through Control of Replication Initiation and Nucleotide Consumption," Molecular and Cellular Biology 32(20):4226-426.

Bellutti, F. et al. (Jul. 2018, e-pub. Jun. 13, 2018). "CDK6 Antagonizes p53-Induced Responses During Tumorigenesis," Cancer Discov. 8(7):884-897.

Bogenberger, J. et al. (2017). "Combined Venetoclax and Alvocidib in Acute Myeloid Leukemia," Oncotarget 8(63):107206-107222.

Bollard, J. et al. (2017, e-pub. Nov. 14, 2016). "Palbociclib (PD-0332991), A Selective CDK4/6 Inhibitor, Restricts Tumuor Growth in Preclinical Models of Hepatocellular Carcinoma," Hepatology 66:1286-1296.

Bouchekioua-Bouzaghou, K. et al. (Jul. 2016). "Abstract 2819: Characterization of the Mechanisms of Early and Later Stages of Resistance to the Selective CDK4/6 Inhibitor Palbociclib," Cancer Research, 6 pages.

Bradley. M. et al. (2017). "Abstract 1143: Targeting the Transcriptional Kinases CDK12 and CDK13 in Breast and Ovarian Cancer," AACR, 1 page.

Cemeli, T. et al. (Apr. 7, 2019). Cytoplasmic Cyclin D1 Regulates Glioblastoma Dissemination, 39 pages.

Chaikovsky, A.C. et al. (2018, e-pub. Jun. 22, 2018). "Beyond the Cell Cycle: Enhancing the Immune Surveillance of Tumors via CDK4/6 Inhibition," Mol. Cancer Res., 15 pages.

Chen, P. et al. (2016, e-pub. Aug. 5, 2016). "Spectrum and Degree of CDK Drug Interactions Predicts Clinical Performance," Molecular Cancer Therapeutics, 10 pages.

Chen, R. et al. (Apr. 17, 2018). "3905/5—Strategic Combination of the Cyclin-Dependent Kinase Inhibitor CYC065 With Venetoclax to Target Anti-Apoptotic Proteins in Chronic Lymphocytic Leukemia," AACR Section 38, 2 pages.

Chen, Y. et al. (2016, e-pub. Jul. 29, 2016). "Pro-Survival Signal Inhibition by CDK Inhibitor Dinaciclib in Chronic Lymphocytic Leukaemia," British Journal of Haematology 175:641-651.

Cheng, W. et al. (2019, e-pub. Jan. 3, 2019). "Recent Development of CDK Inhibitors: An Overview of CDK/Inhibitor Co-Crystal Structures," European Journal of Medicinal Chemistry 164:615-639.

Chi, Y. et al. (Oct. 13, 2008). "Identification of CDK2 Substrates in Human Cell Lysates," Biology 9:R149, 12 pages.

Chohan, T.A. et al. (2015). "Cyclin-Dependent Kinase-2 as a Target for Cancer Therapy: Progress in the Development of CDK2 Inhibitors as Anti-Cancer Agents," Current Medicinal Chemistry 22:237-263.

Choudhary, G.S. et al. (Jul. 15, 2015). "Cyclin E/Cdk2-Dependent Phosphorylation of Mcl-1 Determines Its Stability and Cellular Sensitivity to BH3 Mimetics," Oncotarget 6(19):16912-16925.

Cicenas, J. et al. (2014). "Highlights of the Latest Advances in Research on CDK Inhibitors," Cancers 6:2224-2242.

Corona, S.P. et al. (2018). "Abemaciclib: A CDK4/6 Ihibitor for the Treatment of HR+/HER2—Advanced Breast Cancer," Drug Design, Development and Therapy 12:321-330.

Cretella, D. et al. (2019, e-pub. Sep. 10, 2019). "Pre-Treatment With the CDK4/6 Inhibitor Palbociclib Improves the Efficacy of Paclitaxel in TNBC Cells," Scientific Reports 9:13014, 11 pages . . . .

Cyclacel (Oct. 2, 2018). "Translating Cancer Biology Into Medicines," Laden Thalman 2018 Healthcare Conference, 21 pages.

Danilov, A.V. et al. (2016, e-pub. Aug. 22, 2016). "Dinaciclib Induces Anaphase Catastrophe in Lung Cancer Cells via Inhibition of Cyclin-Dependent Kinases 1 and 2," Molecular Cancer Therapeutics 15:2758-2766.

De Leeuw, R. et al. (2018). "Effect of Bypass Kinases Pathways on Acquired CDK4/6 Inhibitor Resistance," Journal of Clinical Oncology, 5 pages.

Dean, J.L. et al. (2010). "Therapeutic CDK4/6 Inhibition in Breast Cancer: Key Mechanisms of Response and Failure," Oncogene 29:4018-4032.

Del Muro, X.G. et al. (2018). "Abstract 11582: Combination of CDK and Bcl-1 Inhibitors in the Treatment of Soft-Tissue Sarcomas," Journal of Clinical Oncology, 4 pages.

Deng, J. et al. (2017, e-pub. Nov. 3, 2017). "CDK4/6 Inhibitio Augments Antitumour Immunity by Enhancing T-Cell Activation," Cancer Discov. 8(2):1-18.

Deng, J. et al. (2017, e-pub. Nov. 3, 2017). "CDK4/6 Inhibitio Augments Antitumour Immunity by Enhancing T-Cell Activation," Cancer Discov. 8(2):216-233.

(56) References Cited

OTHER PUBLICATIONS

Dey, J. et al. (2017, e-pub. Dec. 21, 2017). "Voruciclib, A Clinical Stage Oral CDK9 Inhibitor, Represses MCL-1 and Sensitizes High-Risk Diffuse Large B-Cell Lymphoma to BCL2 Inhibition," Scientific Reports 7:18007, 11 pages.
Di Sante, G. et al. (2019, e-pub. Jun. 20, 2019). "Recent Advances With Cyclin-Dependent Kinase Inhibitors: Therapeutic Agents for Breast Cancer and Their Role in Immuno-Oncology," Expert Review of Anticancer Therapy 19(7):569-587.
Ding, W. et al. (2018). "The CDK4/6 Inhibitor in HR-Positive Advanced Breast Cancer," Medicine 97:20, 9 pages.
Ehab, M. et al. (May 17, 2016). "Profile of Palbociclib in the Treatment of Metastatic Breast Cancer," Breast Cancer—Targets and Therapy 8:83-91.
Errico, A. et al. (2010). "Identification of Substrates for Cyclin Dependents Kinases," Advances in Enzyme Regulation 50:375-399.
Eschbach, R.S. et al. (2018). "18F-FDG-PET/CT and Diffusion-Weighted MRI for Monitoring a BRAF and CDK4/6 Inhibitor Combination Therapy in a Murine Model of Human Melanoma," Cancer Imaging 18:2, 11 pages.
Fabre, C. et al. (2014). "Clinical Study of the Novel Cyclin-Dependent Kinase Inhibitor Dinaciclib in Combination with Rituximade in Relapsed/Refractory Chronic Lymophocytic Leukemia Patients," Cancer Chemother. Pharmacol 74:1057-1064.
Finn, R.S. et al. (2009). "PD 0332991, A Selective Cyclin D Kinase 4/6 Inhibitor, Preferentially Inhibits Proliferation of Luminal Estrogen Receptor-Positive Human Breast Cancer Cells Lines in vitro," Breast Cancer Research 11(5):R77, 13 pages.
Finn, R.S. et al. (2016). "Targeting the Cyclin-Dependent Kinases (CDK) 4/6 in Estrogen Receptor-Positive Breast Cancers," Breast Cancer Research 18:17, 11 pages.
Finn, R.S. et al. (Nov. 17, 2016). "Palbociclib and Letrozole in Advanced Breast Cancer," The New Eng. J. of Medicine 375(20):1925-1936.
Fitzsimmons, E. et al. (Apr. 4, 2018). "CDK 4/6 Inhibitors What's New and What's Left to Learn," Living Beyond Breast Cancer, 6 pages.
Formisano, L. et la. (2017). "Abstract 1008: Gain-of-Function Kinase Library Screen Identifies FGFR1 Amplication as a Mechanism of Resistance to Antiestrogens and CDK4/6 Inhibitors in ER+ Breast Cancer," Cancer Research, 4 pages.
Fu, Y. et al. (2017, e-pub. Oct. 16, 2017). "Discovery of a Class of Diheteroaromatic Amines as Orally Bioavailable CDK1/4/6 Inhibitors," Bioogranic & Medicinal Chemistry Letter 27:5332-5336.
Gao, S. et al. (2016). "Androgen Receptor Tumor Suppressor Function Is Mediated by Recruitment of Retinoblastoma Protein," Cell Reports 17:966-976.
Goel, S. et al. (Aug. 24, 2017). "CDK4/6 Inhibition Triggers Anti-Tumour Immunity," Nature 548(7668):471-475, 32 pages.
Grant, S. (Jun. 2018). "Rational Combination Strategies to Enhance Venetoclax Activity and Overcome Resistance in Hematologic Malignancies," Leuk. Lymphoma 59(6):1292-1299, 12 pages.
Grossel, M.J. (1998). "Oncogenic Functions of cdK4 and cdK6," U.S. Army Medical Research and Material Command, 56 pages.
Guarducci, C. et al. (2017, e-pub. Oct. 27, 2017 ). "Mechanisms of Resistance to CDK4/6 Inhibitors in Breast Cancer and Potential Biomarkers of Response," Breast Care 12:304-308.
Hafner, M. et al. (Aug. 15, 2019). "Multiomics Profiling Establishes the Polypharmacology of FDA-Approved CDK4/6 Inhibitors and the Potential for Differential Clinical Activity," Cell Chemical Biology 26:1-14, 23 pages.
Haines, E. et al. (2018). "Palbociclib Resistance Confers Dependence on an FGFR-MAP Kinase-mTOR-Driven Pathwasy in KRAS-Mutant Non-Smaill Cell Lung Cancer," Oncotarget 9(60):31572-31589.
He, S. et al. (Apr. 26, 2017). "Transient CDK4/6 Inhibition Protects Hematopoietic Stem Cells from Chemotherapy-Induced Exhaustion," Sci. Transl. Med. 9(387):1-27, 27 pages.
Herrera-Abreu, M.T. et al. (2015). "Preclincial Breast Cancer Biology: PI3 Kinase/mTOR Inhibition Increases Sensitivity of ER Positive Breast Cancers to CDK4/6 Inhibition by Blocking Cell Cycle Re-Entry Driven by CyclinD1 and Inducting Apoptosis," Annals of Oncology 26(Suppl. 3)ii29-ii30.
Herrera-Abreu, M.T. et al. (2016, e-pub. Mar. 28, 2016). "Early Adaptation and Acquired Resistance to CDK4/6 Inhibiton in Estrogen Receptor-Positive Breast Cancer," Cancer Research 76:2301-2313.
Honma, T. et al. (2001, e-pub. Dec. 13, 2001). "A Novel Approach for the Development of Selective Cdk4 Inhibitors: Library Design Based on Locations of Cdk4 Specific Amino Acid Residues," J. Med. Chem. 44:4628-4640.
Hossain, D.M.S. et al. (2018). "Dinaciclib Induces Immunogenic Cell Death and Enhances Anti-PD-1-Mediated Tumor Suppression," the Journal of Clinical Investigation, 11 pages.
Hu, S. et al. (2019). "Discovery and Characterization of SY-1365, a Selective, Covalent Inhibitor of CDK7," AACR, 42 pages.
International Search Report and Written Opinion dated Jun. 13, 2019 for PCT Application No. PCT/US2019/018244, filed on Feb. 15, 2019, 10 pages.
Iyengar, M. et al. (2018). "CDK4/6 Inhibition as Maintenance and Combination Therapy for High Grade Serous Ovarian Cancer," Oncotarget 9(21):15658-15672.
Jansen, V.M. et al. (May 1, 2017, e-pub. Mar. 1, 2017). "Kinome-Wide RNA Interference Screen Reveals a Role for PDK1 in Acquired Resistance to CDK4/6 Inhibition in ER-Positive Breast Cancer," Cancer Research 77(9):1-13.
Ji, W. et al. (2019). "Combined Androgen Receptor Blockade Overcomes the Resistance of Breast Cancer Cells to Palbociclib," International J. Of Biological Sciences 15:522-532.
Kawakami, M. et al. (2017). "Next-Generation CDK2/9 Inhibitors and Anaphase Castastrophe in Lung Cancer," JNCI Natl. Cancer Inst. 109(6):1-11.
Kawakami, M. et al. (Apr. 2018). "Engaging Anaphase Catastrophe Mechanisms to Eradicate Aneuploid Cancers," Mol. Cancer Ther. 17(4):724-731.
Klien, M.E. et al. (Jul. 9, 2018). "CDK4/6 Inhibitors: The Mechanism of Action May Not Be as Simple as Once Thought," Cancer Cell 34:1-12.
Knudsen, E.S. et al. (Jan. 2017). "The Strange Case of CDK4/6 Inhibitors: Mechanisms, Resistance, and Combination Strategies," Trends Cancer 3(1):39-55.
Konecny, G.E. (2019). "Combining PARP and CDK4/6 Inhibitors in MYC Driven Ovarian Cancer," EBioMedicine, 2 pages.
Konecny, G.E. et al. (2011, e-pub. Jan. 28, 2011). "Expression of p16 and Retinoblastoma Determines Response to CDK4/6 Inhibition in Ovarian Cancer," Clinical Cancer Research 17:1591-1602.
Lee, N.V. et al. (Feb. 2016). "Abstract P3-06-01: Mechanisms of Resistance to CDK4/6 Ihhibition in ER+ Breast Cancer," Cancer Research, 5 pages.
Lenihan, C. et al. (Feb. 2016). "Abstract P3-06-02: Characterization of Resistance to the Selective CDK4/6 Inhibitor Palbociclib in ER Positive Breast Cancer," Cancer Research, 6 pages.
Lenihan, C. et al. (Feb. 2017). "Abstract P3-03-12: CDK4/6 Inhibitor Resistant ER-Positive Cells Remain Dependent on Estrogen Signalling and Retain Sensitivity to Endocrine Therapy," Cancer Research, 5 pages.
Li, Z. et al. (2018). "Loss of the FAT1 Tumor Suppressor Promotes Resistance to CDK4/6 Ihibitors via the Hippo Pathway," Cancer Cell 34:893-905.
Lim, S. et al. (2013). "Cdks, Cyclins and CKIS: Roles Beyond Cell Cycle Reguation," Development 140(15):3079-3093.
Liu, C.-Y. et al. (Dec. 20, 2017). "Combination of Palbociclib With Enzalutamide Shows in vitro activity in RB Proficient and Androgen Receptor Positive Triple Negative Breast Cancer Cells," PLoS ONE 12(12):e0189007, 14 pages.
Lu, H. et al. (2006). "Toward Understanding the Structural Basis of Cyclin-Dependent Kinase 6 Specific Inhibition," J. Med. Chem. 49:3826-3831.
Malumbres, M. (2014). "Cyclin-Dependent Kinases," Genome Biol. 15(6):122, 10 pages.
Malumbres, M. et al. (Nov. 2009). "Cyclin-Dependent Kinases: A Family Portrait," Nat Cell Biol. 11(11):1275-1276, 4 pages.

(56) References Cited

OTHER PUBLICATIONS

Martin, L.-A. et al. (Feb. 2017). "Abstract P3-03-09: Resistance to Palbociclib Depends on Mutliple Targetable Mechanisms Highlighting the Potential of Drug Holidays and Drug Switching to Improve Therapeutic Outcome," Cancer Research, 6 pages.

Michaloglou, C. et al. (2018, e-pub. Feb. 26, 2018). "Combined Inhibition of mTOR and CDK4/6 Is Required for Optimal Blockade of E2F Function and Long-Term Growth Inhibition in Estrogen Receptor-Positive Breast Cancer," Molecular Cancer Therapeutics 17(5):1-14.

Michaud, K. et al. (Apr. 15, 2010, e-pub. Mar. 30, 2010). "Pharmacologic Inhibition of Cyclin-Dependent Kinases 4 and 6 Arrests the Growth of Glioblastoma Multiforme Intracranial Xenografts," Cancer Research 70(8):1-12.

Naidoo, K. et al. (Jan. 2018). "Evaluation of CDK12 Protein Expression as a Potential Novel Biomarker for DNA Damage Response Targeted Therapies in Breast Cancer," Mol. Cancer Ther. 17(1):306-305.

Naz, S. et al. (2018, e-pub. May 1, 2018). "Abemaciclib, A Selective CDK4/6 Inhibitor Enhances the Radiosensitivity of Non-Small Cell Lung Cancer in vitro and in vivo," AACR, 36 pages.

Nikitorowicz-Biniak, J. et al. (Feb. 2018). "Abstract P1-09-03: Global Knockdown of Cellular Kinases Identifies MPS1 as a Novel Modulator of Endocrine and Palbociclib Resistance Highlighting a New Role for MPS1 Inhibtors," Cancer Research, 7 pages.

O'Brien, N. et al. (2018, e-pub. Feb. 28, 2018). "Preclinical Activity of Abemaciclib Alone or in Combination With Antimitotic and Targeted Therapies in Breast Cancer," Molecular Cancer Therapeutics 17:897-907.

O'Leary, B. et al. (2016). "Treating Cancer With Selective CDK4/6 Inhibitors," The Institute of Cancer Research, 31 pages.

O'Leary, B. et al. (2018). "Early Circulating Tumor DNA Dynamics and Clonal Selection With Palbociclib and Fulvestrant for Breast Cancer," Nature Communications 9:896, 10 pages.

Pandey, K. et al. (2019). "Molecular Mechanisms of Resistance to CDK4/6 Inhibitors in Breast Cancer: A review," International Journal of Cancer 145:1179-1188.

Patel, P. et al. (2018, e-pub. Jan. 12, 2018). "Dual Inhibition of CDK4 and CDK2 via Targeting p27 Tyrosine Phyosphorylation Induces a Potent and Durable Response in Breast Cancer Cells," SUNY Downstate Medical Center, 43 pages.

Patnaik, A. et al. (Jul. 2016, e-pub. May 23, 2016). "Efficacy and Safety of Abemaciclib, and Inhibitor of CDK4 and CDK6, for Patients with Breast Cancer, Non-Small Cell Lung Cancer, and Other Solid Tumors," Cancer Discovery, 6(7):1-14.

Pernas, S. et al. (2018). "CDK4/6 Inhibition in Breast Cancer: Current Practice and Future Directions," Ther. Adv. Med. Oncol. 10:1-15.

Portman, N. et al. (2019). "Overcoming CDK4/6 Ihibitor Resistance in ER-Positive Breast Cancer," Endocrine-Related Cancer 26(1):R15-R30.

Puyol, M. et al. (Jul. 13, 2010). "A Synthetic Lethal Interaction Between K-Ras Oncogenes and Cdk4 Unveils a Therapeutic Strategy for Non-Small Cell Lung Carcinoma," Cancer Cell 18:63-73.

Raza, A. et al. (2017). "Rigosertib Oral in Transfusion Dependent Lower Risk Myelodysplastic Syndromes (LR-MDS): Optimization of Dose and Rate of Transfusion Independence (TI) or Transfusion Reduction (TR) in a Single-Arm Phase 2 Study," Onoconva Therapeutics, 1 page.

Reddy, M.V. et al. (Jan. 13, 2014). "Discovery of 8-Cyclopentyl-2-[4-(4-methyl-piperazin-1-yl)-phenylamino]-7-oxo-7,8-dihydropyrido[2,3-d]pyrimidine-6-carbonitrile (7x) as a Potent Inhibitor of Cyclin-Dependent Kinase 4 (CDK4) and AMPK-Related Kinase 5 (ARK5)," Journal of Medicinal Chemistry 57:578-599.

Ren, C. et al. (Nov. 12-15, 2017). "Abstract AM-17-1604: Pharmacokinetics/Pharmacodynamics/Drug Metabolism," 2017 AAPS Annual Meeting and Expositions, 3 pages.

Robinson, T.J.W. et al. (Nov. 12, 2013). "RB1 Status in Triple Negative Breast Cancer Cells Dictates Response to Radiation Treatment and Selective Therapeutic Drugs," PLoS ONE 8(11):e78641, 11 pages.

Rocca, A. et al. (2017). "Progress With Palbociclib in Breast Cancer: Latest Evidence and Clincial Considersations," Ther. Adv. Med. Oncol. 9(2):83-105.

Rodgers, J.T. et al. (Jun. 19, 2014). "mTORC1 Controls the Adaptive Transition of Quiescent Stem Cells from G0 to GAlert," Nature 510(7505):393-396, 11 pages.

Roskoski, R. Jr. (2019). "Cyclin-Dependent Protein Serine/Threonine Kinase Ihhibitors as Anticancer Drugs," Pharacological Research 1396:417-488.

Sakurikar, N. et al. (2016, e-pub. Apr. 25, 2016). "Critical Reanalysis of the Methods That Discriminate the Activity of CDK2 From CDK1," Cell Cycle 15(9)1184-1188.

Seyfried, F. et al. (2015). "Synergistic Activity of ABT-199 With Conventional Chemotherapy and Dinaciclib in B-Cell Precursor Acute Lymphoblastic Leukemia," Blood 126:2631, 6 pages.

Shafiq, M.I. et al. (Aug. 14, 2012). "Fascaplysin as a Specific Inhibitor for CDK4: Insights from Molecular Modelling," PLoS ONE 7(8):e42612, 9 pages.

Shapiro, G.I. (Jul. 2018). "Abstract SY19-02: Novel Mechanisms of Acquired Resistance to Selective CDK4/6 Inhibition," Cancer Research, 4 pages.

Sherr, C.J. (2018). "Acquired Palbociclib Resistance in KRAS-Mutant Lung Cancer," Oncotarget 9(67):32734-32735.

Sherr, C.J. et al. (2015, e-pub. Dec. 11, 2015). "Targeting CDK4 and CDK6 From Discovery to Therapy," Cancer Discov. 6(4):353-367.

Tadesse, S. et al. (2018, e-pub. Dec. 13, 2018). "Cyclin Dependent Kinase 2 Inhibitors in Cancer Therapy: An Update," J. Med. Chem., 68 pages.

Tadesse, S. et al. (Feb. 3, 2017). "Highly Potent, Selective, and Orally Bioavailable 4-Thiazol-N-(pyridin-2yl) Pyrimidin-2-amine Cyclin-Dependent Kinases 4 and 6 Inhibitors as Anticancer Drug Candidates: Design, Synthesis, and Evaluation," J. of Med. Chemistry 60:1892-1915.

Tarrado-Castellarnau, M. et al. (2017). " De novo MYC Addiction as an Adaptive Response of Cancer Cells to CDK4/6 Inhibition," Molecular Systems Biology 13:940, 15 pages.

Teo, Z.L. et al. (Nov. 15, 2017, e-pub. Sep. 25, 2017). "Combined CDK4/6 and PI2Kα Inhibition Is Synergistic and Immunogenic in Triple-Negative Breast Cancer," Cancer Research 77(22):1-14.

Toogood, P.L. et al. (2005). "Discovery of a Potent and Selective Inhibitor of Cyclin-Dependent Kinase 4/6," J. Med. Chem. 487:2388-2406.

Toulmonde, M. et al. (2019, e-pub. Apr. 12, 2019). "Activity and Safety of Palbociclib in Patients With Advanced Gastrointestinal Stromal Tumors Resfractory to Imatinib and Sunitinib: A Biomarker-Driven Phase 2 Study," AARC J., 15 pages.

Tripathy, D. et al. (2017, e-pub. Mar. 28, 2017). "Ribociclib (LEE011): Mechanism of Action and Clinical Impact of this Selective Cyclin-Dependent Kinase 4/6 Inhibitor in Various Solid Tumors," AACR J., 29 pages.

Turner, N.C. et al. (Jul. 16, 2015). "Palbociclib in Hormone-Receptor-Positive Advanced Breast Cancer," The New Engl. J. of Med. 373(3):209-219.

Vidula, N. et al. (Feb. 2016, e-pub. Jul. 26, 2015). " Cyclin-Dependent Kinase 4/6 Inhibitors for the Treatment of Breast Cancer: A Review of Preclinical and Clinical Data," Clinical Breast Cancer 16(1):8-17.

Vilgelm, A.E. (Aug. 14, 2019). "MDM2 Antagonists Overcome Intrinsic resistance to CDK4/6 Inhibition by Inducing p21," Sci. Transl. Med. 11(eaav7171):1-15.

Vora, S.R. et al. (Jul. 14, 2014). "CDK 4/6 Inhibitors Sensitize PIK3CA Mutant Breast Cancer to PI3K Inhibitors," Cancer Cell 26:136-149.

Whatcott, C.J. et al. (2016). "Alvocidib Potentiates the Activity of Venetoclax in Preclinical Models of Acute Myeloid Leuemia," Blood 128:1652, 7 pages.

Whittaker, S.R. et al. (2018, e-pub. Jan. 28, 2018). "Molecular Profiling and Combinatorial Activity of CCT068127: A Potent CDK2 and CDK9 Inhibitor," Molecular Oncology 12:287-304.

(56) References Cited

OTHER PUBLICATIONS

Wiedemeyer, W.R. (2018, e-pub. Mar. 29, 2018). "Resistance Mechanisms to Cyclin-Dependent Kinase Inhibitors," Springer, 1 page.
Wood, A.C. et al. (Jun. 1, 2016, e-pub. Dec. 16, 2016). "Dual ALK and CDK4/6 Inhibition Demonstrates Synergy Against Neuroblastoma," Clinical Cancer Research 23(11):2856-2868.
Wood, D.J. et al. (2018). "Difference in the Conformational Energy Landscape of CDK1 and CDK2 Suggest a Mechanism for Achieving Selective CDK Inhibition," Cell Chemical Biology 26:1-10.
Wood, D.J. et al. (2018). "Structural Insights Into the Functional Diversity of the CDK—Cyclin Family," Open Biol. 8:180112, 26 pages.
Xia, P. et al. (Oct. 25, 2018). "Inhibition of Cyclin-Dependent Kinase 2 Protects Against Doxorubicin-Induced Cardiomyocyte Apoptosis and Cardiomyopathy," JBC, 24 pages.
Xie, S. et al. (2016). "Antitumor Action of CDK Inhibitor LS-007 as a Single Agent and in Combination with ABT-199 Against Human Acute Leukemia Cells," Acta Pharmacologica Sinica 37:1481-1489.
Xue, Y. et al. (2019). "CDK4/6 Inhibitors Target SMARCA4-Determined Cyclin D1 Deficiency in Hypercalcemica Small Cell Carcinoma of the Ovary," Nature Communications 10:558, 15 pages.
Xue, Y. et al. (2019). "SMARCA4 Loss is Synthetic Lethal With CDK4/6 Inhibition in Non-Small Cell Lung Cancer," Nature Communications 10:577, 13 pages.
Yang, C. et al. (2017). "Acquired CDK6 Amplification Promotes Breast Cancer Resistance to CDK4/6 Inhibitors and Loss of ER Signaling and Dependence," Oncogene 36:2255-2264.
Yi, J. et al. (2019). "MYC Status as a Determinant of Synergistic Response to Olaparib and Palbociclib in Ovarian Cancer," EBioMedicine 13 pages.
Yin, L. et al. (2018). "A Highly Potent CDK4/6 Inhibitor Was Rationally Designed to Overcome Blood Brain Barrier in Gliobastoma Therapy," Euro. J. Med. Chem. 34, pages.
Zha, C. et al. (2018, e-pub. Feb. 12, 2018). "Design, Synthesis and Biological Evaluation of Tetrahydronaphthyridine Derivatives as Bioavailable CDK4/6 Inhibitors for Cancer Therapy," Euro. J. Med. Chem. 148:140-153.
Zhao, X. et al. (2015). "The Synergistic Effect of Venetoclax Combined With a CDK9 Inhibitor in Primary Diffuse Large B Cell Lymphoma and Folicular Lymphoma Cells," Blood 126:2746, 5 pages.
Zhao, X. et al. (2016). "Inhibition of Cyclin Dependent Kinase 9 Synergistically Enhanced Venetoclax Activity in Mantle Cell Lymphoma Cells," Blood 128:1593, 5 pages.
Zhou, L. et al. (2017, e-pub. Dec. 14, 2017). "Flavopiridol Enhances ABT-199 Sensitivity in Unfavourable-Risk Multiple Myeloma Cells in vitro and in vivo," British J. Cancer, 10 pages.
Zhu, Y. et al. (2018). Tamoxifen-Resistant Breast Cancer Cells are Resistant to DNA-Damaging Chemotherapy Because of Upregulated BARD1 and BRCA1,: Nature Communications 9:1595, 11 pages.
Remington's Pharmaceutical Sciences, Mack Publishing Company, Philadelphia, PA, 20th ed. (2000).
Barroso-Sousa, R. et al. (2016, e-pub Jun. 22, 2016). "Clinical Development of the CDK4/6 Inhibitors Ribociclib and Abemaciclib in Breast Cancer," BreastCare 11:167-173.
Di Giovanni, C. et al. (Sep. 12, 2016, e-pub. Sep. 8, 2016). "Investigational Drugs Targeting Cyclin-Dependent Kinases For The Treatment of Cancer: An Updated on Recent Findings (2013-2016)." Expert Opinion on Investigational Drugs 55 pages.
Gelbert, L.M. et al. (2014). "Preclinical Characterization of the CDK4/6 Inhibitor LY28352219: in-vivo Cell Cycle-Dependent/independent Anti-Tumor Activities Alone/In Combintiaton With Gemcitabine," Invest. New Drugs 32:825-837.
Jhan, J.-R. et al. (2017). "Triple-Negative Breast Cancer and the Potential for Targeted Therapy," Pharmacogenomics 18(17):1595-1609.
PUBCHEM (Dec. 27, 2010). "CID 49802504-(2S-2-[6-(Cycloheptylcarbamayl)-4-(8-fluro-4-methyl-2,3-dihydro-1,4-benzoxazin-6-yl)-2,5-dimethylpyridin-3-yl]-2-[(2-methylpropan-2-yl)oxy]acetic acid," 7 pages.
PUBCHEM (Oct. 25, 2006). "CID 10064398- "6-(2-Anilinopyridin-4-yl)-4H-1,4-Benzoxazin-3-one," 8 pages.

HETEROCYCLIC COMPOUNDS AS KINASE INHIBITORS

CROSS-REFERENCE TO RELATED APPLICATIONS

This application claims priority to U.S. Provisional Application No. 62/631,437, filed Feb. 15, 2018, the contents of which are incorporated herein by reference in their entirety.

FIELD OF THE INVENTION

This disclosure relates generally to therapeutics which play a crucial role in the control of the cell cycle and more particularly, compounds that inhibit cyclin-dependent kinases (CDK). The invention also provides pharmaceutically acceptable compositions comprising compounds of the present invention and methods of using said compositions in the treatment of diseases associated with these pathways.

BACKGROUND OF THE INVENTION

The cell cycle is a period between the successive divisions of a cell. During this period, the contents of the cell must be accurately replicated. The processes that permit the cell to divide are very precisely controlled by a multitude of enzymatic reactions amongst which the protein kinase-triggered protein phosphorylation plays a major role. In eukaryotes, there are four main stages/phases of cell cycle namely the Gap-1 (G1) phase, Synthesis (S) phase, Gap-2 (G2) and Mitosis (M) phases. An extended phase of Gap-1 phase is coined as Gap-0 (G0) phase or Resting phase (Cancers 2014, 6, 2224-2242).

Uncontrolled proliferation is the hallmark of cancer and other proliferative disorders and abnormal cell cycle regulation is, therefore, common in these diseases. Cyclin-dependent kinases (CDK) constitute a heterodimeric family of serine/threonine protein kinases involved in cell cycle and transcription. They include two main groups: cell cycle CDK and transcriptional CDK. The functionality of CDK depends on specific interactions with regulatory proteins named cyclins which form heterodimeric complexes with their partners. These complexes are important regulators of the cellular processes, especially in the cell cycle progression.

The human proteome contains 20 CDK along with 29 cyclins. CDK1, CDK2, CDK4 and CDK6 are generally considered cell cycle CDK, whereas CDK7, CDK8, CDK9 and CDK11 are mainly involved in transcription regulation (Genome Biol 2014; 15(6):122, Nat Cell Biol 2009; 11(11): 1275-6). CDK5 is the prototype of atypical CDK: it is activated by the non-cyclin proteins p35 (or Cdk5R1) and p39 (or Cdk5R2) and has unique post-mitotic functions in neuronal biology, angiogenesis and cell differentiation. Proliferative signals induce the transition from the G0 or G1 phases into S phase through the activation of the structurally related CDK4 and CDK6 [Development, 2013; 140 (15): 3079-93, Biochem Pharmacol 2012; 84(8):985-93, Nature 2014; 510(7505):393-6]. The binding of cyclin D to CDK4 and to CDK6 promotes the phosphorylation of the transcriptional repressor retinoblastoma protein (RB1).

CDK hyperactivity is often observed in cancer, reflecting their prominent role in cell cycle and transcription regulation. In cancer cells, the process of cell division becomes unregulated, resulting in uncontrolled growth that leads to the development of a tumor. A number of mechanisms contribute to the dysregulation of the cell cycle in malignant cells, including the amplification and hyperactivity of CDK4/6, or their genomic instability, which might cause CDK4/6 to become oncogenic drivers of cell replication. Usurping these mechanisms, cancer cells can continue to replicate by triggering the G1 to S phase transition. This process appears to be facilitated by a shortening of the G1 phase. In a cancer cell, CDK4/6 antagonizes intrinsic tumor suppression mechanisms including cell senescence and apoptosis, which further augments the growth of a tumor. Cancer cells also upregulate other CDK and cyclins and decrease suppressive mechanisms such as intrinsic CDK inhibitors and tumor suppressor proteins. The overall effect of this type of cell cycle dysregulation is malignant cell proliferation and the development of cancer (Clinical Breast Cancer, 2016, 1526-8209).

Several CDK inhibitors have been reported (such as in WO2011101409 and WO2011101417) or clinically developed. Flavopiridol and R-Roscovitine (Seliciclib), were the first generation of pan-CDK inhibitors with anti-tumor activity attributed to down-regulation of CDK9-mediated anti-apoptotic proteins, especially Mcl-1. Recently, a new generation of CDK inhibitors have been developed, advanced to clinical trials, and approved for certain types of cancer. Dinaciclib, a selective inhibitor of CDK1, CDK2, CDK5, and CDK9, was directed towards refractory chronic lymphocytic leukemia while palbociclib was tested against advanced estrogen receptor (ER)-positive breast cancer as a selective inhibitor of CDK4 and CDK6. The development of more selective second and third generation CDK inhibitors, including specific CDK4/6 inhibitors, has led to a renewed enthusiasm for manipulating the cyclin D1-CDK4/6 axis in cancer treatment. There are three FDA-approved CDK4/6 inhibitors presently: Palbociclib, Ribociclib and Abemaciclib.

The development of therapies, including monotherapies, for treatment of proliferative disorders using a therapeutic targeted generically at CDK, or specifically at dual inhibition of CDK4 and CDK6, is therefore potentially highly desirable.

There is still a need for new CDK4/6 inhibitors. Compounds for the treatment of hyper-proliferative diseases preferably have at least one advantageous property selected from selectivity, potency, stability, pharmacodynamic properties and safety profile. In this regard, a novel class of CDK4/6 inhibitors is provided herein.

BRIEF SUMMARY OF THE INVENTION

In one embodiment, provided is a compound of Formula (J):

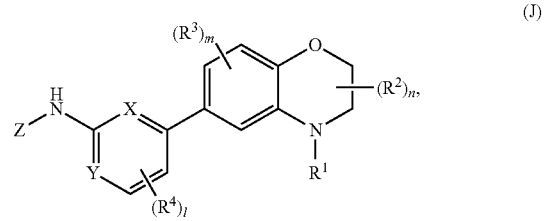

or a salt thereof, wherein X, Y, Z, $R^1$, $R^2$, $R^3$, $R^4$, l, m and n are as detailed herein.

In some embodiments, provided is a compound of Formula (I):

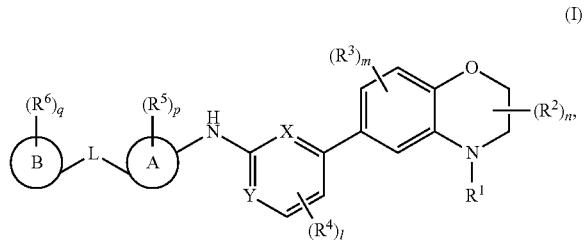
(I)

or a salt thereof, wherein X, Y, A, B, L, $R^1$, $R^2$, $R^3$, $R^4$, $R^5$, $R^6$, l, m, n, p and q are as detailed herein.

In some embodiments, provided is a compound of Formula (II):

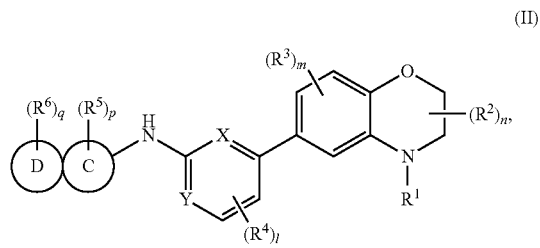
(II)

or a salt thereof, wherein X, Y, C, D, $R^1$, $R^2$, $R^3$, $R^4$, $R^5$, $R^6$, l, m, n, p and q are as detailed herein.

In some embodiments, the compound of Formula (I) or a salt thereof is of Formula (I-A) as detailed herein,

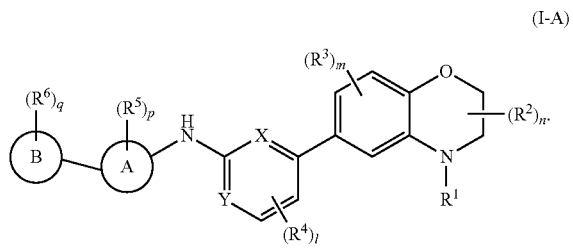
(I-A)

In another aspect, provided is a method of treating cancer in an individual in need thereof comprising administering to the individual a therapeutically effective amount of a compound as detailed herein, such as a compound of any one of Formula (J), Formula (I), Formula (II), (I-A), (I-B1) to (I-B12), (I-C1) to (I-C23), or a pharmaceutically acceptable salt thereof. Also provided is a method of modulating CDK4/6 in an individual, comprising administering to the individual a compound detailed herein, or a salt thereof. Also provided is a method of modulating CDK4/6 and one or more of CDK1, CDK2, and CDK9 in an individual, comprising administering to the individual a compound detailed herein, or a salt thereof. Also provided is a method of inhibiting CDK4/6 in a cell, comprising administering a compound detailed herein, or a salt thereof, to the cell. Also provided is a method of inhibiting CDK4/6 and one or more of CDK1, CDK2, and CDK9 in a cell, comprising administering a compound detailed herein, or a salt thereof, to the cell. In some embodiments of the methods detailed herein, the methods comprise administration of a compound detailed herein, or a salt thereof, as a monotherapy.

In another aspect, provided is a pharmaceutical composition comprising a compound detailed herein, or a pharmaceutically acceptable salt thereof, and a pharmaceutically acceptable carrier or excipient. Kits comprising a compound detailed herein, or a salt thereof, are also provided. Kits may optionally include instructions for use, such as instructions for use in any of the methods detailed herein, for example, for use in the treatment of cancer. A compound as detailed herein, or a salt thereof, is also provided for the manufacture of a medicament for the treatment of cancer.

DETAILED DESCRIPTION OF THE INVENTION

Definitions

Figure 1:
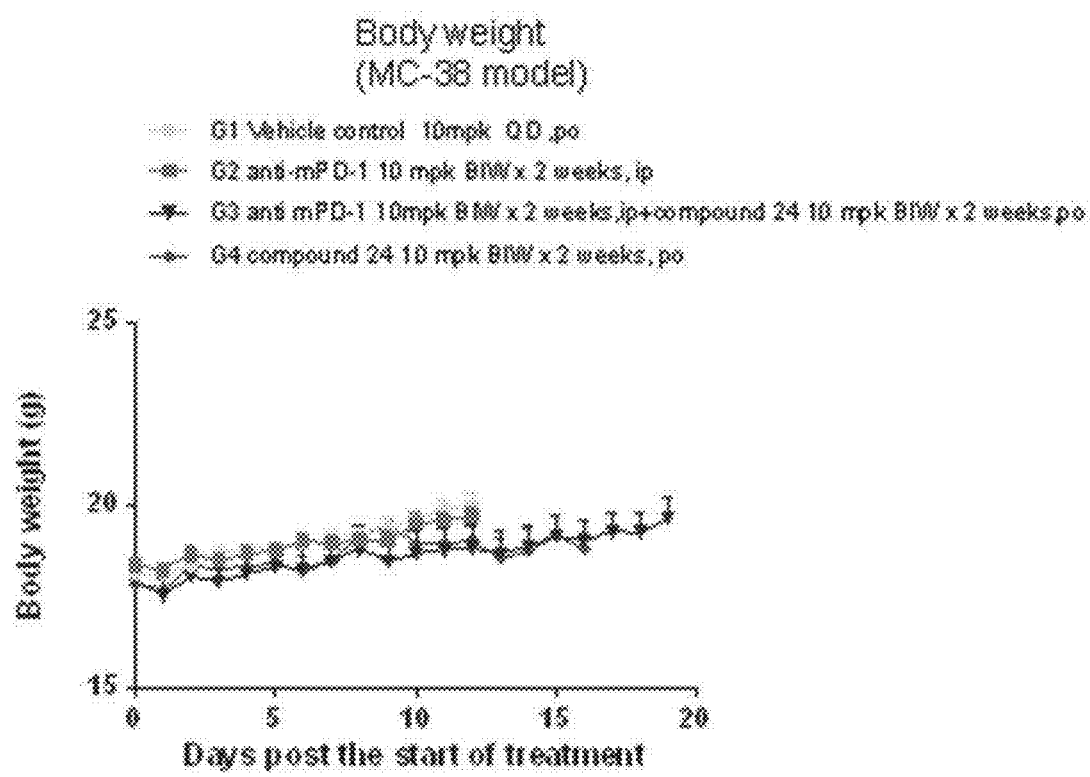
FIG. 1 shows the body weight changes of the mice in the different groups of a pharmacological study of test compound in a MC-38 mouse model.

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C═C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but- 2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_8$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, pyrazolyl, oxazolyl, isooxazolyl, imidazolyl, quinolyl, isoquinolyl, benzimidazolyl, benzpyrazolyl, benzotriazolyl, indole, benzothiazyl, benzoxazolyl, benzisoxazolyl, imidazopyridinyl and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, dihydrooxazolyl, dihydroisoxazolyl, dioxolanyl, morpholinyl, dioxanyl, tetrahydrothiophenyl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different, provided that the group's normal valence is not exceeded. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

As used herein "CDK" refers to one or more cyclin-dependent kinases. CDK4/6 refers to both CDK4 and CDK6. Thus, inhibitors of CDK4/6 inhibit both CDK4 and CDK6.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that embodiments, aspects and variations described herein also include "consisting" and/or "consisting essentially of" embodiments, aspects and variations.

Compounds

In one aspect, provided is a compound of the Formula (J):

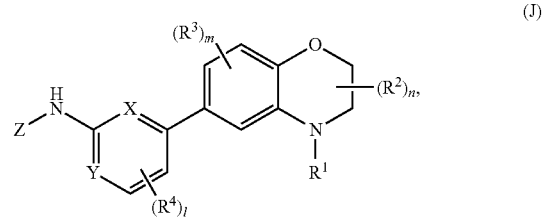

or a salt thereof, wherein:

Z is

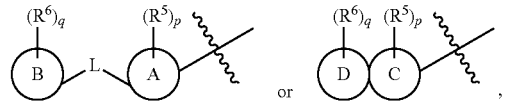

wherein

A is $C_3$-$C_6$ cycloalkyl, 4- to 7-membered heterocyclyl, 5- to 7-membered heteroaryl, or $C_6$ aryl, each of which is optionally substituted with $R^5$;

L is a bond, —$CR^{11}R^{12}$—, —O—, —S—, —$SO_2$—, —C(O)—, —$NR^{10}$—, —$SO_2NR^{10}$—, or —$NR^{10}SO_2$—;

B is hydrogen, $C_3$-$C_6$ cycloalkyl, 3- to 7-membered heterocyclyl, 5- to 7-membered heteroaryl, or $C_6$ aryl, each of which is optionally substituted with $R^6$;

C is $C_3$-$C_6$ cycloalkyl, 5- to 7-membered heterocyclyl, 5- to 7-membered heteroaryl, or $C_6$ aryl, each of which is optionally substituted with $R^5$, wherein C is fused to D; and D is $C_3$-$C_6$ cycloalkyl, 3- to 7-membered heterocyclyl, 5- to 7-membered heteroaryl, or $C_6$ aryl, each of which is optionally substituted with $R^6$;

each X and Y are independently N or CH, provided that at least one of X and Y is N;

$R^1$ is hydrogen, $C_1$-$C_6$ alkyl, $C_2$-$C_6$ alkenyl, $C_2$-$C_6$ alkynyl, $C_1$-$C_8$ alkoxy, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)

(3- to 12-membered heterocyclyl), —C(O)R$^{10}$, —(C$_1$-C$_3$ alkylene)(5- to 10-membered heteroaryl) or —(C$_1$-C$_3$ alkylene)(C$_6$-C$_{14}$ aryl), wherein R$^1$ is independently optionally substituted by halogen, oxo, —OR$^{13}$, —NR$^{13}$R$^{14}$, —C(O)R$^{13}$, —CN, C$_3$-C$_8$ cycloalkyl, or C$_1$-C$_6$ alkyl optionally substituted by oxo, —OH or halogen, provided that when Z is

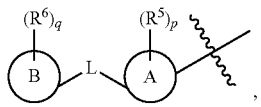

n is 1 and R$^2$ is oxo, then R$^1$ is C$_2$-C$_6$ alkyl, C$_2$-C$_6$ alkenyl, C$_2$-C$_6$ alkynyl, C$_1$-C$_8$ alkoxy, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)(C$_3$-C$_6$ cycloalkyl), —C(O)R$^{10}$, or —(C$_1$-C$_3$ alkylene)(C$_6$-C$_{14}$ aryl), wherein R$_1$ is independently optionally substituted by halogen, oxo, —OR$^{13}$, —C(O)R$^{13}$, —CN, C$_3$-C$_8$ cycloalkyl, or C$_1$-C$_6$ alkyl optionally substituted by oxo, —OH or halogen;

each R$^2$ is independently C$_1$-C$_6$ alkyl, oxo, —NR$^{11}$R$^{12}$, —CN, —C(O)R$^{10}$, —C(O)NR$^{11}$R$^{12}$ or halogen, wherein any two R$^2$ groups are independently attached to same carbon or two different carbons;

each of R$^3$ and R$^4$ is independently C$_1$-C$_6$ alkyl, C$_3$-C$_6$ cycloalkyl, C$_1$-C$_6$ haloalkyl, C$_1$-C$_6$ alkoxy, C$_1$-C$_6$ haloalkoxy, halogen or —OH;

each R$^5$ is independently C$_1$-C$_6$ alkyl, C$_2$-C$_6$ alkenyl, C$_2$-C$_6$ alkynyl, halogen, oxo, —CN, —OR$^{10}$, —SR$^{10}$, —NR$^{11}$R$^{12}$, —C(O)R$^{10}$, —C(O)NR$^{11}$R$^{12}$, —OC(O)NR$^{11}$R$^{12}$, —NR$^{10}$C(O)R$^{11}$, —NR$^{10}$C(O)NR$^{11}$R$^{12}$, —S(O)R$^{10}$, —S(O)$_2$R$^{10}$, —NR$^{10}$S(O)$_2$R$^{10}$, —S(O)$_2$NR$^{11}$R$^{12}$, C$_3$-C$_6$ cycloalkyl, 3- to 12-membered heterocyclyl, —(C$_1$-C$_3$ alkylene)OR$^{10}$, —(C$_1$-C$_3$ alkylene)SR$^{10}$, —(C$_1$-C$_3$ alkylene)NR$^{11}$R$^{12}$, —(C$_1$-C$_3$ alkylene)C(O)R$^{10}$, —(C$_1$-C$_3$ alkylene)C(O)NR$^{11}$R$^{12}$, —(C$_1$-C$_3$ alkylene)NR$^{10}$C(O)R$^{11}$, —(C$_1$-C$_3$ alkylene)NR$^{10}$C(O)NR$^{11}$R$^{12}$, —(C$_1$-C$_3$ alkylene)S(O)$_2$R$^{10}$, —(C$_1$-C$_3$ alkylene)NR$^{10}$S(O)$_2$R$^{11}$, —(C$_1$-C$_3$ alkylene)NR$^{10}$S(O)$_2$NR$^{11}$R$^{12}$, —(C$_1$-C$_3$ alkylene)S(O)$_2$NR$^{11}$R$^{12}$, —(C$_1$-C$_3$ alkylene)(C$_3$-C$_6$ cycloalkyl), —(C$_1$-C$_3$ alkylene)(3- to 12-membered heterocyclyl), wherein each R$^5$ is independently optionally substituted by halogen, oxo, —OR$^{13}$, —NR$^{13}$R$^{14}$, —C(O)R$^{13}$, —CN, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, or C$_1$-C$_6$ alkyl optionally substituted by oxo, —OH or halogen;

each R$^6$ is independently oxo or R$^7$, or any two R$^6$ groups, when bound to the same carbon atom, are taken together with the carbon to which they are attached to form a C$_3$-C$_6$ cycloalkyl;

R$^7$ is independently hydrogen, C$_1$-C$_6$ alkyl, C$_2$-C$_6$ alkenyl, C$_2$-C$_6$ alkynyl, C$_3$-C$_6$ cycloalkyl, 3- to 6-membered heterocyclyl, —OR$^{10}$, —NR$^{11}$R$^{12}$, —NR$^{10}$C(O)R$^{11}$, —NR$^{10}$C(O)NR$^{11}$R$^{12}$, —S(O)$_2$R$^{10}$, —NR$^{10}$S(O)$_2$R$^{11}$, —S(O)$_2$NR$^{11}$R$^{12}$, —C(O)R$^{10}$, —C(O)NR$^{11}$R$^{12}$, —(C$_1$-C$_3$ alkylene)CN, —(C$_1$-C$_3$ alkylene)OR$^{10}$, —(C$_1$-C$_3$ alkylene)SR$^{10}$, —(C$_1$-C$_3$ alkylene)NR$^{11}$R$^{12}$, —(C$_1$-C$_3$ alkylene)CF$_3$, —(C$_1$-C$_3$ alkylene)C(O)R$^{10}$, —(C$_1$-C$_3$ alkylene)C(O)NR$^{11}$R$^{12}$, —(C$_1$-C$_3$ alkylene)NR$^{10}$C(O)R$^{11}$, —(C$_1$-C$_3$ alkylene)NR$^{10}$C(O)NR$^{11}$R$^{12}$, —(C$_1$-C$_3$ alkylene)S(O)$_2$R$^{10}$, —(C$_1$-C$_3$ alkylene)NR$^{10}$S(O)$_2$R$^{11}$, —(C$_1$-C$_3$ alkylene)S(O)$_2$NR$^{11}$R$^{12}$, —(C$_1$-C$_3$ alkylene)(C$_3$-C$_6$ cycloalkyl), or —(C$_1$-C$_3$ alkylene)(3- to 6-membered heterocyclyl), wherein each R$^7$ is independently optionally substituted by halogen, oxo, —OR$^{13}$, —NR$^{13}$R$^{14}$, —C(O)R$^{13}$, —CN, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, or C$_1$-C$_6$ alkyl optionally substituted by oxo, —OH or halogen;

R$^{10}$ is independently hydrogen, C$_1$-C$_6$ alkyl, C$_3$-C$_6$ cycloalkyl, —(C$_1$-C$_3$ alkylene)(C$_3$-C$_6$ cycloalkyl), C$_6$-C$_{14}$ aryl, 5- to 6-membered heteroaryl or 3- to 6-membered heterocyclyl, each of which is independently optionally substituted by halogen, oxo, —CN, —OR$^{15}$, —NR$^{15}$R$^{16}$, or C$_1$-C$_6$ alkyl optionally substituted by halogen, —OH or oxo;

R$^{11}$ and R$^{12}$ are each independently hydrogen, C$_1$-C$_6$ alkyl, C$_3$-C$_6$ cycloalkyl, —(C$_1$-C$_3$ alkylene)(C$_3$-C$_6$ cycloalkyl), C$_6$-C$_{14}$ aryl, 5- to 6-membered heteroaryl or 3- to 6-membered heterocyclyl, each of which is independently optionally substituted by halogen, oxo, —CN, —OR$^{15}$, —NR$^{15}$R$^{16}$ or C$_1$-C$_6$ alkyl optionally substituted by halogen, —OH or oxo;

or R$^{11}$ and R$^{12}$ are taken together with the atom to which they attached to form a 3- to 6-membered heterocyclyl optionally substituted by halogen, oxo, or C$_1$-C$_6$ alkyl optionally substituted by halogen;

R$^{13}$ and R$^{14}$ are each independently hydrogen or C$_1$-C$_6$ alkyl, wherein the C$_1$-C$_6$ alkyl of R$^{13}$ and R$^{14}$ are optionally substituted by halogen, —OR$^{15}$, —NR$^{15}$R$^{16}$, or oxo;

or R$^{13}$ and R$^{14}$ are taken together with the atom to which they attached to form a 3- to 6-membered heterocyclyl optionally substituted by halogen, oxo or C$_1$-C$_6$ alkyl optionally substituted by halogen or oxo; and R$^{15}$ and R$^{16}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{15}$ and R$^{16}$ are taken together with the atom to which they attached to form a 3- to 6-membered heterocyclyl optionally substituted by halogen, oxo or C$_1$-C$_6$ alkyl optionally substituted by oxo or halogen;

l, m, p and q are each independently 0, 1, 2 or 3, provided that at least one of m and 1 is not 0; and n is 0, 1, 2, 3 or 4.

In some embodiments, provided is a compound of Formula (J):

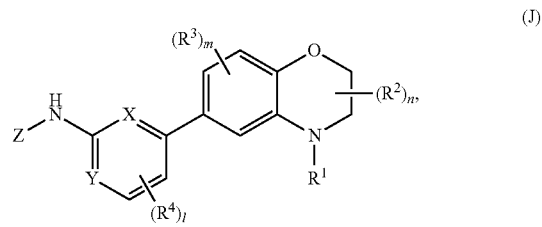

or a salt thereof, wherein:

Z is

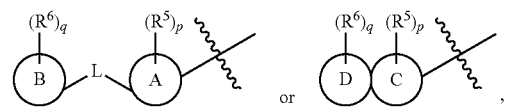

wherein

A is C$_3$-C$_6$ cycloalkyl, 4- to 7-membered heterocyclyl, 5- to 7-membered heteroaryl, or C$_6$ aryl, each of which is optionally substituted with R$^5$;

L is a bond, CH$_2$, NH, O, S, or SO$_2$;

B is hydrogen, C$_3$-C$_6$ cycloalkyl, 3- to 7-membered heterocyclyl, 5- to 7-membered heteroaryl, or C$_6$ aryl, each of which is optionally substituted with R$^6$;

C is C$_3$-C$_6$ cycloalkyl, 5- to 7-membered heterocyclyl, 5- to 7-membered heteroaryl, or C$_6$ aryl, each of which is optionally substituted with R$^5$, wherein C is fused to D; and D is C$_3$-C$_6$ cycloalkyl, 3- to 7-membered heterocyclyl, 5- to 7-membered heteroaryl, or C$_6$ aryl, each of which is optionally substituted with R$^6$;

each X and Y are independently N or CH, provided that at least one of X and Y is N;

R$^1$ is hydrogen, C$_1$-C$_6$ alkyl, C$_2$-C$_6$ alkenyl, C$_2$-C$_6$ alkynyl, C$_1$-C$_8$ alkoxy, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)(C$_3$-C$_6$ cycloalkyl), —(C$_1$-C$_3$ alkylene)(3- to 12-membered heterocyclyl), —C(O)R$^{10}$, —(C$_1$-C$_3$ alkylene)(5- to 10-membered heteroaryl) or —(C$_1$-C$_3$ alkylene)(C$_6$-C$_{14}$ aryl), wherein R$^1$ is independently optionally substituted by halogen, oxo, —OR$^{13}$, —NR$^{13}$R$^{14}$, —C(O)R$^{13}$, —CN, C$_3$-C$_8$ cycloalkyl, or C$_1$-C$_6$ alkyl optionally substituted by oxo, —OH or halogen, provided that when Z is

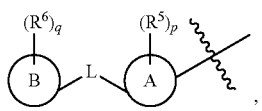

n is 1 and R$^2$ is oxo, then R$^1$ is C$_2$-C$_6$ alkyl, C$_2$-C$_6$ alkenyl, C$_2$-C$_6$ alkynyl, C$_1$-C$_8$ alkoxy, C$_3$-C$_6$ cycloalkyl, 3- to 12-membered heterocyclyl, 5- to 10-membered heteroaryl, C$_6$-C$_{14}$ aryl, —(C$_1$-C$_3$ alkylene)(C$_3$-C$_6$ cycloalkyl), —C(O)R$^{10}$, or —(C$_1$-C$_3$ alkylene)(C$_6$-C$_{14}$ aryl), wherein R$_1$ is independently optionally substituted by halogen, oxo, —OR$^{13}$, —NR$^{13}$R$^{14}$, —C(O)R$^{13}$, —CN, C$_3$-C$_8$ cycloalkyl, or C$_1$-C$_6$ alkyl optionally substituted by oxo, —OH or halogen;

each R$^2$ is independently C$_1$-C$_6$ alkyl, oxo, —NR$^{11}$R$^{12}$, —CN, —C(O)R$^{10}$, —C(O)NR$^{11}$R$^{12}$ or halogen, wherein any two R$^2$ groups are independently attached to same carbon or two different carbons;

each of R$^3$ and R$^4$ is independently C$_1$-C$_6$ alkyl, C$_3$-C$_6$ cycloalkyl, C$_1$-C$_6$ haloalkyl, C$_1$-C$_6$ alkoxy, C$_1$-C$_6$ haloalkoxy, halogen or —OH;

each R$^5$ is independently C$_1$-C$_6$ alkyl, C$_2$-C$_6$ alkenyl, C$_2$-C$_6$ alkynyl, halogen, oxo, —CN, —OR$^{10}$, —SR$^{10}$, —NR$^{11}$R$^{12}$, —C(O)R$^{10}$, —C(O)NR$^{11}$R$^{12}$, —OC(O)NR$^{11}$R$^{12}$, —NR$^{10}$C(O)R$^{11}$, —NR$^{10}$C(O)NR$^{11}$R$^{12}$, —S(O)$_2$R$^{10}$, —NR$^{10}$S(O)$_2$R$^{11}$, —S(O)$_2$NR$^{11}$R$^{12}$, C$_3$-C$_6$ cycloalkyl, 3- to 12-membered heterocyclyl, —(C$_1$-C$_3$ alkylene)OR$^{10}$, —(C$_1$-C$_3$ alkylene)SR$^{10}$, —(C$_1$-C$_3$ alkylene)NR$^{11}$R$^{12}$, —(C$_1$-C$_3$ alkylene)C(O)R$^{10}$, —(C$_1$-C$_3$ alkylene)C(O)NR$^{11}$R$^{12}$, —(C$_1$-C$_3$ alkylene)NR$^{10}$C(O)R$^{11}$, —(C$_1$-C$_3$ alkylene)NR$^{10}$C(O)NR$^{11}$R$^{12}$, —(C$_1$-C$_3$ alkylene)S(O)$_2$R$^{10}$, —(C$_1$-C$_3$ alkylene)NR$^{10}$S(O)$_2$R$^{11}$, —(C$_1$-C$_3$ alkylene)S(O)$_2$NR$^{11}$R$^{12}$, —(C$_1$-C$_3$ alkylene)(C$_3$-C$_6$ cycloalkyl), —(C$_1$-C$_3$ alkylene)(3- to 12-membered heterocyclyl), wherein each R$^5$ is independently optionally substituted by halogen, oxo, —OR$^{13}$, —NR$^{13}$R$^{14}$, —C(O)R$^{13}$, —CN, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, or C$_1$-C$_6$ alkyl optionally substituted by oxo, —OH or halogen;

each R$^6$ is independently oxo or R$^7$, or any two R$^6$ groups, when bound to the same carbon atom, are taken together with the carbon to which they are attached to form a C$_3$-C$_6$ cycloalkyl;

R$^7$ is independently hydrogen, C$_1$-C$_6$ alkyl, C$_2$-C$_6$ alkenyl, C$_2$-C$_6$ alkynyl, C$_3$-C$_6$ cycloalkyl, 3- to 6-membered heterocyclyl, —C(O)R$^{10}$, —C(O)NR$^{11}$R$^{12}$, —(C$_1$-C$_3$ alkylene)CN, —(C$_1$-C$_3$ alkylene)OR$^{10}$, —(C$_1$-C$_3$ alkylene)SR$^{10}$, —(C$_1$-C$_3$ alkylene)NR$^{11}$R$^{12}$, —(C$_1$-C$_3$ alkylene)CF$_3$, —(C$_1$-C$_3$ alkylene)C(O)R$^{10}$, —(C$_1$-C$_3$ alkylene)C(O)NR$^{11}$R$^{12}$, —(C$_1$-C$_3$ alkylene)NR$^{10}$C(O)R$^{11}$, —(C$_1$-C$_3$ alkylene)NR$^{10}$C(O)NR$^{11}$R$^{12}$, —(C$_1$-C$_3$ alkylene)S(O)$_2$R$^{10}$, —(C$_1$-C$_3$ alkylene)NR$^{10}$S(O)$_2$R$^{11}$, —(C$_1$-C$_3$ alkylene)S(O)$_2$NR$^{11}$R$^{12}$, —(C$_1$-C$_3$ alkylene)(C$_3$-C$_6$ cycloalkyl), or —(C$_1$-C$_3$ alkylene)(3- to 6-membered heterocyclyl), wherein each R$^7$ is independently optionally substituted by halogen, oxo, —OR$^{13}$, —NR$^{13}$R$^{14}$, —C(O)R$^{13}$, —CN, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, or C$_1$-C$_6$ alkyl optionally substituted by oxo, —OH or halogen;

R$^{10}$ is independently hydrogen, C$_1$-C$_6$ alkyl, C$_3$-C$_6$ cycloalkyl, —(C$_1$-C$_3$ alkylene)(C$_3$-C$_6$ cycloalkyl), C$_6$-C$_{14}$ aryl, 5- to 6-membered heteroaryl or 3- to 6-membered heterocyclyl, each of which is independently optionally substituted by halogen, oxo, —CN, —OR$^{15}$, —NR$^{15}$R$^{16}$, or C$_1$-C$_6$ alkyl optionally substituted by halogen, —OH or oxo;

R$^{11}$ and R$^{12}$ are each independently hydrogen, C$_1$-C$_6$ alkyl, C$_3$-C$_6$ cycloalkyl, —(C$_1$-C$_3$ alkylene)(C$_3$-C$_6$ cycloalkyl), C$_6$-C$_{14}$ aryl, 5- to 6-membered heteroaryl or 3- to 6-membered heterocyclyl, each of which is independently optionally substituted by halogen, oxo, —CN, —OR$^{15}$, —NR$^{15}$R$^{16}$ or C$_1$-C$_6$ alkyl optionally substituted by halogen, —OH or oxo;

or R$^{11}$ and R$^{12}$ are taken together with the atom to which they attached to form a 3- to 6-membered heterocyclyl optionally substituted by halogen, oxo, or C$_1$-C$_6$ alkyl optionally substituted by halogen;

R$^{13}$ and R$^{14}$ are each independently hydrogen or C$_1$-C$_6$ alkyl, wherein the C$_1$-C$_6$ alkyl of R$^{13}$ and R$^{14}$ are optionally substituted by halogen, —OR$^{15}$, —NR$^{15}$R$^{16}$, or oxo;

or R$^{13}$ and R$^{14}$ are taken together with the atom to which they attached to form a 3- to 6-membered heterocyclyl optionally substituted by halogen, oxo or C$_1$-C$_6$ alkyl optionally substituted by halogen or oxo; and R$^{15}$ and R$^{16}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{15}$ and R$^{16}$ are taken together with the atom to which they attached to form a 3- to 6-membered heterocyclyl optionally substituted by halogen, oxo or C$_1$-C$_6$ alkyl optionally substituted by oxo or halogen;

l, m, p and q are each independently 0, 1, 2 or 3; and n is 0, 1, 2, 3 or 4.

In some embodiments of Formula (J), Z is

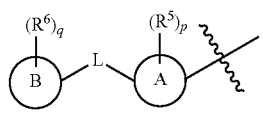

and provides a compound of Formula (I):

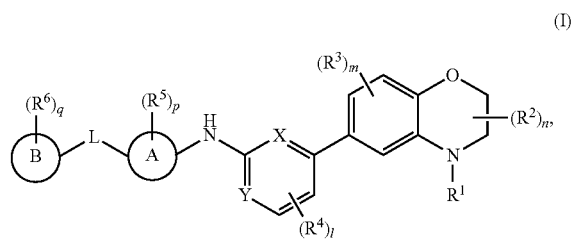

or a salt thereof, wherein X, Y, A, B, L, $R^1$, $R^2$, $R^3$, $R^4$, $R^5$, $R^6$, l, m, n, p and q are as detailed herein for Formula (J).

In some embodiments of Formula (J), Z is

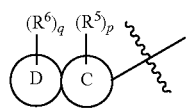

and provides a compound of Formula (II):

or a salt thereof, wherein X, Y, C, D, $R^1$, $R^2$, $R^3$, $R^4$, $R^5$, $R^6$, l, m, n, p and q are as detailed herein for Formula (J).

Specific values listed below are values for a compound of Formula (J), Formula (I), or Formula (II) as well as all related formulae (e.g., Formula (I-A), (I-B1) to (I-B12), and (I-C1) to (I-C23)), or a salt thereof. It is to be understood that two or more values may combined. Thus, it is to be understood that any variable for a compound of Formula (J), Formula (I), or Formula (II) as well as all related formulae may be combined with any other variable for a compound of Formula (J), Formula (I), or Formula (II) as well as all related formulae the same as if each and every combination of variables were specifically and individually listed. For example, it is understood that any specific value of $R^1$ detailed herein for a compound of Formula (J), Formula (I), or Formula (II) as well as all related formulae may be combined with any other specific value for one or more of the variables A, B, C, D, X, Y, $R^2$, $R^3$, $R^4$, $R^5$, $R^6$, l, m, n, p, and q the same as if each and every combination were specifically and individually listed.

In some embodiments of a compound of Formula (I), A is $C_3$-$C_6$ cycloalkyl, 4- to 7-membered heterocyclyl, 5- to 7-membered heteroaryl or $C_6$ aryl, each of which is unsubstituted. In some embodiments of a compound of Formula (I), A is $C_3$-$C_6$ cycloalkyl, 4- to 7-membered heterocyclyl, 5- to 7-membered heteroaryl or $C_6$ aryl, each of which is optionally substituted with $R^5$. In some embodiments of a compound of Formula (I), A is $C_6$ aryl optionally further substituted with $R^5$. In some embodiments of a compound of Formula (I), A is phenyl optionally substituted with $R^5$. In some embodiments of a compound of Formula (I), A is 5- to 7-membered heteroaryl optionally further substituted with $R^5$. In some embodiments of a compound of Formula (I), A is selected from the group consisting of pyridine, pyrimidine, pyrazolyl, thiazolyl, oxazolyl, isooxazolyl or imidazolyl, each of which is optionally substituted with $R^5$. In some embodiments of a compound of Formula (I), A is 4- to 7-membered heterocyclyl, optionally further substituted with $R^5$. In some embodiments of a compound of Formula (I), A is piperidinyl, pyrrolidinyl, azetidinyl, dihydropyridine, or pyridone, each of optionally substituted with $R^5$. In some embodiments of a compound of Formula (I), A is $C_3$-$C_6$ cycloalkyl substituted with $R^5$. In some embodiments A is cyclohexyl or cyclopentyl, each of optionally substituted with $R^5$. In some embodiments of a compound of Formula (I), A is phenyl, pyridine, pyrimidine, pyrazolyl, thiazolyl, oxazolyl, isooxazolyl, imidazolyl, piperidinyl, pyrrolidinyl, azetidinyl, pyridone, cyclohexyl, or cyclopentyl, each of which is unsubstituted. In some embodiments of a compound of Formula (I), A is phenyl, pyridine, pyrimidine, pyrazolyl, thiazolyl, oxazolyl, isooxazolyl, imidazolyl, piperidinyl, pyrrolidinyl, azetidinyl, dihydropyridine, pyridone, cyclohexyl, or cyclopentyl, each of which is optionally substituted with $R^5$.

In some embodiments of a compound of Formula (I), B is hydrogen, $C_3$-$C_6$ cycloalkyl, 3- to 7-membered heterocyclyl, 5- to 7-membered heteroaryl, or $C_6$ aryl, each of which is optionally substituted with $R^6$. In some embodiments of a compound of Formula (I), B is $C_3$-$C_6$ cycloalkyl, 3- to 7-membered heterocyclyl, 5- to 7-membered heteroaryl, or $C_6$ aryl, each of which is unsubstituted. In some embodiments of a compound of Formula (I), B is hydrogen. In some embodiments of a compound of Formula (I), B is 3- to 7-membered heterocyclyl optionally substituted with $R^6$. In some embodiments of a compound of Formula (I), B is diazepanyl, azepanyl, piperazinyl, piperidinyl, pyrrolidinyl or azetidinyl, each of which is optionally substituted with $R^6$. In some embodiments of a compound of Formula (I), B is 5- to 7-membered heteroaryl optionally substituted with $R^6$. In some embodiments of a compound of Formula (I), B is imidazolyl or pyrazolyl, each of which is optionally substituted with $R^6$. In some embodiments of a compound of Formula (I), B is phenyl optionally substituted with $R^6$. In some embodiments of a compound of Formula (I), B is $C_3$-$C_6$ cycloalkyl optionally substituted with $R^6$. In some embodiments of a compound of Formula (I), B is cyclopentyl, cyclohexyl, or cycloheptyl, each of which is optionally substituted with $R^6$. In some embodiments of a compound of Formula (I), B is hydrogen, diazepanyl, azepanyl, piperazinyl, piperidinyl, pyrrolidinyl, azetidinyl, imidazolyl, pyrazolyl, phenyl, cyclopentyl, cyclohexyl, or cycloheptyl, each of which is unsubstituted. In some embodiments of a compound of Formula (I), B is hydrogen, diazepanyl, azepanyl, piperazinyl, piperidinyl, pyrrolidinyl, azetidinyl, imidazolyl, pyrazolyl, phenyl, cyclopentyl, cyclohexyl, or cycloheptyl, each of which is optionally substituted with $R^6$.

In some embodiments of a compound of Formula (I), L is a bond, —$CH_2$—, —NH—, —O—, —S—, —$SO_2$—, —CO—, —$NCH_3$—, —$SO_2NH$—, or —$NHSO_2$—. In some embodiments of a compound of Formula (I), L is a bond, —$CH_2$—, —NH—, —O—, or —S—. In some embodiments, L is a bond. In some embodiments, L is —$CH_2$—. In some embodiments, L is —NH—. In some embodiments, L is —S—. In some embodiments, L is —O—. In some embodiments, L is —$SO_2$—. In some embodiments, L is —CO—. In some embodiments, L is —NCH$_3$—. In some embodiments, L is —NHSO$_2$—. In some embodiments, L is —CR$^{11}$R$^{12}$—. In some embodiments, L is —NR$^{10}$—. In some embodiments, L is —NR$^{10}$SO$_2$—. In some embodiments, L is —SO$_2$NR$^{10}$—. In some embodiments, L is —SO$_2$NH—.

It is understood that any description of A for Formula (I) may be combined with any description of B and L for formula (I), the same as if each and every combination were specifically and individually listed.

In some embodiments of a compound of Formula (II), D is fused with C to form a 7-12 membered bicyclic ring having at least one aromatic ring, wherein C and D are optionally substituted with R$^5$ and R$^6$. In some embodiments of a compound of Formula (II), D is fused with C to form a 7-12 membered bicyclic ring having at least one aromatic ring and at least one heteroatom selected from the group consisting of N, O, and S, wherein C and D are optionally substituted with R$^5$ and R$^6$. In some embodiments of a compound of Formula (II), D is fused with C to form a 7-12 membered bicyclic ring having at least one aromatic ring and at least one nitrogen atom, wherein C and D are optionally substituted with R$^5$ and R$^6$. In some embodiments of a compound of Formula (II), D is fused with C to form a 7-12 membered bicyclic ring having at least one aromatic ring and at least one nitrogen atom, wherein C and D are optionally substituted with R$^5$ and R$^6$.

In some embodiments, provided is a compound of Formula (I-A),

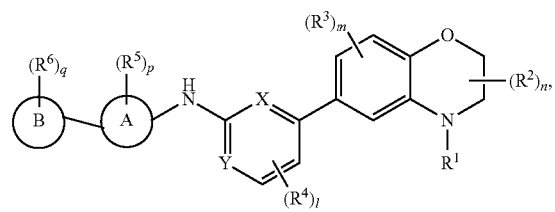
(I-A)

or a salt thereof, wherein A, B, X, Y; R$^1$, R$^2$, R$^3$, R$^4$, R$^5$, R$^6$, l, m, n, p, and q are as detailed herein for Formula (I).

In some embodiments, provided is a compound of any one of Formula (I-B1) to (I-B12), or a salt thereof:

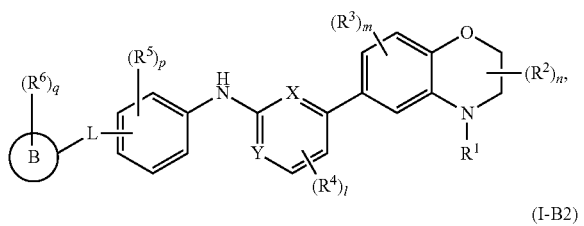
(I-B1)

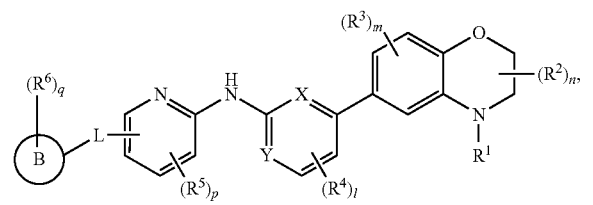
(I-B2)

(I-B3)

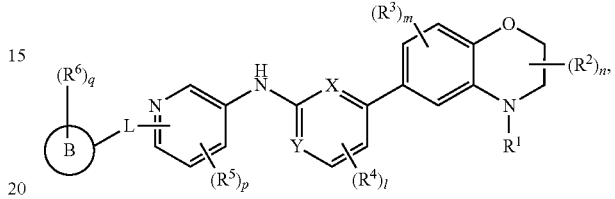
(I-B4)

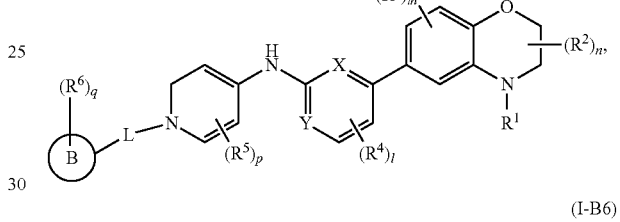
(I-B5)

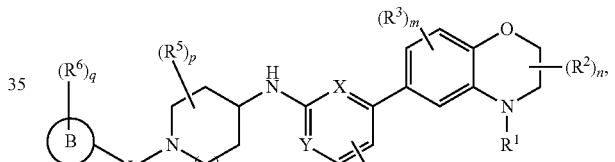
(I-B6)

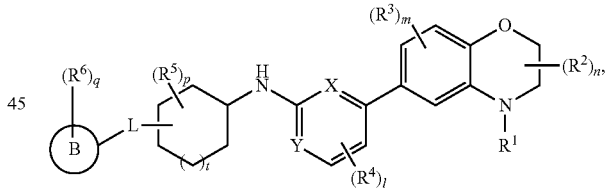
(I-B7)

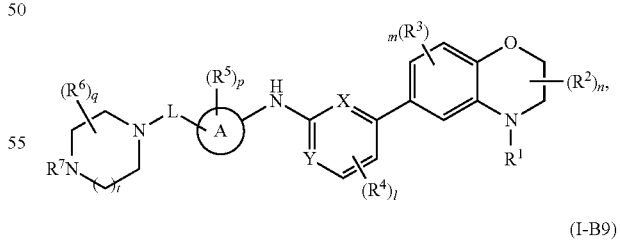
(I-B8)

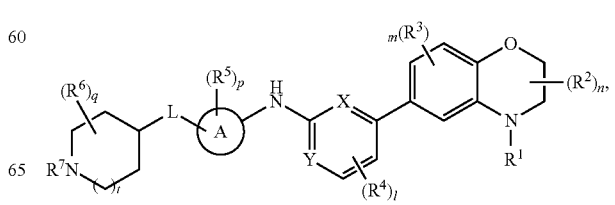
(I-B9)

(I-B10)
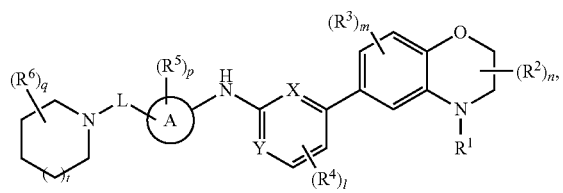
(I-B11)
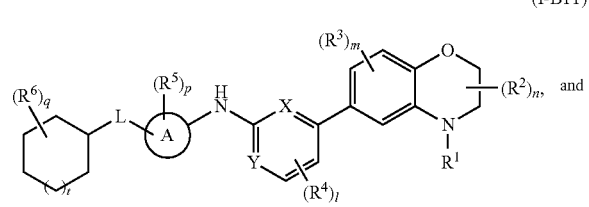
and
(I-B12)
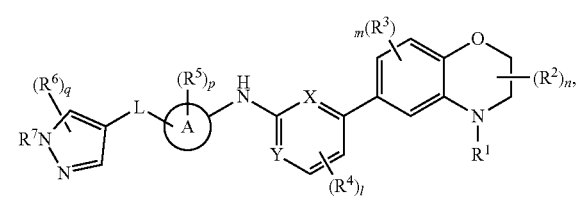
wherein X, Y, A, B, L, $R^1$, $R^2$, $R^3$, $R^4$, $R^5$, $R^6$, $R^7$, l, m, n, p, and q are as described herein for Formula (I) and t is 0, 1, 2 or 3. In some embodiments, t is 0. In some embodiments, t is 0 or 1. In some embodiments, t is 0, 1, or 2.
In some embodiments, provided is a compound of any one of Formula (I-C1) to (I-C23):
(I-C1)
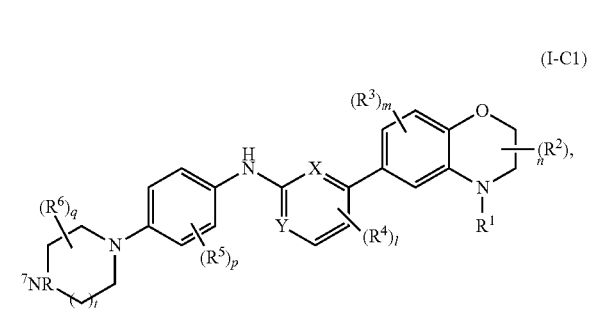
(I-C2)
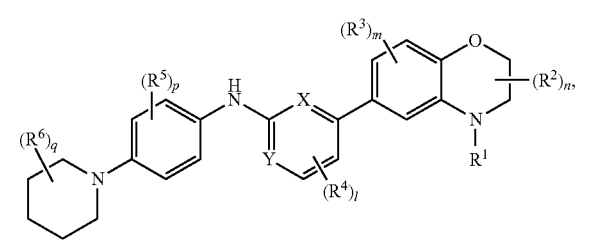
(I-C3)
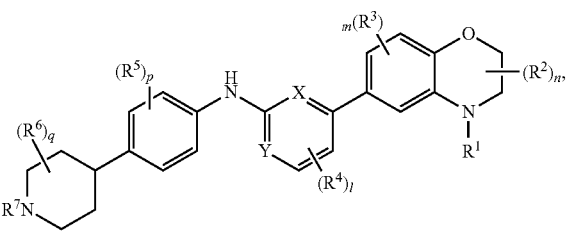
(I-C4)
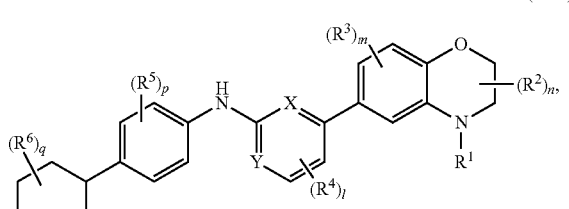
(I-C5)
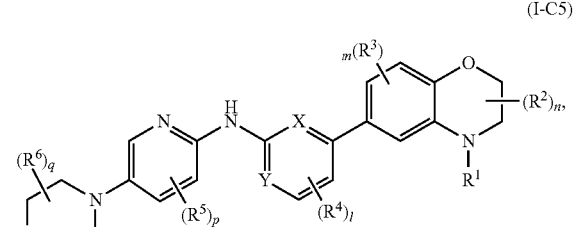
(I-C6)
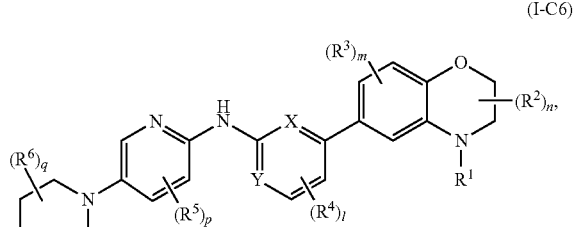
(I-C7)
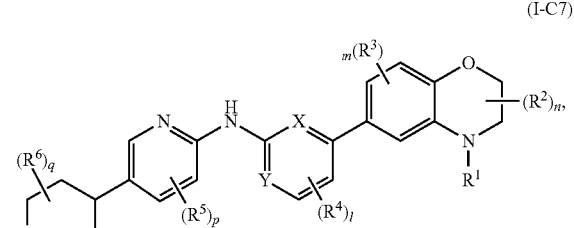
(I-C8)
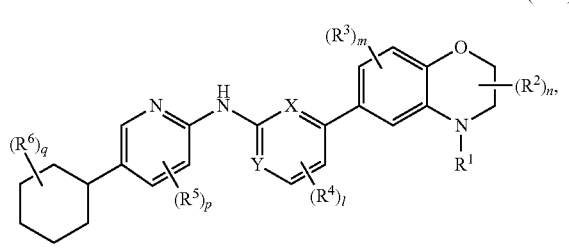

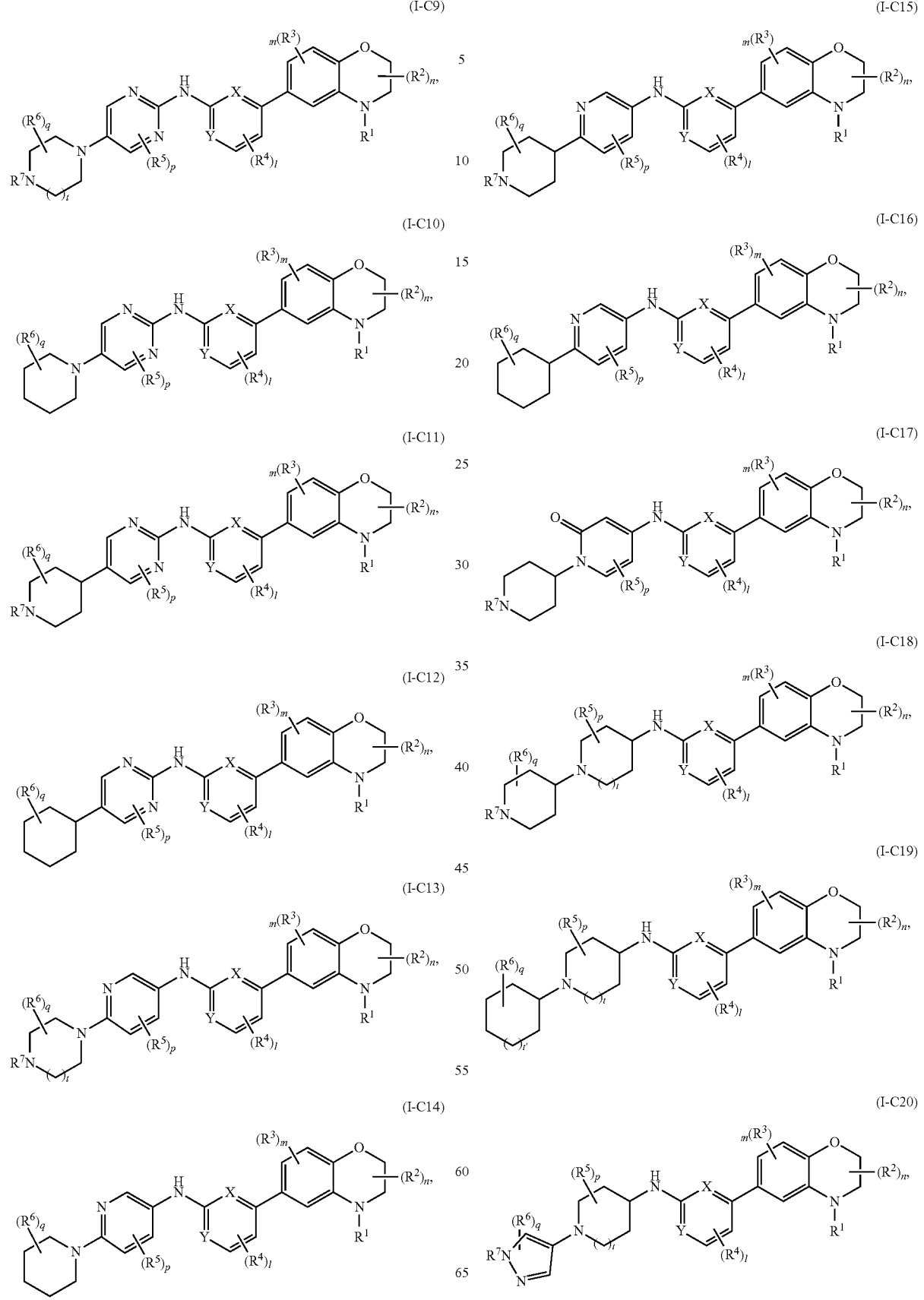

-continued (I-C21)
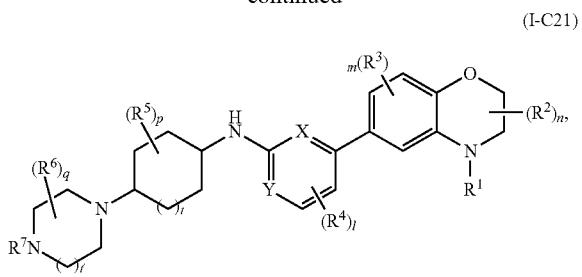

(I-C22)
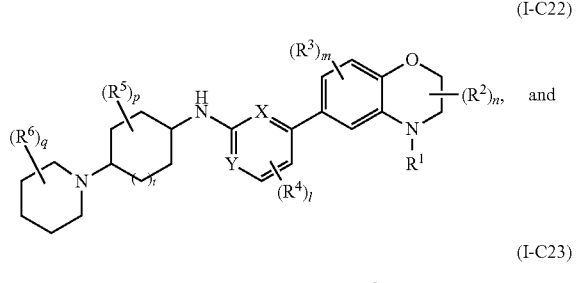
and (I-C23)
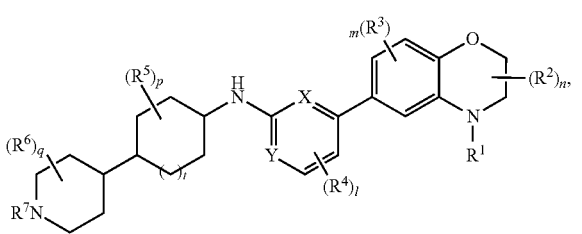

or a salt thereof, wherein X, Y, $R^1$, $R^2$, $R^3$, $R^4$, $R^5$, $R^6$, $R^7$, l, m, n, p, and q are as described herein for Formula (I) and t and t' are each independently 0, 1, 2, or 3. In some embodiments, t is 0. In some embodiments, t is 0 or 1. In some embodiments, t is 0, 1, or 2. In some embodiments, t' is 0. In some embodiments, t' is 0 or 1. In some embodiments, t' is 0, 1, or 2.

In some embodiments of a compound of Formula (I), $R^7$ is hydrogen, $C_1$-$C_6$ alkyl, $C_3$-$C_6$ cycloalkyl, —C(O)$R^{10}$, each of which (except hydrogen) is optionally substituted by halogen, oxo, —OR$^{13}$, —NR$^{13}$R$^{14}$, —C(O)R$^{13}$, —CN, —($C_1$-$C_3$ alkylene)OR$^{13}$, —($C_1$-$C_3$ alkylene)NR$^{13}$R$^{14}$, —($C_1$-$C_3$ alkylene)C(O)R$^{13}$, $C_3$-$C_8$ cycloalkyl, or $C_1$-$C_6$ alkyl optionally substituted by oxo, —OH or halogen. In some embodiments of a compound of Formula (I), $R^7$ is hydrogen, methyl, ethyl, isopropyl, cyclopropyl, —C(O)CH$_2$NHCH$_3$, or —CH$_2$CH$_2$OH.

In some embodiments, provided is a compound of Formula (II):

(II)
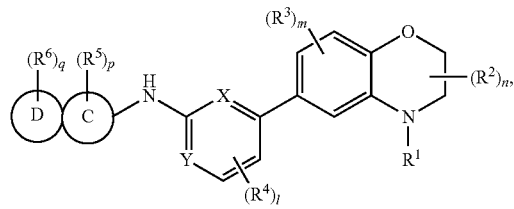

or a salt thereof, wherein C-D, X, Y, $R^1$, $R^2$, $R^3$, $R^4$, $R^5$, $R^6$, l, m, n, p and q are as described for Formula (II).

In some embodiments of a compound of Formula (J), Formula (I), or Formula (II), X is N and Y is N. In some embodiments of a compound of Formula (J), Formula (I), or Formula (II), X is N and Y is CH. In some embodiments of a compound of Formula (J), Formula (I), or Formula (II), X is CH and Y is N.

In some embodiments of a compound of Formula (J), Formula (I), or Formula (II), $R^1$ is hydrogen, $C_1$-$C_6$ alkyl, $C_2$-$C_6$ alkenyl, $C_2$-$C_6$ alkynyl, $C_1$-$C_8$ alkoxy, $C_3$-$C_6$ cycloalkyl, 3- to 12-membered heterocyclyl, 5- to 10-membered heteroaryl, $C_6$-$C_{14}$ aryl, —C(O)$R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), each of which is optionally substituted by halogen, oxo, —OR$^{13}$, —C(O)NR$^{13}$R$^{14}$, —NR$^{13}$R$^{14}$, —C(O)R$^{13}$, —CN, $C_3$-$C_8$ cycloalkyl, or $C_1$-$C_6$ alkyl optionally substituted by oxo, —OH or halogen. In some embodiments of a compound of Formula (J), Formula (I), or Formula (II), $R^1$ is hydrogen, $C_1$-$C_6$ alkyl, $C_3$-$C_6$ cycloalkyl, 3- to 12-membered heterocyclyl, 5- to 10-membered heteroaryl, $C_6$-$C_{14}$ aryl, —C(O)$R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), each of which is unsubstituted. In some embodiments of a compound of Formula (J), Formula (I), or Formula (II), $R^1$ is $C_2$-$C_6$ alkyl, $C_2$-$C_6$ alkenyl, $C_2$-$C_6$ alkynyl, $C_1$-$C_8$ alkoxy, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —C(O)$R^{10}$, or —($C_1$-$C_3$ alkylene)($C_6$-$C_{14}$ aryl), wherein $R_1$ is independently optionally substituted by halogen, oxo, —OR$^{13}$, —NR$^{13}$R$^{14}$, —C(O)R$^{13}$, —CN, $C_3$-$C_8$ cycloalkyl, or $C_1$-$C_6$ alkyl optionally substituted by oxo, —OH or halogen. In some embodiments of a compound of Formula (J), Formula (I), or Formula (II), $R^1$ is $C_2$-$C_6$ alkyl, $C_2$-$C_6$ alkenyl, $C_2$-$C_6$ alkynyl, $C_1$-$C_8$ alkoxy, $C_3$-$C_6$ cycloalkyl, 3- to 12-membered heterocyclyl, 5- to 10-membered heteroaryl, $C_6$-$C_{14}$ aryl, or —C(O)$R^{10}$, wherein $R_1$ is independently optionally substituted by halogen, oxo, —OR$^{13}$, —NR$^{13}$R$^{14}$, —C(O)R$^{13}$, —CN, $C_3$-$C_8$ cycloalkyl, or $C_1$-$C_6$ alkyl optionally substituted by oxo, —OH or halogen. In some embodiments of a compound of Formula (J), Formula (I), or Formula (II), $R^1$ is hydrogen, $C_1$-$C_6$ alkyl, —C(O)$R^{10}$, —($C_1$-$C_3$ alkylene)($C_3$-$C_6$ cycloalkyl), —($C_1$-$C_3$ alkylene)(5- to 10-membered heterocyclyl), or $C_3$-$C_6$ cycloalkyl, each of which is optionally substituted with halogen, oxo, —NH$_2$. In some embodiments, $R^1$ is methyl, ethyl, n-propyl, isopropyl, cyclopropyl, cyclopentyl, cyclohexyl or cyclopropyl-methyl. In some embodiments, $R^1$ is isopropyl. In some embodiments of a compound of Formula (J), Formula (I), or Formula (II), $R^1$ is $C_2$-$C_6$ alkyl.

In some embodiments of a compound of Formula (J), Formula (I), or Formula (II), $R^1$ is selected from the group consisting of

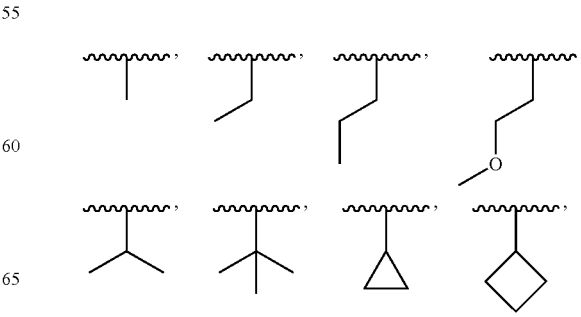

-continued
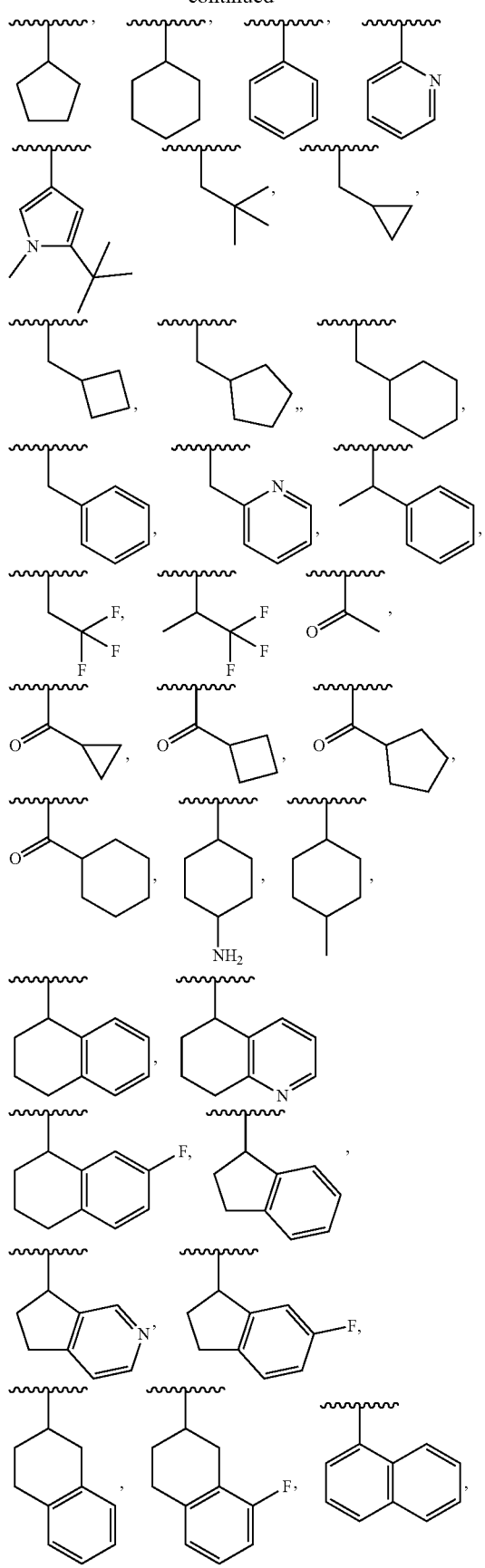
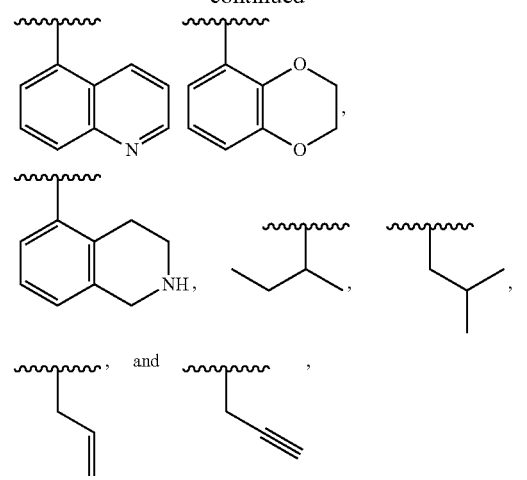
wherein the wavy lines denote attachment points to the parent molecule.
In some embodiments, $R^1$ is selected from the group consisting of
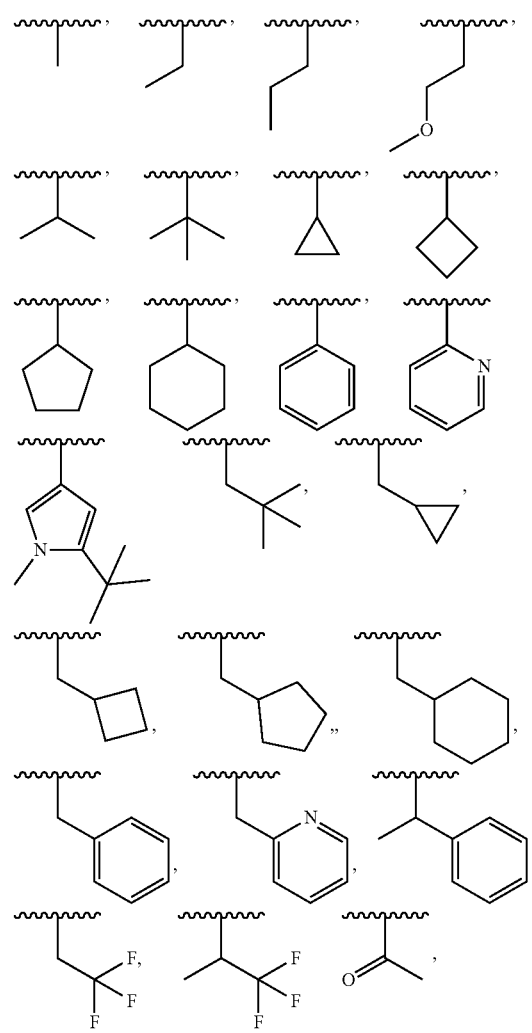

-continued

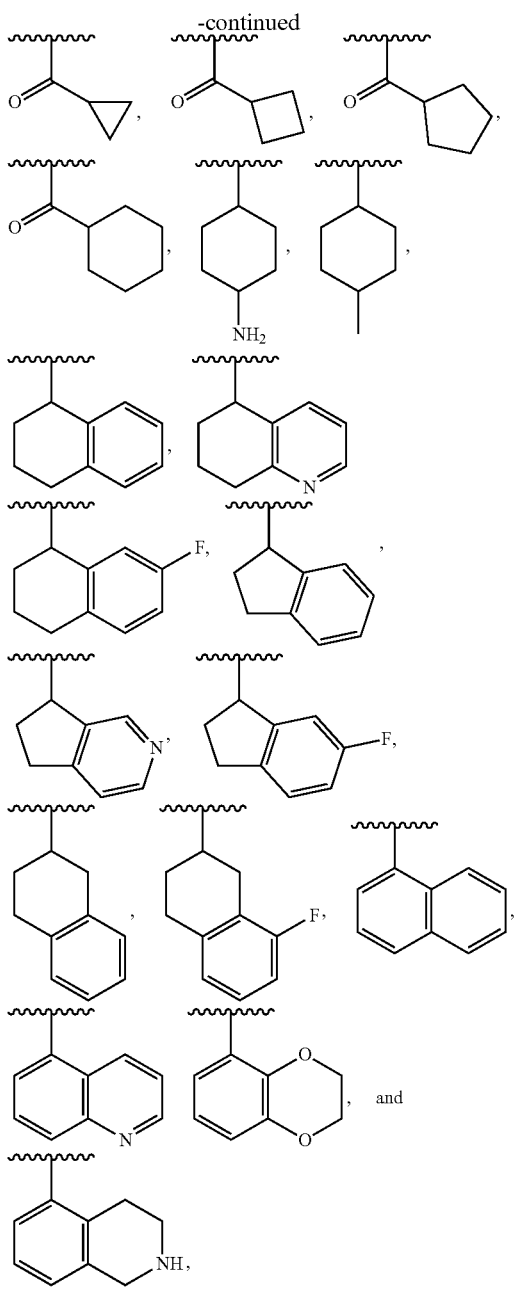

wherein the wavy lines denote attachment points to the parent molecule. In some embodiments, $R^1$ is

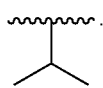

In some embodiments of a compound of Formula (J), Formula (I), or Formula (II), n is 0. In some embodiments, n is 0 or 1. In some embodiments, n is 0, 1, or 2. In some embodiments, n is 0, 1, 2, or 3.

In some embodiments of a compound of Formula (J), Formula (I), or Formula (II), each $R^2$ is independently $C_1$-$C_6$ alkyl, oxo, —$NR^{11}R^{12}$, —CN, or halogen. In some embodiments, each $R^2$ is independently $C_1$-$C_6$ alkyl, oxo, or halogen. In some embodiments of a compound of Formula (J), Formula (I), or Formula (II), $R^2$ is oxo. In some embodiments of a compound of Formula (J), Formula (I), or Formula (II), $R^2$ is —$NR^{11}R^{12}$. In some embodiments of a compound of Formula (J), Formula (I), or Formula (II), $R^2$ is —CN. In some embodiments of a compound of Formula (J), Formula (I), or Formula (II), $R^2$ is —$C(O)R^{10}$. In some embodiments of a compound of Formula (J), Formula (I), or Formula (II), $R^2$ is —$C(O)NR^{11}R^{12}$. In some embodiments of a compound of Formula (J), Formula (I), or Formula (II), $R^2$ is halogen, such as fluoro. In some embodiments of a compound of Formula (J), Formula (I), or Formula (II), $R^2$ is $C_1$-$C_6$ alkyl, preferably methyl or dimethyl attached to the same carbon. In some embodiments of a compound of Formula (J), Formula (I), or Formula (II), groups of $R^2$ (such as when more than one $R^2$ is present) are oxo and methyl, independently attached to two different carbons. In some embodiments of a compound of Formula (J), Formula (I), or Formula (II), groups of $R^2$ are oxo and dimethyl, each independently attached to two different carbons. In some embodiments of a compound of Formula (J), Formula (I), or Formula (II), groups of $R^2$ are oxo and —CN, each independently attached to two different carbons. In some embodiments of a compound of Formula (J), Formula (I), or Formula (II), groups of $R^2$ are oxo and —$NR^{11}R^{12}$, each independently attached to two different carbons. In some embodiments of a compound of Formula (J), Formula (I), or Formula (II), groups of $R^2$ are oxo and —$C(O)R^{10}$, each independently attached two different carbon. In some embodiments of a compound of Formula (J), Formula (I), or Formula (II), groups of $R^2$ are oxo and —$C(O)NR^{11}R^{12}$, each independently attached to two different carbons. In some embodiments of a compound of Formula (J), Formula (I), or Formula (II), groups of $R^2$ are difluoro attached to the same carbon. In some embodiments of a compound of Formula (J), Formula (I), or Formula (II), groups of $R^2$ are oxo and fluoro or difluoro, each independently attached to two different carbons. In some embodiments of a compound of Formula (J), Formula (I), or Formula (II), $R^2$ is H.

In some embodiments of a compound of Formula (J), Formula (I), or Formula (II), m is 0. In some embodiments, m is 0 or 1. In some embodiments, m is 0, 1, or 2. In some embodiments, m is 0, 1, 2, or 3. In some embodiments, m is 0, 1, 2, or 3, provided that at least one of m and l is not 0.

In some embodiments of a compound of Formula (J), Formula (I), or Formula (II), each $R^3$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH. In some embodiments, each $R^3$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy or halogen. In some embodiments, each $R^3$ is independently fluoro, chloro, methyl, trifluoromethyl, trifluoromethoxy, methoxy, and cyclopropyl. In some embodiments, $R^3$ is halogen.

In some embodiments of a compound of Formula (J), Formula (I), or Formula (II), l is 0. In some embodiments, l is 0 or 1. In some embodiments, l is 0, 1, or 2. In some embodiments, l is 0, 1, 2, or 3. In some embodiments, l is 0, 1, 2, or 3, provided that when Z is

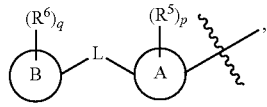

n is 1 and $R^2$ is oxo, then at least one of m and 1 is not 0. In some embodiments, 1 is 0, 1, 2, or 3, provided that at least one of m and 1 is not 0.

In some embodiments of a compound of Formula (J), Formula (I), or Formula (II), each $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH. In some embodiments, each $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy or halogen. In some embodiments, each $R^4$ is independently fluoro, chloro, methyl, trifluoromethyl, trifluoromethoxy, methoxy, or cyclopropyl. In some embodiments, $R^4$ is halogen.

In some embodiments of a compound of Formula (J), Formula (I), or Formula (II), each $R^3$ and $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH and 1 and m are independently 0, 1, 2 or 3. In some embodiments of a compound of Formula (J), Formula (I), or Formula (II), each $R^3$ and $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH and 1 and m are independently 0, 1, 2 or 3, provided that when Z is

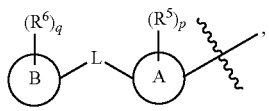

n is 1 and $R^2$ is oxo, then at least one of m and 1 is not 0. In some embodiments of a compound of Formula (J), Formula (I), or Formula (II), each $R^3$ and $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH and 1 and m are independently 0, 1, 2 or 3, provided that at least one of m and 1 is not 0. In some embodiments of a compound of Formula (J), Formula (I), or Formula (II), $R^3$ and $R^4$ are halogen. In some embodiments of a compound of Formula (J), Formula (I), or Formula (II), $R^3$ is F and $R^4$ is Cl. In some embodiments of a compound of Formula (J), Formula (I), or Formula (II), $R^3$ is Cl and $R^4$ is F. In some embodiments, both $R^3$ and $R^4$ are F.

In some embodiments of a compound of Formula (J), Formula (I), or Formula (II), X is CH; Y is N; and $R^3$ and $R^4$ are independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen or —OH. In some embodiments of a compound of Formula (J), Formula (I), or Formula (II), X is N; Y is CH; and $R^3$ and $R^4$ are independently hydrogen, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen or —OH. In some embodiments of a compound of Formula (J), Formula (I), or Formula (II), X is N; Y is N; and $R^3$ and $R^4$ are independently hydrogen, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen or —OH.

In some embodiments of a compound of Formula (J), Formula (I), or Formula (II), X is CH; Y is N; $R^3$ is F; and $R^4$ is F. In some embodiments of a compound of Formula (J), Formula (I), or Formula (II), X is N; Y is CH; $R^3$ is F; and $R^4$ is F. In some embodiments of a compound of Formula (J), Formula (I), or Formula (II), X is N; Y is N; $R^3$ is Cl; and $R^4$ is F. In some embodiments of a compound of Formula (J), Formula (I), or Formula (II), X is N; Y is N; $R^3$ is F; and $R^4$ is Cl. In some embodiments of a compound of Formula (J), Formula (I), or Formula (II), X is CH; Y is N; $R^3$ is Cl; and $R^4$ is F. In some embodiments of a compound of Formula (J), Formula (I), or Formula (II), X is N; Y is CH; $R^3$ is F; and $R^4$ is Cl. In some embodiments of a compound of Formula (J), Formula (I), or Formula (II), X is N; Y is CH; $R^3$ is Cl; and $R^4$ is F. In some embodiments of a compound of Formula (J), Formula (I), or Formula (II), X is N; Y is N; $R^3$ is F; and $R^4$ is F.

In some embodiments of a compound of Formula (J), Formula (I), or Formula (II), X is CH; Y is N; $R^3$ is F and $R^4$ is F; and each $R^2$ is independently hydrogen, $C_1$-$C_6$ alkyl, oxo, —$NR^{11}R^{12}$, —CN, —$C(O)R^{10}$, —$C(O)NR^{11}R^{12}$ or halogen. In some embodiments of a compound of Formula (J), Formula (I), or Formula (II), X is N; Y is CH; $R^3$ is F and $R^4$ is F; and each $R^2$ is independently hydrogen, $C_1$-$C_6$ alkyl, oxo, —$NR^{11}R^{12}$, —CN, —$C(O)R^{10}$, —$C(O)NR^{11}R^{12}$ or halogen. In some embodiments of a compound of Formula (J), Formula (I), or Formula (II), X is N; Y is N; $R^3$ is F and $R^4$ is F; and each $R^2$ is independently hydrogen, $C_1$-$C_6$ alkyl, oxo —$NR^{11}R^{12}$, —CN, —$C(O)R^{10}$, —$C(O)NR^{11}R^{12}$ or halogen. In some embodiments of a compound of Formula (J), Formula (I), or Formula (II), X is N; Y is N; $R^3$ is F; $R^4$ is F; and each $R^2$ is independently F, wherein each F is attached to same carbon or two different carbons. In some embodiments of a compound of Formula (J), Formula (I), or Formula (II), X is N; Y is N; $R^3$ is F; $R^4$ is F; and each $R^2$ is independently $C_1$-$C_6$ alkyl, preferably methyl, each methyl attached to same carbon or two different carbon. In some embodiments of a compound of Formula (J), Formula (I), or Formula (II), X is N; Y is N; $R^3$ is F; $R^4$ is F; each $R^2$ is oxo or methyl, each of which is attached to two different carbons. In some embodiments of a compound of Formula (J), Formula (I), or Formula (II), X is N; Y is N; $R^3$ is F; $R^4$ is F; and each $R^2$ is oxo or F, which are attached to two different carbons. In some embodiments of a compound of Formula (J), Formula (I), or Formula (II), X is N; Y is N; $R^3$ is F; $R^4$ is F; $R^2$ is oxo. In some embodiments of a compound of Formula (J), Formula (I), or Formula (II), X is N; Y is N; $R^3$ is F; $R^4$ is F; each $R^2$ is independently hydrogen.

In some embodiments of a compound of Formula (J), Formula (I), or Formula (II), X is N; Y is N; each $R^3$ and $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH; each $R^2$ is independently hydrogen, $C_1$-$C_6$ alkyl, oxo, —$NR^{11}R^{12}$, —CN, —$C(O)R^{10}$, —$C(O)NR^{11}R^{12}$ or halogen, any two $R^2$ groups are independently attached to same carbon or two different carbon; and $R^1$ is hydrogen, $C_1$-$C_6$ alkyl, $C_2$-$C_6$ alkenyl, $C_2$-$C_6$ alkynyl, $C_1$-$C_8$ alkoxy, $C_3$-$C_6$ cycloalkyl, 3- to 12-membered heterocyclyl, 5- to 10-membered heteroaryl, $C_6$-$C_{14}$ aryl, —$C(O)R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), each of which is optionally substituted by halogen, oxo, —$OR^{13}$, —$C(O)$ $NR^{13}R^{14}$, —$NR^{13}R^{14}$, —$C(O)R^{13}$, —CN, $C_3$-$C_8$ cycloalkyl, or $C_1$-$C_6$ alkyl optionally substituted by oxo, —OH or halogen.

In some embodiments of a compound of Formula (J), Formula (I), or Formula (II), X is CH; Y is N; each $R^3$ and $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, halogen, or —OH; each $R^2$ is independently hydrogen, $C_1$-$C_6$ alkyl, oxo, —$NR^{11}R^{12}$, —CN, —$C(O)R^{10}$, —$C(O)NR^{11}R^{12}$ or halogen, any two $R^2$ groups are independently attached to same carbon or two different carbon; $R^1$ is $C_1$-$C_6$ alkyl, $C_3$-$C_6$ cycloalkyl, 3- to 12-membered heterocyclyl, —$C(O)R^{10}$, —($C_1$-$C_3$ alkylene)($C_3$-$C_6$ cycloalkyl), —($C_1$-$C_3$ alkylene)

(3- to 12-membered heterocyclyl), or —($C_1$-$C_3$ alkylene)($C_6$-$C_{14}$ aryl), each of which is optionally substituted by halogen, oxo, —$OR^{13}$, —C(O) $NR^{13}R^{14}$, —$NR^{13}R^{14}$, —C(O)$R^{13}$, —CN, $C_3$-$C_8$ cycloalkyl, or $C_1$-$C_6$ alkyl optionally substituted by oxo, —OH or halogen.

In some embodiments of a compound of Formula (J), Formula (I), or Formula (II), X is N; Y is CH; each $R^3$ and $R^4$ is independently $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy halogen, or —OH; each $R^2$ is independently hydrogen, $C_1$-$C_6$ alkyl, oxo, —$NR^{11}R^{12}$, —CN, —C(O)$R^{10}$, —C(O)$NR^{11}R^{12}$ or halogen, any two $R^2$ groups are independently attached to same carbon or two different carbon; $R^1$ is $C_1$-$C_6$ alkyl, $C_3$-$C_6$ cycloalkyl, 3- to 12-membered heterocyclyl, —C(O)$R^{10}$, —($C_1$-$C_3$ alkylene)($C_3$-$C_6$ cycloalkyl), —($C_1$-$C_3$ alkylene) (3- to 12-membered heterocyclyl), or —($C_1$-$C_3$ alkylene) ($C_6$-$C_{14}$ aryl), each of which is optionally substituted by halogen, oxo, —$OR^{13}$, —C(O) $NR^{13}R^{14}$, —$NR^{13}R^{14}$, —C(O)$R^{13}$, —CN, $C_3$-$C_8$ cycloalkyl, or $C_1$-$C_6$ alkyl optionally substituted by oxo, —OH or halogen.

In some embodiments of a compound of Formula (J), Formula (I), or Formula (II), X is N; Y is N; each $R^3$ and $R^4$ is independently F; each $R^2$ is independently hydrogen, $C_1$-$C_6$ alkyl, oxo, —$NR^{11}R^{12}$, —CN, —C(O)$R^{10}$, —C(O)$NR^{11}R^{12}$ or halogen, any two $R^2$ groups are independently attached to same carbon or two different carbon; $R^1$ is hydrogen, $C_1$-$C_6$ alkyl, $C_2$-$C_6$ alkenyl, $C_2$-$C_6$ alkynyl, $C_1$-$C_8$ alkoxy, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl) or —($C_1$-$C_3$ alkylene)($C_6$-$C_{14}$ aryl), each of which is optionally substituted by halogen, oxo, —$OR^{13}$, —C(O) $NR^{13}R^{14}$, —$NR^{13}R^{14}$, —C(O)$R^{13}$, —CN, $C_3$-$C_8$ cycloalkyl, or $C_1$-$C_6$ alkyl optionally substituted by oxo, —OH or halogen.

In some embodiments of a compound of Formula (J), Formula (I), or Formula (II), X is N; Y is N; each $R^3$ and $R^4$ is independently F; each $R^2$ is independently hydrogen, $C_1$-$C_6$ alkyl, oxo, —$NR^{11}R^{12}$, —CN, —C(O)$R^{10}$, —C(O)$NR^{11}R^{12}$ or halogen, any two $R^2$ groups are independently attached to same carbon or two different carbon; $R^1$ is $C_1$-$C_6$ alkyl, $C_3$-$C_6$ cycloalkyl, 3- to 12-membered heterocyclyl, —($C_1$-$C_3$ alkylene)($C_3$-$C_6$ cycloalkyl), —($C_1$-$C_3$ alkylene) (3- to 12-membered heterocyclyl), or —($C_1$-$C_3$ alkylene) ($C_6$-$C_{14}$ aryl), each of which is optionally substituted by halogen, oxo, —$OR^{13}$, —C(O) $NR^{13}R^{14}$, —$NR^{13}R^{14}$, —C(O)$R^{13}$, —CN, $C_3$-$C_8$ cycloalkyl, or $C_1$-$C_6$ alkyl optionally substituted by oxo, —OH or halogen.

In some embodiments of a compound of Formula (J), Formula (I), or Formula (II), X is N; Y is N; each $R^3$ and $R^4$ is independently F; each $R^2$ is independently hydrogen or $C_1$-$C_6$ alkyl, any two $R^2$ groups are independently attached to same carbon or two different carbon;

$R^1$ is $C_1$-$C_6$ alkyl, $C_3$-$C_6$ cycloalkyl, 3- to 12-membered heterocyclyl, —($C_1$-$C_3$ alkylene)($C_3$-$C_6$ cycloalkyl), —($C_1$-$C_3$ alkylene)(3- to 12-membered heterocyclyl), or —($C_1$-$C_3$ alkylene)($C_6$-$C_{14}$ aryl), each of which is optionally substituted by halogen, oxo, —$OR^{13}$, —C(O) $NR^{13}R^{14}$, —$NR^{13}R^{14}$, —C(O)$R^{13}$, —CN, $C_3$-$C_8$ cycloalkyl, or $C_1$-$C_6$ alkyl optionally substituted by oxo, —OH or halogen.

In some embodiments of a compound of Formula (J), Formula (I), or Formula (II), X is N; Y is N; each $R^3$ and $R^4$ is independently F; each $R^2$ is independently hydrogen or $C_1$-$C_6$ alkyl, any two $R^2$ groups are independently attached to same carbon or two different carbon;

$R^1$ is $C_1$-$C_6$ alkyl, $C_3$-$C_6$ cycloalkyl or —($C_1$-$C_3$ alkylene) ($C_3$-$C_6$ cycloalkyl), each of which is optionally substituted by halogen, oxo, —$OR^{13}$, —$NR^{13}R^{14}$ or $C_1$-$C_6$ alkyl optionally substituted by oxo, —OH or halogen.

In some embodiments of a compound of Formula (J), Formula (I), or Formula (II), X is N; Y is N; each $R^3$ and $R^4$ is independently F; each $R^2$ is independently hydrogen; $R^1$ is $C_1$-$C_6$ alkyl or $C_3$-$C_6$ cycloalkyl, wherein $R^1$ is independently optionally substituted by halogen, oxo, —$OR^{13}$, —$NR^{13}R^{14}$ or $C_1$-$C_6$ alkyl optionally substituted by oxo, —OH or halogen. In some embodiments of a compound of Formula (J), Formula (I), or Formula (II), X is N; Y is N; each $R^3$ and $R^4$ is independently F; each $R^2$ is independently hydrogen; $R^1$ is $C_1$-$C_6$ alkyl, wherein $R^1$ is independently optionally substituted by halogen, oxo, —$OR^{13}$, —$NR^{13}R^{14}$ or $C_1$-$C_6$ alkyl optionally substituted by oxo, —OH or halogen. In some embodiments of a compound of Formula (J), Formula (I), or Formula (II), X is N; Y is N; each $R^3$ and $R^4$ is independently F; each $R^2$ is independently hydrogen; $R^1$ is selected from the group consisting of:

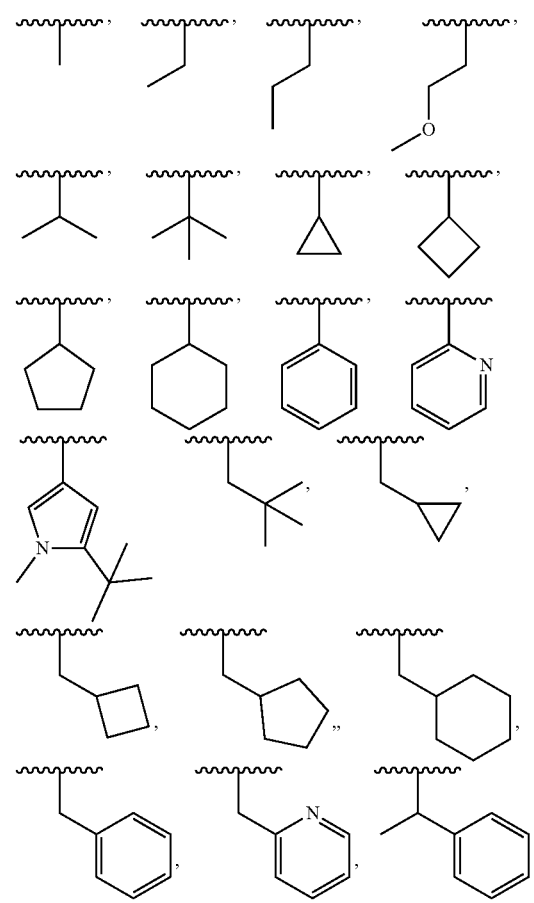

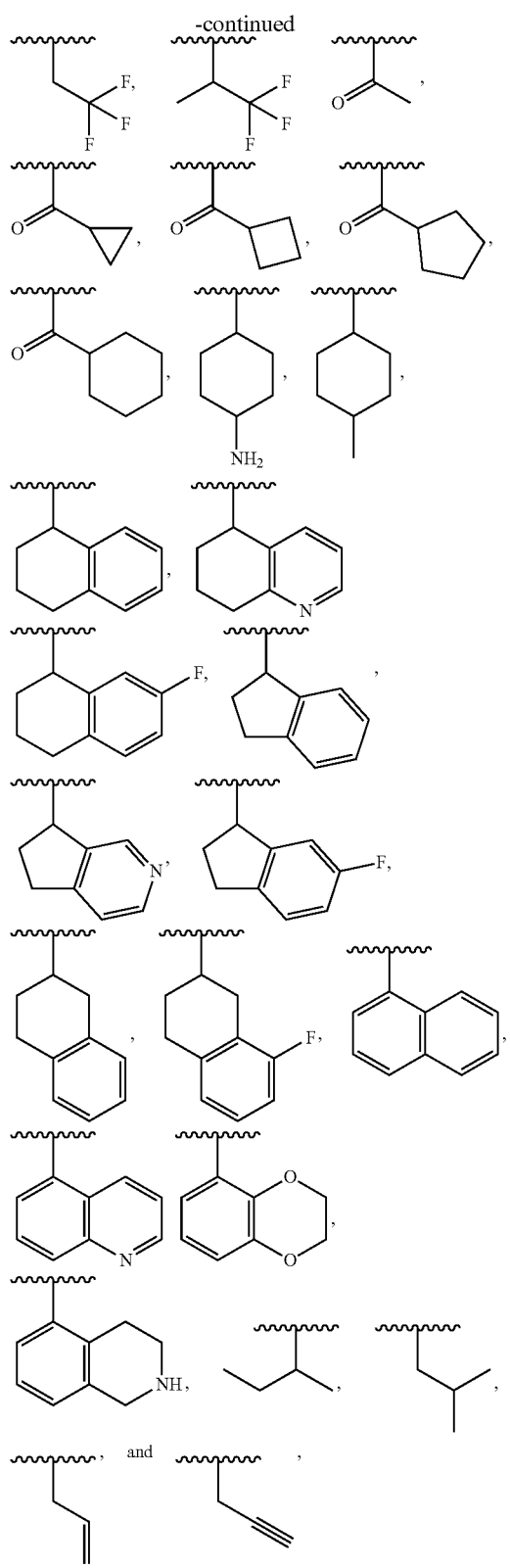
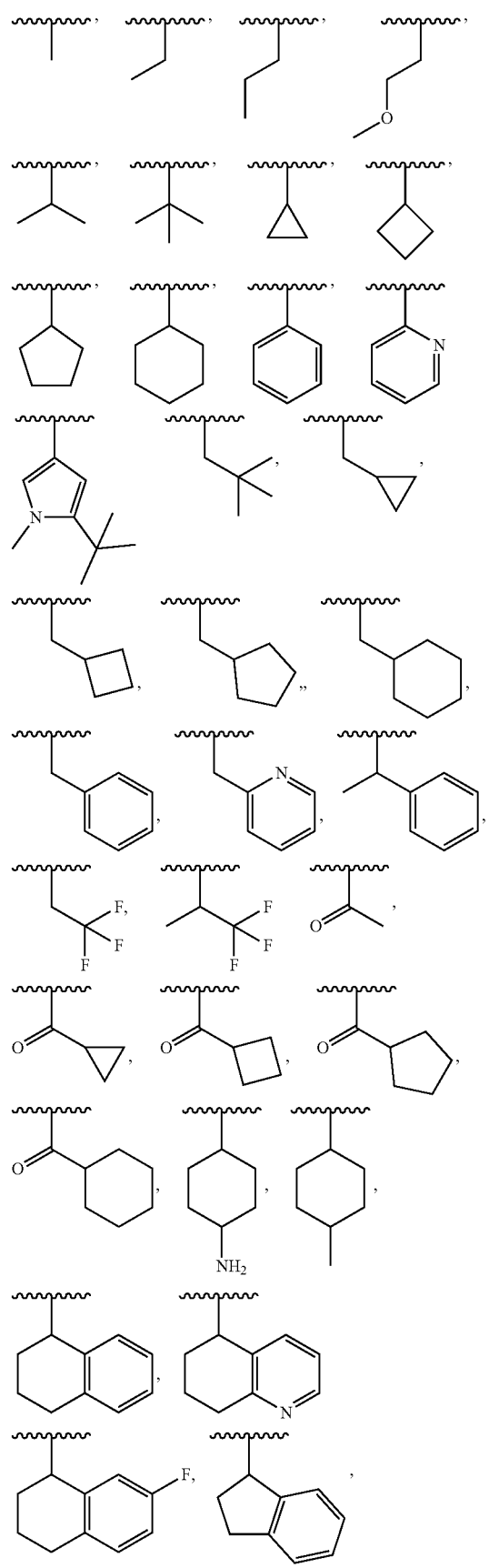
wherein the wavy lines denote attachment points to the parent molecule. In some embodiments of a compound of Formula (J), Formula (I), or Formula (II), X is N; Y is N; each $R^3$ and $R^4$ is independently F; each $R^2$ is independently hydrogen; R is selected from the group consisting of:

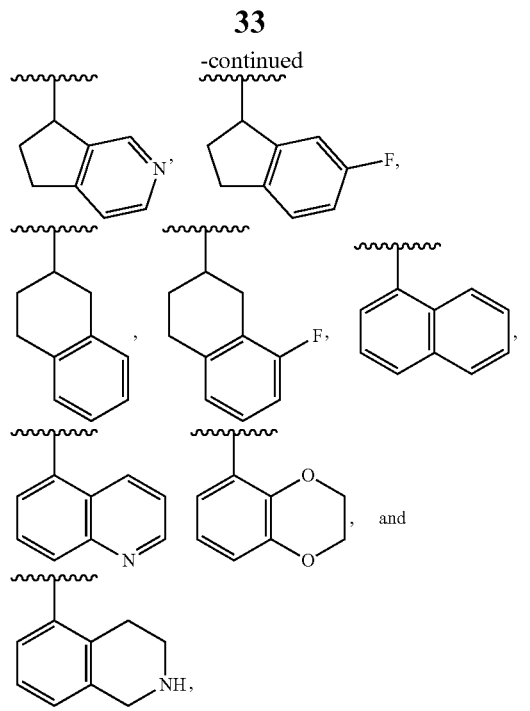

wherein the wavy lines denote attachment points to the parent molecule. In some embodiments of a compound of Formula (J), Formula (I), or Formula (II), X is N; Y is N; each $R^3$ and $R^4$ is independently F; each $R^2$ is independently hydrogen; $R^1$ is $C_1$-$C_6$ alkyl.

In some embodiments of a compound of Formula (J), Formula (I), or Formula (II), p is 0. In some embodiments of a compound of Formula (J), Formula (I), or Formula (II), p is 0 or 1. In some embodiments of a compound of Formula (J), Formula (I), or Formula (II), p is 0, 1, or 2.

In some embodiments of a compound of Formula (J), Formula (I), or Formula (II), each $R^5$ is independently $C_1$-$C_6$ alkyl, halogen, oxo, —CN, —OR$^{10}$, —NR$^{11}$R$^{12}$, —C(O)R$^{10}$, —C(O)NR$^{11}$R$^{12}$, $C_3$-$C_6$ cycloalkyl, 3- to 12-membered heterocyclyl, —($C_1$-$C_3$ alkylene)OR$^{10}$, —($C_1$-$C_3$ alkylene)NR$^{11}$R$^{12}$, —($C_1$-$C_3$ alkylene)C(O)R$^{10}$, —($C_1$-$C_3$ alkylene)($C_3$-$C_6$ cycloalkyl), —($C_1$-$C_3$ alkylene)(3- to 12-membered heterocyclyl), each of which is optionally substituted by halogen, oxo, —OR$^{13}$, —NR$^{13}$R$^{14}$, —C(O)R$^{13}$, —CN, —($C_1$-$C_3$ alkylene)OR$^{13}$, —($C_1$-$C_3$ alkylene)NR$^{13}$R$^{14}$, —($C_1$-$C_3$ alkylene)C(O)R$^{13}$, $C_3$-$C_8$ cycloalkyl, or $C_1$-$C_6$ alkyl optionally substituted by oxo, —OH or halogen. In some embodiments, each $R^5$ is independently —CN, halogen, methoxy, oxo, trifluoromethoxy, —NH(CH$_3$), —N(CH$_3$)$_2$, —(CH$_2$)NH(CH$_3$), —(CH$_2$)NH$_2$, —(CH$_2$)N(CH$_3$)$_2$, —C(O)NH$_2$, —C(O)N(CH$_3$)$_2$, methyl, ethyl, isopropyl, cyclopropyl, —CH$_2$OH, —CH$_2$OCH$_3$, —NH(CH$_2$)$_2$N(CH$_2$CH$_3$)$_2$, —O(CH$_2$)$_2$N(CH$_2$CH$_3$)$_2$, or trifluoromethyl. In some embodiments, each $R^5$ is independently —CN, halogen, methoxy, oxo, trifluoromethoxy, —NH(CH$_3$), —N(CH$_3$)$_2$, —(CH$_2$)NH(CH$_3$), —(CH$_2$)NH$_2$, —(CH$_2$)N(CH$_3$)$_2$, —C(O)NH$_2$, —C(O)N(CH$_3$)$_2$, methyl, ethyl, isopropyl, n-propyl, cyclopropyl, —CH$_2$OH, —CH$_2$OCH$_3$, —NH(CH$_2$)$_2$N(CH$_2$CH$_3$)$_2$, —O(CH$_2$)$_2$N(CH$_2$CH$_3$)$_2$, trifluoromethyl,

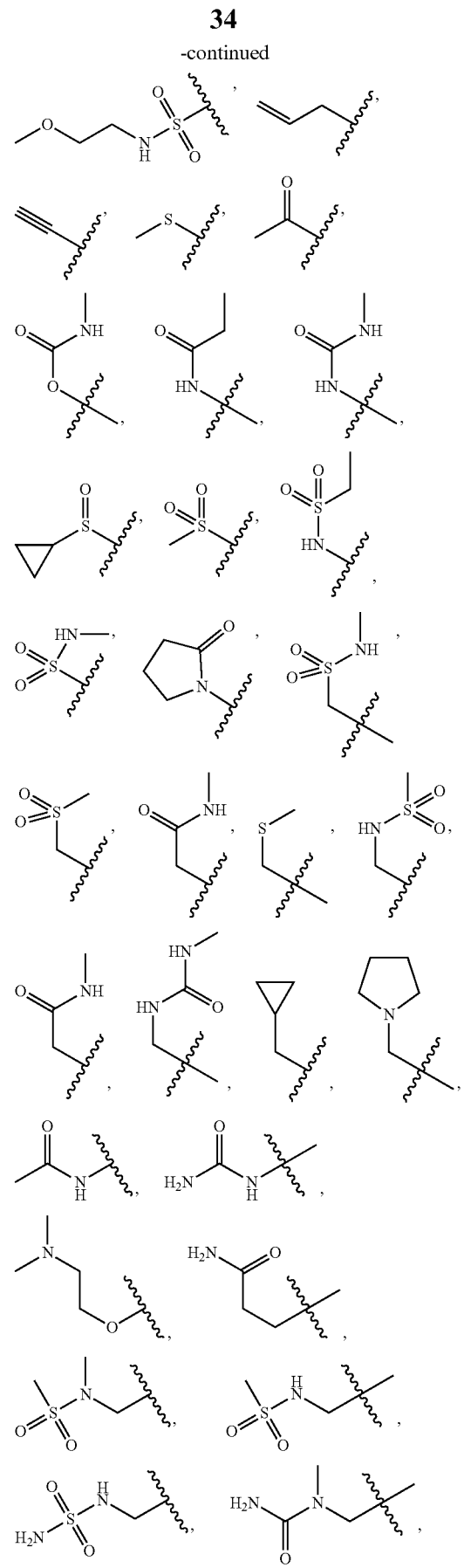

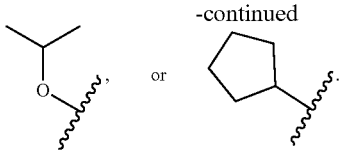

In some embodiments of a compound of Formula (J), Formula (I), or Formula (II), q is 0. In some embodiments of a compound of Formula (J), Formula (I), or Formula (II), q is 0 or 1. In some embodiments of a compound of Formula (J), Formula (I), or Formula (II), q is 0, 1, or 2.

In some embodiments of a compound of Formula (J), Formula (I), or Formula (II), each $R^6$ is independently $C_1$-$C_6$ alkyl, halogen, oxo, —CN, —$NR^{11}R^{12}$, —C(O)$R^{10}$, $C_3$-$C_6$ cycloalkyl, 3- to 12-membered heterocyclyl, —($C_1$-$C_3$ alkylene)$OR^{10}$, —($C_1$-$C_3$ alkylene)$NR^{11}R^{12}$, each of which is optionally substituted by halogen, oxo, —$OR^{13}$, —$NR^{13}R^{14}$, —C(O)$R^{13}$, —CN, —($C_1$-$C_3$ alkylene)$OR^{13}$, —($C_1$-$C_3$ alkylene)$NR^{13}R^{14}$, —($C_1$-$C_3$ alkylene)C(O)$R^{13}$, $C_3$-$C_8$ cycloalkyl, or $C_1$-$C_6$ alkyl optionally substituted by oxo, —OH or halogen; or two $R^6$ groups when bound to the same carbon atom, are taken together with the carbon to which they are attached to form a $C_3$-$C_6$ cycloalkyl. In some embodiments, each $R^6$ is independently ethyl, methyl, isopropyl, pyrrolidinyl, —N(CH$_3$)$_2$, —CH$_2$OH, oxo, —C(O)CH$_2$NHCH$_3$, —CH$_2$CH$_2$OH, difluoroethyl, —CH$_2$N(CH$_3$)$_2$, —OH, or —C(O)CH$_2$OH. In some embodiments, each $R^6$ is independently ethyl, methyl, isopropyl, pyrrolidinyl, cyclopropyl, methoxy, —N(CH$_3$)$_2$, —NHCH$_3$, —CH$_2$OH, oxo, —C(O)CH$_2$NHCH$_3$, —CH$_2$CH$_2$OH, difluoroethyl, —CH$_2$N(CH$_3$)$_2$, —CH$_2$NH$_2$, —OH, —C(O)CH$_2$OH, —C(O)CH$_2$N(CH$_3$)$_2$, —C(O)N(CH$_3$)$_2$, —C(O)NHCH$_3$, —C(O)NH$_2$, —NHC(O)CH$_3$, —C(O)CH$_3$, —S(O)$_2$CH$_3$,

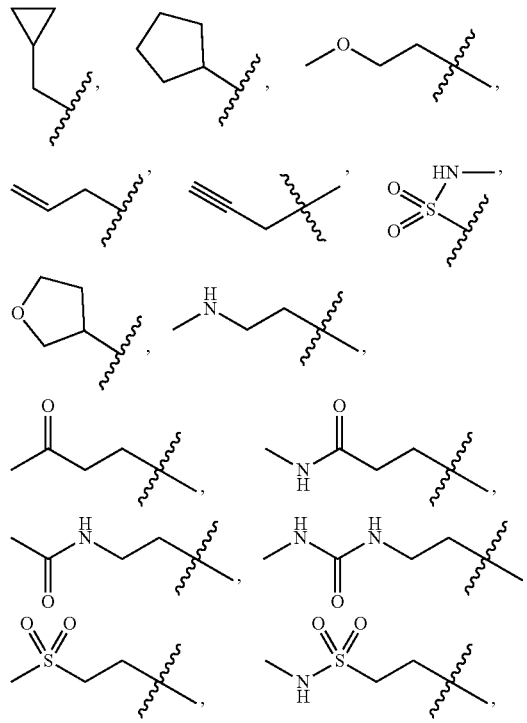

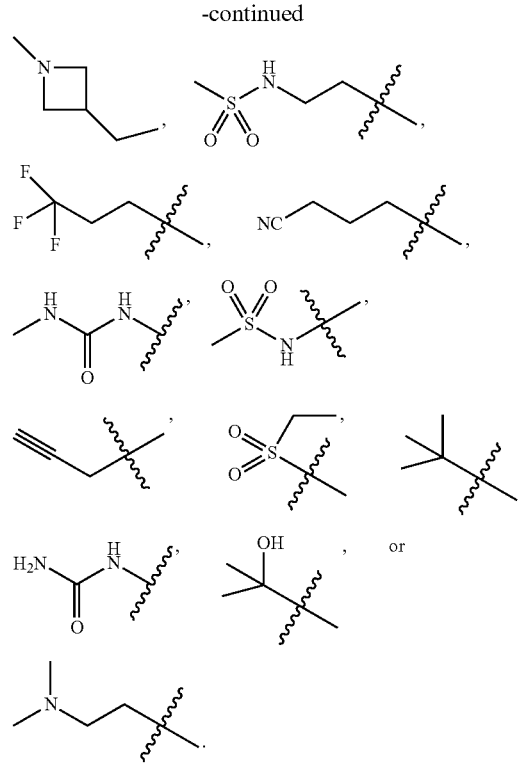

In some embodiments of a compound of Formula (I), A, L, and B together with $R^5$ and $R^6$ are selected from the group consisting of:

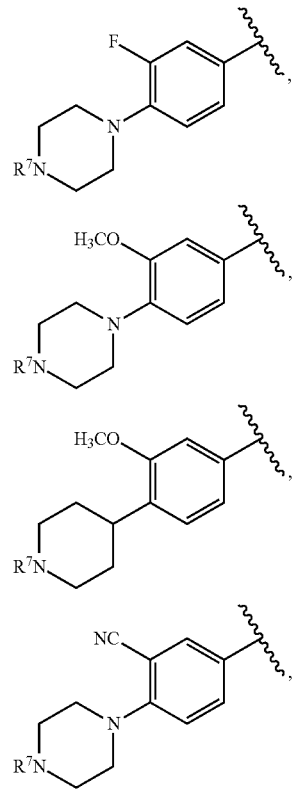

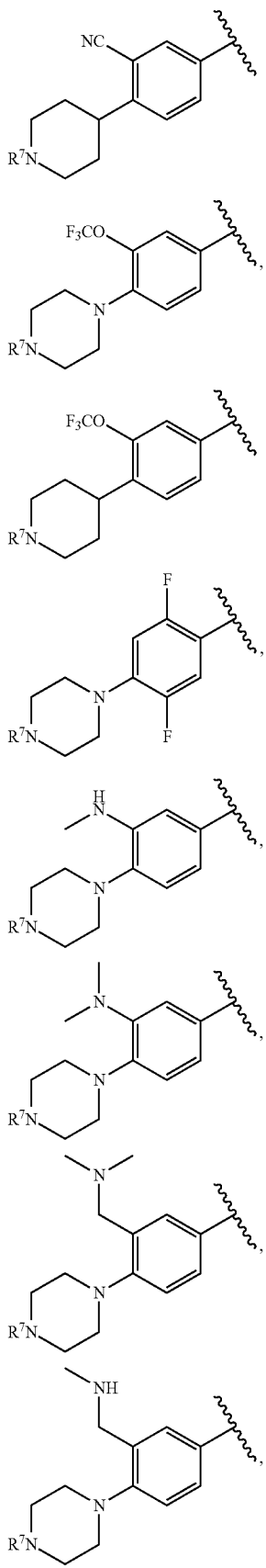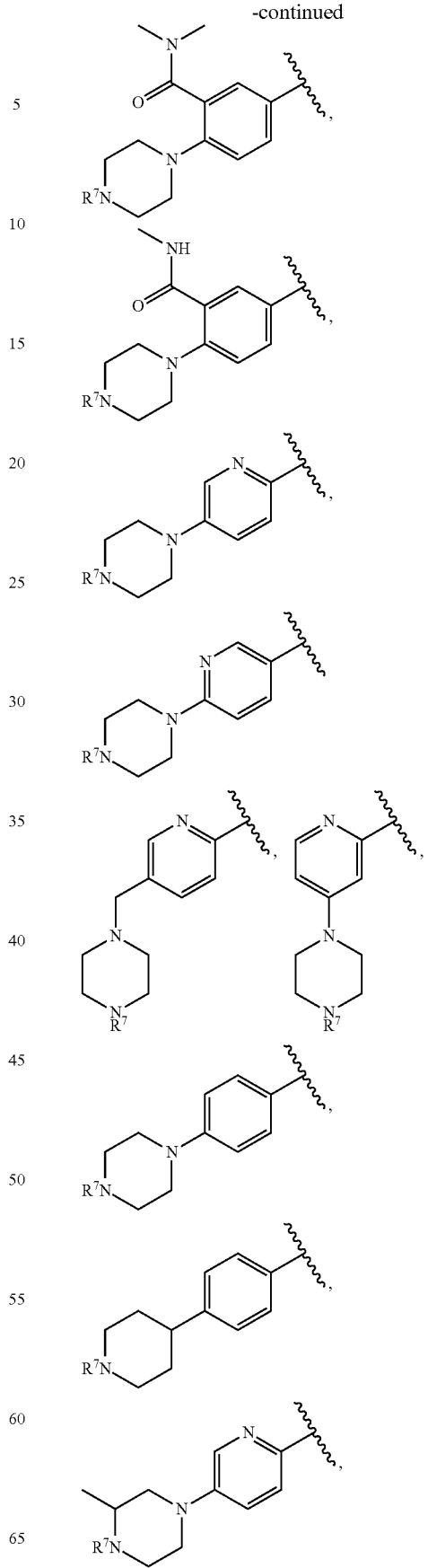

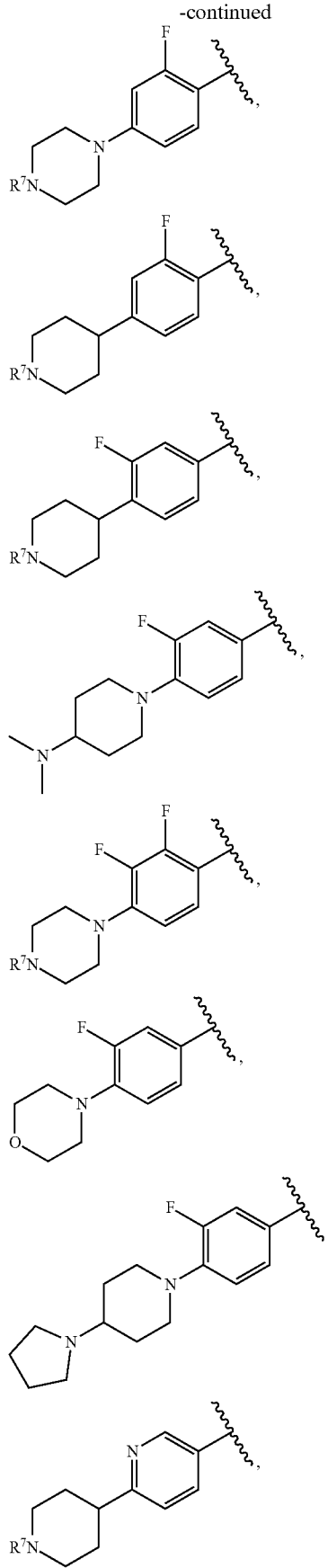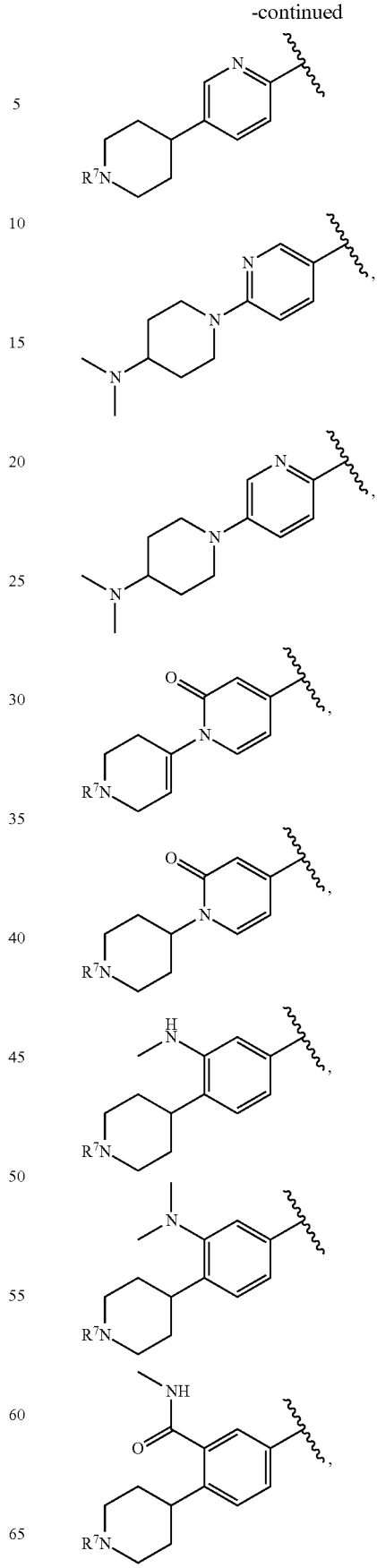

41
-continued
42
-continued
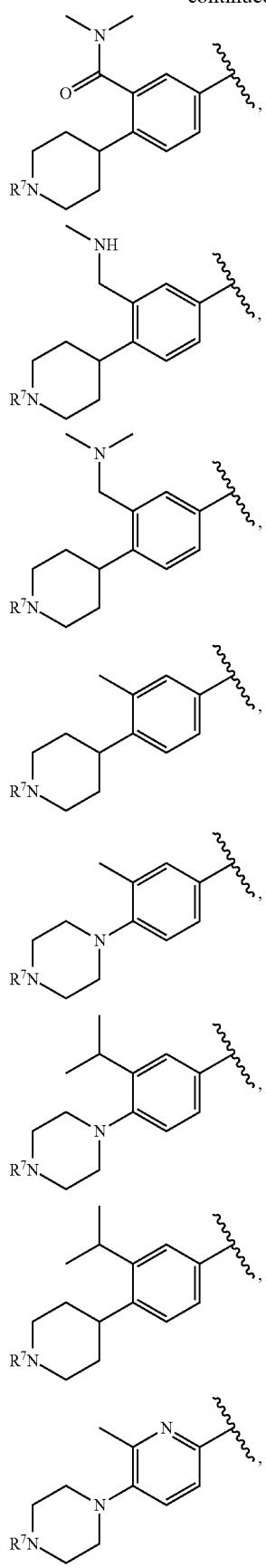
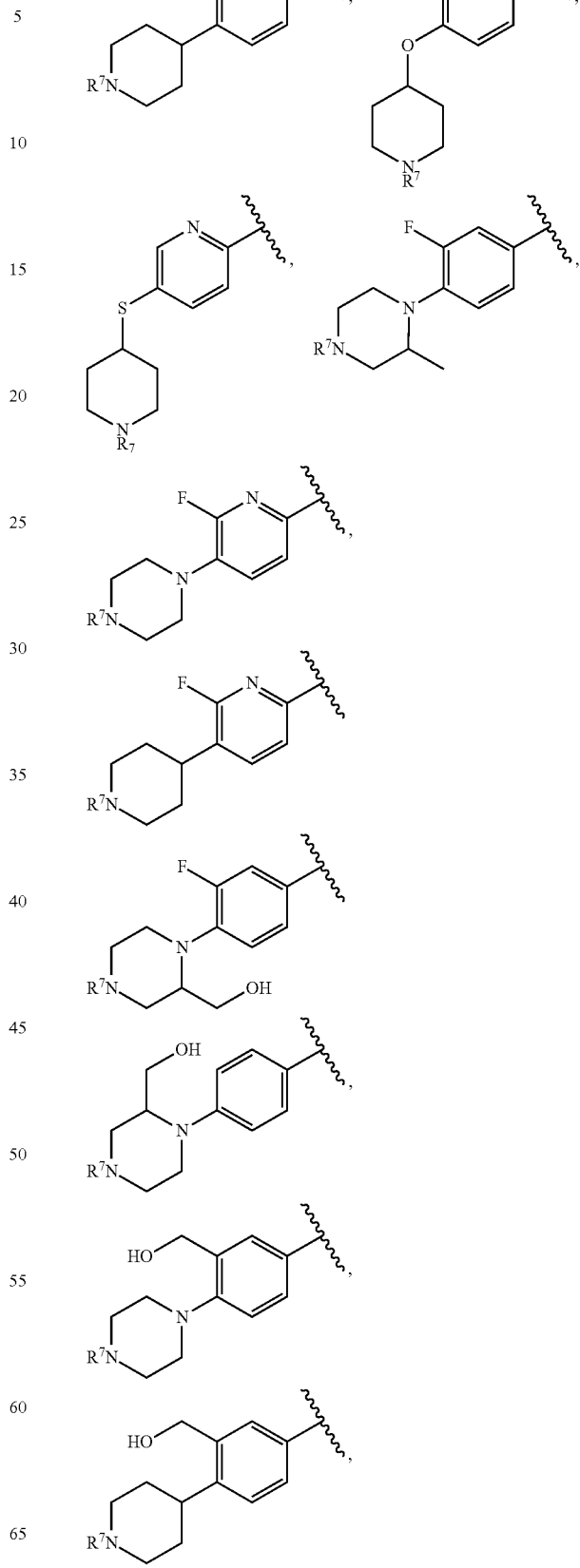

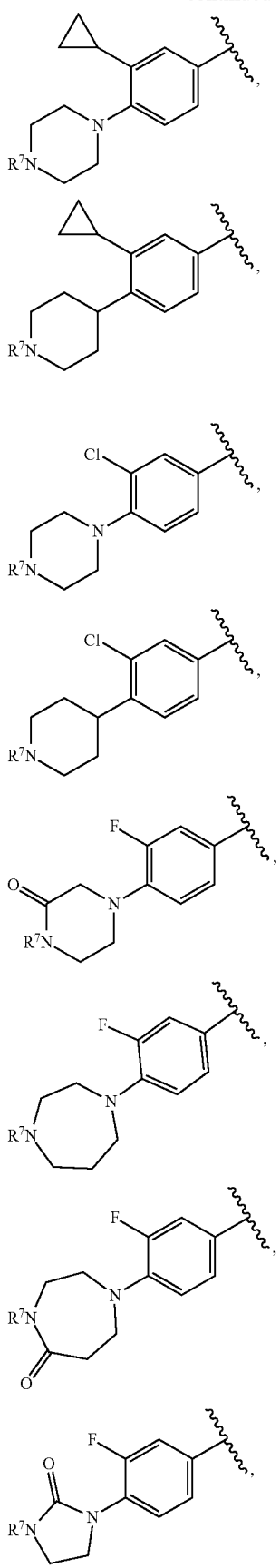
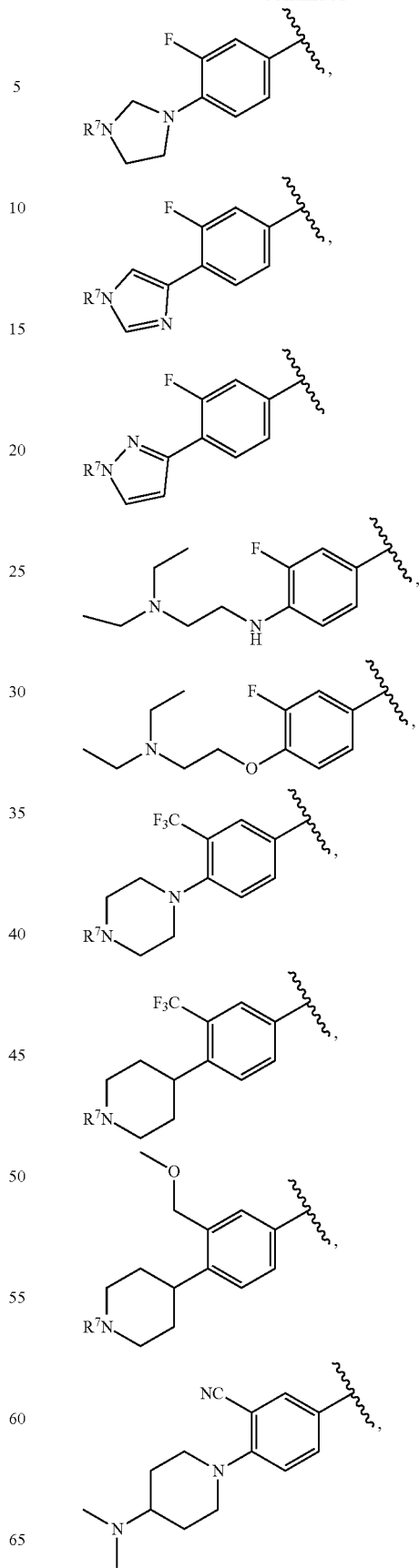

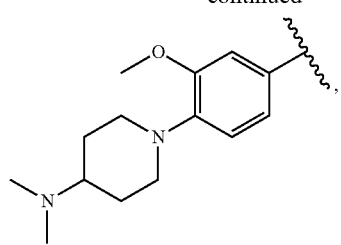,
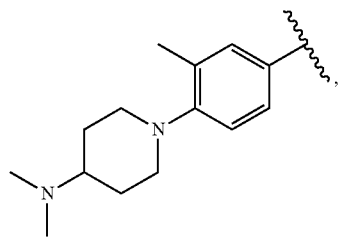,
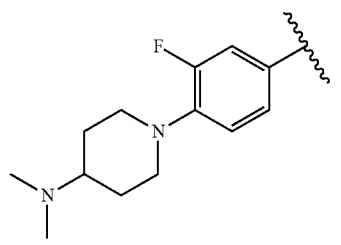,
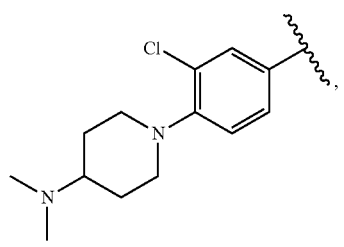,
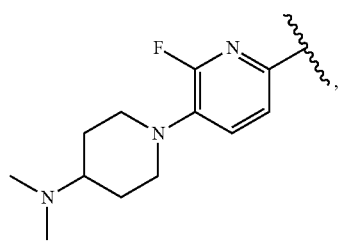,
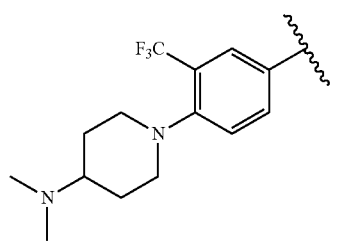,
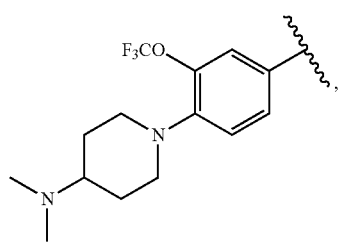,
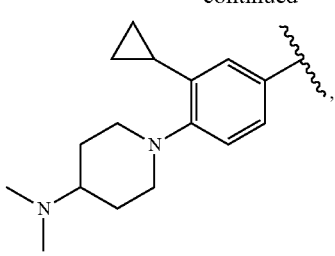,
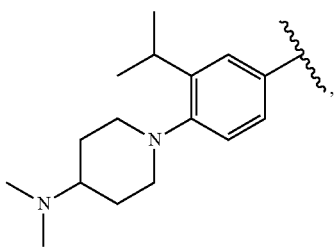,
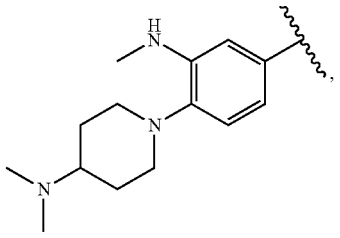,
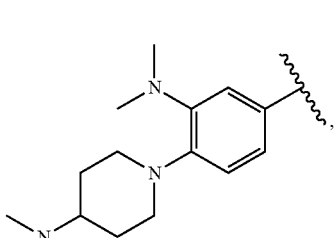,
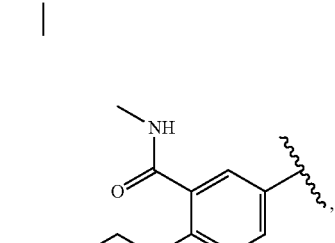,
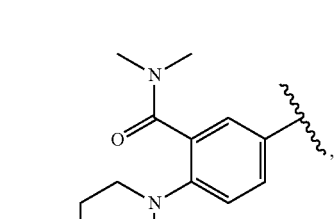
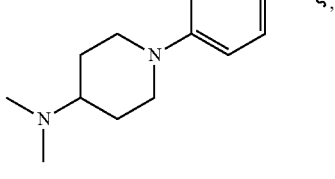,

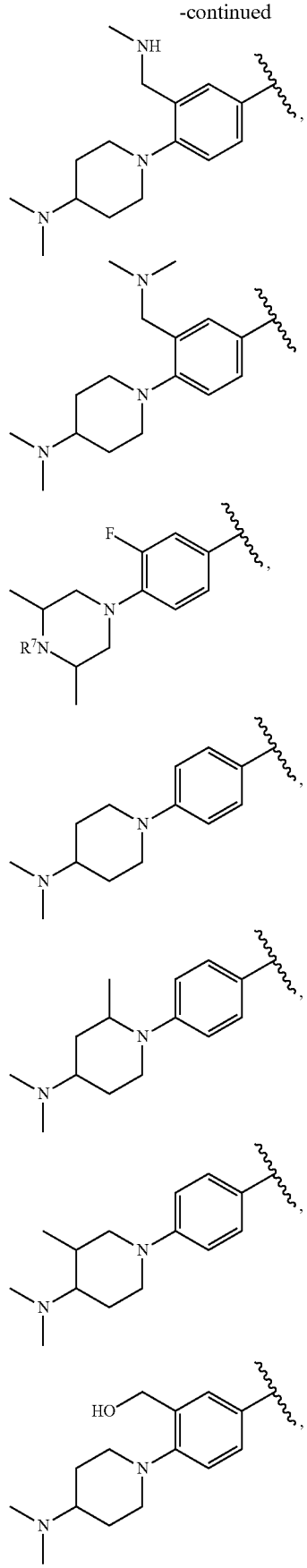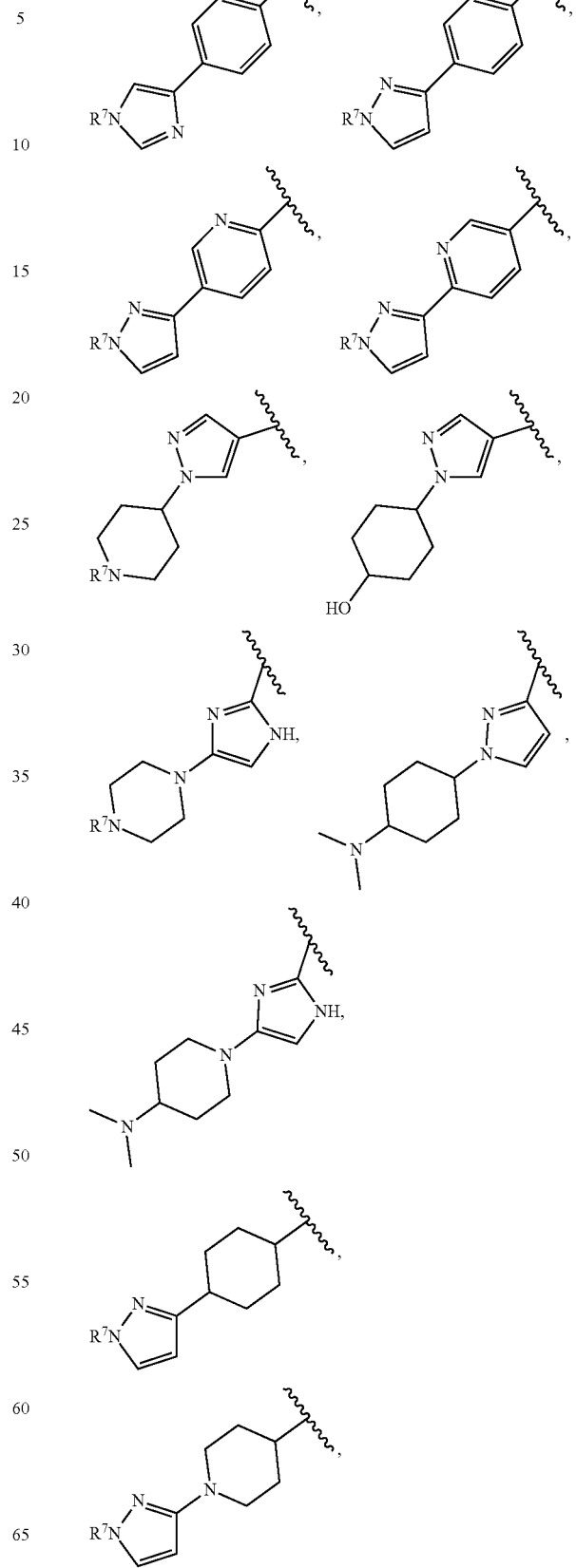

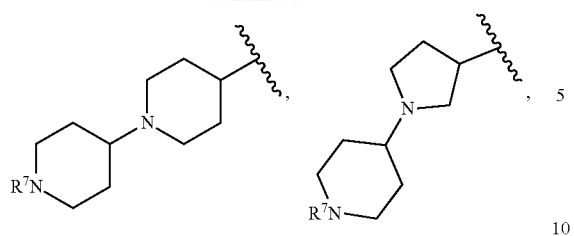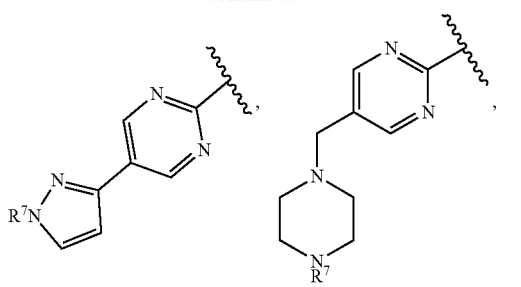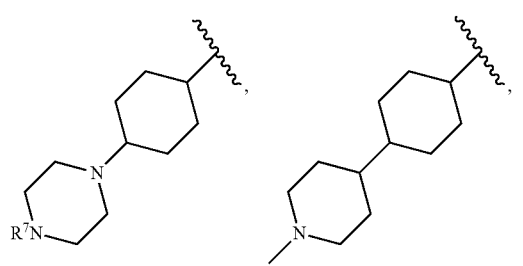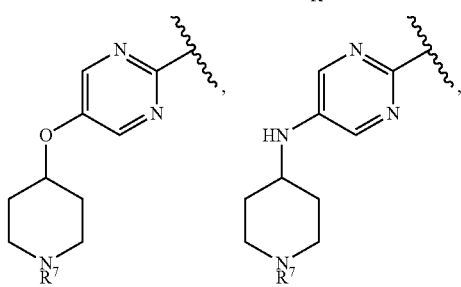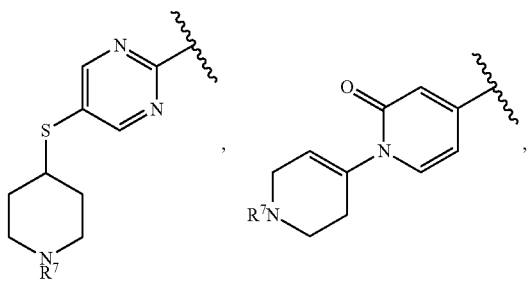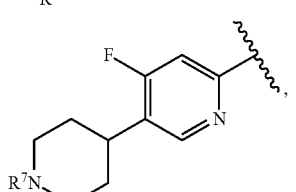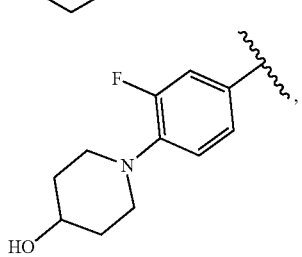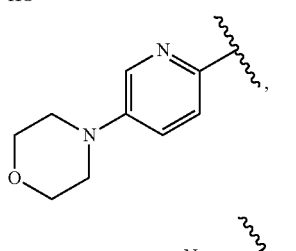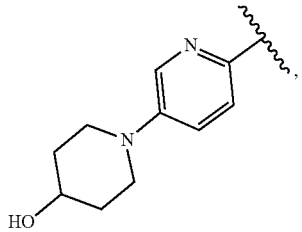

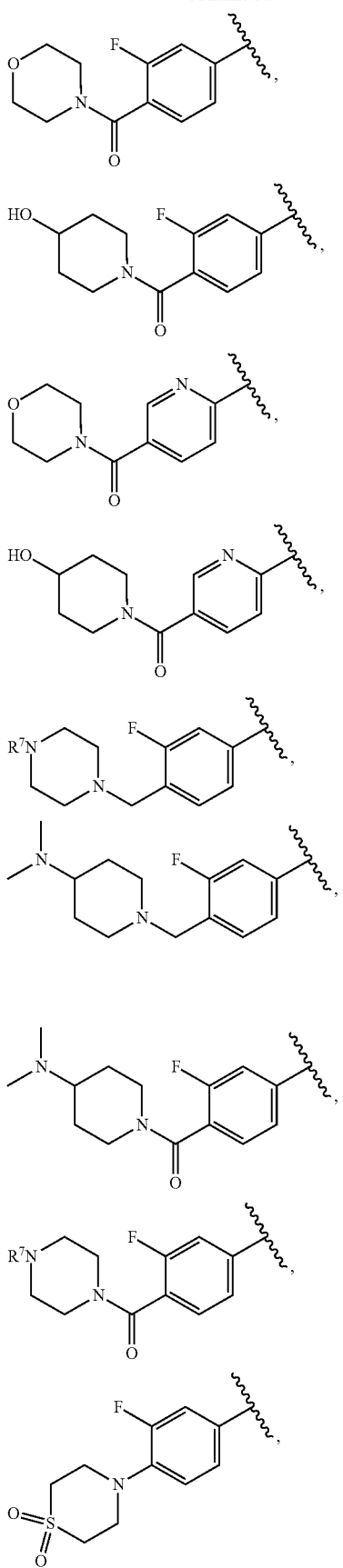
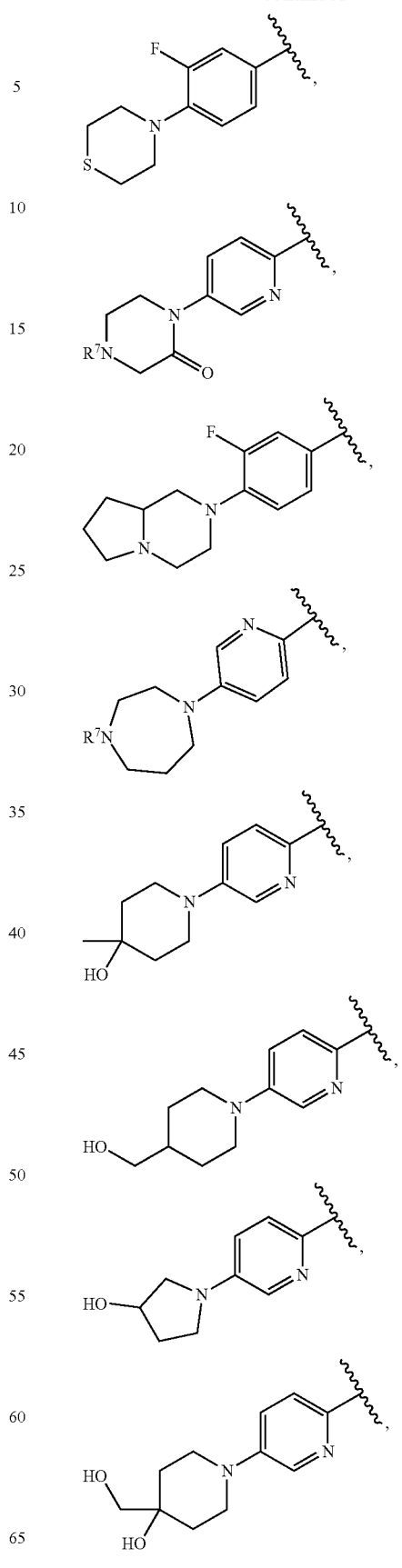

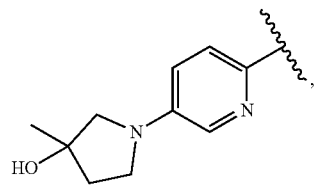
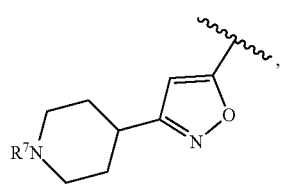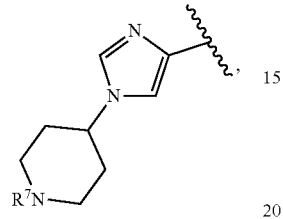
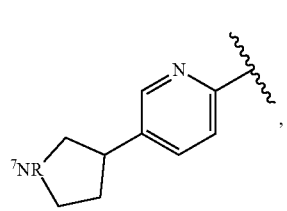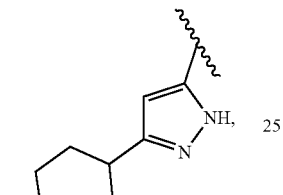
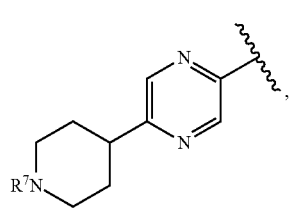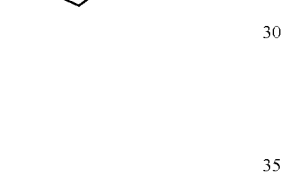
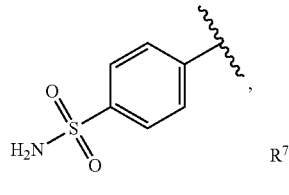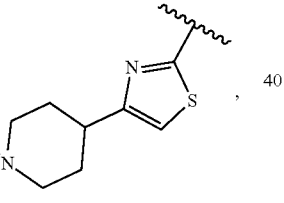
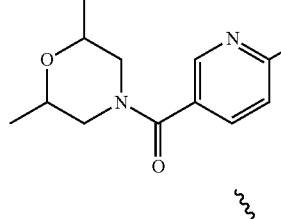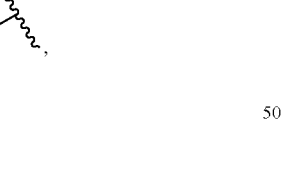
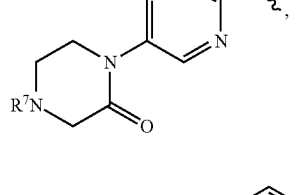
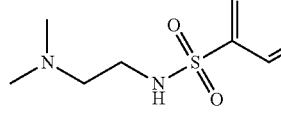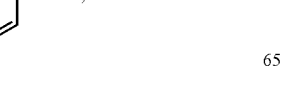
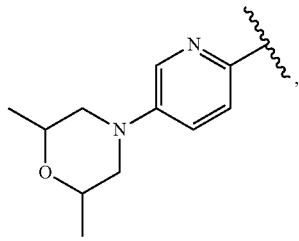
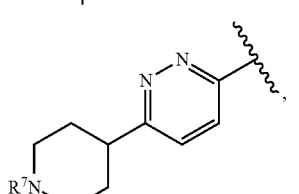
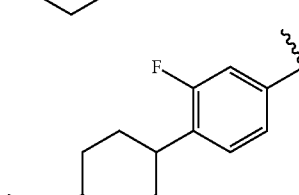

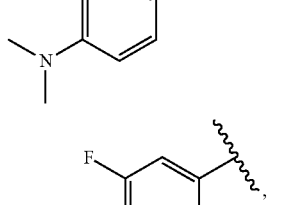
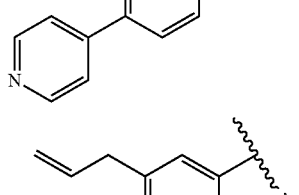
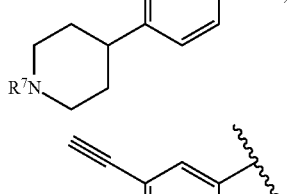
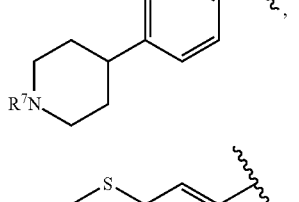

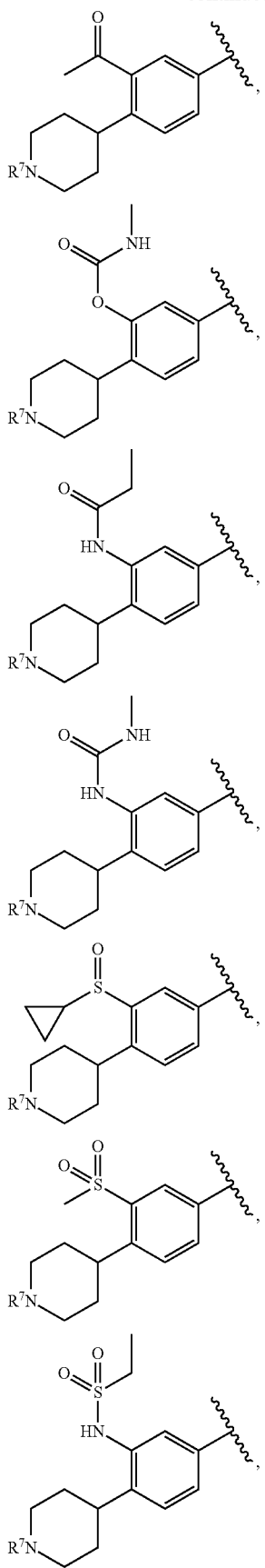
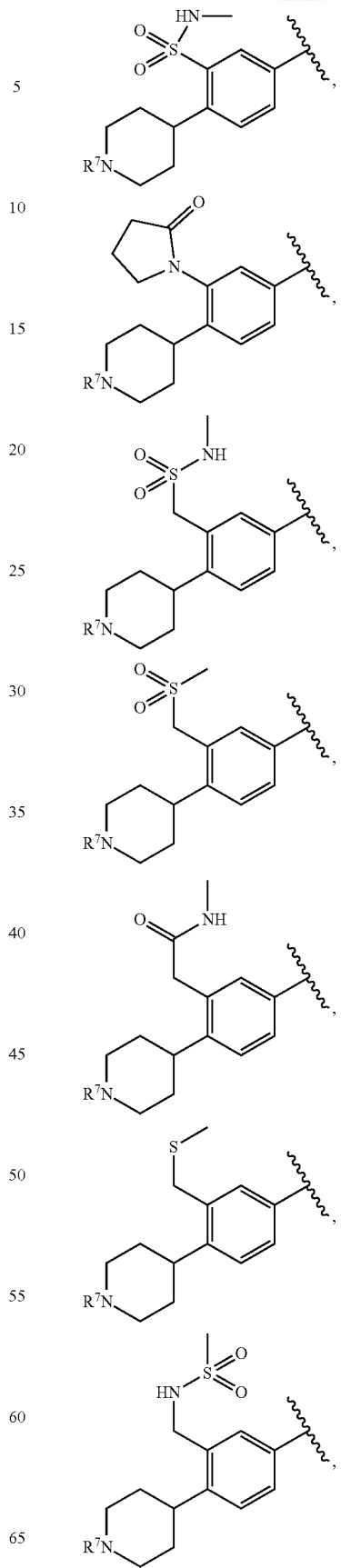

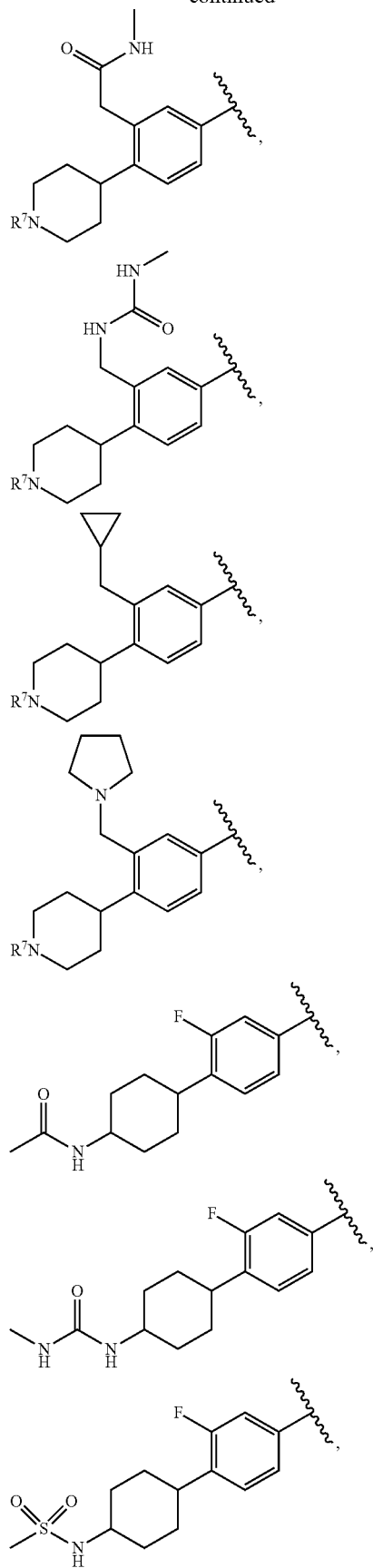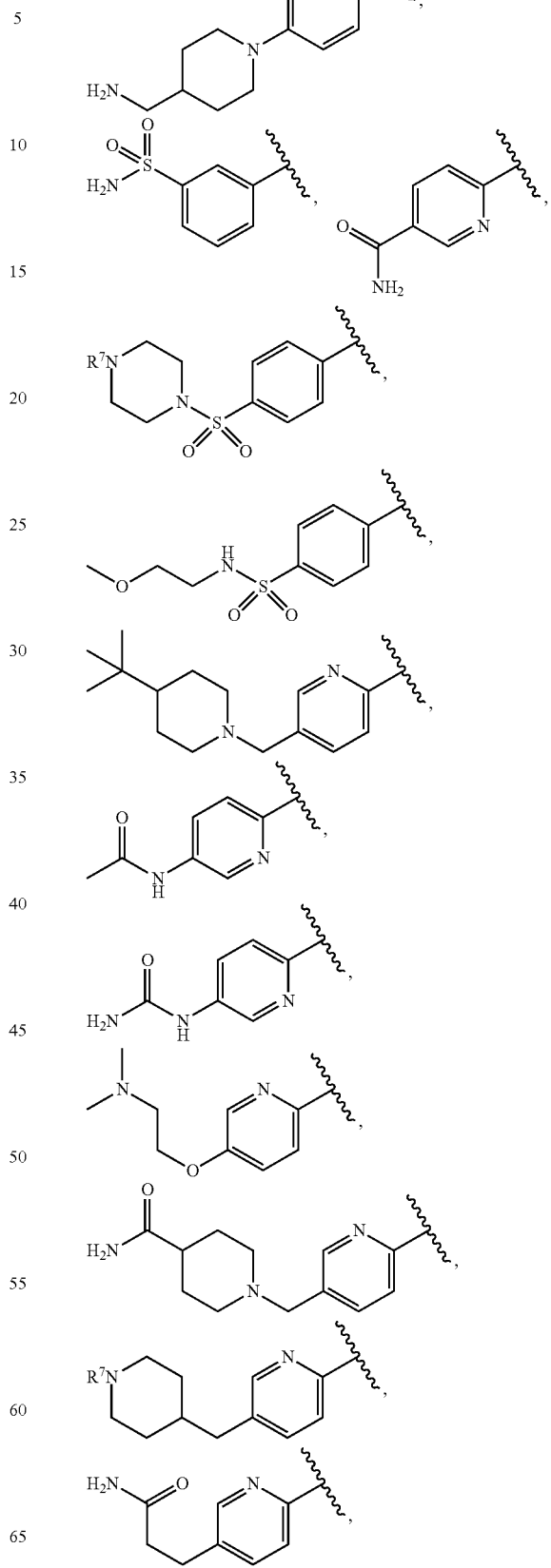

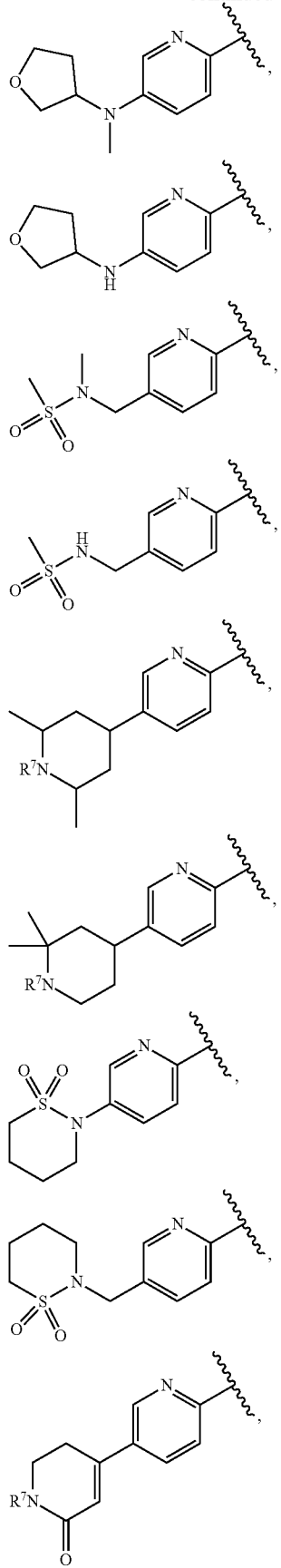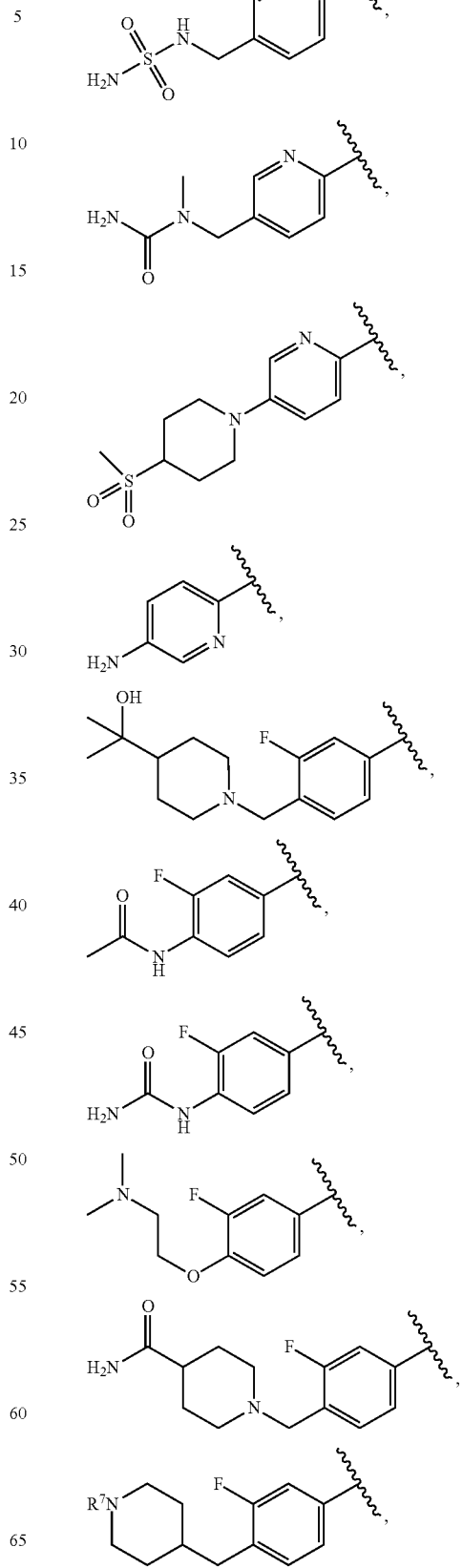

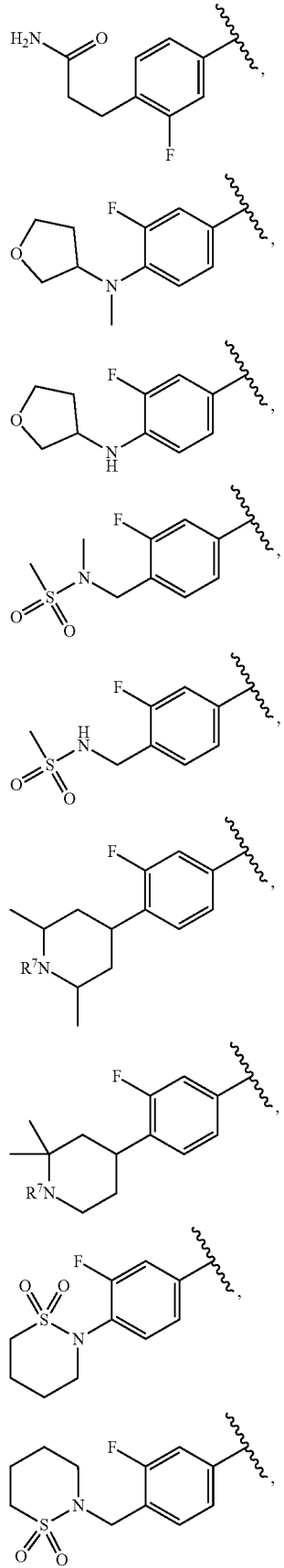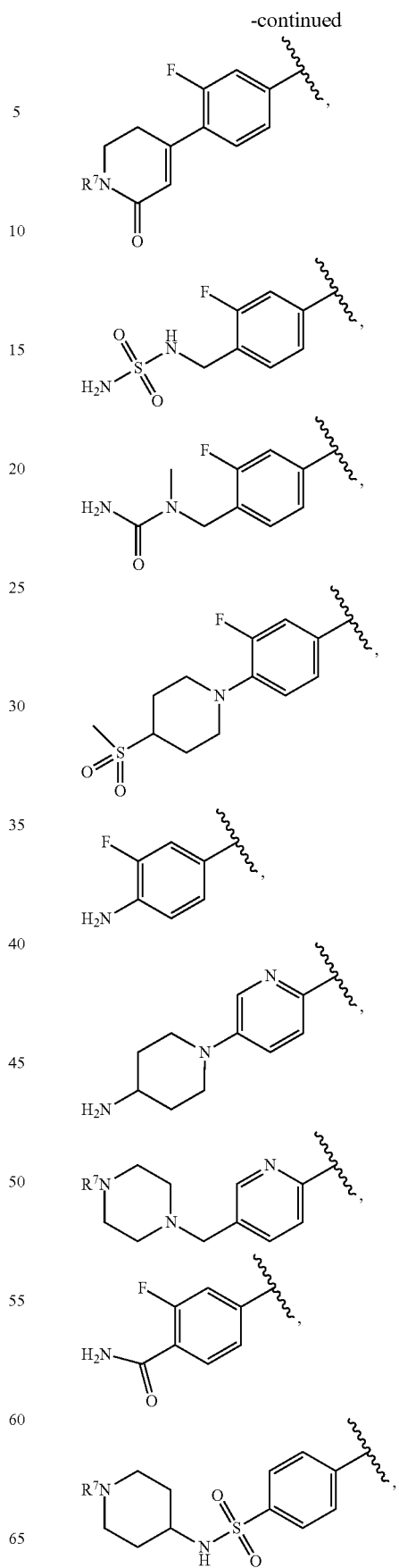

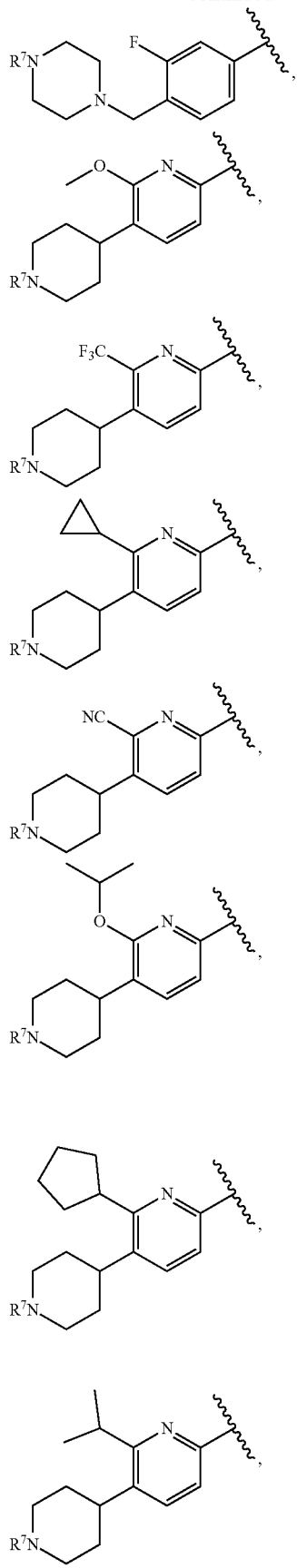

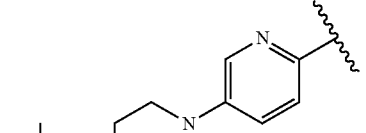

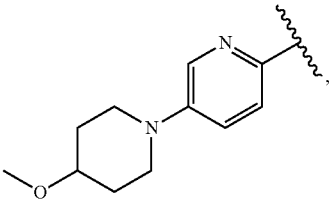 [SMILES: *c1ccc(N2CCC(OC)CC2)cn1]

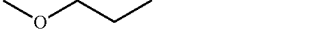

wherein the wavy lines denote attachment points to the parent molecule and R⁷ is as described herein. It is understood that each description of A and B may be combined with each description of X, Y, R², R³, R⁴, R⁵, R⁶, l, m, n, p, and q the same as if each and every combination were specifically and individually listed.

In some embodiments of a compound of Formula (I), A and B together with R⁵ and R⁶ are selected from the group consisting of:

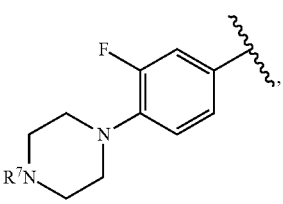

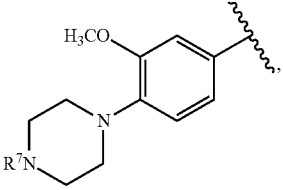

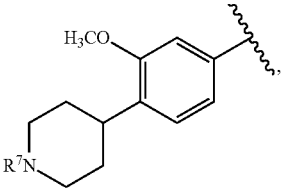

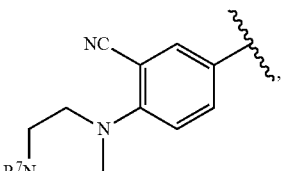

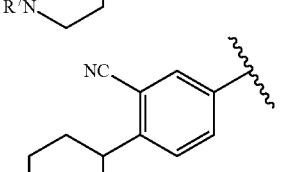

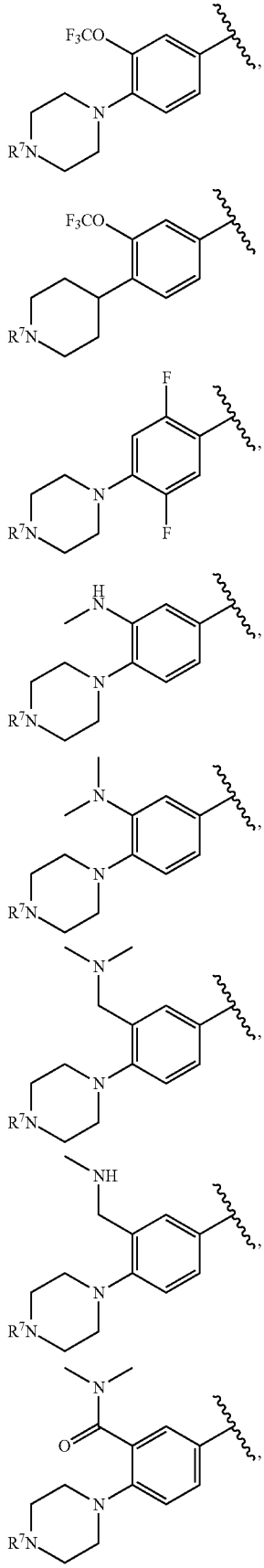
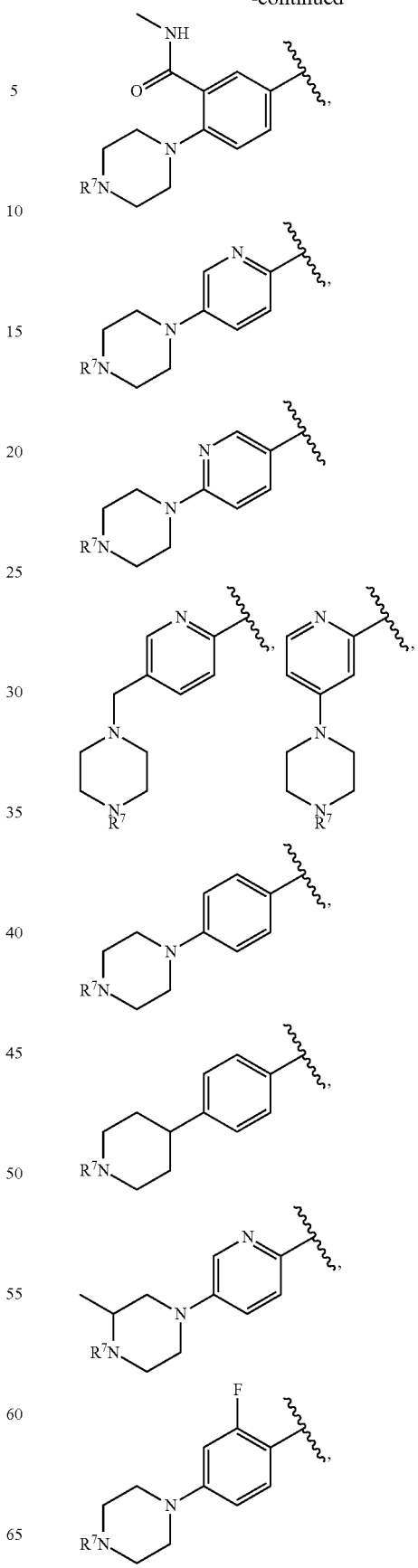

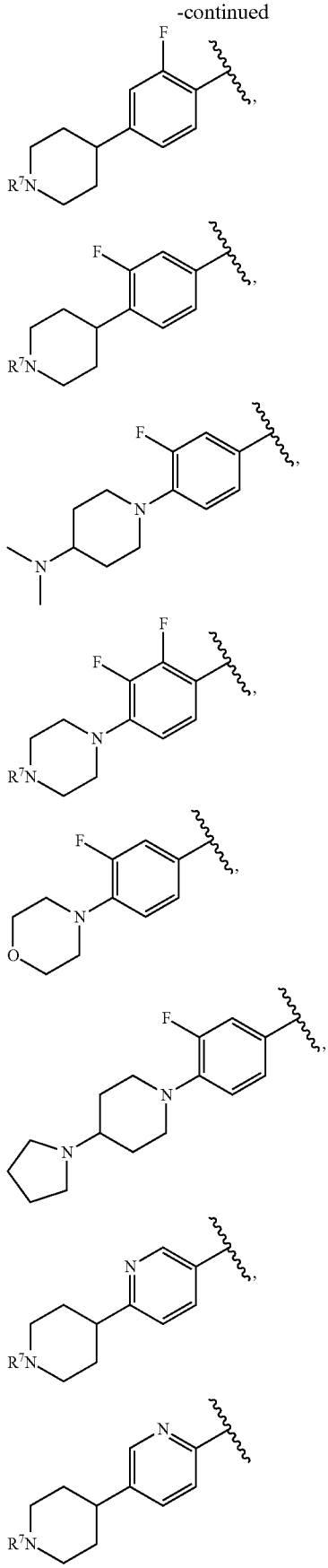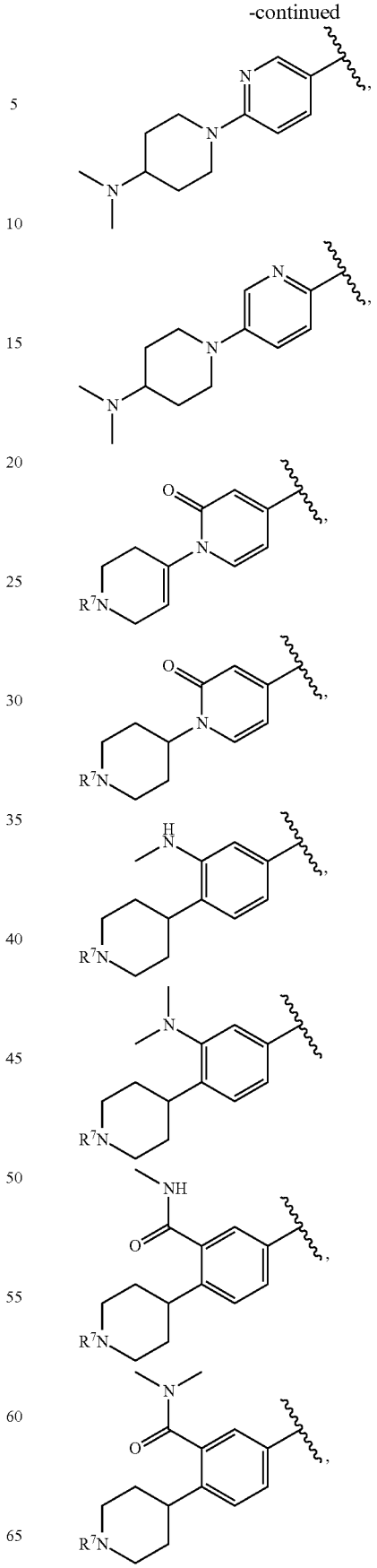

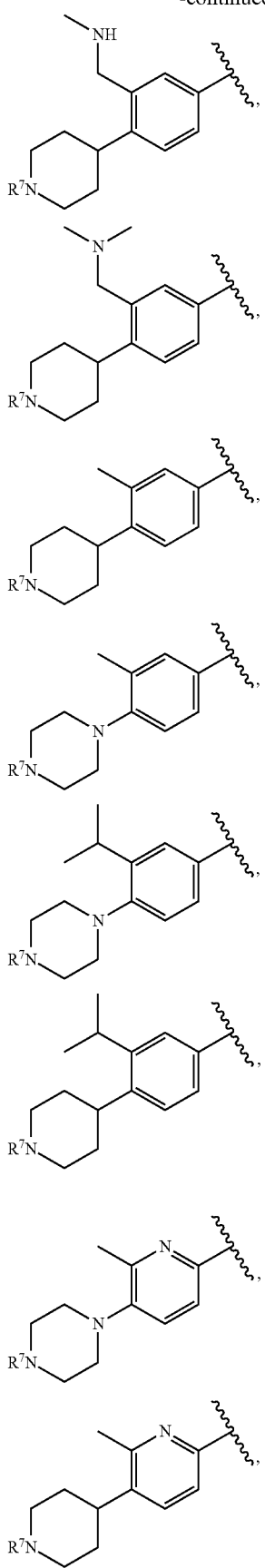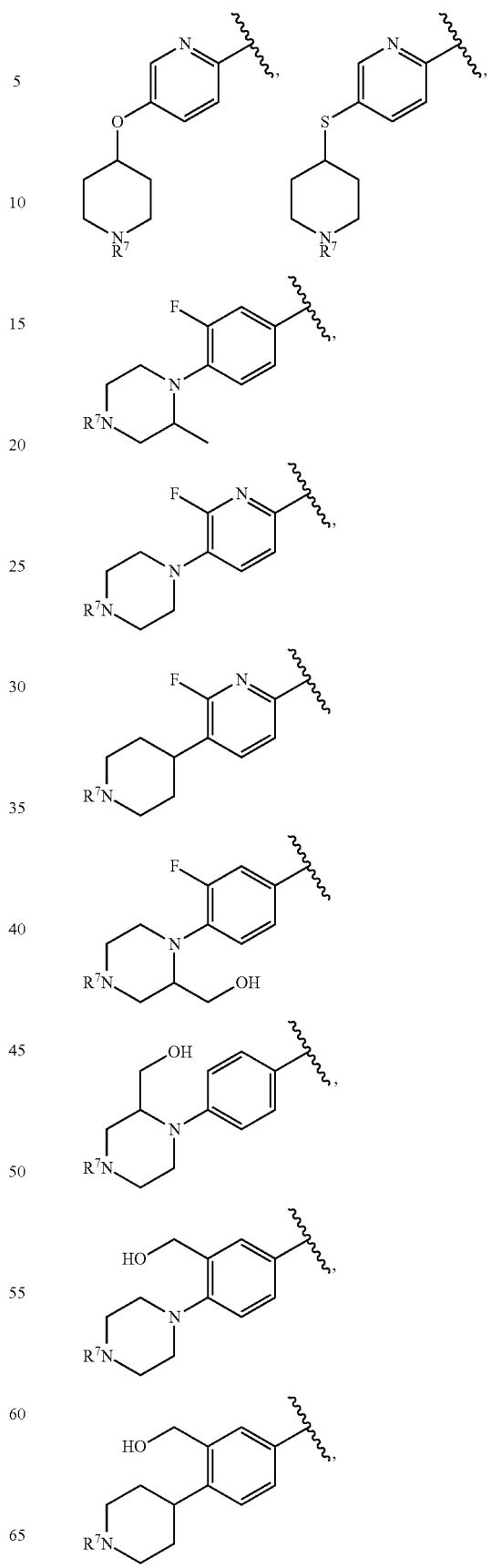

71
-continued
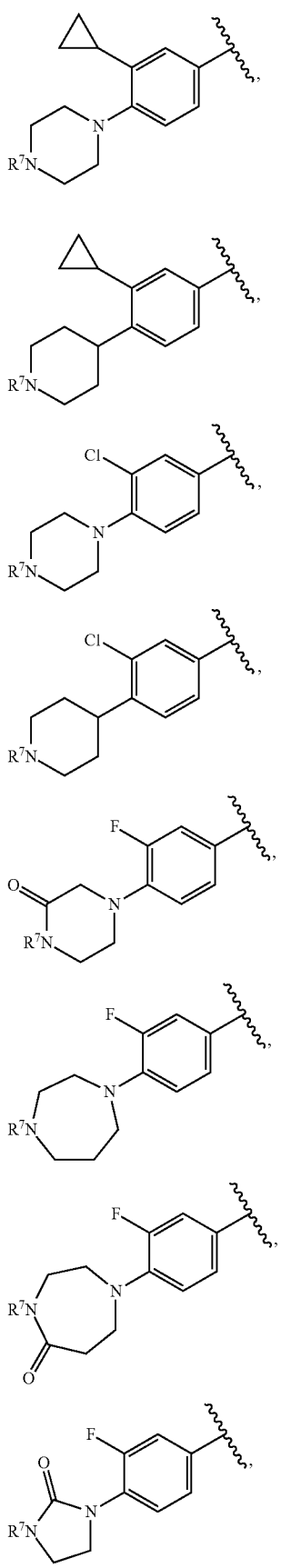
72
-continued
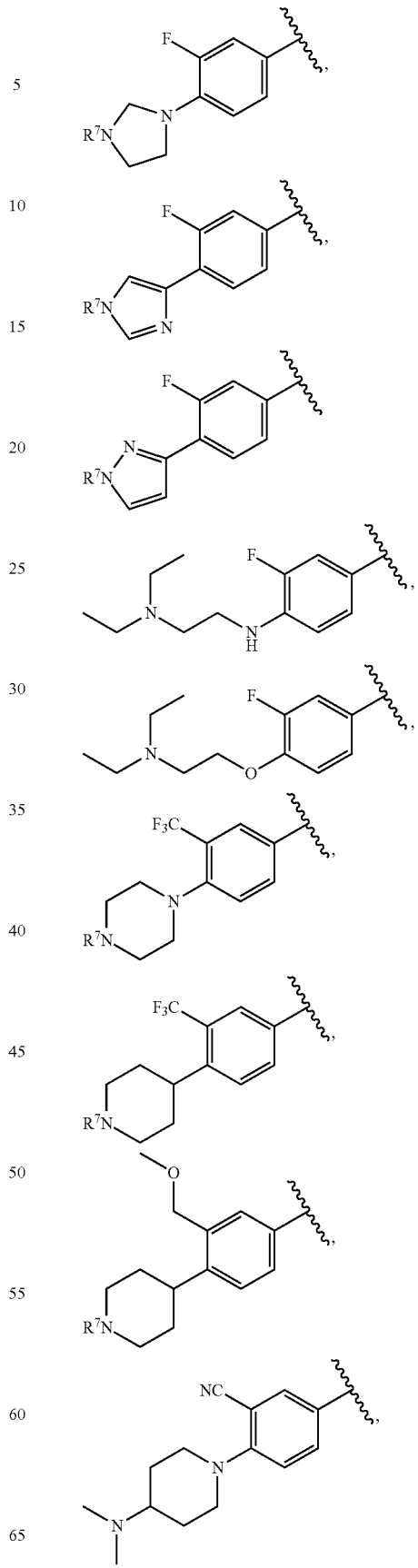

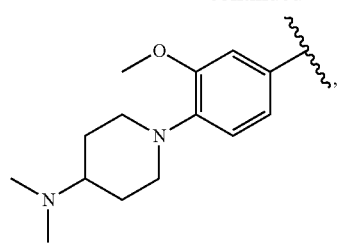
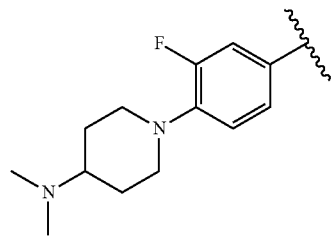
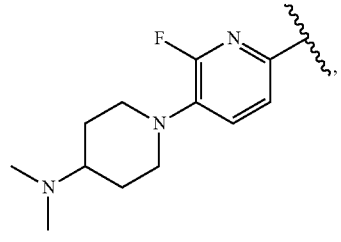
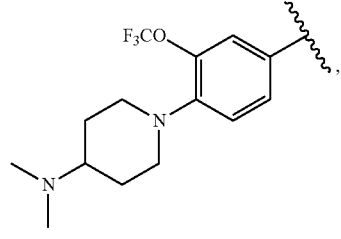
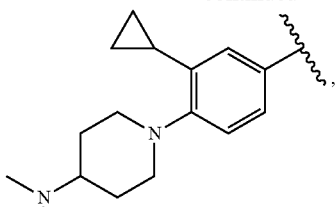
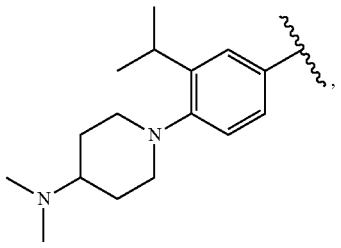
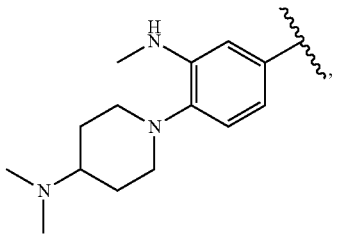
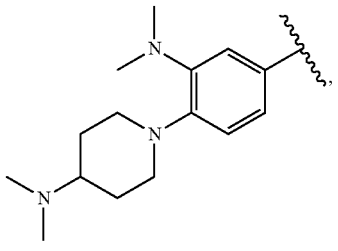
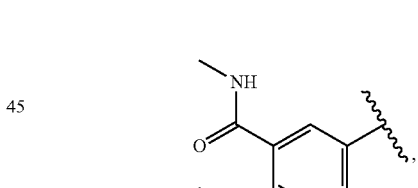
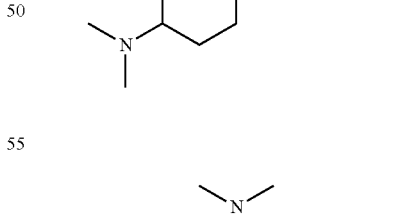
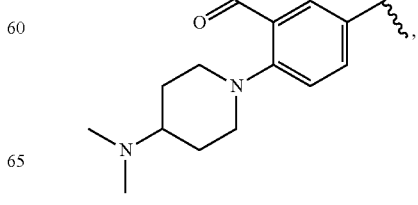

75
-continued
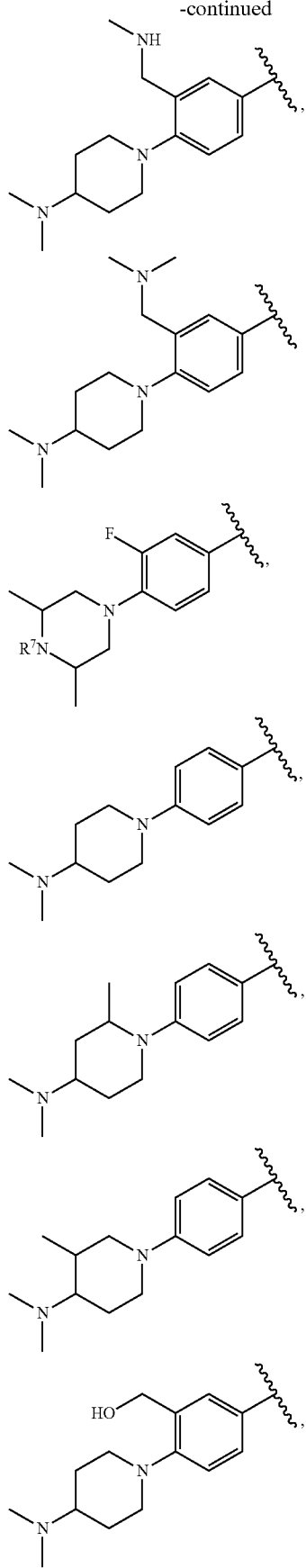
76
-continued
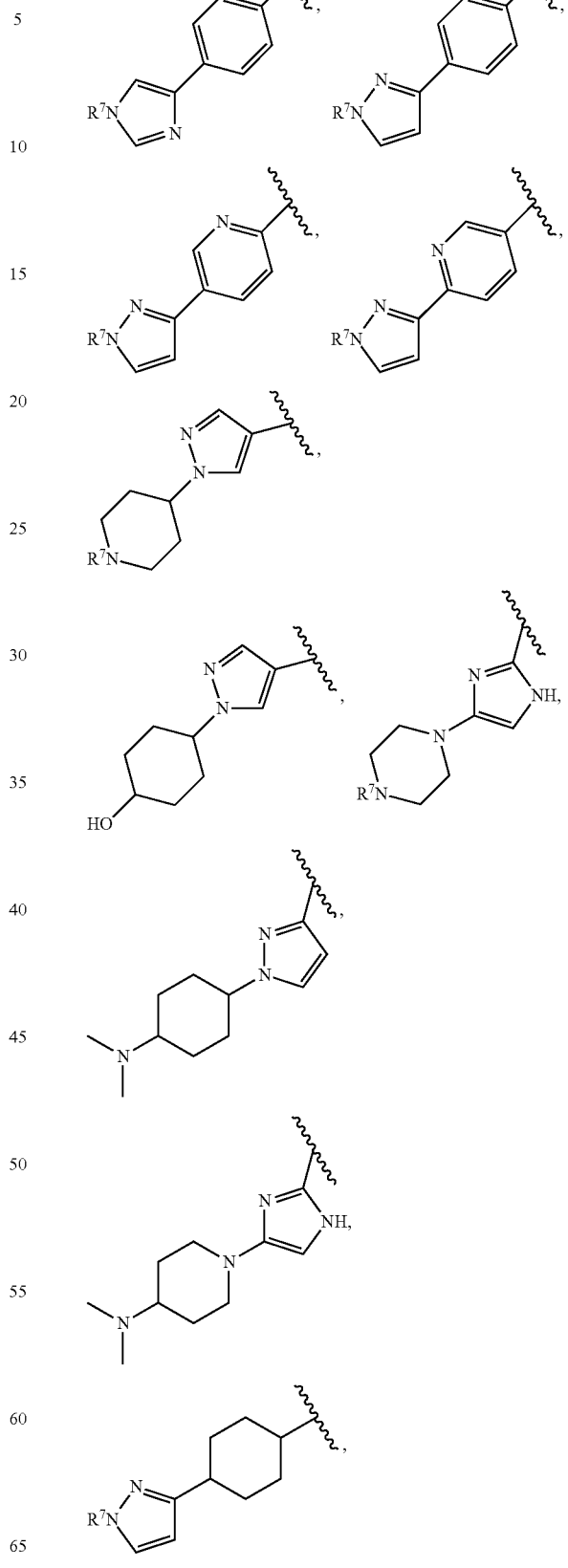

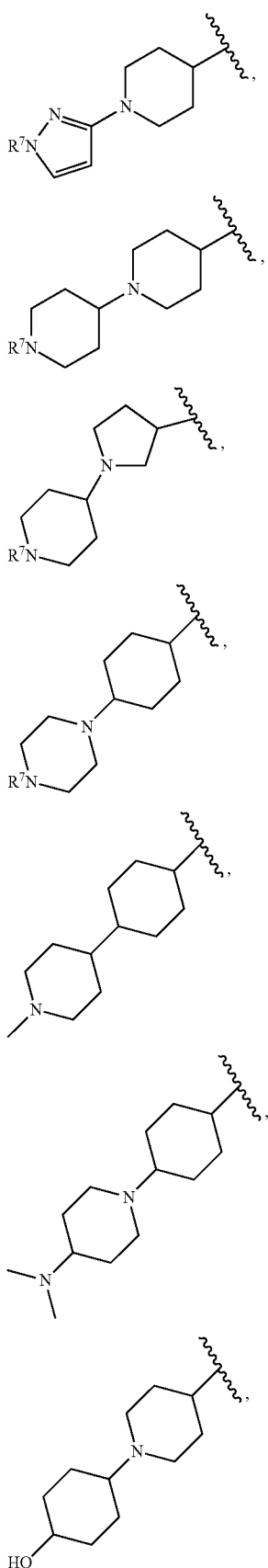
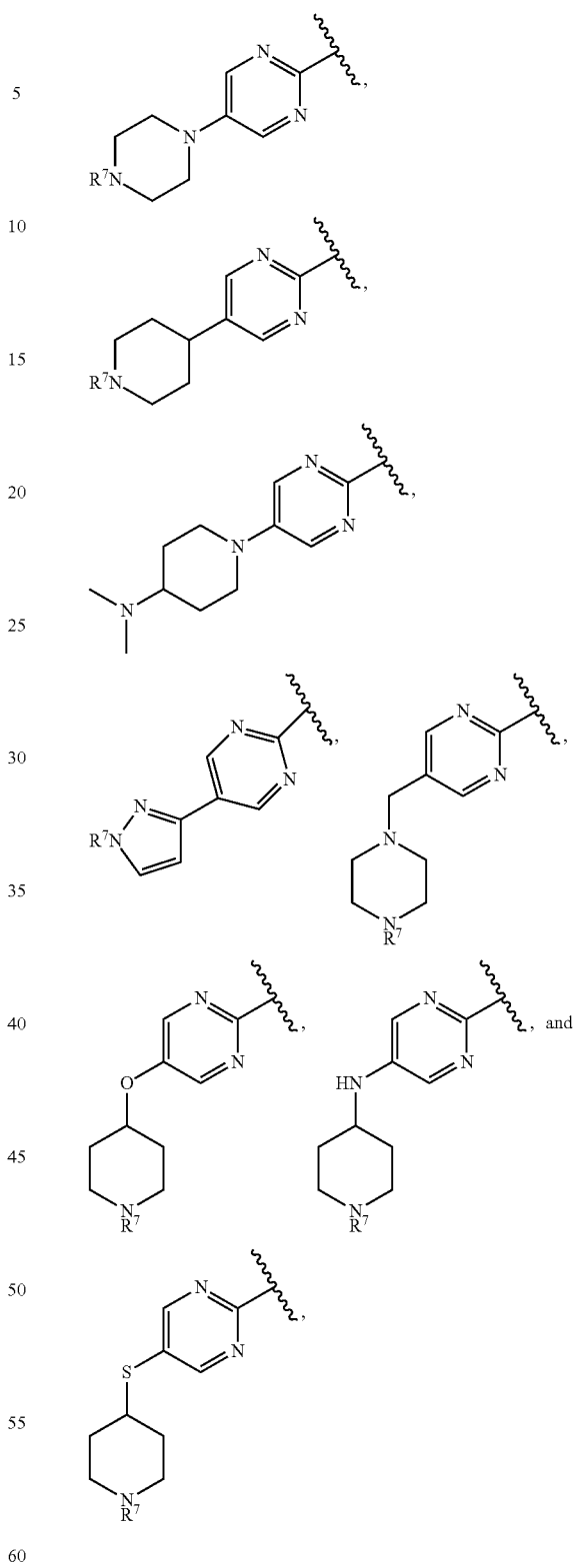
wherein the wavy lines denote attachment points to the parent molecule and $R^7$ is as described herein. It is understood that each description of A and B may be combined with each description of X, Y, $R^2$, $R^3$, $R^4$, $R^5$, $R^6$, l, m, n, p, and q the same as if each and every combination were specifically and individually listed.

In some embodiments of a compound of Formula (II), C-D are selected from the group consisting of:
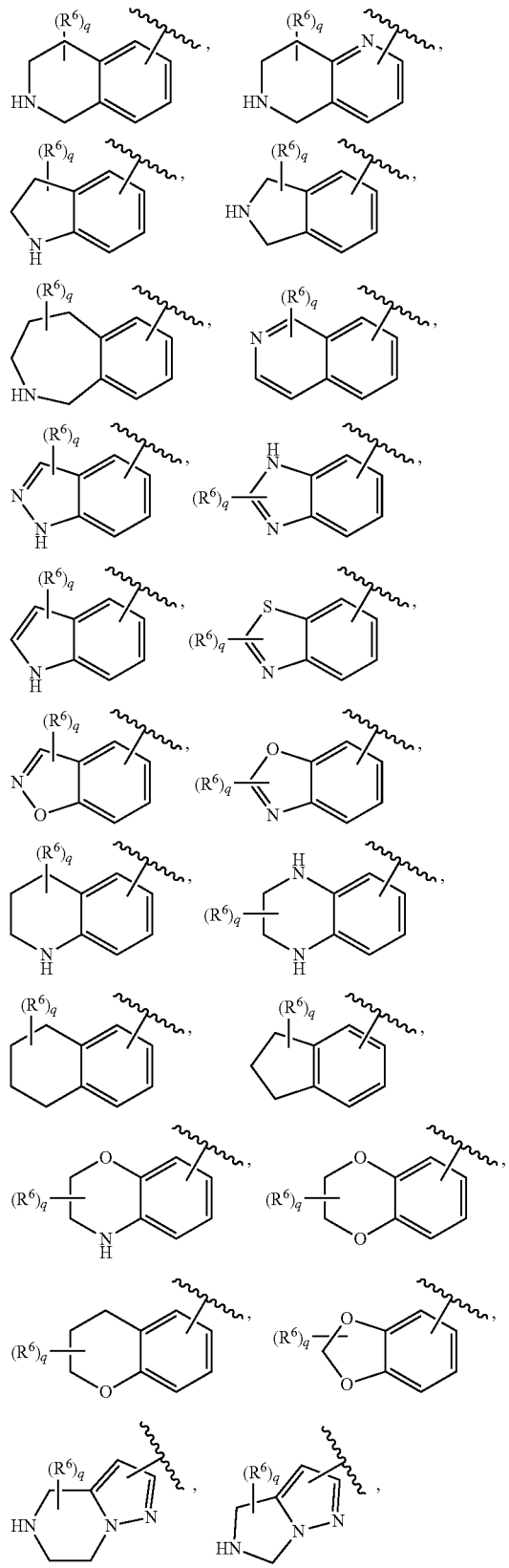
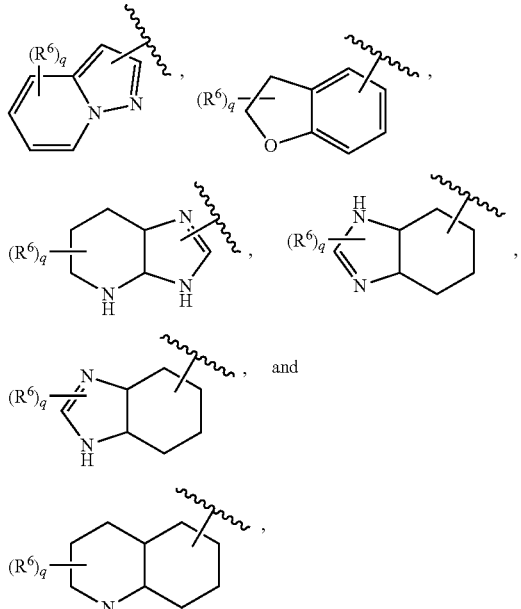
wherein the wavy lines denote attachment points to the parent molecule.
In some embodiments of a compound of Formula (II), C-D are selected from the group consisting of:
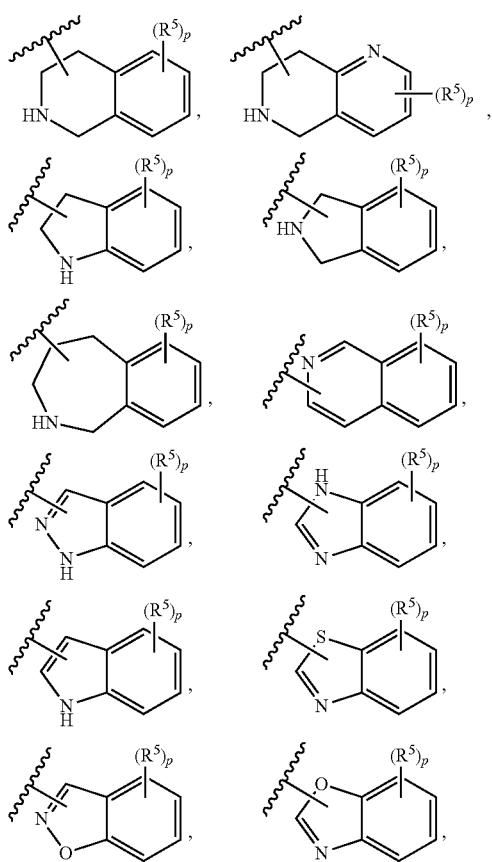

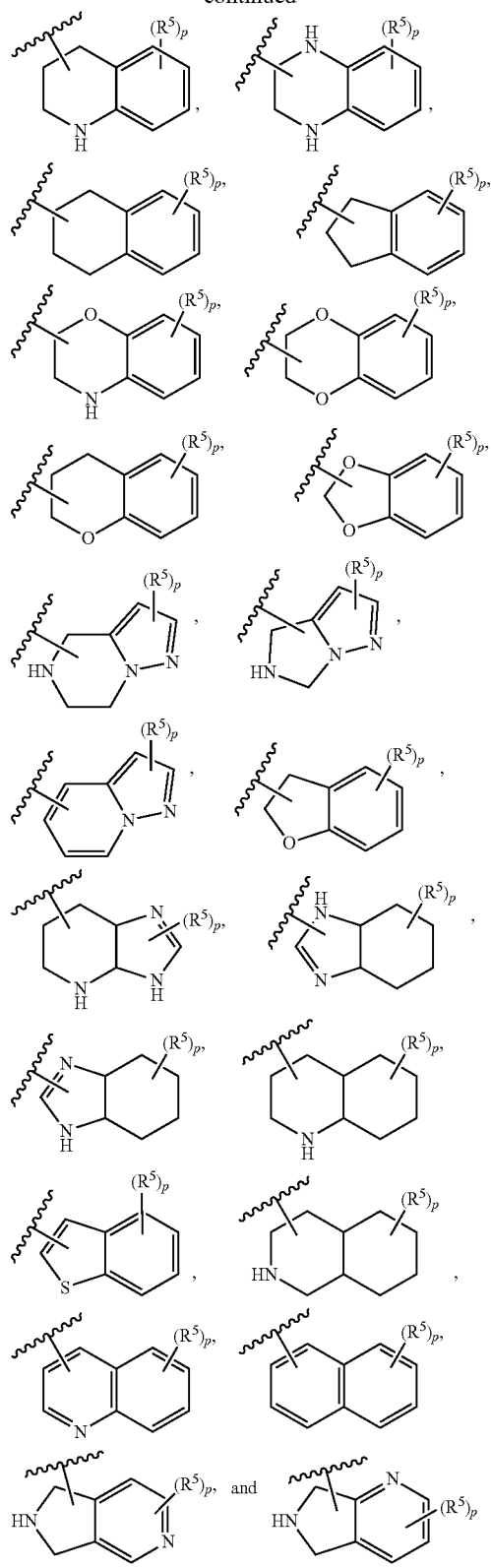
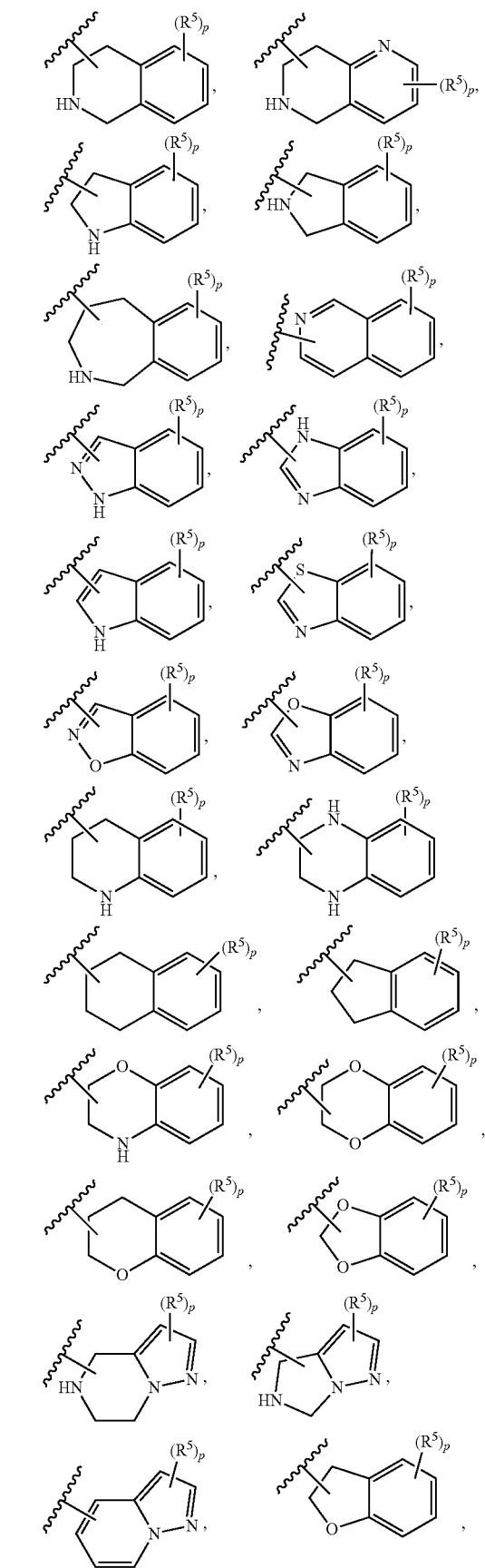
wherein the wavy lines denote attachment points to the parent molecule.
In some embodiments of a compound of Formula (II), C-D are selected from the group consisting of:

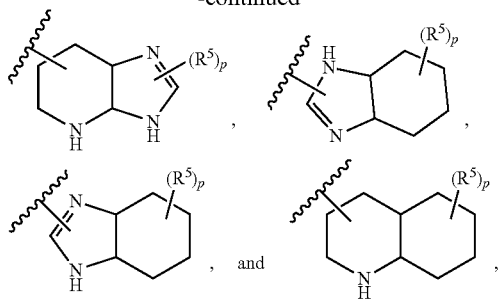
wherein the wavy lines denote attachment points to the parent molecule.
In some embodiments of a compound of Formula (II), C-D are selected from the group consisting of:
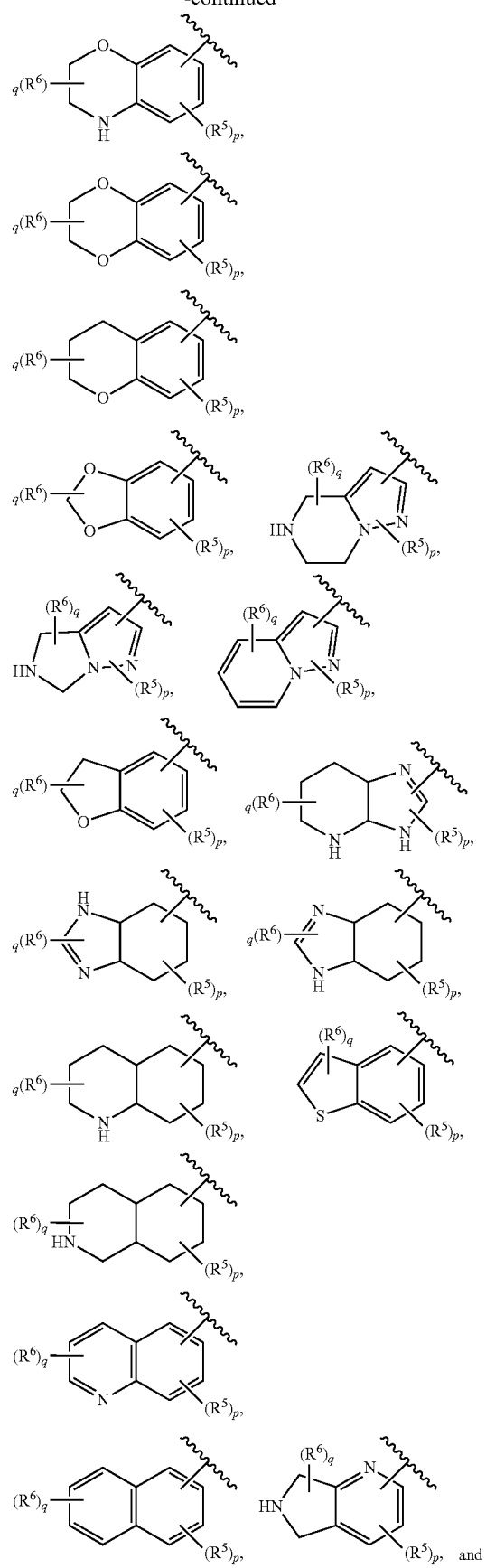

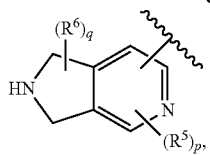
wherein the wavy lines denote attachment points to the parent molecule.
In some embodiments of a compound of Formula (II), C-D are selected from the group consisting of:
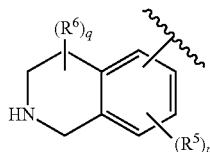 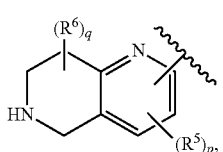
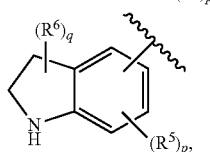 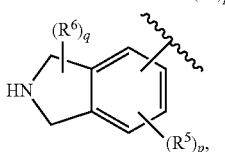
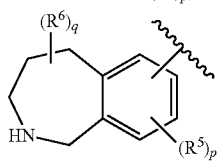 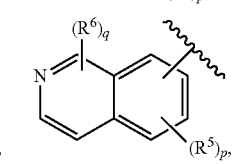
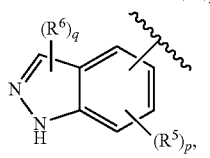 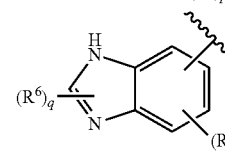
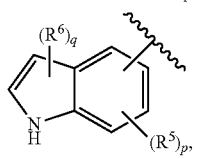 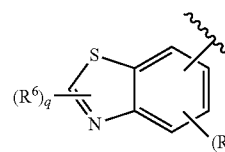
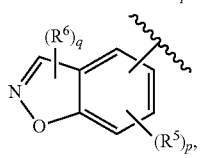 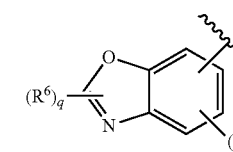
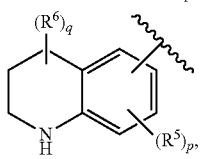 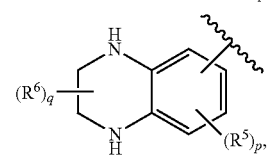
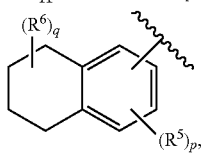 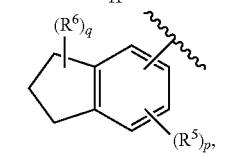
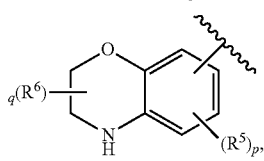
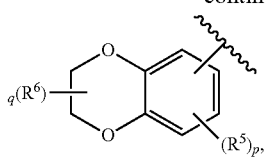
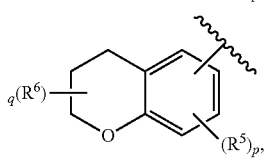
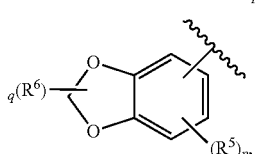 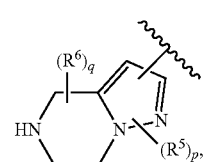
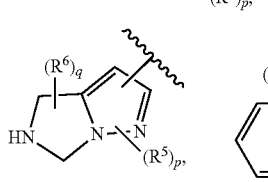
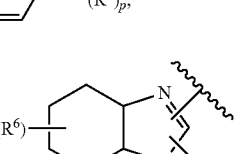
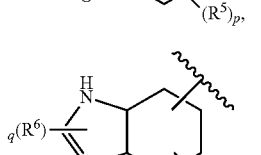 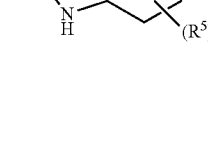
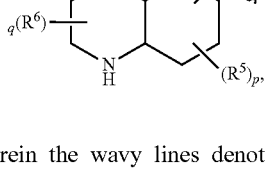
and
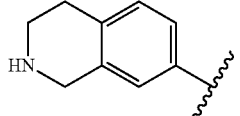
wherein the wavy lines denote attachment points to the parent molecule.
In some embodiments of a compound of Formula (II), C-D, $R^5$ and $R^6$ together are selected from the group consisting of:
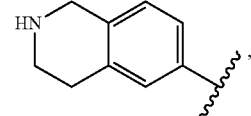
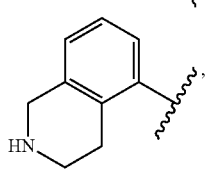 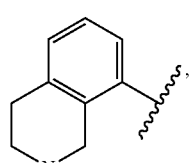

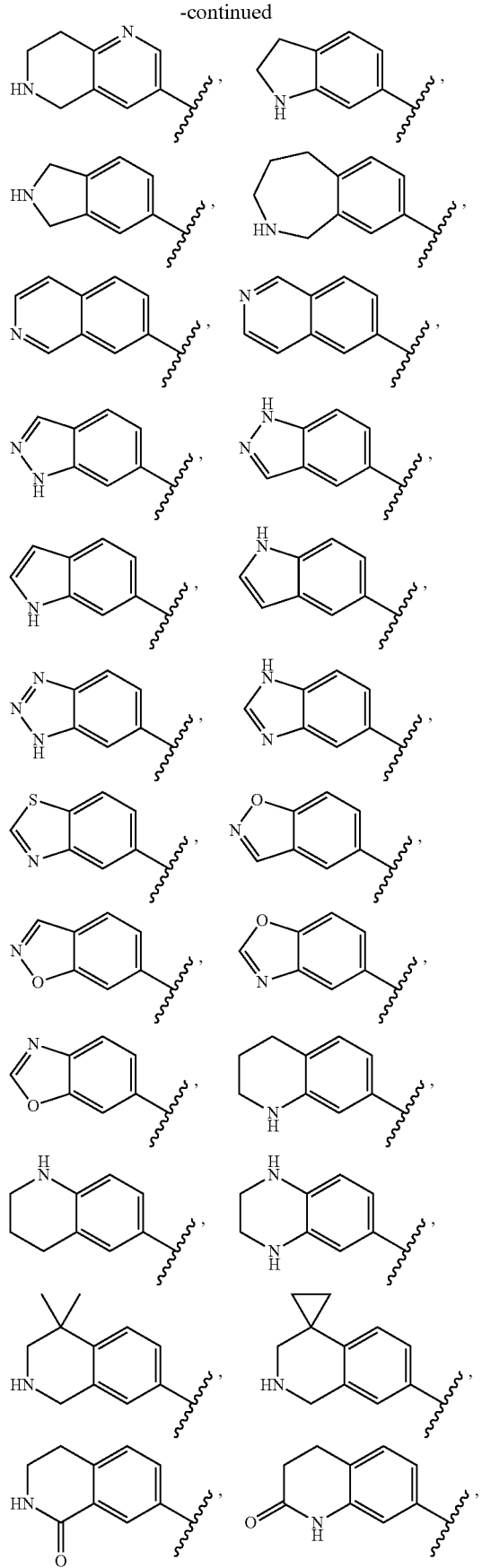
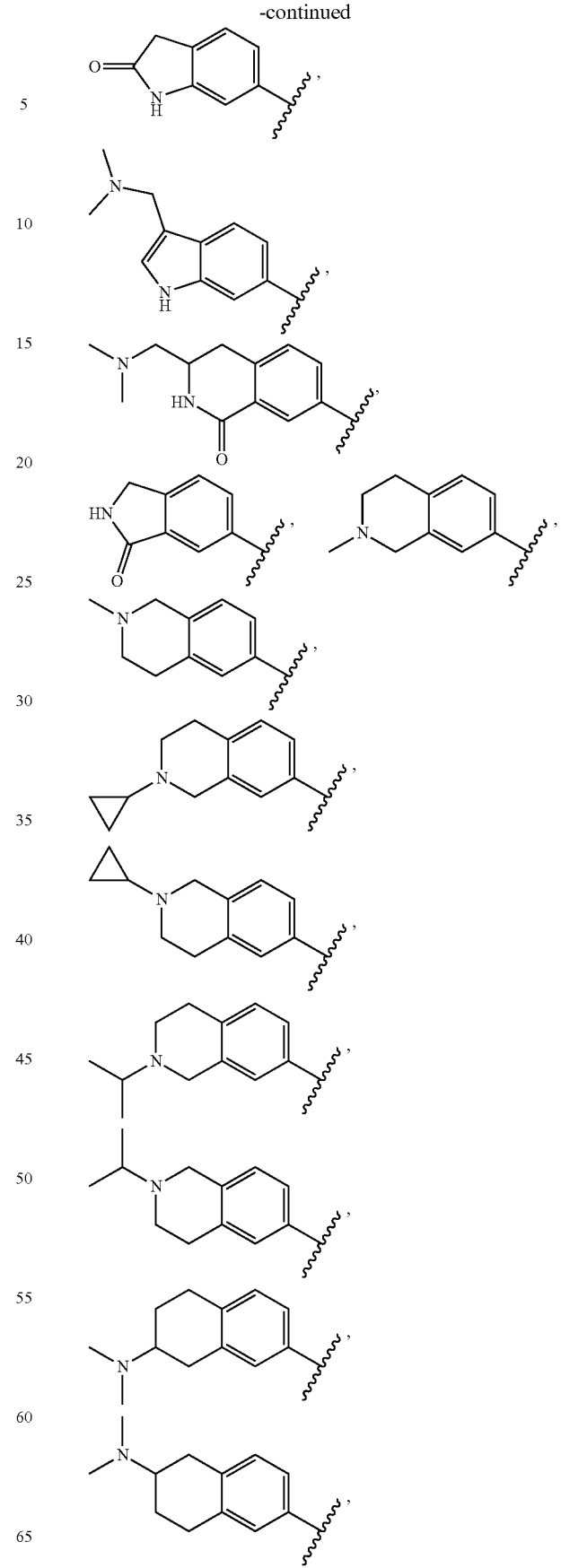

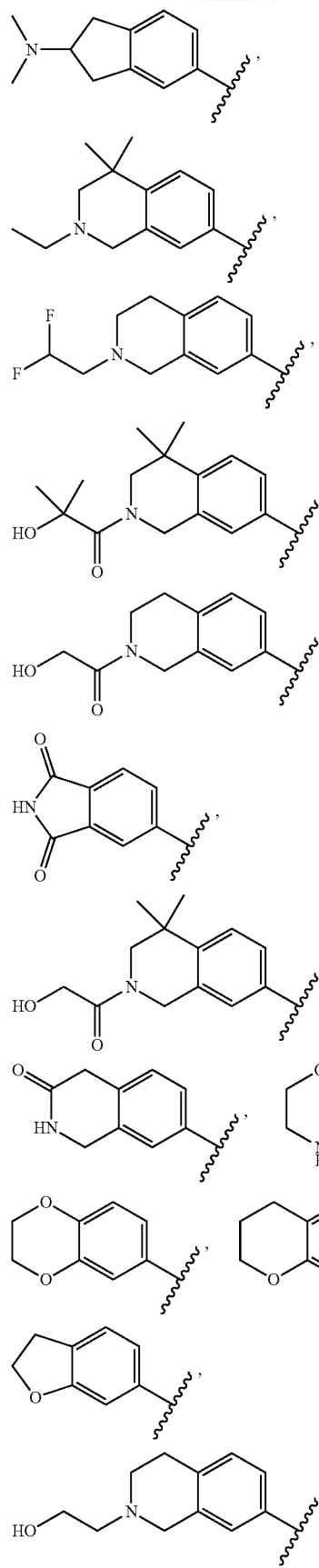
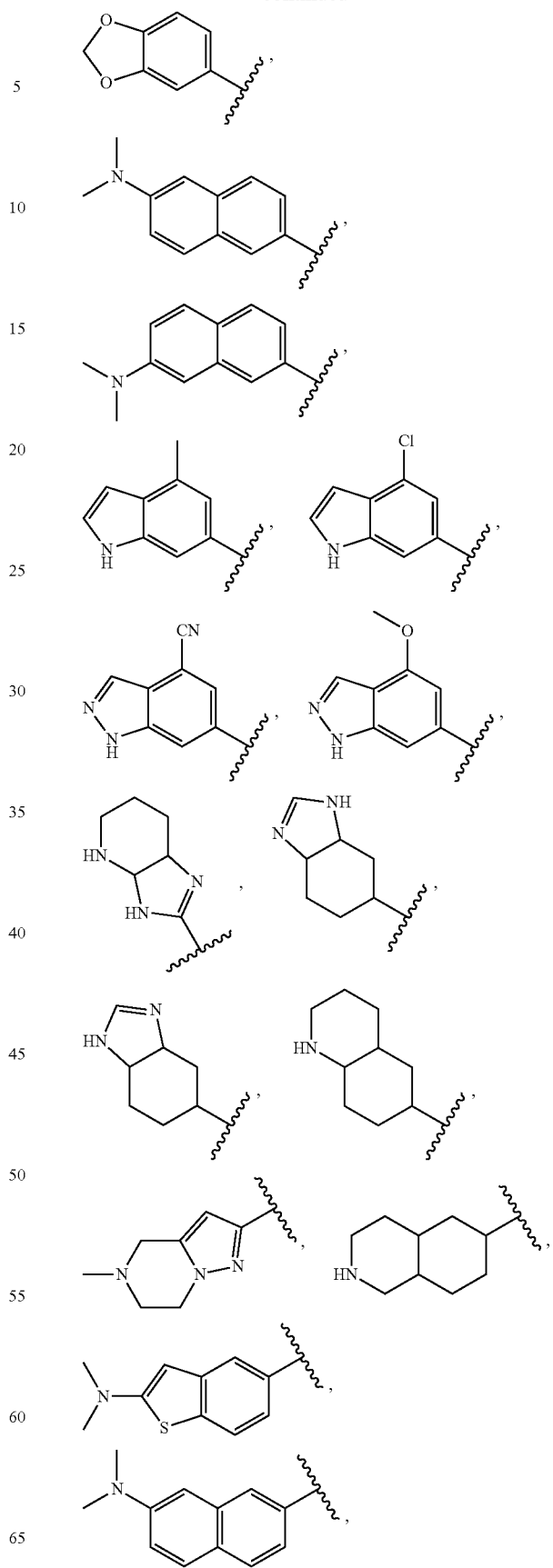

91
-continued
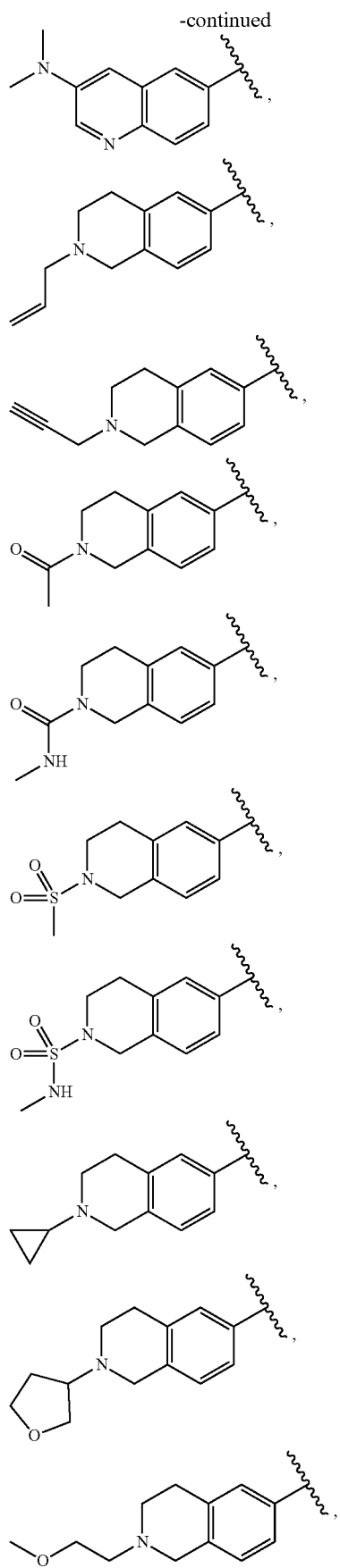
92
-continued
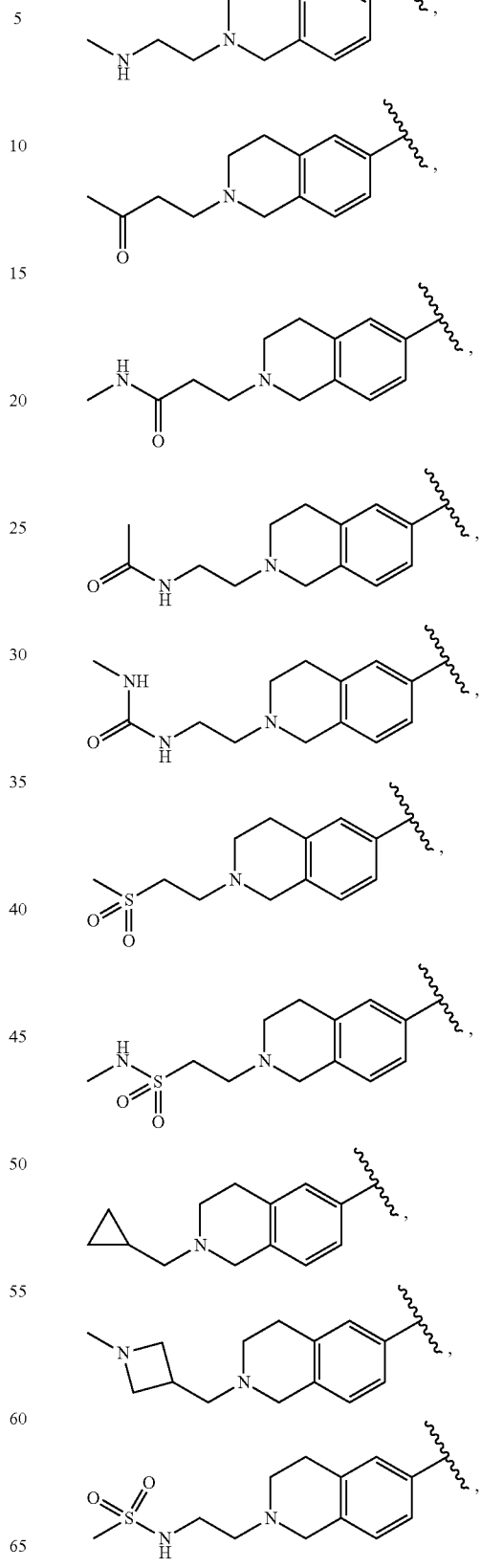

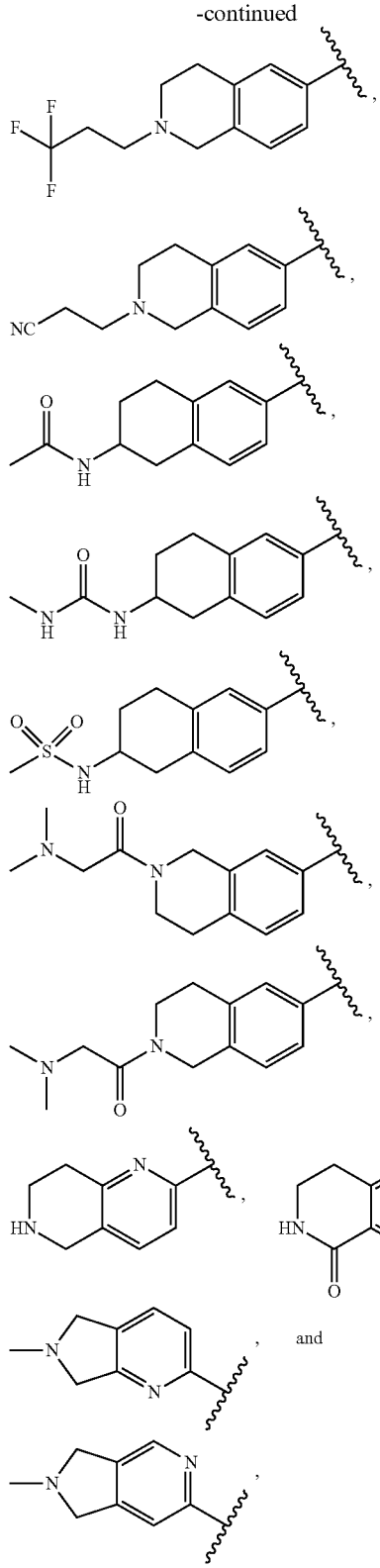
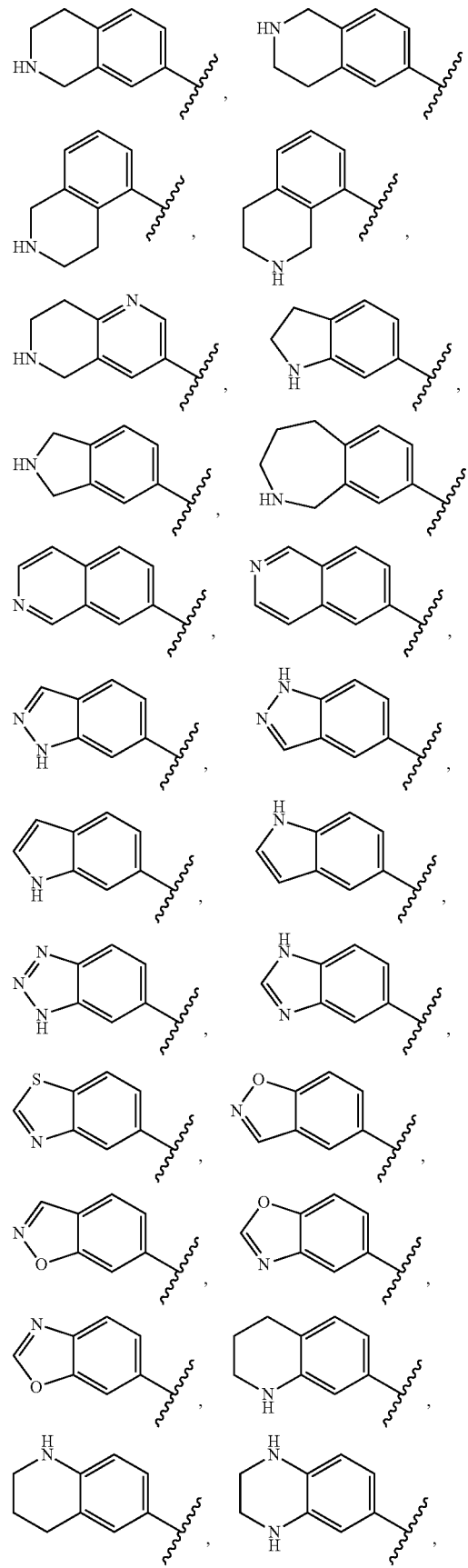
wherein the wavy lines denote attachment points to the parent molecule.
In some embodiments of a compound of Formula (II), C-D, $R^5$ and $R^6$ together are selected from the group consisting of:

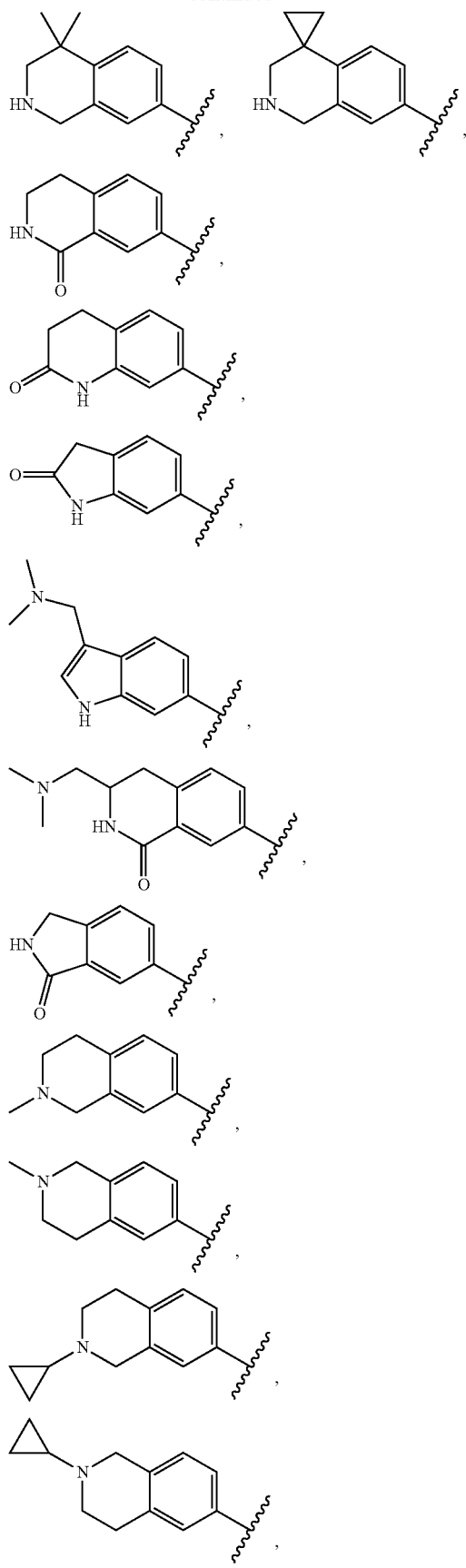
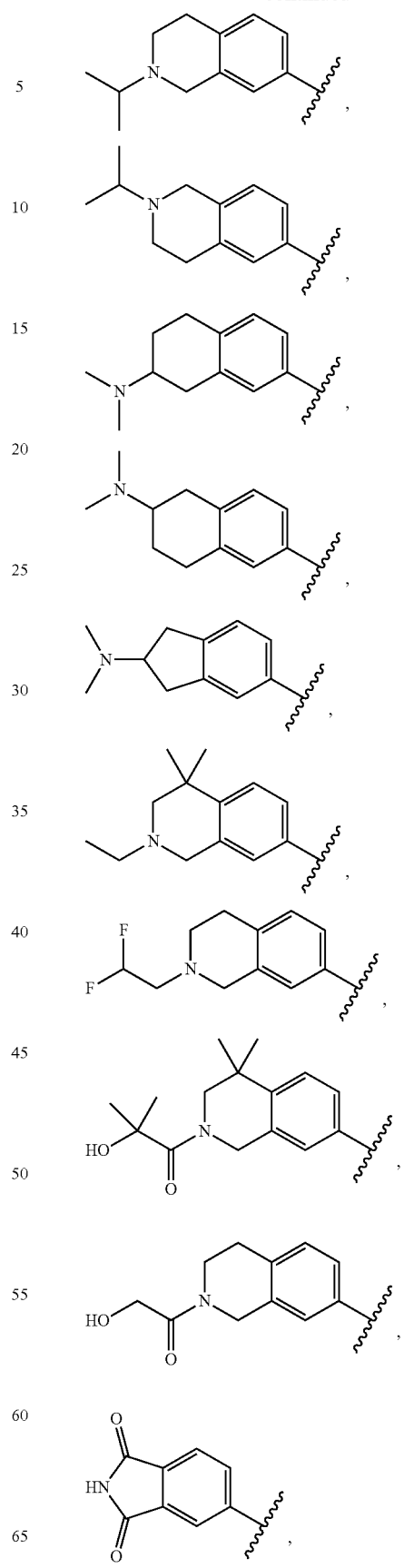

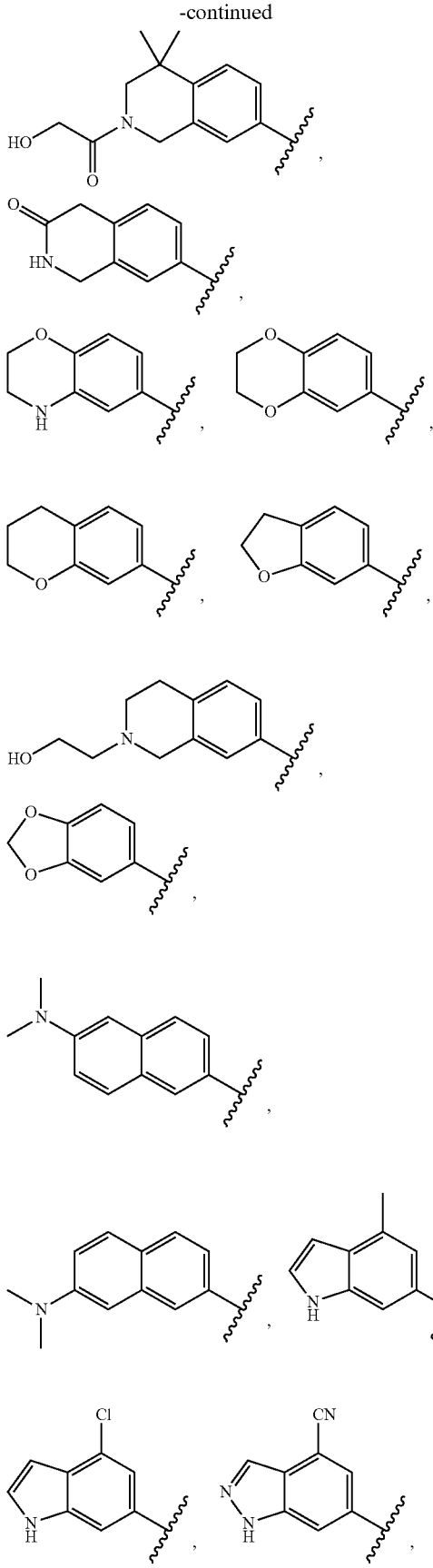

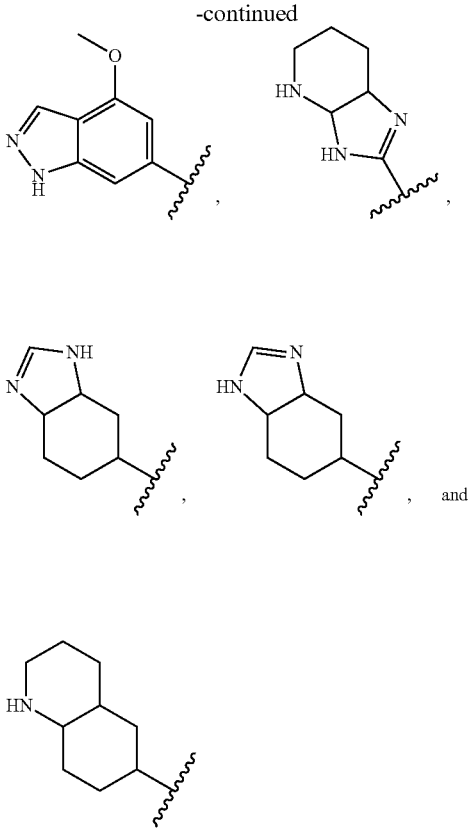

wherein the wavy lines denote attachment points to the parent molecule.

It is understood that each description of C-D may be combined with each description of X, Y, $R^2$, $R^3$, $R^4$, $R^5$, $R^6$, l, m, n, p, and q the same as if each and every combination were specifically and individually listed.

Also provided are salts of compounds referred to herein, such as pharmaceutically acceptable salts. The invention also includes any or all of the stereochemical forms, including any enantiomeric or diastereomeric forms, and any tautomers or other forms of the compounds described. It is understood that individual enantiomers and diastereomers are provided herein and their corresponding structures can be readily determined.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1.

TABLE 1

| Compound No. | Structure |
| --- | --- |
| 1 | 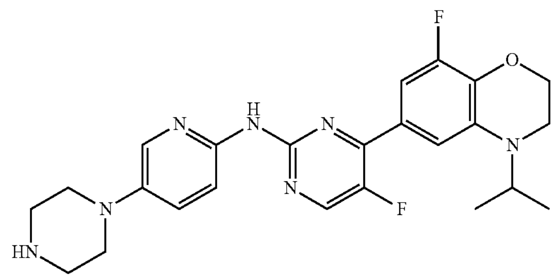 [SMILES: CC(C)N1CCOc2c(F)cc(-c3nc(Nc4ccc(N5CCNCC5)cn4)ncc3F)cc21] |
| 2 | 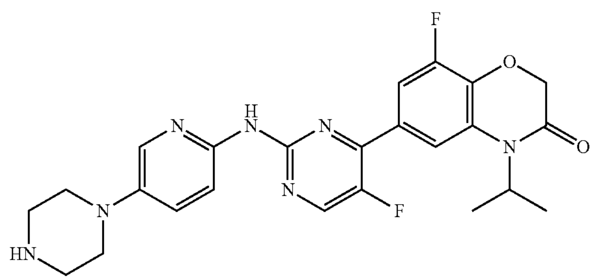 [SMILES: CC(C)N1C(=O)COc2c(F)cc(-c3nc(Nc4ccc(N5CCNCC5)cn4)ncc3F)cc21] |
| 3 | 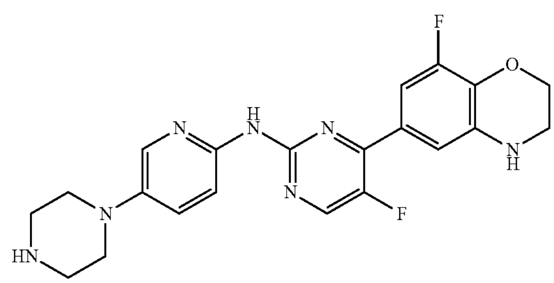 [SMILES: Fc1cnc(Nc2ccc(N3CCNCC3)cn2)nc1-c1cc(F)c2c(c1)NCCO2] |
| 4 | 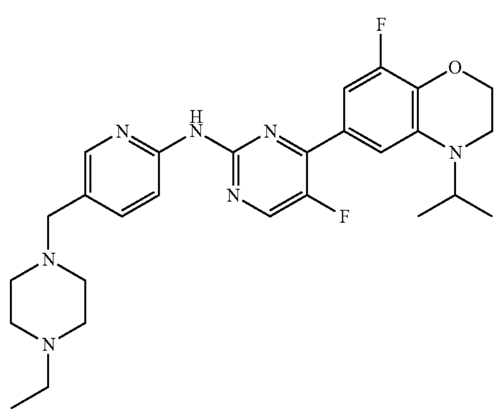 [SMILES: CCN1CCN(Cc2ccc(Nc3ncc(F)c(-c4cc(F)c5c(c4)N(C(C)C)CCO5)n3)nc2)CC1] |
| 5 | 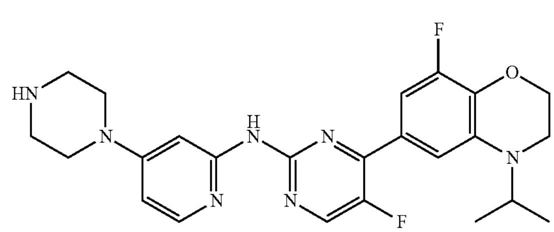 [SMILES: CC(C)N1CCOc2c(F)cc(-c3nc(Nc4cc(N5CCNCC5)ccn4)ncc3F)cc21] |

TABLE 1-continued
| Compound No. | Structure |
|---|---|
| 6 | 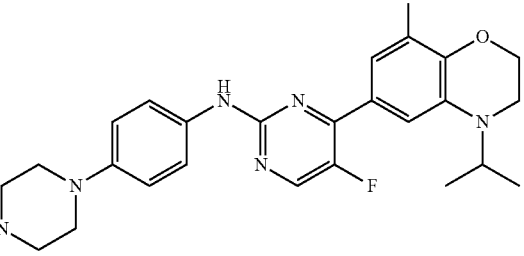 |
| 7 | 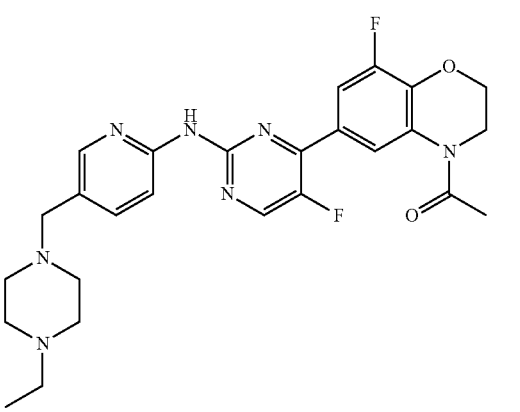 [SMILES: CCN1CCN(Cc2ccc(Nc3ncc(F)c(-c4cc(F)c5c(c4)N(C(C)=O)CCO5)n3)nc2)CC1] |
| 8 | 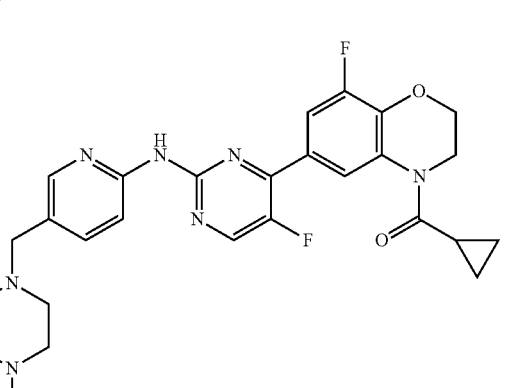 |
| 9 | 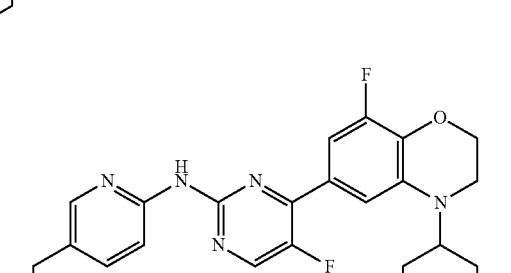 |

TABLE 1-continued
| Compound No. | Structure |
|---|---|
| 10 | 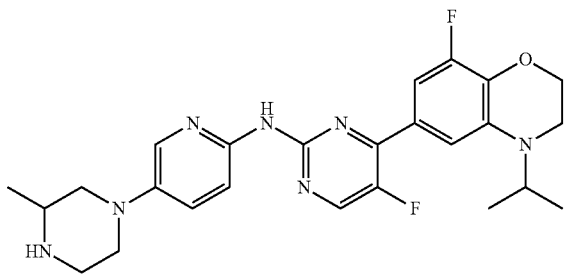 [SMILES: CC1CN(c2ccc(Nc3ncc(F)c(-c4cc(F)c5c(c4)N(C(C)C)CCO5)n3)nc2)CCN1] |
| 11 | 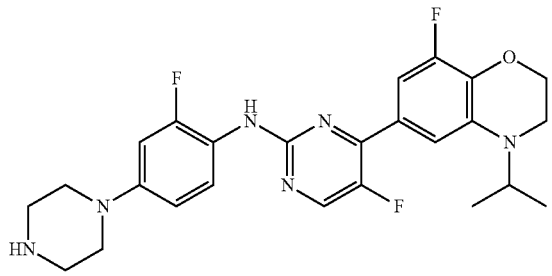 [SMILES: CC(C)N1CCOc2c(F)cc(-c3nc(Nc4ccc(N5CCNCC5)cc4F)ncc3F)cc21] |
| 12 | 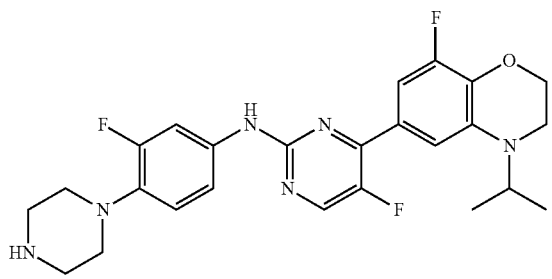 [SMILES: CC(C)N1CCOc2c(F)cc(-c3nc(Nc4ccc(N5CCNCC5)c(F)c4)ncc3F)cc21] |
| 13 | 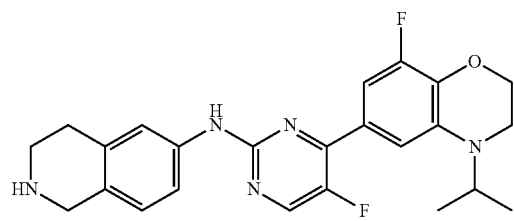 [SMILES: CC(C)N1CCOc2c(F)cc(-c3nc(Nc4ccc5c(c4)CCNC5)ncc3F)cc21] |
| 14 | 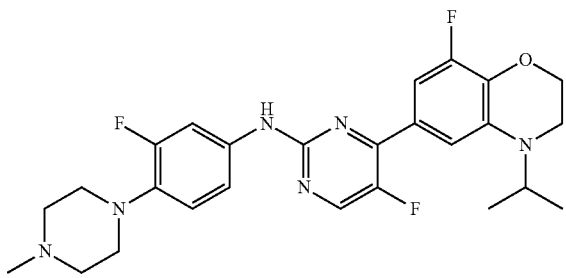 [SMILES: CC(C)N1CCOc2c(F)cc(-c3nc(Nc4ccc(N5CCN(C)CC5)c(F)c4)ncc3F)cc21] |
| 15 | 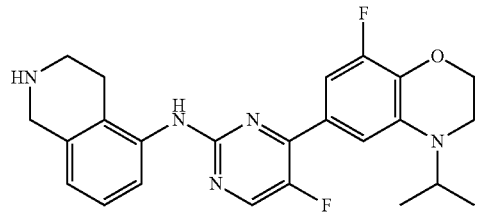 [SMILES: CC(C)N1CCOc2c(F)cc(-c3nc(Nc4cccc5c4CCNC5)ncc3F)cc21] |

TABLE 1-continued
| Compound No. | Structure |
|---|---|
| 16 | 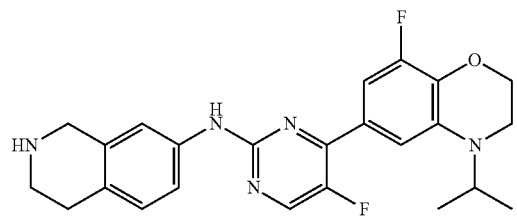 [SMILES: CC(C)N1CCOc2c(F)cc(-c3nc(Nc4ccc5c(c4)CNCC5)ncc3F)cc21] |
| 17 | 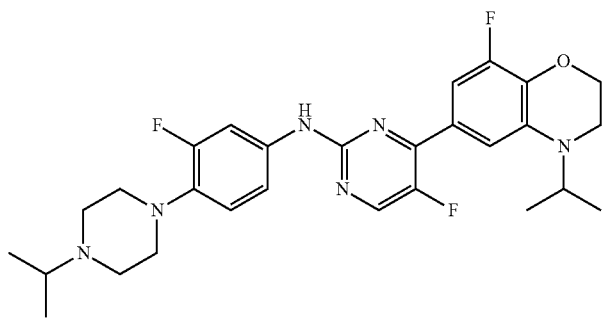 [SMILES: CC(C)N1CCN(c2ccc(Nc3ncc(F)c(-c4cc(F)c5c(c4)N(C(C)C)CCO5)n3)cc2F)CC1] |
| 18 | 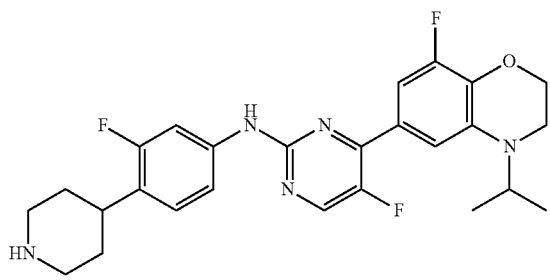 [SMILES: CC(C)N1CCOc2c(F)cc(-c3nc(Nc4ccc(C5CCNCC5)c(F)c4)ncc3F)cc21] |
| 19 | 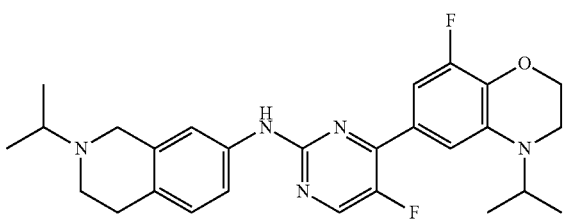 [SMILES: CC(C)N1CCc2ccc(Nc3ncc(F)c(-c4cc(F)c5c(c4)N(C(C)C)CCO5)n3)cc2C1] |
| 20 | 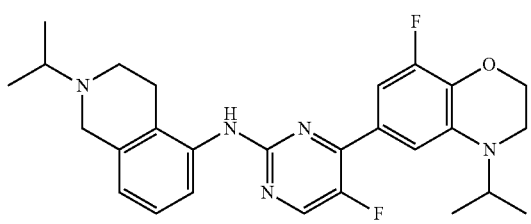 [SMILES: CC(C)N1CCc2c(cccc2Nc2ncc(F)c(-c3cc(F)c4c(c3)N(C(C)C)CCO4)n2)C1] |
| 21 | 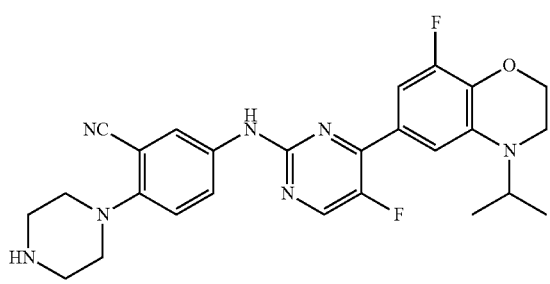 [SMILES: CC(C)N1CCOc2c(F)cc(-c3nc(Nc4ccc(N5CCNCC5)c(C#N)c4)ncc3F)cc21] |

TABLE 1-continued

| Compound No. | Structure |
|---|---|
| 22 | 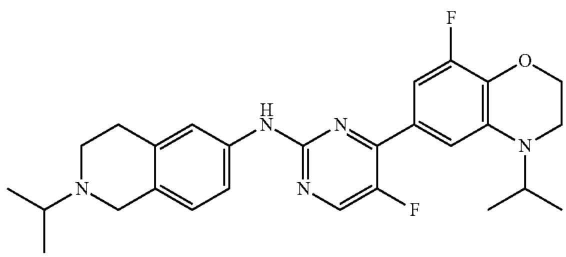 [SMILES: CC(C)N1CCc2cc(Nc3ncc(F)c(-c4cc(F)c5c(c4)N(C(C)C)CCO5)n3)ccc2C1] |
| 23 | 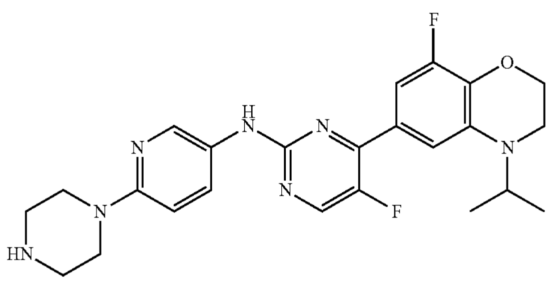 [SMILES: CC(C)N1CCOc2c(F)cc(-c3nc(Nc4ccc(N5CCNCC5)nc4)ncc3F)cc21] |
| 24 | 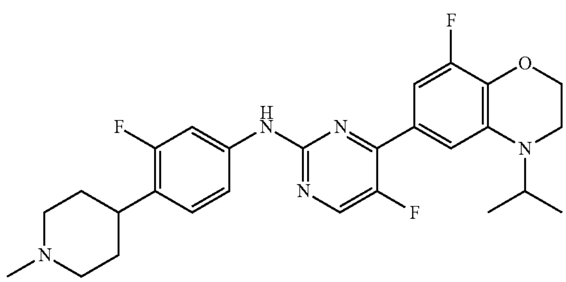 [SMILES: CC(C)N1CCOc2c(F)cc(-c3nc(Nc4ccc(C5CCN(C)CC5)c(F)c4)ncc3F)cc21] |
| 25 | 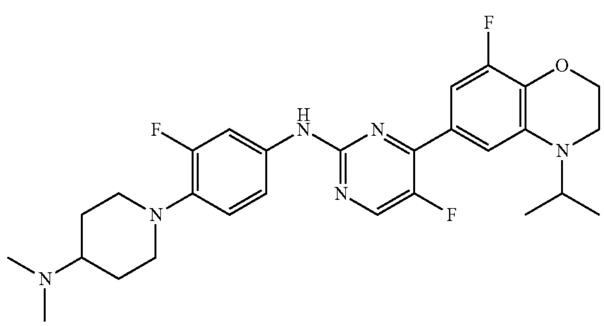 [SMILES: CC(C)N1CCOc2c(F)cc(-c3nc(Nc4ccc(N5CCC(N(C)C)CC5)c(F)c4)ncc3F)cc21] |
| 26 | 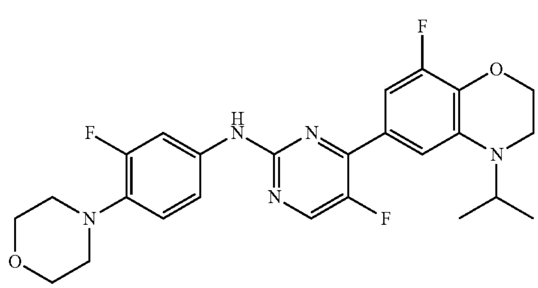 [SMILES: CC(C)N1CCOc2c(F)cc(-c3nc(Nc4ccc(N5CCOCC5)c(F)c4)ncc3F)cc21] |

TABLE 1-continued
| Compound No. | Structure |
|---|---|
| 27 | 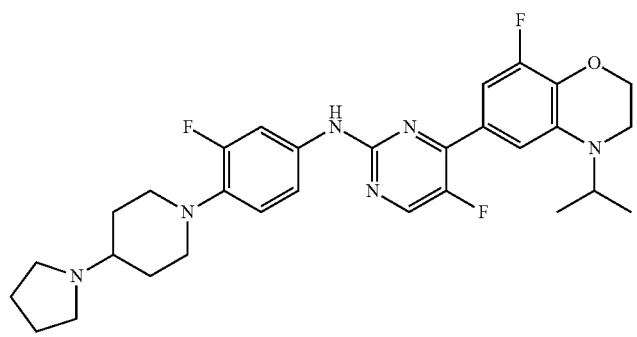 [SMILES: CC(C)N1CCOc2c(F)cc(-c3nc(Nc4ccc(N5CCC(N6CCCC6)CC5)c(F)c4)ncc3F)cc21] |
| 28 | 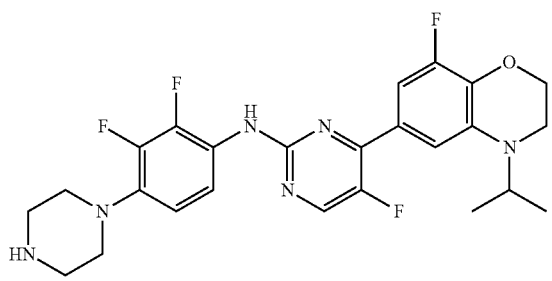 [SMILES: CC(C)N1CCOc2c(F)cc(-c3nc(Nc4ccc(N5CCNCC5)c(F)c4F)ncc3F)cc21] |
| 29 | 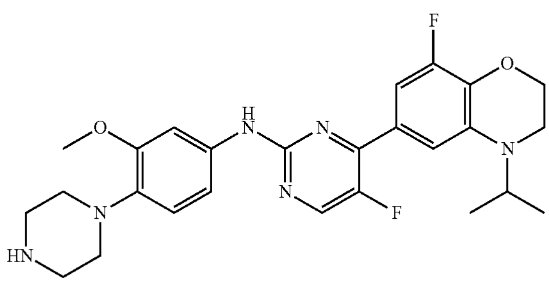 [SMILES: COc1cc(Nc2ncc(F)c(-c3cc(F)c4c(c3)N(C(C)C)CCO4)n2)ccc1N1CCNCC1] |
| 30 | 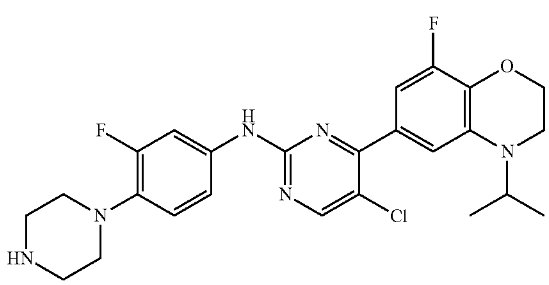 [SMILES: CC(C)N1CCOc2c(F)cc(-c3nc(Nc4ccc(N5CCNCC5)c(F)c4)ncc3Cl)cc21] |
| 31 | 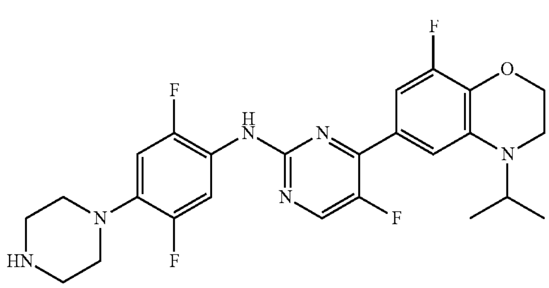 [SMILES: CC(C)N1CCOc2c(F)cc(-c3nc(Nc4cc(F)c(N5CCNCC5)cc4F)ncc3F)cc21] |

TABLE 1-continued
| Compound No. | Structure |
|---|---|
| 32 | 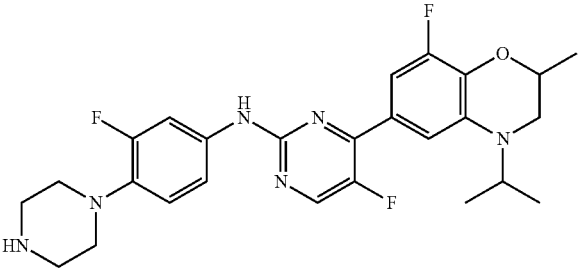 [SMILES: CC1CN(C(C)C)c2cc(-c3nc(Nc4ccc(N5CCNCC5)c(F)c4)ncc3F)cc(F)c2O1] |
| 33 | 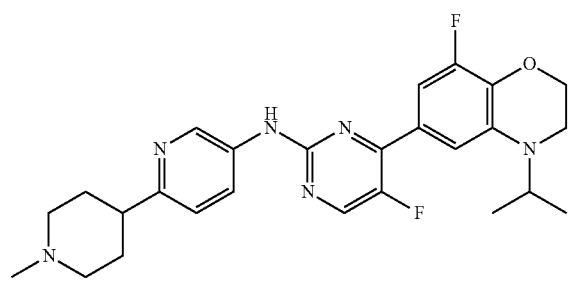 [SMILES: CC(C)N1CCOc2c(F)cc(-c3nc(Nc4ccc(C5CCN(C)CC5)nc4)ncc3F)cc21] |
| 34 | 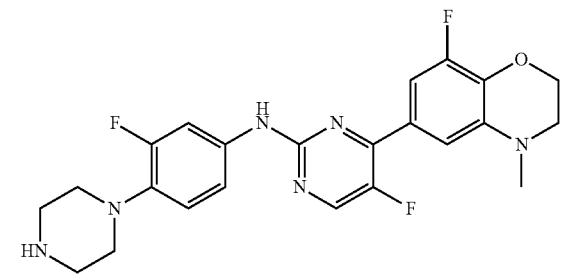 [SMILES: CN1CCOc2c(F)cc(-c3nc(Nc4ccc(N5CCNCC5)c(F)c4)ncc3F)cc21] |
| 35 | 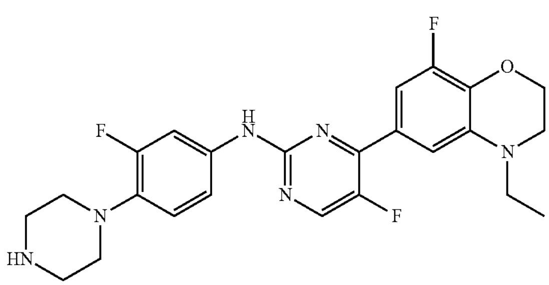 [SMILES: CCN1CCOc2c(F)cc(-c3nc(Nc4ccc(N5CCNCC5)c(F)c4)ncc3F)cc21] |
| 36 | 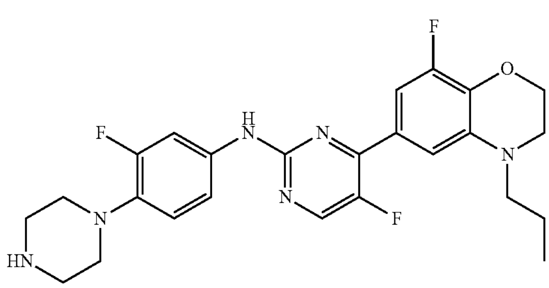 [SMILES: CCCN1CCOc2c(F)cc(-c3nc(Nc4ccc(N5CCNCC5)c(F)c4)ncc3F)cc21] |

TABLE 1-continued
| Compound No. | Structure |
|---|---|
| 37 | 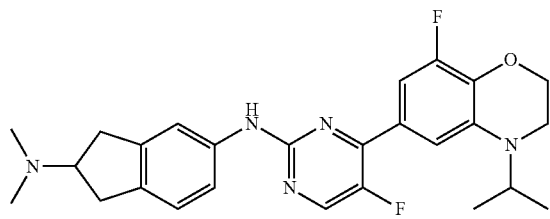 [SMILES: CC(C)N1CCOc2c(F)cc(-c3nc(Nc4ccc5c(c4)CC(N(C)C)C5)ncc3F)cc21] |
| 38 | 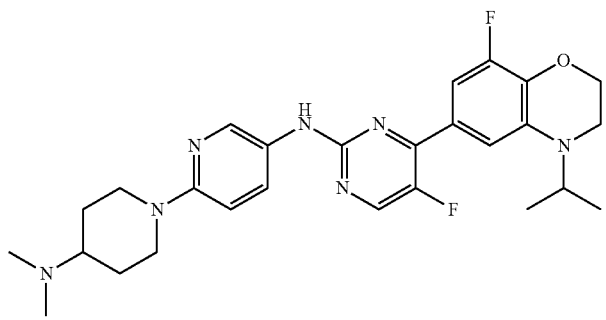 [SMILES: CC(C)N1CCOc2c(F)cc(-c3nc(Nc4ccc(N5CCC(N(C)C)CC5)nc4)ncc3F)cc21] |
| 39 | 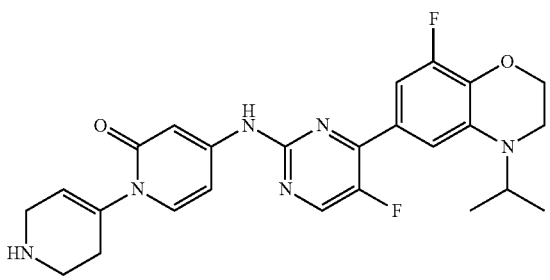 [SMILES: CC(C)N1CCOc2c(F)cc(-c3nc(Nc4ccn(C5=CCNCC5)c(=O)c4)ncc3F)cc21] |
| 40 | 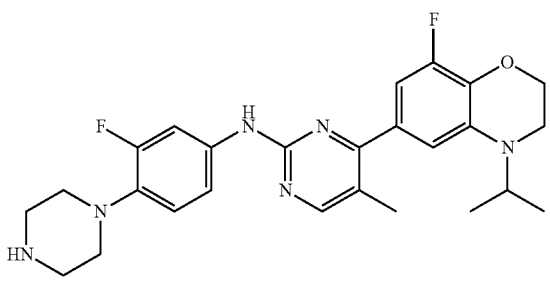 [SMILES: Cc1cnc(Nc2ccc(N3CCNCC3)c(F)c2)nc1-c1cc(F)c2c(c1)N(C(C)C)CCO2] |
| 41 | 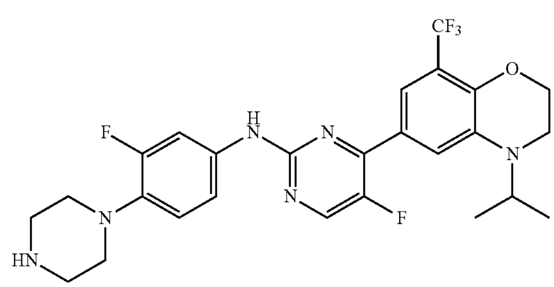 [SMILES: CC(C)N1CCOc2c1cc(-c1nc(Nc3ccc(N4CCNCC4)c(F)c3)ncc1F)cc2C(F)(F)F] |

TABLE 1-continued

| Compound No. | Structure |
|---|---|
| 42 | (structure) |
| 43 | (structure) |
| 44 | (structure) |
| 45 | (structure) |
| 46 | (structure) |

TABLE 1-continued
| Compound No. | Structure |
|---|---|
| 47 | 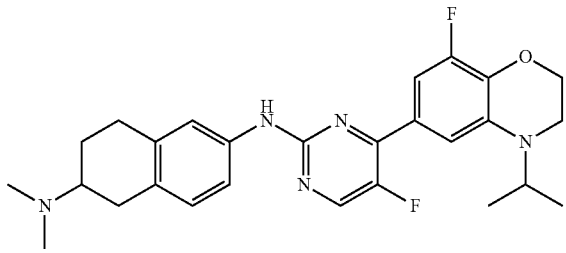 [SMILES: CC(C)N1CCOc2c(F)cc(-c3nc(Nc4ccc5c(c4)CCC(N(C)C)C5)ncc3F)cc21] |
| 48 | 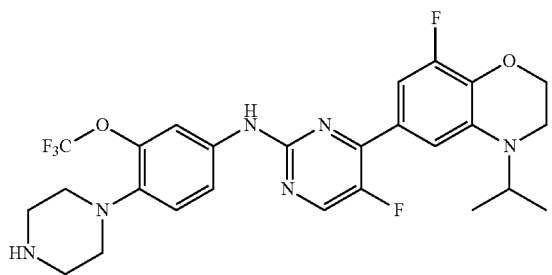 [SMILES: CC(C)N1CCOc2c(F)cc(-c3nc(Nc4ccc(N5CCNCC5)c(OC(F)(F)F)c4)ncc3F)cc21] |
| 49 | 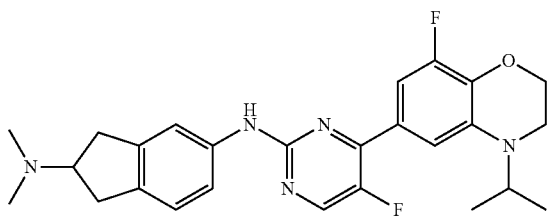 [SMILES: CC(C)N1CCOc2c(F)cc(-c3nc(Nc4ccc5c(c4)CC(N(C)C)C5)ncc3F)cc21] |
| 50 | 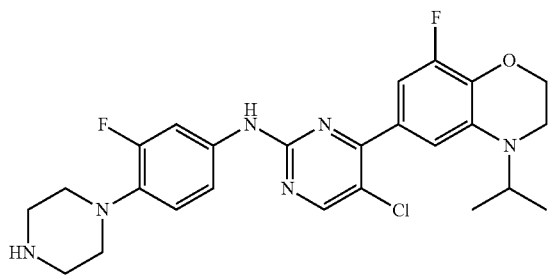 [SMILES: CC(C)N1CCOc2c(F)cc(-c3nc(Nc4ccc(N5CCNCC5)c(F)c4)ncc3Cl)cc21] |
| 51 | 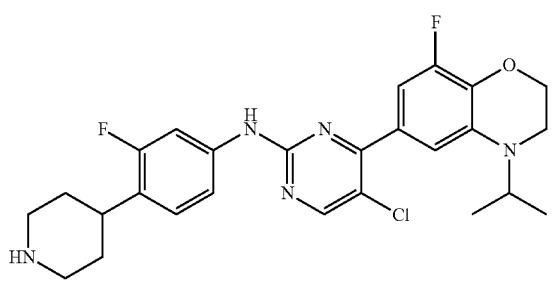 [SMILES: CC(C)N1CCOc2c(Cl)cc(-c3nc(Nc4ccc(N5CCNCC5)c(F)c4)ncc3Cl)cc21] |

TABLE 1-continued
| Compound No. | Structure |
|---|---|
| 52 | 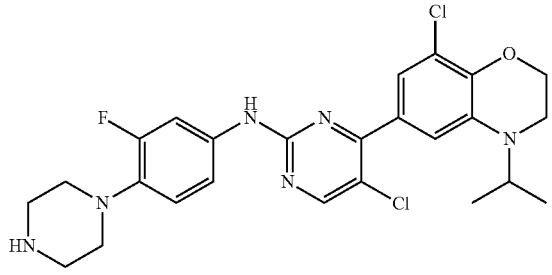 |
| 53 | 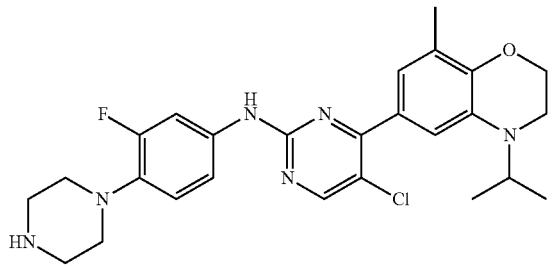 [SMILES: Cc1cc(-c2nc(Nc3ccc(N4CCNCC4)c(F)c3)ncc2Cl)cc2c1OCCN2C(C)C] |
| 54 | 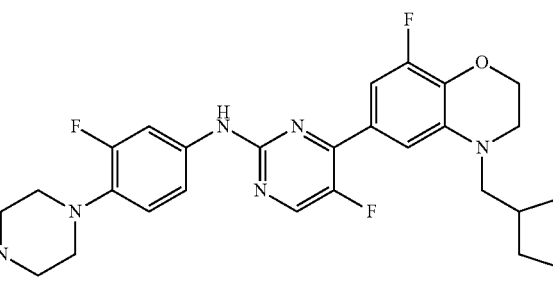 |
| 55 | 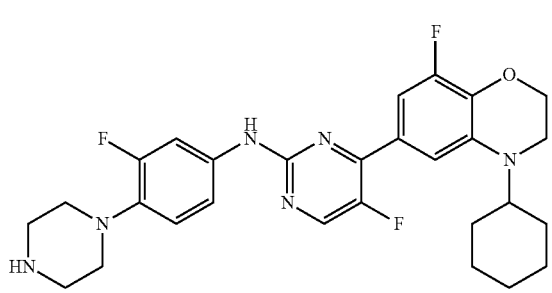 [SMILES: Fc1cc(Nc2ncc(F)c(-c3cc(F)c4c(c3)N(C3CCCCC3)CCO4)n2)ccc1N1CCNCC1] |
| 56 | 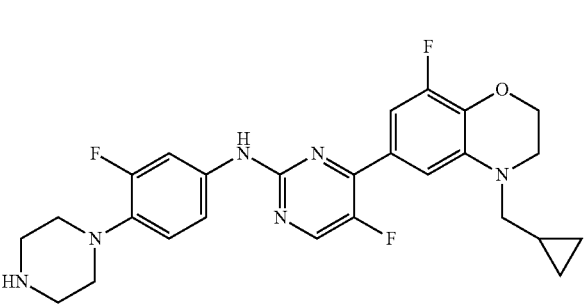 [SMILES: Fc1cc(Nc2ncc(F)c(-c3cc(F)c4c(c3)N(CC3CC3)CCO4)n2)ccc1N1CCNCC1] |

TABLE 1-continued

| Compound No. | Structure |
|---|---|
| 57 | 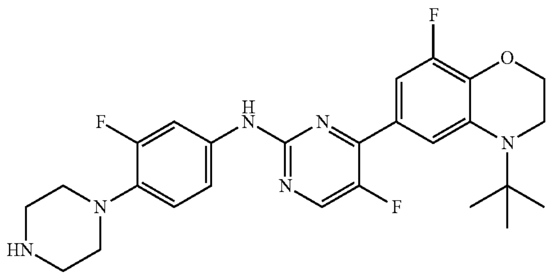 [SMILES: CC(C)(C)N1CCOc2c(F)cc(-c3nc(Nc4ccc(N5CCNCC5)c(F)c4)ncc3F)cc21] |
| 58 | 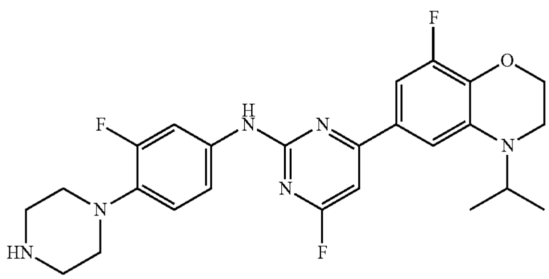 [SMILES: CC(C)N1CCOc2c(F)cc(-c3cc(F)nc(Nc4ccc(N5CCNCC5)c(F)c4)n3)cc21] |
| 59 | 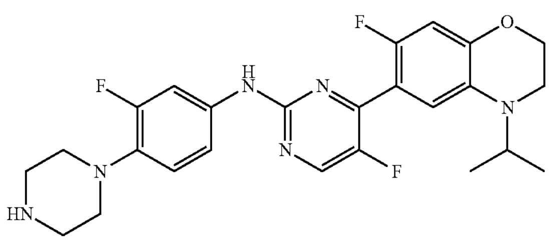 [SMILES: CC(C)N1CCOc2cc(F)c(-c3nc(Nc4ccc(N5CCNCC5)c(F)c4)ncc3F)cc21] |
| 60 | 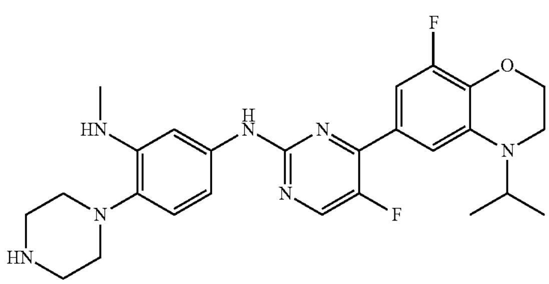 [SMILES: CNc1cc(Nc2ncc(F)c(-c3cc(F)c4c(c3)N(C(C)C)CCO4)n2)ccc1N1CCNCC1] |
| 61 | 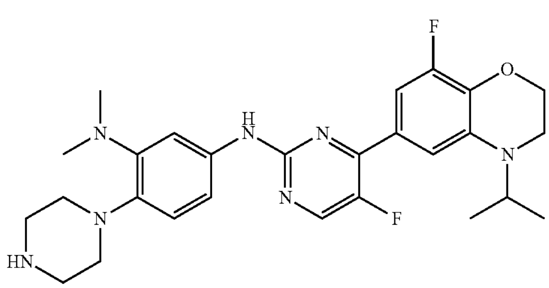 [SMILES: CC(C)c1cc(Nc2ncc(F)c(-c3cc(F)c4c(c3)N(C(C)C)CCO4)n2)ccc1N1CCNCC1] |

TABLE 1-continued

| Compound No. | Structure |
|---|---|
| 62 | *(structure image)* |
| 63 | *(structure image)* |
| 64 | *(structure image)* |
| 65 | *(structure image)* |
| 66 | *(structure image)* |

TABLE 1-continued
| Compound No. | Structure |
|---|---|
| 67 | 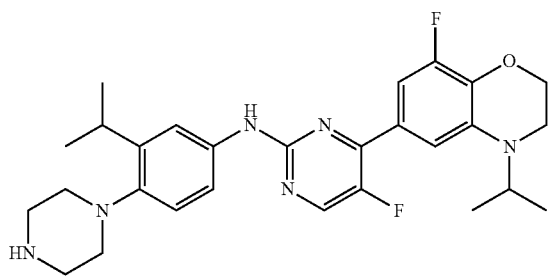 |
| 68 | 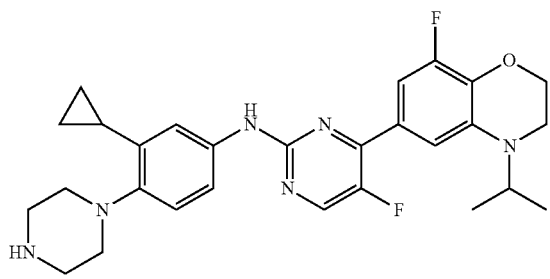 [SMILES: CC(C)N1CCOc2c(F)cc(-c3nc(Nc4ccc(N5CCNCC5)c(C5CC5)c4)ncc3F)cc21] |
| 69 | 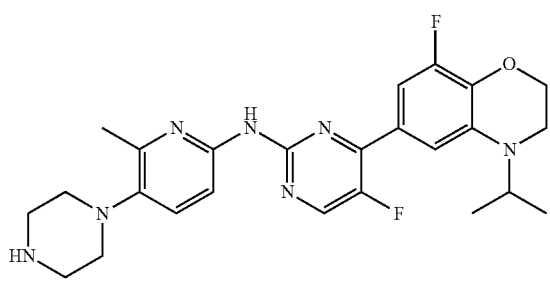 |
| 70 | 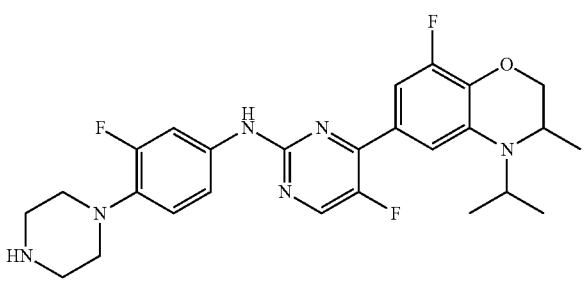 [SMILES: CC(C)N1c2cc(-c3nc(Nc4ccc(N5CCNCC5)c(F)c4)ncc3F)cc(F)c2OCC1C] |
| 71 | 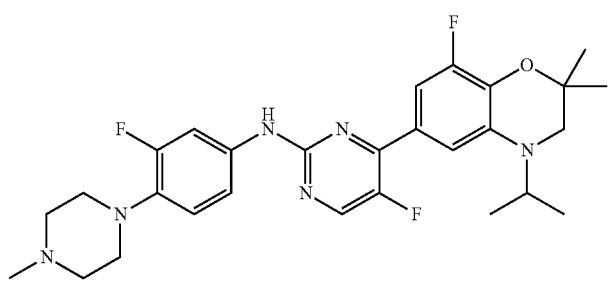 |

TABLE 1-continued
| Compound No. | Structure |
|---|---|
| 72 | 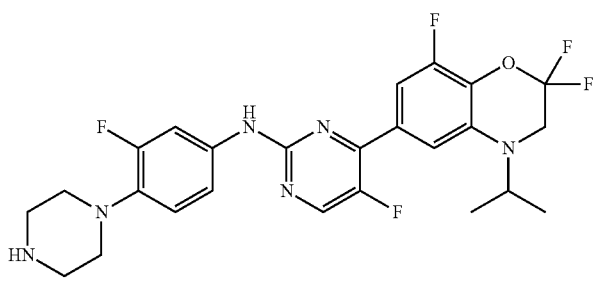 [SMILES: CC(C)N1CC(F)(F)Oc2c(F)cc(-c3nc(Nc4ccc(N5CCNCC5)c(F)c4)ncc3F)cc21] |
| 73 | 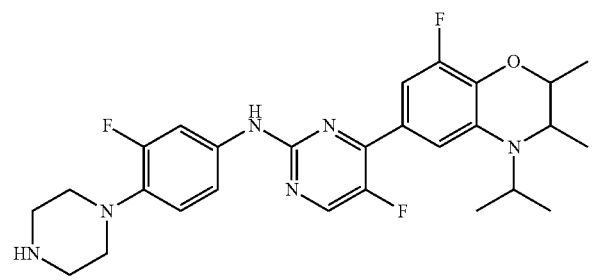 [SMILES: CC1Oc2c(F)cc(-c3nc(Nc4ccc(N5CCNCC5)c(F)c4)ncc3F)cc2N(C(C)C)C1C] |
| 74 | 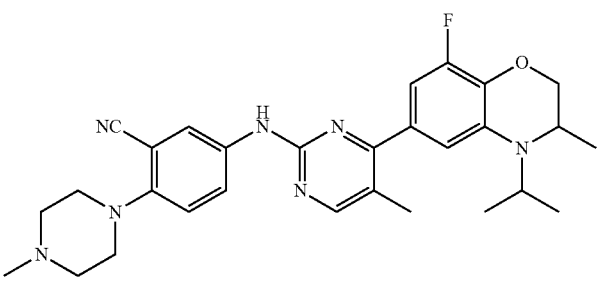 |
| 75 | 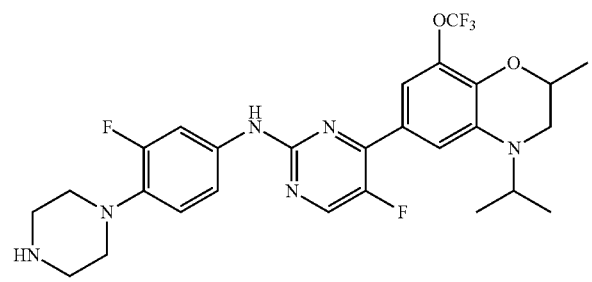 [SMILES: CC1CN(C(C)C)c2cc(-c3nc(Nc4ccc(N5CCNCC5)c(F)c4)ncc3F)cc(OC(F)(F)F)c2O1] |
| 76 | 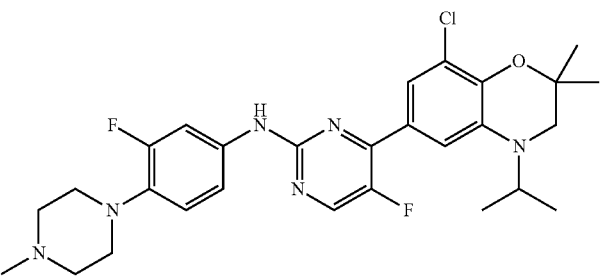 |

TABLE 1-continued
| Compound No. | Structure |
|---|---|
| 77 | 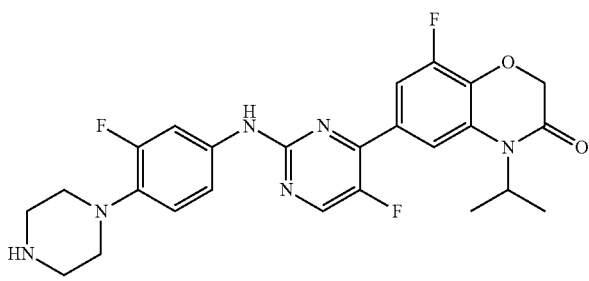 [SMILES: CC(C)N1C(=O)COc2c(F)cc(-c3nc(Nc4ccc(N5CCNCC5)c(F)c4)ncc3F)cc21] |
| 78 | 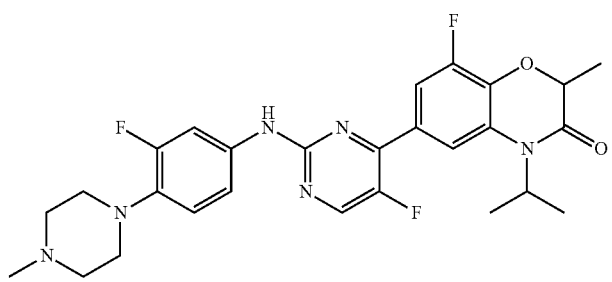 [SMILES: CC1Oc2c(F)cc(-c3nc(Nc4ccc(N5CCN(C)CC5)c(F)c4)ncc3F)cc2N(C(C)C)C1=O] |
| 79 | 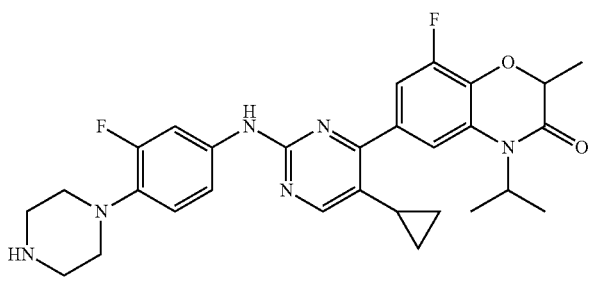 [SMILES: CC1Oc2c(F)cc(-c3nc(Nc4ccc(N5CCNCC5)c(F)c4)ncc3C3CC3)cc2N(C(C)C)C1=O] |
| 80 | 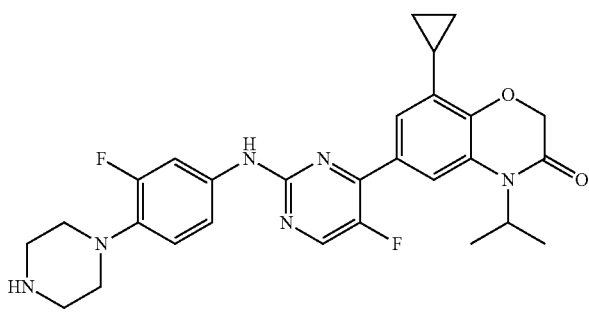 [SMILES: CC(C)N1C(=O)COc2c(C3CC3)cc(-c3nc(Nc4ccc(N5CCNCC5)c(F)c4)ncc3F)cc21] |
| 81 | 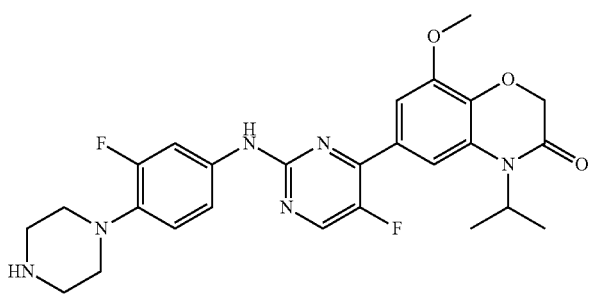 [SMILES: COc1cc(-c2nc(Nc3ccc(N4CCNCC4)c(F)c3)ncc2F)cc2c1OCC(=O)N2C(C)C] |

TABLE 1-continued
| Compound No. | Structure |
|---|---|
| 82 | 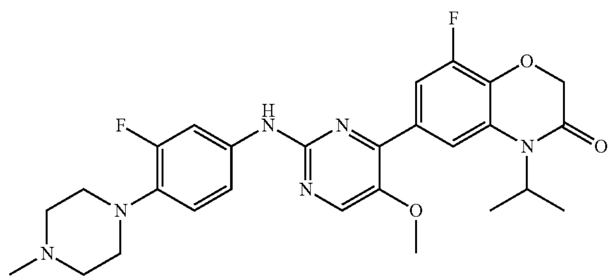 [SMILES: COc1cnc(Nc2ccc(N3CCN(C)CC3)c(F)c2)nc1-c1cc(F)c2c(c1)N(C(C)C)C(=O)CO2] |
| 83 | 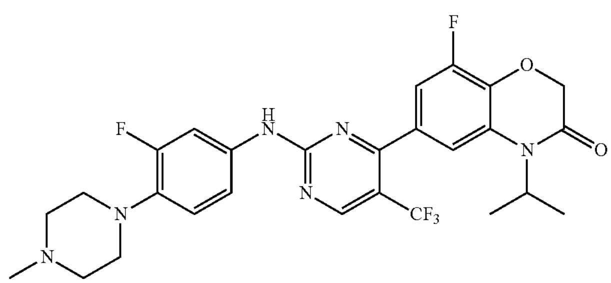 |
| 84 | 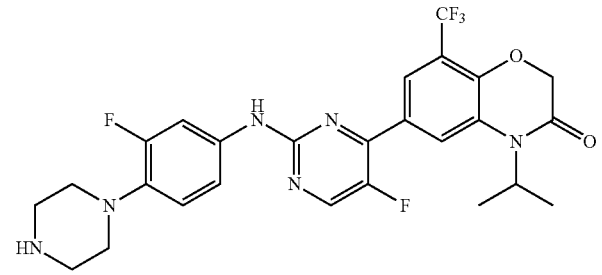 [SMILES: CC(C)N1C(=O)COc2c1cc(-c1nc(Nc3ccc(N4CCNCC4)c(F)c3)ncc1F)cc2C(F)(F)F] |
| 85 | 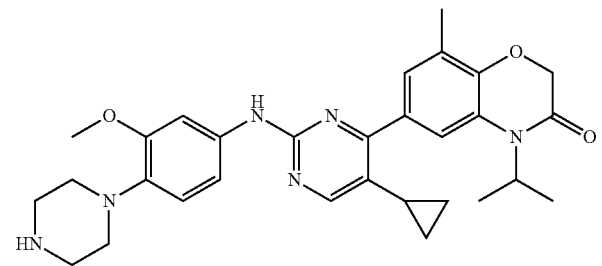 [SMILES: COc1cc(Nc2ncc(C3CC3)c(-c3cc(C)c4c(c3)N(C(C)C)C(=O)CO4)n2)ccc1N1CCNCC1] |
| 86 | 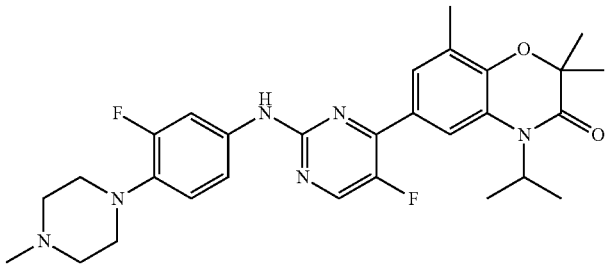 |

TABLE 1-continued
| Compound No. | Structure |
|---|---|
| 87 | 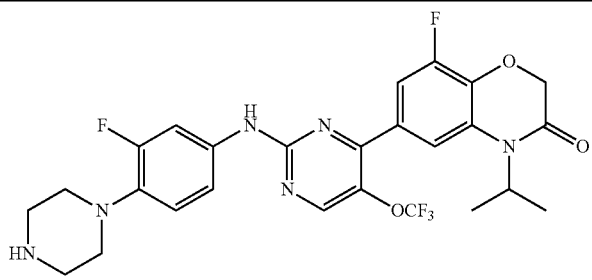 |
| 88 | 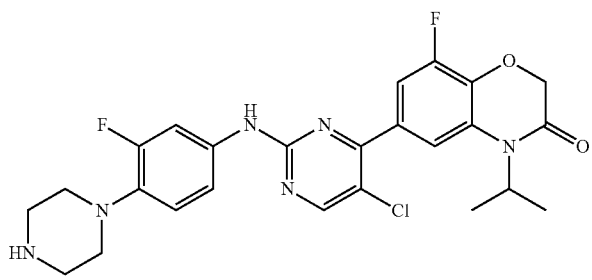 |
| 89 | 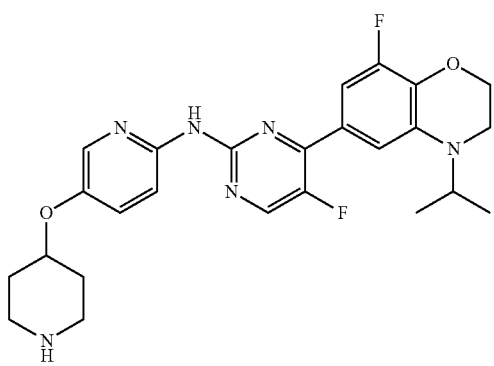 [SMILES: CC(C)N1CCOc2c(F)cc(-c3nc(Nc4ccc(OC5CCNCC5)cn4)ncc3F)cc21] |
| 90 | 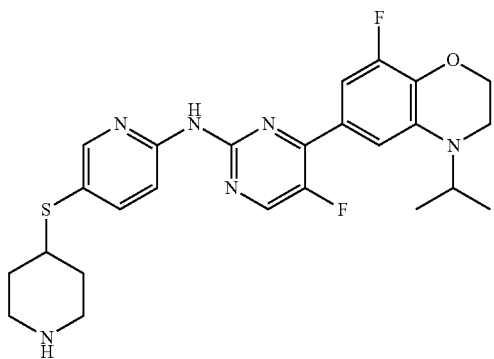 [SMILES: CC(C)N1CCOc2c(F)cc(-c3nc(Nc4ccc(SC5CCNCC5)cn4)ncc3F)cc21] |
| 91 | 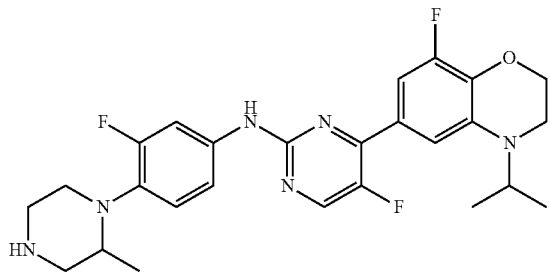 [SMILES: CC(C)N1CCOc2c(F)cc(-c3nc(Nc4ccc(N5CCNCC5C)c(F)c4)ncc3F)cc21] |

TABLE 1-continued
| Compound No. | Structure |
|---|---|
| 92 | 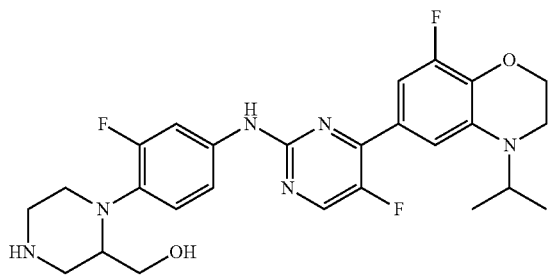 [SMILES: CC(C)N1CCOc2c(F)cc(-c3nc(Nc4ccc(N5CCNCC5CO)c(F)c4)ncc3F)cc21] |
| 93 | 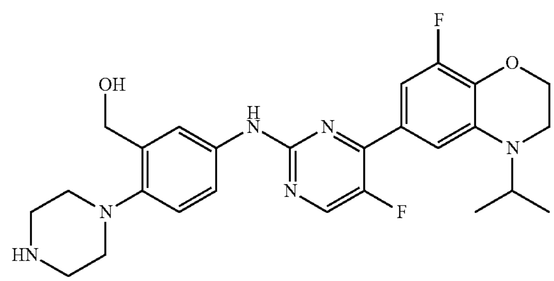 [SMILES: CC(C)N1CCOc2c(F)cc(-c3nc(Nc4ccc(N5CCNCC5)c(CO)c4)ncc3F)cc21] |
| 94 | 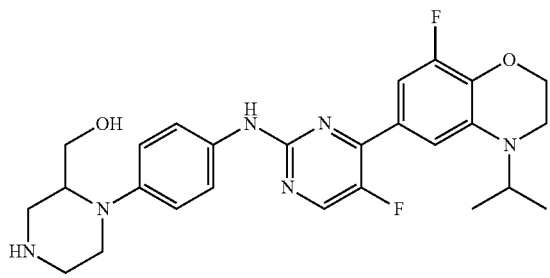 [SMILES: CC(C)N1CCOc2c(F)cc(-c3nc(Nc4ccc(N5CCNCC5CO)cc4)ncc3F)cc21] |
| 95 | 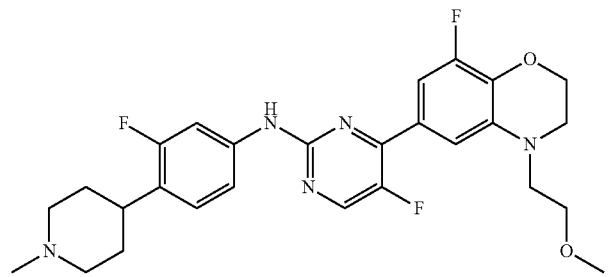 |
| 96 | 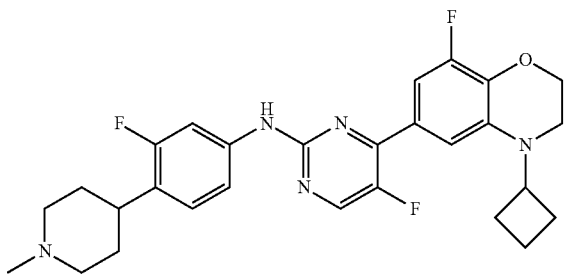 [SMILES: CN1CCC(c2ccc(Nc3ncc(F)c(-c4cc(F)c5c(c4)N(C4CCC4)CCO5)n3)cc2F)CC1] |

TABLE 1-continued
| Compound No. | Structure |
|---|---|
| 97 | 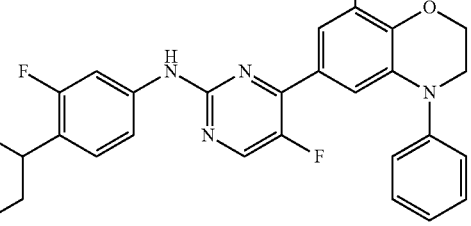 |
| 98 | 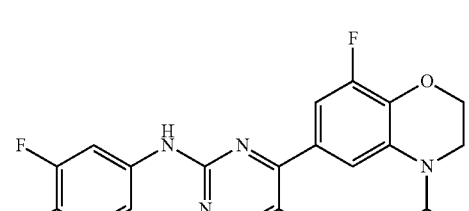 |
| 99 | 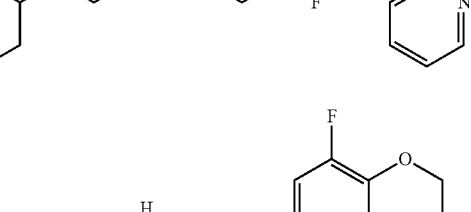 |
| 100 | 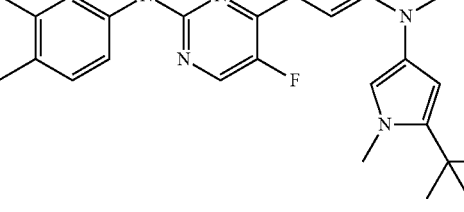 |
| 101 | 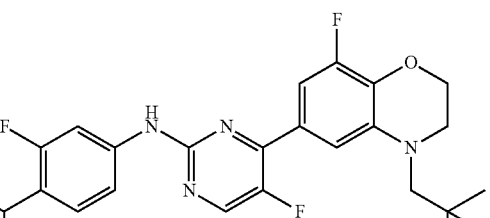 |

TABLE 1-continued
| Compound No. | Structure |
|---|---|
| 102 | 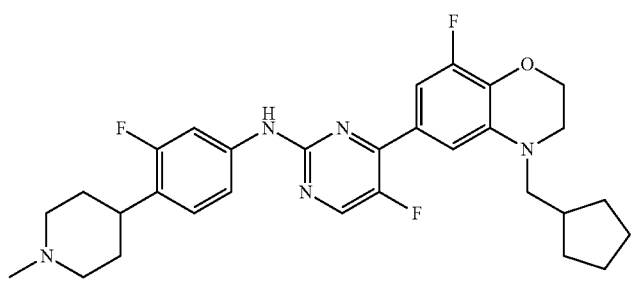 [SMILES: CN1CCC(c2ccc(Nc3ncc(F)c(-c4cc(F)c5c(c4)N(CC4CCCC4)CCO5)n3)cc2F)CC1] |
| 103 | 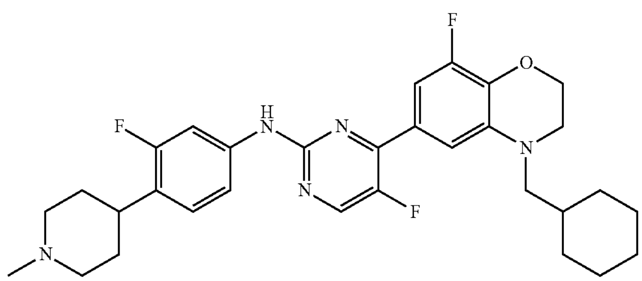 [SMILES: CN1CCC(c2ccc(Nc3ncc(F)c(-c4cc(F)c5c(c4)N(CC4CCCCC4)CCO5)n3)cc2F)CC1] |
| 104 | 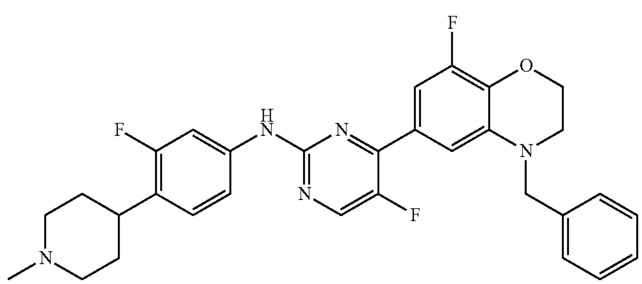 [SMILES: CN1CCC(c2ccc(Nc3ncc(F)c(-c4cc(F)c5c(c4)N(Cc4ccccc4)CCO5)n3)cc2F)CC1] |
| 105 | 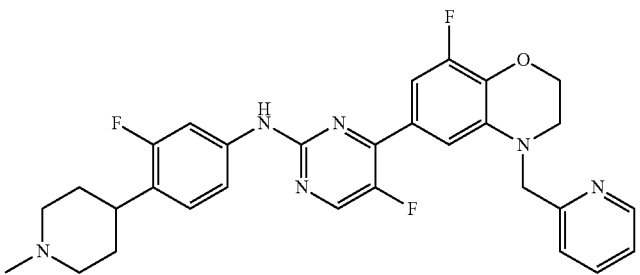 |
| 106 | 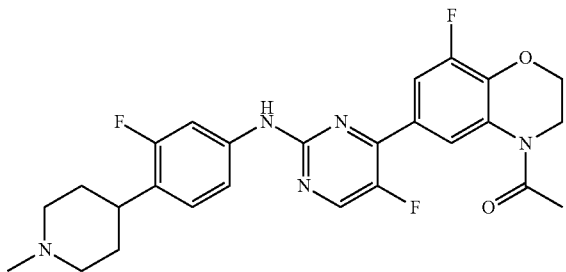 [SMILES: CC(=O)N1CCOc2c(F)cc(-c3nc(Nc4ccc(C5CCN(C)CC5)c(F)c4)ncc3F)cc21] |

TABLE 1-continued
| Compound No. | Structure |
|---|---|
| 107 | 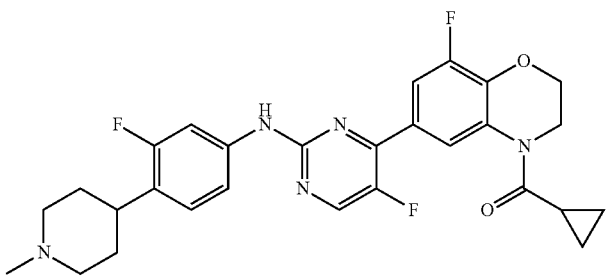 [SMILES: CN1CCC(c2ccc(Nc3ncc(F)c(-c4cc(F)c5c(c4)N(C(=O)C4CC4)CCO5)n3)cc2F)CC1] |
| 108 | 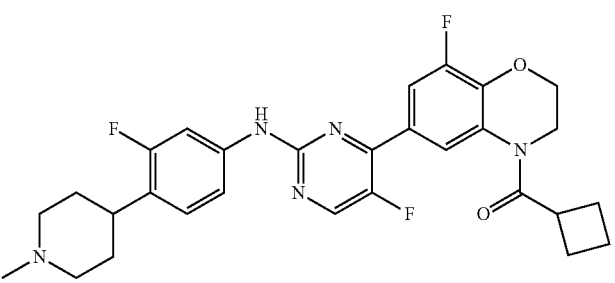 [SMILES: CN1CCC(c2ccc(Nc3ncc(F)c(-c4cc(F)c5c(c4)N(C(=O)C4CCC4)CCO5)n3)cc2F)CC1] |
| 109 | 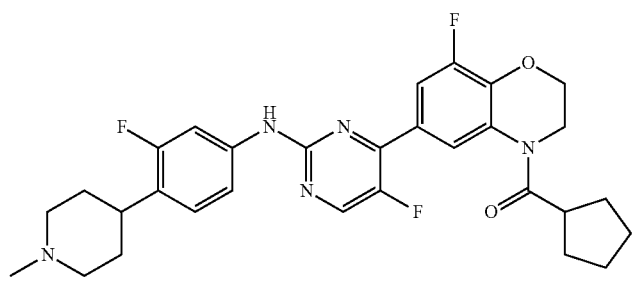 [SMILES: CN1CCC(c2ccc(Nc3ncc(F)c(-c4cc(F)c5c(c4)N(C(=O)C4CCCC4)CCO5)n3)cc2F)CC1] |
| 110 | 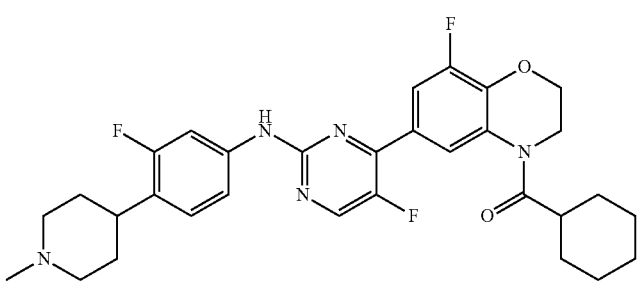 [SMILES: CN1CCC(c2ccc(Nc3ncc(F)c(-c4cc(F)c5c(c4)N(C(=O)C4CCCCC4)CCO5)n3)cc2F)CC1] |
| 111 | 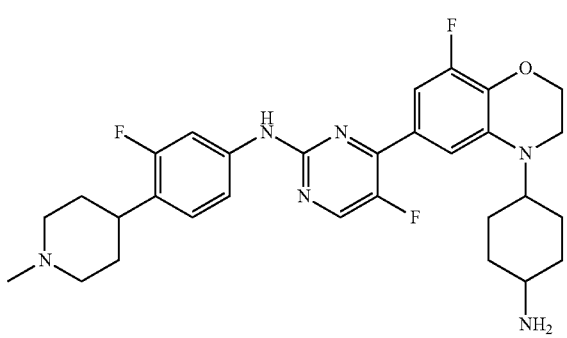 [SMILES: CN1CCC(c2ccc(Nc3ncc(F)c(-c4cc(F)c5c(c4)N(C4CCC(N)CC4)CCO5)n3)cc2F)CC1] |

TABLE 1-continued
| Compound No. | Structure |
|---|---|
| 112 | 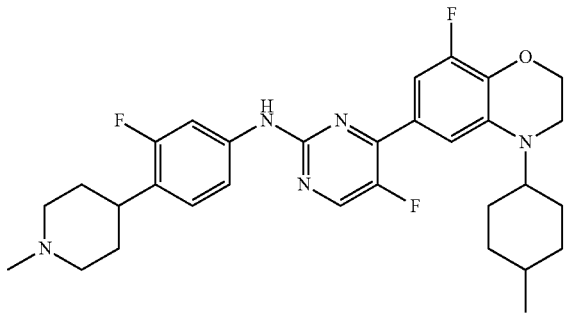 [SMILES: CC1CCC(N2CCOc3c(F)cc(-c4nc(Nc5ccc(C6CCN(C)CC6)c(F)c5)ncc4F)cc32)CC1] |
| 113 | 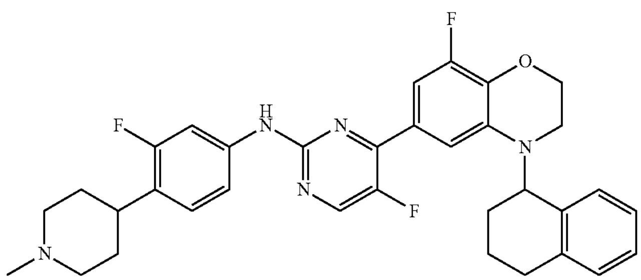 [SMILES: CN1CCC(c2ccc(Nc3ncc(F)c(-c4cc(F)c5c(c4)N(C4CCCc6ccccc64)CCO5)n3)cc2F)CC1] |
| 114 | 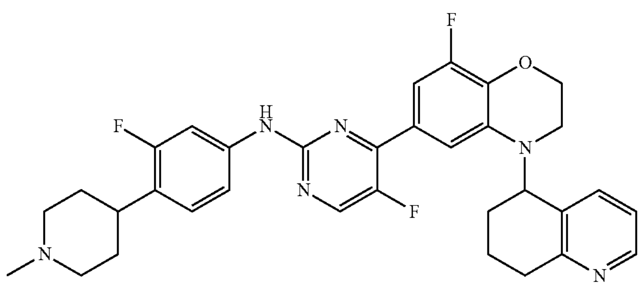 [SMILES: CN1CCC(c2ccc(Nc3ncc(F)c(-c4cc(F)c5c(c4)N(C4CCCc6ncccc64)CCO5)n3)cc2F)CC1] |
| 115 | 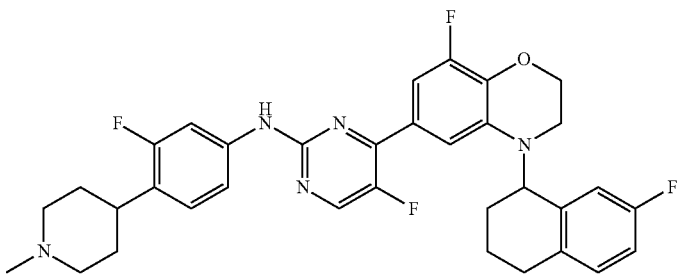 [SMILES: CN1CCC(c2ccc(Nc3ncc(F)c(-c4cc(F)c5c(c4)N(C4CCCc6ccc(F)cc64)CCO5)n3)cc2F)CC1] |
| 116 | 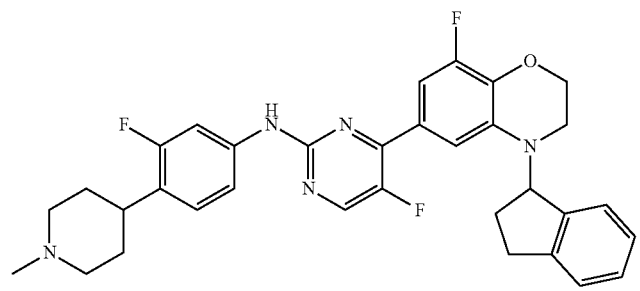 [SMILES: CN1CCC(c2ccc(Nc3ncc(F)c(-c4cc(F)c5c(c4)N(C4CCc6ccccc64)CCO5)n3)cc2F)CC1] |

TABLE 1-continued
| Compound No. | Structure |
|---|---|
| 117 | 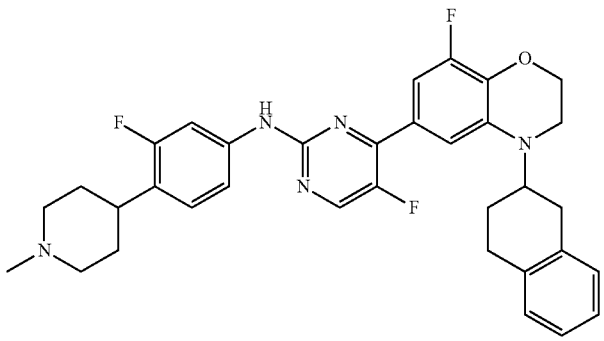 [SMILES: CN1CCC(c2ccc(Nc3ncc(F)c(-c4cc(F)c5c(c4)N(C4CCc6ccccc6C4)CCO5)n3)cc2F)CC1] |
| 118 | 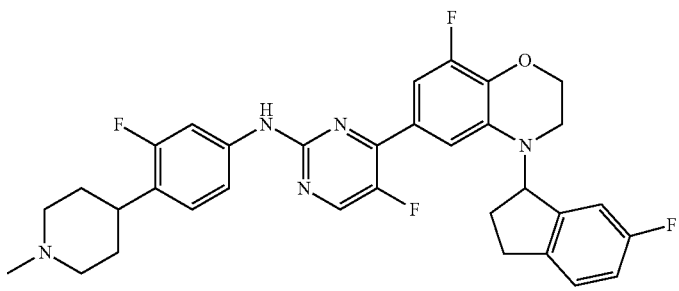 [SMILES: CN1CCC(c2ccc(Nc3ncc(F)c(-c4cc(F)c5c(c4)N(C4CCc6ccc(F)cc64)CCO5)n3)cc2F)CC1] |
| 119 | 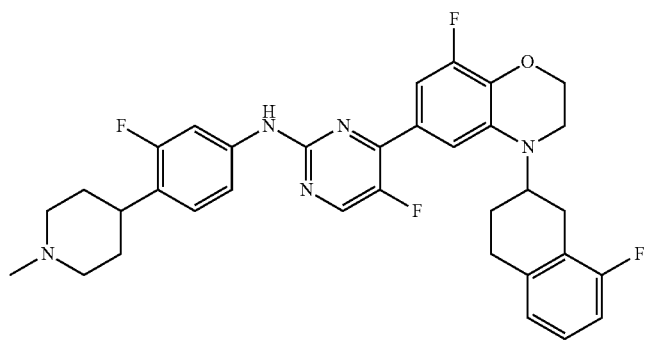 [SMILES: CN1CCC(c2ccc(Nc3ncc(F)c(-c4cc(F)c5c(c4)N(C4CCc6cccc(F)c6C4)CCO5)n3)cc2F)CC1] |
| 120 | 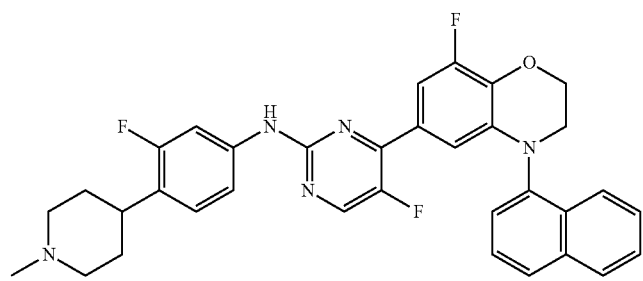 [SMILES: CN1CCC(c2ccc(Nc3ncc(F)c(-c4cc(F)c5c(c4)N(c4cccc6ccccc46)CCO5)n3)cc2F)CC1] |
| 121 | 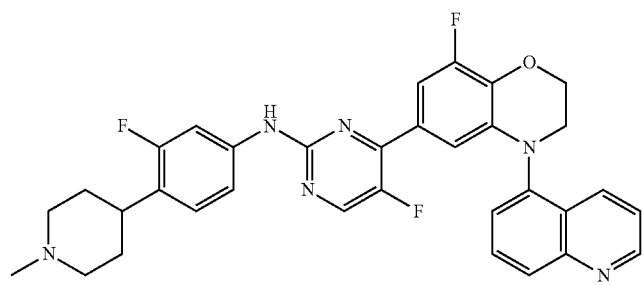 [SMILES: CN1CCC(c2ccc(Nc3ncc(F)c(-c4cc(F)c5c(c4)N(c4cccc6ncccc46)CCO5)n3)cc2F)CC1] |

TABLE 1-continued
| Compound No. | Structure |
|---|---|
| 122 | 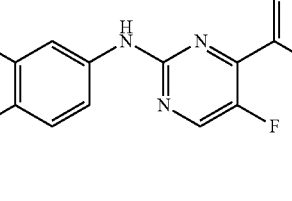 |
| 123 | 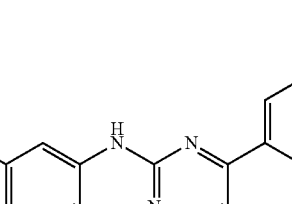 |
| 124 | 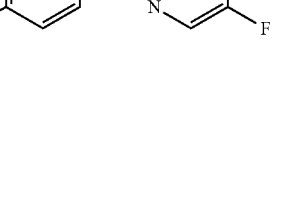 |
| 125 | 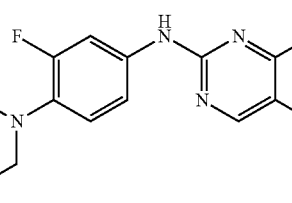 |
| 126 | 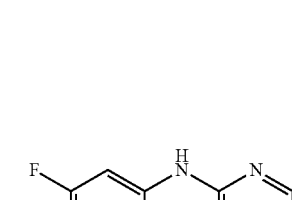 |

TABLE 1-continued
| Compound No. | Structure |
|---|---|
| 127 | 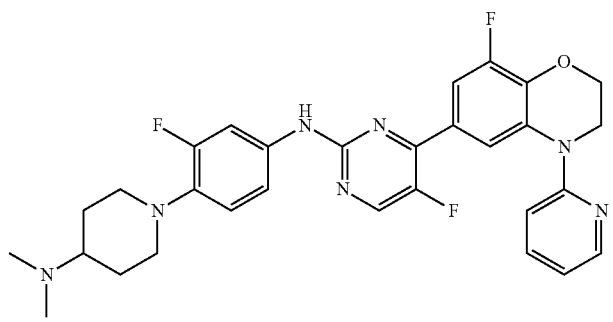 [SMILES: CN(C)C1CCN(c2ccc(Nc3ncc(F)c(-c4cc(F)c5c(c4)N(c4ccccn4)CCO5)n3)cc2F)CC1] |
| 128 | 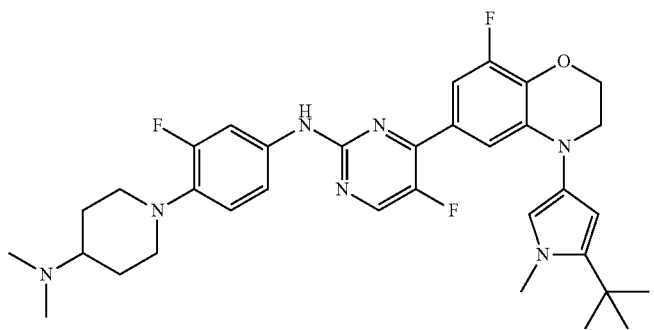 [SMILES: CN(C)C1CCN(c2ccc(Nc3ncc(F)c(-c4cc(F)c5c(c4)N(c4cc(C(C)(C)C)n(C)c4)CCO5)n3)cc2F)CC1] |
| 129 | 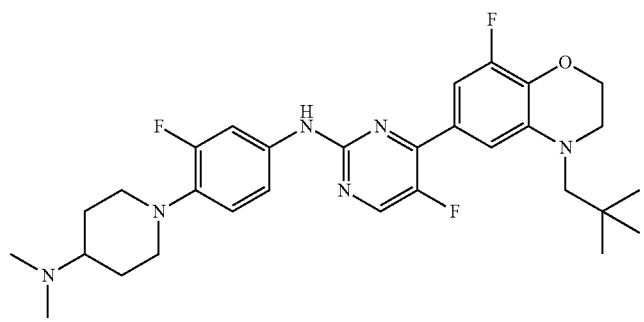 [SMILES: CN(C)C1CCN(c2ccc(Nc3ncc(F)c(-c4cc(F)c5c(c4)N(CC(C)(C)C)CCO5)n3)cc2F)CC1] |
| 130 | 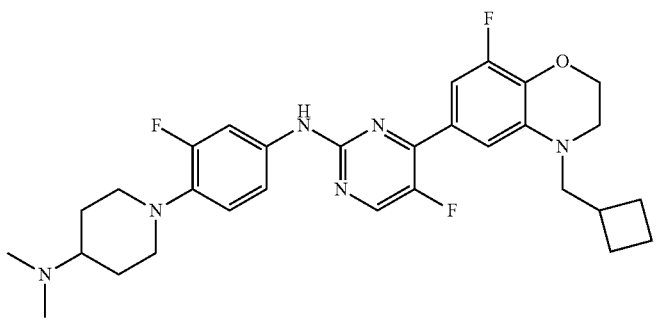 [SMILES: CN(C)C1CCN(c2ccc(Nc3ncc(F)c(-c4cc(F)c5c(c4)N(CC4CCC4)CCO5)n3)cc2F)CC1] |

TABLE 1-continued
| Compound No. | Structure |
|---|---|
| 131 | 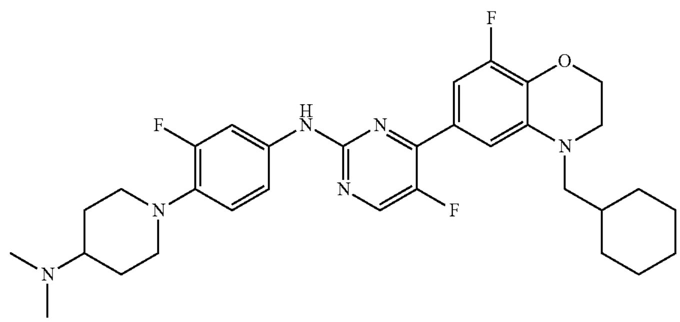 [SMILES: CN(C)C1CCN(c2ccc(Nc3ncc(F)c(-c4cc(F)c5c(c4)N(CC4CCCCC4)CCO5)n3)cc2F)CC1] |
| 132 | 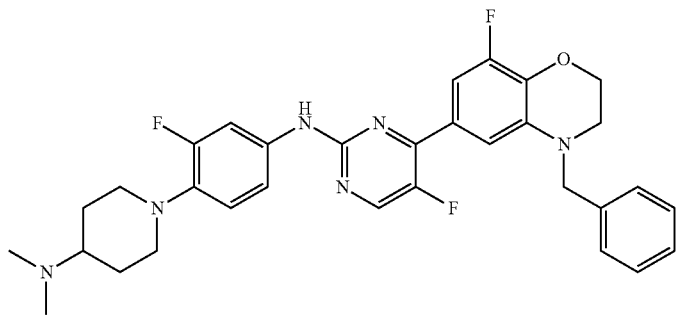 [SMILES: CN(C)C1CCN(c2ccc(Nc3ncc(F)c(-c4cc(F)c5c(c4)N(Cc4ccccc4)CCO5)n3)cc2F)CC1] |
| 133 | 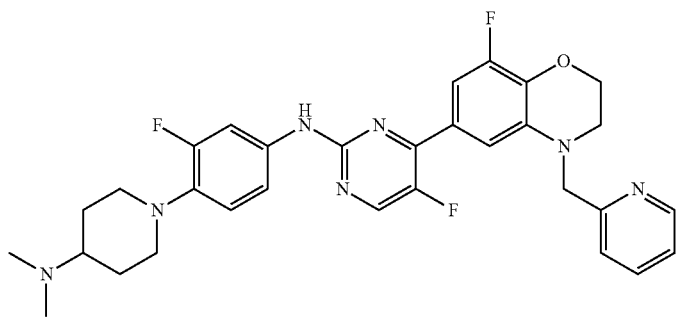 [SMILES: CN(C)C1CCN(c2ccc(Nc3ncc(F)c(-c4cc(F)c5c(c4)N(Cc4ccccn4)CCO5)n3)cc2F)CC1] |
| 134 | 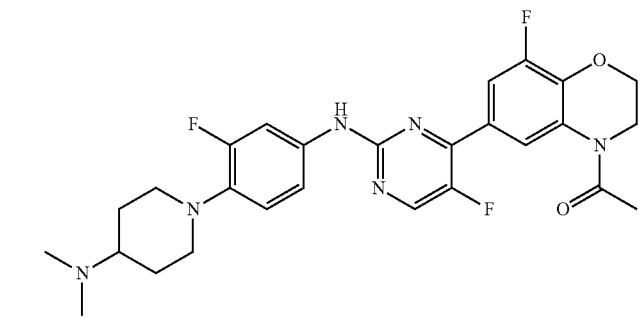 [SMILES: CC(=O)N1CCOc2c(F)cc(-c3nc(Nc4ccc(N5CCC(N(C)C)CC5)c(F)c4)ncc3F)cc21] |

TABLE 1-continued
| Compound No. | Structure |
|---|---|
| 135 | 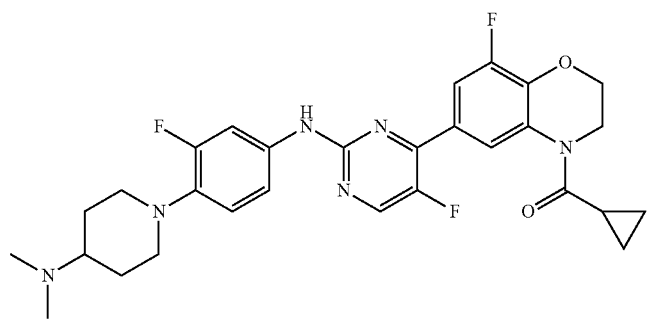 [SMILES: CN(C)C1CCN(c2ccc(Nc3ncc(F)c(-c4cc(F)c5c(c4)N(C(=O)C4CC4)CCO5)n3)cc2F)CC1] |
| 136 | 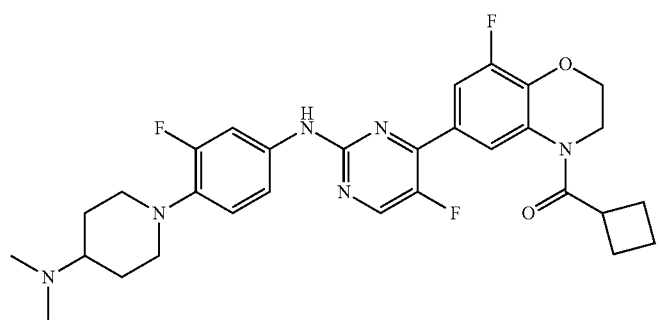 [SMILES: CN(C)C1CCN(c2ccc(Nc3ncc(F)c(-c4cc(F)c5c(c4)N(C(=O)C4CCC4)CCO5)n3)cc2F)CC1] |
| 137 | 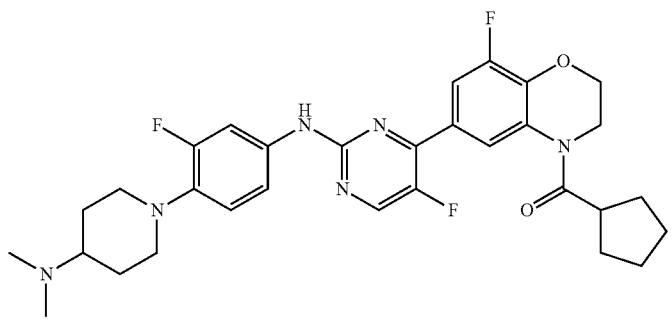 [SMILES: CN(C)C1CCN(c2ccc(Nc3ncc(F)c(-c4cc(F)c5c(c4)N(C(=O)C4CCCC4)CCO5)n3)cc2F)CC1] |
| 138 | 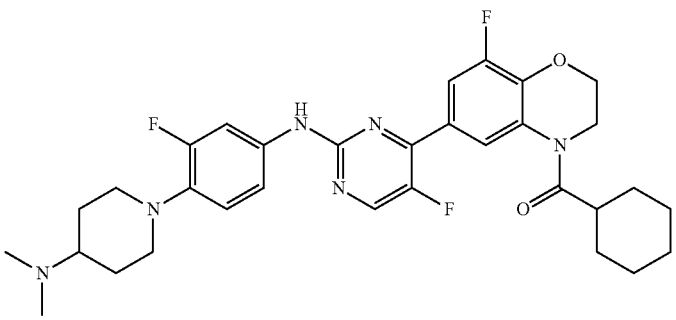 [SMILES: CN(C)C1CCN(c2ccc(Nc3ncc(F)c(-c4cc(F)c5c(c4)N(C(=O)C4CCCCC4)CCO5)n3)cc2F)CC1] |

TABLE 1-continued
| Compound No. | Structure |
|---|---|
| 139 | 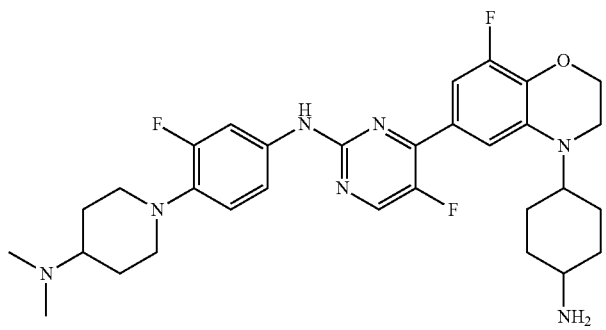 [SMILES: CN(C)C1CCN(c2ccc(Nc3ncc(F)c(-c4cc(F)c5c(c4)N(C4CCC(N)CC4)CCO5)n3)cc2F)CC1] |
| 140 | 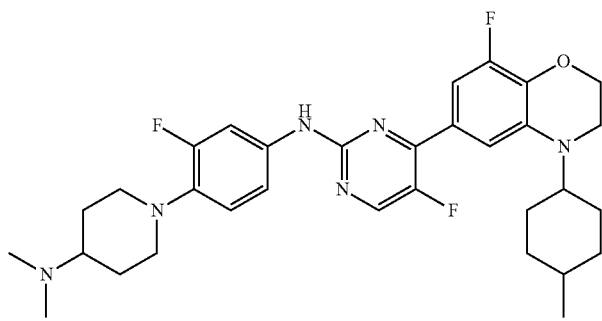 [SMILES: CC1CCC(N2CCOc3c(F)cc(-c4nc(Nc5ccc(N6CCC(N(C)C)CC6)c(F)c5)ncc4F)cc32)CC1] |
| 141 | 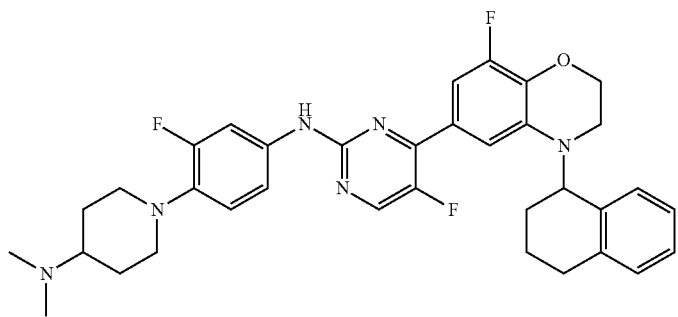 [SMILES: CN(C)C1CCN(c2ccc(Nc3ncc(F)c(-c4cc(F)c5c(c4)N(C4CCCc6ccccc64)CCO5)n3)cc2F)CC1] |
| 142 | 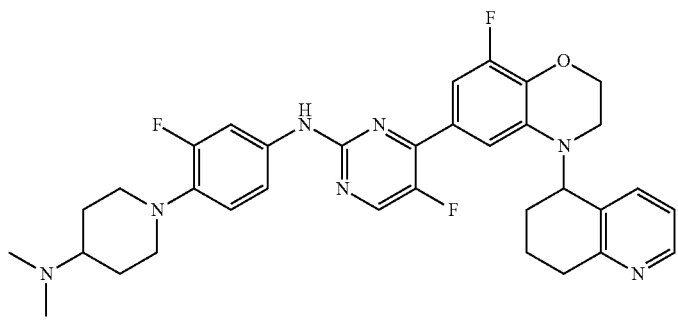 [SMILES: CN(C)C1CCN(c2ccc(Nc3ncc(F)c(-c4cc(F)c5c(c4)N(C4CCCc6ncccc64)CCO5)n3)cc2F)CC1] |

TABLE 1-continued
| Compound No. | Structure |
|---|---|
| 143 | 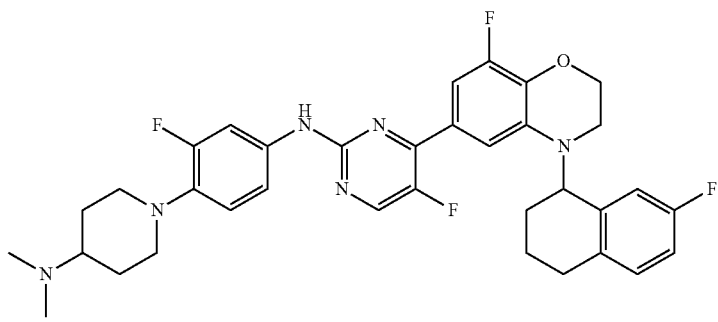 [SMILES: CN(C)C1CCN(c2ccc(Nc3ncc(F)c(-c4cc(F)c5c(c4)N(C4CCCc6ccc(F)cc64)CCO5)n3)cc2F)CC1] |
| 144 | 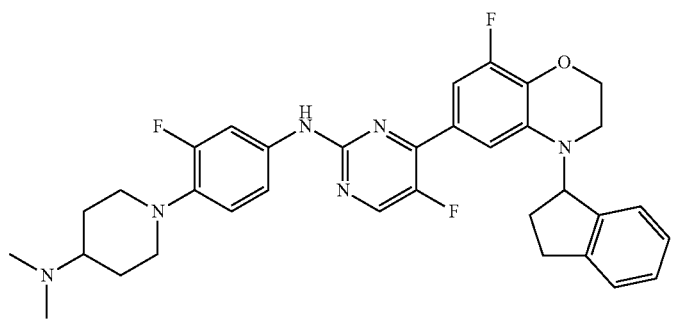 [SMILES: CN(C)C1CCN(c2ccc(Nc3ncc(F)c(-c4cc(F)c5c(c4)N(C4CCc6ccccc64)CCO5)n3)cc2F)CC1] |
| 145 | 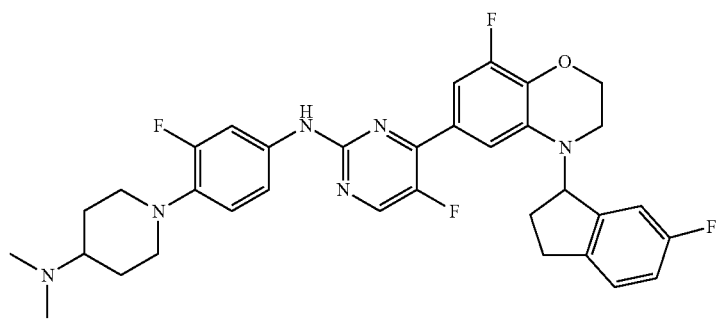 [SMILES: CN(C)C1CCN(c2ccc(Nc3ncc(F)c(-c4cc(F)c5c(c4)N(C4CCc6ccc(F)cc64)CCO5)n3)cc2F)CC1] |
| 146 | 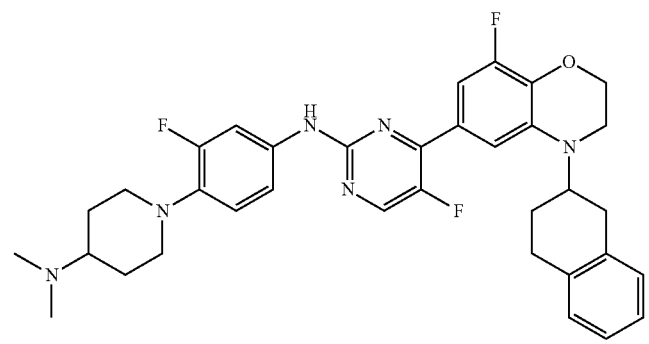 [SMILES: CN(C)C1CCN(c2ccc(Nc3ncc(F)c(-c4cc(F)c5c(c4)N(C4CCc6ccccc6C4)CCO5)n3)cc2F)CC1] |

TABLE 1-continued

| Compound No. | Structure |
|---|---|
| 147 | 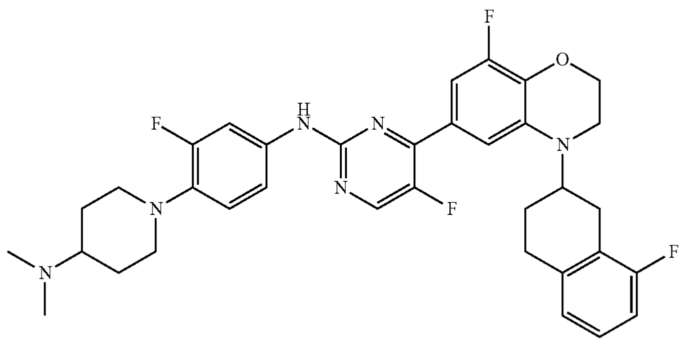 [SMILES: CN(C)C1CCN(c2ccc(Nc3ncc(F)c(-c4cc(F)c5c(c4)N(C4CCc6cccc(F)c6C4)CCO5)n3)cc2F)CC1] |
| 148 | 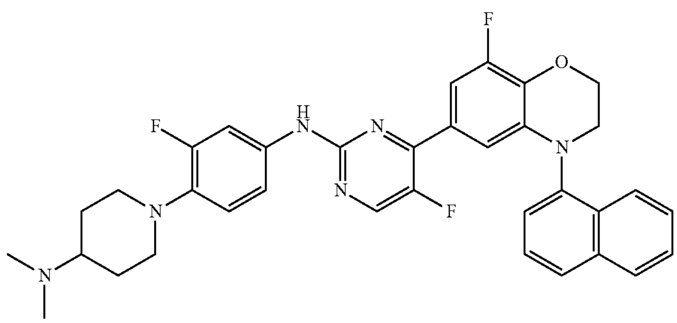 [SMILES: CN(C)C1CCN(c2ccc(Nc3ncc(F)c(-c4cc(F)c5c(c4)N(c4cccc6ccccc46)CCO5)n3)cc2F)CC1] |
| 149 | 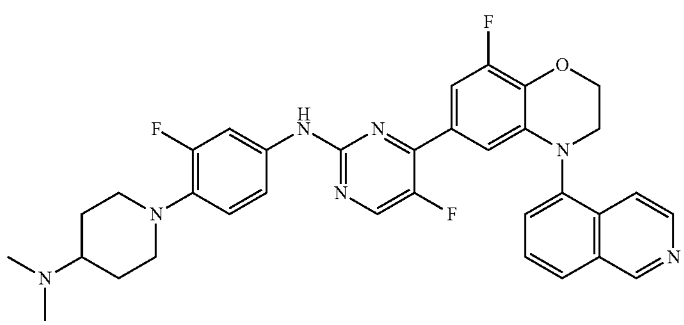 [SMILES: CN(C)C1CCN(c2ccc(Nc3ncc(F)c(-c4cc(F)c5c(c4)N(c4cccc6cnccc46)CCO5)n3)cc2F)CC1] |
| 150 | 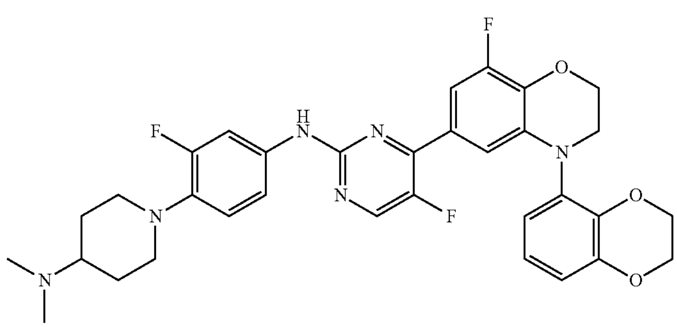 [SMILES: CN(C)C1CCN(c2ccc(Nc3ncc(F)c(-c4cc(F)c5c(c4)N(c4cccc6c4OCCO6)CCO5)n3)cc2F)CC1] |

TABLE 1-continued
| Compound No. | Structure |
|---|---|
| 151 | 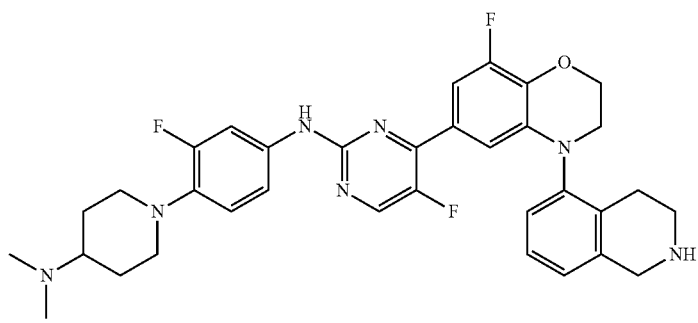 [SMILES: CN(C)C1CCN(c2ccc(Nc3ncc(F)c(-c4cc(F)c5c(c4)N(c4cccc6c4CCNC6)CCO5)n3)cc2F)CC1] |
| 152 | 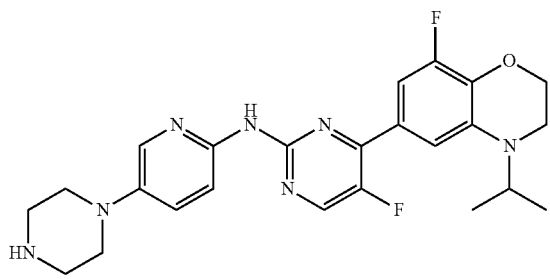 [SMILES: CC(C)N1CCOc2c(F)cc(-c3nc(Nc4ccc(N5CCNCC5)cn4)ncc3F)cc21] |
| 153 | 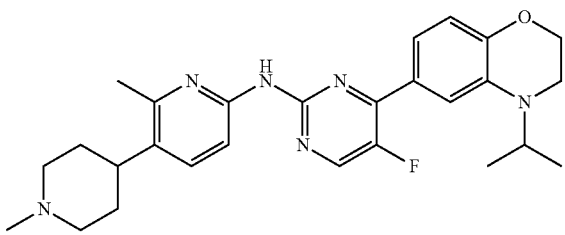 [SMILES: Cc1nc(Nc2ncc(F)c(-c3ccc4c(c3)N(C(C)C)CCO4)n2)ccc1C1CCN(C)CC1] |
| 154 | 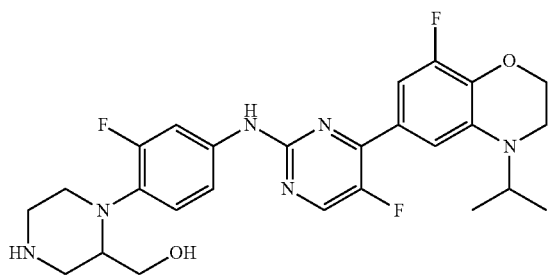 [SMILES: CC(C)N1CCOc2c(F)cc(-c3nc(Nc4ccc(N5CCNCC5CO)c(F)c4)ncc3F)cc21] |
| 155 | 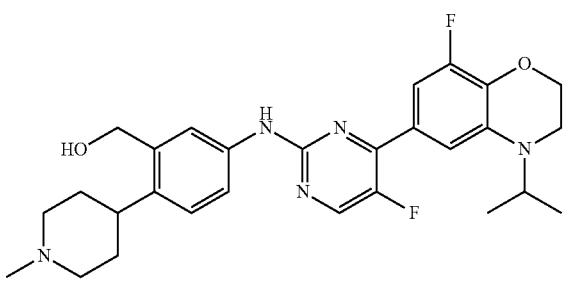 [SMILES: CC(C)N1CCOc2c(F)cc(-c3nc(Nc4ccc(C5CCN(C)CC5)c(CO)c4)ncc3F)cc21] |

TABLE 1-continued
| Compound No. | Structure |
|---|---|
| 156 | 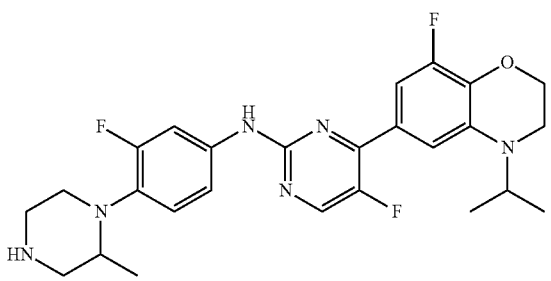 [SMILES: CC(C)N1CCOc2c(F)cc(-c3nc(Nc4ccc(N5CCNCC5C)c(F)c4)ncc3F)cc21] |
| 157 | 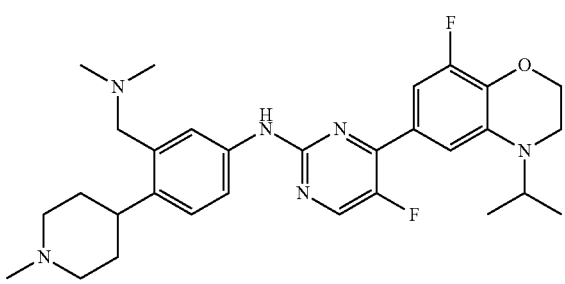 [SMILES: CC(C)N1CCOc2c(F)cc(-c3nc(Nc4ccc(C5CCN(C)CC5)c(CN(C)C)c4)ncc3F)cc21] |
| 158 | 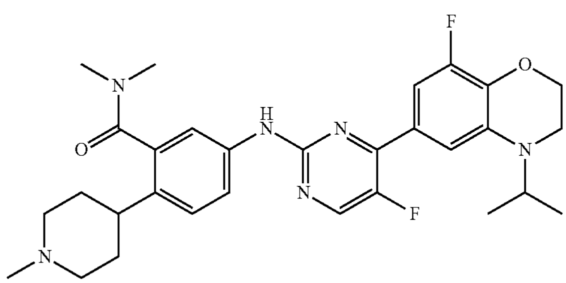 [SMILES: CC(C)N1CCOc2c(F)cc(-c3nc(Nc4ccc(C5CCN(C)CC5)c(C(=O)N(C)C)c4)ncc3F)cc21] |
| 159 | 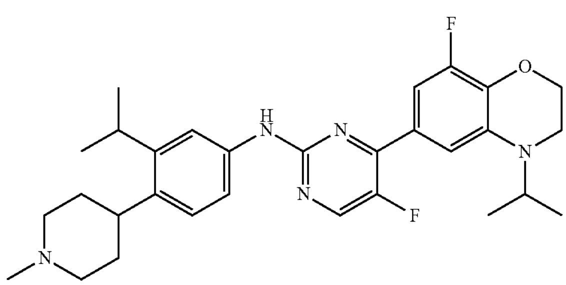 [SMILES: CC(C)c1cc(Nc2ncc(F)c(-c3cc(F)c4c(c3)N(C(C)C)CCO4)n2)ccc1C1CCN(C)CC1] |
| 160 | 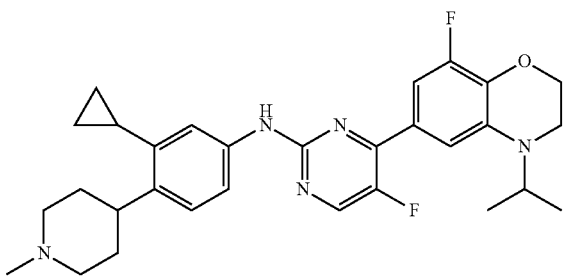 [SMILES: CC(C)N1CCOc2c(F)cc(-c3nc(Nc4ccc(C5CCN(C)CC5)c(C5CC5)c4)ncc3F)cc21] |

TABLE 1-continued
| Compound No. | Structure |
| --- | --- |
| 161 | 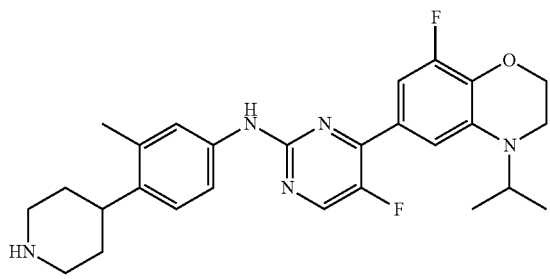 [SMILES: Cc1cc(Nc2ncc(F)c(-c3cc(F)c4c(c3)N(C(C)C)CCO4)n2)ccc1C1CCNCC1] |
| 162 | 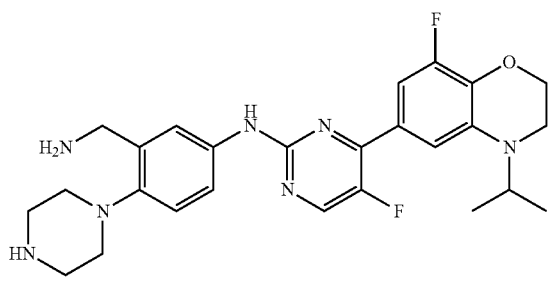 [SMILES: CC(C)N1CCOc2c(F)cc(-c3nc(Nc4ccc(N5CCNCC5)c(CN)c4)ncc3F)cc21] |
| 163 | 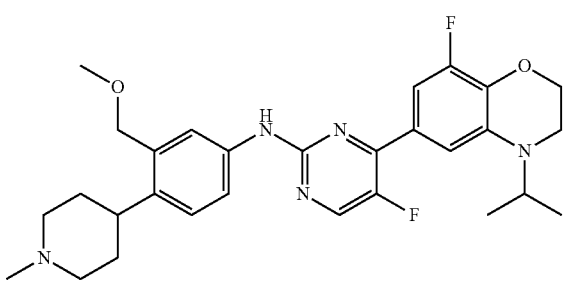 [SMILES: COCc1cc(Nc2ncc(F)c(-c3cc(F)c4c(c3)N(C(C)C)CCO4)n2)ccc1C1CCN(C)CC1] |
| 164 | 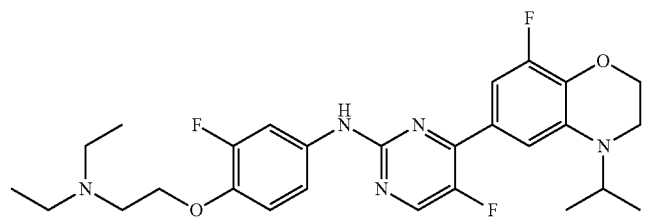 [SMILES: CCN(CC)CCOc1ccc(Nc2ncc(F)c(-c3cc(F)c4c(c3)N(C(C)C)CCO4)n2)cc1F] |
| 165 | 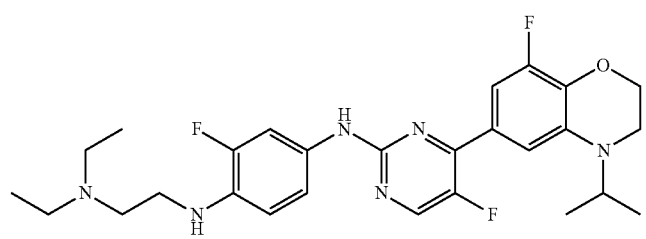 [SMILES: CCN(CC)CCNc1ccc(Nc2ncc(F)c(-c3cc(F)c4c(c3)N(C(C)C)CCO4)n2)cc1F] |

TABLE 1-continued
| Compound No. | Structure |
|---|---|
| 166 | 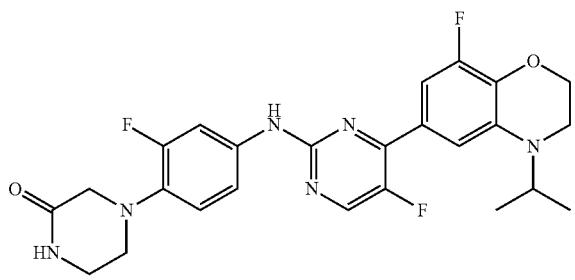 [SMILES: CC(C)N1CCOc2c(F)cc(-c3nc(Nc4ccc(N5CCNC(=O)C5)c(F)c4)ncc3F)cc21] |
| 167 | 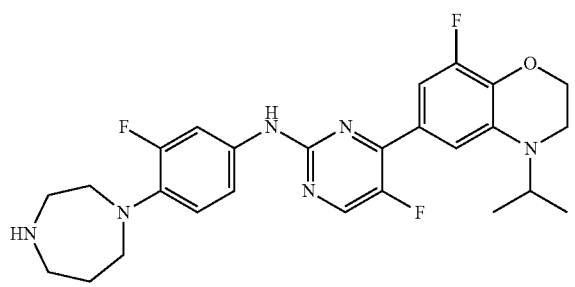 [SMILES: CC(C)N1CCOc2c(F)cc(-c3nc(Nc4ccc(N5CCCNCC5)c(F)c4)ncc3F)cc21] |
| 168 | 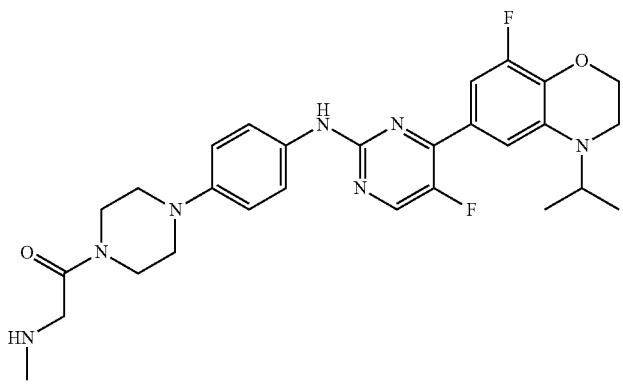 [SMILES: CNCC(=O)N1CCN(c2ccc(Nc3ncc(F)c(-c4cc(F)c5c(c4)N(C(C)C)CCO5)n3)cc2)CC1] |
| 169 | 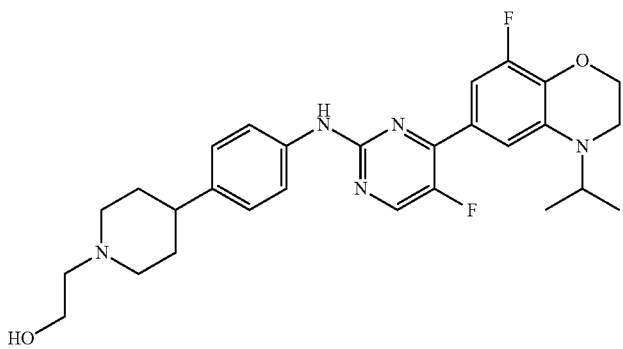 [SMILES: CC(C)N1CCOc2c(F)cc(-c3nc(Nc4ccc(C5CCN(CCO)CC5)cc4)ncc3F)cc21] |

TABLE 1-continued
| Compound No. | Structure |
|---|---|
| 170 | 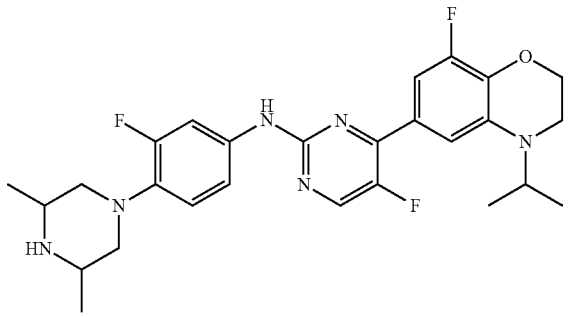 [SMILES: CC1CN(c2ccc(Nc3ncc(F)c(-c4cc(F)c5c(c4)N(C(C)C)CCO5)n3)cc2F)CC(C)N1] |
| 171 | 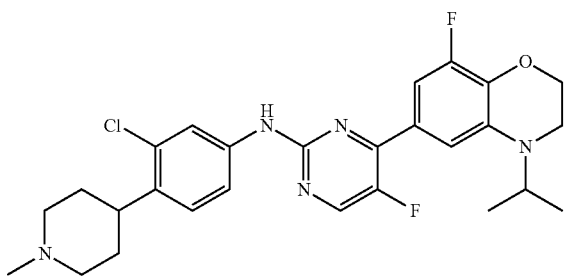 |
| 172 | 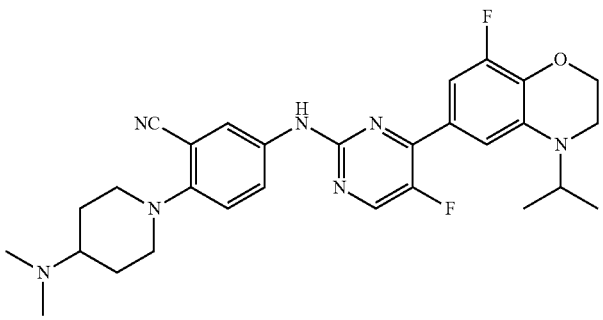 |
| 173 | 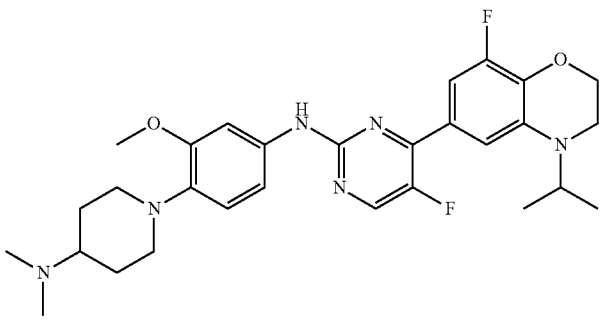 [SMILES: COc1cc(Nc2ncc(F)c(-c3cc(F)c4c(c3)N(C(C)C)CCO4)n2)ccc1N1CCC(N(C)C)CC1] |
| 174 | 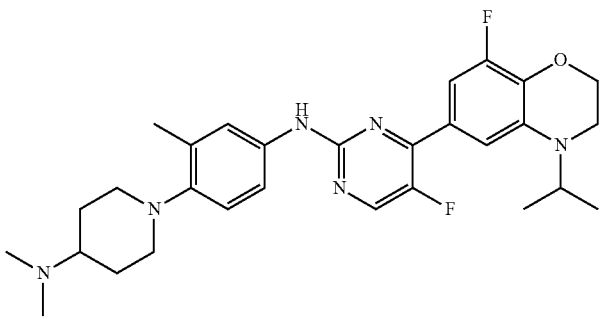 [SMILES: Cc1cc(Nc2ncc(F)c(-c3cc(F)c4c(c3)N(C(C)C)CCO4)n2)ccc1N1CCC(N(C)C)CC1] |

TABLE 1-continued
| Compound No. | Structure |
|---|---|
| 175 | 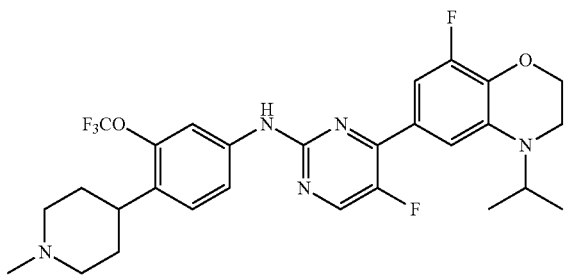 [SMILES: CC(C)N1CCOc2c(F)cc(-c3nc(Nc4ccc(C5CCN(C)CC5)c(OC(F)(F)F)c4)ncc3F)cc21] |
| 176 | 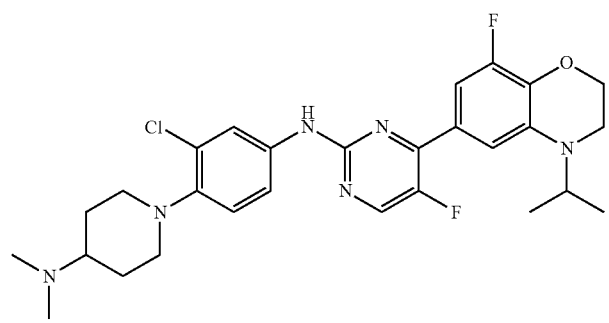 |
| 177 | 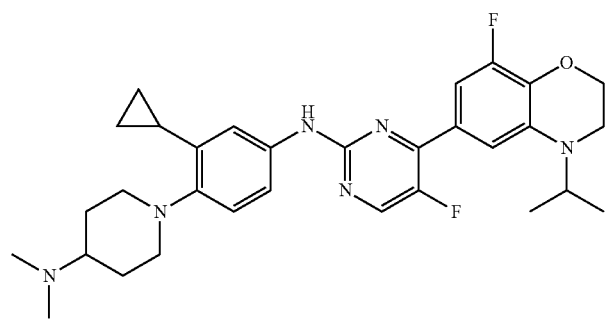 [SMILES: CC(C)N1CCOc2c(F)cc(-c3nc(Nc4ccc(N5CCC(N(C)C)CC5)c(C5CC5)c4)ncc3F)cc21] |
| 178 | 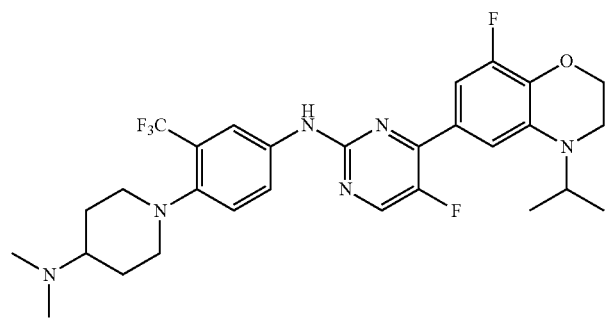 [SMILES: CC(C)N1CCOc2c(F)cc(-c3nc(Nc4ccc(N5CCC(N(C)C)CC5)c(C(F)(F)F)c4)ncc3F)cc21] |
| 179 | 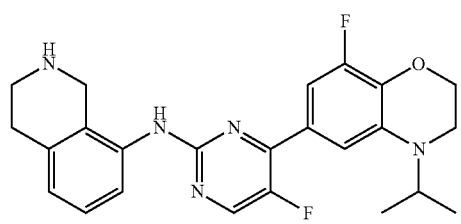 [SMILES: CC(C)N1CCOc2c(F)cc(-c3nc(Nc4cccc5c4CNCC5)ncc3F)cc21] |

TABLE 1-continued
| Compound No. | Structure |
|---|---|
| 180 | 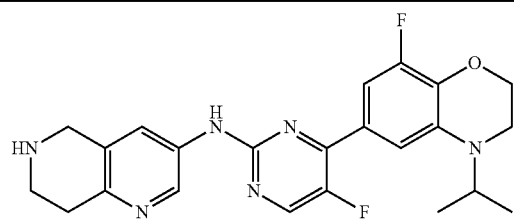 |
| 181 | 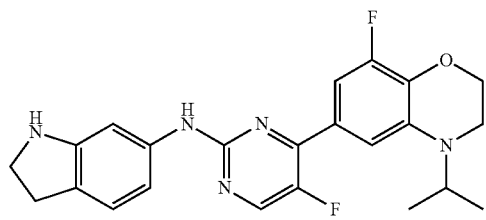 [SMILES: CC(C)N1CCOc2c(F)cc(-c3nc(Nc4ccc5c(c4)NCC5)ncc3F)cc21] |
| 182 | 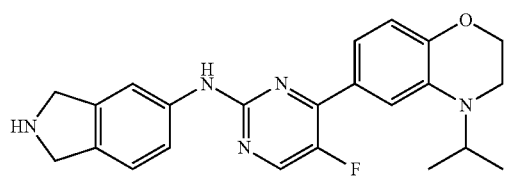 [SMILES: CC(C)N1CCOc2ccc(-c3nc(Nc4ccc5c(c4)CNC5)ncc3F)cc21] |
| 183 | 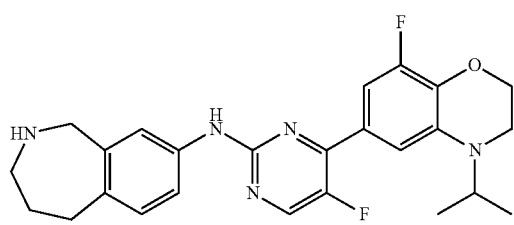 [SMILES: CC(C)N1CCOc2c(F)cc(-c3nc(Nc4ccc5c(c4)CNCCC5)ncc3F)cc21] |
| 184 | 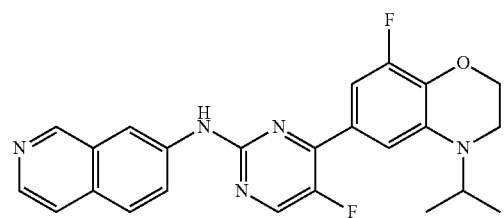 [SMILES: CC(C)N1CCOc2c(F)cc(-c3nc(Nc4ccc5ccncc5c4)ncc3F)cc21] |
| 185 | 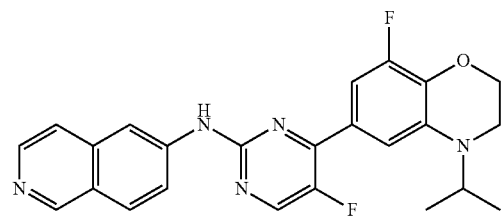 [SMILES: CC(C)N1CCOc2c(F)cc(-c3nc(Nc4ccc5cnccc5c4)ncc3F)cc21] |
| 186 | 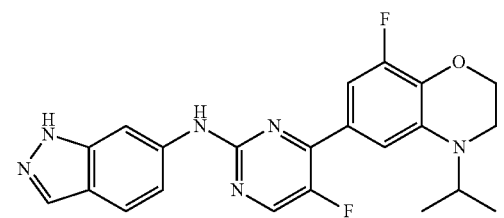 |

US 11,174,252 B2
TABLE 1-continued
| Compound No. | Structure |
|---|---|
| 187 | 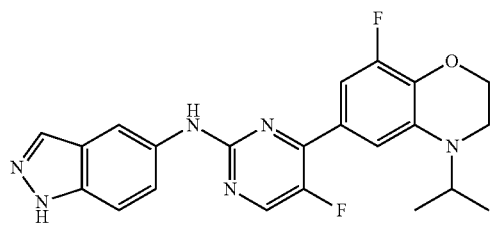 [SMILES: CC(C)N1CCOc2c(F)cc(-c3nc(Nc4ccc5[nH]ncc5c4)ncc3F)cc21] |
| 188 | 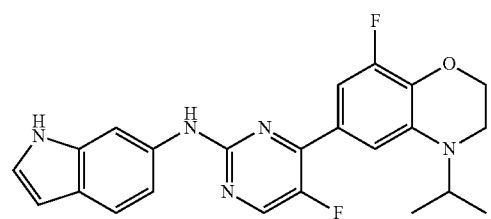 [SMILES: CC(C)N1CCOc2c(F)cc(-c3nc(Nc4ccc5cc[nH]c5c4)ncc3F)cc21] |
| 189 | 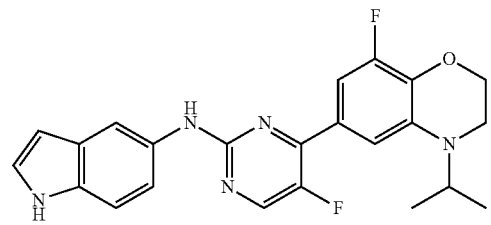 [SMILES: CC(C)N1CCOc2c(F)cc(-c3nc(Nc4ccc5[nH]ccc5c4)ncc3F)cc21] |
| 190 | 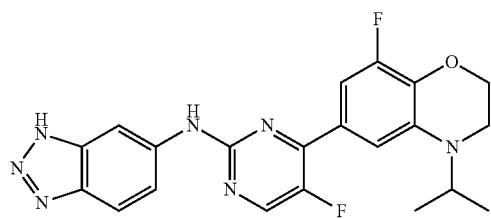 [SMILES: CC(C)N1CCOc2c(F)cc(-c3nc(Nc4ccc5nn[nH]c5c4)ncc3F)cc21] |
| 191 | 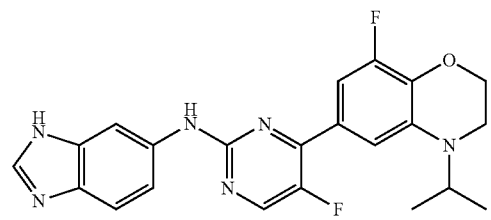 |
| 192 | 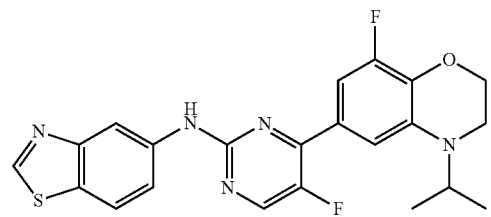 |

TABLE 1-continued
| Compound No. | Structure |
|---|---|
| 193 | 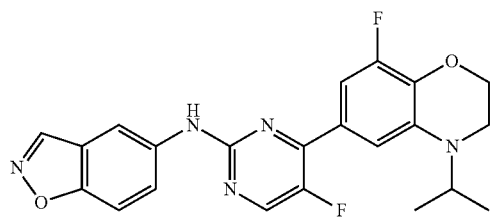 |
| 194 | 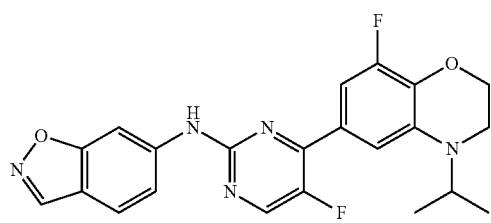 |
| 195 | 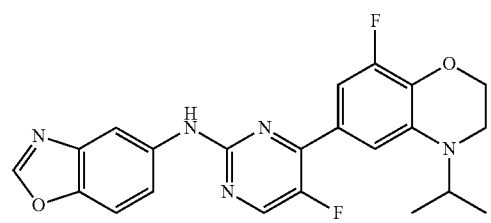 [SMILES: CC(C)N1CCOc2c(F)cc(-c3nc(Nc4ccc5scnc5c4)ncc3F)cc21] |
| 196 | 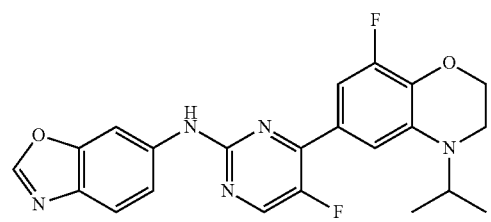 [SMILES: CC(C)N1CCOc2c(F)cc(-c3nc(Nc4ccc5ncoc5c4)ncc3F)cc21] |
| 197 | 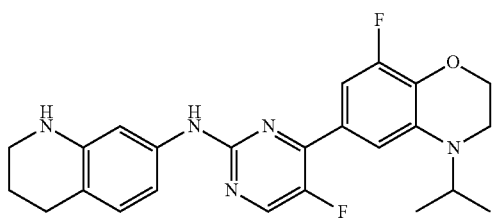 |
| 198 | 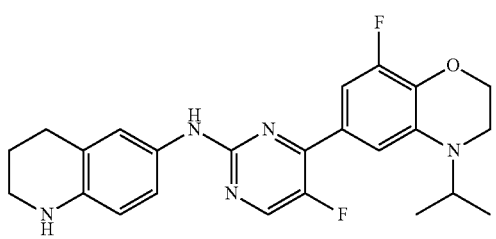 [SMILES: CC(C)N1CCOc2c(F)cc(-c3nc(Nc4ccc5c(c4)CCCN5)ncc3F)cc21] |

TABLE 1-continued

| Compound No. | Structure |
|---|---|
| 199 | (structure) |
| 200 | (structure) |
| 201 | (structure) |
| 202 | (structure) |
| 203 | (structure) |
| 204 | (structure) |

TABLE 1-continued
| Compound No. | Structure |
|---|---|
| 205 | 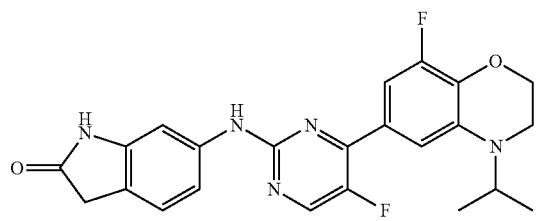 [SMILES: CC(C)N1CCOc2c(F)cc(-c3nc(Nc4ccc5c(c4)NC(=O)C5)ncc3F)cc21] |
| 206 | 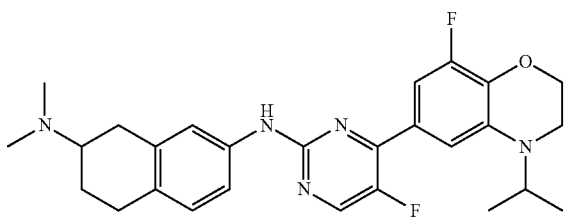 [SMILES: CC(C)N1CCOc2c(F)cc(-c3nc(Nc4ccc5c(c4)CC(N(C)C)CC5)ncc3F)cc21] |
| 207 | 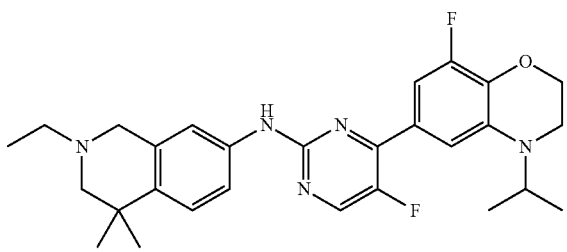 [SMILES: CCN1Cc2cc(Nc3ncc(F)c(-c4cc(F)c5c(c4)N(C(C)C)CCO5)n3)ccc2C(C)(C)C1] |
| 208 | 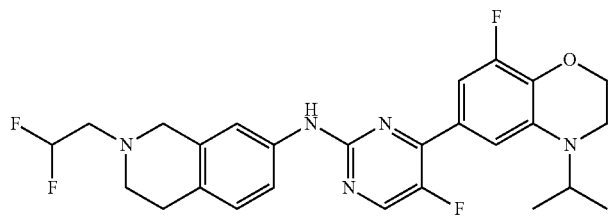 [SMILES: CC(C)N1CCOc2c(F)cc(-c3nc(Nc4ccc5c(c4)CN(CC(F)F)CC5)ncc3F)cc21] |
| 209 | 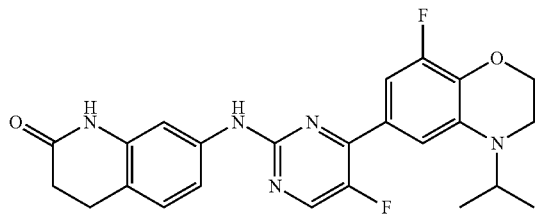 [SMILES: CC(C)N1CCOc2c(F)cc(-c3nc(Nc4ccc5c(c4)NC(=O)CC5)ncc3F)cc21] |
| 210 | 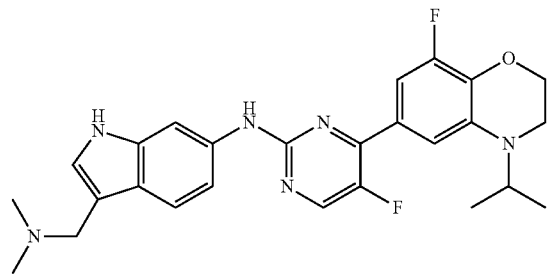 [SMILES: CC(C)N1CCOc2c(F)cc(-c3nc(Nc4ccc5c(CN(C)C)c[nH]c5c4)ncc3F)cc21] |

TABLE 1-continued
| Compound No. | Structure |
|---|---|
| 211 | 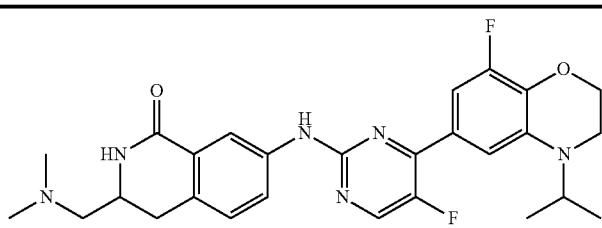 |
| 212 | 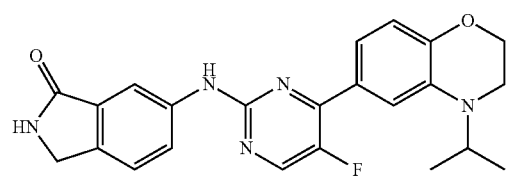 [SMILES: CC(C)N1CCOc2ccc(-c3nc(Nc4ccc5c(c4)C(=O)NC5)ncc3F)cc21] |
| 213 | 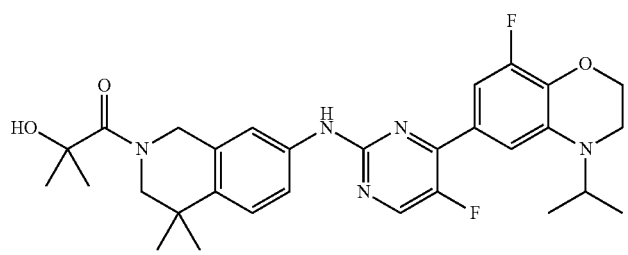 [SMILES: CC(C)N1CCOc2c(F)cc(-c3nc(Nc4ccc5c(c4)CN(C(=O)C(C)(C)O)CC5(C)C)ncc3F)cc21] |
| 214 | 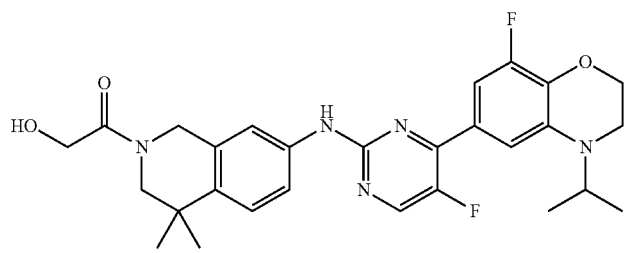 [SMILES: CC(C)N1CCOc2c(F)cc(-c3nc(Nc4ccc5c(c4)CN(C(=O)CO)CC5(C)C)ncc3F)cc21] |
| 215 | 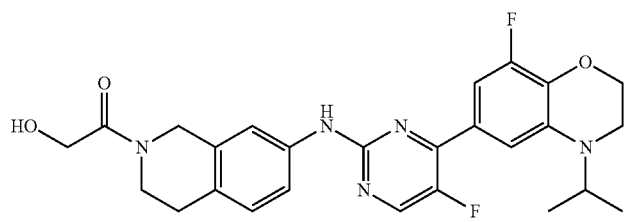 [SMILES: CC(C)N1CCOc2c(F)cc(-c3nc(Nc4ccc5c(c4)CN(C(=O)CO)CC5)ncc3F)cc21] |
| 216 | 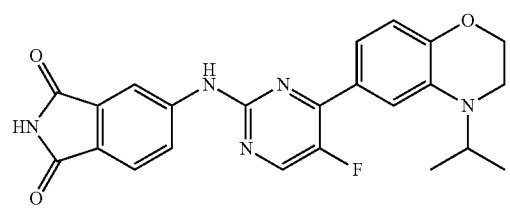 [SMILES: CC(C)N1CCOc2ccc(-c3nc(Nc4ccc5c(c4)C(=O)NC5=O)ncc3F)cc21] |
| 217 | 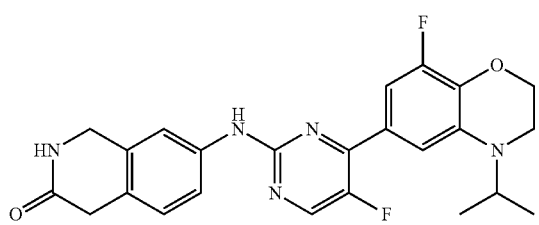 [SMILES: CC(C)N1CCOc2c(F)cc(-c3nc(Nc4ccc5c(c4)CNC(=O)C5)ncc3F)cc21] |

TABLE 1-continued
| Compound No. | Structure |
|---|---|
| 218 | 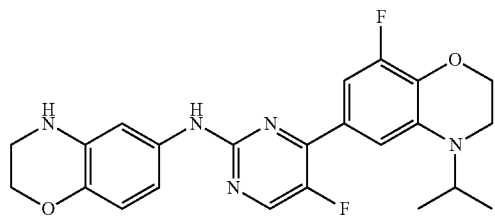 [SMILES: CC(C)N1CCOc2c(F)cc(-c3nc(Nc4ccc5c(c4)NCCO5)ncc3F)cc21] |
| 219 | 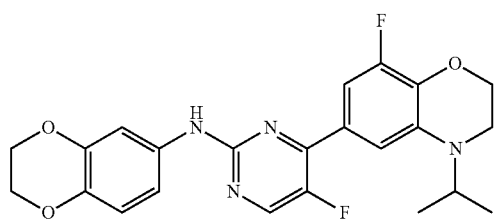 [SMILES: CC(C)N1CCOc2c(F)cc(-c3nc(Nc4ccc5c(c4)OCCO5)ncc3F)cc21] |
| 220 | 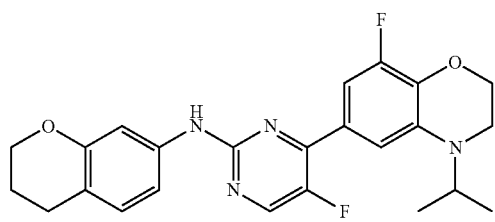 [SMILES: CC(C)N1CCOc2c(F)cc(-c3nc(Nc4ccc5c(c4)OCCC5)ncc3F)cc21] |
| 221 | 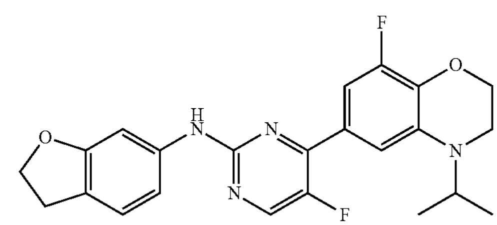 [SMILES: CC(C)N1CCOc2c(F)cc(-c3nc(Nc4ccc5c(c4)OCC5)ncc3F)cc21] |
| 222 | 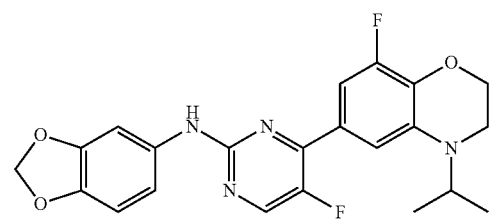 [SMILES: CC(C)N1CCOc2c(F)cc(-c3nc(Nc4ccc5c(c4)OCO5)ncc3F)cc21] |
| 223 | 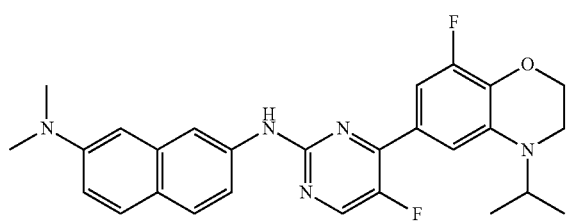 [SMILES: CC(C)N1CCOc2c(F)cc(-c3nc(Nc4ccc5ccc(N(C)C)cc5c4)ncc3F)cc21] |

TABLE 1-continued
| Compound No. | Structure |
|---|---|
| 224 | 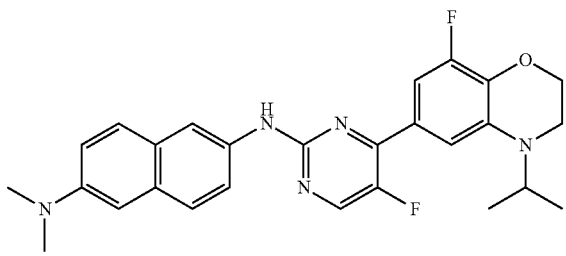 [SMILES: CC(C)N1CCOc2c(F)cc(-c3nc(Nc4ccc5cc(N(C)C)ccc5c4)ncc3F)cc21] |
| 225 | 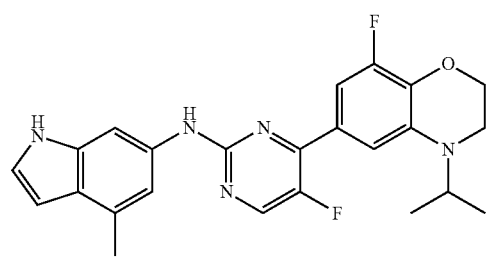 [SMILES: Cc1cc(Nc2ncc(F)c(-c3cc(F)c4c(c3)N(C(C)C)CCO4)n2)cc2[nH]ccc12] |
| 226 | 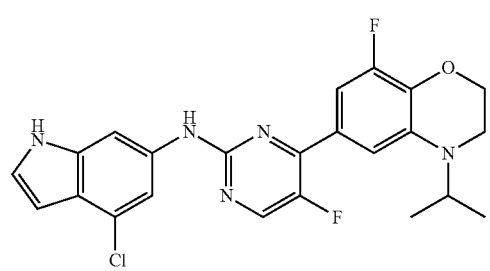 [SMILES: CC(C)N1CCOc2c(F)cc(-c3nc(Nc4cc(Cl)c5cc[nH]c5c4)ncc3F)cc21] |
| 227 | 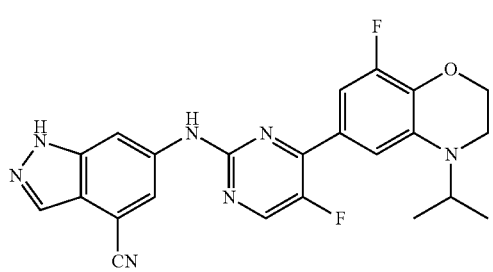 [SMILES: CC(C)N1CCOc2c(F)cc(-c3nc(Nc4cc(C#N)c5cn[nH]c5c4)ncc3F)cc21] |
| 228 | 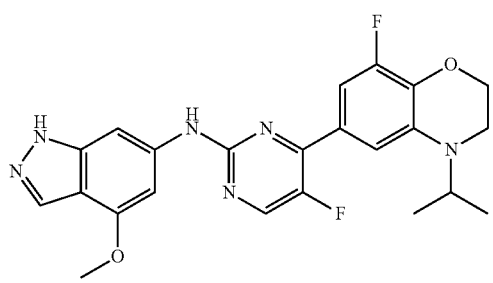 [SMILES: COc1cc(Nc2ncc(F)c(-c3cc(F)c4c(c3)N(C(C)C)CCO4)n2)cc2[nH]ncc12] |

TABLE 1-continued
| Compound No. | Structure |
|---|---|
| 229 | 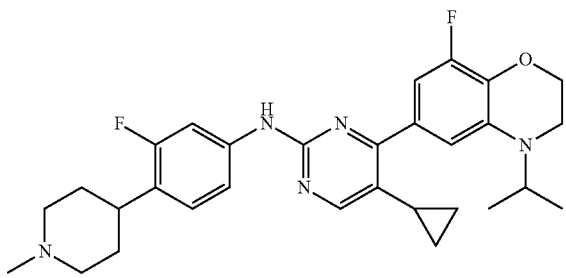 [SMILES: CC(C)N1CCOc2c(F)cc(-c3nc(Nc4ccc(C5CCN(C)CC5)c(F)c4)ncc3C3CC3)cc21] |
| 230 | 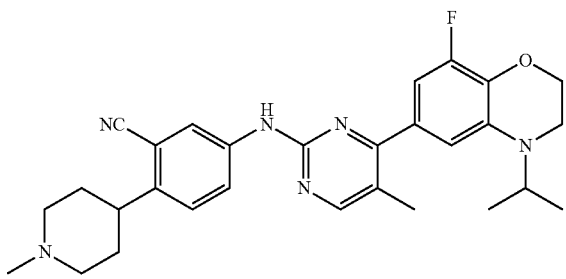 [SMILES: Cc1cnc(Nc2ccc(C3CCN(C)CC3)c(C#N)c2)nc1-c1cc(F)c2c(c1)N(C(C)C)CCO2] |
| 231 | 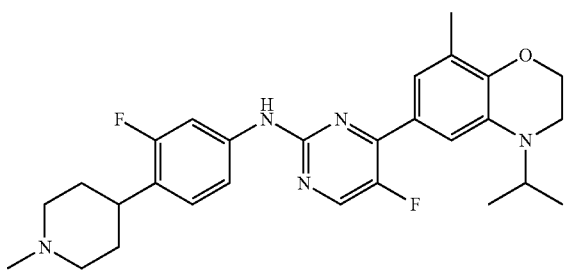 [SMILES: Cc1cc(-c2nc(Nc3ccc(C4CCN(C)CC4)c(F)c3)ncc2F)cc2c1OCCN2C(C)C] |
| 232 | 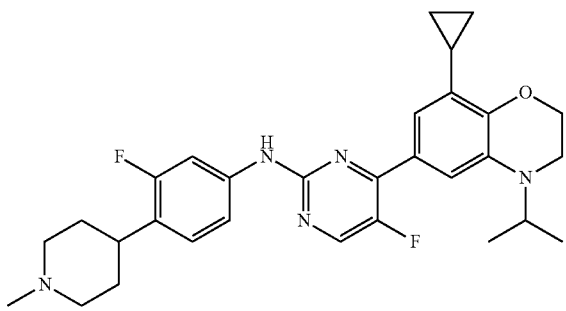 [SMILES: CC(C)N1CCOc2c(C3CC3)cc(-c3nc(Nc4ccc(C5CCN(C)CC5)c(F)c4)ncc3F)cc21] |
| 233 | 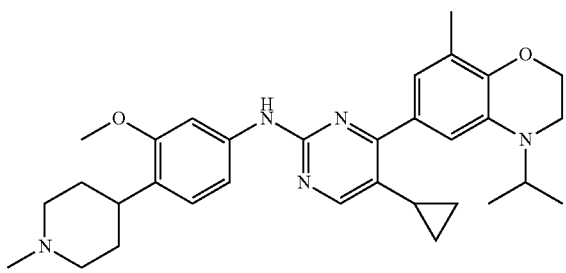 [SMILES: COc1cc(Nc2ncc(C3CC3)c(-c3cc(C)c4c(c3)N(C(C)C)CCO4)n2)ccc1C1CCN(C)CC1] |

TABLE 1-continued
| Compound No. | Structure |
|---|---|
| 234 | 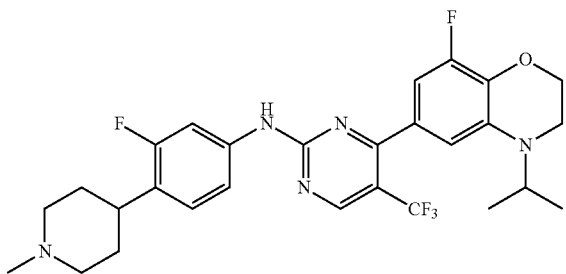 [SMILES: CC(C)N1CCOc2c(F)cc(-c3nc(Nc4ccc(C5CCN(C)CC5)c(F)c4)ncc3C(F)(F)F)cc21] |
| 235 | 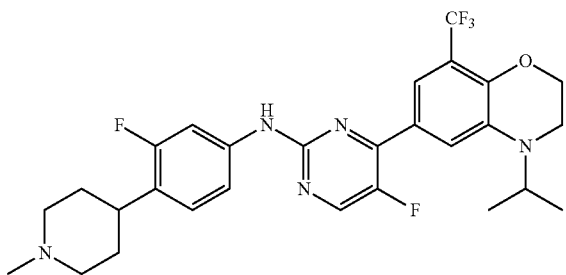 |
| 236 | 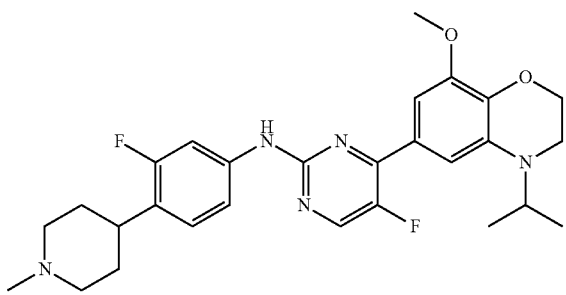 [SMILES: COc1cc(-c2nc(Nc3ccc(C4CCN(C)CC4)c(F)c3)ncc2F)cc2c1OCCN2C(C)C] |
| 237 | 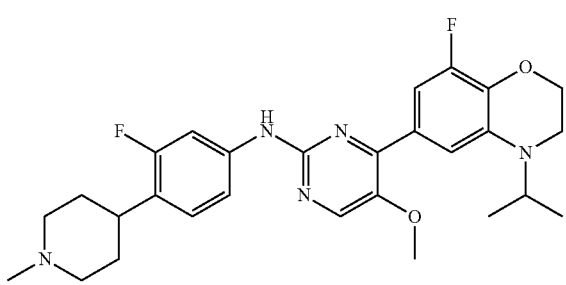 [SMILES: COc1cnc(Nc2ccc(C3CCN(C)CC3)c(F)c2)nc1-c1cc(F)c2c(c1)N(C(C)C)CCO2] |
| 238 | 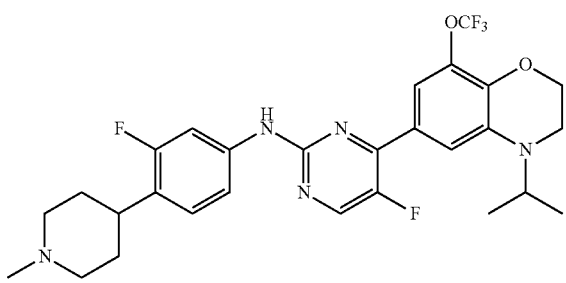 [SMILES: CC(C)N1CCOc2c(OC(F)(F)F)cc(-c3nc(Nc4ccc(C5CCN(C)CC5)c(F)c4)ncc3F)cc21] |

TABLE 1-continued
| Compound No. | Structure |
|---|---|
| 239 | 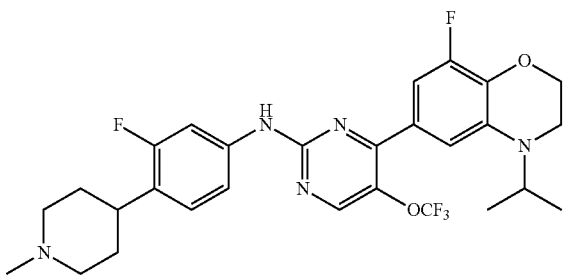 [SMILES: CC(C)N1CCOc2c(F)cc(-c3nc(Nc4ccc(C5CCN(C)CC5)c(F)c4)ncc3OC(F)(F)F)cc21] |
| 240 | 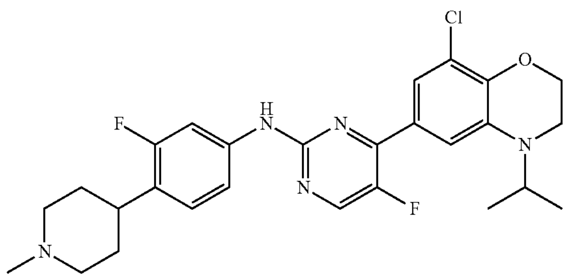 |
| 241 | 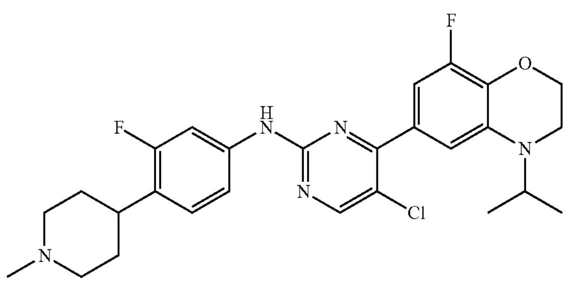 [SMILES: CC(C)N1CCOc2c(F)cc(-c3nc(Nc4ccc(C5CCN(C)CC5)c(F)c4)ncc3Cl)cc21] |
| 242 | 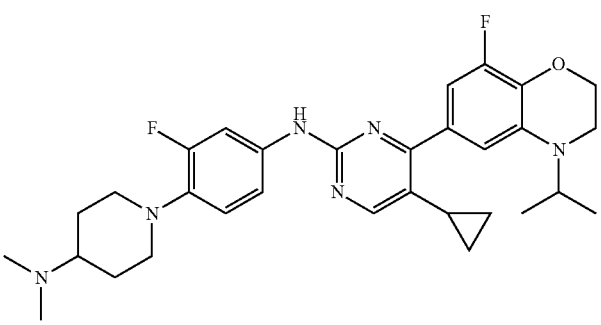 [SMILES: CC(C)N1CCOc2c(F)cc(-c3nc(Nc4ccc(N5CCC(N(C)C)CC5)c(F)c4)ncc3C3CC3)cc21] |
| 243 | 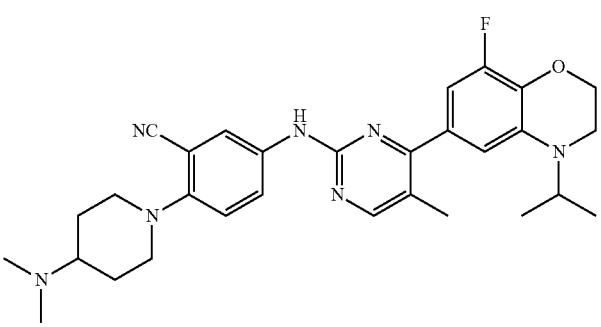 [SMILES: Cc1cnc(Nc2ccc(N3CCC(N(C)C)CC3)c(C#N)c2)nc1-c1cc(F)c2c(c1)N(C(C)C)CCO2] |

TABLE 1-continued
| Compound No. | Structure |
|---|---|
| 244 | 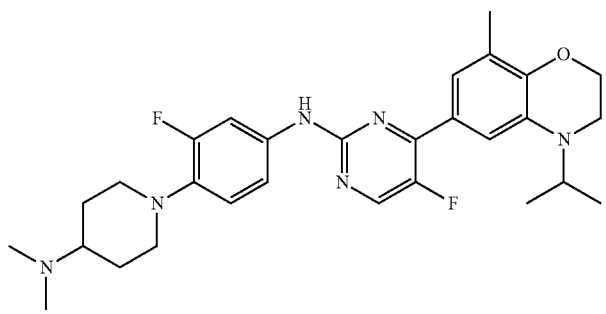 [SMILES: Cc1cc(-c2nc(Nc3ccc(N4CCC(N(C)C)CC4)c(F)c3)ncc2F)cc2c1OCCN2C(C)C] |
| 245 | 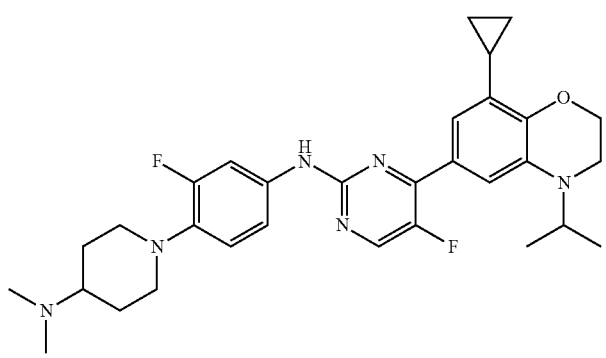 [SMILES: CC(C)N1CCOc2c(C3CC3)cc(-c3nc(Nc4ccc(N5CCC(N(C)C)CC5)c(F)c4)ncc3F)cc21] |
| 246 | 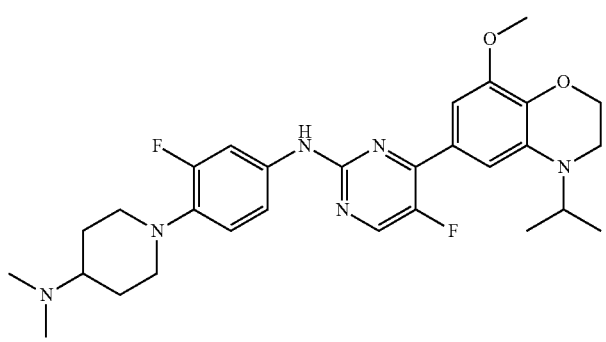 [SMILES: COc1cc(-c2nc(Nc3ccc(N4CCC(N(C)C)CC4)c(F)c3)ncc2F)cc2c1OCCN2C(C)C] |
| 247 | 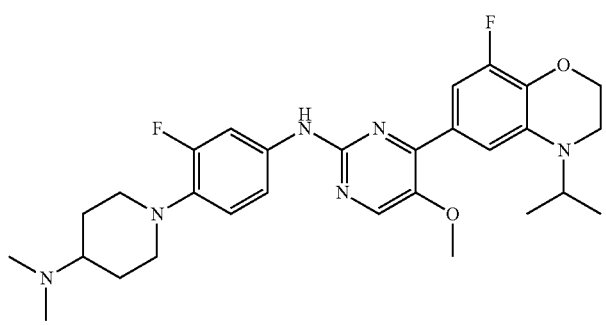 [SMILES: COc1cnc(Nc2ccc(N3CCC(N(C)C)CC3)c(F)c2)nc1-c1cc(F)c2c(c1)N(C(C)C)CCO2] |

TABLE 1-continued
| Compound No. | Structure |
|---|---|
| 248 | 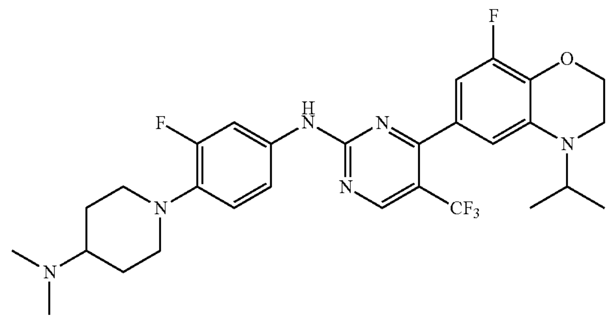 |
| 249 | 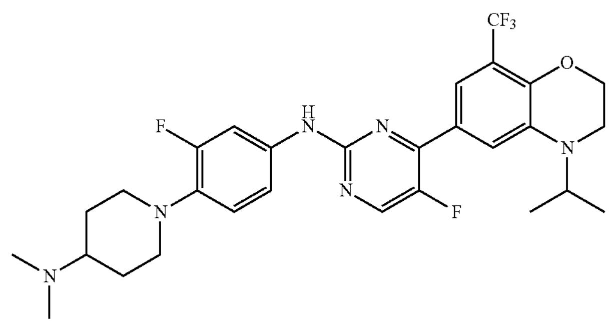 [SMILES: CC(C)N1CCOc2c1cc(-c1nc(Nc3ccc(N4CCC(N(C)C)CC4)c(F)c3)ncc1F)cc2C(F)(F)F] |
| 250 | 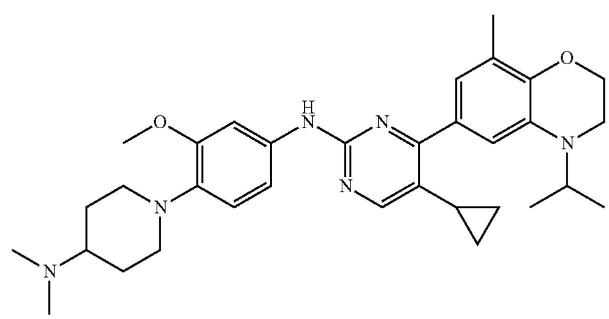 [SMILES: COc1cc(Nc2ncc(C3CC3)c(-c3cc(C)c4c(c3)N(C(C)C)CCO4)n2)ccc1N1CCC(N(C)C)CC1] |
| 251 | 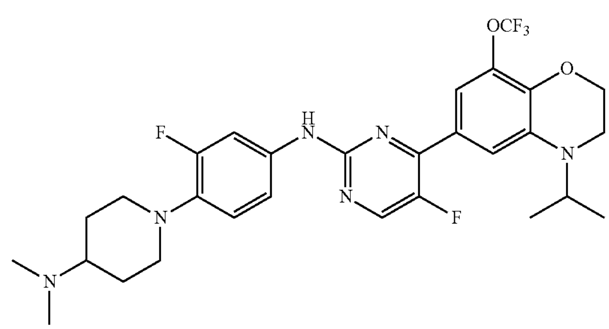 [SMILES: CC(C)N1CCOc2c(OC(F)(F)F)cc(-c3nc(Nc4ccc(N5CCC(N(C)C)CC5)c(F)c4)ncc3F)cc21] |

TABLE 1-continued

| Compound No. | Structure |
|---|---|
| 252 | 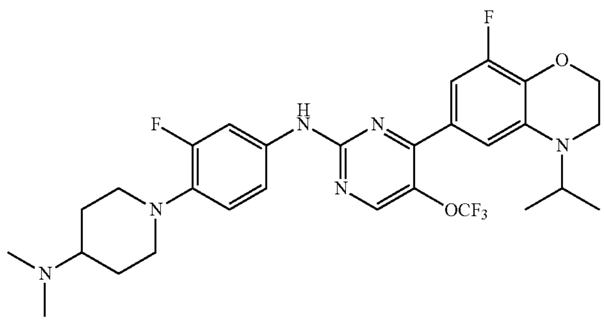 [SMILES: CC(C)N1CCOc2c(F)cc(-c3nc(Nc4ccc(N5CCC(N(C)C)CC5)c(F)c4)ncc3OC(F)(F)F)cc21] |
| 253 | 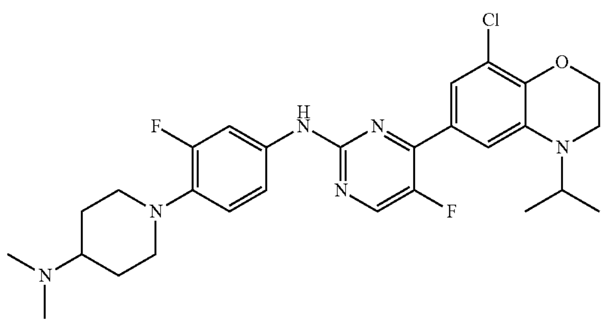 |
| 254 | 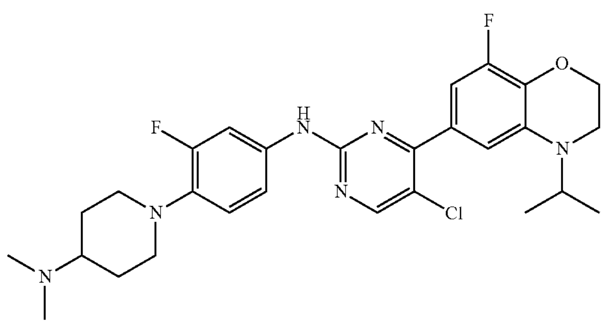 |
| 255 | 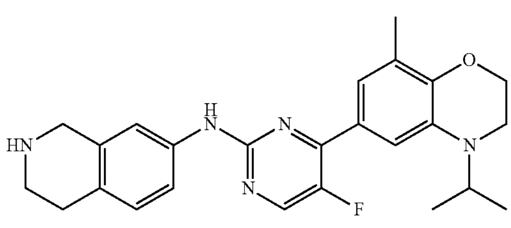 [SMILES: Cc1cc(-c2nc(Nc3ccc4c(c3)CNCC4)ncc2F)cc2c1OCCN2C(C)C] |
| 256 | 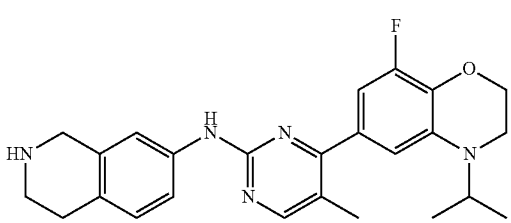 [SMILES: Cc1cnc(Nc2ccc3c(c2)CNCC3)nc1-c1cc(F)c2c(c1)N(C(C)C)CCO2] |

TABLE 1-continued
| Compound No. | Structure |
|---|---|
| 257 | 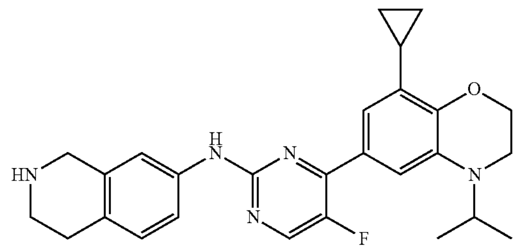 [SMILES: CC(C)N1CCOc2c(C3CC3)cc(-c3nc(Nc4ccc5c(c4)CNCC5)ncc3F)cc21] |
| 258 | 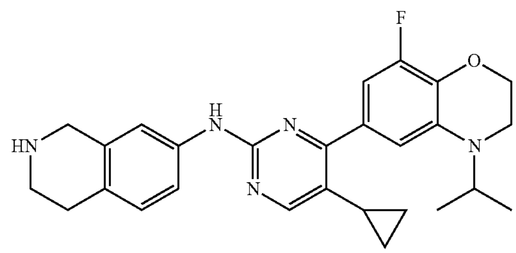 [SMILES: CC(C)N1CCOc2c(F)cc(-c3nc(Nc4ccc5c(c4)CNCC5)ncc3C3CC3)cc21] |
| 259 | 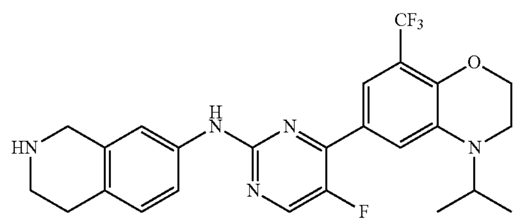 [SMILES: CC(C)N1CCOc2c1cc(-c1nc(Nc3ccc4c(c3)CNCC4)ncc1F)cc2C(F)(F)F] |
| 260 | 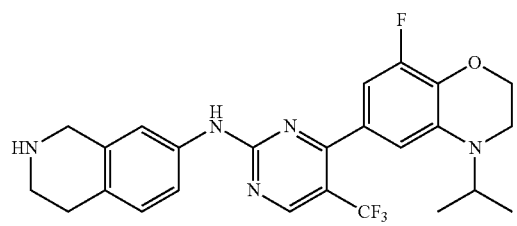 [SMILES: CC(C)N1CCOc2c(F)cc(-c3nc(Nc4ccc5c(c4)CNCC5)ncc3C(F)(F)F)cc21] |
| 261 | 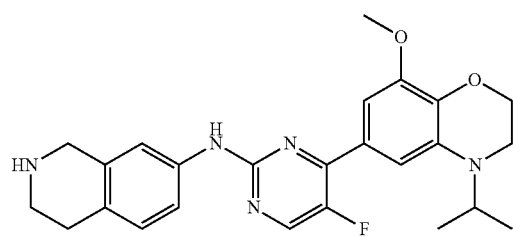 [SMILES: COc1cc(-c2nc(Nc3ccc4c(c3)CNCC4)ncc2F)cc2c1OCCN2C(C)C] |
| 262 | 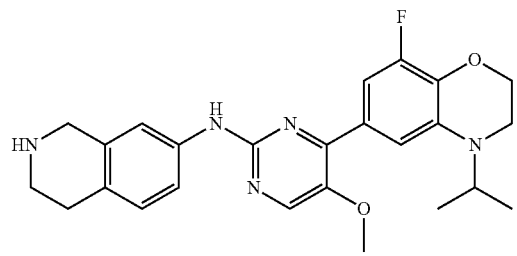 [SMILES: COc1cnc(Nc2ccc3c(c2)CNCC3)nc1-c1cc(F)c2c(c1)N(C(C)C)CCO2] |

TABLE 1-continued

| Compound No. | Structure |
|---|---|
| 263 | 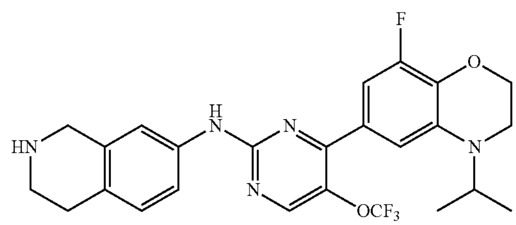 [SMILES: CC(C)N1CCOc2c(F)cc(-c3nc(Nc4ccc5c(c4)CNCC5)ncc3OC(F)(F)F)cc21] |
| 264 | 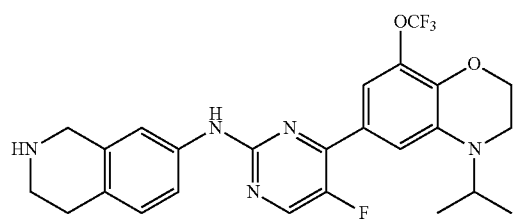 [SMILES: CC(C)N1CCOc2c(OC(F)(F)F)cc(-c3nc(Nc4ccc5c(c4)CNCC5)ncc3F)cc21] |
| 265 | 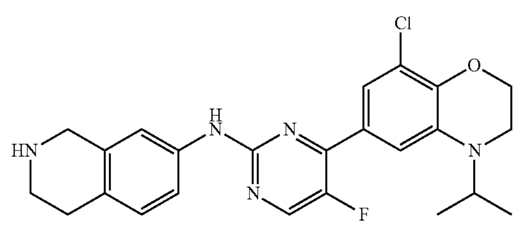 |
| 266 | 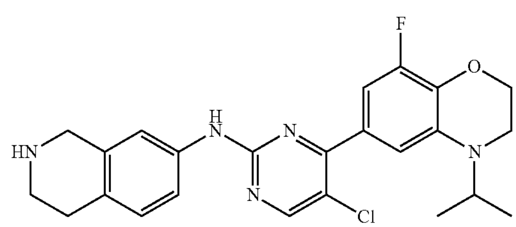 [SMILES: CC(C)N1CCOc2c(F)cc(-c3nc(Nc4ccc5c(c4)CNCC5)ncc3Cl)cc21] |
| 267 | 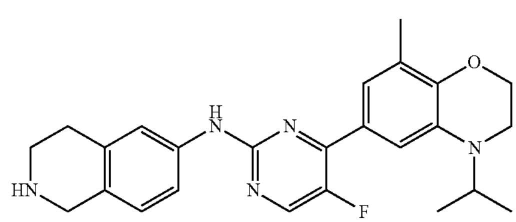 [SMILES: Cc1cc(-c2nc(Nc3ccc4c(c3)CCNC4)ncc2F)cc2c1OCCN2C(C)C] |
| 268 | 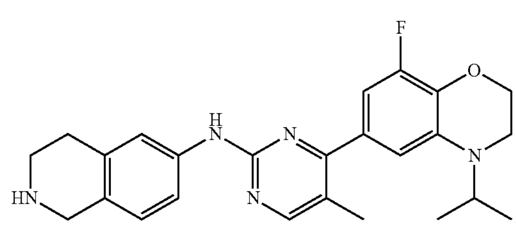 [SMILES: Cc1cnc(Nc2ccc3c(c2)CCNC3)nc1-c1cc(F)c2c(c1)N(C(C)C)CCO2] |

TABLE 1-continued
| Compound No. | Structure |
|---|---|
| 269 | 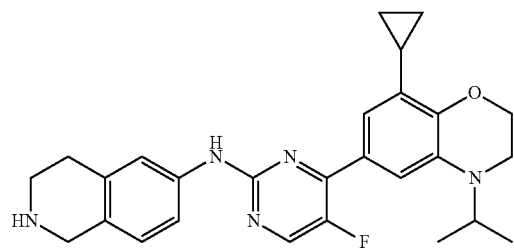 [SMILES: CC(C)N1CCOc2c(C3CC3)cc(-c3nc(Nc4ccc5c(c4)CCNC5)ncc3F)cc21] |
| 270 | 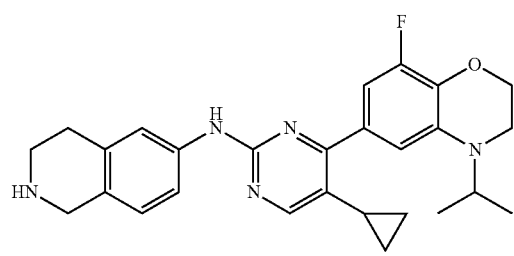 [SMILES: CC(C)N1CCOc2c(F)cc(-c3nc(Nc4ccc5c(c4)CCNC5)ncc3C3CC3)cc21] |
| 271 | 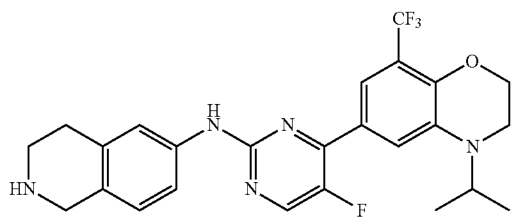 |
| 272 | 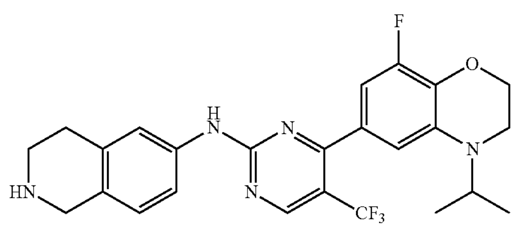 [SMILES: CC(C)N1CCOc2c(F)cc(-c3nc(Nc4ccc5c(c4)CCNC5)ncc3C(F)(F)F)cc21] |
| 273 | 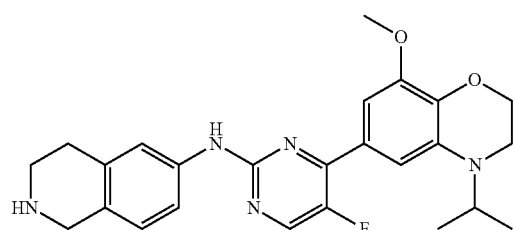 |
| 274 | 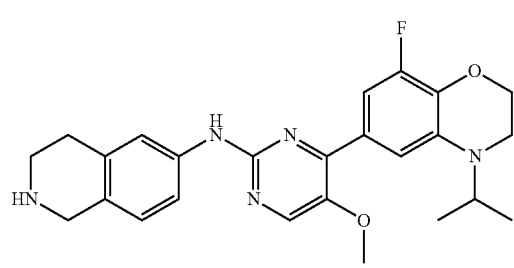 [SMILES: COc1cnc(Nc2ccc3c(c2)CCNC3)nc1-c1cc(F)c2c(c1)N(C(C)C)CCO2] |

TABLE 1-continued
| Compound No. | Structure |
|---|---|
| 275 | 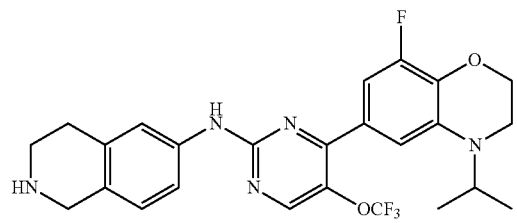 |
| 276 | 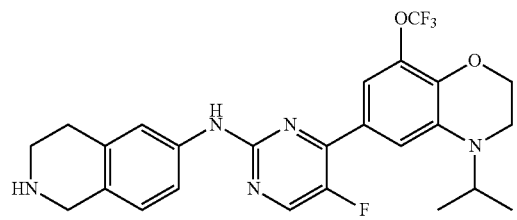 [SMILES: CC(C)N1CCOc2c(OC(F)(F)F)cc(-c3nc(Nc4ccc5c(c4)CCNC5)ncc3F)cc21] |
| 277 | 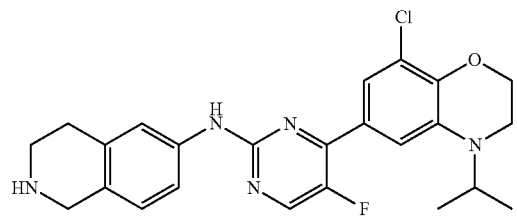 [SMILES: CC(C)N1CCOc2c(Cl)cc(-c3nc(Nc4ccc5c(c4)CCNC5)ncc3F)cc21] |
| 278 | 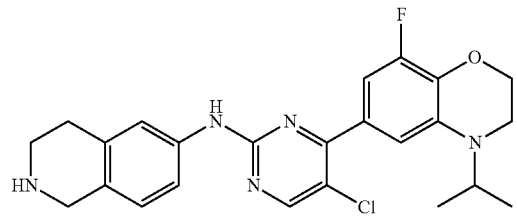 [SMILES: CC(C)N1CCOc2c(F)cc(-c3nc(Nc4ccc5c(c4)CCNC5)ncc3Cl)cc21] |
| 279 | 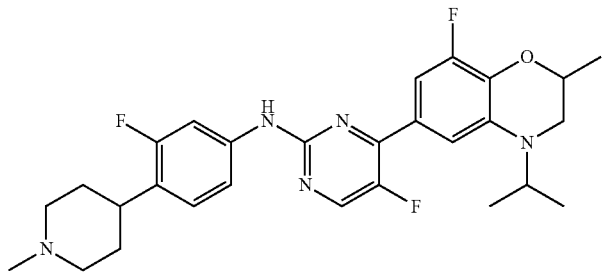 |
| 280 | 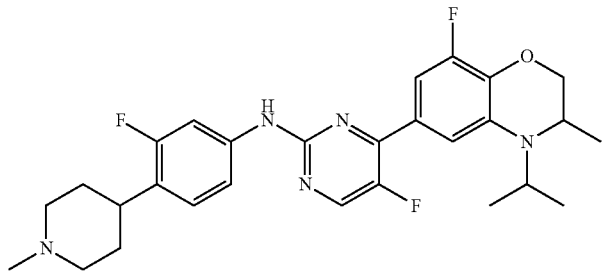 |

TABLE 1-continued
| Compound No. | Structure |
|---|---|
| 281 | 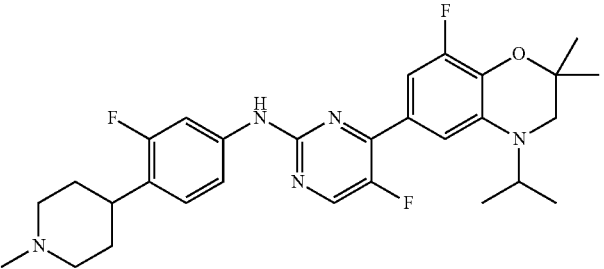 |
| 282 | 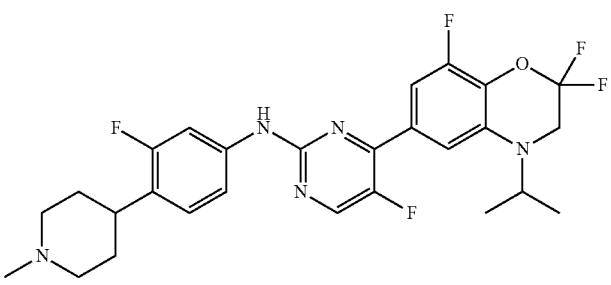 [SMILES: CC(C)N1CC(F)(F)Oc2c(F)cc(-c3nc(Nc4ccc(C5CCN(C)CC5)c(F)c4)ncc3F)cc21] |
| 283 | 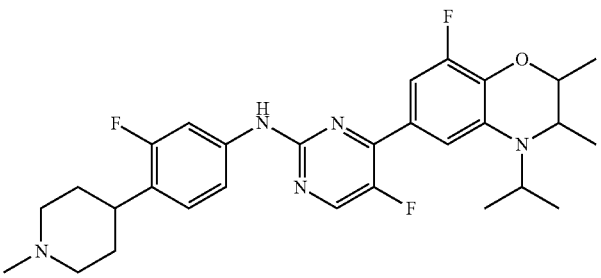 |
| 284 | 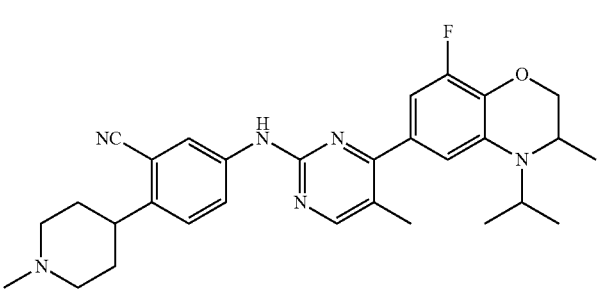 |
| 285 | 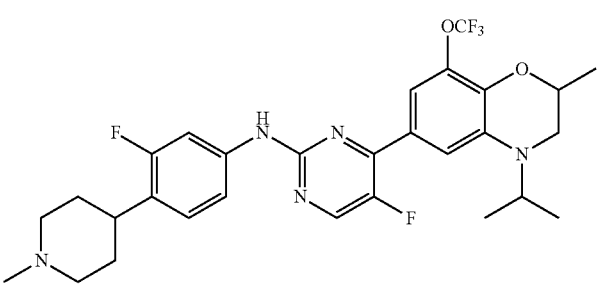 |

TABLE 1-continued
| Compound No. | Structure |
|---|---|
| 286 | 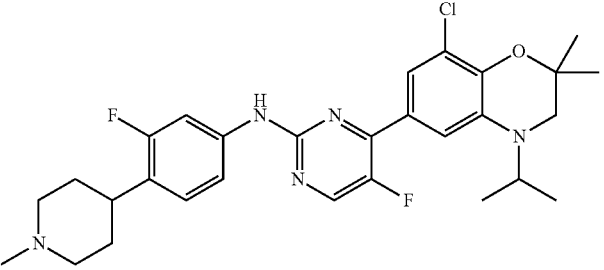 |
| 287 | 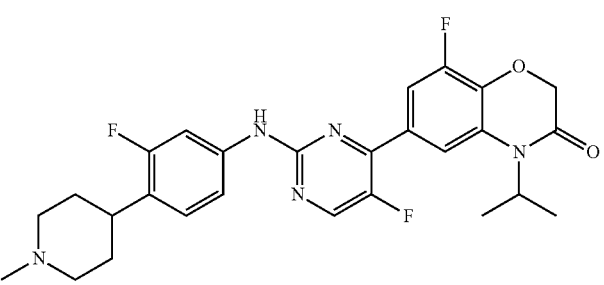 [SMILES: CC(C)N1C(=O)COc2c(F)cc(-c3nc(Nc4ccc(C5CCN(C)CC5)c(F)c4)ncc3F)cc21] |
| 288 | 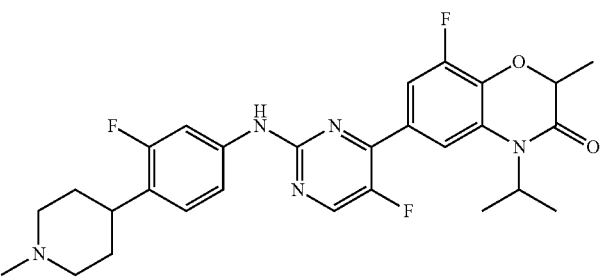 |
| 289 | 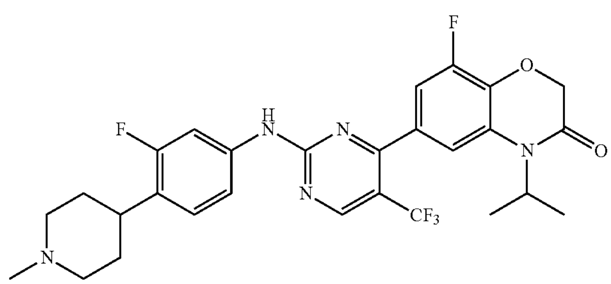 |
| 290 | 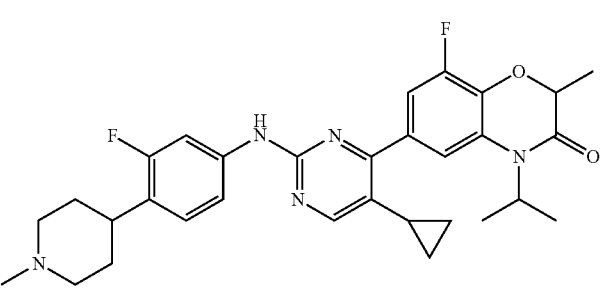 [SMILES: CC1Oc2c(F)cc(-c3nc(Nc4ccc(C5CCN(C)CC5)c(F)c4)ncc3C3CC3)cc2N(C(C)C)C1=O] |

TABLE 1-continued
| Compound No. | Structure |
|---|---|
| 291 | 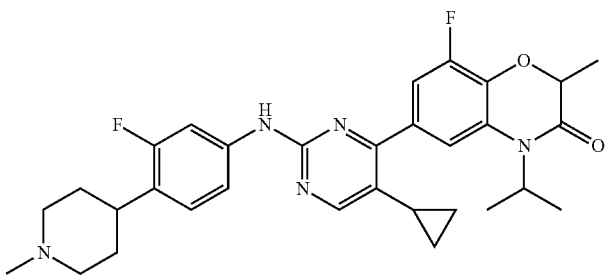 [SMILES: CC1Oc2c(F)cc(-c3nc(Nc4ccc(C5CCN(C)CC5)c(F)c4)ncc3C3CC3)cc2N(C(C)C)C1=O] |
| 292 | 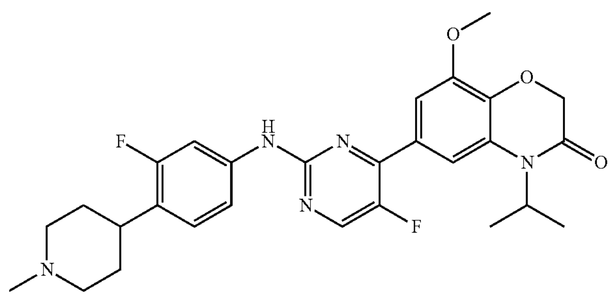 [SMILES: COc1cc(-c2nc(Nc3ccc(C4CCN(C)CC4)c(F)c3)ncc2F)cc2c1OCC(=O)N2C(C)C] |
| 293 | 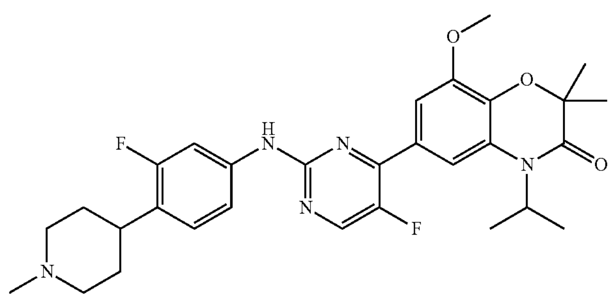 |
| 294 | 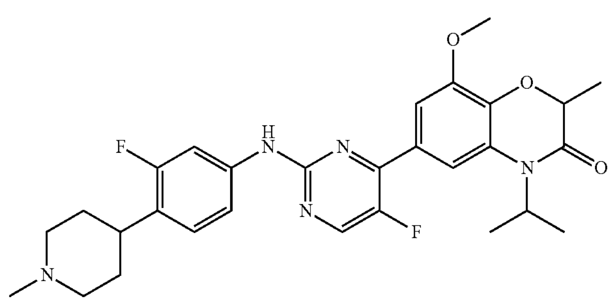 [SMILES: COc1cc(-c2nc(Nc3ccc(C4CCN(C)CC4)c(F)c3)ncc2F)cc2c1OC(C)C(=O)N2C(C)C] |
| 295 | 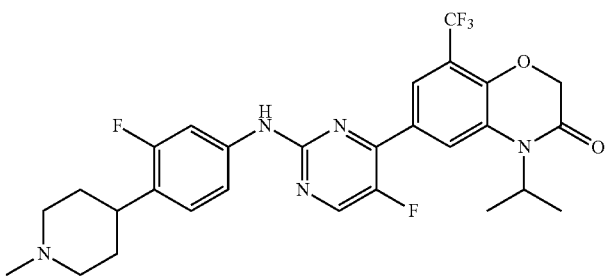 [SMILES: CC(C)N1C(=O)COc2c1cc(-c1nc(Nc3ccc(C4CCN(C)CC4)c(F)c3)ncc1F)cc2C(F)(F)F] |

TABLE 1-continued
| Compound No. | Structure |
|---|---|
| 296 | 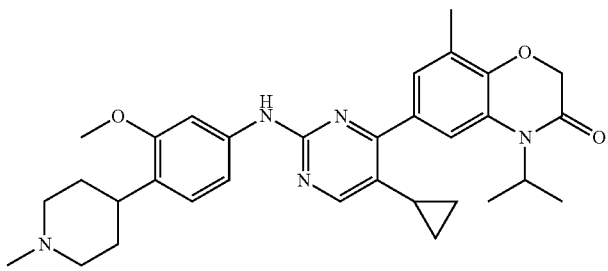 [SMILES: COc1cc(Nc2ncc(C3CC3)c(-c3cc(C)c4c(c3)N(C(C)C)C(=O)CO4)n2)ccc1C1CCN(C)CC1] |
| 297 | 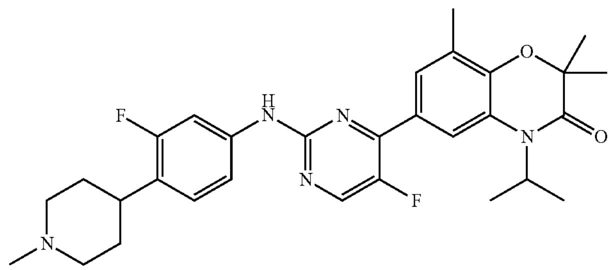 |
| 298 | 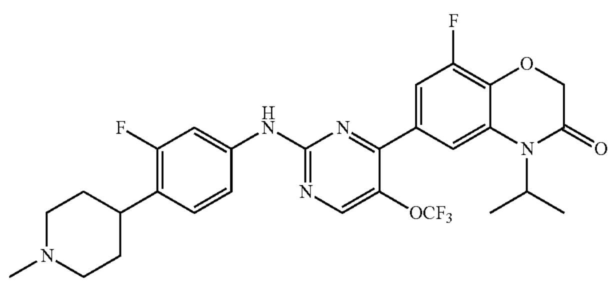 [SMILES: CC(C)N1C(=O)COc2c(F)cc(-c3nc(Nc4ccc(C5CCN(C)CC5)c(F)c4)ncc3OC(F)(F)F)cc21] |
| 299 | 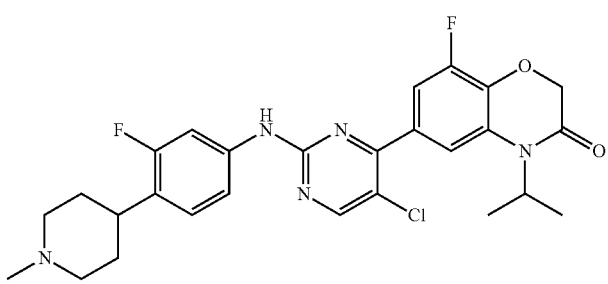 [SMILES: CC(C)N1C(=O)COc2c(F)cc(-c3nc(Nc4ccc(C5CCN(C)CC5)c(F)c4)ncc3Cl)cc21] |
| 300 | 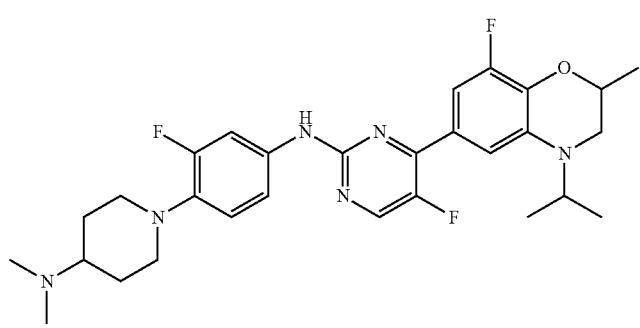 |

TABLE 1-continued
| Compound No. | Structure |
|---|---|
| 301 | 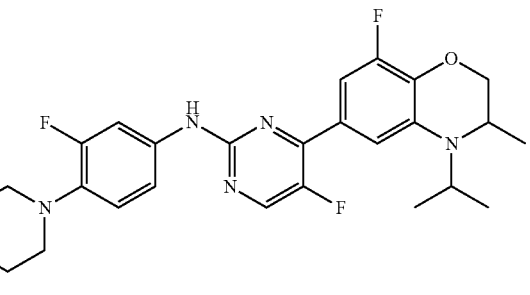 |
| 302 | 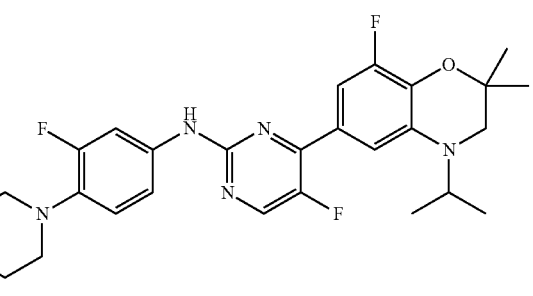 |
| 303 | 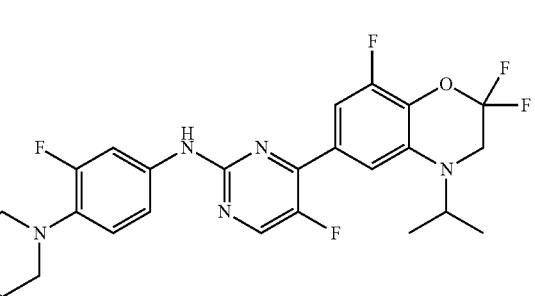 |
| 304 | 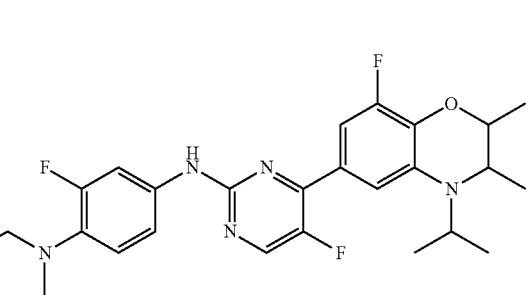 |

TABLE 1-continued
| Compound No. | | Structure |
|---|---|---|
| 305 | | 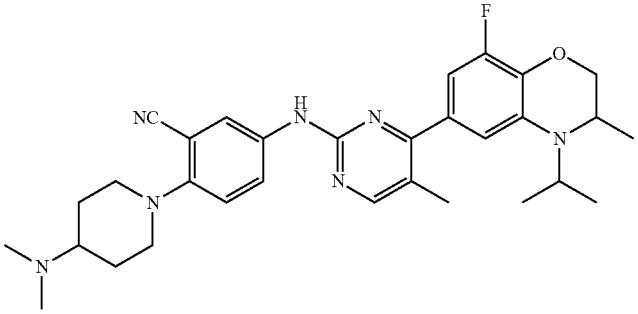 |
| 306 | lp;2p | 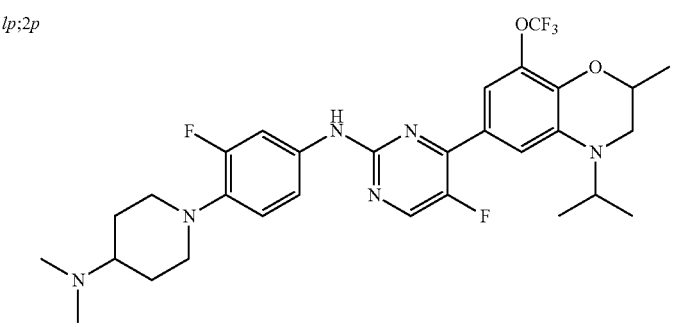 |
| 307 | | 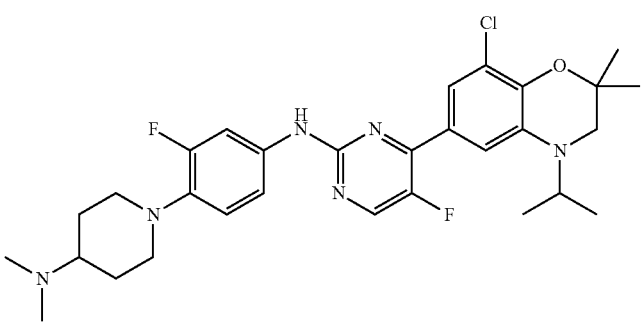 |
| 308 | | 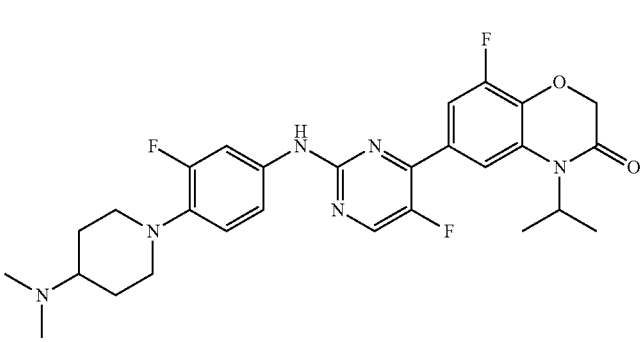 [SMILES: CC(C)N1C(=O)COc2c(F)cc(-c3nc(Nc4ccc(N5CCC(N(C)C)CC5)c(F)c4)ncc3F)cc21] |

TABLE 1-continued

| Compound No. | Structure |
|---|---|
| 309 | 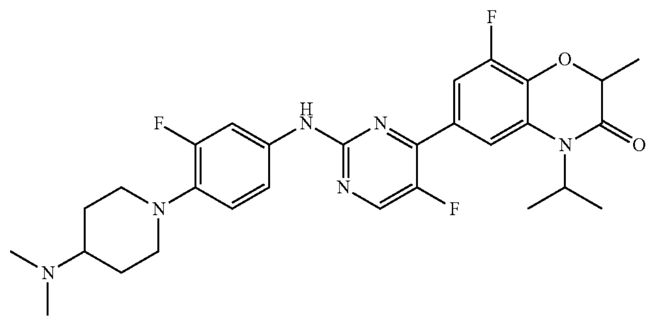 |
| 310 | 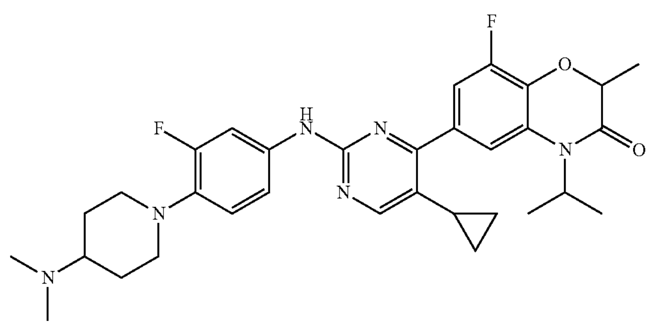 |
| 311 | 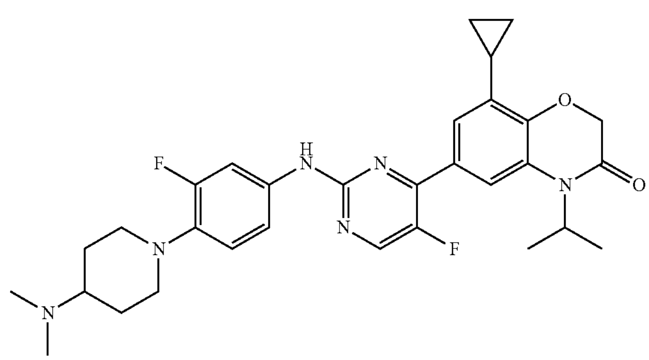 [SMILES: CC(C)N1C(=O)COc2c(C3CC3)cc(-c3nc(Nc4ccc(N5CCC(N(C)C)CC5)c(F)c4)ncc3F)cc21] |
| 312 | 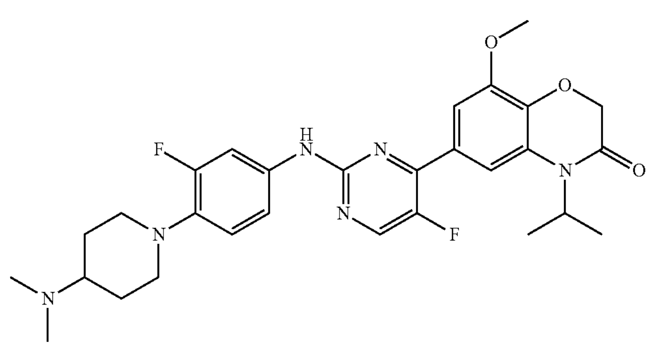 [SMILES: COc1cc(-c2nc(Nc3ccc(N4CCC(N(C)C)CC4)c(F)c3)ncc2F)cc2c1OCC(=O)N2C(C)C] |

TABLE 1-continued

| Compound No. | Structure |
|---|---|
| 313 | 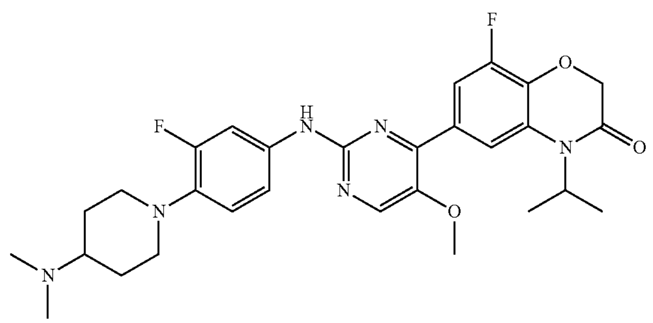 [SMILES: COc1cnc(Nc2ccc(N3CCC(N(C)C)CC3)c(F)c2)nc1-c1cc(F)c2c(c1)N(C(C)C)C(=O)CO2] |
| 314 | 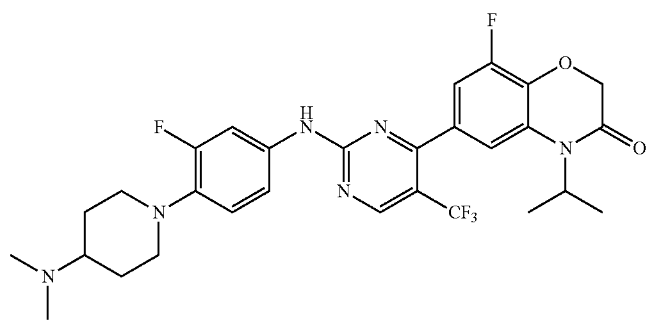 |
| 315 | 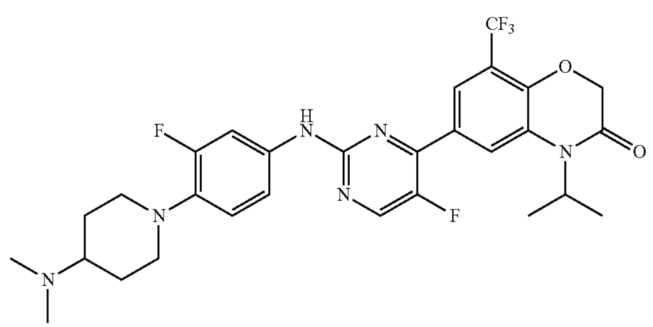 [SMILES: CC(C)N1C(=O)COc2c1cc(-c1nc(Nc3ccc(N4CCC(N(C)C)CC4)c(F)c3)ncc1F)cc2C(F)(F)F] |
| 316 | 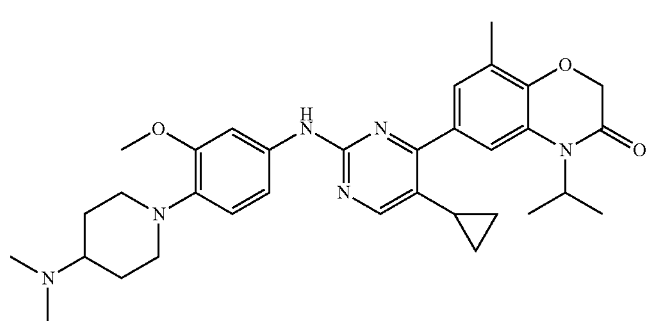 [SMILES: COc1cc(Nc2ncc(C3CC3)c(-c3cc(C)c4c(c3)N(C(C)C)C(=O)CO4)n2)ccc1N1CCC(N(C)C)CC1] |

TABLE 1-continued
| Compound No. | Structure |
|---|---|
| 317 | 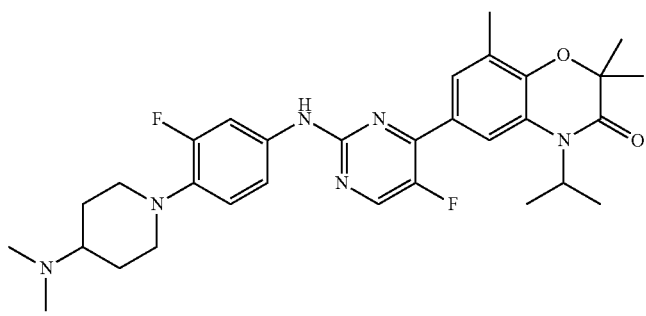 |
| 318 | 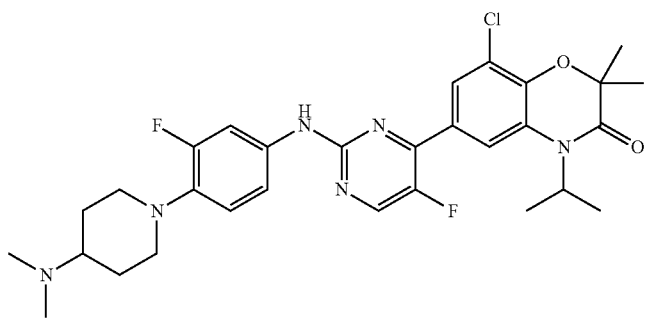 |
| 319 | 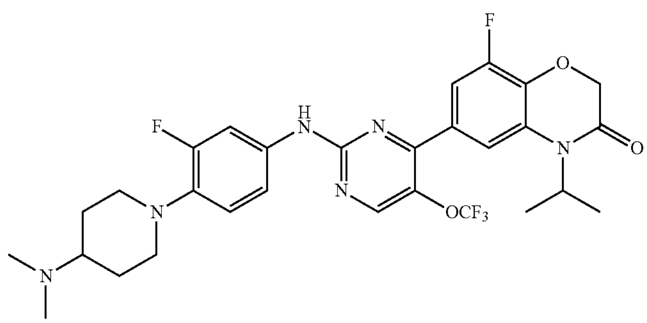 [SMILES: CC(C)N1C(=O)COc2c(F)cc(-c3nc(Nc4ccc(N5CCC(N(C)C)CC5)c(F)c4)ncc3OC(F)(F)F)cc21] |
| 320 | 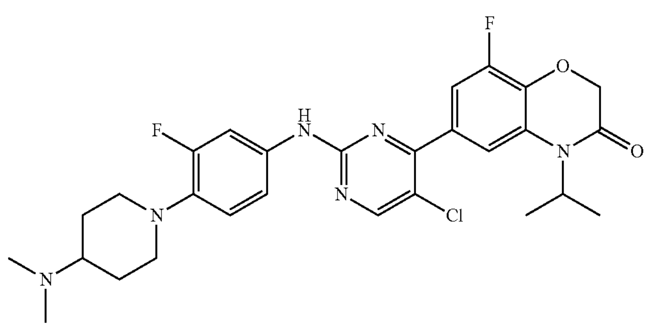 [SMILES: CC(C)N1C(=O)COc2c(F)cc(-c3nc(Nc4ccc(N5CCC(N(C)C)CC5)c(F)c4)ncc3Cl)cc21] |
| 321 | 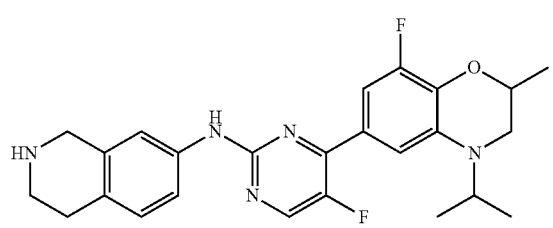 [SMILES: CC1CN(C(C)C)c2cc(-c3nc(Nc4ccc5c(c4)CNCC5)ncc3F)cc(F)c2O1] |

TABLE 1-continued
| Compound No. | Structure |
|---|---|
| 322 | 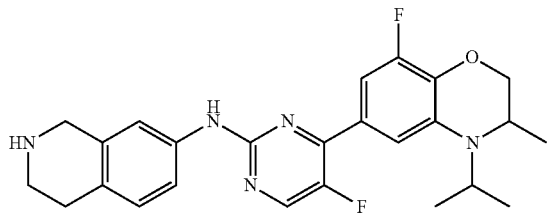 [SMILES: CC(C)N1c2cc(-c3nc(Nc4ccc5c(c4)CNCC5)ncc3F)cc(F)c2OCC1C] |
| 323 | 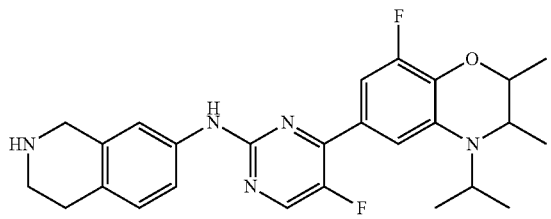 [SMILES: CC1Oc2c(F)cc(-c3nc(Nc4ccc5c(c4)CNCC5)ncc3F)cc2N(C(C)C)C1C] |
| 324 | 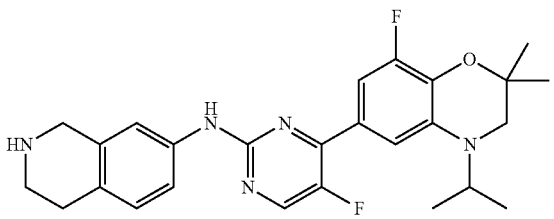 [SMILES: CC(C)N1CC(C)(C)Oc2c(F)cc(-c3nc(Nc4ccc5c(c4)CNCC5)ncc3F)cc21] |
| 325 | 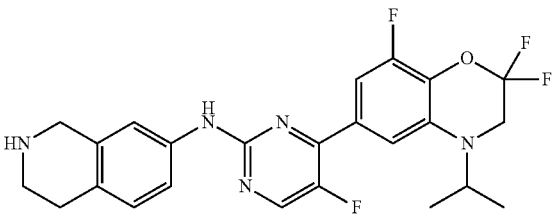 [SMILES: CC(C)N1CC(F)(F)Oc2c(F)cc(-c3nc(Nc4ccc5c(c4)CNCC5)ncc3F)cc21] |
| 326 | 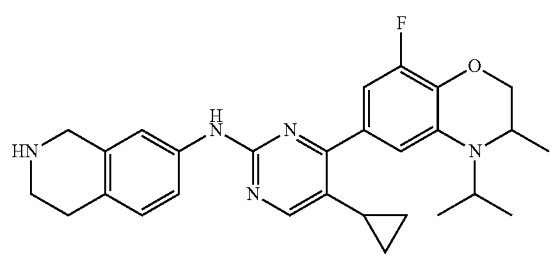 [SMILES: CC(C)N1c2cc(-c3nc(Nc4ccc5c(c4)CNCC5)ncc3C3CC3)cc(F)c2OCC1C] |
| 327 | 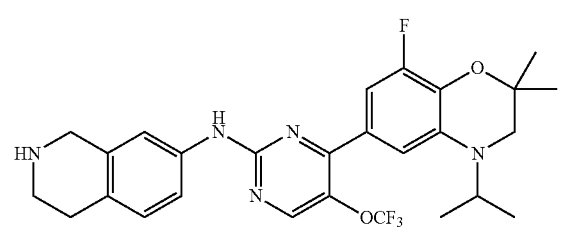 [SMILES: CC(C)N1CC(C)(C)Oc2c(F)cc(-c3nc(Nc4ccc5c(c4)CNCC5)ncc3OC(F)(F)F)cc21] |

TABLE 1-continued
| Compound No. | Structure |
|---|---|
| 328 | 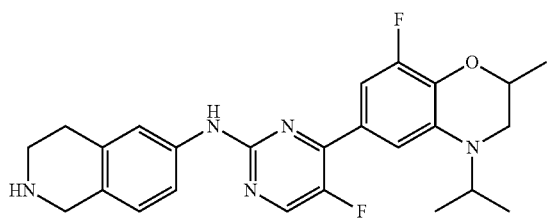 [SMILES: CC1CN(C(C)C)c2cc(-c3nc(Nc4ccc5c(c4)CCNC5)ncc3F)cc(F)c2O1] |
| 329 | 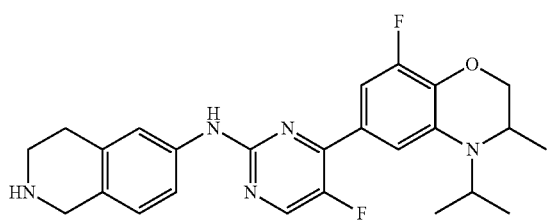 [SMILES: CC(C)N1c2cc(-c3nc(Nc4ccc5c(c4)CCNC5)ncc3F)cc(F)c2OCC1C] |
| 330 | 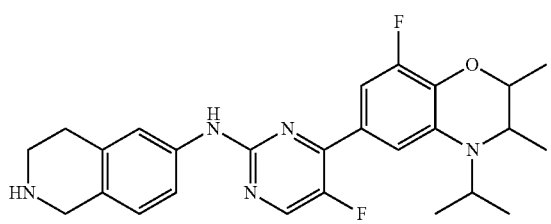 [SMILES: CC1Oc2c(F)cc(-c3nc(Nc4ccc5c(c4)CCNC5)ncc3F)cc2N(C(C)C)C1C] |
| 331 | 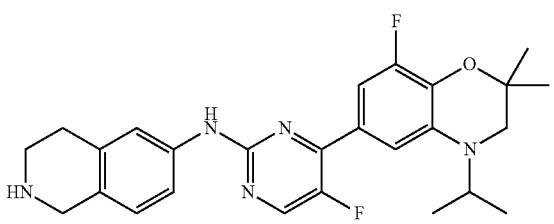 [SMILES: CC(C)N1CC(C)(C)Oc2c(F)cc(-c3nc(Nc4ccc5c(c4)CCNC5)ncc3F)cc21] |
| 332 | 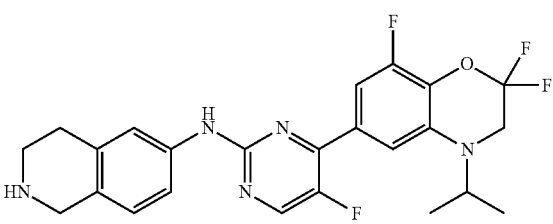 [SMILES: CC(C)N1CC(F)(F)Oc2c(F)cc(-c3nc(Nc4ccc5c(c4)CCNC5)ncc3F)cc21] |
| 333 | 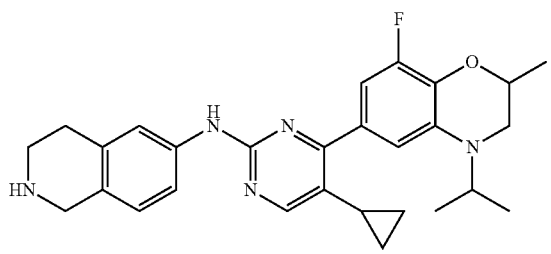 [SMILES: CC1CN(C(C)C)c2cc(-c3nc(Nc4ccc5c(c4)CCNC5)ncc3C3CC3)cc(F)c2O1] |

TABLE 1-continued

| Compound No. | Structure |
|---|---|
| 334 | (structure) |
| 335 | (structure) |
| 336 | (structure) |
| 337 | (structure) |
| 338 | (structure) |
| 339 | (structure) |

TABLE 1-continued
| Compound No. | Structure |
|---|---|
| 340 | 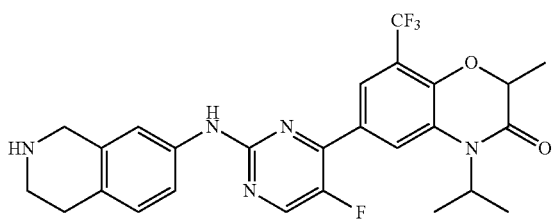 |
| 341 | 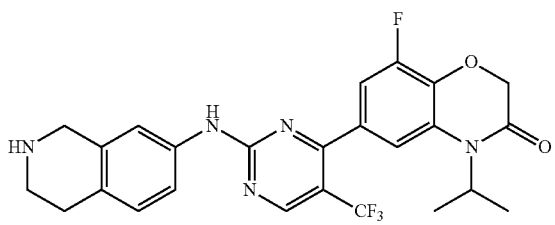 [SMILES: CC(C)N1C(=O)COc2c(F)cc(-c3nc(Nc4ccc5c(c4)CNCC5)ncc3C(F)(F)F)cc21] |
| 342 | 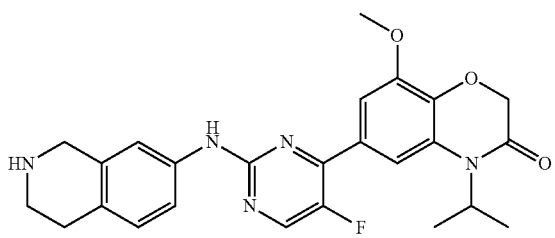 [SMILES: COc1cc(-c2nc(Nc3ccc4c(c3)CNCC4)ncc2F)cc2c1OCC(=O)N2C(C)C] |
| 343 | 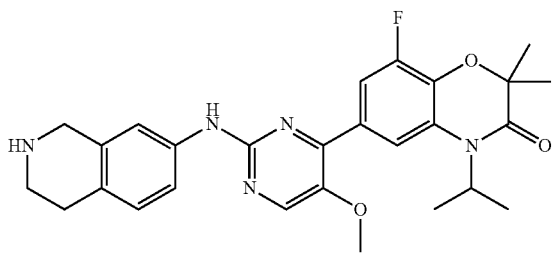 [SMILES: COc1cnc(Nc2ccc3c(c2)CNCC3)nc1-c1cc(F)c2c(c1)N(C(C)C)C(=O)C(C)(C)O2] |
| 344 | 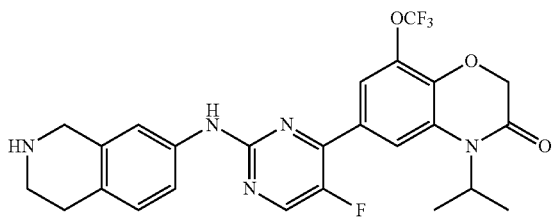 [SMILES: CC(C)N1C(=O)COc2c(OC(F)(F)F)cc(-c3nc(Nc4ccc5c(c4)CNCC5)ncc3F)cc21] |
| 345 | 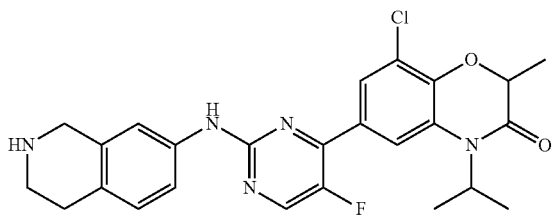 [SMILES: CC1Oc2c(Cl)cc(-c3nc(Nc4ccc5c(c4)CNCC5)ncc3F)cc2N(C(C)C)C1=O] |

TABLE 1-continued
| Compound No. | Structure |
|---|---|
| 346 | 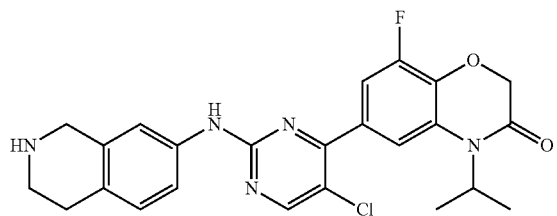 [SMILES: CC(C)N1C(=O)COc2c(F)cc(-c3nc(Nc4ccc5c(c4)CNCC5)ncc3Cl)cc21] |
| 347 | 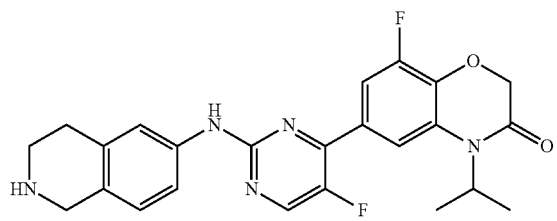 [SMILES: CC(C)N1C(=O)COc2c(F)cc(-c3nc(Nc4ccc5c(c4)CCNC5)ncc3F)cc21] |
| 348 | 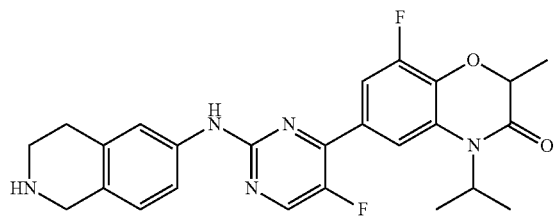 |
| 349 | 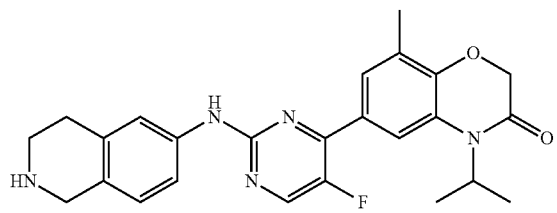 [SMILES: Cc1cc(-c2nc(Nc3ccc4c(c3)CCNC4)ncc2F)cc2c1OCC(=O)N2C(C)C] |
| 350 | 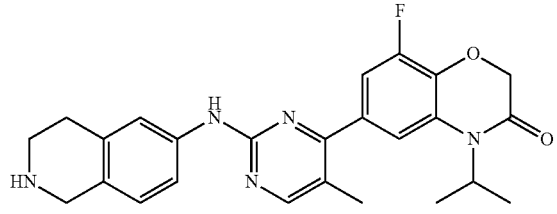 [SMILES: Cc1cnc(Nc2ccc3c(c2)CCNC3)nc1-c1cc(F)c2c(c1)N(C(C)C)C(=O)CO2] |
| 351 | 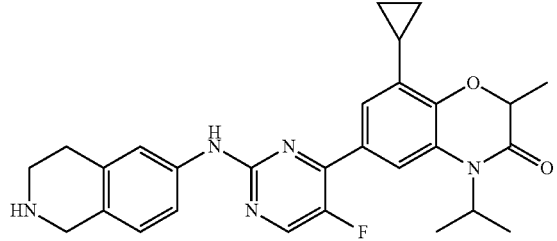 [SMILES: CC1Oc2c(C3CC3)cc(-c3nc(Nc4ccc5c(c4)CCNC5)ncc3F)cc2N(C(C)C)C1=O] |

TABLE 1-continued
| Compound No. | Structure |
|---|---|
| 352 | 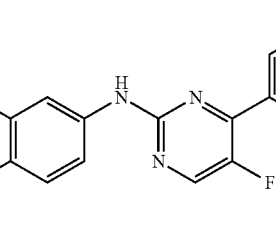 |
| 353 | 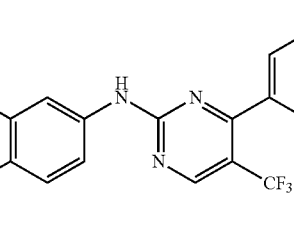 |
| 354 | 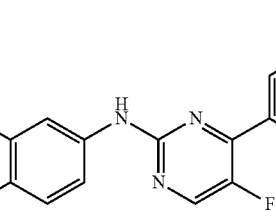 |
| 355 | 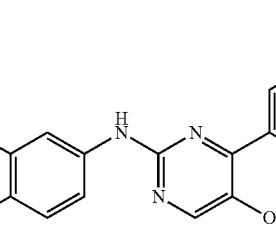 |
| 356 | 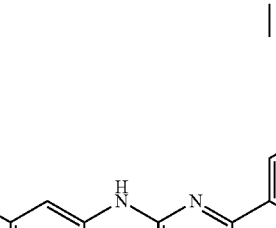 |
| 357 | 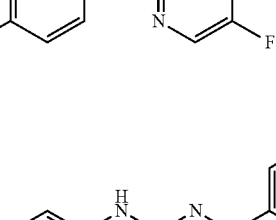 |

TABLE 1-continued

| Compound No. | Structure |
|---|---|
| 358 | 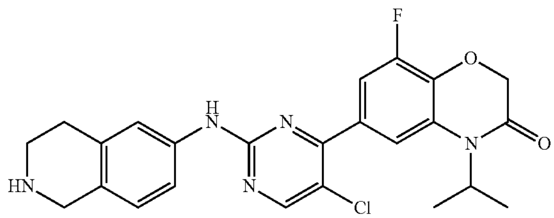 [SMILES: CC(C)N1C(=O)COc2c(F)cc(-c3nc(Nc4ccc5c(c4)CCNC5)ncc3Cl)cc21] |
| 359 | 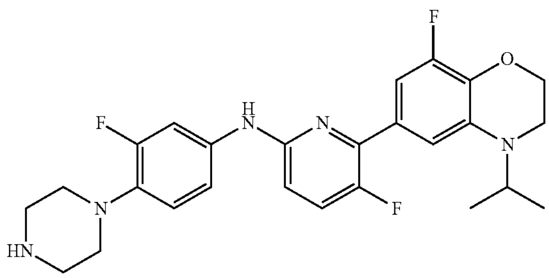 [SMILES: CC(C)N1CCOc2c(F)cc(-c3nc(Nc4ccc(N5CCNCC5)c(F)c4)ccc3F)cc21] |
| 360 | 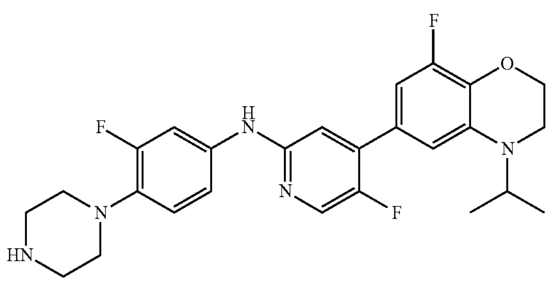 [SMILES: CC(C)N1CCOc2c(F)cc(-c3cc(Nc4ccc(N5CCNCC5)c(F)c4)ncc3F)cc21] |
| 361 | 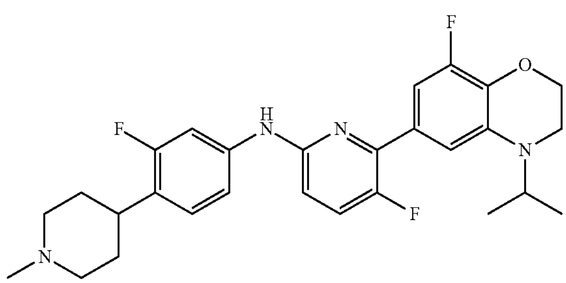 [SMILES: CC(C)N1CCOc2c(F)cc(-c3nc(Nc4ccc(C5CCN(C)CC5)c(F)c4)ccc3F)cc21] |
| 362 | 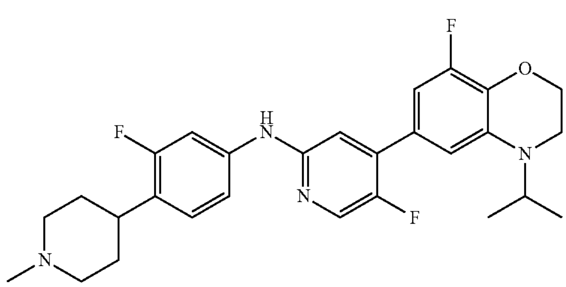 [SMILES: CC(C)N1CCOc2c(F)cc(-c3cc(Nc4ccc(C5CCN(C)CC5)c(F)c4)ncc3F)cc21] |

TABLE 1-continued

| Compound No. | Structure |
|---|---|
| 363 | 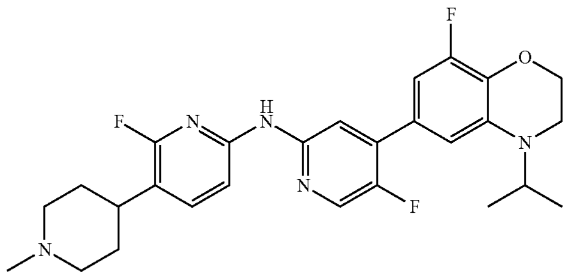 [SMILES: CC(C)N1CCOc2c(F)cc(-c3cc(Nc4ccc(C5CCN(C)CC5)c(F)n4)ncc3F)cc21] |
| 364 | 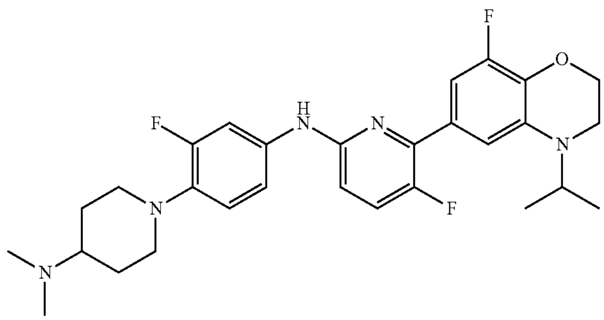 [SMILES: CC(C)N1CCOc2c(F)cc(-c3nc(Nc4ccc(N5CCC(N(C)C)CC5)c(F)c4)ccc3F)cc21] |
| 365 | 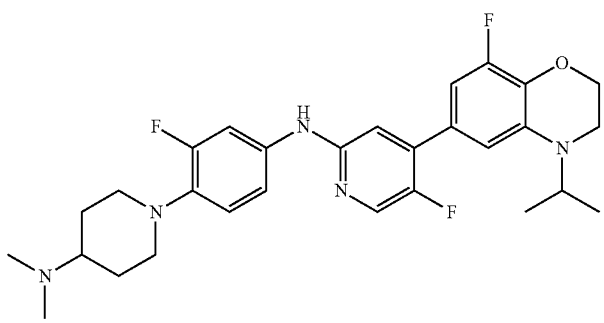 [SMILES: CC(C)N1CCOc2c(F)cc(-c3cc(Nc4ccc(N5CCC(N(C)C)CC5)c(F)c4)ncc3F)cc21] |
| 366 | 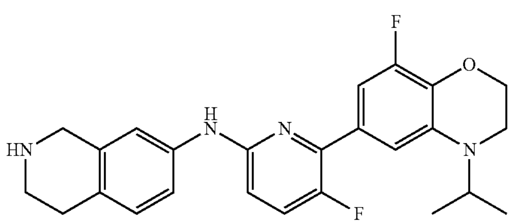 [SMILES: CC(C)N1CCOc2c(F)cc(-c3nc(Nc4ccc5c(c4)CNCC5)ccc3F)cc21] |
| 367 | 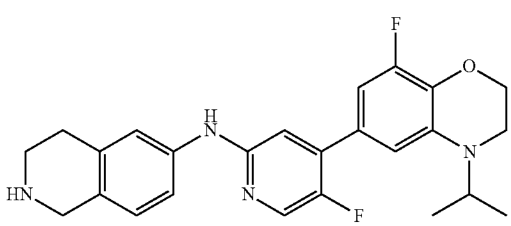 [SMILES: CC(C)N1CCOc2c(F)cc(-c3cc(Nc4ccc5c(c4)CCNC5)ncc3F)cc21] |

TABLE 1-continued
| Compound No. | Structure |
|---|---|
| 368 | 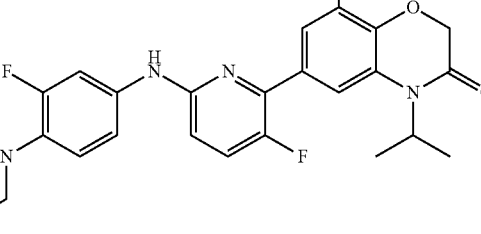 |
| 369 | 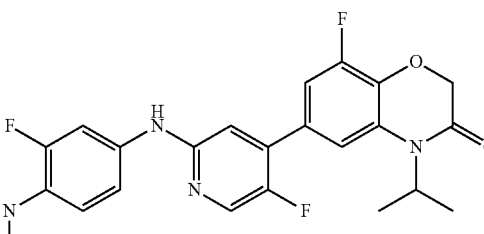 |
| 370 | 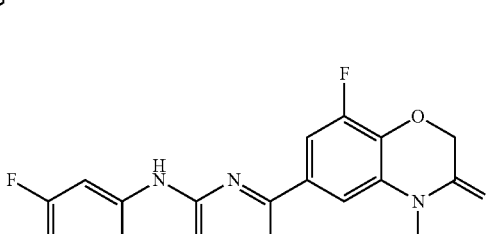 |
| 371 | 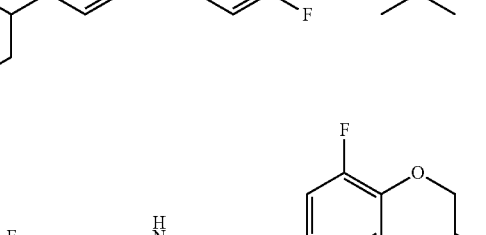 |
| 372 | 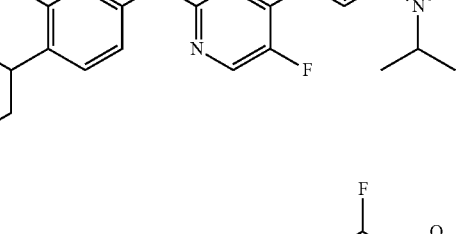 |

TABLE 1-continued

| Compound No. | Structure |
|---|---|
| 373 | 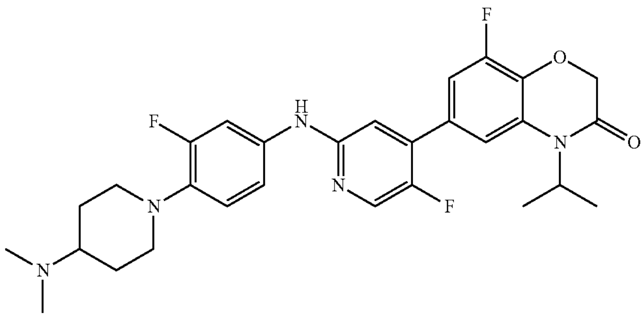 [SMILES: CC(C)N1C(=O)COc2c(F)cc(-c3cc(Nc4ccc(N5CCC(N(C)C)CC5)c(F)c4)ncc3F)cc21] |
| 374 | 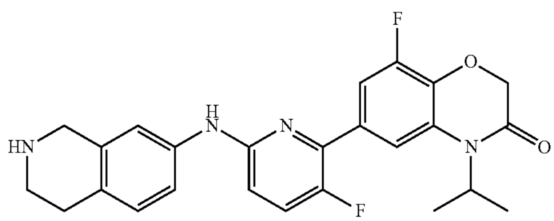 [SMILES: CC(C)N1C(=O)COc2c(F)cc(-c3nc(Nc4ccc5c(c4)CNCC5)ccc3F)cc21] |
| 375 | 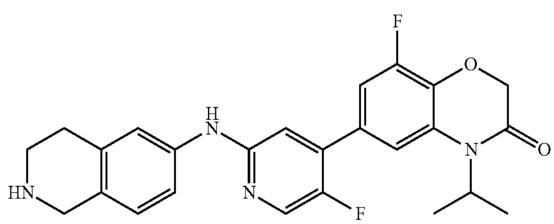 [SMILES: CC(C)N1C(=O)COc2c(F)cc(-c3cc(Nc4ccc5c(c4)CCNC5)ncc3F)cc21] |
| 376 | 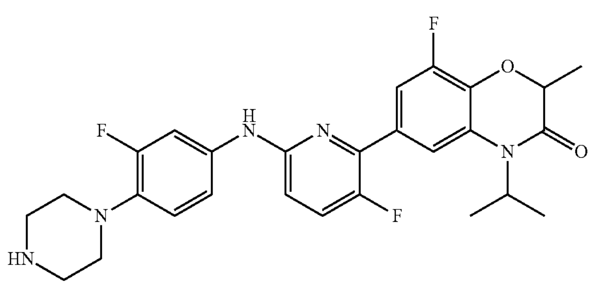 [SMILES: CC1Oc2c(F)cc(-c3nc(Nc4ccc(N5CCNCC5)c(F)c4)ccc3F)cc2N(C(C)C)C1=O] |
| 377 | 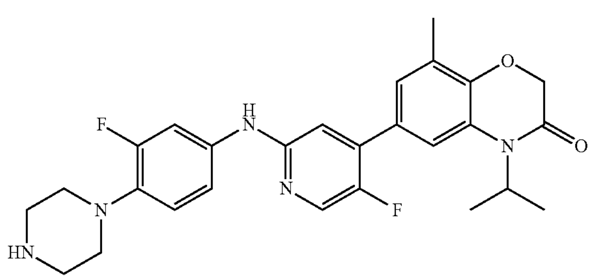 [SMILES: Cc1cc(-c2cc(Nc3ccc(N4CCNCC4)c(F)c3)ncc2F)cc2c1OCC(=O)N2C(C)C] |

TABLE 1-continued
| Compound No. | Structure |
| --- | --- |
| 378 | 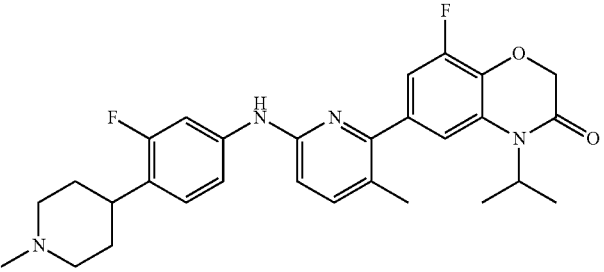 [SMILES: Cc1ccc(Nc2ccc(C3CCN(C)CC3)c(F)c2)nc1-c1cc(F)c2c(c1)N(C(C)C)C(=O)CO2] |
| 379 | 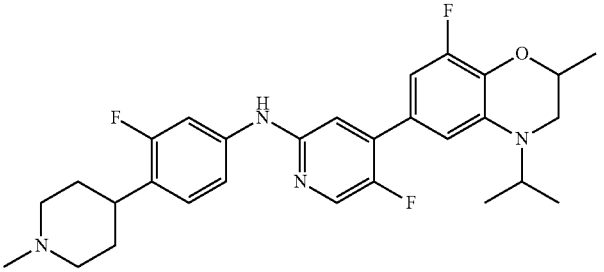 |
| 380 | 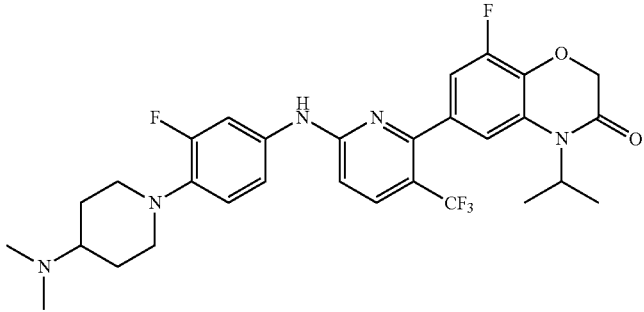 [SMILES: CC(C)N1C(=O)COc2c(F)cc(-c3nc(Nc4ccc(N5CCC(N(C)C)CC5)c(F)c4)ccc3C(F)(F)F)cc21] |
| 381 | 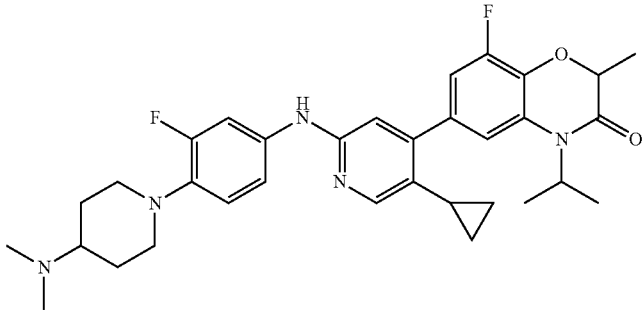 |
| 382 | 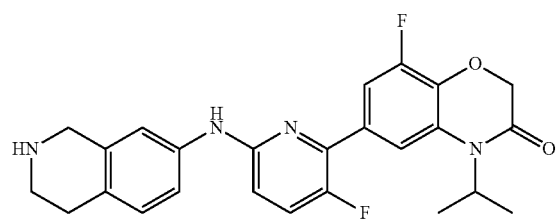 [SMILES: CC(C)N1C(=O)COc2c(F)cc(-c3nc(Nc4ccc5c(c4)CNCC5)ccc3F)cc21] |

TABLE 1-continued
| Compound No. | Structure |
|---|---|
| 383 | 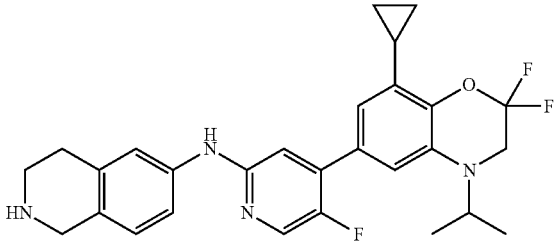 [SMILES: CC(C)N1CC(F)(F)Oc2c(C3CC3)cc(-c3cc(Nc4ccc5c(c4)CCNC5)ncc3F)cc21] |
| 384 | 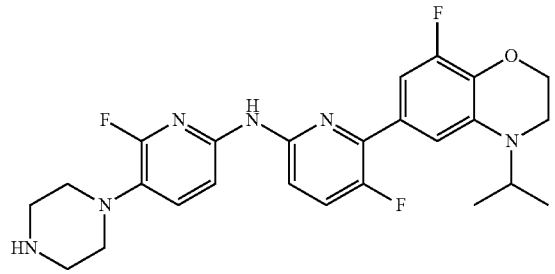 [SMILES: CC(C)N1CCOc2c(F)cc(-c3nc(Nc4ccc(N5CCNCC5)c(F)n4)ccc3F)cc21] |
| 385 | 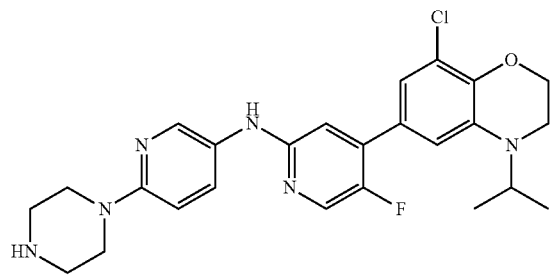 [SMILES: CC(C)N1CCOc2c(Cl)cc(-c3cc(Nc4ccc(N5CCNCC5)nc4)ncc3F)cc21] |
| 386 | 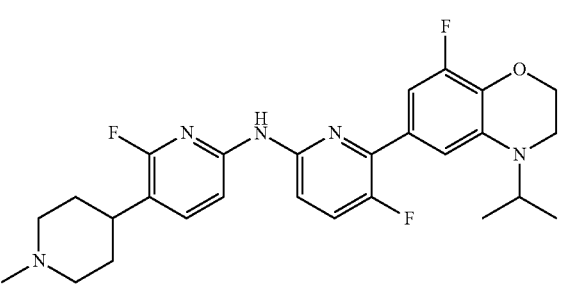 [SMILES: CC(C)N1CCOc2c(F)cc(-c3nc(Nc4ccc(C5CCN(C)CC5)c(F)n4)ccc3F)cc21] |
| 387 | 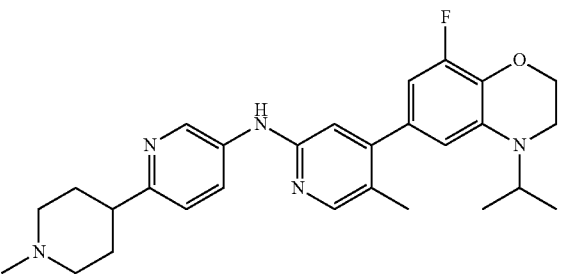 [SMILES: Cc1cnc(Nc2ccc(C3CCN(C)CC3)nc2)cc1-c1cc(F)c2c(c1)N(C(C)C)CCO2] |

TABLE 1-continued
| Compound No. | Structure |
|---|---|
| 388 | 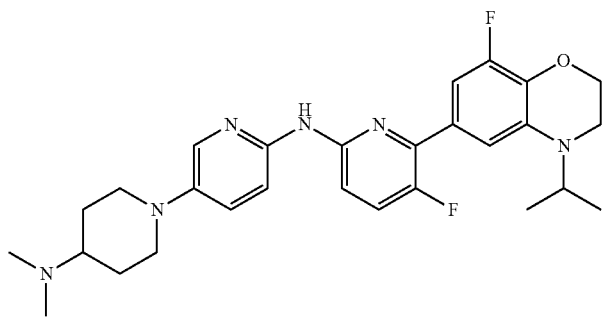 [SMILES: CC(C)N1CCOc2c(F)cc(-c3nc(Nc4ccc(N5CCC(N(C)C)CC5)cn4)ccc3F)cc21] |
| 389 | 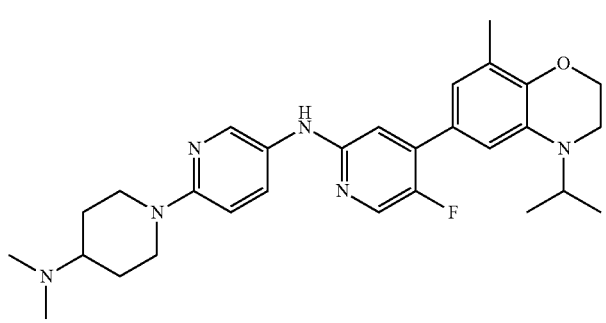 [SMILES: Cc1cc(-c2cc(Nc3ccc(N4CCC(N(C)C)CC4)nc3)ncc2F)cc2c1OCCN2C(C)C] |
| 390 | 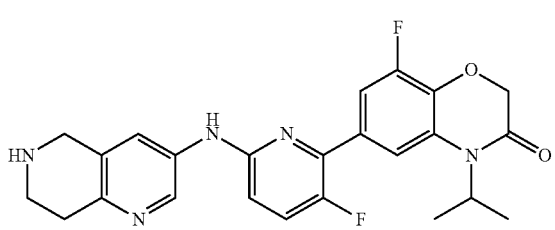 [SMILES: CC(C)N1C(=O)COc2c(F)cc(-c3nc(Nc4cnc5c(c4)CNCC5)ccc3F)cc21] |
| 391 | 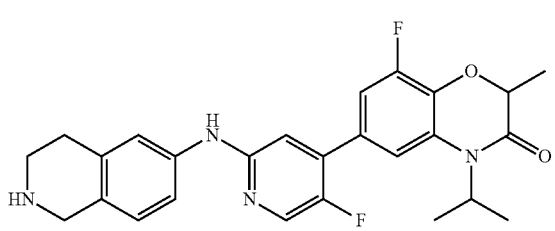 [SMILES: CC1Oc2c(F)cc(-c3cc(Nc4ccc5c(c4)CCNC5)ncc3F)cc2N(C(C)C)C1=O] |
| 392 | 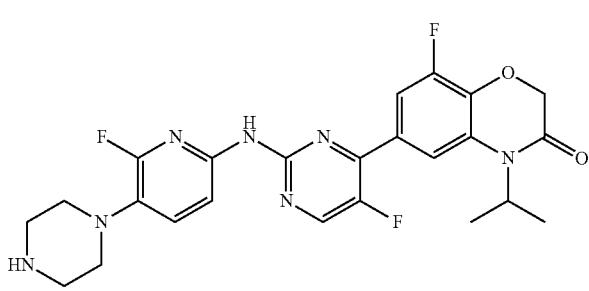 [SMILES: CC(C)N1C(=O)COc2c(F)cc(-c3nc(Nc4ccc(N5CCNCC5)c(F)n4)ncc3F)cc21] |

TABLE 1-continued
| Compound No. | Structure |
|---|---|
| 393 | 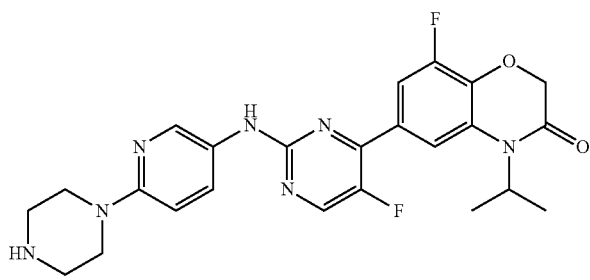 [SMILES: CC(C)N1C(=O)COc2c(F)cc(-c3nc(Nc4ccc(N5CCNCC5)nc4)ncc3F)cc21] |
| 394 | 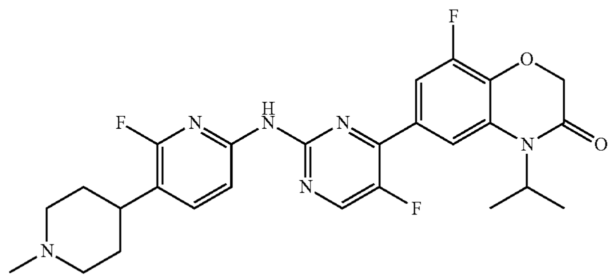 [SMILES: CC(C)N1C(=O)COc2c(F)cc(-c3nc(Nc4ccc(C5CCN(C)CC5)c(F)n4)ncc3F)cc21] |
| 395 | 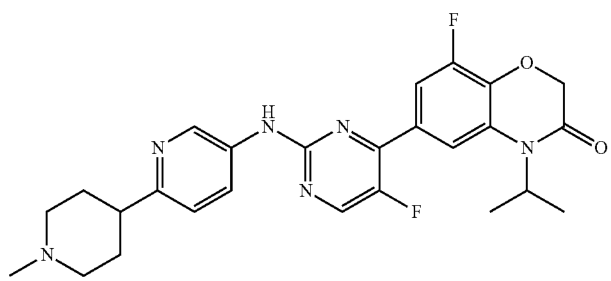 [SMILES: CC(C)N1C(=O)COc2c(F)cc(-c3nc(Nc4ccc(C5CCN(C)CC5)nc4)ncc3F)cc21] |
| 396 | 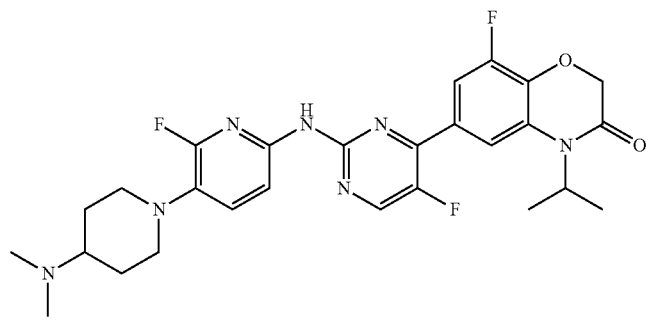 |
| 397 | 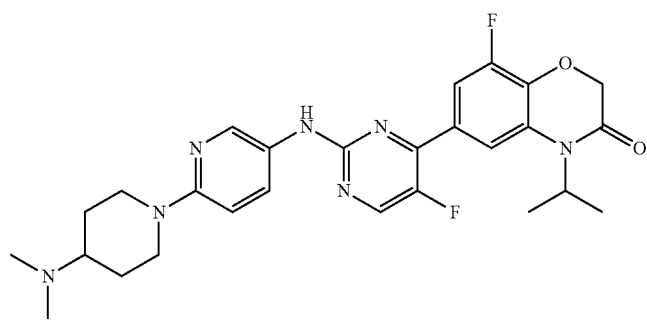 [SMILES: CC(C)N1C(=O)COc2c(F)cc(-c3nc(Nc4ccc(N5CCC(N(C)C)CC5)nc4)ncc3F)cc21] |

TABLE 1-continued

| Compound No. | Structure |
|---|---|
| 398 | 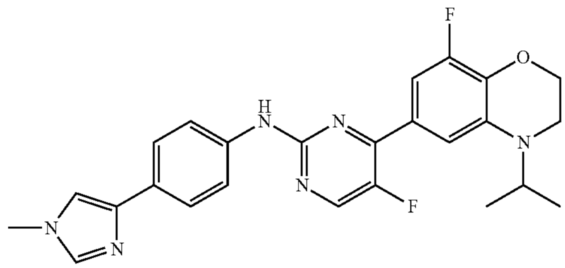 [SMILES: CC(C)N1CCOc2c(F)cc(-c3nc(Nc4ccc(-c5cn(C)cn5)cc4)ncc3F)cc21] |
| 399 | 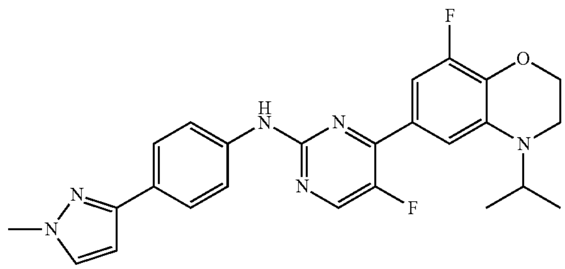 [SMILES: CC(C)N1CCOc2c(F)cc(-c3nc(Nc4ccc(-c5ccn(C)n5)cc4)ncc3F)cc21] |
| 400 | 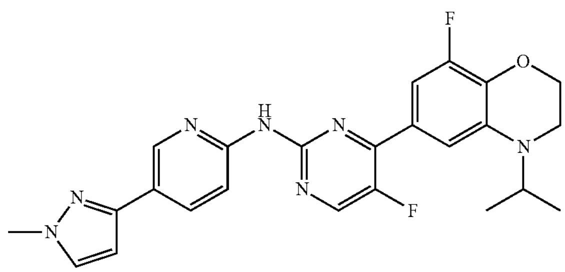 [SMILES: CC(C)N1CCOc2c(F)cc(-c3nc(Nc4ccc(-c5ccn(C)n5)cn4)ncc3F)cc21] |
| 401 | 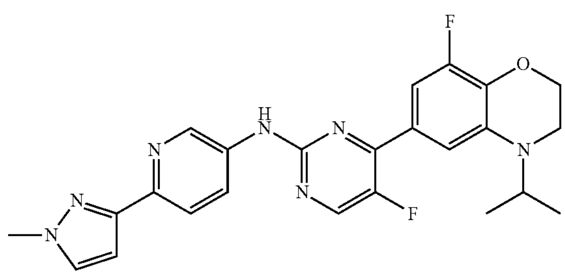 |
| 402 | 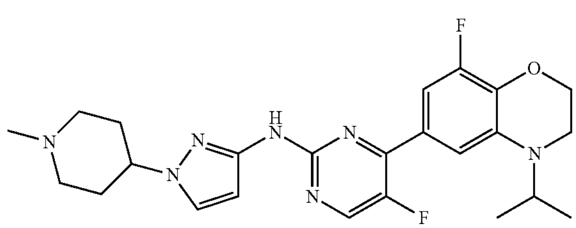 [SMILES: CC(C)N1CCOc2c(F)cc(-c3nc(Nc4ccn(C5CCN(C)CC5)n4)ncc3F)cc21] |
| 403 | 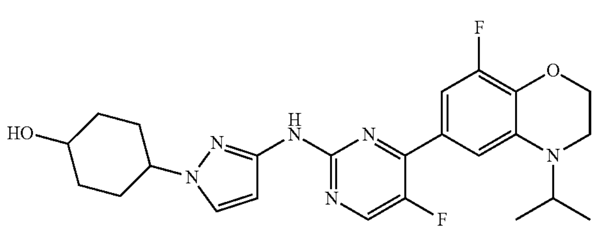 [SMILES: CC(C)N1CCOc2c(F)cc(-c3nc(Nc4ccn(C5CCC(O)CC5)n4)ncc3F)cc21] |

TABLE 1-continued
| Compound No. | Structure |
|---|---|
| 404 | 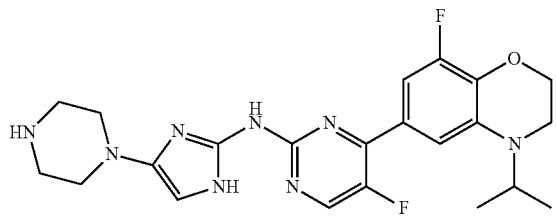 [SMILES: CC(C)N1CCOc2c(F)cc(-c3nc(Nc4nc(N5CCNCC5)c[nH]4)ncc3F)cc21] |
| 405 | 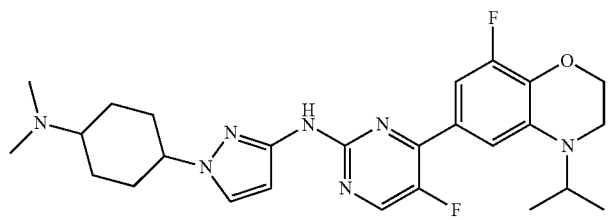 [SMILES: CC(C)N1CCOc2c(F)cc(-c3nc(Nc4ccn(C5CCC(N(C)C)CC5)n4)ncc3F)cc21] |
| 406 | 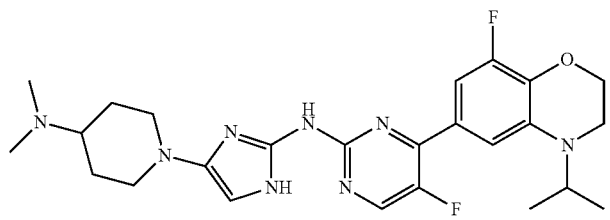 [SMILES: CC(C)N1CCOc2c(F)cc(-c3nc(Nc4nc(N5CCC(N(C)C)CC5)c[nH]4)ncc3F)cc21] |
| 407 | 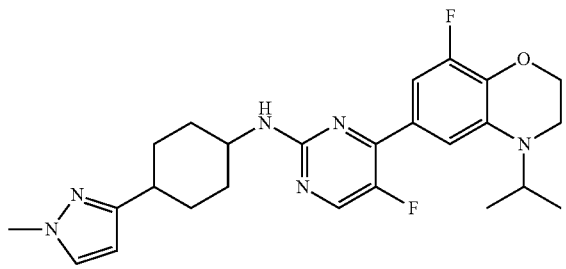 |
| 408 | 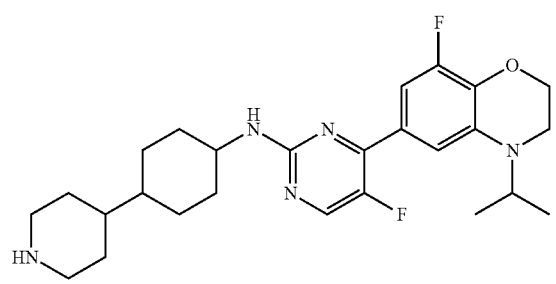 |
| 409 | 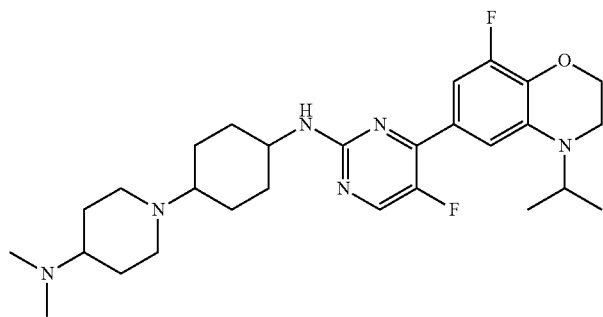 [SMILES: CC(C)N1CCOc2c(F)cc(-c3nc(NC4CCC(N5CCC(N(C)C)CC5)CC4)ncc3F)cc21] |

TABLE 1-continued
| Compound No. | Structure |
|---|---|
| 410 | 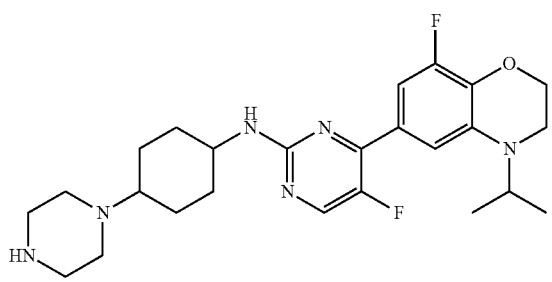 [SMILES: CC(C)N1CCOc2c(F)cc(-c3nc(NC4CCC(N5CCNCC5)CC4)ncc3F)cc21] |
| 411 | 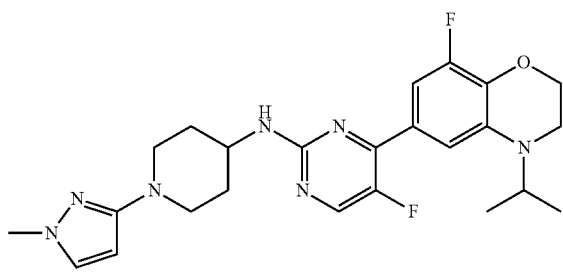 |
| 412 | 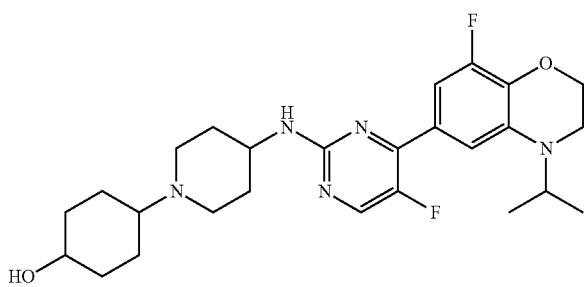 [SMILES: CC(C)N1CCOc2c(F)cc(-c3nc(NC4CCN(C5CCC(O)CC5)CC4)ncc3F)cc21] |
| 413 | 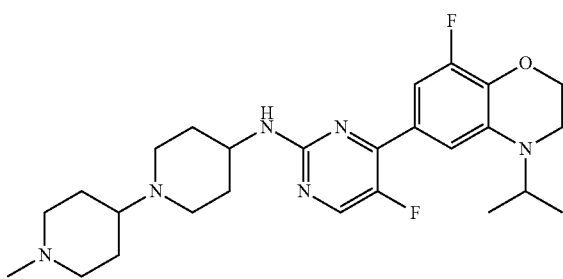 [SMILES: CC(C)N1CCOc2c(F)cc(-c3nc(NC4CCN(C5CCN(C)CC5)CC4)ncc3F)cc21] |
| 414 | 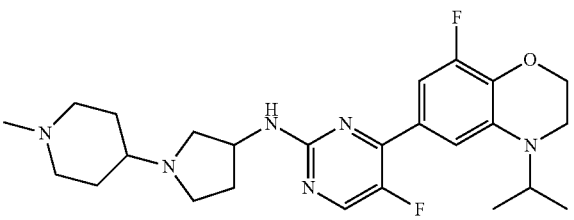 [SMILES: CC(C)N1CCOc2c(F)cc(-c3nc(NC4CCN(C5CCN(C)CC5)C4)ncc3F)cc21] |

TABLE 1-continued
| Compound No. | Structure |
|---|---|
| 415 | 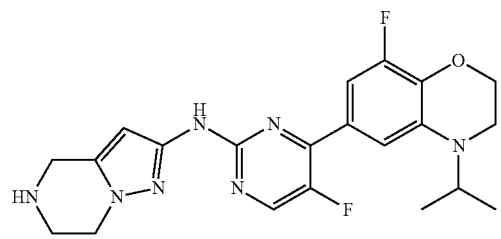 [SMILES: CC(C)N1CCOc2c(F)cc(-c3nc(Nc4cc5n(n4)CCNC5)ncc3F)cc21] |
| 416 | 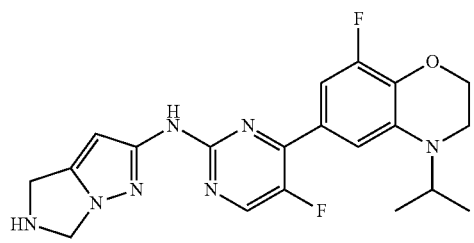 [SMILES: CC(C)N1CCOc2c(F)cc(-c3nc(Nc4cc5n(n4)CNC5)ncc3F)cc21] |
| 417 | 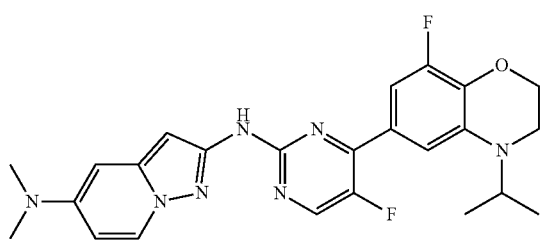 [SMILES: CC(C)N1CCOc2c(F)cc(-c3nc(Nc4cc5cc(N(C)C)ccn5n4)ncc3F)cc21] |
| 418 | 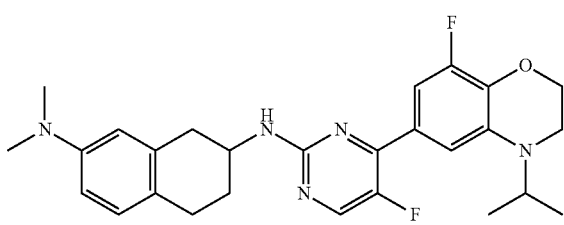 [SMILES: CC(C)N1CCOc2c(F)cc(-c3nc(NC4CCc5ccc(N(C)C)cc5C4)ncc3F)cc21] |
| 419 | 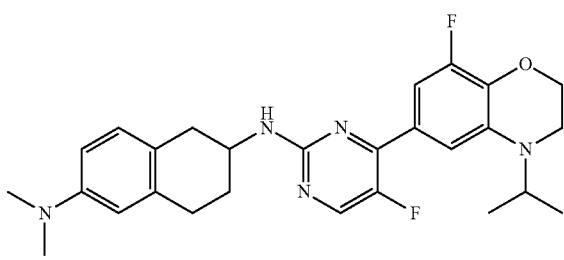 [SMILES: CC(C)N1CCOc2c(F)cc(-c3nc(NC4CCc5cc(N(C)C)ccc5C4)ncc3F)cc21] |
| 420 | 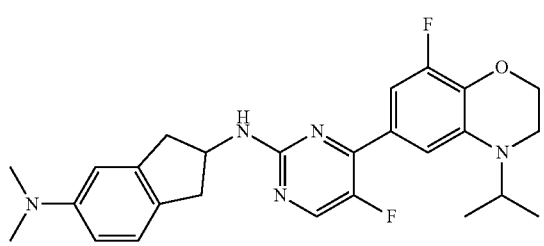 [SMILES: CC(C)N1CCOc2c(F)cc(-c3nc(NC4Cc5ccc(N(C)C)cc5C4)ncc3F)cc21] |

TABLE 1-continued
| Compound No. | Structure |
|---|---|
| 421 | 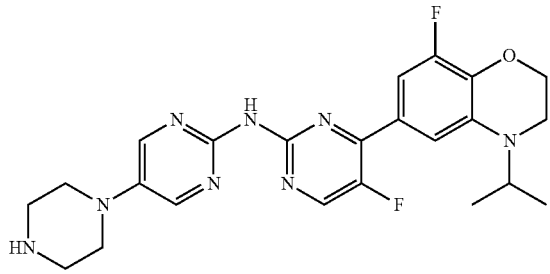 [SMILES: CC(C)N1CCOc2c(F)cc(-c3nc(Nc4ncc(N5CCNCC5)cn4)ncc3F)cc21] |
| 422 | 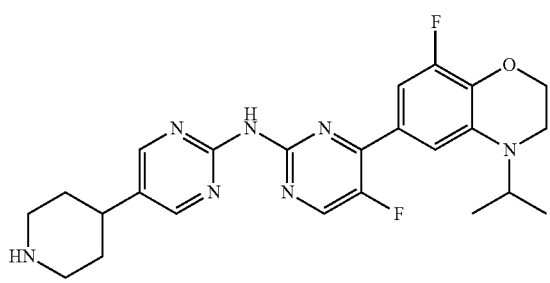 [SMILES: CC(C)N1CCOc2c(F)cc(-c3nc(Nc4ncc(C5CCNCC5)cn4)ncc3F)cc21] |
| 423 | 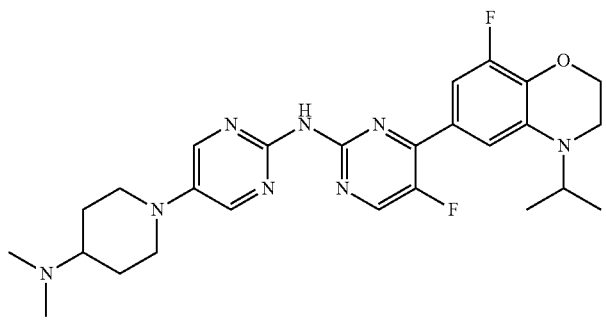 [SMILES: CC(C)N1CCOc2c(F)cc(-c3nc(Nc4ncc(N5CCC(N(C)C)CC5)cn4)ncc3F)cc21] |
| 424 | 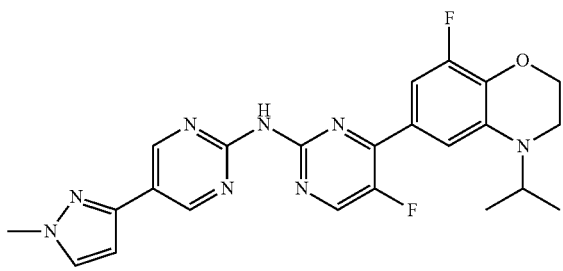 [SMILES: CC(C)N1CCOc2c(F)cc(-c3nc(Nc4ncc(-c5ccn(C)n5)cn4)ncc3F)cc21] |
| 425 | 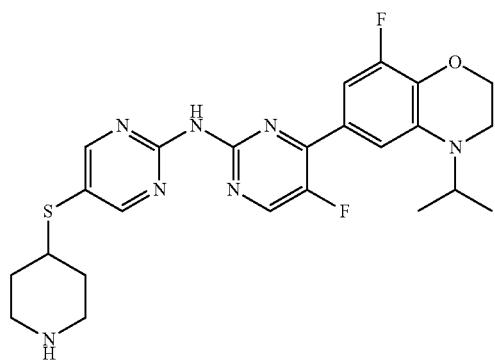 |

TABLE 1-continued
| Compound No. | Structure |
|---|---|
| 426 | 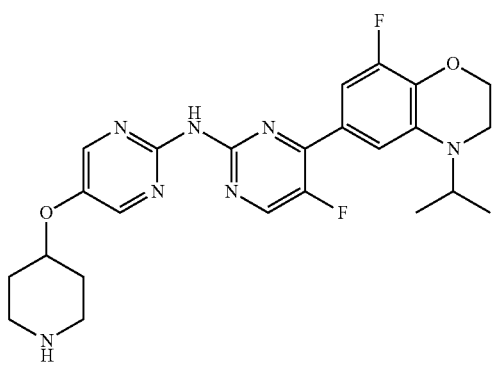 [SMILES: CC(C)N1CCOc2c(F)cc(-c3nc(Nc4ncc(OC5CCNCC5)cn4)ncc3F)cc21] |
| 427 | 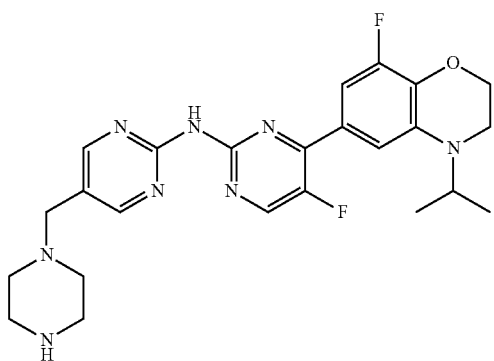 [SMILES: CC(C)N1CCOc2c(F)cc(-c3nc(Nc4ncc(CN5CCNCC5)cn4)ncc3F)cc21] |
| 428 | 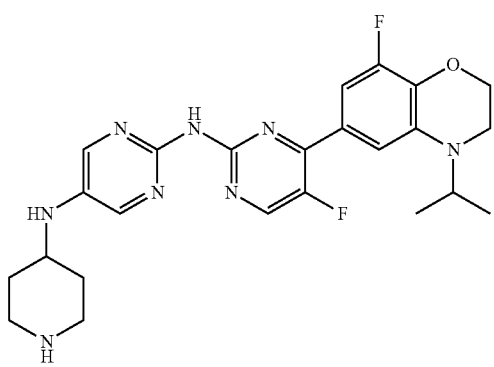 [SMILES: CC(C)N1CCOc2c(F)cc(-c3nc(Nc4ncc(NC5CCNCC5)cn4)ncc3F)cc21] |
| 429 | 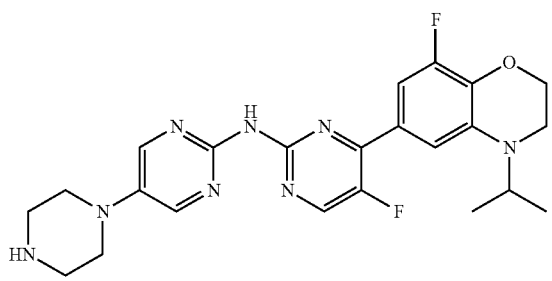 [SMILES: CC(C)N1CCOc2c(F)cc(-c3nc(Nc4ncc(N5CCNCC5)cn4)ncc3F)cc21] |

TABLE 1-continued
| Compound No. | Structure |
|---|---|
| 430 | 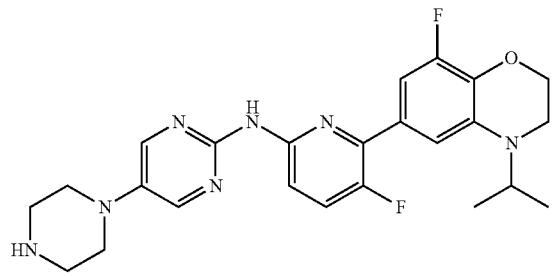 [SMILES: CC(C)N1CCOc2c(F)cc(-c3nc(Nc4ncc(N5CCNCC5)cn4)ccc3F)cc21] |
| 431 | 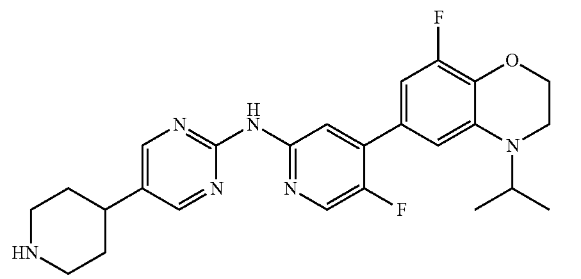 [SMILES: CC(C)N1CCOc2c(F)cc(-c3cc(Nc4ncc(C5CCNCC5)cn4)ncc3F)cc21] |
| 432 | 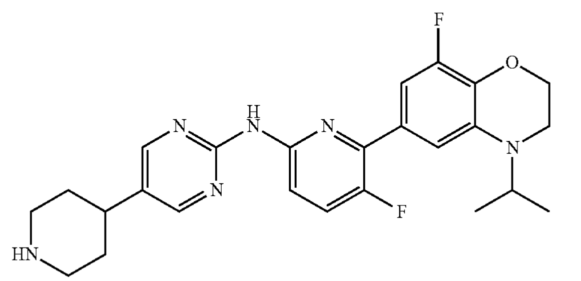 [SMILES: CC(C)N1CCOc2c(F)cc(-c3nc(Nc4ncc(C5CCNCC5)cn4)ccc3F)cc21] |
| 433 | 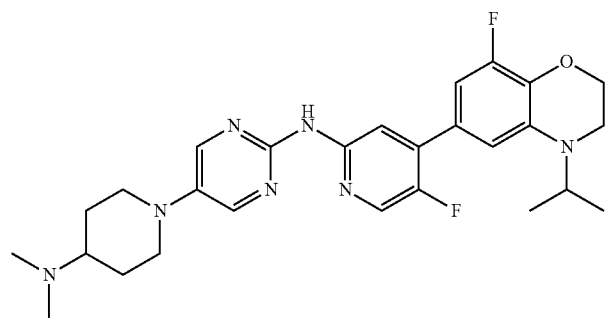 [SMILES: CC(C)N1CCOc2c(F)cc(-c3cc(Nc4ncc(N5CCC(N(C)C)CC5)cn4)ncc3F)cc21] |
| 434 | 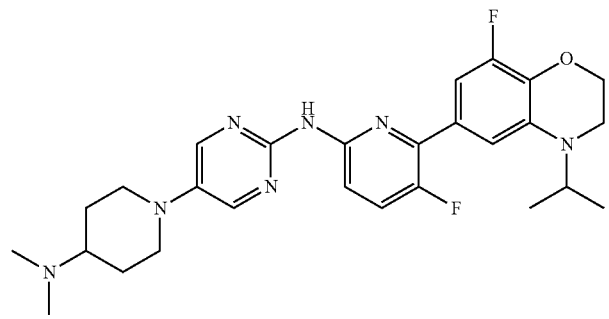 [SMILES: CC(C)N1CCOc2c(F)cc(-c3nc(Nc4ncc(N5CCC(N(C)C)CC5)cn4)ccc3F)cc21] |

TABLE 1-continued
| Compound No. | Structure |
|---|---|
| 435 | 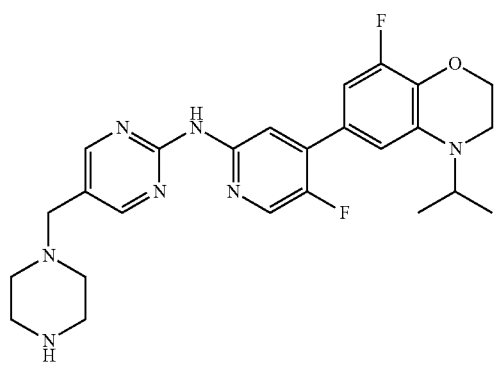 [SMILES: CC(C)N1CCOc2c(F)cc(-c3cc(Nc4ncc(CN5CCNCC5)cn4)ncc3F)cc21] |
| 436 | 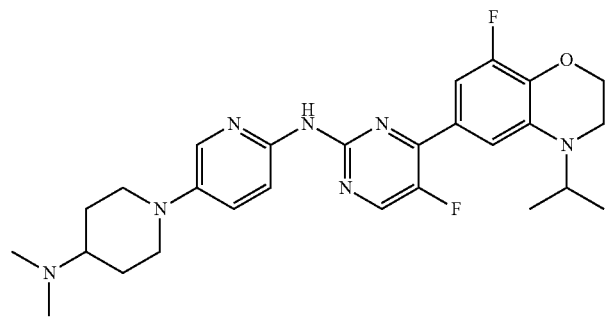 [SMILES: CC(C)N1CCOc2c(F)cc(-c3nc(Nc4ccc(N5CCC(N(C)C)CC5)cn4)ncc3F)cc21] |
| 437 | 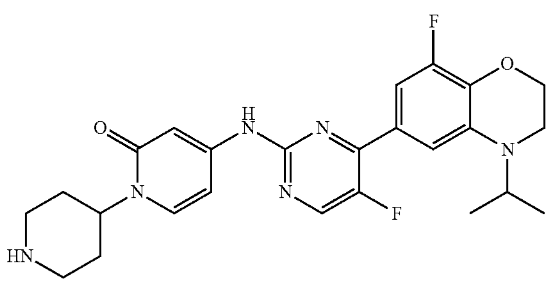 [SMILES: CC(C)N1CCOc2c(F)cc(-c3nc(Nc4ccn(C5CCNCC5)c(=O)c4)ncc3F)cc21] |
| 438 | 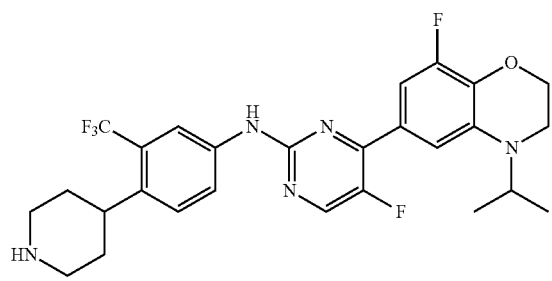 |
| 439 | 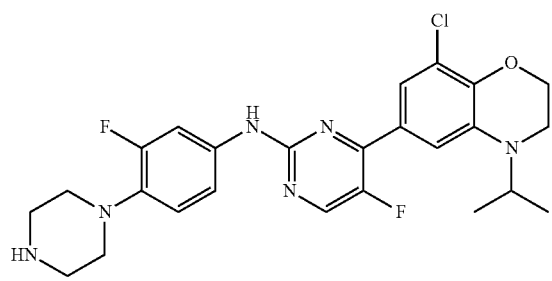 |

TABLE 1-continued
| Compound No. | Structure |
|---|---|
| 440 | 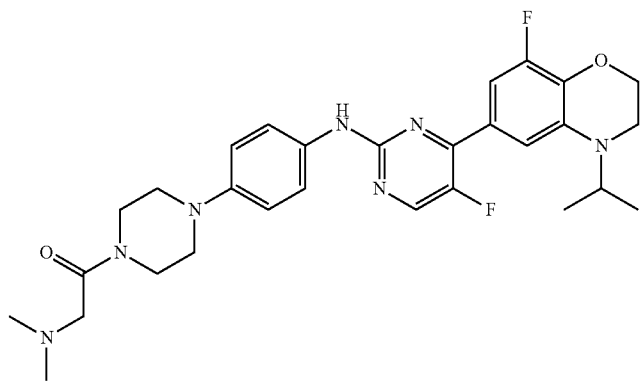 [SMILES: CC(C)N1CCOc2c(F)cc(-c3nc(Nc4ccc(N5CCN(C(=O)CN(C)C)CC5)cc4)ncc3F)cc21] |
| 441 | 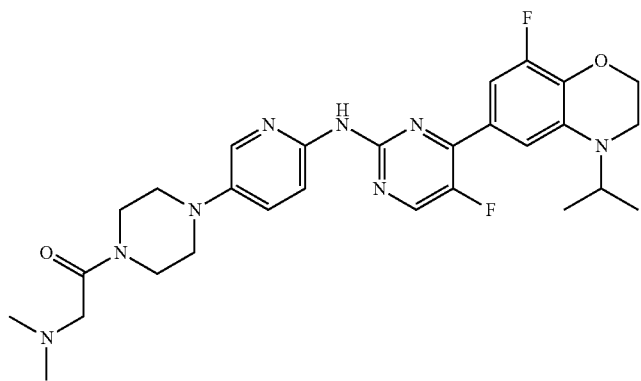 |
| 442 | 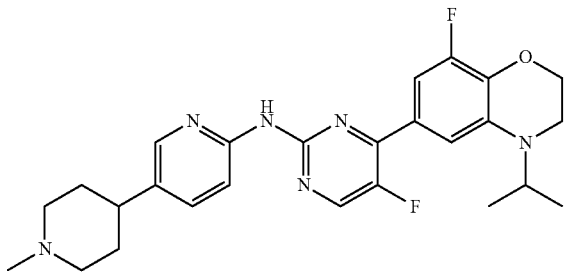 [SMILES: CC(C)N1CCOc2c(F)cc(-c3nc(Nc4ccc(C5CCN(C)CC5)cn4)ncc3F)cc21] |
| 443 | 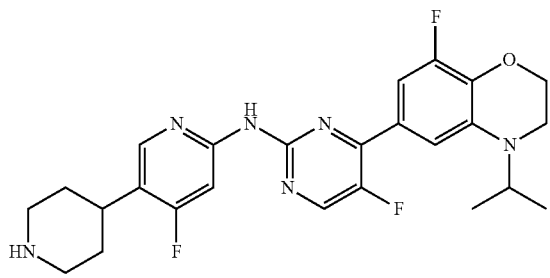 [SMILES: CC(C)N1CCOc2c(F)cc(-c3nc(Nc4cc(F)c(C5CCNCC5)cn4)ncc3F)cc21] |
| 444 | 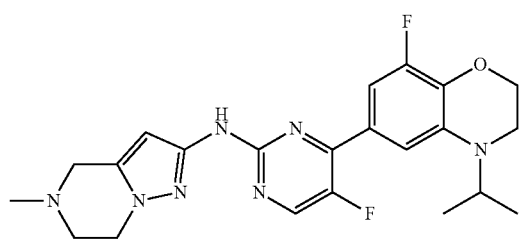 [SMILES: CC(C)N1CCOc2c(F)cc(-c3nc(Nc4cc5n(n4)CCN(C)C5)ncc3F)cc21] |

TABLE 1-continued
| Compound No. | Structure |
|---|---|
| 445 | 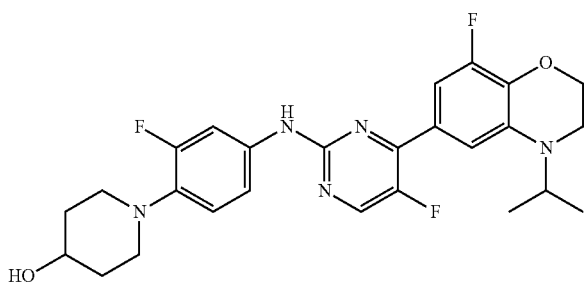 [SMILES: CC(C)N1CCOc2c(F)cc(-c3nc(Nc4ccc(N5CCC(O)CC5)c(F)c4)ncc3F)cc21] |
| 446 | 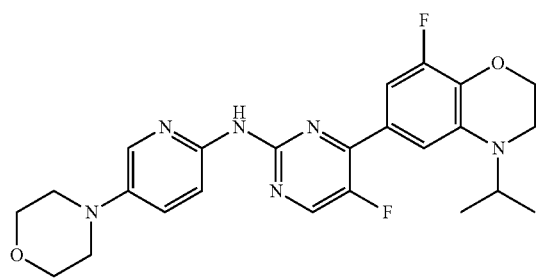 [SMILES: CC(C)N1CCOc2c(F)cc(-c3nc(Nc4ccc(N5CCOCC5)cn4)ncc3F)cc21] |
| 447 | 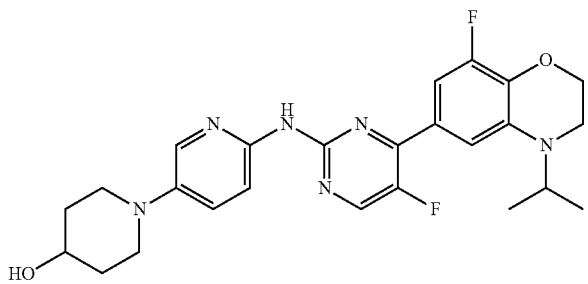 [SMILES: CC(C)N1CCOc2c(F)cc(-c3nc(Nc4ccc(N5CCC(O)CC5)cn4)ncc3F)cc21] |
| 448 | 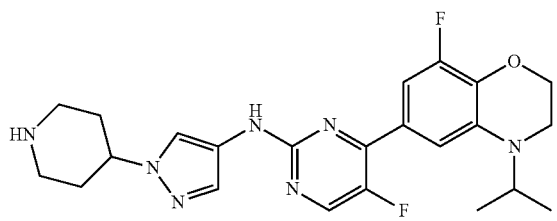 [SMILES: CC(C)N1CCOc2c(F)cc(-c3nc(Nc4cnn(C5CCNCC5)c4)ncc3F)cc21] |
| 449 | 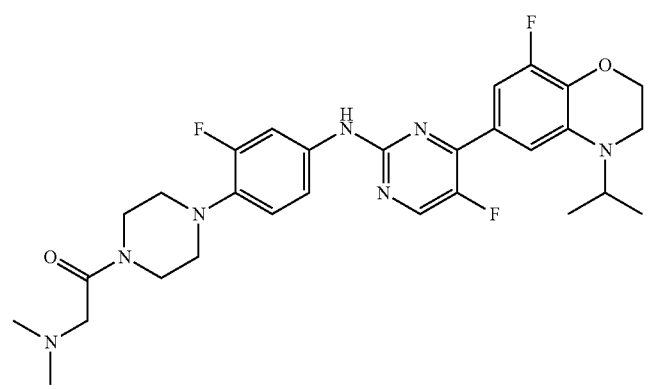 [SMILES: CC(C)N1CCOc2c(F)cc(-c3nc(Nc4ccc(C5CCN(C(=O)CN(C)C)CC5)c(F)c4)ncc3F)cc21] |

TABLE 1-continued
| Compound No. | Structure |
| --- | --- |
| 450 | 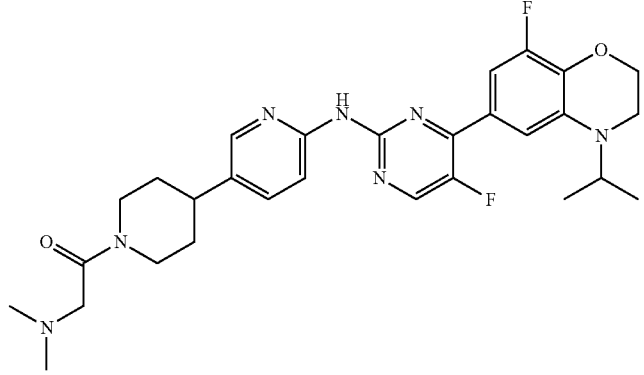 |
| 451 | 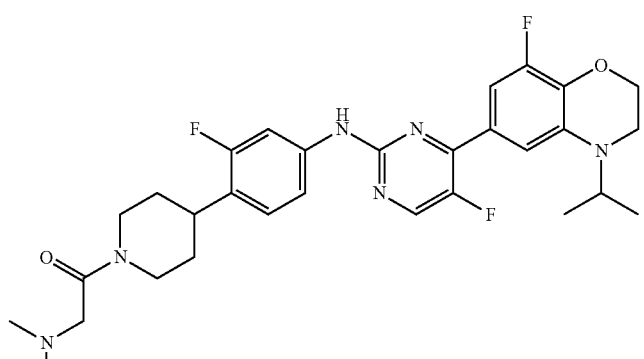 |
| 452 | 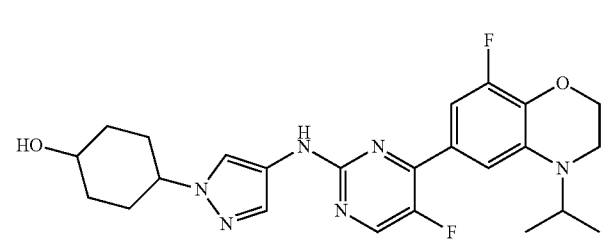 [SMILES: CC(C)N1CCOc2c(F)cc(-c3nc(Nc4cnn(C5CCC(O)CC5)c4)ncc3F)cc21] |
| 453 | 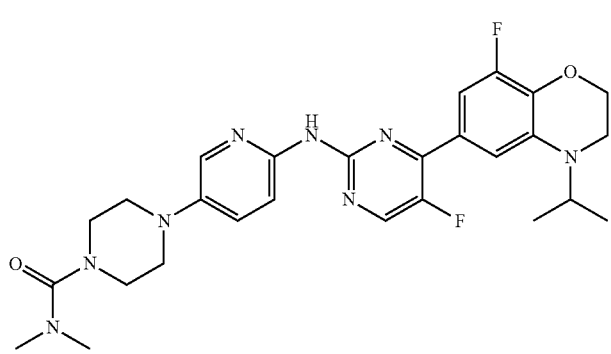 [SMILES: CC(C)N1CCOc2c(F)cc(-c3nc(Nc4ccc(N5CCN(C(=O)N(C)C)CC5)cn4)ncc3F)cc21] |

TABLE 1-continued
| Compound No. | Structure |
|---|---|
| 454 | 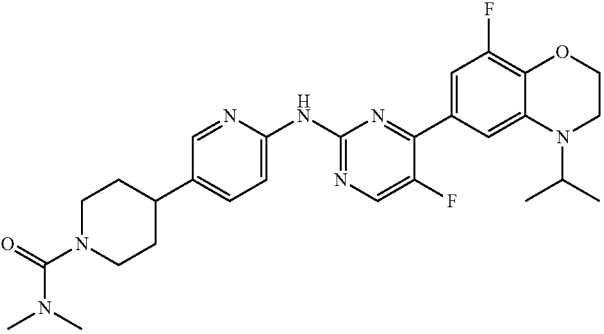 [SMILES: CC(C)N1CCOc2c(F)cc(-c3nc(Nc4ccc(C5CCN(C(=O)N(C)C)CC5)cn4)ncc3F)cc21] |
| 455 | 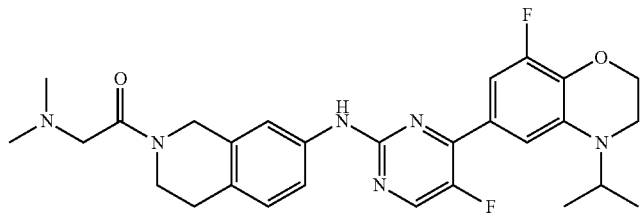 [SMILES: CC(C)N1CCOc2c(F)cc(-c3nc(Nc4ccc5c(c4)CN(C(=O)CN(C)C)CC5)ncc3F)cc21] |
| 456 | 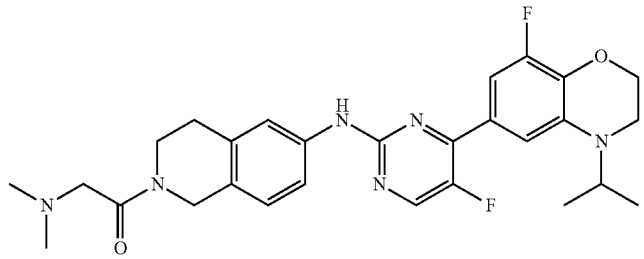 [SMILES: CC(C)N1CCOc2c(F)cc(-c3nc(Nc4ccc5c(c4)CCN(C(=O)CN(C)C)C5)ncc3F)cc21] |
| 457 | 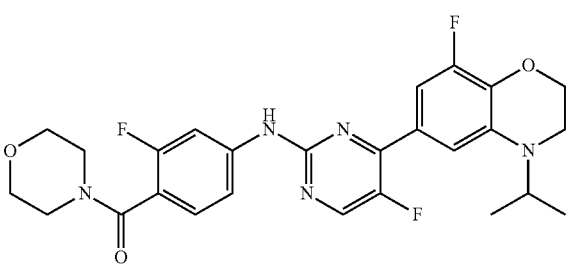 [SMILES: CC(C)N1CCOc2c(F)cc(-c3nc(Nc4ccc(C(=O)N5CCOCC5)c(F)c4)ncc3F)cc21] |
| 458 | 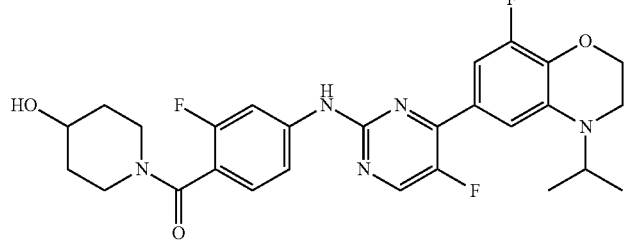 |

TABLE 1-continued
| Compound No. | Structure |
|---|---|
| 459 | 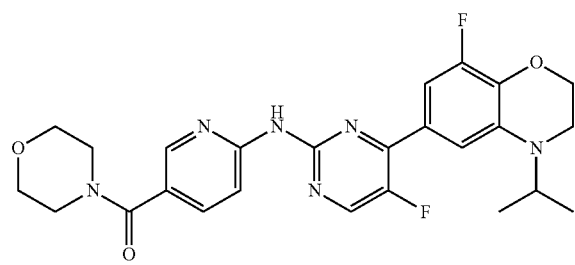 [SMILES: CC(C)N1CCOc2c(F)cc(-c3nc(Nc4ccc(C(=O)N5CCOCC5)cn4)ncc3F)cc21] |
| 460 | 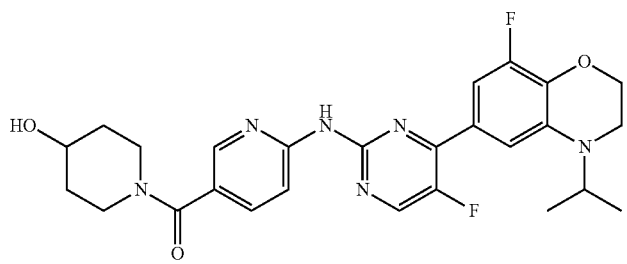 [SMILES: CC(C)N1CCOc2c(F)cc(-c3nc(Nc4ccc(C(=O)N5CCC(O)CC5)cn4)ncc3F)cc21] |
| 461 | 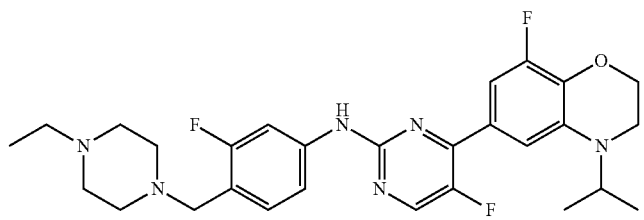 [SMILES: CCN1CCN(Cc2ccc(Nc3ncc(F)c(-c4cc(F)c5c(c4)N(C(C)C)CCO5)n3)cc2F)CC1] |
| 462 | 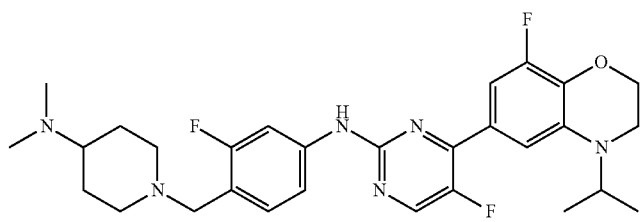 [SMILES: CC(C)N1CCOc2c(F)cc(-c3nc(Nc4ccc(CN5CCC(N(C)C)CC5)c(F)c4)ncc3F)cc21] |
| 463 | 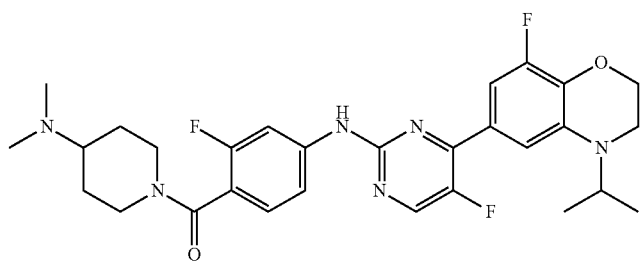 [SMILES: CC(C)N1CCOc2c(F)cc(-c3nc(Nc4ccc(C(=O)N5CCC(N(C)C)CC5)c(F)c4)ncc3F)cc21] |
| 464 | 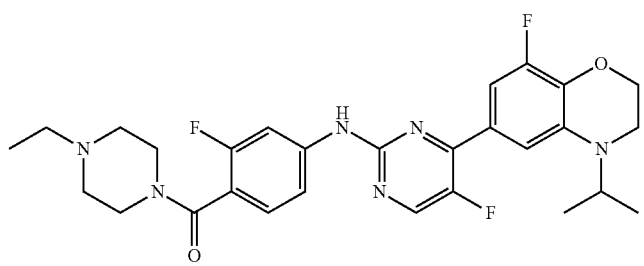 [SMILES: CCN1CCN(C(=O)c2ccc(Nc3ncc(F)c(-c4cc(F)c5c(c4)N(C(C)C)CCO5)n3)cc2F)CC1] |

TABLE 1-continued
| Compound No. | Structure |
|---|---|
| 465 | 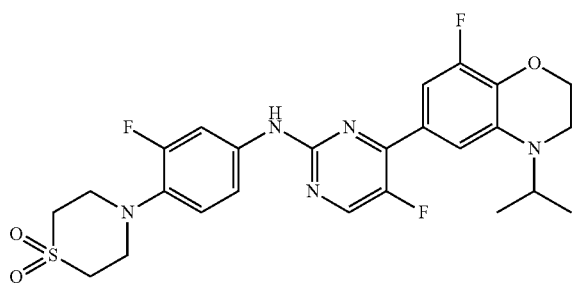 [SMILES: CC(C)N1CCOc2c(F)cc(-c3nc(Nc4ccc(N5CCS(=O)(=O)CC5)c(F)c4)ncc3F)cc21] |
| 466 | 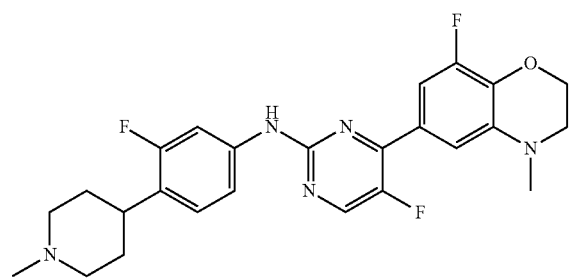 [SMILES: CN1CCC(c2ccc(Nc3ncc(F)c(-c4cc(F)c5c(c4)N(C)CCO5)n3)cc2F)CC1] |
| 467 | 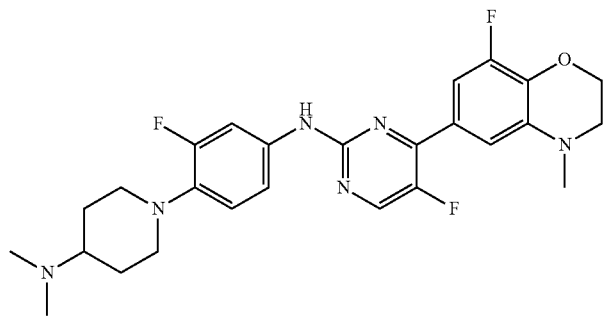 [SMILES: CN1CCOc2c(F)cc(-c3nc(Nc4ccc(N5CCC(N(C)C)CC5)c(F)c4)ncc3F)cc21] |
| 468 | 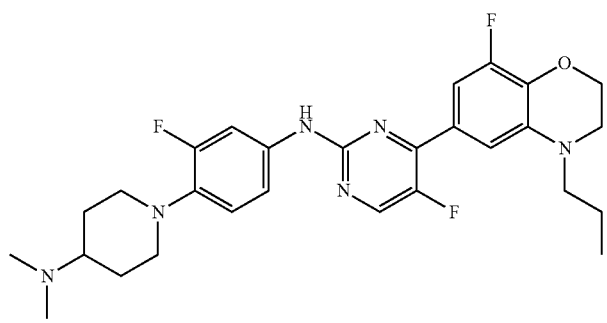 [SMILES: CCCN1CCOc2c(F)cc(-c3nc(Nc4ccc(N5CCC(N(C)C)CC5)c(F)c4)ncc3F)cc21] |
| 469 | 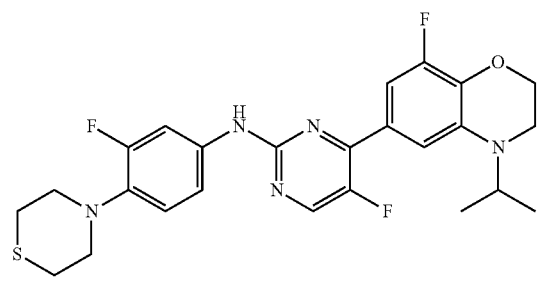 [SMILES: CC(C)N1CCOc2c(F)cc(-c3nc(Nc4ccc(N5CCSCC5)c(F)c4)ncc3F)cc21] |

TABLE 1-continued
| Compound No. | Structure |
|---|---|
| 470 | 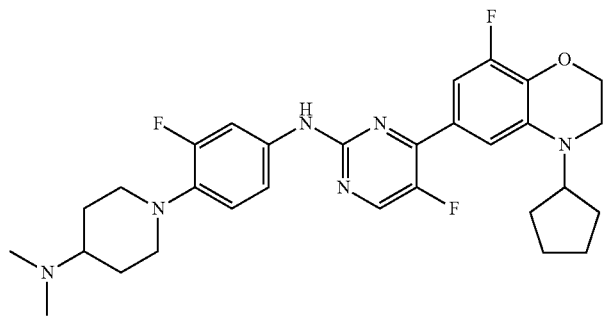 [SMILES: CN(C)C1CCN(c2ccc(Nc3ncc(F)c(-c4cc(F)c5c(c4)N(C4CCCC4)CCO5)n3)cc2F)CC1] |
| 471 | 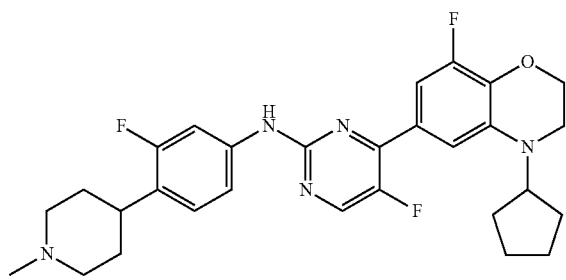 [SMILES: CN1CCC(c2ccc(Nc3ncc(F)c(-c4cc(F)c5c(c4)N(C4CCCC4)CCO5)n3)cc2F)CC1] |
| 472 | 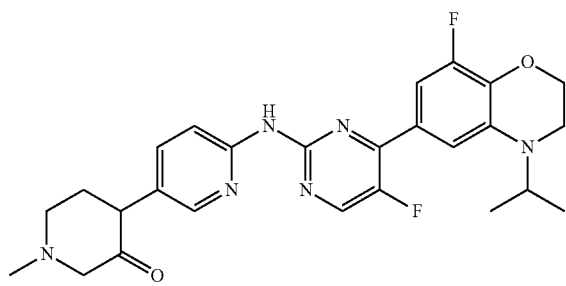 [SMILES: CC(C)N1CCOc2c(F)cc(-c3nc(Nc4ccc(C5CCN(C)CC5=O)cn4)ncc3F)cc21] |
| 473 | 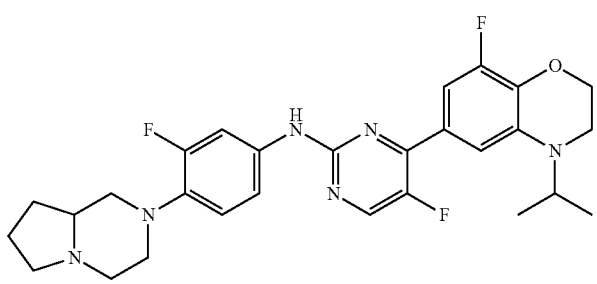 [SMILES: CC(C)N1CCOc2c(F)cc(-c3nc(Nc4ccc(N5CCN6CCCC6C5)c(F)c4)ncc3F)cc21] |
| 474 | 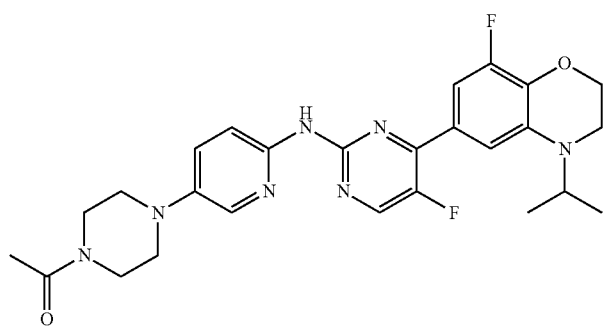 [SMILES: CC(=O)N1CCN(c2ccc(Nc3ncc(F)c(-c4cc(F)c5c(c4)N(C(C)C)CCO5)n3)nc2)CC1] |

TABLE 1-continued
| Compound No. | Structure |
|---|---|
| 475 | 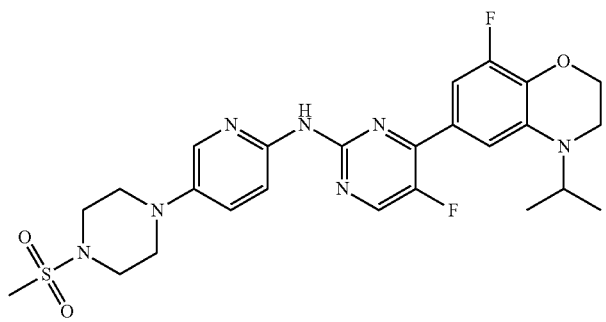 [SMILES: CC(C)N1CCOc2c(F)cc(-c3nc(Nc4ccc(N5CCN(S(C)(=O)=O)CC5)cn4)ncc3F)cc21] |
| 476 | 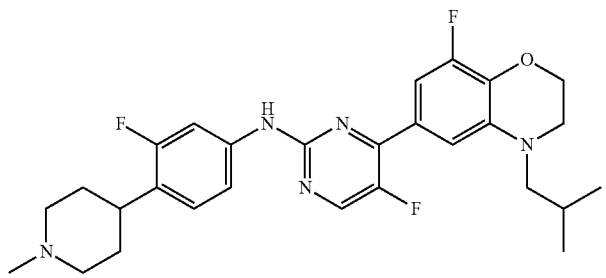 [SMILES: CC(C)CN1CCOc2c(F)cc(-c3nc(Nc4ccc(C5CCN(C)CC5)c(F)c4)ncc3F)cc21] |
| 477 | 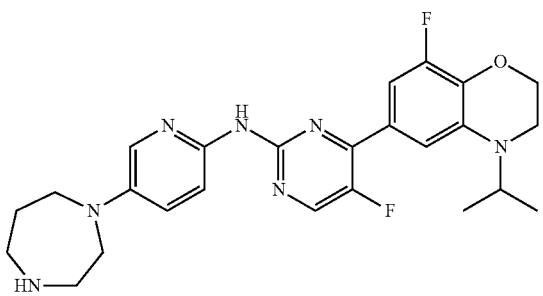 [SMILES: CC(C)N1CCOc2c(F)cc(-c3nc(Nc4ccc(N5CCCNCC5)cn4)ncc3F)cc21] |
| 478 | 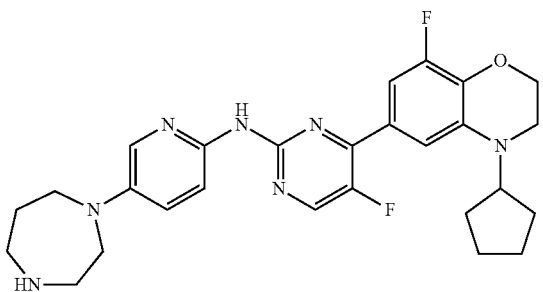 [SMILES: Fc1cnc(Nc2ccc(N3CCCNCC3)cn2)nc1-c1cc(F)c2c(c1)N(C1CCCC1)CCO2] |
| 479 | 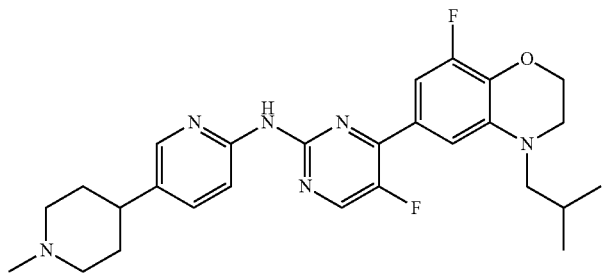 [SMILES: CC(C)CN1CCOc2c(F)cc(-c3nc(Nc4ccc(C5CCN(C)CC5)cn4)ncc3F)cc21] |

TABLE 1-continued
| Compound No. | Structure |
|---|---|
| 480 | 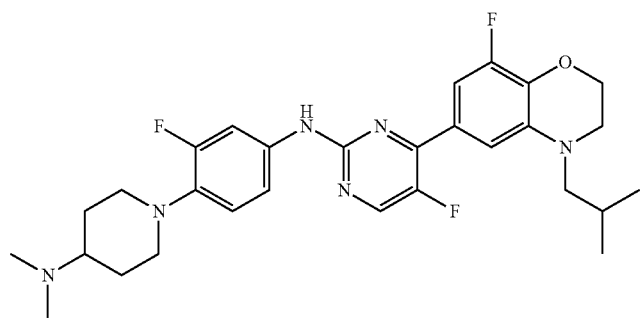 [SMILES: CC(C)CN1CCOc2c(F)cc(-c3nc(Nc4ccc(N5CCC(N(C)C)CC5)c(F)c4)ncc3F)cc21] |
| 481 | 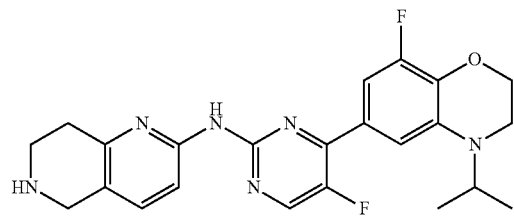 [SMILES: CC(C)N1CCOc2c(F)cc(-c3nc(Nc4ccc5c(n4)CCNC5)ncc3F)cc21] |
| 482 | 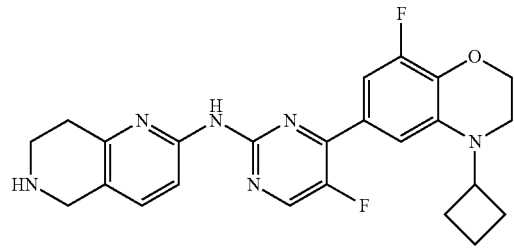 [SMILES: Fc1cnc(Nc2ccc3c(n2)CCNC3)nc1-c1cc(F)c2c(c1)N(C1CCC1)CCO2] |
| 483 | 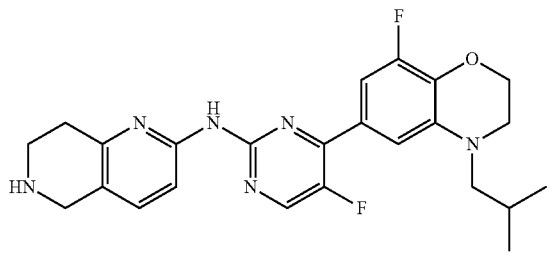 [SMILES: CC(C)CN1CCOc2c(F)cc(-c3nc(Nc4ccc5c(n4)CCNC5)ncc3F)cc21] |
| 484 | 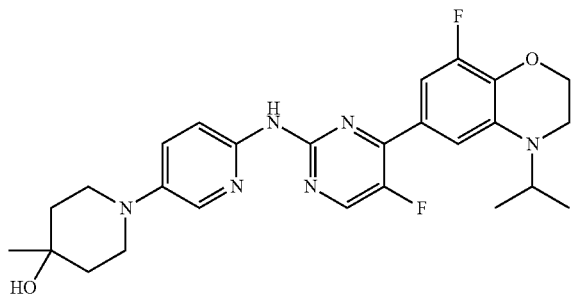 [SMILES: CC(C)N1CCOc2c(F)cc(-c3nc(Nc4ccc(N5CCC(C)(O)CC5)cn4)ncc3F)cc21] |

TABLE 1-continued
| Compound No. | Structure |
|---|---|
| 485 | 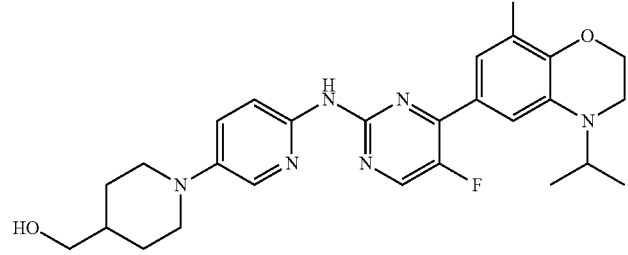 |
| 486 | 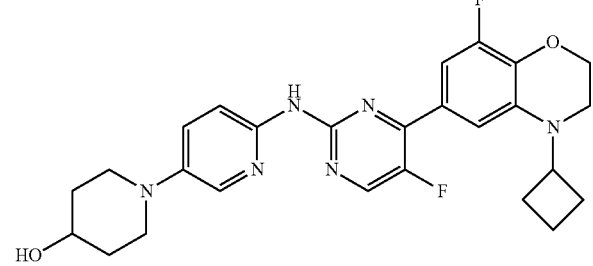 |
| 487 | 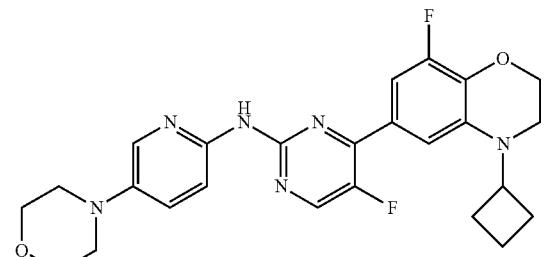 |
| 488 | 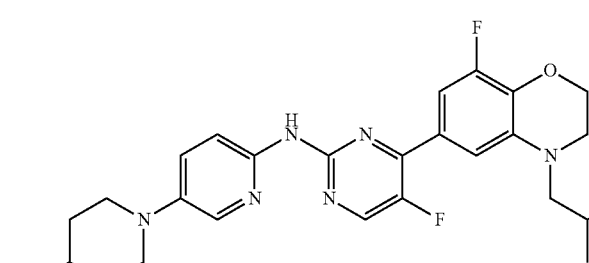 |
| 489 | 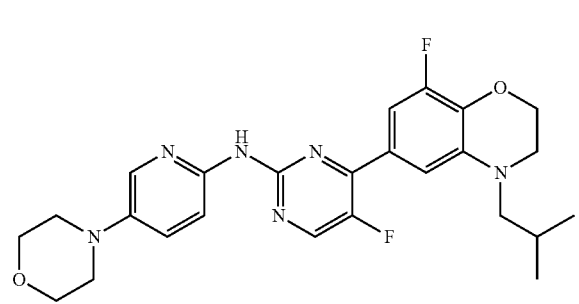 [SMILES: CC(C)CN1CCOc2c(F)cc(-c3nc(Nc4ccc(N5CCOCC5)cn4)ncc3F)cc21] |

TABLE 1-continued
| Compound No. | Structure |
|---|---|
| 490 | 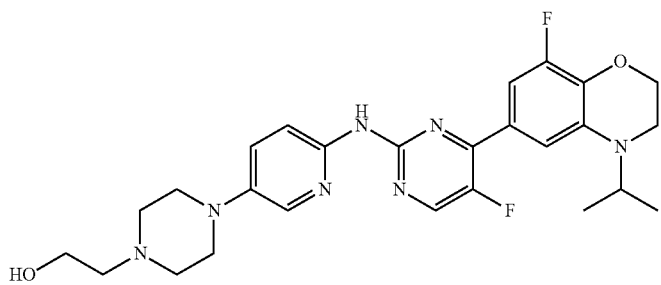 [SMILES: CC(C)N1CCOc2c(F)cc(-c3nc(Nc4ccc(N5CCN(CCO)CC5)cn4)ncc3F)cc21] |
| 491 | 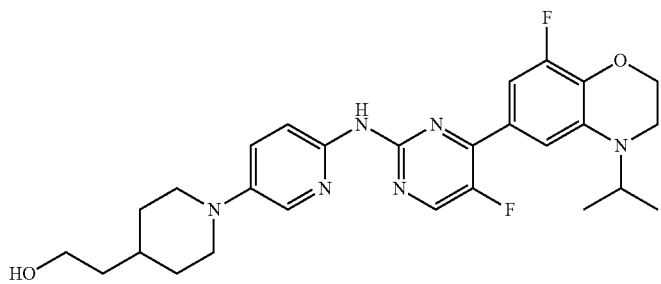 [SMILES: CC(C)N1CCOc2c(F)cc(-c3nc(Nc4ccc(N5CCC(CCO)CC5)cn4)ncc3F)cc21] |
| 492 | 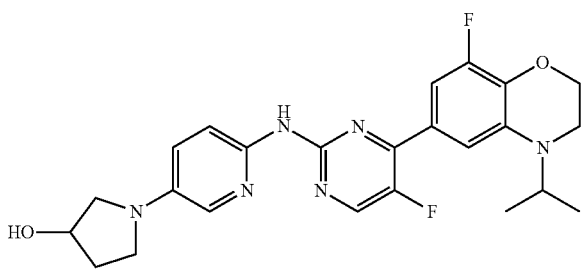 [SMILES: CC(C)N1CCOc2c(F)cc(-c3nc(Nc4ccc(N5CCC(O)C5)cn4)ncc3F)cc21] |
| 493 | 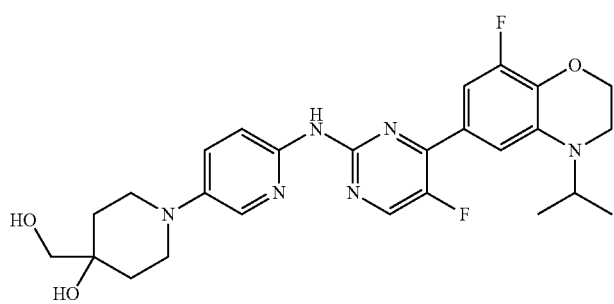 [SMILES: CC(C)N1CCOc2c(F)cc(-c3nc(Nc4ccc(N5CCC(O)(CO)CC5)cn4)ncc3F)cc21] |
| 494 | 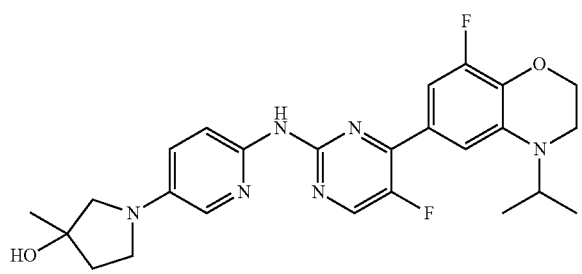 [SMILES: CC(C)N1CCOc2c(F)cc(-c3nc(Nc4ccc(N5CCC(C)(O)C5)cn4)ncc3F)cc21] |

TABLE 1-continued

| Compound No. | Structure |
|---|---|
| 495 | 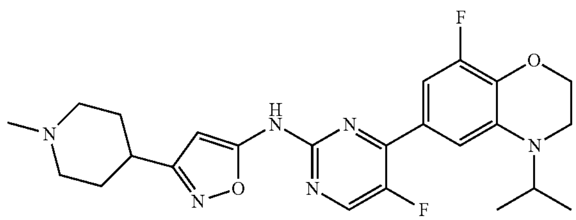 [SMILES: CC(C)N1CCOc2c(F)cc(-c3nc(Nc4cc(C5CCN(C)CC5)no4)ncc3F)cc21] |
| 496 | 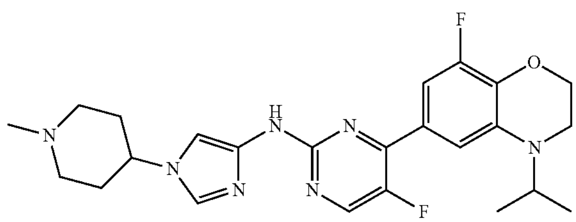 [SMILES: CC(C)N1CCOc2c(F)cc(-c3nc(Nc4cn(C5CCN(C)CC5)cn4)ncc3F)cc21] |
| 497 | 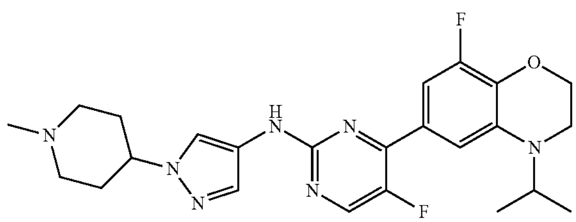 [SMILES: CC(C)N1CCOc2c(F)cc(-c3nc(Nc4cnn(C5CCN(C)CC5)c4)ncc3F)cc21] |
| 498 | 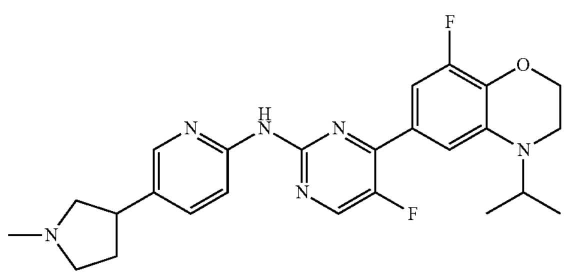 [SMILES: CC(C)N1CCOc2c(F)cc(-c3nc(Nc4ccc(C5CCN(C)C5)cn4)ncc3F)cc21] |
| 499 | 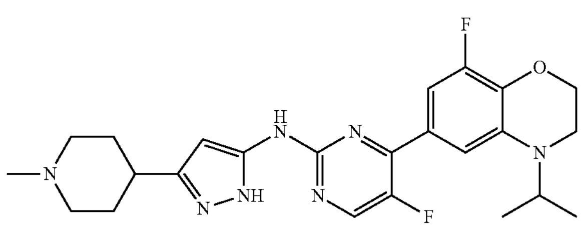 [SMILES: CC(C)N1CCOc2c(F)cc(-c3nc(Nc4cc(C5CCN(C)CC5)n[nH]4)ncc3F)cc21] |
| 500 | 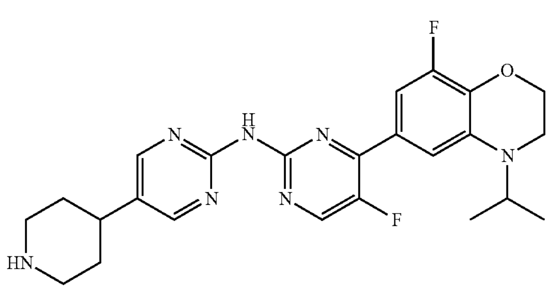 |

TABLE 1-continued
| Compound No. | Structure |
|---|---|
| 501 | 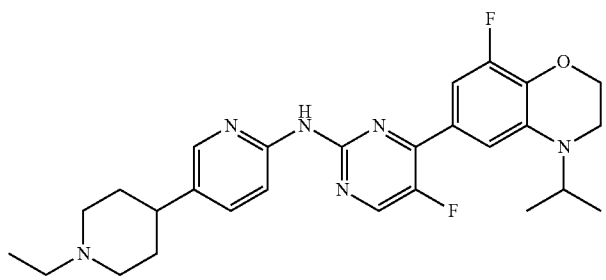 [SMILES: CCN1CCC(c2ccc(Nc3ncc(F)c(-c4cc(F)c5c(c4)N(C(C)C)CCO5)n3)nc2)CC1] |
| 502 | 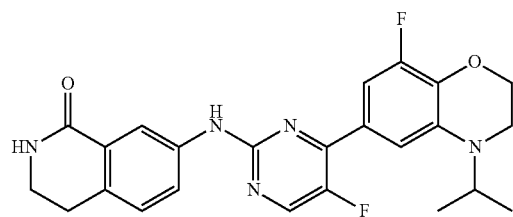 [SMILES: CC(C)N1CCOc2c(F)cc(-c3nc(Nc4ccc5c(c4)C(=O)NCC5)ncc3F)cc21] |
| 503 | 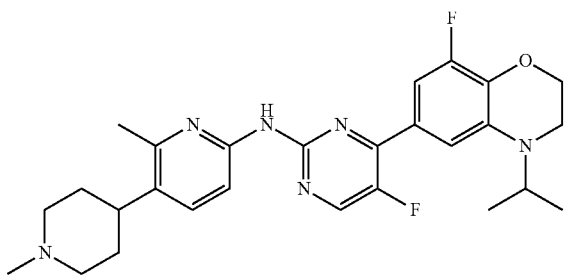 |
| 504 | 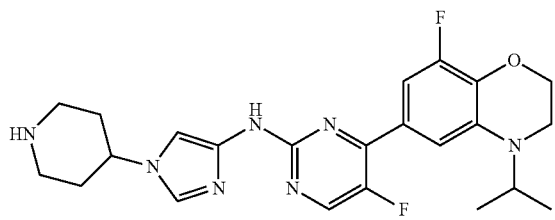 |
| 505 | 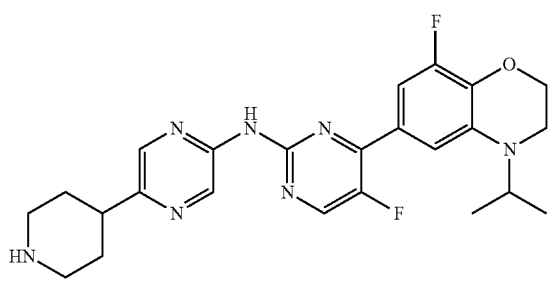 |

TABLE 1-continued
| Compound No. | Structure |
|---|---|
| 506 | 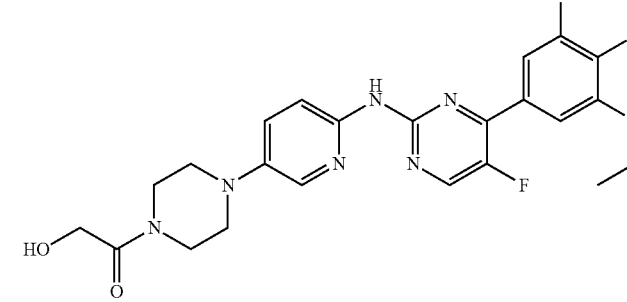 |
| 507 | 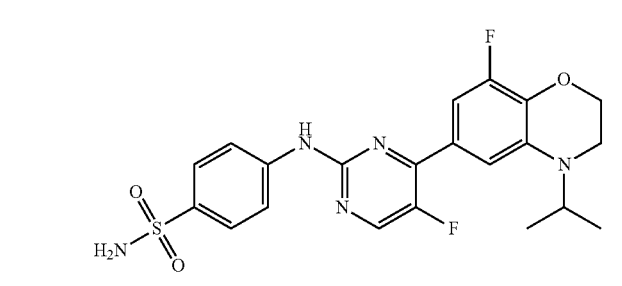 [SMILES: CC(C)N1CCOc2c(F)cc(-c3nc(Nc4ccc(S(N)(=O)=O)cc4)ncc3F)cc21] |
| 508 | 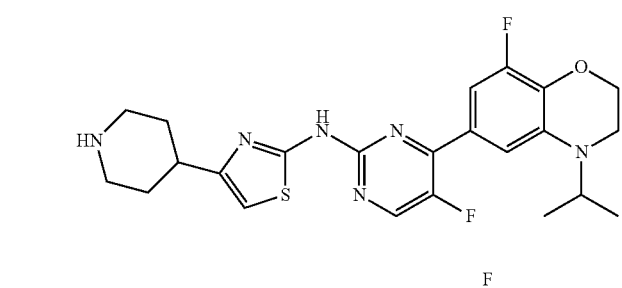 |
| 509 | 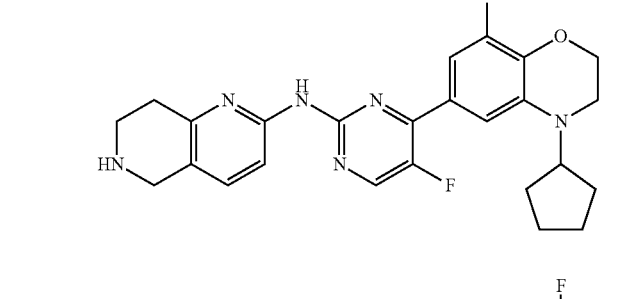 |
| 510 | 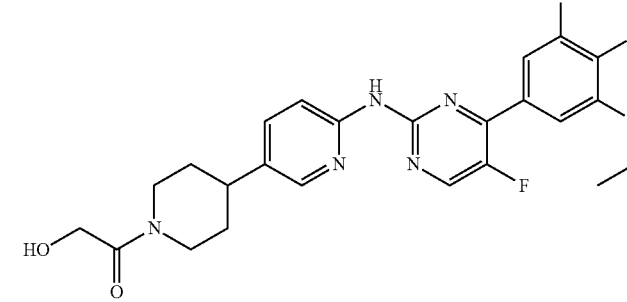 |

| Compound No. | Structure |
|---|---|
| 511 | (2,6-dimethylmorpholine-carbonyl-pyridin-2-yl)amino-pyrimidine with 5-F, 4-(8-fluoro-4-isopropyl-3,4-dihydro-2H-benzo[b][1,4]oxazin-6-yl) |
| 512 | 5-(3-oxopiperazin-1-yl)pyridin-2-yl amino pyrimidine with 5-F, 4-(8-fluoro-4-isopropyl-3,4-dihydro-2H-benzo[b][1,4]oxazin-6-yl) |
| 513 | 4-(N-(2-(dimethylamino)ethyl)sulfamoyl)phenylamino pyrimidine with 5-F, 4-(8-fluoro-4-isopropyl-3,4-dihydro-2H-benzo[b][1,4]oxazin-6-yl) |
| 514 | 5-(piperidin-4-yl)thiazol-2-ylamino pyrimidine with 5-F, 4-(8-fluoro-4-isopropyl-3,4-dihydro-2H-benzo[b][1,4]oxazin-6-yl) |
| 515 | 5-(2,6-dimethylmorpholino)pyridin-2-ylamino pyrimidine with 5-F, 4-(8-fluoro-4-isopropyl-3,4-dihydro-2H-benzo[b][1,4]oxazin-6-yl) |

TABLE 1-continued
| Compound No. | Structure |
|---|---|
| 516 | 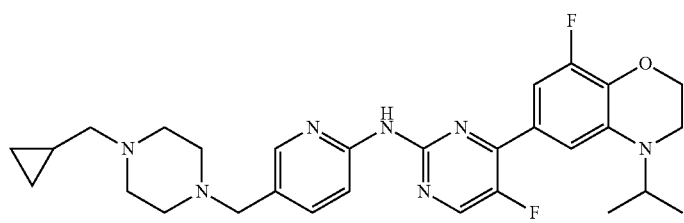 [SMILES: CC(C)N1CCOc2c(F)cc(-c3nc(Nc4ccc(CN5CCN(CC6CC6)CC5)cn4)ncc3F)cc21] |
| 517 | 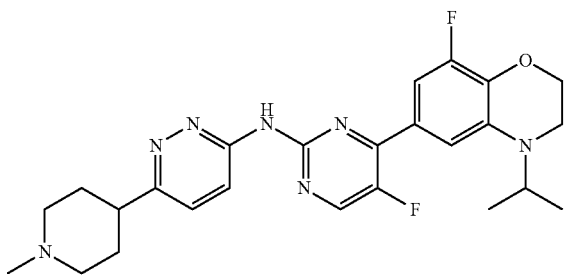 [SMILES: CC(C)N1CCOc2c(F)cc(-c3nc(Nc4ccc(C5CCN(C)CC5)nn4)ncc3F)cc21] |
| 518 | 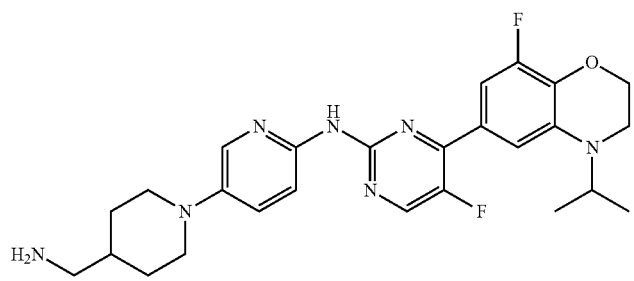 [SMILES: CC(C)N1CCOc2c(F)cc(-c3nc(Nc4ccc(N5CCC(CN)CC5)cn4)ncc3F)cc21] |
| 519 | 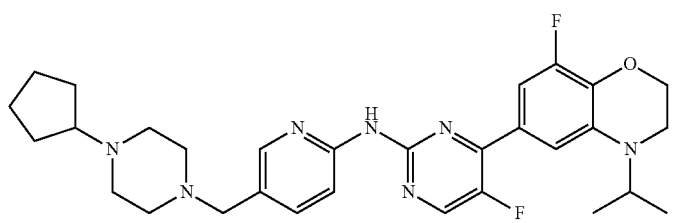 [SMILES: CC(C)N1CCOc2c(F)cc(-c3nc(Nc4ccc(CN5CCN(C6CCCC6)CC5)cn4)ncc3F)cc21] |
| 520 | 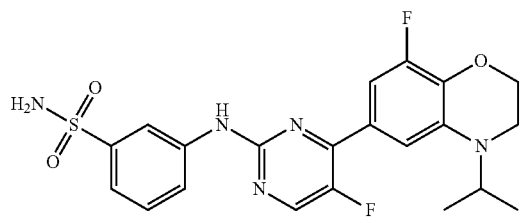 [SMILES: CC(C)N1CCOc2c(F)cc(-c3nc(Nc4cccc(S(N)(=O)=O)c4)ncc3F)cc21] |
| 521 | 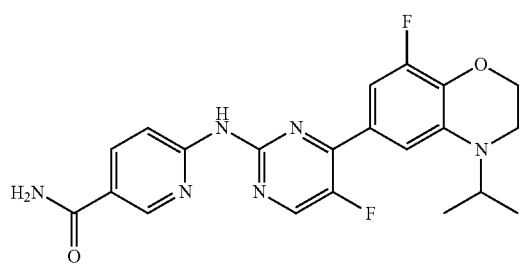 [SMILES: CC(C)N1CCOc2c(F)cc(-c3nc(Nc4ccc(C(N)=O)cn4)ncc3F)cc21] |

TABLE 1-continued

| Compound No. | Structure |
|---|---|
| 522 | 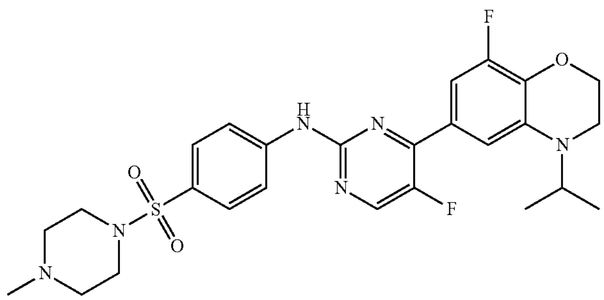 [SMILES: CC(C)N1CCOc2c(F)cc(-c3nc(Nc4ccc(S(=O)(=O)N5CCN(C)CC5)cc4)ncc3F)cc21] |
| 523 | 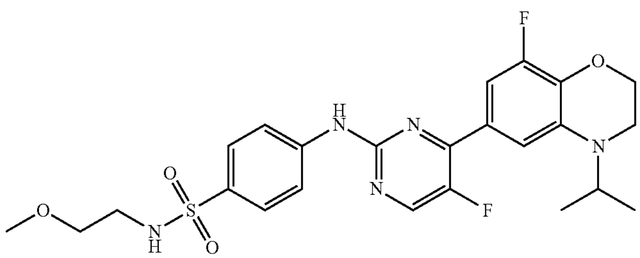 [SMILES: COCCNS(=O)(=O)c1ccc(Nc2ncc(F)c(-c3cc(F)c4c(c3)N(C(C)C)CCO4)n2)cc1] |
| 524 | 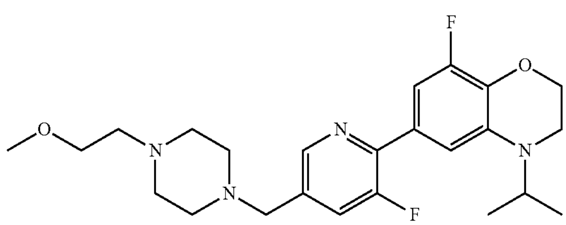 [SMILES: COCCN1CCN(Cc2cnc(-c3cc(F)c4c(c3)N(C(C)C)CCO4)c(F)c2)CC1] |
| 525 | 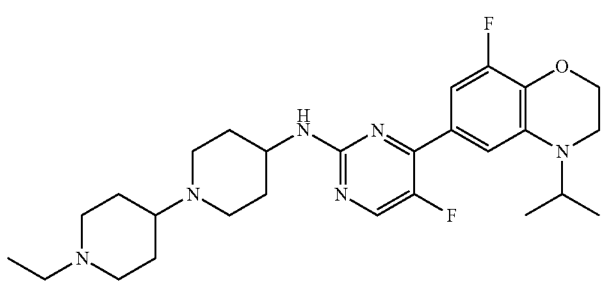 [SMILES: CCN1CCC(N2CCC(Nc3ncc(F)c(-c4cc(F)c5c(c4)N(C(C)C)CCO5)n3)CC2)CC1] |
| 526 | 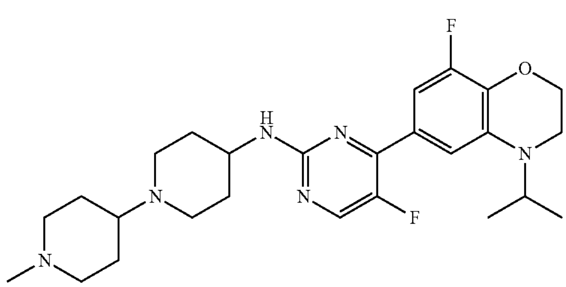 [SMILES: CC(C)N1CCOc2c(F)cc(-c3nc(NC4CCN(C5CCN(C)CC5)CC4)ncc3F)cc21] |

TABLE 1-continued

| Compound No. | Structure |
|---|---|
| 527 | 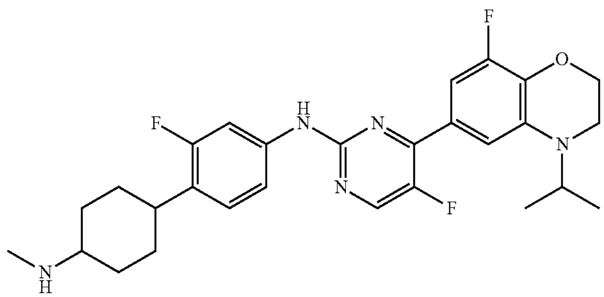 [SMILES: CNC1CCC(c2ccc(Nc3ncc(F)c(-c4cc(F)c5c(c4)N(C(C)C)CCO5)n3)cc2F)CC1] |
| 528 | 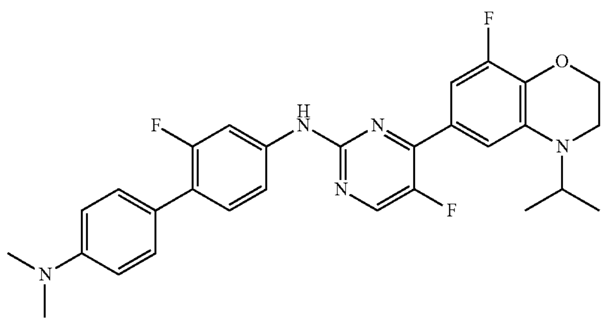 [SMILES: CC(C)N1CCOc2c(F)cc(-c3nc(Nc4ccc(-c5ccc(N(C)C)cc5)c(F)c4)ncc3F)cc21] |
| 529 | 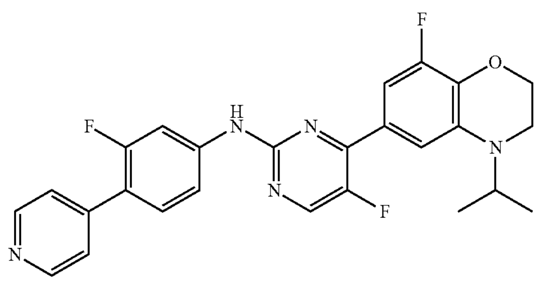 [SMILES: CC(C)N1CCOc2c(F)cc(-c3nc(Nc4ccc(-c5ccncc5)c(F)c4)ncc3F)cc21] |
| 530 | 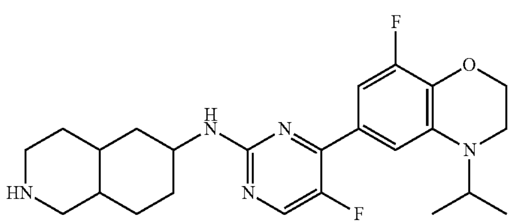 [SMILES: CC(C)N1CCOc2c(F)cc(-c3nc(NC4CCC5CNCCC5C4)ncc3F)cc21] |
| 531 | 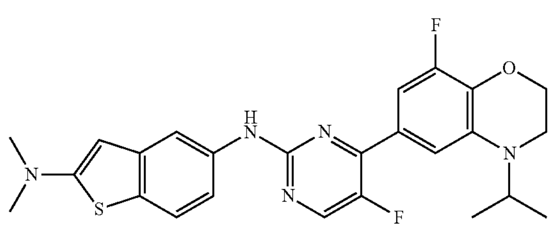 [SMILES: CC(C)N1CCOc2c(F)cc(-c3nc(Nc4ccc5sc(N(C)C)cc5c4)ncc3F)cc21] |
| 532 | 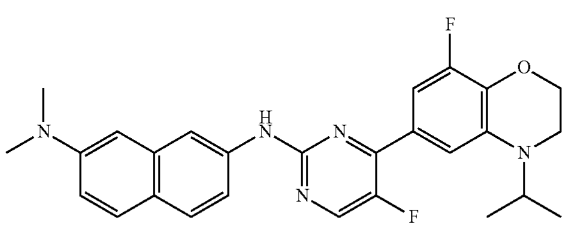 [SMILES: CC(C)N1CCOc2c(F)cc(-c3nc(Nc4ccc5ccc(N(C)C)cc5c4)ncc3F)cc21] |

TABLE 1-continued
| Compound No. | Structure |
|---|---|
| 533 | 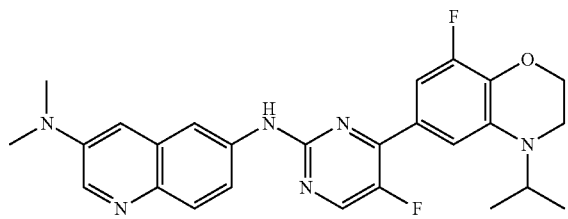 |
| 534 | 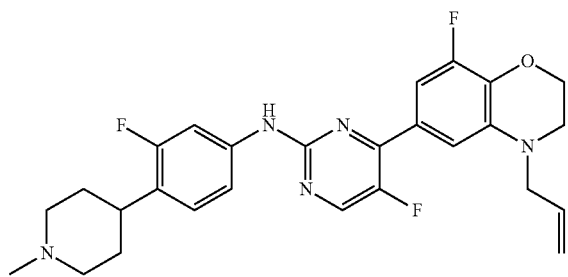 [SMILES: C=CCN1CCOc2c(F)cc(-c3nc(Nc4ccc(C5CCN(C)CC5)c(F)c4)ncc3F)cc21] |
| 535 | 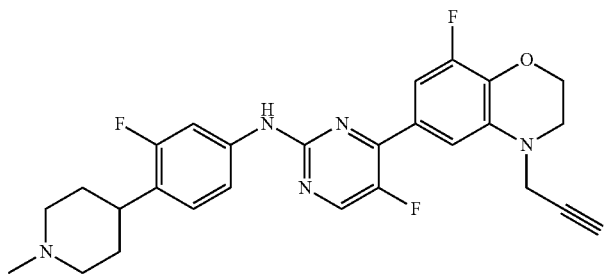 [SMILES: C#CCN1CCOc2c(F)cc(-c3nc(Nc4ccc(C5CCN(C)CC5)c(F)c4)ncc3F)cc21] |
| 536 | 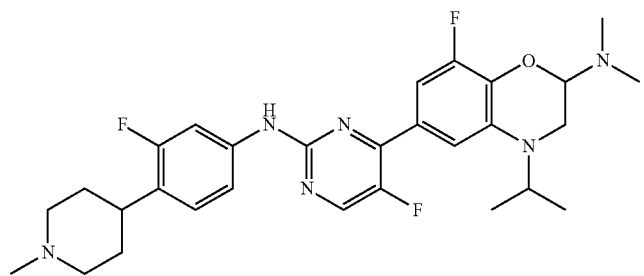 |
| 537 | 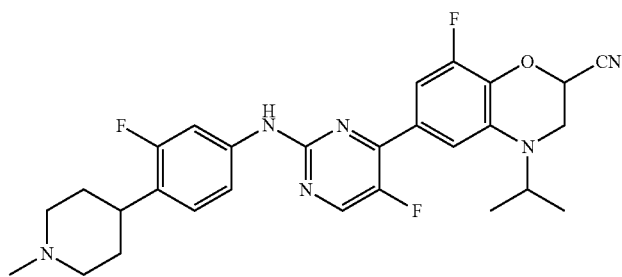 [SMILES: CC(C)N1CC(C#N)Oc2c(F)cc(-c3nc(Nc4ccc(C5CCN(C)CC5)c(F)c4)ncc3F)cc21] |

TABLE 1-continued
| Compound No. | Structure |
|---|---|
| 538 | 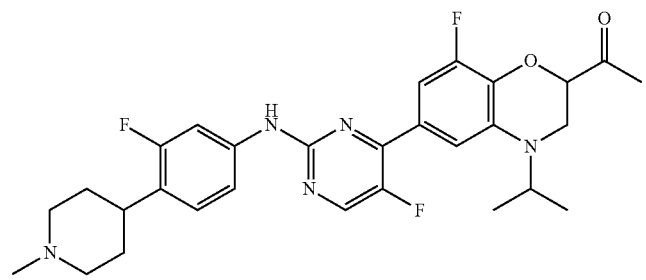 [SMILES: CC(=O)C1CN(C(C)C)c2cc(-c3nc(Nc4ccc(C5CCN(C)CC5)c(F)c4)ncc3F)cc(F)c2O1] |
| 539 | 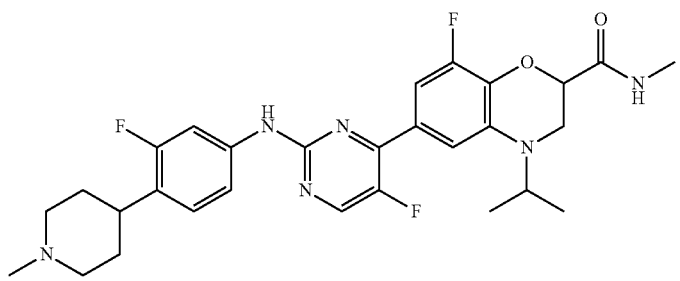 |
| 540 | 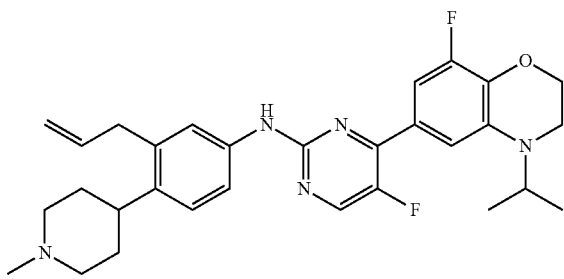 [SMILES: C=CCc1cc(Nc2ncc(F)c(-c3cc(F)c4c(c3)N(C(C)C)CCO4)n2)ccc1C1CCN(C)CC1] |
| 541 | 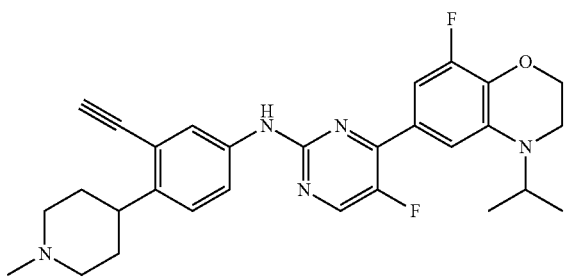 [SMILES: C#Cc1cc(Nc2ncc(F)c(-c3cc(F)c4c(c3)N(C(C)C)CCO4)n2)ccc1C1CCN(C)CC1] |
| 542 | 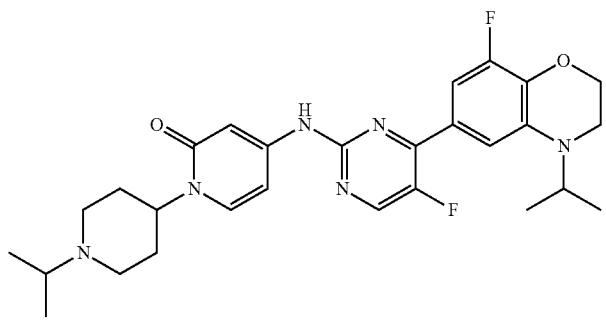 [SMILES: CC(C)N1CCC(n2ccc(Nc3ncc(F)c(-c4cc(F)c5c(c4)N(C(C)C)CCO5)n3)cc2=O)CC1] |

TABLE 1-continued
| Compound No. | Structure |
|---|---|
| 543 | 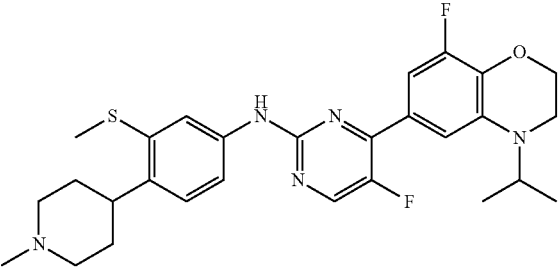 [SMILES: CSc1cc(Nc2ncc(F)c(-c3cc(F)c4c(c3)N(C(C)C)CCO4)n2)ccc1C1CCN(C)CC1] |
| 544 | 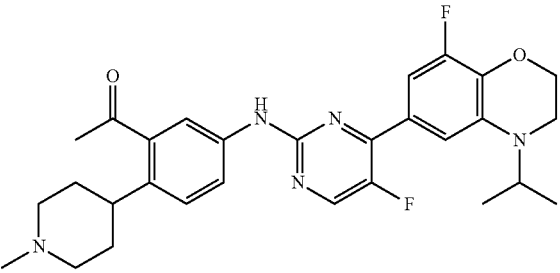 [SMILES: CC(=O)c1cc(Nc2ncc(F)c(-c3cc(F)c4c(c3)N(C(C)C)CCO4)n2)ccc1C1CCN(C)CC1] |
| 545 | 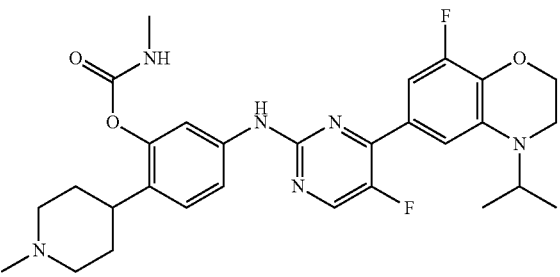 |
| 546 | 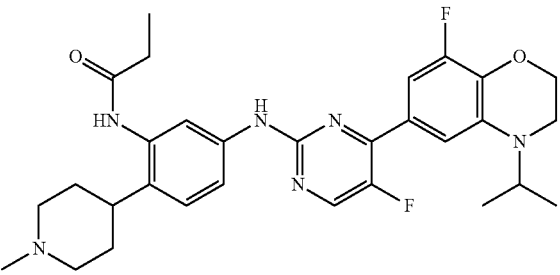 [SMILES: CCC(=O)Nc1cc(Nc2ncc(F)c(-c3cc(F)c4c(c3)N(C(C)C)CCO4)n2)ccc1C1CCN(C)CC1] |
| 547 | 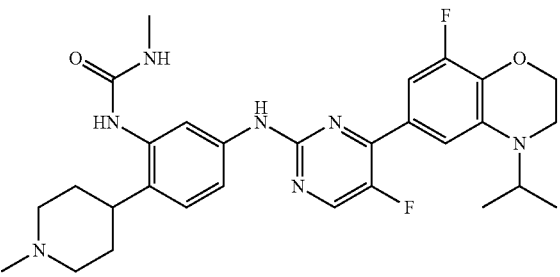 |

TABLE 1-continued
| Compound No. | Structure |
|---|---|
| 548 | 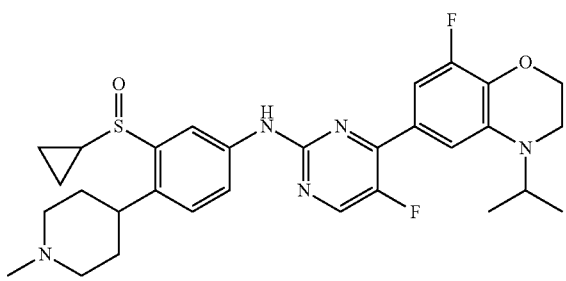 [SMILES: CC(C)N1CCOc2c(F)cc(-c3nc(Nc4ccc(C5CCN(C)CC5)c(S(=O)C5CC5)c4)ncc3F)cc21] |
| 549 | 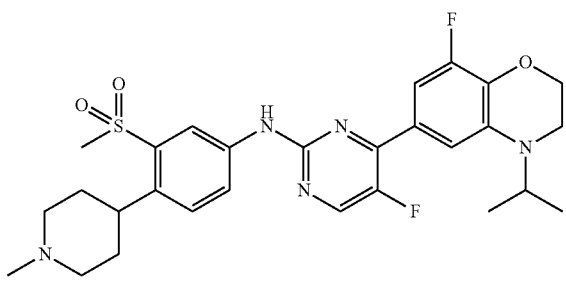 [SMILES: CC(C)N1CCOc2c(F)cc(-c3nc(Nc4ccc(C5CCN(C)CC5)c(S(C)(=O)=O)c4)ncc3F)cc21] |
| 550 | 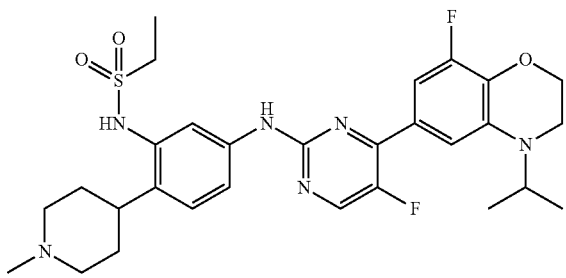 [SMILES: CCS(=O)(=O)Nc1cc(Nc2ncc(F)c(-c3cc(F)c4c(c3)N(C(C)C)CCO4)n2)ccc1C1CCN(C)CC1] |
| 551 | 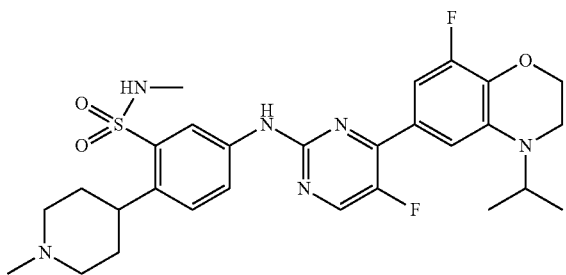 [SMILES: CNS(=O)(=O)c1cc(Nc2ncc(F)c(-c3cc(F)c4c(c3)N(C(C)C)CCO4)n2)ccc1C1CCN(C)CC1] |
| 552 | 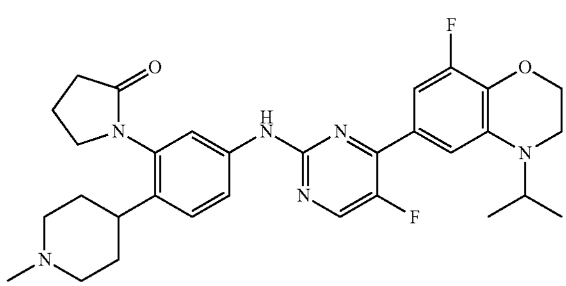 [SMILES: CC(C)N1CCOc2c(F)cc(-c3nc(Nc4ccc(C5CCN(C)CC5)c(N5CCCC5=O)c4)ncc3F)cc21] |

TABLE 1-continued
| Compound No. | Structure |
|---|---|
| 553 | 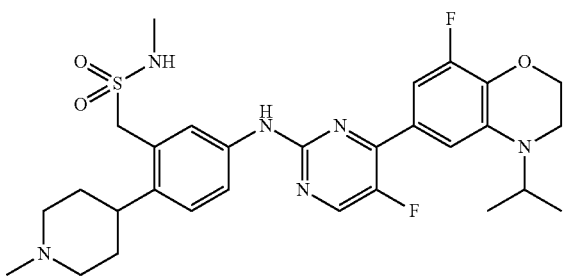 [SMILES: CNS(=O)(=O)Cc1cc(Nc2ncc(F)c(-c3cc(F)c4c(c3)N(C(C)C)CCO4)n2)ccc1C1CCN(C)CC1] |
| 554 | 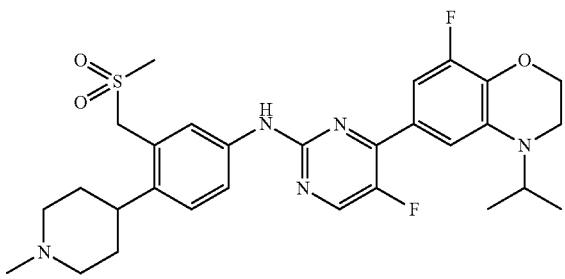 [SMILES: CC(C)N1CCOc2c(F)cc(-c3nc(Nc4ccc(C5CCN(C)CC5)c(CS(C)(=O)=O)c4)ncc3F)cc21] |
| 555 | 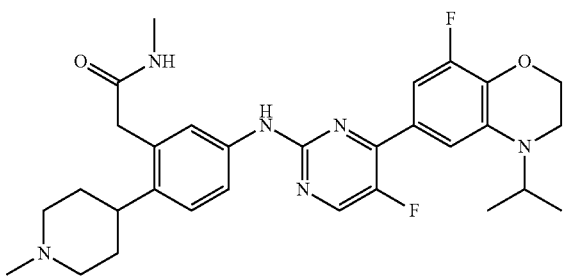 [SMILES: CNC(=O)Cc1cc(Nc2ncc(F)c(-c3cc(F)c4c(c3)N(C(C)C)CCO4)n2)ccc1C1CCN(C)CC1] |
| 556 | 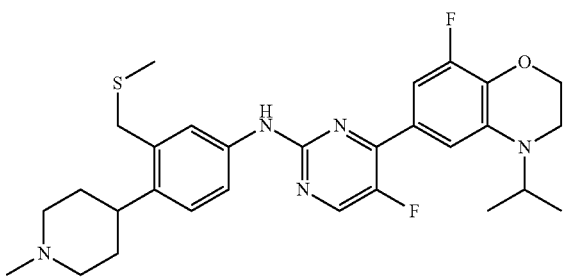 [SMILES: CSCc1cc(Nc2ncc(F)c(-c3cc(F)c4c(c3)N(C(C)C)CCO4)n2)ccc1C1CCN(C)CC1] |
| 557 | 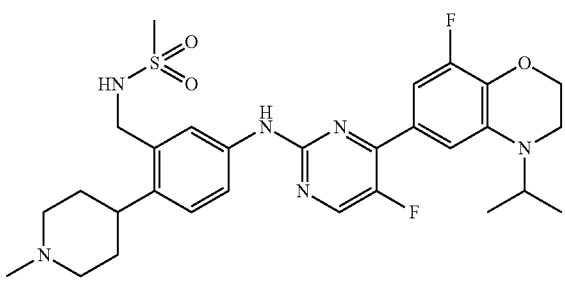 [SMILES: CC(C)N1CCOc2c(F)cc(-c3nc(Nc4ccc(C5CCN(C)CC5)c(CNS(C)(=O)=O)c4)ncc3F)cc21] |

TABLE 1-continued
| Compound No. | Structure |
|---|---|
| 558 | 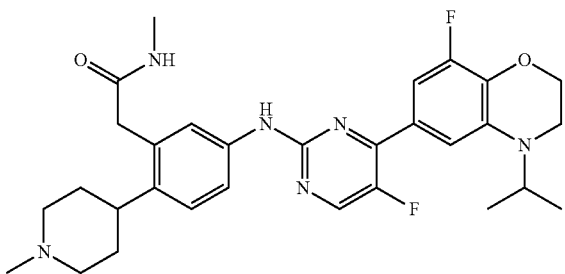 |
| 559 | 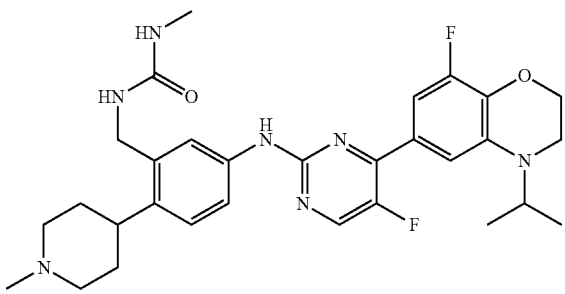 [SMILES: CNC(=O)NCc1cc(Nc2ncc(F)c(-c3cc(F)c4c(c3)N(C(C)C)CCO4)n2)ccc1C1CCN(C)CC1] |
| 560 | 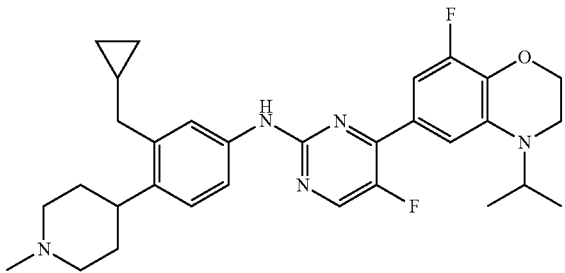 [SMILES: CC(C)N1CCOc2c(F)cc(-c3nc(Nc4ccc(C5CCN(C)CC5)c(CC5CC5)c4)ncc3F)cc21] |
| 561 | 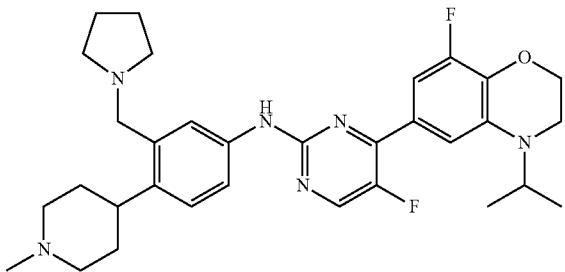 [SMILES: CC(C)N1CCOc2c(F)cc(-c3nc(Nc4ccc(C5CCN(C)CC5)c(CN5CCCC5)c4)ncc3F)cc21] |
| 562 | 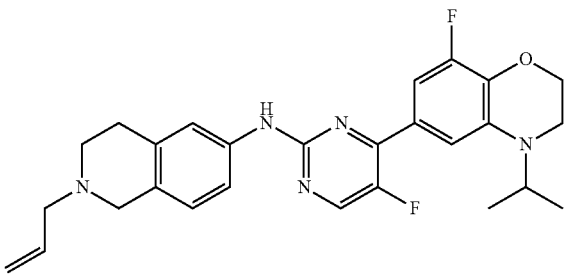 [SMILES: C=CCN1CCc2cc(Nc3ncc(F)c(-c4cc(F)c5c(c4)N(C(C)C)CCO5)n3)ccc2C1] |

TABLE 1-continued
| Compound No. | Structure |
|---|---|
| 563 | 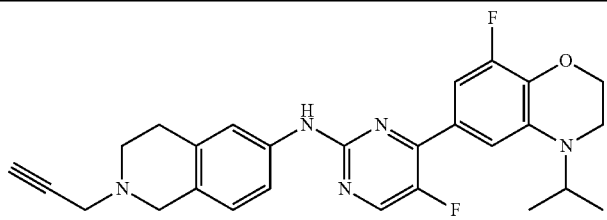 |
| 564 | 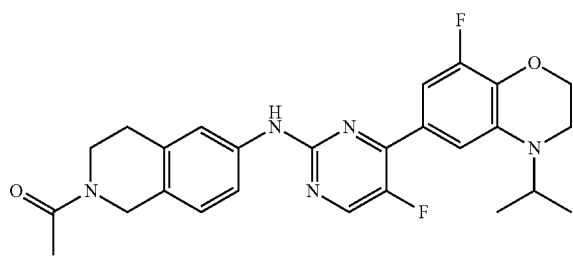 [SMILES: CC(=O)N1CCc2cc(Nc3ncc(F)c(-c4cc(F)c5c(c4)N(C(C)C)CCO5)n3)ccc2C1] |
| 565 | 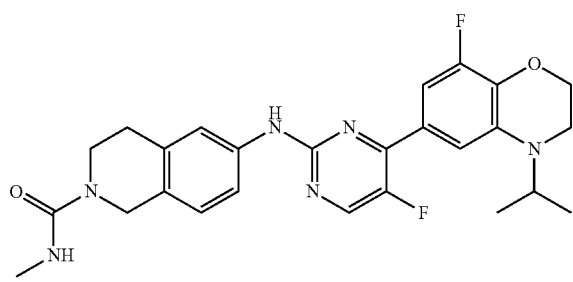 [SMILES: CNC(=O)N1CCc2cc(Nc3ncc(F)c(-c4cc(F)c5c(c4)N(C(C)C)CCO5)n3)ccc2C1] |
| 566 | 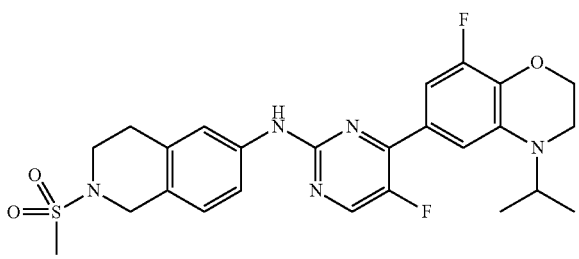 [SMILES: CC(C)N1CCOc2c(F)cc(-c3nc(Nc4ccc5c(c4)CCN(S(C)(=O)=O)C5)ncc3F)cc21] |
| 567 | 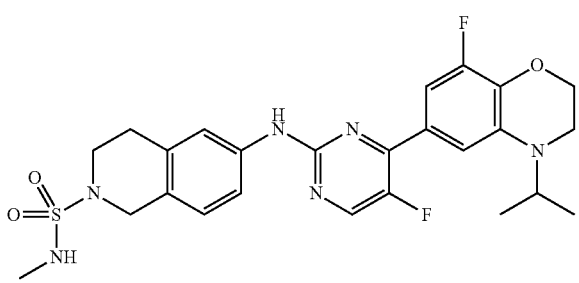 [SMILES: CNS(=O)(=O)N1CCc2cc(Nc3ncc(F)c(-c4cc(F)c5c(c4)N(C(C)C)CCO5)n3)ccc2C1] |
| 568 | 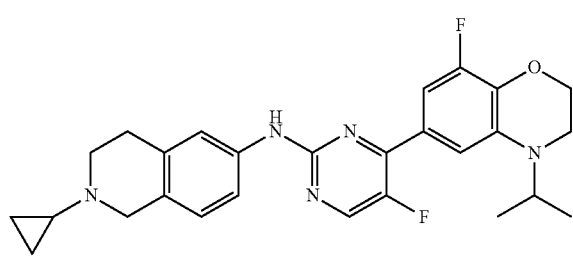 [SMILES: CC(C)N1CCOc2c(F)cc(-c3nc(Nc4ccc5c(c4)CCN(C4CC4)C5)ncc3F)cc21] |

TABLE 1-continued
| Compound No. | Structure |
|---|---|
| 569 | 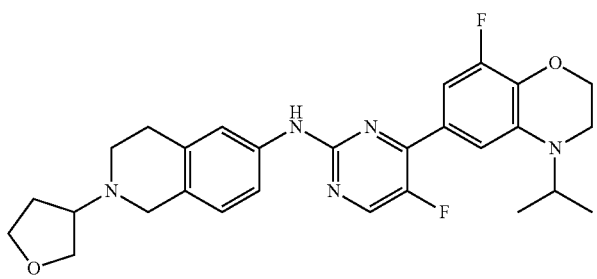 [SMILES: CC(C)N1CCOc2c(F)cc(-c3nc(Nc4ccc5c(c4)CCN(C4CCOC4)C5)ncc3F)cc21] |
| 570 | 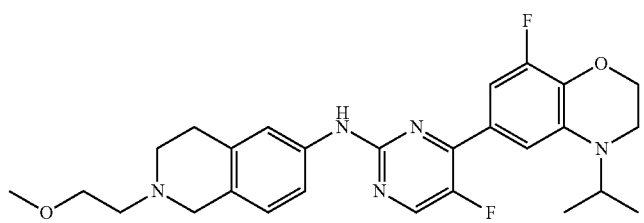 [SMILES: COCCN1CCc2cc(Nc3ncc(F)c(-c4cc(F)c5c(c4)N(C(C)C)CCO5)n3)ccc2C1] |
| 571 | 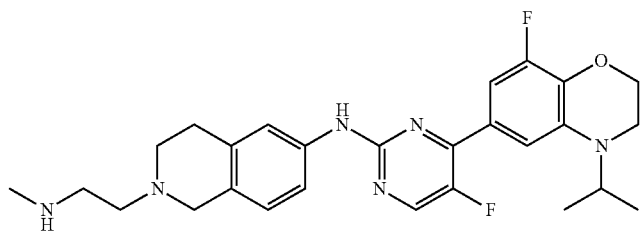 [SMILES: CNCCN1CCc2cc(Nc3ncc(F)c(-c4cc(F)c5c(c4)N(C(C)C)CCO5)n3)ccc2C1] |
| 572 | 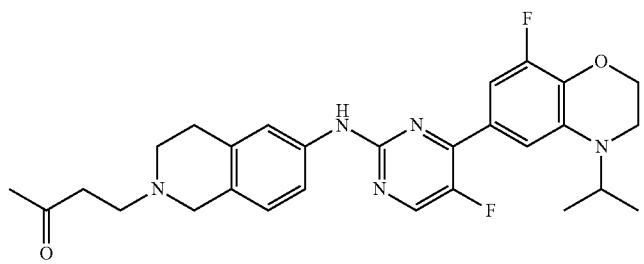 [SMILES: CC(=O)CCN1CCc2cc(Nc3ncc(F)c(-c4cc(F)c5c(c4)N(C(C)C)CCO5)n3)ccc2C1] |
| 573 | 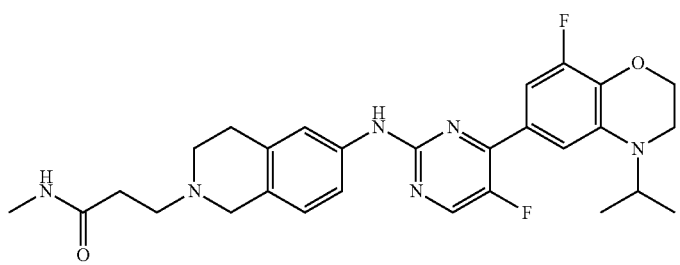 [SMILES: CNC(=O)CCN1CCc2cc(Nc3ncc(F)c(-c4cc(F)c5c(c4)N(C(C)C)CCO5)n3)ccc2C1] |
| 574 | 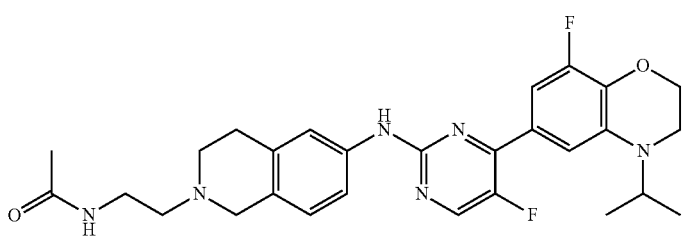 [SMILES: CC(=O)NCCN1CCc2cc(Nc3ncc(F)c(-c4cc(F)c5c(c4)N(C(C)C)CCO5)n3)ccc2C1] |

TABLE 1-continued

| Compound No. | Structure |
|---|---|
| 575 | 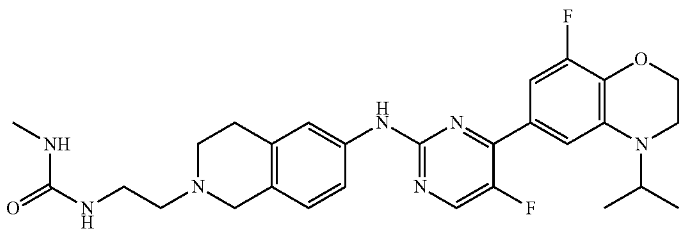 [SMILES: CNC(=O)NCCN1CCc2cc(Nc3ncc(F)c(-c4cc(F)c5c(c4)N(C(C)C)CCO5)n3)ccc2C1] |
| 576 | 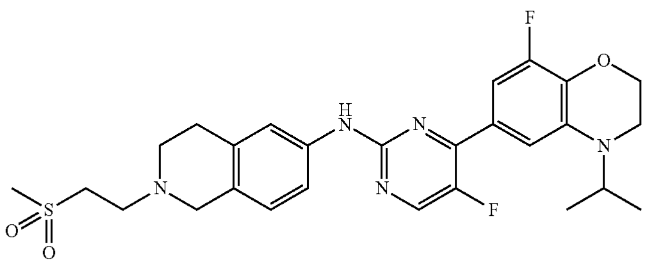 [SMILES: CC(C)N1CCOc2c(F)cc(-c3nc(Nc4ccc5c(c4)CCN(CCS(C)(=O)=O)C5)ncc3F)cc21] |
| 577 | 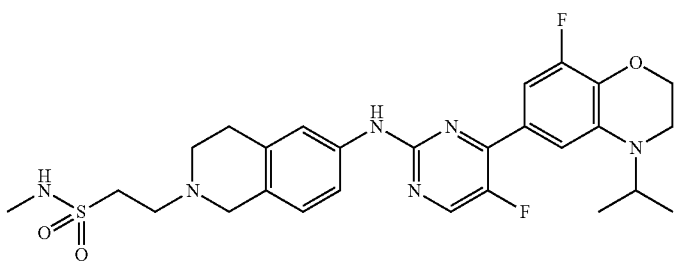 [SMILES: CNS(=O)(=O)CCN1CCc2cc(Nc3ncc(F)c(-c4cc(F)c5c(c4)N(C(C)C)CCO5)n3)ccc2C1] |
| 578 | 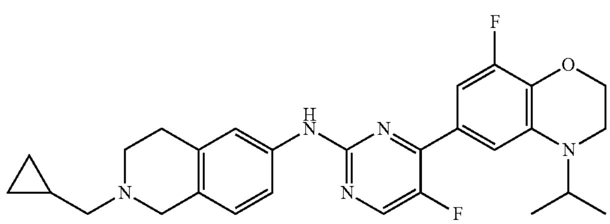 [SMILES: CC(C)N1CCOc2c(F)cc(-c3nc(Nc4ccc5c(c4)CCN(CC4CC4)C5)ncc3F)cc21] |
| 579 | 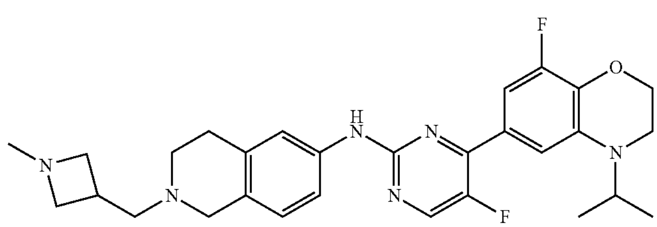 [SMILES: CC(C)N1CCOc2c(F)cc(-c3nc(Nc4ccc5c(c4)CCN(CC4CN(C)C4)C5)ncc3F)cc21] |
| 580 | 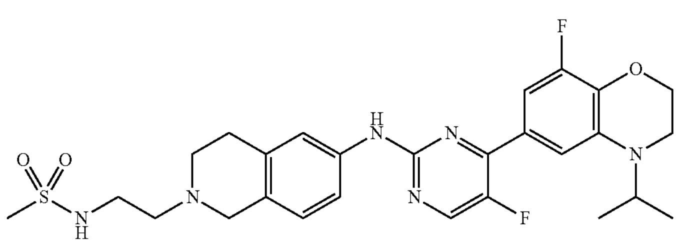 [SMILES: CC(C)N1CCOc2c(F)cc(-c3nc(Nc4ccc5c(c4)CCN(CCNS(C)(=O)=O)C5)ncc3F)cc21] |

TABLE 1-continued
| Compound No. | Structure |
|---|---|
| 581 | 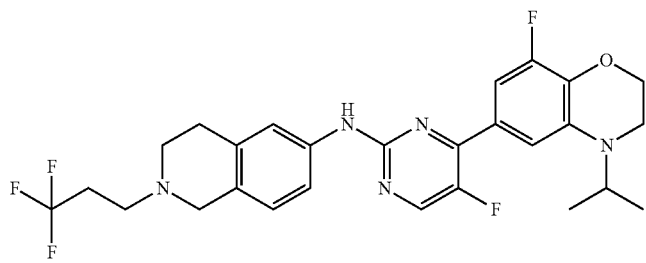 [SMILES: CC(C)N1CCOc2c(F)cc(-c3nc(Nc4ccc5c(c4)CCN(CCC(F)(F)F)C5)ncc3F)cc21] |
| 582 | 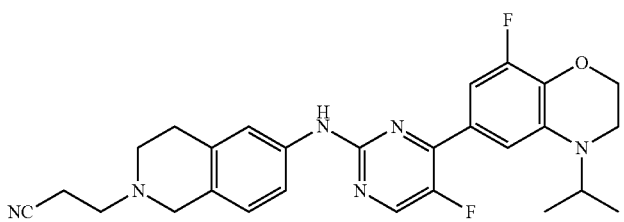 [SMILES: CC(C)N1CCOc2c(F)cc(-c3nc(Nc4ccc5c(c4)CCN(CCC#N)C5)ncc3F)cc21] |
| 583 | 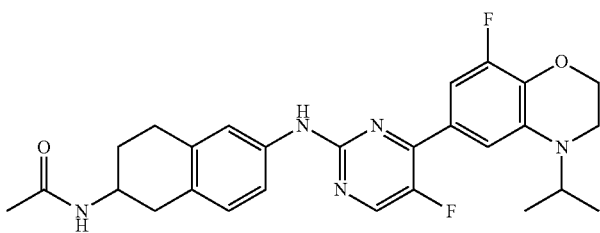 [SMILES: CC(=O)NC1CCc2cc(Nc3ncc(F)c(-c4cc(F)c5c(c4)N(C(C)C)CCO5)n3)ccc2C1] |
| 584 | 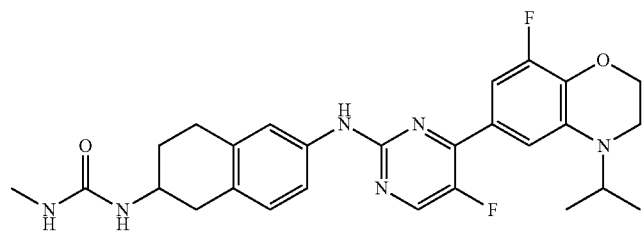 [SMILES: CNC(=O)NC1CCc2cc(Nc3ncc(F)c(-c4cc(F)c5c(c4)N(C(C)C)CCO5)n3)ccc2C1] |
| 585 | 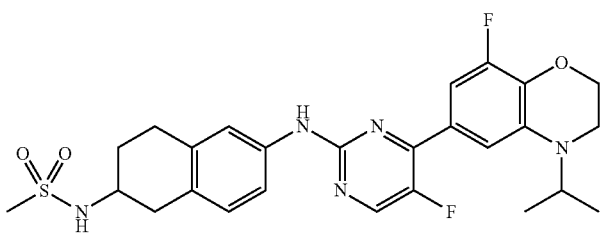 [SMILES: CC(C)N1CCOc2c(F)cc(-c3nc(Nc4ccc5c(c4)CCC(NS(C)(=O)=O)C5)ncc3F)cc21] |
| 586 | 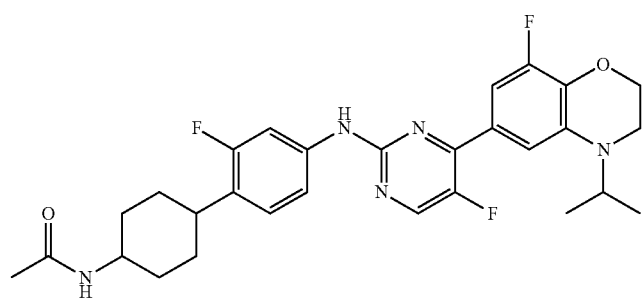 [SMILES: CC(=O)NC1CCC(c2ccc(Nc3ncc(F)c(-c4cc(F)c5c(c4)N(C(C)C)CCO5)n3)cc2F)CC1] |

TABLE 1-continued

| Compound No. | Structure |
|---|---|
| 587 | 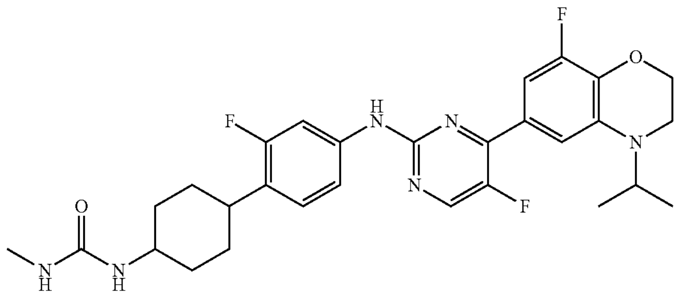 [SMILES: CNC(=O)NC1CCC(c2ccc(Nc3ncc(F)c(-c4cc(F)c5c(c4)N(C(C)C)CCO5)n3)cc2F)CC1] |
| 588 | 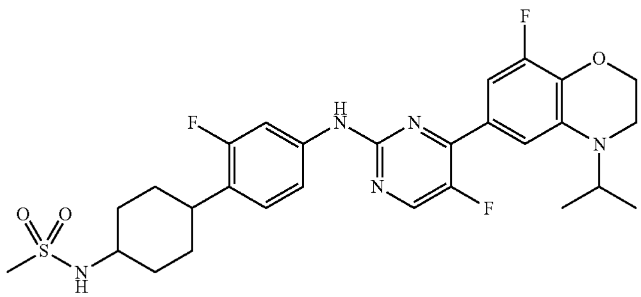 [SMILES: CC(C)N1CCOc2c(F)cc(-c3nc(Nc4ccc(C5CCC(NS(C)(=O)=O)CC5)c(F)c4)ncc3F)cc21] |
| 589 | 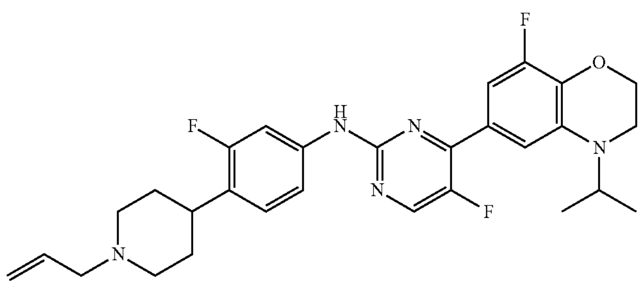 [SMILES: C=CCN1CCC(c2ccc(Nc3ncc(F)c(-c4cc(F)c5c(c4)N(C(C)C)CCO5)n3)cc2F)CC1] |
| 590 | 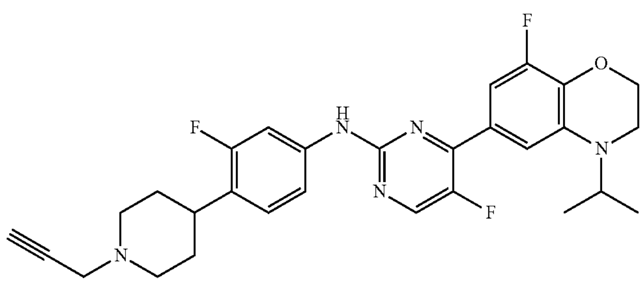 [SMILES: C#CCN1CCC(c2ccc(Nc3ncc(F)c(-c4cc(F)c5c(c4)N(C(C)C)CCO5)n3)cc2F)CC1] |
| 591 | 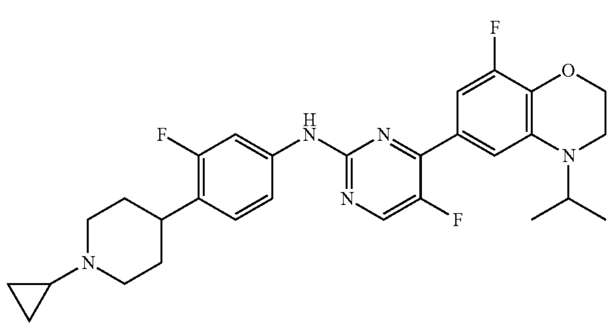 [SMILES: CC(C)N1CCOc2c(F)cc(-c3nc(Nc4ccc(C5CCN(C6CC6)CC5)c(F)c4)ncc3F)cc21] |

TABLE 1-continued
| Compound No. | Structure |
|---|---|
| 592 | 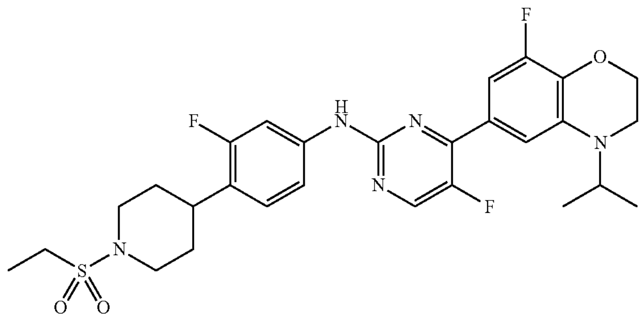 [SMILES: CCS(=O)(=O)N1CCC(c2ccc(Nc3ncc(F)c(-c4cc(F)c5c(c4)N(C(C)C)CCO5)n3)cc2F)CC1] |
| 593 | 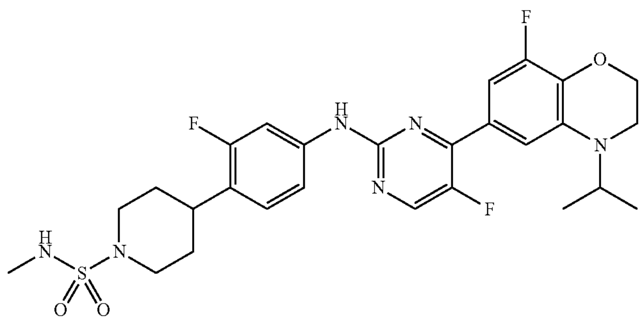 [SMILES: CNS(=O)(=O)N1CCC(c2ccc(Nc3ncc(F)c(-c4cc(F)c5c(c4)N(C(C)C)CCO5)n3)cc2F)CC1] |
| 594 | 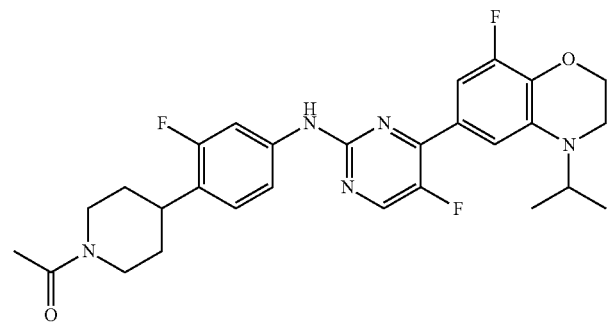 [SMILES: CC(=O)N1CCC(c2ccc(Nc3ncc(F)c(-c4cc(F)c5c(c4)N(C(C)C)CCO5)n3)cc2F)CC1] |
| 595 | 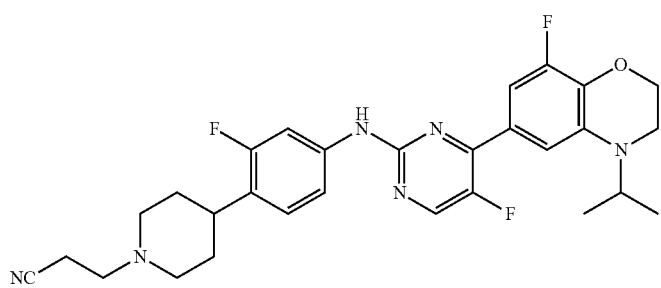 [SMILES: CC(C)N1CCOc2c(F)cc(-c3nc(Nc4ccc(C5CCN(CCC#N)CC5)c(F)c4)ncc3F)cc21] |
| 596 | 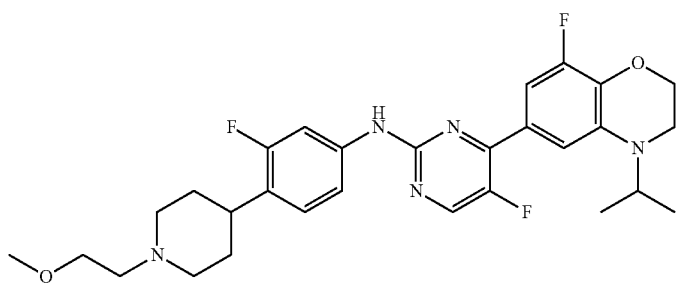 [SMILES: COCCN1CCC(c2ccc(Nc3ncc(F)c(-c4cc(F)c5c(c4)N(C(C)C)CCO5)n3)cc2F)CC1] |

TABLE 1-continued
| Compound No. | Structure |
|---|---|
| 597 | 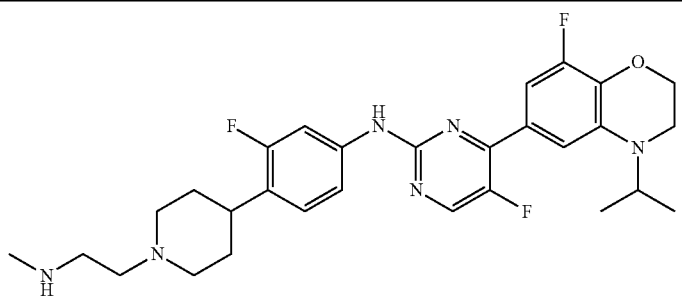 |
| 598 | 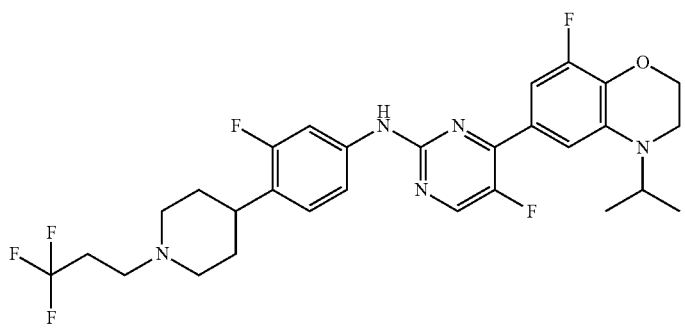 [SMILES: CC(C)N1CCOc2c(F)cc(-c3nc(Nc4ccc(C5CCN(CCC(F)(F)F)CC5)c(F)c4)ncc3F)cc21] |
| 599 | 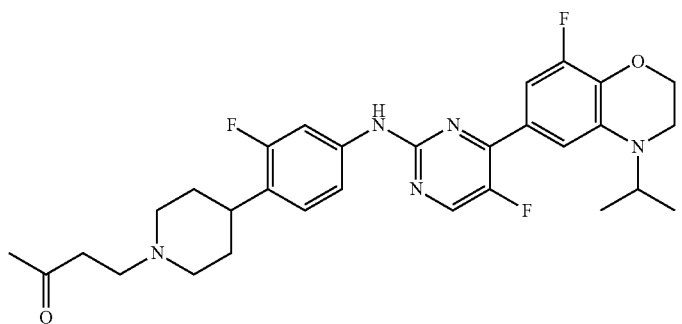 [SMILES: CC(=O)CCN1CCC(c2ccc(Nc3ncc(F)c(-c4cc(F)c5c(c4)N(C(C)C)CCO5)n3)cc2F)CC1] |
| 600 | 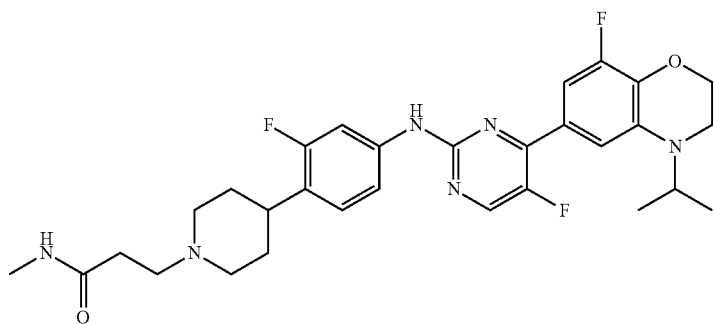 [SMILES: CNC(=O)CCN1CCC(c2ccc(Nc3ncc(F)c(-c4cc(F)c5c(c4)N(C(C)C)CCO5)n3)cc2F)CC1] |
| 601 | 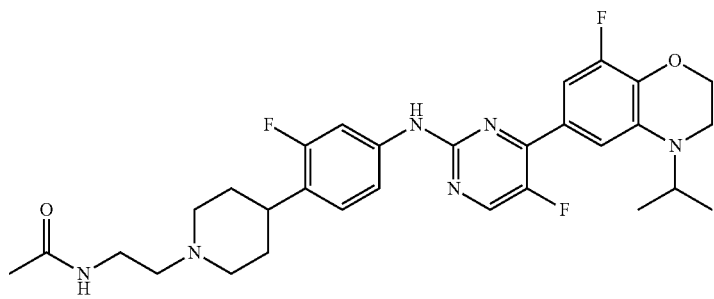 [SMILES: CC(=O)NCCN1CCC(c2ccc(Nc3ncc(F)c(-c4cc(F)c5c(c4)N(C(C)C)CCO5)n3)cc2F)CC1] |

TABLE 1-continued
| Compound No. | Structure |
|---|---|
| 602 | 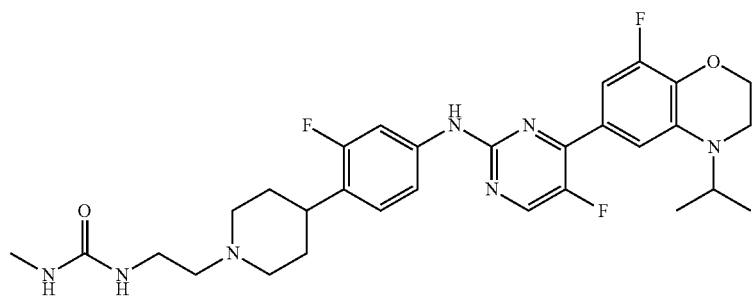 [SMILES: CNC(=O)NCCN1CCC(c2ccc(Nc3ncc(F)c(-c4cc(F)c5c(c4)N(C(C)C)CCO5)n3)cc2F)CC1] |
| 603 | 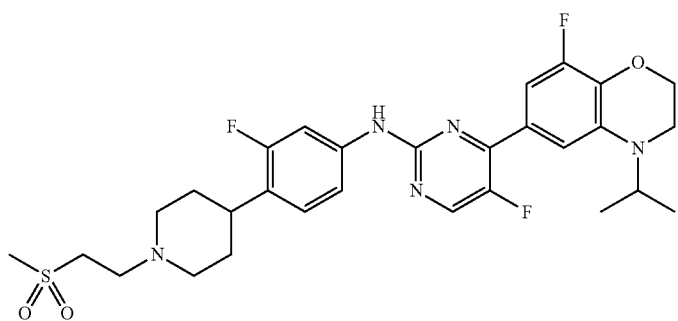 [SMILES: CC(C)N1CCOc2c(F)cc(-c3nc(Nc4ccc(C5CCN(CCS(C)(=O)=O)CC5)c(F)c4)ncc3F)cc21] |
| 604 | 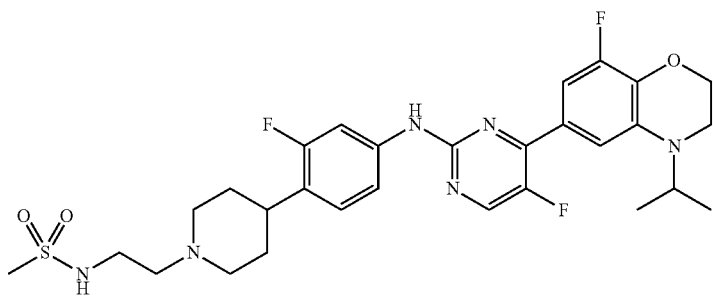 [SMILES: CC(C)N1CCOc2c(F)cc(-c3nc(Nc4ccc(C5CCN(CCNS(C)(=O)=O)CC5)c(F)c4)ncc3F)cc21] |
| 605 | 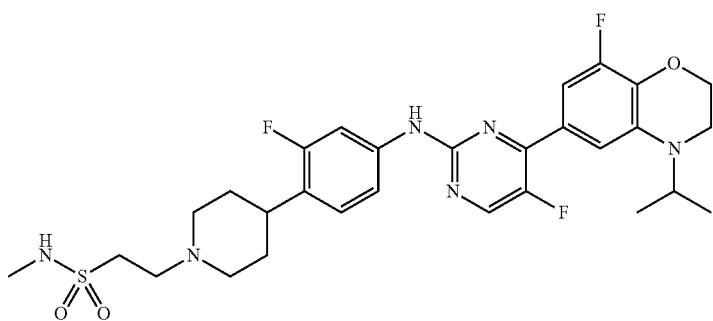 [SMILES: CNS(=O)(=O)CCN1CCC(c2ccc(Nc3ncc(F)c(-c4cc(F)c5c(c4)N(C(C)C)CCO5)n3)cc2F)CC1] |
| 606 | 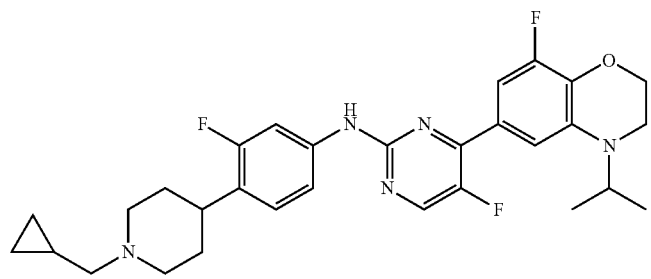 [SMILES: CC(C)N1CCOc2c(F)cc(-c3nc(Nc4ccc(C5CCN(CC6CC6)CC5)c(F)c4)ncc3F)cc21] |

TABLE 1-continued
| Compound No. | Structure |
|---|---|
| 607 | 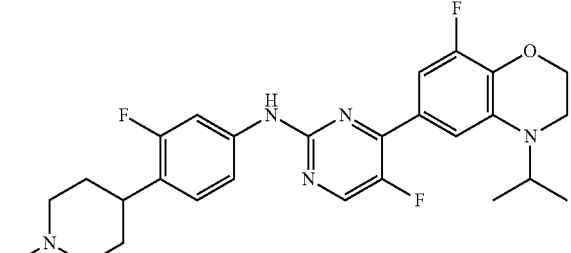 |
| 608 | 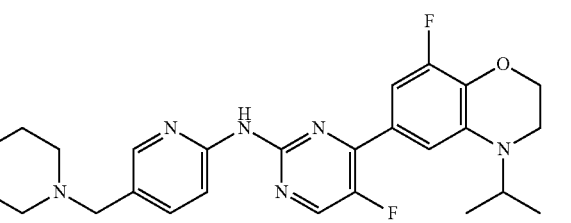 |
| 609 | 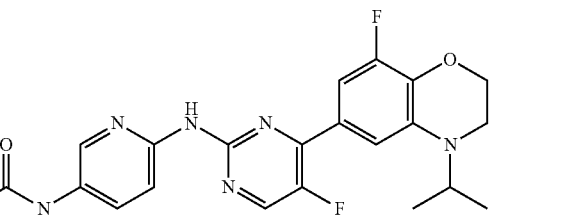 |
| 610 | 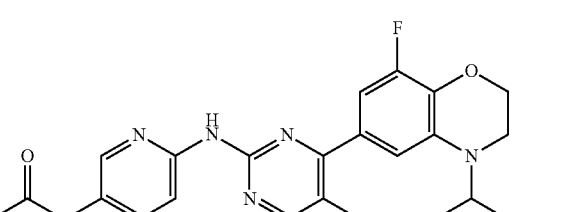 |
| 611 | 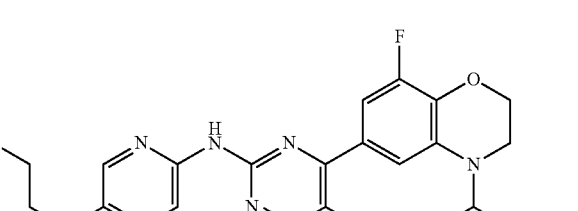 |
| 612 | 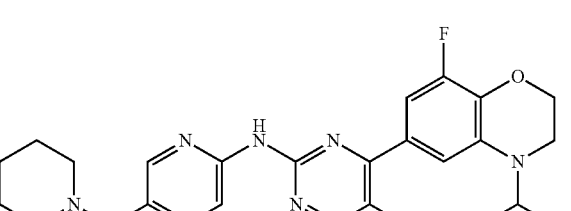 |

TABLE 1-continued

| Compound No. | Structure |
|---|---|
| 613 | 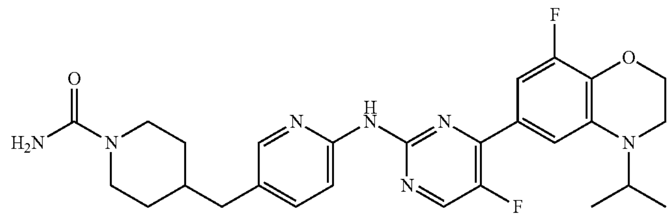 [SMILES: CC(C)N1CCOc2c(F)cc(-c3nc(Nc4ccc(CC5CCN(C(N)=O)CC5)cn4)ncc3F)cc21] |
| 614 | 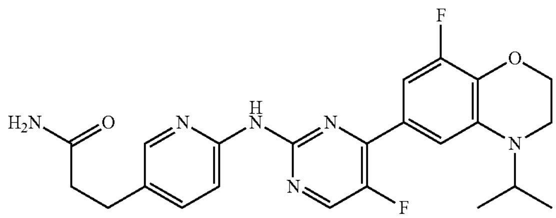 [SMILES: CC(C)N1CCOc2c(F)cc(-c3nc(Nc4ccc(CCC(N)=O)cn4)ncc3F)cc21] |
| 615 | 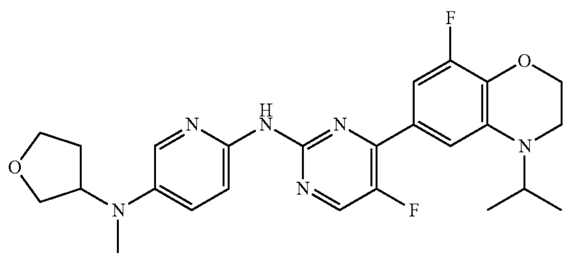 [SMILES: CC(C)N1CCOc2c(F)cc(-c3nc(Nc4ccc(N(C)C5CCOC5)cn4)ncc3F)cc21] |
| 616 | 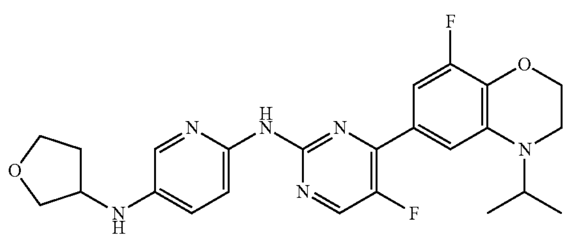 [SMILES: CC(C)N1CCOc2c(F)cc(-c3nc(Nc4ccc(NC5CCOC5)cn4)ncc3F)cc21] |
| 617 | 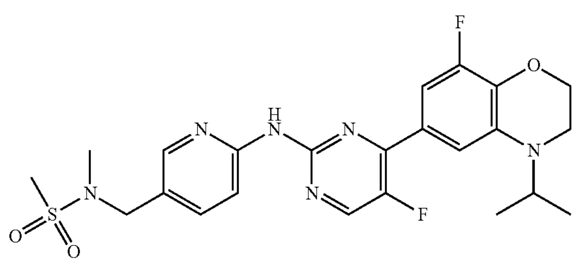 [SMILES: CC(C)N1CCOc2c(F)cc(-c3nc(Nc4ccc(CN(C)S(C)(=O)=O)cn4)ncc3F)cc21] |
| 618 | 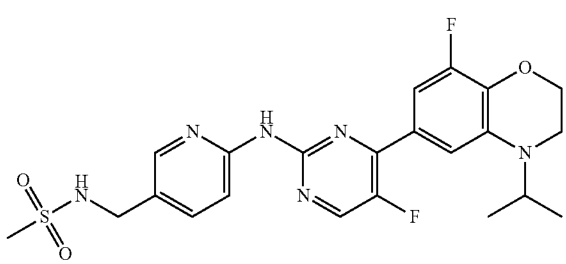 [SMILES: CC(C)N1CCOc2c(F)cc(-c3nc(Nc4ccc(CNS(C)(=O)=O)cn4)ncc3F)cc21] |

TABLE 1-continued
| Compound No. | Structure |
|---|---|
| 619 | 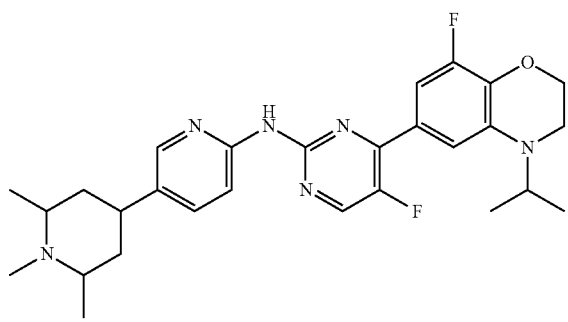 [SMILES: CC(C)N1CCOc2c(F)cc(-c3nc(Nc4ccc(C5CC(C)N(C)C(C)C5)cn4)ncc3F)cc21] |
| 620 | 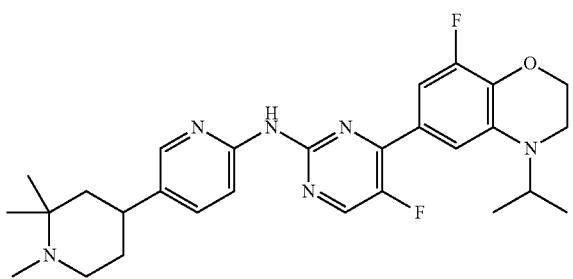 [SMILES: CC(C)N1CCOc2c(F)cc(-c3nc(Nc4ccc(C5CCN(C)C(C)(C)C5)cn4)ncc3F)cc21] |
| 621 | 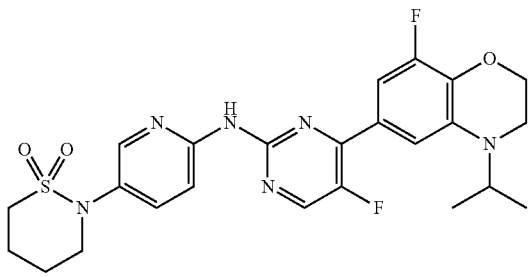 [SMILES: CC(C)N1CCOc2c(F)cc(-c3nc(Nc4ccc(N5CCCCS5(=O)=O)cn4)ncc3F)cc21] |
| 622 | 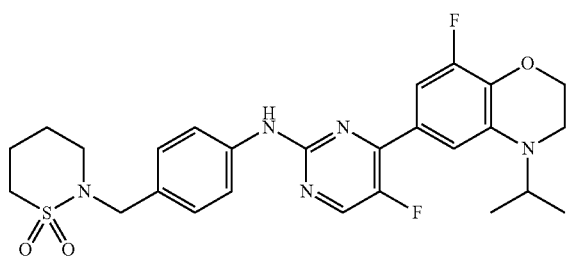 [SMILES: CC(C)N1CCOc2c(F)cc(-c3nc(Nc4ccc(CN5CCCCS5(=O)=O)cc4)ncc3F)cc21] |
| 623 | 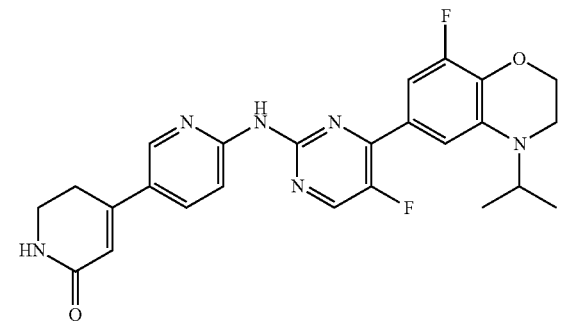 [SMILES: CC(C)N1CCOc2c(F)cc(-c3nc(Nc4ccc(C5=CC(=O)NCC5)cn4)ncc3F)cc21] |

TABLE 1-continued
| Compound No. | Structure |
|---|---|
| 624 | 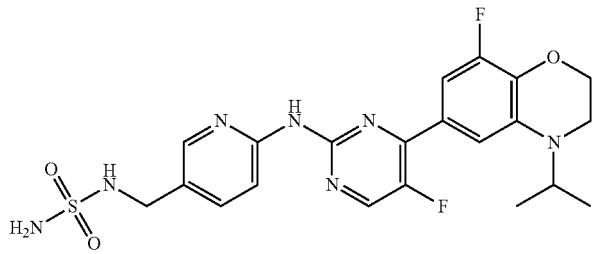 [SMILES: CC(C)N1CCOc2c(F)cc(-c3nc(Nc4ccc(CNS(N)(=O)=O)cn4)ncc3F)cc21] |
| 625 | 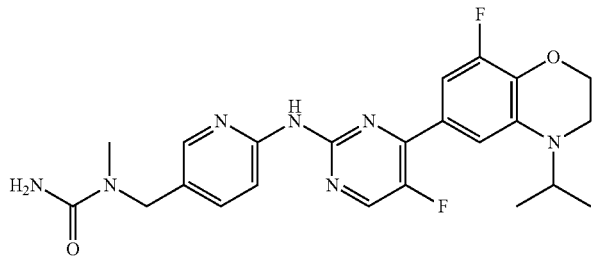 [SMILES: CC(C)N1CCOc2c(F)cc(-c3nc(Nc4ccc(CN(C)C(N)=O)cn4)ncc3F)cc21] |
| 626 | 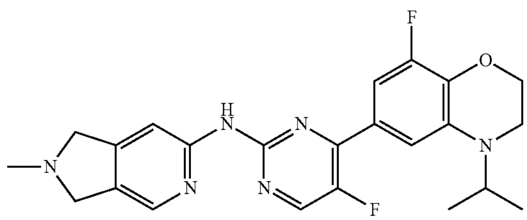 [SMILES: CC(C)N1CCOc2c(F)cc(-c3nc(Nc4cc5c(cn4)CN(C)C5)ncc3F)cc21] |
| 627 | 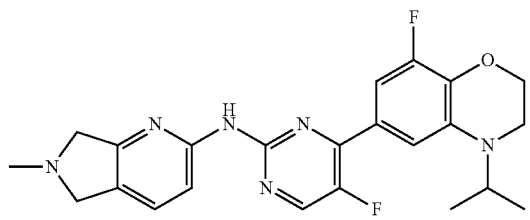 |
| 628 | 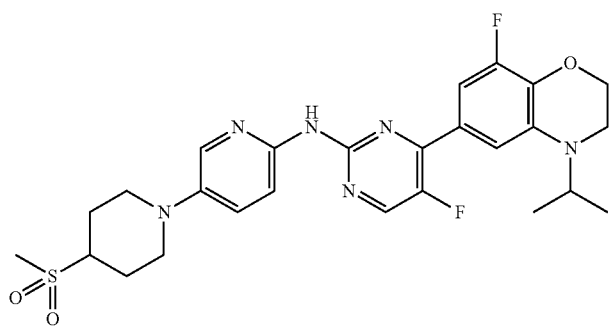 [SMILES: CC(C)N1CCOc2c(F)cc(-c3nc(Nc4ccc(N5CCC(S(C)(=O)=O)CC5)cn4)ncc3F)cc21] |
| 629 | 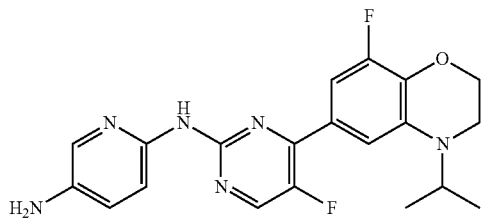 [SMILES: CC(C)N1CCOc2c(F)cc(-c3nc(Nc4ccc(N)cn4)ncc3F)cc21] |

TABLE 1-continued
| Compound No. | Structure |
|---|---|
| 630 | 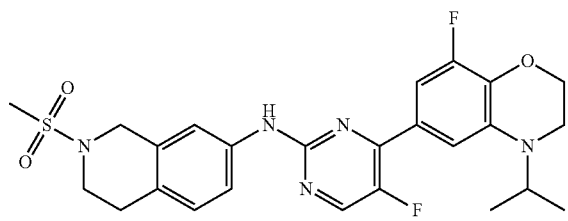 [SMILES: CC(C)N1CCOc2c(F)cc(-c3nc(Nc4ccc5c(c4)CN(S(C)(=O)=O)CC5)ncc3F)cc21] |
| 631 | 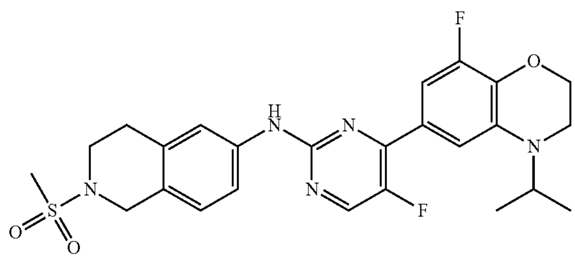 [SMILES: CC(C)N1CCOc2c(F)cc(-c3nc(Nc4ccc5c(c4)CCN(S(C)(=O)=O)C5)ncc3F)cc21] |
| 632 | 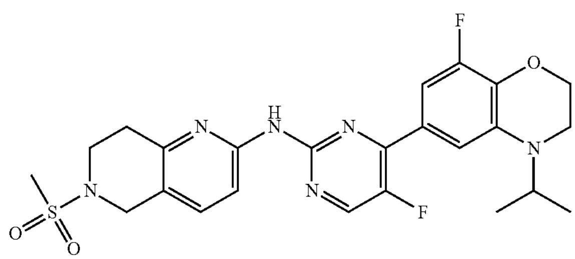 [SMILES: CC(C)N1CCOc2c(F)cc(-c3nc(Nc4ccc5c(n4)CCN(S(C)(=O)=O)C5)ncc3F)cc21] |
| 633 | 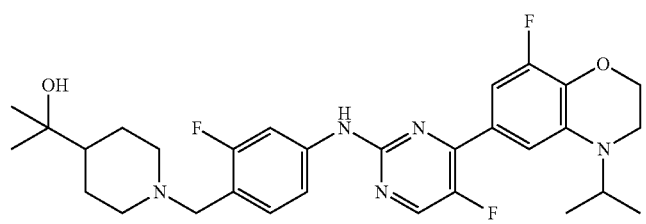 [SMILES: CC(C)N1CCOc2c(F)cc(-c3nc(Nc4ccc(CN5CCC(C(C)(C)O)CC5)c(F)c4)ncc3F)cc21] |
| 634 | 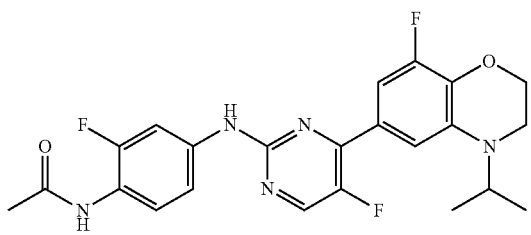 [SMILES: CC(=O)Nc1ccc(Nc2ncc(F)c(-c3cc(F)c4c(c3)N(C(C)C)CCO4)n2)cc1F] |
| 635 | 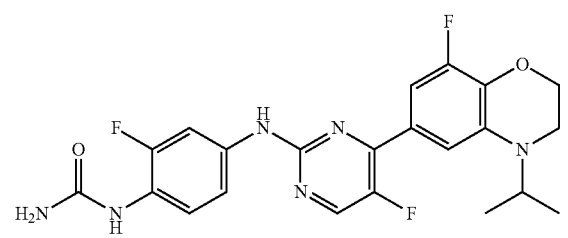 [SMILES: CC(C)N1CCOc2c(F)cc(-c3nc(Nc4ccc(NC(N)=O)c(F)c4)ncc3F)cc21] |

TABLE 1-continued
| Compound No. | Structure |
|---|---|
| 636 | 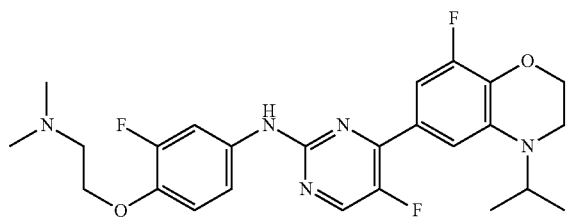 [SMILES: CC(C)N1CCOc2c(F)cc(-c3nc(Nc4ccc(OCCN(C)C)c(F)c4)ncc3F)cc21] |
| 637 | 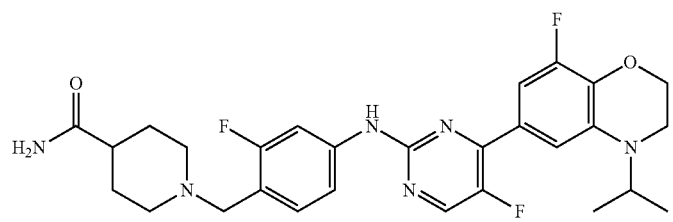 [SMILES: CC(C)N1CCOc2c(F)cc(-c3nc(Nc4ccc(CN5CCC(C(N)=O)CC5)c(F)c4)ncc3F)cc21] |
| 638 | 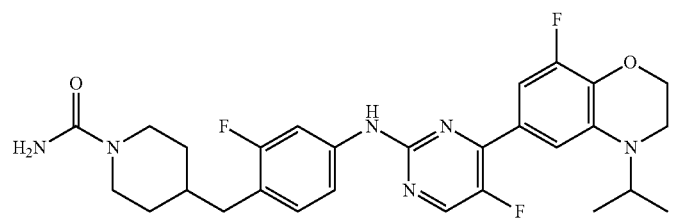 |
| 639 | 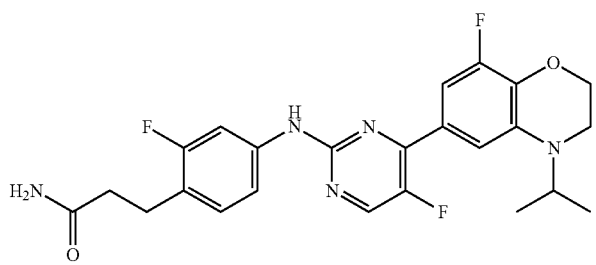 [SMILES: CC(C)N1CCOc2c(F)cc(-c3nc(Nc4ccc(CCC(N)=O)c(F)c4)ncc3F)cc21] |
| 640 | 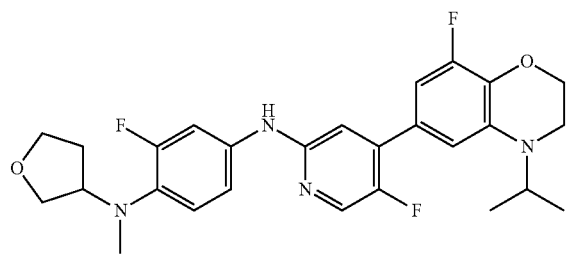 [SMILES: CC(C)N1CCOc2c(F)cc(-c3cc(Nc4ccc(N(C)C5CCOC5)c(F)c4)ncc3F)cc21] |
| 641 | 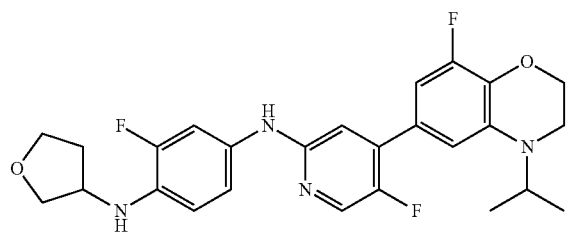 [SMILES: CC(C)N1CCOc2c(F)cc(-c3cc(Nc4ccc(NC5CCOC5)c(F)c4)ncc3F)cc21] |

TABLE 1-continued
| Compound No. | Structure |
|---|---|
| 642 | 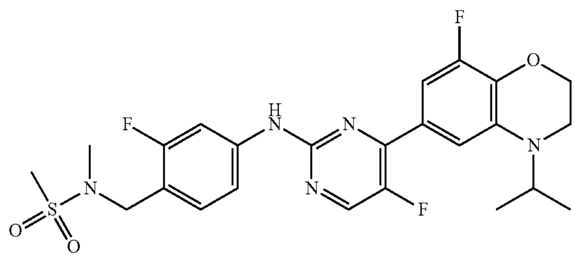 [SMILES: CC(C)N1CCOc2c(F)cc(-c3nc(Nc4ccc(CN(C)S(C)(=O)=O)c(F)c4)ncc3F)cc21] |
| 643 | 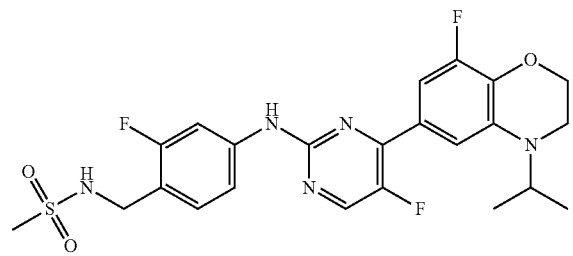 [SMILES: CC(C)N1CCOc2c(F)cc(-c3nc(Nc4ccc(CNS(C)(=O)=O)c(F)c4)ncc3F)cc21] |
| 644 | 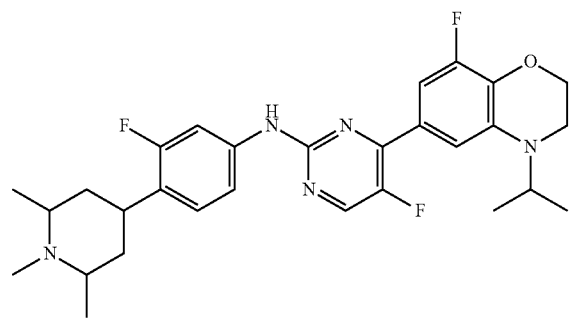 [SMILES: CC(C)N1CCOc2c(F)cc(-c3nc(Nc4ccc(C5CC(C)N(C)C(C)C5)c(F)c4)ncc3F)cc21] |
| 645 | 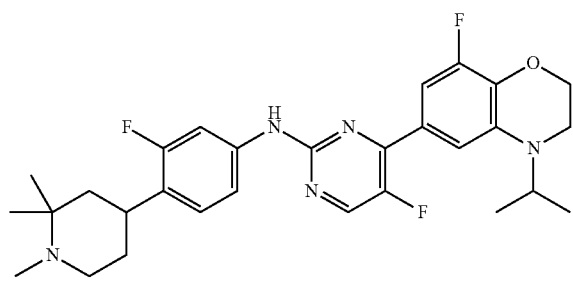 [SMILES: CC(C)N1CCOc2c(F)cc(-c3nc(Nc4ccc(C5CCN(C)C(C)(C)C5)c(F)c4)ncc3F)cc21] |
| 646 | 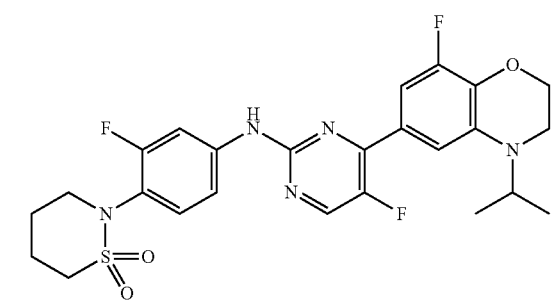 [SMILES: CC(C)N1CCOc2c(F)cc(-c3nc(Nc4ccc(N5CCCCS5(=O)=O)c(F)c4)ncc3F)cc21] |

TABLE 1-continued

| Compound No. | Structure |
|---|---|
| 647 | 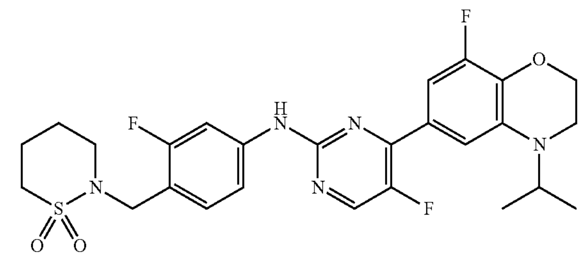 [SMILES: CC(C)N1CCOc2c(F)cc(-c3nc(Nc4ccc(CN5CCCCS5(=O)=O)c(F)c4)ncc3F)cc21] |
| 648 | 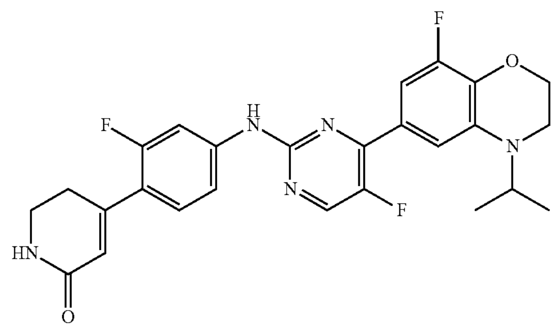 [SMILES: CC(C)N1CCOc2c(F)cc(-c3nc(Nc4ccc(C5=CC(=O)NCC5)c(F)c4)ncc3F)cc21] |
| 649 | 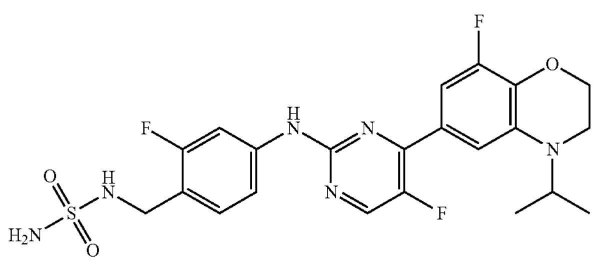 [SMILES: CC(C)N1CCOc2c(F)cc(-c3nc(Nc4ccc(CNS(N)(=O)=O)c(F)c4)ncc3F)cc21] |
| 650 | 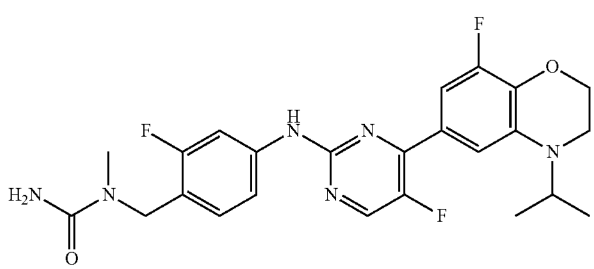 [SMILES: CC(C)N1CCOc2c(F)cc(-c3nc(Nc4ccc(CN(C)C(N)=O)c(F)c4)ncc3F)cc21] |
| 651 | 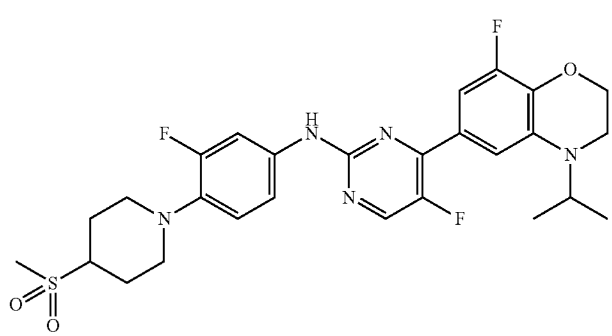 [SMILES: CC(C)N1CCOc2c(F)cc(-c3nc(Nc4ccc(N5CCC(S(C)(=O)=O)CC5)c(F)c4)ncc3F)cc21] |

TABLE 1-continued

| Compound No. | Structure |
|---|---|
| 652 | 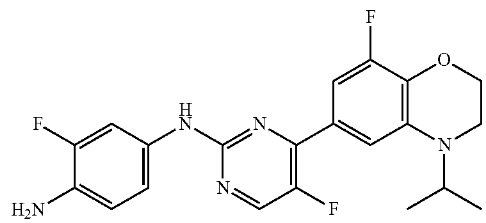 |
| 653 | 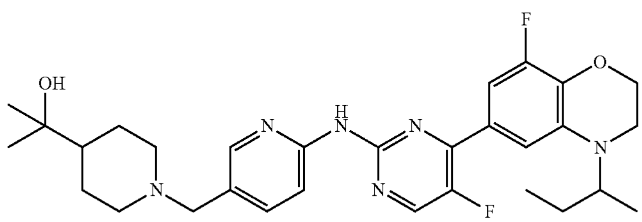 [SMILES: CCC(C)N1CCOc2c(F)cc(-c3nc(Nc4ccc(CN5CCC(C(C)(C)O)CC5)cn4)ncc3F)cc21] |
| 654 | 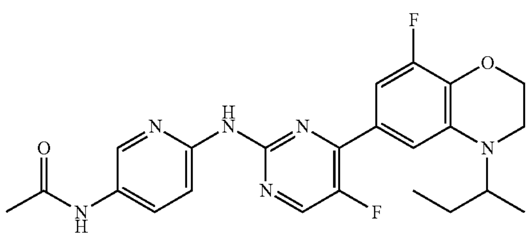 [SMILES: CCC(C)N1CCOc2c(F)cc(-c3nc(Nc4ccc(NC(C)=O)cn4)ncc3F)cc21] |
| 655 | 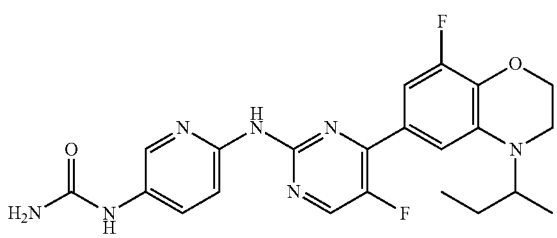 [SMILES: CCC(C)N1CCOc2c(F)cc(-c3nc(Nc4ccc(NC(N)=O)cn4)ncc3F)cc21] |
| 656 | 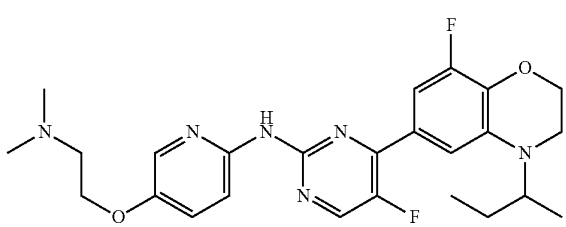 [SMILES: CCC(C)N1CCOc2c(F)cc(-c3nc(Nc4ccc(OCCN(C)C)cn4)ncc3F)cc21] |
| 657 | 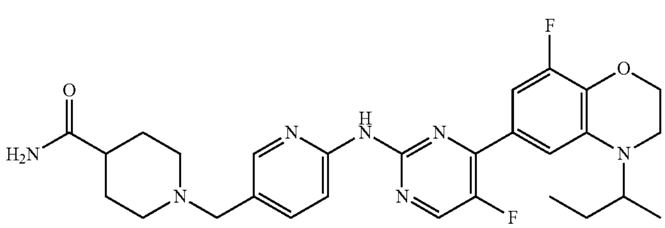 [SMILES: CCC(C)N1CCOc2c(F)cc(-c3nc(Nc4ccc(CN5CCC(C(N)=O)CC5)cn4)ncc3F)cc21] |

TABLE 1-continued
| Compound No. | Structure |
| --- | --- |
| 658 | 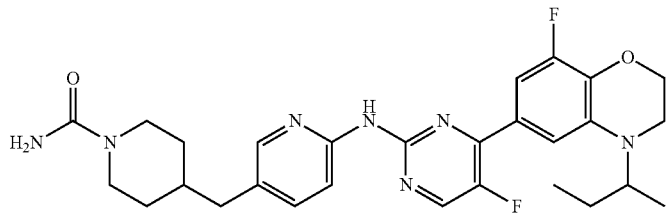 [SMILES: CCC(C)N1CCOc2c(F)cc(-c3nc(Nc4ccc(CC5CCN(C(N)=O)CC5)cn4)ncc3F)cc21] |
| 659 | 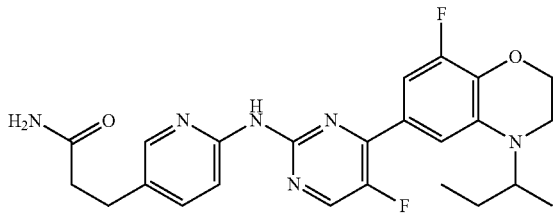 [SMILES: CCC(C)N1CCOc2c(F)cc(-c3nc(Nc4ccc(CCC(N)=O)cn4)ncc3F)cc21] |
| 660 | 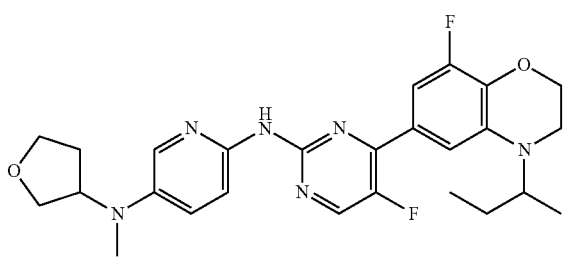 [SMILES: CCC(C)N1CCOc2c(F)cc(-c3nc(Nc4ccc(N(C)C5CCOC5)cn4)ncc3F)cc21] |
| 661 | 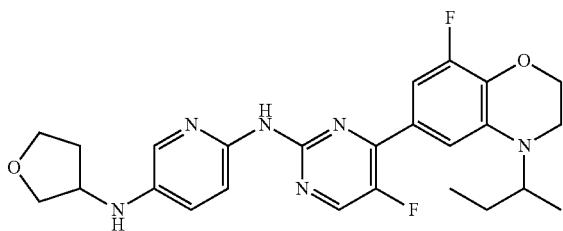 [SMILES: CCC(C)N1CCOc2c(F)cc(-c3nc(Nc4ccc(NC5CCOC5)cn4)ncc3F)cc21] |
| 662 | 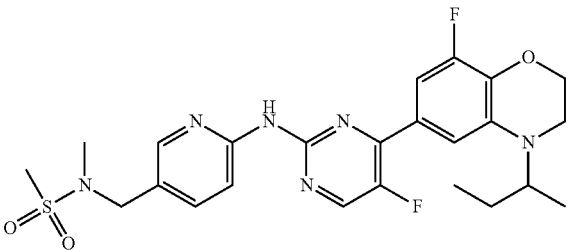 [SMILES: CCC(C)N1CCOc2c(F)cc(-c3nc(Nc4ccc(CN(C)S(C)(=O)=O)cn4)ncc3F)cc21] |
| 663 | 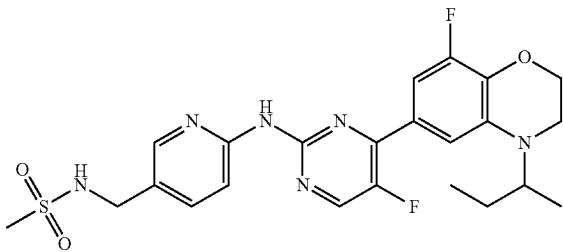 [SMILES: CCC(C)N1CCOc2c(F)cc(-c3nc(Nc4ccc(CNS(C)(=O)=O)cn4)ncc3F)cc21] |

TABLE 1-continued
| Compound No. | Structure |
|---|---|
| 664 | 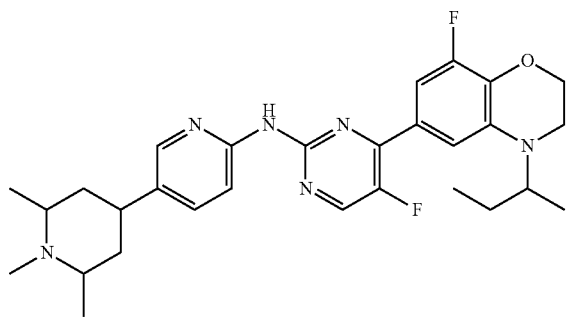 [SMILES: CCC(C)N1CCOc2c(F)cc(-c3nc(Nc4ccc(C5CC(C)N(C)C(C)C5)cn4)ncc3F)cc21] |
| 665 | 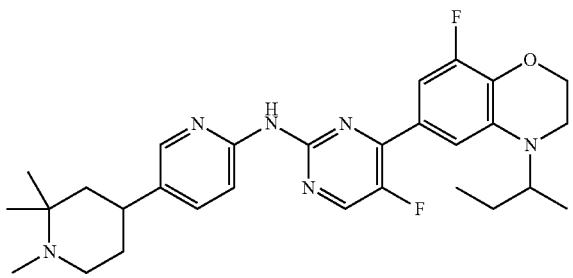 [SMILES: CCC(C)N1CCOc2c(F)cc(-c3nc(Nc4ccc(C5CCN(C)C(C)(C)C5)cn4)ncc3F)cc21] |
| 666 | 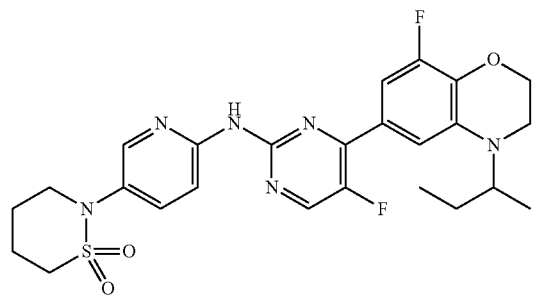 [SMILES: CCC(C)N1CCOc2c(F)cc(-c3nc(Nc4ccc(N5CCCCS5(=O)=O)cn4)ncc3F)cc21] |
| 667 | 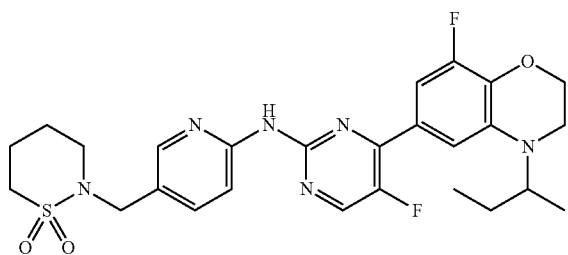 [SMILES: CCC(C)N1CCOc2c(F)cc(-c3nc(Nc4ccc(CN5CCCCS5(=O)=O)cn4)ncc3F)cc21] |
| 668 | 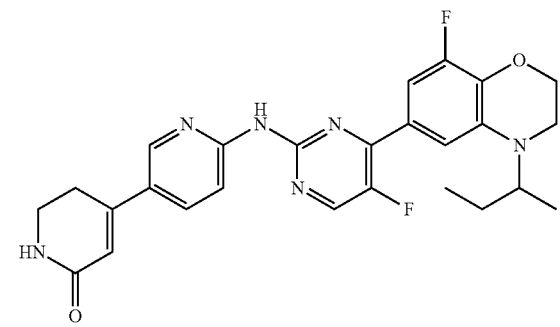 [SMILES: CCC(C)N1CCOc2c(F)cc(-c3nc(Nc4ccc(C5=CC(=O)NCC5)cn4)ncc3F)cc21] |

TABLE 1-continued

| Compound No. | Structure |
| --- | --- |
| 669 | 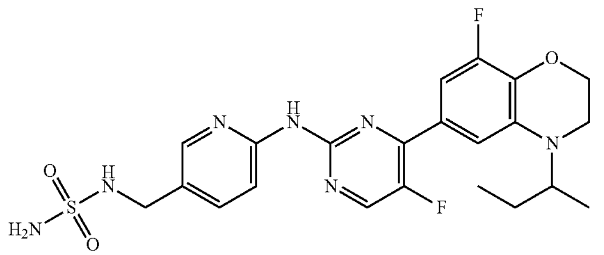 [SMILES: CCC(C)N1CCOc2c(F)cc(-c3nc(Nc4ccc(CNS(N)(=O)=O)cn4)ncc3F)cc21] |
| 670 | 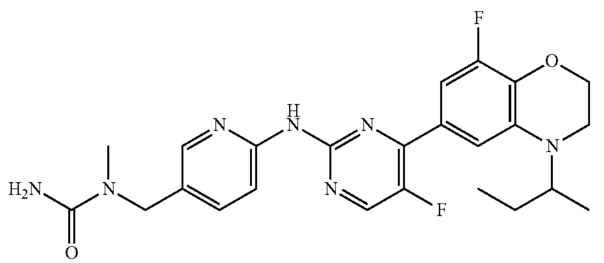 [SMILES: CCC(C)N1CCOc2c(F)cc(-c3nc(Nc4ccc(CN(C)C(N)=O)cn4)ncc3F)cc21] |
| 671 | 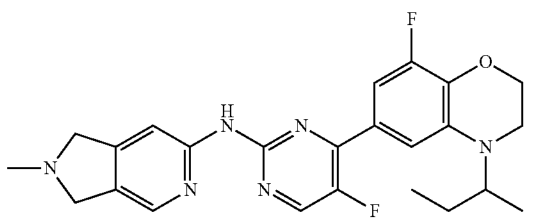 [SMILES: CCC(C)N1CCOc2c(F)cc(-c3nc(Nc4cc5c(cn4)CN(C)C5)ncc3F)cc21] |
| 672 | 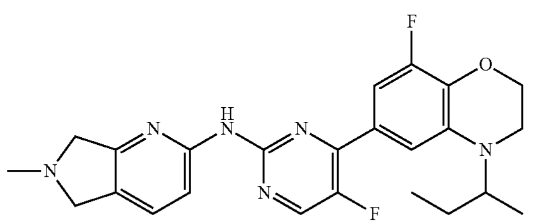 [SMILES: CCC(C)N1CCOc2c(F)cc(-c3nc(Nc4ccc5c(n4)CN(C)C5)ncc3F)cc21] |
| 673 | 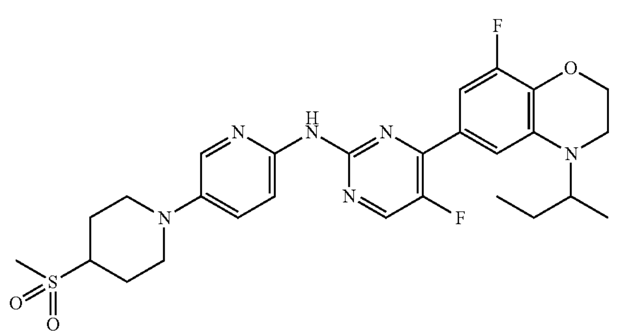 [SMILES: CCC(C)N1CCOc2c(F)cc(-c3nc(Nc4ccc(N5CCC(S(C)(=O)=O)CC5)cn4)ncc3F)cc21] |
| 674 | 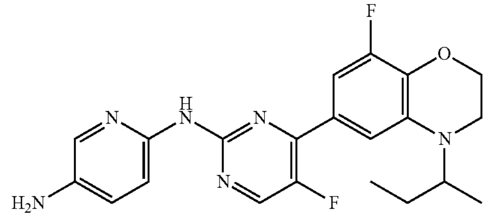 [SMILES: CCC(C)N1CCOc2c(F)cc(-c3nc(Nc4ccc(N)cn4)ncc3F)cc21] |

TABLE 1-continued
| Compound No. | Structure |
|---|---|
| 675 | 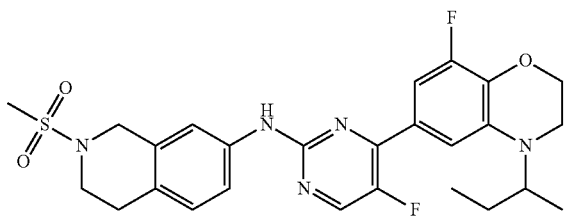 [SMILES: CCC(C)N1CCOc2c(F)cc(-c3nc(Nc4ccc5c(c4)CN(S(C)(=O)=O)CC5)ncc3F)cc21] |
| 676 | 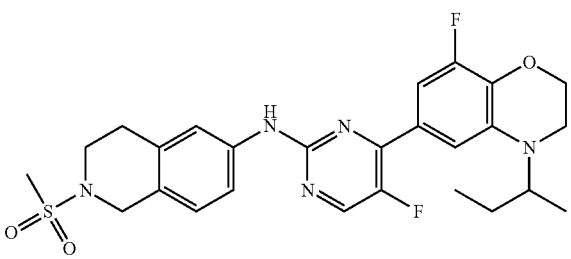 [SMILES: CCC(C)N1CCOc2c(F)cc(-c3nc(Nc4ccc5c(c4)CCN(S(C)(=O)=O)C5)ncc3F)cc21] |
| 677 | 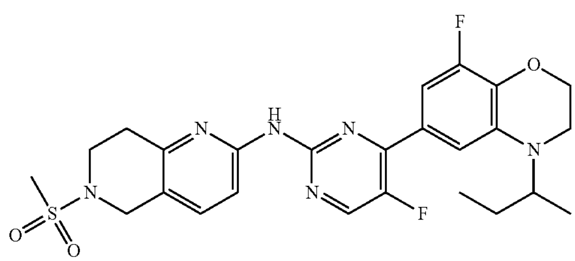 [SMILES: CCC(C)N1CCOc2c(F)cc(-c3nc(Nc4ccc5c(n4)CCN(S(C)(=O)=O)C5)ncc3F)cc21] |
| 678 | 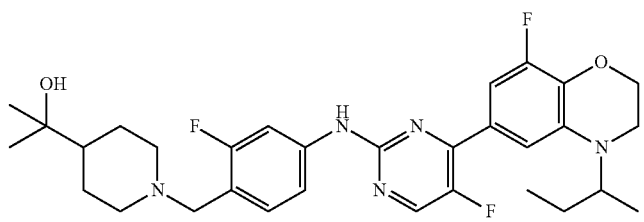 [SMILES: CCC(C)N1CCOc2c(F)cc(-c3nc(Nc4ccc(CN5CCC(C(C)(C)O)CC5)c(F)c4)ncc3F)cc21] |
| 679 | 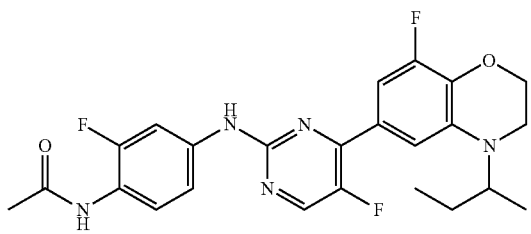 [SMILES: CCC(C)N1CCOc2c(F)cc(-c3nc(Nc4ccc(NC(C)=O)c(F)c4)ncc3F)cc21] |
| 680 | 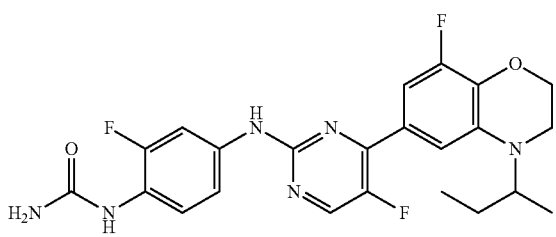 [SMILES: CCC(C)N1CCOc2c(F)cc(-c3nc(Nc4ccc(NC(N)=O)c(F)c4)ncc3F)cc21] |

TABLE 1-continued
| Compound No. | Structure |
|---|---|
| 681 | 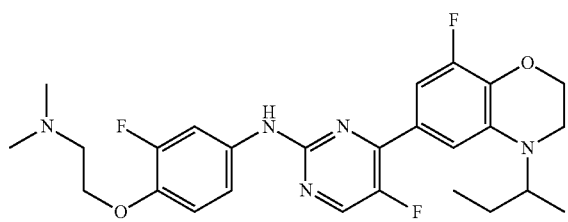 [SMILES: CCC(C)N1CCOc2c(F)cc(-c3nc(Nc4ccc(OCCN(C)C)c(F)c4)ncc3F)cc21] |
| 682 | 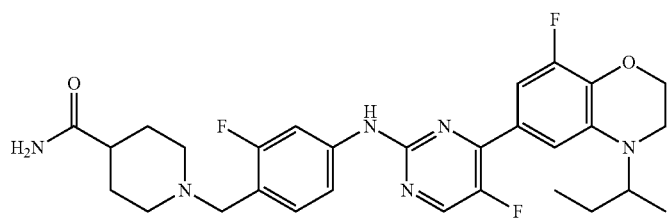 |
| 683 | 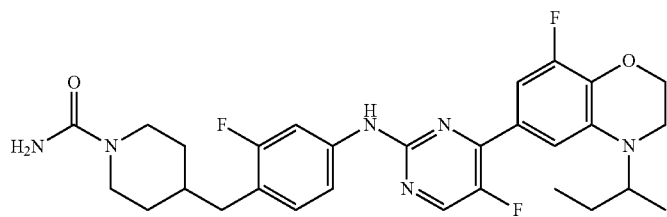 [SMILES: CCC(C)N1CCOc2c(F)cc(-c3nc(Nc4ccc(CC5CCN(C(N)=O)CC5)c(F)c4)ncc3F)cc21] |
| 684 | 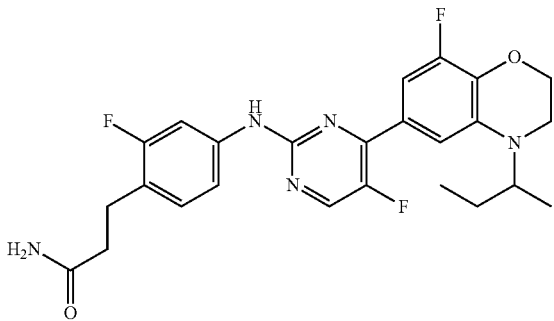 [SMILES: CCC(C)N1CCOc2c(F)cc(-c3nc(Nc4ccc(CCC(N)=O)c(F)c4)ncc3F)cc21] |
| 685 | 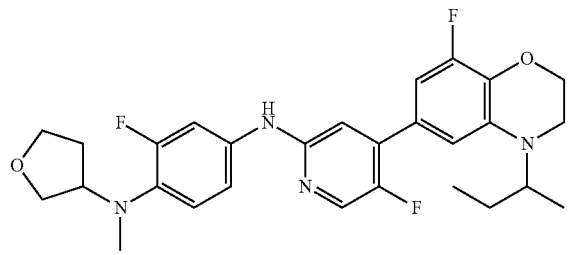 [SMILES: CCC(C)N1CCOc2c(F)cc(-c3cc(Nc4ccc(N(C)C5CCOC5)c(F)c4)ncc3F)cc21] |
| 686 | 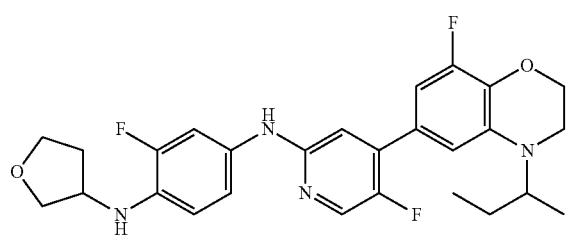 [SMILES: CCC(C)N1CCOc2c(F)cc(-c3cc(Nc4ccc(NC5CCOC5)c(F)c4)ncc3F)cc21] |

TABLE 1-continued
| Compound No. | Structure |
|---|---|
| 687 | 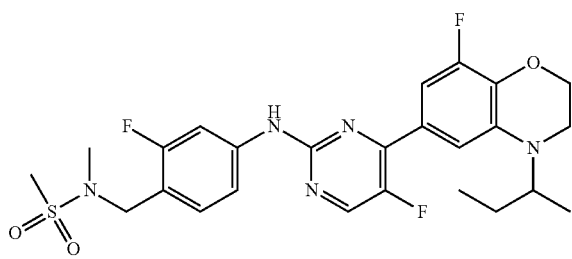 [SMILES: CCC(C)N1CCOc2c(F)cc(-c3nc(Nc4ccc(CN(C)S(C)(=O)=O)c(F)c4)ncc3F)cc21] |
| 688 | 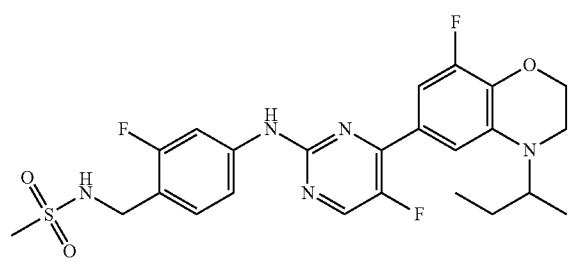 [SMILES: CCC(C)N1CCOc2c(F)cc(-c3nc(Nc4ccc(CNS(C)(=O)=O)c(F)c4)ncc3F)cc21] |
| 689 | 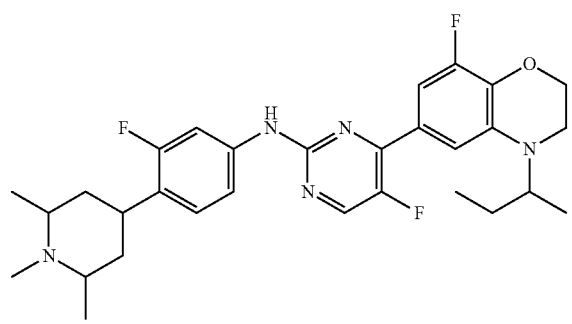 [SMILES: CCC(C)N1CCOc2c(F)cc(-c3nc(Nc4ccc(C5CC(C)N(C)C(C)C5)c(F)c4)ncc3F)cc21] |
| 690 | 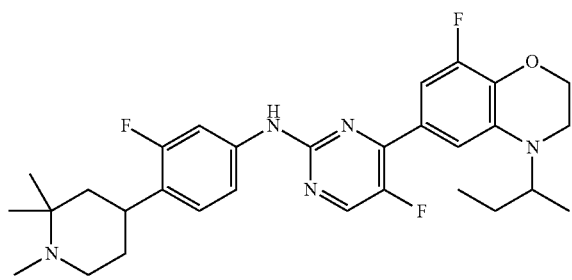 [SMILES: CCC(C)N1CCOc2c(F)cc(-c3nc(Nc4ccc(C5CCN(C)C(C)(C)C5)c(F)c4)ncc3F)cc21] |
| 691 | 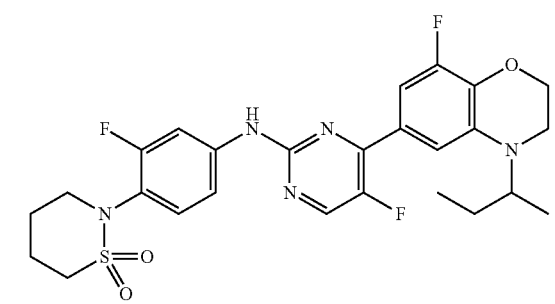 [SMILES: CCC(C)N1CCOc2c(F)cc(-c3nc(Nc4ccc(N5CCCCS5(=O)=O)c(F)c4)ncc3F)cc21] |

TABLE 1-continued
| Compound No. | Structure |
|---|---|
| 692 | 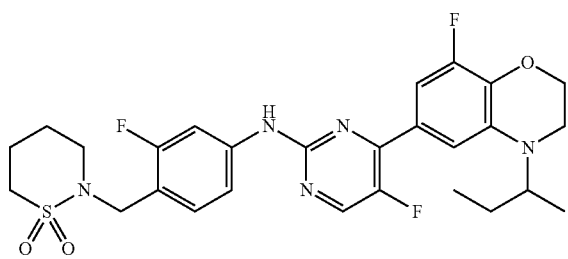 [SMILES: CCC(C)N1CCOc2c(F)cc(-c3nc(Nc4ccc(CN5CCCCS5(=O)=O)c(F)c4)ncc3F)cc21] |
| 693 | 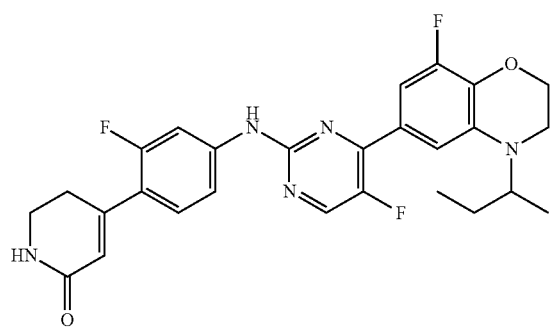 [SMILES: CCC(C)N1CCOc2c(F)cc(-c3nc(Nc4ccc(C5=CC(=O)NCC5)c(F)c4)ncc3F)cc21] |
| 694 | 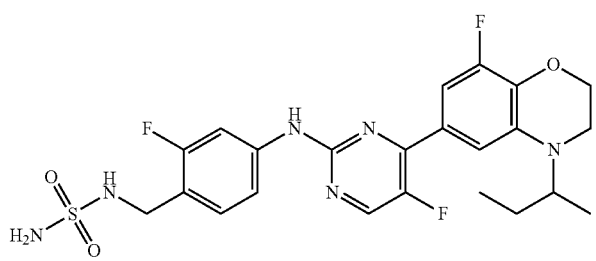 [SMILES: CCC(C)N1CCOc2c(F)cc(-c3nc(Nc4ccc(CNS(N)(=O)=O)c(F)c4)ncc3F)cc21] |
| 695 | 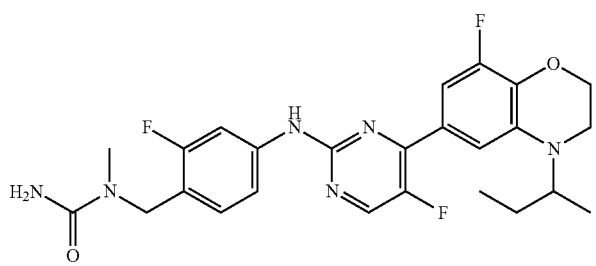 [SMILES: CCC(C)N1CCOc2c(F)cc(-c3nc(Nc4ccc(CN(C)C(N)=O)c(F)c4)ncc3F)cc21] |
| 696 | 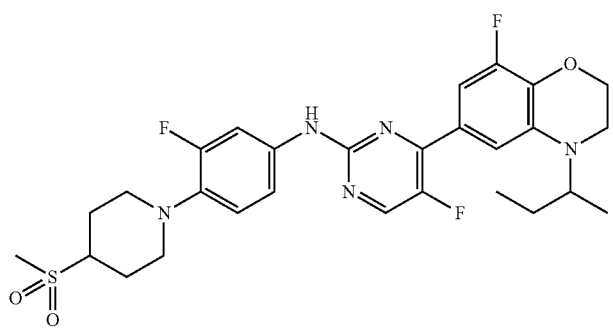 [SMILES: CCC(C)N1CCOc2c(F)cc(-c3nc(Nc4ccc(N5CCC(S(C)(=O)=O)CC5)c(F)c4)ncc3F)cc21] |

TABLE 1-continued

| Compound No. | Structure |
|---|---|
| 697 | 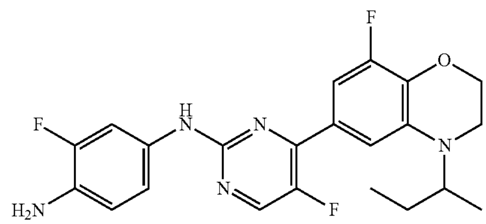 [SMILES: CCC(C)N1CCOc2c(F)cc(-c3nc(Nc4ccc(N)c(F)c4)ncc3F)cc21] |
| 698 | 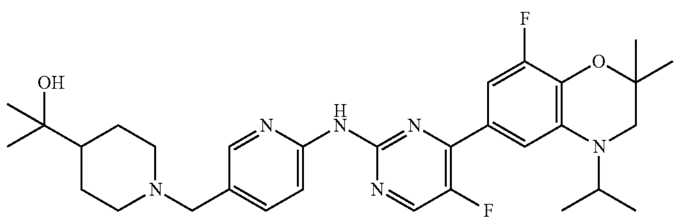 [SMILES: CC(C)N1CC(C)(C)Oc2c(F)cc(-c3nc(Nc4ccc(CN5CCC(C(C)(C)O)CC5)cn4)ncc3F)cc21] |
| 699 | 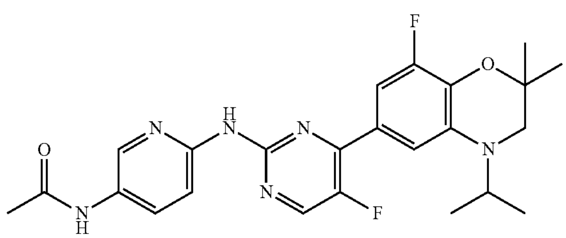 [SMILES: CC(=O)Nc1ccc(Nc2ncc(F)c(-c3cc(F)c4c(c3)N(C(C)C)CC(C)(C)O4)n2)nc1] |
| 700 | 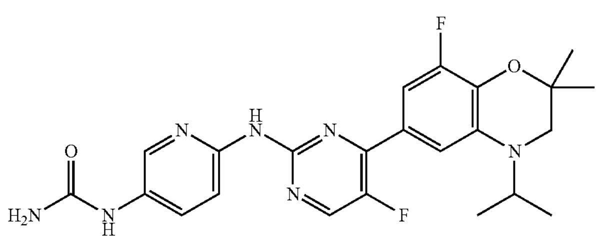 [SMILES: CC(C)N1CC(C)(C)Oc2c(F)cc(-c3nc(Nc4ccc(NC(N)=O)cn4)ncc3F)cc21] |
| 701 | 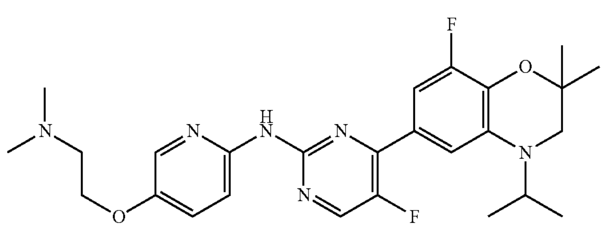 |
| 702 | 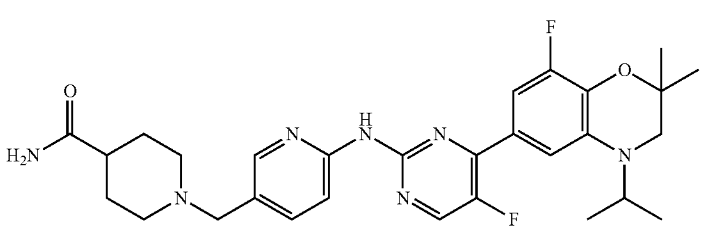 [SMILES: CC(C)N1CC(C)(C)Oc2c(F)cc(-c3nc(Nc4ccc(CN5CCC(C(N)=O)CC5)cn4)ncc3F)cc21] |

TABLE 1-continued

| Compound No. | Structure |
|---|---|
| 703 | 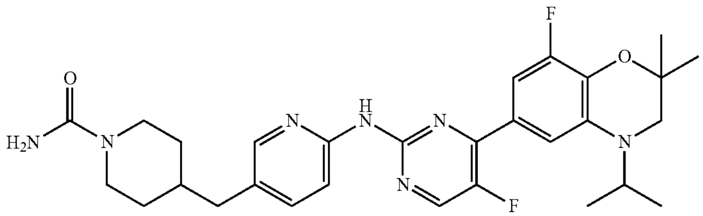 [SMILES: CC(C)N1CC(C)(C)Oc2c(F)cc(-c3nc(Nc4ccc(CC5CCN(C(N)=O)CC5)cn4)ncc3F)cc21] |
| 704 | 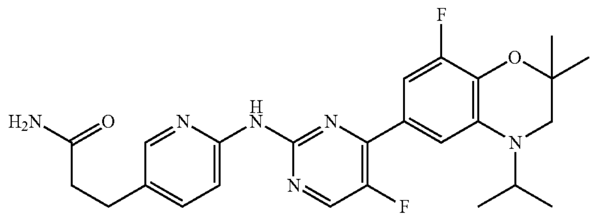 [SMILES: CC(C)N1CC(C)(C)Oc2c(F)cc(-c3nc(Nc4ccc(CCC(N)=O)cn4)ncc3F)cc21] |
| 705 | 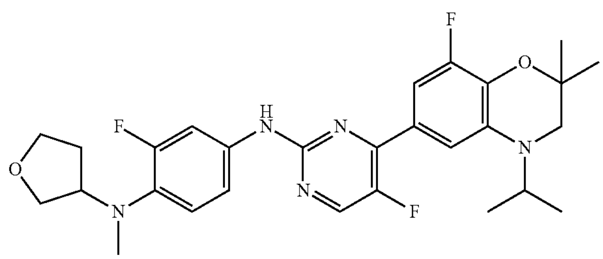 [SMILES: CC(C)N1CC(C)(C)Oc2c(F)cc(-c3nc(Nc4ccc(N(C)C5CCOC5)c(F)c4)ncc3F)cc21] |
| 706 | 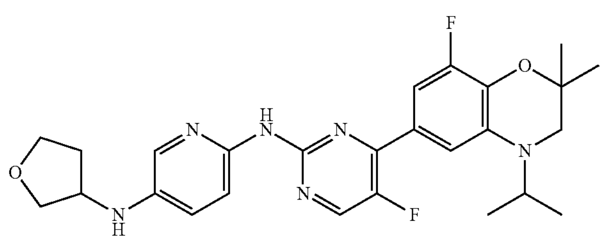 [SMILES: CC(C)N1CC(C)(C)Oc2c(F)cc(-c3nc(Nc4ccc(NC5CCOC5)cn4)ncc3F)cc21] |
| 707 | 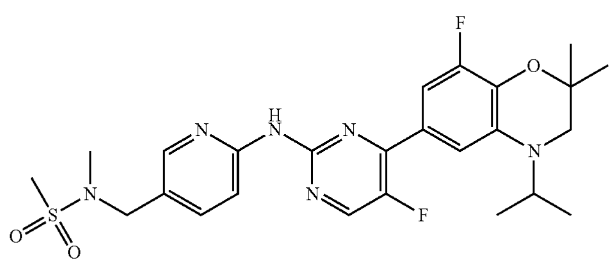 [SMILES: CC(C)N1CC(C)(C)Oc2c(F)cc(-c3nc(Nc4ccc(CN(C)S(C)(=O)=O)cn4)ncc3F)cc21] |
| 708 | 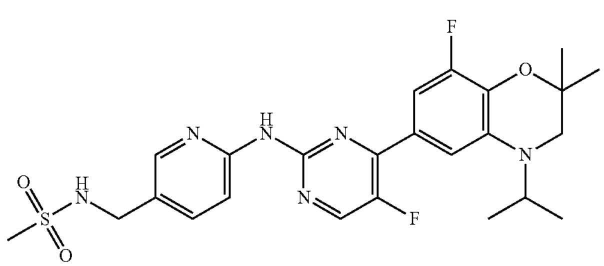 |

TABLE 1-continued
| Compound No. | Structure |
|---|---|
| 709 | 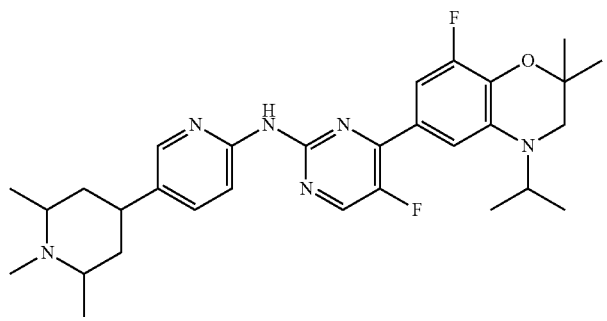 |
| 710 | 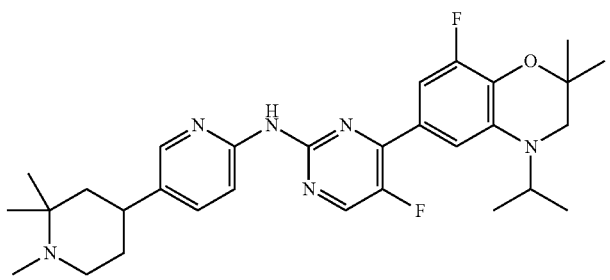 |
| 711 | 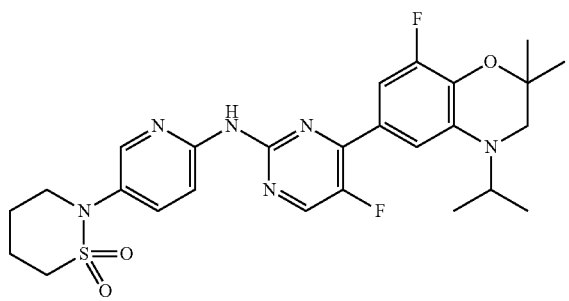 [SMILES: CC(C)N1CC(C)(C)Oc2c(F)cc(-c3nc(Nc4ccc(N5CCCCS5(=O)=O)cn4)ncc3F)cc21] |
| 712 | 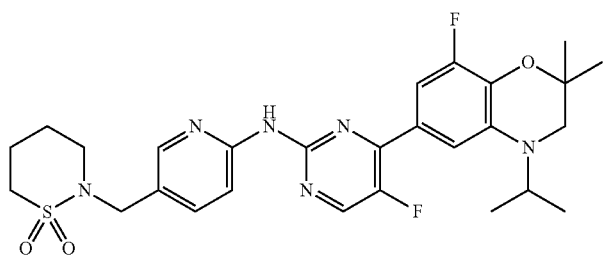 [SMILES: CC(C)N1CC(C)(C)Oc2c(F)cc(-c3nc(Nc4ccc(CN5CCCCS5(=O)=O)cn4)ncc3F)cc21] |
| 713 | 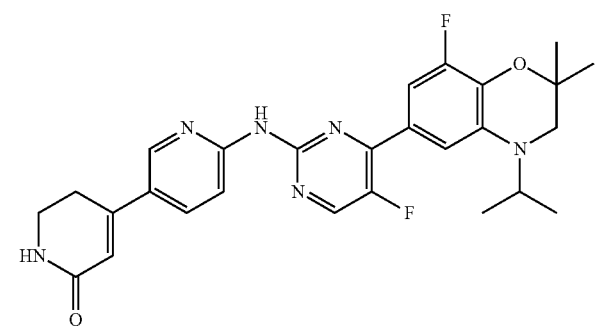 [SMILES: CC(C)N1CC(C)(C)Oc2c(F)cc(-c3nc(Nc4ccc(C5=CC(=O)NCC5)cn4)ncc3F)cc21] |

TABLE 1-continued
| Compound No. | Structure |
|---|---|
| 714 | 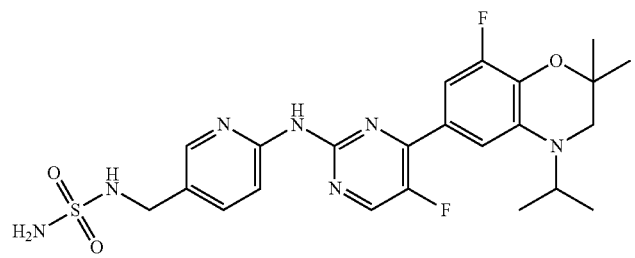 [SMILES: CC(C)N1CC(C)(C)Oc2c(F)cc(-c3nc(Nc4ccc(CNS(N)(=O)=O)cn4)ncc3F)cc21] |
| 715 | 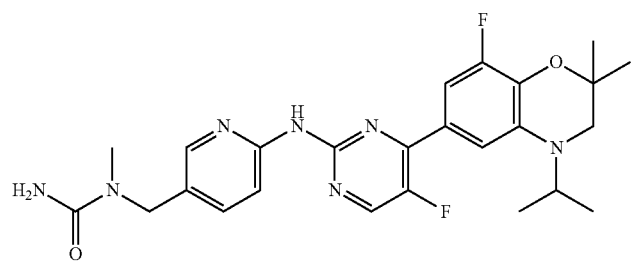 [SMILES: CC(C)N1CC(C)(C)Oc2c(F)cc(-c3nc(Nc4ccc(CN(C)C(N)=O)cn4)ncc3F)cc21] |
| 716 | 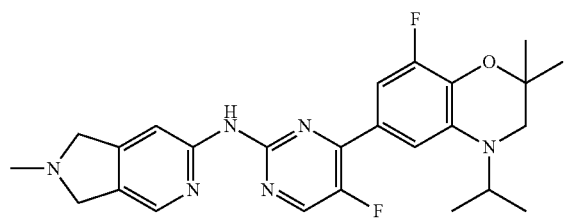 |
| 717 | 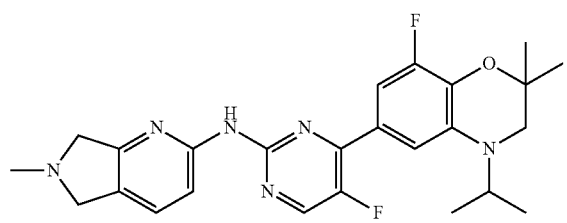 |
| 718 | 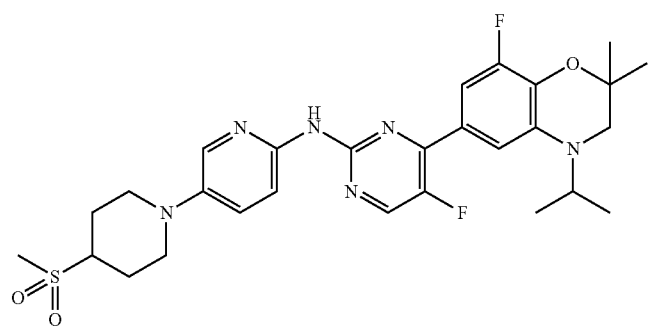 |
| 719 | 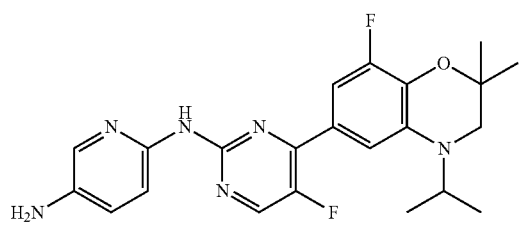 [SMILES: CC(C)N1CC(C)(C)Oc2c(F)cc(-c3nc(Nc4ccc(N)cn4)ncc3F)cc21] |

TABLE 1-continued

| Compound No. | Structure |
|---|---|
| 720 | 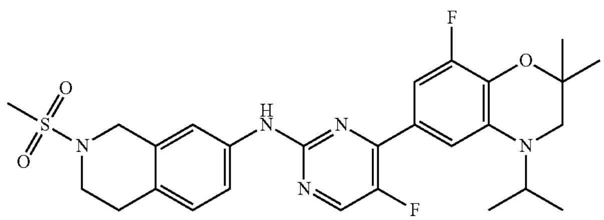 |
| 721 | 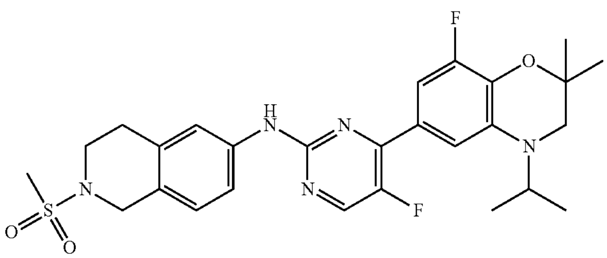 [SMILES: CC(C)N1CC(C)(C)Oc2c(F)cc(-c3nc(Nc4ccc5c(c4)CCN(S(C)(=O)=O)C5)ncc3F)cc21] |
| 722 | 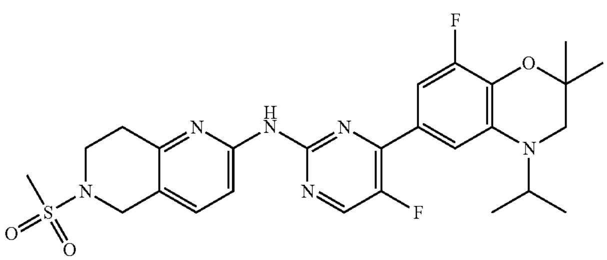 [SMILES: CC(C)N1CC(C)(C)Oc2c(F)cc(-c3nc(Nc4ccc5c(n4)CCN(S(C)(=O)=O)C5)ncc3F)cc21] |
| 723 | 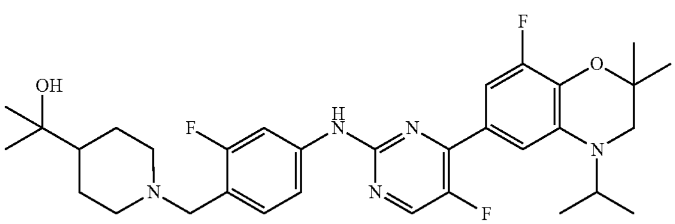 [SMILES: CC(C)N1CC(C)(C)Oc2c(F)cc(-c3nc(Nc4ccc(CN5CCC(C(C)(C)O)CC5)c(F)c4)ncc3F)cc21] |
| 724 | 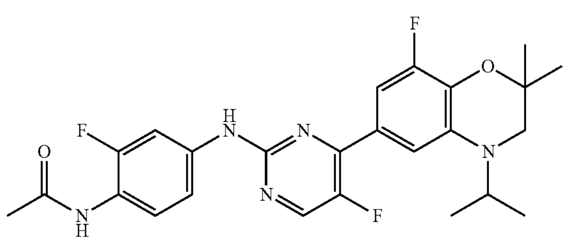 [SMILES: CC(=O)Nc1ccc(Nc2ncc(F)c(-c3cc(F)c4c(c3)N(C(C)C)CC(C)(C)O4)n2)cc1F] |
| 725 | 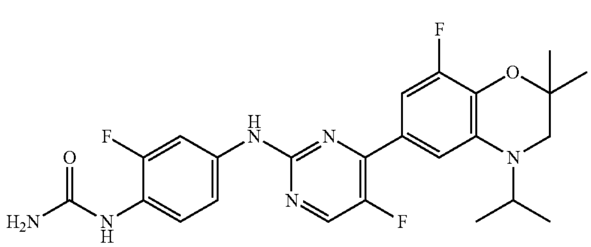 [SMILES: CC(C)N1CC(C)(C)Oc2c(F)cc(-c3nc(Nc4ccc(NC(N)=O)c(F)c4)ncc3F)cc21] |

TABLE 1-continued

| Compound No. | Structure |
|---|---|
| 726 | 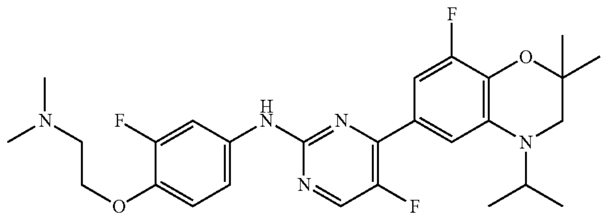 |
| 727 | 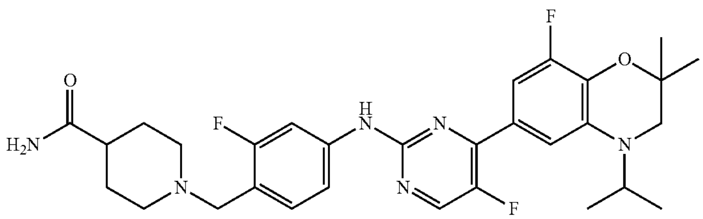 [SMILES: CC(C)N1CC(C)(C)Oc2c(F)cc(-c3nc(Nc4ccc(CN5CCC(C(N)=O)CC5)c(F)c4)ncc3F)cc21] |
| 728 | 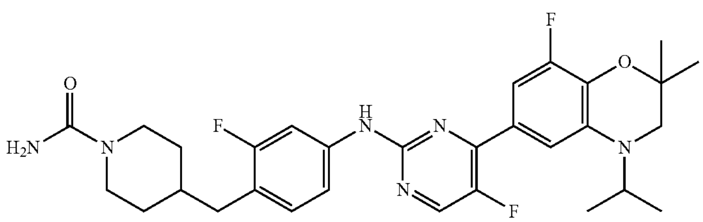 |
| 729 | 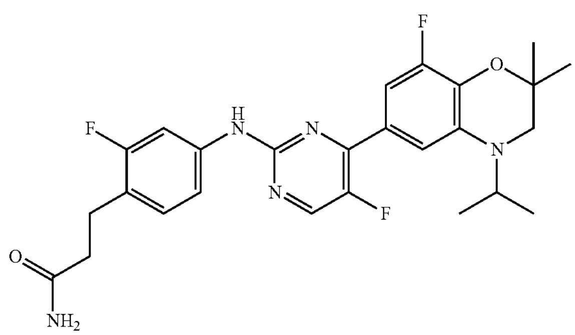 [SMILES: CC(C)N1CC(C)(C)Oc2c(F)cc(-c3nc(Nc4ccc(CCC(N)=O)c(F)c4)ncc3F)cc21] |
| 730 | 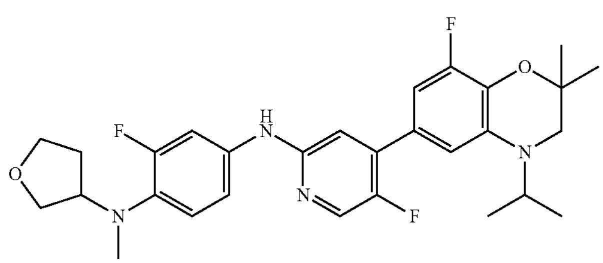 [SMILES: CC(C)N1CC(C)(C)Oc2c(F)cc(-c3cc(Nc4ccc(N(C)C5CCOC5)c(F)c4)ncc3F)cc21] |
| 731 | 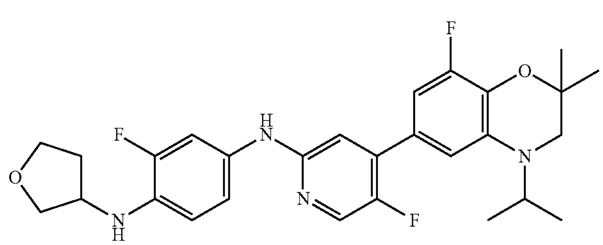 [SMILES: CC(C)N1CC(C)(C)Oc2c(F)cc(-c3cc(Nc4ccc(NC5CCOC5)c(F)c4)ncc3F)cc21] |

TABLE 1-continued

| Compound No. | Structure |
|---|---|
| 732 | 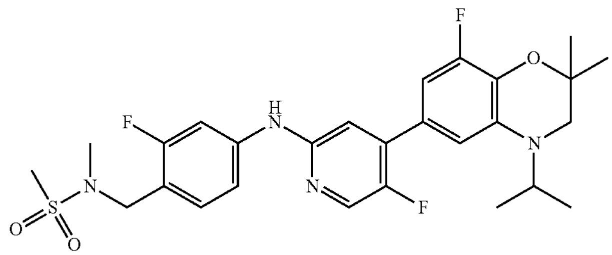 [SMILES: CC(C)N1CC(C)(C)Oc2c(F)cc(-c3cc(Nc4ccc(CN(C)S(C)(=O)=O)c(F)c4)ncc3F)cc21] |
| 733 | 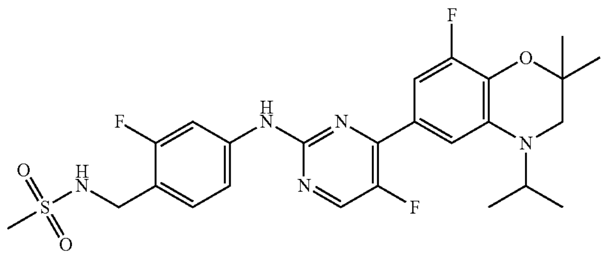 |
| 734 | 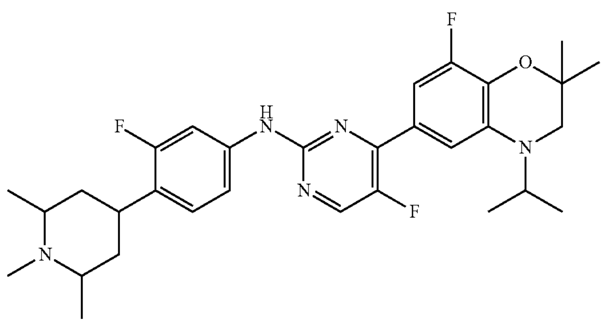 |
| 735 | 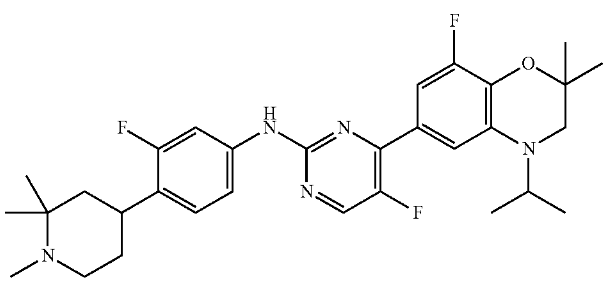 |
| 736 | 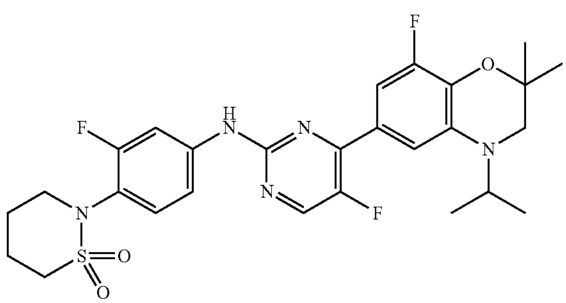 [SMILES: CC(C)N1CC(C)(C)Oc2c(F)cc(-c3nc(Nc4ccc(N5CCCCS5(=O)=O)c(F)c4)ncc3F)cc21] |

TABLE 1-continued

| Compound No. | Structure |
|---|---|
| 737 | 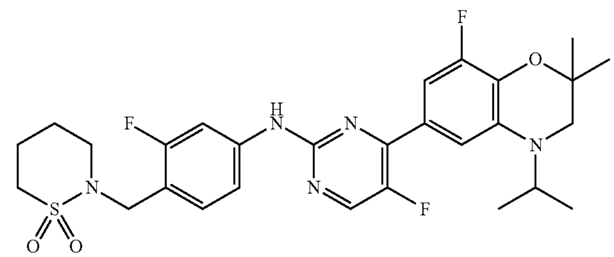 [SMILES: CC(C)N1CC(C)(C)Oc2c(F)cc(-c3nc(Nc4ccc(CN5CCCCS5(=O)=O)c(F)c4)ncc3F)cc21] |
| 738 | 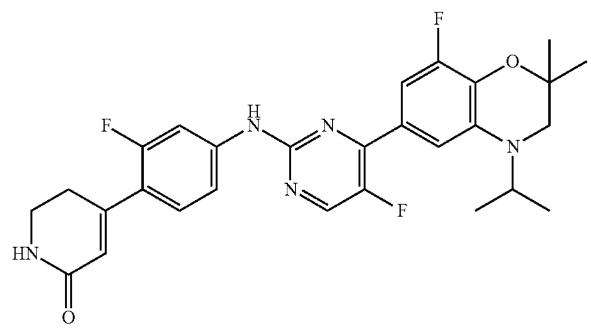 [SMILES: CC(C)N1CC(C)(C)Oc2c(F)cc(-c3nc(Nc4ccc(C5=CC(=O)NCC5)c(F)c4)ncc3F)cc21] |
| 739 | 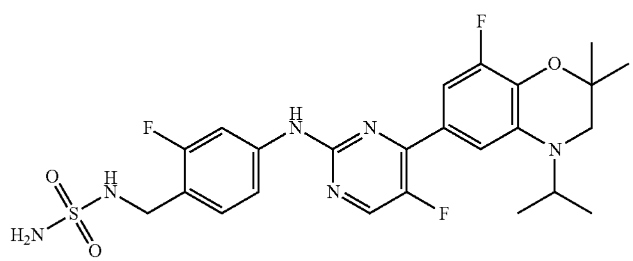 [SMILES: CC(C)N1CC(C)(C)Oc2c(F)cc(-c3nc(Nc4ccc(CNS(N)(=O)=O)c(F)c4)ncc3F)cc21] |
| 740 | 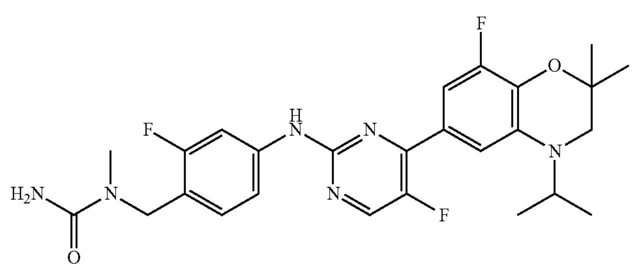 [SMILES: CC(C)N1CC(C)(C)Oc2c(F)cc(-c3nc(Nc4ccc(CN(C)C(N)=O)c(F)c4)ncc3F)cc21] |
| 741 | 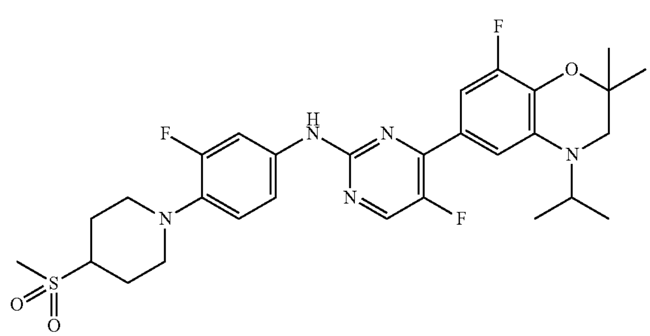 |

TABLE 1-continued

| Compound No. | Structure |
| --- | --- |
| 742 | (structure) |
| 743 | (structure) |
| 744 | (structure) |
| 745 | (structure) |
| 746 | (structure) |
| 747 | (structure) |

TABLE 1-continued

| Compound No. | Structure |
|---|---|
| 748 | 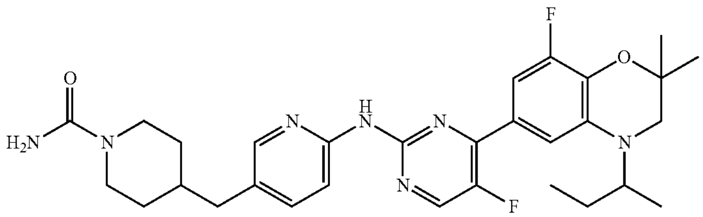 [SMILES: CCC(C)N1CC(C)(C)Oc2c(F)cc(-c3nc(Nc4ccc(CC5CCN(C(N)=O)CC5)cn4)ncc3F)cc21] |
| 749 | 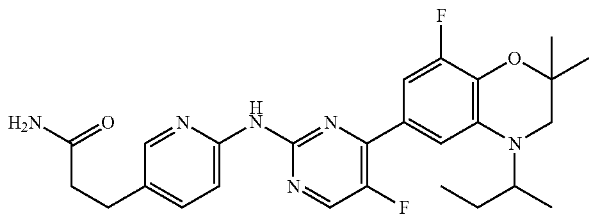 [SMILES: CCC(C)N1CC(C)(C)Oc2c(F)cc(-c3nc(Nc4ccc(CCC(N)=O)cn4)ncc3F)cc21] |
| 750 | 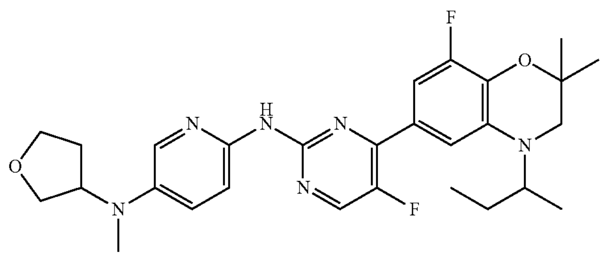 [SMILES: CCC(C)N1CC(C)(C)Oc2c(F)cc(-c3nc(Nc4ccc(N(C)C5CCOC5)cn4)ncc3F)cc21] |
| 751 | 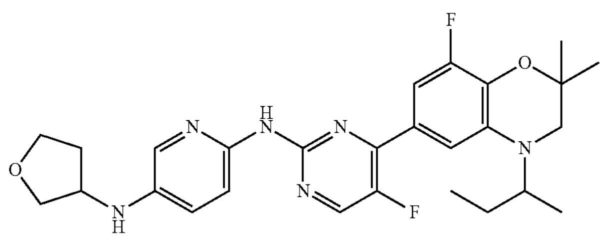 [SMILES: CCC(C)N1CC(C)(C)Oc2c(F)cc(-c3nc(Nc4ccc(NC5CCOC5)cn4)ncc3F)cc21] |
| 752 | 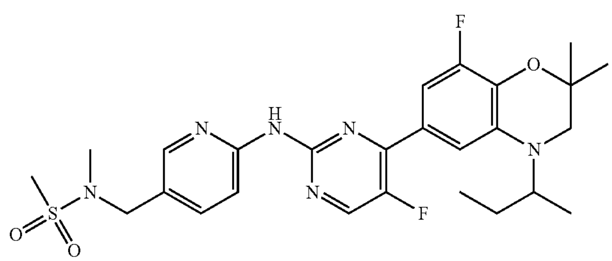 [SMILES: CCC(C)N1CC(C)(C)Oc2c(F)cc(-c3nc(Nc4ccc(CN(C)S(C)(=O)=O)cn4)ncc3F)cc21] |
| 753 | 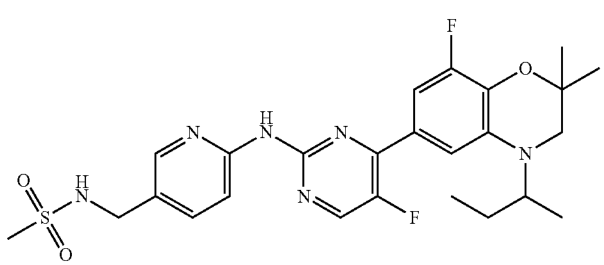 |

TABLE 1-continued
| Compound No. | Structure |
|---|---|
| 754 | 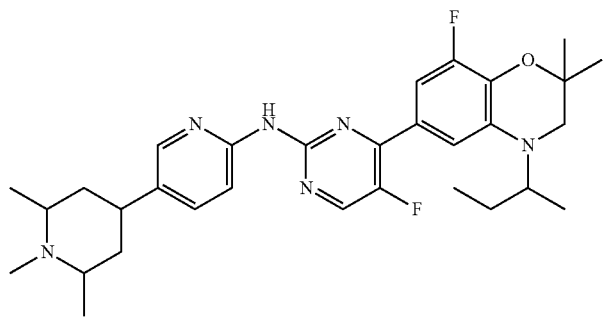 |
| 755 | 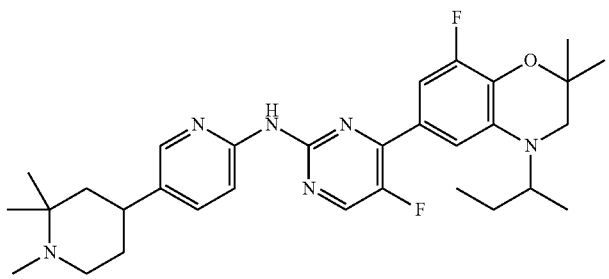 |
| 756 | 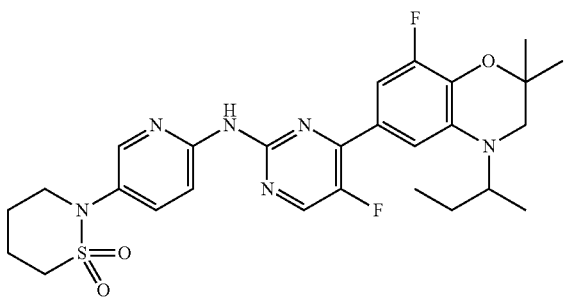 [SMILES: CCC(C)N1CC(C)(C)Oc2c(F)cc(-c3nc(Nc4ccc(N5CCCCS5(=O)=O)cn4)ncc3F)cc21] |
| 757 | 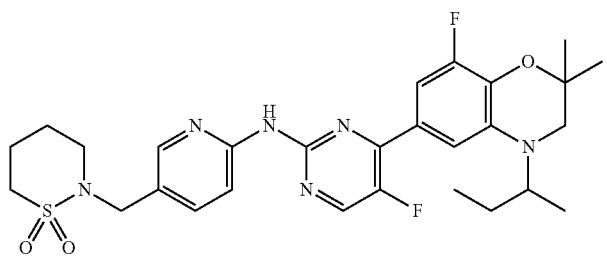 [SMILES: CCC(C)N1CC(C)(C)Oc2c(F)cc(-c3nc(Nc4ccc(CN5CCCCS5(=O)=O)cn4)ncc3F)cc21] |
| 758 | 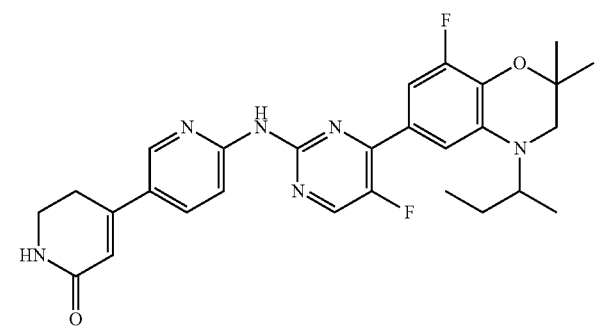 [SMILES: CCC(C)N1CC(C)(C)Oc2c(F)cc(-c3nc(Nc4ccc(C5=CC(=O)NCC5)cn4)ncc3F)cc21] |

TABLE 1-continued
| Compound No. | Structure |
|---|---|
| 759 | 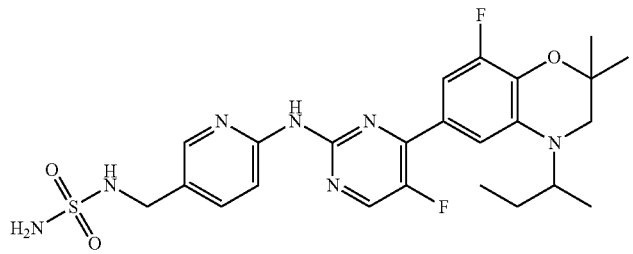 [SMILES: CCC(C)N1CC(C)(C)Oc2c(F)cc(-c3nc(Nc4ccc(CNS(N)(=O)=O)cn4)ncc3F)cc21] |
| 760 | 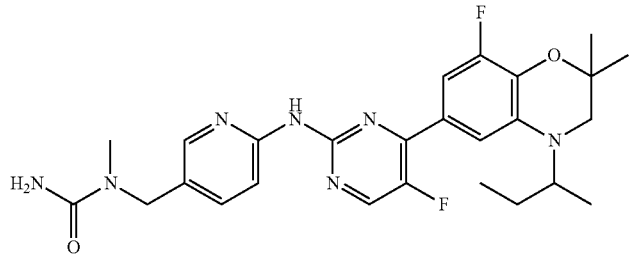 [SMILES: CCC(C)N1CC(C)(C)Oc2c(F)cc(-c3nc(Nc4ccc(CN(C)C(N)=O)cn4)ncc3F)cc21] |
| 761 | 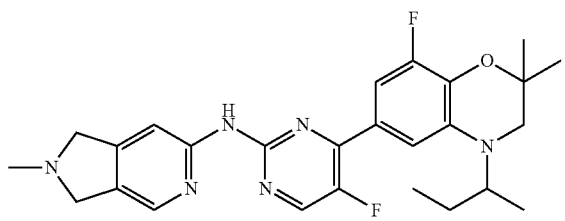 |
| 762 | 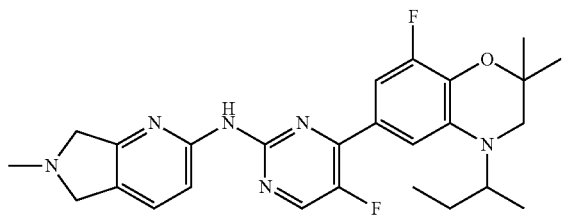 |
| 763 | 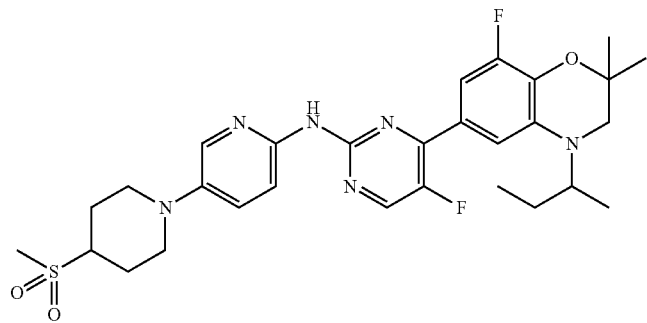 |
| 764 | 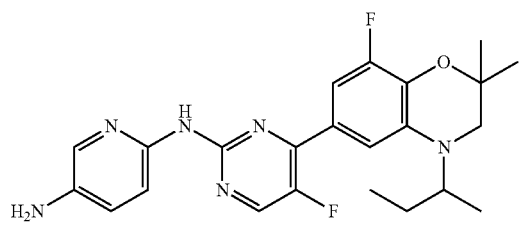 |

TABLE 1-continued
| Compound No. | Structure |
|---|---|
| 765 | 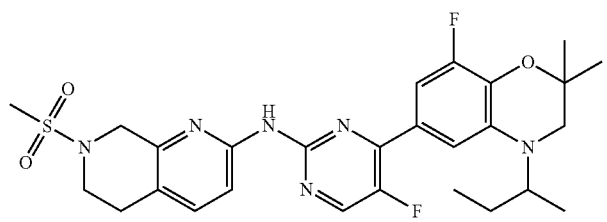 |
| 766 | 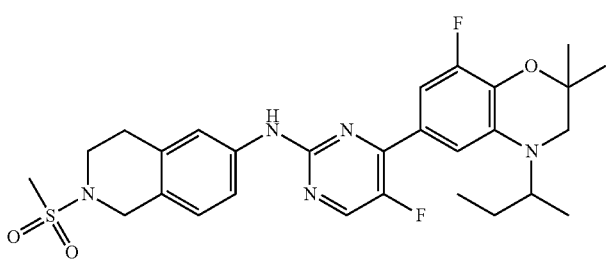 [SMILES: CCC(C)N1CC(C)(C)Oc2c(F)cc(-c3nc(Nc4ccc5c(c4)CCN(S(C)(=O)=O)C5)ncc3F)cc21] |
| 767 | 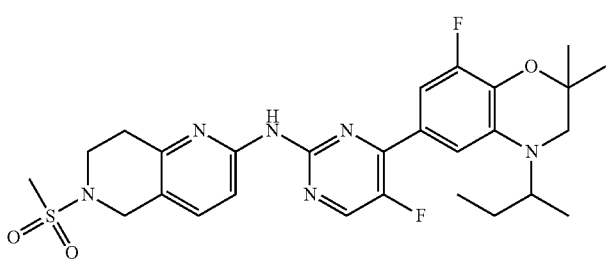 [SMILES: CCC(C)N1CC(C)(C)Oc2c(F)cc(-c3nc(Nc4ccc5c(n4)CCN(S(C)(=O)=O)C5)ncc3F)cc21] |
| 768 | 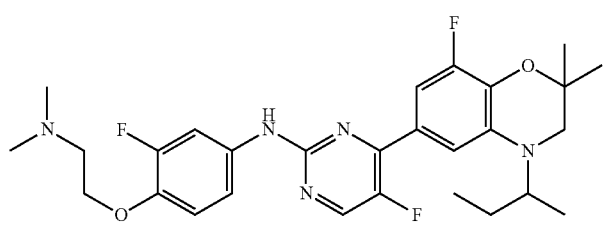 |
| 769 | 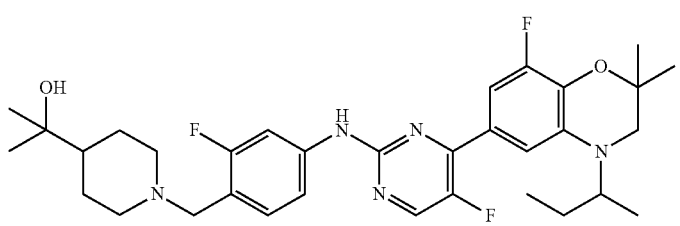 [SMILES: CCC(C)N1CC(C)(C)Oc2c(F)cc(-c3nc(Nc4ccc(CN5CCC(C(C)(C)O)CC5)c(F)c4)ncc3F)cc21] |
| 770 | 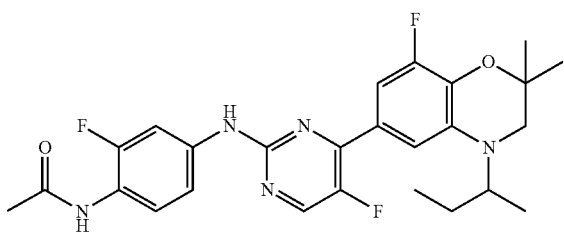 [SMILES: CCC(C)N1CC(C)(C)Oc2c(F)cc(-c3nc(Nc4ccc(NC(C)=O)c(F)c4)ncc3F)cc21] |

TABLE 1-continued
| Compound No. | Structure |
|---|---|
| 771 | 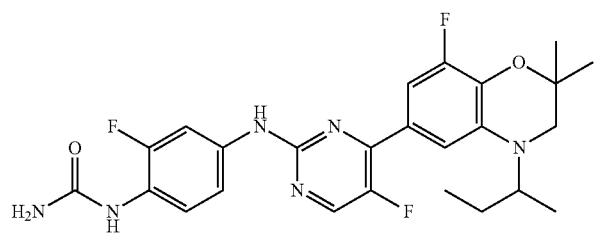 |
| 772 | 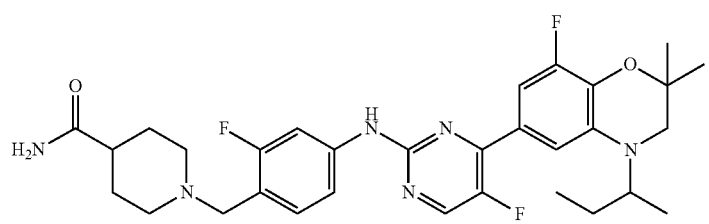 [SMILES: CCC(C)N1CC(C)(C)Oc2c(F)cc(-c3nc(Nc4ccc(CN5CCC(C(N)=O)CC5)c(F)c4)ncc3F)cc21] |
| 773 | 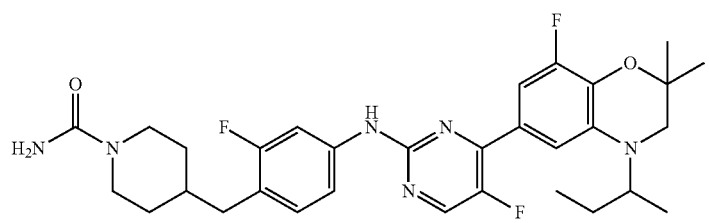 |
| 774 | 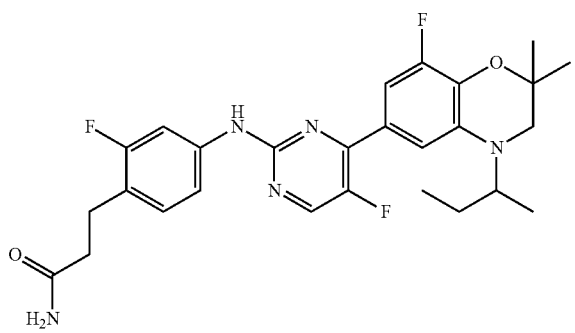 [SMILES: CCC(C)N1CC(C)(C)Oc2c(F)cc(-c3nc(Nc4ccc(CCC(N)=O)c(F)c4)ncc3F)cc21] |
| 775 | 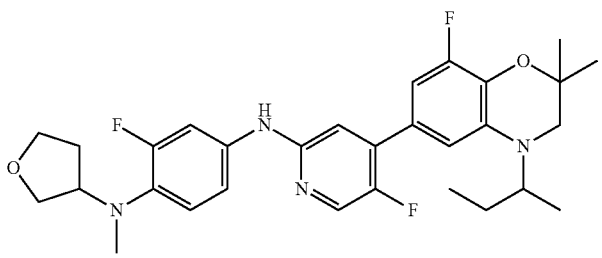 [SMILES: CCC(C)N1CC(C)(C)Oc2c(F)cc(-c3cc(Nc4ccc(N(C)C5CCOC5)c(F)c4)ncc3F)cc21] |
| 776 | 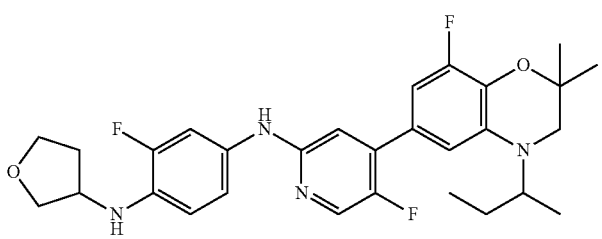 [SMILES: CCC(C)N1CC(C)(C)Oc2c(F)cc(-c3cc(Nc4ccc(NC5CCOC5)c(F)c4)ncc3F)cc21] |

TABLE 1-continued
| Compound No. | Structure |
|---|---|
| 777 | 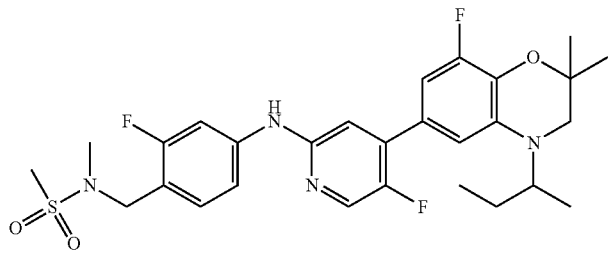 [SMILES: CCC(C)N1CC(C)(C)Oc2c(F)cc(-c3cc(Nc4ccc(CN(C)S(C)(=O)=O)c(F)c4)ncc3F)cc21] |
| 778 | 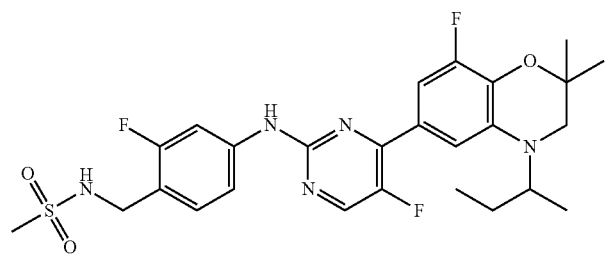 |
| 779 | 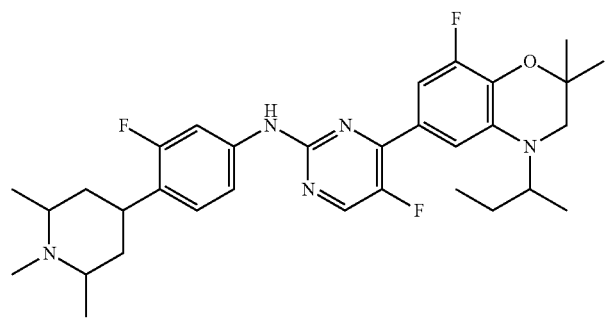 |
| 780 | 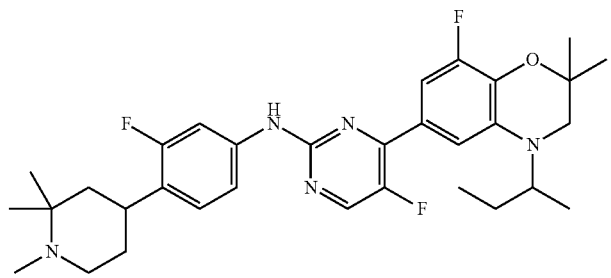 |
| 781 | 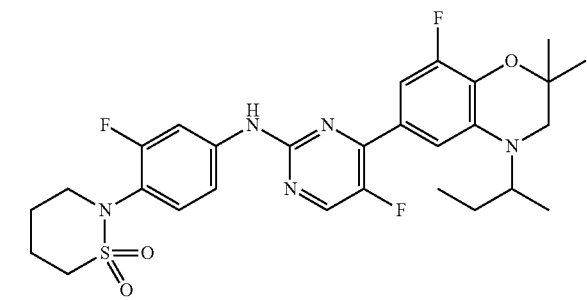 [SMILES: CCC(C)N1CC(C)(C)Oc2c(F)cc(-c3nc(Nc4ccc(N5CCCCS5(=O)=O)c(F)c4)ncc3F)cc21] |

TABLE 1-continued
| Compound No. | Structure |
|---|---|
| 782 | 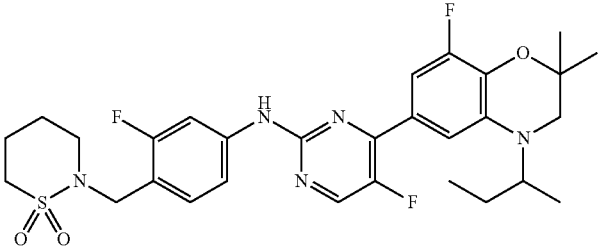 [SMILES: CCC(C)N1CC(C)(C)Oc2c(F)cc(-c3nc(Nc4ccc(CN5CCCCS5(=O)=O)c(F)c4)ncc3F)cc21] |
| 783 | 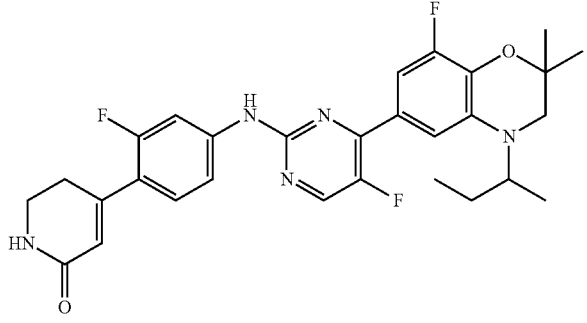 [SMILES: CCC(C)N1CC(C)(C)Oc2c(F)cc(-c3nc(Nc4ccc(C5=CC(=O)NCC5)c(F)c4)ncc3F)cc21] |
| 784 | 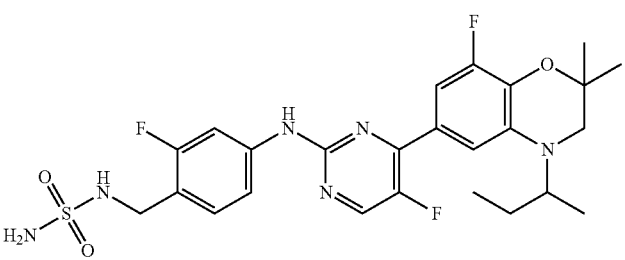 [SMILES: CCC(C)N1CC(C)(C)Oc2c(F)cc(-c3nc(Nc4ccc(CNS(N)(=O)=O)c(F)c4)ncc3F)cc21] |
| 785 | 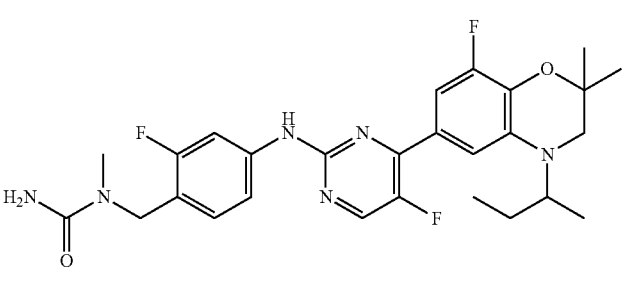 [SMILES: CCC(C)N1CC(C)(C)Oc2c(F)cc(-c3nc(Nc4ccc(CN(C)C(N)=O)c(F)c4)ncc3F)cc21] |
| 786 | 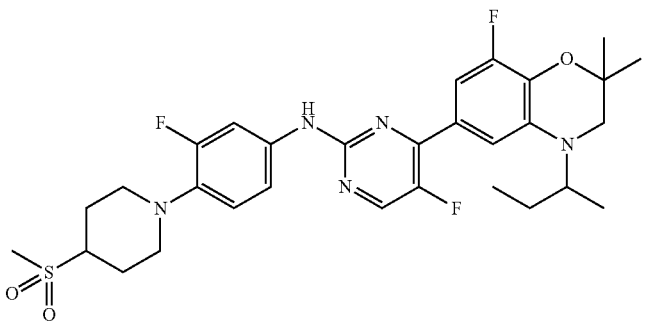 |

TABLE 1-continued
| Compound No. | Structure |
|---|---|
| 787 | 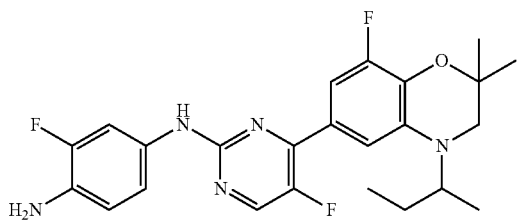 [SMILES: CCC(C)N1CC(C)(C)Oc2c(F)cc(-c3nc(Nc4ccc(N)c(F)c4)ncc3F)cc21] |
| 788 | 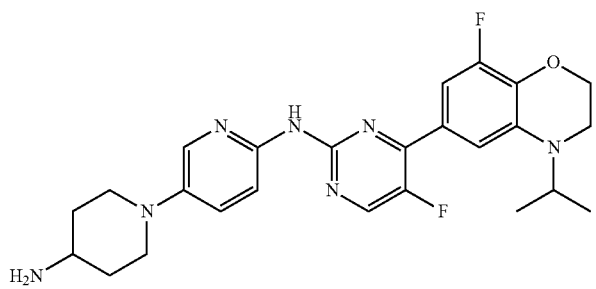 [SMILES: CC(C)N1CCOc2c(F)cc(-c3nc(Nc4ccc(N5CCC(N)CC5)cn4)ncc3F)cc21] |
| 789 | 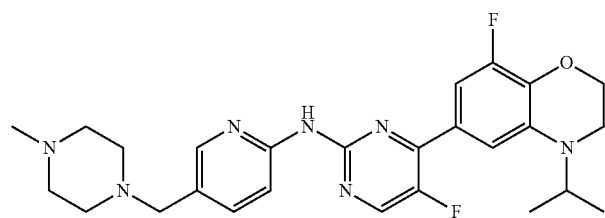 [SMILES: CC(C)N1CCOc2c(F)cc(-c3nc(Nc4ccc(CN5CCN(C)CC5)cn4)ncc3F)cc21] |
| 790 | 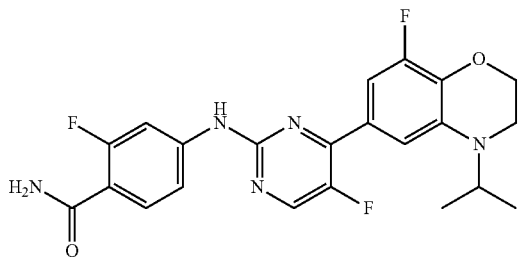 [SMILES: CC(C)N1CCOc2c(F)cc(-c3nc(Nc4ccc(C(N)=O)c(F)c4)ncc3F)cc21] |
| 791 | 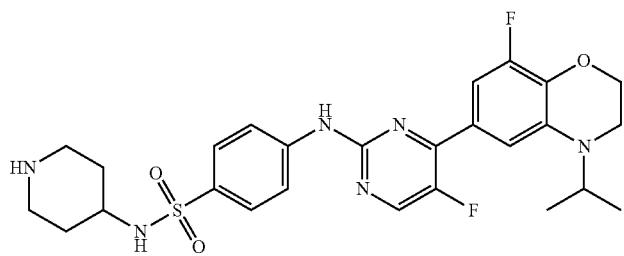 [SMILES: CC(C)N1CCOc2c(F)cc(-c3nc(Nc4ccc(S(=O)(=O)NC5CCNCC5)cc4)ncc3F)cc21] |
| 792 | 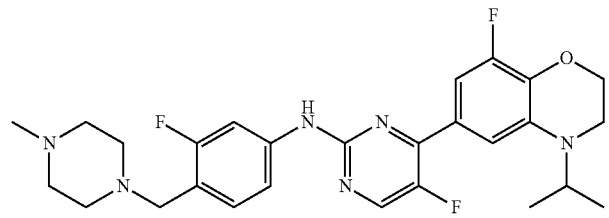 [SMILES: CC(C)N1CCOc2c(F)cc(-c3nc(Nc4ccc(CN5CCN(C)CC5)c(F)c4)ncc3F)cc21] |

TABLE 1-continued

| Compound No. | Structure |
|---|---|
| 793 | 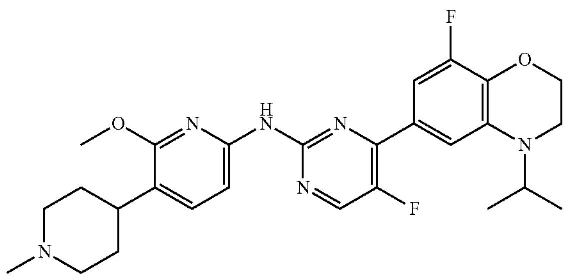 [SMILES: COc1nc(Nc2ncc(F)c(-c3cc(F)c4c(c3)N(C(C)C)CCO4)n2)ccc1C1CCN(C)CC1] |
| 794 | 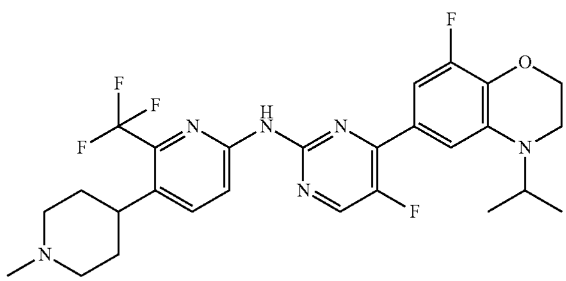 [SMILES: CC(C)N1CCOc2c(F)cc(-c3nc(Nc4ccc(C5CCN(C)CC5)c(C(F)(F)F)n4)ncc3F)cc21] |
| 795 | 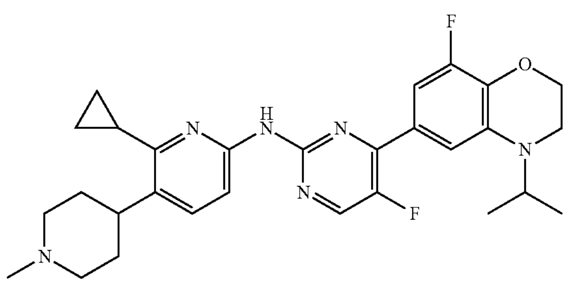 [SMILES: CC(C)N1CCOc2c(F)cc(-c3nc(Nc4ccc(C5CCN(C)CC5)c(C5CC5)n4)ncc3F)cc21] |
| 796 | 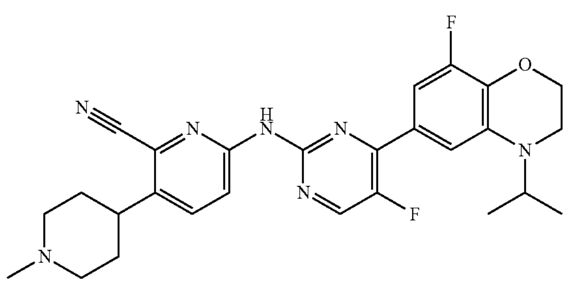 [SMILES: CC(C)N1CCOc2c(F)cc(-c3nc(Nc4ccc(C5CCN(C)CC5)c(C#N)n4)ncc3F)cc21] |
| 797 | 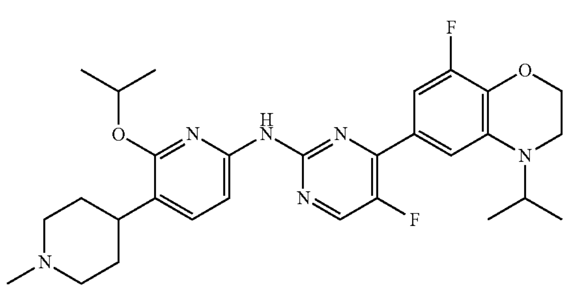 [SMILES: CC(C)Oc1nc(Nc2ncc(F)c(-c3cc(F)c4c(c3)N(C(C)C)CCO4)n2)ccc1C1CCN(C)CC1] |

TABLE 1-continued
| Compound No. | Structure |
|---|---|
| 798 | 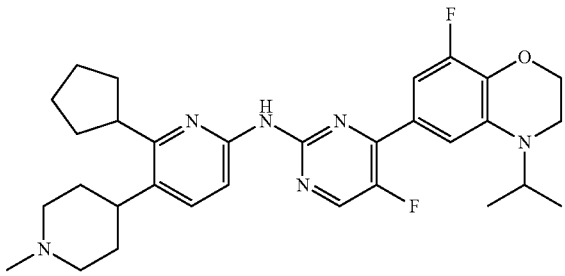 [SMILES: CC(C)N1CCOc2c(F)cc(-c3nc(Nc4ccc(C5CCN(C)CC5)c(C5CCCC5)n4)ncc3F)cc21] |
| 799 | 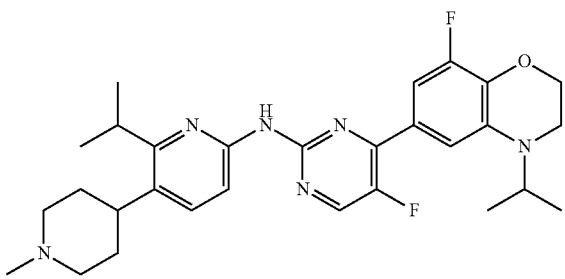 [SMILES: CC(C)c1nc(Nc2ncc(F)c(-c3cc(F)c4c(c3)N(C(C)C)CCO4)n2)ccc1C1CCN(C)CC1] |
| 800 | 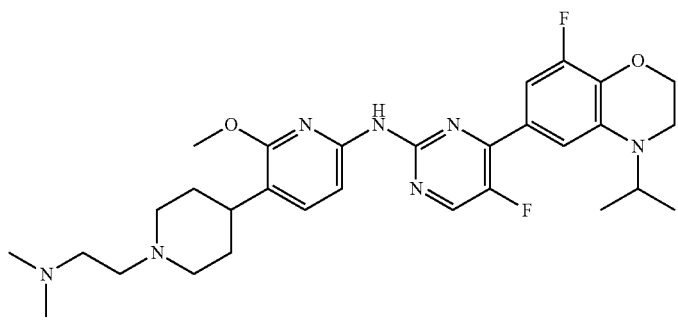 [SMILES: COc1nc(Nc2ncc(F)c(-c3cc(F)c4c(c3)N(C(C)C)CCO4)n2)ccc1C1CCN(CCN(C)C)CC1] |
| 801 | 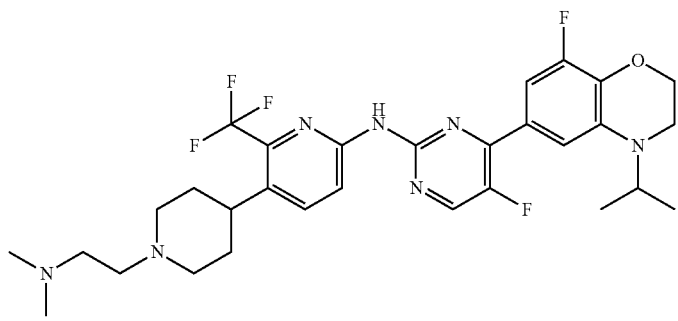 [SMILES: CC(C)N1CCOc2c(F)cc(-c3nc(Nc4ccc(C5CCN(CCN(C)C)CC5)c(C(F)(F)F)n4)ncc3F)cc21] |
| 802 | 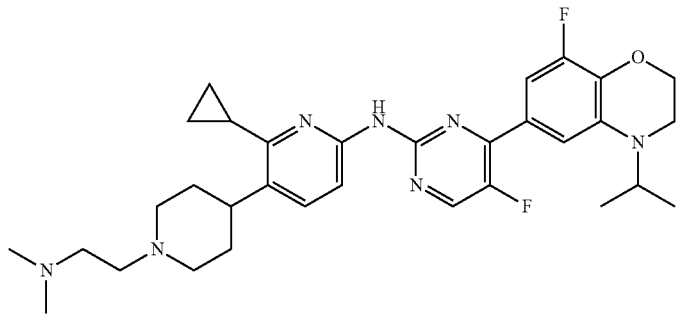 [SMILES: CC(C)N1CCOc2c(F)cc(-c3nc(Nc4ccc(C5CCN(CCN(C)C)CC5)c(C5CC5)n4)ncc3F)cc21] |

TABLE 1-continued
| Compound No. | Structure |
|---|---|
| 803 | 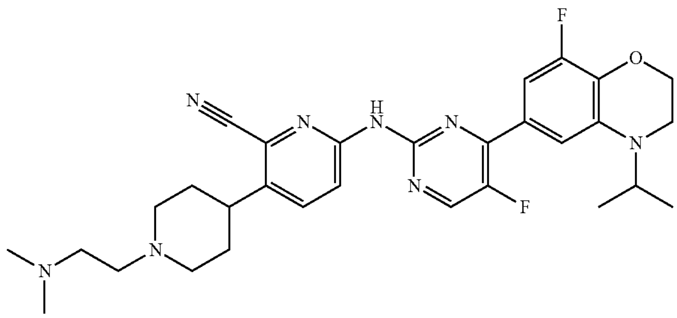 [SMILES: CC(C)N1CCOc2c(F)cc(-c3nc(Nc4ccc(C5CCN(CCN(C)C)CC5)c(C#N)n4)ncc3F)cc21] |
| 804 | 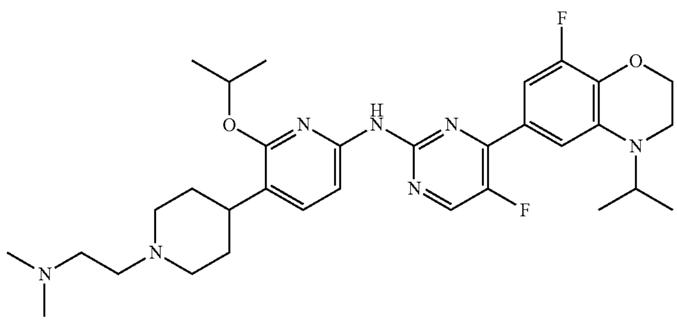 [SMILES: CC(C)Oc1nc(Nc2ncc(F)c(-c3cc(F)c4c(c3)N(C(C)C)CCO4)n2)ccc1C1CCN(CCN(C)C)CC1] |
| 805 | 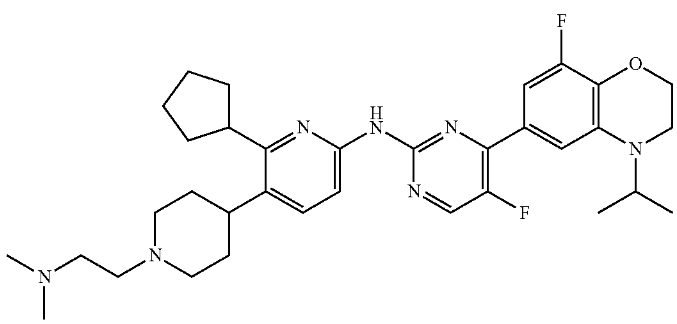 [SMILES: CC(C)N1CCOc2c(F)cc(-c3nc(Nc4ccc(C5CCN(CCN(C)C)CC5)c(C5CCCC5)n4)ncc3F)cc21] |
| 806 | 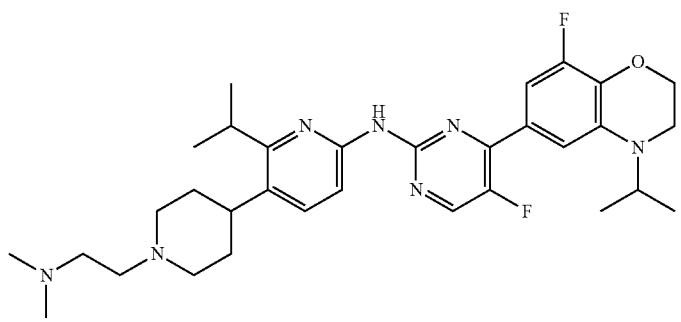 [SMILES: CC(C)c1nc(Nc2ncc(F)c(-c3cc(F)c4c(c3)N(C(C)C)CCO4)n2)ccc1C1CCN(CCN(C)C)CC1] |
| 807 | 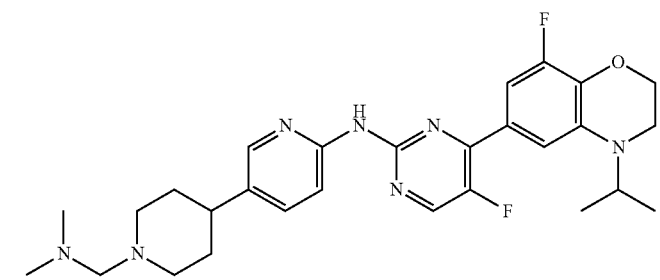 [SMILES: CC(C)N1CCOc2c(F)cc(-c3nc(Nc4ccc(C5CCN(CN(C)C)CC5)cn4)ncc3F)cc21] |

TABLE 1-continued
| Compound No. | Structure |
|---|---|
| 808 | 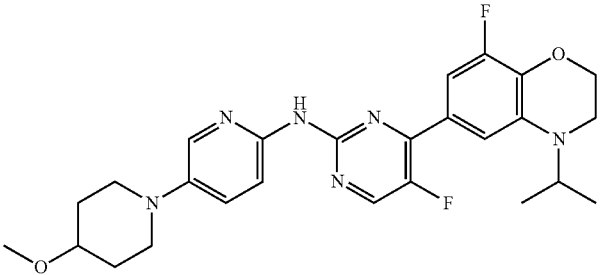 [SMILES: COC1CCN(c2ccc(Nc3ncc(F)c(-c4cc(F)c5c(c4)N(C(C)C)CCO5)n3)nc2)CC1] |
| 809 | 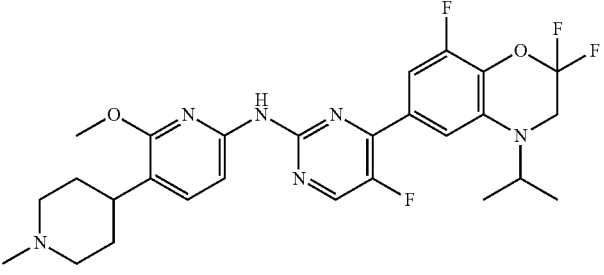 [SMILES: COc1nc(Nc2ncc(F)c(-c3cc(F)c4c(c3)N(C(C)C)CC(F)(F)O4)n2)ccc1C1CCN(C)CC1] |
| 810 | 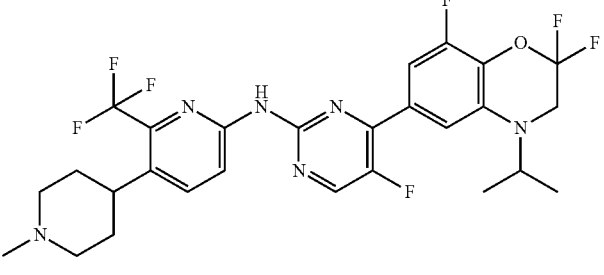 |
| 811 | 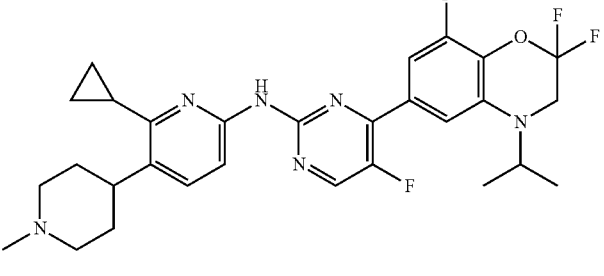 |
| 812 | 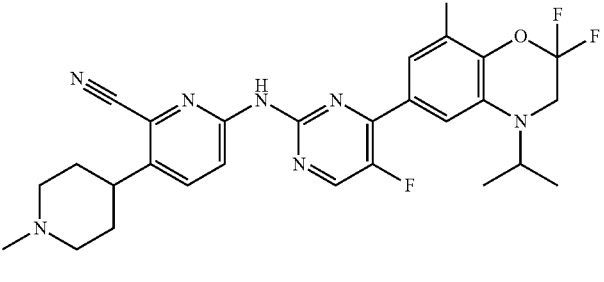 |

TABLE 1-continued

| Compound No. | Structure |
|---|---|
| 813 | 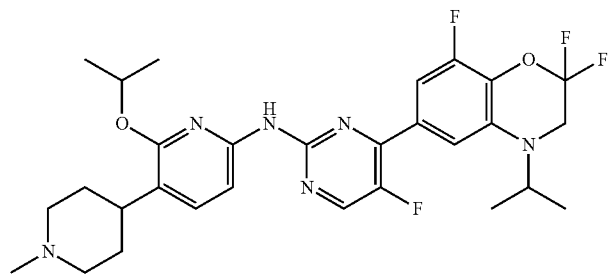 [SMILES: CC(C)Oc1nc(Nc2ncc(F)c(-c3cc(F)c4c(c3)N(C(C)C)CC(F)(F)O4)n2)ccc1C1CCN(C)CC1] |
| 814 | 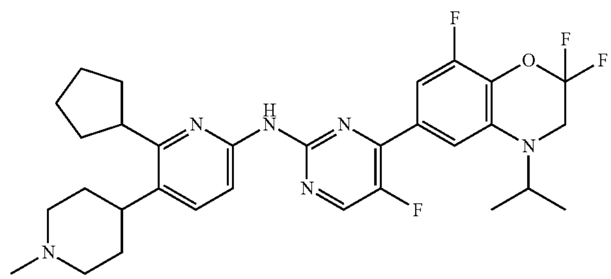 [SMILES: CC(C)N1CC(F)(F)Oc2c(F)cc(-c3nc(Nc4ccc(C5CCN(C)CC5)c(C5CCCC5)n4)ncc3F)cc21] |
| 815 | 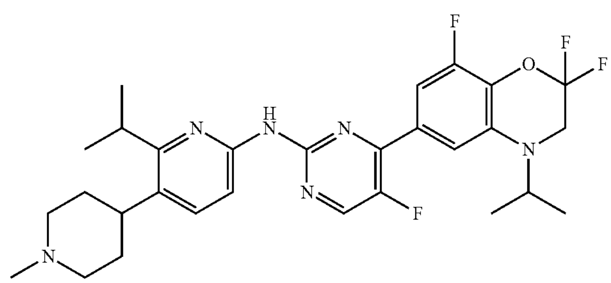 [SMILES: CC(C)c1nc(Nc2ncc(F)c(-c3cc(F)c4c(c3)N(C(C)C)CC(F)(F)O4)n2)ccc1C1CCN(C)CC1] |
| 816 | 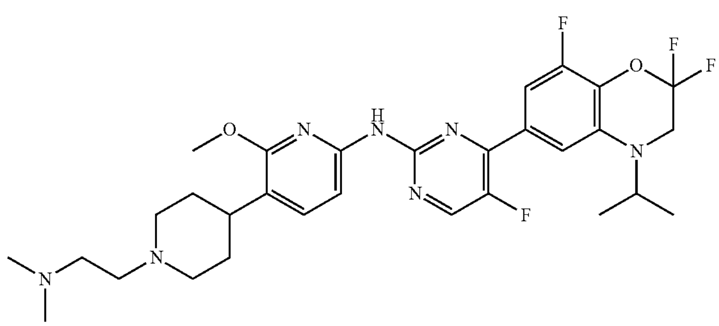 [SMILES: COc1nc(Nc2ncc(F)c(-c3cc(F)c4c(c3)N(C(C)C)CC(F)(F)O4)n2)ccc1C1CCN(CCN(C)C)CC1] |
| 817 | 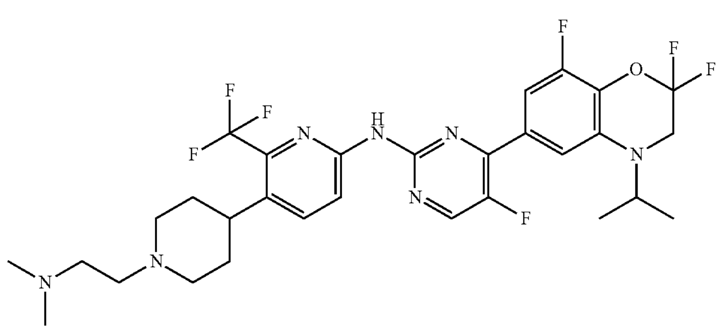 [SMILES: CC(C)N1CC(F)(F)Oc2c(F)cc(-c3nc(Nc4ccc(C5CCN(CCN(C)C)CC5)c(C(F)(F)F)n4)ncc3F)cc21] |

TABLE 1-continued
| Compound No. | Structure |
|---|---|
| 818 | 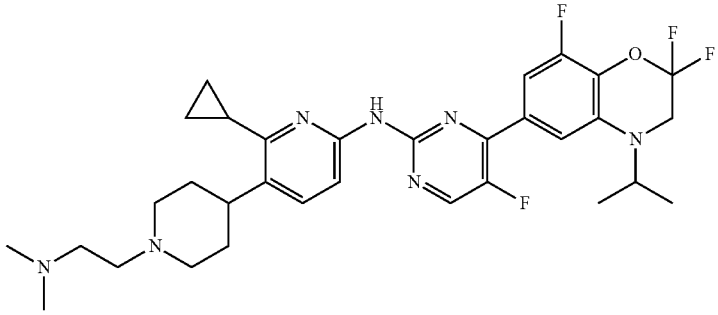 [SMILES: CC(C)N1CC(F)(F)Oc2c(F)cc(-c3nc(Nc4ccc(C5CCN(CCN(C)C)CC5)c(C5CC5)n4)ncc3F)cc21] |
| 819 | 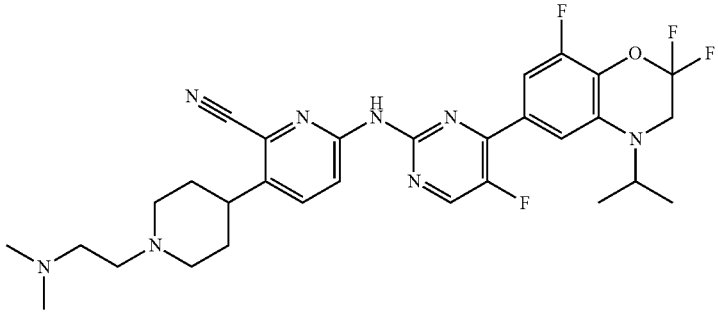 [SMILES: CC(C)N1CC(F)(F)Oc2c(F)cc(-c3nc(Nc4ccc(C5CCN(CCN(C)C)CC5)c(C#N)n4)ncc3F)cc21] |
| 820 | 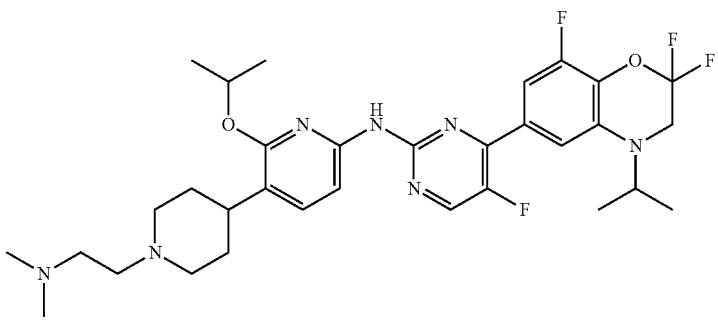 [SMILES: CC(C)Oc1nc(Nc2ncc(F)c(-c3cc(F)c4c(c3)N(C(C)C)CC(F)(F)O4)n2)ccc1C1CCN(CCN(C)C)CC1] |
| 821 | 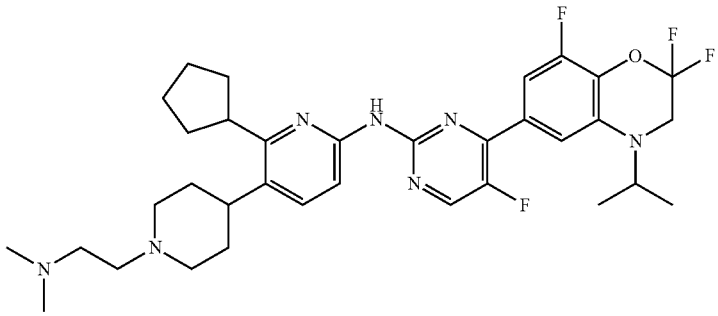 [SMILES: CC(C)N1CC(F)(F)Oc2c(F)cc(-c3nc(Nc4ccc(C5CCN(CCN(C)C)CC5)c(C5CCCC5)n4)ncc3F)cc21] |

TABLE 1-continued
| Compound No. | Structure |
|---|---|
| 822 | 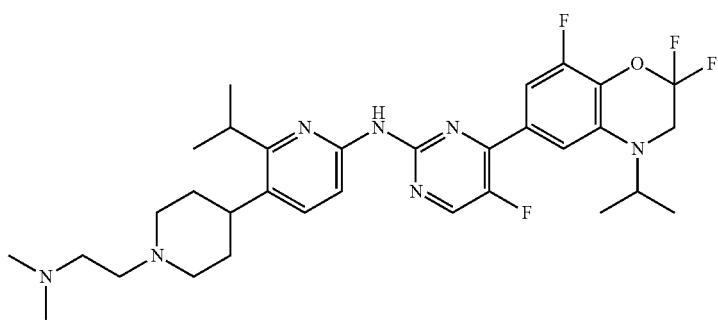 [SMILES: CC(C)c1nc(Nc2ncc(F)c(-c3cc(F)c4c(c3)N(C(C)C)CC(F)(F)O4)n2)ccc1C1CCN(CCN(C)C)CC1] |
| 823 | 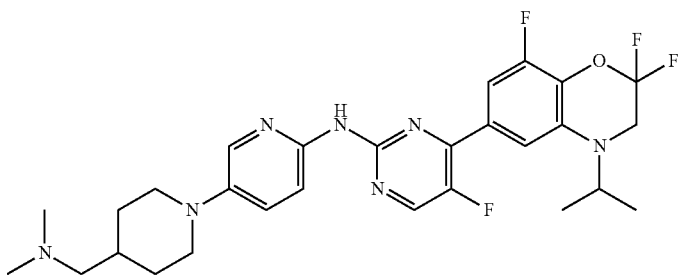 [SMILES: CC(C)N1CC(F)(F)Oc2c(F)cc(-c3nc(Nc4ccc(N5CCC(CN(C)C)CC5)cn4)ncc3F)cc21] |
| 824 | 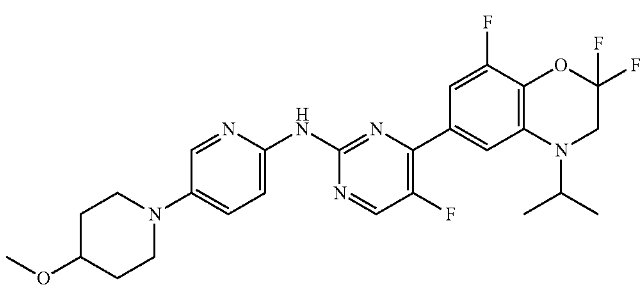 [SMILES: COC1CCN(c2ccc(Nc3ncc(F)c(-c4cc(F)c5c(c4)N(C(C)C)CC(F)(F)O5)n3)nc2)CC1] |
| 825 | 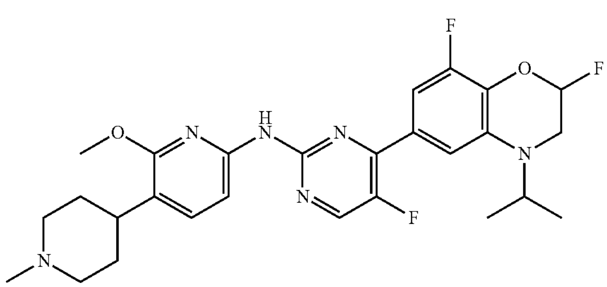 [SMILES: COc1nc(Nc2ncc(F)c(-c3cc(F)c4c(c3)N(C(C)C)CC(F)O4)n2)ccc1C1CCN(C)CC1] |
| 826 | 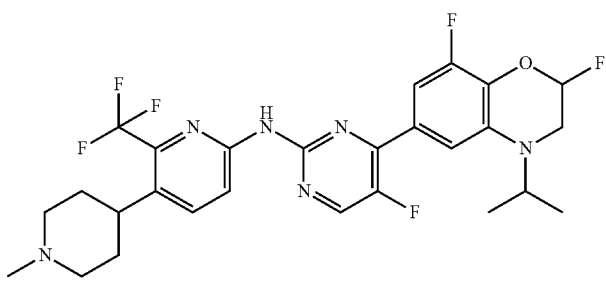 [SMILES: CC(C)N1CC(F)Oc2c(F)cc(-c3nc(Nc4ccc(C5CCN(C)CC5)c(C(F)(F)F)n4)ncc3F)cc21] |

TABLE 1-continued

| Compound No. | Structure |
|---|---|
| 827 | 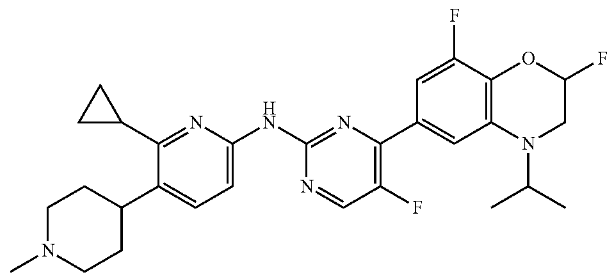 [SMILES: CC(C)N1CC(F)Oc2c(F)cc(-c3nc(Nc4ccc(C5CCN(C)CC5)c(C5CC5)n4)ncc3F)cc21] |
| 828 | 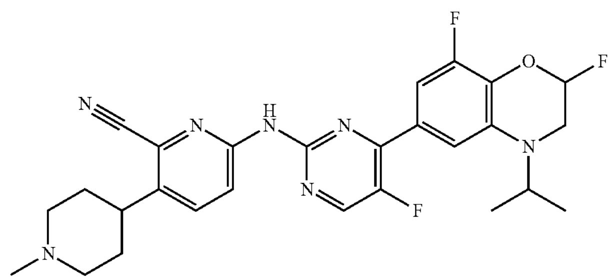 [SMILES: CC(C)N1CC(F)Oc2c(F)cc(-c3nc(Nc4ccc(C5CCN(C)CC5)c(C#N)n4)ncc3F)cc21] |
| 829 | 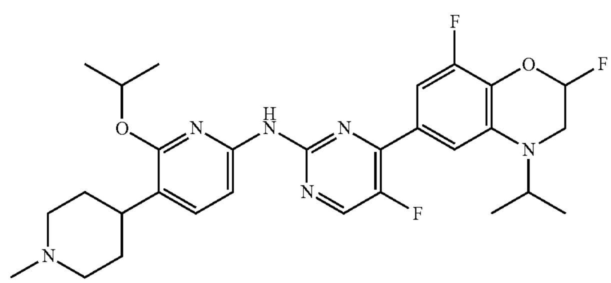 [SMILES: CC(C)Oc1nc(Nc2ncc(F)c(-c3cc(F)c4c(c3)N(C(C)C)CC(F)O4)n2)ccc1C1CCN(C)CC1] |
| 830 | 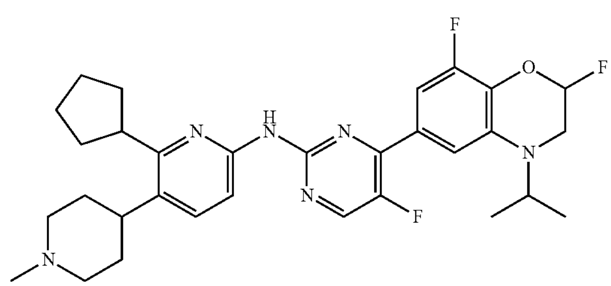 [SMILES: CC(C)N1CC(F)Oc2c(F)cc(-c3nc(Nc4ccc(C5CCN(C)CC5)c(C5CCCC5)n4)ncc3F)cc21] |
| 831 | 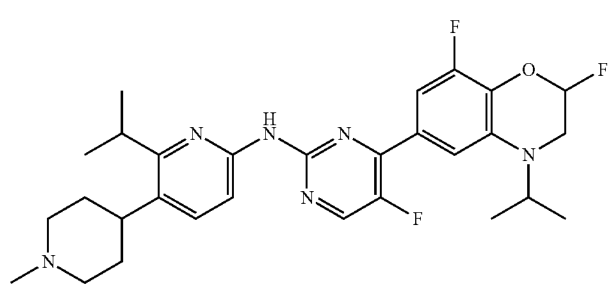 [SMILES: CC(C)c1nc(Nc2ncc(F)c(-c3cc(F)c4c(c3)N(C(C)C)CC(F)O4)n2)ccc1C1CCN(C)CC1] |

TABLE 1-continued
| Compound No. | Structure |
|---|---|
| 832 | 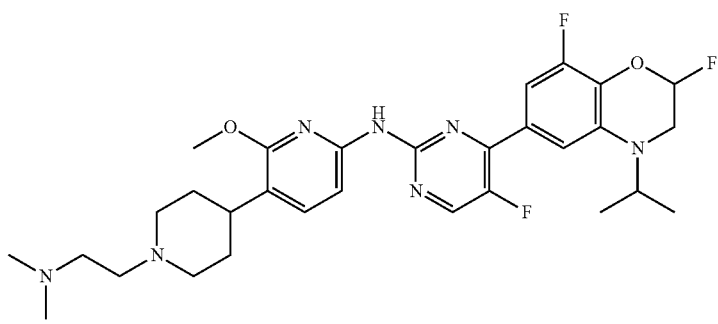 [SMILES: COc1nc(Nc2ncc(F)c(-c3cc(F)c4c(c3)N(C(C)C)CC(F)O4)n2)ccc1C1CCN(CCN(C)C)CC1] |
| 833 | 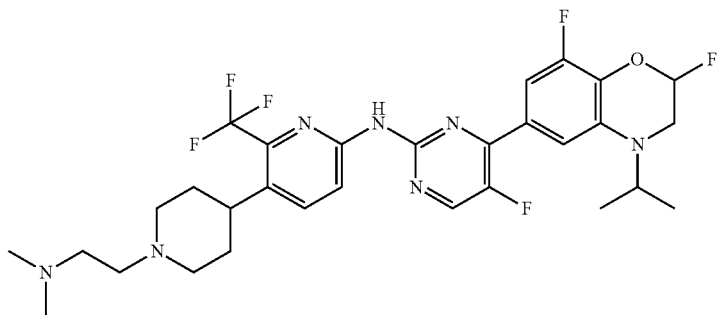 [SMILES: CC(C)N1CC(F)Oc2c(F)cc(-c3nc(Nc4ccc(C5CCN(CCN(C)C)CC5)c(C(F)(F)F)n4)ncc3F)cc21] |
| 834 | 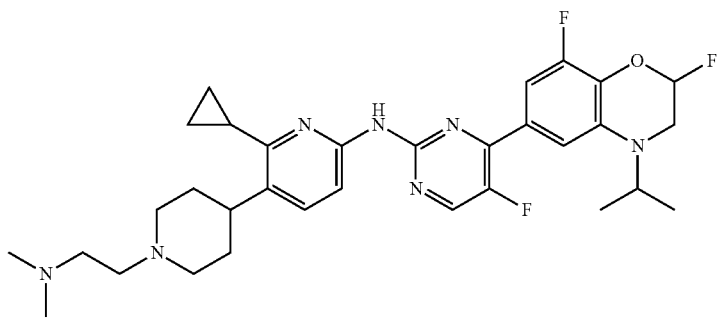 [SMILES: CC(C)N1CC(F)Oc2c(F)cc(-c3nc(Nc4ccc(C5CCN(CCN(C)C)CC5)c(C5CC5)n4)ncc3F)cc21] |
| 835 | 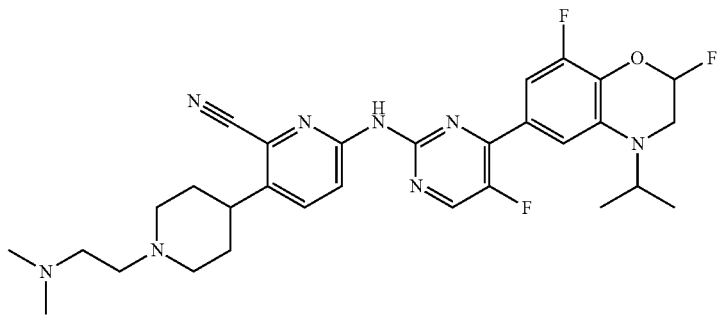 [SMILES: CC(C)N1CC(F)Oc2c(F)cc(-c3nc(Nc4ccc(C5CCN(CCN(C)C)CC5)c(C#N)n4)ncc3F)cc21] |

TABLE 1-continued
| Compound No. | Structure |
|---|---|
| 836 | 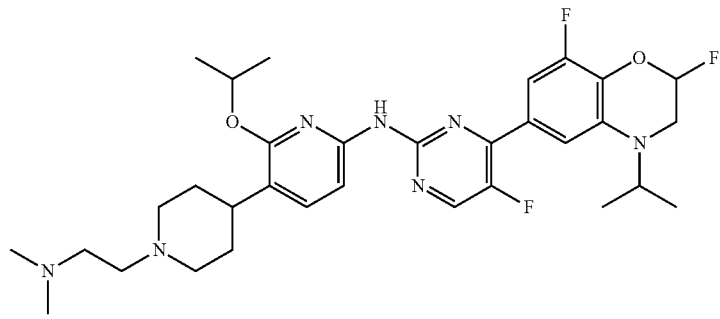 [SMILES: CC(C)Oc1nc(Nc2ncc(F)c(-c3cc(F)c4c(c3)N(C(C)C)CC(F)O4)n2)ccc1C1CCN(CCN(C)C)CC1] |
| 837 | 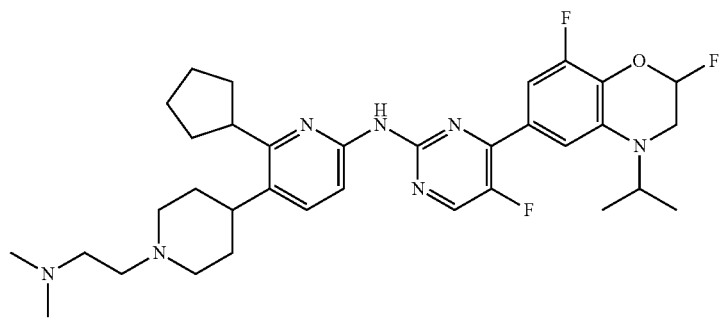 [SMILES: CC(C)N1CC(F)Oc2c(F)cc(-c3nc(Nc4ccc(C5CCN(CCN(C)C)CC5)c(C5CCCC5)n4)ncc3F)cc21] |
| 838 | 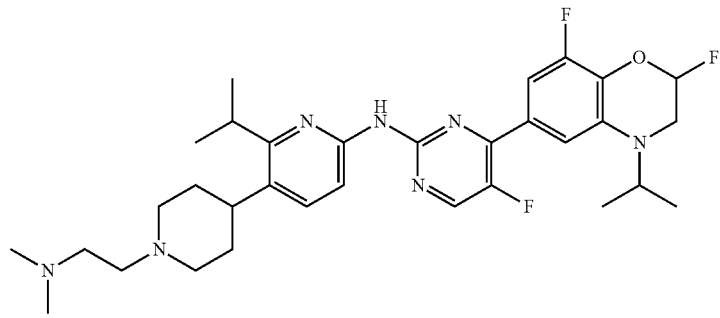 [SMILES: CC(C)c1nc(Nc2ncc(F)c(-c3cc(F)c4c(c3)N(C(C)C)CC(F)O4)n2)ccc1C1CCN(CCN(C)C)CC1] |
| 839 | 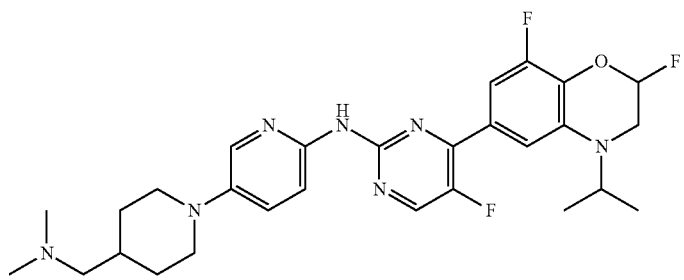 [SMILES: CC(C)N1CC(F)Oc2c(F)cc(-c3nc(Nc4ccc(N5CCC(CN(C)C)CC5)cn4)ncc3F)cc21] |
| 840 | 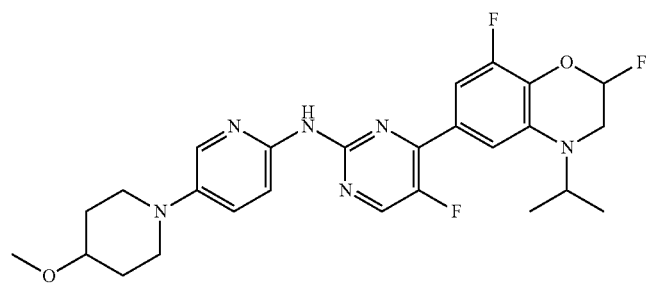 [SMILES: COC1CCN(c2ccc(Nc3ncc(F)c(-c4cc(F)c5c(c4)N(C(C)C)CC(F)O5)n3)nc2)CC1] |

TABLE 1-continued
| Compound No. | Structure |
|---|---|
| 841 | 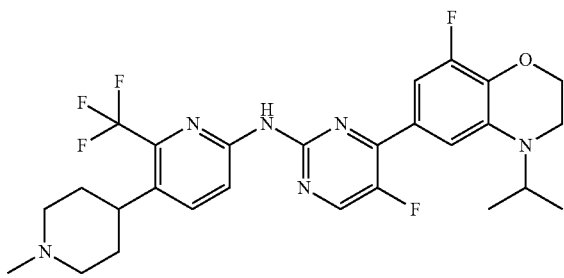 [SMILES: CC(C)N1CCOc2c(F)cc(-c3nc(Nc4ccc(C5CCN(C)CC5)c(C(F)(F)F)n4)ncc3F)cc21] |
| 842 | 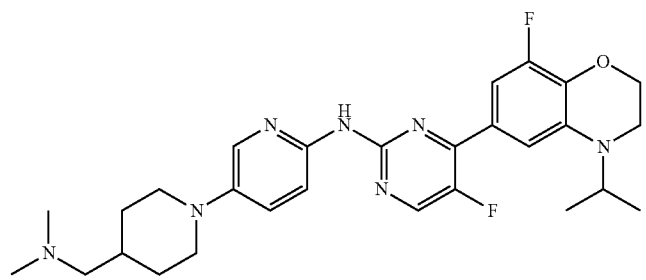 [SMILES: CC(C)N1CCOc2c(F)cc(-c3nc(Nc4ccc(N5CCC(CN(C)C)CC5)cn4)ncc3F)cc21] |
| 843 | 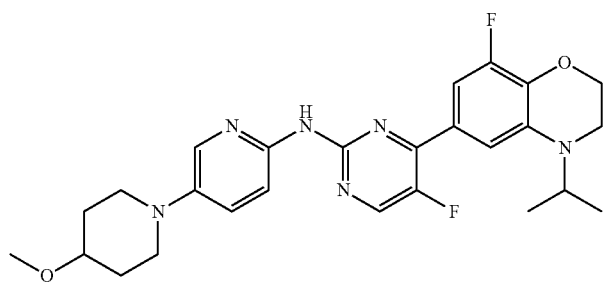 [SMILES: COC1CCN(c2ccc(Nc3ncc(F)c(-c4cc(F)c5c(c4)N(C(C)C)CCO5)n3)nc2)CC1] |
| 844 | 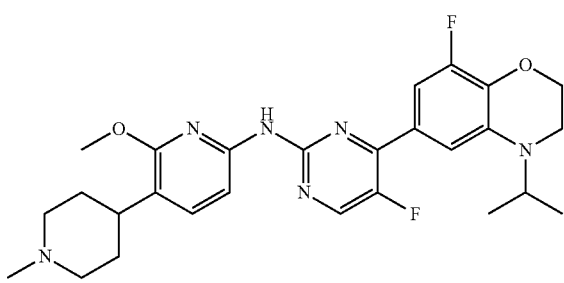 [SMILES: COc1nc(Nc2ncc(F)c(-c3cc(F)c4c(c3)N(C(C)C)CCO4)n2)ccc1C1CCN(C)CC1] |
| 845 | 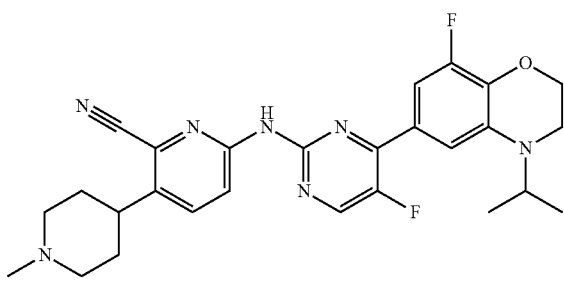 [SMILES: CC(C)N1CCOc2c(F)cc(-c3nc(Nc4ccc(C5CCN(C)CC5)c(C#N)n4)ncc3F)cc21] |

TABLE 1-continued

| Compound No. | Structure |
| --- | --- |
| 846 | 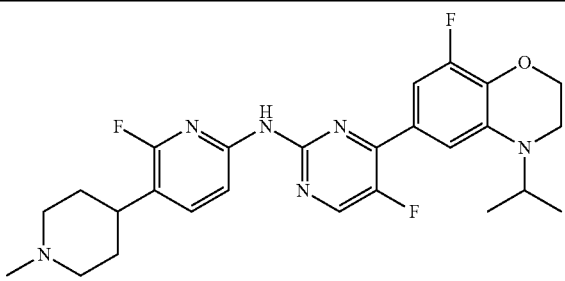 |
| 847 | 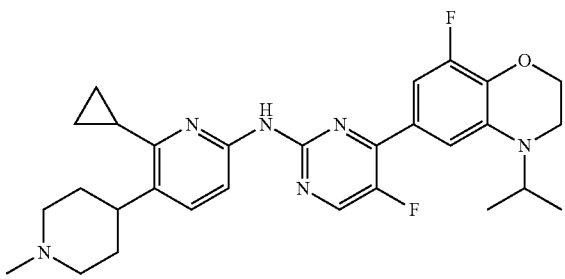 [SMILES: CC(C)N1CCOc2c(F)cc(-c3nc(Nc4ccc(C5CCN(C)CC5)c(C5CC5)n4)ncc3F)cc21] |
| 848 | 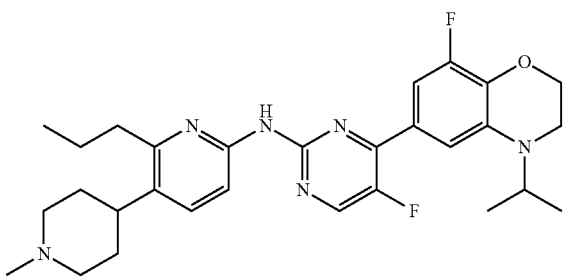 [SMILES: CCCc1nc(Nc2ncc(F)c(-c3cc(F)c4c(c3)N(C(C)C)CCO4)n2)ccc1C1CCN(C)CC1] |

In some embodiments, provided herein are compounds described in Table 1, or a tautomer thereof, or a salt of any of the foregoing, and uses thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible stereoisomers of a compound depicted. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2$H, $^3$H, $^{11}$C, $^{13}$C, $^{14}$C $^{13}$N $^{15}$O, $^{17}$O, $^{32}$P, $^{35}$S, $^{18}$F, $^{36}$Cl. Certain isotope labeled compounds (e.g. $^3$H and $^{14}$C) are useful in compound or substrate tissue distribution studies. Incorporation of heavier isotopes such as deuterium ($^2$H) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of the Formula (I) or (II) may be synthesized according to Scheme 1.

Scheme 1

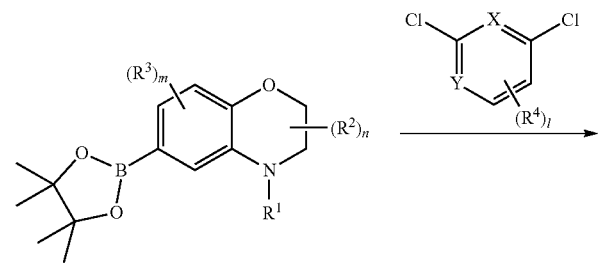

-continued
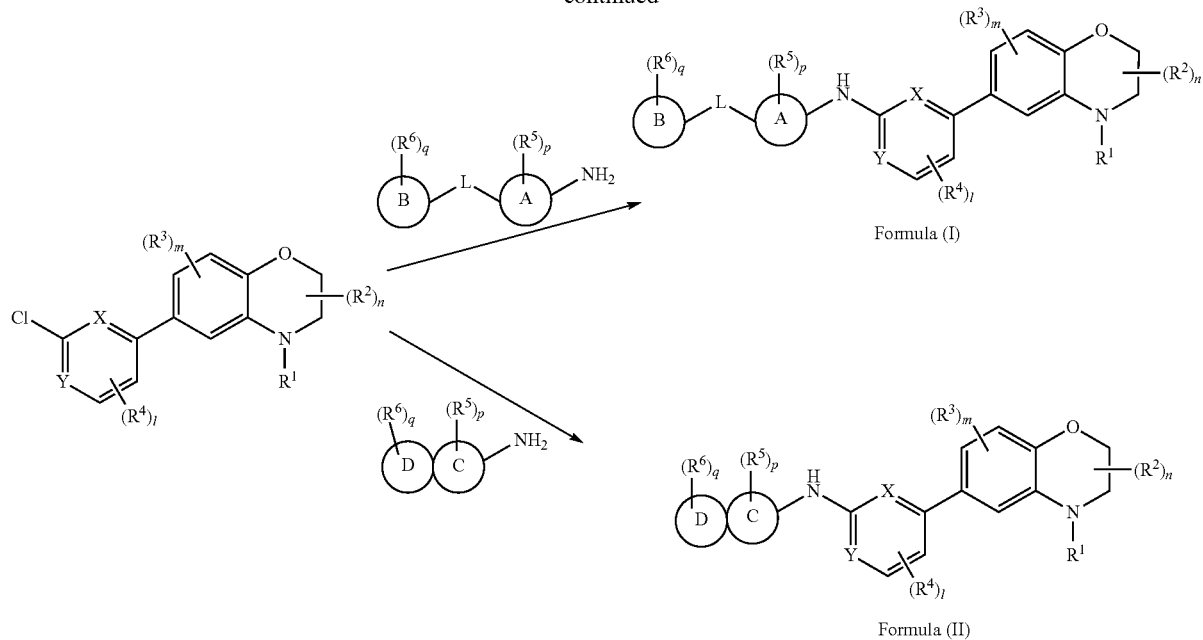
Formula (I)
Formula (II)
wherein A, B, C, D, L, X, Y; $R^1$, $R^2$, $R^3$, $R^4$, $R^5$, $R^6$; l, m, n, p and q are as described for Formula (J), Formula (I), or Formula (II).
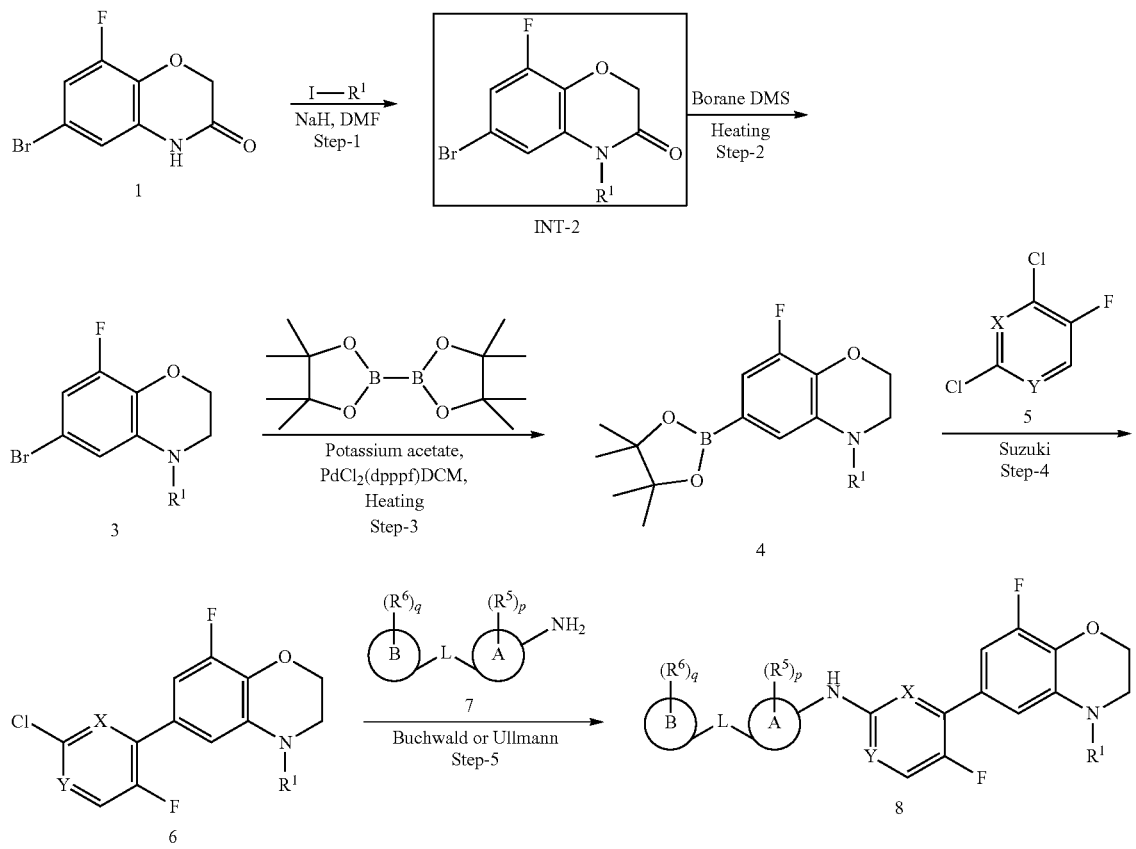

-continued
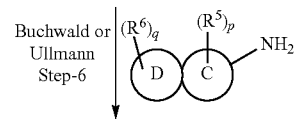
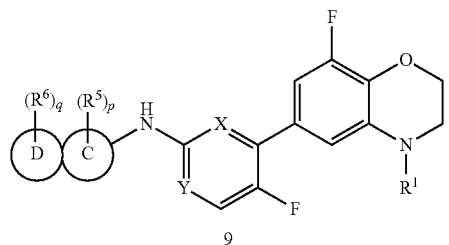
wherein A, B, C, D, L, X, Y; $R^1$, $R^5$, $R^6$; p and q are as described for Formula (J), Formula (I), or Formula (II).
Scheme 3
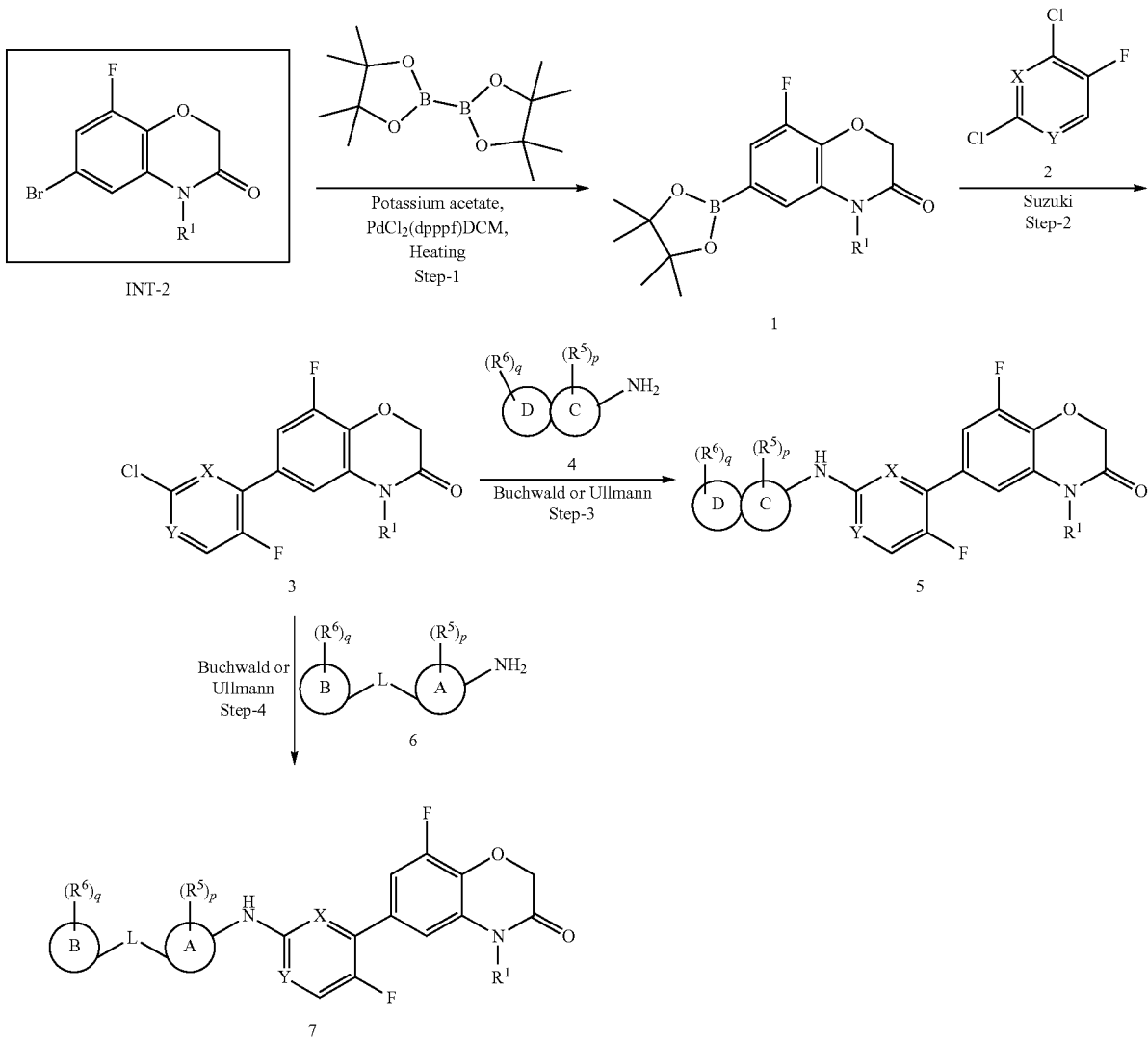

wherein A, B, C, D, L, X, Y; $R^1$, $R^5$, $R^6$; p and q are as described for Formula (J), Formula (I), or Formula (II).
Scheme 4
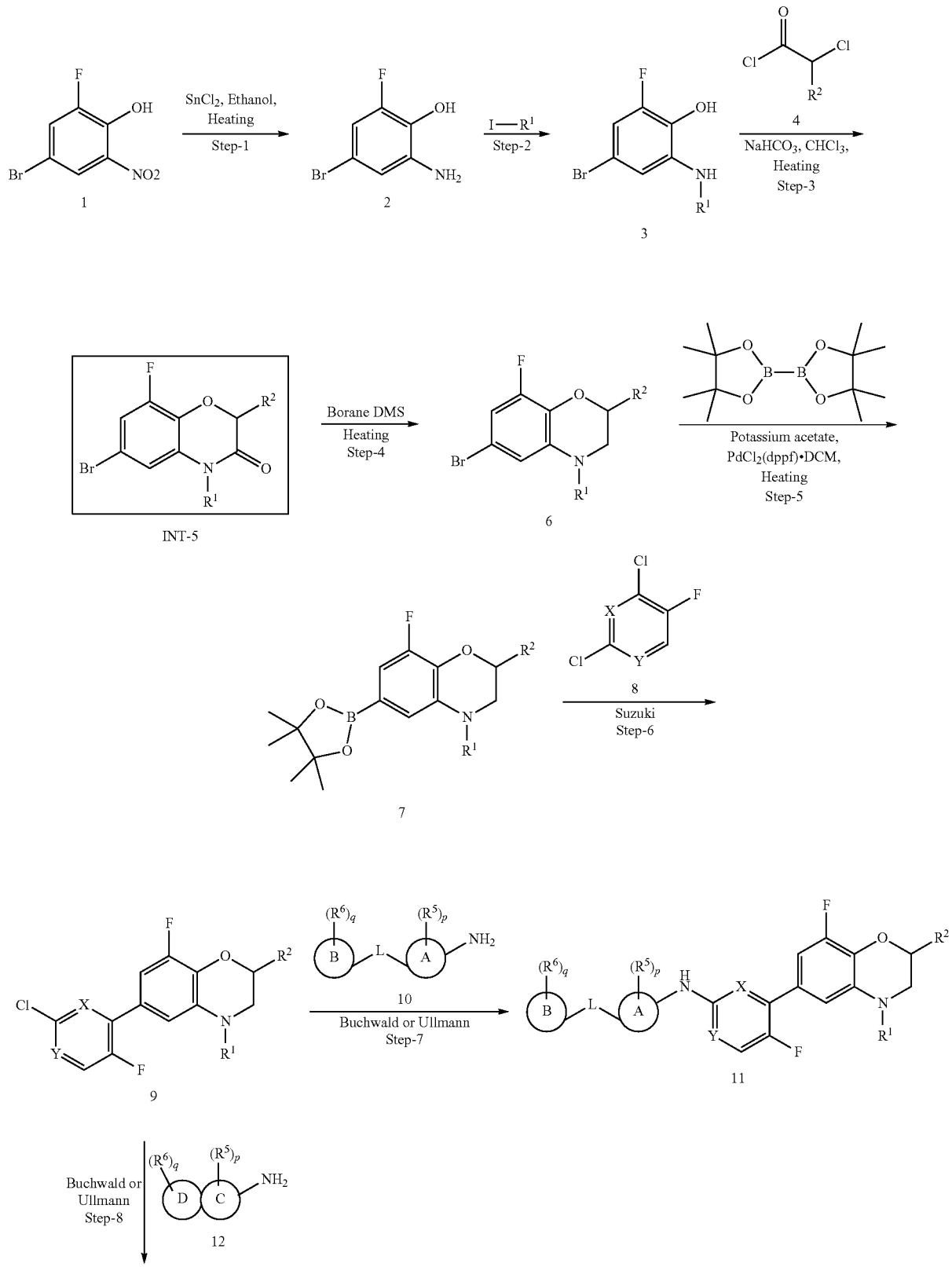

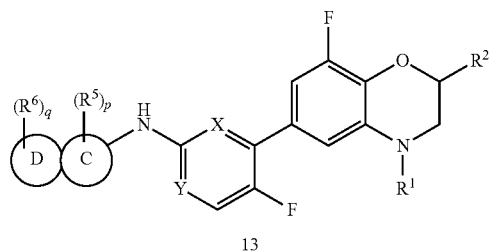
13
wherein A, B, C, D, L, X, Y; $R^1$, $R^2$, $R^5$, $R^6$; p and q are as described for Formula (J), Formula (I), or Formula (II).
Scheme 5
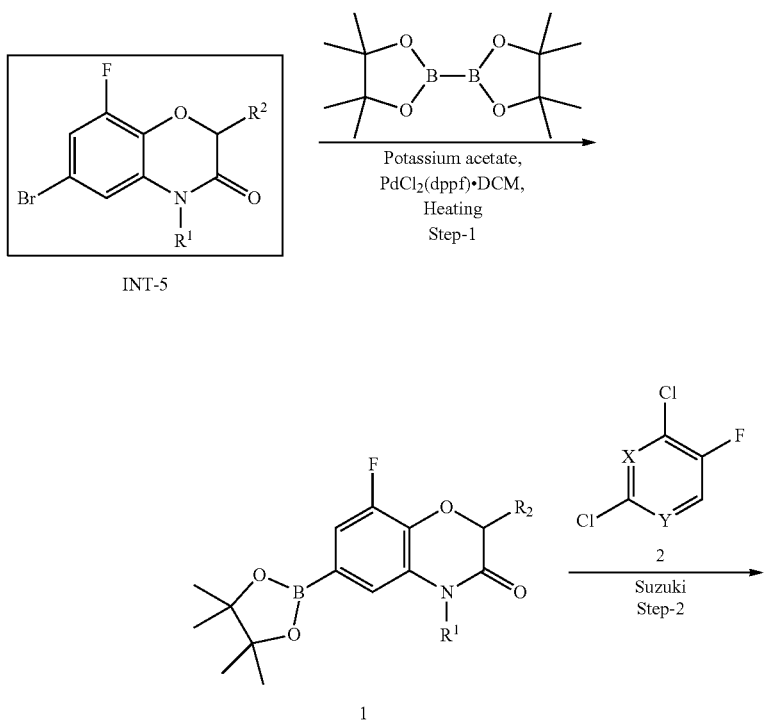
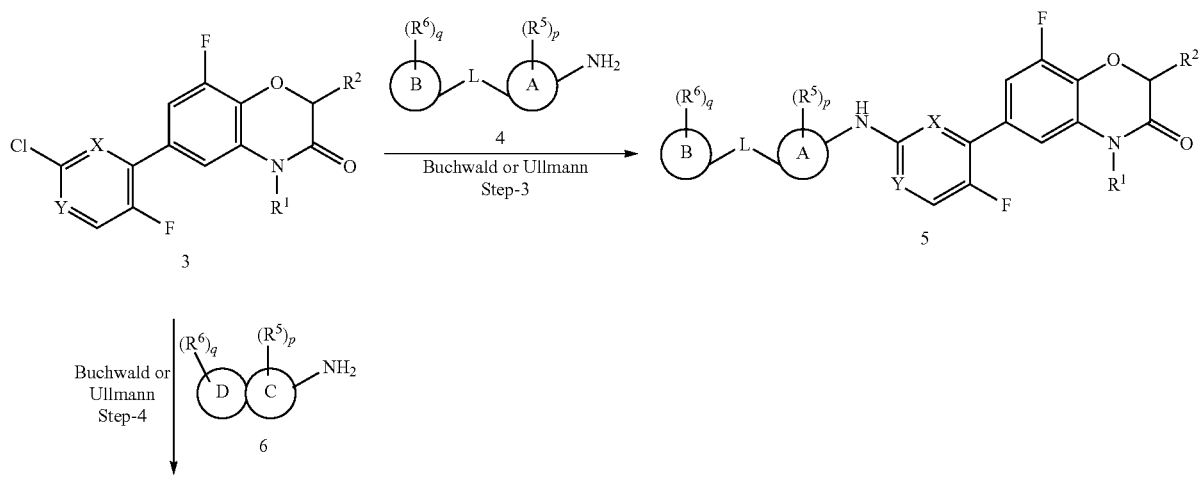

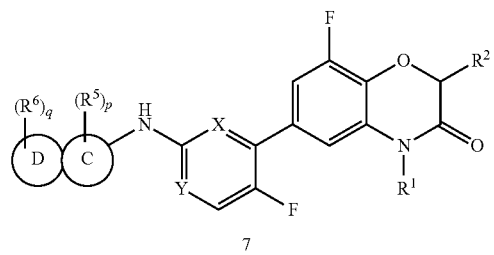
7
wherein A, B, C, D, L, X, Y; R$^1$, R$^2$, R$^5$, R$^6$; p and q are as described for Formula (J), Formula (I), or Formula (II).
Scheme 6
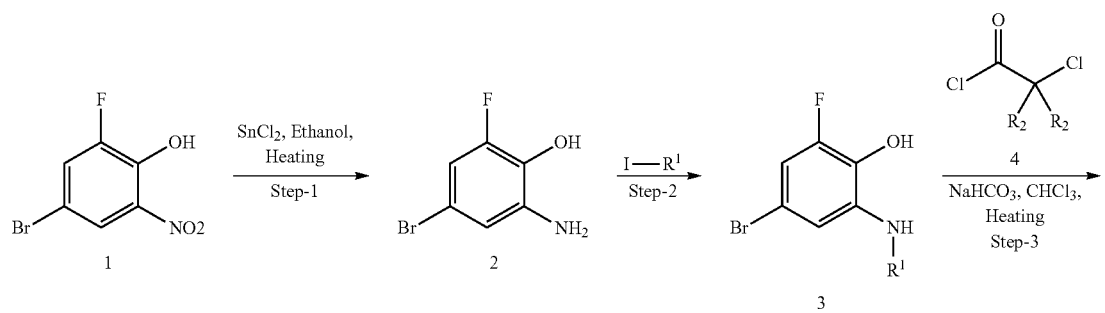

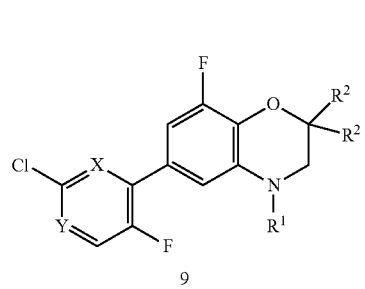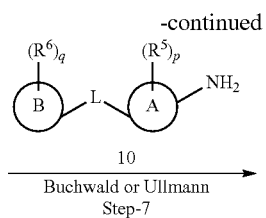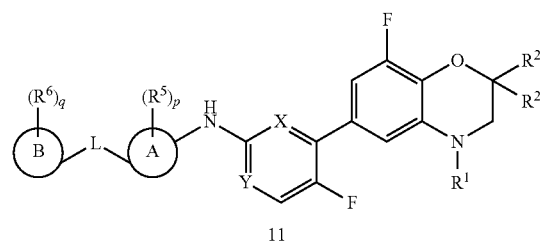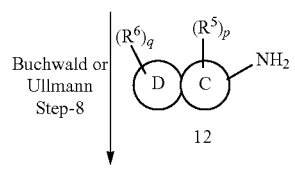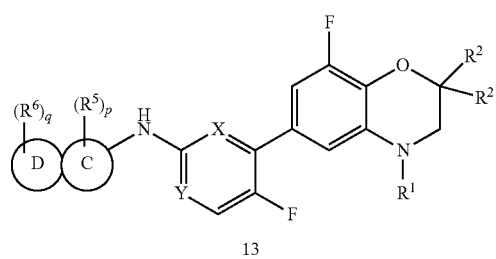
wherein A, B, C, D, L, X, Y; $R^1$, $R^2$, $R^5$, $R^6$; p and q are as described for Formula (J), Formula (I), or Formula (II).
Scheme 7
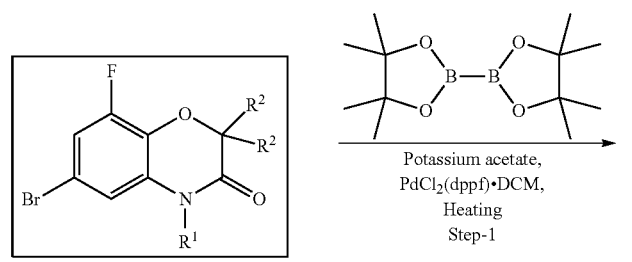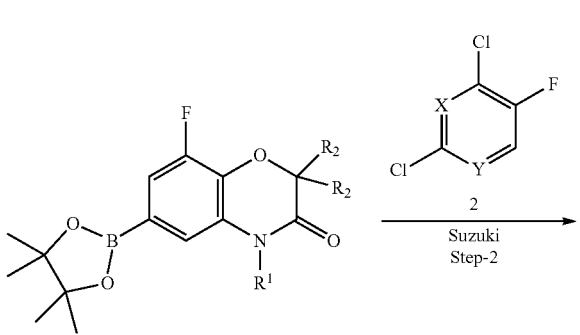

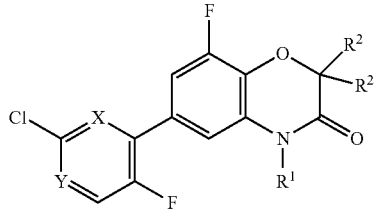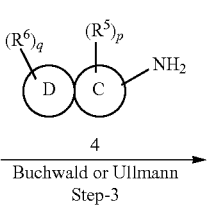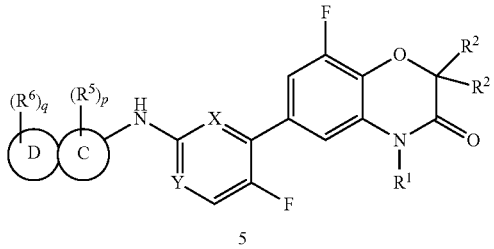

Buchwald or Ullmann Step-3

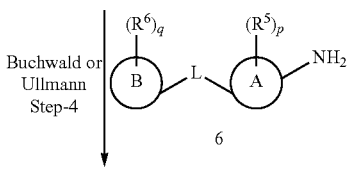

Buchwald or Ullmann Step-4

wherein A, B, C, D, L, X, Y; $R^1$, $R^2$, $R^5$, $R^6$; p and q are as described for Formula (J), Formula (I), or Formula (II). Particular examples are provided in the Example Section below.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays. In some embodiments of the methods detailed herein, the methods comprise administration of a compound detailed herein, or a salt thereof, as a monotherapy.

Provided herein is a method of treating a disease in an individual comprising administering an effective amount of a compound of Formula (J), Formula (I), Formula (II), (I-A), (I-B1) to (I-B12), (I-C1)-(I-C23) or any embodiment, variation or aspect thereof (collectively, a compound of Formula (J), Formula (I), Formula (II), (I-A), (I-B1) to (I-B12), (I-C1)-(I-C23)) or the present compounds or the compounds detailed or described herein) or a pharmaceutically acceptable salt thereof, to the individual. Further provided herein is a method of treating a proliferative disease in an individual, comprising administering an effective amount of the compound of Formula (J), Formula (I), Formula (II), (I-A), (I-B1) to (I-B12), (I-C1)-(I-C23), or a pharmaceutically acceptable salt thereof, to the individual. Also provided herein is a method of treating cancer in an individual comprising administering an effective amount of the compound of Formula (J), Formula (I), Formula (II), (I-A), (I-B1) to (I-B12), (I-C1)-(I-C23) or a pharmaceutically acceptable salt thereof, to the individual. In some embodiments, the compound is administered to the individual according to a dosage and/or method of administration described herein.

In some embodiments, the cancer in the individual has one or more mutations or amplification or overexpression of the genes encoding cyclins or of the genes encoding the CDK or loss of endogenous INK4 inhibitors by gene deletion, mutation, or promoter hypermethylation, or other genetic events leading to overactivity of one or more of CDK1, CDK2, CDK4, CDK6 and CDK9. In some embodiments, the cancer in the individual has one or more mutations or amplification or overexpression of the genes encoding cyclins or of the genes encoding the CDK or loss of endogenous INK4 inhibitors by gene deletion, mutation, or promoter hypermethylation, or other genetic events leading to overactivity of CDK4/6 and one or more of CDK1, CDK2, and CDK9.

In some embodiments, there is provided a method of treating a cancer in an individual, comprising (a) selecting the individual for treatment based on (i) the presence of phosphorylation of the retinoblastoma (Rb) protein in the cancer, or (ii) presence of mutations or amplification or overexpression of CDK4 or CDK6 in the cancer, and administering an effective amount of the compound of Formula (J), Formula (I), Formula (II), (I-A), (I-B1) to (I-B12), (I-C1)-(I-C23), or a pharmaceutically acceptable salt thereof, to the individual. In some embodiments, the cancer is assayed for the expression of phosphorylated Rb. In some embodiments, the cancer is assayed for the expression of CDK4 or CDK6. In some embodiments, the CDK4 or CDK6 gene of the cancer is sequenced to detect the one or more mutations or amplifications. In some embodiments, the CDK4 or CDK6 gene is sequenced by biopsying the cancer and sequencing the CDK4 or CDK6 gene from the biopsied cancer. In some embodiments, the CDK4 or CDK6 gene is sequenced by sequencing circulating-tumor DNA (ctDNA) from the individual.

In some embodiments, provided herein is a method of using a compound of Formula (J), Formula (I), Formula (II), (I-A), (I-B1) to (I-B12), (I-C1)-(I-C23) or any embodiment in the manufacture of a medicament for treatment of a disease. In some embodiments, provided herein is a method of using a compound of Formula (J), Formula (I), Formula (II), (I-A), (I-B1) to (I-B12), (I-C1)-(I-C23) or any embodiment in the manufacture of a medicament for treatment of cancer.

In some embodiments, a compound of Formula (J), Formula (I), Formula (II), (I-A), (I-B1) to (I-B12), (I-C1)-(I-C23) or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma, cutaneous T cell lymphoma, Hodgkin's lymphoma, non-Hodgkin's lymphoma, cancer of the adrenal cortex, ACTH-producing tumors, lung cancer, including small cell carcinoma and nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the cancer is defined by a molecular characteristic. In some embodiments, the cancer is an estrogen receptor-positive breast cancer. In some embodiments, the breast cancer is triple negative breast cancer. In some embodiments, the cancer is a KRAS-mutant non-small cell lung cancer. In some embodiments, the cancer is mantle cell lymphoma defined by a translocation involving CCND1 resulting in cyclin D1 overexpression.

In some embodiments, the compounds and compositions described herein cause $G_1$-S cell cycle arrest in a cell (such as a cancer cell). In some embodiments, the cancer cell is a cancer cell from any of the cancer types described herein. In some embodiments, arrested cells enter a state of apoptosis. In some embodiments, arrested cells enter a state of senescence. In some embodiments, provided herein is a method of causing $G_1$-S checkpoint arrest in a cell comprising administering an effective amount of the compound of Formula (J), Formula (I), Formula (II), (I-A), (I-B1) to (I-B12), (I-C1)-(I-C23) or a pharmaceutically acceptable salt thereof, to the cell. In some embodiments, the $G_1$-S cell cycle arrest occurs in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, the $G_1$-S cell cycle arrest occurs in up to about 99%, up to about 98%, up to about 97%, up to about 96%, up to about 95%, up to about 90%, up to about 85%, or up to about 80% of cells in the cell population.

In some embodiments, provided herein is a method of inducing senescence in a cell comprising administering an effective amount of the compound of Formula (J), Formula (I), Formula (II), (I-A), (I-B1) to (I-B12), (I-C1)-(I-C23) or a pharmaceutically acceptable salt thereof, to the cell. In some embodiments, senescence is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, senescence is induced in up to about 99%, up to about 98%, up to about 97%, up to about 96%, up to about 95%, up to about 90%, up to about 85%, or up to about 80% of cells in the cell population.

In some embodiments, provided herein is a method of inducing apoptosis in a cell comprising administering an effective amount of the compound of Formula (J), Formula (I), Formula (II), (I-A), (I-B1) to (I-B12), (I-C1)-(I-C23)) or a pharmaceutically acceptable salt thereof, to the cell. In some embodiments, apoptosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, apoptosis is induced in up to about 99%, up to about 98%, up to about 97%, up to about 96%, up to about 95%, up to about 90%, up to about 85%, or up to about 80% of cells in the cell population.

In some embodiments, provided herein is a method of inhibiting CDK4 or CDK6 in a cell comprising administering an effective amount of the compound of Formula (J), Formula (I), Formula (II), (I-A), (I-B1) to (I-B12), (I-C1)-(I-C23) or a pharmaceutically acceptable salt thereof, to the cell. In some embodiments, CDK4 or CDK6 is inhibited by about 10% or more, about 20% or more, about 30% or more, about 40% or more, about 50% or more, about 60% or more, about 70% or more, about 75% or more, about 80% or more, about 90% or more, about 95% or more, about 96% or more, about 97% or more, about 98% or more, or about 99% or more. In some embodiments, CDK4 or CDK6 is inhibited up to about 99%, up to about 98%, up to about 97%, up to about 96%, up to about 95%, up to about 90%, up to about 85%, up to about 80%, up to about 70%, or up to about 60%. In some embodiments, the activity of CDK4 or CDK6 is measured according to a kinase assay.

In some embodiments, provided herein is a method of inhibiting one or more of CDK1, CDK2, CDK4, CDK6, and CDK9 in a cell comprising administering an effective amount of the compound of Formula (J), Formula (I), Formula (II), (I-A), (I-B1) to (I-B12), (I-C1)-(I-C23) or a pharmaceutically acceptable salt thereof, to the cell. In some embodiments, one or more of CDK1, CDK2, CDK4, CDK6, and CDK9 is inhibited by about 10% or more, about 20% or more, about 30% or more, about 40% or more, about 50% or more, about 60% or more, about 70% or more, about 75% or more, about 80% or more, about 90% or more, about 95% or more, about 96% or more, about 97% or more, about 98% or more, or about 99% or more. In some embodiments, one or more of CDK1, CDK2, CDK4, CDK6, and CDK9 is inhibited up to about 99%, up to about 98%, up to about 97%, up to about 96%, up to about 95%, up to about 90%, up to about 85%, up to about 80%, up to about 70%, or up to about 60%. In some embodiments, the activity of one or more of CDK1, CDK2, CDK4, CDK6, and CDK9 is measured according to a kinase assay.

In some embodiments, provided herein is a method of inhibiting CDK4 or CDK6 comprising contacting CDK4 or CDK6 with an effective amount of the compound of Formula (J), Formula (I), Formula (II), (I-A), (I-B1) to (I-B12), (I-C1)-(I-C23) or a pharmaceutically acceptable salt thereof. In some embodiments, the compound of Formula (J), Formula (I), Formula (II), (I-A), (I-B1) to (I-B12), (I-C1)-(I-C23) or a pharmaceutically acceptable salt thereof binds to CDK4 or CDK6 with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 50 nM, less than 10 nM, less than 5 nM, less than 1 nM, or less than 0.5 nM. In some embodiments, the compound of Formula (J), Formula (I), Formula (II), (I-A), (I-B1) to (I-B12), (I-C1)-(I-C23) or a pharmaceutically acceptable salt thereof binds to CDK4 or CDK6 with an $IC_{50}$ between 0.1 nM and 1 nM, between 1 nM and 5 nM, between 5 nM and 10 nM, between 10 nM and 50 nM, between 50 nM and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, or between 900 nM and 1 µM. In some embodiments, the IC$_{50}$ is measured according to a kinase assay. In some embodiments, the IC$_{50}$ is measured according to a cell proliferation assay.

In some embodiments, provided herein is a method of inhibiting one or more of CDK1, CDK2, CDK4, CDK6, and CDK9 comprising contacting one or more of CDK1, CDK2, CDK4, CDK6, and CDK9 with an effective amount of the compound of Formula (J), Formula (I), Formula (II), (I-A), (I-B1) to (I-B12), (I-C1)-(I-C23) or a pharmaceutically acceptable salt thereof. In some embodiments, the compound of Formula (J), Formula (I), Formula (II), (I-A), (I-B1) to (I-B12), (I-C1)-(I-C23) or a pharmaceutically acceptable salt thereof binds to one or more of CDK1, CDK2, CDK4, CDK6, and CDK9 with an IC$_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 50 nM, less than 10 nM, less than 5 nM, less than 1 nM, or less than 0.5 nM. In some embodiments, the compound of Formula (J), Formula (I), Formula (II), (I-A), (I-B1) to (I-B12), (I-C1)-(I-C23) or a pharmaceutically acceptable salt thereof binds to one or more of CDK1, CDK2, CDK4, CDK6, and CDK9 with an IC$_{50}$ between 0.1 nM and 1 nM, between 1 nM and 5 nM, between 5 nM and 10 nM, between 10 nM and 50 nM, between 50 nM and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, or between 900 nM and 1 µM. In some embodiments, the IC$_{50}$ is measured according to a kinase assay. In some embodiments, the IC$_{50}$ is measured according to a cell proliferation assay.

In some embodiments, provided herein is a method of modulating CDK4/6 in an individual, comprising administering to the individual a compound of Formula (J), Formula (I), Formula (II), (I-A), (I-B1) to (I-B12), (I-C1)-(I-C23) or a pharmaceutically acceptable salt thereof, or a salt thereof. In some embodiments, provided herein is a method of modulating CDK4 and CDK 6 in an individual, comprising administering to the individual a compound of Formula (J), Formula (I), Formula (II), (I-A), (I-B1) to (I-B12), (I-C1)-(I-C23) or a pharmaceutically acceptable salt thereof, or a salt thereof. In some embodiments, provided herein is a method of modulating CDK4/6 and one or more of CDK1, CDK2, and CDK9 in an individual, comprising administering to the individual a compound detailed herein, or a salt thereof. In some embodiments, provided herein is a method of modulating CDK4 and CDK 6 and one or more of CDK1, CDK2, and CDK9 in an individual, comprising administering to the individual a compound detailed herein, or a salt thereof. In some embodiments, the compound of Formula (J), Formula (I), Formula (II), (I-A), (I-B1) to (I-B12), (I-C1)-(I-C23) or a pharmaceutically acceptable salt thereof binds to one or more of CDK4/6 with an IC$_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 50 nM, less than 10 nM, less than 5 nM, less than 1 nM, or less than 0.5 nM. In some embodiments, the compound of Formula (J), Formula (I), Formula (II), (I-A), (I-B1) to (I-B12), (I-C1)-(I-C23) or a pharmaceutically acceptable salt thereof binds to one or more of CDK4 and CDK6 with an IC$_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 50 nM, less than 10 nM, less than 5 nM, less than 1 nM, or less than 0.5 nM. In some embodiments, the compound of Formula (J), Formula (I), Formula (II), (I-A), (I-B1) to (I-B12), (I-C1)-(I-C23) or a pharmaceutically acceptable salt thereof binds to one or more of CDK1, CDK2, CDK4, CDK6, and CDK9 with an IC$_{50}$ between 0.1 nM and 1 nM, between 1 nM and 5 nM, between 5 nM and 10 nM, between 10 nM and 50 nM, between 50 nM and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, or between 900 nM and 1 µM. In some embodiments, the IC$_{50}$ is measured according to a kinase assay. In some embodiments, the IC$_{50}$ is measured according to a cell proliferation assay.

In one embodiment, the compound or a salt thereof may enhance the antitumour immunity by increasing the functional capacity of tumour cells to present antigen or by reducing the immunosuppressive T$_{Reg}$ population by suppressing their proliferation.

In some embodiments, provided herein is a method of inhibiting the proliferation of a cell, comprising contacting the cell with an effective amount of the compound of Formula (J), Formula (I), Formula (II), (I-A), (I-B1) to (I-B12), (I-C1)-(I-C23) or a pharmaceutically acceptable salt thereof. In some embodiments, the compound of Formula (J), Formula (I), Formula (II), (IA-), (I-B1) to (I-B12), (I-C1)-(I-C23) or a pharmaceutically acceptable salt thereof is effective in inhibiting the proliferation of the cell with an EC$_{50}$ of less than 5 µM, less than 2 µM, less than 1 µM, less than 900 nM, less than 800 nM, less than 700 nM, less than 600 nM, less than 500 nM, less than 400 nM, less than 300 nM, less than 200 nM, less than 100 nM, or less than 50 nM. In some embodiments, the compound of Formula (J), Formula (I), Formula (II), (I-A), (I-B1) to (I-B12), (I-C1)-(I-C23) or a pharmaceutically acceptable salt is effective in inhibiting the proliferation of the cell with an EC$_{50}$ between 10 nM and 20 nM, between 20 nM and 50 nM, between 50 nM and 100 nM, between 100 nM and 500 nM, between 500 nM and 1 µM, between 1 µM and 2 µM, or between 2 µM and 5 µM. In some embodiments, the EC$_{50}$ is measured according to a cell proliferation assay.

Combination Therapy

As provided herein, the presently disclosed compounds or a salt thereof may affect the immune system. Accordingly, the present compounds or a salt thereof may be used in combination with other anti-cancer agents or immunotherapies. In some embodiments, provided herein is a method of treating a disease in an individual comprising administering an effective amount of a compound of Formula (J), Formula (I), Formula (II), (I-A), (I-B1) to (I-B12), (I-C1)-(I-C23), or any embodiment, variation or aspect thereof (collectively, a compound of Formula (J), Formula (I), Formula (II), (I-A), (I-B1) to (I-B12), (I-C1)-(I-C23) or the present compounds or the compounds detailed or described herein) or a pharmaceutically acceptable salt thereof, and an additional therapeutic agent to the individual. In some embodiments, the second therapeutic agent is a cancer immunotherapy agent or an endocrine therapy agent or a chemotherapeutic agent. In some embodiments, the disease is a proliferative disease such as cancer.

In some embodiments, the additional therapeutic agent is a cancer immunotherapy agent. In some embodiments, the additional therapeutic agent is an immunostimulatory agent. In some embodiments, the additional therapeutic agent targets a checkpoint protein (for example an immune checkpoint inhibitor). In some embodiments, the additional therapeutic agent is effective to stimulate, enhance or improve an immune response against a tumor.

In another aspect provided herein is a combination therapy for the treatment of a disease, such as cancer. In some embodiments, there is provide a method of treating a disease in an individual comprising administering an effective amount of Formula (J), Formula (I), Formula (II), (I-A), (I-B1) to (I-B12), (I-C1)-(I-C23), or any embodiment, variation or aspect thereof (collectively, a compound of Formula (J), Formula (I), Formula (II), (IA-), (I-B1) to (I-B12), (I-C1)-(I-C23), or the present compounds or the compounds detailed or described herein) or a pharmaceutically acceptable salt thereof, in combination with a radiation therapy.

In some embodiments, there is provide a method of treating a disease in an individual comprising (a) administering an effective amount of Formula (J), Formula (I), Formula (II), (I-A), (I-B1) to (I-B12), (I-C1)-(I-C23) or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of an endocrine therapy agent. In some embodiments, the endocrine therapy is antiestrogen therapy. In some embodiments, the endocrine therapy is a selective estrogen receptor degrader (SERD, such as fulvestrant). In some embodiments, the endocrine therapy is an aromatase inhibitor (such as letrozole). In some embodiments, the combination of a CDK4/6 inhibitor and endocrine therapy causes enhancement of G1-S cell-cycle arrest. In some embodiments, the combination of a CDK4/6 inhibitor and endocrine therapy causes enhanced entry into a senescent state. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the endocrine therapy agent. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the endocrine therapy agent.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (IA-), (I-B1) to (I-B12), (I-C1)-(I-C23)) or a pharmaceutically acceptable salt thereof, and (b) administering an effective amount of a second chemotherapeutic agent. In some embodiments, the chemotherapeutic agent is another kinase inhibitor. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the second chemotherapeutic agent. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the second chemotherapeutic agent.

Examples of chemotherapeutic agents that can be used in combination with Formula (J), Formula (I), Formula (II), (I-A), (I-B1) to (I-B12), (I-C1)-(I-C23) or a pharmaceutically acceptable salt thereof include DNA-targeted agents, a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or teniposide)), an anthracycline (such as daunorubicin, doxorubicin, epirubicin, idarubicin, mitoxantrone, or valrubicin), a histone deacetylase inhibitor (such as vorinostat or romidepsin), a bromodomain inhibitor, other epigenetic inhibitors, a taxane (such as paclitaxel or docetaxel), a kinase inhibitor (such as bortezomib, erlotinib, gefitinib, imatinib, vemurafenib, vismodegib, ibrutinib), an anti-angiogenic inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof. In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a kinase inhibitor (such as bortezomib, erlotinib, gefitinib, imatinib, vemurafenib, vismodegib, or ibrutinib). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the kinase inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a DNA damaging agent. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the DNA damaging agent. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, there is provide a method of treating a disease in an individual comprising (a) administering an effective amount of Formula (J), Formula (I), Formula (II), (I-A), (I-B1) to (I-B12), (I-C1)-(I-C23)), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the DNA alkylating agent. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the topoisomerase inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the anthracycline. In some embodiments, Formula (J), Formula (I), Formula (II), (IA-), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a histone deacetylase inhibitor (such as vorinostat or romidepsin). In some embodiments, Formula I or a pharmaceutically acceptable salt thereof is administered prior to, after, or simultaneously co-administered with the histone deacetylase inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a taxane (such as paclitaxel or docetaxel). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the taxane. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the nucleotide analog or precursor analog. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a platinum-based chemotherapeutic agent (such as cisplatin, carboplatin, or oxaliplatin). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the platinum-based chemotherapeutic agent. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of pemetrexed. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the pemetrexed. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a Bruton's tyrosine kinase (BTK) inhibitor. In some embodiments, Formula (J), Formula (I), Formula (II), (IA-), (I-B1) to (I-B12), (I-C1)-(I-C23) or a pharmaceutically acceptable salt thereof is administered prior to, after, or simultaneously co-administered with the BTK inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the BTK inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a PI3K or Akt inhibitor. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the PI3K or Akt inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the PI3K or Akt inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23)), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a DNA damage repair (DDR) pathway inhibitor. In some embodiments, Formula (J), Formula (I), Formula (II), (IA-), (I-B1) to (I-B12), (I-C1)-(I-C23) or a pharmaceutically acceptable salt thereof is administered prior to, after, or simultaneously co-administered with the DDR pathway inhibitor. In some embodiments, Formula (J), Formula (I), Formula (II), (IA-), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly (ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a PARP inhibitor (such as olaparib, rucaparib, niraparib, or talazoparib). In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the PARP inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23)), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of an ATM protein inhibitor. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the ATM protein inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of an ATR protein inhibitor. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the ATR protein inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of an Chk1 inhibitor. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the Chk1 inhibitor. In some embodiments, Formula (J), Formula (I), Formula (II), (I-A), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In some embodiments, there is provide a method of treating a disease in an individual comprising (a) administering an effective amount of Formula (J), Formula (I), Formula (II), (I-A), (I-B1) to (I-B12), (I-C1)-(I-C23)), or any embodiment, variation or aspect thereof (collectively, Formula (J), Formula (I), Formula (II), (I-A), (I-B1) to (I-B12), (I-C1)-(I-C23)) or a pharmaceutically acceptable salt thereof, and (b) administering an effective amount of a further CDK4/6 inhibitor. In some embodiments, Formula (J), Formula (I), Formula (II), (I-A), (I-B1) to (I-B12), (I-C1)-(I-C23) or a pharmaceutically acceptable salt thereof is administered prior to, after, or simultaneously co-administered with the further CDK4/6 inhibitor. In some embodiments, Formula (J), Formula (I), Formula (II), (IA-), (I-B1) to (I-B12), (I-C1)-(I-C23) or a pharmaceutically acceptable salt thereof is administered 1 or more hours (such as 2 or more hours, 4 or more hours, 8 or more hours, 12 or more hours, 24 or more hours, or 48 or more hours) prior to or after the further CDK4/6 inhibitor.

In another aspect, provided herein is a combination therapy in which a compound of Formula (J), Formula (I), Formula (II), (I-A), (I-B1) to (I-B12), (I-C1)-(I-C23), or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (J), Formula (I), Formula (II), (I-A), (I-B1) to (I-B12), (I-C1)-(I-C23), or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (J), Formula (I), Formula (II), (I-A), (I-B1) to (I-B12), (I-C1)-(I-C23) or a salt thereof and an anti-PD-1 antibody. In another embodiment, the subject is administered a compound of Formula (J), Formula (I), Formula (II), (I-A), (I-B1) to (I-B12), (I-C1)-(I-C23), or a salt thereof and an anti-PD-L1 antibody. In yet another embodiment, the subject is administered a compound of Formula (J), Formula (I), Formula (II), (I-A), (I-B1) to (I-B12), (I-C1)-(I-C23) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a proliferative disease (e.g., cancer), comprising administering a compound of Formula (J), Formula (I), Formula (II), (I-A), (I-B1) to (I-B12), (I-C1)-(I-C23), or a salt thereof and an anti-PD-1 antibody to a subject. In further embodiments, a compound of Formula (J), Formula (I), Formula (II), (I-A), (I-B1) to (I-B12), (I-C1)-(I-C23) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (J), Formula (I), Formula (II), (I-A), (I-B1) to (I-B12), (I-C1)-(I-C23), or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present invention provides a method for treating a hyperproliferative disease (e.g., cancer), comprising administering a compound of Formula (J), Formula (I), Formula (II), (I-A), (I-B1) to (I-B12), (I-C1)-(I-C23), or a salt thereof and an anti-PD-L1 antibody to a subject. In further embodiments, a compound of Formula (J), Formula (I), Formula (II), (I-A), (I-B1) to (I-B12), (I-C1)-(I-C23) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (J), Formula (I), Formula (II), (I-A), (I-B1) to (I-B12), (I-C1)-(I-C23), or a salt thereof and a subtherapeutic dose of anti-PD-L antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (J), Formula (I), Formula (II), (I-A), (I-B1) to (I-B12), (I-C1)-(I-C23), or a salt thereof can be administered sequentially, such as anti-CTLA-4 antibody being administered first and a compound of Formula (J), Formula (I), Formula (II), (I-A), (I-B1) to (I-B12), (I-C1)-(I-C23), or a salt thereof second, or a compound of Formula (J), Formula (I), Formula (II), (I-A), (I-B1) to (I-B12), (I-C1)-(I-C23), or a salt thereof being administered first and anti-CTLA-4 antibody second. Additionally or alternatively, an anti-PD-1 antibody and a compound of Formula (J), Formula (I), Formula (II), (I-A), (I-B1) to (I-B12), (I-C1)-(I-C23), or a salt thereof can be administered sequentially, such as anti-PD-1 antibody being administered first and a compound of Formula (J), Formula (I), Formula (II), (I-A), (I-B1) to (I-B12), (I-C1)-(I-C23), or a salt thereof second, or a compound of Formula (J), Formula (I), Formula (II), (I-A), (I-B1) to (I-B12), (I-C1)-(I-C23), or a salt thereof being administered first and anti-PD-1 antibody second. Additionally or alternatively, an anti-PD-L1 antibody and a compound of Formula (J), Formula (I), Formula (II), (I-A), (I-B1) to (I-B12), (I-C1)-(I-C23), or a salt thereof can be administered sequentially, such as anti-PD-L1 antibody being administered first and a compound of Formula (J), Formula (I), Formula (II), (I-A), (I-B1) to (I-B12), (I-C1)-(I-C23), or a salt thereof second, or a compound of Formula (J), Formula (I), Formula (II), (I-A), (I-B1) to (I-B12), (I-C1)-(I-C23), or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of Formula (J), Formula (I), Formula (II), (I-A), (I-B1) to (I-B12), (I-C1)-(I-C23), or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of Formula (J), Formula (I), Formula (II), (I-A), (I-B1) to (I-B12), (I-C1)-(I-C23), or a salt thereof can also be further combined with standard cancer treatments. For example, a compound of Formula (J), Formula (I), Formula (II), (I-A), (I-B1) to (I-B12), (I-C1)-(I-C23), or a salt thereof can be effectively combined with chemotherapeutic regimens. In these instances, it is possible to reduce the dose of other chemotherapeutic reagent administered with the combination of the instant disclosure. Other combination therapies with a compound of Formula (J), Formula (I), Formula (II), (I-A), (I-B1) to (I-B12), (I-C1)-(I-C23)), or a salt thereof include radiation, surgery, or hormone deprivation. Angiogenesis inhibitors can also be combined with a compound of Formula (J), Formula (I), Formula (II), (I-A), (I-B1) to (I-B12), (I-C1)-(I-C23), or a salt thereof. Inhibition of angiogenesis leads to tumor cell death, which can be a source of tumor antigen fed into host antigen presentation pathways.

In another example, a compound of Formula (J), Formula (I), Formula (II), (I-A), (I-B1) to (I-B12), (I-C1)-(I-C23)), or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (J), Formula (I), Formula (II), (I-A), (I-B1) to (I-B12), (I-C1)-(I-C23), or a salt thereof. In an exemplary embodiment, a treatment of a hyperproliferative disease (e.g., a cancer tumor) can include an anti-cancer antibody in combination with a compound of Formula (J), Formula (I), Formula (II), (I-A), (I-B1) to (I-B12), (I-C1)-(I-C23) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (J), Formula (I), Formula (II), (I-A), (I-B1) to (I-B12), (I-C1)-(I-C23) or a salt thereof.

In some embodiments, a compound of Formula (J), Formula (I), Formula (II), (I-A), (I-B1) to (I-B12), (I-C1)-(I-C23), or a salt thereof can be combined with an anti-CD73 therapy, such as an anti-CD73 antibody.

In yet further embodiments, the compound of Formula (J), Formula (I), Formula (II), (I-A), (I-B1) to (I-B12), (I-C1)-(I-C23), or a salt thereof is administered in combination with another CDK4 or CDK6 inhibitor or other CDK inhibitor.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Example-1: Synthesis of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (Compound 1)

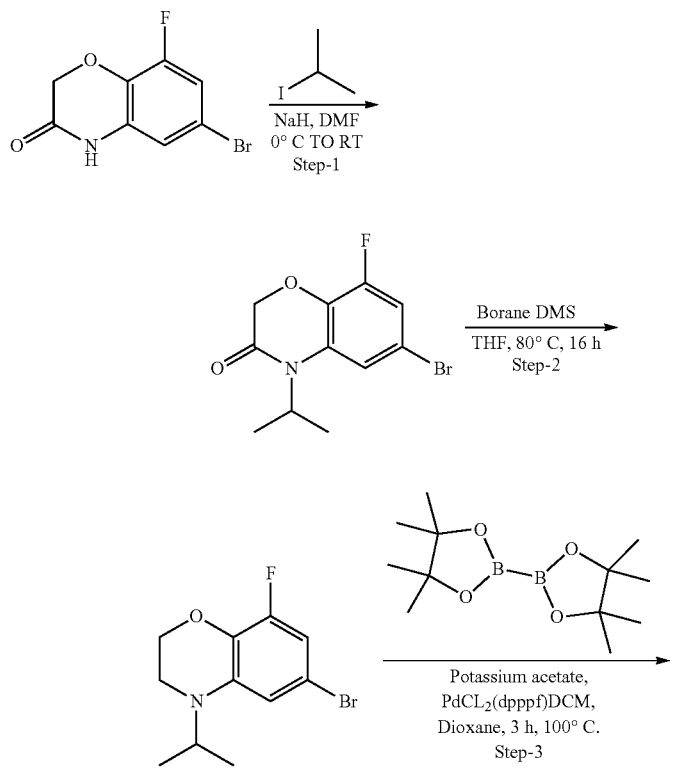

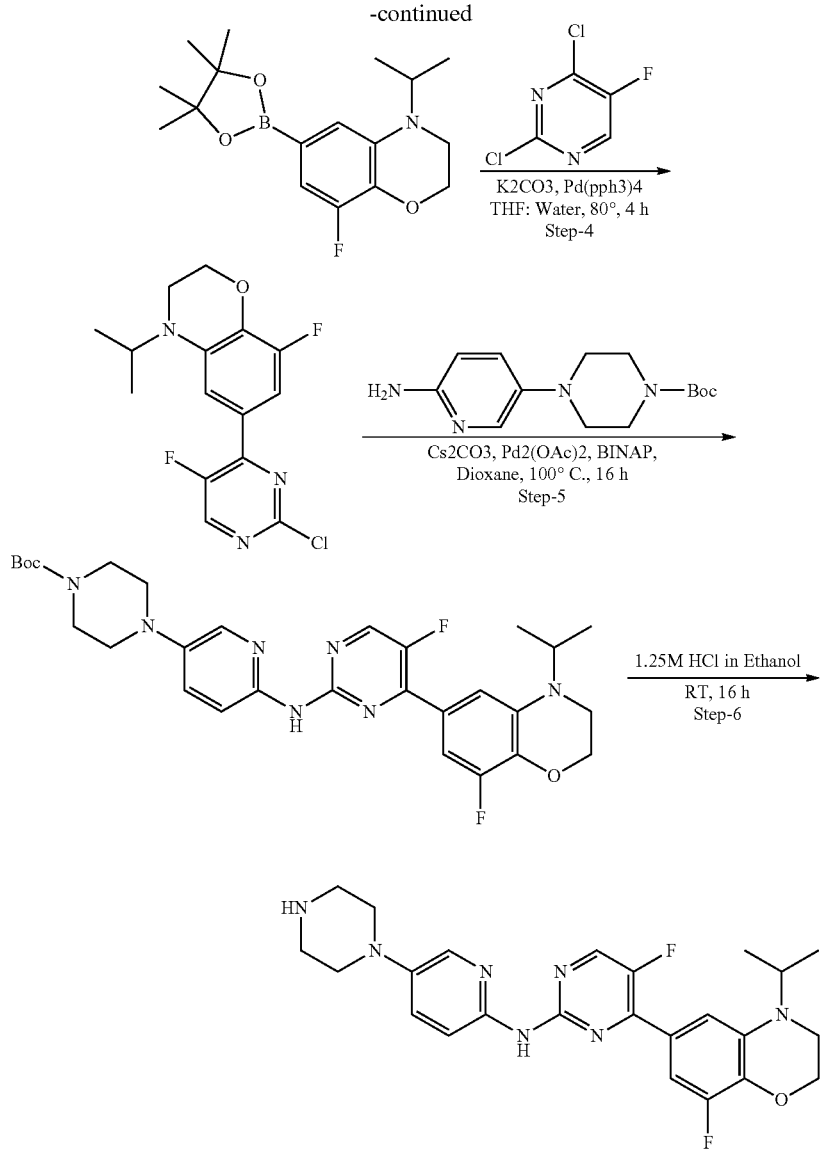

Step-1: Synthesis of 6-bromo-8-fluoro-4-isopropyl-2H-benzo[b][1,4]oxazin-3(4H)-one To a stirred solution of 6-bromo-8-fluoro-2H-benzo[b][1,4]oxazin-3 (4H)-one (7000 mg, 28.56 mmol, 1 equiv) in DMF (70 mL), was added NaH (60%) (2282 mg, 57.12 mmol, 2 equiv) at 0° C. and stirred for 30 min at RT, followed by the addition of 2-iodopropane (5.6 mL, 57.12 mmol, 2 equiv). The reaction mixture was heated to 80° C. for 3 h. Progress of the reaction was monitored by TLC and LCMS. After completion of the reaction, the reaction mixture cooled to RT and quenched with ice-cold water (100 mL) and extracted with EtOAc (150 mL×3). Organic layer was washed with water (150 mL) and brine solution (150 mL). Organic layer was dried over anhydrous $Na_2SO_4$ and concentrated under reduced pressure to obtain crude compound, which was purified by normal phase combi-flash to obtain 6-bromo-8-fluoro-4-isopropyl-2H-benzo[b][1,4]oxazin-3(4H)-one (2400 mg, 29%) as off white solid compound.
LCMS 288 [M+H]+

Step-2: Synthesis of 6-bromo-8-fluoro-4-isopropyl-3,4-dihydro-2H-benzo[b][1,4]oxazine To a stirred solution of 6-bromo-8-fluoro-4-isopropyl-2H-benzo[b][1,4]oxazin-3(4H)-one (1400 mg, 4.87 mmol, 1 equiv) in THF (14 mL), was added $BH_3$.DMS (9.7 mL, 7.66 mmol, 4 equiv) drop wise at 0° C. The reaction mixture was heated to 80° C. for 16 h. Progress of the reaction was monitored by TLC and LCMS. After completion of the reaction, the reaction mixture was quenched with saturated solution of $NaHCO_3$ (100 mL) and extracted with EtOAc (100 mL×3). The combined organic layer was washed with water (100 mL) and brine solution (100 mL). Organic layer was dried over anhydrous $Na_2SO_4$ and concentrated under reduced pressure to obtain 6-bromo-8-fluoro-4-isopropyl-3,4-dihydro-2H-benzo[b][1,4]oxazine (1200 mg, 90%) as a yellow viscous compound.
LCMS 274 [M+H]+

Step-3: Synthesis of 8-fluoro-4-isopropyl-6-(4,4,5,5-tetramethyl-1,3,2-dioxaborolan-2-yl)-3,4-dihydro-2H-benzo[b][1,4]oxazine To a stirred solution of 6-bromo-8-fluoro-4-isopropyl-3,4-dihydro-2H-benzo[b][1,4]oxazine (1200 mg, 4.39 mmol, 1 equiv) in dioxane (12 mL), was added 4,4,5,5-tetramethyl-2-(4,4,5,5-tetramethyl-1,3,2-dioxaborolan-2-yl)-1,3,2-dioxaborolane (1340 mg, 5.27 mmol, 1.2 equiv) and potassium acetate (1291 mg, 13.17 mmol, 3 equiv). Purge the reaction mixture with nitrogen gas for 15 min. After addition of Pd(dppf).DCM (179 mg, 0.219 mmol, 0.5 equiv) again purge with nitrogen for 5 min. The reaction mixture was heated to 100° C. for 4 h. Progress of the reaction was monitored by TLC and LCMS. After completion of the reaction, the reaction mixture was diluted with water (30 mL) and extracted with EtOAc (100 mL×2). Organic layer was washed with brine (100 mL), dried over anhydrous $Na_2SO_4$ and concentrated under reduced pressure to obtain 8-fluoro-4-isopropyl-6-(4,4,5,5-tetramethyl-1,3,2-dioxaborolan-2-yl)-3,4-dihydro-2H-benzo[b][1,4]oxazine (1000 mg, 69%) as a dark brown viscous compound.
LCMS 322.1 $[M+H]^+$

Step-4: Synthesis of 6-(2-chloro-5-fluoropyrimidin-4-yl)-8-fluoro-4-isopropyl-3,4-dihydro-2H-benzo[b][1,4]oxazine To a stirred solution of 2,4-dichloro-5-fluoropyrimidine (500 mg, 3.01 mmol, 1 equiv) and 8-fluoro-4-isopropyl-6-(4,4,5,5-tetramethyl-1,3,2-dioxaborolan-2-yl)-3,4-dihydro-2H-benzo[b][1,4]oxazine (970.1 mg, 3.01 mmol, 1 equiv) in THF:Water (1:1, 16 mL) was added Potassium carbonate (831 mg, 6.02 mmol, 2 equiv) and $Pd(PPh_3)_4$ (174 mg, 0.15 mmol, 0.05 equiv). The reaction mixture was heated to 80° C. for 4 h. Progress of the reaction was monitored by TLC and LCMS. After completion of the reaction, the reaction mixture was diluted with water (30 mL) and extracted with EtOAc (100 mL×2), organic layer was washed with water (100 mL) and brine solution (100 mL). The organic layer dried over anhydrous $Na_2SO_4$ and concentrated under reduced pressure to obtain crude compound, which was purified by normal phase combi-flash to obtain 6-(2-chloro-5-fluoropyrimidin-4-yl)-8-fluoro-4-isopropyl-3,4-dihydro-2H-benzo[b][1,4]oxazine (800 mg, 82%) as a yellow solid compound.
LCMS 326 $[M+H]^+$

Step-5: Synthesis of tert-butyl 4-(6-(5-fluoro-4-(8-fluoro-4-isopropyl-3,4-dihydro-2H-benzo[b][1,4]oxazin-6-yl)pyrimidin-2-ylamino)pyridin-3-yl)piperazine-1-carboxylate To a solution of 6-(2-chloro-5-fluoropyrimidin-4-yl)-8-fluoro-4-isopropyl-3,4-dihydro-2H-benzo[b][1,4]oxazine (300 mg, 0.923 mmol, 1 equiv) in Dioxane (10 mL), was added tert-butyl 4-(6-aminopyridin-3-yl)piperazine-1-carboxylate (282.3 mg, 1.015 mmol, 1.1 equiv) and cesium carbonate (451.4 mg, 1.384 mmol, 1.5 equiv). The reaction mixture was aerated with nitrogen gas for 30 min., followed by the addition of palladium acetate (4.2 mg, 0.018 mmol, 0.02 equiv) and BINAP (23 mg, 0.036 mmol, 0.04 equiv) again purged nitrogen for 5 min. The resultant reaction mixture was heated to 100° C. for 16 h. Progress of the reaction was monitored by TLC and LCMS. After completion of the reaction, the reaction mixture was diluted with EtOAc (25 mL). Solid observed was filtered and washed with EtOAc (20 mL) to obtain tert-butyl 4-(6-(5-fluoro-4-(8-fluoro-4-isopropyl-3,4-dihydro-2H-benzo[b][1,4]oxazin-6-yl)pyrimidin-2-ylamino)pyridin-3-yl)piperazine-1-carboxylate (190 mg, 36%) as a greenish solid compound.
LCMS 568.3 $[M+H]^+$

Step-6: Synthesis of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine Tert-butyl 4-(6-(5-fluoro-4-(8-fluoro-4-isopropyl-3,4-dihydro-2H-benzo[b][1,4]oxazin-6-yl)pyrimidin-2-ylamino)pyridin-3-yl)piperazine-1-carboxylate (190 mg, 0.335 mmol, 1 equiv) was taken in 1.25 M HCl in ethanol (5 mL) and the resultant reaction mixture was stirred at RT for 16 h. Progress of the reaction was monitored by LCMS. After completion of the reaction, the reaction mixture was concentrated under vacuum to obtain 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (180 mg, 100%) as a pale yellow solid compound.
LCMS 468.2 $[M+H]^+$
$^1$HNMR (400 MHz, DMSO-$d_6$) δ 9.04 (d, J=7.4 Hz, 2H), 8.67 (d, J=3.7 Hz, 1H), 8.01 (d, J=2.9 Hz, 1H), 7.91 (s, 1H), 7.77 (d, J=9.5 Hz, 1H), 7.42 (s, 1H), 7.19 (d, J=11.5 Hz, 1H), 4.36-4.21 (s, 2H), 4.17-4.07 (m, 1H), 3.38 (t, J=5.1 Hz, 4H), 3.32 (d, J=4.3 Hz, 2H), 3.26 (s, 4H), 1.19 (d, J=6.5 Hz, 6H).

Example-2: Synthesis of 8-fluoro-6-(5-fluoro-2-(5-(piperazin-1-yl)pyridin-2-ylamino)pyrimidin-4-yl)-4-isopropyl-2H-benzo[b][1,4]oxazin-3(4H)-one (Compound 2)

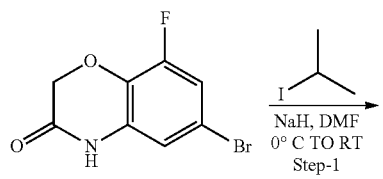

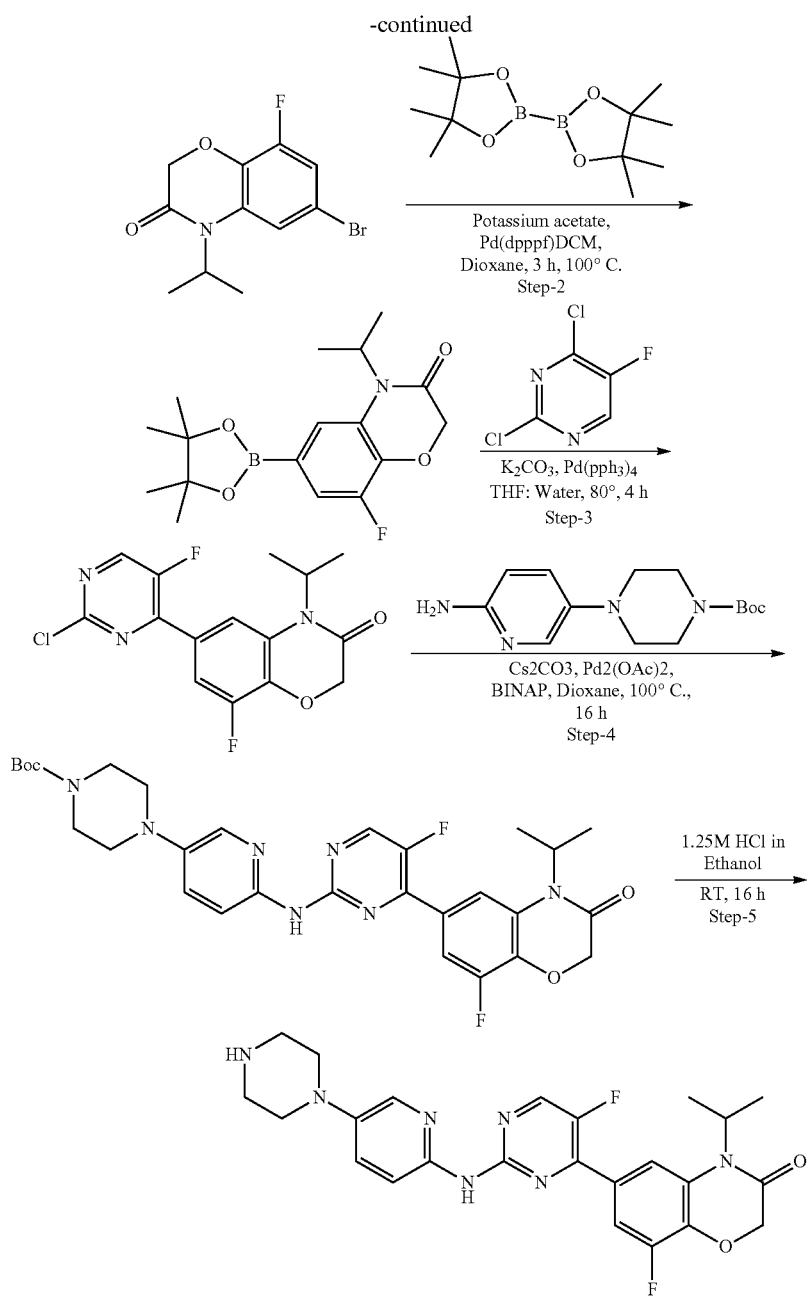

Step-1: Synthesis of 6-bromo-8-fluoro-4-isopropyl-2H-benzo[b][1,4]oxazin-3(4H)-one To a stirred solution of 6-bromo-8-fluoro-2H-benzo[b][1,4]oxazin-3(4H)-one (7000 mg, 28.56 mmol, 1 equiv) in DMF (70 mL), was added NaH (60%) (2282 mg, 57.12 mmol, 2 equiv) at 0° C. and stirred at RT for 30 min, followed by the addition of 2-iodopropane (5.6 mL, 57.12 mmol, 2 equiv). The reaction mixture was heated to 80° C. for 3 h. Progress of the reaction was monitored by TLC and LCMS. After completion of the reaction, the reaction mixture was diluted with water (100 mL) and extracted wit EtOAc (150 mL×3). Organic layer was washed with water (150 mL), brine solution (150 mL). Organic layer was dried over anhydrous $Na_2SO_4$ and concentrated under reduced pressure to obtain crude compound, which was purified by normal phase combi-flash to obtain 6-bromo-8-fluoro-4-isopropyl-2H-benzo[b][1,4]oxazin-3(4H)-one (2400 mg, 29%) as an off white solid compound.

LCMS 288 [M+H]$^+$

Step-2: Synthesis of 8-fluoro-4-isopropyl-6-(4,4,5,5-tetramethyl-1,3,2-dioxaborolan-2-yl)-2H-benzo[b][1,4]oxazin-3(4H)-one To a stirred solution of 6-bromo-8-fluoro-4-isopropyl-2H-benzo[b][1,4]oxazin-3(4H)-one (1000 mg, 3.48 mmol, 1 equiv) and 4,4,5,5-tetramethyl-2-(4,4,5,5-tetramethyl-1,3,2-dioxaborolan-2-yl)-1,3,2-dioxaborolane (1062 mg, 4.18 mmol, 1.2 equiv) in Dioxane was added Potassium acetate (1023 mg, 10.44 mmol, 3 equiv). Purge the reaction mixture with nitrogen gas for 15 min. After addition of Pd(dppf)

DCM (142 mg, 0.174 mmol, 0.05 equiv) again purged nitrogen for 5 min. The reaction mixture was stirred at 100° C. for 4 h. Progress of the reaction was monitored by TLC and LCMS. After completion of the reaction, the reaction mixture was diluted with water (30 mL) and extracted with EtOAc (100 mL×2). Organic layer was washed with brine (100 mL), dried over anhydrous $Na_2SO_4$ and concentrated under reduced pressure to obtain 8-fluoro-4-isopropyl-6-(4,4,5,5-tetramethyl-1,3,2-dioxaborolan-2-yl)-2H-benzo[b][1,4]oxazin-3(4H)-one (950 mg, 76%) as a dark brown viscous compound.

LCMS 336.1 [M+H]$^+$

Step-3: Synthesis of 6-(2-chloro-5-fluoropyrimidin-4-yl)-8-fluoro-4-isopropyl-2H-benzo[b][1,4]oxazin-3(4H)-one To a stirred solution of 2, 4-dichloro-5-fluoropyrimidine (450 mg, 2.71 mmol, 1 equiv), 8-fluoro-4-isopropyl-6-(4,4,5,5-tetramethyl-1,3,2-dioxaborolan-2-yl)-2H-benzo[b][1,4]oxazin-3(4H)-one (908.4 mg, 2.71 mmol, 1 equiv), Potassium carbonate (748 mg, 5.42 mmol, 2 equiv) in THF:Water (1:1) (16 mL), was added (8:8 mL) $Pd(PPh_3)_4$ (157 mg, 0.135 mmol, 0.05 equiv). The reaction mixture was heated to 80° C. for 4 h. Progress of the reaction was monitored by TLC and LCMS. After completion of the reaction, the reaction mixture was diluted with water (30 mL) and extracted with EtOAc (100 mL×2). Organic layer was washed with water (100 mL) and brine solution (100 mL). Organic layer was dried over anhydrous $Na_2SO_4$ and concentrated under reduced pressure to obtain crude compound, which was purified by normal phase combiflash to obtain 6-(2-chloro-5-fluoropyrimidin-4-yl)-8-fluoro-4-isopropyl-2H-benzo[b][1,4]oxazin-3(4H)-one (270 mg, 29%) as a white solid compound.

LCMS 340 [M+H]$^+$

Step-4: Synthesis of tert-butyl 4-(6-(5-fluoro-4-(8-fluoro-4-isopropyl-3-oxo-3,4-dihydro-2H-benzo[b][1,4]oxazin-6-yl)pyrimidin-2-ylamino)pyridin-3-yl)piperazine-1-carboxylate To a solution of 6-(2-chloro-5-fluoropyrimidin-4-yl)-8-fluoro-4-isopropyl-2H-benzo[b][1,4]oxazin-3(4H)-one (240 mg, 0.707 mmol, 1 equiv) in Dioxane (10 mL), was added tert-butyl 4-(6-aminopyridin-3-yl)piperazine-1-carboxylate (217 mg, 0.778 mmol, 1.1 equiv) and cesium carbonate (346 mg, 1.06 mmol, 1.5 equiv). The reaction mixture was aerated with nitrogen gas for 30 min., followed by the addition of palladium acetate (3.2 mg, 0.014 mmol, 0.02 equiv) and BINAP (17.6 mg, 0.028 mmol, 0.04 equiv) again purged nitrogen for 5 min. The resultant reaction mixture was heated to 100° C. for 16 h. Progress of the reaction was monitored by TLC and LCMS. After completion of the reaction, the reaction mixture was diluted with EtOAc (25 mL). Solid observed was filtered and washed with EtOAc (20 mL) to obtain tert-butyl 4-(6-(5-fluoro-4-(8-fluoro-4-isopropyl-3-oxo-3,4-dihydro-2H-benzo[b][1,4]oxazin-6-yl)pyrimidin-2-ylamino)pyridin-3-yl)piperazine-1-carboxylate (125 mg, 30%) yellow solid compound.

LCMS 582.3 [M+H]$^+$

Step-5: Synthesis of 8-fluoro-6-(5-fluoro-2-(5-(piperazin-1-yl)pyridin-2-ylamino)pyrimidin-4-yl)-4-isopropyl-2H-benzo[b][1,4]oxazin-3(4H)-one Tert-butyl 4-(6-(5-fluoro-4-(8-fluoro-4-isopropyl-3-oxo-3,4-dihydro-2H-benzo[b][1,4]oxazin-6-yl)pyrimidin-2-ylamino)pyridin-3-yl)piperazine-1-carboxylate (125 mg, 0.215 mmol, 1 equiv) was taken in 1.25M HCl in ethanol (5 mL) and the resultant reaction mixture was stirred at RT for 16 h. Progress of the reaction was monitored by LCMS. After completion of the reaction, the reaction mixture was concentrated under vacuum to obtain 8-fluoro-6-(5-fluoro-2-(5-(piperazin-1-yl) pyridin-2-ylamino) pyrimidin-4-yl)-4-isopropyl-2H-benzo[b][1,4]oxazin-3(4H)-one (120 mg, 100%) as a yellow solid compound.

LCMS 482.2 [M+H]$^+$ $^1$HNMR (400 MHz, DMSO-$d_6$) δ 8.97 (s, 2H), 8.72 (d, J=3.5 Hz, 1H), 8.04 (d, J=3.0 Hz, 1H), 7.96 (d, J=9.1 Hz, 1H), 7.84 (s, 1H), 7.66 (d, J=10.8 Hz, 2H), 4.83-4.81 (M, 1H), 4.78-4.76 (s, 2H), 3.36 (t, J=5.0 Hz, 4H), 3.26 (q, J=4.4 Hz, 4H), 1.51 (d, J=7.0 Hz, 6H).

Example-3: Synthesis of 5-fluoro-4-(8-fluoro-3,4-dihydro-2H-benzo[b][1,4]oxazin-6-yl)-N-(5 (piperazin-1-yl)pyridin-2-yl)pyrimidin-2-amine (Compound 3)

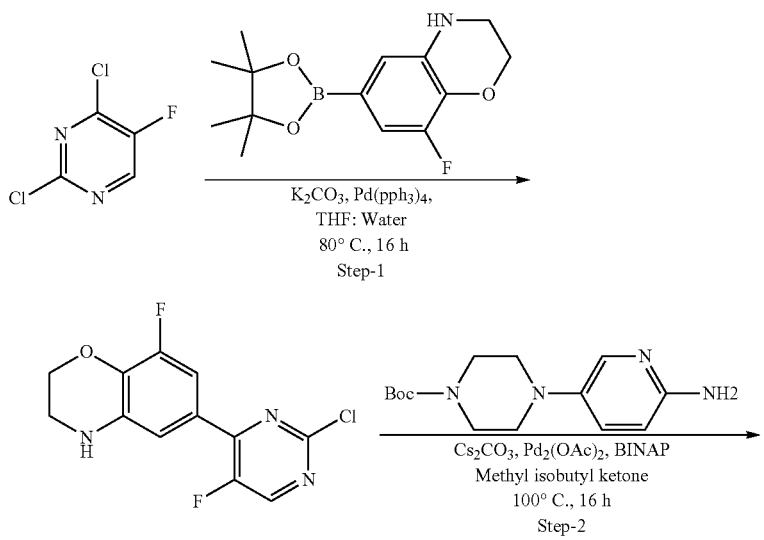

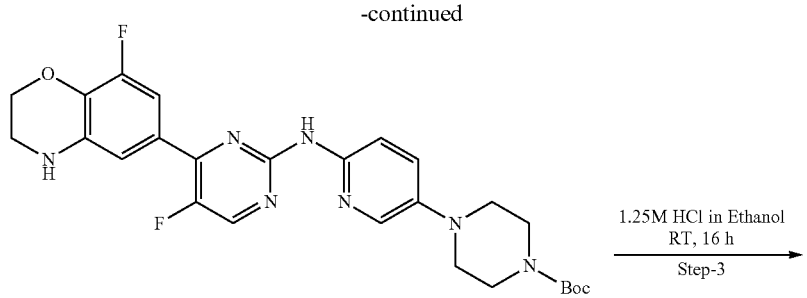

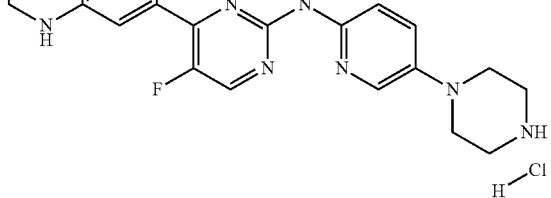

Step-1: Synthesis of 6-(2-chloro-5-fluoropyrimidin-4-yl)-8-fluoro-3,4-dihydro-2H-benzo[b][1,4]oxazine To a stirred solution of 2, 4-dichloro-5-fluoropyrimidine (4000 mg, 24.09 mmol, 1 equiv), 8-fluoro-6-(4,4,5,5-tetramethyl-1,3,2-dioxaborolan-2-yl)-3,4-dihydro-2H-benzo[b][1,4]oxazine (6722 mg, 24.09 mmol, 1 equiv), Potassium carbonate (6649 mg, 48.18 mmol, 2 equiv), Pd(PPh$_3$)$_4$ (1391 mg, 1.2 mmol, 0.05 equiv) in THF:Water (1:1.40 mL) were charged. The reaction mixture was heated to 80° C. for 16 h. Progress of the reaction was monitored by TLC and LCMS. After completion of the reaction, the reaction mixture was diluted with water (100 mL) and extracted wit EtOAc (150 mL×3). Organic layer was washed with water (150 mL), brine solution (150 mL). Organic layer was dried over anhydrous Na$_2$SO$_4$ and concentrated under reduced pressure to obtain crude compound, which was purified by normal phase combi-flash to obtain 6-(2-chloro-5-fluoropyrimidin-4-yl)-8-fluoro-3,4-dihydro-2H-benzo[b][1,4]oxazine (3400 mg, 50%) as a brown color solid compound.

LCMS 284 [M+H]$^+$

Step-2: Synthesis of tert-butyl 4-(6-(5-fluoro-4-(8-fluoro-3,4-dihydro-2H-benzo[b][1,4]oxazin-6-yl)pyrimidin-2-ylamino)pyridin-3-yl)piperazine-1-carboxylate To a solution of 6-(2-chloro-5-fluoropyrimidin-4-yl)-8-fluoro-3,4-dihydro-2H-benzo[b][1,4]oxazine (200 mg, 0.706 mmol, 1 equiv) in Methyl isobutyl ketone (6 mL), was added tert-butyl 4-(6-aminopyridin-3-yl)piperazine-1-carboxylate (216 mg, 0.776 mmol, 1.1 equiv) and cesium carbonate (345 mg, 1.059 mmol, 1.5 equiv). The reaction mixture was aerated with nitrogen gas for 30 min., followed by the addition of palladium acetate (3.1 mg, 0.014 mmol, 0.02 equiv) and BINAP (18 mg, 0.028 mmol, 0.04 equiv) again purged nitrogen for 5 min. The resultant reaction mixture was heated to 100° C. for 16 h. Progress of the reaction was monitored by TLC and LCMS. After completion of the reaction, the reaction mixture was diluted with water (25 mL) and extracted with EtOAc (50 mL×3). Organic layer was washed with water (50 mL) and brine solution (50 mL). Organic layer was dried over anhydrous Na$_2$SO$_4$ and concentrated under reduced pressure to obtain crude compound, which was purified with reverse phase HPLC to obtain tert-butyl 4-(6-(5-fluoro-4-(8-fluoro-3,4-dihydro-2H-benzo[b][1,4]oxazin-6-yl)pyrimidin-2-ylamino)pyridin-3-yl)piperazine-1-carboxylate (90 mg, 25%) as a yellow solid compound.

LCMS 526 [M+H]$^+$

Step-3: Synthesis of 5-fluoro-4-(8-fluoro-3,4-dihydro-2H-benzo[b][1,4]oxazin-6-yl)-N-(5-(piperazin-1-yl)pyridin-2-yl)pyrimidin-2-amine Tert-butyl 4-(6-(5-fluoro-4-(8-fluoro-3,4-dihydro-2H-benzo[b][1,4]oxazin-6-yl)pyrimidin-2-ylamino)pyridin-3-yl)piperazine-1-carboxylate (90 mg, 0.133 mmol, 1 equiv) was taken in 1.25M HCl in ethanol (5 mL) and the resultant reaction mixture was stirred at RT for 16 h. Progress of the reaction was monitored by LCMS. After completion of the reaction, the reaction mixture was concentrated under vacuum to obtain 5-fluoro-4-(8-fluoro-3,4-dihydro-2H-benzo[b][1,4]oxazin-6-yl)-N-(5-(piperazin-1-yl)pyridin-2-yl)pyrimidin-2-amine (70 mg, 97%) as a pale yellow solid compound.

LCMS 426 [M+H]$^+$ $^1$HNMR (400 MHz, Methanol-d$_4$) δ 8.65 (d, J=3.9 Hz, 1H), 8.25 (dd, J=9.7, 2.6 Hz, 1H), 7.89 (d, J=2.7 Hz, 1H), 7.51 (d, J=9.6 Hz, 1H), 7.33 (d, J=11.3 Hz, 2H), 4.33 (t, J=4.3 Hz, 2H), 3.56-3.49 (m, 4H), 3.48-3.41 (m, 4H), 1.29 (t, J=3.2 Hz, 2H).

Example-4: Synthesis of N-(5-((4-ethylpiperazin-1-yl) methyl) pyridin-2-yl)-5-fluoro-4-(8-fluoro-4-isopropyl-3,4-dihydro-2H-benzo[b][1,4]oxazin-6-yl) pyrimidin-2-amine (Compound 4)

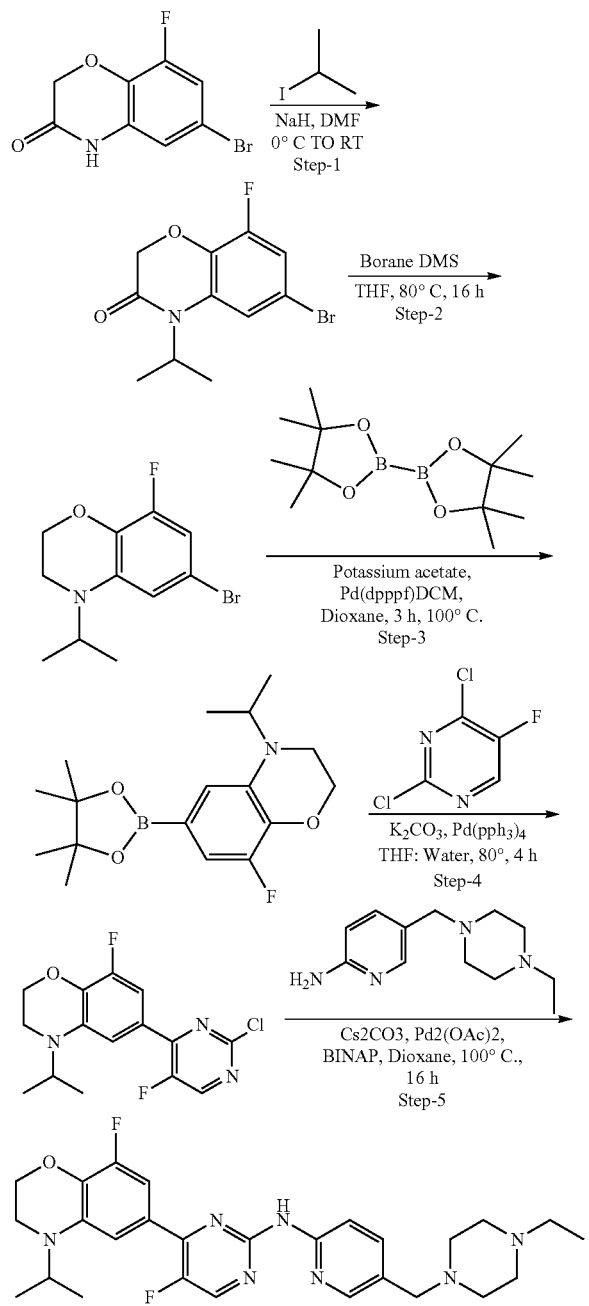

Step-1: Synthesis of 6-bromo-8-fluoro-4-isopropyl-2H-benzo[b][1,4]oxazin-3(4H)-one To a stirred solution of 6-bromo-8-fluoro-2H-benzo[b][1,4]oxazin-3(4H)-one (7.0 g, 28.56 mmol, 1 equiv) in DMF (70 mL), was added NaH (60%) (2.282 g, 57.12 mmol, 2 equiv) at 0° C. and stirred for 30 min. at RT, followed by the addition of 2-iodopropane (5.6 mL, 57.12 mmol, 2 equiv). The reaction mixture was heated to 80° C. for 3 h. Progress of the reaction was monitored by TLC and LCMS. After completion of the reaction, the reaction mixture cooled to RT and quenched with ice-cold water (100 mL) and extracted wit EtOAc (150 mL×3), organic layer was washed with water (150 mL) and brine solution (150 mL). Organic layer dried over anhydrous $Na_2SO_4$ and concentrated under reduced pressure to obtain crude compound, which was purified by normal phase combi-flash to obtain 6-bromo-8-fluoro-4-isopropyl-2H-benzo[b][1,4]oxazin-3(4H)-one (2.40 g, 29%) as off white solid compound.

LCMS 288 $[M+H]^+$

Step-2: Synthesis of 6-bromo-8-fluoro-4-isopropyl-3,4-dihydro-2H-benzo[b][1,4]oxazine To a stirred solution of 6-bromo-8-fluoro-4-isopropyl-2H-benzo[b][1,4]oxazin-3(4H)-one (1400 mg, 4.87 mmol, 1 equiv) in THF (14 mL), was drop wise added $BH_3.DMS$ (9.7 mL, 7.66 mmol, 4 equiv) at 0° C. The reaction mixture was heated to 80° C. for 16 h. Progress of the reaction was monitored by TLC and LCMS. After completion of the reaction, the reaction mixture was quenched with saturated solution of $NaHCO_3$ (100 mL) and extracted with EtOAc (100 mL×3). The combined organic layer was washed with water (100 mL) and brine solution (100 mL). Organic layer dried over anhydrous $Na_2SO_4$ and concentrated under reduced pressure to obtain 6-bromo-8-fluoro-4-isopropyl-3,4-dihydro-2H-benzo[b][1,4]oxazine (1200 mg, 90%) as a yellow viscous compound.

LCMS 274 $[M+H]^+$

Step-3: Synthesis of 8-fluoro-4-isopropyl-6-(4,4,5,5-tetramethyl-1,3,2-dioxaborolan-2-yl)-3,4-dihydro-2H-benzo[b][1,4]oxazine To a stirred solution of 6-bromo-8-fluoro-4-isopropyl-3,4-dihydro-2H-benzo[b][1,4]oxazine (1200 mg, 4.39 mmol, 1 equiv) in dioxane (12 mL), was added 4,4,5,5-tetramethyl-2-(4,4,5,5-tetramethyl-1,3,2-dioxaborolan-2-yl)-1,3,2-di-oxaborolane (1340 mg, 5.27 mmol, 1.2 equiv) and Potassium acetate (1291 mg, 13.17 mmol, 3 equiv). Aerated the reaction mixture with nitrogen gas for 15 minutes. After addition of Pd(dppf) DCM (179 mg, 0.219 mmol, 0.5 equiv) again purge nitrogen for 5 min. The reaction mixture was heated to 100° C. for 4 h. Progress of the reaction was monitored by TLC and LCMS. After completion of the reaction, the reaction mixture was diluted with water (30 mL) and extracted with EtOAc (100 mL×2), organic layer was washed with brine (100 mL). The organic layer dried over anhydrous $Na_2SO_4$ and concentrated under reduced pressure to obtain 8-fluoro-4-isopropyl-6-(4,4,5,5-tetramethyl-1,3,2-dioxaborolan-2-yl)-3,4-dihydro-2H-benzo[b][1,4]oxazine (1000 mg, 69%) as a dark brown viscous compound.

LCMS 322.1 $[M+H]^+$

Step-4: Synthesis of 6-(2-chloro-5-fluoropyrimidin-4-yl)-8-fluoro-4-isopropyl-3, 4-dihydro-2H-benzo[b][1,4]oxazine To a stirred solution of 2, 4-dichloro-5-fluoropyrimidine (500 mg, 3.01 mmol, 1 equiv) and 8-fluoro-4-isopropyl-6-(4,4,5,5-tetramethyl-1,3,2-dioxaborolan-2-yl)-3,4-dihydro-2H-benzo[b][1,4]oxazine (970.1 mg, 3.01 mmol, 1 equiv) in THF:Water (1:1, 16 mL) was added Potassium carbonate (831 mg, 6.02 mmol, 2 equiv) and $Pd(PPh_3)_4$ (174 mg, 0.15 mmol, 0.05 equiv). The reaction mixture was heated to 80°

C. for 4 h. Progress of the reaction was monitored by TLC and LCMS. After completion of the reaction, the reaction mixture was diluted with water (30 mL) and extracted with EtOAc (100 mL×2), organic layer was washed with water (100 mL) and brine solution (100 mL). The organic layer dried over anhydrous $Na_2SO_4$ and concentrated under reduced pressure to obtain crude compound, which was purified by normal phase combi-flash to obtain 6-(2-chloro-5-fluoropyrimidin-4-yl)-8-fluoro-4-isopropyl-3,4-dihydro-2H-benzo[b][1,4]oxazine (800 mg, 82%) as a yellow solid compound.

LCMS 326 [M+H]+

Step-5: Synthesis of N-(5-((4-ethylpiperazin-1-yl) methyl) pyridin-2-yl)-5-fluoro-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (200 mg, 0.676 mmol, 1 equiv) in Dioxane (10 mL), was added 5-((4-ethylpiperazin-1-yl)methyl)pyridin-2-amine (149 mg, 1.015 mmol, 1.1 equiv) and cesium carbonate (301 mg, 0.923 mmol, 1.5 equiv). The reaction mixture was aerated with nitrogen gas for 30 min., followed by the addition of palladium acetate (3 mg, 0.012 mmol, 0.02 equiv) and BINAP (15.3 mg, 0.024 mmol, 0.04 equiv) again purge nitrogen for 5 min. The resultant reaction mixture was heated to 100° C. for 16 h. Progress of the reaction was monitored by TLC and LCMS. After completion of the reaction, the reaction mixture was diluted with water (25 mL) extracted with EtOAc (100 mL), organic layer was dried over anhydrous $Na_2SO_4$ and concentrated under reduced pressure to obtain crude which was purified by reversed phase HPLC to obtain N-(5-((4-ethylpiperazin-1-yl)methyl)pyridin-2-yl)-5-fluoro-4-(8-fluoro-4-isopropyl-3,4-dihydro-2H-benzo[b][1,4]oxazin-6-yl)pyrimidin-2-amine (35 mg) as a yellow solid compound.

LCMS 510.1 [M+H]+

$^1$HNMR (400 MHz, Methanol-$d_4$) δ 8.45 (s, 1H), 8.32 (s, 1H), 8.21 (s, 1H), 7.76 (d, J=8.7 Hz, 1H), 7.54 (s, 1H), 7.30-7.22 (m, 1H), 4.33 (t, J=4.3 Hz, 2H), 4.23 (p, J=6.7 Hz, 1H), 3.57 (s, 2H), 3.35 (t, J=4.5 Hz, 2H), 2.85 (s, 2H), 2.66-2.59 (m, 8H), 1.27 (d, J=6.6 Hz, 6H), 1.15 (t, J=7.2 Hz, 3H).

Example-5: Synthesis of 5-fluoro-4-(8-fluoro-4-isopropyl-3,4-dihydro-2H-benzo[b][1,4]oxazin-6-yl)-N-(4-(piperazin-1-yl)pyridin-2-yl)pyrimidin-2-amine (Compound 5)

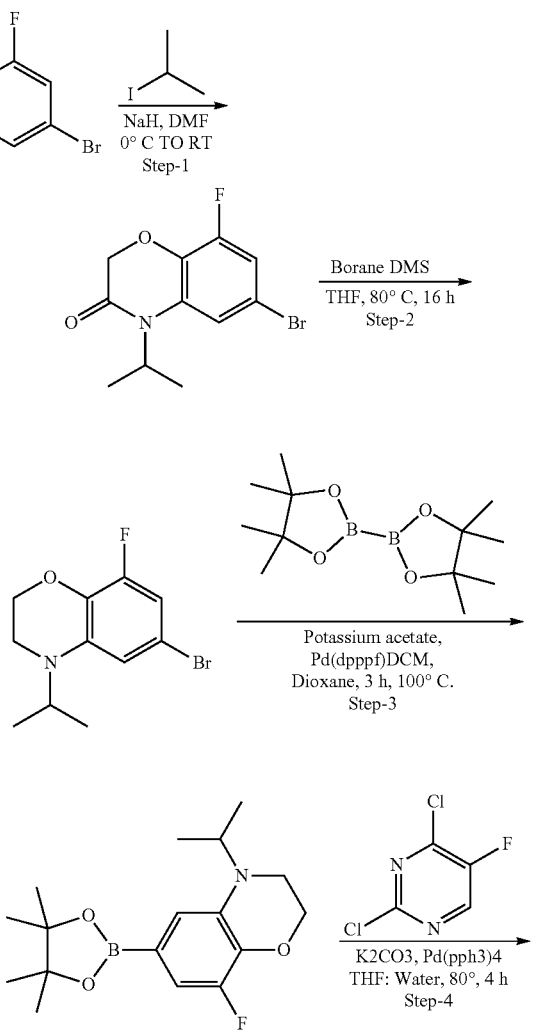

-continued

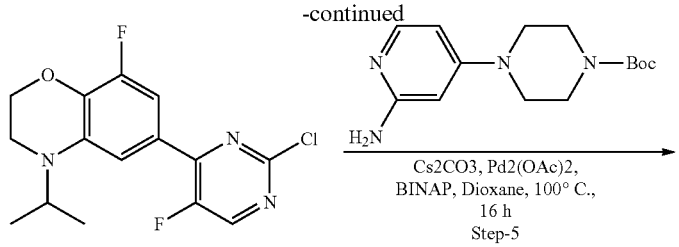

Cs2CO3, Pd2(OAc)2,
BINAP, Dioxane, 100° C.,
16 h
Step-5

1.25M HCl in Ethanol
RT, 16 h
Step-6

Step-1: Synthesis of 6-bromo-8-fluoro-4-isopropyl-2H-benzo[b][1,4]oxazin-3(4H)-one To a stirred solution of 6-bromo-8-fluoro-2H-benzo[b][1,4]oxazin-3(4H)-one (7000 mg, 28.56 mmol, 1 equiv) in DMF (70 mL), was added NaH (60%) (2282 mg, 57.12 mmol, 2 equiv) at 0° C. and stirred for 30 min. at RT, followed by the addition of 2-iodopropane (5.6 mL, 57.12 mmol, 2 equiv). The reaction mixture was heated to 80° C. for 3 h. Progress of the reaction was monitored by TLC and LCMS. After completion of the reaction, the reaction mixture cooled to RT and quenched with ice-cold water (100 mL) and extracted wit EtOAc (150 mL×3), organic layer was washed with water (150 mL) and brine solution (150 mL). Organic layer dried over anhydrous $Na_2SO_4$ and concentrated under reduced pressure to obtain crude compound, which was purified by normal phase combi-flash to obtain 6-bromo-8-fluoro-4-isopropyl-2H-benzo[b][1,4]oxazin-3(4H)-one (2400 mg, 29%) as off white solid compound.

LCMS 288 [M+H]$^+$

Step-2: Synthesis of 6-bromo-8-fluoro-4-isopropyl-3,4-dihydro-2H-benzo[b][1,4]oxazine To a stirred solution of 6-bromo-8-fluoro-4-isopropyl-2H-benzo[b][1,4]oxazin-3(4H)-one (1400 mg, 4.87 mmol, 1 equiv) in THF (14 mL), was drop wise added $BH_3$.DMS (9.7 mL, 7.66 mmol, 4 equiv) at 0° C. The reaction mixture was heated to 80° C. for 16 h. Progress of the reaction was monitored by TLC and LCMS. After completion of the reaction, the reaction mixture was quenched with saturated solution of $NaHCO_3$ (100 mL) and extracted with EtOAc (100 mL×3). The combined organic layer was washed with water (100 mL) and brine solution (100 mL). Organic layer dried over anhydrous $Na_2SO_4$ and concentrated under reduced pressure to obtain 6-bromo-8-fluoro-4-isopropyl-3,4-dihydro-2H-benzo[b][1,4]oxazine (1200 mg, 90%) as a yellow viscous compound.

LCMS 274 [M+H]$^+$

Step-3: Synthesis of 8-fluoro-4-isopropyl-6-(4,4,5,5-tetramethyl-1,3,2-dioxaborolan-2-yl)-3,4-dihydro-2H-benzo[b][1,4]oxazine To a stirred solution of 6-bromo-8-fluoro-4-isopropyl-3,4-dihydro-2H-benzo[b][1,4]oxazine (1200 mg, 4.39 mmol, 1 equiv) in dioxane (12 mL), was added 4,4,5,5-tetramethyl-2-(4,4,5,5-tetramethyl-1,3,2-dioxaborolan-2-yl)-1,3,2-dioxaborolane (1340 mg, 5.27 mmol, 1.2 equiv) and Potassium acetate (1291 mg, 13.17 mmol, 3 equiv). Aerated the reaction mixture with nitrogen gas for 15 minutes. After addition of Pd(dppf) DCM (179 mg, 0.219 mmol, 0.5 equiv) again purge nitrogen for 5 min. The reaction mixture was heated to 100° C. for 4 h. Progress of the reaction was monitored by TLC and LCMS. After completion of the reaction, the reaction mixture was diluted with water (30 mL) and extracted with EtOAc (100 mL×2), organic layer was washed with brine (100 mL). The organic layer dried over anhydrous $Na_2SO_4$ and concentrated under reduced pressure to obtain 8-fluoro-4-isopropyl-6-(4,4,5,5-tetramethyl-1,3,2-dioxaborolan-2-yl)-3,4-dihydro-2H-benzo[b][1,4]oxazine (1000 mg, 69%) as a dark brown viscous compound.

LCMS 322.1 [M+H]$^+$

Step-4: Synthesis of 6-(2-chloro-5-fluoropyrimidin-4-yl)-8-fluoro-4-isopropyl-3, 4-dihydro-2H-benzo[b][1,4]oxazine To a stirred solution of 2, 4-dichloro-5-fluoropyrimidine (500 mg, 3.01 mmol, 1 equiv) and 8-fluoro-4-isopropyl-6-

(4,4,5,5-tetramethyl-1,3,2-dioxaborolan-2-yl)-3,4-dihydro-2H-benzo[b][1,4]oxazine (970.1 mg, 3.01 mmol, 1 equiv) in THF:Water (1:1, 16 mL) was added Potassium carbonate (831 mg, 6.02 mmol, 2 equiv) and Pd(PPh₃)₄(174 mg, 0.15 mmol, 0.05 equiv). The reaction mixture was heated to 80° C. for 4 h. Progress of the reaction was monitored by TLC and LCMS. After completion of the reaction, the reaction mixture was diluted with water (30 mL) and extracted with EtOAc (100 mL×2), organic layer was washed with water (100 mL) and brine solution (100 mL). The organic layer dried over anhydrous Na₂SO₄ and concentrated under reduced pressure to obtain crude compound, which was purified by normal phase combi-flash to obtain 6-(2-chloro-5-fluoropyrimidin-4-yl)-8-fluoro-4-isopropyl-3,4-dihydro-2H-benzo[b][1,4]oxazine (800 mg, 82%) as a yellow solid compound.

LCMS 326 [M+H]⁺

Step-5: Synthesis of tert-butyl 4-(2-((5-fluoro-4-(8-fluoro-4-isopropyl-3,4-dihydro-2H-benzo[b][1,4]oxazin-6-yl)pyrimidin-2-yl)amino)pyridin-4-yl)piperazine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.461 mmol, 1 equiv) in Dioxane (10 mL), was added tert-butyl 4-(2-aminopyridin-4-yl)piperazine-1-carboxylate (141 mg, 0.507 mmol, 1.1 equiv) and cesium carbonate (225.4 mg, 0.691 mmol, 1.5 equiv). The reaction mixture was aerated with nitrogen gas for 30 min., followed by the addition of palladium acetate (2 mg, 0.009 mmol, 0.02 equiv) and BINAP (12 mg, 0.018 mmol, 0.04 equiv) again purge nitrogen for 5 min. The resultant reaction mixture was stir at 100° C. for 16 h. Progress of the reaction was monitored by TLC and LCMS. After completion of the reaction, the reaction mixture was diluted with EtOAc (25 mL). Solid observed was filtered and washed with EtOAc (20 mL) to obtain tert-butyl 4-(2-((5-fluoro-4-(8-fluoro-4-isopropyl-3,4-dihydro-2H-benzo[b][1,4]oxazin-6-yl)pyrimidin-2-yl)amino)pyridin-4-yl)piperazine-1-carboxylate (140 mg, 53%) as a yellow solid compound.

LCMS 568.3 [M+H]⁺

Step-6: Synthesis of 5-fluoro-4-(8-fluoro-4-isopropyl-3,4-dihydro-2H-benzo[b][1, 4]oxazin-6-yl)-N-(4-(piperazin-1-yl)pyridin-2-yl)pyrimidin-2-amine Tert-butyl 4-(2-((5-fluoro-4-(8-fluoro-4-isopropyl-3,4-dihydro-2H-benzo[b][1,4]oxazin-6-yl)pyrimidin-2-yl)amino)pyridin-4-yl)piperazine-1-carboxylate (140 mg, 0.246 mmol, 1 equiv) was taken in 1.25M HCl in ethanol (5 mL) and the resultant reaction mixture was stirred at RT for 16 h. Progress of the reaction was monitored by LCMS. After completion of the reaction, the reaction mixture was concentrated under vacuum to obtain 5-fluoro-4-(8-fluoro-4-isopropyl-3,4-dihydro-2H-benzo[b][1,4]oxazin-6-yl)-N-(4-(piperazin-1-yl)pyridin-2-yl)pyrimidin-2-amine (110 mg, 83%) as a yellow solid compound.

LCMS 468.2 [M+H]⁺

¹HNMR (400 MHz, METHANOL-d₄) δ 8.61 (d, J=3.95 Hz, 1H), 8.02 (d, J=7.24 Hz, 1H), 7.50 (s, 1H), 7.31 (d, J=11.40 Hz, 1H), 6.95-7.03 (m, 1H), 6.66 (d, J=2.19 Hz, 1H), 4.31-4.37 (m, 2H), 4.22 (m, 1H), 3.92 (s, 4H), 3.42 (s, 4H), 3.37-3.50 (m, 2H), 1.22-1.33 (d, 6H).

Example-6: Synthesis of 5-fluoro-4-(8-fluoro-4-isopropyl-3,4-dihydro-2H-benzo[b][1,4]oxazin-6-yl)-N-(4-(4-methylpiperazin-1-yl)phenyl)pyrimidin-2-amine (Compound 6)

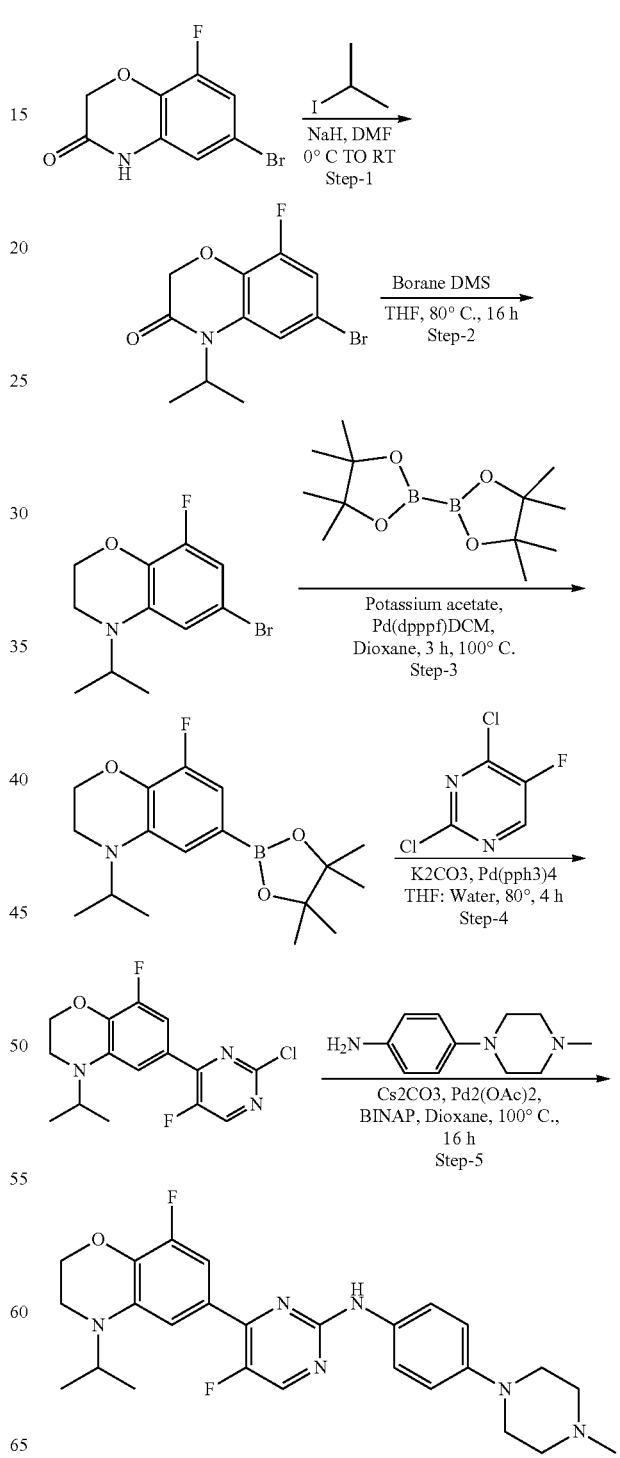

Step-1: Synthesis of 6-bromo-8-fluoro-4-isopropyl-2H-benzo[b][1,4]oxazin-3(4H)-one To a stirred solution of 6-bromo-8-fluoro-2H-benzo[b][1,4]oxazin-3(4H)-one (7000 mg, 28.56 mmol, 1 equiv) in DMF (70 mL), was added NaH (60%) (2282 mg, 57.12 mmol, 2 equiv) at 0° C. and stirred for 30 min. at RT, followed by the addition of 2-iodopropane (5.6 mL, 57.12 mmol, 2 equiv). The reaction mixture was heated to 80° C. for 3 h. Progress of the reaction was monitored by TLC and LCMS. After completion of the reaction, the reaction mixture cooled to RT and quenched with ice-cold water (100 mL) and extracted wit EtOAc (150 mL×3), organic layer was washed with water (150 mL) and brine solution (150 mL). Organic layer dried over anhydrous $Na_2SO_4$ and concentrated under reduced pressure to obtain crude compound, which was purified by normal phase combi-flash to obtain 6-bromo-8-fluoro-4-isopropyl-2H-benzo[b][1,4]oxazin-3(4H)-one (2400 mg, 29%) as off white solid compound.

LCMS 288 $[M+H]^+$

Step-2: Synthesis of 6-bromo-8-fluoro-4-isopropyl-3,4-dihydro-2H-benzo[b][1,4]oxazine To a stirred solution of 6-bromo-8-fluoro-4-isopropyl-2H-benzo[b][1,4]oxazin-3(4H)-one (1400 mg, 4.87 mmol, 1 equiv) in THF (14 mL), was drop wise added $BH_3.DMS$ (9.7 mL, 7.66 mmol, 4 equiv) at 0° C. The reaction mixture was heated to 80° C. for 16 h. Progress of the reaction was monitored by TLC and LCMS. After completion of the reaction, the reaction mixture was quenched with saturated solution of $NaHCO_3$ (100 mL) and extracted with EtOAc (100 mL×3). The combined organic layer was washed with water (100 mL) and brine solution (100 mL). Organic layer dried over anhydrous $Na_2SO_4$ and concentrated under reduced pressure to obtain 6-bromo-8-fluoro-4-isopropyl-3,4-dihydro-2H-benzo[b][1,4]oxazine (1200 mg, 90%) as a yellow viscous compound.

LCMS 274 $[M+H]^+$

Step-3: Synthesis of 8-fluoro-4-isopropyl-6-(4,4,5,5-tetramethyl-1,3,2-dioxaborolan-2-yl)-3,4-dihydro-2H-benzo[b][1,4]oxazine To a stirred solution of 6-bromo-8-fluoro-4-isopropyl-3,4-dihydro-2H-benzo[b][1,4]oxazine (1200 mg, 4.39 mmol, 1 equiv) in dioxane (12 mL), was added 4,4,5,5-tetramethyl-2-(4,4,5,5-tetramethyl-1,3,2-dioxaborolan-2-yl)-1,3,2-dioxaborolane (1340 mg, 5.27 mmol, 1.2 equiv) and Potassium acetate (1291 mg, 13.17 mmol, 3 equiv). Aerated the reaction mixture with nitrogen gas for 15 minutes. After addition of Pd(dppf) DCM (179 mg, 0.219 mmol, 0.5 equiv) again purge nitrogen for 5 min. The reaction mixture was heated to 100° C. for 4 h. Progress of the reaction was monitored by TLC and LCMS. After completion of the reaction, the reaction mixture was diluted with water (30 mL) and extracted with EtOAc (100 mL×2), organic layer was washed with brine (100 mL). The organic layer dried over anhydrous $Na_2SO_4$ and concentrated under reduced pressure to obtain 8-fluoro-4-isopropyl-6-(4,4,5,5-tetramethyl-1,3,2-dioxaborolan-2-yl)-3,4-dihydro-2H-benzo[b][1,4]oxazine (1000 mg, 69%) as a dark brown viscous compound.

LCMS 322.1 $[M+H]^+$

Step-4: Synthesis of 6-(2-chloro-5-fluoropyrimidin-4-yl)-8-fluoro-4-isopropyl-3,4-dihydro-2H-benzo[b][1,4]oxazine To a stirred solution of 2,4-dichloro-5-fluoropyrimidine (500 mg, 3.01 mmol, 1 equiv) and 8-fluoro-4-isopropyl-6-(4,4,5,5-tetramethyl-1,3,2-dioxaborolan-2-yl)-3,4-dihydro-2H-benzo[b][1,4]oxazine (970.1 mg, 3.01 mmol, 1 equiv) in THF:Water (1:1, 16 mL) was added Potassium carbonate (831 mg, 6.02 mmol, 2 equiv) and $Pd(PPh_3)_4$ (174 mg, 0.15 mmol, 0.05 equiv). The reaction mixture was heated to 80° C. for 4 h. Progress of the reaction was monitored by TLC and LCMS. After completion of the reaction, the reaction mixture was diluted with water (30 mL) and extracted with EtOAc (100 mL×2), organic layer was washed with water (100 mL) and brine solution (100 mL). The organic layer dried over anhydrous $Na_2SO_4$ and concentrated under reduced pressure to obtain crude compound, which was purified by normal phase combi-flash to obtain 6-(2-chloro-5-fluoropyrimidin-4-yl)-8-fluoro-4-isopropyl-3,4-dihydro-2H-benzo[b][1,4]oxazine (800 mg, 82%) as a yellow solid compound.

LCMS 326 $[M+H]^+$

Step-5: Synthesis of 5-fluoro-4-(8-fluoro-4-isopropyl-3,4-dihydro-2H-benzo[b][1,4]oxazin-6-yl)-N-(4-(4-methylpiperazin-1-yl)phenyl)pyrimidin-2-amine To a solution of 6-(2-chloro-5-fluoropyrimidin-4-yl)-8-fluoro-4-isopropyl-3,4-dihydro-2H-benzo[b][1,4]oxazine (150 mg, 0.461 mmol, 1 equiv) in Dioxane (10 mL), was added 4-(4-methylpiperazin-1-yl)aniline (97 mg, 0.507 mmol, 1.1 equiv) and cesium carbonate (225.4 mg, 0.691 mmol, 1.5 equiv). The reaction mixture was aerated with nitrogen gas for 30 min., followed by the addition of palladium acetate (2 mg, 0.009 mmol, 0.02 equiv) and BINAP (12 mg, 0.018 mmol, 0.04 equiv) again purge nitrogen for 5 min. The resultant reaction mixture was heated to 100° C. for 16 h. Progress of the reaction was monitored by TLC and LCMS. After completion of the reaction, the reaction mixture was diluted with EtOAc (25 mL). Solid observed was filtered and washed with EtOAc (20 mL) to obtain crude compound, which was purified by reverse phase HPLC to afford 5-fluoro-4-(8-fluoro-4-isopropyl-3,4-dihydro-2H-benzo[b][1,4]oxazin-6-yl)-N-(4-(4-methylpiperazin-1-yl)phenyl)pyrimidin-2-amine (100 mg, 45%) as a yellow solid compound.

LCMS 481.2 $[M+H]^+$ $^1$HNMR (400 MHz, Methanol-$d_4$) δ 8.40 (d, J=3.95 Hz, 1H), 7.44-7.59 (m, J=8.77 Hz, 2H), 7.40 (s, 1H), 7.12 (d, J=11.62 Hz, 1H), 6.74-6.90 (m, J=8.99 Hz, 2H), 4.25 (s, 2H), 4.03-4.12 (m, 1H), 3.25 (s, 2H), 3.03 (s, 4H), 2.44 (s, 4H), 2.18 (s, 3H), 1.14 (d, J=6.36 Hz, 6H).

Example-7: Synthesis of 1-(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)ethan-1-one (Compound 7)

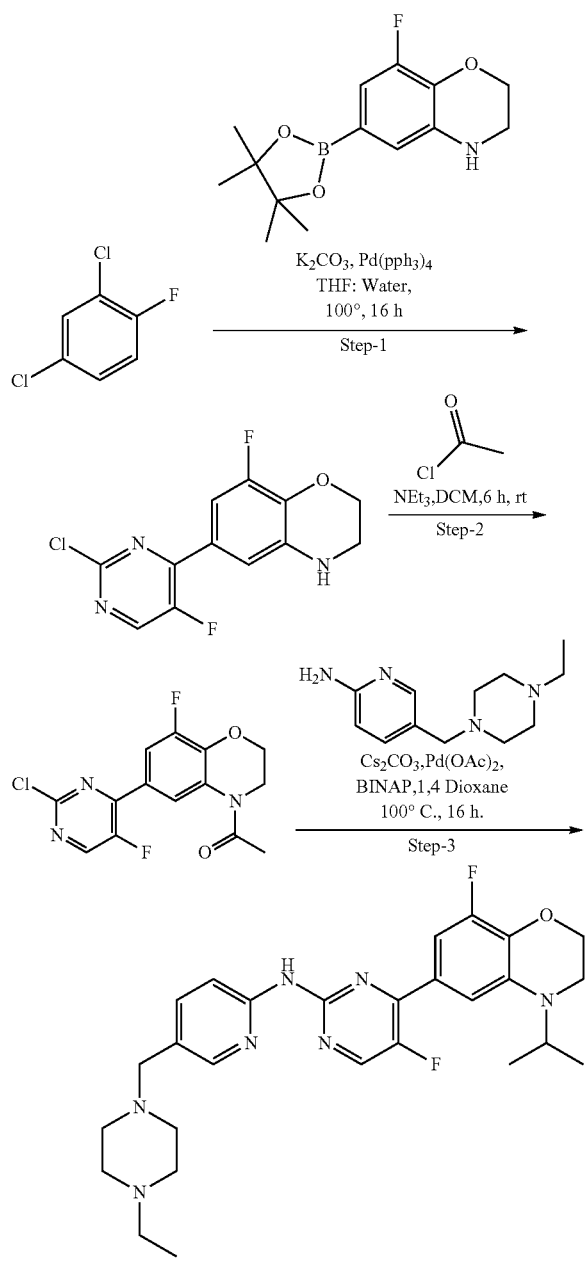

Step-1: Synthesis of 6-(2-chloro-5-fluoropyrimidin-4-yl)-8-fluoro-3,4-dihydro-2H-benzo[b][1,4]oxazine 6-(2-chloro-5-fluoropyrimidin-4-yl)-8-fluoro-3,4-dihydro-2H-benzo[b][1,4]oxazine (9243 mg, 33.12 mmol, 1.1 equiv), 2,4-dichloro-5-fluoropyrimidine (5.0 g, 30.12 mmol, 1.0 equiv), Potassium carbonate (8.3 g, 60.24 mmol, 2 equiv), Pd(PPh₃)₄ (1.74 g, 1.50 mmol, 0.05 equiv) and THF:Water (1:1=40 mL) were charged. The reaction mixture was allowed to stir at 80° C. for overnight. Progress of the reaction was monitored by TLC and LCMS. After completion of the reaction, the reaction mixture was diluted with water (100 mL) and extracted with EtOAc (100 mL×2), organic layer was washed with water (200 mL), brine solution (200 mL) and dried over anhydrous Na₂SO₄. Concentrated under reduced pressure to obtain crude compound, which was purified by ether and pentane washing, recrystallization to obtain 6-(2-chloro-5-fluoropyrimidin-4-yl)-8-fluoro-3,4-dihydro-2H-benzo[b][1,4]oxazine (4000 mg,) as a yellow solid compound.
LCMS 284 [M+H]⁺

Step-2: Synthesis of 1-(6-(2-chloro-5-fluoropyrimidin-4-yl)-8-fluoro-2,3-dihydro-4H-benzo[b][1,4]oxazin-4-yl)ethan-1-one To a stirred solution of 6-(2-chloro-5-fluoropyrimidin-4-yl)-8-fluoro-3,4-dihydro-2H-benzo[b][1,4]oxazine (300 mg, 1.06 mmol, 1 equiv) in DCM (20 mL), was added triethyl amine (0.37 ml, 2.65 mmol, 2.5 equiv) at 0° C. Stir the reaction mixture for 30 min. at RT, followed by the addition of acetyl chloride (124 mg, 1.59 mmol). The reaction mixture was allowed to stir at RT for 16 h. Progress of the reaction was monitored by TLC and LCMS. After completion of the reaction, the reaction mixture was diluted with water (50 mL) and extracted wit EtOAc (50 mL×3), organic layer was washed with NaHCO₃ (100 mL), brine solution (100 mL) and dried over anhydrous Na₂SO₄. Concentrated under reduced pressure to obtain crude compound, which was purified by recrystallization in ether and pentane to obtain 1-(6-(2-chloro-5-fluoropyrimidin-4-yl)-8-fluoro-2,3-dihydro-4H-benzo[b][1,4]oxazin-4-yl)ethan-1-one (200 mg) as off white solid compound.
LCMS 326 [M+H]⁺

Step-3: Synthesis of 1-(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)ethan-1-one To a solution of 1-(6-(2-chloro-5-fluoropyrimidin-4-yl)-8-fluoro-2,3-dihydro-4H-benzo[b][1,4]oxazin-4-yl)ethan-1-one (200 mg, 0.676 mmol, 1 equiv) in Dioxane (10 mL), was added 5-((4-ethylpiperazin-1-yl)methyl)pyridin-2-amine (162 mg, 0.738 mmol, 1.1 equiv) and cesium carbonate (299 mg, 0.918 mmol, 1.5 equiv). The reaction mixture was aerated with nitrogen gas for 30 min., followed by the addition of palladium acetate (6.8 mg, 0.030 mmol, 0.05 equiv) and BINAP (19.12 mg, 0.030 mmol, 0.05 equiv). The resultant reaction mixture was stir at 100° C. for 16 h. Progress of the reaction was monitored by TLC and LCMS. After completion of the reaction, the reaction mixture was diluted with water (50 mL) and extracted wit EtOAc (50 mL×2), organic layer was washed with NaHCO₃ (100 mL), brine solution (50 mL×3) and dried over anhydrous Na₂SO₄. Concentrated under reduced pressure to obtain crude compound, which was purified by reverse phase combi-flash chromatography to obtain 1-(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)ethan-1-one (50 mg, 97.84%) as a yellow solid compound.
LCMS 510.1 [M+H]⁺
¹HNMR (400 MHz, DMSO-d₆) δ 9.96 (s, 1H), 8.66 (d, J=3.95 Hz, 1H), 8.12-8.28 (m, 2H), 7.62-7.77 (m, 2H), 4.34-4.54 (m, 2H), 3.92-4.03 (m, 1H), 3.43 (s, 2H), 2.21-2.44 (m, 7H), 0.97 (t, J=7.24 Hz, 2H) 21-2.44 (m, 10H), 0.97 (t, J=7.24 Hz, 3H).

Example-8: Synthesis of cyclopropyl(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)methanone (Compound 8)

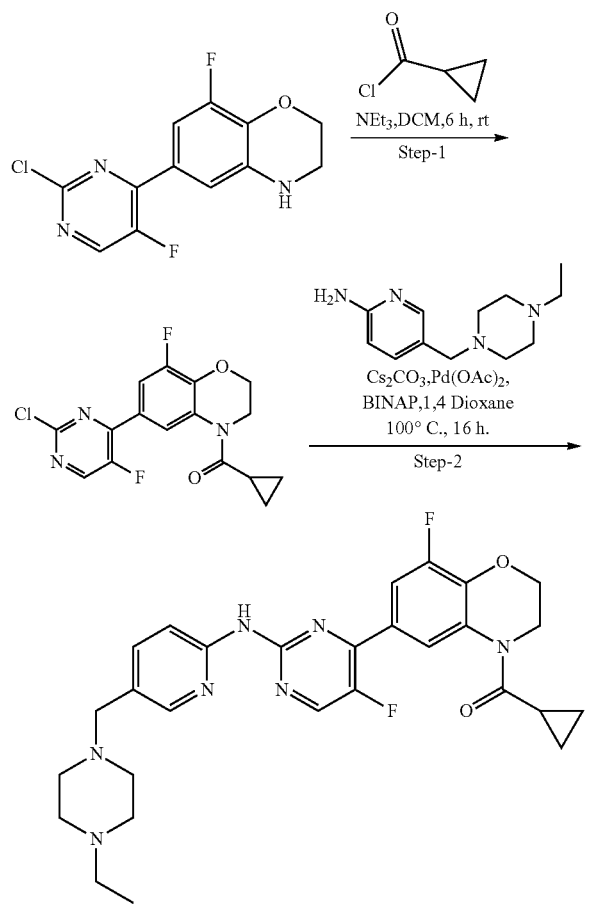

Step-1: Synthesis of (6-(2-chloro-5-fluoropyrimidin-4-yl)-8-fluoro-2,3-dihydro-4H-benzo[b][1,4]oxazin-4-yl)(cyclopropyl)methanone To a stirred solution of 6-(2-chloro-5-fluoropyrimidin-4-yl)-8-fluoro-3,4-dihydro-2H-benzo[b][1,4]oxazine (300 mg, 1.06 mmol, 1 equiv) in DCM (10 mL), was added triethyl amine (0.37 ml, 2.65 mmol, 2.5 equiv) at 0° C. Stirred the reaction mixture for 30 min at RT, followed by addition of cyclopropanecarbonyl chloride (165 mg, 1.59 mmol). The reaction mixture was allowed to stir at RT for 16 h. Progress of the reaction was monitored by TLC and LCMS. After completion of the reaction, the reaction mixture was diluted with water (50 mL) and extracted wit EtOAc (50 mL×3), organic layer was washed with NaHCO$_3$ (100 mL), brine solution (100 mL) and dried over anhydrous Na$_2$SO$_4$. Concentrated under reduced pressure to obtain crude compound, which was purified by recrystallization in ether and pentane to obtain (6-(2-chloro-5-fluoropyrimidin-4-yl)-8-fluoro-2,3-dihydro-4H-benzo[b][1,4]oxazin-4-yl)(cyclopropyl)methanone (300 mg) as off white solid compound.

LCMS 352 [M+H]$^+$

Step-2: Synthesis of cyclopropyl(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)methanone To a solution of (6-(2-chloro-5-fluoropyrimidin-4-yl)-8-fluoro-2,3-dihydro-4H-benzo[b][1,4]oxazin-4-yl)(cyclopropyl)methanone (200 mg, 0.676 mmol, 1 equiv) in Dioxane (10 mL), was added 5-((4-ethylpiperazin-1-yl)methyl)pyridin-2-amine (162 mg, 0.738 mmol, 1.1 equiv) and cesium carbonate (299 mg, 0.918 mmol, 1.5 equiv). The reaction mixture was aerated with nitrogen gas for 30 min., followed by the addition of palladium acetate (6.8 mg, 0.030 mmol, 0.05 equiv) and BINAP (19.12 mg, 0.030 mmol, 0.05 equiv). The resultant reaction mixture was stir at 100° C. for 16 h. Progress of the reaction was monitored by TLC and LCMS. After completion of the reaction, the reaction mixture was diluted with water (50 mL) and extracted wit EtOAc (50 mL×2), organic layer was washed with NaHCO$_3$ (100 mL), brine solution (50 mL×3) and dried over anhydrous Na$_2$SO$_4$. Concentrated under reduced pressure to obtain crude compound, which was purified by reverse phase combi-flash chromatography to obtain cyclopropyl(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)methanone (80 mg) as a yellow solid compound.

LCMS 536 [M+H]$^+$ $^1$H NMR (400 MHz, DMSO-d$_6$) δ 9.98 (s, 1H), 8.66 (d, J=3.95 Hz, 1H), 8.43 (br. s., 1H), 8.11-8.27 (m, 2H), 7.63-7.80 (m, 2H), 4.47 (t, J=4.17 Hz, 2H), 4.09 (br. s., 2H), 3.42 (s, 3H), 2.38 (br. s., 3H), 2.24-2.35 (m, 4H), 2.11-2.24 (m, 5H), 0.94-1.06 (m, 3H), 0.89 (dd, J=3.73, 6.80 Hz, 2H).

Example-9: Synthesis of 4-(4-(4-aminocyclohexyl)-8-fluoro-3,4-dihydro-2H-benzo[b][,4]oxazin-6-yl)-N-(5-((4-ethylpiperazin-1-yl)methyl)pyridin-2-yl)-5-fluoropyrimidin-2-amine (Compound 9)

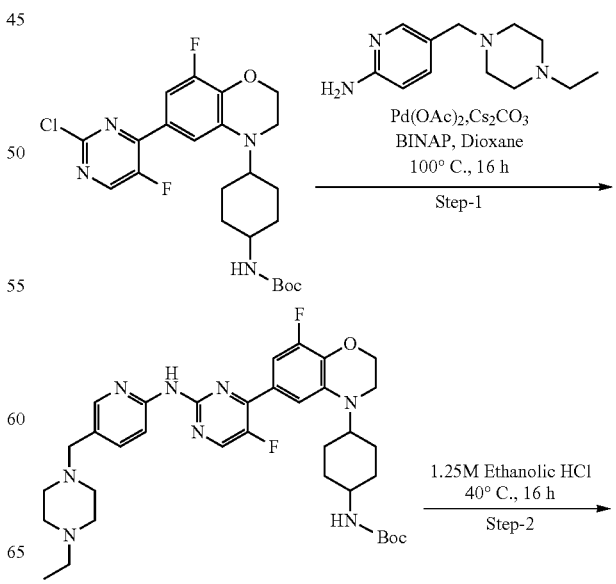

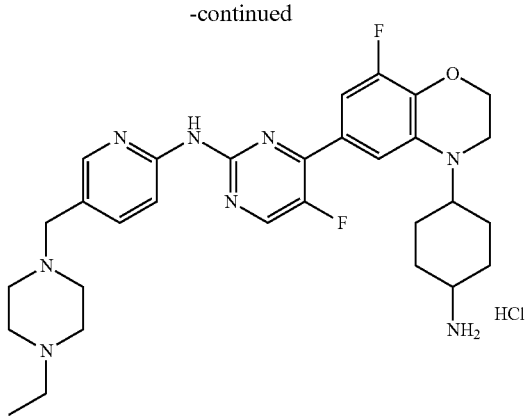

Step-1: Synthesis of tert-butyl (4-(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)cyclohexyl)carbamate To a solution of 4-(4-((tert-butoxycarbonyl)amino)cyclohexyl)-6-(2-chloro-5-fluoropyrimidin-4-yl)-8-fluoro-2H-benzo[b][1,4]oxazin-4-ium (100 mg, 0.31 mmol, 1 equiv) in dioxane (4 mL), was added 5-((4-ethylpiperazin-1-yl)methyl)pyridin-2-amine (82 mg, 0.34 mmol, 1.1 equiv), and cesium carbonate (151 mg, 0.47 mmol, 1.5 equiv). The reaction mass was degassed by the purging nitrogen for 10 min. After 10 min, BINAP (6.5 mg, 0.0123 mmol, 0.04 equiv), and Pd(OAc)$_2$ (1.4 mg, 0.0062 mmol, 0.02 equiv) were added, followed by nitrogen purging for 10 min. Resultant reaction mixture was stirred at 100° C. for 16 h. Reaction was monitored by LCMS. After completion of reaction, reaction mass was diluted with water (5 mL) and extracted with EtOAc (3×10 mL). Organic layer was passed through the anhydrous Na$_2$SO$_4$, filtered and concentrated the organic layer under reduced pressure to afford 200 mg crude desired product. Crude compound was purified by combiflash and further purified by reverse phase HPLC to afford 30 mg tert-butyl (4-(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)cyclohexyl)carbamate.

LCMS 665 [M+H]$^+$

Step-2: Synthesis of 4-(4-(4-aminocyclohexyl)-8-fluoro-3,4-dihydro-2H-benzo[b][1,4]oxazin-6-yl)-N-(5-((4-ethylpiperazin-1-yl)methyl)pyridin-2-yl)-5-fluoropyrimidin-2-amine To a solution of tert-butyl (4-(6-(2-((5-((4-ethylpiperazin-1-yl)methyl)pyridin-2-yl)amino)-5-fluoropyrimidin-4-yl)-8-fluoro-2,3-dihydro-4H-benzo[b][1,4]oxazin-4-yl)cyclohexyl)carbamate (20 mg) in 1.25M ethanolic HCl (3 mL). The resultant reaction mixture was stirred at 40° C. for 16 h. Reaction was monitored by LCMS. After completion of reaction, filtered the solid product and washed with diethyl ether and dried under reduced pressure to afford 10 mg of 4-(4-(4-aminocyclohexyl)-8-fluoro-3,4-dihydro-2H-benzo[b][1,4]oxazin-6-yl)-N-(5-((4-ethylpiperazin-1-yl)methyl)pyridin-2-yl)-5-fluoropyrimidin-2-amine hydrochloride.

LCMS 565 [M+H]$^+$ $^1$H NMR (400 MHz, Methanol-d4) δ 8.73 (s, 1H), 8.65-8.42 (m, 2H), 7.69 (t, J=13.2 Hz, 1H), 7.57 (s, 1H), 7.38 (d, J=11.3 Hz, 1H), 4.36 (d, J=25.9 Hz, 4H), 3.96-3.36 (m, 14H), 3.20 (d, J=18.4 Hz, 5H), 2.18 (s, 2H), 2.03-1.88 (m, 5H), 1.76 (s, 7H), 1.45-1.22 (m, 6H), 1.21 (s, 4H), 0.89 (dd, J=16.3, 7.6 Hz, 2H).

Example-10: Synthesis of 5-fluoro-4-(8-fluoro-4-isopropyl-3,4-dihydro-2H-benzo[b][1,4]oxazin-6-yl)-N-(5-(3-methylpiperazin-1-yl)pyridin-2-yl)pyrimidin-2-amine (Compound 10)

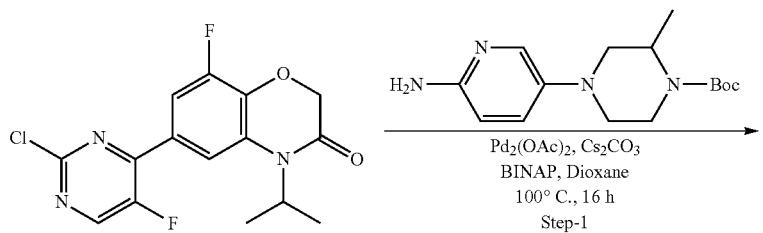

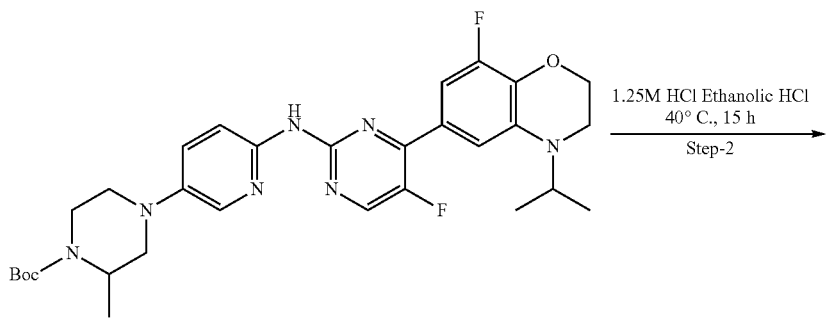

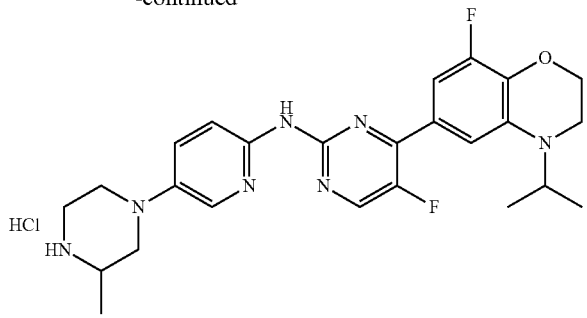

Step-1: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-2-methylpiperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.31 mmol, 1 equiv) in dioxane (5 mL), was tert-butyl 4-(6-aminopyridin-3-yl)-2-methylpiperazine-1-carboxylate (98 mg, 0.34 mmol, 1.1 equiv), and cesium carbonate (151 mg, 0.47 mmol, 1.5 equiv). The reaction mass was degassed by the purging nitrogen for 10 min. After 10 min, BINAP (7.7 mg, 0.0123 mmol, 0.04 equiv), and Pd(OAc)$_2$ (1.4 mg, 0.0062 mmol, 0.02 equiv) were added, followed by nitrogen purging for 10 min. Resultant reaction mixture was stirred at 100° C. for 28 h. Reaction was monitored by LCMS. After completion of reaction, reaction mass was diluted with water (5 mL) and extracted with EtOAc (3×10 mL). Organic layer was passed through the anhydrous Na$_2$SO$_4$, filtered and concentrated the organic layer under reduced pressure to afford 200 mg crude desired product. Crude compound was purified by combi-flash and further purified by reverse phase HPLC to afford 50 mg of tert-butyl 4-(6-((5-fluoro-4-(8-fluoro-4-isopropyl-3,4-dihydro-2H-benzo[b][1,4]oxazin-6-yl)pyrimidin-2-yl) amino)pyridin-3-yl)-2-methylpiperazine-1-carboxylate.

LCMS 582 [M+H]$^+$

Step-2: Synthesis of 5-fluoro-4-(8-fluoro-4-isopropyl-3,4-dihydro-2H-benzo[b][1,4]oxazin-6-yl)-N-(5-(3-methylpiperazin-1-yl)pyridin-2-yl)pyrimidin-2-amine To a solution of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-2-methylpiperazine-1-carboxylate (50 mg) in 1.25M ethanolic HCl (3 mL). The resultant reaction mixture was stirred at RT for 16 h. Reaction was monitored by LCMS. After completion of reaction, filtered the solid product and purified by reverse phase HPLC to afford 13 mg of 5-fluoro-4-(8-fluoro-4-isopropyl-3,4-dihydro-2H-benzo[b][1,4]oxazin-6-yl)-N-(5-(3-methylpiperazin-1-yl)pyridin-2-yl)pyrimidin-2-amine hydrochloride.

LCMS 482 [M+H]$^+$ $^1$H NMR (400 MHz, Methanol-d4) δ 8.40 (d, J=4.0 Hz, 1H), 8.18 (d, J=9.1 Hz, 1H), 8.04-7.98 (m, 1H), 7.50 (q, J=4.2, 3.5 Hz, 2H), 7.24 (d, J=11.6 Hz, 1H), 4.36-4.29 (m, 2H), 4.21 (p, J=6.8 Hz, 1H), 3.62 (t, J=13.8 Hz, 2H), 3.39-3.33 (m, 2H), 3.26 (s, 3H), 3.21-3.13 (m, 1H), 2.88 (t, J=11.6 Hz, 1H), 2.59 (t, J=11.3 Hz, 1H), 1.94 (s, 4H), 1.27 (dd, J=10.9, 6.4 Hz, 12H), 0.90 (s, 1H).

Example-11: Synthesis of 5-fluoro-N-(2-fluoro-4-(piperazin-1-yl)phenyl)-4-(8-fluoro-4-isopropyl-3,4-dihydro-2H-benzo[b][1,4]oxazin-6-yl)pyrimidin-2-amine (Compound 11)

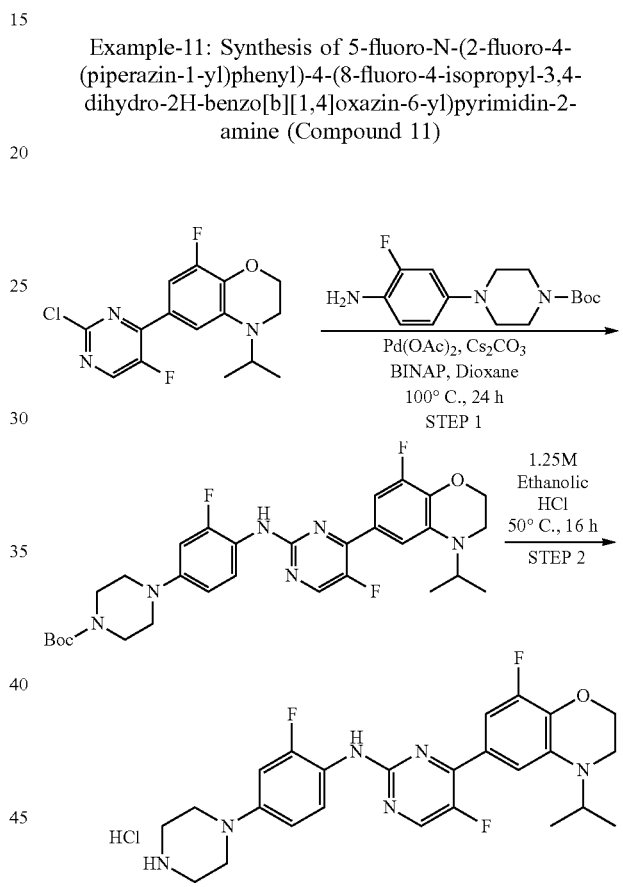

Step-1: Synthesis of tert-butyl 4-(3-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.31 mmol, 1 equiv) in dioxane (4 mL), was tert-butyl 4-(4-amino-3-fluorophenyl)piperazine-1-carboxylate (101 mg, 0.34 mmol, 1.1 equiv), and cesium carbonate (151 mg, 0.47 mmol, 1.5 equiv). The reaction mass was degassed by the purging nitrogen for 10 min. After 10 min, BINAP (7.7 mg, 0.0123 mmol, 0.04 equiv), and Pd(OAc)$_2$ (1.4 mg, 0.0062 mmol, 0.02 equiv) were added, followed by nitrogen purging for 10 min. Resultant reaction mixture was stirred at 100° C. for 24 h. Reaction was monitored by LCMS. After completion of reaction, reaction mass was diluted with water (5 mL) and extracted with EtOAc (20 mL×3). Organic layer was passed through the anhydrous Na₂SO₄, filtered and concentrated the organic layer under reduced pressure to afford crude desired product. Crude compound was purified by purified by reverse phase HPLC to afford 75 mg of tert-butyl 4-(3-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate.

LCMS 585 [M+H]⁺

Step-2: Synthesis of 5-fluoro-N-(2-fluoro-4-(piperazin-1-yl)phenyl)-4-(8-fluoro-4-isopropyl-3,4-dihydro-2H-benzo[b][1,4]oxazin-6-yl)pyrimidin-2-amine To a solution of tert-butyl 4-(3-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (75 mg) in 1.25M ethanolic HCl (3 mL). The resultant reaction mixture was stirred at 50° C. for 1 h. Reaction was monitored by LCMS. After completion of reaction, filtered the solid product and dried under reduced pressure to afford 71 mg of 5-fluoro-N-(2-fluoro-4-(piperazin-1-yl)phenyl)-4-(8-fluoro-4-isopropyl-3,4-dihydro-2H-benzo[b][1,4]oxazin-6-yl)pyrimidin-2-aminehydrochloride.

LCMS 485 [M+H]⁺

¹H NMR (400 MHz, Methanol-d4) δ 8.40 (d, J=4.5 Hz, 1H), 7.64 (d, J=9.3 Hz, 1H), 7.50 (s, 1H), 7.30 (d, J=11.4 Hz, 1H), 7.02-6.89 (m, 2H), 4.37-4.30 (m, 2H), 4.10 (h, J=5.6 Hz, 1H), 3.50 (s, 4H), 3.39 (s, 3H), 1.22 (d, J=6.1 Hz, 6H).

Example-12: Synthesis of 5-fluoro-N-(3-fluoro-4-(piperazin-1-yl)phenyl)-4-(8-fluoro-4-isopropyl-3,4-dihydro-2H-benzo[b][1,4]oxazin-6-yl)pyrimidin-2-amine hydrochloride (Compound 12)

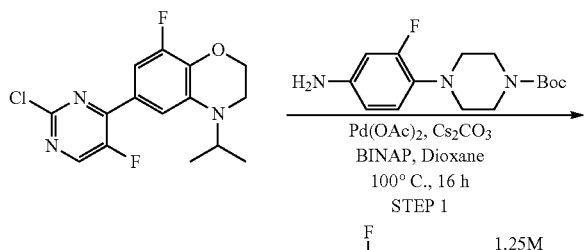

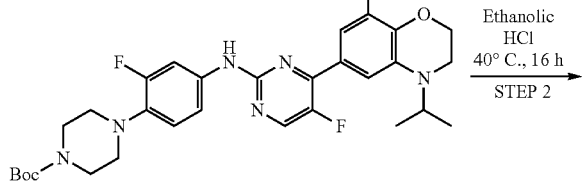

Step-1: Synthesis of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.31 mmol, 1 equiv) in dioxane (4 mL), was added tert-butyl 4-(4-amino-2-fluorophenyl)piperazine-1-carboxylate (82 mg, 0.34 mmol, 1.1 equiv), and cesium carbonate (151 mg, 0.47 mmol, 1.5 equiv). The reaction mass was degassed by the purging nitrogen for 10 min. After 10 min, BINAP (6.5 mg, 0.0123 mmol, 0.04 equiv), and Pd(OAc)₂ (1.4 mg, 0.0062 mmol, 0.02 equiv) were added, followed by nitrogen purging for 10 min. Resultant reaction mixture was stirred at 100° C. for 16 h. Reaction was monitored by LCMS. After completion of reaction, reaction mass was diluted with water (5 mL) and extracted with EtOAc (10 mL×3). Organic layer was passed through the anhydrous Na₂SO₄, filtered and concentrated the organic layer under reduced pressure to afford 200 mg crude desired product. Crude compound was purified by combi-flash and further purified by reverse phase HPLC to afford 30 mg of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate.

LCMS 585 [M+H]⁺

Step-2: Synthesis of 5-fluoro-N-(3-fluoro-4-(piperazin-1-yl)phenyl)-4-(8-fluoro-4-isopropyl-3,4-dihydro-2H-benzo[b][1,4]oxazin-6-yl)pyrimidin-2-amine hydrochloride To a solution of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (20 mg) in 1.25M ethanolic HCl (3 mL). The resultant reaction mixture was stirred at 40° C. for 16 h. Reaction was monitored by LCMS. After completion of reaction, filtered the solid product and washed with diethyl ether and dried under reduced pressure to afford 10 mg of 5-fluoro-N-(3-fluoro-4-(piperazin-1-yl)phenyl)-4-(8-fluoro-4-isopropyl-3,4-dihydro-2H-benzo[b][1,4]oxazin-6-yl)pyrimidin-2-amine hydrochloride.

LCMS 485 [M+H]⁺

¹H NMR (400 MHz, Methanol-d4) δ 8.38 (d, J=4.3 Hz, 1H), 7.82 (dd, J=14.9, 2.5 Hz, 1H), 7.56 (s, 1H), 7.36-7.29 (m, 1H), 7.29-7.23 (m, 1H), 7.07 (t, J=9.2 Hz, 1H), 4.37-4.19 (m, 3H), 3.44-3.25 (m, 10H), 2.68 (d, J=15.3 Hz, 1H), 1.55 (s, 2H), 1.32-1.27 (m, 3H), 1.26 (d, J=6.6 Hz, 6H), 0.88 (dd, J=12.7, 6.8 Hz, 2H).

Example-13: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine (Compound 13)

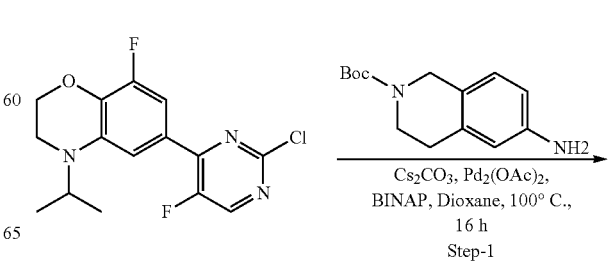

Step-1

-continued

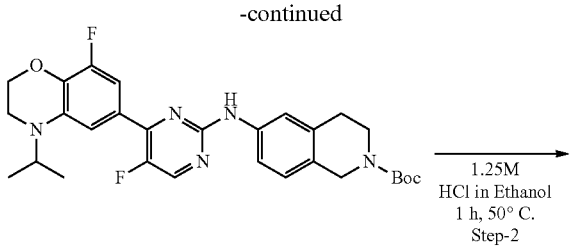

Step-1: Synthesis of tert-butyl 6-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (10 mL), was added tert-butyl 6-amino-3,4-dihydroisoquinoline-2(1H)-carboxylate (168 mg, 0.67 mmol, 1.1 equiv) and cesium carbonate (298 mg, 0.91 mmol, 1.5 equiv). The reaction mixture was degassed with nitrogen gas for 30 min., followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with EtOAc (100 mL). Organic layer was washed with water (50 mL) and brine solution (50 mL). Organic layer was dried over anhydrous Na$_2$SO$_4$ and concentrated under reduced pressure to obtain crude, which was purified by normal phase combi flash to obtain tert-butyl 6-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (80 mg, 24%) as a yellow solid compound.
LCMS 538.4[M+H]$^+$ Step-2: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine A solution of tert-butyl 6-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (90 mg, 0.11 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine (40 mg, 91%) as a brick red color solid compound.
LCMS 438.4 [M+H]$^+$
$^1$HNMR (400 MHz, DMSO-d6) δ 9.75 (s, 1H), 9.41 (s, 1H), 8.58 (d, J=3.9 Hz, 1H), 7.68-7.59 (m, 2H), 7.40 (s, 1H), 7.15 (dd, J=15.4, 10.0 Hz, 2H), 4.30 (t, J=4.2 Hz, 2H), 4.16 (dt, J=25.2, 5.7 Hz, 3H), 3.33 (dt, J=17.4, 4.3 Hz, 4H), 2.98 (t, J=6.3 Hz, 2H), 1.19 (d, J=6.5 Hz, 6H).

Example-14: Synthesis of 5-fluoro-N-(3-fluoro-4-(4-methylpiperazin-1-yl) phenyl)-4-(8-fluoro-4-isopropyl-3,4-dihydro-2H-benzo[b][1,4]oxazin-6-yl) pyrimidin-2-amine (Compound 14)

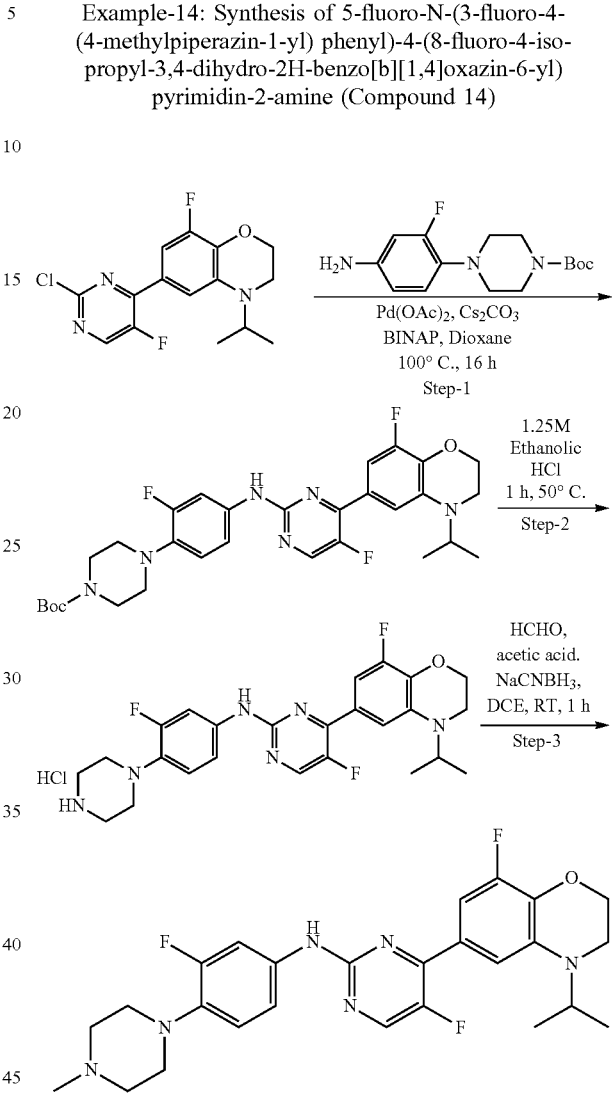

Step-1: Synthesis of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (300 mg, 0.92 mmol, 1 equiv) in dioxane (10 mL), was added tert-butyl 4-(4-amino-2-fluorophenyl)piperazine-1-carboxylate (300 mg, 1.01 mmol, 1.1 equiv) and cesium carbonate (450 mg, 1.38 mmol, 1.5 equiv). The reaction mixture was degassed with nitrogen gas for 30 min., followed by the addition of palladium acetate (4 mg, 0.01 mmol, 0.02 equiv) and BINAP (23 mg, 0.03 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with EtOAc (100 mL). Organic layer was washed with water (50 mL) and brine solution (50 mL). Organic layer was dried over anhydrous Na₂SO₄ and concentrated under reduced pressure to obtain crude, which was purified by normal phase combi flash to obtain tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (95 mg, 18%) as a yellow solid compound.

LCMS 584 [M+H]⁺

Step-2: Synthesis of 5-fluoro-N-(3-fluoro-4-(piperazin-1-yl) phenyl)-4-(8-fluoro-4-isopropyl-3,4-dihydro-2H-benzo[b][1,4]oxazin-6-yl)pyrimidin-2-amine A solution of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (85 mg, 0.15 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-N-(3-fluoro-4-(piperazin-1-yl) phenyl)-4-(8-fluoro-4-isopropyl-3,4-dihydro-2H-benzo[b][1,4]oxazin-6-yl)pyrimidin-2-amine (80 mg, 95%) as an orange colour solid compound.

LCMS 484 [M+H]⁺

Step-3: Synthesis of 5-fluoro-N-(3-fluoro-4-(4-methylpiperazin-1-yl) phenyl)-4-(8-fluoro-4-isopropyl-3,4-dihydro-2H-benzo[b][1,4]oxazin-6-yl) pyrimidin-2-amine To a stirred solution of 5-fluoro-N-(3-fluoro-4-(piperazin-1-yl) phenyl)-4-(8-fluoro-4-isopropyl-3,4-dihydro-2H-benzo[b][1,4]oxazin-6-yl)pyrimidin-2-amine (80 mg, 0.15 mmol, 1 equiv) in DCE (5 mL), was added HCHO in water (0.02 mL, 0.46 mmol, 3 equiv), acetic acid (0.05 mL, 0.75 mmol, 5 equiv). The reaction mixture was allowed to stir at RT for 1 h. The reaction mixture was cooled to 0° C. NaCNBH₃ (29 mg, 0.46 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with EtOAc (50 mL×2). Organic layer was washed with water (50 mL) and brine solution (50 mL). Organic layer was dried over anhydrous Na₂SO₄ and concentrated under reduced pressure to obtain crude, which was purified by reverse phase HPLC to afford 5-fluoro-N-(3-fluoro-4-(4-methylpiperazin-1-yl)phenyl)-4-(8-fluoro-4-isopropyl-3,4-dihydro-2H-benzo[b][1,4]oxazin-6-yl)pyrimidin-2-amine (15 mg, 19%) as a yellow solid compound.
LCMS 499 [M+H]+

¹HNMR (400 MHz, DMSO-d6) δ 9.78 (s, 1H), 8.57 (d, J=3.9 Hz, 1H), 7.78 (dd, J=15.2, 2.5 Hz, 1H), 7.45-7.35 (m, 2H), 7.16 (d, J=11.6 Hz, 1H), 7.03 (t, J=9.3 Hz, 1H), 4.30 (t, J=4.1 Hz, 2H), 4.15 (p, J=6.7 Hz, 1H), 3.13-2.95 (m, 10H), 2.63 (s, 3H), 1.19 (d, J=6.4 Hz, 6H).

Example-15: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-5-amine (Compound 15)

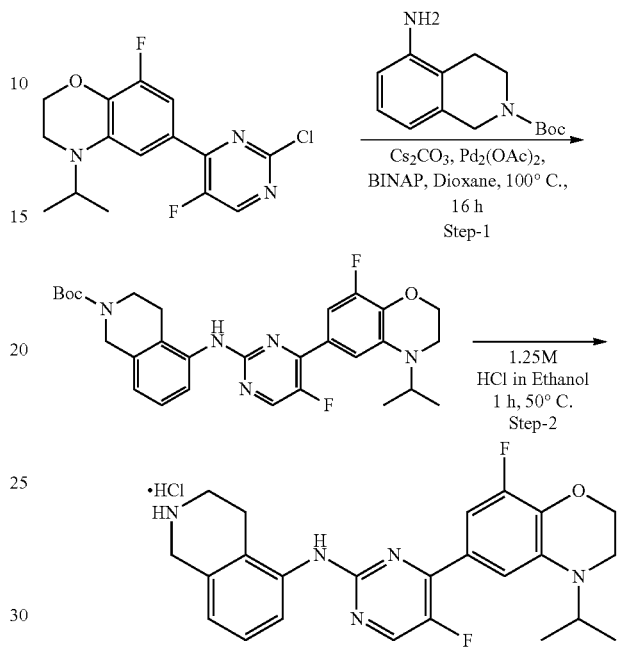

Step-1: Synthesis of tert-butyl 5-((5-fluoro-4-(8-fluoro-4-isopropyl-3,4-dihydro-2H-benzo[b][1,4] oxazin-6-yl)pyrimidin-2-yl)amino)-3,4-dihydroisoquinoline-2(1H)-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (10 mL), was added tert-butyl 5-amino-3,4-dihydroisoquinoline-2(1H)-carboxylate (168 mg, 0.67 mmol, 1.1 equiv) and cesium carbonate (298 mg, 0.91 mmol, 1.5 equiv). The reaction mixture was degassed with nitrogen gas for 30 min., followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with EtOAc (100 mL). Organic layer was washed with water (50 mL) and brine solution (50 mL). Organic layer was dried over anhydrous Na₂SO₄ and concentrated under reduced pressure to obtain crude, which was purified by normal phase combi flash to tert-butyl 5-((5-fluoro-4-(8-fluoro-4-isopropyl-3,4-dihydro-2H-benzo[b][1,4]oxazin-6-yl)pyrimidin-2-yl) amino)-3,4-dihydroisoquinoline-2(1H)-carboxylate (120 mg, 36%) as a yellow solid compound.
LCMS 538.4[M+H]⁺

Step-2: Synthesis of N-(5-fluoro-4-(8-fluoro-4-isopropyl-3,4-dihydro-2H-benzo[b][1,4]oxazin-6-yl) pyrimidin-2-yl)-1,2,3,4-tetrahydroisoquinolin-5-amine A solution of tert-butyl 5-((5-fluoro-4-(8-fluoro-4-isopropyl-3,4-dihydro-2H-benzo[b][1,4]oxazin-6-yl)pyrimidin-2- yl)amino)-3,4-dihydroisoquinoline-2(1H)-carboxylate (70 mg, 0.13 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-5-amine (55 mg, 89%) as a brick red color solid compound.

LCMS 438.4 [M+H]⁺

¹HNMR (400 MHz, DMSO-d6) δ 9.45 (d, J=5.7 Hz, 1H), 9.01 (s, 1H), 8.48 (d, J=4.0 Hz, 1H), 7.59 (d, J=7.9 Hz, 1H), 7.33 (s, 1H), 7.25 (t, J=7.8 Hz, 1H), 7.07 (dd, J=28.2, 9.6 Hz, 2H), 4.27 (q, J=5.3, 4.6 Hz, 4H), 4.04 (h, J=6.8 Hz, 1H), 3.31 (dt, J=24.7, 4.6 Hz, 4H), 2.97 (t, J=6.3 Hz, 2H), 1.15 (d, J=6.5 Hz, 6H).

Example-16: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine (Compound 16)

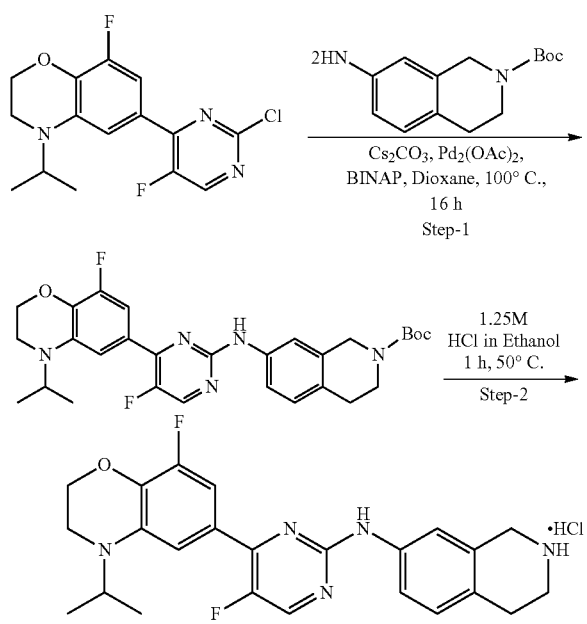

Step-1: Synthesis of tert-butyl 7-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (10 mL), was added tert-butyl 7-amino-3,4-dihydroisoquinoline-2(1H)-carboxylate (168 mg, 0.67 mmol, 1.1 equiv) and cesium carbonate (298 mg, 0.91 mmol, 1.5 equiv). The reaction mixture was degassed with nitrogen gas for 30 min., followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with EtOAc (100 mL). Organic layer was washed with water (50 mL) and brine solution (50 mL). Organic layer was dried over anhydrous Na₂SO₄ and concentrated under reduced pressure to obtain crude, which was purified by normal phase combi flash to obtain tert-butyl 7-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (100 mg, 30%) as a yellow solid compound.

LCMS 538.4 [M+H]⁺

Step-2: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine A solution of tert-butyl 7-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (90 mg, 0.11 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine (80 mg, 79%) as a brick red color solid compound.

LCMS 438.4 [M+H]⁺

¹HNMR (400 MHz, DMSO-d6) δ 9.75 (s, 1H), 9.41 (s, 1H), 8.58 (d, J=3.9 Hz, 1H), 7.68-7.59 (m, 2H), 7.40 (s, 1H), 7.15 (dd, J=15.4, 10.0 Hz, 2H), 4.30 (t, J=4.2 Hz, 4H), 4.16 (dt, J=25.2, 5.7 Hz, 1H), 3.33 (dt, J=17.4, 4.3 Hz, 4H), 2.98 (t, J=6.3 Hz, 2H), 1.19 (d, J=6.5 Hz, 6H).

Example-17: Synthesis of 5-fluoro-N-(3-fluoro-4-(4-isopropylpiperazin-1-yl) phenyl)-4-(8-fluoro-4-isopropyl-3,4-dihydro-2H-benzo[b][1,4]oxazin-6-yl)pyrimidin-2-amine (Compound 17)

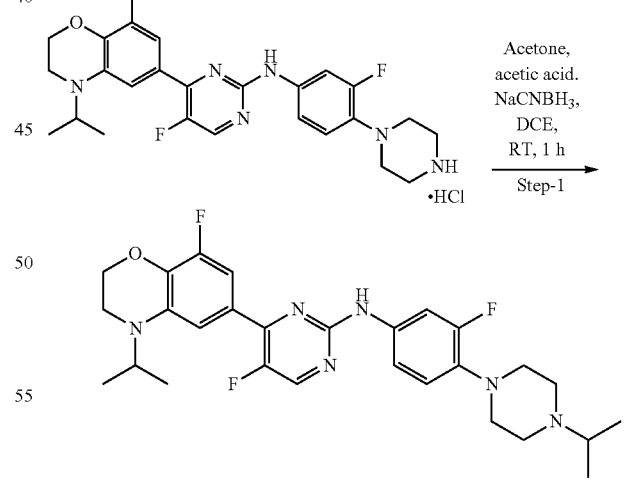

Step-1: Synthesis of 5-fluoro-N-(3-fluoro-4-(4-isopropylpiperazin-1-yl) phenyl)-4-(8-fluoro-4-isopropyl-3,4-dihydro-2H-benzo[b][1,4]oxazin-6-yl)pyrimidin-2-amine To a stirred solution of 5-fluoro-N-(3-fluoro-4-(piperazin-1-yl)phenyl)-4-(8-fluoro-4-isopropyl-3,4-dihydro-2H- benzo[b][1,4]oxazin-6-yl)pyrimidin-2-amine (30 mg, 0.06 mmol, 1 equiv) in DCE (5 mL), was added Acetone (0.01 mL, 0.18 mmol, 3 equiv), acetic acid (0.01 mL, 0.3 mmol, 5 equiv). The reaction mixture was allowed to stir at RT for 1 h. The reaction mixture was cooled to 0° C. NaCNBH$_3$ (11 mg, 0.18 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with EtOAc (50 mL×2). Organic layer was washed with water (50 mL) and brine solution (50 mL). Organic layer was dried over anhydrous Na$_2$SO$_4$ and concentrated under reduced pressure to obtain crude, which was purified by reverse phase HPLC to afford 5-fluoro-N-(3-fluoro-4-(4-isopropylpiperazin-1-yl)phenyl)-4-(8-fluoro-4-isopropyl-3,4-dihydro-2H-benzo[b][1,4]oxazin-6-yl)pyrimidin-2-amine (5 mg, 15%) as a yellow solid compound.

LCMS 527 [M+H]$^+$ $^1$HNMR (400 MHz, DMSO-d6) δ 9.71 (s, 1H), 8.56 (d, J=4.0 Hz, 1H), 7.72 (dd, J=15.4, 2.5 Hz, 1H), 7.44 (s, 1H), 7.37 (d, J=8.2 Hz, 1H), 7.15 (d, J=11.5 Hz, 1H), 6.96 (t, J=9.4 Hz, 1H), 4.30 (t, J=4.4 Hz, 2H), 4.13 (dp, J=15.2, 5.9, 5.3 Hz, 1H), 3.18-3.04 (m, 2H), 2.94 (t, J=4.6 Hz, 4H), 2.58 (t, J=4.8 Hz, 4H), 2.08 (s, 1H), 1.18 (d, J=6.5 Hz, 6H), 1.00 (d, J=6.5 Hz, 6H).

Example-18: Synthesis of 5-fluoro-N-(3-fluoro-4-(piperidin-4-yl) phenyl)-4-(8-fluoro-4-isopropyl-3,4-dihydro-2H-benzo[b][1,4]oxazin-6-yl) pyrimidin-2-amine (Compound 18)

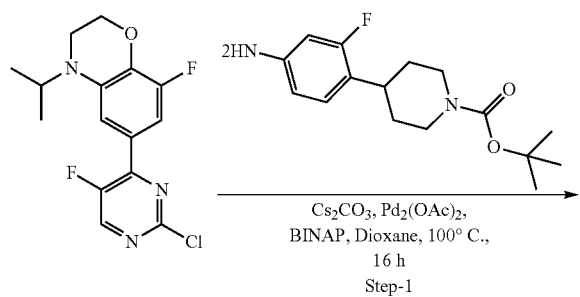

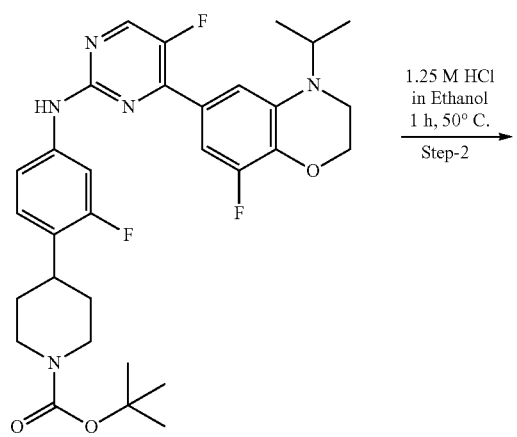

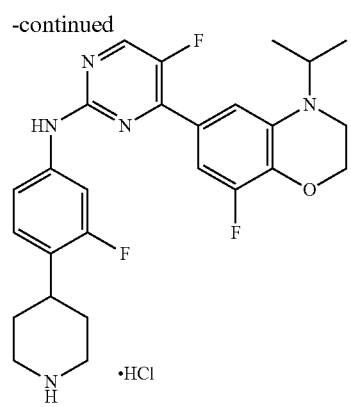

Step-1: Synthesis of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino) phenyl)piperidine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) in dioxane (10 mL), was added tert-butyl 4-(4-amino-2-fluorophenyl)piperidine-1-carboxylate (148 mg, 0.50 mmol, 1.1 equiv) and cesium carbonate (225 mg, 0.69 mmol, 1.5 equiv). The reaction mixture was degassed with nitrogen gas for 30 min., followed by the addition of palladium acetate (3 mg, 0.009 mmol, 0.02 equiv) and BINAP (12 mg, 0.018 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidine-1-carboxylate (80 mg, 30%) as a yellow solid compound.

LCMS: 584[M+H]$^+$

Step-2: Synthesis of 5-fluoro-N-(3-fluoro-4-(piperidin-4-yl) phenyl)-4-(8-fluoro-4-isopropyl-3,4-dihydro-2H-benzo[b][1,4]oxazin-6-yl) pyrimidin-2-amine A solution of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidine-1-carboxylate (50 mg, 0.08 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-N-(3-fluoro-4-(piperidin-4-yl) phenyl)-4-(8-fluoro-4-isopropyl-3,4-dihydro-2H-benzo[b][1,4]oxazin-6-yl)pyrimidin-2-amine (34 mg, 83%) as a brick red color solid compound.

LCMS: 484 [M+H]$^+$ $^1$H NMR: (400 MHz, DMSO-d6) δ 9.93 (s, 1H), 8.84 (d, J=11.4 Hz, 1H), 8.62 (dd, J=15.0, 7.6 Hz, 1H), 7.80 (dd, J=13.6, 2.4 Hz, 1H), 7.45 (d, J=7.5 Hz, 2H), 7.16 (dd, J=11.0, 5.6 Hz, 2H), 4.30 (t, J=4.1 Hz, 2H), 4.17 (p, J=6.6

Hz, 1H), 3.40-3.28 (m, 4H), 3.13-2.96 (m, 3H), 1.88 (h, J=4.0 Hz, 4H), 1.19 (d, J=6.5 Hz, 6H).

Example-19: Synthesis of N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-7-amine (Compound 19)

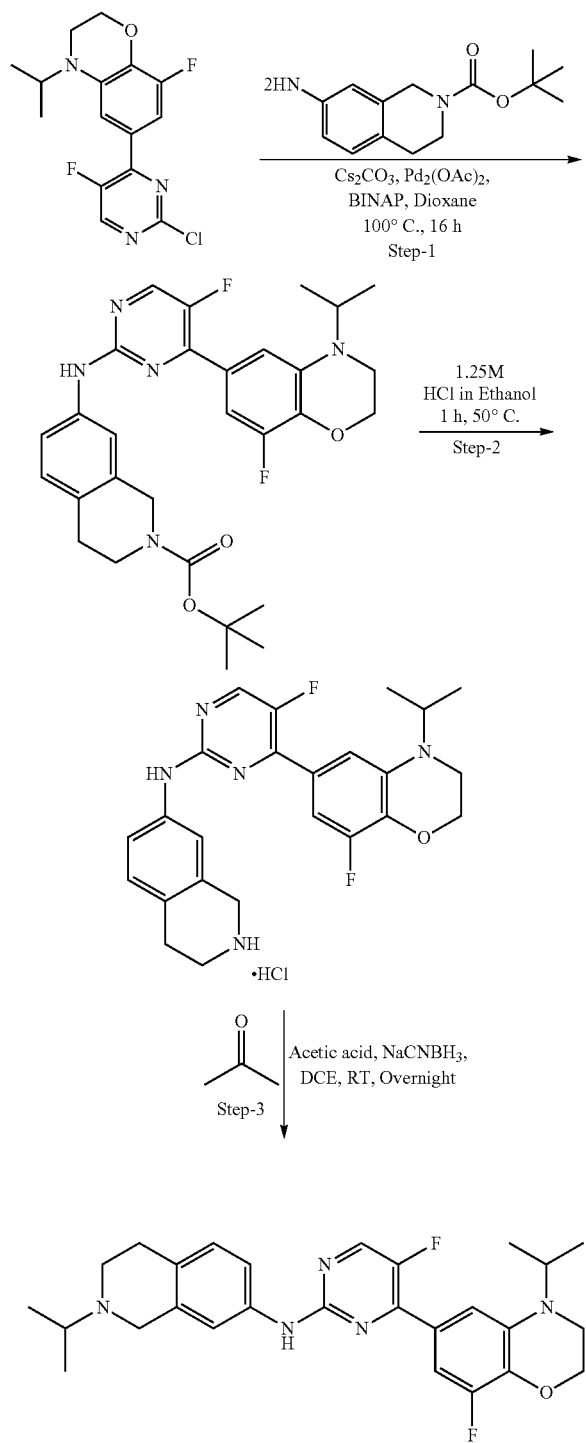

Step-1: Synthesis of tert-butyl 7-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (10 mL), was added tert-butyl 7-amino-3,4-dihydroisoquinoline-2(1H)-carboxylate (168 mg, 0.67 mmol, 1.1 equiv) and cesium carbonate (298 mg, 0.91 mmol, 1.5 equiv). The reaction mixture was degassed with nitrogen gas for 30 min., followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 7-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (100 mg, 30%) as a yellow solid compound.
LCMS: 538.4[M+H]$^+$ Step-2: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine A solution of tert-butyl 7-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (40 mg, 0.07 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine (30 mg, 94%) as a brick red color solid compound.
LCMS: 438.4 [M+H]$^+$ Step-3: Synthesis of N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-7-amine To a stirred solution of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine (50 mg, 0.1 mmol, 1 equiv) in DCE (5 mL), was added Acetone (0.02 mL, 0.3 mmol, 3 equiv), acetic acid (0.03 mL, 0.5 mmol, 5 equiv). The reaction mixture was allowed to stir at RT for 1 h. The reaction mixture was cooled to 0° C. NaCNBH$_3$ (19 mg, 0.3 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-7-amine (10 mg, 20%) as a yellow solid compound.

LCMS: 480 [M+H]⁺

¹HNMR: (400 MHz, DMSO-d6) δ 9.57 (s, 1H), 8.54 (d, J=3.9 Hz, 1H), 7.49 (dd, J=8.3, 2.3 Hz, 1H), 7.44-7.37 (m, 2H), 7.16 (d, J=11.5 Hz, 1H), 6.98 (d, J=8.3 Hz, 1H), 4.29 (t, J=4.4 Hz, 2H), 4.12 (p, J=6.7 Hz, 1H), 3.60 (s, 2H), 3.30 (t, J=4.4 Hz, 2H), 2.84 (dq, J=14.6, 8.1, 7.3 Hz, 1H), 2.72 (t, J=5.5 Hz, 2H), 2.67 (t, J=5.7 Hz, 2H), 1.18 (d, J=6.5 Hz, 6H), 1.05 (d, J=6.5 Hz, 6H).

Example-20: Synthesis of N-(5-fluoro-4-(8-fluoro-4-isopropyl-3,4-dihydro-2H-benzo[b][1,4]oxazin-6-yl)pyrimidin-2-yl)-2-isopropyl-, 2,3,4-tetrahydroisoquinolin-5-amine (Compound 20)

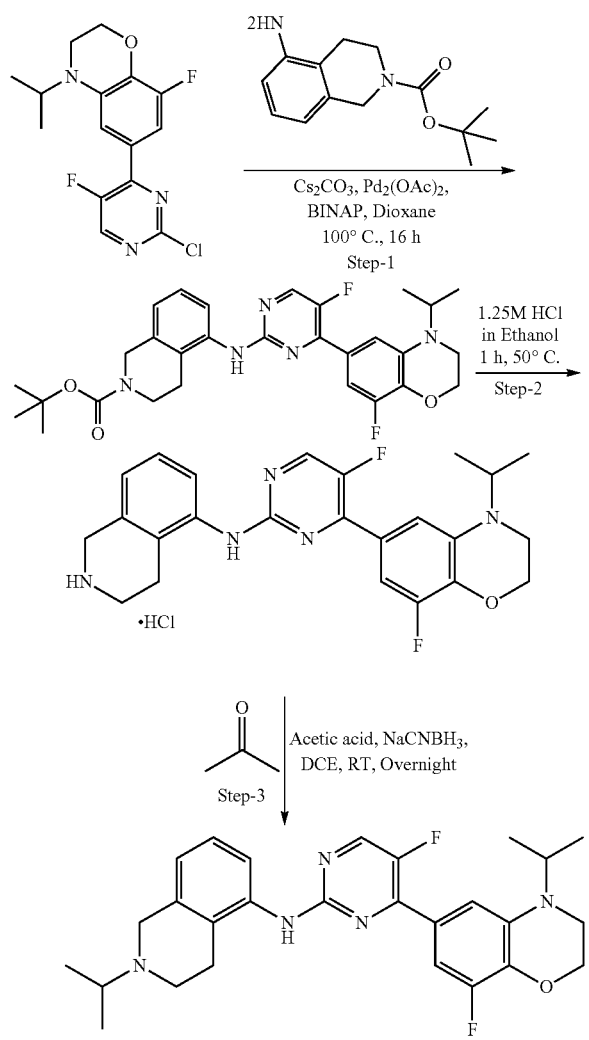

Step-1: Synthesis of tert-butyl 5-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (10 mL), was added tert-butyl 5-amino-3,4-dihydroisoquinoline-2(1H)-carboxylate (168 mg, 0.67 mmol, 1.1 equiv) and cesium carbonate (298 mg, 0.91 mmol, 1.5 equiv). The reaction mixture was degassed with nitrogen gas for 30 min, followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to tert-butyl 5-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (120 mg, 36%) as a yellow solid compound.

LCMS: 538.4 [M+H]⁺

Step-2 Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-5-amine A solution of tert-butyl 5-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (50 mg, 0.09 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-5-amine (35 mg, 88%) as a brick red color solid compound.

LCMS: 438.4 [M+H]⁺

Step-3: Synthesis of N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-5-amin To a stirred solution of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-5-amine (50 mg, 0.1 mmol, 1 equiv) in DCE (5 mL), was added Acetone (0.02 mL, 0.3 mmol, 3 equiv), acetic acid (0.03 mL, 0.5 mmol, 5 equiv). The reaction mixture was allowed to stir at RT for 1 h. The reaction mixture was cooled to 0° C. NaCNBH₃ (19 mg, 0.3 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-5-amine (15 mg, 30%) as a yellow solid compound.

LCMS: 480 [M+H]⁺

¹HNMR: (400 MHz, DMSO-d6) δ 8.78 (s, 1H), 8.46 (d, J=4.0 Hz, 1H), 7.38-7.29 (m, 2H), 7.13-7.06 (m, 2H), 6.89 (d, J=7.6 Hz, 1H), 4.27 (t, J=4.4 Hz, 2H), 4.03-3.97 (m, 1H), 3.64 (s, 2H), 3.26 (t, J=4.3 Hz, 2H), 2.86-2.79 (m, 1H), 2.69 (d, J=5.7 Hz, 2H), 2.65 (d, J=5.4 Hz, 2H), 1.11 (d, J=6.5 Hz, 6H), 1.04 (d, J=6.5 Hz, 6H).

Example-21: Synthesis of 5-((5-fluoro-4-(8-fluoro-4-isopropyl-3,4-dihydro-2H-benzo[b][1,4]oxazin-6-yl) pyrimidin-2-yl) amino)-2-(piperazin-1-yl) benzonitrile (Compound 21)

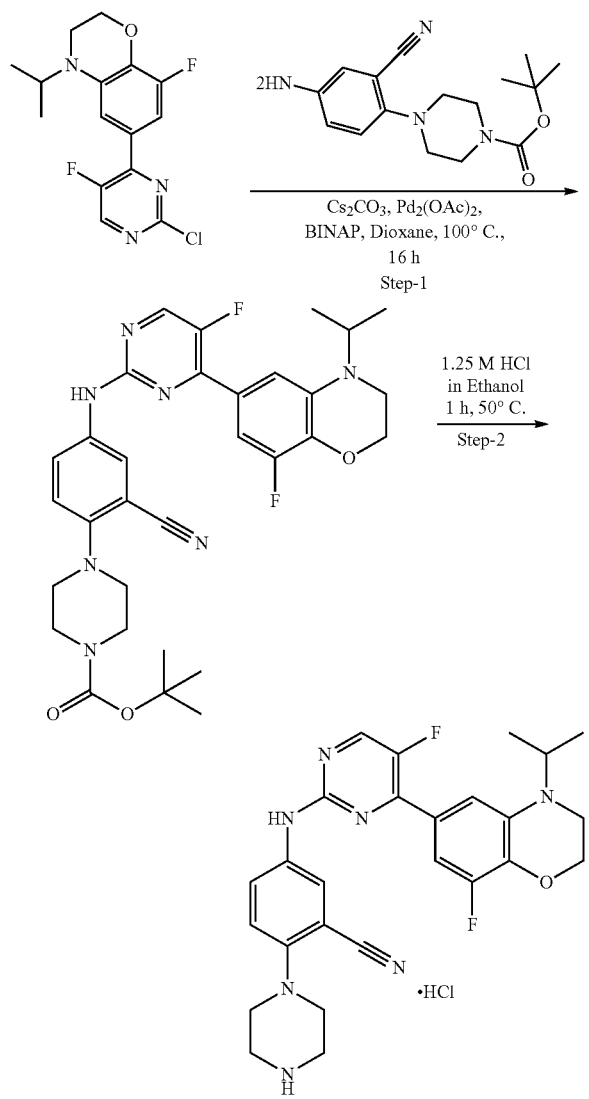

Step-1: Synthesis of tert-butyl 4-(2-cyano-4-((5-fluoro-4-(8-fluoro-4-isopropyl-3,4-dihydro-2H-benzo[b][1,4]oxazin-6-yl)pyrimidin-2-yl)amino) phenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) in dioxane (10 mL), was added tert-butyl 4-(4-amino-2-cyanophenyl)piperazine-1-carboxylate (168 mg, 0.67 mmol, 1.1 equiv) and cesium carbonate (225 mg, 0.69 mmol, 1.5 equiv). The reaction mixture was degassed with nitrogen gas for 30 min., followed by the addition of palladium acetate (2 mg, 0.009 mmol, 0.02 equiv) and BINAP (12 mg, 0.018 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(2-cyano-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (100 mg, 37%) as a yellow solid compound.

LCMS: 592 [M+H]⁺

Step-2: Synthesis of 5-((5-fluoro-4-(8-fluoro-4-isopropyl-3,4-dihydro-2H-benzo[b][1,4]oxazin-6-yl) pyrimidin-2-yl) amino)-2-(piperazin-1-yl) benzonitrile A solution of tert-butyl 4-(2-cyano-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (100 mg, 0.16 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-((5-fluoro-4-(8-fluoro-4-isopropyl-3,4-dihydro-2H-benzo[b][1,4]oxazin-6-yl)pyrimidin-2-yl)amino)-2-(piperazin-1-yl)benzonitrile (80 mg, 97%) as a brick red compound.

LCMS: 492 [M+H]⁺

¹HNMR: (400 MHz, DMSO-d6) δ 9.95 (s, 1H), 9.28 (s, 1H), 8.61 (d, J=3.7 Hz, 1H), 8.18 (d, J=2.4 Hz, 1H), 7.91 (dd, J=9.1, 2.6 Hz, 1H), 7.35 (s, 1H), 7.23 (d, J=8.9 Hz, 1H), 7.14 (d, J=11.3 Hz, 1H), 4.29 (t, J=3.9 Hz, 2H), 4.12 (p, J=6.6 Hz, 1H), 3.28 (d, J=17.2 Hz, 10H), 1.18 (d, J=6.4 Hz, 6H).

Example-22: Synthesis of N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-6-amine (Compound 22)

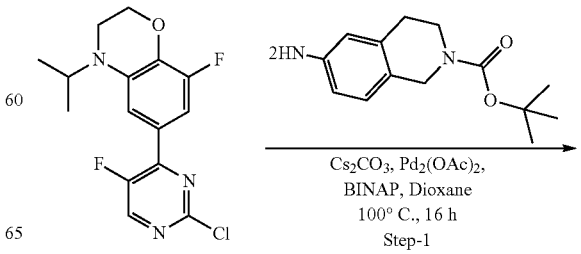

-continued

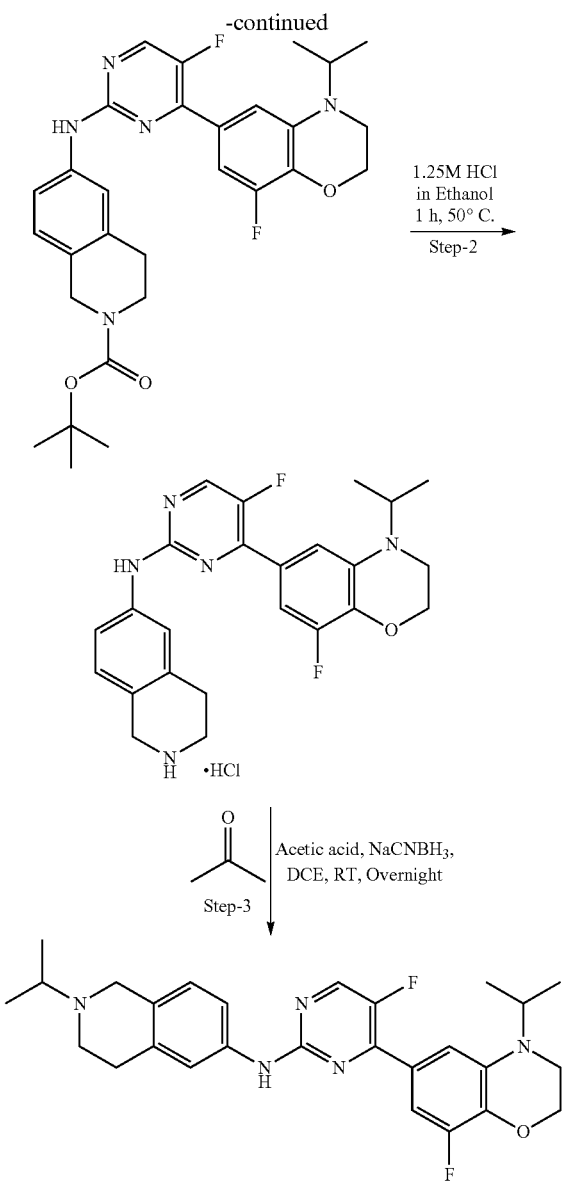

Step-1: Synthesis of tert-butyl 6-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (10 mL), was added tert-butyl 6-amino-3,4-dihydroisoquinoline-2(1H)-carboxylate (168 mg, 0.67 mmol, 1.1 equiv) and cesium carbonate (298 mg, 0.91 mmol, 1.5 equiv). The reaction mixture was degassed with nitrogen gas for 30 min., followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi-flash to obtain tert-butyl 6-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (80 mg, 24%) as a yellow solid compound.

LCMS: 538.4[M+H]$^+$

Step-2: Synthesis of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine A solution of tert-butyl 6-((5-fluoro-4-(8-fluoro-4-isopropyl-3,4-dihydro-2H-benzo[b][1,4]oxazin-6-yl)pyrimidin-2-yl)amino)-3,4-dihydroisoquinoline-2(1H)-carboxylate (30 mg, 0.05 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine (22 mg, 92%) as a brick red color solid compound.

LCMS: 439.4 [M+H]$^+$

Step-3: Synthesis of N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-6-amine To a stirred solution of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine (50 mg, 0.1 mmol, 1 equiv) in DCE (5 mL), was added acetone (0.02 mL, 0.3 mmol, 3 equiv), acetic acid (0.03 mL, 0.5 mmol, 5 equiv). The reaction mixture was allowed to stir at RT for 1 h. The reaction mixture was cooled to 0° C. NaCNBH$_3$ (19 mg, 0.3 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-2-isopropyl-1,2,3,4-tetrahydroisoquinolin-6-amine (10 mg, 20%) as a yellow solid compound.

LCMS: 480 [M+H]$^+$ $^1$HNMR: (400 MHz, DMSO-d6) δ 9.57 (s, 1H), 8.55 (d, J=3.9 Hz, 1H), 7.49 (d, J=7.4 Hz, 2H), 7.41 (s, 1H), 7.16 (d, J=11.6 Hz, 1H), 6.96 (d, J=8.4 Hz, 1H), 4.30 (t, J=4.3 Hz, 2H), 4.13 (p, J=6.5, 6.0 Hz, 1H), 3.58 (s, 2H), 3.33-3.24 (m, 2H), 2.84 (p, J=6.5 Hz, 1H), 2.75 (t, J=5.7 Hz, 2H), 2.67 (t, J=5.6 Hz, 2H), 1.18 (d, J=6.5 Hz, 6H), 1.05 (d, J=6.5 Hz, 6H).

Example-23: Synthesis of 5-fluoro-4-(8-fluoro-4-isopropyl-3,4-dihydro-2H-benzo[b][1,4]oxazin-6-yl)-N-(6-(piperazin-1-yl)pyridin-3-yl)pyrimidin-2-amine (Compound 23)

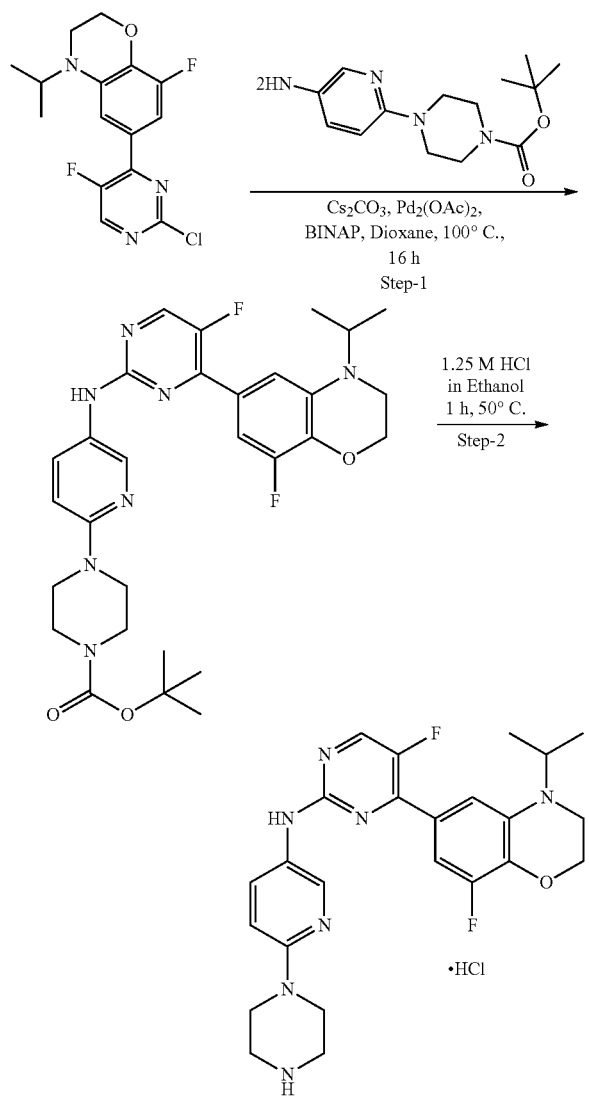

Step-1: Synthesis of tert-butyl 4-(5-((5-fluoro-4-(8-fluoro-4-isopropyl-3,4-dihydro-2H-benzo[b][1,4]oxazin-6-yl)pyrimidin-2-yl)amino)pyridin-2-yl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(5-aminopyridin-2-yl)piperazine-1-carboxylate (94 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(5-((5-fluoro-4-(8-fluoro-4-isopropyl-3,4-dihydro-2H-benzo[b][1,4]oxazin-6-yl)pyrimidin-2-yl)amino)pyridin-2-yl)piperazine-1-carboxylate (50 mg, 29%) as a yellow solid compound.

LCMS: 568 [M+H]$^+$

Step-2: Synthesis of 5-fluoro-4-(8-fluoro-4-isopropyl-3,4-dihydro-2H-benzo[b][1,4]oxazin-6-yl)-N-(6-(piperazin-1-yl)pyridin-3-yl)pyrimidin-2-amine A solution of tert-butyl 4-(5-((5-fluoro-4-(8-fluoro-4-isopropyl-3,4-dihydro-2H-benzo[b][1,4]oxazin-6-yl)pyrimidin-2-yl)amino)pyridin-2-yl)piperazine-1-carboxylate (50 mg, 0.08 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(6-(piperazin-1-yl)pyridin-3-yl)pyrimidin-2-amine (40 mg, 91%) as a yellow solid compound.

LCMS: 468 [M+H]$^+$ $^1$HNMR: (400 MHz, DMSO-d6) δ 9.67 (s, 1H), 9.14 (s, 1H), 8.57 (dd, J=9.2, 3.3 Hz, 2H), 8.01 (d, J=9.2 Hz, 1H), 7.37 (s, 1H), 7.17-7.10 (m, 1H), 7.07 (s, 1H), 4.29 (t, J=4.3 Hz, 2H), 4.11 (p, J=6.6 Hz, 1H), 3.71 (d, J=6.0 Hz, 4H), 3.30 (t, J=4.4 Hz, 2H), 3.21 (d, J=5.4 Hz, 4H), 1.17 (d, J=6.5 Hz, 6H).

Example-24: Synthesis of 5-fluoro-N-(3-fluoro-4-(1-methylpiperidin-4-yl) phenyl)-4-(8-fluoro-4-isopropyl-3,4-dihydro-2H-benzo[b][1,4]oxazin-6-yl) pyrimidin-2-amine (Compound 24)

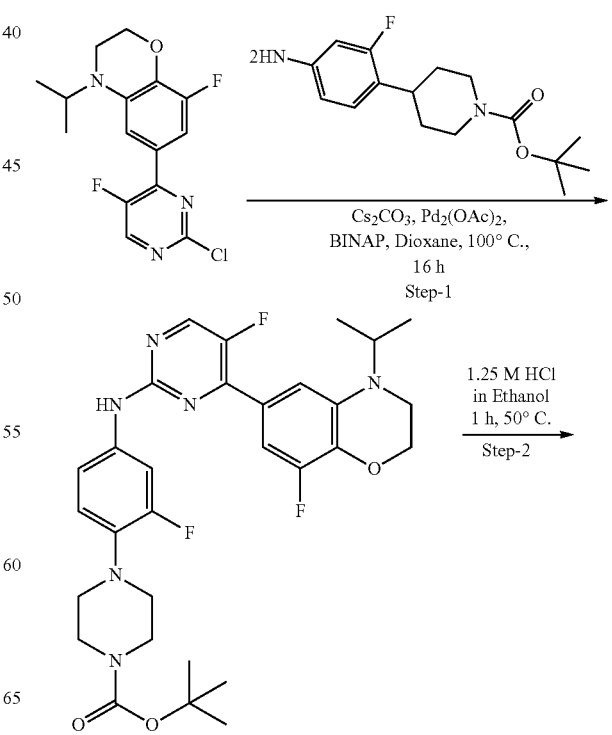

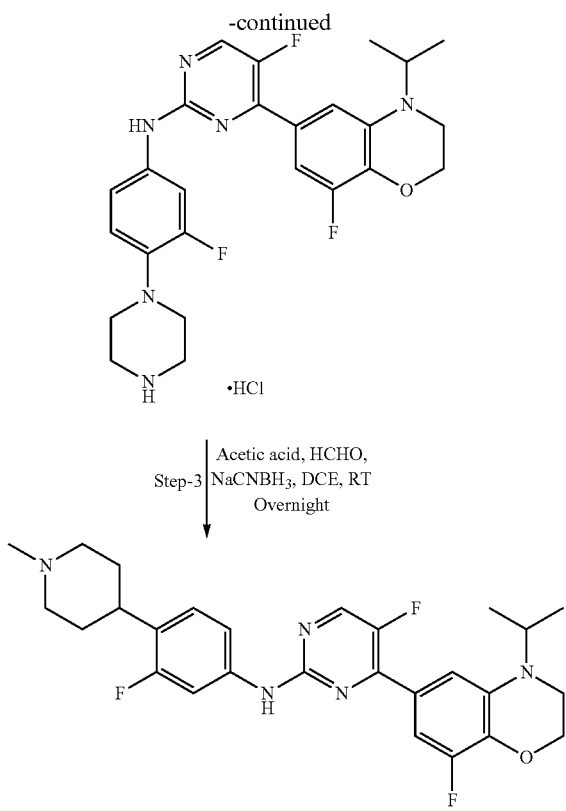

Step-1: Synthesis of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) in dioxane (10 mL), was added tert-butyl 4-(4-amino-2-fluorophenyl)piperidine-1-carboxylate (148 mg, 0.50 mmol, 1.1 equiv) and cesium carbonate (225 mg, 0.69 mmol, 1.5 equiv). The reaction mixture was degassed with nitrogen gas for 30 min., followed by the addition of palladium acetate (3 mg, 0.009 mmol, 0.02 equiv) and BINAP (12 mg, 0.018 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidine-1-carboxylate (200 mg, 74%) as a yellow solid compound.

LCMS: 584[M+H]$^+$

Step-2: Synthesis of 5-fluoro-N-(3-fluoro-4-(piperidin-4-yl) phenyl)-4-(8-fluoro-4-isopropyl-3,4-dihydro-2H-benzo[b][1,4]oxazin-6-yl) pyrimidin-2-amine A solution of tert-butyl 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidine-1-carboxylate (200 mg, 0.34 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-N-(3-fluoro-4-(piperidin-4-yl) phenyl)-4-(8-fluoro-4-isopropyl-3,4-dihydro-2H-benzo[b][1,4]oxazin-6-yl)pyrimidin-2-amine (150 mg, 90%) as a yellow solid compound.

LCMS: 484 [M+H]$^+$

Step-3: Synthesis of 5-fluoro-N-(3-fluoro-4-(1-methylpiperidin-4-yl) phenyl)-4-(8-fluoro-4-isopropyl-3,4-dihydro-2H-benzo[b][1,4]oxazin-6-yl)pyrimidin-2-amine To a stirred solution of 5-fluoro-N-(3-fluoro-4-(piperidin-4-yl) phenyl)-4-(8-fluoro-4-isopropyl-3,4-dihydro-2H-benzo[b][1,4]oxazin-6-yl)pyrimidin-2-amine (100 mg, 0.2 mmol, 1 equiv) in DCE (5 mL), was added Formaldehyde (40% in water) (0.02 mL, 0.61 mmol, 3 equiv), acetic acid (0.05 mL, 1.0 mmol, 5 equiv). The reaction mixture was allowed to stir at RT for 1 h. The reaction mixture was cooled to 0° C. NaCNBH$_3$ (38 mg, 0.61 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-N-(3-fluoro-4-(1-methylpiperidin-4-yl)phenyl)-4-(8-fluoro-4-isopropyl-3,4-dihydro-2H-benzo[b][1,4]oxazin-6-yl)pyrimidin-2-amine (15 mg, 15%) as a yellow solid compound.

LCMS: 498 [M+H]$^+$ $^1$HNMR: (400 MHz, DMSO-d6) δ 9.88 (s, 1H), 8.60 (d, J=3.9 Hz, 1H), 8.28 (s, 1H), 7.75 (dd, J=13.7, 2.2 Hz, 1H), 7.45 (s, 1H), 7.40 (dd, J=8.6, 2.2 Hz, 1H), 7.24-7.13 (m, 2H), 4.30 (t, J=4.3 Hz, 2H), 4.17 (p, J=6.5 Hz, 1H), 3.31 (t, J=4.5 Hz, 2H), 2.87 (d, J=11.1 Hz, 2H), 2.40 (s, 1H), 2.20 (s, 3H), 1.98 (td, J=10.9, 4.4 Hz, 2H), 1.69 (dd, J=12.0, 8.3 Hz, 4H), 1.18 (d, J=6.5 Hz, 6H).

Example-25: Synthesis of N-(4-(4-(dimethylamino)piperidin-1-yl)-3-fluorophenyl)-5-fluoro-4-(8-fluoro-4-isopropyl-3,4-dihydro-2H-benzo[b][1,4]oxazin-6-yl)pyrimidin-2-amine (Compound 25)

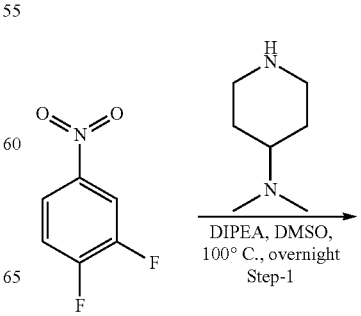

DIPEA, DMSO,
100° C., overnight
Step-1

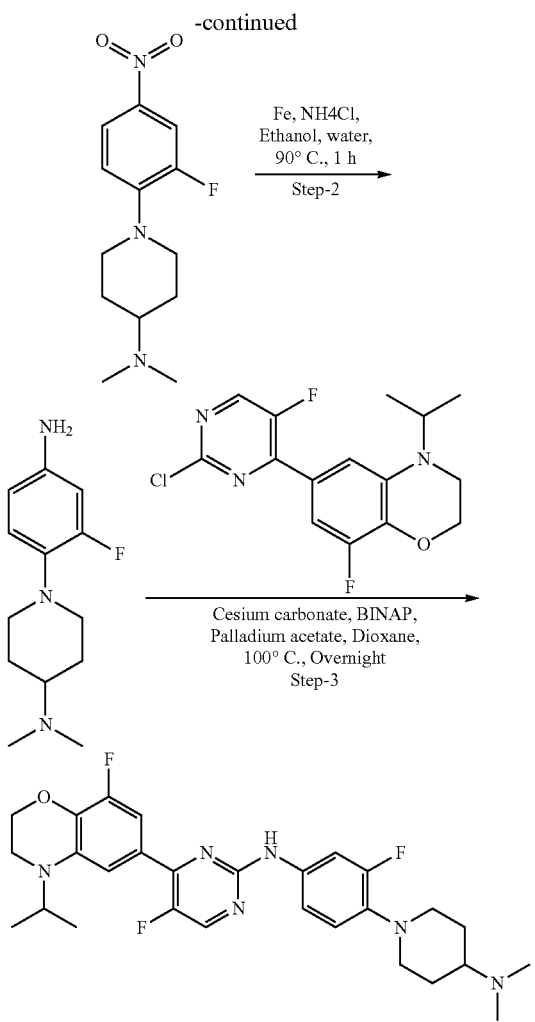

Step-1: Synthesis 1-(2-fluoro-4-nitrophenyl)-N, N-dimethylpiperidin-4-amine

To a stirred solution of 1, 2-difluoro-4-nitrobenzene (400 mg, 2.5 mmol, 1 equiv) in DMSO (10 mL), was added DIPEA (1.7 mL, 10 mmol, 4 equiv) and N, N-dimethylpiperidin-4-amine (556 mg, 2.76 mmol, 1.1 equiv). The resultant reaction mixture was allowed to stir at 1000 for overnight. Progress of the reaction was monitored by TLC and LCMS. After completion of the reaction, the mixture was diluted with ice water (10 mL), solid observed was filtered and dried under vacuum to obtain 1-(2-fluoro-4-nitrophenyl)-N, N-dimethylpiperidin-4-amine (600 mg, 89%) as a yellow solid compound.

LCMS: 268 [M+H]$^+$

Step-2: Synthesis of 1-(4-amino-2-fluorophenyl)-N, N-dimethylpiperidin-4-amine To a stirred solution of 1-(2-fluoro-4-nitrophenyl)-N, N-dimethylpiperidin-4-amine (500 mg, 1.87 mmol, 1 equiv) in ethanol (8 mL), water (2 mL), was added iron powder (315 mg, 5.61 mmol, 3 equiv) and ammonium chloride (202 mg, 3.74 mmol, 2 equiv). The resultant reaction mixture was allowed to stir at 900 for 1 h. Progress of the reaction was monitored by TLC and LCMS. After completion of the reaction, the mixture was diluted with water (30 mL) and extracted with EtoAc (100 mL). Organic layer was washed with water (50 mL) and brine (50 mL). Organic layer was dried over anhydrous sodium sulphate and concentrated under reduced pressure to obtain 1-(4-amino-2-fluorophenyl)-N, N-dimethylpiperidin-4-amine (400 mg, 90%) as a dark brown solid compound.

LCMS: 238 [M+H]$^+$

Step-3: Synthesis of N-(4-(4-(dimethylamino) piperidin-1-yl)-3-fluorophenyl)-5-fluoro-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 1-(4-amino-2-fluorophenyl)-N, N-dimethylpiperidin-4-amine (78 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N-(4-(4-(dimethylamino)piperidin-1-yl)-3-fluorophenyl)-5-fluoro-4-(8-fluoro-4-isopropyl-3,4-dihydro-2H-benzo[b][1,4]oxazin-6-yl)pyrimidin-2-amine (20 mg, 12%) as a yellow solid compound.

LCMS: 527 [M+H]$^+$ $^1$HNMR: (400 MHz, DMSO-d6) δ 9.74 (s, 1H), 8.57 (d, J=4.0 Hz, 1H), 8.29 (s, 1H), 7.72 (dd, J=15.3, 2.5 Hz, 1H), 7.44 (s, 1H), 7.36 (dd, J=8.8, 2.5 Hz, 1H), 7.16 (d, J=11.4 Hz, 1H), 6.97 (t, J=9.4 Hz, 1H), 4.30 (t, J=4.4 Hz, 2H), 4.16 (p, J=6.6 Hz, 1H), 3.30 (dd, J=9.6, 5.2 Hz, 4H), 2.63-2.54 (m, 2H), 2.22 (s, 7H), 1.84 (dd, J=12.7, 3.6 Hz, 2H), 1.54 (tt, J=13.3, 6.7 Hz, 2H), 1.18 (d, J=6.5 Hz, 6H).

Example-26: Synthesis of 5-fluoro-4-(8-fluoro-4-isopropyl-3,4-dihydro-2H-benzo[b][1,4]oxazin-6-yl)-N-(3-fluoro-4-morpholinophenyl)pyrimidin-2-amine (Compound 26)

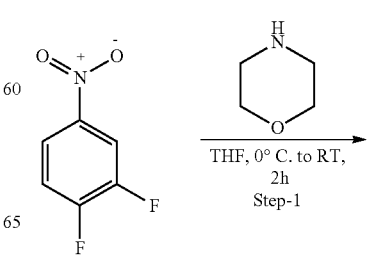

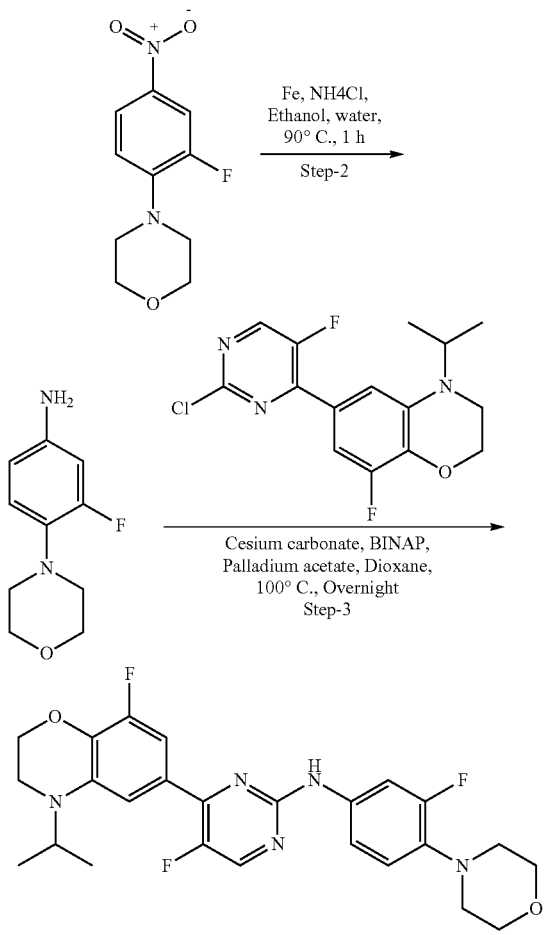

Step-1: Synthesis 4-(2-fluoro-4-nitrophenyl) morpholine

To a stirred solution of morpholine (2.5 mL, 28 mmol, 4.5 equiv) in THF (15 mL), was added 1, 2-difluoro-4-nitrobenzene (1000 mg, 6.28 mmol, 1 equiv) at 0° C. Raise the temp to RT and the mixture was allowed to stir for 2 h at RT. Progress of the reaction was monitored by TLC and LCMS. After completion of the reaction, the mixture was diluted with water (100 mL) and extracted with EtoAc (200 mL). Organic layer was washed with water (50 mL) and brine (50 mL). Organic layer was dried over anhydrous sodium sulphate and concentrated under reduced pressure to obtain 4-(2-fluoro-4-nitrophenyl) morpholine (1000 mg, 70%) as a yellow solid compound.

LCMS: 227 [M+H]$^+$

Step-2: Synthesis of 3-fluoro-4-morpholinoaniline

To a stirred solution of 4-(2-fluoro-4-nitrophenyl) morpholine (400 mg, 1.76 mmol, 1 equiv) in ethanol (8 mL), water (2 mL), was added iron powder (297 mg, 5.3 mmol, 3 equiv) and ammonium chloride (190 mg, 3.52 mmol, 2 equiv). The resultant reaction mixture was allowed to stir at 900 for 1 h. Progress of the reaction was monitored by TLC and LCMS. After completion of the reaction, the mixture was diluted with water (30 mL) and extracted with EtoAc (100 mL). Organic layer was washed with water (50 mL) and brine (50 mL). Organic layer was dried over anhydrous sodium sulphate and concentrated under reduced pressure to obtain crude, which was purified by normal phase combi flash to obtain 3-fluoro-4-morpholinoaniline (240 mg, 69%) as a dark brown solid compound.

LCMS: 197 [M+H]$^+$

Step-3: Synthesis of 5-fluoro-4-(8-fluoro-4-isopropyl-3,4-dihydro-2H-benzo[b][1,4]oxazin-6-yl)-N-(3-fluoro-4-morpholinophenyl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 3-fluoro-4-morpholinoaniline (66 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(3-fluoro-4-morpholinophenyl)pyrimidin-2-amine (20 mg, 13%) as a yellow solid compound.

LCMS: 486 [M+H]$^+$ $^1$HNMR: (400 MHz, DMSO-d6) δ 9.75 (s, 1H), 8.56 (d, J=3.9 Hz, 1H), 7.75 (dd, J=15.5, 2.5 Hz, 1H), 7.43 (s, 1H), 7.41-7.35 (m, 1H), 7.20-7.12 (m, 1H), 6.98 (t, J=9.4 Hz, 1H), 4.30 (t, J=4.2 Hz, 2H), 4.15 (p, J=7.7, 7.1 Hz, 1H), 3.74 (t, J=4.6 Hz, 4H), 3.30 (d, J=4.5 Hz, 2H), 2.94 (t, J=4.6 Hz, 4H), 1.18 (d, J=6.5 Hz, 6H).

Example-27: Synthesis of 5-fluoro-N-(3-fluoro-4-(4-(pyrrolidin-1-yl) piperidin-1-yl) phenyl)-6-(8-fluoro-4-isopropyl-3,4-dihydro-2H-benzo[b][1,4]oxazin-6-yl)pyridin-2-amine (Compound 27)

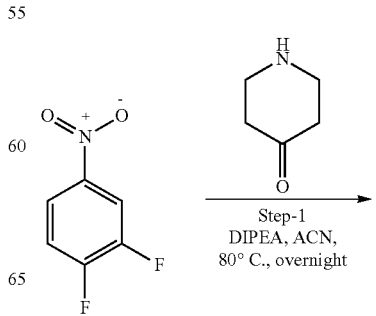

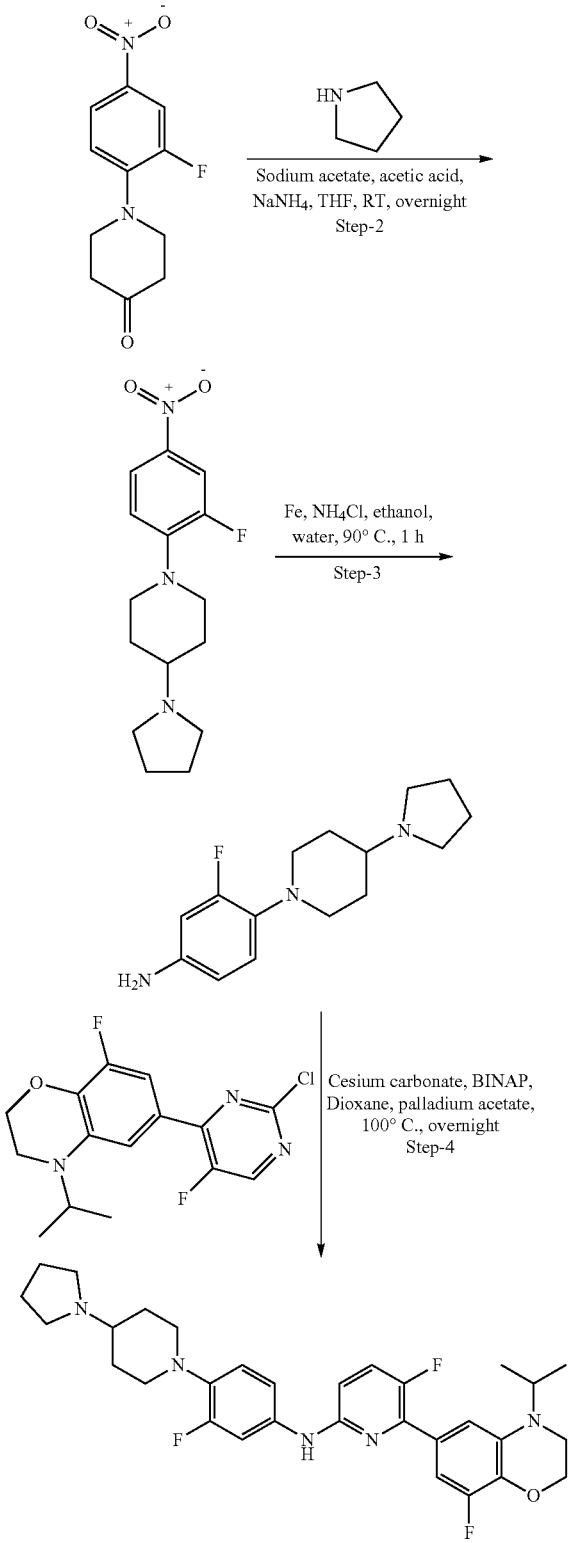

Step-1: Synthesis of 1-(2-fluoro-4-nitrophenyl) piperidin-4-one

To a stirred solution of 1, 2-difluoro-4-nitrobenzene (3000 mg, 18.8 mmol, 1 equiv) in ACN (30 mL), was added DIPEA (6.6 mL, 37.6 mmol, 2 equiv) and piperidin-4-one (2906 mg, 18.8 mmol, 1 equiv). The resultant reaction mixture was allowed to stir at 80° for overnight. Progress of the reaction was monitored by TLC and LCMS. After completion of the reaction, the mixture was diluted with EtoAc (200 mL), washed with 10% HCl (100 mL) and brine (100 mL). Organic layer was dried over anhydrous sodium sulphate and concentrated under reduced pressure to obtain 1-(2-fluoro-4-nitrophenyl) piperidin-4-one (4200 mg, 94%) as a yellow solid compound.

LCMS: 239 [M+H]$^+$

Step-2: Synthesis 1-(2-fluoro-4-nitrophenyl)-4-(pyrrolidin-1-yl) piperidine

To a stirred solution of 1-(2-fluoro-4-nitrophenyl) piperidin-4-one (2000 mg, 8.4 mmol, 1 equiv) in THF (20 mL), was added pyrrolidine (1 mL, 11.76 mmol, 1.4 equiv), sodium acetate (1033 mg, 12.6 mmol, 1.5 equiv), and acetic acid (1 mL). The resultant reaction mixture was allowed to stir at RT for 1 h. Sodium borohydride (570 mg, 15 mmol, 1.5 equiv) was added to above mixture and the resultant reaction mixture was allowed to stir at RT for overnight. Progress of the reaction was monitored by LCMS. After completion of the reaction, the mixture was diluted with water (100 mL) and extracted with EtoAc (100 mL×2). Organic layer was washed with water (100 mL) and brine (100 mL). Organic layer was dried over anhydrous sodium sulphate and concentrated under reduced pressure to obtain 1-(2-fluoro-4-nitrophenyl)-4-(pyrrolidin-1-yl) piperidine (2000 mg, 81%) as a yellow solid compound.

LCMS: 294 [M+H]$^+$

Step-3: Synthesis of 3-fluoro-4-(4-(pyrrolidin-1-yl) piperidin-1-yl) aniline

To a stirred solution of 1-(2-fluoro-4-nitrophenyl)-4-(pyrrolidin-1-yl) piperidine (1000 mg, 3.4 mmol, 1 equiv) in ethanol (10 mL), water (3 mL), was added iron powder (573 mg, 10.2 mmol, 3 equiv) and ammonium chloride (367 mg, 6.8 mmol, 2 equiv). The resultant reaction mixture was allowed to stir at 900 for 1 h. Progress of the reaction was monitored by TLC and LCMS. After completion of the reaction, the mixture was diluted with water (50 mL) and extracted with EtoAc (100 mL×2). Organic layer was washed with water (50 mL) and brine (50 mL). Organic layer was dried over anhydrous sodium sulphate and concentrated under reduced pressure to obtain 3-fluoro-4-(4-(pyrrolidin-1-yl) piperidin-1-yl) aniline (700 mg, 78%) as a dark brown solid compound.

LCMS: 264 [M+H]$^+$

Step-4: Synthesis 5-fluoro-N-(3-fluoro-4-(4-(pyrrolidin-1-yl) piperidin-1-yl) phenyl)-6-(8-fluoro-4-isopropyl-3,4-dihydro-2H-benzo[b][1,4]oxazin-6-yl) pyridin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 3-fluoro-4-(4-(pyrrolidin-1-yl) piperidin-1-yl) aniline (87 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h.

Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-N-(3-fluoro-4-(4-(pyrrolidin-1-yl)piperidin-1-yl) phenyl)-6-(8-fluoro-4-isopropyl-3,4-dihydro-2H-benzo[b] [1,4]oxazin-6-yl)pyridin-2-amine (40 mg, 24%) as a yellow solid compound.

LCMS: 553.5 [M+H]+

$^1$HNMR: (400 MHz, DMSO-d6) δ 9.71 (s, 1H), 8.56 (d, J=4.0 Hz, 1H), 7.71 (d, J=15.3 Hz, 1H), 7.44 (s, 1H), 7.36 (d, J=8.9 Hz, 1H), 7.16 (d, J=11.6 Hz, 1H), 6.97 (t, J=9.4 Hz, 1H), 4.33-4.26 (m, 2H), 4.15 (dq, J=14.0, 7.5, 6.9 Hz, 1H), 3.33-3.21 (m, 3H), 2.65 (s, 3H), 2.56 (d, J=5.1 Hz, 4H), 2.12 (d, J=10.6 Hz, 1H), 1.98-1.90 (m, 2H), 1.69 (t, J=5.1 Hz, 4H), 1.56 (q, J=10.8, 9.4 Hz, 2H), 1.18 (d, J=6.4 Hz, 6H).

Example-28: Synthesis of N-(2, 3-difluoro-4-(piperazin-1-yl) phenyl)-5-fluoro-4-(8-fluoro-4-isopropyl-3,4-dihydro-2H-benzo[b][1,4]oxazin-6-yl)pyrimidin-2-amine (Compound 28)

Step-1: Synthesis tert-butyl 4-(2,3-difluoro-4-((5-fluoro-4-(8-fluoro-4-isopropyl-3,4-dihydro-2H-benzo[b][1,4]oxazin-6-yl)pyrimidin-2-yl)amino) phenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(4-amino-2,3-difluorophenyl)piperazine-1-carboxylate (103 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain tert-butyl 4-(2,3-difluoro-4-((5-fluoro-4-(8-fluoro-4-isopropyl-3,4-dihydro-2H-benzo[b][1,

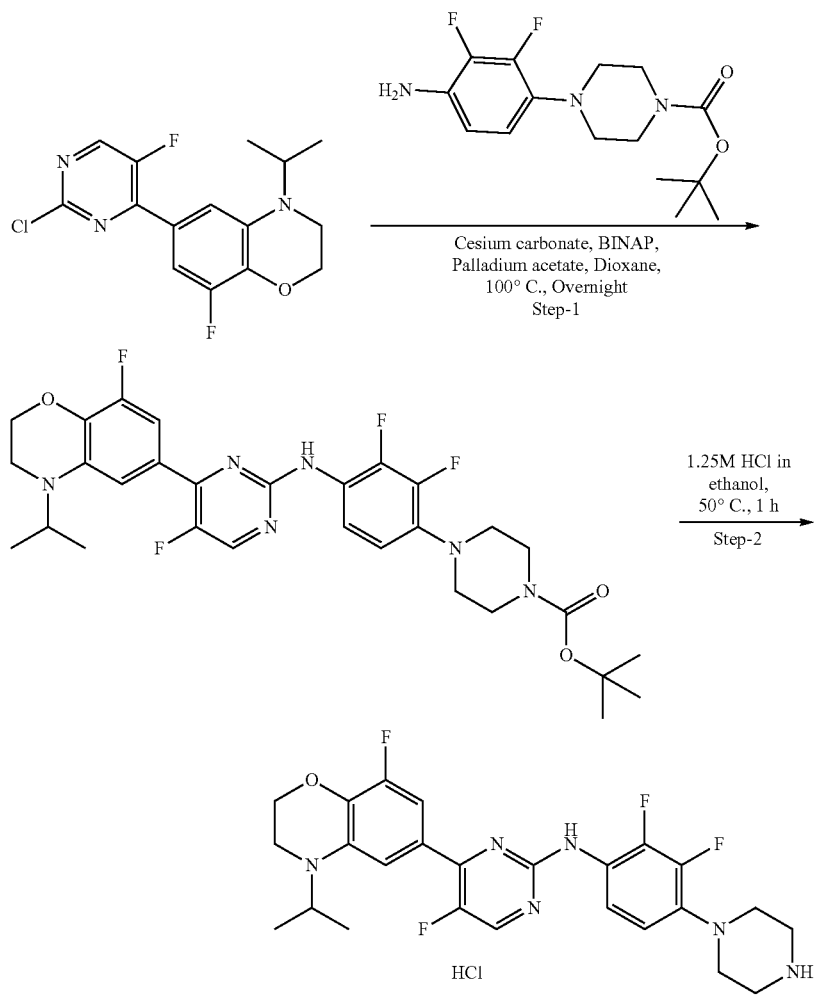

4]oxazin-6-yl)pyrimidin-2-yl)amino)phenyl)piperazine-1-carboxylate (90 mg, 48%) as a yellow color solid compound.

LCMS: 603 [M+H]+

Step-2: Synthesis of N-(2, 3-difluoro-4-(piperazin-1-yl) phenyl)-5-fluoro-4-(8-fluoro-4-isopropyl-3,4-dihydro-2H-benzo[b][1,4]oxazin-6-yl)pyrimidin-2-amine A solution of obtain tert-butyl 4-(2,3-difluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (90 mg, 0.14 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(2, 3-difluoro-4-(piperazin-1-yl) phenyl)-5-fluoro-4-(8-fluoro-4-isopropyl-3,4-dihydro-2H-benzo[b][1,4]oxazin-6-yl)pyrimidin-2-amine (60 mg, 75%) as a brown color solid compound.

LCMS: 503 [M+H]+

¹HNMR: (400 MHz, DMSO-d6) δ 9.35 (s, 1H), 8.88 (d, J=19.7 Hz, 1H), 8.51 (d, J=3.9 Hz, 1H), 7.33 (d, J=7.0 Hz, 2H), 7.10 (d, J=11.7 Hz, 1H), 6.90 (t, J=8.9 Hz, 1H), 4.31-4.23 (m, 2H), 4.03 (p, J=6.8 Hz, 1H), 3.26 (q, J=6.4, 5.7 Hz, 10H), 1.15 (d, J=6.4 Hz, 6H).

Example-29: Synthesis of 5-fluoro-4-(8-fluoro-4-isopropyl-3,4-dihydro-2H-benzo[b][1,4]oxazin-6-yl)-N-(3-methoxy-4-(piperazin-1-yl)phenyl)pyrimidin-2-amine (Compound 29)

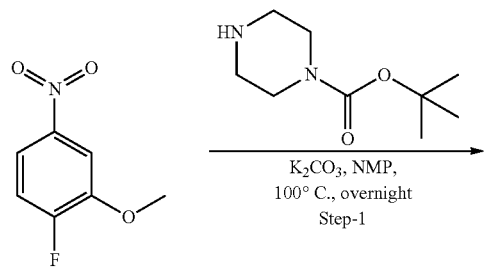

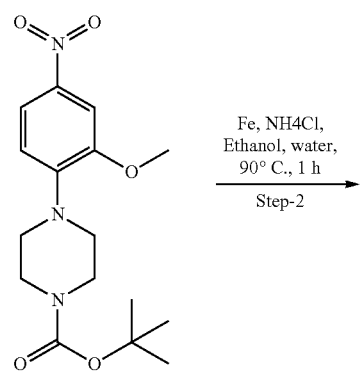

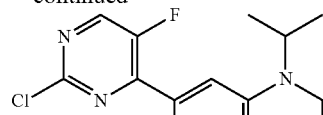

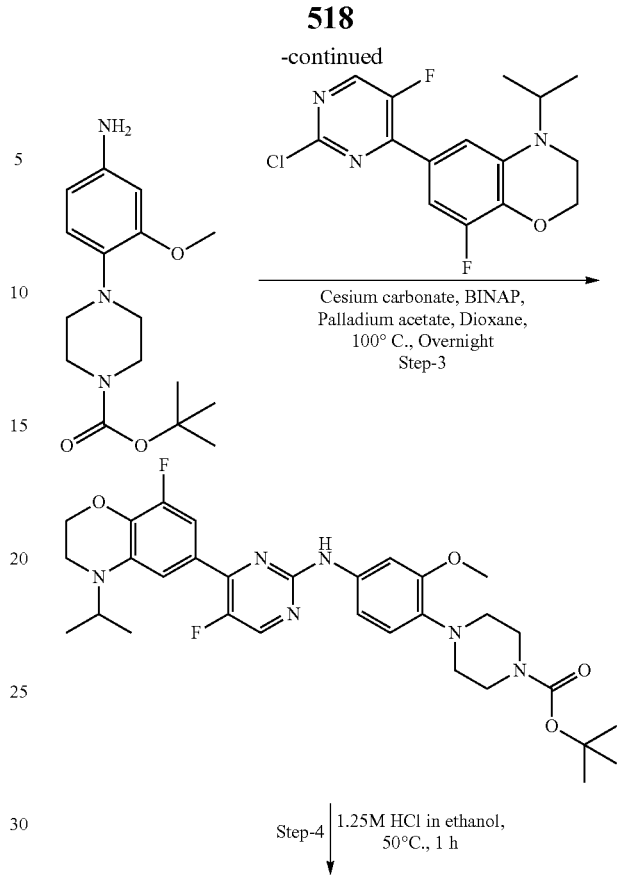

Step-1: Synthesis tert-butyl 4-(2-methoxy-4-nitrophenyl) piperazine-1-carboxylate To a stirred solution of 1-fluoro-2-methoxy-4-nitrobenzene (1000 mg, 5.8 mmol, 1 equiv) in NMP (15 mL), was added K2CO3 (1601 mg, 11.6 mmol, 2 equiv) and tert-butyl piperazine-1-carboxylate (1632 mg, 8.77 mmol, 1.5 equiv). The resultant reaction mixture was allowed to stir at 100° C. for 3 h. Progress of the reaction was monitored by TLC and LCMS. After completion of the reaction, the mixture was diluted with water (50 mL) and extracted with EtOAc (100 mL×2). Organic layer was washed with water (50 mL) and brine (50 mL). Organic layer was dried over anhydrous sodium sulphate and concentrated under reduced pressure to obtain tert-butyl 4-(2-methoxy-4-nitrophenyl) piperazine-1-carboxylate (1200 mg, 61%) as a dark brown solid compound.

LCMS: 338 [M+H]+

Step-2: Synthesis of tert-butyl 4-(4-amino-2-methoxyphenyl)piperazine-1-carboxylate To a stirred solution of tert-butyl 4-(2-methoxy-4-nitrophenyl) piperazine-1-carboxylate (400 mg, 1.18 mmol, 1 equiv) in ethanol (8 mL), water (2 mL), was added iron powder (297 mg, 3.56 mmol, 3 equiv) and ammonium chloride (190 mg, 2.36 mmol, 2 equiv). The resultant reaction mixture was allowed to stir at 900 for 1 h. Progress of the reaction was monitored by TLC and LCMS. After completion of the reaction, the mixture was diluted with water (30 mL) and extracted with EtoAc (100 mL). Organic layer was washed with water (50 mL) and brine (50 mL). Organic layer was dried over anhydrous sodium sulphate and concentrated under reduced pressure to obtain crude, which was purified by normal phase combi flash to obtain tert-butyl 4-(4-amino-2-methoxyphenyl)piperazine-1-carboxylate (250 mg, 69%) as a dark brown solid compound.
LCMS: 308 [M+H]$^+$

Step-3: Synthesis of tert-butyl 4-(4-((5-fluoro-4-(8-fluoro-4-isopropyl-3,4-dihydro-2H-benzo[b][1,4]oxazin-6-yl)pyrimidin-2-yl)amino)-2-methoxyphenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(4-amino-2-methoxyphenyl)piperazine-1-carboxylate (101 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain tert-butyl 4-(4-((5-fluoro-4-(8-fluoro-4-isopropyl-3,4-dihydro-2H-benzo[b][1,4]oxazin-6-yl)pyrimidin-2-yl)amino)-2-methoxyphenyl)piperazine-1-carboxylate (40 mg, 22%) as a yellow color solid compound.
LCMS: 597 [M+H]$^+$

Step-4: Synthesis of 5-fluoro-4-(8-fluoro-4-isopropyl-3,4-dihydro-2H-benzo[b][1,4]oxazin-6-yl)-N-(3-methoxy-4-(piperazin-1-yl)phenyl)pyrimidin-2-amine A solution of obtain tert-butyl 4-(4-((5-fluoro-4-(8-fluoro-4-isopropyl-3,4-dihydro-2H-benzo[b][1,4]oxazin-6-yl)pyrimidin-2-yl)amino)-2-methoxyphenyl)piperazine-1-carboxylate (40 mg, 0.06 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(3-methoxy-4-(piperazin-1-yl)phenyl)pyrimidin-2-amine (20 mg, 56%) as a brown color solid compound.
LCMS: 497 [M+H]$^+$ $^1$HNMR: (400 MHz, DMSO-d6) δ 9.59 (s, 1H), 9.00 (d, J=5.7 Hz, 1H), 8.55 (d, J=3.8 Hz, 1H), 7.46 (d, J=2.3 Hz, 1H), 7.39 (s, 1H), 7.37-7.25 (m, 1H), 7.19 (d, J=11.4 Hz, 1H), 6.88 (d, J=8.6 Hz, 1H), 4.34-4.25 (m, 2H), 4.12 (p, J=6.3 Hz, 1H), 3.79 (s, 4H), 3.34-3.27 (m, 2H), 3.27-3.17 (m, 4H), 3.13 (t, J=4.6 Hz, 3H), 1.18 (d, J=6.4 Hz, 6H).

Example-30: Synthesis of 5-chloro-N-(3-fluoro-4-(piperazin-1-yl) phenyl)-4-(8-fluoro-4-isopropyl-3, 4-dihydro-2H-benzo[b][1,4]oxazin-6-yl)pyrimidin-2-amine (Compound 30)

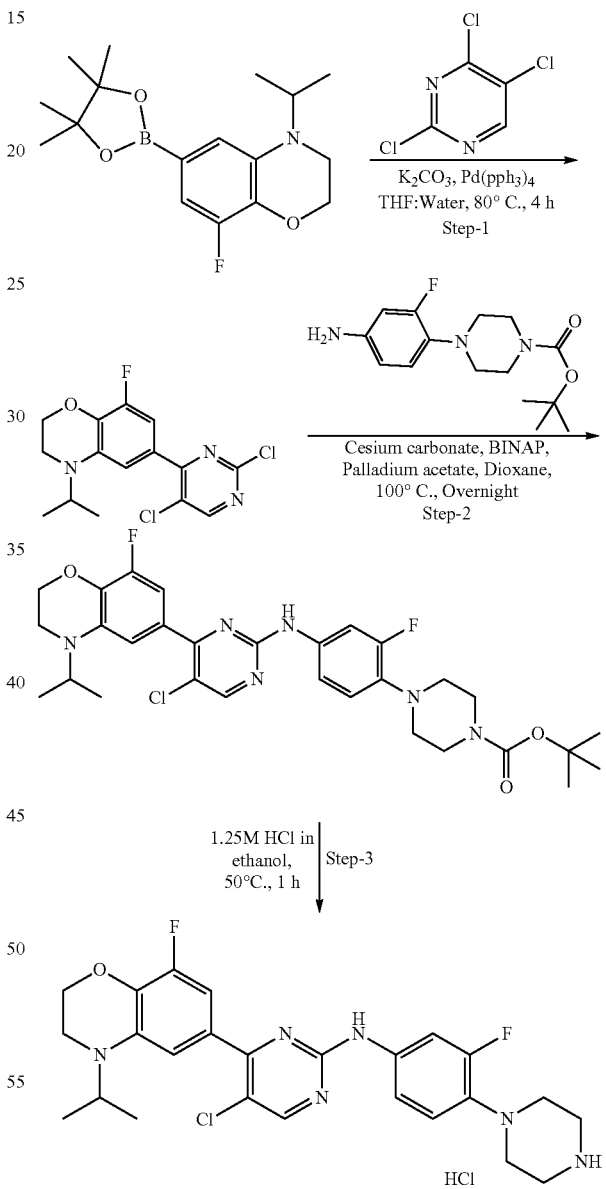

Step-1: Synthesis of 6-(2, 5-dichloropyrimidin-4-yl)-8-fluoro-4-isopropyl-3,4-dihydro-2H-benzo[b][1,4]oxazine To a stirred solution of 2,4,5-trichloropyrimidine (300 mg, 1.64 mmol, 1 equiv) in THF:Water (1:1=10 mL) was added, 8-fluoro-4-isopropyl-6-(4,4,5,5-tetramethyl-1,3,2-dioxaborolan-2-yl)-3,4-dihydro-2H-benzo[b][1,4]oxazine (529 mg, 1.64 mmol, 1 equiv), Potassium carbonate (453 mg, 3.28 mmol, 2 equiv) and Pd(PPh$_3$)$_4$ (95 mg, 0.08 mmol, 0.05 equiv). The reaction mixture was allowed to stir at 80° C. for 4 h. Progress of the reaction was monitored by TLC and LCMS. After completion of the reaction, the reaction mixture was diluted with water (30 mL) and extracted wit ethyl acetate (100 mL×2). Organic layer was washed with water (100 mL) and brine solution (100 mL). Organic layer was dried over anhydrous sodium sulphate and concentrated under reduced pressure to obtain crude compound, which was purified by normal phase combi-flash to obtain 6-(2,5-dichloropyrimidin-4-yl)-8-fluoro-4-isopropyl-3,4-dihydro-2H-benzo[b][1,4]oxazine (350 mg, 62%) as a yellow solid.
LCMS: 342 [M+H]$^+$ Step-2: Synthesis tert-butyl 4-(4-((5-chloro-4-(8-fluoro-4-isopropyl-3,4-dihydro-2H-benzo[b][1,4]oxazin-6-yl)pyrimidin-2-yl)amino)-2-fluorophenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(4-amino-2,3-difluorophenyl)piperazine-1-carboxylate (103 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to tert-butyl 4-(4-((5-chloro-4-(8-fluoro-4-isopropyl-3,4-dihydro-2H-benzo[b][1,4]oxazin-6-yl)pyrimidin-2-yl)amino)-2-fluorophenyl)piperazine-1-carboxylate (70 mg, 40%) a yellow color solid compound.
LCMS: 601 [M+H]$^+$ Step-3: Synthesis of 5-chloro-N-(3-fluoro-4-(piperazin-1-yl) phenyl)-4-(8-fluoro-4-isopropyl-3,4-dihydro-2H-benzo[b][1,4]oxazin-6-yl)pyrimidin-2-amine A solution of obtain tert-butyl 4-(4-((5-chloro-4-(8-fluoro-4-isopropyl-3,4-dihydro-2H-benzo[b][1,4]oxazin-6-yl)pyrimidin-2-yl)amino)-2-fluorophenyl)piperazine-1-carboxylate (70 mg, 0.11 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-chloro-N-(3-fluoro-4-(piperazin-1-yl) phenyl)-4-(8-fluoro-4-isopropyl-3,4-dihydro-2H-benzo[b][1,4]oxazin-6-yl)pyrimidin-2-amine (50 mg, 79%) as a brick red color solid compound.
LCMS: 501 [M+H]$^+$
$^1$HNMR: (400 MHz, DMSO-d6) δ 9.97 (s, 1H), 9.10 (s, 1H), 8.58 (s, 1H), 7.78 (dd, J=15.2, 2.5 Hz, 1H), 7.41 (dd, J=8.8, 2.3 Hz, 1H), 7.13 (s, 1H), 7.04 (t, J=9.4 Hz, 1H), 6.99 (d, J=11.2 Hz, 1H), 4.32-4.25 (m, 2H), 4.09 (s, 1H), 3.34-3.27 (m, 2H), 3.27-3.19 (m, 4H), 3.16 (dd, J=6.9, 3.4 Hz, 4H), 1.17 (d, J=6.5 Hz, 6H).

Example-31: Synthesis of N-(2, 5-difluoro-4-(piperazin-1-yl)phenyl)-5-fluoro-4-(8-fluoro-4-isopropyl-3,4-dihydro-2H-benzo[b][1,4]oxazin-6-yl)pyrimidin-2-amine (Compound 31)

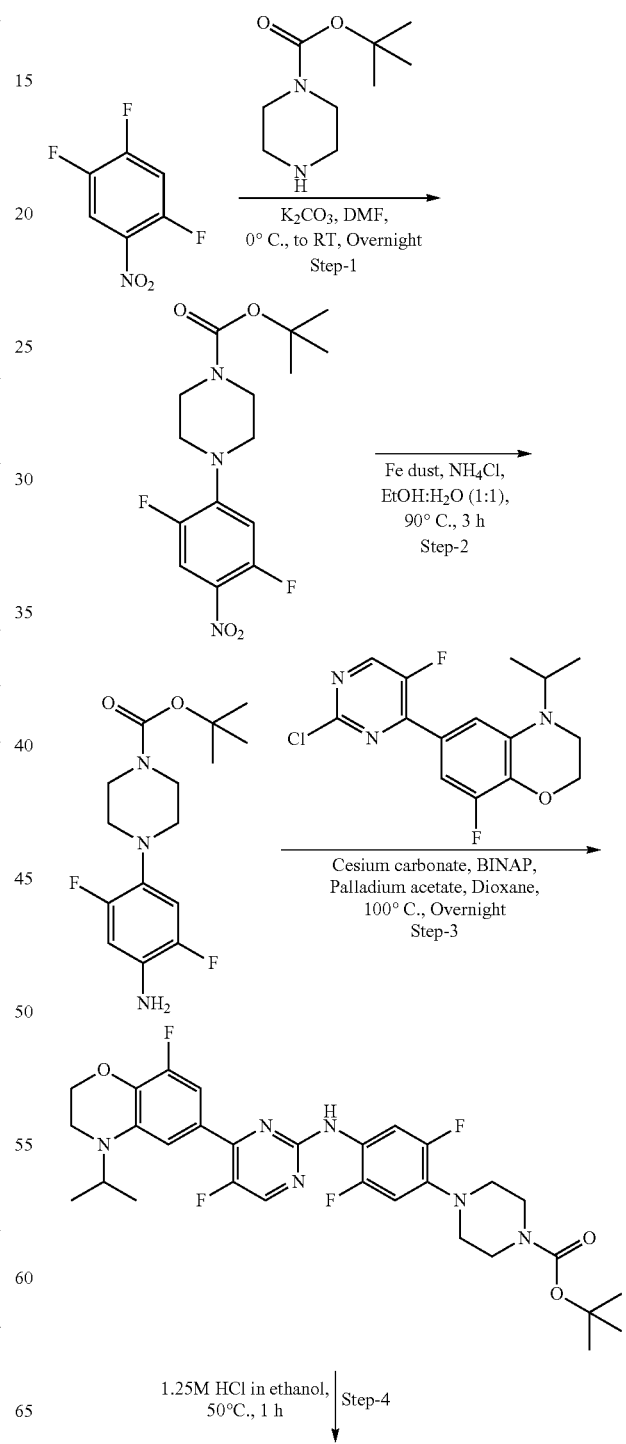

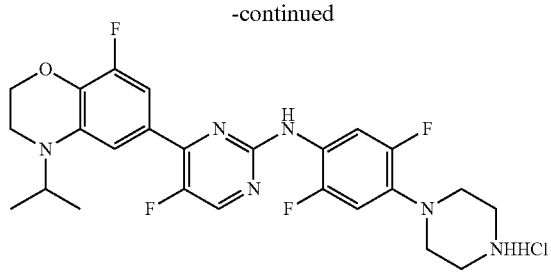

Step-1: Synthesis of tert-butyl 4-(2,5-difluoro-4-nitrophenyl)piperazine-1-carboxylate To a solution of 1,2,4-trifluoro-5-nitrobenzene (500 mg, 2.85 mmol, 1 equiv) and K$_2$CO$_3$ (432 mg, 3.13 mmol, 1.1 equiv) in DMF (10 mL), was added a solution of tert-butyl piperazine-1-carboxylate (526 mg, 2.85 mmol, 1 equiv) in DMF (5 mL) at 0° C. The resultant reaction mixture was allowed to stir at 0° C. for 15 min. followed by RT overnight. Progress of the reaction was monitored by TLC and LCMS. After completion of the reaction, precipitated salt removed by filtration and filtrate diluted with ethyl acetate (50 mL). Organic layer was washed with cold water (30 mL×3) and brine solution (30 mL). Organic layer was dried over anhydrous sodium sulphate and concentrated under reduced pressure to obtain tert-butyl 4-(2,5-difluoro-4-nitrophenyl)piperazine-1-carboxylate (950 mg, 97.3%) as a yellow color solid compound.
LCMS: 344.2 [M+H]$^+$

Step-2: Synthesis of tert-butyl 4-(4-amino-2,5-difluorophenyl)piperazine-1-carboxylate To a solution of tert-butyl 4-(2,5-difluoro-4-nitrophenyl)piperazine-1-carboxylate (200 mg, 0.538 mmol, 1 equiv) in Ethanol:Water (1:1) (20 mL), was added NH$_4$Cl (63 mg, 1.66 mmol, 2 equiv) and Fe dust (98 mg, 1.166 mmol, 3 equiv) at RT. The resultant reaction mixture was allowed to reflux at 90° C. for 3 h. Progress of the reaction was monitored by TLC and LCMS. After completion of the reaction, reaction mixture filtered through celite bed and filtrate concentrated up to dry. Residue obtained dissolved in EtOAc (50 mL) and organic layer washed with water (30 mL) and brine solution (30 mL). Organic layer was dried over anhydrous sodium sulphate and concentrated under reduced pressure to obtain crude, which was purified by column chromatography (eluted in 20% EtOAc in Hexane) to obtained tert-butyl 4-(4-amino-2,5-difluorophenyl)piperazine-1-carboxylate (130 mg, 71.4%) as a brown color solid compound.
LCMS: 314.4 [M+H]$^+$

Step-3: Synthesis of tert-butyl 4-(2,5-difluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.31 mmol, 1 equiv) in dioxane (10 mL), was added tert-butyl 4-(4-amino-2,5-difluorophenyl)piperazine-1-carboxylate (106 mg, 0.34 mmol, 1.1 equiv) and cesium carbonate (150 mg, 0.46 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to tert-butyl 4-(2,5-difluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (50 mg, 27%) as a yellow color solid compound.
LCMS: 603.5 [M+H]$^+$

Step-4: Synthesis of N-(2,5-difluoro-4-(piperazin-1-yl)phenyl)-5-fluoro-4-(8-fluoro-4-isopropyl-3,4-dihydro-2H-benzo[b][1,4]oxazin-6-yl)pyrimidin-2-amine A solution of tert-butyl 4-(2,5-difluoro-4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (50 mg, 0.083 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain N-(2,5-difluoro-4-(piperazin-1-yl)phenyl)-5-fluoro-4-(8-fluoro-4-isopropyl-3,4-dihydro-2H-benzo[b][1,4]oxazin-6-yl)pyrimidin-2-amine (30 mg, 72.11%) as a red color solid compound.
LCMS: 503.4 [M+H]$^+$
$^1$HNMR: (400 MHz, DMSO-d6) δ 9.24 (br. s., 2H), 8.53 (d, J=3.51 Hz, 1H), 7.68 (dd, J=7.45, 13.59 Hz, 1H), 7.36 (s, 1H), 6.98-7.20 (m, 2H), 4.26 (br. s., 2H), 4.04 (br. s., 1H), 3.22 (d, J=7.89 Hz, 10H), 1.09-1.25 (m, 6H).

Example-32: Synthesis of 5-fluoro-N-(3-fluoro-4-(piperazin-1-yl) phenyl)-4-(8-fluoro-4-isopropyl-2-methyl-3,4-dihydro-2H-benzo[b][1,4]oxazin-6-yl)pyrimidin-2-amine (Compound 32)

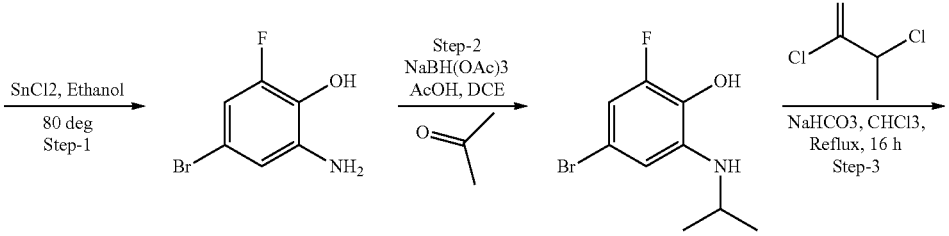

-continued

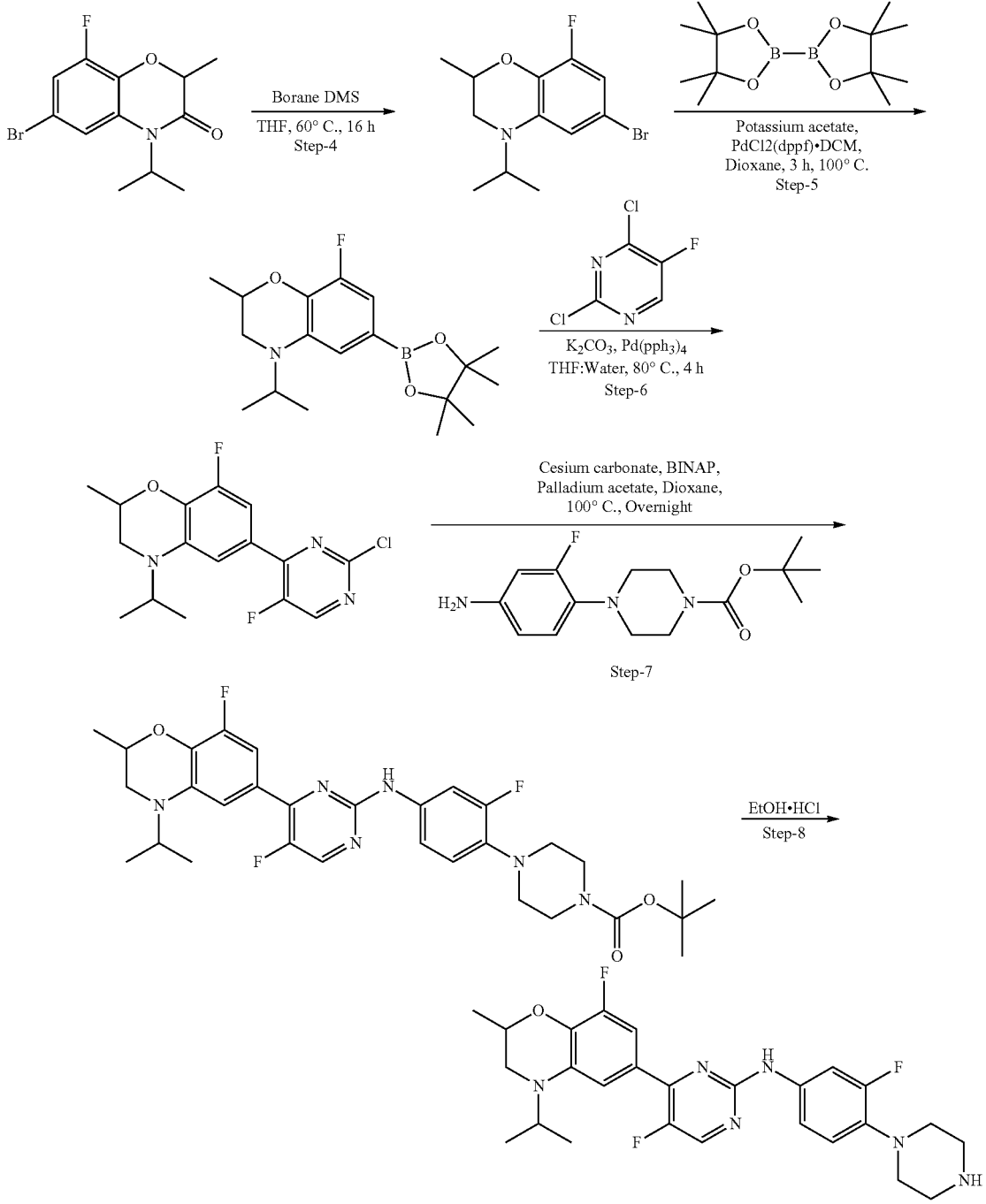

Step-1: Synthesis of 2-amino-4-bromo-6-fluorophenol

To a stirred suspension of 4-bromo-2-fluoro-6-nitrophenol (15 g, 63.55 mmol, 1 equiv) in ethanol (400 mL), was added stannous chloride monohydrate (60 g, 317.8 mmol, 5 equiv) at room temperature. The reaction mixture was refluxed at 80° C. for 3 h. Progress of the reaction was monitored by TLC and LCMS. After completion of the reaction, reaction mass concentrated, the reaction poured on ice-cold water (500 mL) and was basified by 3N NaOH solution up to pH 10 and was extracted with ethyl acetate (350 mL×3), organic layer was washed with water (150 mL) and brine solution (150 mL). Organic layer dried over anhydrous sodium sulphate and concentrated under reduced pressure to afford 2-amino-4-bromo-6-fluorophenol (11 g). LCMS: 207 [M+H]$^+$, 209 [M+2H]$^+$

Step-2: Synthesis of 4-bromo-2-fluoro-6-(isopropylamino)phenol

To a stirred solution of 2-amino-4-bromo-6-fluorophenol (500 mg, 2.4 mmol, 1 equiv) in 1,2 dichloroethane (10 mL), was added acetone (211.1 mg, 4.8 mmol, 2 equiv) followed by addition of acetic acid (540 mg, 12 mmol, 5 equiv) at 0° C. The reaction mixture was stirred at room temperature for 30 minutes. To this was added sodium triacetoxyborohydride (1010 mg, 4.8 mmol, 2 equiv) at 0° C. Resultant mixture was stirred at room temperature for 16 h. Progress of the reaction was monitored by TLC and LCMS. After completion of the reaction, the reaction mixture was quenched with water (40 mL) and was extracted with ethyl acetate (40 mL×2). The combined organic layer was washed with water (15 mL) and brine solution (15 mL). Organic layer was dried over anhydrous sodium sulphate and concentrated under reduced pressure to afford 4-bromo-2-fluoro-6-(isopropylamino)phenol (480 mg).

LCMS: 248 [M+H]$^+$, 250 [M+2H]$^+$

Step-3: Synthesis of 6-bromo-8-fluoro-4-isopropyl-2-methyl-2H-benzo[b][1,4]oxazin-3(4H)-one To a stirred solution of 4-bromo-2-fluoro-6-(isopropylamino)phenol (2 g, 8.1 mmol, 1 equiv) in chloroform (40 mL), was added NaHCO$_3$ (3.4 g, 40.5 mmol, 5 equiv) at 0° C., followed by addition of benzyl triethyl ammonium chloride (1.84 g, 8.1 mmol, 1 equiv) at 0° C. The reaction mixture was stirred at 0° C. for 5 min. To this was added 2-chloropropanoyl chloride (1.02 g, 8.1 mmol, 1 equiv) at 0° C. Resultant mixture was stirred at 0° C. for 1 h and then at 60° C. for 16 h. Progress of the reaction was monitored by TLC and LCMS. After completion of the reaction, the reaction mixture was quenched with saturated Na2CO3 solution (100 mL) and was extracted with DCM (100 mL×2). The combined organic layer was washed with water (15 mL) and brine solution (15 mL). Organic layer was dried over anhydrous sodium sulphate and concentrated under reduced pressure to afford 6-bromo-8-fluoro-4-isopropyl-2-methyl-2H-benzo[b][1,4]oxazin-3(4H)-one (1.5 g).

LCMS: 302 [M+H]$^+$, 304 [M+2H]$^+$

Step-4: Synthesis of 6-bromo-8-fluoro-4-isopropyl-2-methyl-3,4-dihydro-2H-benzo[b][1,4]oxazine To a stirred solution of 6-bromo-8-fluoro-4-isopropyl-2-methyl-2H-benzo[b][1,4]oxazin-3(4H)-one (1000 mg, 3.32 mmol, 1 equiv) in THF (14 mL), was drop wise added BH$_3$.DMS (1 mL, 13.3 mmol, 4 equiv) at 0° C. The reaction mixture was stirred at 50° C. for 16 h. Progress of the reaction was monitored by TLC and LCMS. After completion of the reaction, the reaction mixture was quenched with water (50 mL) and extracted with ethyl acetate (100 mL×3). The combined organic layer was washed with water (50 mL) and brine solution (50 mL). Organic layer dried over anhydrous sodium sulphate and concentrated under reduced pressure to afford 6-bromo-8-fluoro-4-isopropyl-2-methyl-3,4-dihydro-2H-benzo[b][1,4]oxazine (700 mg).

LCMS: 288 [M+H]$^+$, 290 [M+2H]$^+$

Step-5: Synthesis of 8-fluoro-4-isopropyl-2-methyl-6-(4,4,5,5-tetramethyl-1,3,2-dioxaborolan-2-yl)-3,4-dihydro-2H-benzo[b][1,4]oxazine To a stirred solution of 6-bromo-8-fluoro-4-isopropyl-2-methyl-3,4-dihydro-2H-benzo[b][1,4]oxazine (200 mg, 0.7 mmol, 1 equiv) in dioxane (4 mL), was added 4,4,5,5-tetramethyl-2-(4,4,5,5-tetramethyl-1,3,2-dioxaborolan-2-yl)-1,3,2-dioxaborolane (194 mg, 0.76 mmol, 1.1 equiv) and potassium acetate (100 mg, 1.05 mmol, 1.5 equiv). Aerated the reaction mixture with nitrogen gas for 15 minutes. After addition of PdCl2(dppf) DCM (24 mg, 0.034 mmol, 0.05 equiv) again purge nitrogen for 5 min. The reaction mixture was stirred at 100° C. for 4 h. Progress of the reaction was monitored by TLC and LCMS. After completion of the reaction, the reaction mixture was diluted with water (30 mL) and extracted with ethyl acetate (20 mL×2), organic layer was washed with brine (20 mL). The organic layer dried over anhydrous sodium sulphate and concentrated under reduced pressure purified by combiflash to afford 8-fluoro-4-isopropyl-2-methyl-6-(4,4,5,5-tetramethyl-1,3,2-dioxaborolan-2-yl)-3,4-dihydro-2H-benzo[b][1,4]oxazine (170 mg).

LCMS: 336 [M+H]$^+$

Step-6: Synthesis of 6-(2-chloro-5-fluoropyrimidin-4-yl)-8-fluoro-4-isopropyl-2-methyl-3,4-dihydro-2H-benzo[b][1,4]oxazine To a stirred solution of 2, 4-dichloro-5-fluoropyrimidine (0.75 g, 4.5 mmol, 1 equiv) and 8-fluoro-4-isopropyl-2-methyl-6-(4,4,5,5-tetramethyl-1,3,2-dioxaborolan-2-yl)-3,4-dihydro-2H-benzo[b][1,4]oxazine (1.5 g, 4.5 mmol, 1 equiv) in THF:Water (1:1, 20 mL) was added potassium carbonate (0.93 g, 6.75 mmol, 1.5 equiv) and Pd(PPh$_3$)$_4$ (0.259 g, 0.226 mmol, 0.05 equiv). The reaction mixture was heated to 80° C. for 4 h. Progress of the reaction was monitored by TLC and LCMS. After completion of the reaction, the reaction mixture was diluted with water (30 mL) and extracted with ethyl acetate (100 mL×2), organic layer was washed with water (100 mL) and brine solution (100 mL). The organic layer dried over anhydrous sodium sulphate and concentrated under reduced pressure to obtain crude compound, which was purified by normal phase combi-flash to afford 6-(2-chloro-5-fluoropyrimidin-4-yl)-8-fluoro-4-isopropyl-2-methyl-3,4-dihydro-2H-benzo[b][1,4]oxazine (0.8 g) as a yellow solid compound.

LCMS: 340 [M+H]$^+$

Step-7: Synthesis of tert-butyl 4-(2-fluoro-4-((5-fluoro-4-(8-fluoro-4-isopropyl-2-methyl-3,4-dihydro-2H-benzo[b][1,4]oxazin-6-yl)pyrimidin-2-yl)amino)phenyl)piperazine-1-carboxylate To a solution of 6-(2-chloro-5-fluoropyrimidin-4-yl)-8-fluoro-4-isopropyl-2-methyl-3,4-dihydro-2H-benzo[b][1,4]oxazine (60 mg, 0.18 mmol, 1 equiv) in Dioxane (3 mL), was added tert-butyl 4-(4-amino-2-fluorophenyl)piperazine-1-carboxylate (57 mg, 0.19 mmol, 1.1 equiv) and cesium carbonate (88 mg, 0.27 mmol, 1.5 equiv). The reaction mixture was aerated with nitrogen gas for 10 min. followed by the addition of palladium acetate (4 mg, 0.02 mmol, 0.1 equiv) and BINAP (22 mg, 0.036 mmol, 0.2 equiv) again purged nitrogen for 5 min. The resultant reaction mixture was stirred at 100° C. for 16 h. Progress of the reaction was monitored by TLC and LCMS. After completion of the reaction, the reaction mixture was diluted with water (10 mL) and extracted with EtOAc (15 mL). The organic layer dried over anhydrous sodium sulphate and concentrated under reduced pressure to obtain crude compound, which was purified by reverse phase HPLC to afford of tert-butyl 4-(2-fluoro-4-((5-fluoro-4-(8-fluoro-4-isopropyl-2-methyl-3,4-dihydro-2H-benzo[b][1,4]oxazin-6-yl)pyrimidin-2-yl)amino)phenyl)piperazine-1-carboxylate (50 mg).

LCMS: 599 [M+H]$^+$

529

Step-8: Synthesis of 5-fluoro-N-(3-fluoro-4-(piperazin-1-yl)phenyl)-4-(8-fluoro-4-isopropyl-2-methyl-3,4-dihydro-2H-benzo[b][1,4]oxazin-6-yl)pyrimidin-2-amine Tert-butyl 4-(2-fluoro-4-((5-fluoro-4-(8-fluoro-4-isopropyl-2-methyl-3,4-dihydro-2H-benzo[b][1,4]oxazin-6-yl)pyrimidin-2-yl)amino)phenyl)piperazine-1-carboxylate (50 mg, 0.083 mmol, 1 equiv) was taken in 1.25 M HCl in ethanol (4 mL) and the resultant reaction mixture was stirred at 50° C. for 2 h. Progress of the reaction was monitored by LCMS. After completion of the reaction, the reaction mixture was concentrated under vacuum to obtain 5-fluoro-N-(3-fluoro-4-(piperazin-1-yl)phenyl)-4-(8-fluoro-4-isopropyl-2-methyl-3,4-dihydro-2H-benzo[b][1,4]oxazin-6-yl)pyrimidin-2-amine (20 mg) as a HCl salt.

LCMS: 499 [M+H]$^+$ $^1$HNMR: (400 MHz, DMSO-d6) δ 9.82 (s, 1H), 9.03 (d, J=8.5 Hz, 2H), 8.58 (d, J=3.9 Hz, 1H), 7.81 (dd, J=15.3, 2.4 Hz, 1H), 7.41 (d, J=9.2 Hz, 2H), 7.16 (d, J=11.7 Hz, 1H), 7.05 (t, J=9.4 Hz, 1H), 4.29 (p, J=7.5 Hz, 1H), 4.16 (p, J=6.7 Hz, 1H), 3.45 (d, J=12.2 Hz, 1H), 3.27-3.21 (m, 4H), 3.16 (t, J=4.7 Hz, 4H), 2.88 (dd, J=12.7, 7.5 Hz, 1H), 1.36 (d, J=6.2 Hz, 3H), 1.21 (d, J=6.7 Hz, 3H), 1.15 (d, J=6.5 Hz, 3H).

Example-33: Synthesis of 5-fluoro-4-(8-fluoro-4-isopropyl-3,4-dihydro-2H-benzo[b][1,4]oxazin-6-yl)-N-(6-(1-methylpiperidin-4-yl)pyridin-3-yl)pyrimidin-2-amine (Compound 33)

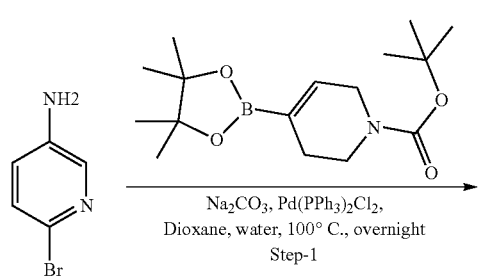

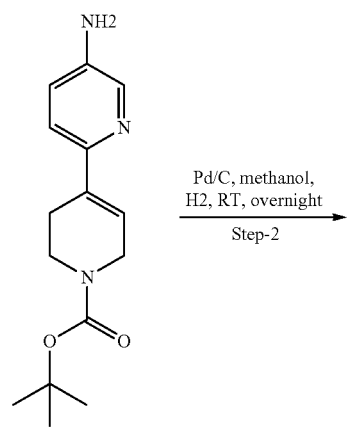

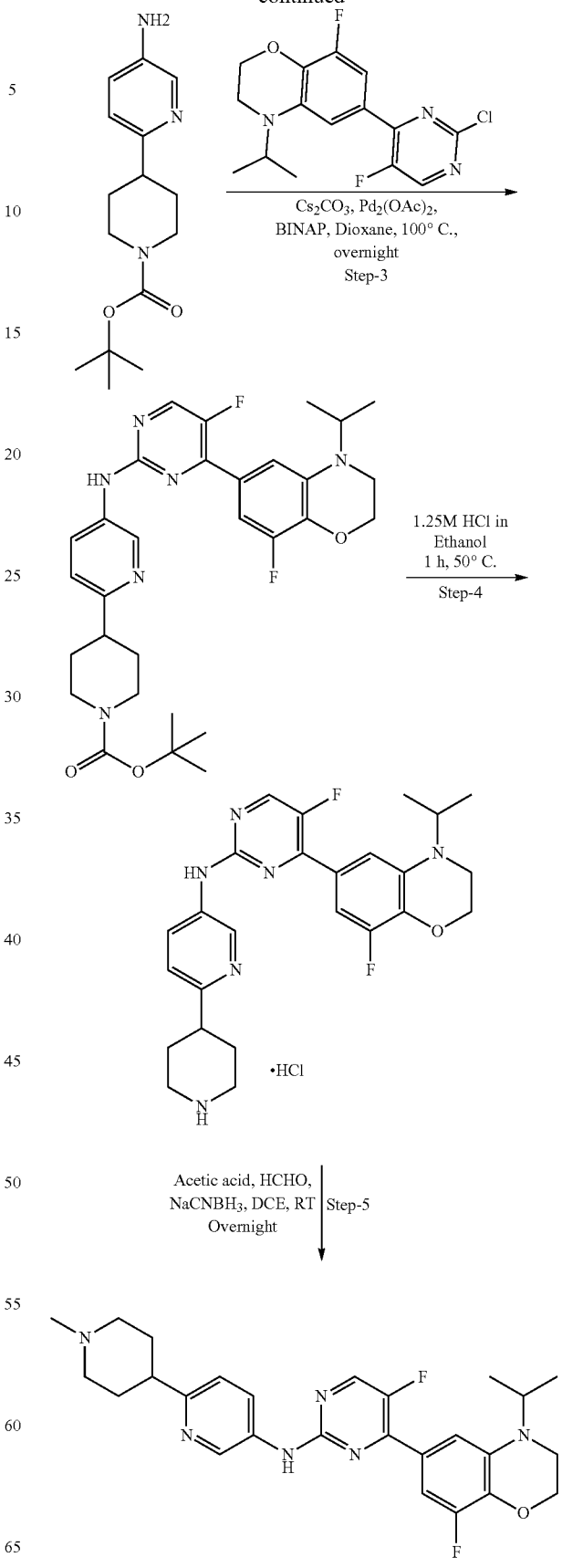

Step-1: Synthesis of tert-butyl 5-amino-3', 6'-dihydro-[2, 4'-bipyridine]-1'(2'H)-carboxylate To a solution of 6-bromopyridin-3-amine (1000 mg, 5.8 mmol, 1 equiv) in dioxane (15 mL), was added tert-butyl 4-(4, 4, 5, 5-tetramethyl-1, 3, 2-dioxaborolan-2-yl)-3, 6-dihydropyridine-1(2H)-carboxylate (1797 mg, 5.8 mmol, 1 equiv) and sodium carbonate (1844 mg, 17.4 mmol, 3 equiv). The reaction mixture was degassed with nitrogen gas for 30 min., followed by the addition of Pd(PPh$_3$)$_2$Cl$_2$ (204 mg, 0.29 mmol, 0.05 equiv). The resultant reaction mixture was allowed to stir at 100° C. for overnight. Progress of the reaction was monitored by TLC and LCMS. After completion of the reaction, reaction mixture was diluted with water (30 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to tert-butyl 5-amino-3',6'-dihydro-[2,4'-bipyridine]-1'(2'H)-carboxylate (900 mg, 56%) as a yellow oil compound.

LCMS: 276 [M+H]$^+$

Step-2: Synthesis of tert-butyl 4-(5-aminopyridin-2-yl) piperidine-1-carboxylate To a stirred solution of tert-butyl 5-amino-3', 6'-dihydro-[2, 4'-bipyridine]-1'(2'H)-carboxylate (900 mg, 3.2 mmol, 1 equiv) in methanol (10 mL), was added Pd/C (20% w/w) (180 mg) under H$_2$ atm. The resultant reaction mixture was allowed to stir at RT for overnight. Progress of the reaction was monitored by LCMS. After completion of the reaction, the mixture was passes through celite bed and the filtrate was concentrated under reduced pressure to obtain tert-butyl 4-(5-aminopyridin-2-yl) piperidine-1-carboxylate (800 mg, 88%) as a transparent oil compound.

LCMS: 278 [M+H]$^+$

Step-3: Synthesis of tert-butyl 4-(5-((5-fluoro-4-(8-fluoro-4-isopropyl-3,4-dihydro-2H-benzo[b][1,4]oxazin-6-yl)pyrimidin-2-yl)amino)227yridine-2-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) in dioxane (10 mL), was added tert-butyl 4-(5-aminopyridin-2-yl) piperidine-1-carboxylate (141 mg, 0.50 mmol, 1.1 equiv) and cesium carbonate (225 mg, 0.69 mmol, 1.5 equiv). The reaction mixture was degassed with nitrogen gas for 30 min., followed by the addition of palladium acetate (2 mg, 0.009 mmol, 0.02 equiv) and BINAP (12 mg, 0.018 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(5-((5-fluoro-4-(8-fluoro-4-isopropyl-3,4-dihydro-2H-benzo[b][1,4]oxazin-6-yl)pyrimidin-2-yl)amino)pyridin-2-yl)piperidine-1-carboxylate (60 mg, 23%) as a yellow solid compound.

LCMS: 567 [M+H]$^+$

Step-4: Synthesis of 5-fluoro-4-(8-fluoro-4-isopropyl-3,4-dihydro-2H-benzo[b][1,4]oxazin-6-yl)-N-(6-(piperidin-4-yl)pyridin-3-yl)pyrimidin-2-amine A solution of tert-butyl 4-(5-((5-fluoro-4-(8-fluoro-4-isopropyl-3,4-dihydro-2H-benzo[b][1,4]oxazin-6-yl)pyrimidin-2-yl)amino)pyridin-2-yl)piperidine-1-carboxylate (60 mg, 0.1 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(6-(piperidin-4-yl)pyridin-3-yl)pyrimidin-2-amine (50 mg, 94%) as a yellow solid compound.

LCMS: 467 [M+H]$^+$

Step-5: Synthesis of 5-fluoro-4-(8-fluoro-4-isopropyl-3,4-dihydro-2H-benzo[b][1,4]oxazin-6-yl)-N-(6-(1-methylpiperidin-4-yl)pyridin-3-yl)pyrimidin-2-amine To a stirred solution of 5-fluoro-4-(8-fluoro-4-isopropyl-3,4-dihydro-2H-benzo[b][1,4]oxazin-6-yl)-N-(6-(piperidin-4-yl)pyridin-3-yl)pyrimidin-2-amine (50 mg, 0.09 mmol, 1 equiv) in DCE (5 mL), was added Formaldehyde (40% in water) (0.01 mL, 0.29 mmol, 3 equiv), acetic acid (0.02 mL, 0.45 mmol, 5 equiv). The reaction mixture was allowed to stir at RT for 1 h. The reaction mixture was cooled to 0° C. NaCNBH$_3$ (18 mg, 0.29 mmol, 3 equiv) was added to above mixture and raise the temperature to RT. The reaction mixture was allowed to stir at RT for overnight. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(6-(1-methylpiperidin-4-yl)pyridin-3-yl)pyrimidin-2-amine (7 mg, 15%) as a yellow color solid compound.

LCMS: 481 [M+H]$^+$ $^1$HNMR: (400 MHz, DMSO-d$_6$) δ 9.79 (s, 1H), 8.84 (br. s., 1H), 8.57 (d, J=3.9 Hz, 1H), 8.05 (d, J=6.1 Hz, 1H), 7.44 (br. s., 1H), 7.27-7.01 (m, 2H), 4.30 (br. s., 2H), 4.17-4.02 (m, 1H), 3.30 (br. s., 3H), 2.88 (d, J=11.0 Hz, 2H), 2.21 (s, 3H), 2.00 (br. s., 2H), 1.88-1.59 (m, 4H), 1.19 (d, J=6.6 Hz, 6H).

Example-34: Synthesis of 5-fluoro-N-(3-fluoro-4-(piperazin-1-yl) phenyl)-4-(8-fluoro-4-methyl-3,4-dihydro-2H-benzo[b][1,4]oxazin-6-yl)pyrimidin-2-amine (Compound 34)

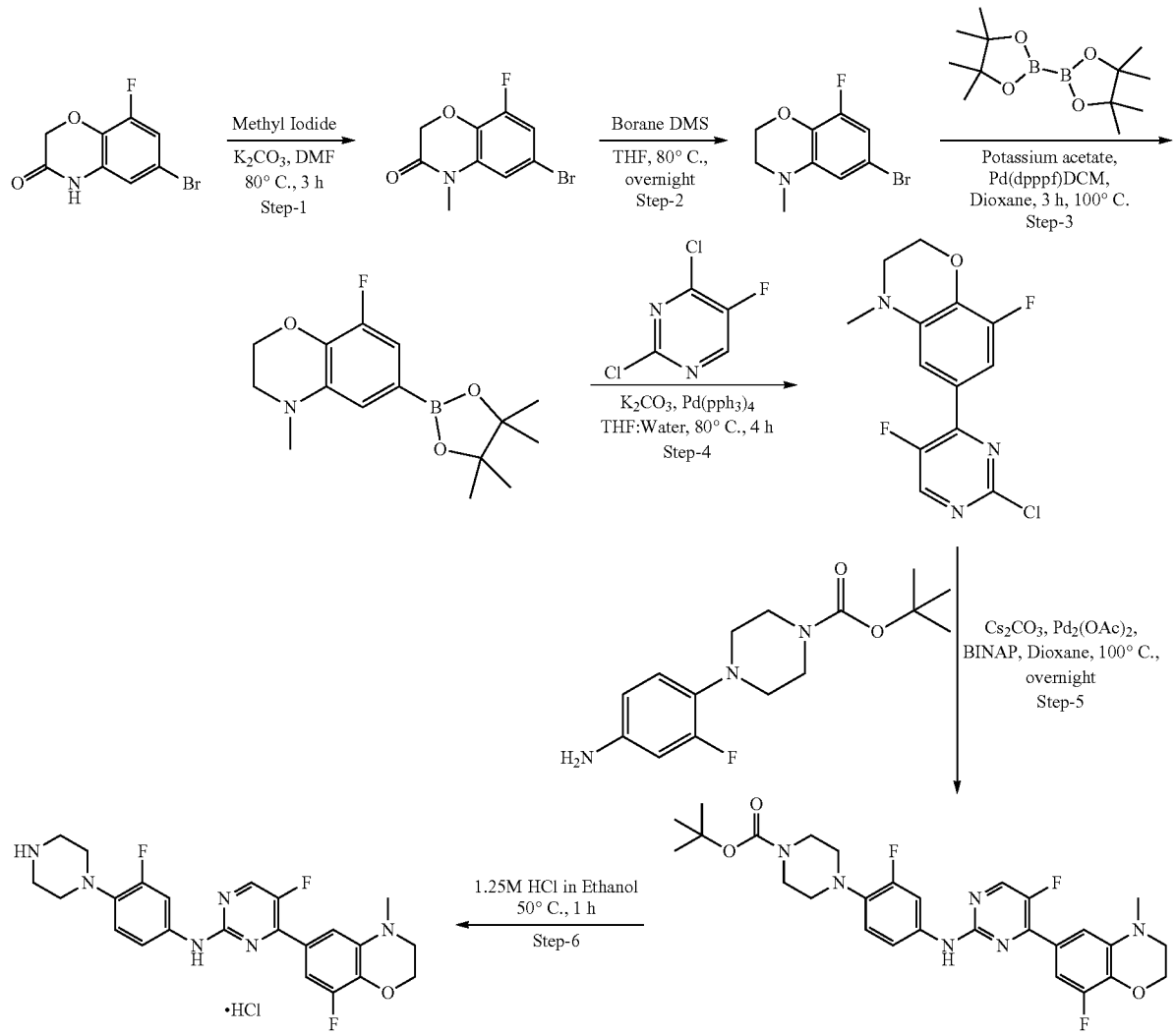

Step-1: Synthesis of 6-bromo-8-fluoro-4-isopropyl-2H-benzo[b][1,4]oxazin-3(4H)-o6-bromo-8-fluoro-4-methyl-2H-benzo[b][1,4]oxazin-3(4H)-onene To a stirred solution of 6-bromo-8-fluoro-2H-benzo[b][1,4]oxazin-3(4H)-one (700 mg, 2.85 mmol, 1 equiv) in DMF (10 mL), was added K$_2$CO$_3$ (789 mg, 5.71 mmol, 2 equiv) and methyl iodide (0.4 mL, 5.71 mmol, 2 equiv). The reaction mixture was allowed to stir at 80° C. for 3 h. Progress of the reaction was monitored by TLC and LCMS. After completion of the reaction, the reaction mixture was diluted with water (50 mL), solid observed was filtered dried under vacuum to obtain 6-bromo-8-fluoro-4-methyl-2H-benzo[b][1,4]oxazin-3(4H)-one (700 mg, 95%) as an off white solid compound.

LCMS: 260 [M+H]$^+$

Step-2: Synthesis of 6-bromo-8-fluoro-4-methyl-3,4-dihydro-2H-benzo[b][1,4]oxazine To a stirred solution of 6-bromo-8-fluoro-4-methyl-2H-benzo[b][1,4]oxazin-3(4H)-one (700 mg, 2.7 mmol, 1 equiv) in THF (15 mL), was added BH$_3$.DMS (1 mL, 10.8 mmol, 4 equiv) at 0° C. drop wise. The reaction mixture was allowed to stir at 80° C. for overnight. Progress of the reaction was monitored by TLC and LCMS. After completion of the reaction, the reaction mixture was quenched with saturated solution of NaHCO$_3$ (100 mL) and extracted with ethyl acetate (100 mL×2). Organic layer was washed with water (100 mL), dried over anhydrous sodium sulphate and concentrated under reduced pressure to obtain 6-bromo-8-fluoro-4-methyl-3,4-dihydro-2H-benzo[b][1,4]oxazine (650 mg, 98%) as a yellow viscous compound.

LCMS: 246 [M+H]$^+$

Step-3; Synthesis of 8-fluoro-4-methyl-6-(4,4,5,5-tetramethyl-1,3,2-dioxaborolan-2-yl)-3,4-dihydro-2H-benzo[b][1,4]oxazine 6-bromo-8-fluoro-4-methyl-3,4-dihydro-2H-benzo[b][1,4]oxazine (650 mg, 2.65 mmol, 1 equiv), 4,4,5,5-tetramethyl-2-(4,4,5,5-tetramethyl-1,3,2-dioxaborolan-2-yl)-1,3,2-dioxaborolane (809 mg, 3.18 mmol, 1.2 equiv), Potassium acetate (779 mg, 7.95 mmol, 3 equiv) and dioxane (10 mL) were charged in a 25 mL glass bottle. Purged the reaction mixture with nitrogen gas for 15 min., Pd(dppf)Cl2. DCM (108 mg, 0.13 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (50 mL) and water (50 mL). Organic layer was dried over anhydrous sodium sulphate and concentrated under reduced pressure to obtain 8-fluoro-4-methyl-6-(4,4,5,5-tetramethyl-1,3,2-dioxaborolan-2-yl)-3,4-dihydro-2H-benzo[b][1,4]oxazine (700 mg, 90%) as a dark brown viscous compound.

LCMS: 294 [M+H]$^+$

Step-4: Synthesis of 6-(2-chloro-5-fluoropyrimidin-4-yl)-8-fluoro-4-methyl-3,4-dihydro-2H-benzo[b][1,4]oxazine To a stirred solution of 2, 4-dichloro-5-fluoropyrimidine (400 mg, 2.19 mmol, 1 equiv) in THF:Water (5 mL:5 mL) was added 8-fluoro-4-methyl-6-(4,4,5,5-tetramethyl-1,3,2-dioxaborolan-2-yl)-3,4-dihydro-2H-benzo[b][1,4]oxazine (642 mg, 2.19 mmol, 1 equiv), Potassium carbonate (607 mg, 4.39 mmol, 2 equiv) and Pd(PPh$_3$)$_4$ (127 mg, 0.1 mmol, 0.05 equiv). The reaction mixture was allowed to stir at 80° C. for 3 h. Progress of the reaction was monitored by TLC and LCMS. After completion of the reaction, the reaction mixture was diluted with water (30 mL) and extracted wit ethyl acetate (100 mL×2). Organic layer was washed with water (100 mL) and brine (100 mL). Organic layer was dried over anhydrous sodium sulphate and concentrated under reduced pressure to obtain crude compound, which was purified by normal phase combi-flash to obtain 6-(2-chloro-5-fluoropyrimidin-4-yl)-8-fluoro-4-methyl-3,4-dihydro-2H-benzo[b][1,4]oxazine (360 mg, 55%) as a yellow solid compound.

LCMS: 298 [M+H]$^+$

Step-5: Synthesis of tert-butyl 4-(2-fluoro-4-((5-fluoro-4-(8-fluoro-4-methyl-3,4-dihydro-2H-benzo[b][1,4]oxazin-6-yl)pyrimidin-2-yl)amino)phenyl)piperazine-1-carboxylate To a solution of 6-(2-chloro-5-fluoropyrimidin-4-yl)-8-fluoro-4-methyl-3,4-dihydro-2H-benzo[b][1,4]oxazine (100 mg, 0.33 mmol, 1 equiv) in Dioxane (10 mL), was added tert-butyl 4-(4-amino-2-fluorophenyl)piperazine-1-carboxylate (109 mg, 0.37 mmol, 1.1 equiv) and cesium carbonate (161 mg, 0.49 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain tert-butyl 4-(2-fluoro-4-((5-fluoro-4-(8-fluoro-4-methyl-3,4-dihydro-2H-benzo[b][1,4]oxazin-6-yl)pyrimidin-2-yl)amino)phenyl)piperazine-1-carboxylate (70 mg, 70%) as a yellow solid compound.

LCMS: 557[M+H]$^+$

Step-6: Synthesis of 5-fluoro-N-(3-fluoro-4-(piperazin-1-yl) phenyl)-4-(8-fluoro-4-methyl-3,4-dihydro-2H-benzo[b][1,4]oxazin-6-yl)pyrimidin-2-amine tert-butyl 4-(2-fluoro-4-((5-fluoro-4-(8-fluoro-4-methyl-3,4-dihydro-2H-benzo[b][1,4]oxazin-6-yl)pyrimidin-2-yl)amino)phenyl)piperazine-1-carboxylate (70 mg, 0.12 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-fluoro-N-(3-fluoro-4-(piperazin-1-yl)phenyl)-4-(8-fluoro-4-methyl-3,4-dihydro-2H-benzo[b][1,4]oxazin-6-yl)pyrimidin-2-amine (45 mg, 73%) as a brick red color solid compound.

LCMS: 457[M+H]$^+$ $^1$HNMR: (400 MHz, DMSO-d6) δ 9.83 (s, 1H), 9.33 (s, 1H), 8.58 (d, J=3.9 Hz, 1H), 7.86 (dd, J=15.5, 2.5 Hz, 1H), 7.42-7.34 (m, 1H), 7.30 (s, 1H), 7.26-7.17 (m, 1H), 7.06 (t, J=9.4 Hz, 1H), 4.37 (t, J=4.3 Hz, 2H), 3.37 (t, J=4.3 Hz, 2H), 3.26-3.14 (m, 8H), 2.96 (s, 3H).

Example-35: Synthesis of 4-(4-ethyl-8-fluoro-3,4-dihydro-2H-benzo[b][1,4]oxazin-6-yl)-5-fluoro-N-(3-fluoro-4-(piperazin-1-yl)phenyl)pyrimidin-2-amine (Compound 35)

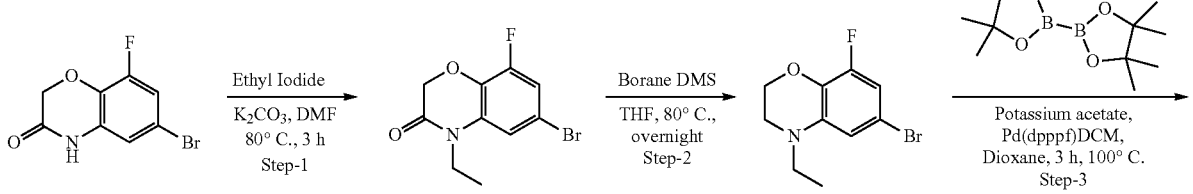

537

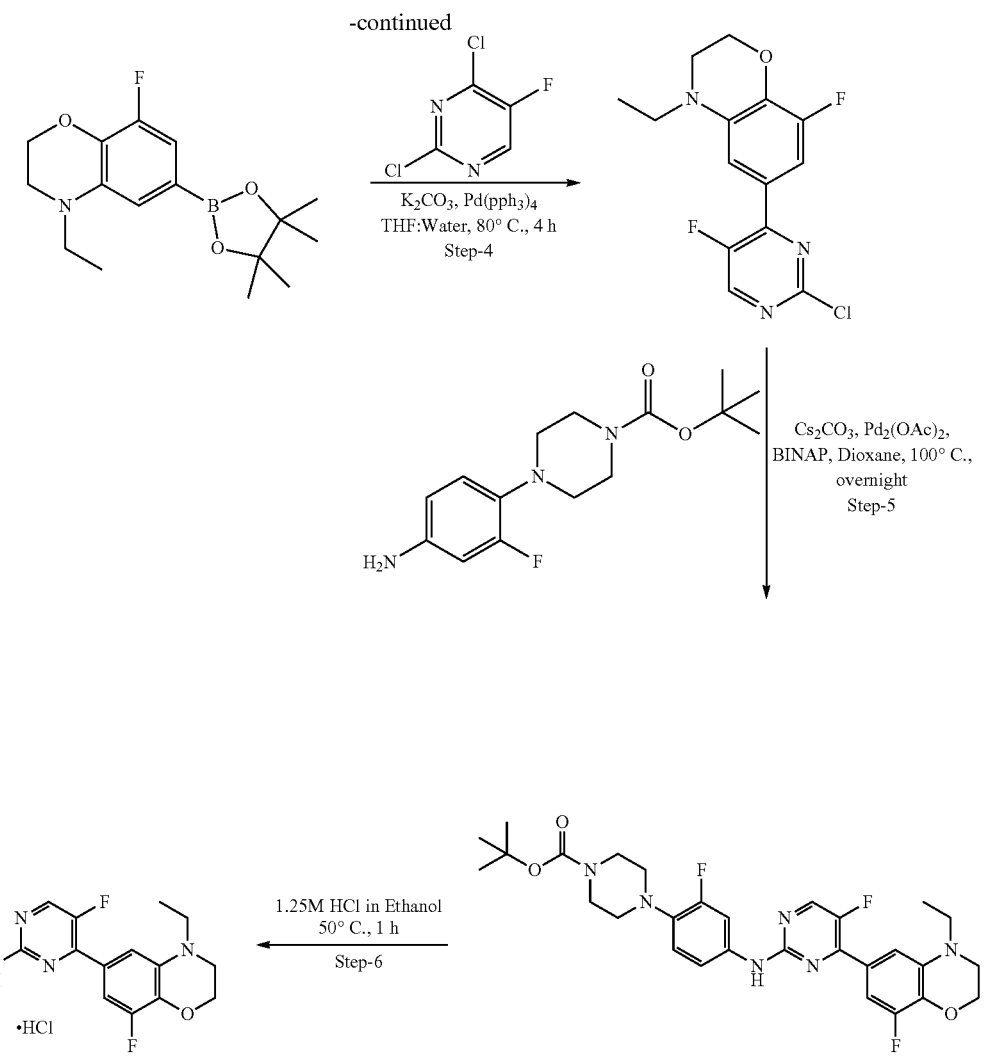

538

Step-1: Synthesis of 6-6-bromo-4-ethyl-8-fluoro-2H-benzo[b][1,4]oxazin-3(4H)-one To a stirred solution of 6-bromo-8-fluoro-2H-benzo[b][1,4]oxazin-3 (4H)-one (700 mg, 2.85 mmol, 1 equiv) in DMF (10 mL), was added K₂CO₃ (789 mg, 5.71 mmol, 2 equiv) and ethyl iodide (0.5 mL, 5.71 mmol, 2 equiv). The reaction mixture was allowed to stir at 80° C. for 3 h. Progress of the reaction was monitored by TLC and LCMS. After completion of the reaction, the reaction mixture was diluted with water (50 mL), solid observed was filtered dried under vacuum to obtain 6-bromo-4-ethyl-8-fluoro-2H-benzo[b][1, 4]oxazin-3 (4H)-one (700 mg, 90%) as an off white solid compound.

LCMS: 274 [M+H]⁺

Step-2: Synthesis of 6-bromo-4-ethyl-8-fluoro-3,4-dihydro-2H-benzo[b][1,4]oxazine To a stirred solution of 6-bromo-4-ethyl-8-fluoro-2H-benzo[b][1,4]oxazin-3(4H)-one (700 mg, 2.7 mmol, 1 equiv) in THF (10 mL), was added BH₃.DMS (1 mL, 10.8 mmol, 4 equiv) at 0° C. drop wise. The reaction mixture was allowed to stir at 80° C. for overnight. Progress of the reaction was monitored by TLC and LCMS. After completion of the reaction, the reaction mixture was quenched with saturated solution of NaHCO₃ (100 mL) and extracted with ethyl acetate (100 mL×2). Organic layer was washed with water (100 mL), dried over anhydrous sodium sulphate and concentrated under reduced pressure to obtain 6-bromo-4-ethyl-8-fluoro-3,4-dihydro-2H-benzo[b][1,4]oxazine (600 mg, 90%) as a transparent oil compound.

LCMS: 260 [M+H]⁺

Step-3: Synthesis of 4-ethyl-8-fluoro-6-(4,4,5,5-tetramethyl-1,3,2-dioxaborolan-2-yl)-3,4-dihydro-2H-benzo[b][1,4]oxazine 6-bromo-4-ethyl-8-fluoro-3,4-dihydro-2H-benzo[b][1,4]oxazine (600 mg, 2.31 mmol, 1 equiv), 4,4,5,5-tetramethyl-2-(4,4,5,5-tetramethyl-1,3,2-dioxaborolan-2-yl)-1,3,2-dioxaborolane (706 mg, 2.77 mmol, 1.2 equiv), Potassium acetate (679 mg, 6.93 mmol, 3 equiv) and dioxane (15 mL) were charged in a 25 mL glass bottle. Purged the reaction mixture with nitrogen gas for 15 min., Pd(dppf)Cl2. DCM (94 mg, 0.11 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (50 mL) and water (50 mL). Organic layer was dried over anhydrous sodium sulphate and concentrated under reduced pressure to obtain 4-ethyl-8-fluoro-6-(4,4,5,5-tetramethyl-1,3,2-dioxaborolan-2-yl)-3,4-dihydro-2H-benzo[b][1,4]oxazine (700 mg, 90%) as a dark brown viscous compound.

LCMS: 308 [M+H]$^+$

Step-4: Synthesis of 6-(2-chloro-5-fluoropyrimidin-4-yl)-4-ethyl-8-fluoro-3,4-dihydro-2H-benzo[b][1,4]oxazine To a stirred solution of 2, 4-dichloro-5-fluoropyrimidine (300 mg, 1.8 mmol, 1 equiv) in THF:Water (1:1=10 mL) was added 4-ethyl-8-fluoro-6-(4,4,5,5-tetramethyl-1,3,2-dioxaborolan-2-yl)-3,4-dihydro-2H-benzo[b][1,4]oxazine (555 mg, 1.8 mmol, 1 equiv), Potassium carbonate (499 mg, 3.6 mmol, 2 equiv) and Pd(PPh$_3$)$_4$ (104 mg, 0.09 mmol, 0.05 equiv). The reaction mixture was allowed to stir at 80° C. for 3 h. Progress of the reaction was monitored by TLC and LCMS. After completion of the reaction, the reaction mixture was diluted with water (30 mL) and extracted wit ethyl acetate (100 mL×2). Organic layer was washed with water (100 mL) and brine (100 mL). Organic layer was dried over anhydrous sodium sulphate and concentrated under reduced pressure to obtain crude compound, which was purified by normal phase combi-flash to obtain 6-(2-chloro-5-fluoropyrimidin-4-yl)-4-ethyl-8-fluoro-3,4-dihydro-2H-benzo[b][1,4]oxazine (150 mg, 27%) as a yellow solid compound.

LCMS: 312 [M+H]$^+$

Step-5: Synthesis of tert-butyl 4-(4-((4-(4-ethyl-8-fluoro-3,4-dihydro-2H-benzo[b][1,4]oxazin-6-yl)-5-fluoropyrimidin-2-yl)amino)-2-fluorophenyl)piperazine-1-carboxylate To a solution of 6-(2-chloro-5-fluoropyrimidin-4-yl)-4-ethyl-8-fluoro-3,4-dihydro-2H-benzo[b][1,4]oxazine (100 mg, 0.32 mmol, 1 equiv) in Dioxane (10 mL), was added tert-butyl 4-(4-amino-2-fluorophenyl)piperazine-1-carboxylate (104 mg, 0.35 mmol, 1.1 equiv) and cesium carbonate (157 mg, 0.48 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain tert-butyl 4-(4-((4-(4-ethyl-8-fluoro-3,4-dihydro-2H-benzo[b][1,4]oxazin-6-yl)-5-fluoropyrimidin-2-yl)amino)-2-fluorophenyl)piperazine-1-carboxylate (60 mg, 33%) as a yellow solid compound.

LCMS: 571[M+H]$^+$

Step-6: Synthesis of 4-(4-ethyl-8-fluoro-3,4-dihydro-2H-benzo[b][1,4]oxazin-6-yl)-5-fluoro-N-(3-fluoro-4-(piperazin-1-yl)phenyl)pyrimidin-2-amine Tert-butyl 4-(4-((4-(4-ethyl-8-fluoro-3,4-dihydro-2H-benzo[b][1,4]oxazin-6-yl)-5-fluoropyrimidin-2-yl)amino)-2-fluorophenyl)piperazine-1-carboxylate (60 mg, 0.1 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 4-(4-ethyl-8-fluoro-3,4-dihydro-2H-benzo[b][1,4]oxazin-6-yl)-5-fluoro-N-(3-fluoro-4-(piperazin-1-yl)phenyl)pyrimidin-2-amine (40 mg, 75%) as a brick red color solid compound.

LCMS: 471[M+H]$^+$ $^1$HNMR: (400 MHz, DMSO-d6) δ 9.81 (s, 1H), 9.19 (d, J=6.7 Hz, 1H), 8.58 (d, J=3.9 Hz, 1H), 7.80 (dd, J=15.1, 2.4 Hz, 1H), 7.39 (dd, J=11.6, 9.1 Hz, 1H), 7.30 (s, 1H), 7.19-7.00 (m, 2H), 4.32 (t, J=4.1 Hz, 2H), 3.49-3.37 (m, 4H), 3.26-3.13 (m, 8H), 1.13 (t, J=7.0 Hz, 3H).

Example-36: Synthesis of 5-fluoro-N-(3-fluoro-4-(piperazin-1-yl) phenyl)-4-(8-fluoro-4-propyl-3,4-dihydro-2H-benzo[b][1,4]oxazin-6-yl)pyrimidin-2-amine (Compound 36)

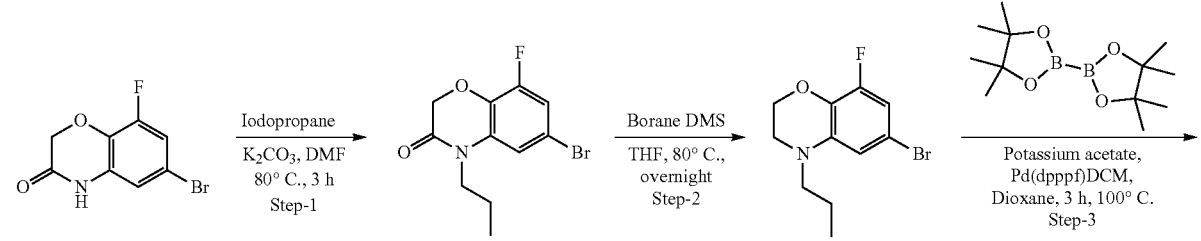

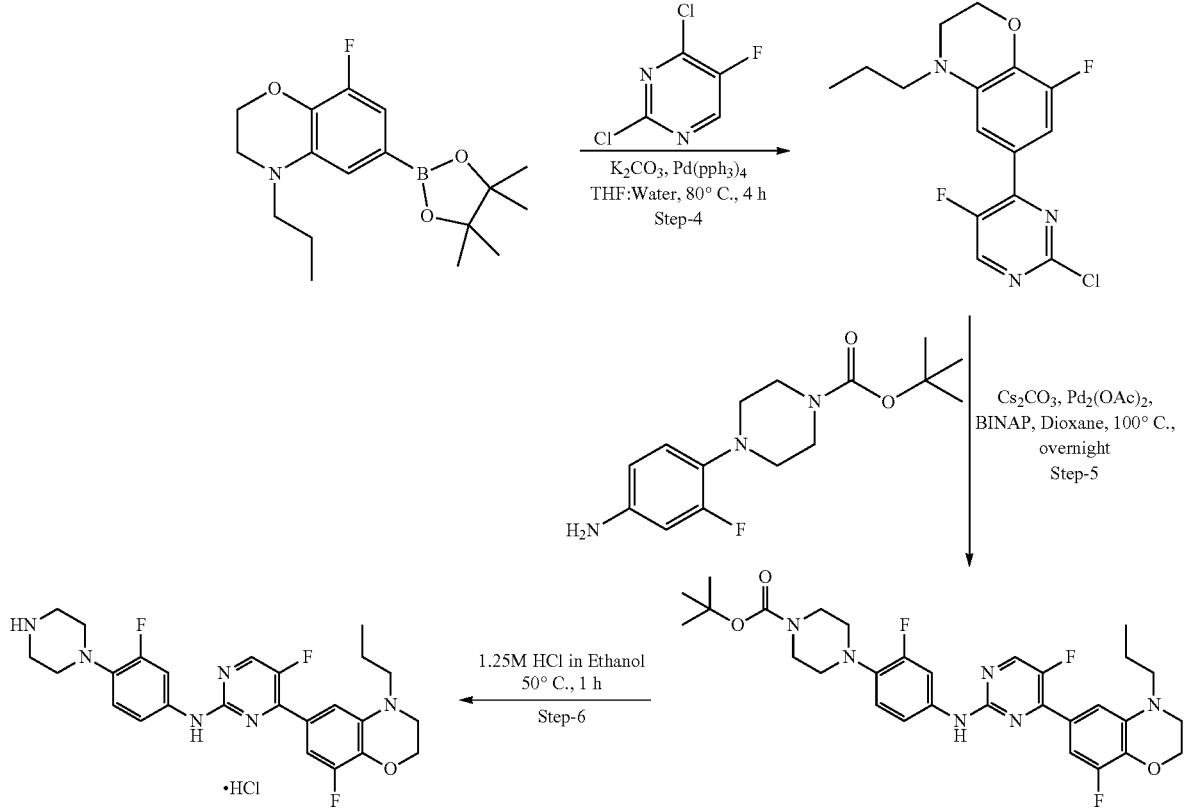

Step-1: Synthesis of 6-bromo-8-fluoro-4-propyl-2H-benzo[b][1,4]oxazin-3(4H)-one

To a stirred solution of 6-bromo-8-fluoro-2H-benzo[b][1,4]oxazin-3(4H)-one (700 mg, 2.85 mmol, 1 equiv) in DMF (10 mL), was added K$_2$CO$_3$ (789 mg, 5.71 mmol, 2 equiv) and iodopropane (0.6 mL, 5.71 mmol, 2 equiv). The reaction mixture was allowed to stir at 80° C. for 3 h. Progress of the reaction was monitored by TLC and LCMS. After completion of the reaction, the reaction mixture was diluted with water (50 mL), solid observed was filtered dried under vacuum to obtain 6-bromo-8-fluoro-4-propyl-2H-benzo[b][1,4]oxazin-3 (4H)-one (750 mg, 92%) as an off white solid compound.

LCMS: 288 [M+H]$^+$

Step-2: Synthesis of 6-bromo-8-fluoro-4-propyl-3,4-dihydro-2H-benzo[b][1,4]oxazine To a stirred solution of 6-bromo-8-fluoro-4-propyl-2H-benzo[b][1,4]oxazin-3(4H)-one (750 mg, 2.6 mmol, 1 equiv) in THF (10 mL), was added BH$_3$.DMS (1 mL, 10.4 mmol, 4 equiv) at 0° C. drop wise. The reaction mixture was allowed to stir at 80° C. for overnight. Progress of the reaction was monitored by TLC and LCMS. After completion of the reaction, the reaction mixture was quenched with saturated solution of NaHCO$_3$ (100 mL) and extracted with ethyl acetate (100 mL×2). Organic layer was washed with water (100 mL), dried over anhydrous sodium sulphate and concentrated under reduced pressure to obtain 6-bromo-8-fluoro-4-propyl-3,4-dihydro-2H-benzo[b][1,4]oxazine (650 mg, 91%) as a transparent oil compound.

LCMS: 274 [M+H]$^+$

Step-3: Synthesis of 8-fluoro-4-propyl-6-(4,4,5,5-tetramethyl-1,3,2-dioxaborolan-2-yl)-3,4-dihydro-2H-benzo[b][1,4]oxazine 6-bromo-8-fluoro-4-propyl-3,4-dihydro-2H-benzo[b][1,4]oxazine (650 mg, 2.31 mmol, 1 equiv), 4,4,5,5-tetramethyl-2-(4,4,5,5-tetramethyl-1,3,2-dioxaborolan-2-yl)-1,3,2-dioxaborolane (725 mg, 2.85 mmol, 1.2 equiv), Potassium acetate (676 mg, 6.93 mmol, 3 equiv) and dioxane (15 mL) were charged in a 25 mL glass bottle. Purged the reaction mixture with nitrogen gas for 15 min., Pd(dppf)Cl2. DCM (94 mg, 0.11 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (50 mL) and water (50 mL). Organic layer was dried over anhydrous sodium sulphate and concentrated under reduced pressure to obtain 8-fluoro-4-propyl-6-(4,4,5,5-tetramethyl-1,3,2-dioxaborolan-2-yl)-3,4-dihydro-2H-benzo[b][1,4] oxazine (650 mg, 85%) as a dark brown viscous compound.

LCMS: 322.1 [M+H]$^+$

Step-4: Synthesis of 6-(2-chloro-5-fluoropyrimidin-4-yl)-8-fluoro-4-propyl-3,4-dihydro-2H-benzo[b][1,4]oxazine To a stirred solution of 2, 4-dichloro-5-fluoropyrimidine (300 mg, 1.8 mmol, 1 equiv) in THF:Water (1:1=10 mL) was added 8-fluoro-4-propyl-6-(4,4,5,5-tetramethyl-1,3,2-dioxaborolan-2-yl)-3,4-dihydro-2H-benzo[b][1,4]oxazine (580 mg, 1.8 mmol, 1 equiv), Potassium carbonate (499 mg, 3.6 mmol, 2 equiv) and Pd(PPh$_3$)$_4$ (104 mg, 0.09 mmol, 0.05 equiv). The reaction mixture was allowed to stir at 80° C. for 3 h. Progress of the reaction was monitored by TLC and LCMS. After completion of the reaction, the reaction mixture was diluted with water (30 mL) and extracted wit ethyl acetate (100 mL×2). Organic layer was washed with water (100 mL) and brine (100 mL). Organic layer was dried over anhydrous sodium sulphate and concentrated under reduced pressure to obtain crude compound, which was purified by normal phase combi-flash to obtain 6-(2-chloro-5-fluoropyrimidin-4-yl)-8-fluoro-4-propyl-3,4-dihydro-2H-benzo[b] [1,4]oxazine (200 mg, 34%) as a yellow solid compound.

LCMS: 326 [M+H]$^+$

Step-5: Synthesis of tert-butyl 4-(2-fluoro-4-((5-fluoro-4-(8-fluoro-4-propyl-3,4-dihydro-2H-benzo [b][1,4]oxazin-6-yl)pyrimidin-2-yl)amino)phenyl) piperazine-1-carboxylate To a solution of 6-(2-chloro-5-fluoropyrimidin-4-yl)-8-fluoro-4-propyl-3,4-dihydro-2H-benzo[b][1,4]oxazine (100 mg, 0.32 mmol, 1 equiv) in Dioxane (10 mL), was added tert-butyl 4-(4-amino-2-fluorophenyl)piperazine-1-carboxylate (100 mg, 0.33 mmol, 1.1 equiv) and cesium carbonate (147 mg, 0.45 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain tert-butyl 4-(2-fluoro-4-((5-fluoro-4-(8-fluoro-4-propyl-3,4-dihydro-2H-benzo[b][1,4]oxazin-6-yl)pyrimidin-2-yl)amino)phenyl) piperazine-1-carboxylate (50 mg, 28%) as a yellow solid compound.

LCMS: 585[M+H]$^+$

Step-6: Synthesis of 5-fluoro-N-(3-fluoro-4-(piperazin-1-yl) phenyl)-4-(8-fluoro-4-propyl-3,4-dihydro-2H-benzo[b][1,4]oxazin-6-yl)pyrimidin-2-amine tert-butyl 4-(2-fluoro-4-((5-fluoro-4-(8-fluoro-4-propyl-3,4-dihydro-2H-benzo[b][1,4]oxazin-6-yl)pyrimidin-2-yl) amino)phenyl)piperazine-1-carboxylate (50 mg, 0.08 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-fluoro-N-(3-fluoro-4-(piperazin-1-yl)phenyl)-4-(8-fluoro-4-propyl-3,4-dihydro-2H-benzo[b][1,4]oxazin-6-yl)pyrimidin-2-amine (35 mg, 78%) as a brick red color solid compound.

LCMS: 485[M+H]$^+$ $^1$HNMR: (400 MHz, DMSO-d6) δ 9.82 (s, 1H), 9.30-9.23 (m, 1H), 8.58 (d, J=3.9 Hz, 1H), 7.79 (dd, J=15.3, 2.4 Hz, 1H), 7.42 (dd, J=8.8, 2.4 Hz, 1H), 7.27 (s, 1H), 7.14 (d, J=11.2 Hz, 1H), 7.05 (t, J=9.4 Hz, 1H), 4.30 (t, J=4.3 Hz, 2H), 3.43 (t, J=4.3 Hz, 2H), 3.31 (t, J=7.3 Hz, 2H), 3.26-3.13 (m, 8H), 1.61 (h, J=7.4 Hz, 2H), 0.89 (t, J=7.3 Hz, 3H).

Example-37: Synthesis of N$^5$-(5-fluoro-4-(8-fluoro-4-isopropyl-3,4-dihydro-2H-benzo[b][1,4]oxazin-6-yl)pyrimidin-2-yl)-N$^2$,N$^2$-dimethyl-2, 3-dihydro-1H-indene-2, 5-diamine (Compound 37)

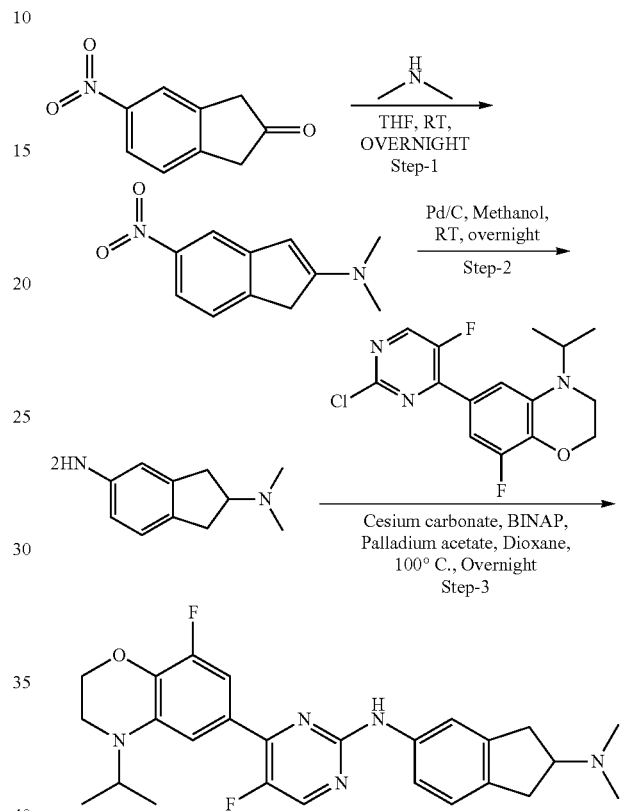

Step-1: Synthesis N, N-dimethyl-5-nitro-1H-inden-2-amine

To a stirred solution of 5-nitro-1,3-dihydro-2H-inden-2-one (1000 mg, 5.64 mmol, 1 equiv) in THF (15 mL), was added dimethyl amine (2 M in THF) (5.6 mL, 11.2 mmol, 2 equiv). The resultant reaction mixture was allowed to stir at RT for overnight. Progress of the reaction was monitored by TLC and LCMS. After completion of the reaction, the mixture was diluted with ice water (50 mL) and extracted with EtoAc (100 mL×2). Organic layer was washed with water (100 mL) and brine (100 mL). Organic layer was dried over anhydrous sodium sulphate and concentrated under reduced pressure to obtain N, N-dimethyl-5-nitro-1H-inden-2-amine (800 mg, 69%) as a brown crystal solid compound.

LCMS: 205 [M+H]$^+$

Step-2: Synthesis of N2, N2-dimethyl-2, 3-dihydro-1H-indene-2, 5-diamine

To a stirred solution of N, N-dimethyl-5-nitro-1H-inden-2-amine (800 mg, 3.9 mmol, 1 equiv) in methanol (10 mL), was added Pd/C (20% w/w) (160 mg) under H$_2$ atm. The resultant reaction mixture was allowed to stir at RT for overnight. Progress of the reaction was monitored by TLC and LCMS. After completion of the reaction, the mixture was passes through celite bed and the filtrate was concentrated under reduced pressure to obtain N2, N2-dimethyl-2,3-dihydro-1H-indene-2, 5-diamine (600 mg, 87%) as a dark brown solid compound.

LCMS: 177 [M+H]+

Step-3: Synthesis of N5-(5-fluoro-4-(8-fluoro-4-isopropyl-3,4-dihydro-2H-benzo[b][1,4]oxazin-6-yl) pyrimidin-2-yl)-N2,N2-dimethyl-2,3-dihydro-1H-indene-2,5-diamine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added N2, N2-dimethyl-2, 3-dihydro-1H-indene-2, 5-diamine (58 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N5-(5-fluoro-4-(8-fluoro-4-isopropyl-3,4-dihydro-2H-benzo[b][1,4]oxazin-6-yl)pyrimidin-2-yl)-N2,N2-dimethyl-2,3-dihydro-1H-indene-2,5-diamine (5 mg, 4%) as a brown solid compound.

LCMS: 466 [M+H]+

¹HNMR (400 MHz, DMSO-d6) δ 9.57 (s, 1H), 8.53 (d, J=4.1 Hz, 1H), 8.43-8.32 (m, 1H), 7.63 (s, 1H), 7.46 (d, J=8.1 Hz, 1H), 7.41 (s, 1H), 7.15 (d, J=11.7 Hz, 1H), 7.08 (d, J=8.1 Hz, 1H), 4.33-4.21 (m, 2H), 4.13 (dt, J=13.1, 7.3 Hz, 1H), 3.34-3.27 (m, 3H), 2.95 (h, J=6.7, 5.6 Hz, 2H), 2.73 (td, J=14.5, 13.6, 6.1 Hz, 2H), 2.20 (s, 6H), 1.19 (d, J=6.5 Hz, 6H).

Example-38: Synthesis of N-(6-(4-(dimethyl amino) piperidin-1-yl) pyridin-3-yl)-5-fluoro-4-(8-fluoro-4-isopropyl-3,4-dihydro-2H-benzo[b][1,4]oxazin-6-yl) pyrimidin-2-amine (Compound 38)

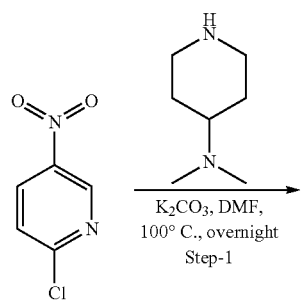

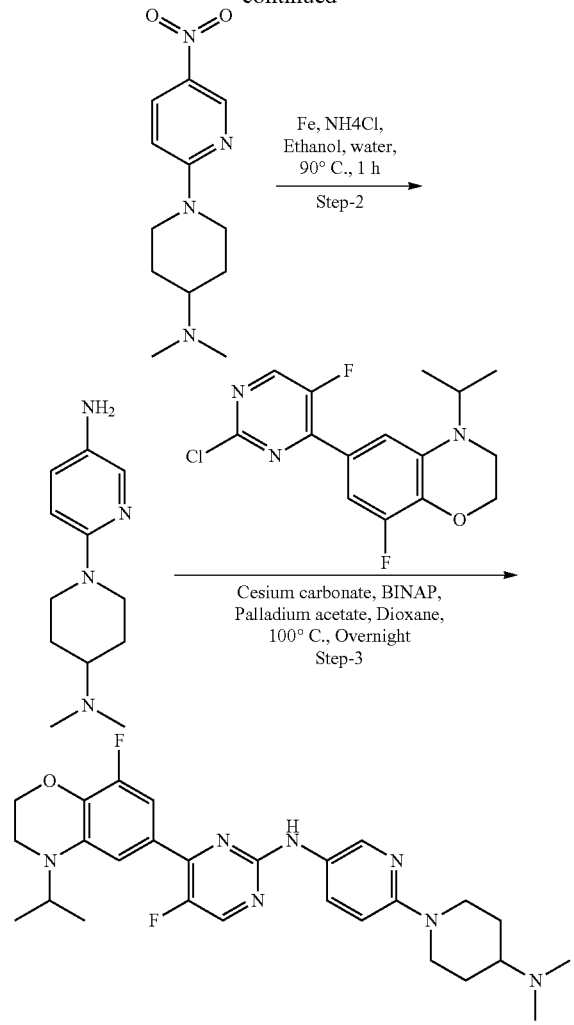

Step-1: Synthesis N, N-dimethyl-1-(5-nitropyridin-2-yl) piperidin-4-amine

To a stirred solution of 2-chloro-5-nitropyridine (500 mg, 3.16 mmol, 1 equiv) in DMF (10 mL), was added K2CO3 (654 mg, 4.74 mmol, 1.5 equiv) and N, N-dimethylpiperidin-4-amine (405 mg, 3.16 mmol, 1 equiv). The resultant reaction mixture was allowed to stir at 100° C. for overnight. Progress of the reaction was monitored by TLC and LCMS. After completion of the reaction, the mixture was diluted with ice water (50 mL), solid observed was filtered and dried under vacuum to obtain N,N-dimethyl-1-(5-nitropyridin-2-yl)piperidin-4-amine (700 mg, 89%) as a yellow solid compound.

LCMS: 251 [M+H]+

Step-2: Synthesis of 6-(4-(dimethyl amino) piperidin-1-yl) pyridin-3-amine

To a stirred solution of N,N-dimethyl-1-(5-nitropyridin-2-yl)piperidin-4-amine (500 mg, 2 mmol, 1 equiv) in ethanol (9 mL), water (3 mL), was added iron powder (336 mg, 6 mmol, 3 equiv) and ammonium chloride (216 mg, 4 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 6-(4-(dimethyl amino) piperidin-1-yl) pyridin-3-amine (400 mg, 91%) as a dark brown viscous compound.

LCMS: 221 [M+H]+

Step-3: Synthesis of N-(6-(4-(dimethyl amino) piperidin-1-yl) pyridin-3-yl)-5-fluoro-4-(8-fluoro-4-isopropyl-3,4-dihydro-2H-benzo[b][1,4]oxazin-6-yl) pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 6-(4-(dimethyl amino) piperidin-1-yl) 239yridine-3-amine (73 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N-(6-(4-(dimethylamino)piperidin-1-yl)$_{239}$yridine-3-yl)-5-fluoro-4-(8-fluoro-4-isopropyl-3,4-dihydro-2H-benzo[b][1,4]oxazin-6-yl)pyrimidin-2-amine (3 mg, 2%) as a yellow solid compound.

LCMS: 510 [M+H]+

$^1$HNMR (400 MHz, DMSO-d6) δ 9.37 (s, 1H), 8.48 (d, J=4.4 Hz, 2H), 8.32 (br. S., 1H), 7.79 (dd, J=9.0, 2.4 Hz, 1H), 7.42 (br. S., 1H), 7.13 (d, J=11.0 Hz, 1H), 6.82 (d, J=8.8 Hz, 1H), 4.29 (br. S., 2H), 4.22 (d, J=12.3 Hz, 2H), 4.04-4.14 (m, 1H), 3.29 (br. S., 2H), 2.74 (t, J=11.6 Hz, 2H), 2.34 (d, J=12.7 Hz, 1H), 2.22 (s, 6H), 1.82 (d, J=11.0 Hz, 2H), 1.38 (d, J=9.2 Hz, 2H), 1.05-1.23 (m, 6H).

Example-39: Synthesis of 4-((5-fluoro-4-(8-fluoro-4-isopropyl-3,4-dihydro-2H-benzo[b][1,4]oxazin-6-yl)pyrimidin-2-yl)amino)-1',2',3',6'-tetrahydro-2H-[1,4'-bipyridin]-2-one (Compound 39)

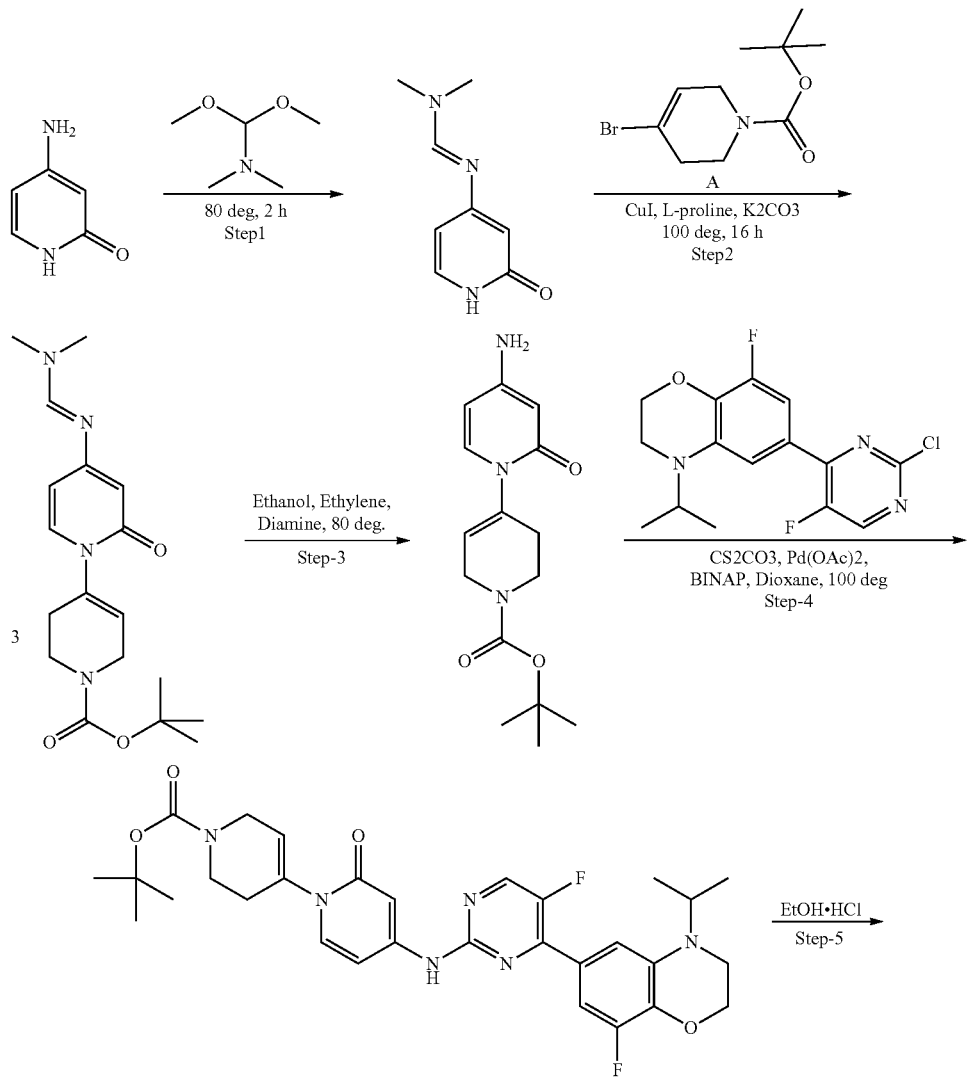

-continued

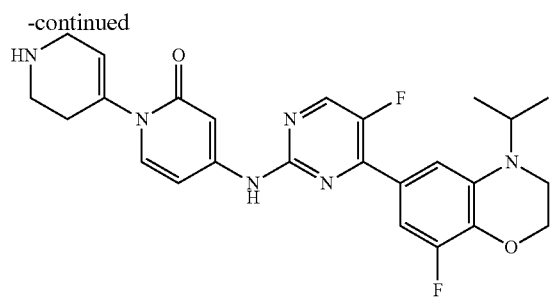

Step-1: Synthesis of (E/Z)—N,N-dimethyl-N'-(2-oxo-1,2-dihydropyridin-4-yl)formimidamide 4-aminopyridin-2(1H)-one (200 mg, 1.8 mmol, 1 equiv) was taken in 1,1-dimethoxy-N,N-dimethylmethanamine (4 mL) and the resultant reaction mixture was stirred at 80° C. for 2 h. Progress of the reaction was monitored by LCMS. After completion of the reaction, the reaction mixture was concentrated under vacuum to afford (E/Z)—N,N-dimethyl-N'-(2-oxo-1,2-dihydropyridin-4-yl)formimidamide (220 mg).

LCMS: 166 [M+H]$^+$

Step-2: Synthesis of tert-butyl (E/Z)-4-(4-(((dimethylamino)methylene)amino)-2-oxopyridin-1(2H)-yl)piperidine-1-carboxylate To a solution of (E/Z)—N,N-dimethyl-N'-(2-oxo-1,2-dihydropyridin-4-yl)formimidamide (500 mg, 3 mmol, 1 equiv) in DMF (10 mL), was added tert-butyl 4-bromo-3,6-dihydropyridine-1(2H)-carboxylate (730 mg, 4.5 mmol, 1.5 equiv) followed by addition of potassium carbonate (700 mg, 5.1 mmol, 1.7 equiv), CuI (57 mg, 0.3 mmol, 0.1 equiv), L-proline (68 mg, 0.6 mmol, 0.2 equiv). The resultant reaction mixture was stirred at 100° C. for 16 h. Progress of the reaction was monitored by TLC and LCMS. After completion of the reaction, the reaction mixture was diluted with water (30 mL) and extracted with EtOAc (50 mL). The organic layer dried over anhydrous sodium sulphate and concentrated under reduced pressure to obtain crude compound, which was purified by making HCL salt to afford tert-butyl (E)-4-(4-(((dimethylamino)methylene)amino)-2-oxopyridin-1(2H)-yl)piperidine-1-carboxylate (150 mg). LCMS: 347 [M+H]+

Step-3: Synthesis tert-butyl 4-amino-2-oxo-3',6'-dihydro-2H-[1,4'-bipyridine]-1'(2'H)-carboxylate To a solution of tert-butyl (E)-4-(4-(((dimethylamino)methylene)amino)-2-oxopyridin-1(2H)-yl)piperidine-1-carboxylate (135 mg, 0.4 mmol, 1 equiv) in ethanol (5 mL), was added ethylene diamine (35 mg, 0.6 mmol, 1.5 equiv. The resultant reaction mixture was stirred at 80° C. for 3 h. Progress of the reaction was monitored by TLC and LCMS. After completion of the reaction, the reaction mixture was concentrated, diluted with water (10 mL) and extracted with EtOAc (10 mL). The organic layer dried over anhydrous sodium sulphate and concentrated under reduced pressure to obtain tert-butyl 4-amino-2-oxo-3',6'-dihydro-2H-[1,4'-bipyridine]-1'(2'H)-carboxylate (98 mg). LCMS: 292 [M+H]+

Step-4: Synthesis of tert-butyl 4-((5-fluoro-4-(8-fluoro-4-isopropyl-3,4-dihydro-2H-benzo[b][1,4]oxazin-6-yl)pyrimidin-2-yl)amino)-2-oxo-3',6'-dihydro-2H-[1,4'-bipyridine]-1'(2'H)-carboxylate To a solution of 6-(2-chloro-5-fluoropyrimidin-4-yl)-8-fluoro-4-isopropyl-2-methyl-3,4-dihydro-2H-benzo[b][1,4]oxazine (100 mg, 0.3 mmol, 1 equiv) in dioxane (3 mL), was added tert-butyl 4-amino-2-oxo-3',6'-dihydro-2H-[1,4'-bipyridine]-1'(2'H)-carboxylate (98 mg, 0.33 mmol, 1.1 equiv) and cesium carbonate (146 mg, 0.45 mmol, 1.5 equiv). The reaction mixture was aerated with nitrogen gas for 10 min. followed by the addition of palladium acetate (6 mg, 0.03 mmol, 0.1 equiv) and BINAP (37 mg, 0.06 mmol, 0.2 equiv) again purged nitrogen for 5 min. The resultant reaction mixture was stirred at 100° C. for 16 h. Progress of the reaction was monitored by TLC and LCMS. After completion of the reaction, the reaction mixture was diluted with water (10 mL) and extracted with EtOAc (15 mL). The organic layer dried over anhydrous sodium sulphate and concentrated under reduced pressure to obtain crude compound used directly for next step. 100 mg of tert-butyl 4-((5-fluoro-4-(8-fluoro-4-isopropyl-3,4-dihydro-2H-benzo[b][1,4]oxazin-6-yl)pyrimidin-2-yl) amino)-2-oxo-3',6'-dihydro-2H-[1,4'-bipyridine]-1'(2'H)-carboxylate obtained as a crude. LCMS: 581 [M+H]$^+$

Step-5: Synthesis of 4-((5-fluoro-4-(8-fluoro-4-isopropyl-3,4-dihydro-2H-benzo[b][1,4]oxazin-6-yl)pyrimidin-2-yl)amino)-1',2',3',6'-tetrahydro-2H-[1,4'-bipyridin]-2-one tert-butyl 4-((5-fluoro-4-(8-fluoro-4-isopropyl-3,4-dihydro-2H-benzo[b][1,4]oxazin-6-yl)pyrimidin-2-yl)amino)-2-oxo-3',6'-dihydro-2H-[1,4'-bipyridine]-1'(2'H)-carboxylate (100 mg, 0.17 mmol, 1 equiv) was taken in 1.25 M HCl in ethanol (4 mL) and the resultant reaction mixture was stirred at 50° C. for 2 h. Progress of the reaction was monitored by LCMS. After completion of the reaction, the reaction mixture was concentrated under vacuum purified by reverse phase HPLC to afford 4-((5-fluoro-4-(8-fluoro-4-isopropyl-3,4-dihydro-2H-benzo[b][1,4]oxazin-6-yl)pyrimidin-2-yl)amino)-1',2',3',6'-tetrahydro-2H-[1,4'-bipyridin]-2-one (4 mg). LCMS: 481 [M+H]$^+$ $^1$HNMR: (400 MHz, METHANOL-d$_4$) δ 8.50 (d, J=3.9 Hz, 1H), 7.53 (s, 1H), 7.41-7.34 (m, 1H), 7.26 (br. s., 1H), 6.73 (d, J=7.5 Hz, 1H), 5.95 (br. s., 1H), 4.58 (br. s., 1H), 4.41-4.19 (m, 2H), 3.81 (br. s., 1H), 3.48 (br. s., 1H), 3.41 (d, J=6.6 Hz, 1H), 2.69 (br. s., 1H), 1.39-1.12 (m, 3H).

Example-40: Synthesis of 5-chloro-4-(8-chloro-4-isopropyl-3,4-dihydro-2H-benzo[b][1,4]oxazin-6-yl)-N-(3-fluoro-4-(piperazin-1-yl)phenyl)pyrimidin-2-amine (Compound 52)

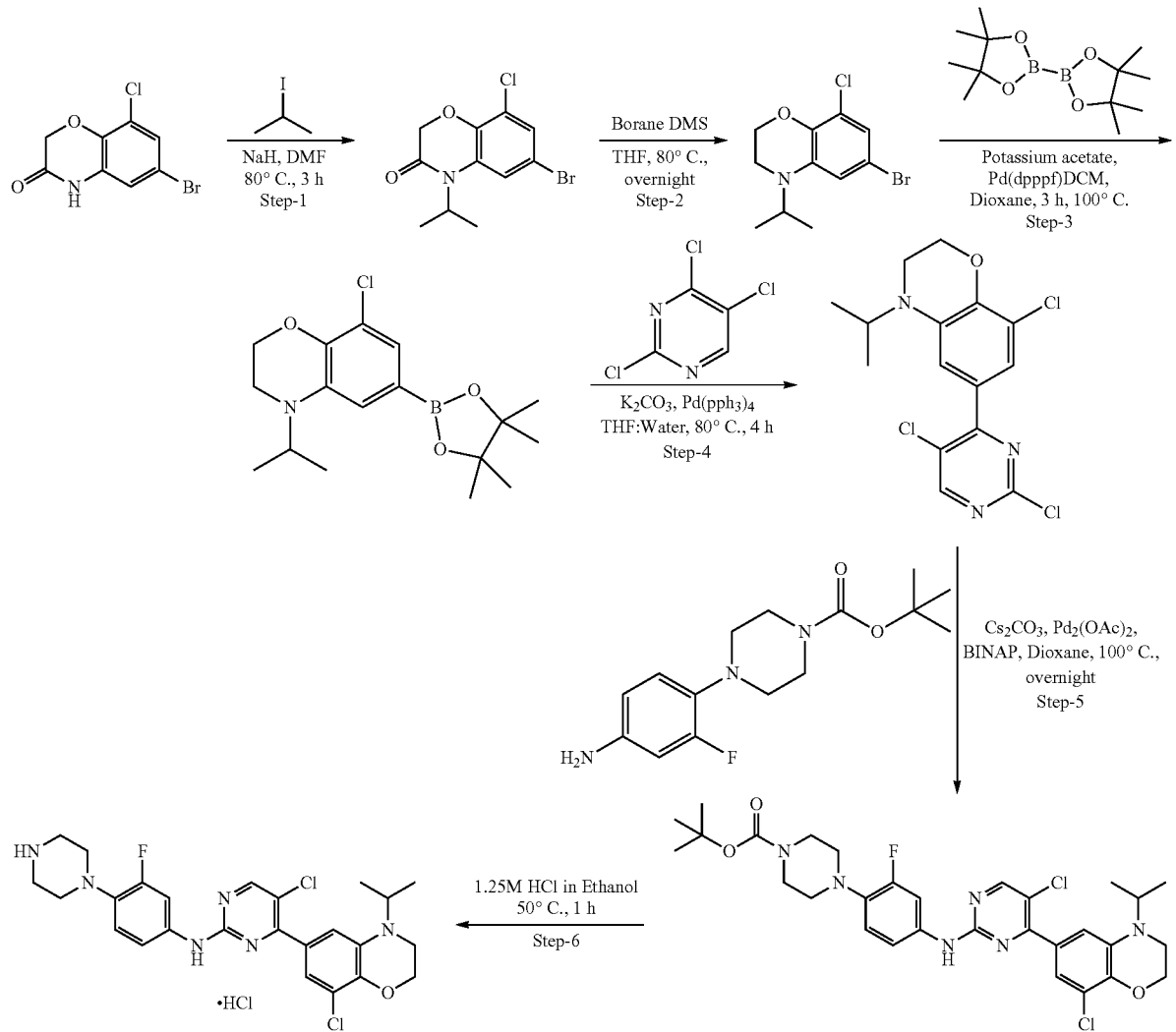

Step-1: Synthesis of 6-bromo-8-chloro-4-isopropyl-2H-benzo[b][1,4]oxazin-3(4H)-one To a stirred solution of 6-bromo-8-chloro-2H-benzo[b][1,4]oxazin-3(4H)-one (2000 mg, 7.6 mmol, 1 equiv) in DMF (20 mL), was added NaH (610 mg, 15.2 mmol, 2 equiv) and isopropyl iodide (1.5 mL, 15.2 mmol, 2 equiv). The reaction mixture was allowed to stir at 80° C. for 3 h. Progress of the reaction was monitored by TLC and LCMS. After completion of the reaction, the reaction mixture was diluted with water (100 mL) and extracted with ethyl acetate (100 mL×2). Organic layer was washed with brine (100 mL) and water (100 mL). Organic layer was dried over anhydrous sodium sulphate and concentrated under reduced pressure to obtain 6-bromo-8-chloro-4-isopropyl-2H-benzo[b][1,4]oxazin-3 (4H)-one (700 mg, 95%) as an off white solid compound. LCMS: 260 [M+H]$^+$ Step-2: Synthesis of 6-bromo-8-chloro-4-isopropyl-3,4-dihydro-2H-benzo[b][1,4]oxazine To a stirred solution of 6-bromo-8-chloro-4-isopropyl-2H-benzo[b][1,4]oxazin-3(4H)-one (650 mg, 2.1 mmol, 1 equiv) in THF (15 mL), was added BH$_3$.DMS (2 M in THF) (4 mL, 8.5 mmol, 4 equiv) at 0° C. drop wise. The reaction mixture was allowed to stir at 80° C. for overnight. Progress of the reaction was monitored by TLC and LCMS. After completion of the reaction, the reaction mixture was quenched with saturated solution of NaHCO$_3$ (50 mL) and extracted with ethyl acetate (100 mL×2). Organic layer was washed with water (100 mL), dried over anhydrous sodium sulphate and concentrated under reduced pressure to obtain 6-bromo-8-chloro-4-isopropyl-3,4-dihydro-2H-benzo[b][1,4]oxazine (550 mg, 89%) as a transparent oil compound. LCMS: 290 [M+H]$^+$

Step-3: Synthesis of 8-chloro-4-isopropyl-6-(4,4,5,5-tetramethyl-1,3,2-dioxaborolan-2-yl)-3,4-dihydro-2H-benzo[b][1,4]oxazine 6-bromo-8-chloro-4-isopropyl-3,4-dihydro-2H-benzo[b][1,4]oxazine (550 mg, 1.9 mmol, 1 equiv), 4,4,5,5-tetramethyl-2-(4,4,5,5-tetramethyl-1,3,2-dioxaborolan-2-yl)-1,3,2-dioxaborolane (725 mg, 2.8 mmol, 1.5 equiv), Potassium acetate (466 mg, 4.7 mmol, 2.5 equiv) and dioxane (10 mL) were charged in a 25 mL glass bottle. Purged the reaction mixture with nitrogen gas for 15 min., Pd(dppf)Cl2. DCM (78 mg, 0.09 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (100 mL) and water (100 mL). Organic layer was dried over anhydrous sodium sulphate and concentrated under reduced pressure to obtain 8-chloro-4-isopropyl-6-(4,4,5,5-tetramethyl-1,3,2-dioxaborolan-2-yl)-3,4-dihydro-2H-benzo[b][1,4]oxazine (600 mg, 94%) as a dark brown viscous compound. LCMS: 338 [M+H]$^+$

Step-4: Synthesis of 8-chloro-6-(2, 5-dichloropyrimidin-4-yl)-4-isopropyl-3,4-dihydro-2H-benzo[b][1,4]oxazine To a stirred solution of 2,4,5-trichloropyrimidine (160 mg, 0.87 mmol, 1 equiv) in THF:Water (1:1=10 mL) was added 8-chloro-4-isopropyl-6-(4,4,5,5-tetramethyl-1,3,2-dioxaborolan-2-yl)-3,4-dihydro-2H-benzo[b][1,4]oxazine (296 mg, 0.87 mmol, 1 equiv), Potassium carbonate (240 mg, 1.74 mmol, 2 equiv) and Pd(PPh$_3$)$_4$ (50 mg, 0.04 mmol, 0.05 equiv). The reaction mixture was allowed to stir at 80° C. for 3 h. Progress of the reaction was monitored by TLC and LCMS. After completion of the reaction, the reaction mixture was diluted with water (30 mL) and extracted wit ethyl acetate (100 mL×2). Organic layer was washed with water (100 mL) and brine (100 mL). Organic layer was dried over anhydrous sodium sulphate and concentrated under reduced pressure to obtain crude compound, which was purified by normal phase combi-flash to obtain 8-chloro-6-(2,5-dichloropyrimidin-4-yl)-4-isopropyl-3,4-dihydro-2H-benzo[b][1,4]oxazine (300 mg, 80%) as a yellow solid compound.
LCMS: 358 [M+H]$^+$

Step-5: Synthesis of tert-butyl 4-(4-((5-chloro-4-(8-chloro-4-isopropyl-3,4-dihydro-2H-benzo[b][1,4]oxazin-6-yl)pyrimidin-2-yl)amino)-2-fluorophenyl)piperazine-1-carboxylate To a solution of 8-chloro-6-(2,5-dichloropyrimidin-4-yl)-4-isopropyl-3,4-dihydro-2H-benzo[b][1,4]oxazine (100 mg, 0.28 mmol, 1 equiv) in Dioxane (10 mL), was added tert-butyl 4-(4-amino-2-fluorophenyl)piperazine-1-carboxylate (91 mg, 0.3 mmol, 1.1 equiv) and cesium carbonate (137 mg, 0.42 mmol, 1.5 equiv). The reaction mixture was purged with nitrogen gas for 30 min., followed by the addition of palladium acetate (1.2 mg, 0.005 mmol, 0.02 equiv) and BINAP (7 mg, 0.011 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain tert-butyl 4-(4-((5-chloro-4-(8-chloro-4-isopropyl-3,4-dihydro-2H-benzo[b][1,4]oxazin-6-yl)pyrimidin-2-yl)amino)-2-fluorophenyl)piperazine-1-carboxylate (30 mg, 16%) as a yellow solid compound. LCMS: 617 [M+H]$^+$

Step-6: Synthesis of 5-chloro-4-(8-chloro-4-isopropyl-3,4-dihydro-2H-benzo[b][1,4]oxazin-6-yl)-N-(3-fluoro-4-(piperazin-1-yl)phenyl)pyrimidin-2-amine Tert-butyl 4-(4-((5-chloro-4-(8-chloro-4-isopropyl-3,4-dihydro-2H-benzo[b][1,4]oxazin-6-yl)pyrimidin-2-yl)amino)-2-fluorophenyl)piperazine-1-carboxylate (30 mg, 0.04 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-chloro-4-(8-chloro-4-isopropyl-3,4-dihydro-2H-benzo[b][1,4]oxazin-6-yl)-N-(3-fluoro-4-(piperazin-1-yl)phenyl)pyrimidin-2-amine (25 mg, 93%) as an orange color solid compound. LCMS: 517 [M+H]$^+$; $^1$HNMR (400 MHz, DMSO-d6) δ 9.97 (s, 1H), 8.93 (s, 1H), 8.58 (s, 1H), 7.79 (dd, J=15.3, 2.5 Hz, 1H), 7.40 (dd, J=9.0, 2.5 Hz, 1H), 7.25 (s, 1H), 7.16 (d, J=2.0 Hz, 1H), 7.04 (t, J=9.3 Hz, 1H), 4.33 (t, J=4.2 Hz, 2H), 4.11 (p, J=6.7 Hz, 1H), 3.30 (t, J=4.1 Hz, 2H), 3.24 (s, 4H), 3.15 (t, J=4.9 Hz, 4H), 1.17 (d, J=6.4 Hz, 6H).

Example-41: Synthesis of N-(5-(4-(dimethylamino)piperidin-1-yl) pyridin-2-yl)-5-fluoro-4-(8-fluoro-4-isopropyl-3,4-dihydro-2H-benzo[b][1,4]oxazin-6-yl)pyrimidin-2-amine. (Compound 436)

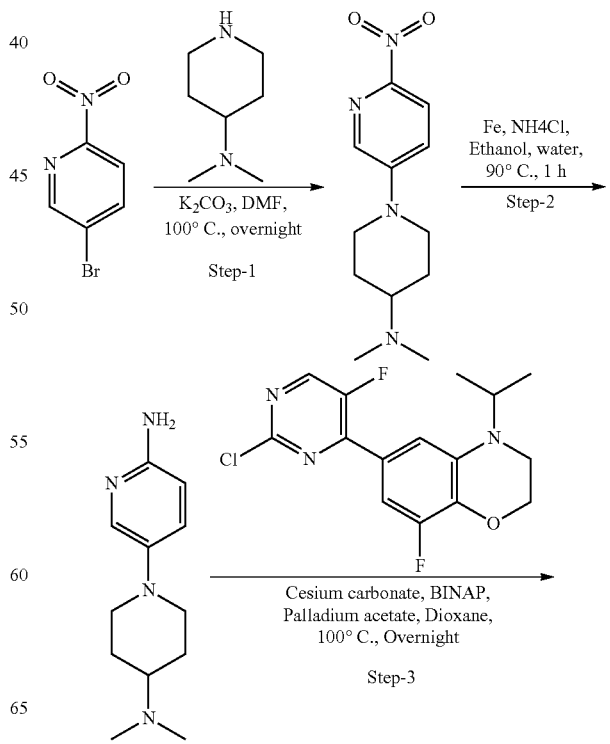

-continued

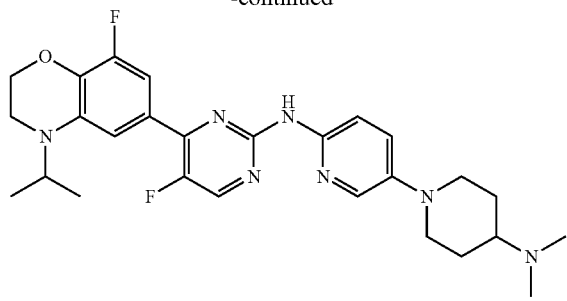

Step-1: Synthesis N, N-dimethyl-1-(6-nitropyridin-3-yl) piperidin-4-amine

To stirred solution of 5-bromo-2-nitropyridine (500 mg, 2.47 mmol, 1 equiv) in DMF (10 mL), was added $K_2CO_3$ (683 mg, 4.95 mmol, 2 equiv) and N, N-dimethylpiperidin-4-amine (316 mg, 2.47 mmol, 1 equiv). The resultant reaction mixture was allowed to stir at 100° C. for overnight. Progress of the reaction was monitored by TLC and LCMS. After completion of the reaction, the mixture was diluted with ice water (50 mL) and extracted with ethyl acetate (100 mL). Organic layer was washed with water (50 mL) and brine solution (50 mL). Organic layer was dried over anhydrous sodium sulphate and concentrated under reduced pressure to obtain N, N-dimethyl-1-(6-nitropyridin-3-yl) piperidin-4-amine (500 mg, 81%) as a yellow solid compound. LCMS: 251 $[M+H]^+$ Step-2: Synthesis of 5-(4-(dimethylamino) piperidin-1-yl) pyridin-2-amine To a stirred solution of N, N-dimethyl-1-(6-nitropyridin-3-yl) piperidin-4-amine (500 mg, 2 mmol, 1 equiv) in ethanol (7 mL), water (3 mL), was added iron powder (336 mg, 6 mmol, 3 equiv) and ammonium chloride (216 mg, 4 mmol, 2 equiv). The resultant reaction mixture was allowed to stir at 90° C. for 1 h. Progress of the reaction was monitored by TLC and LCMS. After completion of the reaction, the mixture was passes through celite bed and the filtrate was concentrated under reduced pressure to obtain 5-(4-(dimethylamino) piperidin-1-yl) pyridin-2-amine (350 mg, 80%) as a dark brown solid compound. LCMS: 221 $[M+H]^+$ Step-3: Synthesis of N-(5-(4-(dimethylamino) piperidin-1-yl) pyridin-2-yl)-5-fluoro-4-(8-fluoro-4-isopropyl-3,4-dihydro-2H-benzo[b][1,4]oxazin-6-yl) pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 5-(4-(dimethylamino) piperidin-1-yl) pyridin-2-amine (73 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N-(5-(4-(dimethylamino)piperidin-1-yl)pyridin-2-yl)-5-fluoro-4-(8-fluoro-4-isopropyl-3,4-dihydro-2H-benzo[b][1,4]oxazin-6-yl)pyrimidin-2-amine (12 mg, 8%) as a yellow solid compound. LCMS: 510 $[M+H]^+$; $^1$HNMR (400 MHz, DMSO-d6) δ 9.64 (s, 1H), 8.55 (d, J=4.0 Hz, 1H), 8.46 (s, 1H), 8.04-7.96 (m, 2H), 7.46 (s, 1H), 7.38 (dd, J=9.1, 3.1 Hz, 1H), 7.17 (d, J=11.6 Hz, 1H), 4.30 (t, J=4.3 Hz, 2H), 4.15 (p, J=6.6 Hz, 1H), 3.64 (dd, J=12.3, 4.4 Hz, 2H), 3.34-3.27 (m, 3H), 2.72-2.61 (m, 2H), 2.19 (s, 6H), 1.89-1.80 (m, 2H), 1.50 (qd, J=12.1, 3.8 Hz, 2H), 1.19 (d, J=6.5 Hz, 6H).

Example-42: Synthesis of 4-((5-fluoro-4-(8-fluoro-4-isopropyl-3,4-dihydro-2H-benzo[b][1,4]oxazin-6-yl)pyrimidin-2-yl)amino)-1-(piperidin-4-yl)pyridin-2(1H)-one: (Compound 437)

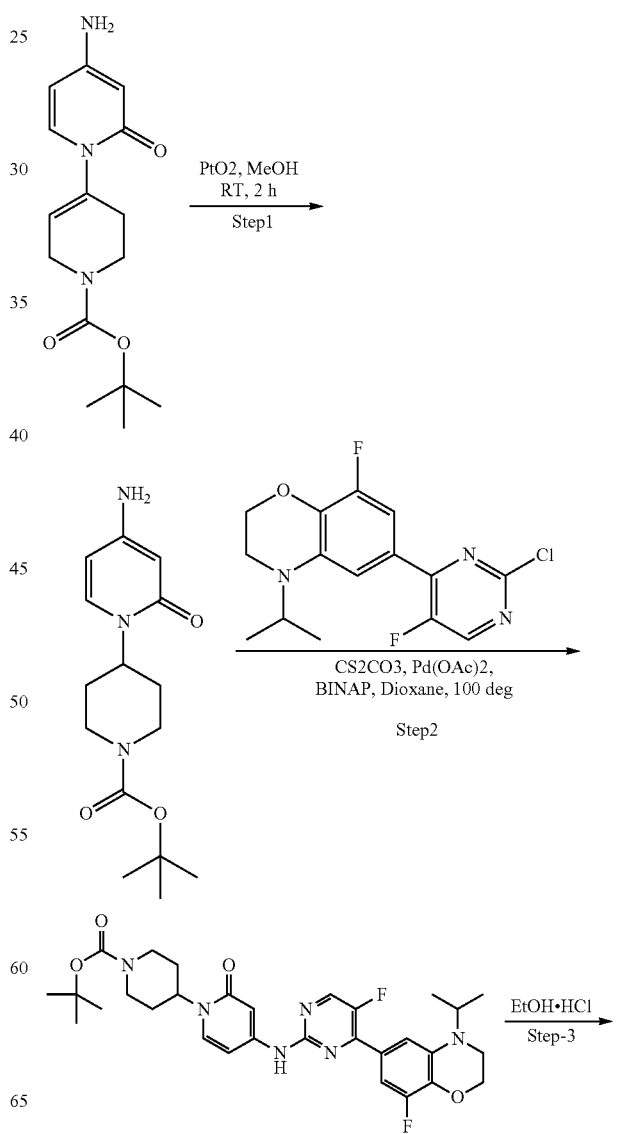

-continued

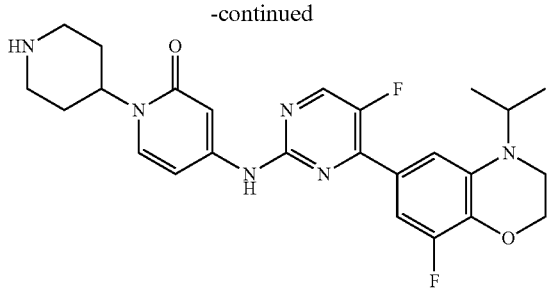

Step-1: Synthesis of tert-butyl 4-(4-amino-oxopyridin-1(2H)-yl) piperidine-1-carboxylate To a stirred solution of tert-butyl 4-amino-2-oxo-3',6'-dihydro-2H-[1,4'-bipyridine]-1'(2'H)-carboxylate (95 mg, 0.33 mmol, 1 equiv) in methanol (4 mL), was added Platinum oxide (25 mg, 0.11 mmol, 0.3 equiv) at RT. The reaction mixture was allowed to stir at RT for 2 h. Progress of the reaction was monitored by TLC and LCMS. After completion of the reaction, the reaction mixture was passed through cealite bed. Filtrate was concentrated to afford tert-butyl 4-(4-amino-2-oxopyridin-1(2H)-yl) piperidine-1-carboxylate (90 mg) as off white solid compound. LCMS: 294 [M+H]$^+$

Step-2: Synthesis of tert-butyl 4-(4-((5-fluoro-4-(8-fluoro-4-isopropyl-3,4-dihydro-2H-benzo[b][1,4]oxazin-6-yl)pyrimidin-2-yl)amino)-2-oxopyridin-1(2H)-yl)piperidine-1-carboxylate To a solution of 6-(2-chloro-5-fluoropyrimidin-4-yl)-8-fluoro-4-isopropyl-2-methyl-3,4-dihydro-2H-benzo[b][1,4]oxazine (70 mg, 0.21 mmol, 1 equiv) in dioxane (3 mL), was added 4-(4-amino-2-oxopyridin-1 (2H)-yl)piperidine-1-carboxylate (68 mg, 0.23 mmol, 1.1 equiv) and cesium carbonate (102 mg, 0.31 mmol, 1.5 equiv). The reaction mixture was aerated with nitrogen gas for 10 min. followed by the addition of palladium acetate (5 mg, 0.03 mmol, 0.1 equiv) and BINAP (26 mg, 0.06 mmol, 0.2 equiv) again purged nitrogen for 5 min. The resultant reaction mixture was stirred at 100° C. for 16 h. Progress of the reaction was monitored by TLC and LCMS. After completion of the reaction, the reaction mixture was diluted with water (10 mL) and extracted with EtOAc (15 mL). The organic layer dried over anhydrous sodium sulphate and concentrated under reduced pressure to obtain crude compound used directly for next step. 140 mg of tert-butyl 4-(4-((5-fluoro-4-(8-fluoro-4-isopropyl-3,4-dihydro-2H-benzo[b][1,4]oxazin-6-yl)pyrimidin-2-yl) amino)-2-oxopyridin-1(2H)-yl) piperidine-1-carboxylate obtained as a crude. LCMS: 583 [M+H]$^+$

Step-3: Synthesis of 4-((5-fluoro-4-(8-fluoro-4-isopropyl-3,4-dihydro-2H-benzo[b][1,4]oxazin-6-yl)pyrimidin-2-yl)amino)-1-(piperidin-4-yl)pyridin-2 (1H)-one A solution of tert-butyl 4-(4-((5-chloro-4-(8-fluoro-4-isopropyl-3,4-dihydro-2H-benzo[b][1,4]oxazin-6-yl)pyrimidin-2-yl)amino)-2-fluorophenyl)piperazine-1-carboxylate (70 mg, 0.11 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure and crude was purified by reverse phase HPLC to obtain 4-((5-fluoro-4-(8-fluoro-4-isopropyl-3,4-dihydro-2H-benzo[b][1,4]oxazin-6-yl)pyrimidin-2-yl)amino)-1-(piperidin-4-yl)pyridin-2(1H)-one (16 mg) as an off white solid compound. LCMS: 483 [M+H]$^+$; $^1$HNMR (400 MHz, DMSO-d6) δ 9.98 (s, 1H), 8.68 (d, J=3.9 Hz, 1H), 8.35 (d, J=10.8 Hz, 2H), 7.52 (d, J=7.6 Hz, 1H), 7.44 (s, 1H), 7.17 (d, J=11.8 Hz, 1H), 7.13 (d, J=2.5 Hz, 1H), 6.49 (dd, J=7.8, 2.5 Hz, 1H), 4.75-4.66 (m, 1H), 4.31 (t, J=4.3 Hz, 2H), 4.21 (p, J=6.5 Hz, 1H), 3.31 (t, J=4.4 Hz, 3H), 3.19-3.06 (m, 3H), 2.44 (s, 1H), 1.68 (d, J=8.2 Hz, 4H), 1.24 (d, J=4.0 Hz, 0H), 1.19 (d, J=6.5 Hz, 7H).

Example-43: Synthesis of 5-fluoro-4-(8-fluoro-4-isopropyl-3,4-dihydro-2H-benzo[b][1,4]oxazin-6-yl)-N-(4-(piperidin-4-yl)-3-(trifluoromethyl)phenyl)pyrimidin-2-amine. (Compound 438)

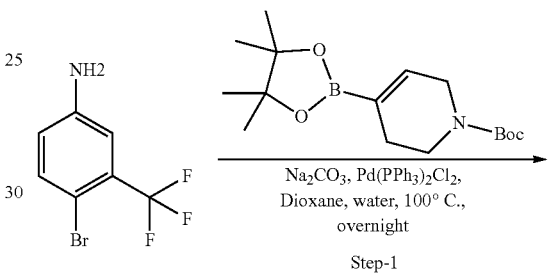

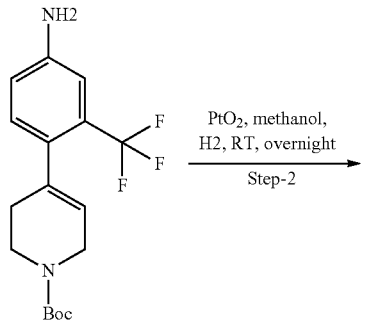

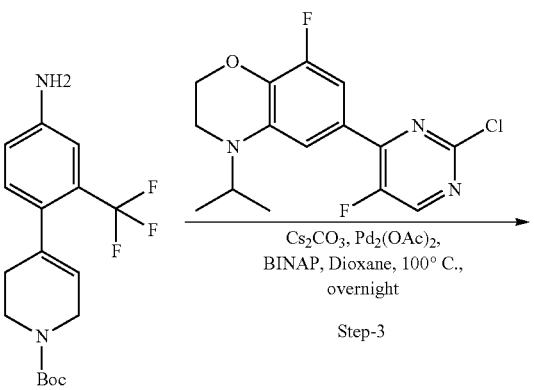

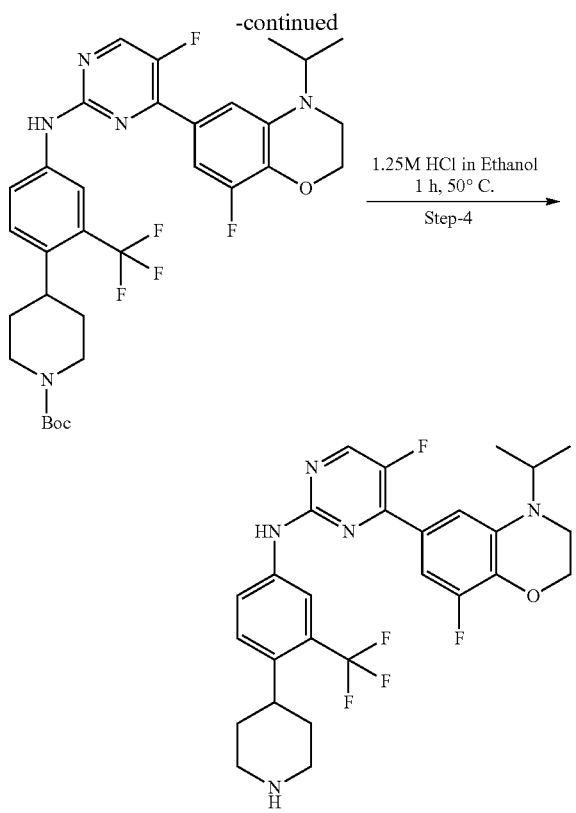

1.25M HCl in Ethanol
1 h, 50° C.
Step-4

Step-1: Synthesis of tert-butyl 4-(4-amino-2-(trifluoromethyl) phenyl)-3, 6-dihydropyridine-1(2H)-carboxylate To a solution of 4-bromo-3-(trifluoromethyl)aniline (1000 mg, 4.18 mmol, 1 equiv) in dioxane (15 mL), was added tert-butyl 4-(4, 4, 5, 5-tetramethyl-1, 3, 2-dioxaborolan-2-yl)-3, 6-dihydropyridine-1(2H)-carboxylate (1292 mg, 4.18 mmol, 1 equiv) and sodium carbonate (1053 mg, 12.5 mmol, 3 equiv). The reaction mixture was degassed with nitrogen gas for 30 min., followed by the addition of Pd (PPh$_3$)$_2$Cl$_2$ (242 mg, 0.2 mmol, 0.05 equiv). The resultant reaction mixture was allowed to stir at 100° C. for overnight. Progress of the reaction was monitored by TLC and LCMS. After completion of the reaction, reaction mixture was diluted with water (50 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 4-(4-amino-2-(trifluoromethyl) phenyl)-3, 6-dihydropyridine-1(2H)-carboxylate (1200 mg, 87%) as a brown solid compound.
LCMS: 373 [M+H]$^+$

Step-2: Synthesis of tert-butyl 4-(4-amino-2-(trifluoromethyl) phenyl) piperidine-1-carboxylate To a stirred solution of tert-butyl 4-(4-amino-2-(trifluoromethyl) phenyl)-3, 6-dihydropyridine-1(2H)-carboxylate (500 mg, 1.34 mmol, 1 equiv) in methanol (5 mL), was added PtO$_2$ (20% w/w) (100 mg) under H$_2$ atm. The resultant reaction mixture was allowed to stir at RT for overnight. Progress of the reaction was monitored by LCMS. After completion of the reaction, the mixture was passes through celite bed and the filtrate was concentrated under reduced pressure to obtain tert-butyl 4-(4-amino-2-(trifluoromethyl) phenyl) piperidine-1-carboxylate (400 mg, 87%) as a transparent oil compound. LCMS: 345 [M+H]$^+$

Step-3: Synthesis of tert-butyl 4-(4-((5-fluoro-4-(8-fluoro-4-isopropyl-3,4-dihydro-2H-benzo[b][1,4]oxazin-6-yl)pyrimidin-2-yl)amino)-2-(trifluoromethyl)phenyl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(4-amino-2-(trifluoromethyl) phenyl) piperidine-1-carboxylate (114 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(4-((5-fluoro-4-(8-fluoro-4-isopropyl-3,4-dihydro-2H-benzo [b][1,4]oxazin-6-yl)pyrimidin-2-yl)amino)-2-(trifluoromethyl)phenyl)piperidine-1-carboxylate (100 mg, 51%) as a yellow solid compound. LCMS: 634 [M+H]$^+$

Step-4: Synthesis of 5-fluoro-4-(8-fluoro-4-isopropyl-3,4-dihydro-2H-benzo[b][1,4]oxazin-6-yl)-N-(4-(piperidin-4-yl)-3-(trifluoromethyl)phenyl)pyrimidin-2-amine A solution of tert-butyl 4-(4-((5-fluoro-4-(8-fluoro-4-isopropyl-3,4-dihydro-2H-benzo[b][1,4]oxazin-6-yl)pyrimidin-2-yl)amino)-2-(trifluoromethyl)phenyl)piperidine-1-carboxylate (100 mg, 0.15 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(4-(piperidin-4-yl)-3-(trifluoromethyl)phenyl)pyrimidin-2-amine (10 mg, 12%) as a yellow solid compound. LCMS: 534 [M+H]$^+$; $^1$HNMR (400 MHz, DMSO-d$_6$) δ 10.04 (s, 1H), 8.63 (d, J=3.9 Hz, 1H), 8.54-8.40 (m, 1H), 8.25 (d, J=2.4 Hz, 1H), 8.05-7.97 (m, 1H), 7.42 (d, J=8.7 Hz, 1H), 7.37 (s, 1H), 7.18 (d, J=11.6 Hz, 1H), 4.30 (t, J=4.2 Hz, 2H), 4.12 (h, J=6.6 Hz, 1H), 3.37 (d, J=12.0 Hz, 2H), 3.14-3.00 (m, 3H), 1.98-1.78 (m, 4H), 1.18 (d, J=6.5 Hz, 6H).

Example-44: Synthesis of N-(4-(4-(dimethylamino) piperidin-1-yl)-3-(trifluoromethyl)phenyl)-5-fluoro-4-(8-fluoro-4-isopropyl-3,4-dihydro-2H-benzo[b][1,4]oxazin-6-yl)pyrimidin-2-amine. (Compound 178)

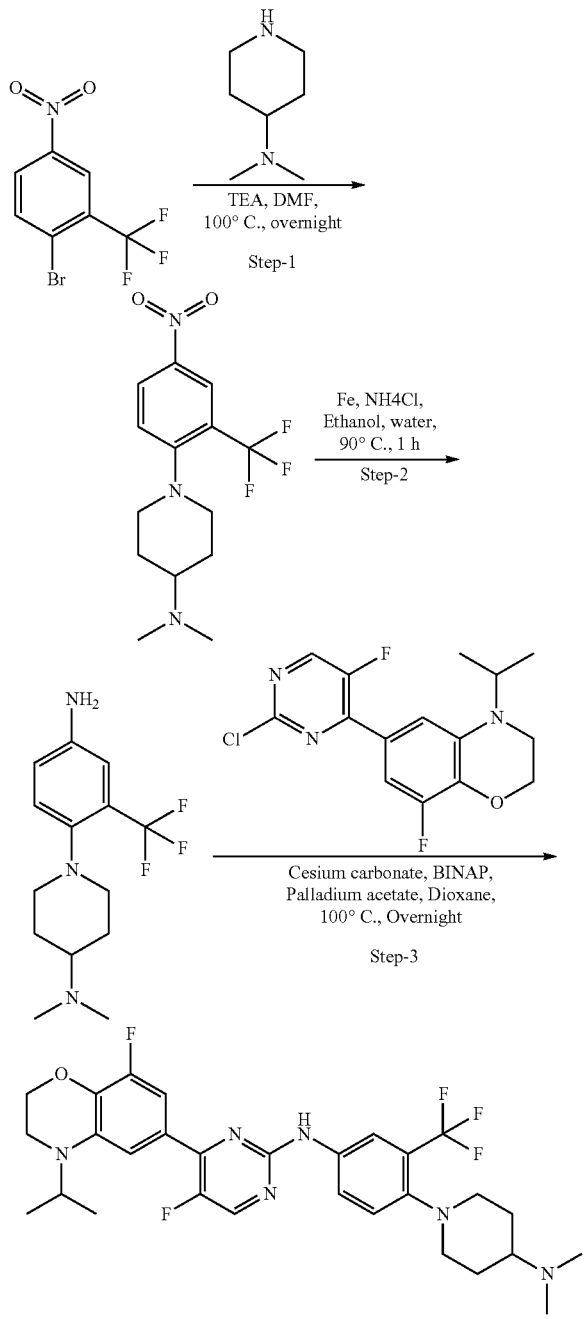

Step-1: Synthesis N, N-dimethyl-1-(4-nitro-2-(trifluoromethyl) phenyl) piperidin-4-amine To a stirred solution of 1-bromo-4-nitro-2-(trifluoromethyl) benzene (500 mg, 1.85 mmol, 1 equiv) in DMF (10 mL), was added TEA (0.5 mL) and N, N-dimethylpiperidin-4-amine (237 mg, 1.85 mmol, 1 equiv). The resultant reaction mixture was allowed to stir at 1000 for overnight. Progress of the reaction was monitored by TLC and LCMS. After completion of the reaction, diluted with water (30 mL) and extracted with ethyl acetate (100 mL×2). Organic layer was washed with water (50 mL) and brine solution (50 mL). Organic layer was dried over anhydrous sodium sulphate and concentrated under reduced pressure to obtain N, N-dimethyl-1-(4-nitro-2-(trifluoromethyl) phenyl) piperidin-4-amine (500 mg, 85%) as a yellow viscous compound. LCMS: 318 [M+H]$^+$ Step-2: Synthesis of 1-(4-amino-2-(trifluoromethyl) phenyl)-N, N-dimethylpiperidin-4-amine To a stirred solution of N, N-dimethyl-1-(4-nitro-2-(trifluoromethyl) phenyl) piperidin-4-amine (500 mg, 1.5 mmol, 1 equiv) in ethanol (7 mL), water (3 mL), was added iron powder (265 mg, 4.7 mmol, 3 equiv) and ammonium chloride (162 mg, 3 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 1-(4-amino-2-(trifluoromethyl) phenyl)-N, N-dimethylpiperidin-4-amine (400 mg, 88%) as a dark brown solid compound. LCMS: 288 [M+H]$^+$ Step-3: Synthesis of N-(4-(4-(dimethylamino)piperidin-1-yl)-3-(trifluoromethyl)phenyl)-5-fluoro-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 1-(4-amino-2-(trifluoromethyl) phenyl)-N, N-dimethylpiperidin-4-amine (95 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N-(4-(4-(dimethylamino)piperidin-1-yl)-3-(trifluoromethyl)phenyl)-5-fluoro-4-(8-fluoro-4-isopropyl-3,4-dihydro-2H-benzo[b][1,4]oxazin-6-yl)pyrimidin-2-amine (40 mg, 23%) as a yellow solid compound. LCMS: 577 [M+H]$^{+1}$HNMR (400 MHz, DMSO-d$_6$) δ 9.92 (s, 1H), 8.60 (d, J=4.0 Hz, 1H), 8.24 (s, 1H), 8.17 (s, 1H), 7.97-7.90 (m, 1H), 7.46 (d, J=8.8 Hz, 1H), 7.37 (s, 1H), 7.17 (d, J=11.5 Hz, 1H), 4.30 (t, J=4.2 Hz, 2H), 4.12 (p, J=6.8 Hz, 1H), 3.63-3.55 (m, 1H), 3.30 (t, J=4.8 Hz, 4H), 2.93 (d, J=11.1 Hz, 2H), 2.72 (t, J=11.1 Hz, 2H), 2.23 (s, 7H), 1.82 (d, J=12.0 Hz, 2H), 1.58-1.43 (m, 2H), 1.17 (d, J=6.5 Hz, 6H).

Example-45: Synthesis of N7-(5-fluoro-4-(8-fluoro-4-isopropyl-3,4-dihydro-2H-benzo[b][1,4]oxazin-6-yl)pyrimidin-2-yl)-N2,N2-dimethyl-1,2,3,4-tetrahydronaphthalene-2, 7-diamine (Peak-1) (Compound 206) and Example-46: Synthesis of N6-(5-fluoro-4-(8-fluoro-4-isopropyl-3,4-dihydro-2H-benzo[b][1,4]oxazin-6-yl)pyrimidin-2-yl)-N2,N2-dimethyl-1,2,3,4-tetrahydronaphthalene-2,6-diamine (Peak-2) (Compound 47)

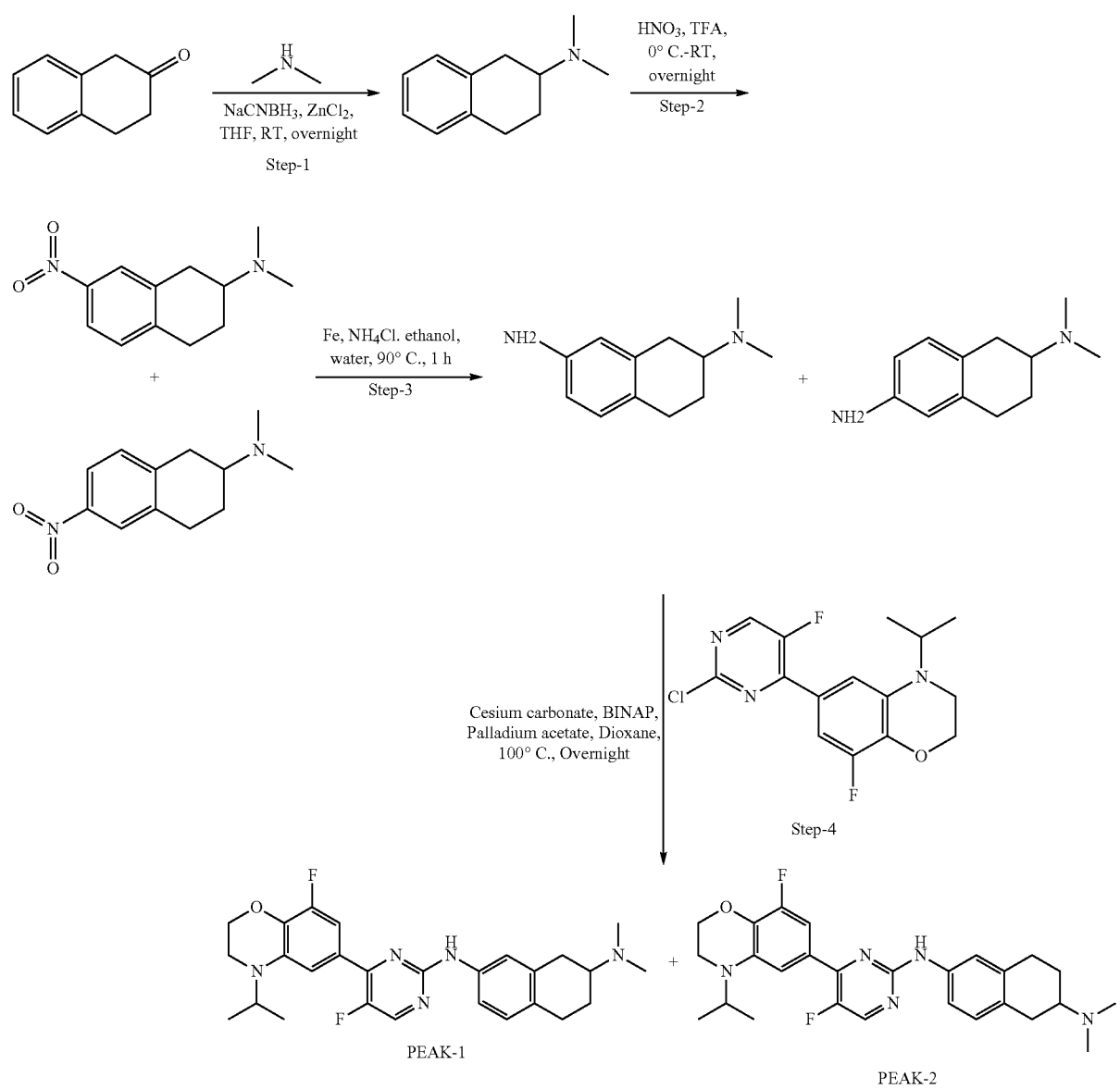

Step-1: Synthesis of N, N-dimethyl-1, 2, 3, 4-tetrahydronaphthalen-2-amine

To a stirred solution of 3, 4-dihydronaphthalen-2(1H)-one (5000 mg, 34.2 mmol, 1 equiv) in THF (50 mL), was added NaCNBH₃ (2155 mg, 34.2 mmol, 1 equiv), ZnCl₂ (2326 mg, 17.1 mmol, 0.5 equiv) and dimethyl amine (2M in TFH) (17 mL, 34.2 mmol, 1 equiv). The resultant reaction mixture was allowed to stir at RT for overnight. Progress of the reaction was monitored by LCMS. After completion of the reaction, solvent was removed under reduced pressure and 1N HCl (100 mL) was added to above residue. The acidic solution was washed with ethyl acetate (100 mL×2), then made alkaline with aq. 5M NaOH solution (50 mL) and extracted with EtoAC (100 mL×3). Organic layer was dried over anhydrous sodium sulphate and concentrated under reduced pressure to obtain N, N-dimethyl-1, 2, 3, 4-tetrahydronaphthalen-2-amine (950 mg, 15%) as a yellow oil compound. LCMS: 176 [M+H]⁺

Step-2: Synthesis of N, N-dimethyl-7-nitro-1, 2, 3, 4-tetrahydronaphthalen-2-amine and N, N-dimethyl-6-nitro-1, 2, 3, 4-tetrahydronaphthalen-2-amine To a stirred solution of N, N-dimethyl-1, 2, 3, 4-tetrahydronaphthalen-2-amine (950 mg, 5.4 mmol, 1 equiv) in THF (5 mL), was added HNO3 (0.9 mL, 21.7 mmol, 4 equiv) at 0° C. The resultant reaction mixture was allowed to stir at RT for overnight. Progress of the reaction was monitored by LCMS. After completion of the reaction, the mixture was diluted with ice water (20 mL), then made alkaline with aq. 5M NaOH solution (10 mL) and extracted with EtoAC (100 mL×2). Organic layer was dried over anhydrous sodium sulphate and concentrated under reduced pressure to obtain a mixture of N, N-dimethyl-7-nitro-1, 2, 3, 4-tetrahydronaphthalen-2-amine and N, N-dimethyl-6-nitro-1, 2, 3, 4-tetrahydronaphthalen-2-amine (700 mg, 58%) as a yellow oil compound. LCMS: 221 [M+H]$^+$ Step-3: Synthesis of N2,N2-dimethyl-1,2,3,4-tetrahydronaphthalene-2,7-diamine and N2,N2-dimethyl-1,2,3,4-tetrahydronaphthalene-2,6-diamine To a stirred solution of a mixture of N, N-dimethyl-7-nitro-1, 2, 3, 4-tetrahydronaphthalen-2-amine and N, N-dimethyl-6-nitro-1, 2, 3, 4-tetrahydronaphthalen-2-amine (500 mg, 1.87 mmol, 1 equiv) in ethanol (9 mL), water (3 mL), was added iron powder (535 mg, 9.5 mmol, 3 equiv) and ammonium chloride (335 mg, 6.2 mmol, 2 equiv). The resultant reaction mixture was allowed to stir at 900 for 1 h. Progress of the reaction was monitored by TLC and LCMS. After completion of the reaction, the reaction mixture was passes through celite bed and the filtrate was concentrated under reduced pressure to obtain a mixture of N2,N2-dimethyl-1,2,3,4-tetrahydronaphthalene-2,7-diamine and N2,N2-dimethyl-1,2,3,4-tetrahydronaphthalene-2,6-diamine (550 mg, 91%) as a brown solid compound. LCMS: 191 [M+H]$^+$ Step-4: Synthesis of N7-(5-fluoro-4-(8-fluoro-4-isopropyl-3,4-dihydro-2H-benzo[b][1,4]oxazin-6-yl)pyrimidin-2-yl)-N2,N2-dimethyl-1,2,3,4-tetrahydronaphthalene-2,7-diamine and N6-(5-fluoro-4-(8-fluoro-4-isopropyl-3,4-dihydro-2H-benzo[b][1,4]oxazin-6-yl)pyrimidin-2-yl)-N2,N2-dimethyl-1,2,3,4-tetrahydronaphthalene-2,6-diamine To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) and in dioxane (10 mL), was added a mixture of N2,N2-dimethyl-1,2,3,4-tetrahydronaphthalene-2,7-diamine and N2,N2-dimethyl-1,2,3,4-tetrahydronaphthalene-2,6-diamine (97 mg, 0.5 mmol, 1.1 equiv), followed by the addition of cesium carbonate (225 mg, 0.69 mmol, 1.5 equiv). The reaction mixture was degassed with nitrogen gas for 30 min., followed by the addition of palladium acetate (2 mg, 0.009 mmol, 0.02 equiv) and BINAP (11 mg, 0.018 mmol, 0.04 equiv). The resultant reaction mixture was allowed to stir at 100° C. for 16 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain two peaks as N7-(5-fluoro-4-(8-fluoro-4-isopropyl-3,4-dihydro-2H-benzo[b][1,4]oxazin-6-yl)pyrimidin-2-yl)-N2,N2-dimethyl-1,2,3,4-tetrahydronaphthalene-2,7-diamine and N6-(5-fluoro-4-(8-fluoro-4-isopropyl-3,4-dihydro-2H-benzo[b][1,4]oxazin-6-yl)pyrimidin-2-yl)-N2,N2-dimethyl-1,2,3,4-tetrahydronaphthalene-2,6-diamine (5 mg and 15 mg, 9%) as a yellow solid compound. LCMS: 480 [M+H]$^+$; PEAK-1: $^1$HNMR (DMSO-d$_6$, 400 MHz): δ 9.86 (br. s., 1H), 8.46 (d, J=4.0 Hz, 1H), 7.46 (d, J=7.5 Hz, 1H), 7.32 (s, 1H), 7.17 (t, J=7.7 Hz, 1H), 7.10 (d, J=12.3 Hz, 1H), 6.98 (d, J=7.9 Hz, 1H), 4.27 (br. s., 2H), 4.01 (p, J=6.5 Hz, 1H), 3.51 (br. s., 2H), 3.16 (d, J=11.0 Hz, 1H), 2.90-3.05 (m, 2H), 2.82 (d, J=4.1 Hz, 6H), 2.28 (br. s., 1H), 1.93 (br. s., 1H), 1.71 (d, J=6.6 Hz, 1H), 1.49 (br. s., 1H), 1.14 ppm (t, J=7.0 Hz, 6H).

PEAK-2: $^1$HNMR (DMSO-d$_6$, 400 MHz): δ 9.61 (br. s., 1H), 8.55 (d, J=3.5 Hz, 1H), 7.50-7.63 (m, 1H), 7.47 (br. s., 1H), 7.39 (d, J=6.6 Hz, 1H), 7.17 (d, J=11.4 Hz, 1H), 6.93-7.05 (m, 1H), 4.29 (d, J=3.5 Hz, 2H), 4.07-4.20 (m, 1H), 3.51 (br. s., 2H), 2.97 (br. s., 1H), 2.85 (br. s., 2H), 2.69 (d, J=11.8 Hz, 6H), 2.17 (d, J=7.5 Hz, 1H), 1.91 (br. s., 1H), 1.72 (br. s., 1H), 1.49 (br. s., 1H), 1.19 ppm (d, J=6.6 Hz, 6H).

Example-47: Synthesis of 4-(8-chloro-4-isopropyl-3,4-dihydro-2H-benzo[b][1,4]oxazin-6-yl)-5-fluoro-N-(3-fluoro-4-(piperazin-1-yl)phenyl)pyrimidin-2-amine. (Compound 439)

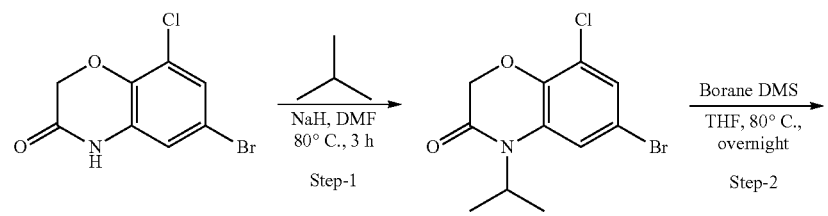

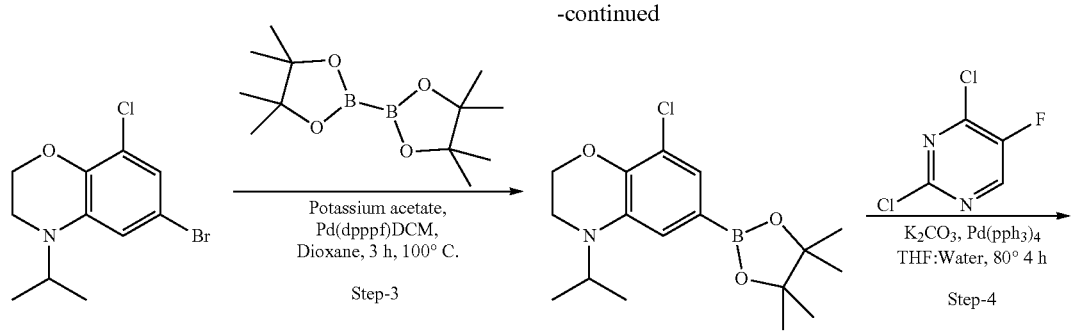

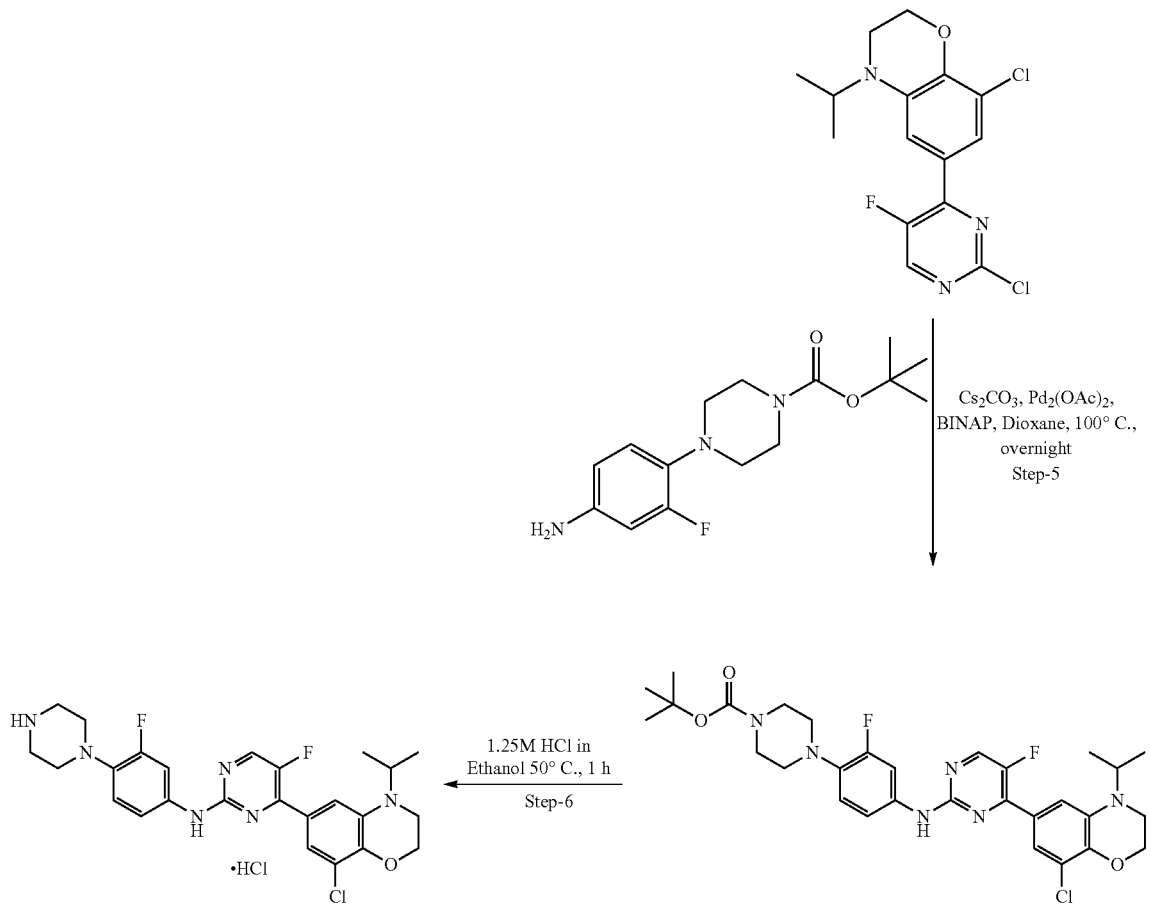

Step-1: Synthesis of 6-bromo-8-chloro-4-isopropyl-2H-benzo[b][1,4]oxazin-3(4H)-one To a stirred solution of 6-bromo-8-chloro-2H-benzo[b][1,4]oxazin-3(4H)-one (2000 mg, 7.6 mmol, 1 equiv) in DMF (20 mL), was added NaH (610 mg, 15.2 mmol, 2 equiv) and isopropyl iodide (1.5 mL, 15.2 mmol, 2 equiv). The reaction mixture was allowed to stir at 80° C. for 3 h. Progress of the reaction was monitored by TLC and LCMS. After completion of the reaction, the reaction mixture was diluted with water (100 mL) and extracted with ethyl acetate (100 mL×2). Organic layer was washed with brine (100 mL) and water (100 mL). Organic layer was dried over anhydrous sodium sulphate and concentrated under reduced pressure to obtain 6-bromo-8-chloro-4-isopropyl-2H-benzo[b][1,4]oxazin-3 (4H)-one (700 mg, 95%) as an off white solid compound. LCMS: 260 [M+H]$^+$ Step-2: Synthesis of 6-bromo-8-chloro-4-isopropyl-3,4-dihydro-2H-benzo[b][1,4]oxazine To a stirred solution of 6-bromo-8-chloro-4-isopropyl-2H-benzo[b][1,4]oxazin-3(4H)-one (650 mg, 2.1 mmol, 1 equiv) in THF (15 mL), was added BH$_3$.DMS (2 M in THF) (4 mL, 8.5 mmol, 4 equiv) at 0° C. drop wise. The reaction mixture was allowed to stir at 80° C. for overnight. Progress of the reaction was monitored by TLC and LCMS. After completion of the reaction, the reaction mixture was quenched with saturated solution of $NaHCO_3$ (50 mL) and extracted with ethyl acetate (100 mL×2). Organic layer was washed with water (100 mL), dried over anhydrous sodium sulphate and concentrated under reduced pressure to obtain 6-bromo-8-chloro-4-isopropyl-3,4-dihydro-2H-benzo[b][1,4]oxazine (550 mg, 89%) as a transparent oil compound. LCMS: 290 [M+H]$^+$

Step-3: Synthesis of 8-chloro-4-isopropyl-6-(4,4,5,5-tetramethyl-1,3,2-dioxaborolan-2-yl)-3,4-dihydro-2H-benzo[b][1,4]oxazine 6-bromo-8-chloro-4-isopropyl-3,4-dihydro-2H-benzo[b][1,4]oxazine (550 mg, 1.9 mmol, 1 equiv), 4,4,5,5-tetramethyl-2-(4,4,5,5-tetramethyl-1,3,2-dioxaborolan-2-yl)-1,3,2-dioxaborolane (725 mg, 2.8 mmol, 1.5 equiv), Potassium acetate (466 mg, 4.7 mmol, 2.5 equiv) and dioxane (10 mL) were charged in a 25 mL glass bottle. Purged the reaction mixture with nitrogen gas for 15 min., Pd(dppf)Cl2. DCM (78 mg, 0.09 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (100 mL) and water (100 mL). Organic layer was dried over anhydrous sodium sulphate and concentrated under reduced pressure to obtain 8-chloro-4-isopropyl-6-(4,4,5,5-tetramethyl-1,3,2-dioxaborolan-2-yl)-3,4-dihydro-2H-benzo[b][1,4]oxazine (600 mg, 94%) as a dark brown viscous compound. LCMS: 338 [M+H]$^+$

Step-4: Synthesis of 8-chloro-6-(2-chloro-5-fluoropyrimidin-4-yl)-4-isopropyl-3,4-dihydro-2H-benzo[b][1,4]oxazine To a stirred solution of 2,4-dichloro-5-fluoropyrimidine (150 mg, 0.9 mmol, 1 equiv) in THF:Water (1:1=10 mL) was added 8-chloro-4-isopropyl-6-(4,4,5,5-tetramethyl-1,3,2-dioxaborolan-2-yl)-3,4-dihydro-2H-benzo[b][1,4]oxazine (305 mg, 0.9 mmol, 1 equiv), Potassium carbonate (248 mg, 1.8 mmol, 2 equiv) and Pd(PPh$_3$)$_4$ (52 mg, 0.04 mmol, 0.05 equiv). The reaction mixture was allowed to stir at 80° C. for 3 h. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi-flash to obtain 8-chloro-6-(2-chloro-5-fluoropyrimidin-4-yl)-4-isopropyl-3,4-dihydro-2H-benzo[b][1,4]oxazine (300 mg, 81%) as a yellow solid compound. LCMS: 342 [M+H]$^+$

Step-5: Synthesis of tert-butyl 4-(4-((4-(8-chloro-4-isopropyl-3,4-dihydro-2H-benzo[b][1,4]oxazin-6-yl)-5-fluoropyrimidin-2-yl)amino)-2-fluorophenyl)piperazine-1-carboxylate To a solution of 8-chloro-6-(2-chloro-5-fluoropyrimidin-4-yl)-4-isopropyl-3,4-dihydro-2H-benzo[b][1,4]oxazine (100 mg, 0.29 mmol, 1 equiv) in Dioxane (10 mL), was added tert-butyl 4-(4-amino-2-fluorophenyl)piperazine-1-carboxylate (95 mg, 0.32 mmol, 1.1 equiv) and cesium carbonate (142 mg, 0.43 mmol, 1.5 equiv). The reaction mixture was purged with nitrogen gas for 30 min., followed by the addition of palladium acetate (1.3 mg, 0.005 mmol, 0.02 equiv) and BINAP (7 mg, 0.01 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain tert-butyl 4-(4-((4-(8-chloro-4-isopropyl-3,4-dihydro-2H-benzo[b][1,4]oxazin-6-yl)-5-fluoropyrimidin-2-yl)amino)-2-fluorophenyl)piperazine-1-carboxylate (30 mg, 17%) as a yellow solid compound. LCMS: 601 [M+H]$^+$

Step-6: Synthesis of 4-(8-chloro-4-isopropyl-3,4-dihydro-2H-benzo[b][1,4]oxazin-6-yl)-5-fluoro-N-(3-fluoro-4-(piperazin-1-yl)phenyl)pyrimidin-2-amine tert-butyl 4-(4-((4-(8-chloro-4-isopropyl-3,4-dihydro-2H-benzo[b][1,4]oxazin-6-yl)-5-fluoropyrimidin-2-yl)amino)-2-fluorophenyl)piperazine-1-carboxylate (30 mg, 0.05 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 4-(8-chloro-4-isopropyl-3,4-dihydro-2H-benzo[b][1,4]oxazin-6-yl)-5-fluoro-N-(3-fluoro-4-(piperazin-1-yl)phenyl)pyrimidin-2-amine (25 mg, 93%) as a brick red color solid compound. LCMS: 501 [M+H]$^+$; $^1$HNMR (400 MHz, DMSO-d6) δ 9.82 (s, 1H), 9.18 (s, 1H), 8.58 (d, J=3.8 Hz, 1H), 7.81 (dd, J=15.0, 2.5 Hz, 1H), 7.51 (s, 1H), 7.39 (dd, J=8.7, 2.3 Hz, 1H), 7.36 (s, 1H), 7.04 (t, J=9.3 Hz, 1H), 4.33 (d, J=4.0 Hz, 2H), 4.16 (p, J=6.7 Hz, 1H), 3.31 (t, J=4.2 Hz, 2H), 3.23 (q, J=4.3 Hz, 4H), 3.20-3.13 (m, 4H), 1.19 (d, J=6.5 Hz, 6H).

Example-48: Synthesis of 2-(dimethylamino)-1-(4-(4-((5-fluoro-4-(8-fluoro-4-isopropyl-3,4-dihydro-2H-benzo[b][1,4]oxazin-6-yl)pyrimidin-2-yl)amino)phenyl)piperazin-1-yl)ethan-1-one. (Compound 440)

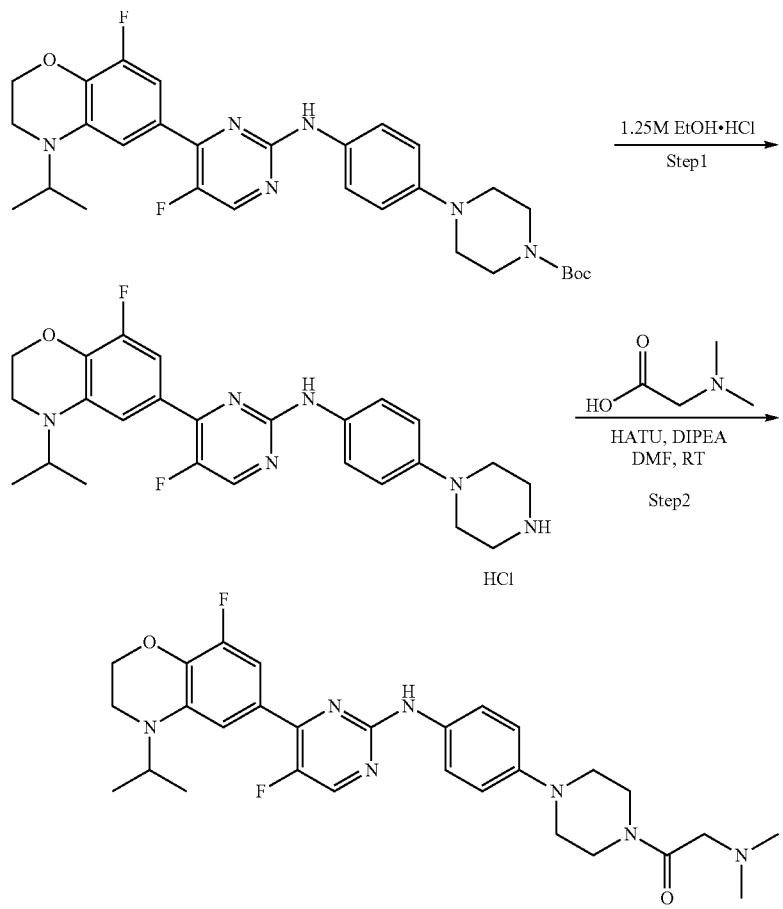

Step-1: Synthesis of 5-fluoro-4-(8-fluoro-4-isopropyl-3,4-dihydro-2H-benzo[b][1,4]oxazin-6-yl)-N-(4-(piperazin-1-yl)phenyl)pyrimidin-2-amine A solution of tert-butyl 4-(4-((5-fluoro-4-(8-fluoro-4-isopropyl-3,4-dihydro-2H-benzo[b][1,4]oxazin-6-yl)pyrimidin-2-yl)amino)phenyl)piperazine-1-carboxylate (110 mg, 0.19 mmol, 1 equiv) in 1.25 M HCl in ethanol (4 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(4-(piperazin-1-yl)phenyl)pyrimidin-2-amine (70 mg) as an oily residue. LCMS: 467 [M+H]$^+$ Step-2: Synthesis of 2-(dimethylamino)-1-(4-(4-((5-fluoro-4-(8-fluoro-4-isopropyl-3,4-dihydro-2H-benzo[b][1,4]oxazin-6-yl)pyrimidin-2-yl)amino)phenyl)piperazin-1-yl)ethan-1-one To a solution of 5-fluoro-4-(8-fluoro-4-isopropyl-3,4-dihydro-2H-benzo[b][1,4]oxazin-6-yl)-N-(4-(piperazin-1-yl)phenyl)pyrimidin-2-amine (70 mg, 0.15 mmol, 1 equiv) in DMF (4 mL) was added dimethyl glycine (24 mg, 0.22 mmol, 1.5 equiv) followed by addition of HATU (84 mg, 0.22 mmol, 1.5 equiv) and DIPEA (48 mg, 0.37 mmol, 2.5 equiv). Resultant mixture was allowed to stir at room temperature for 2 h. Progress of the reaction was monitored by LCMS. After completion of the reaction, the reaction mixture was diluted with water (10 mL) and extracted with EtOAc (15 mL). Organic layer was washed with water (50 mL×6) and brine (50 mL), dried over anhydrous sodium sulphate and concentrated under reduced pressure to obtain crude compound was purified by reverse phase HPLC to afford 2-(dimethylamino)-1-(4-(4-((5-fluoro-4-(8-fluoro-4-isopropyl-3,4-dihydro-2H-benzo[b][1,4]oxazin-6-yl)pyrimidin-2-yl)amino)phenyl)piperazin-1-yl)ethan-1-one (10 mg) as a pale yellow solid. LCMS: 552 [M+H]$^+$; $^1$HNMR (400 MHz, DMSO-d6) δ 9.45 (s, 1H), 8.50 (d, J=4.0 Hz, 1H), 8.34 (s, 1H), 7.60 (d, J=8.5 Hz, 2H), 7.43 (s, 1H), 7.15 (d, J=11.6 Hz, 1H), 6.91 (d, J=8.5 Hz, 2H), 4.29 (t, J=4.3 Hz, 2H), 4.13 (p, J=6.6 Hz, 1H), 3.68 (t, J=4.9 Hz, 2H), 3.59 (t, J=4.9 Hz, 2H), 3.30 (t, J=4.4 Hz, 2H), 3.10 (s, 2H), 3.06 (t, J=4.9 Hz, 2H), 3.03 (d, J=5.5 Hz, 2H), 2.19 (s, 6H), 1.19 (d, J=6.5 Hz, 6H).

Example-49: Synthesis of 2-(dimethylamino)-1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)ethan-1-one. (Compound 441)

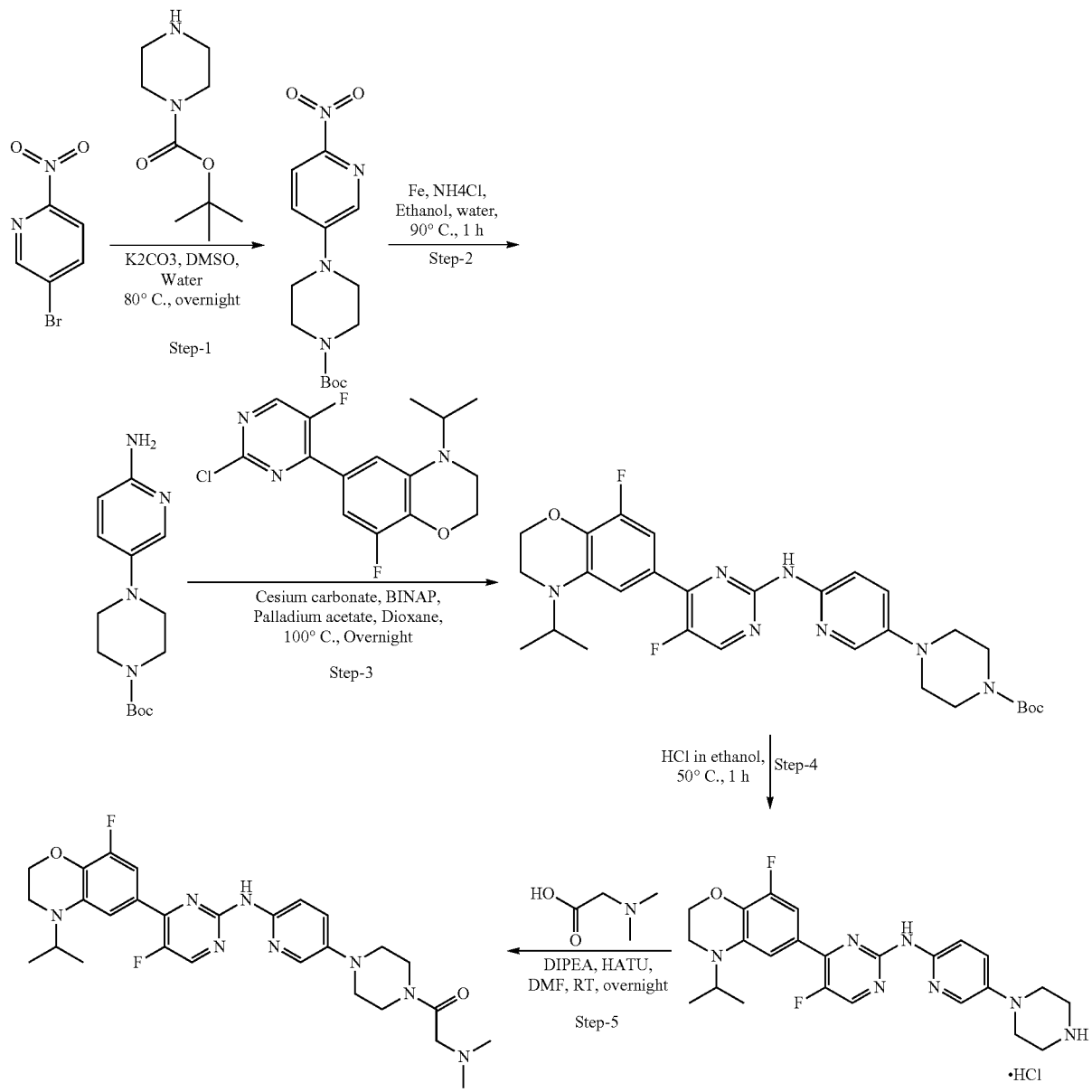

Step-1: Synthesis tert-butyl 4-(6-nitropyridin-3-yl) piperazine-1-carboxylate

To a stirred solution of 5-bromo-2-nitropyridine (1500 mg, 7.4 mmol, 1 equiv) in DMSO (10 mL), was added $K_2CO_3$ (1532 mg, 11.1 mmol, 1 equiv), water (5 mL) and tert-butyl piperazine-1-carboxylate (2072 mg, 11.1 mmol, 1 equiv). The resultant reaction mixture was allowed to stir at 100° C. for overnight. Progress of the reaction was monitored by LCMS. After completion of the reaction, diluted with water (100 mL), solid observed was filtered and dried under vacuum to obtain tert-butyl 4-(6-nitropyridin-3-yl) piperazine-1-carboxylate (1800 mg, 79%) as a yellow solid compound. LCMS: 309 [M+H]+

Step-2: Synthesis of tert-butyl 4-(6-aminopyridin-3-yl) piperazine-1-carboxylate To a stirred solution of tert-butyl 4-(6-nitropyridin-3-yl) piperazine-1-carboxylate (500 mg, 1.6 mmol, 1 equiv) in ethanol (8 mL), water (2 mL), was added iron powder (269 mg, 4.8 mmol, 3 equiv) and ammonium chloride (173 mg, 3.2 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain tert-butyl 4-(6-aminopyridin-3-yl) piperazine-1-carboxylate (350 mg, 78%) as a dark brown solid compound. LCMS: 279 [M+H]+

Step-3: Synthesis of tert-butyl 4-(6-((5-fluoro-4-(8-fluoro-4-isopropyl-3,4-dihydro-2H-benzo[b][1,4] oxazin-6-yl)pyrimidin-2-yl)amino)pyridin-3-yl)piperazine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) in dioxane (10 mL), was added tert-butyl 4-(6-aminopyridin-3-yl) piperazine-1-carboxylate (141 mg, 0.5 mmol, 1.1 equiv) and cesium carbonate (225 mg, 0.69 mmol, 1.5 equiv). The reaction mixture was degassed with nitrogen gas for 30 min., followed by the addition of palladium acetate (2 mg, 0.009 mmol, 0.02 equiv) and BINAP (12 mg, 0.018 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazine-1-carboxylate (100 mg, 38%) as a yellow color solid compound. LCMS: 568 [M+H]+

Step-4: Synthesis of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazine-1-carboxylate (100 mg, 0.17 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (85 mg, 97%) as a brown solid compound. LCMS: 468 [M+H]+

Step-5: Synthesis of 2-(dimethylamino)-1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)ethan-1-one To a stirred solution of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (70 mg, 0.13 mmol, 1 equiv) in DMF (5 mL), was added dimethylglycine (17 mg, 0.16 mmol, 1.2 equiv), DIPEA (0.09 mL, 0.52 mmol, 4 equiv) and HATU (89 mg, 0.23 mmol, 1.8 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by reverse phase HPLC to obtain 2-(dimethylamino)-1-(4-(6-((5-fluoro-4-(8-fluoro-4-isopropyl-3,4-dihydro-2H-benzo[b][1,4]oxazin-6-yl)pyrimidin-2-yl) amino)pyridin-3-yl) piperazin-1-yl)ethan-1-one (25 mg, 32%) as yellow color solid compound. LCMS: 553 [M+H]+; 1HNMR (400 MHz, DMSO-d6) δ 9.71 (s, 1H), 8.56 (d, J=4.0 Hz, 1H), 8.07-8.00 (m, 2H), 7.46 (s, 1H), 7.42 (dd, J=9.2, 3.0 Hz, 1H), 7.17 (d, J=11.5 Hz, 1H), 4.30 (t, J=4.2 Hz, 2H), 4.15 (p, J=6.6 Hz, 1H), 3.70 (t, J=4.8 Hz, 2H), 3.61 (t, J=5.3 Hz, 2H), 3.23 (t, J=4.8 Hz, 2H), 3.16-3.04 (m, 6H), 2.19 (s, 6H), 1.19 (d, J=6.5 Hz, 6H).

Example-50: Synthesis of 5-fluoro-4-(8-fluoro-4-isopropyl-3,4-dihydro-2H-benzo[b][1,4]oxazin-6-yl)-N-(5-(1-methylpiperidin-4-yl)pyridin-2-yl)pyrimidin-2-amine. (Compound 442)

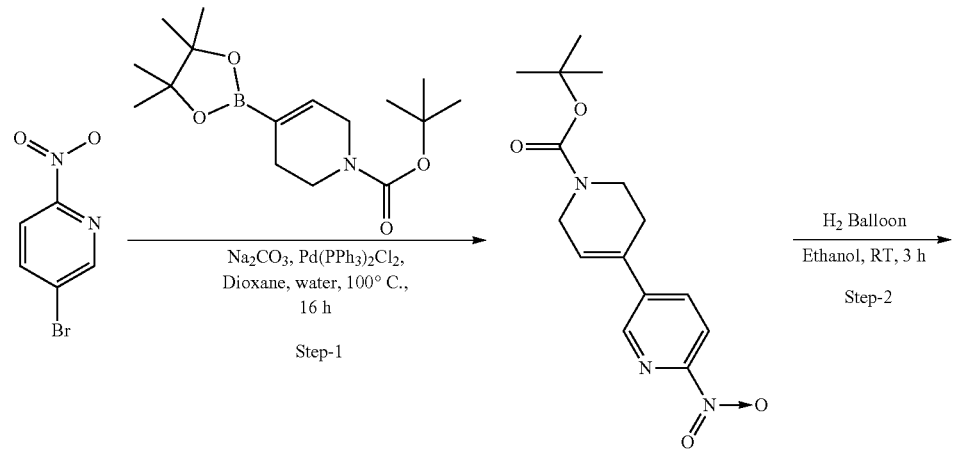

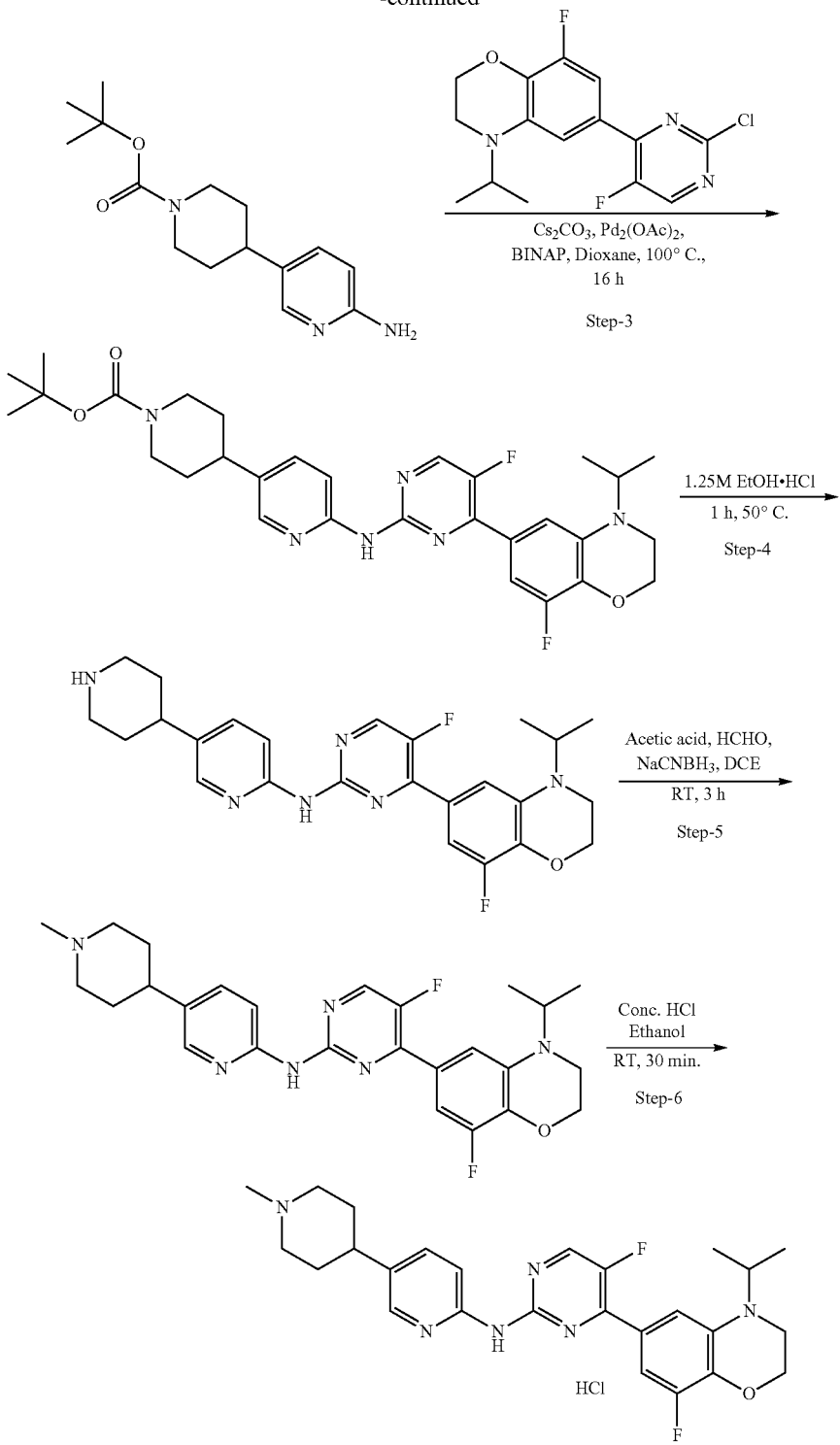

Step-1: Synthesis of tert-butyl 6-nitro-3',6'-dihydro-[3,4'-bipyridine]-1'(2'H)-carboxylate To a solution of 5-bromo-2-nitropyridine (10 g, 49 mmol, 1 equiv) in dioxane (90 mL) and water (10 mL), was added tert-butyl 4-(4, 4, 5, 5-tetramethyl-1, 3, 2-dioxaborolan-2-yl)-3, 6-dihydropyridine-1(2H)-carboxylate (15.23 g, 49 mmol, 1 equiv). Sodium carbonate (15.58 g, 147 mmol, 3 eq.) was added to reaction mixture at ambient temperature and nitrogen was purged for 15 minutes. Pd(PPh$_3$)$_2$Cl$_2$ (343 mg, 0.49 mmol, 1 mol %) was added and nitrogen was again purged for 10 minutes. Reaction mixture was heated at 100° C. for 16 h. TLC (50% ethyl acetate:hexane) showed that starting material was consumed. After completion of reaction, solvent was removed under reduced pressure. Ethyl acetate (1000 mL) was added to reaction mixture and organic phase was separated. Ethyl acetate layer was washed with water (200 mL×3), dried over anhydrous sodium sulphate, filtered and concentrated under reduced pressure to afford crude. Crude product was purified by Combi-Flash to afford tert-butyl 6-nitro-3',6'-dihydro-[3,4'-bipyridine]-1'(2'H)-carboxylate (10.2 g, 67.5%) as white solid. LCMS: 276 [M+H]$^+$ Step-2: Synthesis of tert-butyl tert-butyl 4-(6-aminopyridin-3-yl)piperidine-1-carboxylate To a stirred solution of tert-butyl 6-nitro-3',6'-dihydro-[3,4'-bipyridine]-1'(2'H)-carboxylate (10.2 g, 33.4 mmol, 1 equiv) in ethanol (400 mL), was added Pd/C (10% w/w, 2 g). The resultant reaction mixture was stir at ambient temperature for 2 h under hydrogen balloon. TLC (50% EA:hexane) showed that starting material was consumed. After completion of the reaction, the mixture was passes through celite bed which was washed with ethanol (100 mL×2). Filtrate was concentrated under reduced pressure to afford tert-butyl tert-butyl 4-(6-aminopyridin-3-yl)piperidine-1-carboxylate (10 g, >100%) as a transparent oil. LCMS: 278 [M+H]$^+$ Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (10.6 g, 32 mmol, 1 equiv) in dioxane (160 mL), was added tert-butyl 4-(5-aminopyridin-2-yl) piperidine-1-carboxylate (10 g, 36 mmol, 1.1 equiv) and cesium carbonate (20.8 g, 64 mmol, 2 equiv) and nitrogen was purged for 15 minutes. Palladium acetate (2 mg, 0.009 mmol, 0.02 equiv) and BINAP (12 mg, 0.018 mmol, 0.04 equiv) were added and nitrogen was again purged for 10 minutes. Reaction mixture was heated at 100° C. for 16 h. TLC (50% ethyl acetate:hexane) showed that starting material was consumed. After completion of reaction, solvent was removed under reduced pressure. Ethyl acetate (1000 mL) was added to reaction mixture and organic phase was separated. Ethyl acetate layer was washed with water (200 mL×3), dried over anhydrous sodium sulphate, filtered and concentrated under reduced pressure to afford crude. Crude product was purified by Combi-Flash using 0-40% ethyl acetate:Hexane to afford tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate (7 g, 38%) as a yellow solid compound. LCMS: 567 [M+H]$^+$ Step-4: Synthesis of 5-fluoro-4-(8-fluoro-4-isopropyl-3,4-dihydro-2H-benzo[b][1,4]oxazin-6-yl)-N-(5-(piperidin-4-yl)pyridin-2-yl)pyrimidin-2-amine hydrochloride A solution of tert-butyl tert-butyl 4-(6-((5-fluoro-4-(8-fluoro-4-isopropyl-3,4-dihydro-2H-benzo[b][1,4]oxazin-6-yl)pyrimidin-2-yl) amino)pyridin-3-yl)piperidine-1-carboxylate (7 g, 0.1 mmol, 1 equiv) was charged in ethanol (60 mL) and 4 M HCl in Dioxane (40 mL) was added into it. Solution was stirred for 1 h at 50° C. TLC (50% ethyl acetate:hexane) and LCMS showed that starting material was consumed. After completion of the reaction, solvent was removed under reduced pressure and basified with saturated NaHCO$_3$ (~100 mL) till pH=7-8. Solid obtained was filtered under vacuum and washed with water (100 mL×3). Compound was further dried in vacuum to afford 5-fluoro-4-(8-fluoro-4-isopropyl-3,4-dihydro-2H-benzo[b][1,4]oxazin-6-yl)-N-(5-(piperidin-4-yl)pyridin-2-yl)pyrimidin-2-amine hydrochloride (5.2 g, 90.2%) as a yellow solid. LCMS: 467 [M+H]$^+$ Step-5: Synthesis of 5-fluoro-4-(8-fluoro-4-isopropyl-3,4-dihydro-2H-benzo[b][1,4]oxazin-6-yl)-N-(5-(1-methylpiperidin-4-yl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(6-(piperidin-4-yl)pyridin-3-yl)pyrimidin-2-amine (4 g, 8.56 mmol, 1 equiv) in DCE (40 mL), was added Formaldehyde (40% in water) (2.31 g, 77.04 mmol, 9 equiv), acetic acid (2.57 g, 42.8 mmol, 5 equiv). The reaction mixture was stirred at ambient temperature for 1 h. The reaction mixture was cooled to 0° C. NaCNBH$_3$ (1.61 g, 25.68 mmol, 3 equiv) was added to above mixture and reaction mixture was allowed to come at ambient temperature. The reaction mixture was stirred at ambient temperature for 2 h. TLC (10% MeOH:DCM) and LCMS showed that starting material was consumed. After completion, the reaction mixture was diluted with water (50 mL) and concentrated under reduced pressure. Saturated bicarbonate solution (100 mL) was added in to crude material and solid obtained was filtered under vacuum. Crude material was purified by silica gel chromatography (#100-200) using 0-7% MeOH:DCM to afford free base of 5-fluoro-4-(8-fluoro-4-isopropyl-3,4-dihydro-2H-benzo[b][1,4]oxazin-6-yl)-N-(5-(1-methylpiperidin-4-yl)pyridin-2-yl)pyrimidin-2-amine (1.42 g, 34.5%) as a yellow solid.

LCMS: 481 [M+H]$^+$

Step-6: Synthesis of 5-fluoro-4-(8-fluoro-4-isopropyl-3,4-dihydro-2H-benzo[b][1,4]oxazin-6-yl)-N-(5-(1-methylpiperidin-4-yl)pyridin-2-yl)pyrimidin-2-amine hydrochloride In 250 mL RBF, 5-fluoro-4-(8-fluoro-4-isopropyl-3,4-dihydro-2H-benzo[b][1,4]oxazin-6-yl)-N-(5-(1-methylpiperidin-4-yl)pyridin-2-yl)pyrimidin-2-amine free base (1.41 g, 2.93 mmol, 1 eq.) was suspended in ethanol (100 mL) and heated to reflux till the suspension became clear solution. Reaction mixture was cooled to ambient temperature. Hydrochloric acid, 35% (611 mg, 5.86 mmol, 2 eq.) dissolved in ethanol (10 mL) was added to reaction mixture drop wise at ambient temperature. Reaction mixture was stirred at same temperature for 30 minutes. Reaction mixture was concentrated under reduced pressure. MTBE (100 mL) was added to reaction mixture and solid obtained was filtered under vacuum. Solid compound was washed with Methyl tert butyl ether (100 mL) and dried in vacuum oven at 55° C. for 16 h to afford 5-fluoro-4-(8-fluoro-4-isopropyl-3,4-dihydro-2H-benzo[b][1,4]oxazin-6-yl)-N-(5-(1-methylpiperidin-4-yl)pyridin-2-yl)pyrimidin-2-amine hydrochloride salt of tittle compound (1.57 g, 96.9%) as yellow solid. LCMS: 481 [M+1]$^+$; $^1$H NMR (400 MHz, DMSO-d6, HCl salt): δ 10.61 (br. s., 1H), 8.75 (d, J=3.51 Hz, 1H), 8.24 (s., 1H), 8.01 (s., 1H), 7.92 (d, J=8.77 Hz, 1H), 7.44 (s., 1H), 7.22 (d, J=11.40 Hz, 1H), 4.31 (s., 2H), 4.06-4.23 (m, 1H), 3.50 (d, J=12.28 Hz, 2H), 3.32 (m, 2H), 3.06 (m, 1H), 2.90 (m, 3H), 2.77 (m, 2H), 2.03 (m, 2H), 1.97 (m, 2H), 1.20 (d, J=6.58 Hz, 6H); UPLC-LCMS: 99.93%; HPLC: 99.05%

Example-51: Synthesis of 5-fluoro-4-(8-fluoro-4-isopropyl-3,4-dihydro-2H-benzo[b][1,4]oxazin-6-yl)-N-(4-fluoro-5-(piperidin-4-yl)pyridin-2-yl)pyrimidin-2-amine. (Compound 443)

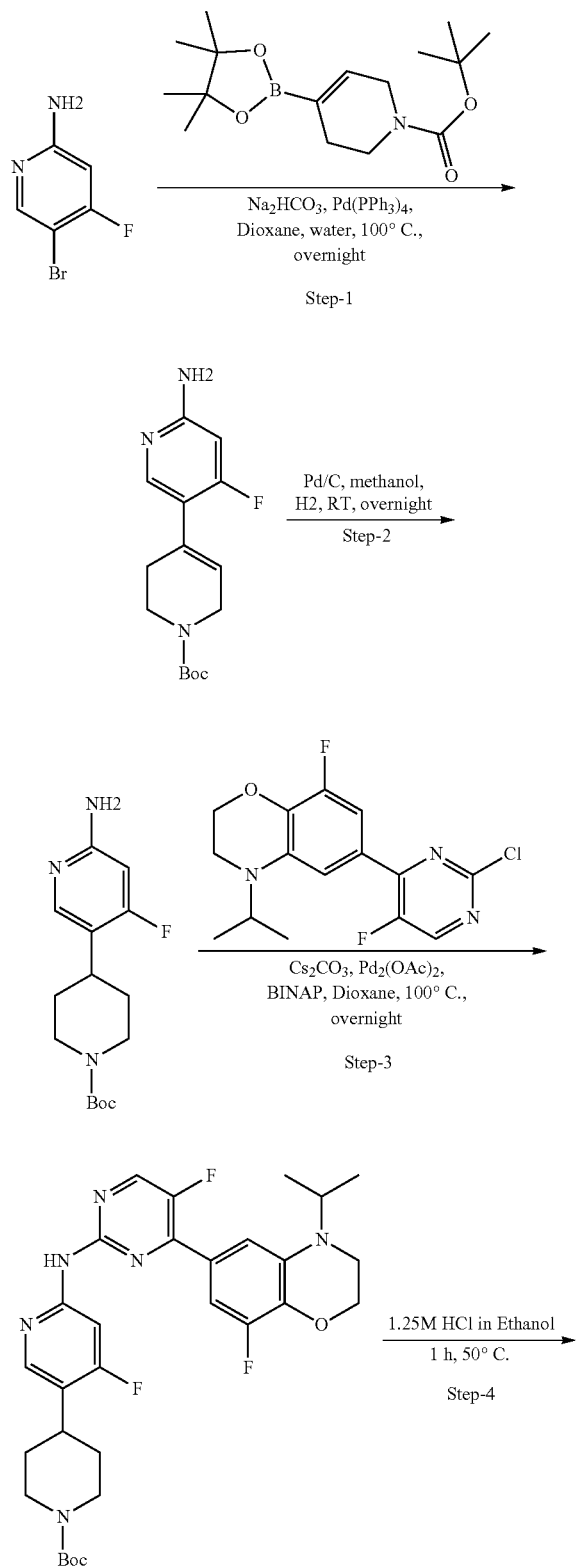

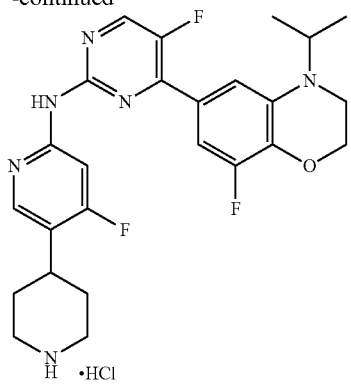

Step-1: Synthesis of tert-butyl 6-amino-4-fluoro-3',6'-dihydro-[3, 4'-bipyridine]-1'(2'H)-carboxylate To a solution of 5-bromo-4-fluoropyridin-2-amine (500 mg, 2.6 mmol, 1 equiv) in dioxane (10 mL), was added tert-butyl 4-(4,4,5,5-tetramethyl-1,3,2-dioxaborolan-2-yl)-3,6-dihydropyridine-1(2H)-carboxylate (809 mg, 2.6 mmol, 1 equiv) and sodium bicarbonate (655 mg, 7.8 mmol, 3 equiv). The reaction mixture was degassed with nitrogen gas for 30 min., followed by the addition of Pd (PPh$_3$)$_4$ (150 mg, 0.13 mmol, 0.05 equiv). The resultant reaction mixture was allowed to stir at 100° C. for overnight. Progress of the reaction was monitored by TLC and LCMS. After completion of the reaction, reaction mixture was diluted with water (30 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 6-amino-4-fluoro-3',6'-dihydro-[3, 4'-bipyridine]-1'(2'H)-carboxylate (600 mg, 78%) as a yellow oil compound. LCMS: 294 [M+H]$^+$

Step-2: Synthesis of tert-butyl 4-(6-amino-4-fluoropyridin-3-yl) piperidine-1-carboxylate To a stirred solution of tert-butyl 6-amino-4-fluoro-3',6'-dihydro-[3, 4'-bipyridine]-1'(2'H)-carboxylate (300 mg, 1.02 mmol, 1 equiv) in methanol (10 mL), was added Pd/C (20% w/w) (60 mg) under H$_2$ atm. The resultant reaction mixture was allowed to stir at RT for overnight. Progress of the reaction was monitored by LCMS. After completion of the reaction, the mixture was passes through celite bed and the filtrate was concentrated under reduced pressure to obtain tert-butyl 4-(6-amino-4-fluoropyridin-3-yl) piperidine-1-carboxylate (150 mg, 50%) as a white solid compound. LCMS: 296 [M+H]$^+$

Step-3: Synthesis of tert-butyl 4-(4-fluoro-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(6-amino-4-fluoropyridin-3-yl) piperidine-1-carboxylate (97 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(4-fluoro-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate (17 mg, 9%) as a yellow solid compound. LCMS: 585 [M+H]$^+$ Step-4: Synthesis of 5-fluoro-4-(8-fluoro-4-isopropyl-3,4-dihydro-2H-benzo[b][1,4]oxazin-6-yl)-N-(4-fluoro-5-(piperidin-4-yl)pyridin-2-yl)pyrimidin-2-amine A solution of tert-butyl 4-(4-fluoro-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate (17 mg, 0.02 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(4-fluoro-5-(piperidin-4-yl)pyridin-2-yl)pyrimidin-2-amine (13 mg, 87%) as a yellow solid compound. LCMS: 485 [M+H]$^{+1}$HNMR (400 MHz, DMSO-d$_6$) δ 10.48 (s, 1H), 8.86 (d, J=11.2 Hz, 1H), 8.69 (d, J=3.8 Hz, 1H), 8.21 (d, J=10.6 Hz, 1H), 8.08 (d, J=13.6 Hz, 1H), 7.48 (s, 1H), 7.19 (d, J=11.6 Hz, 1H), 4.31 (t, J=4.2 Hz, 2H), 4.19 (p, J=6.7 Hz, 1H), 3.37 (d, J=12.5 Hz, 1H), 3.32 (t, J=4.4 Hz, 2H), 3.06 (dt, J=19.1, 8.9 Hz, 4H), 2.01-1.90 (m, 4H), 1.19 (d, J=6.5 Hz, 6H).

Example-52: Synthesis of N-(5-fluoro-4-(8-fluoro-4-isopropyl-3,4-dihydro-2H-benzo[b][1,4]oxazin-6-yl)pyrimidin-2-yl)-5-methyl-4,5,6,7-tetrahydropyrazolo[1,5-a]pyrazin-2-amine. (Compound 444)

To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 5-methyl-4,5,6,7-tetrahydropyrazolo[1,5-a]pyrazin-2-amine (97 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain N-(5-fluoro-4-(8-fluoro-4-isopropyl-3,4-dihydro-2H-benzo[b][1,4]oxazin-6-yl)pyrimidin-2-yl)-5-methyl-4,5,6,7-tetrahydropyrazolo[1,5-a]pyrazin-2-amine (30 mg, 22%) as a yellow solid compound. LCMS: 442 [M+H]$^+$; $^1$HNMR (400 MHz, DMSO-d$_6$) δ 9.82 (s, 1H), 8.49 (d, J=4.0 Hz, 1H), 7.45 (s, 1H), 7.15 (d, J=11.5 Hz, 1H), 6.41 (s, 1H), 4.30 (t, J=4.3 Hz, 2H), 4.12 (dq, J=10.1, 5.3, 4.6 Hz, 1H), 3.96 (t, J=5.4 Hz, 2H), 3.54 (s, 2H), 3.25 (s, 2H), 2.83 (t, J=5.5 Hz, 2H), 2.38 (s, 3H), 1.19 (d, J=6.5 Hz, 6H).

Example-53: Synthesis of 1-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidin-4-ol. (Compound 445)

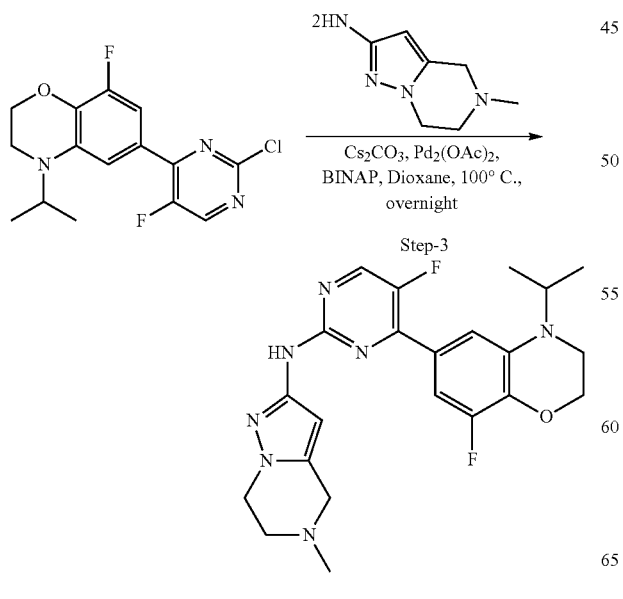

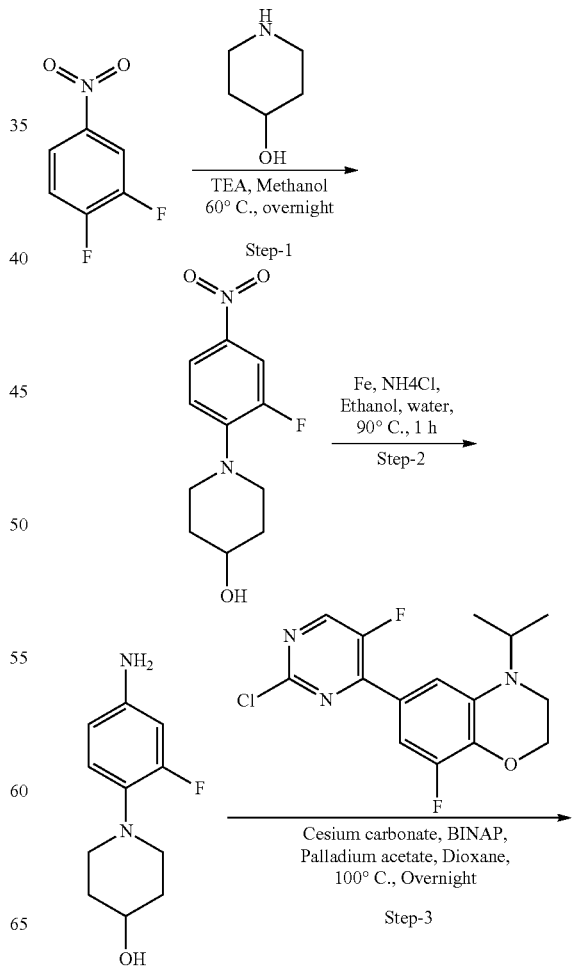

-continued

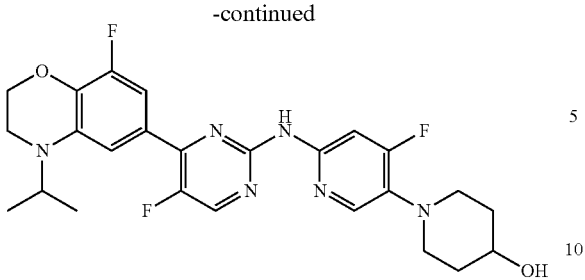

Step-1: Synthesis of 1-(2-fluoro-4-nitrophenyl)piperidin-4-ol

To a stirred solution of 1, 2-difluoro-4-nitrobenzene (1000 mg, 6.28 mmol, 1 equiv) in methanol (15 mL), was added TEA (1.7 mL, 9.43 mmol, 2 equiv) and piperidin-4-ol (953 mg, 12.5 mmol, 1.5 equiv). The resultant reaction mixture was allowed to stir at 60° C. for overnight. Progress of the reaction was monitored by LCMS. After completion of the reaction, diluted with water (100 mL), solid observed was filtered and dried under vacuum to obtain 1-(2-fluoro-4-nitrophenyl)piperidin-4-ol (1300 mg, 86%) as a yellow solid compound. LCMS: 241 [M+H]$^+$

Step-2: Synthesis of 1-(4-amino-2-fluorophenyl)piperidin-4-ol

To a stirred solution of 1-(2-fluoro-4-nitrophenyl)piperidin-4-ol (500 mg, 2.08 mmol, 1 equiv) in ethanol (8 mL), water (2 mL), was added iron powder (350 mg, 6.25 mmol, 3 equiv) and ammonium chloride (225 mg, 4.16 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 1-(4-amino-2-fluorophenyl) piperidin-4-ol (350 mg, 80%) as a dark brown solid compound. LCMS: 211 [M+H]$^+$

Step-3: Synthesis of 1-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidin-4-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 1-(4-amino-2-fluorophenyl)piperidin-4-ol (69 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 1-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidin-4-ol (70 mg, 45%) as a yellow color solid compound. LCMS: 500 [M+H]$^+$; $^1$HNMR (400 MHz, DMSO-d6) δ 9.72 (s, 1H), 8.56 (d, J=4.0 Hz, 1H), 7.71 (dd, J=15.2, 2.5 Hz, 1H), 7.43 (s, 1H), 7.35 (dd, J=8.9, 2.4 Hz, 1H), 7.16 (d, J=11.5 Hz, 1H), 6.97 (t, J=9.4 Hz, 1H), 4.68 (d, J=4.1 Hz, 1H), 4.33-4.26 (m, 2H), 4.15 (h, J=6.7 Hz, 1H), 3.58 (tt, J=8.5, 4.3 Hz, 1H), 3.31 (s, 2H), 3.16 (dt, J=10.0, 4.4 Hz, 2H), 2.71 (d, J=9.5 Hz, 2H), 1.83 (dt, J=12.2, 4.2 Hz, 2H), 1.61-1.47 (m, 2H), 1.18 (d, J=6.4 Hz, 6H).

Example-54: Synthesis of 5-fluoro-4-(8-fluoro-4-isopropyl-3,4-dihydro-2H-benzo[b][1,4]oxazin-6-yl)-N-(5-morpholinopyridin-2-yl)pyrimidin-2-amine. (Compound 446)

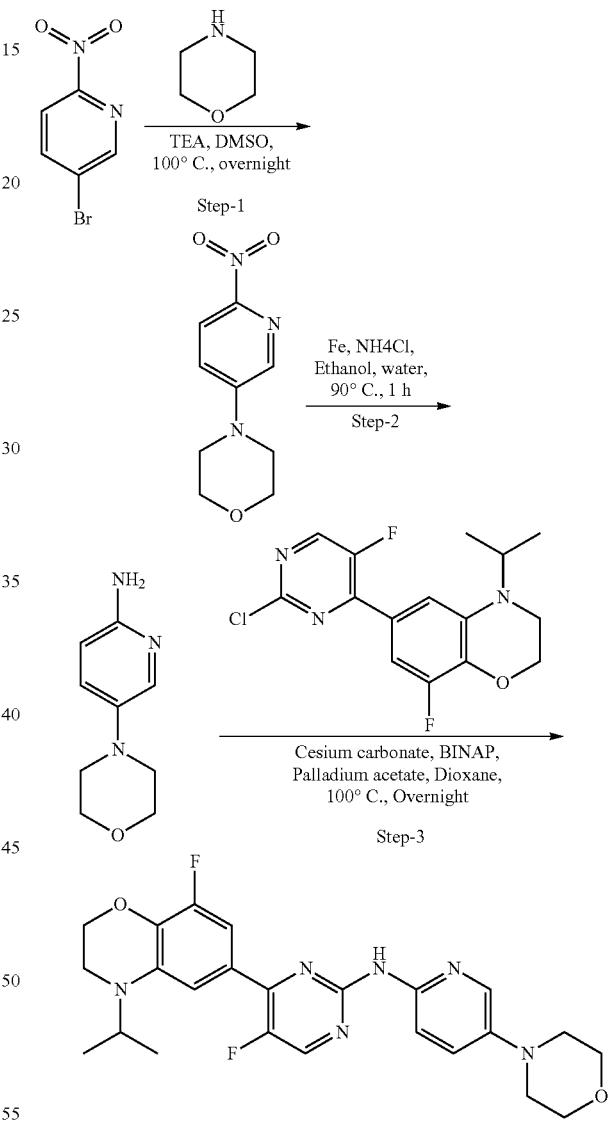

Step-1: Synthesis of 4-(6-nitropyridin-3-yl)morpholine

To a stirred solution of 5-bromo-2-nitropyridine (500 mg, 2.47 mmol, 1 equiv) in DMSO (10 mL), was added TEA (0.7 mL, 4.94 mmol, 2 equiv) and morpholine (323 mg, 3.7 mmol, 1.5 equiv). The resultant reaction mixture was allowed to stir at 100° C. for overnight. Progress of the reaction was monitored by TLC and LCMS. After completion of the reaction, diluted with water (100 mL), solid observed was filtered and dried under vacuum to obtain 4-(6-nitropyridin-3-yl)morpholine (500 mg, 97%) as a yellow solid compound. LCMS: 210 [M+H]⁺

Step-2: Synthesis of 5-morpholinopyridin-2-amine

To a stirred solution of 4-(6-nitropyridin-3-yl)morpholine (500 mg, 2.39 mmol, 1 equiv) in ethanol (8 mL), water (2 mL), was added iron powder (402 mg, 7.17 mmol, 3 equiv) and ammonium chloride (258 mg, 4.78 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 5-morpholinopyridin-2-amine (300 mg, 70%) as a dark brown solid compound. LCMS: 180 [M+H]⁺

Step-3: Synthesis of 5-fluoro-4-(8-fluoro-4-isopropyl-3,4-dihydro-2H-benzo[b][1,4]oxazin-6-yl)-N-(5-morpholinopyridin-2-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 5-morpholinopyridin-2-amine (59 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(5-morpholinopyridin-2-yl)pyrimidin-2-amine (40 mg, 28%) as a yellow color solid compound.
LCMS: 469 [M+H]⁺; ¹HNMR (400 MHz, DMSO-d6) δ 8.53 (d, J=3.9 Hz, 1H), 8.00 (d, J=9.3 Hz, 2H), 7.42 (s, 1H), 7.38 (dd, J=9.1, 3.1 Hz, 1H), 7.15 (d, J=11.7 Hz, 1H), 4.31-4.24 (m, 2H), 4.11 (p, J=6.6 Hz, 1H), 3.74 (t, J=4.7 Hz, 4H), 3.28 (t, J=4.3 Hz, 2H), 3.07 (t, J=4.8 Hz, 4H), 1.16 (d, J=6.5 Hz, 6H).

Example-55: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-ol. (Compound 447)

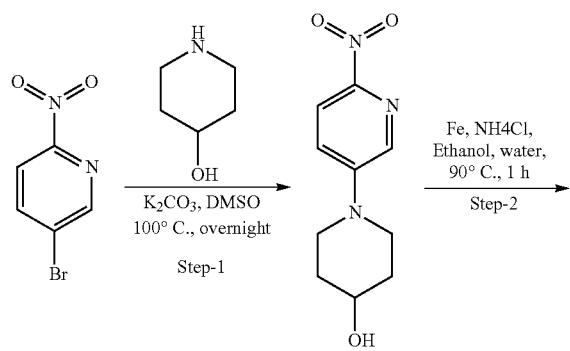

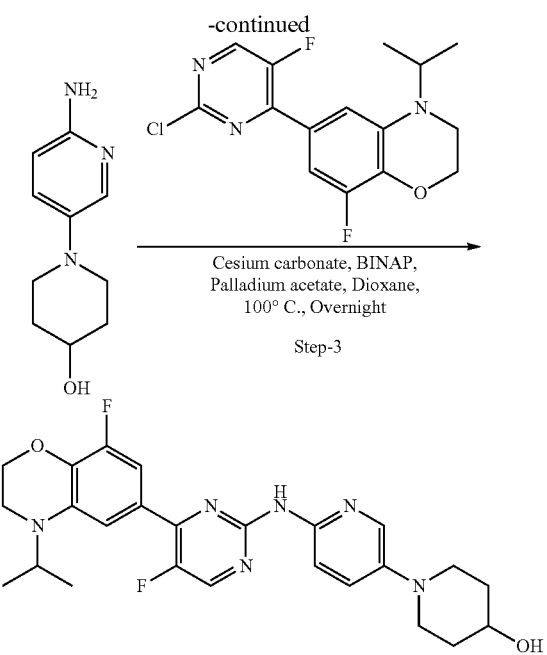

Step-1: Synthesis of 1-(6-nitropyridin-3-yl)piperidin-4-ol

To a stirred solution of 5-bromo-2-nitropyridine (1000 mg, 4.95 mmol, 1 equiv) in DMSO (15 mL), was added K₂CO₃ (1366 mg, 9.9 mmol, 2 equiv) and piperidin-4-ol (750 mg, 7.42 mmol, 1.5 equiv). The resultant reaction mixture was allowed to stir at 100° C. for overnight. Progress of the reaction was monitored by LCMS. After completion of the reaction, diluted with water (100 mL), solid observed was filtered and dried under vacuum to obtain 1-(6-nitropyridin-3-yl)piperidin-4-ol (900 mg, 82%) as a yellow solid compound. LCMS: 224 [M+H]⁺

Step-2: Synthesis of 1-(6-aminopyridin-3-yl)piperidin-4-ol

To a stirred solution of 1-(6-nitropyridin-3-yl)piperidin-4-ol (500 mg, 2.24 mmol, 1 equiv) in ethanol (8 mL), water (2 mL), was added iron powder (377 mg, 6.72 mmol, 3 equiv) and ammonium chloride (242 mg, 4.48 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 1-(6-aminopyridin-3-yl)piperidin-4-ol (350 mg, 81%) as a dark brown solid compound. LCMS: 194 [M+H]⁺

Step-3: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 1-(6-aminopyridin-3-yl)piperidin-4-ol (64 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-ol (20 mg, 14%) as a yellow color solid compound. LCMS: 483 [M+H]$^+$; $^1$HNMR (400 MHz, DMSO-d6) δ 8.69 (d, J=3.6 Hz, 1H), 8.00-7.91 (m, 1H), 7.88 (d, J=3.0 Hz, 1H), 7.70 (d, J=9.3 Hz, 1H), 7.38 (s, 1H), 7.19 (d, J=11.4 Hz, 1H), 4.29 (t, J=4.2 Hz, 2H), 4.12 (p, J=6.6 Hz, 1H), 3.67 (p, J=6.8, 6.1 Hz, 3H), 3.30 (t, J=4.2 Hz, 2H), 2.95 (t, J=10.7 Hz, 2H), 1.85 (dd, J=12.8, 4.9 Hz, 2H), 1.51 (dtd, J=13.1, 9.0, 3.8 Hz, 2H), 1.17 (d, J=6.5 Hz, 6H).

Example-56: Synthesis of 5-fluoro-4-(8-fluoro-4-isopropyl-3,4-dihydro-2H-benzo[b][1,4]oxazin-6-yl)-N-(1-(piperidin-4-yl)-1H-pyrazol-4-yl)pyrimidin-2-amine. (Compound 448)

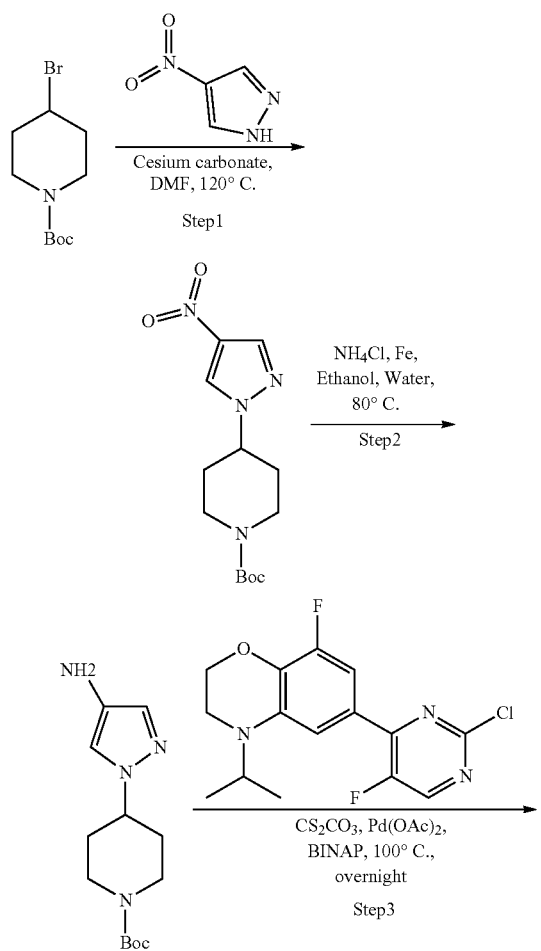

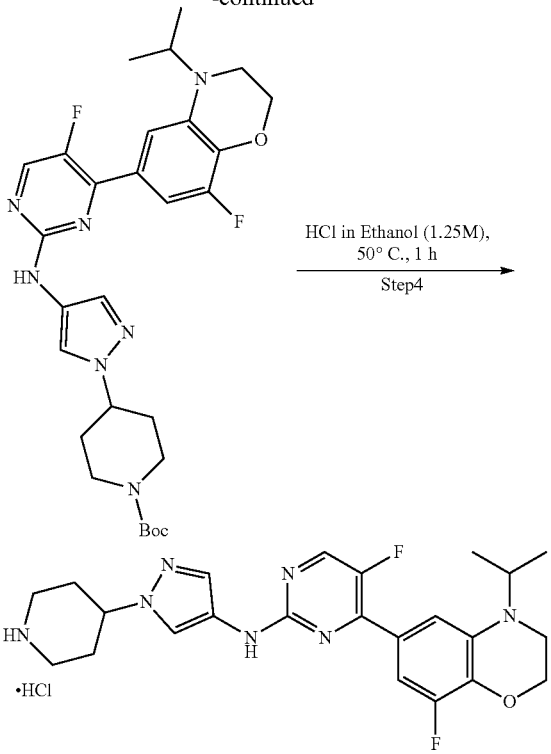

Step-1: Synthesis of tert-butyl 4-(4-nitro-1H-pyrazol-1-yl) piperidine-1-carboxylate To a stirred solution of tert-butyl 4-bromopiperidine-1-carboxylate (1000 mg, 8.7 mmol, 1 equiv) in DMF (15 mL), was added Cs$_2$CO$_3$ (5672 mg, 17.4 mmol, 1 equiv) and 4-nitro-1H-pyrazole (2693 mg, 10.2 mmol, 1.2 equiv). The resultant reaction mixture was allowed to stir at 120° C. for overnight. Progress of the reaction was monitored by TLC and LCMS. After completion of the reaction, diluted with water (100 mL) and extracted with ethyl acetate (150 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 4-(4-nitro-1H-pyrazol-1-yl)piperidine-1-carboxylate (2500 mg, 96%) as a white solid compound. LCMS: 241 [M-t-But+H]$^+$ Step-2: Synthesis of tert-butyl 4-(4-amino-1H-pyrazol-1-yl) piperidine-1-carboxylate To a stirred solution of tert-butyl 4-(4-nitro-1H-pyrazol-1-yl)piperidine-1-carboxylate (1000 mg, 3.37 mmol, 1 equiv) in ethanol (10 mL), water (3 mL), was added iron powder (566 mg, 10.11 mmol, 3 equiv) and ammonium chloride (364 mg, 6.74 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain tert-butyl 4-(4-amino-1H-pyrazol-1-yl) piperidine-1-carboxylate (400 mg, 44%) as a dark brown solid compound. LCMS: 267 [M+H]$^+$ Step-3: Synthesis of tert-butyl 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(4-amino-1H-pyrazol-1-yl) piperidine-1-carboxylate (88 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain tert-butyl 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl)piperidine-1-carboxylate (20 mg, 12%) as a yellow color solid compound. LCMS: 556 [M+H]$^+$ Step-4: Synthesis of 5-fluoro-4-(8-fluoro-4-isopropyl-3,4-dihydro-2H-benzo[b][1,4]oxazin-6-yl)-N-(1-(piperidin-4-yl)-1H-pyrazol-4-yl)pyrimidin-2-amine tert-butyl 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl)piperidine-1-carboxylate (mg, mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-fluoro-4-(8-fluoro-4-isopropyl-3,4-dihydro-2H-benzo[b][1,4]oxazin-6-yl)-N-(1-(piperidin-4-yl)-1H-pyrazol-4-yl)pyrimidin-2-amine (15 mg, 83%) as an orange color solid compound. LCMS: 456 [M+H]$^+$; $^1$HNMR (400 MHz, DMSO-d6) δ 9.53 (s, 1H), 8.50 (d, J=3.9 Hz, 1H), 7.88 (s, 1H), 7.64 (s, 1H), 7.34 (s, 1H), 7.13 (d, J=11.6 Hz, 1H), 4.44 (tt, J=10.0, 5.1 Hz, 1H), 4.30 (t, J=4.3 Hz, 2H), 4.12 (p, J=6.6 Hz, 1H), 3.39 (d, J=12.7 Hz, 2H), 3.31 (t, J=4.3 Hz, 2H), 3.04 (q, J=11.1 Hz, 2H), 2.14 (tt, J=11.0, 5.2 Hz, 4H), 1.18 (d, J=6.5 Hz, 6H).

Example-57: Synthesis of 2-(dimethylamino)-1-(4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazin-1-yl)ethan-1-one. (Compound 449)

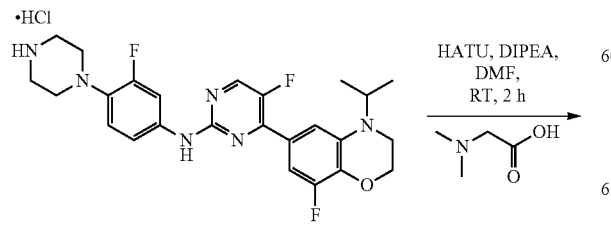

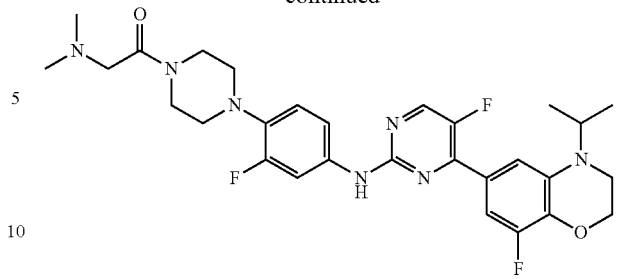

To a solution of 5-fluoro-N-(3-fluoro-4-(piperazin-1-yl)phenyl)-4-(8-fluoro-4-isopropyl-3,4-dihydro-2H-benzo[b][1,4]oxazin-6-yl)pyrimidin-2-amine hydrochloride (50 mg, 0.1 mmol, 1 equiv) in DMF (3 mL) was added dimethyl glycine (16 mg, 0.15 mmol, 1.5 equiv) followed by addition of HATU (57 mg, 0.15 mmol, 1.5 equiv) and DIPEA (33 mg, 0.25 mmol, 2.5 equiv). Resultant mixture was allowed to stir at room temperature for 2 h. Progress of the reaction was monitored by LCMS. After completion of the reaction, the reaction mixture was diluted with water (10 mL) and extracted with EtOAc (12 mL). Organic layer was washed with water (5 mL×6) and brine (5 mL), dried over anhydrous sodium sulphate and concentrated under reduced pressure to obtain crude compound was purified by reverse phase HPLC to afford 2-(dimethylamino)-1-(4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperazin-1-yl)ethan-1-one (30 mg) as a pale yellow solid. LCMS: 570 [M+H]$^+$; $^1$HNMR (400 MHz, DMSO-d6) δ 9.76 (s, 1H), 8.57 (d, J=3.9 Hz, 1H), 7.77 (dd, J=15.0, 2.5 Hz, 1H), 7.43 (s, 1H), 7.41-7.34 (m, 1H), 7.16 (d, J=11.8 Hz, 1H), 6.99 (t, J=9.4 Hz, 1H), 4.34-4.27 (m, 2H), 4.16 (p, J=6.7 Hz, 1H), 3.67 (s, 2H), 3.60 (t, J=5.0 Hz, 2H), 3.22 (s, 2H), 2.93 (dt, J=18.9, 5.3 Hz, 8H), 2.25 (s, 6H), 1.19 (d, J=6.5 Hz, 6H).

Example-58: Synthesis of 2-(dimethylamino)-1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-1-yl)ethan-1-one. (Compound 450)

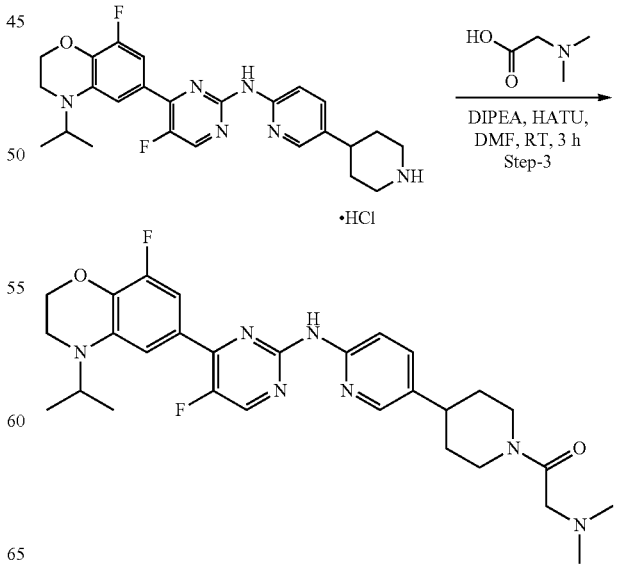

Step-1: Synthesis of 2-(dimethylamino)-1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-1-yl)ethan-1-one To a stirred solution of 5-fluoro-4-(8-fluoro-4-isopropyl-3,4-dihydro-2H-benzo[b][1,4]oxazin-6-yl)-N-(5-(piperidin-4-yl)pyridin-2-yl)pyrimidin-2-amine (160 mg, 0.31 mmol, 1 equiv) in DMF (3 mL), was added dimethylglycine (39 mg, 0.38 mmol, 1.2 equiv), DIPEA (0.2 mL, 1.24 mmol, 4 equiv) and HATU (212 mg, 0.55 mmol, 1.8 equiv). The reaction mixture was allowed to stir for 3 h at RT. Progress of the reaction was monitored by TLC and LCMS. After completion of the reaction, the reaction mixture was diluted with water (10 mL), solid observed was filtered and purified by recrystallization with methanol to obtain 2-(dimethylamino)-1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-1-yl)ethan-1-one (100 mg, 65%) as an off white color solid compound. LCMS: 552 [M+H]$^+$; $^1$HNMR (400 MHz, DMSO-d6) δ 9.92 (s, 1H), 8.61 (d, J=3.8 Hz, 1H), 8.20 (d, J=2.5 Hz, 1H), 8.14 (d, J=8.6 Hz, 1H), 7.61 (dd, J=8.6, 2.6 Hz, 1H), 7.47 (s, 1H), 7.19 (d, J=11.8 Hz, 1H), 4.52 (d, J=13.0 Hz, 1H), 4.30 (t, J=4.3 Hz, 2H), 4.16 (p, J=6.4 Hz, 1H), 3.86 (d, J=14.0 Hz, 2H), 3.39 (d, J=12.7 Hz, 2H), 3.15 (dd, J=15.7, 9.1 Hz, 1H), 2.93-2.67 (m, 3H), 2.62 (s, 6H), 1.90-1.81 (m, 2H), 1.64 (t, J=12.2 Hz, 1H), 1.57-1.43 (m, 1H), 1.19 (d, J=6.5 Hz, 6H).

Example-59: Synthesis of 2-(dimethylamino)-1-(4-(2-fluoro-4-((5-fluoro-4-(8-fluoro-4-isopropyl-3,4 dihydro-2H-benzo[b][ ][1,4]oxazin-6-yl)pyrimidin-2-yl)amino)phenyl)piperidin-1-yl)ethan-1-one. (Compound 451)

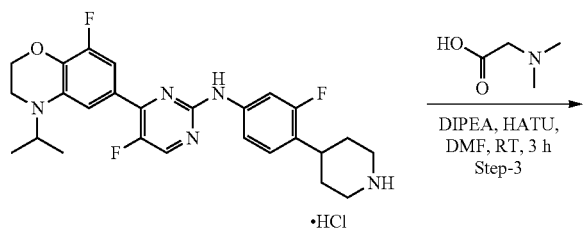

Step-1: Synthesis of 2-(dimethylamino)-1-(4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidin-1-yl)ethan-1-one

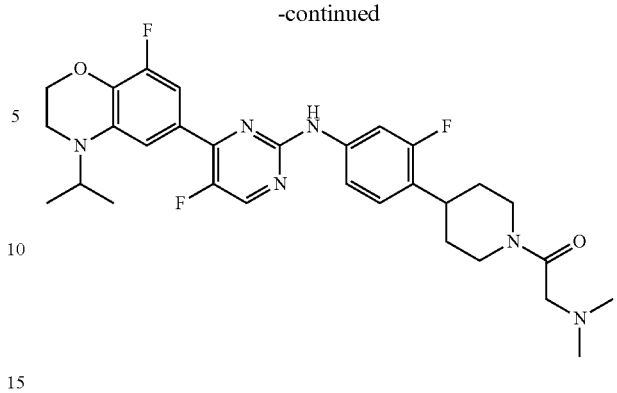

To a stirred solution of 5-fluoro-N-(3-fluoro-4-(piperidin-4-yl)phenyl)-4-(8-fluoro-4-isopropyl-3,4-dihydro-2H-benzo[b][1,4]oxazin-6-yl)pyrimidin-2-amine (180 mg, 0.34 mmol, 1 equiv) in DMF (3 mL), was added dimethyl glycine (43 mg, 0.41 mmol, 1.2 equiv), DIPEA (0.2 mL, 1.24 mmol, 4 equiv) and HATU (233 mg, 0.61 mmol, 1.8 equiv). The reaction mixture was allowed to stir for 3 h at RT. Progress of the reaction was monitored by TLC and LCMS. After completion of the reaction the reaction mixture was diluted with water (10 mL), solid observed was filtered and purified by reverse phase HPLC to obtain 2-(dimethylamino)-1-(4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)piperidin-1-yl)ethan-1-one (40 mg, 23%) as a yellow color solid compound. LCMS: 569 [M+H]$^+$; $^1$HNMR (400 MHz, DMSO-d6) δ 9.87 (s, 1H), 8.59 (d, J=3.9 Hz, 1H), 7.76 (dd, J=13.6, 2.1 Hz, 1H), 7.45 (s, 1H), 7.40 (dd, J=8.7, 2.2 Hz, 1H), 7.23-7.12 (m, 2H), 4.50 (d, J=12.1 Hz, 1H), 4.33-4.26 (m, 2H), 4.17 (dd, J=12.9, 6.5 Hz, 2H), 3.34-3.27 (m, 2H), 3.07 (dq, J=45.8, 11.8, 10.5 Hz, 4H), 2.61 (d, J=12.4 Hz, 1H), 2.19 (s, 6H), 1.79-1.70 (m, 2H), 1.61 (dt, J=14.4, 7.3 Hz, 1H), 1.49 (td, J=12.5, 4.3 Hz, 1H), 1.18 (d, J=6.5 Hz, 6H).

Example-60: Synthesis of 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl)cyclohexan-1-ol. (Compound 452)

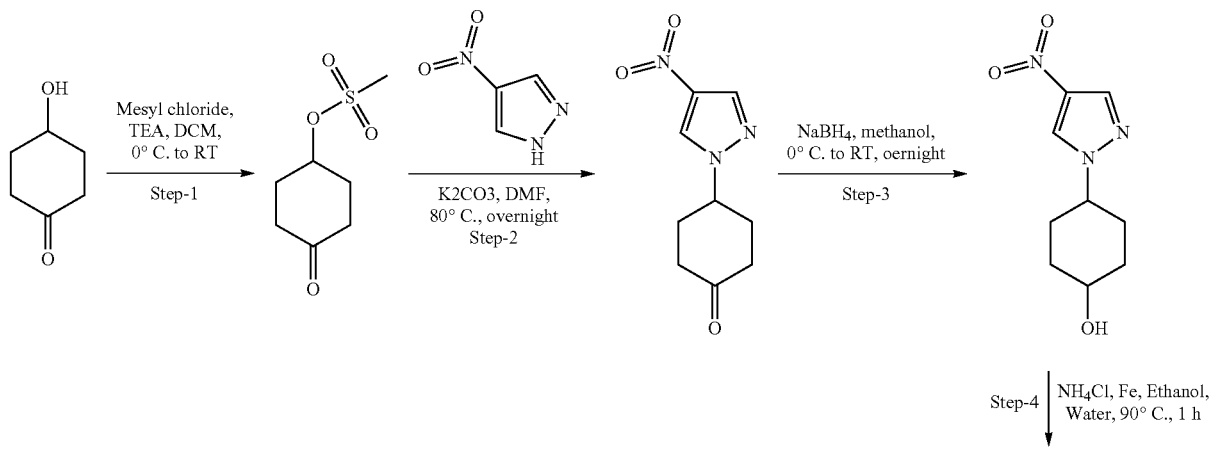

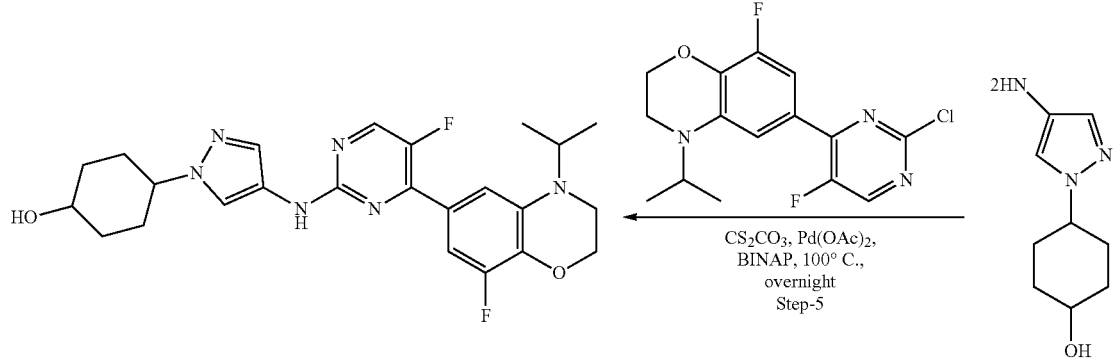

Step-1: Synthesis of 4-oxocyclohexyl methanesulfonate

To a stirred solution of 4-hydroxycyclohexan-1-one (1000 mg, 8.7 mmol, 1 equiv) in DCM (15 mL), was added TEA (1.2 mL, 8.7 mmol, 1 equiv). Cool the reaction mixture to 0° C., followed by the addition of mesyl chloride (0.7 mL, 8.7 mmol, 1 equiv). Raise the temp. To RT and the resultant reaction mixture was allowed to stir for overnight. Progress of the reaction was monitored by LCMS. After completion of the reaction, diluted with water (50 mL) and extracted with DCM (100 mL×2). Organic layer was washed with water (100 mL) and brine solution (100 mL). Organic layer was dried over anhydrous sodium sulphate and concentrated under reduced pressure to obtain 4-oxocyclohexyl methanesulfonate (1300 mg, 77%) as a yellow oil compound.

Step-2: Synthesis of 4-(4-nitro-1H-pyrazol-1-yl) cyclohexan-1-one

To a stirred solution of 4-oxocyclohexyl methanesulfonate (600 mg, 5.3 mmol, 1 equiv) in DMF (10 mL), was added $K_2CO_3$ (1463 mg, 10.6 mmol, 2 equiv) and 4-nitro-1H-pyrazole (1223 mg, 6.37 mmol, 1.2 equiv). The resultant reaction mixture was allowed to stir at 80° C. for overnight. Progress of the reaction was monitored by LCMS. After completion of the reaction, diluted with water (50 mL) and extracted with EtOAc (100 mL×2). Organic layer was washed with water (100 mL) and brine solution (100 mL). Organic layer was dried over anhydrous sodium sulphate and concentrated under reduced pressure to obtain crude, which was purified by normal phase Combi flash to obtain 4-(4-nitro-1H-pyrazol-1-yl)cyclohexan-1-one (400 mg, 36%) as a brown solid compound. LCMS: 210 [M+H]$^+$

Step-3: Synthesis of 4-(4-nitro-1H-pyrazol-1-yl) cyclohexan-1-ol

To a stirred solution of 4-(4-nitro-1H-pyrazol-1-yl) cyclohexan-1-one (400 mg, 1.91 mmol, 1 equiv) in methanol (10 mL), was added $NaBH_4$ (145 mg, 3.82 mmol, 2 equiv) at 0° C. Raise the temp. to RT the resultant reaction mixture was allowed to stir at RT for overnight. Progress of the reaction was monitored by TLC and LCMS. After completion of the reaction, solvent was removed under reduced pressure, residue obtain was diluted with water (50 mL) and extracted with ethyl acetate (150 mL). Organic layer was washed with water (50 mL) and brine solution (50 mL). Organic layer was dried over anhydrous sodium sulphate and concentrated under reduced pressure to obtain crude, which was purified by normal phase Combi flash to obtain 4-(4-nitro-1H-pyrazol-1-yl)cyclohexan-1-ol (400 mg, 87%) as an off white solid compound.
LCMS: 212 [M+H]$^+$

Step-4: Synthesis of 4-(4-amino-1H-pyrazol-1-yl) cyclohexan-1-ol

To a stirred solution of 4-(4-nitro-1H-pyrazol-1-yl)cyclohexan-1-ol (300 mg, 1.42 mmol, 1 equiv) in ethanol (8 mL), water (2 mL), was added iron powder (239 mg, 4.26 mmol, 3 equiv) and ammonium chloride (154 mg, 2.84 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 4-(4-amino-1H-pyrazol-1-yl) cyclohexan-1-ol (350 mg, 78%) as a dark brown solid. LCMS: 182 [M+H]$^+$

Step-5: Synthesis of 4-(4-((5-fluoro-4-(8-fluoro-4-isopropyl-3,4-dihydro-2H-benzo[b][1,4]oxazin-6-yl) pyrimidin-2-yl)amino)-1H-pyrazol-1-yl)cyclohexan-1-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 4-(4-amino-1H-pyrazol-1-yl)cyclohexan-1-ol (60 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 4-(4-((5-fluoro-4-(8-fluoro-4-isopropyl-3,4-dihydro-2H-benzo[b][1,4]oxazin-6-yl)pyrimidin-2-yl) amino)-1H-pyrazol-1-yl)cyclohexan-1-ol (10 mg, 7%) as a yellow color solid compound. LCMS: 471 [M+H]$^+$; $^1$HNMR (400 MHz, DMSO-d6) δ 9.48 (s, 1H), 8.48 (d, J=3.9 Hz, 1H), 7.88 (s, 1H), 7.53 (s, 1H), 7.35 (s, 1H), 7.13 (d, J=11.6 Hz, 1H), 4.65 (d, J=4.4 Hz, 1H), 4.30 (t, J=4.3 Hz, 2H), 4.18-4.00 (m, 2H), 3.48 (td, J=10.2, 9.6, 4.4 Hz, 1H), 3.39 (d, J=12.7 Hz, 2H), 1.95 (dt, J=25.3, 7.8 Hz, 4H), 1.75 (td, J=14.3, 13.7, 7.0 Hz, 2H), 1.40-1.25 (m, 2H), 1.18 (d, J=6.5 Hz, 6H).

Example-61: Synthesis of 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-N,N-dimethylpiperazine-1-carboxamide. (Compound 453)

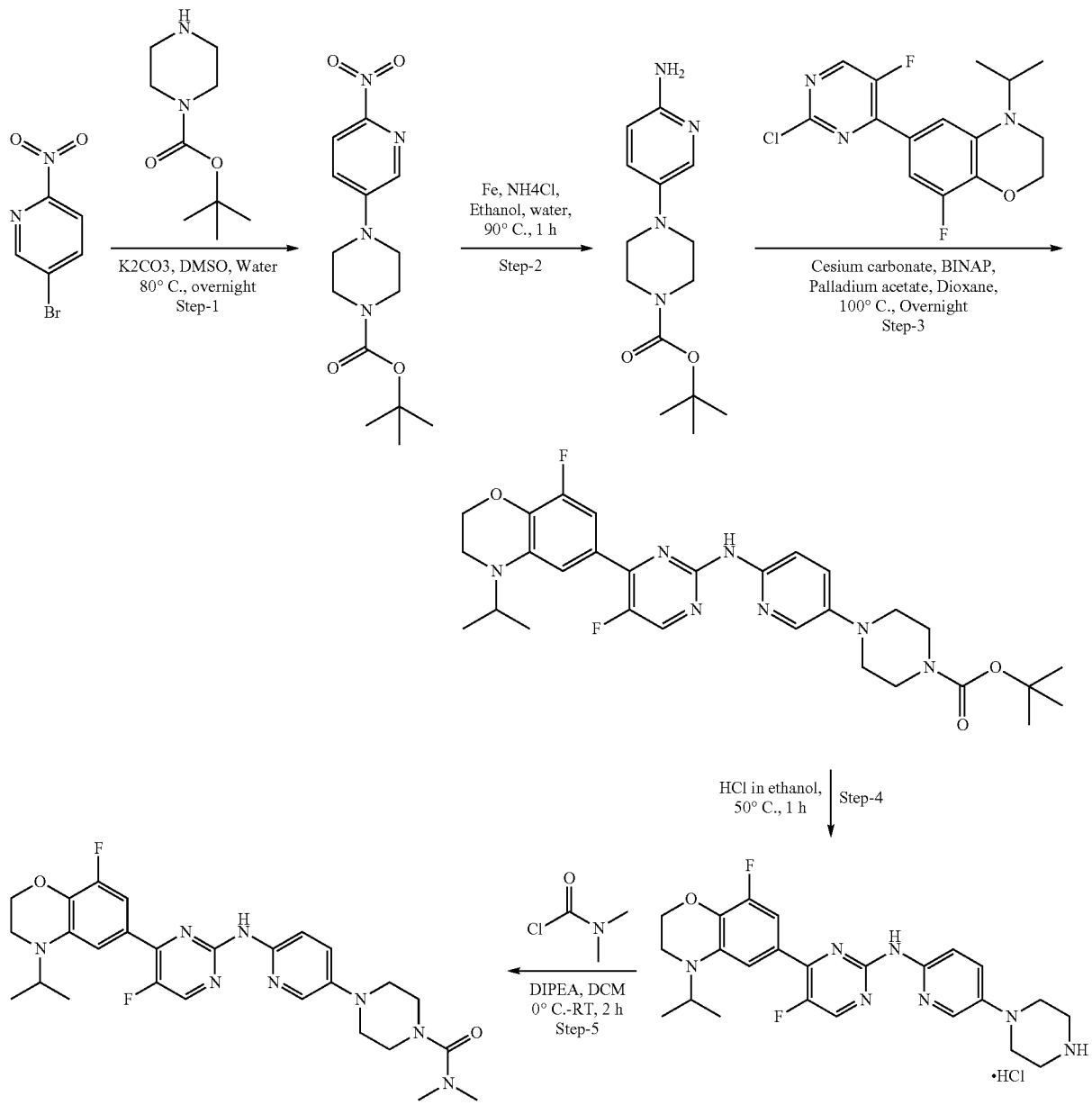

Step-1: Synthesis tert-butyl 4-(6-nitropyridin-3-yl) piperazine-1-carboxylate

To a stirred solution of 5-bromo-2-nitropyridine (1500 mg, 7.4 mmol, 1 equiv) in DMSO (10 mL), was added K₂CO₃ (1532 mg, 11.1 mmol, 1 equiv), water (5 mL) and tert-butyl piperazine-1-carboxylate (2072 mg, 11.1 mmol, 1 equiv). The resultant reaction mixture was allowed to stir at 100° C. for overnight. Progress of the reaction was monitored by LCMS. After completion of the reaction, diluted with water (100 mL), solid observed was filtered and dried under vacuum to obtain tert-butyl 4-(6-nitropyridin-3-yl) piperazine-1-carboxylate (1800 mg, 79%) as a yellow solid compound. LCMS: 309 [M+H]⁺

Step-2: Synthesis of tert-butyl 4-(6-aminopyridin-3-yl) piperazine-1-carboxylate To a stirred solution of tert-butyl 4-(6-nitropyridin-3-yl) piperazine-1-carboxylate (500 mg, 1.6 mmol, 1 equiv) in ethanol (8 mL), water (2 mL), was added iron powder (269 mg, 4.8 mmol, 3 equiv) and ammonium chloride (173 mg, 3.2 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain tert-butyl 4-(6-aminopyridin-3-yl) piperazine-1-carboxylate (300 mg, 67%) as a dark brown solid compound. LCMS: 279 [M+H]$^+$ Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(6-aminopyridin-3-yl) piperazine-1-carboxylate (97 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazine-1-carboxylate (100 mg, 57%) as a yellow color solid compound. LCMS: 568 [M+H]$^+$ Step-4: Synthesis of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazine-1-carboxylate (100 mg, 0.17 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (80 mg, 90%) as a brown solid compound. LCMS: 468 [M+H]$^+$ Step-5: Synthesis of 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-N,N-dimethylpiperazine-1-carboxamide To a stirred solution of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (60 mg, 0.11 mmol, 1 equiv) in DCM (3 mL), was added DIPEA (0.05 mL, 0.33 mmol, 3 equiv). Cool the temp to 0° C., followed by the addition of dimethylcarbamic chloride (0.01 mL, 0.17 mmol, 1.5 equiv). Raise the temp to RT and the reaction mixture was allowed to stir for 2 h at RT. Progress of the reaction was monitored by LCMS. After completion of the reaction, the reaction mixture was diluted with DCM (30 mL) and washed with water (30 mL). Organic layer was dried over anhydrous sodium sulphate and concentrated under reduced pressure to obtain crude compound, which was purified by reverse phase HPLC to obtain 4-(6-((5-fluoro-4-(8-fluoro-4-isopropyl-3,4-dihydro-2H-benzo[b][1,4]oxazin-6-yl)pyrimidin-2-yl) amino)pyridin-3-yl)-N,N-dimethylpiperazine-1-carboxamide (12 mg, 19%) as a yellow color solid compound. LCMS: 539 [M+H]$^+$; $^1$HNMR (400 MHz, DMSO-d6) δ 9.70 (s, 1H), 8.56 (d, J=4.0 Hz, 1H), 8.07-8.00 (m, 2H), 7.46 (s, 1H), 7.41 (dd, J=9.2, 3.0 Hz, 1H), 7.17 (d, J=11.8 Hz, 1H), 4.30 (t, J=4.5 Hz, 2H), 4.14 (p, J=6.7 Hz, 1H), 3.27 (q, J=6.6, 5.1 Hz, 6H), 3.11 (t, J=5.0 Hz, 4H), 2.78 (s, 6H), 1.19 (d, J=6.5 Hz, 6H).

Example-62: Synthesis of 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-N,N-dimethylpiperidine-1-carboxamide. (Compound 454)

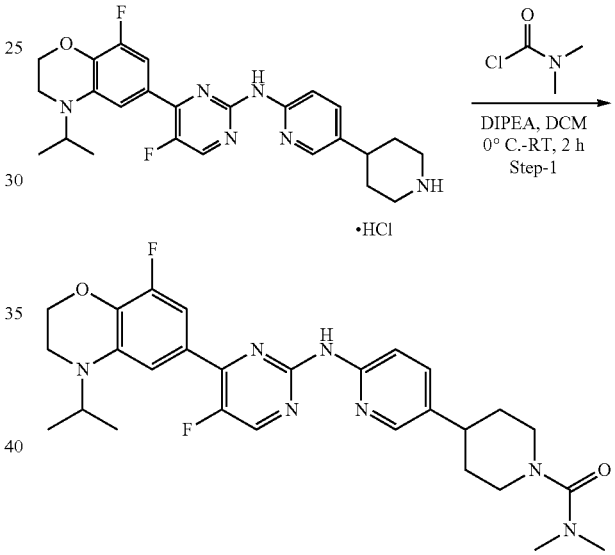

Step-1: Synthesis of 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-N,N-dimethylpiperidine-1-carboxamide To a stirred solution of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (60 mg, 0.11 mmol, 1 equiv) in DCM (3 mL), was added DIPEA (0.05 mL, 0.33 mmol, 3 equiv). Cool the temp to 0° C., followed by the addition of dimethylcarbamic chloride (0.01 mL, 0.17 mmol, 1.5 equiv). Raise the temp to RT and the reaction mixture was allowed to stir for 2 h at RT. Progress of the reaction was monitored by LCMS. After completion of the reaction, the reaction mixture was diluted with DCM (30 mL) and washed with water (30 mL). Organic layer was dried over anhydrous sodium sulphate and concentrated under reduced pressure to obtain crude compound, which was purified by reverse phase HPLC to obtain 4-(6-((5-fluoro-4-(8-fluoro-4-isopropyl-3,4-dihydro-2H-benzo[b][1, 4]oxazin-6-yl)pyrimidin-2-yl) amino)pyridin-3-yl)-N,N-dimethylpiperidine-1-carboxamide (35 mg, 55%) as a yellow color solid compound. LCMS: 538 [M+H]+; ¹HNMR (400 MHz, DMSO-d6) δ 9.91 (s, 1H), 8.61 (d, J=4.0 Hz, 1H), 8.20 (d, J=2.5 Hz, 1H), 8.12 (d, J=8.6 Hz, 1H), 7.63 (dd, J=8.7, 2.6 Hz, 1H), 7.48 (s, 1H), 7.19 (d, J=11.5 Hz, 1H), 4.30 (t, J=4.2 Hz, 2H), 4.16 (p, J=6.7 Hz, 1H), 3.66 (d, J=12.7 Hz, 2H), 3.30 (d, J=4.8 Hz, 2H), 2.85-2.67 (m, 9H), 1.77 (dd, J=13.0, 4.0 Hz, 2H), 1.60 (qd, J=12.5, 3.9 Hz, 2H), 1.19 (d, J=6.5 Hz, 6H).

Example-63: Synthesis of 2-(dimethylamino)-1-(7-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-2(1H)-yl)ethan-1-one. (Compound 455)

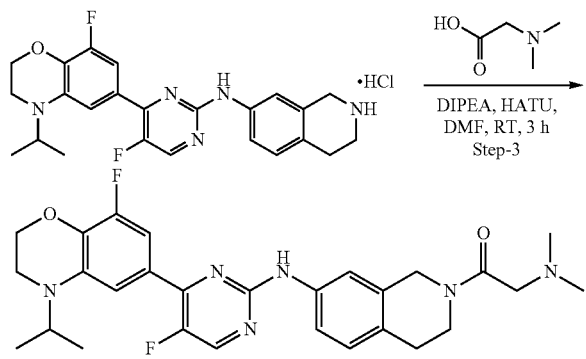

Step-1: Synthesis of 2-(dimethylamino)-1-(7-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-2(1H)-yl)ethan-1-one To a stirred solution of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-7-amine (80 mg, 0.16 mmol, 1 equiv) in DMF (2 mL), was added dimethylglycine (21 mg, 0.2 mmol, 1 equiv), ET₃N (0.02 mL, 0.2 mmol, 1.2 equiv), HOBt (27 mg, 0.2 mmol, 1.2 equiv) and EDC.HCl (38 mg, 0.2 mmol, 1.2 equiv). Allow to stir the mixture for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by reverse phase HPLC to obtain 2-(dimethylamino)-1-(7-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-2(1H)-yl)ethan-1-one (15 mg, 17%) as a yellow color solid compound.

LCMS: 523 [M+H]+; ¹HNMR (400 MHz, DMSO-d6) δ 9.64 (d, J=2.9 Hz, 1H), 8.56 (d, J=4.0 Hz, 1H), 7.62-7.53 (m, 2H), 7.41 (s, 1H), 7.20-7.04 (m, 2H), 4.62 (d, J=59.5 Hz, 2H), 4.30 (t, J=4.3 Hz, 2H), 4.14 (p, J=7.0 Hz, 1H), 3.70 (dt, J=34.7, 5.8 Hz, 2H), 3.30 (d, J=4.8 Hz, 2H), 3.15 (s, 2H), 2.78 (dt, J=39.7, 5.5 Hz, 2H), 2.20 (s, 6H), 1.19 (d, J=6.5 Hz, 6H).

Example-64: Synthesis of 2-(dimethylamino)-1-(6-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-2(1H)-yl)ethan-1-one. (Compound 456)

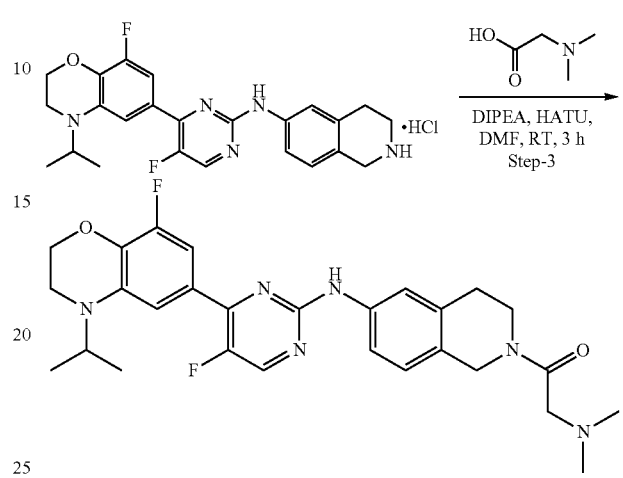

To a stirred solution of N-(5-fluoro-4-(8-fluoro-4-isopropyl-3,4-dihydro-2H-benzo[b][1,4]oxazin-6-yl)pyrimidin-2-yl)-1,2,3,4-tetrahydroisoquinolin-6-amine (80 mg, 0.16 mmol, 1 equiv) in DMF (2 mL), was added dimethylglycine (21 mg, 0.2 mmol, 1 equiv), ET₃N (0.02 mL, 0.2 mmol, 1.2 equiv), HOBt (27 mg, 0.2 mmol, 1.2 equiv) and EDC.HCl (38 mg, 0.2 mmol, 1.2 equiv). Allow to stir the mixture for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by reverse phase HPLC to obtain 2-(dimethylamino)-1-(6-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-2(1H)-yl)ethan-1-one (20 mg, 23%) as a yellow color solid compound. LCMS: 523 [M+H]+; ¹HNMR (400 MHz, DMSO-d6) δ 9.63 (s, 1H), 8.56 (d, J=3.9 Hz, 1H), 7.64-7.46 (m, 2H), 7.40 (s, 1H), 7.21-7.12 (m, 1H), 7.07 (d, J=8.2 Hz, 1H), 4.65 (d, J=64.5 Hz, 2H), 4.30 (t, J=4.3 Hz, 2H), 4.12 (dt, J=11.3, 6.3 Hz, 1H), 3.70 (dt, J=32.6, 5.8 Hz, 2H), 3.30 (d, J=4.8 Hz, 2H), 3.16 (s, 2H), 2.75 (dt, J=39.4, 5.5 Hz, 2H), 2.19 (d, J=6.3 Hz, 6H), 1.19 (d, J=6.5 Hz, 6H).

Example-65: Synthesis of (2-fluoro-4-((5-fluoro-4-(8-fluoro-4-isopropyl-3,4-dihydro-2H-benzo[b][1,4]oxazin-6-yl)pyrimidin-2-yl)amino)phenyl)(morpholino)methanone. (Compound 457)

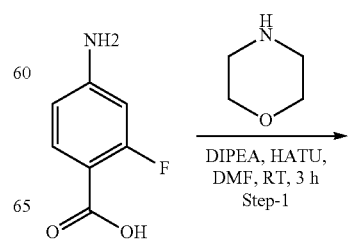

603

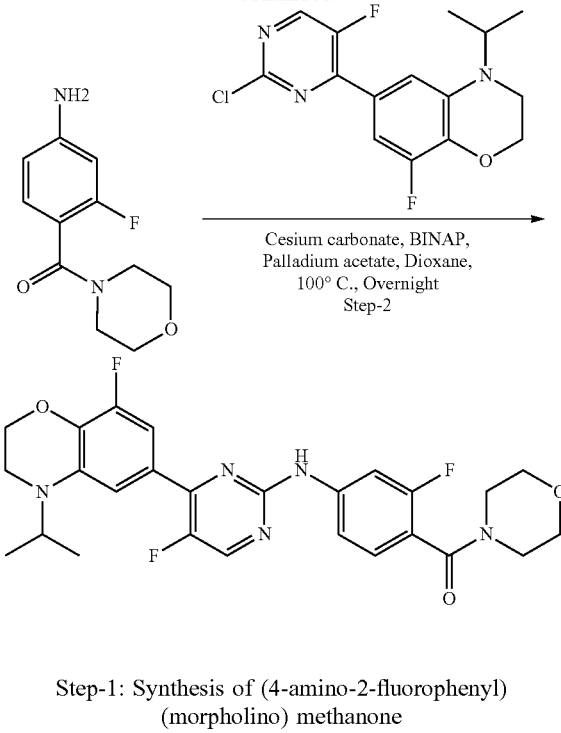

Step-1: Synthesis of (4-amino-2-fluorophenyl)(morpholino) methanone

To a stirred solution of 4-amino-2-fluorobenzoic acid (1000 mg, 6.45 mmol, 1 equiv) in DMF (5 mL), was added morpholine (0.8 mL, 9.67 mmol, 1.5 equiv), DIPEA (4.5 mL, 25.8 mmol, 4 equiv) and HATU (4408 mg, 11.6 mmol, 1.8 equiv). The reaction mixture was allowed to stir for 3 h at RT. Progress of the reaction was monitored by TLC and LCMS. After completion of the reaction, the reaction mixture was diluted with water (50 mL) and extracted with ethyl acetate (100 mL×3). Organic layer was washed with water (100 mL), brine solution (100 mL). Organic layer was dried over anhydrous sodium sulphate and concentrated under reduced pressure to obtain (4-amino-2-fluorophenyl)(morpholino)methanone (1200 mg, 83%) as a brown color viscous compound. LCMS: 225 [M+H]$^+$ Step-2: Synthesis of (2-fluoro-4-((5-fluoro-4-(8-fluoro-4-isopropyl-3,4-dihydro-2H-benzo[b][1,4]oxazin-6-yl)pyrimidin-2-yl)amino)phenyl)(morpholino)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (4-amino-2-fluorophenyl)(morpholino)methanone (74 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain

604

(2-fluoro-4-((5-fluoro-4-(8-fluoro-4-isopropyl-3,4-dihydro-2H-benzo[b][1,4]oxazin-6-yl)pyrimidin-2-yl)amino)phenyl)(morpholino)methanone (50 mg, 32%) as a yellow color solid compound. LCMS: 514 [M+H]$^+$; $^1$HNMR (400 MHz, DMSO-d6) δ 10.18 (s, 1H), 8.65 (d, J=3.8 Hz, 1H), 7.96 (dd, J=13.2, 2.0 Hz, 1H), 7.49 (dd, J=8.3, 2.0 Hz, 1H), 7.43 (s, 1H), 7.32 (t, J=8.2 Hz, 1H), 7.17 (d, J=11.5 Hz, 1H), 4.30 (t, J=4.3 Hz, 2H), 4.16 (h, J=6.6 Hz, 1H), 3.58-3.52 (m, 8H), 3.29 (d, J=7.8 Hz, 2H), 1.18 (d, J=6.5 Hz, 6H).

Example-66: Synthesis of (2-fluoro-4-((5-fluoro-4-(8-fluoro-4-isopropyl-3,4-dihydro-2H-benzo[b][,4]oxazin-6-yl)pyrimidin-2-yl)amino)phenyl)(4-hydroxypiperidin-1-yl)methanone. (Compound 458)

Step-1: Synthesis of (4-amino-2-fluorophenyl)(4-hydroxypiperidin-1-yl) methanone To a stirred solution of 4-amino-2-fluorobenzoic acid (1000 mg, 6.45 mmol, 1 equiv) in DMF (5 mL), was added piperidin-4-ol (967 mg, 9.67 mmol, 1.5 equiv), DIPEA (4.5 mL, 25.8 mmol, 4 equiv) and HATU (4408 mg, 11.6 mmol, 1.8 equiv). The reaction mixture was allowed to stir for 3 h at RT. Progress of the reaction was monitored by TLC and LCMS. After completion of the reaction, the reaction mixture was diluted with water (50 mL) and extracted with ethyl acetate (100 mL×3). Organic layer was washed with water (100 mL), brine solution (100 mL). Organic layer was dried over anhydrous sodium sulphate and concentrated under reduced pressure to obtain (4-amino-2-fluorophenyl) (4-hydroxypiperidin-1-yl) methanone (1200 mg, 78%) as a brown color viscous compound. LCMS: 239 [M+H]+

Step-2: Synthesis of (2-fluoro-4-((5-fluoro-4-(8-fluoro-4-isopropyl-3,4-dihydro-2H-benzo[b][1,4]oxazin-6-yl)pyrimidin-2-yl)amino)phenyl)(4-hydroxypiperidin-1-yl)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (4-amino-2-fluorophenyl)(4-hydroxypiperidin-1-yl)methanone (79 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain (2-fluoro-4-((5-fluoro-4-(8-fluoro-4-isopropyl-3,4-dihydro-2H-benzo[b][1,4]oxazin-6-yl)pyrimidin-2-yl)amino)phenyl)(4-hydroxypiperidin-1-yl)methanone (40 mg, 25%) as a pale yellow color solid compound LCMS: 528 [M+H]+; 1HNMR (400 MHz, DMSO-d6) δ 10.15 (s, 1H), 8.65 (d, J=3.9 Hz, 1H), 7.94 (dd, J=13.1, 2.0 Hz, 1H), 7.51-7.41 (m, 2H), 7.28 (t, J=8.2 Hz, 1H), 7.17 (d, J=11.6 Hz, 1H), 4.30 (t, J=4.3 Hz, 2H), 4.16 (h, J=6.6 Hz, 1H), 4.03 (d, J=12.9 Hz, 1H), 3.73 (dp, J=8.6, 4.2, 3.7 Hz, 2H), 3.32 (t, J=4.3 Hz, 2H), 3.21 (t, J=11.3 Hz, 1H), 3.09 (t, J=11.6 Hz, 1H), 1.77 (s, 1H), 1.68 (d, J=7.3 Hz, 1H), 1.35 (dt, J=24.5, 10.6 Hz, 2H), 1.18 (d, J=6.5 Hz, 6H).

Example-67: Synthesis of (6-((5-fluoro-4-(8-fluoro-4-isopropyl-3,4-dihydro-2H-benzo[b][1,4]oxazin-6-yl)pyrimidin-2-yl)amino)pyridin-3-yl)(morpholino)methanone. (Compound 459)

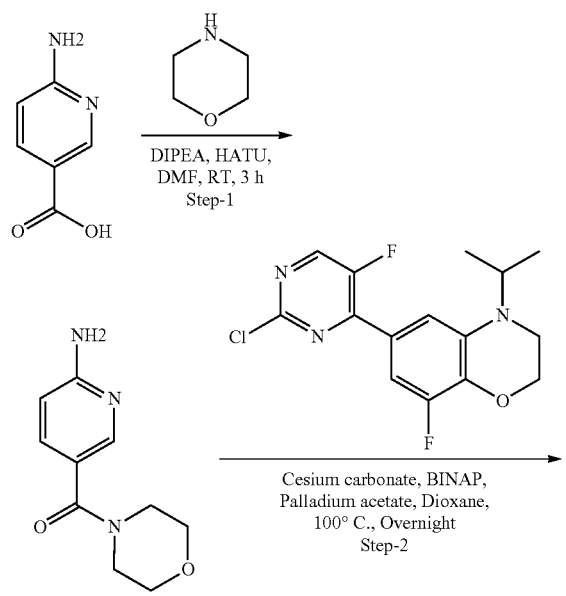

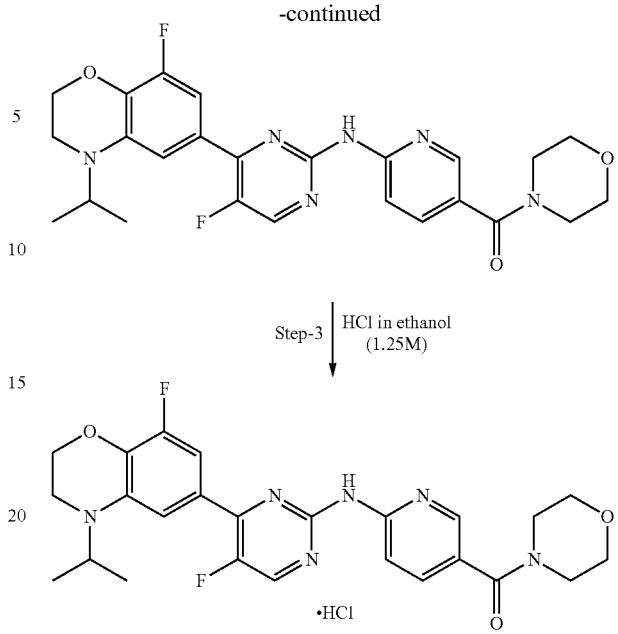

Step-1: Synthesis of (6-aminopyridin-3-yl)(morpholino) methanone

To a stirred solution of 6-aminonicotinic acid (1000 mg, 7.24 mmol, 1 equiv) in DMF (5 mL), was added morpholine (0.8 mL, 9.65 mmol, 1.5 equiv), DIPEA (5 mL, 29 mmol, 4 equiv) and HATU (4940 mg, 13 mmol, 1.8 equiv). The reaction mixture was allowed to stir for 3 h at RT. Progress of the reaction was monitored by TLC and LCMS. After completion of the reaction, the reaction mixture was diluted with water (50 mL) and extracted with ethyl acetate (100 mL×3). Organic layer was washed with water (100 mL), brine solution (100 mL). Organic layer was dried over anhydrous sodium sulphate and concentrated under reduced pressure to obtain (6-aminopyridin-3-yl) (morpholino) methanone (1200 mg, 80%) as a brown color viscous compound. LCMS: 208 [M+H]+

Step-2: Synthesis of (6-((5-fluoro-4-(8-fluoro-4-isopropyl-3,4-dihydro-2H-benzo[b][1,4]oxazin-6-yl)pyrimidin-2-yl)amino)pyridin-3-yl)(morpholino)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (6-aminopyridin-3-yl)(morpholino)methanone (68 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain (6-((5-fluoro-4-(8-fluoro-4-isopropyl-3,4-dihydro-2H-benzo[b][1,4]oxazin-6-yl)pyrimidin-2-yl)amino)pyridin-3-yl)(morpholino)methanone (40 mg, 26%) as an off white color solid compound. LCMS: 497 [M+H]+; 1HNMR (400 MHz, DMSO-d6) δ 10.34 (s, 1H), 8.67 (d, J=3.9 Hz, 1H), 8.38 (s, 1H), 8.28 (d, J=8.7 Hz, 1H), 7.85-7.78 (m, 1H), 7.48 (s, 1H), 7.20 (d, J=11.7 Hz, 1H), 4.31 (t, J=4.3 Hz, 2H), 4.17 (p, J=8.2, 7.5 Hz, 1H), 3.62 (d, J=4.7 Hz, 4H), 3.54 (s, 4H), 3.30 (d, J=4.8 Hz, 2H) 1.23 (s, 6H).

Step-3: Synthesis of (6-((5-fluoro-4-(8-fluoro-4-isopropyl-3,4-dihydro-2H-benzo[b][1,4]oxazin-6-yl)pyrimidin-2-yl)amino)pyridin-3-yl)(morpholino) methanone (6-((5-fluoro-4-(8-fluoro-4-isopropyl-3,4-dihydro-2H-benzo[b][1,4]oxazin-6-yl)pyrimidin-2-yl)amino)pyridin-3-yl)(Morpholino) methanone (10 mg, 0.02 mmol, 1 equiv) was taken in 1.25 M HCl in ethanol (5 mL) and the resultant reaction mixture was allowed to stir at RT for 1 h. Solvent was removed under reduced pressure and the residue was dried under lyophilizer to obtain (6-((5-fluoro-4-(8-fluoro-4-isopropyl-3,4-dihydro-2H-benzo[b][1,4]oxazin-6-yl)pyrimidin-2-yl)amino)pyridin-3-yl)(morpholino)methanone (HCl salt) (5 mg, 45%) as a yellow color solid compound. LCMS: 497 [M+H]+; 1HNMR (400 MHz, DMSO-d6) δ 10.89 (s, 1H), 8.72 (d, J=3.8 Hz, 1H), 8.41 (d, J=2.2 Hz, 1H), 8.15 (d, J=8.7 Hz, 1H), 7.95 (dd, J=8.6, 2.3 Hz, 1H), 7.46 (s, 1H), 7.25-7.17 (m, 1H), 4.31 (t, J=4.2 Hz, 2H), 4.17 (p, J=6.4 Hz, 1H), 3.62 (s, 4H), 3.54 (s, 4H), 3.31 (t, J=4.2 Hz, 2H), 1.19 (d, J=6.5 Hz, 6H).

Example-68: Synthesis of (6-((5-fluoro-4-(8-fluoro-4-isopropyl-3,4-dihydro-2H-benzo[b][,4]oxazin-6-yl)pyrimidin-2-yl)amino)pyridin-3-yl)(4-hydroxypiperidin-1-yl)methanone. (Compound 460)

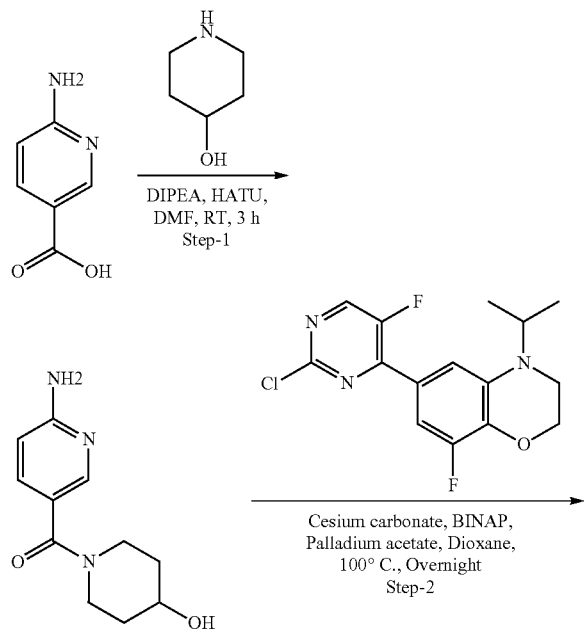

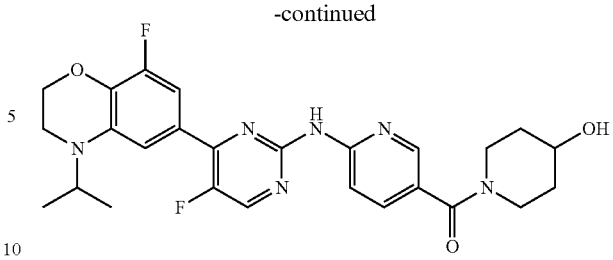

Step-1: Synthesis of (6-aminopyridin-3-yl) (4-hydroxypiperidin-1-yl) methanone

To a stirred solution of 6-aminonicotinic acid (1000 mg, 7.24 mmol, 1 equiv) in DMF (5 mL), was added piperidin-4-ol (975 mg, 9.65 mmol, 1.5 equiv), DIPEA (5 mL, 29 mmol, 4 equiv) and HATU (4940 mg, 13 mmol, 1.8 equiv). The reaction mixture was allowed to stir for 3 h at RT. Progress of the reaction was monitored by TLC and LCMS. After completion of the reaction, the reaction mixture was diluted with water (50 mL) and extracted with ethyl acetate (100 mL×3). Organic layer was washed with water (100 mL), brine solution (100 mL). Organic layer was dried over anhydrous sodium sulphate and concentrated under reduced pressure to obtain (6-aminopyridin-3-yl)(4-hydroxypiperidin-1-yl)methanone (1200 mg, 75%) as a brown color viscous compound. LCMS: 222 [M+H]+

Step-2: Synthesis of (6-((5-fluoro-4-(8-fluoro-4-isopropyl-3,4-dihydro-2H-benzo[b][1,4]oxazin-6-yl)pyrimidin-2-yl)amino)pyridin-3-yl)(4-hydroxypiperidin-1-yl)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (6-aminopyridin-3-yl)(4-hydroxypiperidin-1-yl)methanone (73 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain (6-((5-fluoro-4-(8-fluoro-4-isopropyl-3,4-dihydro-2H-benzo[b][1,4]oxazin-6-yl)pyrimidin-2-yl)amino)pyridin-3-yl)(4-hydroxypiperidin-1-yl)methanone (50 mg, 32%) as a yellow color solid compound LCMS: 511 [M+H]+; 1HNMR (400 MHz, DMSO-d6) δ 10.31 (s, 1H), 8.64 (d, J=3.8 Hz, 1H), 8.33 (d, J=2.4 Hz, 1H), 8.25 (d, J=8.7 Hz, 1H), 7.76 (dd, J=8.4, 2.5 Hz, 1H), 7.46 (s, 1H), 7.19 (d, J=11.5 Hz, 1H), 4.80 (d, J=3.9 Hz, 1H), 4.29 (t, J=4.2 Hz, 2H), 4.15 (p, J=7.1 Hz, 1H), 3.74 (dt, J=9.9, 5.3 Hz, 2H), 3.30 (t, J=4.2 Hz, 2H), 3.21 (td, J=10.2, 9.4, 5.3 Hz, 3H), 1.76 (d, J=11.9 Hz, 2H), 1.45-1.30 (m, 2H), 1.18 (d, J=6.5 Hz, 6H).

Example-69: Synthesis of N-(4-((4-ethylpiperazin-1-yl) methyl)-3-fluorophenyl)-5-fluoro-4-(8-fluoro-4-isopropyl-3,4-dihydro-2H-benzo[b][1,4]oxazin-6-yl)pyrimidin-2-amine. (Compound 461)

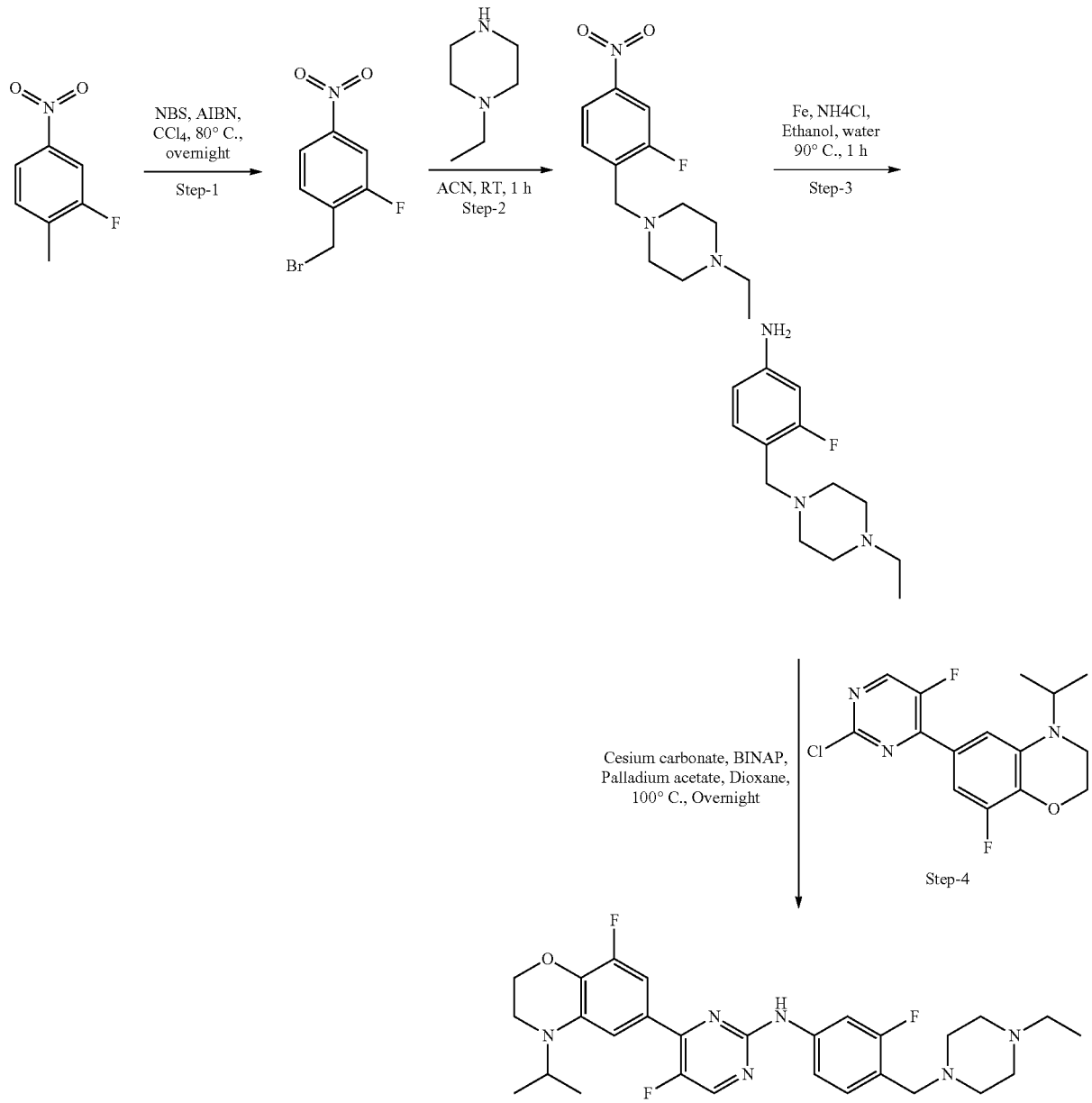

Step-1: Synthesis of 1-(bromomethyl)-2-fluoro-4-nitrobenzene

To a stirred solution of 2-fluoro-1-methyl-4-nitrobenzene (1000 mg, 6.4 mmol, 1 equiv) in CCl$_4$ (15 mL), was added NBS (1139 mg, 6.4 mmol, 1 equiv) and AIBN (210 mg, 1.28 mmol, 0.2 equiv). The resultant reaction mixture was allowed to stir at 80° C. for overnight. Progress of the reaction was monitored by LCMS and TLC. After completion of the reaction, diluted with water (50 mL), and extracted with ethyl acetate (150 mL). Organic layer was washed with water (50 mL) and brine solution (50 mL). Organic layer was dried over anhydrous sodium sulphate and concentrated under reduced pressure to obtain crude, which was purified by normal phase combi flash to obtain 1-(bromomethyl)-2-fluoro-4-nitrobenzene (400 mg, 27%) as an off white solid compound.

Step-2: Synthesis of 1-ethyl-4-(2-fluoro-4-nitrobenzyl) piperazine

To a stirred solution of 1-(bromomethyl)-2-fluoro-4-nitrobenzene (300 mg, 1.29 mmol, 1 equiv) in ACN (5 mL), was added 1-ethylpiperazine (442 mg, 3.87 mmol, 3 equiv). The resultant reaction mixture was allowed to stir at RT for 1 h. Progress of the reaction was monitored by LCMS and NMR. After completion of the reaction, diluted with water (30 mL), and extracted with ethyl acetate (100 mL). Organic layer was washed with water (50 mL) and brine solution (50 mL). Organic layer was dried over anhydrous sodium sulphate and concentrated under reduced pressure to obtain 1-ethyl-4-(2-fluoro-4-nitrobenzyl) piperazine (300 mg, 87%) as a yellow oily compound.

LCMS: 268 [M+H]+

Step-3: Synthesis of 4-((4-ethylpiperazin-1-yl) methyl)-3-fluoroaniline

To a stirred solution of 1-ethyl-4-(2-fluoro-4-nitrobenzyl) piperazine (300 mg, 1.12 mmol, 1 equiv) in ethanol (5 mL), water (1 mL), was added iron powder (189 mg, 3.37 mmol, 3 equiv) and ammonium chloride (121 mg, 2.24 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 4-((4-ethylpiperazin-1-yl) methyl)-3-fluoroaniline (200 mg, 75%) as a dark brown solid compound. LCMS: 238 [M+H]+

Step-4: Synthesis of N-(4-((4-ethylpiperazin-1-yl) methyl)-3-fluorophenyl)-5-fluoro-4-(8-fluoro-4-isopropyl-3,4-dihydro-2H-benzo[b][1,4]oxazin-6-yl) pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 4-((4-ethylpiperazin-1-yl)methyl)-3-fluoroaniline (78 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain N-(4-((4-ethylpiperazin-1-yl)methyl)-3-fluorophenyl)-5-fluoro-4-(8-fluoro-4-isopropyl-3,4-dihydro-2H-benzo[b][1,4]oxazin-6-yl)pyrimidin-2-amine (40 mg, 25%) as a yellow color solid compound.

LCMS: 527 [M+H]+; 1HNMR (400 MHz, DMSO-d6) δ 9.93 (s, 1H), 8.61 (d, J=4.0 Hz, 1H), 7.82-7.73 (m, 1H), 7.49-7.39 (m, 2H), 7.30-7.13 (m, 2H), 4.30 (t, J=4.2 Hz, 2H), 4.16 (h, J=7.9, 7.3 Hz, 1H), 3.45 (s, 2H), 3.31 (d, J=4.6 Hz, 2H), 2.38 (s, 8H), 2.31 (q, J=6.9 Hz, 2H), 1.18 (d, J=6.4 Hz, 6H), 0.97 (t, J=7.1 Hz, 3H).

Example-70: Synthesis of N-(4-((4-(dimethyl amino) piperidin-1-yl) methyl)-3-fluorophenyl)-5-fluoro-4-(8-fluoro-4-isopropyl-3,4-dihydro-2H-benzo[b][1,4]oxazin-6-yl)pyrimidin-2-amine. (Compound 462)

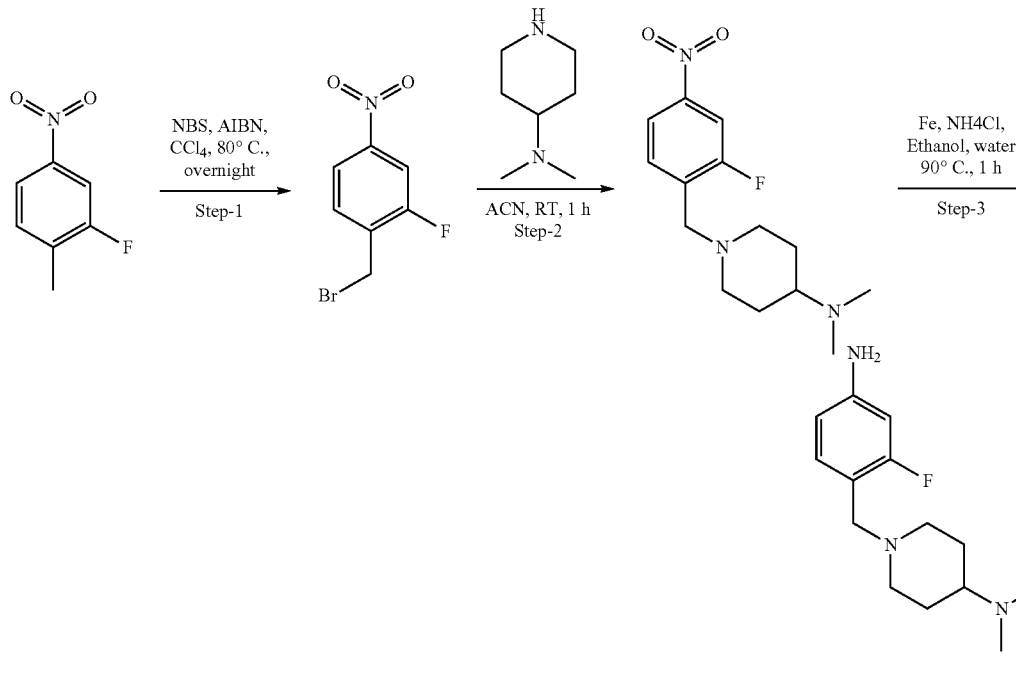

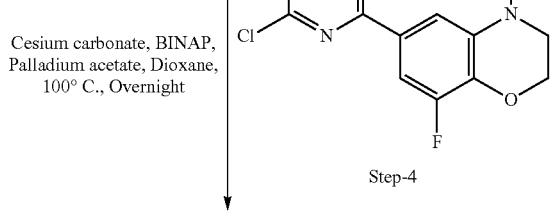

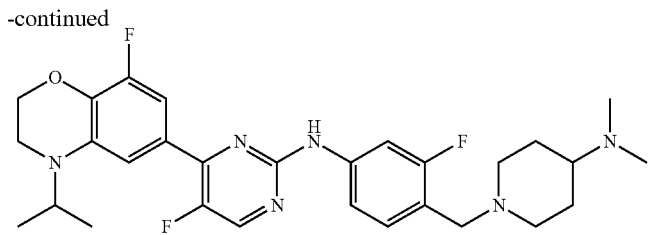

Step-1: Synthesis of 1-(bromomethyl)-2-fluoro-4-nitrobenzene

To a stirred solution of 2-fluoro-1-methyl-4-nitrobenzene (1000 mg, 6.4 mmol, 1 equiv) in CCl₄ (15 mL), was added NBS (1139 mg, 6.4 mmol, 1 equiv) and AIBN (210 mg, 1.28 mmol, 0.2 equiv). The resultant reaction mixture was allowed to stir at 80° C. for overnight. Progress of the reaction was monitored by LCMS and TLC. After completion of the reaction, diluted with water (50 mL), and extracted with ethyl acetate (150 mL). Organic layer was washed with water (50 mL) and brine solution (50 mL). Organic layer was dried over anhydrous sodium sulphate and concentrated under reduced pressure to obtain crude, which was purified by normal phase combi flash to obtain 1-(bromomethyl)-2-fluoro-4-nitrobenzene (400 mg, 27%) as an off white solid compound.
LCMS: 234 [M+H]⁺

Step-2: Synthesis of 1-(2-fluoro-4-nitrobenzyl)-N,N-dimethylpiperidin-4-amine To a stirred solution of 1-(bromomethyl)-2-fluoro-4-nitrobenzene (300 mg, 1.29 mmol, 1 equiv) in ACN (5 mL), was added N,N-dimethylpiperidin-4-amine (495 mg, 3.87 mmol, 3 equiv). The resultant reaction mixture was allowed to stir at RT for 1 h. Progress of the reaction was monitored by LCMS and NMR. After completion of the reaction, diluted with water (30 mL), and extracted with ethyl acetate (100 mL). Organic layer was washed with water (50 mL) and brine solution (50 mL). Organic layer was dried over anhydrous sodium sulphate and concentrated under reduced pressure to obtain 1-(2-fluoro-4-nitrobenzyl)-N, N-dimethylpiperidin-4-amine (300 mg, 83%) as a yellow oily compound. LCMS: 282 [M+H]⁺

Step-3: Synthesis of 1-(4-amino-2-fluorobenzyl)-N,N-dimethylpiperidin-4-amine To a stirred solution of 1-(2-fluoro-4-nitrobenzyl)-N,N-dimethylpiperidin-4-amine (300 mg, 1.06 mmol, 1 equiv) in ethanol (5 mL), water (1 mL), was added iron powder (179 mg, 3.2 mmol, 3 equiv) and ammonium chloride (114 mg, 2.12 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 1-(4-amino-2-fluorobenzyl)-N, N-dimethylpiperidin-4-amine (250 mg, 93%) as a dark brown solid compound. LCMS: 252 [M+H]+

Step-3: Synthesis of N-(4-((4-(dimethyl amino) piperidin-1-yl) methyl)-3-fluorophenyl)-5-fluoro-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 1-(4-amino-2-fluorobenzyl)-N,N-dimethylpiperidin-4-amine (83 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain N-(4-((4-(dimethylamino)piperidin-1-yl)methyl)-3-fluorophenyl)-5-fluoro-4-(8-fluoro-4-isopropyl-3,4-dihydro-2H-benzo[b][1,4]oxazin-6-yl)pyrimidin-2-amine (50 mg, 30%) as a yellow color solid compound.
LCMS: 541 [M+H]⁺; ¹HNMR (400 MHz, DMSO-d6) δ 9.92 (s, 1H), 8.61 (d, J=3.5 Hz, 1H), 8.23 (s, 1H), 7.77 (d, J=13.2 Hz, 1H), 7.36-7.50 (m, 2H), 7.25 (s, 1H), 7.17 (d, J=11.8 Hz, 1H), 4.30 (br. s., 2H), 4.17 (br. s., 1H), 3.44 (s, 3H), 3.31 (br. s., 2H), 2.84 (d, J=11.0 Hz, 2H), 2.11-2.28 (m, 6H), 1.94 (t, J=11.2 Hz, 2H), 1.72 (d, J=11.8 Hz, 2H), 1.38 (d, J=9.2 Hz, 2H), 1.18 ppm (d, J=6.6 Hz, 6H).

Example-71: Synthesis of (4-(dimethylamino)piperidin-1-yl)(2-fluoro-4-((5-fluoro-4-(8-fluoro-4-isopropyl-3,4-dihydro-2H-benzo[b][1,4]oxazin-6-yl)pyrimidin-2-yl)amino)phenyl)methanone. (Compound 463)

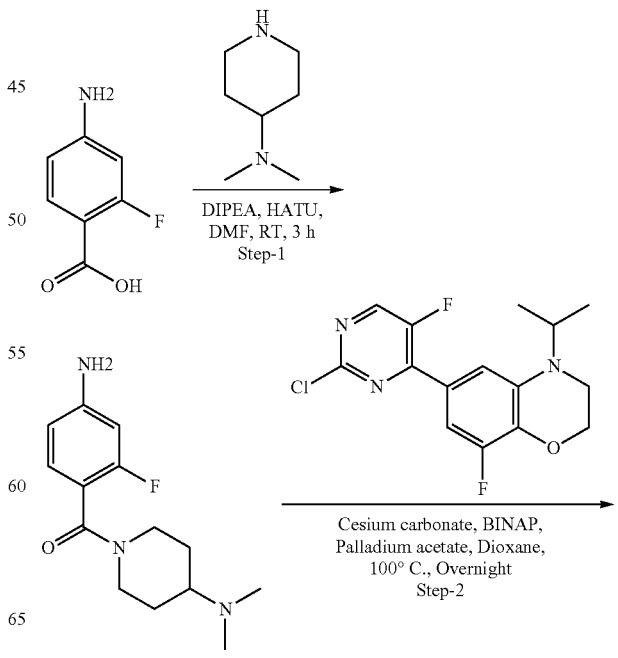

-continued

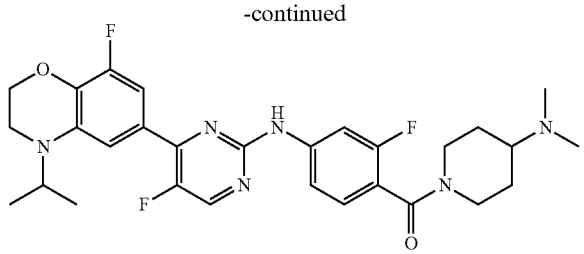

Step-1: Synthesis of (4-amino-2-fluorophenyl) (4-(dimethylamino) piperidin-1-yl) methanone To a stirred solution of 4-amino-2-fluorobenzoic acid (500 mg, 3.22 mmol, 1 equiv) in DMF (5 mL), was added N,N-dimethylpiperidin-4-amine (619 mg, 4.83 mmol, 1.5 equiv), DIPEA (2.2 mL, 13 mmol, 4 equiv) and HATU (2203 mg, 6 mmol, 1.8 equiv). The reaction mixture was allowed to stir for 3 h at RT. Progress of the reaction was monitored by TLC and LCMS. After completion of the reaction, the reaction mixture was diluted with water (50 mL) and extracted with ethyl acetate (100 mL×3). Organic layer was washed with water (100 mL), brine solution (100 mL). Organic layer was dried over anhydrous sodium sulphate and concentrated under reduced pressure to obtain (4-amino-2-fluorophenyl) (4-(dimethylamino) piperidin-1-yl) methanone (700 mg, 82%) as a brown color viscous compound. LCMS: 266 [M+H]$^+$

Step-2: Synthesis of (4-(dimethylamino)piperidin-1-yl)(2-fluoro-4-((5-fluoro-4-(8-fluoro-4-isopropyl-3,4-dihydro-2H-benzo[b][1,4]oxazin-6-yl)pyrimidin-2-yl)amino)phenyl)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (4-amino-2-fluorophenyl)(4-(dimethylamino)piperidin-1-yl)methanone (88 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain (4-(dimethylamino)piperidin-1-yl)(2-fluoro-4-((5-fluoro-4-(8-fluoro-4-isopropyl-3,4-dihydro-2H-benzo[b][1,4]oxazin-6-yl)pyrimidin-2-yl)amino)phenyl)methanone (35 mg, 21%) as a yellow color solid compound. LCMS: 555 [M+H]$^{+1}$HNMR (400 MHz, DMSO-d6) δ 10.16 (s, 1H), 8.65 (d, J=3.5 Hz, 1H), 8.18 (s, 1H), 7.95 (d, J=13.2 Hz, 1H), 7.37-7.55 (m, 2H), 7.30 (d, J=8.3 Hz, 1H), 7.17 (d, J=11.8 Hz, 1H), 4.44 (br. s., 1H), 4.30 (br. s., 2H), 4.06-4.20 (m, 1H), 3.50 (br. s., 2H), 3.31 (br. s., 2H), 3.03 (br. s., 1H), 2.79 (d, J=11.4 Hz, 1H), 2.20 (s, 6H), 1.83 (br. s., 1H), 1.73 (d, J=11.4 Hz, 1H), 1.31 (br. s., 2H), 1.18 ppm (d, J=6.6 Hz, 6H).

Example-72: Synthesis of (4-ethylpiperazin-1-yl)(2-fluoro-4-((5-fluoro-4-(8-fluoro-4-isopropyl-3,4-dihydro-2H-benzo[b][1,4]oxazin-6-yl)pyrimidin-2-yl)amino)phenyl)methanone. (Compound 464)

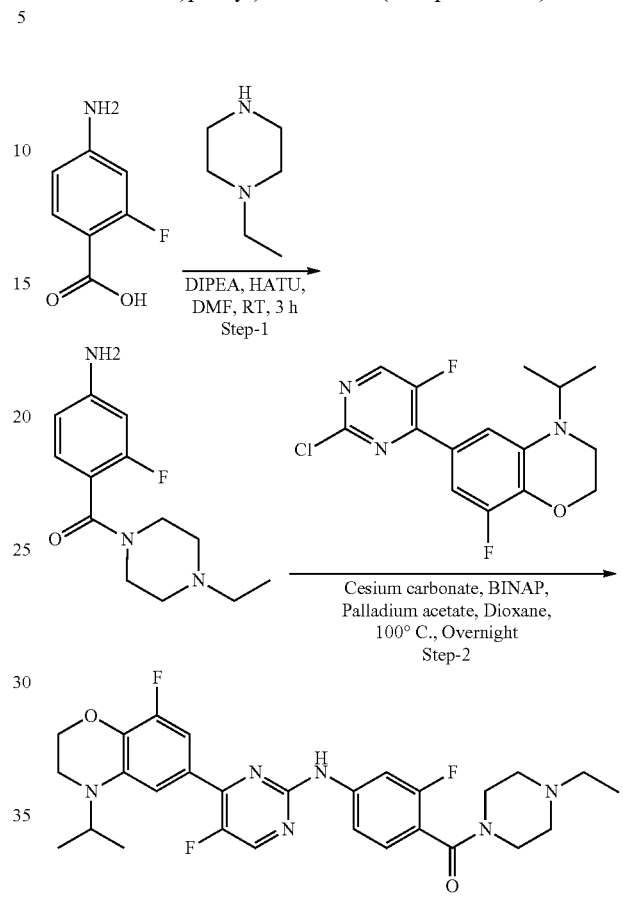

Step-1: Synthesis of (4-amino-2-fluorophenyl) (4-ethylpiperazin-1-yl) methanone To a stirred solution of 4-amino-2-fluorobenzoic acid (500 mg, 3.22 mmol, 1 equiv) in DMF (5 mL), was added 1-ethylpiperazine (551 mg, 4.83 mmol, 1.5 equiv), DIPEA (2.2 mL, 13 mmol, 4 equiv) and HATU (2203 mg, 6 mmol, 1.8 equiv). The reaction mixture was allowed to stir for 3 h at RT. Progress of the reaction was monitored by TLC and LCMS. After completion of the reaction, the reaction mixture was diluted with water (50 mL) and extracted with ethyl acetate (100 mL×3). Organic layer was washed with water (100 mL), brine solution (100 mL). Organic layer was dried over anhydrous sodium sulphate and concentrated under reduced pressure to obtain (4-amino-2-fluorophenyl) (4-ethylpiperazin-1-yl) methanone (700 mg, 86%) as a brown color viscous compound. LCMS: 252 [M+H]$^+$

Step-2: Synthesis of (4-ethylpiperazin-1-yl)(2-fluoro-4-((5-fluoro-4-(8-fluoro-4-isopropyl-3,4-dihydro-2H-benzo[b][1,4]oxazin-6-yl)pyrimidin-2-yl)amino)phenyl)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (4-amino-2-fluorophenyl)(4-ethylpiperazin-1-yl)methanone (83 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain (4-ethylpiperazin-1-yl)(2-fluoro-4-((5-fluoro-4-(8-fluoro-4-isopropyl-3,4-dihydro-2H-benzo[b][1,4]oxazin-6-yl)pyrimidin-2-yl)amino)phenyl)methanone (50 mg, 30%) as a yellow color solid compound LCMS: 541 [M+H]+; $^1$HNMR (400 MHz, DMSO-d6) δ 10.17 (s, 1H), 8.65 (d, J=3.9 Hz, 1H), 7.95 (d, J=12.7 Hz, 1H), 7.38-7.52 (m, 2H), 7.29 (t, J=8.3 Hz, 1H), 7.17 (d, J=11.4 Hz, 1H), 4.30 (br. s., 2H), 4.04-4.20 (m, 1H), 3.62 (br. s., 2H), 3.31 (br. s., 4H), 2.15-2.43 (m, 6H), 1.18 (d, J=6.6 Hz, 6H), 1.00 ppm (t, J=7.2 Hz, 3H).

Example-73: Synthesis of 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)thiomorpholine 1,1-dioxide. (Compound 465)

mixture was allowed to stir at 80° for overnight. Progress of the reaction was monitored by TLC and LCMS. After completion of the reaction, the mixture was diluted with ice water (50 mL) and extracted with ethyl acetate (100 mL). Organic layer was washed with water (50 mL) and brine solution (50 mL). Organic layer was dried over anhydrous sodium sulphate and concentrated under reduced pressure to obtain to obtain 4-(2-fluoro-4-nitrophenyl) thiomorpholine (700 mg, 92%) as a brown oily compound. LCMS: 243[M+H]+

Step-2: Synthesis 4-(2-fluoro-4-nitrophenyl) thiomorpholine 1, 1-dioxide

To a stirred solution of 4-(2-fluoro-4-nitrophenyl) thiomorpholine (500 mg, 2.06 mmol, 1 equiv) in methanol; water (1:1=10 mL), was added oxone (1586 mg, 5.16 mmol, 2.5 equiv). The resultant reaction mixture was allowed to stir at RT for overnight. Progress of the reaction was monitored by TLC and LCMS. After completion of the reaction, solvent was completely removed under reduced pressure and the residue mixture was diluted with ice water (50 mL) and extracted with ethyl acetate (100 mL). Organic layer was washed with water (50 mL) and brine solution (50 mL). Organic layer was dried over anhydrous sodium sulphate and concentrated under reduced pressure to obtain to obtain 4-(2-fluoro-4-nitrophenyl) thiomorpholine 1, 1-dioxide (400 mg, 71%) as a yellow solid compound. LCMS: 251 [M+H]+

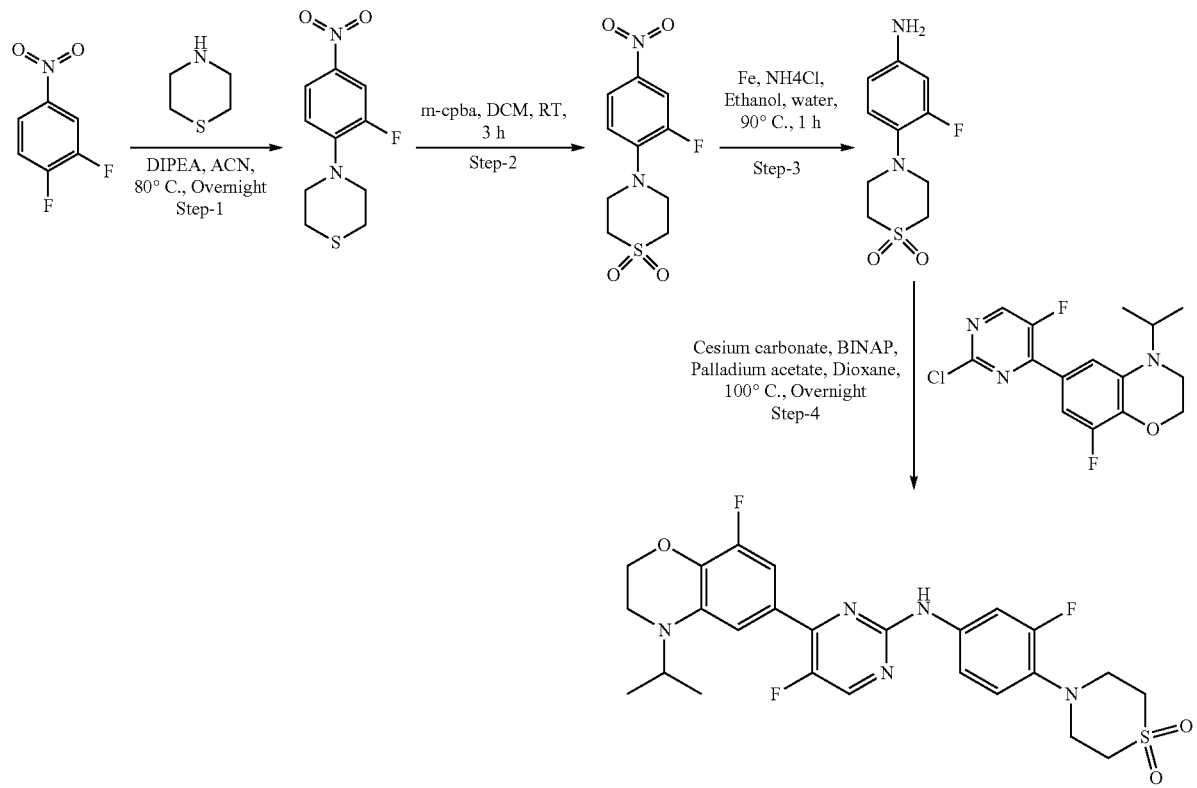

Step-1: Synthesis 4-(2-fluoro-4-nitrophenyl) thiomorpholine

To a stirred solution of 1, 2-difluoro-4-nitrobenzene (500 mg, 3.14 mmol, 1 equiv) in ACN (10 mL), was added DIPEA (0.8 mL, 4.71 mmol, 1.5 equiv) and thiomorpholine (388 mg, 3.76 mmol, 1.2 equiv). The resultant reaction Step-3: Synthesis of 4-(4-amino-2-fluorophenyl) thiomorpholine 1, 1-dioxide To a stirred solution of 4-(2-fluoro-4-nitrophenyl) thiomorpholine 1, 1-dioxide (200 mg, 0.72 mmol, 1 equiv) in ethanol (6 mL), water (2 mL), was added iron powder (123 mg, 2.1 mmol, 3 equiv) and ammonium chloride (78 mg, 1.44 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 4-(4-amino-2-fluorophenyl) thiomorpholine 1, 1-dioxide (150 mg, 84%) as an off white solid compound. LCMS: 245 [M+H]+

Step-4: Synthesis of 4-(2-fluoro-4-((5-fluoro-4-(8-fluoro-4-isopropyl-3,4-dihydro-2H-benzo[b][1,4]oxazin-6-yl)pyrimidin-2-yl)amino)phenyl)thiomorpholine 1,1-dioxide To a solution of 6-(2-chloro-5-fluoropyrimidin-4-yl)-8-fluoro-4-isopropyl-3,4-dihydro-2H-benzo[b][1,4]oxazine

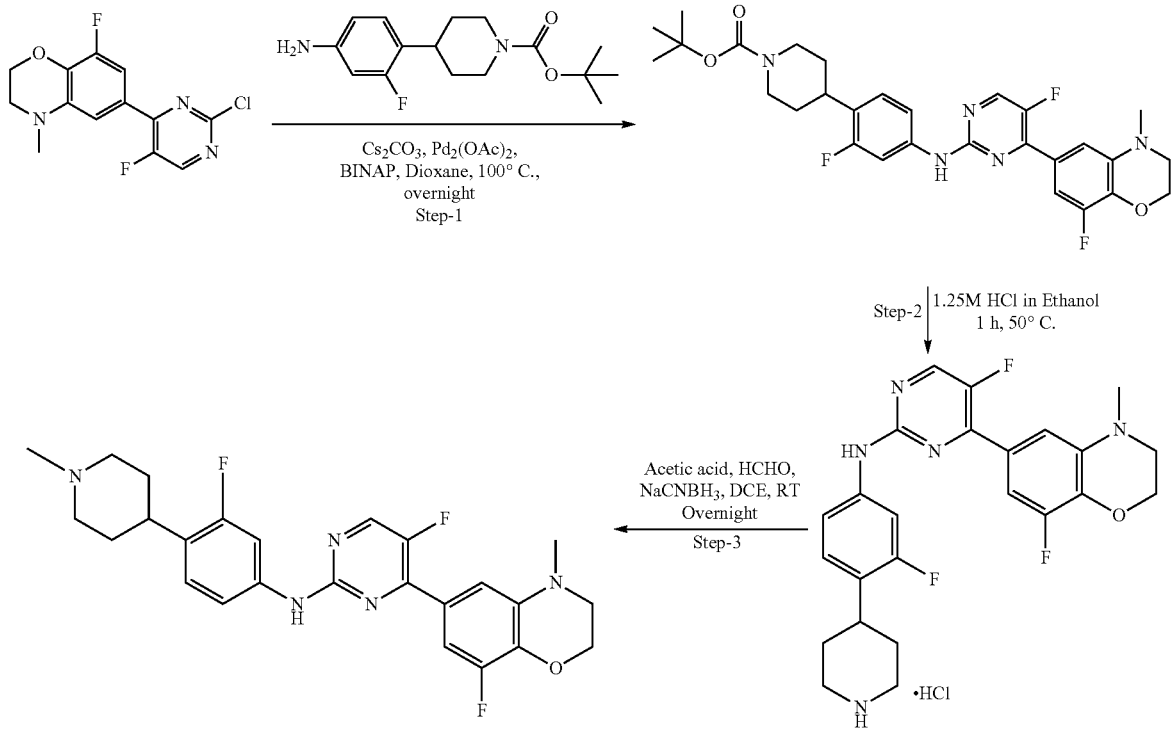

(100 mg, 0.3 mmol, 1 equiv) in dioxane (10 mL), was added 4-(4-amino-2-fluorophenyl)thiomorpholine 1,1-dioxide (81 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 4-(2-fluoro-4-((5-fluoro-4-(8-fluoro-4-isopropyl-3,4-dihydro-2H-benzo[b][1,4]oxazin-6-yl)pyrimidin-2-yl) amino)phenyl)thiomorpholine 1,1-dioxide (45 mg, 27%) as a yellow color solid compound. LCMS: 534 [M+H]+; 1HNMR (400 MHz, DMSO-d6) δ 9.82 (s, 1H), 8.58 (d, J=3.5 Hz, 1H), 7.81 (dd, J=15.1, 2.4 Hz, 1H), 7.28-7.47 (m, 2H), 6.99-7.21 (m, 2H), 4.30 (d, J=4.4 Hz, 2H), 4.15 (d, J=6.6 Hz, 1H), 3.37-3.52 (m, 4H), 3.26 (br. s., 6H), 1.06-1.26 ppm (m, 6H).

Example-74: Synthesis of 5-fluoro-N-(3-fluoro-4-(1-methylpiperidin-4-yl) phenyl)-4-(8-fluoro-4-methyl-3,4-dihydro-2H-benzo[b][1,4]oxazin-6-yl) pyrimidin-2-amine. (Compound 466)

Step-1: Synthesis of tert-butyl 4-(2-fluoro-4-((5-fluoro-4-(8-fluoro-4-methyl-3,4-dihydro-2H-benzo[b][1,4]oxazin-6-yl)pyrimidin-2-yl)amino)phenyl) piperidine-1-carboxylate To a solution of 6-(2-chloro-5-fluoropyrimidin-4-yl)-8-fluoro-4-methyl-3,4-dihydro-2H-benzo[b][1,4]oxazine (100 mg, 0.33 mmol, 1 equiv) in Dioxane (10 mL), was added tert-butyl 4-(4-amino-2-fluorophenyl)piperidine-1-carboxylate (109 mg, 0.37 mmol, 1.1 equiv) and cesium carbonate (161 mg, 0.49 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi flash to obtain tert-butyl 4-(2-fluoro-4-((5-fluoro-4-(8-fluoro-4-methyl-3,4-dihydro-2H-benzo[b][1,4]oxazin-6-yl)pyrimidin-2-yl)amino)phenyl)piperidine-1-carboxylate (150 mg, 80%) as a yellow solid compound. LCMS: 556 [M+H]+

Step-2: Synthesis of 5-fluoro-N-(3-fluoro-4-(piperidin-4-yl) phenyl)-4-(8-fluoro-4-methyl-3,4-dihydro-2H-benzo[b][1,4]oxazin-6-yl)pyrimidin-2-amine tert-butyl 4-(2-fluoro-4-((5-fluoro-4-(8-fluoro-4-methyl-3,4-dihydro-2H-benzo[b][1,4]oxazin-6-yl)pyrimidin-2-yl)amino)phenyl)piperidine-1-carboxylate (150 mg, 0.27 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 5-fluoro-N-(3-fluoro-4-(piperidin-4-yl)phenyl)-4-(8-fluoro-4-methyl-3,4-dihydro-2H-benzo[b][1,4]oxazin-6-yl)pyrimidin-2-amine (100 mg, 75%) as a brick red color solid compound. LCMS: 456 [M+H]+

Step-3: Synthesis of 5-fluoro-N-(3-fluoro-4-(1-methylpiperidin-4-yl) phenyl)-4-(8-fluoro-4-methyl-3,4-dihydro-2H-benzo[b][1,4]oxazin-6-yl)pyrimidin-2-amine To a stirred solution of 5-fluoro-N-(3-fluoro-4-(piperidin-4-yl)phenyl)-4-(8-fluoro-4-methyl-3,4-dihydro-2H-benzo[b][1,4]oxazin-6-yl)pyrimidin-2-amine (100 mg, 0.2 mmol, 1 equiv) in DCE (5 mL), was added Formaldehyde (40% in water) (0.02 mL, 0.61 mmol, 3 equiv), acetic acid (0.05 mL, 1.0 mmol, 5 equiv). The reaction mixture was allowed to stir at RT for 1 h. The reaction mixture was cooled to 0° C. NaCNBH₃ (38 mg, 0.61 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-N-(3-fluoro-4-(1-methylpiperidin-4-yl)phenyl)-4-(8-fluoro-4-methyl-3,4-dihydro-2H-benzo[b][1,4]oxazin-6-yl)pyrimidin-2-amine (40 mg, 42%) as a yellow color solid compound. LCMS: 470 [M+H]+; ¹HNMR (400 MHz, DMSO-d6) δ 9.90 (s, 1H), 8.60 (d, J=3.9 Hz, 1H), 8.16 (s, 1H), 7.83 (d, J=13.6 Hz, 1H), 7.39 (d, J=6.6 Hz, 1H), 7.32 (s, 1H), 7.15-7.28 (m, 2H), 4.28-4.43 (m, 2H), 3.30-3.44 (m, 2H), 3.11 (d, J=11.4 Hz, 2H), 2.96 (s, 3H), 2.80 (br. s., 1H), 2.43 (s, 5H), 1.78 ppm (br. s., 4H).

Example-75: Synthesis of N-(4-(4-(dimethylamino) piperidin-1-yl)-3-fluorophenyl)-5-fluoro-4-(8-fluoro-4-methyl-3,4-dihydro-2H-benzo[b][1,4]oxazin-6-yl) pyrimidin-2-amine. (Compound 467)

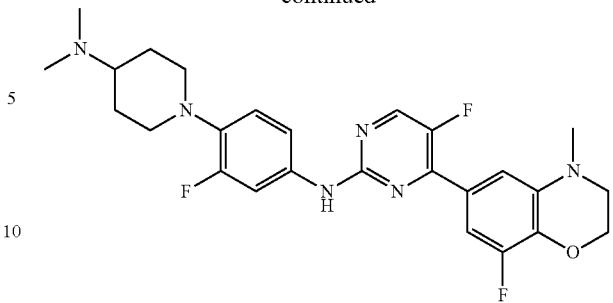

-continued

Step-1: Synthesis of N-(4-(4-(dimethylamino) piperidin-1-yl)-3-fluorophenyl)-5-fluoro-4-(8-fluoro-4-methyl-3,4-dihydro-2H-benzo[b][1,4]oxazin-6-yl) pyrimidin-2-amine To a solution of 6-(2-chloro-5-fluoropyrimidin-4-yl)-8-fluoro-4-methyl-3,4-dihydro-2H-benzo[b][1,4]oxazine (100 mg, 0.33 mmol, 1 equiv) in Dioxane (10 mL), was added 1-(4-amino-2-fluorophenyl)-N,N-dimethylpiperidin-4-amine (88 mg, 0.37 mmol, 1.1 equiv) and cesium carbonate (161 mg, 0.49 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain N-(4-(4-(dimethylamino)piperidin-1-yl)-3-fluorophenyl)-5-fluoro-4-(8-fluoro-4-methyl-3,4-dihydro-2H-benzo[b][1,4]oxazin-6-yl) pyrimidin-2-amine (30 mg, 18%) as a yellow color solid compound. LCMS: 499 [M+H]+; ¹HNMR (400 MHz, DMSO-d6) δ 9.73 (s, 1H), 8.57 (d, J=3.9 Hz, 1H), 8.23 (br. s., 1H), 7.79 (d, J=14.5 Hz, 1H), 7.30-7.38 (m, 2H), 7.22 (d, J=11.8 Hz, 1H), 6.99 (t, J=9.4 Hz, 1H), 4.38 (br. s., 2H), 3.37 (br. s., 2H), 3.30 (d, J=11.0 Hz, 2H), 2.96 (s, 3H), 2.54-2.69 (m, 3H), 2.24 (s, 6H), 1.85 (d, J=10.5 Hz, 2H), 1.55 ppm (d, J=9.2 Hz, 2H)

Example-76: Synthesis of N-(4-(4-(dimethylamino) piperidin-1-yl)-3-fluorophenyl)-5-fluoro-4-(8-fluoro-4-propyl-3,4-dihydro-2H-benzo[b][1,4]oxazin-6-yl) pyrimidin-2-amine. (Compound 468)

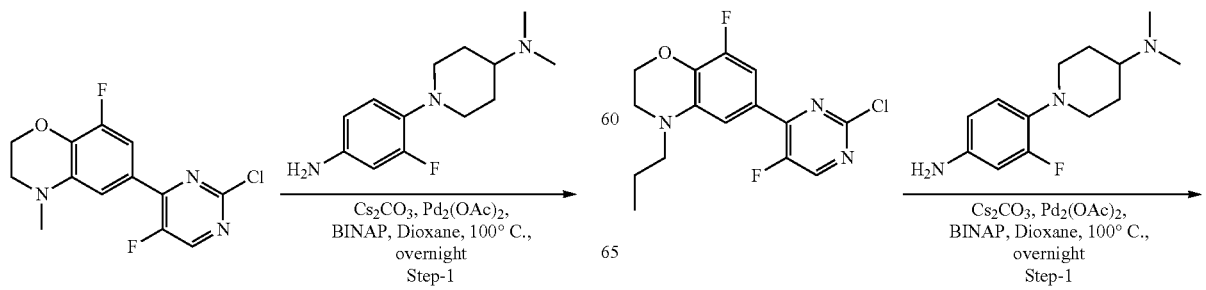

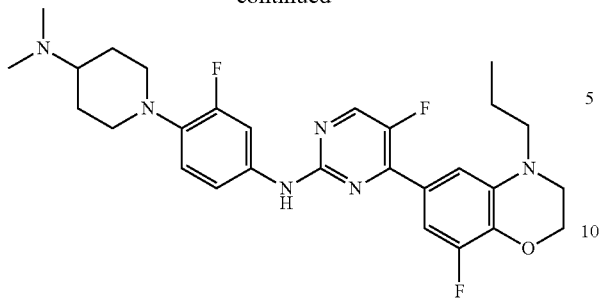

To a solution of 6-(2-chloro-5-fluoropyrimidin-4-yl)-8-fluoro-4-propyl-3,4-dihydro-2H-benzo[b][1,4]oxazine (100 mg, 0.32 mmol, 1 equiv) in Dioxane (10 mL), was added 1-(4-amino-2-fluorophenyl)-N,N-dimethylpiperidin-4-amine (78 mg, 0.33 mmol, 1.1 equiv) and cesium carbonate (147 mg, 0.47 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain N-(4-(4-(dimethylamino)piperidin-1-yl)-3-fluorophenyl)-5-fluoro-4-(8-fluoro-4-propyl-3,4-dihydro-2H-benzo[b][1,4]oxazin-6-yl)pyrimidin-2-amine (30 mg, 19%) as a yellow color solid compound. LCMS: 527 [M+H]⁺; ¹HNMR (400 MHz, DMSO-d6) δ 9.72 (s, 1H), 8.56 (d, J=3.5 Hz, 1H), 8.26 (br. s., 1H), 7.71 (d, J=15.3 Hz, 1H), 7.38 (d, J=8.3 Hz, 1H), 7.28 (br. s., 1H), 7.14 (d, J=11.4 Hz, 1H), 6.98 (t, J=9.4 Hz, 1H), 4.30 (br. s., 2H), 3.43 (br. s., 2H), 3.31 (br. s., 4H), 2.56-2.71 (m, 3H), 2.23 (s, 6H), 1.84 (d, J=11.4 Hz, 2H), 1.42-1.70 (m, 4H), 0.89 ppm (t, J=7.2 Hz, 3H).

Example-77: Synthesis of 5-fluoro-4-(8-fluoro-4-isopropyl-3,4-dihydro-2H-benzo[b][1,4]oxazin-6-yl)-N-(3-fluoro-4-thiomorpholinophenyl)pyrimidin-2-amine. (Compound 469)

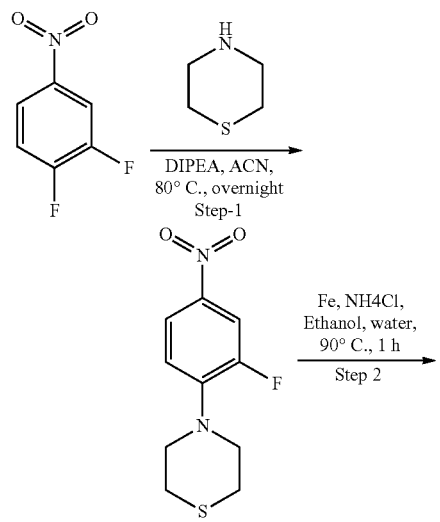

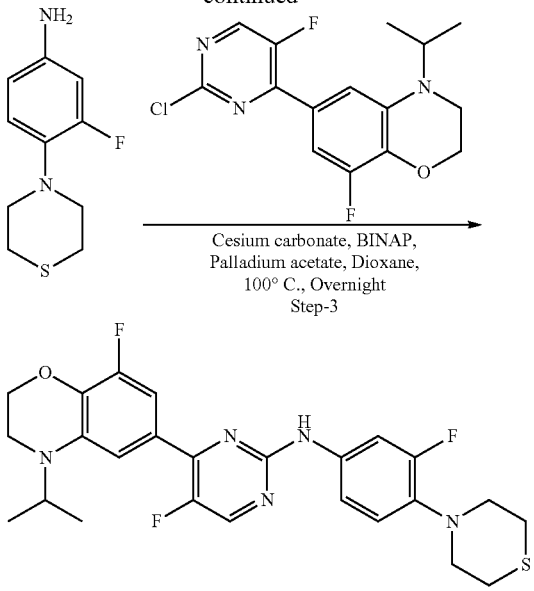

Step-1: Synthesis 4-(2-fluoro-4-nitrophenyl) thiomorpholine

To a stirred solution of 1, 2-difluoro-4-nitrobenzene (500 mg, 3.14 mmol, 1 equiv) in ACN (10 mL), was added DIPEA (0.8 mL, 4.71 mmol, 1.5 equiv) and thiomorpholine (388 mg, 3.76 mmol, 1.2 equiv). The resultant reaction mixture was allowed to stir at 80° for overnight. Progress of the reaction was monitored by TLC and LCMS. After completion of the reaction, the mixture was diluted with ice water (50 mL) and extracted with ethyl acetate (100 mL). Organic layer was washed with water (50 mL) and brine solution (50 mL). Organic layer was dried over anhydrous sodium sulphate and concentrated under reduced pressure to obtain to obtain 4-(2-fluoro-4-nitrophenyl) thiomorpholine (700 mg, 92%) as a brown oily compound. LCMS: 243[M+H]⁺

Step-2: Synthesis of 3-fluoro-4-thiomorpholinoaniline

To a stirred solution of 4-(2-fluoro-4-nitrophenyl)thiomorpholine (300 mg, 1.23 mmol, 1 equiv) in ethanol (6 mL), water (2 mL), was added iron powder (208 mg, 3.7 mmol, 3 equiv) and ammonium chloride (133 mg, 2.45 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 3-fluoro-4-thiomorpholinoaniline (200 mg, 76%) as a yellow color solid compound. LCMS: 213 [M+H]⁺

Step-3: Synthesis of 5-fluoro-4-(8-fluoro-4-isopropyl-3,4-dihydro-2H-benzo[b][1,4]oxazin-6-yl)-N-(3-fluoro-4-thiomorpholinophenyl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 3-fluoro-4-thiomorpholinoaniline (70 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(3-fluoro-4-thiomorpholinophenyl)pyrimidin-2-amine (10 mg, 6%) as a yellow color solid compound. LCMS: 502 [M+H]$^+$; $^1$HNMR (400 MHz, DMSO-d6) δ 9.69 (br. s., 1H), 8.52 (d, J=3.9 Hz, 1H), 7.70 (s, 1H), 7.74 (s, 1H), 7.41 (br. s., 1H), 7.34 (d, J=8.3 Hz, 1H), 7.14 (d, J=11.8 Hz, 1H), 7.00 (t, J=9.2 Hz, 2H), 4.28 (br. s., 2H), 4.06-4.17 (m, 1H), 3.29 (br. s., 2H), 3.09-3.20 (m, 4H), 2.73 (br. s., 4H), 1.16 ppm (d, J=6.6 Hz, 6H).

Example-78: Synthesis of 4-(4-cyclopentyl-8-fluoro-3,4-dihydro-2H-benzo[b][1,4]oxazin-6-yl)-N-(4-(4-(dimethylamino)piperidin-1-yl)-3-fluorophenyl)-5-fluoropyrimidin-2-amine. (Compound 470)

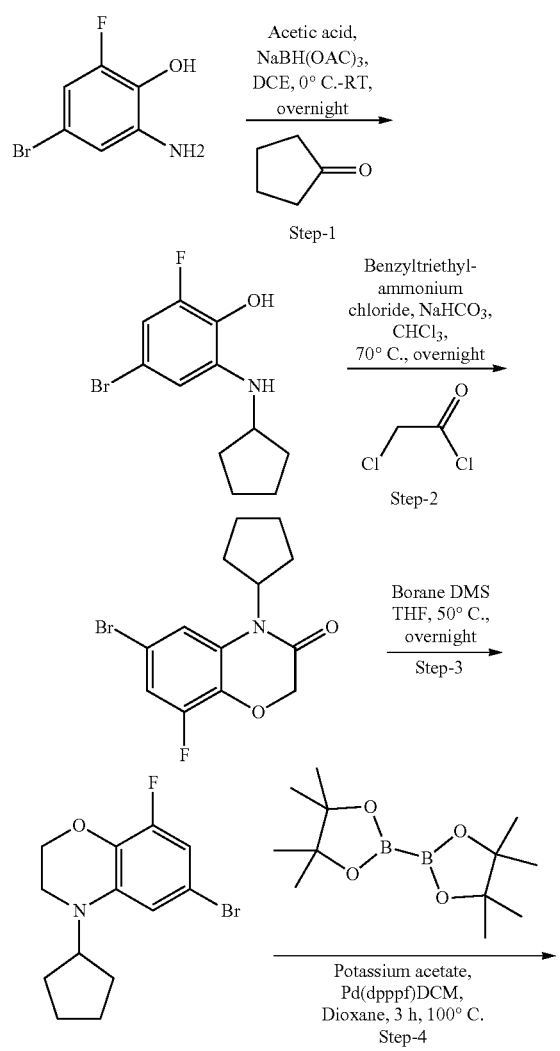

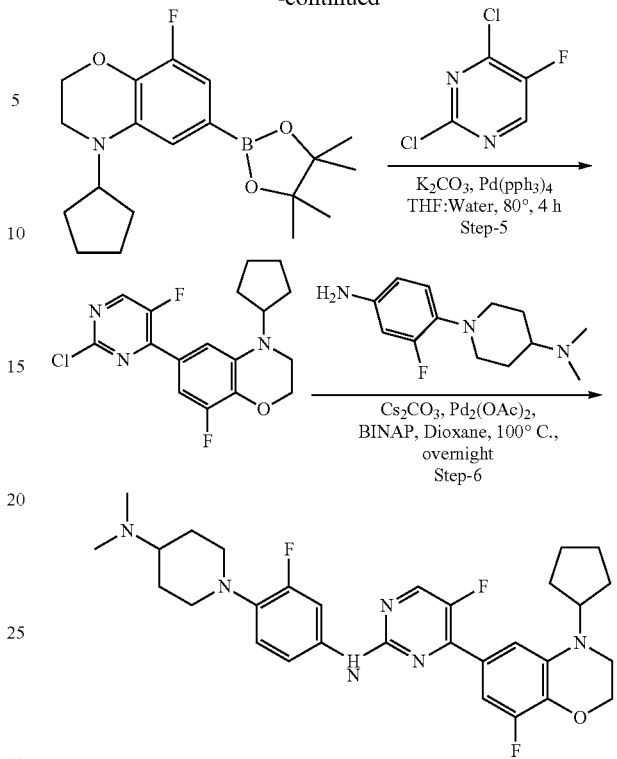

Step-1: Synthesis of 4-bromo-2-(cyclopentylamino)-6-fluorophenol

To a stirred solution of 2-amino-4-bromo-6-fluorophenol (3000 mg, 14.63 mmol, 1 equiv) in DCE (30 mL), was added cyclopentanone (3687 mg, 43.89 mmol, 3 equiv), acetic acid (4.2 mL, 1.0 mmol, 73.15 equiv). The reaction mixture was allowed to stir at RT for 1 h. The reaction mixture was cooled to 0° C. NaBH (OAc)$_3$ (9305 mg, 43.89 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (100 mL) and extracted with ethyl acetate (150 mL×3). Organic layer was washed with water (150 mL) and brine solution (150 mL). Organic layer was dried over anhydrous sodium sulphate and concentrated under reduced pressure to obtain crude, which was purified by normal phase combi flash to afford 4-bromo-2-(cyclopentylamino)-6-fluorophenol (3600 mg, 90%) as a dark brown viscous compound. LCMS: 274 [M+H]$^+$ Step-2: Synthesis of 6-bromo-4-cyclopentyl-8-fluoro-2H-benzo[b][1,4]oxazin-3(4H)-one To a stirred solution of 4-bromo-2-(cyclopentylamino)-6-fluorophenol (3000 mg, 10.9 mmol, 1 equiv) in chloroform (30 mL), was added NaHCO$_3$ (4578 mg, 54.5 mmol, 5 equiv) and Benzyltriethyl ammonium chloride (2485 mg, 10.9 mmol, 1 equiv). The reaction mixture was allowed to stir at RT for 1 h. The reaction mixture was cooled to 0° C., followed by the addition of chloroacetyl chloride (0.9 mL, 10.9 mmol, 1 equiv). The reaction mixture was allowed to stir at 0° C. for 1 h. Raise the temp. to 70° C. and reaction mixture was allowed to stir for overnight. Progress of the reaction was monitored by LCMS. After completion of the reaction, the reaction mixture was diluted with water (100 mL) and extracted with ethyl acetate (150 mL×3). Organic layer was washed with water (150 mL) and brine solution (150 mL). Organic layer was dried over anhydrous sodium sulphate and concentrated under reduced pressure to obtain crude, which was purified by column chromatography to afford 6-bromo-4-cyclopentyl-8-fluoro-2H-benzo[b][1,4]oxazin-3(4H)-one (1000 mg, 29%) as a brown color solid compound. LCMS: 314 [M+H]$^+$ Step-3: Synthesis of 6-bromo-4-cyclopentyl-8-fluoro-3,4-dihydro-2H-benzo[b][1,4]oxazine To a stirred solution of 6-bromo-4-cyclopentyl-8-fluoro-2H-benzo[b][1,4]oxazin-3(4H)-one (1000 mg, 3.19 mmol, 1 equiv) in THF (15 mL), was added BH$_3$.DMS (2 M in THF) (6.3 mL, 12.7 mmol, 4 equiv) at 0° C. drop wise. The reaction mixture was allowed to stir at 50° C. for overnight. Progress of the reaction was monitored by TLC and LCMS. After completion of the reaction, the reaction mixture was quenched with saturated solution of NaHCO$_3$ (50 mL) and extracted with ethyl acetate (100 mL×2). Organic layer was washed with water (100 mL), dried over anhydrous sodium sulphate and concentrated under reduced pressure to obtain 6-bromo-4-cyclopentyl-8-fluoro-3,4-dihydro-2H-benzo[b][1,4]oxazine (900 mg, 94%) as a transparent oil compound. LCMS: 300 [M+H]$^+$ Step-4: Synthesis of 4-cyclopentyl-8-fluoro-6-(4,4,5,5-tetramethyl-1,3,2-dioxaborolan-2-yl)-3,4-dihydro-2H-benzo[b][1,4]oxazine 6-bromo-4-cyclopentyl-8-fluoro-3,4-dihydro-2H-benzo[b][1,4]oxazine (900 mg, 3.01 mmol, 1 equiv), 4,4,5,5-tetramethyl-2-(4,4,5,5-tetramethyl-1,3,2-dioxaborolan-2-yl)-1,3,2-dioxaborolane (1147 mg, 4.51 mmol, 1.5 equiv), Potassium acetate (735 mg, 7.5 mmol, 2.5 equiv) and dioxane (10 mL) were charged in a 25 mL glass bottle. Purged the reaction mixture with nitrogen gas for 15 min., Pd(dppf)Cl2. DCM (123 mg, 0.15 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (100 mL) and water (100 mL). Organic layer was dried over anhydrous sodium sulphate and concentrated under reduced pressure to obtain 4-cyclopentyl-8-fluoro-6-(4,4,5,5-tetramethyl-1,3,2-dioxaborolan-2-yl)-3,4-dihydro-2H-benzo[b][1,4]oxazine (1000 mg, 96%) as a dark brown viscous compound. LCMS: 348 [M+H]$^+$ Step-5: Synthesis of 6-(2-chloro-5-fluoropyrimidin-4-yl)-4-cyclopentyl-8-fluoro-3,4-dihydro-2H-benzo[b][1,4]oxazine To a stirred solution of 2, 4-dichloro-5-fluoropyrimidine (450 mg, 2.7 mmol, 1 equiv) in THF:Water (1:1=10 mL) was added 4-cyclopentyl-8-fluoro-6-(4,4,5,5-tetramethyl-1,3,2-dioxaborolan-2-yl)-3,4-dihydro-2H-benzo[b][1,4]oxazine (941 mg, 2.7 mmol, 1 equiv), Potassium carbonate (745 mg, 5.4 mmol, 2 equiv) and Pd(PPh$_3$)$_4$ (156 mg, 0.13 mmol, 0.05 equiv). The reaction mixture was allowed to stir at 80° C. for 3 h. Progress of the reaction was monitored by TLC and LCMS. After completion of the reaction, the reaction mixture was diluted with water (50 mL) and extracted wit ethyl acetate (150 mL). Organic layer was washed with water (50 mL) and brine (50 mL). Organic layer was dried over anhydrous sodium sulphate and concentrated under reduced pressure to obtain crude compound, which was purified by normal phase combi-flash to obtain 6-(2-chloro-5-fluoropyrimidin-4-yl)-4-cyclopentyl-8-fluoro-3,4-dihydro-2H-benzo[b][1,4]oxazine (300 mg, 32%) as a yellow solid compound. LCMS: 352 [M+H]$^+$ Step-6: Synthesis of 4-(4-cyclopentyl-8-fluoro-3,4-dihydro-2H-benzo[b][1,4]oxazin-6-yl)-N-(4-(4-(dimethylamino)piperidin-1-yl)-3-fluorophenyl)-5-fluoropyrimidin-2-amine To a solution of 6-(2-chloro-5-fluoropyrimidin-4-yl)-4-cyclopentyl-8-fluoro-3,4-dihydro-2H-benzo[b][1,4]oxazine (100 mg, 0.28 mmol, 1 equiv) in Dioxane (10 mL), was added 1-(4-amino-2-fluorophenyl)-N,N-dimethylpiperidin-4-amine (74 mg, 0.31 mmol, 1.1 equiv) and cesium carbonate (137 mg, 0.42 mmol, 1.5 equiv). The reaction mixture was purged with nitrogen gas for 30 min., followed by the addition of palladium acetate (1.3 mg, 0.005 mmol, 0.02 equiv) and BINAP (7 mg, 0.01 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain 4-(4-cyclopentyl-8-fluoro-3,4-dihydro-2H-benzo[b][1,4]oxazin-6-yl)-N-(4-(4-(dimethylamino)piperidin-1-yl)-3-fluorophenyl)-5-fluoropyrimidin-2-amine (20 mg, 13%) as a brick red color solid compound. LCMS: 553 [M+H]$^+$; $^1$HNMR (400 MHz, DMSO-d6) δ 9.76 (s, 1H), 8.57 (s, 1H), 7.73 (dd, J=15.1, 2.4 Hz, 1H), 7.34-7.48 (m, 2H), 7.16 (d, J=11.8 Hz, 1H), 7.02 (d, J=9.6 Hz, 1H), 4.31 (br. s., 2H), 4.27 (br. s., 1H), 3.34-3.48 (m, 4H), 3.33 (br. s., 1H), 2.78 (d, J=4.8 Hz, 6H), 2.53-2.69 (m, 2H), 2.09 (d, J=11.0 Hz, 2H), 1.89 (d, J=8.3 Hz, 2H), 1.78 (d, J=8.3 Hz, 2H), 1.45-1.74 ppm (m, 6H).

Example-79: Synthesis of 4-(4-cyclopentyl-8-fluoro-3,4-dihydro-2H-benzo[b][1,4]oxazin-6-yl)-5-fluoro-N-(3-fluoro-4-(1-methylpiperidin-4-yl)phenyl)pyrimidin-2-amine. (Compound 471)

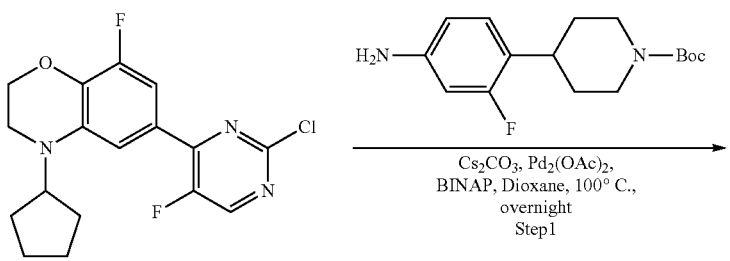

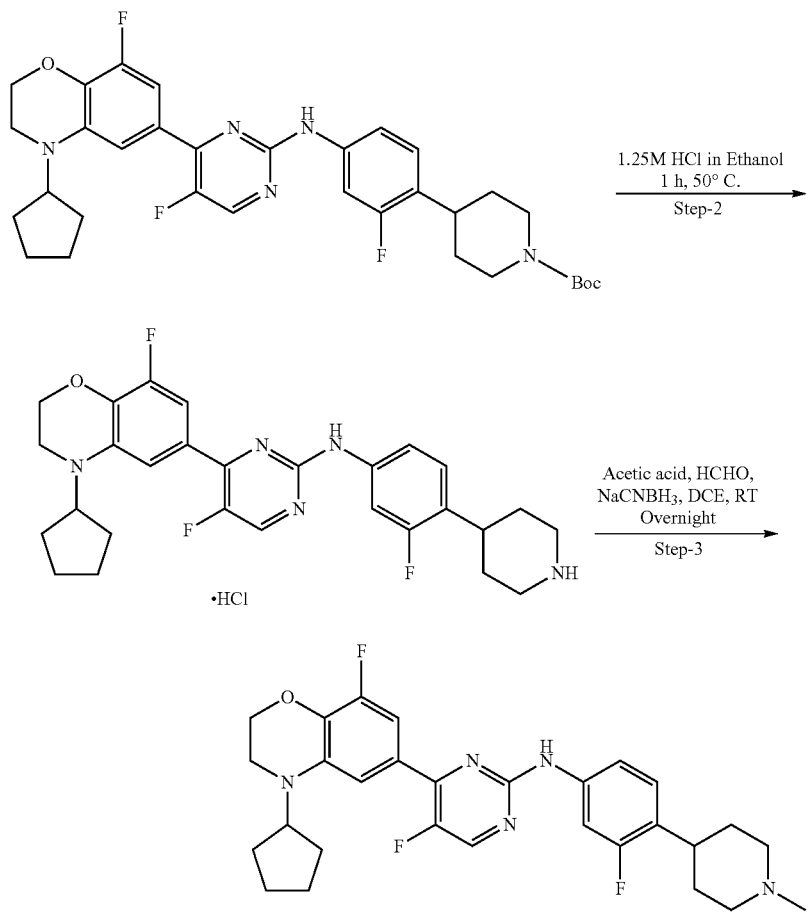

Step-1: Synthesis of tert-butyl 4-(4-((4-(4-cyclopentyl-8-fluoro-3,4-dihydro-2H-benzo[b][1,4]oxazin-6-yl)-5-fluoropyrimidin-2-yl)amino)-2-fluorophenyl)piperidine-1-carboxylate To a solution of 6-(2-chloro-5-fluoropyrimidin-4-yl)-4-cyclopentyl-8-fluoro-3,4-dihydro-2H-benzo[b][1,4]oxazine (200 mg, 0.56 mmol, 1 equiv) in Dioxane (10 mL), was added tert-butyl 4-(4-amino-2-fluorophenyl)piperidine-1-carboxylate (184 mg, 0.62 mmol, 1.1 equiv) and cesium carbonate (274 mg, 0.84 mmol, 1.5 equiv). The reaction mixture was purged with nitrogen gas for 30 min., followed by the addition of palladium acetate (3 mg, 0.011 mmol, 0.02 equiv) and BINAP (14 mg, 0.022 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified column chromatography to obtain tert-butyl 4-(4-((4-(4-cyclopentyl-8-fluoro-3,4-dihydro-2H-benzo[b][1,4]oxazin-6-yl)-5-fluoropyrimidin-2-yl)amino)-2-fluorophenyl)piperidine-1-carboxylate (170 mg, 49%) as a yellow solid compound. LCMS: 610 [M+H]+

Step-2: Synthesis of 4-(4-cyclopentyl-8-fluoro-3,4-dihydro-2H-benzo[b][1,4]oxazin-6-yl)-5-fluoro-N-(3-fluoro-4-(piperidin-4-yl)phenyl)pyrimidin-2-amine tert-butyl 4-(4-((4-(4-cyclopentyl-8-fluoro-3,4-dihydro-2H-benzo[b][1,4]oxazin-6-yl)-5-fluoropyrimidin-2-yl)amino)-2-fluorophenyl)piperidine-1-carboxylate (170 mg, 0.27 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 4-(4-cyclopentyl-8-fluoro-3,4-dihydro-2H-benzo[b][1,4]oxazin-6-yl)-5-fluoro-N-(3-fluoro-4-(piperidin-4-yl)phenyl)pyrimidin-2-amine (130 mg, 86%) as a brick red color solid compound. LCMS: 510 [M+H]+

Step-3: Synthesis of 4-(4-cyclopentyl-8-fluoro-3,4-dihydro-2H-benzo[b][1,4]oxazin-6-yl)-5-fluoro-N-(3-fluoro-4-(1-methylpiperidin-4-yl)phenyl)pyrimidin-2-amine To a stirred solution of 4-(4-cyclopentyl-8-fluoro-3,4-dihydro-2H-benzo[b][1,4]oxazin-6-yl)-5-fluoro-N-(3-fluoro-4-(piperidin-4-yl)phenyl)pyrimidin-2-amine (70 mg, 0.12 mmol, 1 equiv) in DCE (5 mL), was added Formaldehyde (40% in water) (0.01 mL, 0.38 mmol, 3 equiv), acetic acid (0.03 mL, 0.6 mmol, 5 equiv). The reaction mixture was allowed to stir at RT for 1 h. The reaction mixture was cooled to 0° C. NaCNBH$_3$ (23 mg, 0.38 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 4-(4-cyclopentyl-8-fluoro-3,4-dihydro-2H-benzo[b][1,4]oxazin-6-yl)-5-fluoro-N-(3-fluoro-4-(1-methylpiperidin-4-yl)phenyl)pyrimidin-2-amine (7 mg, 10%) as a light orange color solid compound. LCMS: 524 [M+H]$^+$; $^1$HNMR (400 MHz, DMSO-d6) δ 9.94 (s, 1H), 8.61 (d, J=3.9 Hz, 1H), 7.82 (s, 1H), 7.36-7.54 (m, 2H), 7.18 (d, J=8.8 Hz, 2H), 4.32 (br. s., 3H), 3.51 (d, J=13.2 Hz, 2H), 3.34 (br. s., 2H), 3.12 (d, J=11.0 Hz, 2H), 3.00 (br. s., 1H), 2.81 (s, J=4.8 Hz, 3H), 1.80-2.04 (m, 6H), 1.69-1.60 ppm (m, 6H).

Example-80: Synthesis of 1-(6-(((5-fluoro-4-(8-fluoro-4-isopropyl-3,4-dihydro-2H-benzo[b][,4]oxazin-6-yl)pyrimidin-2-yl)amino)pyridin-3-yl)-4-methylpiperazin-2-one. (Compound 472)

Step-1: Synthesis tert-butyl 4-(6-nitropyridin-3-yl)-3-oxopiperazine-1-carboxylate To a solution of 5-bromo-2-nitropyridine (1000 mg, 4.95 mmol, 1 equiv) in Dioxane (10 mL), was added tert-butyl 3-oxopiperazine-1-carboxylate (990 mg, 4.95 mmol, 1 equiv) and cesium carbonate (4034 mg, 12.3 mmol, 2.5 equiv). The reaction mixture was purged with nitrogen gas for 30 min., followed by the addition of Pd$_2$(dba)$_3$ (227 mg, 0.24 mmol, 0.05 equiv) and Xantphos (230 mg, 0.39 mmol, 0.08 equiv). The resultant reaction mixture was allowed to stir at 100° C. for overnight. Progress of the reaction was monitored by TLC and LCMS. After completion of the reaction, the reaction mixture was diluted with water (50 mL) and extracted wit ethyl acetate (150 mL×2). Organic layer was washed with water (100 mL) and brine (100 mL). Organic layer was dried over anhydrous sodium sulphate and concentrated under reduced pressure to obtain crude compound, which was purified by normal phase combi flash to obtain tert-butyl 4-(6-nitropyridin-3-yl)-3-oxopiperazine-1-carboxylate (500 mg, 37%) as a yellow solid compound. LCMS: 323 [M+H]$^+$ Step-2: Synthesis of tert-butyl 4-(6-aminopyridin-3-yl)-3-oxopiperazine-1-carboxylate To a stirred solution of tert-butyl 4-(6-nitropyridin-3-yl)-3-oxopiperazine-1-carboxylate (500 mg, 1.55 mmol, 1 equiv) in ethanol (8 mL), water (2 mL), was added iron powder (261 mg, 4.65 mmol, 3 equiv) and ammonium chloride (167 mg, 3.1 mmol, 2 equiv). The resultant reaction mixture was allowed to stir at 900 for 1 h. Progress of the reaction was monitored by TLC and LCMS. After comple-

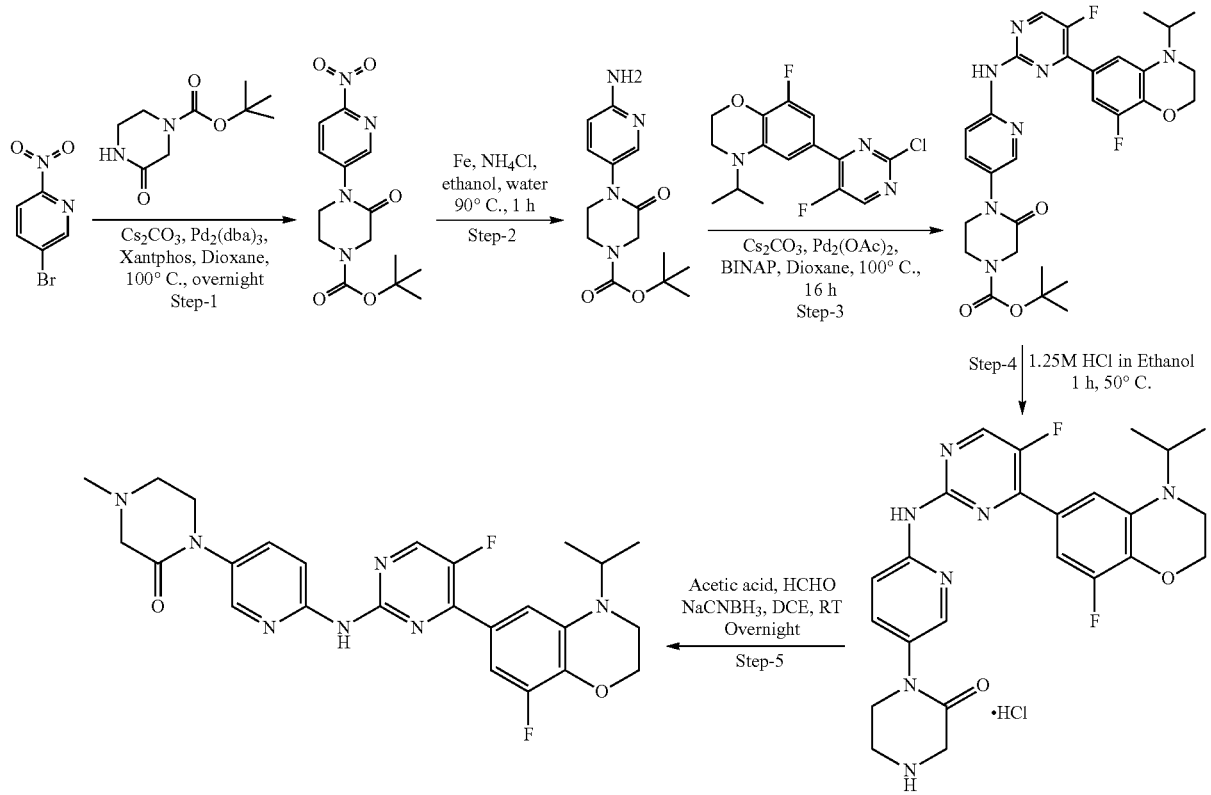

tion of the reaction, the mixture was passes through celite bed and the filtrate was concentrated under reduced pressure to obtain tert-butyl 4-(6-aminopyridin-3-yl)-3-oxopiperazine-1-carboxylate (300 mg, 77%) as a brown color solid compound. LCMS: 293 [M+H]$^+$ Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.33 mmol, 1 equiv) in Dioxane (10 mL), was added tert-butyl 4-(6-aminopyridin-3-yl)-3-oxopiperazine-1-carboxylate (96 mg, 0.37 mmol, 1.1 equiv) and cesium carbonate (161 mg, 0.49 mmol, 1.5 equiv). The reaction mixture was purged with nitrogen gas for 30 min., followed by the addition of palladium acetate (2 mg, 0.006 mmol, 0.02 equiv) and BINAP (8 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi flash to obtain tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate (140 mg, 79%) as a yellow solid compound. LCMS: 582 [M+H]$^+$ Step-4: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-2-one hydrochloride tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate (140 mg, 0.24 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-2-one hydrochloride (120 mg, 96%) as a brick red color solid compound. LCMS: 482 [M+H]$^+$ Step-5: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-methylpiperazin-2-one To a stirred solution of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-2-one (60 mg, 0.11 mmol, 1 equiv) in DCE (3 mL), was added Formaldehyde (40% in water) (0.01 mL, 0.33 mmol, 3 equiv), acetic acid (0.03 mL, 0.55 mmol, 5 equiv). The reaction mixture was allowed to stir at RT for 1 h. The reaction mixture was cooled to 0° C. NaCNBH$_3$ (21 mg, 0.33 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (15 mL) and extracted with DCM (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-methylpiperazin-2-one (5 mg, 9%) as a yellow color solid compound. LCMS: 496 [M+H]$^+$; $^1$HNMR (400 MHz, DMSO-d6) δ 10.21 (s, 1H), 8.65 (d, J=3.9 Hz, 1H), 8.18-8.34 (m, 2H), 7.73 (dd, J=9.0, 2.4 Hz, 1H), 7.48 (br. s., 1H), 7.20 (d, J=11.4 Hz, 1H), 4.30 (br. s., 2H), 4.15 (d, J=6.6 Hz, 1H), 3.93 (br. s., 3H), 3.78 (m, 3H). 3.30 (t, J=4.2 Hz, 2H), 2.86 (br. s., 3H), 1.01-1.30 ppm (m, 6H).

Example-81: Synthesis of 5-fluoro-N-(3-fluoro-4-(hexahydropyrrolo[1,2-a]pyrazin-2(1H)-yl)phenyl)-4-(8-fluoro-4-isopropyl-3,4-dihydro-2H-benzo[b][,4]oxazin-6-yl)pyrimidin-2-amine. (Compound 473)

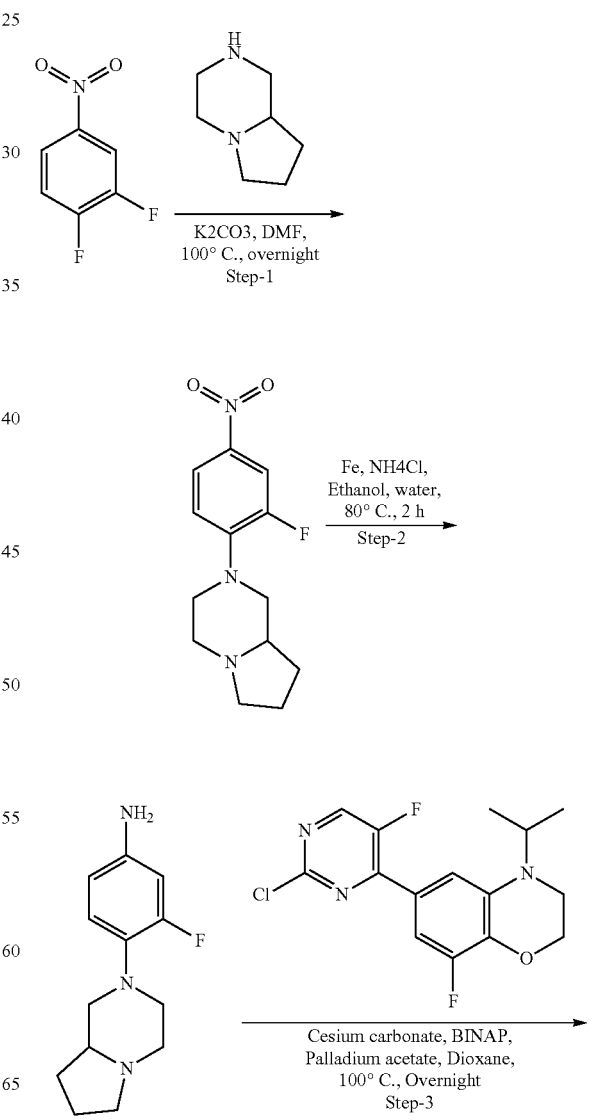

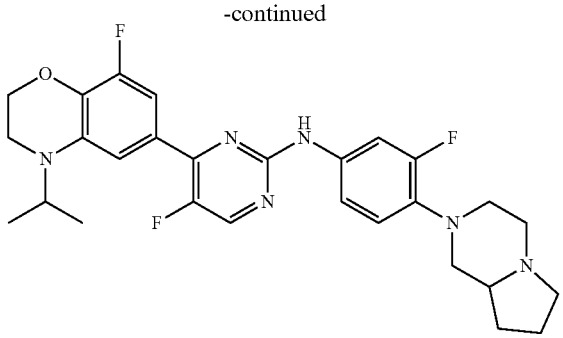

Step-1: Synthesis of 2-(2-fluoro-4-nitrophenyl)octahydropyrrolo[1,2-a]pyrazine To a stirred solution of 1,2-difluoro-4-nitrobenzene (1000 mg, 6.28 mmol, 1 equiv) in DMF (10 mL), was added octahydropyrrolo[1,2-a]pyrazine (950 mg, 7.54 mmol, 1.2 equiv) followed by addition of K2CO3 (1300 mg, 9.42 mmol, 1.5 equiv). Resultant mixture was allowed to stir at 100° for overnight. Progress of the reaction was monitored by TLC and LCMS. After completion of the reaction, the mixture was diluted with water (20 mL), and was extracted with EtOAc (25 mL). Organic layer was washed with water (20 mL×6) and brine (5 mL), dried over anhydrous sodium sulphate and concentrated under reduced pressure to obtain crude compound was triturated from hexane to afford 2-(2-fluoro-4-nitrophenyl)octahydropyrrolo[1,2-a]pyrazine (1000 mg) as a colorless oil. LCMS: 267 [M+H]+

Step-2: Synthesis of 3-fluoro-4-(hexahydropyrrolo[1,2-a]pyrazin-2(1H)-yl)aniline To a stirred solution of 2-(2-fluoro-4-nitrophenyl)octahydropyrrolo[1,2-a]pyrazine (1000 mg, 3.77 mmol, 1 equiv) in ethanol (8 mL), water (3 mL), was added iron fillings (2000 mg, 37.7 mmol, 10 equiv) and ammonium chloride (2000 mg, 37.7 mmol, 10 equiv). The resultant reaction mixture was allowed to stir at 90° C. for 2 h. Progress of the reaction was monitored by TLC and LCMS. After completion of the reaction, the mixture was concentrated under vacuum diluted with water (20 mL) and extracted with EtoAc (20 mL). Organic layer was washed with water (10 mL) and brine (10 mL). Organic layer was dried over anhydrous sodium sulphate and concentrated under reduced pressure to obtain 3-fluoro-4-(hexahydropyrrolo[1,2-a]pyrazin-2(1H)-yl)aniline (800 mg, 82%) as a dark brown solid compound. LCMS: 236 [M+H]

Step-3: Synthesis of 5-fluoro-N-(3-fluoro-4-(hexahydropyrrolo[1,2-a]pyrazin-2(1H)-yl)phenyl)-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (60 mg, 0.18 mmol, 1 equiv) in dioxane (4 mL), was added 3-fluoro-4-(hexahydropyrrolo[1,2-a]pyrazin-2(1H)-yl)aniline (51 mg, 0.24 mmol, 1.2 equiv) and cesium carbonate (90 mg, 0.27 mmol, 1.5 equiv). The reaction mixture was degassed with nitrogen gas for 10 min., followed by the addition of palladium acetate (6 mg, 0.018 mmol, 0.1 equiv) and BINAP (24 mg, 0.036 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain crude, which was purified by reverse phase HPLC to obtain 5-fluoro-N-(3-fluoro-4-(hexahydropyrrolo[1,2-a]pyrazin-2 (1H)-yl)phenyl)-4-(8-fluoro-4-isopropyl-3,4-dihydro-2H-benzo[b][1,4]oxazin-6-yl)pyrimidin-2-amine (15 mg, 11%) as a yellow solid compound. LCMS: 525 [M+H]+; 1HNMR: (400 MHz, DMSO-d6) δ 10.16 (s, 1H), 9.83 (d, J=3.1 Hz, 1H), 9.74 (s, 1H), 8.59 (d, J=3.9 Hz, 1H), 7.83 (dd, J=15.1, 2.4 Hz, 1H), 7.40 (d, J=10.7 Hz, 2H), 7.16 (d, J=11.5 Hz, 1H), 7.13-7.04 (m, 1H), 4.30 (t, J=4.2 Hz, 2H), 4.16 (p, J=6.6 Hz, 1H), 3.90-3.83 (m, 1H), 3.66 (dd, J=19.4, 12.3 Hz, 2H), 3.45 (dd, J=26.2, 11.2 Hz, 2H), 3.34 (s, 14H), 3.17 (t, J=3.8 Hz, 1H), 3.12-2.91 (m, 2H), 2.23-1.95 (m, 4H), 1.63 (t, J=10.2 Hz, 0H), 1.19 (d, J=6.5 Hz, 7H).

Example-82: Synthesis of 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)ethan-1-one. (Compound 474)

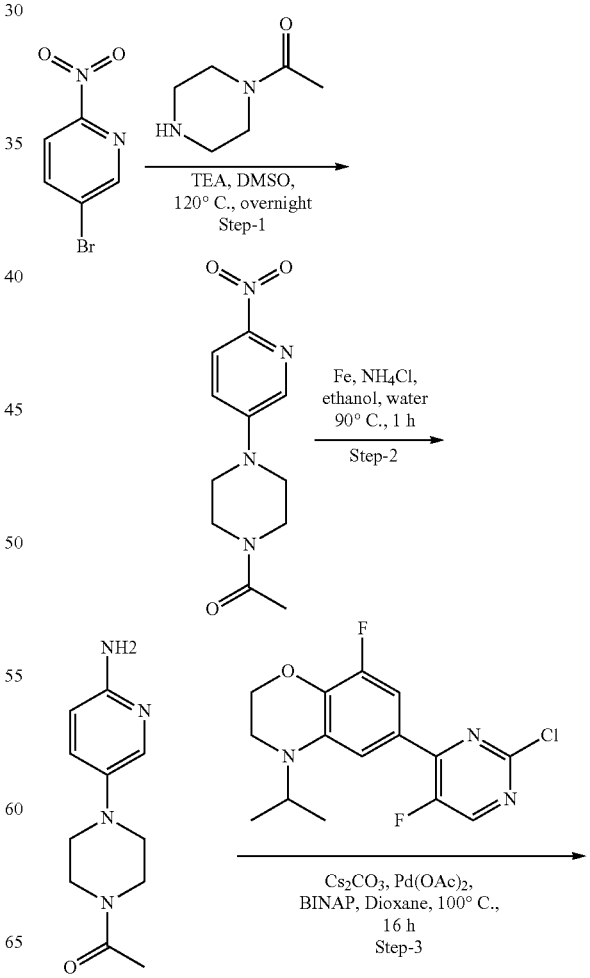

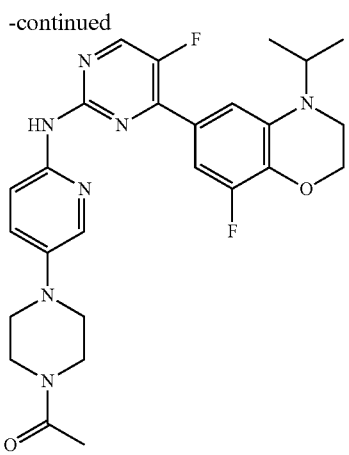

Step-1: Synthesis 1-(4-(6-nitropyridin-3-yl) piperazin-1-yl) ethan-1-one

To a stirred solution of 5-bromo-2-nitropyridine (500 mg, 2.47 mmol, 1 equiv) in DMSO (10 mL), was added TEA (0.7 mL, 4.9 mmol, 1.5 equiv) and 1-(piperazin-1-yl)ethan-1-one (474 mg, 3.7 mmol, 1.2 equiv). The resultant reaction mixture was allowed to stir at 120° C. for overnight. Progress of the reaction was monitored by TLC and LCMS. After completion of the reaction, the mixture was diluted with ice water (50 mL) and extracted with ethyl acetate (100 mL). Organic layer was washed with water (50 mL) and brine solution (50 mL). Organic layer was dried over anhydrous sodium sulphate and concentrated under reduced pressure to obtain to obtain 1-(4-(6-nitropyridin-3-yl) piperazin-1-yl) ethan-1-one (250 mg, 40%) as a brown solid compound.
LCMS: 251 [M+H]$^+$

Step-2: Synthesis of 1-(4-(6-aminopyridin-3-yl) piperazin-1-yl) ethan-1-one

To a stirred solution of 1-(4-(6-nitropyridin-3-yl)piperazin-1-yl)ethan-1-one (250 mg, 1 mmol, 1 equiv) in ethanol (6 mL), water (2 mL), was added iron powder (168 mg, 3 mmol, 3 equiv) and ammonium chloride (108 mg, 2 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain 1-(4-(6-aminopyridin-3-yl)piperazin-1-yl)ethan-1-one (200 mg, 91%) as a dark brown color solid compound. LCMS: 221 [M+H]$^+$

Step-3: Synthesis of 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl) ethan-1-one To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 1-(4-(6-aminopyridin-3-yl)piperazin-1-yl)ethan-1-one (73 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)ethan-1-one (10 mg, 6%) as an off white color solid compound. LCMS: 510 [M+H]$^+$; $^1$HNMR (400 MHz, DMSO-d$_6$) δ 9.73 (s, 1H), 8.57 (d, J=3.9 Hz, 1H), 7.98-8.11 (m, 2H), 7.36-7.50 (m, 2H), 7.17 (d, J=11.0 Hz, 1H), 4.30 (br. s., 2H), 4.15 (br. s., 1H), 3.59 (br. s., 4H), 3.31 (d, J=4.6 Hz, 2H), 3.13 (br. s., 2H), 3.07 (br. s., 2H), 2.05 (s, 3H), 1.19 ppm (d, J=6.6 Hz, 6H).

Example-83: Synthesis of 5-fluoro-4-(8-fluoro-4-isopropyl-3,4-dihydro-2H-benzo[b][1,4]oxazin-6-yl)-N-(5-(4-(methylsulfonyl)piperazin-1-yl)pyridin-2-yl)pyrimidin-2-amine. (Compound 475)

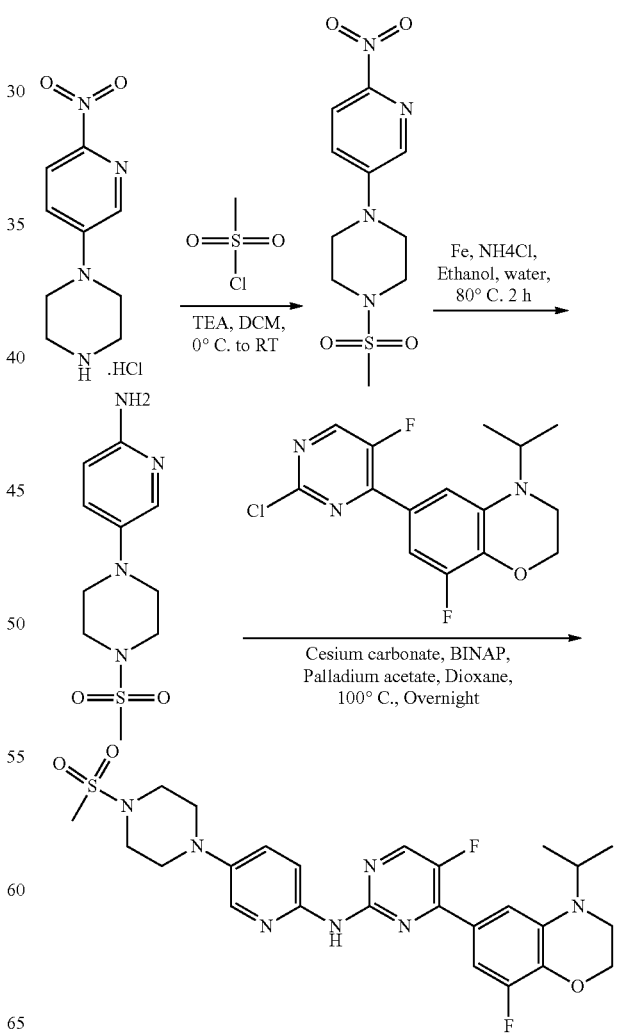

Step-1: Synthesis of 1-(methylsulfonyl)-4-(6-nitropyridin-3-yl)piperazine

To a cooled suspension of 1-(6-nitropyridin-3-yl)piperazine (1600 mg, 6.55 mmol, 1 equiv) in DCM (30 mL) was added TEA (3.5 mL, 19.65 mmol, 3 equiv) at 0° C. followed by addition of mesyl chloride (905 mg, 7.85 mmol, 1.2 equiv) at 0° C. Resultant mixture was allowed to stir at room temperature for 16 h. Progress of the reaction was monitored by LCMS. After completion of the reaction, the reaction mixture was diluted with water (20 mL) and extracted with DCM (30 mL). Organic layer was washed with water (20 mL×3) and brine (5 mL), dried over anhydrous sodium sulphate and concentrated under reduced pressure to obtain 1-(methylsulfonyl)-4-(6-nitropyridin-3-yl)piperazine (1600 mg) as an oil. LCMS: 588 [M+H]$^+$

Step-2: Synthesis of 5-(4-(methylsulfonyl)piperazin-1-yl)pyridin-2-amine

To a stirred solution of 1-(methylsulfonyl)-4-(6-nitropyridin-3-yl)piperazine (1000 mg, 3.5 mmol, 1 equiv) in ethanol (8 mL), water (3 mL), was added iron fillings (1900 mg, 35 mmol, 10 equiv) and ammonium chloride (1960 mg, 35 mmol, 10 equiv). The resultant reaction mixture was allowed to stir at 80° C. for 2 h. Progress of the reaction was monitored by TLC and LCMS. After completion of the reaction, the mixture was concentrated under vacuum diluted with water (20 mL) and extracted with EtoAc (20 mL). Organic layer was washed with water (10 mL) and brine (10 mL). Organic layer was dried over anhydrous sodium sulphate and concentrated under reduced pressure to obtain 5-(4-(methylsulfonyl)piperazin-1-yl)pyridin-2-amine (800 mg, 82%) as a dark brown solid compound. LCMS: 257 [M+H]$^+$

Step-3: Synthesis of 5-fluoro-4-(8-fluoro-4-isopropyl-3,4-dihydro-2H-benzo[b][1,4]oxazin-6-yl)-N-(5-(4-(methylsulfonyl)piperazin-1-yl)pyridin-2-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (37 mg, 0.11 mmol, 1 equiv) in dioxane (3 mL), was added 5-(4-(methylsulfonyl)piperazin-1-yl)pyridin-2-amine (32 mg, 0.13 mmol, 1.2 equiv) and cesium carbonate (71 mg, 0.22 mmol, 2 equiv). The reaction mixture was degassed by nitrogen gas for 10 min., followed by the addition of palladium acetate (2.4 mg, 0.011 mmol, 0.1 equiv) and BINAP (14 mg, 0.022 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(5-(4-(methylsulfonyl)piperazin-1-yl)pyridin-2-yl)pyrimidin-2-amine (5 mg, 8%) as a yellow solid compound. LCMS: 546 [M+H]$^+$; $^1$HNMR: (400 MHz, CHLOROFORM-d) δ 8.24 (t, J=7.3 Hz, 1H), 7.90 (s, 1H), 7.35 (s, 1H), 7.31 (s, OH), 7.22 (d, J=12.6 Hz, 1H), 4.30 (t, J=4.4 Hz, 1H), 4.12 (s, OH), 3.32 (d, J=10.8 Hz, 53H), 3.21 (s, 2H), 2.80 (s, 1H), 1.18 (d, J=6.4 Hz, 4H).

Example-84: Synthesis of 5-fluoro-N-(3-fluoro-4-(1-methylpiperidin-4-yl) phenyl)-4-(8-fluoro-4-isobutyl-3,4-dihydro-2H-benzo[b][1,4]oxazin-6-yl) pyrimidin-2-amine. (Compound 476)

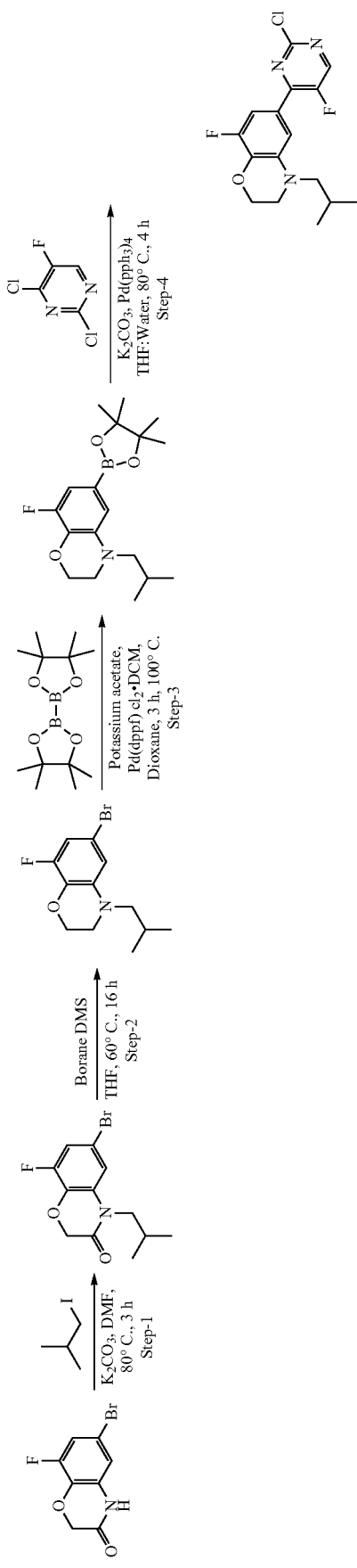
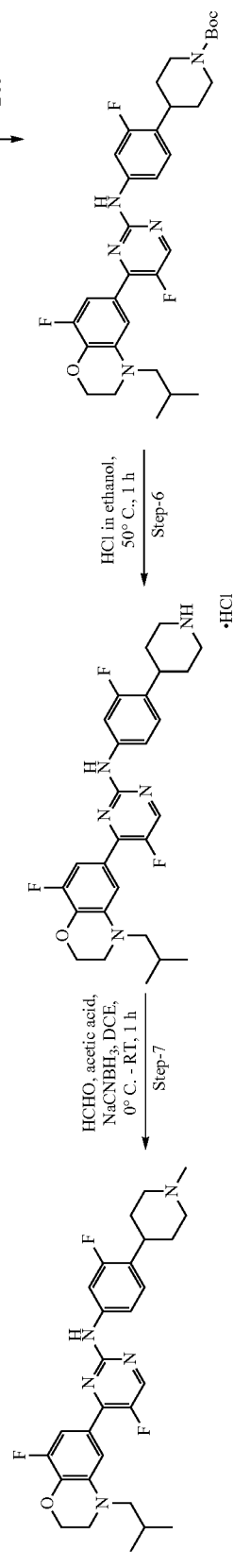

Step-1: Synthesis of 6-bromo-8-fluoro-4-isobutyl-2H-benzo[b][1,4]oxazin-3(4H)-one To a stirred solution of 6-bromo-8-fluoro-2H-benzo[b][1,4]oxazin-3(4H)-one (2500 mg, 10.1 mmol, 1 equiv) in DMF (20 mL), was added $K_2CO_3$ (2801 mg, 20.3 mmol, 2 equiv) and 1-iodo-2-methylpropane (2.3 mL, 20.3 mmol, 2 equiv). The reaction mixture was allowed to stir at 80° C. for 3 h. Progress of the reaction was monitored by TLC and LCMS. After completion of the reaction, the reaction mixture was diluted with water (100 mL) and extracted with ethyl acetate (150 mL×2). Organic layer was washed with water (100 mL), dried over anhydrous sodium sulphate and concentrated under reduced pressure to obtain 6-bromo-8-fluoro-4-isobutyl-2H-benzo[b][1,4]oxazin-3(4H)-one (2300 mg, 75%) as a brown color solid compound. LCMS: 302 $[M+H]^+$

Step-2: Synthesis of 6-bromo-8-fluoro-4-isobutyl-3,4-dihydro-2H-benzo[b][1,4]oxazine To a stirred solution of 6-bromo-8-fluoro-4-isobutyl-2H-benzo[b][1,4]oxazin-3(4H)-one (2000 mg, 6.6 mmol, 1 equiv) in THF (20 mL), was added $BH_3$.DMS (2M in THF) (13 mL, 26.6 mmol, 4 equiv) at 0° C. drop wise. The reaction mixture was allowed to stir at 60° C. for overnight. Progress of the reaction was monitored by TLC and LCMS. After completion of the reaction, the reaction mixture was quenched with saturated solution of $NaHCO_3$ (100 mL) and extracted with ethyl acetate (100 mL×2). Organic layer was washed with water (100 mL), dried over anhydrous sodium sulphate and concentrated under reduced pressure to obtain 6-bromo-8-fluoro-4-isobutyl-3,4-dihydro-2H-benzo[b][1,4]oxazine (1800 mg, 94%) as a transparent oily compound. LCMS: 288 $[M+H]^+$

Step-3: Synthesis of 8-fluoro-4-isobutyl-6-(4,4,5,5-tetramethyl-1,3,2-dioxaborolan-2-yl)-3,4-dihydro-2H-benzo[b][1,4]oxazine To a stirred solution of 6-bromo-8-fluoro-4-isobutyl-3,4-dihydro-2H-benzo[b][1,4]oxazine (1800 mg, 6.27 mmol, 1 equiv) in dioxane (20 mL), was added 4,4,5,5-tetramethyl-2-(4,4,5,5-tetramethyl-1,3,2-dioxaborolan-2-yl)-1,3,2-dioxaborolane (2390 mg, 9.4 mmol, 1.5 equiv), Potassium acetate (1536 mg, 15.6 mmol, 2.5 equiv) and). Purged the reaction mixture with nitrogen gas for 15 min., Pd(dppf)Cl2.DCM (256 mg, 0.78 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (100 mL) and extracted with ethyl acetate (150 mL×2). Organic layer was washed with brine (150 mL) and water (150 mL). Organic layer was dried over anhydrous sodium sulphate and concentrated under reduced pressure to obtain 8-fluoro-4-isobutyl-6-(4,4,5,5-tetramethyl-1,3,2-dioxaborolan-2-yl)-3,4-dihydro-2H-benzo[b][1,4]oxazine (2000 mg, 95%) as a dark brown viscous compound. LCMS: 336 $[M+H]^+$

Step-4: Synthesis of 6-(2-chloro-5-fluoropyrimidin-4-yl)-8-fluoro-4-isobutyl-3,4-dihydro-2H-benzo[b][1,4]oxazine To a stirred solution of 2, 4-dichloro-5-fluoropyrimidine (1000 mg, 6.02 mmol, 1 equiv) in THF:Water (1:1=20 mL) was added 8-fluoro-4-isobutyl-6-(4,4,5,5-tetramethyl-1,3,2-dioxaborolan-2-yl)-3,4-dihydro-2H-benzo[b][1,4]oxazine (2018 mg, 6.02 mmol, 1 equiv), Potassium carbonate (1662 mg, 12.04 mmol, 2 equiv) and $Pd(PPh_3)_4$ (347 mg, 0.3 mmol, 0.05 equiv). The reaction mixture was allowed to stir at 80° C. for 4 h. Progress of the reaction was monitored by TLC and LCMS. After completion of the reaction, the reaction mixture was diluted with water (100 mL) and extracted wit ethyl acetate (150 mL×2). Organic layer was washed with water (100 mL) and brine (100 mL). Organic layer was dried over anhydrous sodium sulphate and concentrated under reduced pressure to obtain crude compound, which was purified by normal phase combi-flash to obtain 6-(2-chloro-5-fluoropyrimidin-4-yl)-8-fluoro-4-isobutyl-3,4-dihydro-2H-benzo[b][1,4]oxazine (1300 mg, 64%) as a yellow solid compound. LCMS: 340 $[M+H]^+$

Step-5: Synthesis of tert-butyl 4-(2-fluoro-4-((5-fluoro-4-(8-fluoro-4-isobutyl-3,4-dihydro-2H-benzo[b][1,4]oxazin-6-yl)pyrimidin-2-yl)amino)phenyl)piperidine-1-carboxylate To a solution of 6-(2-chloro-5-fluoropyrimidin-4-yl)-8-fluoro-4-isobutyl-3,4-dihydro-2H-benzo[b][1,4]oxazine (70 mg, 0.2 mmol, 1 equiv) in Dioxane (5 mL), was added tert-butyl 4-(4-amino-2-fluorophenyl)piperidine-1-carboxylate (63 mg, 0.22 mmol, 1.1 equiv) and cesium carbonate (98 mg, 0.3 mmol, 1.5 equiv). The reaction mixture was purged with nitrogen gas for 30 min., followed by the addition of palladium acetate (1 mg, 0.008 mmol, 0.02 equiv) and BINAP (5 mg, 0.004 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi flash to obtain tert-butyl 4-(2-fluoro-4-((5-fluoro-4-(8-fluoro-4-isobutyl-3,4-dihydro-2H-benzo[b][1,4]oxazin-6-yl)pyrimidin-2-yl)amino)phenyl)piperidine-1-carboxylate (100 mg, 83%) as a yellow solid compound. LCMS: 598 $[M+H]^+$

Step-6: Synthesis of 5-fluoro-N-(3-fluoro-4-(piperidin-4-yl) phenyl)-4-(8-fluoro-4-isobutyl-3,4-dihydro-2H-benzo[b][1,4]oxazin-6-yl)pyrimidin-2-amine tert-butyl 4-(2-fluoro-4-((5-fluoro-4-(8-fluoro-4-isobutyl-3,4-dihydro-2H-benzo[b][1,4]oxazin-6-yl)pyrimidin-2-yl)amino)phenyl)piperidine-1-carboxylate (100 mg, 0.16 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain crude compound, which was purified by making HCl salt to afford 5-fluoro-N-(3-fluoro-4-(piperidin-4-yl) phenyl)-4-(8-fluoro-4-isobutyl-3,4-dihydro-2H-benzo[b][1,4]oxazin-6-yl)pyrimidin-2-amine (90 mg, 83%) as a yellow color solid compound. LCMS: 498 $[M+H]^+$

Step-7: Synthesis of 5-fluoro-N-(3-fluoro-4-(1-methylpiperidin-4-yl) phenyl)-4-(8-fluoro-4-isobutyl-3,4-dihydro-2H-benzo[b][1,4]oxazin-6-yl) pyrimidin-2-amine To a stirred solution of 5-fluoro-N-(3-fluoro-4-(piperidin-4-yl)phenyl)-4-(8-fluoro-4-isobutyl-3,4-dihydro-2H-benzo[b][1,4]oxazin-6-yl)pyrimidin-2-amine (70 mg, 0.14 mmol, 1 equiv) in DCE (5 mL), was added Formaldehyde (40% in water) (0.02 mL, 0.42 mmol, 3 equiv), acetic acid (0.04 mL, 0.72 mmol, 5 equiv). The reaction mixture was allowed to stir at RT for 1 h. The reaction mixture was cooled to 0° C. NaCNBH$_3$ (27 mg, 0.43 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-N-(3-fluoro-4-(1-methylpiperidin-4-yl)phenyl)-4-(8-fluoro-4-isobutyl-3,4-dihydro-2H-benzo[b][1,4]oxazin-6-yl)pyrimidin-2-amine (5 mg, 7%) as a yellow solid compound. LCMS: 512 [M+H]$^+$; $^1$HNMR (400 MHz, DMSO-d$_6$) δ 9.93 (s, 1H), 8.61 (d, J=3.9 Hz, 1H), 7.78 (d, J=13.6 Hz, 1H), 7.46 (d, J=7.5 Hz, 1H), 7.21-7.32 (m, 2H), 7.01-7.21 (m, 1H), 4.30 (br. s., 2H), 3.47 (br. s., 2H), 3.33 (br. s., 2H), 3.13 (d, J=6.6 Hz, 2H), 2.85 (br. s., 2H), 2.67 (br. s., 3H), 2.08 (d, J=6.1 Hz, 2H), 1.86 (br. s., 4H), 0.90 ppm (d, J=6.6 Hz, 6H).

Example-85: Synthesis of N-(5-(1,4-diazepan-1-yl)pyridin-2-yl)-5-fluoro-4-(8-fluoro-4-isopropyl-3,4-dihydro-2H-benzo[b][1,4]oxazin-6-yl)pyrimidin-2-amine. (Compound 477)

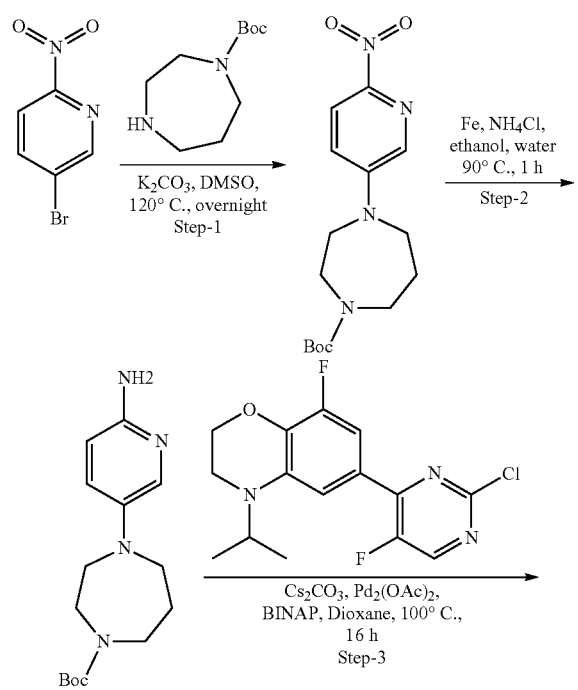

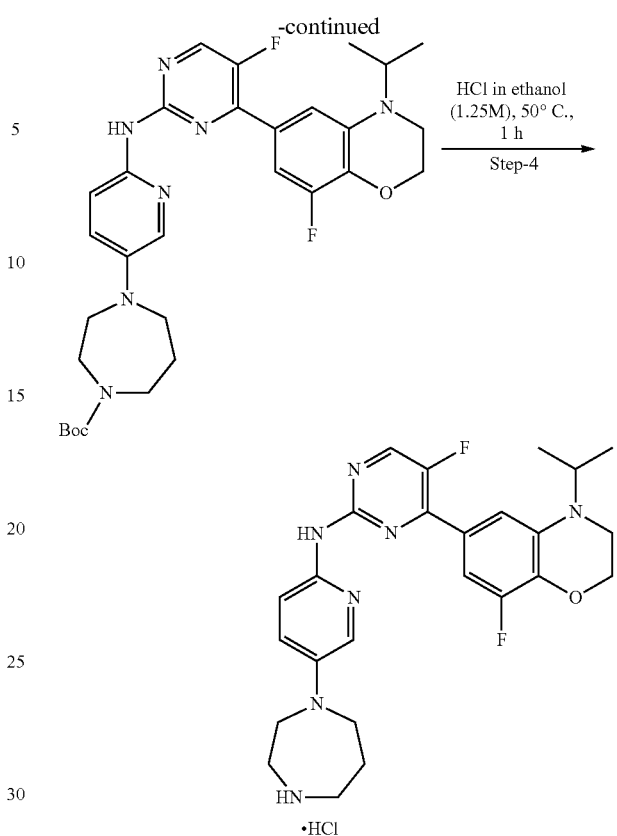

Step-1: Synthesis tert-butyl 4-(6-nitropyridin-3-yl)-1,4-diazepane-1-carboxylate To a stirred solution of 1,2-difluoro-4-nitrobenzene (500 mg, 2.47 mmol, 1 equiv) in DMSO (10 mL), was added K$_2$CO$_3$ (682 mg, 4.9 mmol, 2 equiv) and tert-butyl 1,4-diazepane-1-carboxylate (743 mg, 3.76 mmol, 1.5 equiv). The resultant reaction mixture was allowed to stir at 100° C. for overnight. Progress of the reaction was monitored by TLC and LCMS. After completion of the reaction, the mixture was diluted with ice water (50 mL) and extracted with ethyl acetate (150 mL). Organic layer was washed with water (50 mL) and brine solution (50 mL). Organic layer was dried over anhydrous sodium sulphate and concentrated under reduced pressure to obtain to obtain tert-butyl 4-(6-nitropyridin-3-yl)-1,4-diazepane-1-carboxylate (550 mg, 69%) as a brown oily compound.

LCMS: 323 [M+H]$^+$

Step-2: Synthesis of tert-butyl 4-(6-aminopyridin-3-yl)-1,4-diazepane-1-carboxylate To a stirred solution of tert-butyl 4-(6-nitropyridin-3-yl)-1,4-diazepane-1-carboxylate (550 mg, 1.7 mmol, 1 equiv) in ethanol (6 mL), water (2 mL), was added iron powder (287 mg, 5.12 mmol, 3 equiv) and ammonium chloride (184 mg, 3.4 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain tert-butyl 4-(6-aminopyridin-3-yl)-1, 4-diazepane-1-carboxylate (400 mg, 80%) as a dark brown color viscous compound. LCMS: 293 [M+H]+

Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-1,4-diazepane-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(6-aminopyridin-3-yl)-1,4-diazepane-1-carboxylate (96 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-1,4-diazepane-1-carboxylate (50 mg, 28%) as a yellow color solid compound. LCMS: 582 [M+H]+

Step-4: Synthesis of N-(5-(1,4-diazepan-1-yl)pyridin-2-yl)-5-fluoro-4-(8-fluoro-4-isopropyl-3,4-dihydro-2H-benzo[b][1,4]oxazin-6-yl)pyrimidin-2-amine tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-1,4-diazepane-1-carboxylate (35 mg, 0.06 mmol, 1 equiv) was taken in 1.25 M HCl in ethanol (5 mL) and the resultant reaction mixture was allowed to stir at RT for 1 h. Solvent was removed under reduced pressure and the residue was dried under lyophilizer to obtain N-(5-(1,4-diazepan-1-yl)pyridin-2-yl)-5-fluoro-4-(8-fluoro-4-isopropyl-3,4-dihydro-2H-benzo[b][1,4]oxazin-6-yl)pyrimidin-2-amine (HCl salt) (30 mg, 97%) as a yellow color solid compound. LCMS: 482 [M+H]+; 1HNMR (400 MHz, DMSO-$d_6$) δ 9.26 (br. s., 1H), 8.72 (d, J=3.1 Hz, 1H), 7.86 (br. s., 1H), 7.68-7.84 (m, 2H), 7.39 (s, 1H), 7.19 (d, J=11.4 Hz, 1H), 4.31 (d, J=3.5 Hz, 2H), 4.06-4.21 (m, 1H), 3.77 (br. s., 2H), 3.53 (br. s., 2H), 3.28-3.37 (m, 4H), 3.16 (br. s., 2H), 2.11 (br. s., 2H), 1.06-1.26 ppm (m, 6H).

Example-86: Synthesis of N-(5-(1,4-diazepan-1-yl)pyridin-2-yl)-4-(4-cyclopentyl-8-fluoro-3,4-dihydro-2H-benzo[b][1,4]oxazin-6-yl)-5-fluoropyrimidin-2-amine. (Compound 478)

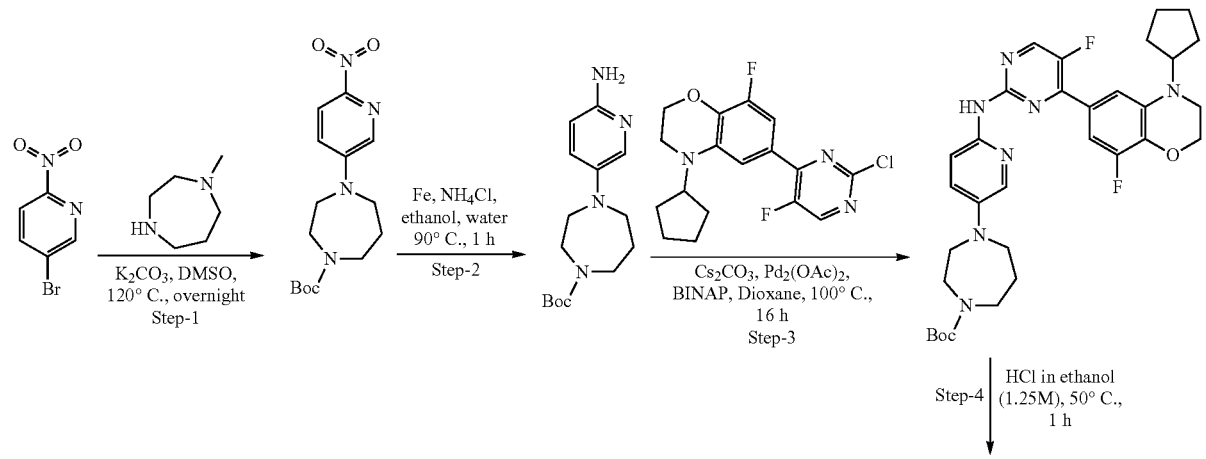

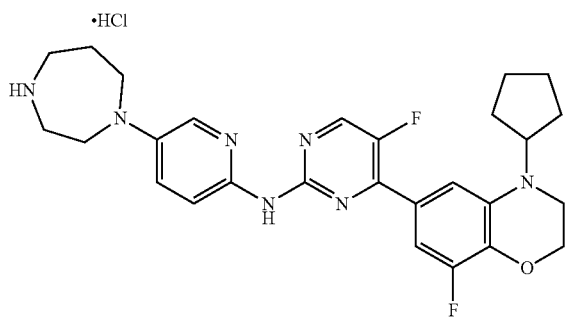

Step-1: Synthesis of tert-butyl 4-(6-nitropyridin-3-yl)-1, 4-diazepane-1-carboxylate To a stirred solution of 1, 2-difluoro-4-nitrobenzene (500 mg, 2.47 mmol, 1 equiv) in DMSO (10 mL), was added $K_2CO_3$ (682 mg, 4.9 mmol, 2 equiv) and tert-butyl 1, 4-diazepane-1-carboxylate (743 mg, 3.76 mmol, 1.5 equiv). The resultant reaction mixture was allowed to stir at 100° C. for overnight. Progress of the reaction was monitored by TLC and LCMS. After completion of the reaction, the mixture was diluted with ice water (50 mL) and extracted with ethyl acetate (150 mL). Organic layer was washed with water (50 mL) and brine solution (50 mL). Organic layer was dried over anhydrous sodium sulphate and concentrated under reduced pressure to obtain to obtain tert-butyl 4-(6-nitropyridin-3-yl)-1, 4-diazepane-1-carboxylate (550 mg, 69%) as a brown oily compound. LCMS: 323 $[M+H]^+$

Step-2: Synthesis of tert-butyl 4-(6-aminopyridin-3-yl)-1, 4-diazepane-1-carboxylate To a stirred solution of tert-butyl 4-(6-nitropyridin-3-yl)-1,4-diazepane-1-carboxylate (550 mg, 1.7 mmol, 1 equiv) in ethanol (6 mL), water (2 mL), was added iron powder (287 mg, 5.12 mmol, 3 equiv) and ammonium chloride (184 mg, 3.4 mmol, 2 equiv). The resultant reaction mixture was allowed to stir at 900 for 1 h. Progress of the reaction was monitored by TLC and LCMS. After completion of the reaction, the mixture was passes through celite bed and the filtrate was concentrated under reduced pressure to obtain tert-butyl 4-(6-aminopyridin-3-yl)-1, 4-diazepane-1-carboxylate (400 mg, 80%) as a dark brown color viscous compound. LCMS: 293 $[M+H]^+$

Step-3: Synthesis of tert-butyl 4-(6-((4-(4-cyclopentyl-8-fluoro-3,4-dihydro-2H-benzo[b][1,4]oxazin-6-yl)-5-fluoropyrimidin-2-yl)amino)pyridin-3-yl)-1,4-diazepane-1-carboxylate To a solution of 6-(2-chloro-5-fluoropyrimidin-4-yl)-4-cyclopentyl-8-fluoro-3,4-dihydro-2H-benzo[b][1,4]oxazine (100 mg, 0.3 mmol, 1 equiv) in dioxane (10 mL), was added tert-butyl 4-(6-aminopyridin-3-yl)-1,4-diazepane-1-carboxylate (92 mg, 0.33 mmol, 1.1 equiv) and cesium carbonate (147 mg, 0.45 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain tert-butyl 4-(6-((4-(4-cyclopentyl-8-fluoro-3,4-dihydro-2H-benzo[b][1,4]oxazin-6-yl)-5-fluoropyrimidin-2-yl)amino)pyridin-3-yl)-1,4-diazepane-1-carboxylate (20 mg, 12%) as a yellow color solid compound. LCMS: 608 $[M+H]^+$

Step-4: Synthesis of N-(5-(1, 4-diazepan-1-yl) pyridin-2-yl)-4-(4-cyclopentyl-8-fluoro-3,4-dihydro-2H-benzo[b][1,4]oxazin-6-yl)-5-fluoropyrimidin-2-amine tert-butyl 4-(6-((4-(4-cyclopentyl-8-fluoro-3,4-dihydro-2H-benzo[b][1,4]oxazin-6-yl)-5-fluoropyrimidin-2-yl)amino)pyridin-3-yl)-1,4-diazepane-1-carboxylate (mg, mmol, 1 equiv) was taken in 1.25 M HCl in ethanol (5 mL) and the resultant reaction mixture was allowed to stir at RT for 1 h. Solvent was removed under reduced pressure and the residue was dried under lyophilizer to obtain N-(5-(1,4-diazepan-1-yl)pyridin-2-yl)-4-(4-cyclopentyl-8-fluoro-3,4-dihydro-2H-benzo[b][1,4]oxazin-6-yl)-5-fluoropyrimidin-2-amine (HCl salt) (7 mg, 78%) as a yellow color solid compound. LCMS: 508 $[M+H]^+$; $^1$HNMR (400 MHz, DMSO-$d_6$) δ 9.12 (br. s., 1H), 8.69 (br. s., 1H), 7.84 (br. s., 3H), 7.43 (br. s., 1H), 7.20 (d, J=10.1 Hz, 1H), 4.33 (br. s., 2H), 4.26 (br. s., 1H), 3.76 (br. s., 2H), 3.52 (d, J=5.3 Hz, 1H), 3.35 (br. s., 3H), 3.26 (br. s., 2H), 3.17 (br. s., 3H), 2.10 (br. s., 2H), 1.88 (br. s., 1H), 1.71 (br. s., 2H), 1.62 ppm (br. s., 4H).

Example-87: Synthesis of 5-fluoro-4-(8-fluoro-4-isobutyl-3,4-dihydro-2H-benzo[b][1,4]oxazin-6-yl)-N-(5-(1-methylpiperidin-4-yl)pyridin-2-yl)pyrimidin-2-amine. (Compound 479)

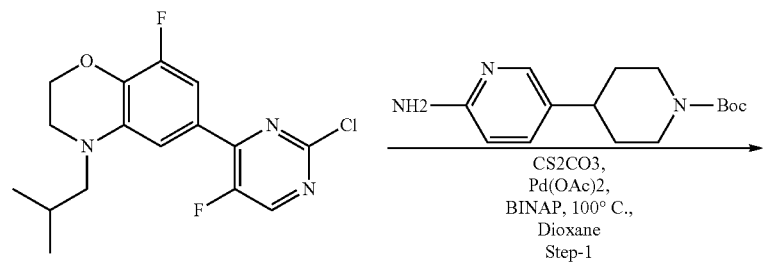

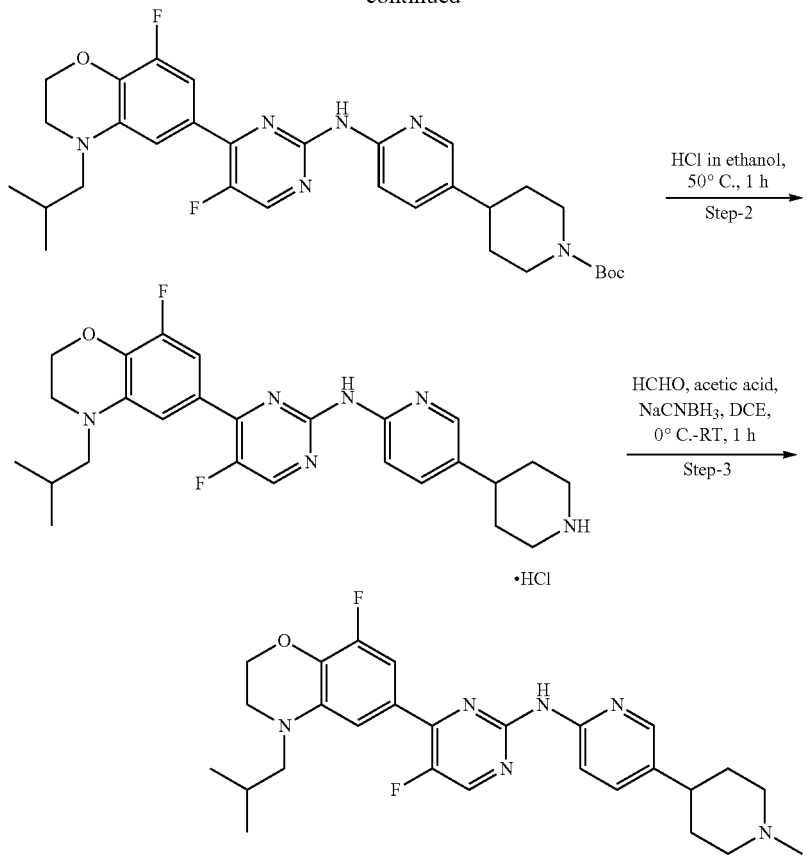

Step-1: Synthesis of tert-butyl 4-(6-((5-fluoro-4-(8-fluoro-4-isobutyl-3,4-dihydro-2H-benzo[b][1,4]oxazin-6-yl)pyrimidin-2-yl)amino)pyridin-3-yl)piperidine-1-carboxylate To a solution of 6-(2-chloro-5-fluoropyrimidin-4-yl)-8-fluoro-4-isobutyl-3,4-dihydro-2H-benzo[b][1,4]oxazine (70 mg, 0.2 mmol, 1 equiv) in Dioxane (5 mL), was added tert-butyl 4-(6-aminopyridin-3-yl)piperidine-1-carboxylate (63 mg, 0.22 mmol, 1.1 equiv) and cesium carbonate (98 mg, 0.3 mmol, 1.5 equiv). The reaction mixture was purged with nitrogen gas for 30 min., followed by the addition of palladium acetate (1 mg, 0.008 mmol, 0.02 equiv) and BINAP (5 mg, 0.004 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi flash to obtain tert-butyl 4-(6-((5-fluoro-4-(8-fluoro-4-isobutyl-3,4-dihydro-2H-benzo[b][1,4]oxazin-6-yl)pyrimidin-2-yl)amino)pyridin-3-yl)piperidine-1-carboxylate (100 mg, 83%) as a yellow solid compound. LCMS: 581 [M+H]$^+$

Step-2: Synthesis of 5-fluoro-4-(8-fluoro-4-isobutyl-3,4-dihydro-2H-benzo[b][1,4]oxazin-6-yl)-N-(5-(piperidin-4-yl)pyridin-2-yl)pyrimidin-2-amine tert-butyl 4-(6-((5-fluoro-4-(8-fluoro-4-isobutyl-3,4-dihydro-2H-benzo[b][1,4]oxazin-6-yl)pyrimidin-2-yl)amino)pyridin-3-yl)piperidine-1-carboxylate (100 mg, 0.17 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain crude compound, which was purified by making HCl salt to afford 5-fluoro-4-(8-fluoro-4-isobutyl-3,4-dihydro-2H-benzo[b][1,4]oxazin-6-yl)-N-(5-(piperidin-4-yl)pyridin-2-yl)pyrimidin-2-amine (70 mg, 84%) as a yellow color solid compound. LCMS: 481 [M+H]$^+$

Step-3: Synthesis of 5-fluoro-4-(8-fluoro-4-isobutyl-3,4-dihydro-2H-benzo[b][1,4]oxazin-6-yl)-N-(5-(1-methylpiperidin-4-yl)pyridin-2-yl)pyrimidin-2-amine To a stirred solution of 5-fluoro-4-(8-fluoro-4-isobutyl-3,4-dihydro-2H-benzo[b][1,4]oxazin-6-yl)-N-(5-(piperidin-4-yl)pyridin-2-yl)pyrimidin-2-amine (70 mg, 0.14 mmol, 1 equiv) in DCE (3 mL), was added Formaldehyde (40% in water) (0.02 mL, 0.42 mmol, 3 equiv), acetic acid (0.04 mL, 0.72 mmol, 5 equiv). The reaction mixture was allowed to stir at RT for 1 h. The reaction mixture was cooled to 0° C. NaCNBH$_3$ (27 mg, 0.42 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-4-(8-fluoro-4-isobutyl-3,4-dihydro-2H-benzo[b][1,4]oxazin-6-yl)-N-(5-(1-methylpiperidin-4-yl)pyridin-2-yl)pyrimidin-2-amine (3 mg, 4%) as a yellow color solid compound. LCMS: 495 M+H]$^+$; $^1$HNMR (400 MHz, DMSO-$d_6$) δ 9.88 (s, 1H), 8.61 (d, J=3.5 Hz, 1H), 8.32 (br. s., 1H), 8.05-8.21 (m, 1H), 7.63 (d, J=8.8 Hz, 1H), 7.29 (br. s., 1H), 7.16 (d, J=11.4 Hz, 1H), 4.30 (br. s., 2H), 3.46 (br. s., 2H), 3.13 (d, J=7.5 Hz, 2H), 2.96 (br. s., 1H), 2.85 (br. s., 1H), 2.19 (s, 3H), 2.05 (d, J=14.5 Hz, 1H), 1.96 (t, J=10.1 Hz, 1H), 1.54-1.77 (m, 4H), 1.45 (br. s., 2H), 0.91 ppm (d, J=6.6 Hz, 6H).

Example-88: Synthesis of N-(4-(4-(dimethylamino)piperidin-1-yl)-3-fluorophenyl)-5-fluoro-4-(8-fluoro-4-isobutyl-3,4-dihydro-2H-benzo[b][1,4]oxazin-6-yl)pyrimidin-2-amine. (Compound 480)

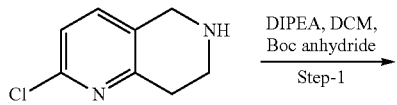

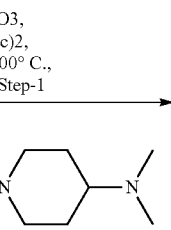

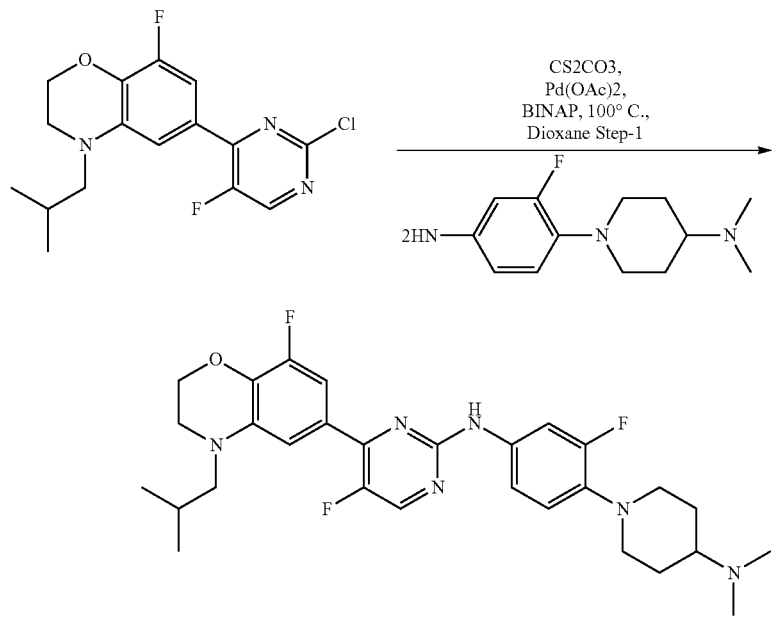

To a solution of 6-(2-chloro-5-fluoropyrimidin-4-yl)-8-fluoro-4-isobutyl-3,4-dihydro-2H-benzo[b][1,4]oxazine (100 mg, 0.29 mmol, 1 equiv) in Dioxane (5 mL), was added 1-(4-amino-2-fluorophenyl)-N,N-dimethylpiperidin-4-amine (76 mg, 0.32 mmol, 1.1 equiv) and cesium carbonate (141 mg, 0.43 mmol, 1.5 equiv). The reaction mixture was purged with nitrogen gas for 30 min., followed by the addition of palladium acetate (1.3 mg, 0.005 mmol, 0.02 equiv) and BINAP (7 mg, 0.01 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by reverse phase HPLC to obtain N-(4-(4-(dimethylamino)piperidin-1-yl)-3-fluorophenyl)-5-fluoro-4-(8-fluoro-4-isobutyl-3,4-dihydro-2H-benzo[b][1,4]oxazin-6-yl)pyrimidin-2-amine (12 mg, 8%) as a yellow solid compound. LCMS: 541 [M+H]$^+$; $^1$HNMR (400 MHz, DMSO-$d_6$) δ 9.72 (s, 1H), 8.56 (d, J=3.9 Hz, 1H), 7.68 (s, 1H), 7.71 (s, 1H), 7.39 (d, J=7.5 Hz, 1H), 7.12 (d, J=11.4 Hz, 1H), 6.86-7.01 (m, 1H), 4.29 (br. s., 2H), 3.46-3.33 (br. s., 4H), 3.13 (d, J=6.6 Hz, 2H), 2.52-2.76 (m, 3H), 2.21 (s, 6H), 2.05 (d, J=6.6 Hz, 1H), 1.83 (d, J=11.0 Hz, 2H), 1.53 (d, J=12.3 Hz, 2H), 0.90 ppm (d, J=6.6 Hz, 6H).

Example-89: Synthesis N-(5-fluoro-4-(8-fluoro-4-isopropyl-3,4-dihydro-2H-benzo[b][1,4]oxazin-6-yl)pyrimidin-2-yl)-5,6,7,8-tetrahydro-1, 6-naphthyridin-2-amine. (Compound 481)

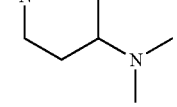

-continued

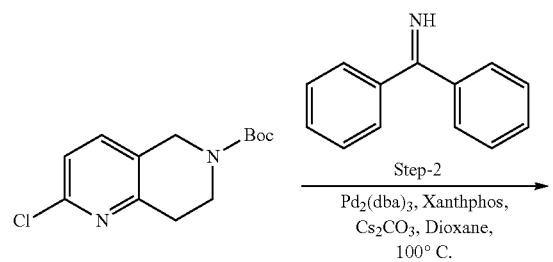

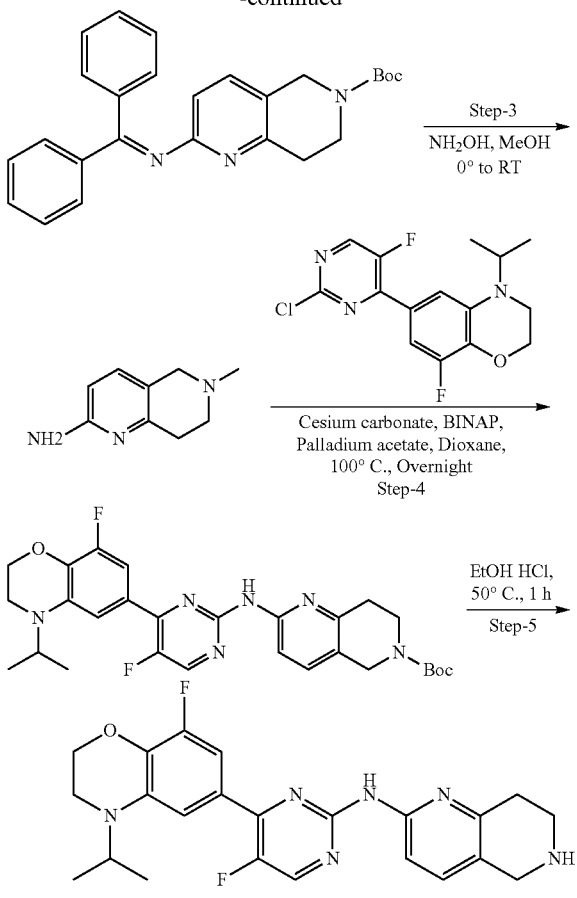

Step-1: Synthesis of tert-butyl 2-chloro-7,8-dihydro-1,6-naphthyridine-6(5H)-carboxylate To the solution of 2-chloro-5,6,7,8-tetrahydro-1,6-naphthyridine (2000 mg, 11.9 mol, 1 equiv), taken in DCM (30 mL), was added DIPEA (1.84 g, 14.28 mmol, 1.2 equiv) At 0° C. then was added Boc Anhydride (2.850 mg, 18.08 mmol, 1.1 equiv), Resulted reaction mixture was allow to stir RT for 2 h. Progress of Reaction was monitored by LCMs/TLC. After completion the reaction mixture was diluted with water and extracted with DCM (200 mL). organic layer was washed with water (30 mL) and brine solution (40 mL), resulted organic layer was dried over anhydrous sodium sulphate and purified by combi-flash column to tert-butyl 2-chloro-7,8-dihydro-1,6-naphthyridine-6(5H)-carboxylate (2.2 g of x %) as yellow colour solid LCMS: 269 [M+H]$^+$

Step-2: Synthesis of tert-butyl 2-((diphenylmethylene)amino)-7,8-dihydro-1,6-naphthyridine-6(5H)-carboxylate To the solution of tert-butyl 2-chloro-7,8-dihydro-1,6-naphthyridine-6(5H)-carboxylate (1 g, 3.73 mmol, 1 equiv), taken in dioxane (20 mL) was added diphenylmethanimine (0.74 g, 4.13 mmol, 1.1 equiv), cesium carbonate (2.42 g, 7.46 mmol, 1.5 equiv). The reaction mixture was degassed with nitrogen gas for 5 min., followed by the addition of Pd$_2$dba$_3$ (340 mg, 0.37 mmol, 0.1 equiv) and xanthphos (740 mg, 0.74 mmol, 0.2 equiv). The resultant reaction mixture was allowed to stir at 100° C. for 16 h. Progress of the reaction was monitored by TLC and LCMS. After completion of the reaction, diluted with water (50 mL) and extracted with ethyl acetate (200 mL). Organic layer was washed with water (100 mL) and brine solution (50 mL). Organic layer was dried over anhydrous sodium sulphate and concentrated under reduced pressure to obtain crude, which was purified by normal phase combi flash to obtain tert-butyl 2-((diphenylmethylene)amino)-7,8-dihydro-1,6-naphthyridine-6(5H)-carboxylate (1.1 g) as a yellow solid compound. LCMS: 414 [M+H]$^+$

Step-3: Synthesis of tert-butyl 2-amino-7,8-dihydro-1,6-naphthyridine-6(5H)-carboxylate To a solution of tert-butyl 2-((diphenylmethylene)amino)-7,8-dihydro-1,6-naphthyridine-6(5H)-carboxylate (1469 mg, 3.5 mmol, 1 equiv) taken in methanol (25 mL), was added hydroxylamine hydrochloride (476 mg, 7 mmol, 2 equiv), resulted reaction mixture allowed to stir at RT for 3 h. Progress of the reaction was monitored by TLC and LCMS. After completion of the reaction, diluted with water (30 mL) and extracted with ethyl acetate (100 mL). Organic layer was washed with water (20 mL) and brine solution (30 mL). Organic layer was dried over anhydrous sodium sulphate and concentrated under reduced pressure to obtain crude, which was purified by normal phase combi flash to obtain tert-butyl 2-((diphenylmethylene)amino)-7,8-dihydro-1,6-naphthyridine-6(5H)-carboxylate (0.57 g of 95.83%) as a yellow solid compound LCMS: 250 [M+H]$^+$

Step-4: Synthesis of tert-butyl 2-((5-fluoro-4-(8-fluoro-4-isopropyl-3,4-dihydro-2H-benzo[b][1,4]oxazin-6-yl)pyrimidin-2-yl)amino)-7,8-dihydro-1,6-naphthyridine-6(5H)-carboxylate To a solution of 6-(2-chloro-5-fluoropyrimidin-4-yl)-8-fluoro-4-isopropyl-3,4-dihydro-2H-benzo[b][1,4]oxazine (100 mg, 0.31 mmol, 1 equiv) in dioxane (4 mL), was added tert-butyl 2-((diphenylmethylene)amino)-7,8-dihydro-1,6-naphthyridine-6(5H)-carboxylate (84 mg, 0.33 mmol, 1.2 equiv) and cesium carbonate (151 mg, 0.46 mmol, 1.5 equiv). The reaction mixture was degassed by nitrogen gas for 10 min., followed by the addition of palladium acetate (7 mg, 0.031 mmol, 0.1 equiv) and BINAP (39 mg, 0.062 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain tert-butyl 2-((5-fluoro-4-(8-fluoro-4-isopropyl-3,4-dihydro-2H-benzo[b][1,4]oxazin-6-yl)pyrimidin-2-yl)amino)-7,8-dihydro-1,6-naphthyridine-6(5H)-carboxylate (135 mg crude). Used directly for next step LCMS: 539 [M+H]$^+$

Step-5: Synthesis of N-(5-fluoro-4-(8-fluoro-4-isopropyl-3,4-dihydro-2H-benzo[b][1,4]oxazin-6-yl)pyrimidin-2-yl)-5,6,7,8-tetrahydro-1,6-naphthyridin-2-amine A solution of tert-butyl 2-((5-fluoro-4-(8-fluoro-4-isopropyl-3,4-dihydro-2H-benzo[b][1,4]oxazin-6-yl)pyrimidin-2-yl)amino)-7,8-dihydro-1,6-naphthyridine-6(5H)-carboxylate (135 mg crude) in 1.25 M HCl in ethanol (5 mL) was allowed to stir for 1 h at 50° C. Progress of the reaction was monitored by LCMS. After completion of the reaction, solvent was removed under reduced pressure to obtain crude which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-5,6,7,8-tetrahydro-1,6-naphthyridin-2-amine (20 mg) as a pale yellow solid compound. LCMS: 439 [M+H]$^+$;

$^1$HNMR: (400 MHz, DMSO-d6) δ 9.83 (s, 1H), 8.59 (d, J=4.0 Hz, 1H), 8.30-8.20 (m, 1H), 8.01 (d, J=8.4 Hz, 1H), 7.51 (s, 1H), 7.41 (d, J=8.5 Hz, 1H), 7.19 (d, J=11.6 Hz, 1H), 4.30 (t, J=4.3 Hz, 2H), 4.17 (p, J=6.5 Hz, 1H), 3.86 (s, 2H), 3.34-3.20 (m, 4H), 3.07 (s, 2H), 2.74 (t, J=5.8 Hz, 2H), 1.19 (d, J=6.5 Hz, 7H).

Example-90: Synthesis of N-(4-(4-cyclobutyl-8-fluoro-3,4-dihydro-2H-benzo[b][1,4]oxazin-6-yl)-5-fluoropyrimidin-2-yl)-5,6,7,8-tetrahydro-1,6-naphthyridin-2-amine. (Compound 482)

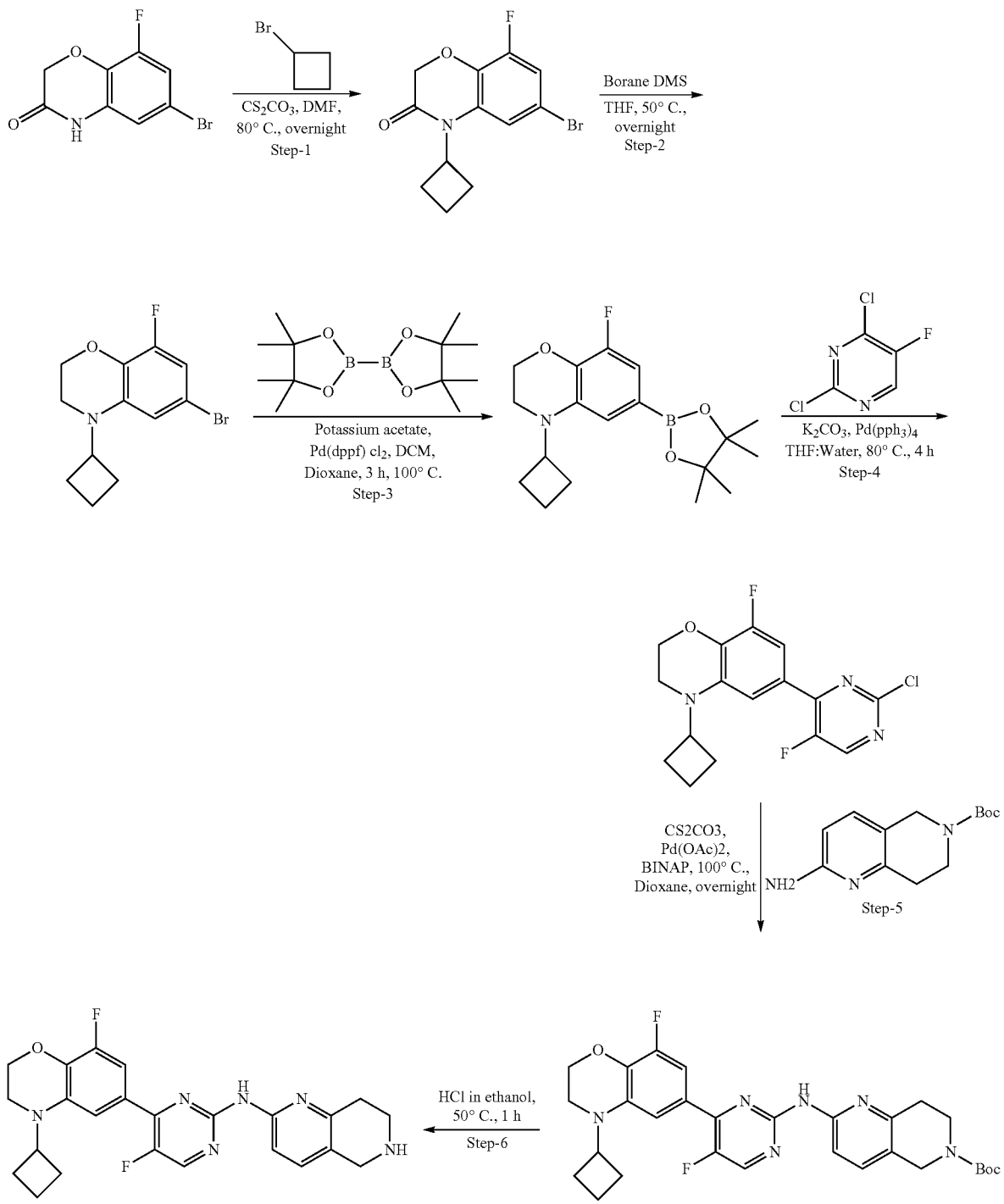

Step-1: Synthesis of 6-bromo-4-cyclobutyl-8-fluoro-2H-benzo[b][1,4]oxazin-3(4H)-one To a stirred solution of 6-bromo-8-fluoro-2H-benzo[b][1,4]oxazin-3 (4H)-one (2500 mg, 10.1 mmol, 1 equiv) in DMF (20 mL), was added $CS_2CO_3$ (6618 mg, 20.3 mmol, 2 equiv) and bromocyclobutane (1.9 mL, 20.3 mmol, 2 equiv). The reaction mixture was allowed to stir at 80° C. for overnight. Progress of the reaction was monitored by TLC and LCMS. After completion of the reaction, the reaction mixture was diluted with water (100 mL) and extracted with ethyl acetate (150 mL×2). Organic layer was washed with water (100 mL), dried over anhydrous sodium sulphate and concentrated under reduced pressure to obtain 6-bromo-4-cyclobutyl-8-fluoro-2H-benzo[b][1,4]oxazin-3(4H)-one (2500 mg, 82%) as a brown color viscous compound. LCMS: 300 $[M+H]^+$

Step-2: Synthesis of 6-bromo-4-cyclobutyl-8-fluoro-3,4-dihydro-2H-benzo[b][1,4]oxazine To a stirred solution of 6-bromo-4-cyclobutyl-8-fluoro-2H-benzo[b][1,4]oxazin-3(4H)-one (2000 mg, 6.6 mmol, 1 equiv) in THF (20 mL), was added $BH_3.DMS$ (2M in THF) (13 mL, 26.8 mmol, 4 equiv) at 0° C. drop wise. The reaction mixture was allowed to stir at 50° C. for overnight. Progress of the reaction was monitored by TLC and LCMS. After completion of the reaction, the reaction mixture was quenched with saturated solution of $NaHCO_3$ (100 mL) and extracted with ethyl acetate (100 mL×2). Organic layer was washed with water (100 mL), dried over anhydrous sodium sulphate and concentrated under reduced pressure to obtain 6-bromo-4-cyclobutyl-8-fluoro-3,4-dihydro-2H-benzo[b][1,4]oxazine (1100 mg, 58%) as a transparent oily compound. LCMS: 286 $[M+H]^+$

Step-3: Synthesis of 4-cyclobutyl-8-fluoro-6-(4,4,5,5-tetramethyl-1,3,2-dioxaborolan-2-yl)-3,4-dihydro-2H-benzo[b][1,4]oxazine 6-bromo-4-cyclobutyl-8-fluoro-3,4-dihydro-2H-benzo[b][1,4]oxazine (1100 mg, 3.8 mmol, 1 equiv), 4,4,5,5-tetramethyl-2-(4,4,5,5-tetramethyl-1,3,2-dioxaborolan-2-yl)-1,3,2-dioxaborolane (1471 mg, 5.7 mmol, 1.5 equiv), Potassium acetate (931 mg, 9.5 mmol, 2.5 equiv) and dioxane (15 mL) were charged in a 25 mL glass bottle. Purged the reaction mixture with nitrogen gas for 15 min., Pd(dppf)Cl2. DCM (155 mg, 0.19 mmol, 0.05 equiv) was added to above mixture and the reaction mixture was allowed to stir at 100° C. for 3 h. Progress of the reaction was monitored by TLC and LCMS. After completion of the reaction, the reaction mixture was diluted with water (30 mL) and extracted with ethyl acetate (100 mL×2). Organic layer was washed with brine (50 mL) and water (50 mL). Organic layer was dried over anhydrous sodium sulphate and concentrated under reduced pressure to obtain 4-cyclobutyl-8-fluoro-6-(4,4,5,5-tetramethyl-1,3,2-dioxaborolan-2-yl)-3,4-dihydro-2H-benzo[b][1,4]oxazine (1200 mg, 93%) as a dark brown viscous compound. LCMS: 334 $[M+H]^+$

Step-4: Synthesis of 6-(2-chloro-5-fluoropyrimidin-4-yl)-4-cyclobutyl-8-fluoro-3, 4-dihydro-2H-benzo[b][1,4]oxazine To a stirred solution of 2, 4-dichloro-5-fluoropyrimidine (600 mg, 3.16 mmol, 1 equiv) in THF:Water (1:1=16 mL) was added 4-cyclobutyl-8-fluoro-6-(4,4,5,5-tetramethyl-1,3,2-dioxaborolan-2-yl)-3,4-dihydro-2H-benzo[b][1,4]oxazine (1200 mg, 3.6 mmol, 1 equiv), Potassium carbonate (998 mg, 7.22 mmol, 2 equiv) and $Pd(PPh_3)_4$ (208 mg, 0.18 mmol, 0.05 equiv). The reaction mixture was allowed to stir at 80° C. for 4 h. Progress of the reaction was monitored by TLC and LCMS. After completion of the reaction, the reaction mixture was diluted with water (30 mL) and extracted wit ethyl acetate (100 mL×2). Organic layer was washed with water (100 mL) and brine (100 mL). Organic layer was dried over anhydrous sodium sulphate and concentrated under reduced pressure to obtain crude compound, which was purified by normal phase combi-flash to obtain 6-(2-chloro-5-fluoropyrimidin-4-yl)-4-cyclobutyl-8-fluoro-3,4-dihydro-2H-benzo[b][1,4]oxazine (500 mg, 41%) as a yellow color solid compound. LCMS: 338 $[M+H]^+$

Step-5: Synthesis of 1-(2-((4-(4-cyclobutyl-8-fluoro-3,4-dihydro-2H-benzo[b][1,4]oxazin-6-yl)-5-fluoropyrimidin-2-yl)amino)-7,8-dihydro-1,6-naphthyridin-6(5H)-yl)-2,2-dimethylpropan-1-one To a solution of 6-(2-chloro-5-fluoropyrimidin-4-yl)-4-cyclobutyl-8-fluoro-3,4-dihydro-2H-benzo[b][1,4]oxazine (100 mg, 0.29 mmol, 1 equiv) in Dioxane (5 mL), was added tert-butyl 2-amino-7,8-dihydro-1,6-naphthyridine-6(5H)-carboxylate (81 mg, 0.32 mmol, 1.1 equiv) and cesium carbonate (142 mg, 0.43 mmol, 1.5 equiv). The reaction mixture was purged with nitrogen gas for 30 min., followed by the addition of palladium acetate (2 mg, 0.006 mmol, 0.02 equiv) and BINAP (7 mg, 0.013 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi flash to obtain 1-(2-((4-(4-cyclobutyl-8-fluoro-3,4-dihydro-2H-benzo[b][1,4]oxazin-6-yl)-5-fluoropyrimidin-2-yl)amino)-7,8-dihydro-1,6-naphthyridin-6(5H)-yl)-2,2-dimethylpropan-1-one (100 mg, 61%) as a yellow color solid compound. LCMS: 551 $[M+H]^+$

Step-6: Synthesis of N-(4-(4-cyclobutyl-8-fluoro-3,4-dihydro-2H-benzo[b][1,4]oxazin-6-yl)-5-fluoropyrimidin-2-yl)-5,6,7,8-tetrahydro-1,6-naphthyridin-2-amine 1-(2-((4-(4-cyclobutyl-8-fluoro-3,4-dihydro-2H-benzo[b][1,4]oxazin-6-yl)-5-fluoropyrimidin-2-yl)amino)-7,8-dihydro-1,6-naphthyridin-6(5H)-yl)-2,2-dimethylpropan-1-one (100 mg, 0.18 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure to obtain the residue, which was purified by reverse phase HPLC to obtain N-(4-(4-cyclobutyl-8-fluoro-3,4-dihydro-2H-benzo[b][1,4]oxazin-6-yl)-5-fluoropyrimidin-2-yl)-5,6,7,8-tetrahydro-1,6-naphthyridin-2-amine (20 mg, 24%) as a light orange color solid compound. LCMS: 451 $[M+H]^+$; $^1$HNMR (400 MHz, DMSO-$d_6$) δ 10.12 (s, 1H), 9.04 (br. s., 1H), 8.64 (d, J=3.9 Hz, 1H), 8.15 (d, J=8.3 Hz, 1H), 7.64 (d, J=8.8 Hz, 1H), 7.36 (s, 1H), 7.27 (s, 1H), 4.37 (d, J=3.9 Hz, 2H), 4.27 (br. s., 2H), 3.89-4.09 (m, 1H), 3.51 (br. s., 2H), 3.31 (br. s., 2H), 3.01 (t, J=5.7 Hz, 2H), 2.27 (br. s., 2H), 2.14 (d, J=11.0 Hz, 2H), 1.73 ppm (dt, J=9.4, 4.9 Hz, 2H).

Example-91: Synthesis of N-(5-fluoro-4-(8-fluoro-4-isobutyl-3,4-dihydro-2H-benzo[b][1,4]oxazin-6-yl)pyrimidin-2-yl)-5,6,7,8-tetrahydro-1,6-naphthyridin-2-amine. (Compound 483)

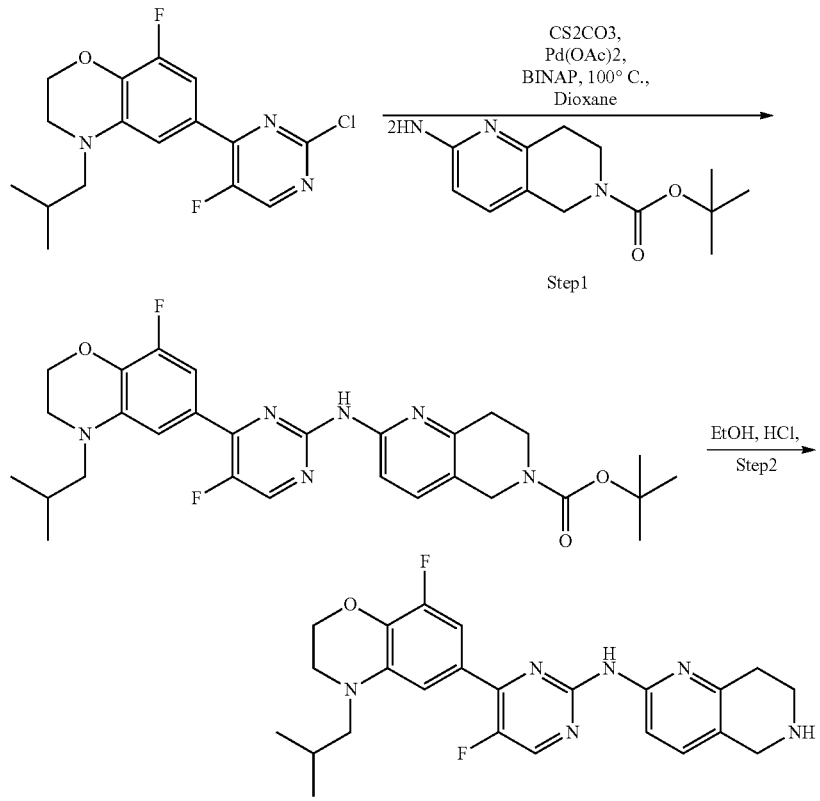

Step-1: Synthesis of tert-butyl 2-((5-fluoro-4-(8-fluoro-4-isobutyl-3,4-dihydro-2H-benzo[b][1,4]oxazin-6-yl)pyrimidin-2-yl)amino)-7,8-dihydro-1,6-naphthyridine-6(5H)-carboxylate To a solution of 6-(2-chloro-5-fluoropyrimidin-4-yl)-8-fluoro-4-isobutyl-3,4-dihydro-2H-benzo[b][1,4]oxazine (100 mg, 0.31 mmol, 1 equiv) in dioxane (4 mL), was added tert-butyl 2-amino-7,8-dihydro-1,6-naphthyridine-6(5H)-carboxylate (81 mg, 0.33 mmol, 1.1 equiv) and cesium carbonate (188 mg, 0.58 mmol, 2 equiv). The reaction mixture was degassed by nitrogen gas for 10 min., followed by the addition of palladium acetate (7 mg, 0.03 mmol, 0.1 equiv) and BINAP (36 mg, 0.06 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain tert-butyl 2-((5-fluoro-4-(8-fluoro-4-isobutyl-3,4-dihydro-2H-benzo[b][1,4]oxazin-6-yl)pyrimidin-2-yl)amino)-7,8-dihydro-1,6-naphthyridine-6(5H)-carboxylate (135 mg crude). Used directly for next step. LCMS: 553 [M+H]$^+$ Step-2: Synthesis of N-(5-fluoro-4-(8-fluoro-4-isobutyl-3,4-dihydro-2H-benzo[b][1,4]oxazin-6-yl)pyrimidin-2-yl)-5,6,7,8-tetrahydro-1,6-naphthyridin-2-amine A solution of tert-butyl 2-((5-fluoro-4-(8-fluoro-4-isobutyl-3,4-dihydro-2H-benzo[b][1,4]oxazin-6-yl)pyrimidin-2-yl)amino)-7,8-dihydro-1,6-naphthyridine-6(5H)-carboxylate (135 mg crude) in 1.25 M HCl in ethanol (5 mL) was allowed to stir for 1 h at 50° C. Progress of the reaction was monitored by LCMS. After completion of the reaction, solvent was removed under reduced pressure to obtain crude which was purified by reverse phase HPLC to afford N-(5-fluoro-4-(8-fluoro-4-isobutyl-3,4-dihydro-2H-benzo[b][1,4]oxazin-6-yl)pyrimidin-2-yl)-5,6,7,8-tetrahydro-1,6-naphthyridin-2-amine (10 mg) as a pale yellow solid compound. LCMS: 453 [M+H]$^+$;

$^1$HNMR: (400 MHz, DMSO-d6) δ 9.74 (s, 1H), 8.57 (d, J=4.0 Hz, 1H), 8.29 (s, 1H), 7.72 (dd, J=15.3, 2.5 Hz, 1H), 7.44 (s, 1H), 7.36 (dd, J=8.8, 2.5 Hz, 1H), 7.16 (d, J=11.4 Hz, 1H), 6.97 (t, J=9.4 Hz, 1H), 4.30 (t, J=4.4 Hz, 2H), 4.16 (p, J=6.6 Hz, 1H), 3.30 (dd, J=9.6, 5.2 Hz, 4H), 2.63-2.54 (m, 2H), 2.22 (s, 7H), 1.84 (dd, J=12.7, 3.6 Hz, 2H), 1.54 (tt, J=13.3, 6.7 Hz, 2H), 1.18 (d, J=6.5 Hz, 6H).

Example-92: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-methylpiperidin-4-ol. (Compound 484)

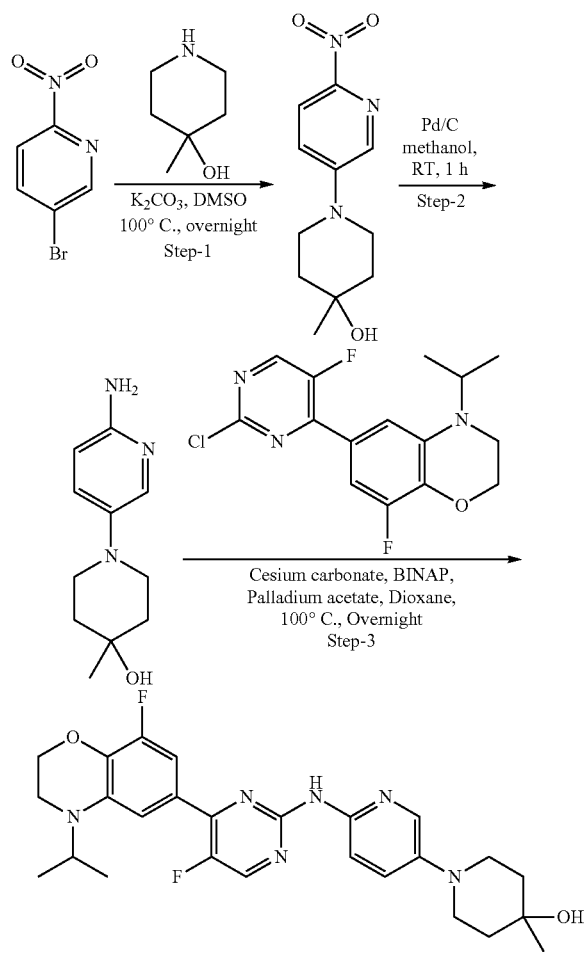

Step-1: Synthesis of 4-methyl-1-(6-nitropyridin-3-yl) piperidin-4-ol

To a stirred solution of 5-bromo-2-nitropyridine (500 mg, 2.47 mmol, 1 equiv) in DMSO (10 mL), was added $K_2CO_3$ (683 mg, 4.95 mmol, 2 equiv) and 4-methylpiperidin-4-ol (427 mg, 3.7 mmol, 1.5 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain 4-methyl-1-(6-nitropyridin-3-yl)piperidin-4-ol (500 mg, 85%) as a yellow solid compound. LCMS: 238 [M+H]$^+$ Step-2: Synthesis of 1-(6-aminopyridin-3-yl)-4-methylpiperidin-4-ol To a stirred solution of 4-methyl-1-(6-nitropyridin-3-yl) piperidin-4-ol (200 mg, 0.84 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 1-(6-aminopyridin-3-yl)-4-methylpiperidin-4-ol (150 mg, 86%) as a white color solid compound. LCMS: 208 [M+H]$^+$ Step-3: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-methylpiperidin-4-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (3 mL), was added 1-(6-aminopyridin-3-yl)-4-methylpiperidin-4-ol (68 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 1-(6-((5-fluoro-4-(8-fluoro-4-isopropyl-3,4-dihydro-2H-benzo[b][1,4]oxazin-6-yl)pyrimidin-2-yl) amino)pyridin-3-yl)-4-methylpiperidin-4-ol (120 mg, 78%) as a yellow color solid compound. LCMS: 497 [M+H]$^+$; $^1$HNMR (400 MHz, DMSO-$d_6$) δ 9.63 (s, 1H), 8.55 (d, J=3.9 Hz, 1H), 7.90-8.08 (m, 2H), 7.46 (s, 1H), 7.37 (dd, J=9.0, 2.9 Hz, 1H), 7.17 (d, J=11.8 Hz, 1H), 5.75 (s, 1H), 4.23-4.32 (m, 2H), 4.05-4.17 (m, 1H), 3.24 (d, J=12.3 Hz, 4H), 2.97-3.12 (m, 2H), 1.57 (d, J=4.4 Hz, 4H), 1.05-1.30 ppm (m, 9H).

Example-93: Synthesis of (1-(6-((5-fluoro-4-(8-fluoro-4-isopropyl-3,4-dihydro-2H-benzo[b][,4]oxazin-6-yl)pyrimidin-2-yl)amino)pyridin-3-yl) piperidin-4-yl)methanol. (Compound 485)

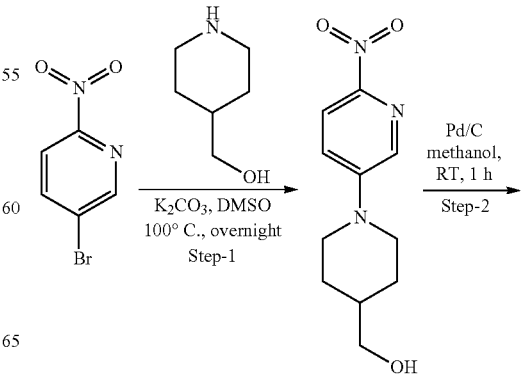

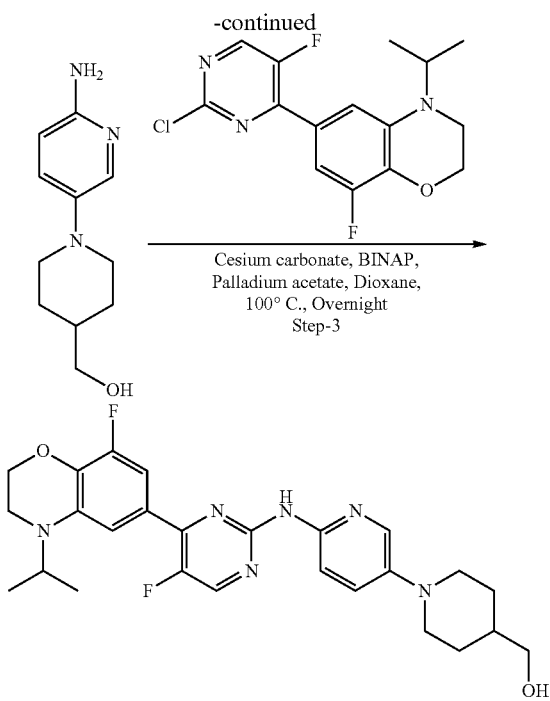

Step-1: Synthesis of (1-(6-nitropyridin-3-yl) piperidin-4-yl) methanol

To a stirred solution of 5-bromo-2-nitropyridine (500 mg, 2.47 mmol, 1 equiv) in DMSO (10 mL), was added K₂CO₃ (683 mg, 4.95 mmol, 2 equiv) and piperidin-4-ylmethanol (427 mg, 3.71 mmol, 1.5 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain (1-(6-nitropyridin-3-yl)piperidin-4-yl)methanol (330 mg, 56%) as a yellow solid compound. LCMS: 238 [M+H]⁺

Step-2: Synthesis of (1-(6-aminopyridin-3-yl) piperidin-4-yl) methanol

To a stirred solution of (1-(6-nitropyridin-3-yl) piperidin-4-yl) methanol (200 mg, 0.84 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain (1-(6-aminopyridin-3-yl) piperidin-4-yl) methanol (150 mg, 86%) as a white color solid compound. LCMS: 208 [M+H]⁺

Step-3: Synthesis of (1-(6-((5-fluoro-4-(8-fluoro-4-isopropyl-3,4-dihydro-2H-benzo[b][1,4]oxazin-6-yl) pyrimidin-2-yl)amino)pyridin-3-yl)piperidin-4-yl) methanol To a solution of 6-(2-chloro-5-fluoropyrimidin-4-yl)-8-fluoro-4-isopropyl-3,4-dihydro-2H-benzo[b][1,4]oxazine (50 mg, 0.15 mmol, 1 equiv) in dioxane (3 mL), was added (1-(6-aminopyridin-3-yl)piperidin-4-yl)methanol (35 mg, 0.16 mmol, 1.1 equiv) and cesium carbonate (73 mg, 0.23 mmol, 1.5 equiv). The reaction mixture was degassed with nitrogen gas for 30 min., followed by the addition of palladium acetate (1 mg, 0.003 mmol, 0.02 equiv) and BINAP (4 mg, 0.006 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain (1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)methanol (8 mg, 11%) as a yellow color solid compound. LCMS: 497 [M+H]⁺; ¹HNMR (400 MHz, DMSO-d₆) δ 9.64 (s, 1H), 8.55 (d, J=4.0 Hz, 1H), 8.03-7.95 (m, 2H), 7.46 (s, 1H), 7.37 (dd, J=9.1, 3.2 Hz, 1H), 7.17 (d, J=11.7 Hz, 1H), 4.49 (t, J=5.4 Hz, 1H), 4.33-4.26 (m, 2H), 4.15 (p, J=6.6 Hz, 1H), 3.63 (d, J=11.9 Hz, 2H), 3.30 (s, 3H), 2.68-2.57 (m, 2H), 1.81-1.72 (m, 2H), 1.48 (d, J=11.2 Hz, 2H), 1.27 (dt, J=12.2, 6.4 Hz, 2H), 1.18 (d, J=6.5 Hz, 6H).

Example-94: Synthesis of 1-(6-((4-(4-cyclobutyl-8-fluoro-3,4-dihydro-2H-benzo[b][1,4]oxazin-6-yl)-5-fluoropyrimidin-2-yl)amino)pyridin-3-yl)piperidin-4-ol. (Compound 486)

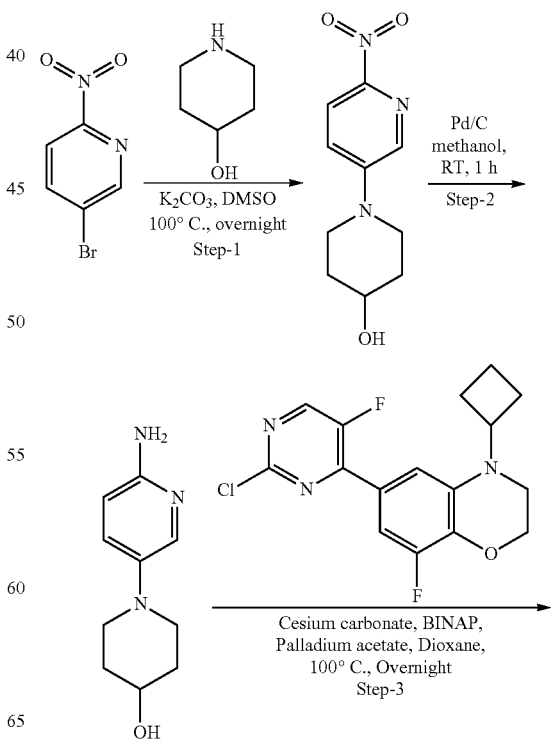

-continued

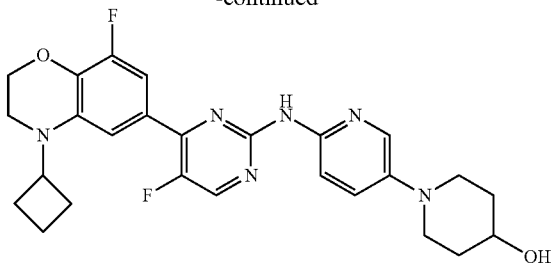

Step-1: Synthesis of 1-(6-nitropyridin-3-yl) piperidin-4-ol

To a stirred solution of 5-bromo-2-nitropyridine (500 mg, 2.47 mmol, 1 equiv) in DMSO (10 mL), was added $K_2CO_3$ (683 mg, 4.95 mmol, 2 equiv) and piperidin-4-ol (500 mg, 4.95 mmol, 2 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain 1-(6-nitropyridin-3-yl)piperidin-4-ol (400 mg, 73%) as a yellow solid compound. LCMS: 224 [M+H]$^+$

Step-2: Synthesis of 1-(6-aminopyridin-3-yl) piperidin-4-ol

To a stirred solution of 1-(6-nitropyridin-3-yl)piperidin-4-ol (400 mg, 1.79 mmol, 1 equiv) in methanol (10 mL), was added Pd/C (20% w/w) (80 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 1-(6-aminopyridin-3-yl) piperidin-4-ol (300 mg, 87%) as a white color solid compound.
LCMS: 194 [M+H]$^+$

Step-3: Synthesis of 1-(6-((4-(4-cyclobutyl-8-fluoro-3,4-dihydro-2H-benzo[b][1,4]oxazin-6-yl)-5-fluoropyrimidin-2-yl)amino)pyridin-3-yl)piperidin-4-ol To a solution of 6-(2-chloro-5-fluoropyrimidin-4-yl)-4-cyclobutyl-8-fluoro-3,4-dihydro-2H-benzo[b][1,4]oxazine (70 mg, 0.2 mmol, 1 equiv) in dioxane (3 mL), was added 1-(6-aminopyridin-3-yl)piperidin-4-ol (44 mg, 0.22 mmol, 1.1 equiv) and cesium carbonate (98 mg, 0.3 mmol, 1.5 equiv). The reaction mixture was degassed with nitrogen gas for 30 min., followed by the addition of palladium acetate (1 mg, 0.004 mmol, 0.02 equiv) and BINAP (5 mg, 0.008 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 1-(6-((4-(4-cyclobutyl-8-fluoro-3,4-dihydro-2H-benzo[b][1,4]oxazin-6-yl)-5-fluoropyrimidin-2-yl)amino)pyridin-3-yl)piperidin-4-ol (30 mg, 30%) as a yellow color solid compound. LCMS: 495 [M+H]$^+$; $^1$HNMR (400 MHz, DMSO-d$_6$) δ 9.65 (s, 1H), 8.56 (d, J=3.9 Hz, 1H), 7.90-8.08 (m, 2H), 7.41 (dd, J=9.2, 2.6 Hz, 1H), 7.35 (s, 1H), 7.25 (d, J=12.7 Hz, 1H), 4.69 (d, J=3.9 Hz, 1H), 4.36 (d, J=3.9 Hz, 2H), 3.87-4.09 (m, 1 H), 3.62 (d, J=3.9 Hz, 1H), 3.47 (d, J=11.8 Hz, 2H), 3.34 (s, 2H), 2.82 (t, J=9.6 Hz, 2H), 2.25 (br. s., 2H), 2.13 (d, J=9.2 Hz, 2H), 1.83 (d, J=10.1 Hz, 2H), 1.61-1.75 (m, 2H), 1.50 ppm (d, J=9.2 Hz, 2H).

Example-95: Synthesis of 4-(4-cyclobutyl-8-fluoro-3,4-dihydro-2H-benzo[b][1,4]oxazin-6-yl)-5-fluoro-N-(5-morpholinopyridin-2-yl)pyrimidin-2-amine. (Compound 487)

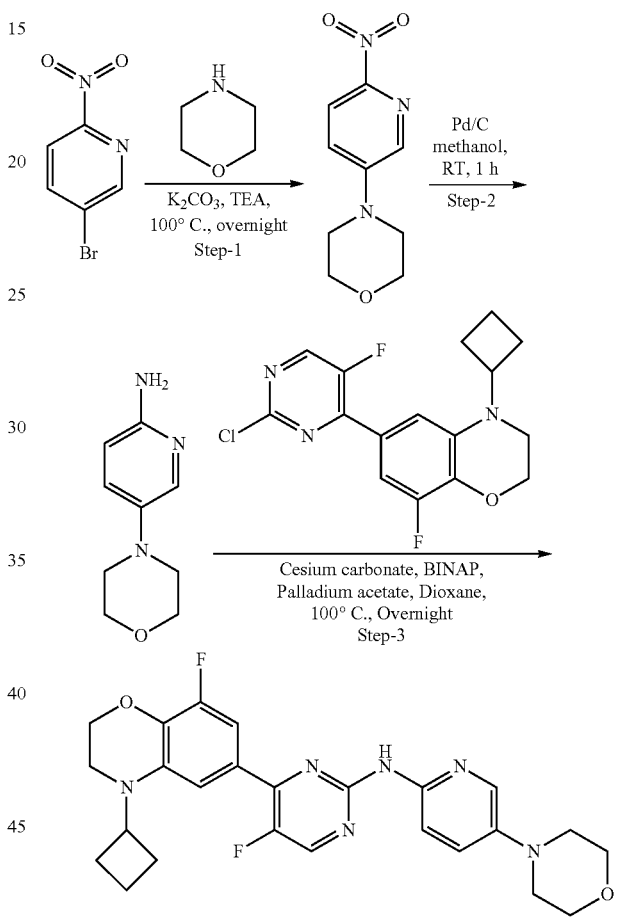

Step-1: Synthesis of 4-(6-nitropyridin-3-yl) morpholine

To a stirred solution of 5-bromo-2-nitropyridine (500 mg, 2.47 mmol, 1 equiv) in DMSO (10 mL), was added TEA (0.7 mL, 4.94 mmol, 2 equiv) and morpholine (323 mg, 3.7 mmol, 1.5 equiv). The resultant reaction mixture was allowed to stir at 100° C. for overnight. Progress of the reaction was monitored by TLC and LCMS. After completion of the reaction, diluted with water (50 mL), solid observed was filtered and dried under vacuum to obtain 4-(6-nitropyridin-3-yl)morpholine (400 mg, 77%) as a yellow solid compound. LCMS: 210 [M+H]$^+$

Step-2: Synthesis of 5-morpholinopyridin-2-amine

To a stirred solution of 4-(6-nitropyridin-3-yl)morpholine (400 mg, 1.9 mmol, 1 equiv) in methanol (10 mL), was added Pd/C (20% w/w) (80 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 5-morpholinopyridin-2-amine (300 mg, 88%) as a white color solid compound. LCMS: 180 [M+H]+

Step-3: Synthesis of 4-(4-cyclobutyl-8-fluoro-3,4-dihydro-2H-benzo[b][1,4]oxazin-6-yl)-5-fluoro-N-(5-morpholinopyridin-2-yl)pyrimidin-2-amine To a solution of 6-(2-chloro-5-fluoropyrimidin-4-yl)-4-cyclobutyl-8-fluoro-3,4-dihydro-2H-benzo[b][1,4]oxazine (70 mg, 0.2 mmol, 1 equiv) in dioxane (3 mL), was added 1-(6-aminopyridin-3-yl)piperidin-4-ol (39 mg, 0.22 mmol, 1.1 equiv) and cesium carbonate (98 mg, 0.3 mmol, 1.5 equiv). The reaction mixture was degassed with nitrogen gas for 30 min., followed by the addition of palladium acetate (1 mg, 0.004 mmol, 0.02 equiv) and BINAP (5 mg, 0.008 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 4-(4-cyclobutyl-8-fluoro-3,4-dihydro-2H-benzo[b][1,4]oxazin-6-yl)-5-fluoro-N-(5-morpholinopyridin-2-yl)pyrimidin-2-amine (30 mg, 30%) as a yellow color solid compound. LCMS: 481 [M+H]+; 1HNMR (400 MHz, DMSO-$d_6$) δ 9.71 (s, 1H), 8.56 (d, J=3.5 Hz, 1H), 7.93-8.12 (m, 2H), 7.43 (d, J=8.8 Hz, 1H), 7.35 (s, 1H), 7.26 (d, J=11.8 Hz, 1H), 4.37 (br. s., 2H), 3.92-4.09 (m, 1H), 3.61-3.77 (m, 4H), 3.35 (s., 2H), 2.98-3.18 (m, 4H), 2.25 (br. s., 2H), 1.99-2.20 (m, 2H), 1.58-1.81 ppm (m, 2H).

Example-96: Synthesis of 1-(6-((5-fluoro-4-(8-fluoro-4-isobutyl-3,4-dihydro-2H-benzo[b][1,4]oxazin-6-yl)pyrimidin-2-yl)amino)pyridin-3-yl)piperidin-4-ol. (Compound 488)

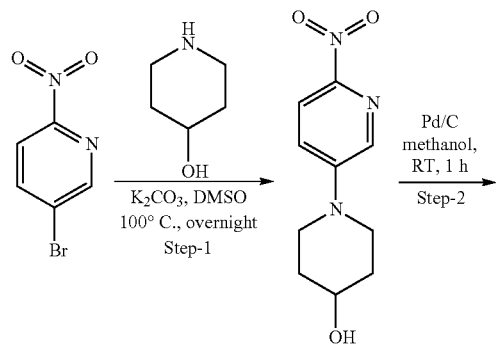

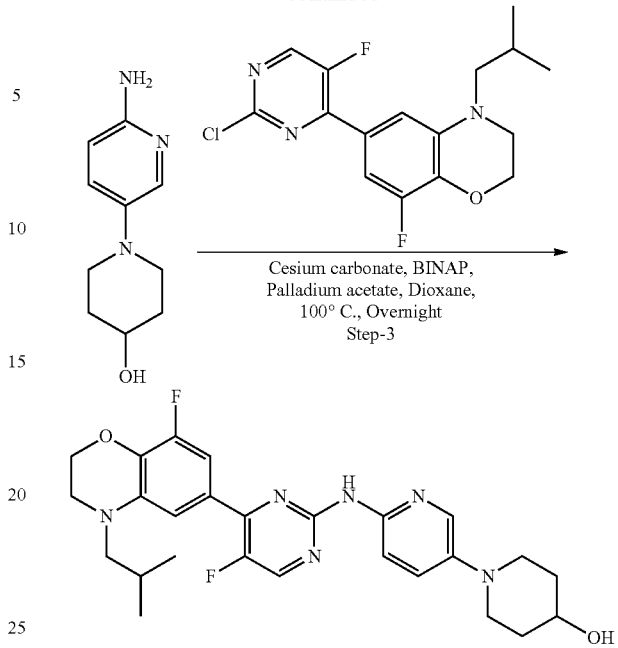

Step-1: Synthesis of 1-(6-nitropyridin-3-yl)piperidin-4-ol

To a stirred solution of 5-bromo-2-nitropyridine (500 mg, 2.47 mmol, 1 equiv) in DMSO (10 mL), was added $K_2CO_3$ (683 mg, 4.95 mmol, 2 equiv) and piperidin-4-ol (500 mg, 4.95 mmol, 2 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain 1-(6-nitropyridin-3-yl)piperidin-4-ol (400 mg, 73%) as a yellow solid compound. LCMS: 224 [M+H]+

Step-2: Synthesis of 1-(6-aminopyridin-3-yl)piperidin-4-ol

To a stirred solution of 1-(6-nitropyridin-3-yl)piperidin-4-ol (400 mg, 1.79 mmol, 1 equiv) in methanol (10 mL), was added Pd/C (20% w/w) (80 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 1-(6-aminopyridin-3-yl) piperidin-4-ol (300 mg, 87%) as a white color solid compound.

LCMS: 194 [M+H]+

Step-3: Synthesis of 1-(6-((5-fluoro-4-(8-fluoro-4-isobutyl-3,4-dihydro-2H-benzo[b][1,4]oxazin-6-yl)pyrimidin-2-yl)amino)pyridin-3-yl)piperidin-4-ol To a solution of 6-(2-chloro-5-fluoropyrimidin-4-yl)-8-fluoro-4-isobutyl-3,4-dihydro-2H-benzo[b][1,4]oxazine (80 mg, 0.23 mmol, 1 equiv) in dioxane (3 mL), was added 1-(6-aminopyridin-3-yl)piperidin-4-ol (50 mg, 0.25 mmol, 1.1 equiv) and cesium carbonate (113 mg, 0.35 mmol, 1.5 equiv). The reaction mixture was degassed with nitrogen gas for 30 min., followed by the addition of palladium acetate (1 mg, 0.005 mmol, 0.02 equiv) and BINAP (6 mg, 0.009 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 1-(6-((5-fluoro-4-(8-fluoro-4-isobutyl-3,4-dihydro-2H-benzo[b][1,4]oxazin-6-yl)pyrimidin-2-yl)amino)pyridin-3-yl)piperidin-4-ol (50 mg, 43%) as a yellow color solid compound. LCMS: 497 [M+H]$^+$; $^1$HNMR (400 MHz, DMSO-d$_6$) δ 9.64 (s, 1H), 8.56 (d, J=3.9 Hz, 1H), 7.93-8.08 (m, 2H), 7.38 (dd, J=9.0, 2.9 Hz, 1H), 7.25 (s, 1H), 7.14 (d, J=11.8 Hz, 1H), 4.69 (d, J=3.9 Hz, 1H), 4.29 (br. s., 2H), 3.52-3.69 (m, 1H), 3.45 (br. s., 4H), 3.12 (d, J=7.0 Hz, 2H), 2.82 (t, J=9.6 Hz, 2H), 1.98-2.14 (m, 1H), 1.83 (d, J=9.2 Hz, 2H), 1.33-1.58 (m, 2H), 0.91 ppm (d, J=6.6 Hz, 6H).

Example-97: Synthesis of 5-fluoro-4-(8-fluoro-4-isobutyl-3,4-dihydro-2H-benzo[b][1,4]oxazin-6-yl)-N-(5-morpholinopyridin-2-yl)pyrimidin-2-amine. (Compound 489)

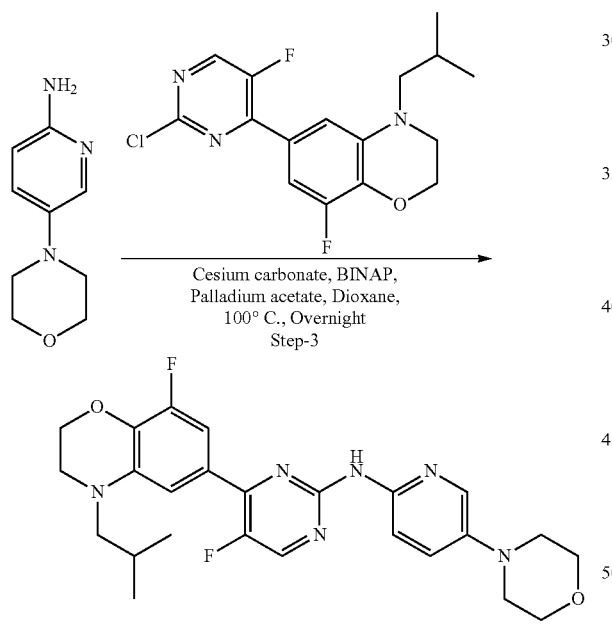

To a solution of 6-(2-chloro-5-fluoropyrimidin-4-yl)-8-fluoro-4-isobutyl-3,4-dihydro-2H-benzo[b][1,4]oxazine (80 mg, 0.23 mmol, 1 equiv) in dioxane (3 mL), was added 1-(6-aminopyridin-3-yl)piperidin-4-ol (45 mg, 0.25 mmol, 1.1 equiv) and cesium carbonate (113 mg, 0.35 mmol, 1.5 equiv). The reaction mixture was degassed with nitrogen gas for 30 min., followed by the addition of palladium acetate (1 mg, 0.005 mmol, 0.02 equiv) and BINAP (6 mg, 0.009 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-4-(8-fluoro-4-isobutyl-3,4-dihydro-2H-benzo[b][1,4]oxazin-6-yl)-N-(5-morpholinopyridin-2-yl)pyrimidin-2-amine (60 mg, 53%) as a yellow color solid compound. LCMS: 483 [M+H]$^+$; $^1$HNMR (400 MHz, DMSO-d$_6$) δ 9.69 (s, 1H), 8.57 (d, J=3.9 Hz, 1H), 7.89-8.11 (m, 2H), 7.63 (br. s., 1H), 7.27 (s, 1H), 7.15 (d, J=11.0 Hz, 1H), 4.29 (br. s., 2H), 3.66-3.91 (m, 4H), 3.45 (br. s., 2H), 2.87-3.16 (m, 6H), 1.89-2.13 (m, 1H), 0.91 ppm (d, J=6.6 Hz, 6H).

Example-98: Synthesis of 2-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)ethan-1-ol. (Compound 490)

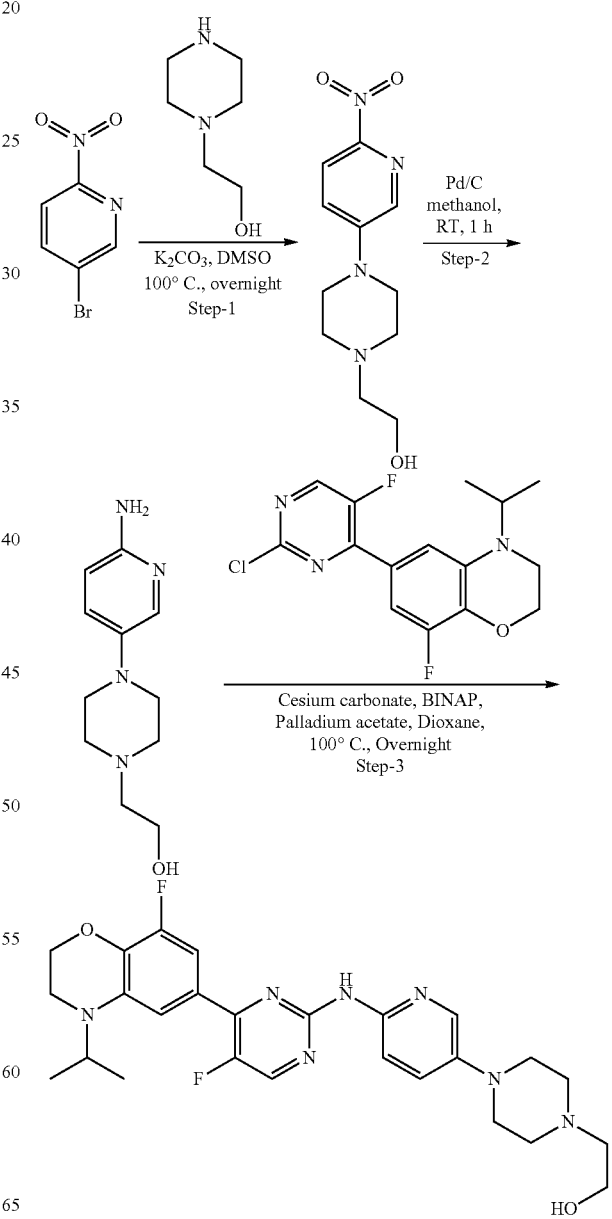

Step-1: Synthesis of 2-(4-(6-nitropyridin-3-yl) piperazin-1-yl) ethan-1-ol

To a stirred solution of 5-bromo-2-nitropyridine (500 mg, 2.47 mmol, 1 equiv) in DMSO (10 mL), was added $K_2CO_3$ (683 mg, 4.95 mmol, 2 equiv) and 2-(piperazin-1-yl) ethan-1-ol (482 mg, 3.71 mmol, 1.5 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain 2-(4-(6-nitropyridin-3-yl)piperazin-1-yl)ethan-1-ol (300 mg, 48%) as a yellow solid compound. LCMS: 253 [M+H]+

Step-2: Synthesis of 2-(4-(6-aminopyridin-3-yl) piperazin-1-yl) ethan-1-ol

To a stirred solution of 2-(4-(6-nitropyridin-3-yl) piperazin-1-yl) ethan-1-ol (200 mg, 0.79 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 2-(4-(6-aminopyridin-3-yl) piperazin-1-yl) ethan-1-ol (150 mg, 85%) as a white color solid compound. LCMS: 223 [M+H]+

Step-3: Synthesis of 2-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl) ethan-1-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (3 mL), was added 2-(4-(6-aminopyridin-3-yl)piperazin-1-yl)ethan-1-ol (73 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 2-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)ethan-1-ol (30 mg, 19%) as a yellow color solid compound. LCMS: 512 [M+H]+; 1HNMR (400 MHz, DMSO-d6) δ 9.69 (s, 1H), 8.56 (d, J=3.9 Hz, 1H), 7.93-8.09 (m, 2H), 7.46 (br. s., 1H), 7.36 (d, J=2.6 Hz, 1H), 7.17 (d, J=11.8 Hz, 1H), 4.44 (t, J=5.0 Hz, 1H), 4.30 (br. s., 2H), 4.05-4.20 (m, 1H), 3.47-3.61 (m, 2H), 3.30 (s, 2H), 3.11 (br. s., 4H), 2.57 (br. s., 4H), 2.29-2.46 ppm (m, 2H), 1.18 (d, J=6.5 Hz, 6H).

Example-99: Synthesis of 2-(1-(6-((5-fluoro-4-(8-fluoro-4-isopropyl-3,4-dihydro-2H-benzo[b][, 4]oxazin-6-yl)pyrimidin-2-yl)amino)pyridin-3-yl) piperidin-4-yl)ethan-1-ol. (Compound 491)

Step-1: Synthesis of 2-(1-(6-nitropyridin-3-yl) piperidin-4-yl) ethan-1-ol

To a stirred solution of 5-bromo-2-nitropyridine (500 mg, 2.47 mmol, 1 equiv) in DMSO (10 mL), was added $K_2CO_3$ (683 mg, 4.95 mmol, 2 equiv) and 2-(piperidin-4-yl) ethan-1-ol (449 mg, 3.71 mmol, 1.5 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain 2-(1-(6-nitropyridin-3-yl)piperidin-4-yl)ethan-1-ol (500 mg, 81%) as a yellow solid compound. LCMS: 252 [M+H]+

Step-2: Synthesis of 2-(1-(6-aminopyridin-3-yl) piperidin-4-yl) ethan-1-ol

To a stirred solution of 2-(1-(6-nitropyridin-3-yl) piperidin-4-yl) ethan-1-ol (200 mg, 0.79 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 2-(1-(6-aminopyridin-3-yl) piperidin-4-yl) ethan-1-ol (150 mg, 85%) as a white color solid compound. LCMS: 222 [M+H]+

Step-3: Synthesis of 2-(1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl) ethan-1-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (3 mL), was added 2-(1-(6-aminopyridin-3-yl)piperidin-4-yl)ethan-1-ol (73 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain 2-(1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)ethan-1-ol (40 mg, 25%) as a yellow color solid compound. LCMS: 511 [M+H]+; 1HNMR (400 MHz, DMSO-$d_6$) δ 9.64 (s, 1H), 8.55 (d, J=3.9 Hz, 1H), 7.90-8.04 (m, 2H), 7.47 (s, 1H), 7.37 (dd, J=9.0, 2.9 Hz, 1H), 7.17 (d, J=11.4 Hz, 1H), 4.37 (br. s., 1H), 4.30 (br. s., 2H), 3.95-4.21 (m, 1H), 3.60 (d, J=12.3 Hz, 2H), 3.48 (br. s., 2H), 3.30 (s, 2H), 2.56-2.71 (m, 2H), 1.75 (d, J=11.8 Hz, 2H), 1.51 (br. s., 1H), 1.31-1.42 (m, 2H), 1.20-1.31 (m, 2H), 1.18 ppm (s, 6H).

Example-100: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)pyrrolidin-3-ol. (Compound 492)

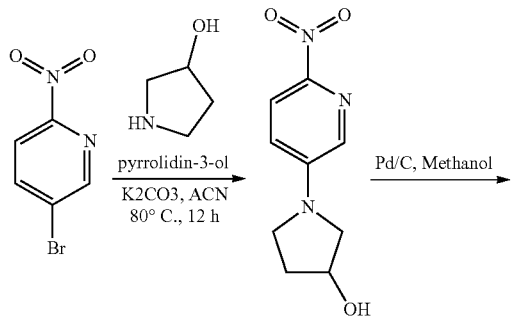

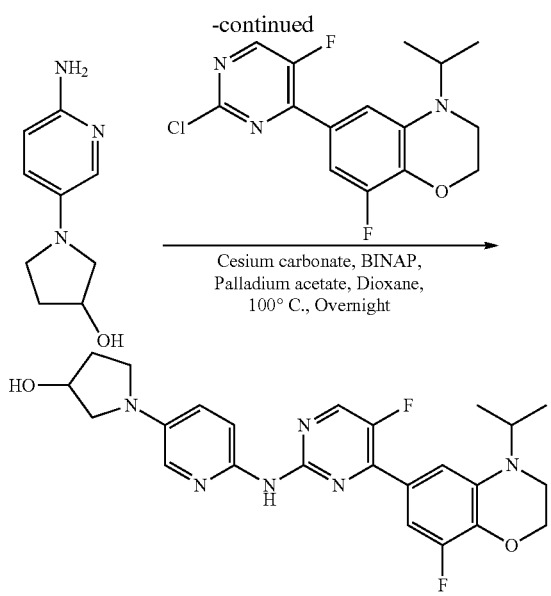

Step-1: Synthesis of 1-(6-nitropyridin-3-yl)pyrrolidin-3-ol

To a stirred solution of 5-bromo-2-nitropyridine (1000 mg, 4.9 mmol, 1 equiv) in ACN (10 mL), was added pyrrolidin-3-ol (640 mg, 7.4 mmol, 1.5 equiv) followed by addition of K2CO3 (1010 mg, 7.4 mmol, 1.5 equiv). Resultant mixture was allowed to stir at 800 for 12 h. Progress of the reaction was monitored by TLC and LCMS. After completion of the reaction, the mixture was diluted with water (15 mL), and was extracted with EtOAc (25 mL). Organic layer dried over anhydrous sodium sulphate and concentrated under reduced pressure to obtain crude compound was triturated from hexane to afford 1-(6-nitropyridin-3-yl) pyrrolidin-3-ol (1000 mg) as a yellow solid compound. LCMS: 588 [M+H]+

Step-2: Synthesis 1-(6-aminopyridin-3-yl) pyrrolidin-3-ol

To a stirred solution of 1-(6-nitropyridin-3-yl) pyrrolidin-3-ol (100 mg, 0.47 mmol, 1 equiv) in methanol (8 mL), was added 10 wt. % Pd/C (20 mg). 2 L hydrogen balloon was pressurized over reaction. The resultant reaction mixture was allowed to stir at room temperature for 4 h. Progress of the reaction was monitored by TLC and LCMS. After completion of the reaction, the mixture was filtered carefully through cealite bed. Filtrate was concentrated under reduced pressure to obtain 1-(6-aminopyridin-3-yl) pyrrolidin-3-ol (85 mg, 82%) as a dark brown solid compound. LCMS: 180 [M+H]+

Step-3: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)pyrrolidin-3-ol To a solution of 6-(2-chloro-5-fluoropyrimidin-4-yl)-8-fluoro-4-isopropyl-3,4-dihydro-2H-benzo[b][1,4]oxazine (120 mg, 0.37 mmol, 1 equiv) in dioxane (3 mL), was added 1-(6-aminopyridin-3-yl)pyrrolidin-3-ol (72 mg, 0.4 mmol, 1.2 equiv) and cesium carbonate (240 mg, 0.74 mmol, 2 equiv). The reaction mixture was degassed by nitrogen gas for 10 min., followed by the addition of palladium acetate (8 mg, 0.037 mmol, 0.1 equiv) and BINAP (46 mg, 0.074 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain crude, which was purified by reverse phase HPLC to obtain 1-(6-((5-fluoro-4-(8-fluoro-4-isopropyl-3,4-dihydro-2H-benzo[b][1,4]oxazin-6-yl)pyrimidin-2-yl)amino)pyridin-3-yl)pyrrolidin-3-ol (25 mg, 19%) as an off white solid compound. LCMS: 469 [M+H]$^+$; $^1$HNMR (400 MHz, DMSO-d$_6$) δ ppm 1.19 (d, J=6.58 Hz, 4H) 1.91 (br. s., 2H) 2.06 (br. s., 2H) 3.08 (d, J=9.65 Hz, 2H) 3.43 (br. s., 2H) 4.15 (br. s., 2H) 4.30 (br. s., 1H) 4.41 (br. s., 1H) 4.97 (d, J=3.51 Hz, 1H) 6.96 (d, J=11.84 Hz, 1H) 7.48 (br. s., 1H) 7.65 (br. s., 1H) 7.93 (d, J=8.77 Hz, 1H) 8.52 (d, J=3.95 Hz, 1H) 9.46 (s, 1H)

Example-101: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-(hydroxymethyl)piperidin-4-ol. (Compound 493)

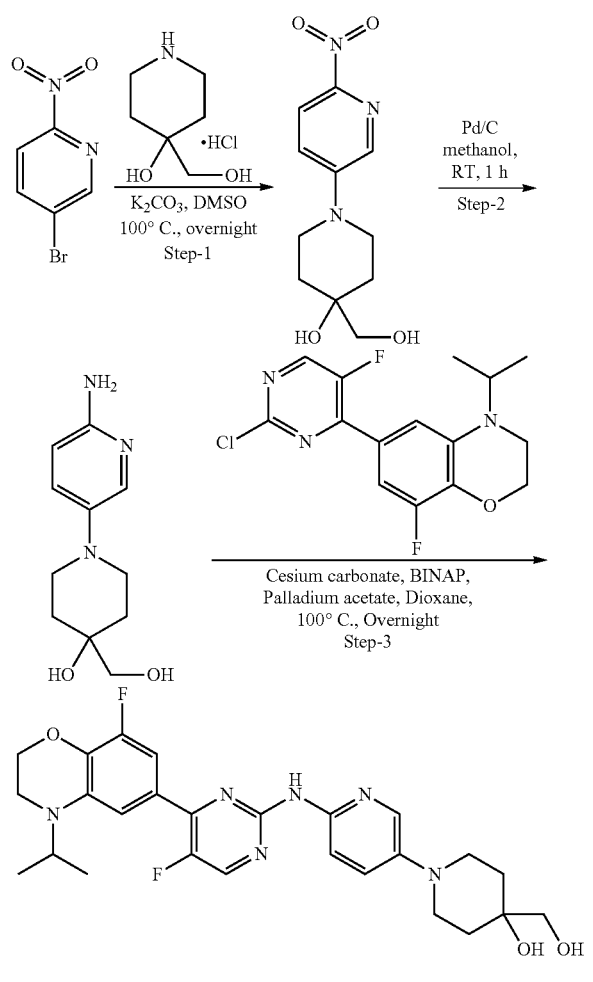

Step-1: Synthesis of 4-(hydroxymethyl)-1-(6-nitropyridin-3-yl) piperidin-4-ol

To a stirred solution of 5-bromo-2-nitropyridine (400 mg, 1.98 mmol, 1 equiv) in DMSO (10 mL), was added K$_2$CO$_3$ (820 mg, 5.95 mmol, 2 equiv) and 4-(hydroxymethyl) piperidin-4-ol (661 mg, 3.96 mmol, 2 equiv). The resultant reaction mixture was allowed to stir at 100° C. for overnight. Progress of the reaction was monitored by LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain 4-(hydroxymethyl)-1-(6-nitropyridin-3-yl) piperidin-4-ol (200 mg, 40%) as a yellow solid compound. LCMS: 254 [M+H]$^+$ Step-2: Synthesis of 1-(6-aminopyridin-3-yl)-4-(hydroxymethyl) piperidin-4-ol To a stirred solution of 4-(hydroxymethyl)-1-(6-nitropyridin-3-yl) piperidin-4-ol (200 mg, 0.79 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 1-(6-aminopyridin-3-yl)-4-(hydroxymethyl) piperidin-4-ol (120 mg, 68%) as a dark brown color viscous compound.

LCMS: 224 [M+H]$^+$

Step-3: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-(hydroxymethyl)piperidin-4-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (3 mL), was added 1-(6-aminopyridin-3-yl)-4-(hydroxymethyl)piperidin-4-ol (74 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-4-(hydroxymethyl)piperidin-4-ol (8 mg, 5%) as a yellow color solid compound. LCMS: 513 [M+H]$^+$; $^1$HNMR (400 MHz, DMSO-d$_6$) δ 9.62 (s, 1H), 8.55 (d, J=3.9 Hz, 1H), 7.83-8.04 (m, 2H), 7.46 (s, 1H), 7.26-7.39 (m, 1H), 7.17 (d, J=11.4 Hz, 1H), 4.29 (d, J=3.9 Hz, 2H), 4.05-4.21 (m, 1H), 3.30 (s, 2H), 3.22 (br. s., 4H), 2.91-3.12 (m, 2H), 1.59-1.76 (m, 2H), 1.44 (d, J=13.2 Hz, 2H), 1.18 ppm (d, J=6.6 Hz, 6H).

Example-102: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-methylpyrrolidin-3-ol. (Compound 494)

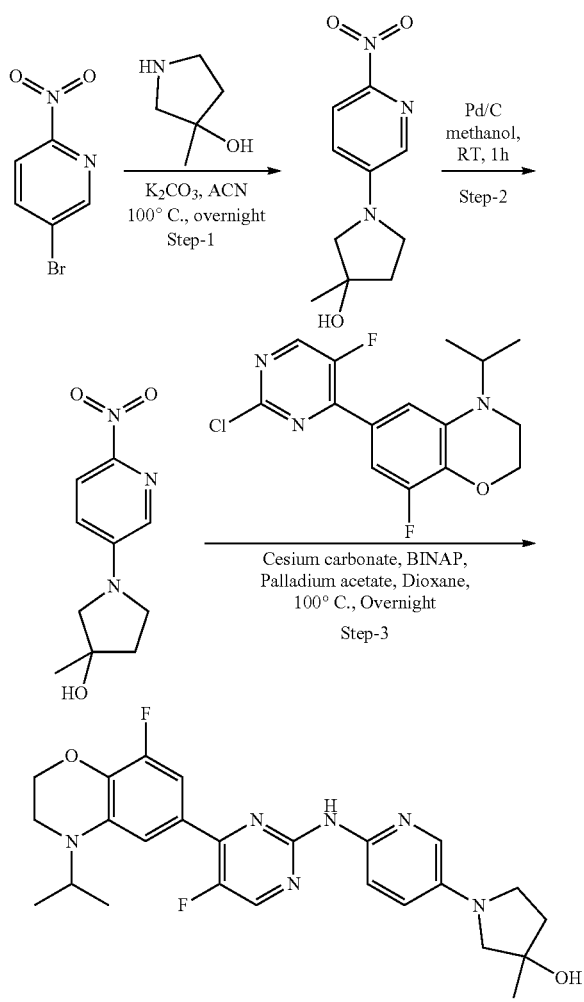

Step-1: Synthesis of 3-methyl-1-(6-nitropyridin-3-yl) pyrrolidin-3-ol

To a stirred solution of 5-bromo-2-nitropyridine (500 mg, 2.47 mmol, 1 equiv) in ACN (10 mL), was added K$_2$CO$_3$ (1023 mg, 7.41 mmol, 3 equiv) and 3-methylpyrrolidin-3-ol (500 mg, 4.95 mmol, 2 equiv). The resultant reaction mixture was allowed to stir at 100° C. for overnight. Progress of the reaction was monitored by LCMS. After completion of the reaction, diluted with water (50 mL) and extracted with ethyl acetate (100 mL). Organic layer was washed with water (50 mL) and brine solution (50 mL). Organic layer was dried over anhydrous sodium sulphate and concentrated under reduced pressure to obtain 3-methyl-1-(6-nitropyridin-3-yl) pyrrolidin-3-ol (500 mg, 91%) as a brown viscous compound. LCMS: 224 [M+H]$^+$ Step-2: Synthesis of 1-(6-aminopyridin-3-yl)-3-methylpyrrolidin-3-ol To a stirred solution of 3-methyl-1-(6-nitropyridin-3-yl) pyrrolidin-3-ol (200 mg, 0.89 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain 1-(6-aminopyridin-3-yl)-3-methylpyrrolidin-3-ol (150 mg, 87%) as color a dark brown solid compound. LCMS: 194 [M+H]$^+$ Step-3: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-methylpyrrolidin-3-ol To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (3 mL), was added 1-(6-aminopyridin-3-yl)-3-methylpyrrolidin-3-ol (64 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 1-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-methylpyrrolidin-3-ol (25 mg, 17%) as a yellow color solid compound. LCMS: 483 [M+H]$^+$;
$^1$HNMR (400 MHz, DMSO-d$_6$) δ 9.45 (s, 1H), 8.52 (d, J=3.9 Hz, 1H), 7.92 (d, J=8.8 Hz, 1H), 7.62 (d, J=2.6 Hz, 1H), 7.47 (s, 1H), 7.16 (d, J=12.3 Hz, 1H), 6.75-7.00 (m, 1H), 4.30 (br. s., 2H), 4.03-4.21 (m, 1H), 3.38 (d, J=7.9 Hz, 2H), 3.24-3.37 (m, 2H), 3.09-3.23 (m, 2H), 1.79-2.04 (m, 2H), 1.36 (s, 3H), 1.19 ppm (d, J=6.6 Hz, 6H).

Example-103: Synthesis of N-(5-fluoro-4-(8-fluoro-4-isopropyl-3,4-dihydro-2H-benzo[b][1,4]oxazin-6-yl)pyrimidin-2-yl)-3-(1-methylpiperidin-4-yl)isoxazol-5-amine. (Compound 495)

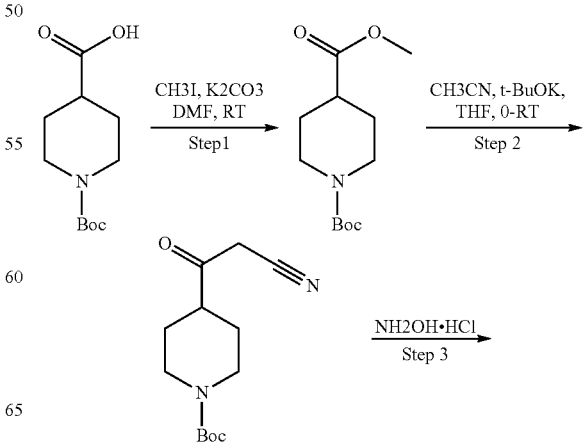

-continued

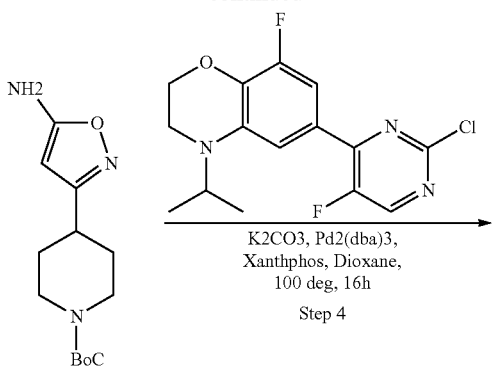

K2CO3, Pd2(dba)3,
Xanthphos, Dioxane,
100 deg, 16h
Step 4

EtOH·HCl
Step 5

HCHO, AcOH,
NaBH3CN, DCE
Step 6

Step-1: Synthesis of 1-(tert-butyl) 4-methyl piperidine-1,4-dicarboxylate

To a solution 1-(tert-butoxycarbonyl)piperidine-4-carboxylic acid (2000 mg, 8.69 mmol, 1 equiv) in DMF (25 mL), was methyl iodide (0.694 ml, 10.25 mmol) 1.2 equiv) was added drop wise under nitrogen and potassium carbonate (1200 mg, 8.69 mmol, 1 equiv). The resultant reaction mixture was allowed to stir at RT for 3 h. Progress of the reaction was monitored by NMR and TLC. After completion of the reaction, reaction mixture was diluted with water (30 mL) and extracted with ethyl acetate (100 mL×2). Organic layer was washed with water (100 mL). Organic layer was dried over anhydrous sodium sulphate and concentrated under reduced pressure to obtained desired product 1-(tert-butyl) 4-methyl piperidine-1,4-dicarboxylate (1760 mg,) as a yellow oil compound. LCMS: ELSD 244 [M+H]+

Step-2: Synthesis of tert-butyl 4-(2-cyanoacetyl) piperidine-1-carboxylate

To a stirred solution of 1-(tert-butyl) 4-methyl piperidine-1,4-dicarboxylate (500 mg, 2.04 mmol, 1 equiv) in THF (10 mL), was added methyl cyanide (0.56 mg, 5 equiv.), and potassium-terbutoxide (689 mg, 3 equiv). The resultant reaction mixture was allowed to stir at RT for 1 h. Progress of the reaction was monitored by $^1$H NMR. After completion of the reaction, the mixture was added aquas ammonium chloride solution (60 mL) resulted solution was diluted with water (20 mL) and extracted with ethyl acetate (100 mL). Organic layer was washed with brine solution (50 mL). Organic layer was dried over anhydrous sodium sulphate and concentrated under reduced pressure to obtain crude, which was purified by normal phase combi flash to obtain of tert-butyl 4-(2-cyanoacetyl)piperidine-1-carboxylate as a light yellow oil compound.

LCMS: ELSD 253 [M+H]+

Step-3: Synthesis of tert-butyl 4-(5-aminoisoxazol-3-yl) piperidine-1-carboxylate To a solution of tert-butyl 4-(2-cyanoacetyl) piperidine-1-carboxylate (500 mg, 1.98 mmol, 1 equiv) in methanol (10 mL) in sealed tube, was added hydroxylamine hydrochloride (275 mg, 3.96 mmol, 2 equiv), sodium acetate (324 mg, 3.96 mmol, 2 equiv). The resultant reaction mixture was allowed to stir at RT for 20-24 h. Progress of the reaction was monitored by TLC and LCMS. After completion of the reaction, diluted with water (30 mL) and extracted with ethyl acetate (100 mL). Organic layer was washed with water (20 mL) and brine solution (30 mL). Organic layer was dried over anhydrous sodium sulphate and concentrated under reduced pressure to obtain crude, which was purified by normal phase combi flash to obtain tert-butyl 4-(5-aminoisoxazol-3-yl)piperidine-1-carboxylate (80 mg, 73%) as a yellow solid compound. LCMS: 267 [M+H]+

Step-4: Synthesis of tert-butyl 4-(5-((5-fluoro-4-(8-fluoro-4-isopropyl-3,4-dihydro-2H-benzo[b][1,4]oxazin-6-yl)pyrimidin-2-yl)amino)isoxazol-3-yl)piperidine-1-carboxylate To the solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) was added dioxane (6 ml) and tert-butyl 4-(5-aminoisoxazol-3-yl)piperidine-1-carboxylate (90 mg, 0.33 mmol, 1.1 equiv), cesium carbonate (149 mg, 0.45 mmol, 1.5 equiv), resulted reaction mixture was degassed with nitrogen for 5 min thereafter was added Pd(Oac)$_2$, (8 mg, 0.03 mmol, 0.1 equiv), BINAP (38 mg, 0.06 mmol, 0.2 mmol), resulted reaction mixture was allowed to stir for 15 h at 100° C. Progress of the reaction was monitored by LCMS. After completion of the reaction, the reaction mixture was diluted with water (25 mL) and extracted with ethyl acetate (50 mL×2). Organic layer was washed with water (20 mL) and brine solution (25 mL). Organic layer was dried over anhydrous sodium sulphate and concentrated under reduced pressure to obtain crude, which was purified by combi-flash to obtain tert-butyl 4-(5-((5-fluoro-4-(8-fluoro-4-isopropyl-3,4-dihydro-2H-benzo[b][1,4]oxazin-6-yl)pyrimidin-2-yl)amino)isoxazol-3-yl)piperidine-1-carboxylate (180 mg, 22%) as a yellow solid compound. LCMS: 556 [M+H]$^+$ Step-5: N-(5-fluoro-4-(8-fluoro-4-isopropyl-3,4-dihydro-2H-benzo[b][1,4]oxazin-6-yl)pyrimidin-2-yl)-3-(piperidin-4-yl)isoxazol-5-amine tert-butyl 4-(5-((5-fluoro-4-(8-fluoro-4-isopropyl-3,4-dihydro-2H-benzo[b][1,4]oxazin-6-yl)pyrimidin-2-yl)amino)isoxazol-3-yl)piperidine-1-carboxylate (200 mg, 0.179 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain N-(5-fluoro-4-(8-fluoro-4-isopropyl-3,4-dihydro-2H-benzo[b][1,4]oxazin-6-yl)pyrimidin-2-yl)-3-(1-methylpiperidin-4-yl)isoxazol-5-amine (150 mg, 81%) as a brick red color solid compound. LCMS: 456 [M+H]$^+$ Step-6: Synthesis of N-(5-fluoro-4-(8-fluoro-4-isopropyl-3,4-dihydro-2H-benzo[b][1,4]oxazin-6-yl)pyrimidin-2-yl)-3-(1-methylpiperidin-4-yl)isoxazol-5-amine To a stirred solution of N-(5-fluoro-4-(8-fluoro-4-isopropyl-3,4-dihydro-2H-benzo[b][1,4]oxazin-6-yl)pyrimidin-2-yl)-3-(1-methylpiperidin-4-yl)isoxazol-5-amine (50 mg, 0.109 mmol, 1 equiv) in DCE (3 mL), was added Formaldehyde (40% in water) (0.01 mL, 0.29 mmol, 3 equiv), acetic acid (0.02 mL, 0.45 mmol, 5 equiv). The reaction mixture was allowed to stir at RT for 1 h. The reaction mixture was cooled to 0° C. NaCNBH$_3$ (18 mg, 0.29 mmol, 3 equiv) was added to above mixture and raise the temperature to RT. The reaction mixture was allowed to stir at RT for overnight. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-3-(1-methylpiperidin-4-yl)isoxazol-5-amine (7 mg, 61%) as a yellow color solid compound. LCMS: 471 [M+H]$^+$; $^1$H NMR (400 MHz, Methanol-d4) δ 8.48 (d, J=3.9 Hz, 1H), 7.48 (s, 1H), 7.29-7.21 (m, 1H), 6.36 (d, J=3.4 Hz, 1H), 4.33 (t, J=4.3 Hz, 2H), 4.22 (p, J=6.7 Hz, 1H), 3.35 (d, J=4.0 Hz, 5H), 3.15 (d, J=12.4 Hz, 3H), 2.83 (t, J=12.0 Hz, 1H), 2.54-2.46 (m, 5H), 2.08 (t, J=16.7 Hz, 3H), 1.90 (q, J=12.4 Hz, 2H), 1.29 (s, 1H), 1.26 (dd, J=6.6, 3.3 Hz, 6H).

Example-104: Synthesis of 5-fluoro-4-(8-fluoro-4-isopropyl-3,4-dihydro-2H-benzo[b][1,4]oxazin-6-yl)-N-(1-(1-methylpiperidin-4-yl)-1H-imidazol-4-yl)pyrimidin-2-amine. (Compound 496)

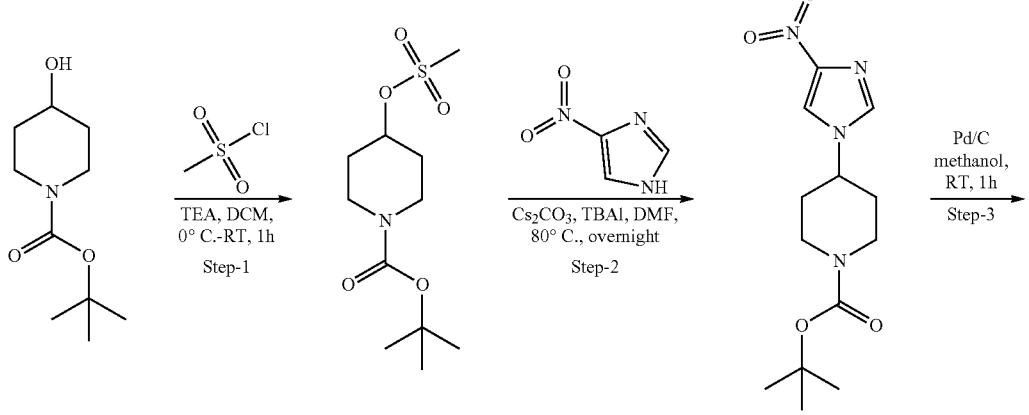

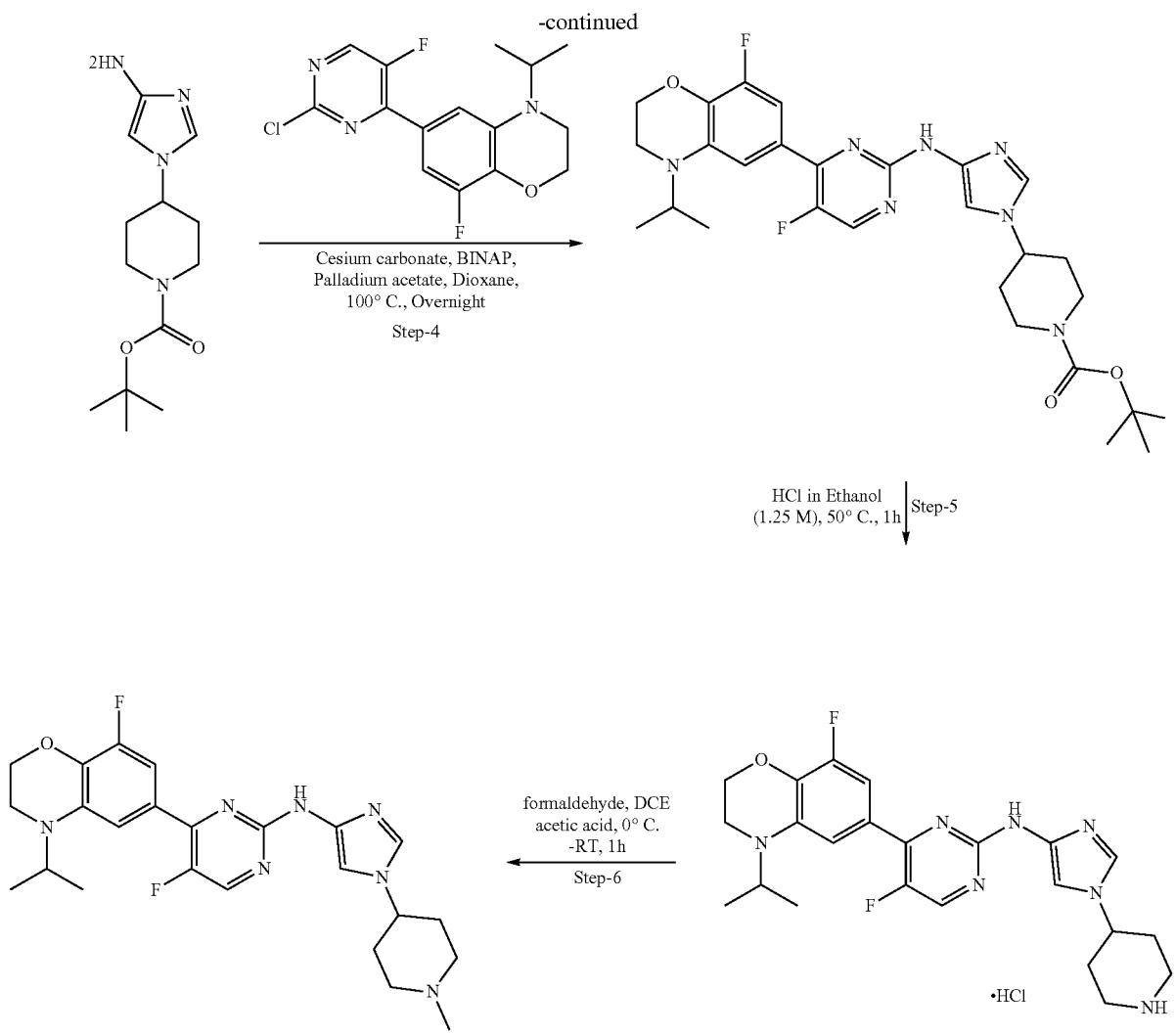

Step-1: Synthesis of tert-butyl 4-((methylsulfonyl)oxy) piperidine-1-carboxylate To a stirred solution of tert-butyl 4-hydroxypiperidine-1-carboxylate (5000 mg, 24.87 mmol, 1 equiv) in DCM (50 mL), was added TEA (5 mL, 34.8 mmol, 1.4 equiv). Cool the reaction mixture to 0° C., followed by the addition of mesyl chloride (2.5 mL, 34.8 mmol, 1.4 equiv). Raise the temp. to RT and the resultant reaction mixture was allowed to stir for overnight. Progress of the reaction was monitored by LCMS. After completion of the reaction, diluted with water (100 mL) and extracted with DCM (150 mL×2). Organic layer was washed with water (100 mL) and brine solution (100 mL). Organic layer was dried over anhydrous sodium sulphate and concentrated under reduced pressure to obtain tert-butyl 4-((methylsulfonyl)oxy)piperidine-1-carboxylate (5000 mg, 72%) as an off white solid compound. LCMS: ELSD 280 [M+H]$^+$

Step-2: Synthesis of tert-butyl 4-(4-nitro-1H-imidazol-1-yl) piperidine-1-carboxylate To a stirred solution of tert-butyl 4-((methylsulfonyl) oxy) piperidine-1-carboxylate (4000 mg, 14.3 mmol, 1 equiv) in DMF (30 mL), was added Cs$_2$CO3 (9324 mg, 28.6 mmol, 2 equiv), TBAI (1055 mg, 2.86 mmol, 0.2 equiv) and 4-nitro-1H-imidazole (810 mg, 7.16 mmol, 0.5 equiv). The resultant reaction mixture was allowed to stir at 80° C. for overnight. Progress of the reaction was monitored by LCMS. After completion of the reaction, diluted with water (100 mL) and extracted with EtOAc (150 mL×2). Organic layer was washed with water (100 mL) and brine solution (100 mL). Organic layer was dried over anhydrous sodium sulphate and concentrated under reduced pressure to obtain crude, which was purified by normal phase Combi flash to obtain tert-butyl 4-(4-nitro-1H-imidazol-1-yl)piperidine-1-carboxylate (550 mg, 13%) as an off white solid compound. LCMS: 297 [M+H]$^+$

Step-3: Synthesis of tert-butyl 4-(4-amino-1H-imidazol-1-yl) piperidine-1-carboxylate To a stirred solution of tert-butyl 4-(4-nitro-1H-imidazol-1-yl) piperidine-1-carboxylate (550 mg, 1.85 mmol, 1 equiv) in methanol (10 mL), was added Pd/C (20% w/w) (110 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain tert-butyl 4-(4-amino-1H- imidazol-1-yl) piperidine-1-carboxylate (450 mg, 91%) as a brown color viscous compound. LCMS: 267 [M+H]⁺

Step-4: Synthesis of tert-butyl 4-(4-((5-fluoro-4-(8-fluoro-4-isopropyl-3,4-dihydro-2H-benzo[b][1,4]oxazin-6-yl)pyrimidin-2-yl)amino)-1H-imidazol-1-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (500 mg, 1.53 mmol, 1 equiv) in dioxane (5 mL), was added tert-butyl 4-(4-amino-1H-imidazol-1-yl)piperidine-1-carboxylate (450 mg, 1.69 mmol, 1.1 equiv) and cesium carbonate (748 mg, 2.29 mmol, 1.5 equiv). The reaction mixture was degassed with nitrogen gas for 30 min., followed by the addition of palladium acetate (7 mg, 0.03 mmol, 0.02 equiv) and BINAP (38 mg, 0.06 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(4-((5-fluoro-4-(8-fluoro-4-isopropyl-3,4-dihydro-2H-benzo[b][1,4]oxazin-6-yl)pyrimidin-2-yl)amino)-1H-imidazol-1-yl)piperidine-1-carboxylate (600 mg, 70%) as a brown color viscous compound. LCMS: 556 [M+H]⁺

Step-5: Synthesis of 5-fluoro-4-(8-fluoro-4-isopropyl-3,4-dihydro-2H-benzo[b][1,4]oxazin-6-yl)-N-(1-(piperidin-4-yl)-1H-imidazol-4-yl)pyrimidin-2-amine tert-butyl 4-(4-((5-fluoro-4-(8-fluoro-4-isopropyl-3,4-dihydro-2H-benzo[b][1,4]oxazin-6-yl)pyrimidin-2-yl)amino)-1H-imidazol-1-yl)piperidine-1-carboxylate (600 mg, 1.08 mmol, 1 equiv) was taken in 1.25 M HCl in ethanol (10 mL) and the resultant reaction mixture was allowed to stir at 50° C. for 1 h. Progress of the reaction was monitored by LCMS. After completion of the reaction, solvent was removed under reduced pressure to obtain crude compound, which was purified by making HCl salt to afford 5-fluoro-4-5-fluoro-4-(8-fluoro-4-isopropyl-3,4-dihydro-2H-benzo[b][1,4]oxazin-6-yl)-N-(1-(piperidin-4-yl)-1H-imidazol-4-yl)pyrimidin-2-amine (400 mg, 81%) as an orange color solid compound. LCMS: 456 [M+H]⁺

Step-6: Synthesis of 5-fluoro-4-(8-fluoro-4-isopropyl-3,4-dihydro-2H-benzo[b][1,4]oxazin-6-yl)-N-(1-(1-methylpiperidin-4-yl)-1H-imidazol-4-yl)pyrimidin-2-amine To a stirred solution of 5-fluoro-4-(8-fluoro-4-isopropyl-3,4-dihydro-2H-benzo[b][1,4]oxazin-6-yl)-N-(1-(piperidin-4-yl)-1H-imidazol-4-yl)pyrimidin-2-amine (50 mg, 0.1 mmol, 1 equiv) in DCE (5 mL), was added Formaldehyde (40% in water) (0.01 mL, 0.3 mmol, 3 equiv), acetic acid (0.03 mL, 0.5 mmol, 5 equiv). The reaction mixture was allowed to stir at RT for 1 h. The reaction mixture was cooled to 0° C. NaCNBH₃ (19 mg, 0.3 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(1-(1-methylpiperidin-4-yl)-1H-imidazol-4-yl)pyrimidin-2-amine (6 mg, 13%) as a yellow color solid compound. LCMS: 470 [M+H]⁺; ¹HNMR (400 MHz, DMSO-d₆) δ 9.68 (br. s., 1H), 8.50 (br. s., 1H), 7.56 (br. s., 1H), 7.39 (br. s., 1H), 7.32 (br. s., 1H), 7.17 (s, 1H), 4.30 (br. s., 2H), 4.13 (d, J=7.8 Hz, 1H), 3.31 (br. s., 2H), 3.08 (br. s., 2H), 2.90 (d, J=7.3 Hz, 2H), 2.08 (br. s., 3H), 2.00 (br. s., 2H), 1.97 (br. s., 2H), 1.01-1.29 ppm (m, 7H).

Example-105: Synthesis of 5-fluoro-4-(8-fluoro-4-isopropyl-3,4-dihydro-2H-benzo[b][1,4]oxazin-6-yl)-N-(1-(1-methylpiperidin-4-yl)-1H-pyrazol-4-yl)pyrimidin-2-amine. (Compound 497)

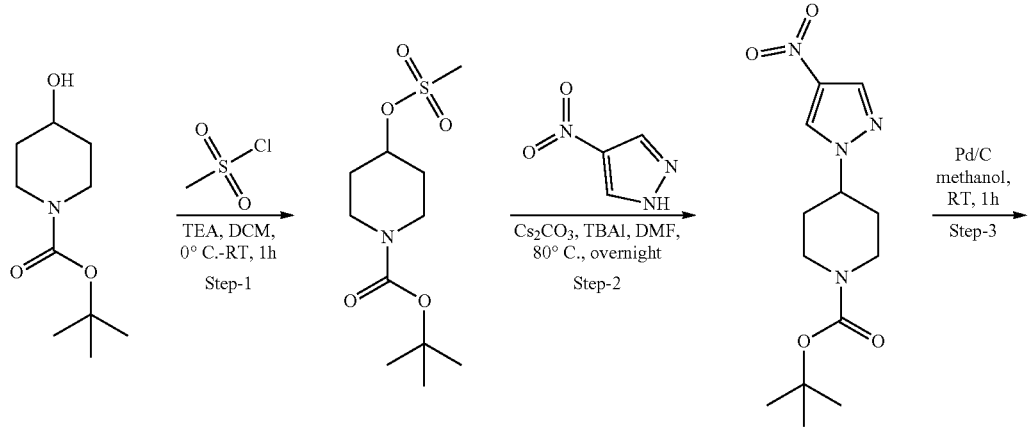

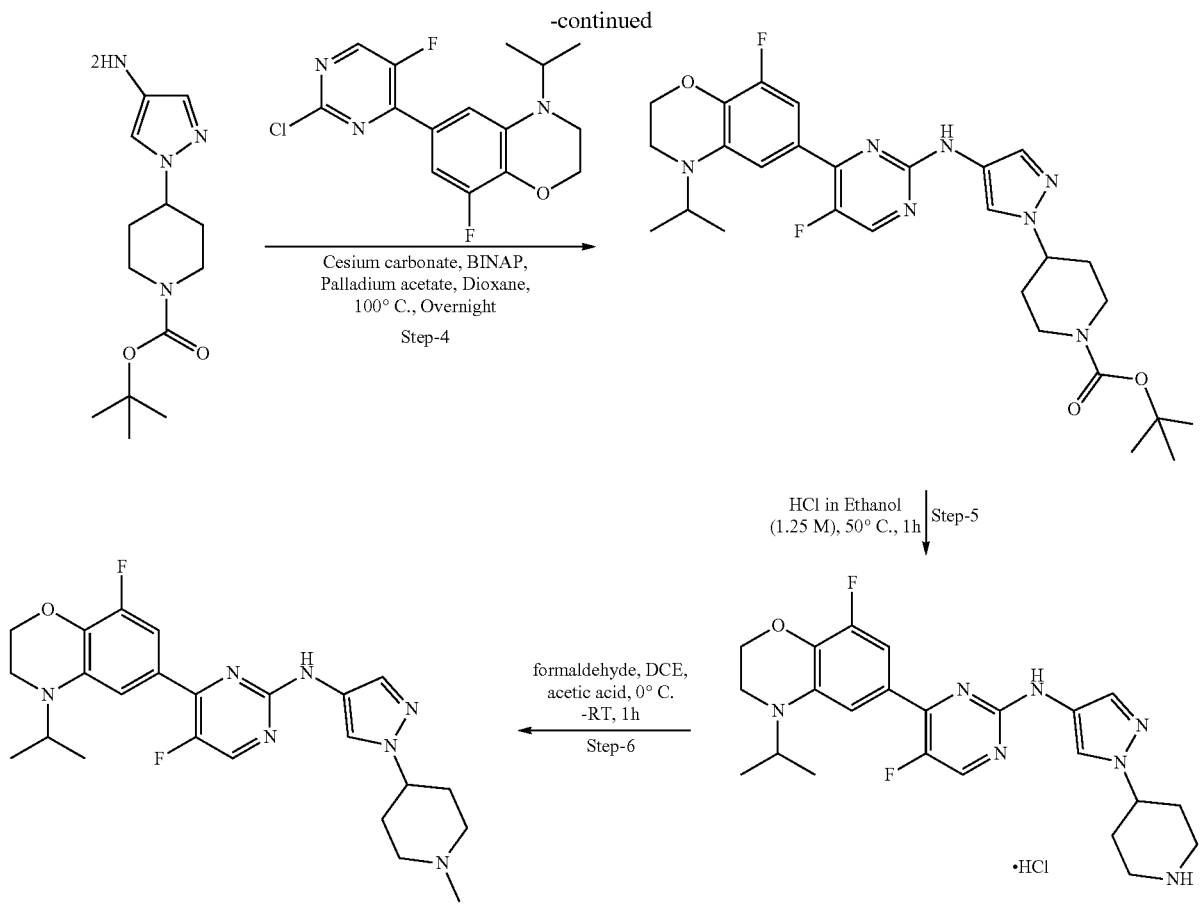

Step-1: Synthesis of tert-butyl 4-((methylsulfonyl)oxy) piperidine-1-carboxylate To a stirred solution of tert-butyl 4-hydroxypiperidine-1-carboxylate (1000 mg, 4.97 mmol, 1 equiv) in DCM (15 mL), was added TEA (1 mL, 6.96 mmol, 1.4 equiv). Cool the reaction mixture to 0° C., followed by the addition of mesyl chloride (0.5 mL, 6.96 mmol, 1.4 equiv). Raise the temp. to RT and the resultant reaction mixture was allowed to stir for overnight. Progress of the reaction was monitored by LCMS. After completion of the reaction, diluted with water (50 mL) and extracted with DCM (100 mL×2). Organic layer was washed with water (100 mL) and brine solution (100 mL). Organic layer was dried over anhydrous sodium sulphate and concentrated under reduced pressure to obtain tert-butyl 4-((methylsulfonyl)oxy)piperidine-1-carboxylate (1200 mg, 86%) as an off white solid compound.

Step-2: Synthesis of tert-butyl 4-(4-nitro-1H-pyrazol-1-yl) piperidine-1-carboxylate To a stirred solution of tert-butyl 4-hydroxypiperidine-1-carboxylate (500 mg, 1.79 mmol, 1 equiv) in DMF (10 mL), was added $Cs_2CO_3$ (1167 mg, 3.58 mmol, 2 equiv), TBAI (133 mg, 0.36 mmol, 0.2 equiv) and 4-nitro-1H-pyrazole (101 mg, 0.89 mmol, 0.5 equiv). The resultant reaction mixture was allowed to stir at 80° C. for overnight. Progress of the reaction was monitored by LCMS. After completion of the reaction, diluted with water (50 mL) and extracted with EtOAc (100 mL×2). Organic layer was washed with water (100 mL) and brine solution (100 mL). Organic layer was dried over anhydrous sodium sulphate and concentrated under reduced pressure to obtain crude, which was purified by normal phase Combi flash to obtain tert-butyl 4-(4-nitro-1H-pyrazol-1-yl)piperidine-1-carboxylate (400 mg, 75%) as a brown viscous compound. LCMS: 297 [M+H]$^+$

Step-3: Synthesis of tert-butyl 4-(4-amino-1H-pyrazol-1-yl) piperidine-1-carboxylate To a stirred solution of tert-butyl 4-(4-nitro-1H-pyrazol-1-yl) piperidine-1-carboxylate (200 mg, 0.67 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain tert-butyl 4-(4-amino-1H-pyrazol-1-yl) piperidine-1-carboxylate (150 mg, 83%) as a brown color viscous compound. LCMS: 267 [M+H]$^+$

Step-4: Synthesis of tert-butyl 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl) piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added tert-butyl 4-(4-amino-1H-pyrazol-1-yl)piperidine-1-carboxylate (90 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by recrystallization with methanol to obtain tert-butyl 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl)piperidine-1-carboxylate (150 mg, 88%) as a yellow color solid compound. LCMS: 556 [M+H]$^+$ Step-5: Synthesis of 5-fluoro-4-(8-fluoro-4-isopropyl-3,4-dihydro-2H-benzo[b][1,4]oxazin-6-yl)-N-(1-(piperidin-4-yl)-1H-pyrazol-4-yl)pyrimidin-2-amine tert-butyl 4-(4-((5-fluoro-4-(8-fluoro-4-isopropyl-3,4-dihydro-2H-benzo[b][1,4]oxazin-6-yl)pyrimidin-2-yl)amino)-1H-pyrazol-1-yl)piperidine-1-carboxylate (150 mg, 0.27 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer to obtain crude compound, which was purified by making HCl salt to afford 5-fluoro-4-(8-fluoro-4-isopropyl-3,4-dihydro-2H-benzo[b][1,4]oxazin-6-yl)-N-(1-(piperidin-4-yl)-1H-pyrazol-4-yl)pyrimidin-2-amine (100 mg, 81%) as an orange color solid compound. LCMS: 456 [M+H]$^+$ Step-6: Synthesis of 5-fluoro-4-(8-fluoro-4-isopropyl-3,4-dihydro-2H-benzo[b][1,4]oxazin-6-yl)-N-(1-(1-methylpiperidin-4-yl)-1H-pyrazol-4-yl)pyrimidin-2-amine To a stirred solution of 5-fluoro-4-(8-fluoro-4-isopropyl-3,4-dihydro-2H-benzo[b][1,4]oxazin-6-yl)-N-(1-(piperidin-4-yl)-1H-pyrazol-4-yl)pyrimidin-2-amine (100 mg, 0.2 mmol, 1 equiv) in DCE (5 mL), was added Formaldehyde (40% in water) (0.03 mL, 0.6 mmol, 3 equiv), acetic acid (0.05 mL, 1.0 mmol, 5 equiv). The reaction mixture was allowed to stir at RT for 1 h. The reaction mixture was cooled to 0° C. NaCNBH$_3$ (38 mg, 0.6 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(1-(1-methylpiperidin-4-yl)-1H-pyrazol-4-yl)pyrimidin-2-amine (10 mg, 10%) as a yellow color solid compound. LCMS: 470 [M+H]$^+$;

$^1$HNMR (400 MHz, DMSO-d$_6$) δ 9.48 (s, 1H), 8.48 (d, J=3.9 Hz, 1H), 7.90 (s, 1H), 7.56 (br. s., 1H), 7.35 (s, 1H), 7.13 (d, J=11.8 Hz, 1H), 4.29 (br. s., 2H), 3.98-4.17 (m, 2H), 3.30 (br. s., 2H), 2.85 (d, J=11.4 Hz, 2H), 2.20 (s, 3H), 1.98-2.11 (m, 2H), 1.69-1.98 (m, 4H), 1.18 ppm (d, J=6.6 Hz, 6H).

Example-106: Synthesis of 5-fluoro-4-(8-fluoro-4-isopropyl-3,4-dihydro-2H-benzo[b][,4]oxazin-6-yl)-N-(5-(1-methylpyrrolidin-3-yl)pyridin-2-yl)pyrimidin-2-amine. (Compound 498)

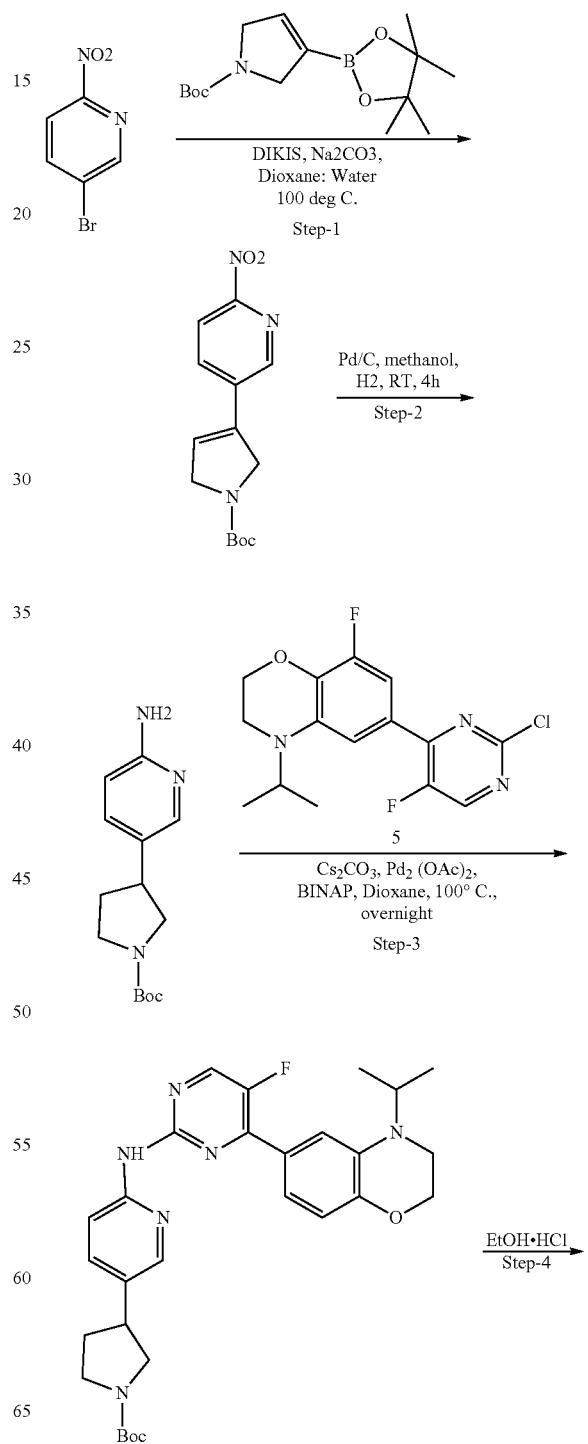

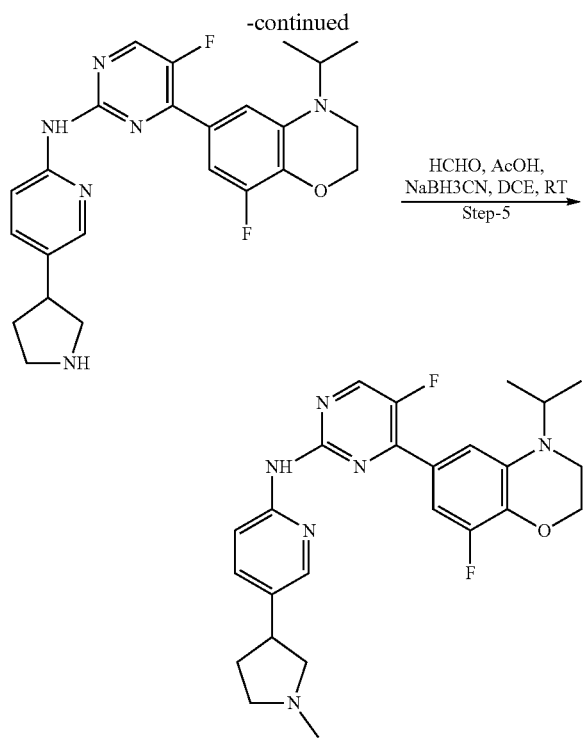

HCHO, AcOH,
NaBH3CN, DCE, RT
Step-5

Step-1: Synthesis of tert-butyl 3-(6-nitropyridin-3-yl)-2,5-dihydro-1H-pyrrole-1-carboxylate To a stirred solution of 6-bromo-8-fluoro-2H-benzo[b][1,4]oxazin-3(4H)-one (700 mg, 2.85 mmol, 1 equiv) in DMF (10 mL), was added $K_2CO_3$ (789 mg, 5.71 mmol, 2 equiv) and ethyl iodide (0.5 mL, 5.71 mmol, 2 equiv). The reaction mixture was allowed to stir at 80° C. for 3 h. Progress of the reaction was monitored by TLC and LCMS. After completion of the reaction, the reaction mixture was diluted with water (50 mL), solid observed was filtered dried under vacuum to obtain 6-bromo-4-ethyl-8-fluoro-2H-benzo[b][1,4]oxazin-3(4H)-one (700 mg, 90%) as an off white solid compound. LCMS: 274 [M+H]$^+$

Step-2: Synthesis of tert-butyl 3-(6-aminopyridin-3-yl) pyrrolidine-1-carboxylate To a stirred solution of tert-butyl 3-(6-nitropyridin-3-yl)-2,5-dihydro-1H-pyrrole-1-carboxylate (100 mg, 0.3 mmol, 1 equiv) in ethanol (3 mL), was added PdC (20 mg, 0.2 mmol, 1 equiv) The resultant reaction mixture was allowed to stir at RT for 3 h. Progress of the reaction was monitored by TLC and LCMS. After completion of the reaction, the mixture was passes through celite bed and the filtrate was concentrated under reduced pressure to obtain tert-butyl 3-(6-aminopyridin-3-yl) pyrrolidine-1-carboxylate (90 mg, 91%) as a brown Solid compound. LCMS: 264 [M+H]$^+$

Step-3: Synthesis of tert-butyl 3-(6-((5-fluoro-4-(8-fluoro-4-isopropyl-3,4-dihydro-2H-benzo[b][1,4]oxazin-6-yl)pyrimidin-2-yl)amino)pyridin-3-yl)pyrrolidine-1-carboxylate To the solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) was added dioxane (5 ml) and tert-butyl 3-(6-aminopyridin-3-yl)pyrrolidine-1-carboxylate (145 mg, 0.50 mmol, 1.1 equiv), cesium carbonate (224 mg, 0.69 mmol, 1.5 equiv), resulted reaction mixture was degassed with nitrogen for 5 min thereafter was added Pd(Oac)$_2$, (11 mg, 0.046 mmol, 0.1 equiv), BINAP (57 mg, 0.09 mmol, 0.2 mmol), resulted reaction mixture was allowed to stir for 15 h at 100° C. Progress of the reaction was monitored by LCMS. After completion of the reaction, the reaction mixture was diluted with water (25 mL) and extracted with ethyl acetate (40 mL×2). Organic layer was washed with water (35 mL) and brine solution (25 mL). Organic layer was dried over anhydrous sodium sulphate and concentrated under reduced pressure to obtain crude, which was purified by combi-flash to get tert-butyl 3-(6-((5-fluoro-4-(8-fluoro-4-isopropyl-3,4-dihydro-2H-benzo[b][1,4]oxazin-6-yl)pyrimidin-2-yl)amino)pyridin-3-yl)pyrrolidine-1-carboxylate (190 mg, 16%) as a yellow solid compound. LCMS: 553 [M+H]$^+$

Step-4: Synthesis of 5-fluoro-4-(8-fluoro-4-isopropyl-3,4-dihydro-2H-benzo[b][1,4]oxazin-6-yl)-N-(5-(pyrrolidin-3-yl)pyridin-2-yl)pyrimidin-2-amine To the solution tert-butyl 3-(6-((5-fluoro-4-(8-fluoro-4-isopropyl-3,4-dihydro-2H-benzo[b][1,4]oxazin-6-yl)pyrimidin-2-yl)amino)pyridin-3-yl)pyrrolidine-1-carboxylate (190 mg, 0.44 mmol, 1 equiv) was taken in 1.25 M HCl in ethanol (5 mL) and the resultant reaction mixture was allowed to stir at 50° C. for 3 h. Progress of the reaction was monitored by LCMS. After completion of the reaction, solvent was removed under reduced pressure and the residue was dried under lyophilizer to get 5-fluoro-4-(8-fluoro-4-isopropyl-3,4-dihydro-2H-benzo[b][1,4]oxazin-6-yl)-N-(5-(pyrrolidin-3-yl)pyridin-2-yl)pyrimidin-2-amine (99 mg, 39%) as a brick red color solid compound. LCMS: 453 [M+H]$^+$

Step-5: Synthesis of 5-fluoro-4-(8-fluoro-4-isopropyl-3,4-dihydro-2H-benzo[b][1,4]oxazin-6-yl)-N-(5-(1-methylpyrrolidin-3-yl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(5-(pyrrolidin-3-yl)pyridin-2-yl)pyrimidin-2-amine (99 mg, 0.44 mmol, 1 equiv) in DCE (5 mL), was added Formaldehyde (40% in water) (0.66 mL, 0.19 mmol, 3 equiv), acetic acid (0.2 mL, 1.1 mmol, 5 equiv). The reaction mixture was allowed to stir at RT for 1 h. The reaction mixture was cooled to 0° C. NaCNBH$_3$ (41 mg, 0.66 mmol, 3 equiv) was added to above mixture and raise the temperature to RT. The reaction mixture was allowed to stir at RT for 4 h. Progress of the reaction was monitored by LCMS. After completion of the reaction, the reaction mixture was diluted with water (20 mL) and extracted with ethyl acetate (25 mL×2). Organic layer was washed with water (15 mL) and brine solution (20 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(5-(1-methylpyrrolidin-3-yl)pyridin-2-yl)pyrimidin-2-amine (18 mg, 99%) as a yellow color solid compound. LCMS: 471[M+H]$^+$; $^1$HNMR (400 MHz, Methanol-d4) δ 8.44 (d, J=4.1 Hz, 1H), 8.30 (d, J=8.8 Hz, 1H), 8.18 (s, 1H), 7.79-7.71 (m, 1H), 7.52 (s, 1H), 7.29-7.21 (m, 1H), 4.33 (t, J=4.3 Hz, 2H), 4.22 (p, J=6.6 Hz, 1H), 3.57-3.44 (m, 1H), 3.35 (t, J=4.4 Hz, 4H), 3.14-3.03

(m, 1H), 3.03-2.93 (m, 1H), 2.77 (t, J=9.5 Hz 1H), 2.61 (s, 3H), 2.43 (dq, J=14.3, 8.2 Hz, 1H), 2.02 (dt, J=13.3, 7.6 Hz, 1H), 1.26 (d, J=6.6 Hz, 7H).

Example-107: Synthesis of 5-fluoro-4-(8-fluoro-4-isopropyl-3,4-dihydro-2H-benzo[b][1,4]oxazin-6-yl)-N-(3-(1-methylpiperidin-4-yl)-1H-pyrazol-5-yl)pyrimidin-2-amine. (Compound 499)

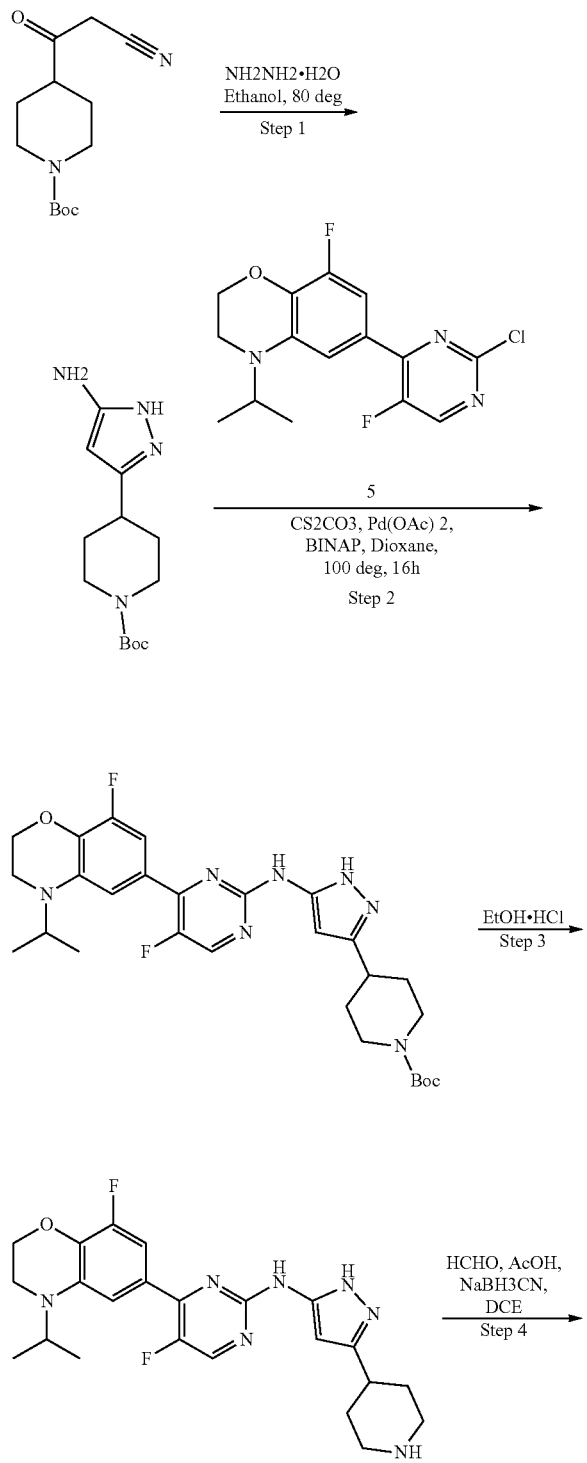

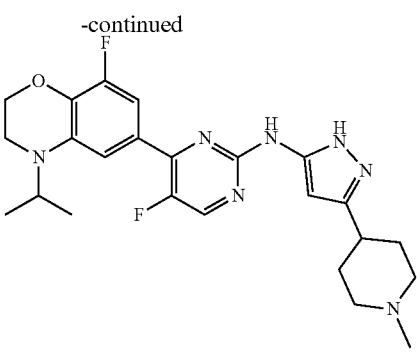

Step-1: Synthesis of tert-butyl 4-(5-amino-1H-pyrazol-3-yl) piperidine-1-carboxylate To a solution of tert-butyl 4-(2-cyanoacetyl) piperidine-1-carboxylate (100 mg, 0.4 mmol, 1 equiv) in ethanol (4 mL) in sealed tube, was added hydrazine hydrate (0.12 mL, 2.4 mmol, 6 equiv). The resultant reaction mixture was allowed to stir at 80° C. for 4 h. Progress of the reaction was monitored by TLC and LCMS. After completion of the reaction, diluted with water (30 mL) and extracted with ethyl acetate (100 mL). Organic layer was washed with water (20 mL) and brine solution (30 mL). Organic layer was dried over anhydrous sodium sulphate and concentrated under reduced pressure to obtain crude, which was purified by normal phase combi flash to obtain tert-butyl 4-(5-amino-1H-pyrazol-3-yl)piperidine-1-carboxylate (80 mg, 73%) as a yellow solid compound. LCMS: 267 [M+H]$^+$

Step-2: Synthesis of tert-butyl 4-(5-((5-fluoro-4-(8-fluoro-4-isopropyl-3,4-dihydro-2H-benzo[b][1,4]oxazin-6-yl)pyrimidin-2-yl)amino)-1H-pyrazol-3-yl)piperidine-1-carboxylate To the solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) was added dioxane (5 ml) and tert-butyl 4-(5-amino-1H-pyrazol-3-yl)piperidine-1-carboxylate (145 mg, 0.50 mmol, 1.1 equiv), cesium carbonate (223 mg, 0.69 mmol, 1.5 equiv), resulted reaction mixture was degassed with nitrogen for 5 min thereafter was added Pd(Oac)$_2$, (10 mg, 0.046 mmol, 0.1 equiv), BINAP (57 mg, 0.09 mmol, 0.2 mmol), resulted reaction mixture was allowed to stir for 15 h at 100° C. Progress of the reaction was monitored by LCMS. After completion of the reaction, the reaction mixture was diluted with water (25 mL) and extracted with ethyl acetate (50 mL×2). Organic layer was washed with water (30 mL) and brine solution (20 mL). Organic layer was dried over anhydrous sodium sulphate and concentrated under reduced pressure to obtain crude, which was purified by combi-flash to tert-butyl 4-(5-((5-fluoro-4-(8-fluoro-4-isopropyl-3,4-dihydro-2H-benzo[b][1,4]oxazin-6-yl)pyrimidin-2-yl)amino)-1H-pyrazol-3-yl)piperidine-1-carboxylate (180 mg, 46%) as a yellow solid compound. LCMS: 556 [M+H]$^+$

Step-3: 5-fluoro-4-(8-fluoro-4-isopropyl-3,4-dihydro-2H-benzo[b][1,4]oxazin-6-yl)-N-(3-(piperidin-4-yl)-1H-pyrazol-5-yl)pyrimidin-2-amine tert-butyl 4-(5-((5-fluoro-4-(8-fluoro-4-isopropyl-3,4-dihydro-2H-benzo[b][1,4]oxazin-6-yl)pyrimidin-2-yl)

amino)-1H-pyrazol-3-yl)piperidine-1-carboxylate (250 mg, 0.44 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure and the residue was dried under lyophilizer 5-fluoro-4-(8-fluoro-4-isopropyl-3,4-dihydro-2H-benzo[b][1,4]oxazin-6-yl)-N-(3-(piperidin-4-yl)-1H-pyrazol-5-yl)pyrimidin-2-amine (200 mg, 44%) as a brick red color solid compound. LCMS: 456 [M+H]+

Step-4: Synthesis of 5-fluoro-4-(8-fluoro-4-isopropyl-3,4-dihydro-2H-benzo[b][1,4]oxazin-6-yl)-N-(3-(1-methylpiperidin-4-yl)-1H-pyrazol-5-yl)pyrimidin-2-amine To a stirred solution of 5-fluoro-4-(8-fluoro-4-isopropyl-3,4-dihydro-2H-benzo[b][1,4]oxazin-6-yl)-N-(3-(piperidin-4-yl)-1H-pyrazol-5-yl)pyrimidin-2-amine (200 mg, 0.44 mmol, 1 equiv) in DCE (35 mL), was added Formaldehyde (40% in water) (0.3 mL, 0.19 mmol, 3 equiv), acetic acid (0.013 mL, 2.1 mmol, 5 equiv). The reaction mixture was allowed to stir at RT for 1 h. The reaction mixture was cooled to 0° C. NaCNBH$_3$ (79 mg, 1.29 mmol, 3 equiv) was added to above mixture and raise the temperature to RT. The reaction mixture was allowed to stir at RT for 4 h. Progress of the reaction was monitored by LCMS. After completion of the reaction, the reaction mixture was diluted with water (30 mL) and extracted with ethyl acetate (40 mL×2). Organic layer was washed with water (30 mL) and brine solution (30 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(3-(1-methylpiperidin-4-yl)-1H-pyrazol-5-yl)pyrimidin-2-amine. (14 mg, 93%) as a yellow color solid compound. LCMS: 470 [M+H]+; $^1$HNMR (400 MHz, Methanol-d4) δ 8.48 (d, J=3.9 Hz, 1H), 7.48 (s, 1H), 7.29-7.21 (m, 1H), 6.36 (d, J=3.4 Hz, 1H), 4.33 (t, J=4.3 Hz, 2H), 4.22 (p, J=6.7 Hz, 1H), 3.35 (d, J=4.0 Hz, 5H), 3.15 (d, J=12.4 Hz, 3H), 2.83 (t, J=12.0 Hz, 1H), 2.54-2.46 (m, 5H), 2.08 (t, J=16.7 Hz, 3H), 1.90 (q, J=12.4 Hz, 2H), 1.29 (s, 1H), 1.26 (dd, J=6.6, 3.3 Hz, 6H).

Example-108: Synthesis of 5-fluoro-4-(8-fluoro-4-isopropyl-3,4-dihydro-2H-benzo[b][1,4]oxazin-6-yl)-N-(5-(piperidin-4-yl)pyrimidin-2-yl)pyrimidin-2-amine. (Compound 500)

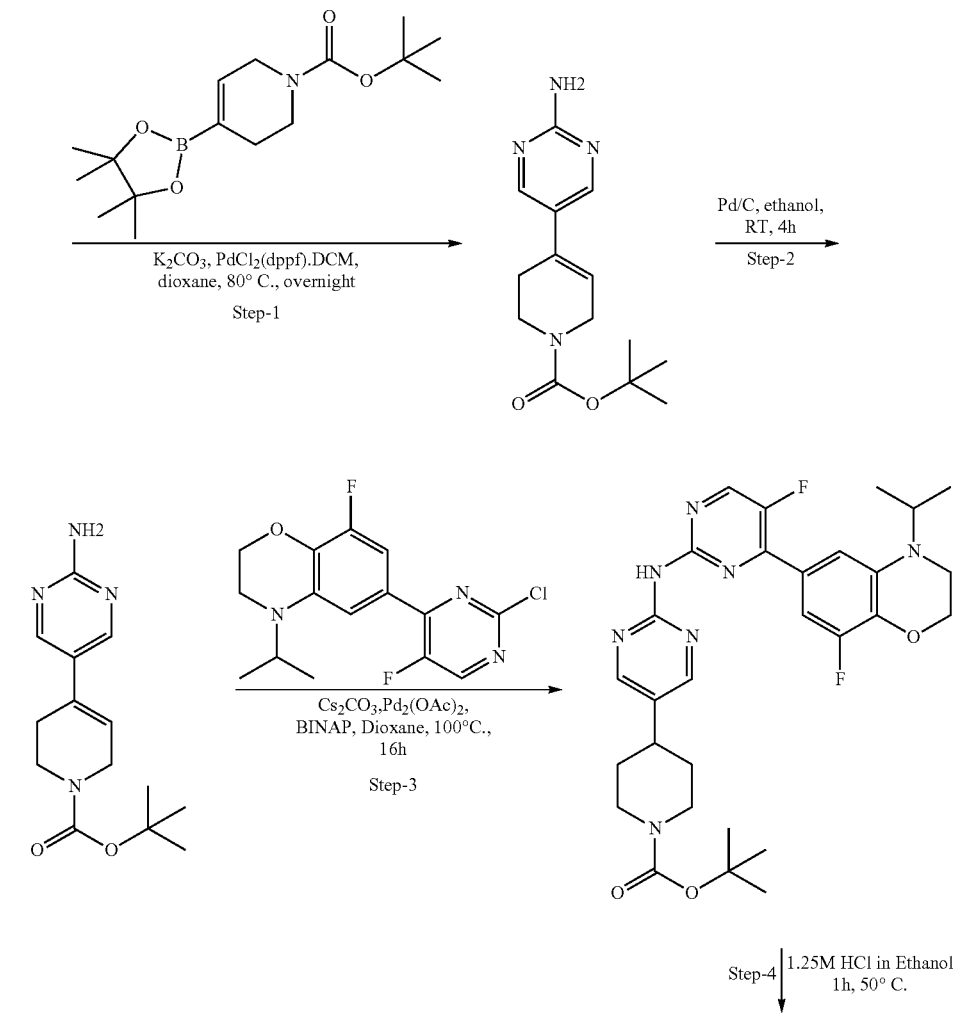

-continued

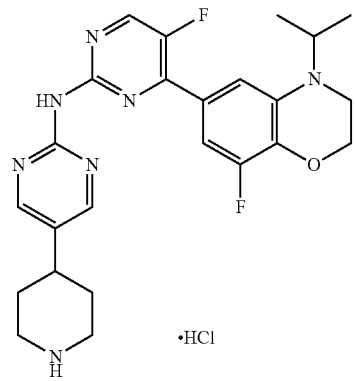

Step-1: Synthesis of tert-butyl 4-(2-aminopyrimidin-5-yl)-3, 6-dihydropyridine-1(2H)-carboxylate To a solution of 5-bromopyrimidin-2-amine (1000 mg, 5.7 mmol, 1 equiv) in dioxane (12 mL), water (2 mL) was added tert-butyl 4-(4,4,5,5-tetramethyl-1,3,2-dioxaborolan-2-yl)-3,6-dihydropyridine-1(2H)-carboxylate (2143 mg, 6.93 mmol, 1.2 equiv) and potassium carbonate (2360 mg, 17.1 mmol, 3 equiv). The reaction mixture was degassed with nitrogen gas for 30 min., followed by the addition of Pd (dppf) $Cl_2$.DCM (233 mg, 0.28 mmol, 0.05 equiv). The resultant reaction mixture was allowed to stir at 100° C. for overnight. Progress of the reaction was monitored by TLC and LCMS. After completion of the reaction, reaction mixture was diluted with water (50 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to tert-butyl 4-(2-aminopyrimidin-5-yl)-3, 6-dihydropyridine-1(2H)-carboxylate (1000 mg, 63%) as a brown solid compound. LCMS: 277 [M+H]$^+$

Step-2: Synthesis of tert-butyl 4-(2-aminopyrimidin-5-yl) piperidine-1-carboxylate To a stirred solution of tert-butyl 4-(2-aminopyrimidin-5-yl)-3, 6-dihydropyridine-1(2H)-carboxylate (400 mg, 0.72 mmol, 1 equiv) in ethanol (5 mL), was added Pd/C (20% w/w) (85 mg) under $H_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain tert-butyl 4-(2-aminopyrimidin-5-yl) piperidine-1-carboxylate (360 mg, 90%) as an off white color solid compound. LCMS: 279 [M+H]$^+$

Step-3: Synthesis of tert-butyl 4-(2-((5-fluoro-4-(8-fluoro-4-isopropyl-3,4-dihydro-2H-benzo[b][1,4]oxazin-6-yl)pyrimidin-2-yl)amino)pyrimidin-5-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (5 mL), was added tert-butyl 4-(2-aminopyrimidin-5-yl)piperidine-1-carboxylate (188 mg, 0.67 mmol, 1.1 equiv) and cesium carbonate (298 mg, 0.91 mmol, 1.5 equiv). The reaction mixture was degassed with nitrogen gas for 30 min., followed by the addition of palladium acetate (3 mg, 0.01 mmol, 0.02 equiv) and BINAP (15 mg, 0.02 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(2-((5-fluoro-4-(8-fluoro-4-isopropyl-3,4-dihydro-2H-benzo[b][1,4]oxazin-6-yl)pyrimidin-2-yl)amino)pyrimidin-5-yl)piperidine-1-carboxylate (150 mg, 43%) as a yellow solid compound. LCMS: 568 [M+H]$^+$

Step-4: Synthesis of 5-fluoro-4-(8-fluoro-4-isopropyl-3,4-dihydro-2H-benzo[b][1,4]oxazin-6-yl)-N-(5-(piperidin-4-yl)pyrimidin-2-yl)pyrimidin-2-amine A solution of tert-butyl 4-(2-((5-fluoro-4-(8-fluoro-4-isopropyl-3,4-dihydro-2H-benzo[b][1,4]oxazin-6-yl)pyrimidin-2-yl)amino)pyrimidin-5-yl)piperidine-1-carboxylate (150 mg, 0.26 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(5-(piperidin-4-yl)pyrimidin-2-yl)pyrimidin-2-amine (25 mg, 20%) as a yellow color solid compound. LCMS: 468 [M+H]$^+$; $^1$HNMR (400 MHz, DMSO-$d_6$) δ 10.35 (s, 1H), 8.63 (d, J=3.9 Hz, 1H), 8.48 (s, 2H), 7.57 (s, 1H), 7.21 (d, J=11.7 Hz, 1H), 4.29 (br. s., 2H), 3.99-4.16 (m, 1H), 3.30 (br. s., 2H), 3.18 (d, J=9.3 Hz, 2H), 2.56-2.84 (m, 3H), 1.84 (d, J=12.2 Hz, 2H), 1.66 (d, J=12.7 Hz, 2H), 1.19 ppm (d, J=6.8 Hz, 6H).

Example-109: Synthesis of N-(5-(1-ethylpiperidin-4-yl) pyridin-2-yl)-5-fluoro-4-(8-fluoro-4-isopropyl-3,4-dihydro-2H-benzo[b][1,4]oxazin-6-yl)pyrimidin-2-amine. (Compound 501)

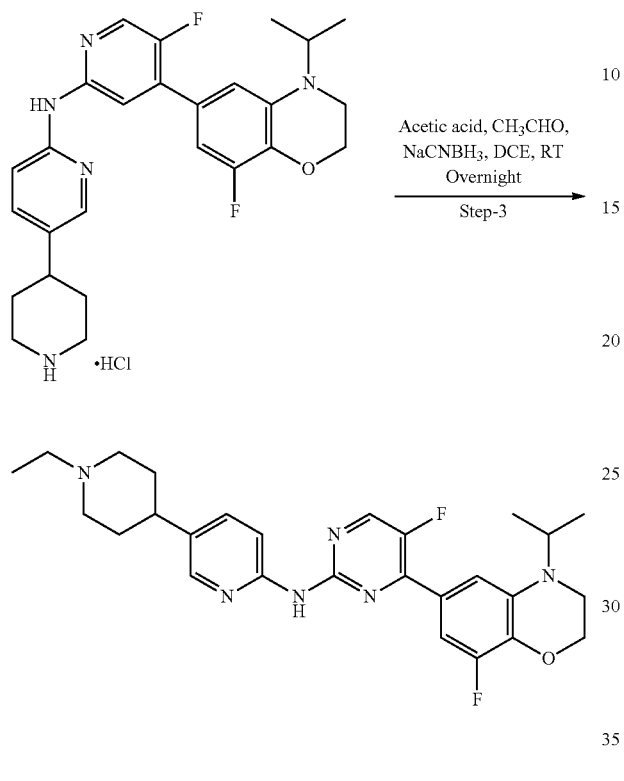

Step-1: Synthesis of N-(5-(1-ethylpiperidin-4-yl) pyridin-2-yl)-5-fluoro-4-(8-fluoro-4-isopropyl-3,4-dihydro-2H-benzo[b][1,4]oxazin-6-yl)pyrimidin-2-amine To a stirred solution of 5-fluoro-4-(8-fluoro-4-isopropyl-3,4-dihydro-2H-benzo[b][1,4]oxazin-6-yl)-N-(5-(piperidin-4-yl)pyridin-2-yl)pyrimidin-2-amine (80 mg, 0.16 mmol, 1 equiv) in DCE (5 mL), was added Acetaldehyde (0.01 mL, 0.48 mmol, 3 equiv), acetic acid (0.04 mL, 0.8 mmol, 5 equiv). The reaction mixture was allowed to stir at RT for 1 h. The reaction mixture was cooled to 0° C. NaCNBH$_3$ (18 mg, 0.48 mmol, 3 equiv) was added to above mixture and raise the temperature to room temperature. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by recrystallization with methanol to afford N-(5-(1-ethylpiperidin-4-yl)pyridin-2-yl)-5-fluoro-4-(8-fluoro-4-isopropyl-3,4-dihydro-2H-benzo[b][1,4]oxazin-6-yl)pyrimidin-2-amine (70 mg, 82%) as a yellow color solid compound. LCMS: 495 [M+H]$^+$; $^1$HNMR (400 MHz, DMSO-d$_6$) δ 9.89 (s, 1H), 8.60 (d, J=3.9 Hz, 1H), 8.18 (s, 1H), 8.11 (d, J=8.8 Hz, 1H), 7.62 (d, J=8.8 Hz, 1H), 7.48 (s, 1H), 7.18 (d, J=11.4 Hz, 1H), 4.30 (br. s., 2H), 4.02-4.21 (m, 1H), 3.30 (br. s., 2H) 2.98 (d, J=10.1 Hz, 2H), 2.35 (br. s., 2H), 1.97 (br. s., 3H), 1.76 (d, J=10.5 Hz, 2H), 1.65 (d, J=9.2 Hz, 2H), 1.19 (d, J=6.6 Hz, 6H), 1.02 ppm (t, J=7.2 Hz, 3H).

Example-110: Synthesis of 7-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-1(2H)-one. (Compound 502)

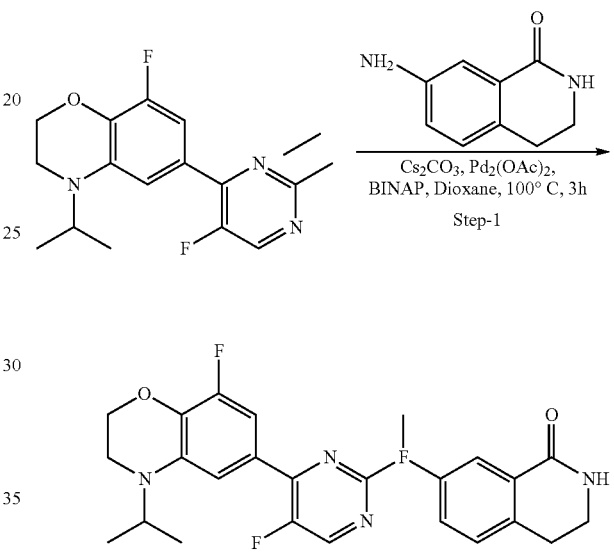

To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added 7-amino-3,4-dihydroisoquinolin-1(2H)-one (54 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for 3 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to afford 7-((5-fluoro-4-(8-fluoro-4-isopropyl-3,4-dihydro-2H-benzo[b][1,4]oxazin-6-yl)pyrimidin-2-yl)amino)-3,4-dihydroisoquinolin-1(2H)-one (5 mg, 4%) as a yellow color solid compound. LCMS: 452 [M+H]$^+$; $^1$HNMR (400 MHz, DMSO-d$_6$) δ 9.76 (s, 1H), 8.57 (d, J=3.9 Hz, 1H), 8.25 (d, J=2.2 Hz, 1H), 7.89 (br. s., 1H), 7.81 (dd, J=8.3, 2.6 Hz, 1H), 7.41 (s, 1H), 7.12-7.25 (m, 1H), 4.23-4.32 (m, 2H), 4.05-4.21 (m, 1H), 3.30-3.39 (br. s., 4H), 2.85 (t, J=6.4 Hz, 2H), 1.16 (d, J=6.6 Hz, 6H).

703

Example-111: Synthesis of 5-fluoro-4-(8-fluoro-4-isopropyl-3,4-dihydro-2H-benzo[b][1,4]oxazin-6-yl)-N-(6-methyl-5-(1-methylpiperidin-4-yl)pyridin-2-yl)pyrimidin-2-amine. (Compound 503)

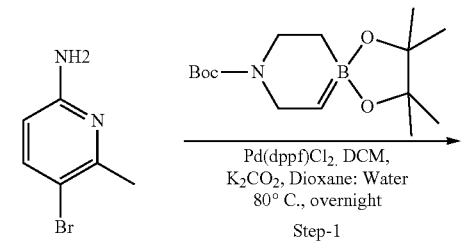

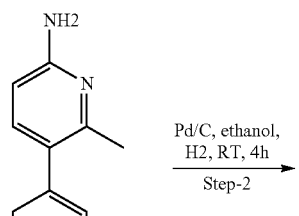

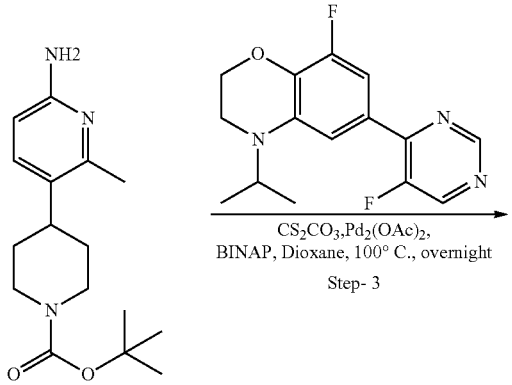

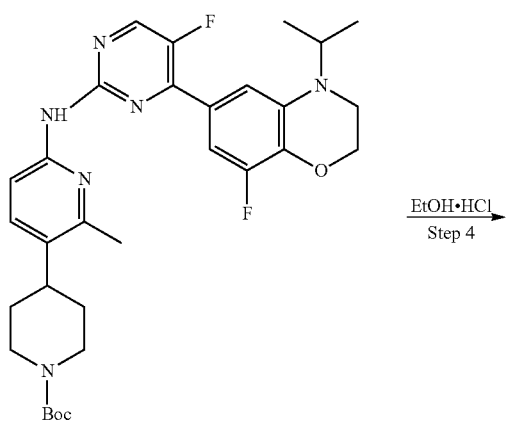

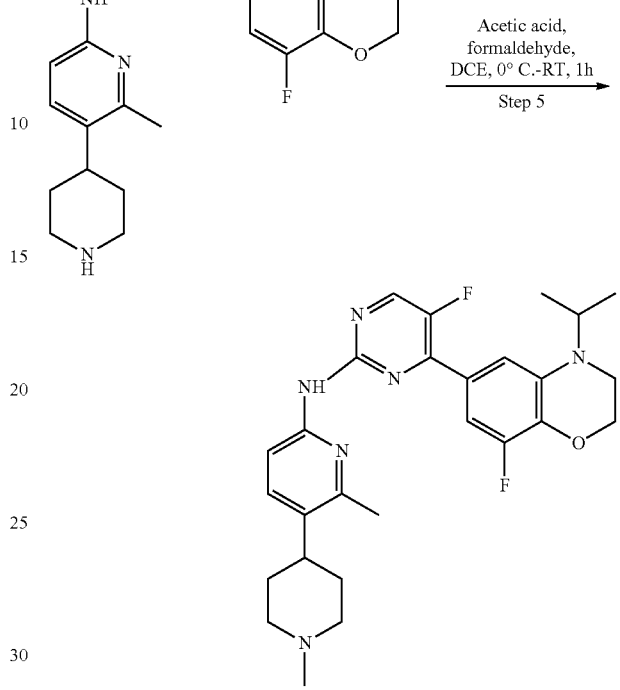

Step-1: Synthesis of tert-butyl 6-amino-2-methyl-3',6'-dihydro-[3,4'-bipyridine]-1'(2'H)-carboxylate To a solution of 5-bromopyrimidin-2-amine (1000 mg, 5.37 mmol, 1 equiv) in dioxane (12 mL), water (2 mL) was added tert-butyl 4-(4,4,5,5-tetramethyl-1,3,2-dioxaborolan-2-yl)-3,6-dihydropyridine-1(2H)-carboxylate (1994 mg, 6.45 mmol, 1.2 equiv) and potassium carbonate (1482 mg, 17.1 mmol, 2 equiv). The reaction mixture was degassed with nitrogen gas for 30 min., followed by the addition of Pd (dppf) $Cl_2$.DCM (219 mg, 0.26 mmol, 0.05 equiv). The resultant reaction mixture was allowed to stir at 100° C. for overnight. Progress of the reaction was monitored by TLC and LCMS. After completion of the reaction, reaction mixture was diluted with water (50 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 6-amino-2-methyl-3',6'-dihydro-[3,4'-bipyridine]-1'(2'H)-carboxylate (1300 mg, 84%) as an off white color solid compound. LCMS: 277 [M+H]$^+$ Step-2: Synthesis of tert-butyl 4-(6-amino-2-methylpyridin-3-yl) piperidine-1-carboxylate To a stirred solution of tert-butyl 6-amino-2-methyl-3',6'-dihydro-[3,4'-bipyridine]-1'(2'H)-carboxylate (400 mg, 1.38 mmol, 1 equiv) in ethanol (5 mL), was added Pd/C (20% w/w) (40 mg) under $H_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain tert-butyl 4-(6-amino-2-methylpyridin-3-yl) piperidine-1-carboxylate (380 mg, 94%) as an off white color solid compound. LCMS: 292 [M+H]⁺

Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)-2-methylpyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added tert-butyl 4-(6-amino-2-methylpyridin-3-yl)piperidine-1-carboxylate (96 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(6-((5-fluoro-4-(8-fluoro-4-isopropyl-3,4-dihydro-2H-benzo[b][1,4]oxazin-6-yl)pyrimidin-2-yl)amino)-2-methylpyridin-3-yl)piperidine-1-carboxylate (120 mg, 67%) as a yellow solid compound. LCMS: 581 [M+H]⁺

Step-4: Synthesis of 5-fluoro-4-(8-fluoro-4-isopropyl-3,4-dihydro-2H-benzo[b][1,4]oxazin-6-yl)-N-(6-methyl-5-(piperidin-4-yl)pyridin-2-yl)pyrimidin-2-amine A solution of tert-butyl 4-(6-((5-fluoro-4-(8-fluoro-4-isopropyl-3,4-dihydro-2H-benzo[b][1,4]oxazin-6-yl)pyrimidin-2-yl)amino)-2-methylpyridin-3-yl)piperidine-1-carboxylate (120 mg, 0.22 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(6-methyl-5-(piperidin-4-yl)pyridin-2-yl)pyrimidin-2-amine (100 mg, quantitative yield) as a yellow color solid compound. LCMS: 481 [M+H]⁺

Step-5: Synthesis of 5-fluoro-4-(8-fluoro-4-isopropyl-3,4-dihydro-2H-benzo[b][1,4]oxazin-6-yl)-N-(6-methyl-5-(1-methylpiperidin-4-yl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(6-methyl-5-(piperidin-4-yl)pyridin-2-yl)pyrimidin-2-amine (60 mg, 0.12 mmol, 1 equiv) in DCE (5 mL), was added Formaldehyde (40% in water) (0.01 mL, 0.37 mmol, 3 equiv), acetic acid (0.03 mL, 0.6 mmol, 5 equiv). The reaction mixture was allowed to stir at RT for 1 h. The reaction mixture was cooled to 0° C. NaCNBH₃ (23 mg, 0.37 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by recrystallization with methanol to afford 5-fluoro-4-(8-fluoro-4-isopropyl-3,4-dihydro-2H-benzo[b][1,4]oxazin-6-yl)-N-(6-methyl-5-(1-methylpiperidin-4-yl)pyridin-2-yl)pyrimidin-2-amine (20 mg, 32%) as a yellow color solid compound. LCMS: 495 [M+H]⁺; ¹HNMR (400 MHz, DMSO-d₆) δ 9.74 (s, 1H), 8.58 (d, J=3.9 Hz, 1H), 8.00 (d, J=8.3 Hz, 1H), 7.41-7.61 (m, 1H), 7.19 (d, J=11.7 Hz, 1H), 4.30 (br. s., 2H), 4.02-4.22 (m, 1H), 3.31 (br. s., 2H), 2.88 (d, J=11.2 Hz, 2H), 2.59 (d, J=11.2 Hz, 2H), 2.44 (s, 3H), 2.20 (s, 3H), 1.99 (t, J=10.3 Hz, 2H), 1.46-1.75 (m, 3H), 1.19 ppm (d, J=6.4 Hz, 6H).

Example-112: Synthesis of 5-fluoro-4-(8-fluoro-4-isopropyl-3,4-dihydro-2H-benzo[b][1,4]oxazin-6-yl)-N-(1-(piperidin-4-yl)-1H-imidazol-4-yl)pyrimidin-2-amine. (Compound 504)

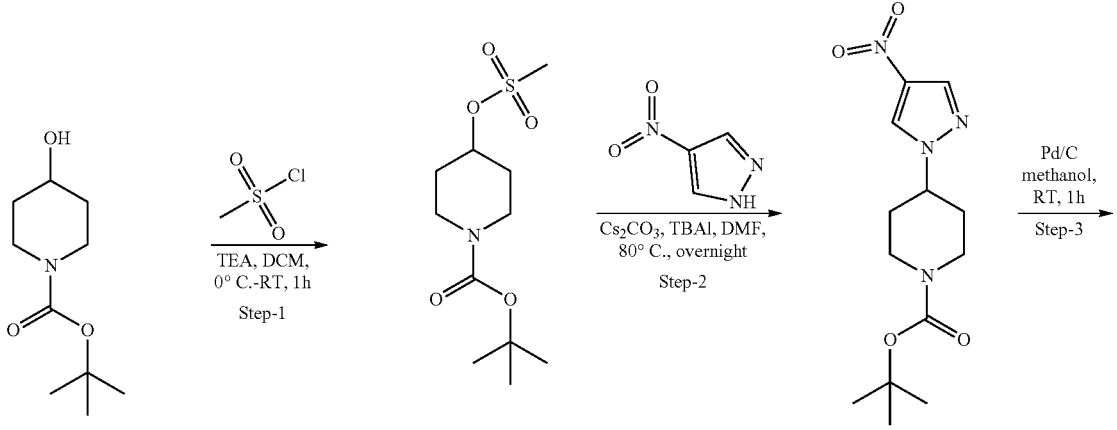

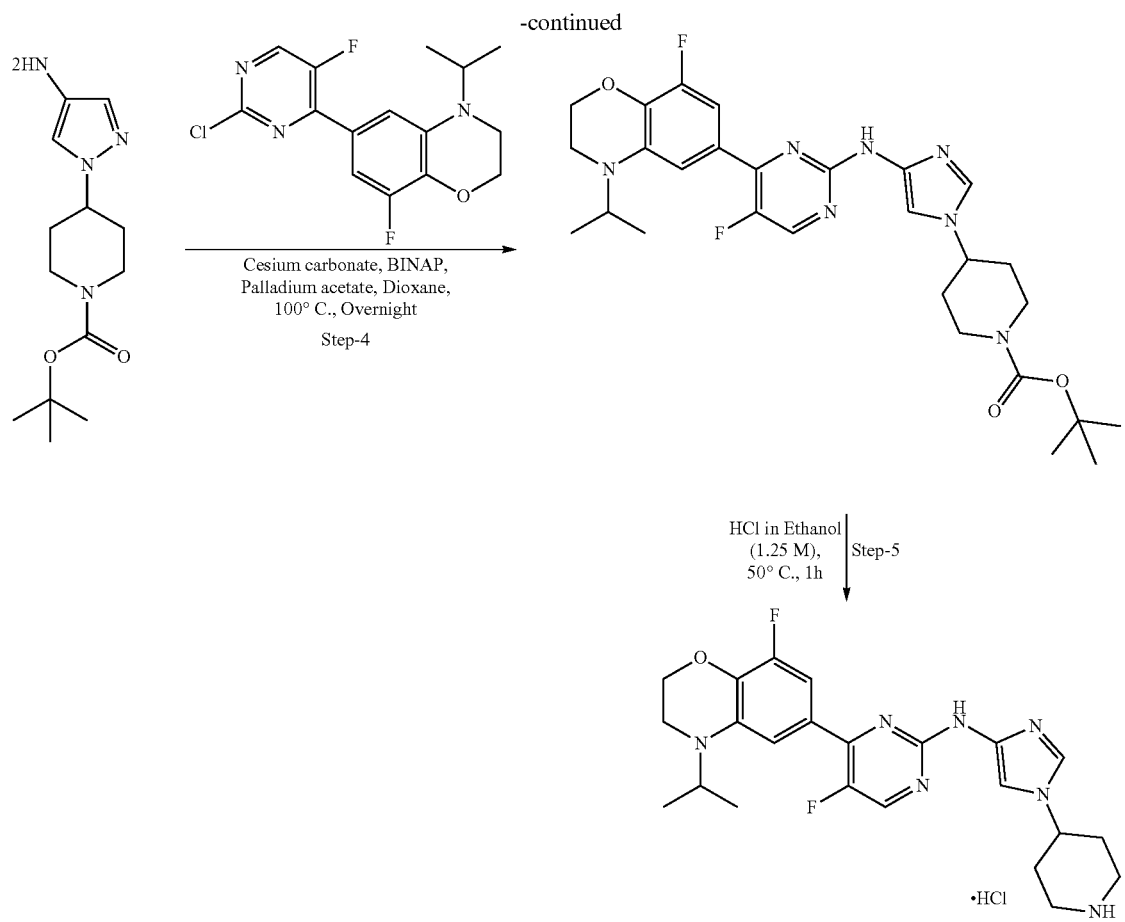

Step-1: Synthesis of tert-butyl 4-((methylsulfonyl) oxy) piperidine-1-carboxylate To a stirred solution of 4-hydroxycyclohexan-1-one (5000 mg, 24.87 mmol, 1 equiv) in DCM (50 mL), was added TEA (5 mL, 34.8 mmol, 1.4 equiv). Cool the reaction mixture to 0° C., followed by the addition of mesyl chloride (2.5 mL, 34.8 mmol, 1.4 equiv). Raise the temp. to RT and the resultant reaction mixture was allowed to stir for overnight. Progress of the reaction was monitored by LCMS. After completion of the reaction, diluted with water (100 mL) and extracted with DCM (150 mL×2). Organic layer was washed with water (100 mL) and brine solution (100 mL). Organic layer was dried over anhydrous sodium sulphate and concentrated under reduced pressure to obtain tert-butyl 4-((methylsulfonyl) oxy) piperidine-1-carboxylate (5000 mg, 72%) as an off white solid compound.

Step-2: Synthesis of tert-butyl 4-(4-nitro-1H-imidazol-1-yl) piperidine-1-carboxylate To a stirred solution of tert-butyl 4-((methylsulfonyl) oxy) piperidine-1-carboxylate (4000 mg, 14.3 mmol, 1 equiv) in DMF (30 mL), was added Cs$_2$CO3 (9324 mg, 28.6 mmol, 2 equiv), TBAI (1055 mg, 2.86 mmol, 0.2 equiv) and 4-nitro-1H-imidazole (810 mg, 7.16 mmol, 0.5 equiv). The resultant reaction mixture was allowed to stir at 80° C. for overnight. Progress of the reaction was monitored by LCMS. After completion of the reaction, diluted with water (100 mL) and extracted with EtOAc (150 mL×2). Organic layer was washed with water (100 mL) and brine solution (100 mL). Organic layer was dried over anhydrous sodium sulphate and concentrated under reduced pressure to obtain crude, which was purified by normal phase Combi flash to obtain tert-butyl 4-(4-nitro-1H-imidazol-1-yl)piperidine-1-carboxylate (550 mg, 13%) as an off white solid compound. LCMS: 297 [M+H]$^+$

Step-3: Synthesis of tert-butyl 4-(4-amino-1H-imidazol-1-yl) piperidine-1-carboxylate To a stirred solution of tert-butyl 4-(4-nitro-1H-imidazol-1-yl) piperidine-1-carboxylate (550 mg, 1.85 mmol, 1 equiv) in methanol (10 mL), was added Pd/C (20% w/w) (110 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain tert-butyl 4-(4-amino-1H-imidazol-1-yl) piperidine-1-carboxylate (450 mg, 91%) as a brown color viscous compound. LCMS: 267 [M+H]$^+$

Step-4: Synthesis of tert-butyl 4-(4-((5-fluoro-4-(8-fluoro-4-isopropyl-3,4-dihydro-2H-benzo[b][1,4] oxazin-6-yl)pyrimidin-2-yl)amino)-1H-imidazol-1-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (500 mg, 1.53 mmol, 1 equiv) in dioxane (5 mL), was added tert-butyl 4-(4-amino-1H-imidazol-1-yl)piperidine-1-carboxylate (450 mg, 1.69 mmol, 1.1 equiv) and cesium carbonate (748 mg, 2.29 mmol, 1.5 equiv). The reaction mixture was degassed with nitrogen gas for 30 min., followed by the addition of palladium acetate (7 mg, 0.03 mmol, 0.02 equiv) and BINAP (38 mg, 0.06 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(4-((5-fluoro-4-(8-fluoro-4-isopropyl-3,4-dihydro-2H-benzo[b][1,4]oxazin-6-yl)pyrimidin-2-yl)amino)-1H-imidazol-1-yl)piperidine-1-carboxylate (600 mg, 70%) as a brown color viscous compound. LCMS: 556 [M+H]$^+$ Step-5: Synthesis of 5-fluoro-4-(8-fluoro-4-isopropyl-3,4-dihydro-2H-benzo[b][1,4]oxazin-6-yl)-N-(1-(piperidin-4-yl)-1H-imidazol-4-yl)pyrimidin-2-amine tert-butyl 4-(4-((5-fluoro-4-(8-fluoro-4-isopropyl-3,4-dihydro-2H-benzo[b][1,4]oxazin-6-yl)pyrimidin-2-yl)amino)-1H-imidazol-1-yl)piperidine-1-carboxylate (100 mg, 0.18 mmol, 1 equiv) was taken in 1.25 M HCl in ethanol (10 mL) and the resultant reaction mixture was allowed to stir at 50° C. for 1 h. Progress of the reaction was monitored by LCMS. After completion of the reaction, solvent was removed under reduced pressure to obtain crude compound, which was purified by making HCl salt to afford 5-fluoro-4 5-fluoro-4-(8-fluoro-4-isopropyl-3,4-dihydro-2H-benzo[b][1,4]oxazin-6-yl)-N-(1-(piperidin-4-yl)-1H-imidazol-4-yl)pyrimidin-2-amine (15 mg, 18%) as a yellow color solid compound. LCMS: 456 [M+H]$^+$;

$^1$HNMR (400 MHz, DMSO-d$_6$) δ 9.65 (br. s., 1H), 8.50 (br. s., 1H), 7.53 (br. s., 1H), 7.39 (br. s., 1H), 7.31 (br. s., 1H), 7.15 (d, J=11.2 Hz, 1H), 4.30 (br. s., 2H), 3.92-4.19 (m, 1H), 3.31 (br. s., 2H), 3.10 (d, J=10.3 Hz, 2H), 2.65 (d, J=11.7 Hz, 2H), 1.97 (br. s., 2H), 1.76 (d, J=10.3 Hz, 2H), 1.18 ppm (d, J=6.4 Hz, 6H).

Example-113: Synthesis of 5-fluoro-4-(8-fluoro-4-isopropyl-3,4-dihydro-2H-benzo[b][1,4]oxazin-6-yl)-N-(5-(piperidin-4-yl)pyrazin-2-yl)pyrimidin-2-amine. (Compound 505)

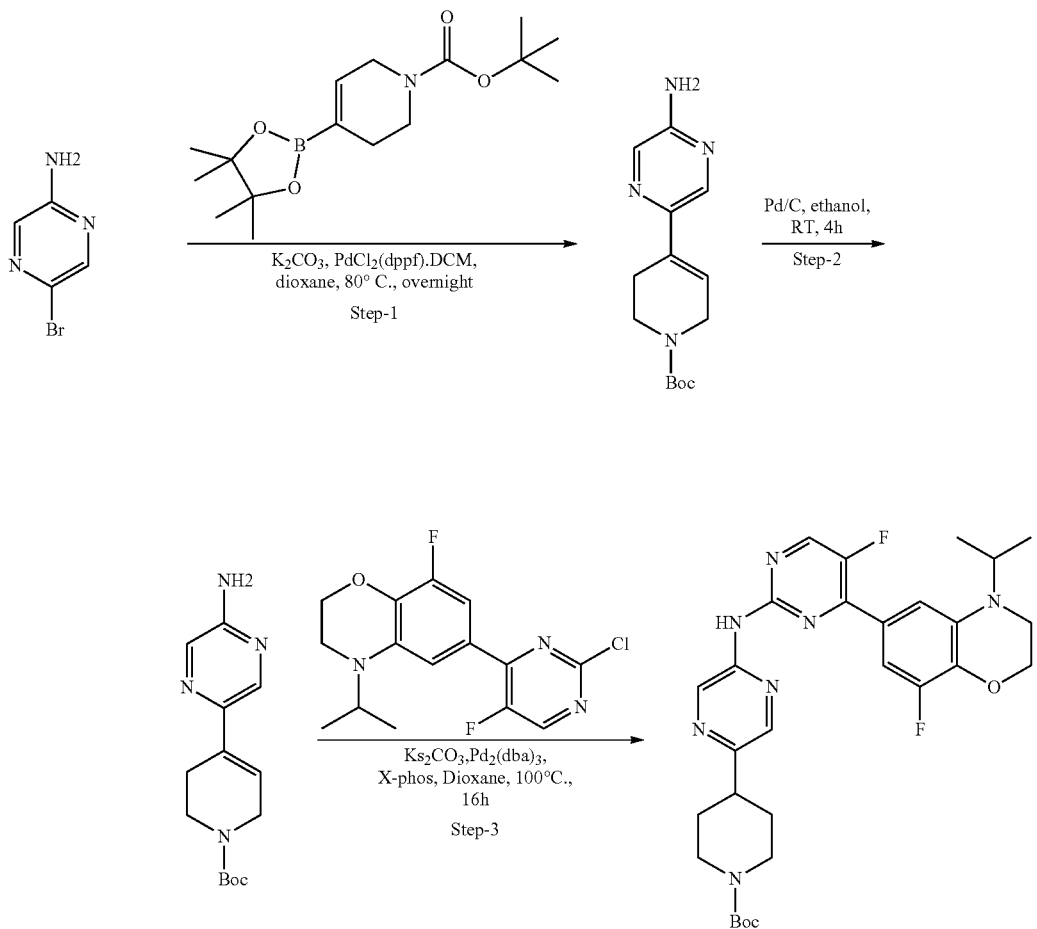

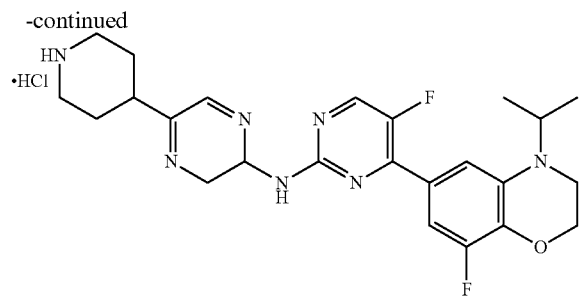

Step-1; Synthesis of tert-butyl 4-(5-aminopyrazin-2-yl)-3,6-dihydropyridine-1(2H)-carboxylate To a solution of 5-bromopyrimidin-2-amine (1000 mg, 5.7 mmol, 1 equiv) in dioxane (12 mL), water (2 mL) was added tert-butyl 4-(4,4,5,5-tetramethyl-1,3,2-dioxaborolan-2-yl)-3,6-dihydropyridine-1(2H)-carboxylate (2143 mg, 6.93 mmol, 1.2 equiv) and potassium carbonate (2360 mg, 17.1 mmol, 3 equiv). The reaction mixture was degassed with nitrogen gas for 30 min., followed by the addition of Pd (dppf) $Cl_2$.DCM (233 mg, 0.28 mmol, 0.05 equiv). The resultant reaction mixture was allowed to stir at 100° C. for overnight. Progress of the reaction was monitored by TLC and LCMS. After completion of the reaction, reaction mixture was diluted with water (50 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 4-(5-aminopyrazin-2-yl)-3,6-dihydropyridine-1(2H)-carboxylate (1000 mg, 63%) as a brown solid compound. LCMS: 277 $[M+H]^+$

Step-2: Synthesis of tert-butyl 4-(5-aminopyrazin-2-yl) piperidine-1-carboxylate To a stirred solution of tert-butyl 4-(5-aminopyrazin-2-yl)-3, 6-dihydropyridine-1(2H)-carboxylate (400 mg, 1.44 mmol, 1 equiv) in ethanol (5 mL), was added Pd/C (20% w/w) (80 mg) under $H_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain tert-butyl 4-(5-aminopyrazin-2-yl) piperidine-1-carboxylate (400 mg, 99%) as an off white color solid compound. LCMS: 279 $[M+H]^+$

Step-3: Synthesis of tert-butyl 4-(5-((5-fluoro-4-(8-fluoro-4-isopropyl-3,4-dihydro-2H-benzo[b][1,4]oxazin-6-yl)pyrimidin-2-yl)amino)pyrazin-2-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (200 mg, 0.61 mmol, 1 equiv) in dioxane (5 mL), was added tert-butyl 4-(5-aminopyrazin-2-yl)piperidine-1-carboxylate (187 mg, 0.67 mmol, 1.1 equiv) and potassium carbonate (168 mg, 1.22 mmol, 2 equiv). The reaction mixture was degassed with nitrogen gas for 30 min., followed by the addition of $Pd_2(dba)_3$ (56 mg, 0.06 mmol, 0.1 equiv) and X-phos (58 mg, 0.12 mmol, 0.2 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(5-((5-fluoro-4-(8-fluoro-4-isopropyl-3,4-dihydro-2H-benzo[b][1,4]oxazin-6-yl)pyrimidin-2-yl)amino)pyrazin-2-yl)piperidine-1-carboxylate (250 mg, 72%) as a yellow solid compound. LCMS: 568 $[M+H]^+$

Step-4: Synthesis of 5-fluoro-4-(8-fluoro-4-isopropyl-3,4-dihydro-2H-benzo[b][1,4]oxazin-6-yl)-N-(5-(piperidin-4-yl)pyrazin-2-yl)pyrimidin-2-amine A solution of tert-butyl 4-(5-((5-fluoro-4-(8-fluoro-4-isopropyl-3,4-dihydro-2H-benzo[b][1,4]oxazin-6-yl)pyrimidin-2-yl)amino)pyrazin-2-yl)piperidine-1-carboxylate (250 mg, 0.44 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(5-(piperidin-4-yl)pyrazin-2-yl)pyrimidin-2-amine (2 mg, 1%) as a yellow color solid compound. LCMS: 468 $[M+H]^+$;

$^1$HNMR (DMSO-$d_6$,400 MHz): δ 10.31 (br. s., 1H), 9.38 (br. s., 1H), 8.65 (d, J=3.4 Hz, 1H), 8.25 (br. s., 1H), 7.50 (br. s., 1H), 7.20 (d, J=10.8 Hz, 1H), 4.31 (br. s., 2H), 4.15 (d, J=7.3 Hz, 1H), 3.31 (br. s., 7H), 3.17 (br. s., 2H), 2.86 (br. s., 2H), 1.02-1.30 ppm (m, 6H).

Example-114: Synthesis of 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)-2-hydroxyethan-1-one. (Compound 506)

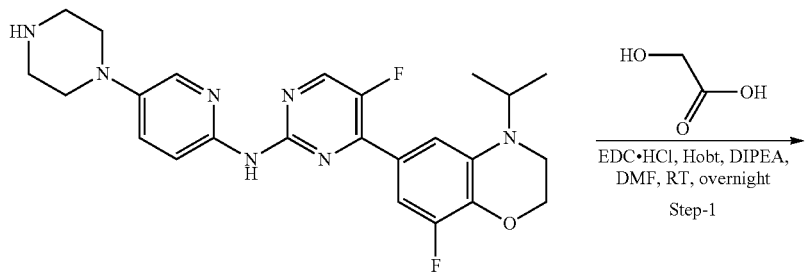

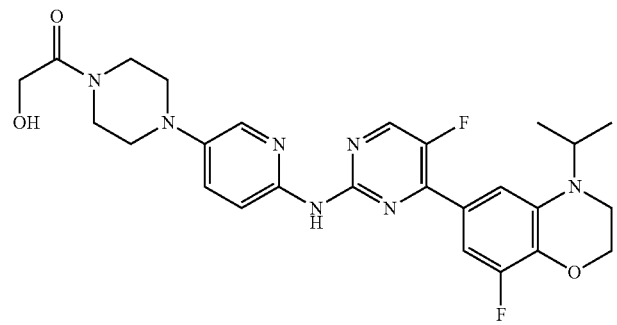

To a stirred solution of 5-fluoro-4-(8-fluoro-4-isopropyl-3,4-dihydro-2H-benzo[b][1,4]oxazin-6-yl)-N-(5-(piperazin-1-yl)pyridin-2-yl)pyrimidin-2-amine (50 mg, 0.1 mmol, 1 equiv) in DMF (5 mL), was added 2-hydroxyacetic acid (12 mg, 0.16 mmol, 1.2 equiv), DIPEA (0.05 mL, 0.3 mmol, 3 equiv), HOBt (22 mg, 0.16 mmol, 1.5 equiv) and EDC.HCL (31 mg, 0.16 mmol, 1.5 equiv). The reaction mixture was allowed to stir for overnight at RT. Progress of the reaction was monitored by TLC and LCMS. After completion of the reaction, solid observed in the reaction mixture was filtered, washed with water (10 mL) and dried under vacuum to obtain 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-1-yl)-2-hydroxyethan-1-one (20 mg, 36%) as yellow color solid compound. LCMS: 525 [M+H]$^+$; $^1$HNMR (400 MHz, DMSO-$d_6$) δ 9.74 (s, 1H), 8.57 (d, J=3.9 Hz, 1H), 7.92-8.15 (m, 2H), 7.29-7.55 (m, 2H), 7.17 (d, J=12.2 Hz, 1H), 4.64 (t, J=5.4 Hz, 1H), 4.30 (br. s., 2H), 4.14 (d, J=5.9 Hz, 3H), 3.63 (br. s., 2H), 3.51 (br. s., 2H), 3.31 (br. s., 2H), 3.11 (br. s., 4H), 1.19 ppm (d, J=6.4 Hz, 6H).

Example-115: Synthesis of 4-((5-fluoro-4-(8-fluoro-4-isopropyl-3,4-dihydro-2H-benzo[b][1,4]oxazin-6-yl)pyrimidin-2-yl)amino)benzenesulfonamide. (Compound 507)

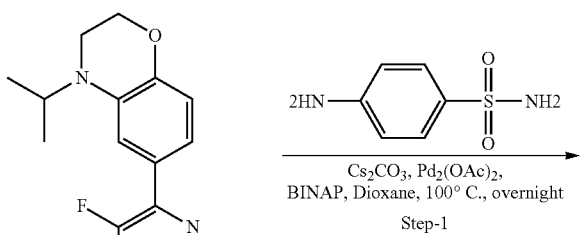

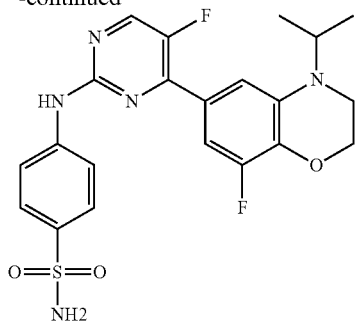

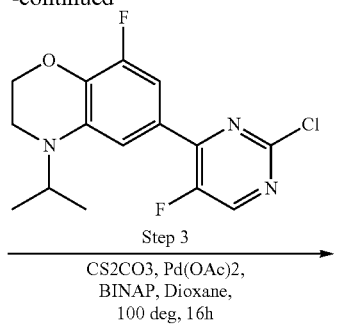

To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added 4-aminobenzenesulfonamide (57 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to afford 4-((5-fluoro-4-(8-fluoro-4-isopropyl-3,4-dihydro-2H-benzo[b][1,4]oxazin-6-yl)pyrimidin-2-yl)amino)benzenesulfonamide (25 mg, 18%) as a yellow color solid compound.

LCMS: 462 [M+H]$^+$; $^1$HNMR (400 MHz, DMSO-d$_6$) δ 10.14 (s, 1H), 8.65 (d, J=3.9 Hz, 1H), 7.81-7.98 (m, J=8.8 Hz, 2H), 7.63-7.81 (m, J=8.8 Hz, 2H), 7.45 (s, 1H), 7.06-7.24 (m, 3H), 4.31 (br. s., 2H), 4.15 (d, J=7.3 Hz, 1H), 3.31 (br. s., 2H), 1.21 ppm (d, J=6.4 Hz, 6H).

Example-116: Synthesis of N-(5-fluoro-4-(8-fluoro-4-isopropyl-3,4-dihydro-2H-benzo[b][1,4]oxazin-6-yl)pyrimidin-2-yl)-4-(piperidin-4-yl)thiazol-2-amine. (Compound 508)

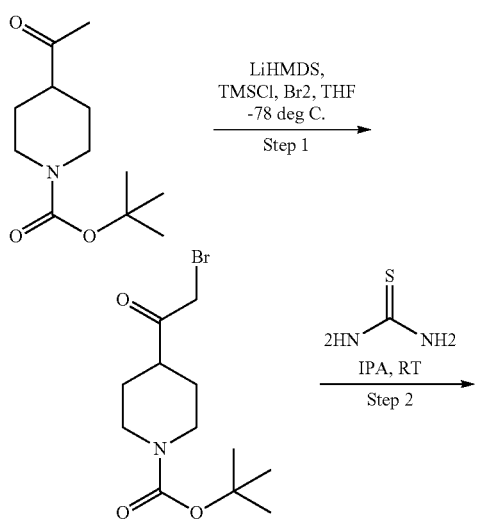

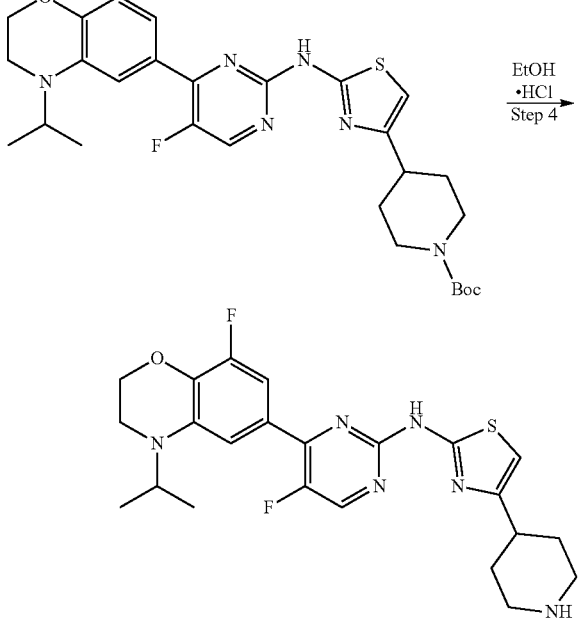

Step-1: Synthesis of tert-butyl 4-(2-bromoacetyl) piperidine-1-carboxylate

To a solution of tert-butyl 4-acetylpiperidine-1-carboxylate (500 mg, 2.21 mmol, 1 equiv) in dry THF (5 mL), was added LiHMDS (4 mL, 2.42 mmol, 1.1 equiv) dropwise at −78° C. within 15 min., resulting mixture was stirred at −78° C. for 1 h. To this was added TMSCl (0.5 mL, 2.42 mmol, 1.1 equiv) dropwise at −78° C. The reaction mixture was warmed to 0° C. for 10 min and then at room temperature for 20 min. Again was cooled to −78° C. To this was added Bromine (0.06 mL, 2.21 mmol, 1 equiv) dropwise at −78° C. The resultant reaction mixture was allowed to stir at room temperature for 15 min. Progress of the reaction was monitored by TLC and LCMS. After completion of the reaction, diluted with Na2S2O3 solution (10 mL) and NH4Cl solution (10 mL). Reaction mass extracted with ethyl acetate (15 mL). Organic layer was washed with water (5 mL) and brine solution (5 mL). Organic layer was dried over anhydrous sodium sulphate and concentrated under reduced pressure to obtain tert-butyl 4-(2-bromoacetyl) piperidine-1-carboxylate as crude, which was purified by combiflash by using 100-200 mesh silica gel column. Yield: 350 mg. LCMS: ELSD 306 [M+H]+

Step-2: Synthesis of tert-butyl 4-(2-aminothiazol-4-yl) piperidine-1-carboxylate To a stirred solution of tert-butyl 4-(2-bromoacetyl) piperidine-1-carboxylate (200 mg, 0.65 mmol, 1 equiv) in IPA (5 mL), was added thiourea (99 mg, 1.3 mmol, 2 equiv). Resultant mixture was allowed to stir at room temperature for 2 h. Progress of the reaction was monitored by TLC and LCMS. After completion of the reaction, the mixture was concentrated, diluted with water (10 mL), and was extracted with EtOAc (15 mL). Organic layer dried over anhydrous sodium sulphate and concentrated under reduced pressure to obtain crude compound was triturated from hexane to afford tert-butyl 4-(2-aminothiazol-4-yl) piperidine-1-carboxylate (150 mg) as an oily compound. LCMS: 284 [M+H]+

Step-3: Synthesis of tert-butyl 4-(2-((5-fluoro-4-(8-fluoro-4-isopropyl-3,4-dihydro-2H-benzo[b][1,4]oxazin-6-yl)pyrimidin-2-yl)amino)thiazol-4-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (4 mL), was added tert-butyl 4-(2-aminothiazol-4-yl)piperidine-1-carboxylate (94 mg, 0.33 mmol, 1.1 equiv) and potassium carbonate (62 mg, 0.45 mmol, 1.5 equiv). The reaction mixture was degassed by nitrogen gas for 10 min., followed by the addition of Pd2(dba)3 (27 mg, 0.03 mmol, 0.1 equiv) and Xphos (28 mg, 0.06 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain tert-butyl 4-(2-((5-fluoro-4-(8-fluoro-4-isopropyl-3,4-dihydro-2H-benzo[b][1,4]oxazin-6-yl)pyrimidin-2-yl)amino)thiazol-4-yl)piperidine-1-carboxylate (130 mg) as an oily crude residue which used directly for next step. LCMS: 573 [M+H]+

Step-4: Synthesis of N-(5-fluoro-4-(8-fluoro-4-isopropyl-3,4-dihydro-2H-benzo[b][1,4]oxazin-6-yl)pyrimidin-2-yl)-4-(piperidin-4-yl)thiazol-2-amine A solution of tert-butyl 4-(2-((5-fluoro-4-(8-fluoro-4-isopropyl-3,4-dihydro-2H-benzo[b][1,4]oxazin-6-yl)pyrimidin-2-yl)amino)thiazol-4-yl)piperidine-1-carboxylate (130 mg crude) in 1.25 M HCl in ethanol (5 mL) was allowed to stir for 1 h at 50° C. Progress of the reaction was monitored by LCMS. After completion of the reaction, solvent was removed under reduced pressure to obtain crude which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-4-(piperidin-4-yl)thiazol-2-amine (18 mg) as an off white solid compound. LCMS: 473 [M+H]+; 1HNMR (400 MHz, DMSO-d6) δ 8.61-8.55 (m, 2H), 8.50 (s, OH), 8.63-8.55 (m, 2H), 8.59-8.53 (m, 2H), 8.51 (s, OH), 8.65-8.52 (m, 3H), 7.71 (s, 1H), 7.36 (d, J=11.7 Hz, 1H), 6.67 (s, 1H), 4.38-4.32 (m, 2H), 2.73-2.63 (m, 4H), 2.61-2.59 (m, 1H), 4.32-4.24 (m, 1H), 3.40-3.32 (m, 3H), 2.82 (d, J=9.4 Hz, 1H), 2.61 (s, 4H), 8.62-8.53 (m, 2H), 2.22-2.13 (m, 2H), 1.91 (t, J=12.7 Hz, 2H), 8.63-8.52 (m, 3H), 1.28 (d, J=6.6 Hz, 7H).

Example-117: Synthesis of N-(4-(4-cyclopentyl-8-fluoro-3,4-dihydro-2H-benzo[b][1,4]oxazin-6-yl)-5-fluoropyrimidin-2-yl)-5,6,7,8-tetrahydro-1,6-naphthyridin-2-amine. (Compound 509)

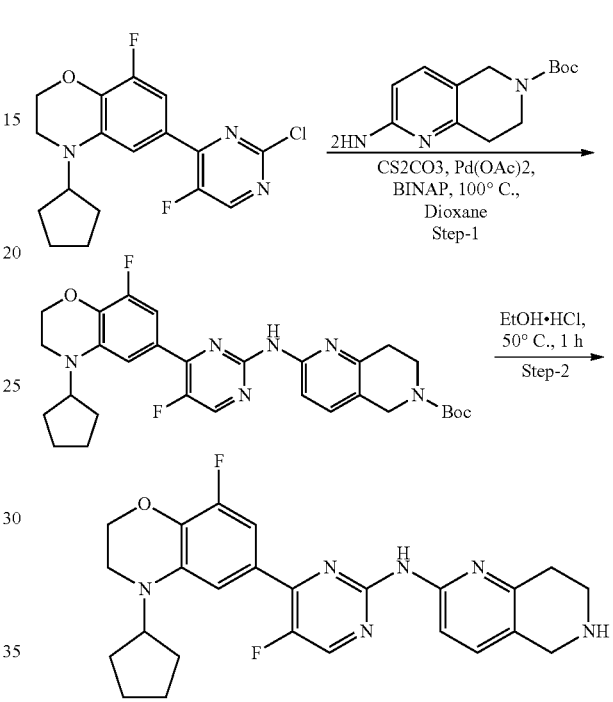

Step-1: Synthesis of tert-butyl 2-((4-(4-cyclopentyl-8-fluoro-3,4-dihydro-2H-benzo[b][1,4]oxazin-6-yl)-5-fluoropyrimidin-2-yl)amino)-7,8-dihydro-1,6-naphthyridine-6(5H)-carboxylate To a solution of 6-(2-chloro-5-fluoropyrimidin-4-yl)-4-cyclopentyl-8-fluoro-3,4-dihydro-2H-benzo[b][1,4]oxazine (40 mg, 0.11 mmol, 1 equiv) in dioxane (5 mL), was added tert-butyl 2-amino-7,8-dihydro-1,6-naphthyridine-6(5H)-carboxylate (31 mg, 0.12 mmol, 1.1 equiv) and cesium carbonate (54 mg, 0.16 mmol, 1.5 equiv). The reaction mixture was degassed with nitrogen gas for 30 min., followed by the addition of palladium acetate (1 mg, 0.002 mmol, 0.02 equiv) and BINAP (3 mg, 0.004 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to tert-butyl 2-((4-(4-cyclopentyl-8-fluoro-3,4-dihydro-2H-benzo[b][1,4]oxazin-6-yl)-5-fluoropyrimidin-2-yl)amino)-7,8-dihydro-1,6-naphthyridine-6(5H)-carboxylate (50 mg, 78%) as a yellow color solid compound. LCMS: 565 [M+H]+

Step-2: Synthesis of N-(4-(4-cyclopentyl-8-fluoro-3,4-dihydro-2H-benzo[b][1,4]oxazin-6-yl)-5-fluoropyrimidin-2-yl)-5,6,7,8-tetrahydro-1,6-naphthyridin-2-amine A solution of tert-butyl 2-((4-(4-cyclopentyl-8-fluoro-3,4-dihydro-2H-benzo[b][1,4]oxazin-6-yl)-5-fluoropyrimidin-2-yl)amino)-7,8-dihydro-1,6-naphthyridine-6(5H)-carboxylate (50 mg, 0.08 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain crude compound, which was purified by reverse phase HPLC to obtain N-(4-(4-cyclopentyl-8-fluoro-3,4-dihydro-2H-benzo[b][1,4]oxazin-6-yl)-5-fluoropyrimidin-2-yl)-5,6,7,8-tetrahydro-1,6-naphthyridin-2-amine (8 mg, 20%) as a yellow color solid compound. LCMS: 465 [M+H]+; 1HNMR (400 MHz, DMSO-$d_6$) δ 9.76 (s, 1H), 8.53 (d, J=3.9 Hz, 1H), 7.94 (d, J=8.3 Hz, 1H), 7.46 (br. s., 1H), 7.33 (d, J=8.3 Hz, 1H), 7.13 (d, J=12.2 Hz, 1H), 4.30 (br. s., 2H), 4.02-4.22 (m, 1H), 3.81 (br. s., 2H), 3.31 (br. s., 2H), 3.00 (br. s., 2H), 2.67 (br. s., 2H), 1.83 (br. s., 2H), 1.64 (br. s., 2H), 1.54 ppm (br. s., 4H).

Example-118: Synthesis of 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-1-yl)-2-hydroxyethan-1-one. (Compound 510)

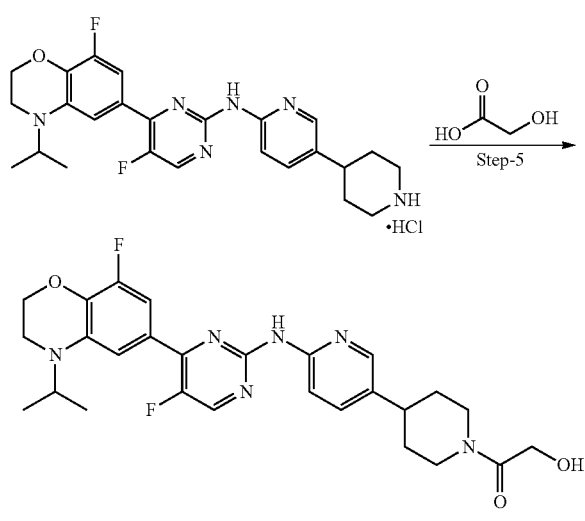

Step-1: Synthesis of 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-1-yl)-2-hydroxyethan-1-one To a stirred solution of 5-fluoro-4-(8-fluoro-4-isopropyl-3,4-dihydro-2H-benzo[b][1,4]oxazin-6-yl)-N-(5-(piperidin-4-yl)pyridin-2-yl)pyrimidin-2-amine hydrochloride (80 mg, 0.17 mmol, 1 equiv) in DMF (5 mL), was added EDC/HCl (49 mg, 0.256 mmol, 1.5 equiv), HOBt (35 mg, 0.256 mmol, 1.5 equiv), DIPEA (0.2 mL, 0.513 mmol, 3 equiv). The reaction mixture was allowed to stir at RT for overnight. Progress of the reaction was monitored by LCMS. After completion of the reaction, the reaction mixture was filtered and washed with water to get yellow solid of 1-(4-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-1-yl)-2-hydroxyethan-1-one. (05 mg, 94.60%) as a yellow color solid compound. LCMS: 525 [M+H]+; 1H NMR (400 MHz, DMSO-d6) δ 9.93 (s, 1H), 8.61 (d, J=4.0 Hz, 1H), 8.20 (d, J=2.5 Hz, 1H), 8.13 (d, J=8.6 Hz, 1H), 7.62 (dd, J=8.6, 2.5 Hz, 1H), 7.48 (s, 1H), 7.19 (d, J=11.5 Hz, 1H), 4.55-4.45 (m, 2H), 4.34-4.27 (m, 2H), 4.14 (dt, J=13.2, 6.5 Hz, 3H), 3.79 (d, J=13.2 Hz, 1H), 3.31 (d, J=4.6 Hz, 2H), 3.07 (t, J=12.8 Hz, 1H), 2.81 (tt, J=12.3, 3.5 Hz, 1H), 2.68 (d, J=11.2 Hz, 1H), 1.81 (d, J=13.0 Hz, 2H), 1.68-1.43 (m, 2H), 1.23 (s, 1H), 1.19 (d, J=6.5 Hz, 6H).

Example-119: Synthesis of (2,6-dimethylmorpholino)(6-((5-fluoro-4-(8-fluoro-4-isopropyl-3,4-dihydro-2H-benzo[b][1,4]oxazin-6-yl)pyrimidin-2-yl)amino)pyridin-3-yl)methanone. (Compound 511)

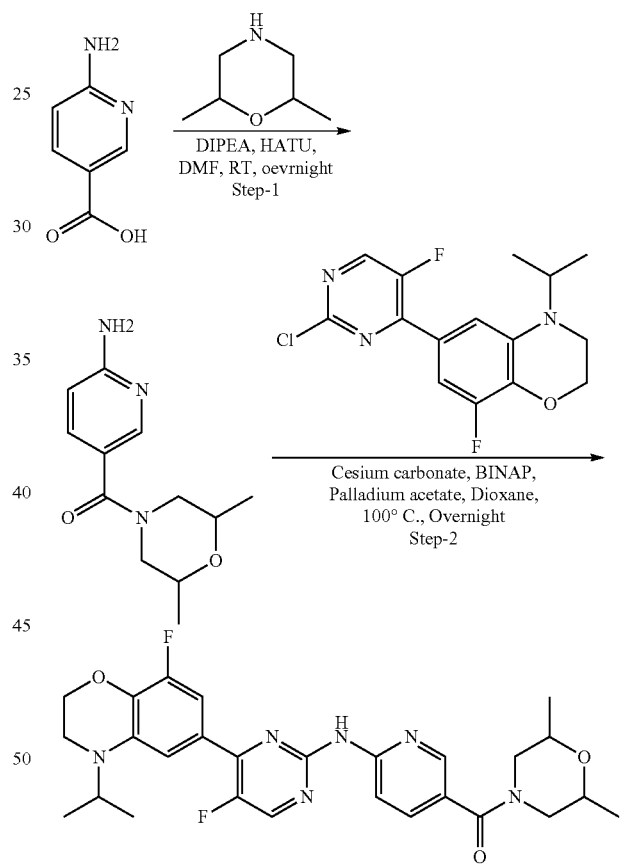

Step-1: Synthesis of (6-aminopyridin-3-yl)(2,6-dimethylmorpholino)methanone

To a stirred solution of 6-aminonicotinic acid (1000 mg, 7.24 mmol, 1 equiv) in DMF (10 mL), was added 2,6-dimethylmorpholine (1250 mg, 10.8 mmol, 1.5 equiv), DIPEA (5 mL, 29 mmol, 4 equiv) and HATU (4952 mg, 13 mmol, 1.8 equiv). The reaction mixture was allowed to stir for overnight at RT. Progress of the reaction was monitored by TLC and LCMS. After completion of the reaction, diluted with water (50 mL), solid observed was filtered and dried under vacuum to obtain (6-aminopyridin-3-yl)(2,6-dimethylmorpholino)methanone (800 mg, 69%) as an off white color solid compound. LCMS: 236 [M+H]+

Step-2: Synthesis of (2,6-dimethylmorpholino)(6-((5-fluoro-4-(8-fluoro-4-isopropyl-3,4-dihydro-2H-benzo[b][1,4]oxazin-6-yl)pyrimidin-2-yl)amino)pyridin-3-yl)methanone To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added (6-aminopyridin-3-yl)(2,6-dimethylmorpholino)methanone (78 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase Combi flash to obtain (2,6-dimethylmorpholino)(6-((5-fluoro-4-(8-fluoro-4-isopropyl-3,4-dihydro-2H-benzo[b][1,4]oxazin-6-yl)pyrimidin-2-yl)amino)pyridin-3-yl)methanone (20 mg, 12%) as a yellow color solid compound. LCMS: 525 [M+H]+; 1HNMR (400 MHz, DMSO-$d_6$) δ 10.34 (s, 1H), 8.67 (d, J=3.4 Hz, 1H), 8.37 (s, 1H), 8.28 (d, J=8.8 Hz, 1H), 7.80 (dd, J=8.8, 2.0 Hz, 1H), 7.49 (s, 1H), 7.20 (d, J=11.7 Hz, 1H), 4.31 (br. s., 2H), 4.05-4.21 (m, 1H), 3.55 (d, J=5.9 Hz, 2H), 3.31 (br. s., 4H), 2.51 (br. s., 2H), 1.19 (d, J=6.4 Hz, 6H), 0.91-1.16 ppm (m, 6H).

Example-120: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-2-one. (Compound 512)

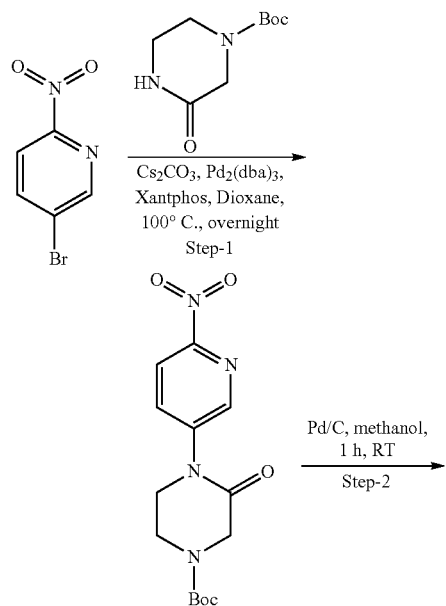

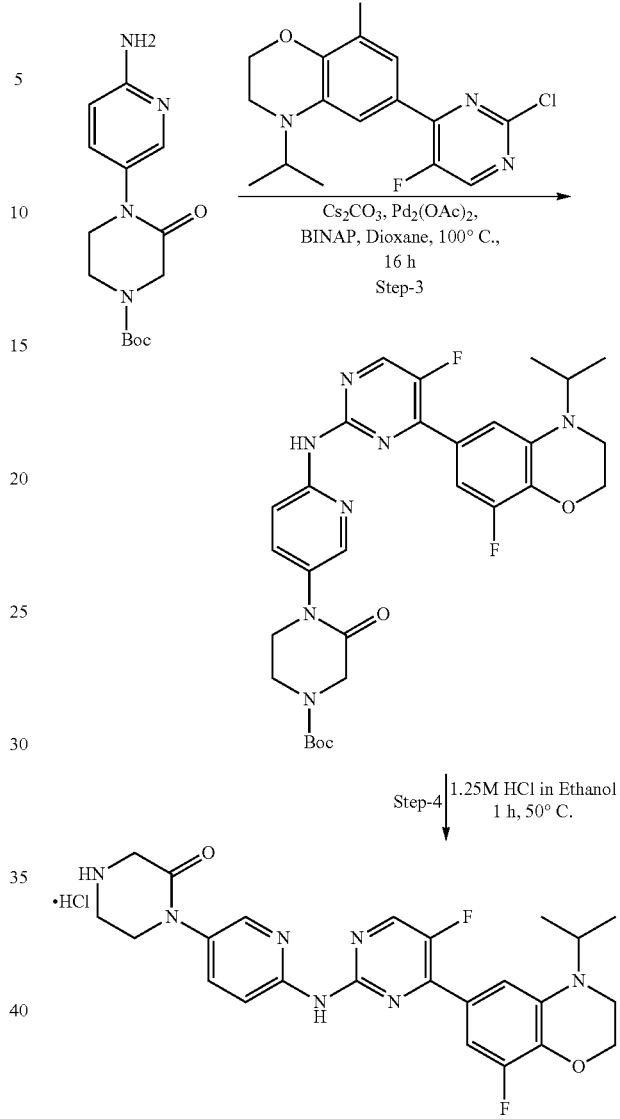

Step-1: Synthesis tert-butyl 4-(6-nitropyridin-3-yl)-3-oxopiperazine-1-carboxylate To a solution of 5-bromo-2-nitropyridine (500 mg, 4.95 mmol, 1 equiv) in Dioxane (10 mL), was added tert-butyl 3-oxopiperazine-1-carboxylate (990 mg, 4.95 mmol, 1 equiv) and cesium carbonate (4034 mg, 12.3 mmol, 2.5 equiv). The reaction mixture was purged with nitrogen gas for 30 min., followed by the addition of $Pd_2$(dba)$_3$ (227 mg, 0.24 mmol, 0.05 equiv) and XATPHOS (230 mg, 0.39 mmol, 0.08 equiv). The resultant reaction mixture was allowed to stir at 100° C. for overnight. Progress of the reaction was monitored by TLC and LCMS. After completion of the reaction, the reaction mixture was diluted with water (50 mL) and extracted wit ethyl acetate (150 mL×2). Organic layer was washed with water (100 mL) and brine (100 mL). Organic layer was dried over anhydrous sodium sulphate and concentrated under reduced pressure to obtain crude compound, which was purified by normal phase combi flash to obtain tert-butyl 4-(6-nitropyridin-3-yl)-3- oxopiperazine-1-carboxylate (250 mg, 37%) as a yellow solid compound. LCMS: 323 [M+H]+

Step-2: Synthesis of tert-butyl 4-(6-aminopyridin-3-yl)-3-oxopiperazine-1-carboxylate To a stirred solution of tert-butyl 4-(6-nitropyridin-3-yl)-3-oxopiperazine-1-carboxylate (250 mg, 0.77 mmol, 1 equiv) in methanol (5 mL), was added Pd/C (20% w/w) (50 mg) under $H_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain tert-butyl 4-(6-aminopyridin-3-yl)-3-oxopiperazine-1-carboxylate (200 mg, 88%) as an off white color solid compound. LCMS: 293 [M+H]+

Step-3; Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate To a solution of 6-(2-chloro-5-fluoropyrimidin-4-yl)-8-fluoro-4-isopropyl-3,4-dihydro-2H-benzo[b][1,4]oxazine (200 mg, 0.6 mmol, 1 equiv) in Dioxane (10 mL), was added tert-butyl 4-(6-aminopyridin-3-yl)-3-oxopiperazine-1-carboxylate (198 mg, 0.66 mmol, 1.1 equiv) and cesium carbonate (293 mg, 0.9 mmol, 1.5 equiv). The reaction mixture was purged with nitrogen gas for 30 min., followed by the addition of palladium acetate (3 mg, 0.012 mmol, 0.02 equiv) and BINAP (15 mg, 0.024 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain crude compound, which was purified by normal phase combi flash to obtain tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate (100 mg, 28%) as a yellow solid compound. LCMS: 582 [M+H]+

Step-4: Synthesis of 1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperazin-2-one tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate (100 mg, 0.17 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(5-(piperidin-4-yl)pyrazin-2-yl)pyrimidin-2-amine (40 mg, 48%) as a yellow color solid compound. LCMS: 482 [M+H]+; 1HNMR (400 MHz, DMSO-d6) δ 10.11 (s, 1H), 8.64 (d, J=3.9 Hz, 1H), 8.27 (d, J=2.4 Hz, 1H), 8.21 (d, J=8.8 Hz, 1H), 7.72 (dd, J=9.3, 2.4 Hz, 1H), 7.49 (s, 1H), 7.19 (d, J=11.2 Hz, 1H), 4.30 (br. s., 2H), 4.16 (br. s., 1H), 3.62 (t, J=5.4 Hz, 2H), 3.40 (br. s., 2H), 3.35 (m, 2H), 3.03 (t, J=5.1 Hz, 2H), 1.19 ppm (d, J=6.4 Hz, 6H).

Example-121: Synthesis of N-(2-(dimethylamino)ethyl)-4-((5-fluoro-4-(8-fluoro-4-isopropyl-3,4-dihydro-2H-benzo[b][1,4]oxazin-6-yl)pyrimidin-2-yl)amino)benzenesulfonamide. (Compound 513)

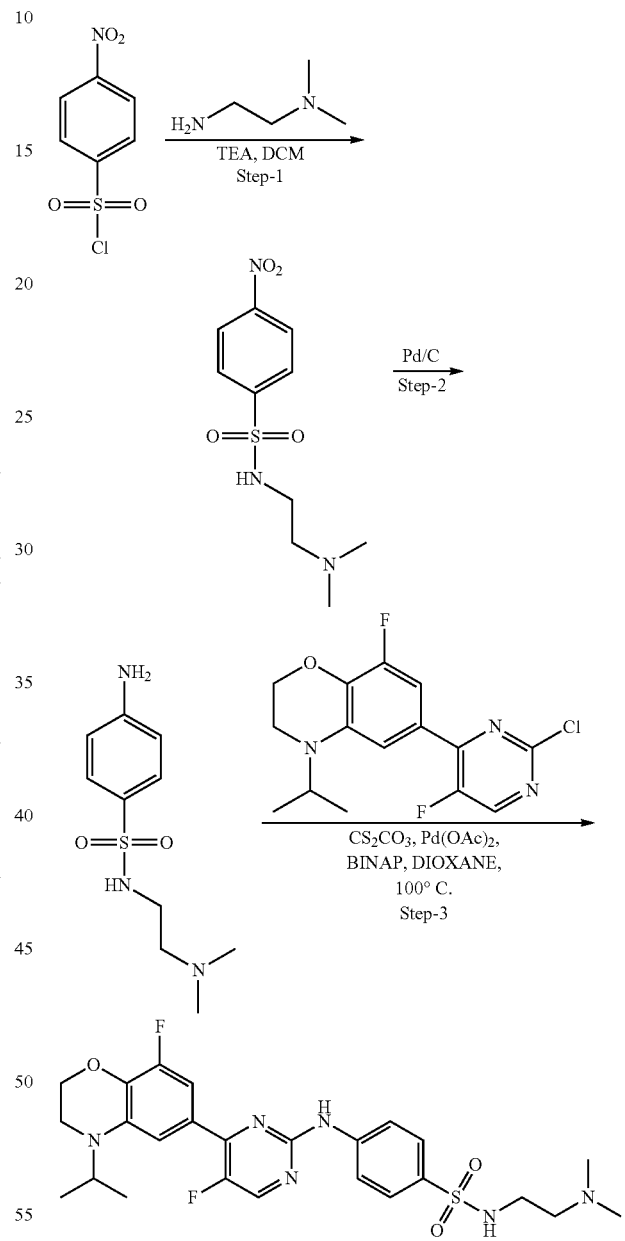

Step-1: Synthesis of N-(2-(dimethylamino)ethyl)-4-nitrobenzenesulfonamide

To a stirred solution of 4-nitrobenzenesulfonyl chloride (500 mg, 2.26 mmol, 1 equiv) in DCM (06 mL), was added Triethylamine (0.4 ml, 4.52 mmol, 2 equiv) and N1, N1-dimethylethane-1, 2-diamine (0.4 ml, 4.52 mmol, 2 equiv). The reaction mixture was allowed to stir at RT for 5 h. Progress of the reaction was monitored by TLC and LCMS.

After completion of the reaction, the reaction mixture was diluted with water (20 ml) extracted with ethyl acetate (25 mL×2). Organic layer was washed with water (15 mL) and brine solution (20 mL). Organic layer was dried over anhydrous sodium sulphate and concentrated under reduced pressure to obtain crude, which was purified by reverse phase HPLC to afford of N-(2-(dimethylamino)ethyl)-4-nitrobenzenesulfonamide. LCMS: 274 [M+H]⁺

Step-2: Synthesis of 4-amino-N-(2-(dimethylamino) ethyl) benzenesulfonamide

To a stirred solution of N-(2-(dimethylamino) ethyl)-4-nitrobenzenesulfonamide (470 mg, 1.74 mmol, 1 equiv) in ethanol (08 mL), was added Pd/C (100 mg, 0.087 mmol, 0.05 equiv) at RT. The reaction mixture was allowed to stir at RT for 3 h. Progress of the reaction was monitored by TLC and LCMS. After completion of the reaction, the reaction mixture was passed through celide filter. Organic layer was washed with water (20), dried over anhydrous sodium sulphate and concentrated under reduced pressure to obtain 4-amino-N-(2-(dimethylamino) ethyl) benzenesulfonamide (277 mg, 99%) as brown compound. LCMS: 244 [M+H]⁺

Step-3: Synthesis of N-(2-(dimethylamino)ethyl)-4-((5-fluoro-4-(8-fluoro-4-isopropyl-3,4-dihydro-2H-benzo[b][1,4]oxazin-6-yl)pyrimidin-2-yl)amino) benzenesulfonamide To the solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) was added dioxane (5 ml) and 4-amino-N-(2-(dimethylamino)ethyl)benzenesulfonamide (82 mg, 0.033 mmol, 1.1 equiv), cesium carbonate (146 mg, 0.0.46 mmol, 1.5 equiv), resulted reaction mixture was degassed with nitrogen for 5 min thereafter was added Pd(Oac)₂, (07 mg, 0.03 mmol, 0.1 equiv), BINAP (38 mg, 0.056 mmol, 0.2 equiv), resulted reaction mixture was allowed to stir for 15 h at 100° C. Progress of the reaction was monitored by LCMS. After completion of the reaction, the reaction mixture was diluted with water (25 mL) and extracted with ethyl acetate (40 mL×2). Organic layer was washed with water (35 mL) and brine solution (25 mL). Organic layer was dried over anhydrous sodium sulphate and concentrated under reduced pressure to obtain crude, which was purified by combi-flash to get N-(2-(dimethylamino)ethyl)-4-((5-fluoro-4-(8-fluoro-4-isopropyl-3,4-dihydro-2H-benzo[b][1,4]oxazin-6-yl)pyrimidin-2-yl)amino) benzenesulfonamide (35 mg, 99.90%) as a yellow solid compound. LCMS: 533 [M+H]⁺; ¹H NMR (400 MHz, Methanol-d4) δ 8.44 (d, J=4.1 Hz, 1H), 8.30 (d, J=8.8 Hz, 1H), 8.18 (s, 1H), 7.79-7.71 (m, 1H), 7.52 (s, 1H), 7.29-7.21 (m, 1H), 4.33 (t, J=4.3 Hz, 2H), 4.22 (p, J=6.6 Hz, 1H), 3.57-3.44 (m, 1H), 3.35 (t, J=4.4 Hz, 4H), 3.14-3.03 (m, 1H), 3.03-2.93 (m, 1H), 2.77 (t, J=9.5 Hz, 1H), 2.61 (s, 3H), 2.43 (dq, J=14.3, 8.2 Hz, 1H), 2.02 (dt, J=13.3, 7.6 Hz, 1H), 1.26 (d, J=6.6 Hz, 7H).

Example-122: Synthesis of N-(5-fluoro-4-(8-fluoro-4-isopropyl-3,4-dihydro-2H-benzo[b][1,4]oxazin-6-yl)pyrimidin-2-yl)-5-(piperidin-4-yl)thiazol-2-amine. (Compound 514)

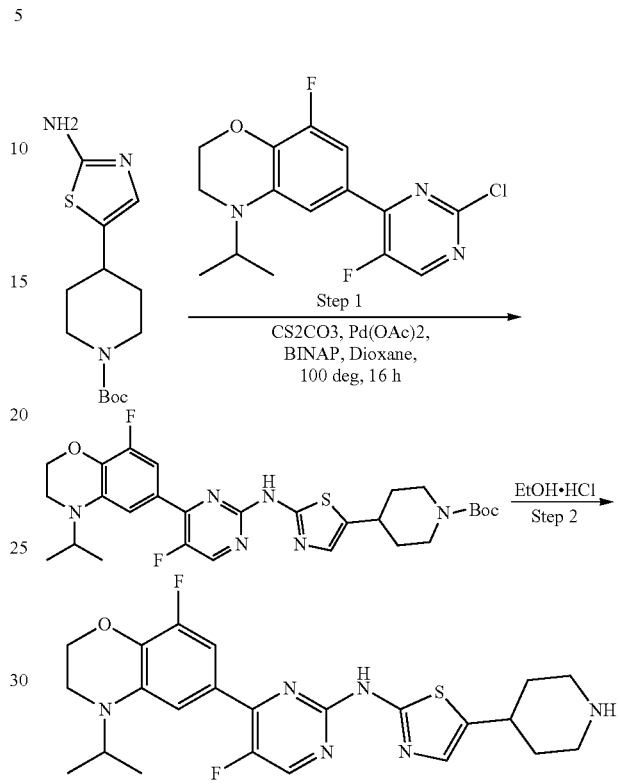

Step-1: Synthesis of tert-butyl 4-(2-((5-fluoro-4-(8-fluoro-4-isopropyl-3,4-dihydro-2H-benzo[b][1,4] oxazin-6-yl)pyrimidin-2-yl)amino)thiazol-5-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (4 mL), was added tert-butyl 4-(2-aminothiazol-4-yl)piperidine-1-carboxylate (94 mg, 0.33 mmol, 1.1 equiv) and potassium carbonate (62 mg, 0.45 mmol, 1.5 equiv). The reaction mixture was degassed by nitrogen gas for 10 min., followed by the addition of Pd2(dba)₃ (27 mg, 0.03 mmol, 0.1 equiv) and Xphos (28 mg, 0.06 mmol, 0.2 equiv). The resultant reaction mixture was allowed to stir at 100° C. for 16 h. Progress of the reaction was monitored by TLC and LCMS. After completion of the reaction, diluted with water (10 mL) and extracted with ethyl acetate (10 mL). Organic layer was washed with water (5 mL) and brine solution (5 mL). Organic layer was dried over anhydrous sodium sulphate and concentrated under reduced pressure to obtain tert-butyl 4-(2-((5-fluoro-4-(8-fluoro-4-isopropyl-3,4-dihydro-2H-benzo[b][1,4]oxazin-6-yl)pyrimidin-2-yl)amino)thiazol-5-yl)piperidine-1-carboxylate (135 mg) as an viscous crude residue which used directly for next step. LCMS: 573 [M+H]⁺

Step-2: Synthesis of N-(5-fluoro-4-(8-fluoro-4-isopropyl-3,4-dihydro-2H-benzo[b][1,4]oxazin-6-yl) pyrimidin-2-yl)-5-(piperidin-4-yl)thiazol-2-amine A solution of tert-butyl 4-(2-((5-fluoro-4-(8-fluoro-4-isopropyl-3,4-dihydro-2H-benzo[b][1,4]oxazin-6-yl)pyrimidin-2-yl)amino)thiazol-5-yl)piperidine-1-carboxylate (135 mg crude) in 1.25 M HCl in ethanol (5 mL) was allowed to stir for 1 h at 50° C. Progress of the reaction was monitored by LCMS. After completion of the reaction, solvent was removed under reduced pressure to obtain crude which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-5-(piperidin-4-yl)thiazol-2-amine (10 mg) as an off white solid compound. LCMS: 473 [M+H]+; 1HNMR (400 MHz, DMSO-d6) δ 9.74 (s, 1H), 8.57 (d, J=4.0 Hz, 1H), 8.29 (s, 1H), 7.72 (dd, J=15.3, 2.5 Hz, 1H), 7.44 (s, 1H), 7.36 (dd, J=8.8, 2.5 Hz, 1H), 7.16 (d, J=11.4 Hz, 1H), 6.97 (t, J=9.4 Hz, 1H), 4.30 (t, J=4.4 Hz, 2H), 4.16 (p, J=6.6 Hz, 1H), 3.30 (dd, J=9.6, 5.2 Hz, 4H), 2.63-2.54 (m, 2H), 2.22 (s, 7H), 1.84 (dd, J=12.7, 3.6 Hz, 2H), 1.54 (tt, J=13.3, 6.7 Hz, 2H), 1.18 (d, J=6.5 Hz, 6H).

Example-123: Synthesis of N-(5-(2,6-dimethylmorpholino)pyridin-2-yl)-5-fluoro-4-(8-fluoro-4-isopropyl-3,4-dihydro-2H-benzo[b][1,4]oxazin-6-yl)pyrimidin-2-amine. (Compound 515)

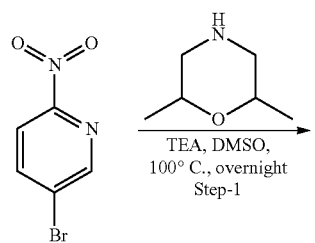

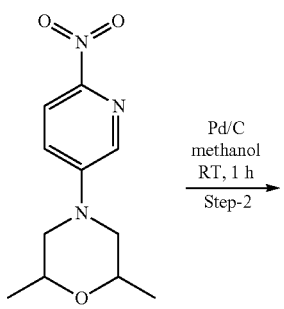

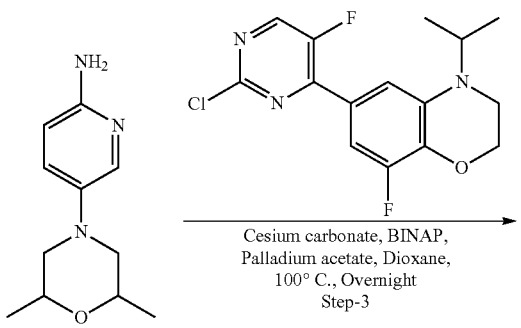

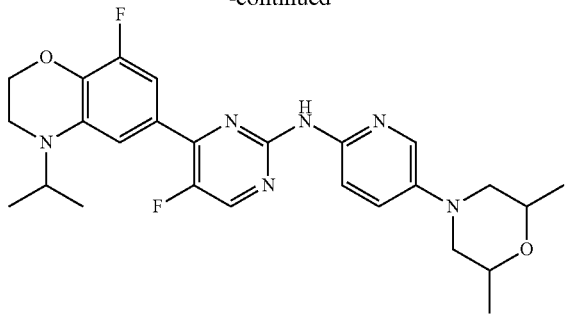

Step-1: Synthesis of 2,6-dimethyl-4-(6-nitropyridin-3-yl)morpholine

To a stirred solution of 5-bromo-2-nitropyridine (500 mg, 2.47 mmol, 1 equiv) in DMSO (10 mL), was added TEA (0.7 mL, 4.94 mmol, 2 equiv) and 2,6-dimethylmorpholine (426 mg, 3.7 mmol, 1.5 equiv). The resultant reaction mixture was allowed to stir at 100° C. for overnight. Progress of the reaction was monitored by TLC and LCMS. After completion of the reaction, diluted with water (100 mL), solid observed was filtered and dried under vacuum to obtain 2,6-dimethyl-4-(6-nitropyridin-3-yl)morpholine (500 mg, 85%) as a yellow solid compound. LCMS: 238 [M+H]+

Step-2: Synthesis of 5-(2,6-dimethylmorpholino)pyridin-2-amine

To a stirred solution of 2,6-dimethyl-4-(6-nitropyridin-3-yl) morpholine (200 mg, 0.84 mmol, 1 equiv) in methanol (5 mL), was added Pd/C (20% w/w) (50 mg) under H2 atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain 5-(2,6-dimethylmorpholino) pyridin-2-amine (150 mg, 86%) as an off white color solid compound. LCMS: 208 [M+H]+

Step-3: Synthesis of N-(5-(2,6-dimethylmorpholino)pyridin-2-yl)-5-fluoro-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added 5-(2,6-dimethylmorpholino)pyridin-2-amine (68 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N-(5-(2,6-dimethylmorpholino)pyridin-2-yl)-5-fluoro-4-(8-fluoro-4-isopropyl-3,4-dihydro-2H-benzo[b][1,4]oxazin-6- yl)pyrimidin-2-amine (80 mg, 52%) as a yellow color solid compound. LCMS: 497 [M+H]⁺; ¹HNMR (400 MHz, DMSO-d₆) δ 9.69 (s, 1H), 8.56 (d, J=3.9 Hz, 1H), 7.92-8.06 (m, 2H), 7.46 (s, 1H), 7.38 (d, J=2.4 Hz, 1H), 7.17 (d, J=11.2 Hz, 1H), 4.18-4.39 (m, 2H), 3.99-4.15 (m, 1H), 3.64-3.76 (m, 2H), 3.54 (d, J=10.8 Hz, 2H), 3.16 (d, J=8.3 Hz, 1H), 2.82 (dd, J=11.5, 5.6 Hz, 1H), 2.26 (t, J=11.0 Hz, 2H), 1.09-1.30 ppm (m, 12H).

Example-124: Synthesis of N-(5-((4-(cyclopropylmethyl) piperazin-1-yl) methyl) pyridin-2-yl)-5-fluoro-4-(8-fluoro-4-isopropyl-3,4-dihydro-2H-benzo[b][1,4]oxazin-6-yl)pyrimidin-2-amine. (Compound 516)

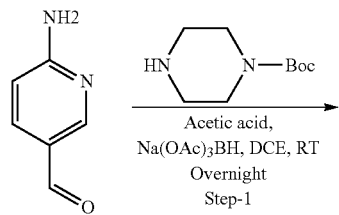

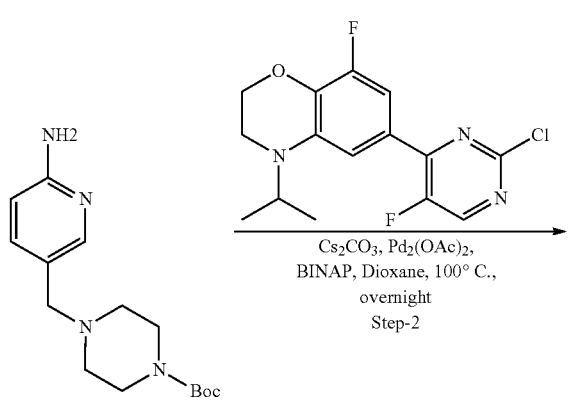

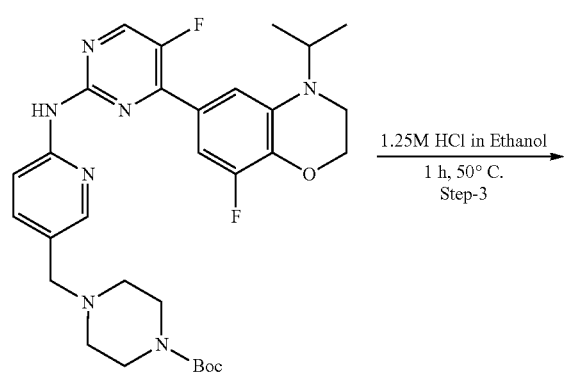

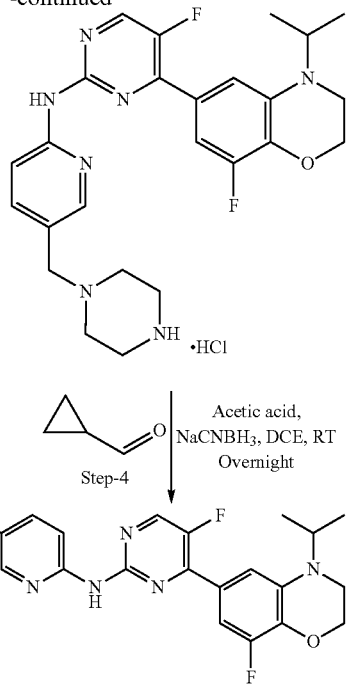

Step-1: Synthesis of tert-butyl 4-((6-aminopyridin-3-yl) methyl) piperazine-1-carboxylate To a stirred solution of 6-aminonicotinaldehyde (500 mg, 8.19 mmol, 1 equiv) in DCE (15 mL), was added tert-butyl piperazine-1-carboxylate (1830 mg, 9.8 mmol, 1.2 equiv), acetic acid (2.3 mL, 41 mmol, 5 equiv). The reaction mixture was allowed to stir at RT for 1 h. The reaction mixture was cooled to 0° C., followed by the addition of Na (OAC)₃BH (2604 mg, 12.2 mmol, 1.5 equiv) was added to above mixture and raise the temperature to RT. The reaction mixture was allowed to stir at RT for 1 h. Progress of the reaction was monitored by LCMS. After completion of the reaction, the reaction mixture was diluted with saturated solution of NaHCO₃ (50 mL) and extracted with ethyl acetate (100 mL×2). Organic layer was washed with water (50 mL) and brine solution (50 mL). Organic layer was dried over anhydrous sodium sulphate and concentrated under reduced pressure to obtain tert-butyl 4-((6-aminopyridin-3-yl) methyl) piperazine-1-carboxylate (500 mg, 21%) as a brown color viscous compound. LCMS: 293 [M+H]⁺

Step-2: Synthesis of tert-butyl 4-((6-((5-fluoro-4-(8-fluoro-4-isopropyl-3,4-dihydro-2H-benzo[b][1,4]oxazin-6-yl)pyrimidin-2-yl)amino)pyridin-3-yl)methyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (500 mg, 1.53 mmol, 1 equiv) in dioxane (10 mL), was added tert-butyl 4-((6-aminopyridin-3-yl)methyl)piperazine-1-carboxylate (494 mg, 1.69 mmol, 1.1 equiv) and cesium carbonate (748 mg, 2.29 mmol, 1.5 equiv). The reaction mixture was degassed with nitrogen gas for 30 min., followed by the addition of palladium acetate (7 mg, 0.03 mmol, 0.02 equiv) and BINAP (38 mg, 0.06 mmol, 0.04 equiv). The resultant reaction mixture was allowed to stir at 100° C. for overnight. Progress of the reaction was monitored by TLC and LCMS. After completion of the reaction, diluted with water (50 mL) and extracted with ethyl acetate (100 mL×2). Organic layer was washed with water (50 mL) and brine solution (50 mL). Organic layer was dried over anhydrous sodium sulphate and concentrated under reduced pressure to obtain tert-butyl 4-((6-((5-fluoro-4-(8-fluoro-4-isopropyl-3,4-dihydro-2H-benzo[b][1,4]oxazin-6-yl)pyrimidin-2-yl)amino)pyridin-3-yl)methyl)piperazine-1-carboxylate (700 mg, 78%) as a brown solid compound. LCMS: 582 [M+H]+

Step-3; Synthesis of 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine A solution of tert-butyl 4-((6-((5-fluoro-4-(8-fluoro-4-isopropyl-3,4-dihydro-2H-benzo[b][1,4]oxazin-6-yl)pyrimidin-2-yl)amino)pyridin-3-yl)methyl)piperazine-1-carboxylate (700 mg, 1.2 mmol, 1 equiv) in 1.25 M HCl in ethanol (10 mL) was allowed to stir for 1 h at 50° C. Progress of the reaction was monitored by LCMS. After completion of the reaction, solvent was removed under reduced pressure to obtain crude compound, which was purified by making HCl salt to afford 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine (500 mg, 86%) as a yellow solid compound. LCMS: 482 [M+H]+

Step-4: Synthesis of N-(5-((4-(cyclopropylmethyl) piperazin-1-yl) methyl) pyridin-2-yl)-5-fluoro-4-(8-fluoro-4-isopropyl-3,4-dihydro-2H-benzo[b][1,4] oxazin-6-yl)pyrimidin-2-amine To a stirred solution of 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine (100 mg, 0.2 mmol, 1 equiv) in DCE (3 mL), was added cyclopropanecarbaldehyde (52 mg, 0.61 mmol, 3 equiv), acetic acid (0.06 mL, 1.0 mmol, 5 equiv). The reaction mixture was allowed to stir at RT for 1 h. The reaction mixture was cooled to 0° C. NaCNBH$_3$ (38 mg, 0.61 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford N-(5-((4-(cyclopropylmethyl)piperazin-1-yl)methyl) pyridin-2-yl)-5-fluoro-4-(8-fluoro-4-isopropyl-3,4-dihydro-2H-benzo[b][1,4]oxazin-6-yl)pyrimidin-2-amine (45 mg, 41%) as a yellow solid compound. LCMS: 536 [M+H]+; $^1$HNMR (400 MHz, DMSO-d$_6$) δ 10.01 (s, 1H), 8.62 (d, J=3.8 Hz, 1H), 8.17 (d, J=8.4 Hz, 2H), 7.64 (dd, J=8.6, 2.4 Hz, 1H), 7.51 (s, 1H), 7.19 (d, J=11.5 Hz, 1H), 4.30 (t, J=4.3 Hz, 2H), 4.17 (p, J=6.6 Hz, 1H), 3.43 (s, 2H), 3.31 (t, J=4.4 Hz, 2H), 2.40 (s, 8H), 2.14 (d, J=6.5 Hz, 2H), 1.19 (d, J=6.5 Hz, 6H), 0.79 (p, J=6.2 Hz, 1H), 0.43 (d, J=7.6 Hz, 2H), 0.04 (d, J=4.9 Hz, 2H).

Example-125: Synthesis of N-(5-fluoro-4-(8-fluoro-4-isopropyl-3,4-dihydro-2H-benzo[b][1,4]oxazin-6-yl)pyrimidin-2-yl)-6-(1-methylpiperidin-4-yl) pyridazin-3-amine. (Compound 517)

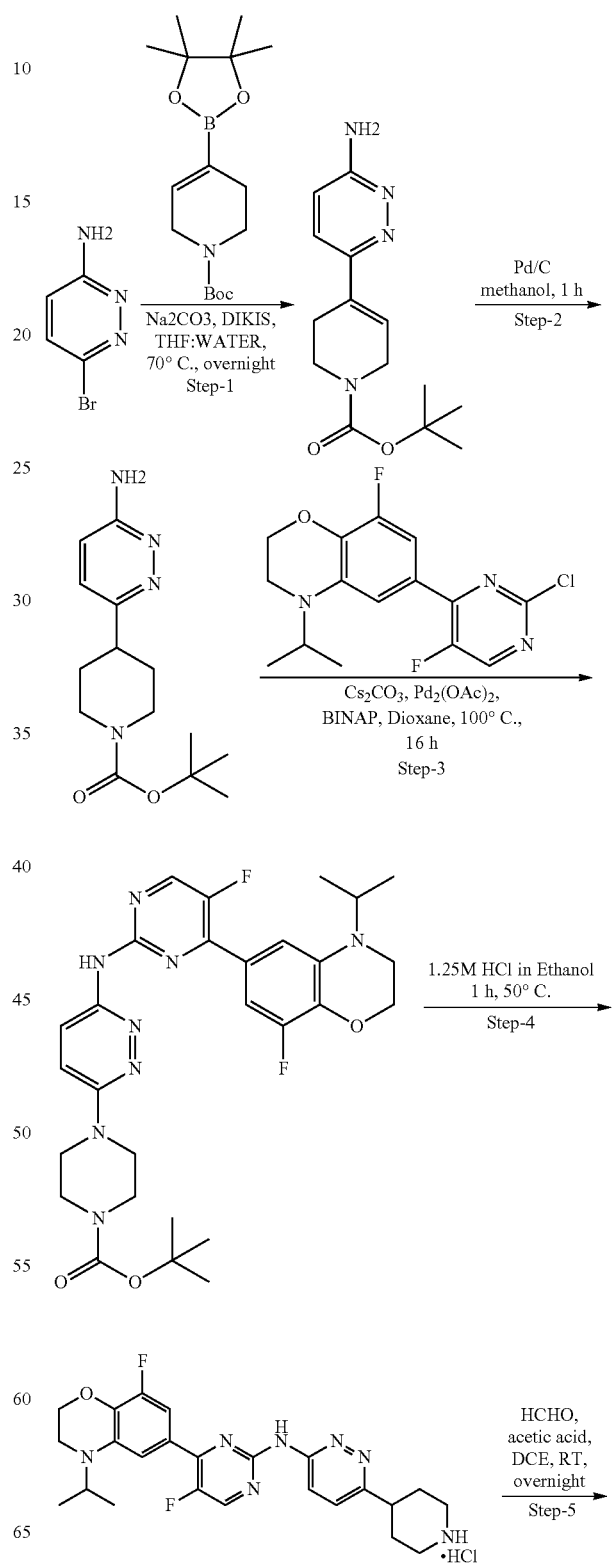

-continued

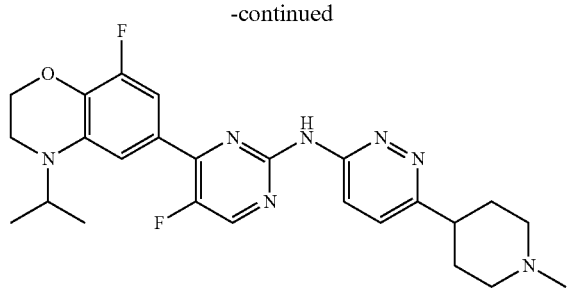

Step-1: Synthesis of tert-butyl 4-(6-aminopyridazin-3-yl)-3,6-dihydropyridine-1(2H)-carboxylate To a stirred solution of 6-bromopyridazin-3-amine (668 mg, 3.34 mmol, 1 equiv) in Dioxane:water (8+2 mL), was added tert-butyl 4-(4,4,5,5-tetramethyl-1,3,2-dioxaborolan-2-yl)-3,6-dihydropyridine-1(2H)-carboxylate (1200 mg, 3.34 mmol, 1 equiv), $Na_2CO_3$ (1062 mg, 10.02 mmol, 3 equiv.) and $Pd(PPh_3)Cl_2$ (120 mg, 0.167 mmol, 0.05 equiv). The resultant reaction mixture was allowed to stir at 100° C. for 16 h. Progress of the reaction was monitored by TLC and LCMS. After completion of the reaction, the mixture was diluted water (50 mL) and extracted with EtOAc (50 mL×2). Organic layer was washed with water (30 mL) and brine (50 mL). Organic layer was dried over anhydrous sodium sulphate and concentrated under reduced pressure to obtain of tert-butyl 4-(6-aminopyridazin-3-yl)-3,6-dihydropyridine-1(2H)-carboxylate (10 mg, 96.17%) as a brown solid compound. LCMS: 277 $[M+H]^+$

Step-2: Synthesis of tert-butyl 4-(6-aminopyridazin-3-yl) piperidine-1-carboxylate To a stirred solution of tert-butyl 4-(6-aminopyridazin-3-yl)-3,6-dihydropyridine-1(2H)-carboxylate (200 mg, 0.72 mmol, 1 equiv) in ethanol (04 mL), was added PdC (100 mg, 0.087 mmol, 0.05 equiv) at RT. The reaction mixture was allowed to stir at RT for 3 h. Progress of the reaction was monitored by TLC and LCMS. After completion of the reaction, the reaction mixture was passed through celide filter. Organic layer was washed with water (20), dried over anhydrous sodium sulphate and concentrated under reduced pressure to obtain tert-butyl 4-(6-aminopyridazin-3-yl) piperidine-1-carboxylate (140 mg, 97.10%) as brown compound. LCMS: 279 $[M+H]^+$

Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)pyridazin-3-yl)piperidine-1-carboxylate To the solution of 6-(2-chloro-5-fluoropyrimidin-4-yl)-8-fluoro-4-isopropyl-3,4-dihydro-2H-benzo[b][1,4]oxazine (200 mg, 0.6 mmol, 1 equiv) was added dioxane (5 ml) and tert-butyl 4-(6-aminopyridazin-3-yl)piperidine-1-carboxylate (185 mg, 0.67 mmol, 1.1 equiv), cesium carbonate (297 mg, 0.91 mmol, 1.5 equiv), resulted reaction mixture was degassed with nitrogen for 5 min thereafter was added $Pd(Oac)_2$, (14 mg, 0.061 mmol, 0.1 equiv), BINAP (76 mg, 0.122 mmol, 0.2 equiv), resulted reaction mixture was allowed to stir for 15 h at 100° C. Progress of the reaction was monitored by LCMS. After completion of the reaction, the reaction mixture was diluted with water (20 mL) and extracted with ethyl acetate (30 mL×3). Organic layer was washed with water (35 mL) and brine solution (15 mL). Organic layer was dried over anhydrous sodium sulphate and concentrated under reduced pressure to obtain crude, which was purified by combi-flash to get tert-butyl 4-(6-((5-fluoro-4-(8-fluoro-4-isopropyl-3,4-dihydro-2H-benzo[b][1,4]oxazin-6-yl)pyrimidin-2-yl)amino)pyridazin-3-yl)piperazine-1-carboxylate. (360 mg, 33.41%) as a light Brown solid compound. LCMS: 568 $[M+H]^+$

Step-4: Synthesis of N-(5-fluoro-4-(8-fluoro-4-isopropyl-3,4-dihydro-2H-benzo[b][1,4]oxazin-6-yl) pyrimidin-2-yl)-6-(piperidin-4-yl)pyridazin-3-amine hydrochloride To the solution of tert-butyl 4-(6-((5-fluoro-4-(8-fluoro-4-isopropyl-3,4-dihydro-2H-benzo[b][1,4]oxazin-6-yl)pyrimidin-2-yl) amino)pyridazin-3-yl)piperazine-1-carboxylate (360 mg, 0.81 mmol, 1 equiv) was taken in 1.25 M HCl in ethanol (5 mL) and the resultant reaction mixture was allowed to stir at 50° C. for 3 h. Progress of the reaction was monitored by LCMS. After completion of the reaction, solvent was removed under reduced pressure and the residue was dried under lyophilizer to get N-(5-fluoro-4-(8-fluoro-4-isopropyl-3, 4-dihydro-2H-benzo[b][1,4]oxazin-6-yl)pyrimidin-2-yl)-6-(1-methylpiperidin-4-yl)pyridazin-3-amine as a brick red color solid compound. LCMS: 468 $[M+H]^+$

Step-5: Synthesis of N-(5-fluoro-4-(8-fluoro-4-isopropyl-3,4-dihydro-2H-benzo[b][1,4]oxazin-6-yl) pyrimidin-2-yl)-6-(1-methylpiperidin-4-yl)pyridazin-3-amine To a stirred solution of N-(5-fluoro-4-(8-fluoro-4-isopropyl-3,4-dihydro-2H-benzo[b][1,4]oxazin-6-yl)pyrimidin-2-yl)-6-(1-methylpiperidin-4-yl)pyridazin-3-amine (150 mg, 0.32 mmol, 1 equiv) in DCE (6 mL), was added Formaldehyde (40% in water) (0.33 mL, 0.96 mmol, 3 equiv), acetic acid (0.2 mL, 1.1 mmol, 5 equiv). The reaction mixture was allowed to stir at RT for 1 h. The reaction mixture was cooled to 0° C. $NaCNBH_3$ (60 mg, 0.91 mmol, 3 equiv) was added to above mixture and raise the temperature to RT. The reaction mixture was allowed to stir at RT for 4 h. Progress of the reaction was monitored by LCMS. After completion of the reaction, the reaction mixture was diluted with water (20 mL) and extracted with ethyl acetate (25 mL×2). Organic layer was washed with water (15 mL) and brine solution (20 mL). Organic layer was dried over anhydrous sodium sulphate and concentrated under reduced pressure to obtain crude, which was purified by reverse phase HPLC to afford N-(5-fluoro-4-(8-fluoro-4-isopropyl-3,4-dihydro-2H-benzo[b][1,4]oxazin-6-yl)pyrimidin-2-yl)-6-(1-methylpiperidin-4-yl)pyridazin-3-amine (8 mg, 98.22%) as a yellow color solid compound. LCMS: 482 $[M+H]^+$; $^1$HNMR (500 MHz, DMSO-d6) δ 10.58 (s, 1H), 8.64 (d, J=3.7 Hz, 1H), 8.32 (d, J=9.2 Hz, 1H), 7.56 (d, J=9.3 Hz, 1H), 7.45 (s, 1H), 7.18 (d, J=11.5 Hz, 1H), 4.30 (t, J=4.3 Hz, 2H), 4.14 (p, J=6.6 Hz, 1H), 2.89 (d, J=11.3 Hz, 2H), 2.79 (t, J=11.8 Hz, 1H), 2.20 (s, 3H), 2.00 (dd, J=12.7, 9.8 Hz, 2H), 1.87-1.73 (m, 5H), 1.18 (d, J=6.5 Hz, 6H).

Example-126: Synthesis of N-(5-(4-(aminomethyl) piperidin-1-yl) pyridin-2-yl)-5-fluoro-4-(8-fluoro-4-isopropyl-3,4-dihydro-2H-benzo[b][1,4]oxazin-6-yl) pyrimidin-2-amine. (Compound 518)

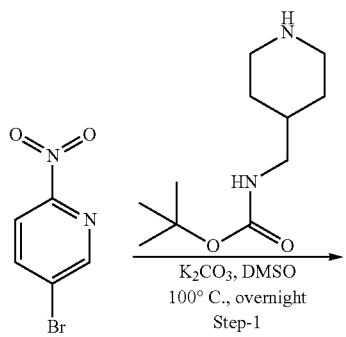

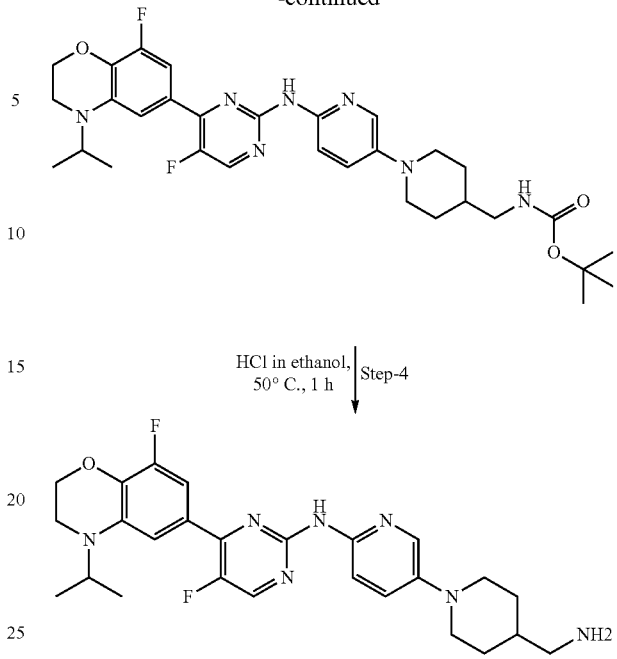

Step-1: Synthesis of tert-butyl ((1-(6-nitropyridin-3-yl) piperidin-4-yl) methyl) carbamate To a stirred solution of 5-bromo-2-nitropyridine (200 mg, 0.99 mmol, 1 equiv) in DMSO (5 mL), was added $K_2CO_3$ (273 mg, 1.98 mmol, 2 equiv) and tert-butyl (piperidin-4-ylmethyl) carbamate (424 mg, 1.98 mmol, 2 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain tert-butyl ((1-(6-nitropyridin-3-yl)piperidin-4-yl) methyl)carbamate (200 mg, 59%) as a yellow color solid compound. LCMS: 337 [M+H]$^+$

Step-2: Synthesis of tert-butyl ((1-(6-aminopyridin-3-yl) piperidin-4-yl) methyl) carbamate To a stirred solution of tert-butyl ((1-(6-nitropyridin-3-yl) piperidin-4-yl) methyl) carbamate (200 mg, 0.59 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain tert-butyl ((1-(6-amino-pyridin-3-yl) piperidin-4-yl) methyl) carbamate (150 mg, 82%) as a brown color viscous compound. LCMS: 307 [M+H]$^+$

Step-3: Synthesis of tert-butyl ((1-(6-((5-fluoro-4-(8-fluoro-4-isopropyl-3,4-dihydro-2H-benzo[b][1,4] oxazin-6-yl)pyrimidin-2-yl)amino)pyridin-3-yl)piperidin-4-yl)methyl)carbamate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added tert-butyl ((1-(6-aminopyridin-3-yl)piperidin-4-yl)methyl)

carbamate (101 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain tert-butyl ((1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)methyl)carbamate (160 mg, 87%) as a brown color viscous compound. LCMS: 596 [M+H]+

Step-4: Synthesis of N-(5-(4-(aminomethyl) piperidin-1-yl) pyridin-2-yl)-5-fluoro-4-(8-fluoro-4-isopropyl-3,4-dihydro-2H-benzo[b][1,4]oxazin-6-yl) pyrimidin-2-amine tert-butyl ((1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)methyl)carbamate (160 mg, 0.26 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure to obtain crude, which was purified by reverse phase HPLC to obtain N-(5-(4-(aminomethyl)piperidin-1-yl)pyridin-2-yl)-5-fluoro-4-(8-fluoro-4-isopropyl-3,4-dihydro-2H-benzo[b][1,4]oxazin-6-yl)pyrimidin-2-amine (80 mg, 60%) as a yellow color solid compound. LCMS: 496 [M+H]+; 1HNMR (400 MHz, DMSO-d6) δ 9.66 (s, 1H), 8.55 (d, J=4.0 Hz, 1H), 8.05-7.96 (m, 2H), 7.46 (s, 1H), 7.39 (dd, J=9.1, 3.0 Hz, 1H), 7.21-7.13 (m, 1H), 4.30 (t, J=4.3 Hz, 2H), 4.14 (hept, J=7.0 Hz, 1H), 3.64 (d, J=12.0 Hz, 2H), 3.30 (t, J=4.2 Hz, 2H), 2.75-2.57 (m, 4H), 1.82 (d, J=12.6 Hz, 2H), 1.62 (s, 1H), 1.37-1.20 (m, 2H), 1.18 (d, J=6.5 Hz, 6H).

Example-127: Synthesis of N-(5-((4-cyclopentylpiperazin-1-yl) methyl) pyridin-2-yl)-5-fluoro-4-(8-fluoro-4-isopropyl-3,4-dihydro-2H-benzo[b][1,4] oxazin-6-yl)pyrimidin-2-amine. (Compound 519)

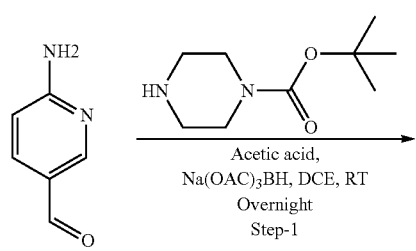

Step-1: Synthesis of tert-butyl 4-((6-aminopyridin-3-yl) methyl) piperazine-1-carboxylate To a stirred solution of 6-aminonicotinaldehyde (500 mg, 8.19 mmol, 1 equiv) in DCE (15 mL), was added tert-butyl piperazine-1-carboxylate (1830 mg, 9.8 mmol, 1.2 equiv), acetic acid (2.3 mL, 41 mmol, 5 equiv). The reaction mixture was allowed to stir at RT for 1 h. The reaction mixture was cooled to 0° C., followed by the addition of Na (OAC)3BH (2604 mg, 12.2 mmol, 1.5 equiv) was added to above mixture and raise the temperature to RT. The reaction

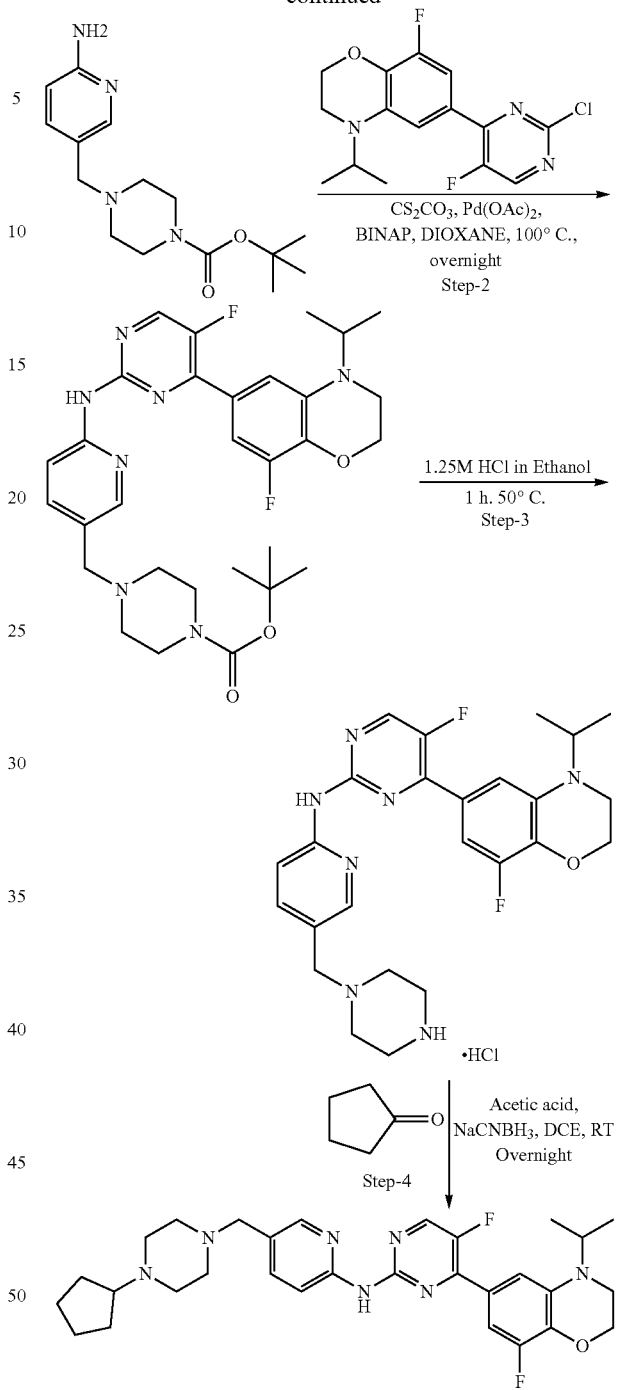

mixture was allowed to stir at RT for 1 h. Progress of the reaction was monitored by LCMS. After completion of the reaction, the reaction mixture was diluted with saturated solution of NaHCO$_3$ (50 mL) and extracted with ethyl acetate (100 mL×2). Organic layer was washed with water (50 mL) and brine solution (50 mL). Organic layer was dried over anhydrous sodium sulphate and concentrated under reduced pressure to obtain tert-butyl 4-((6-aminopyridin-3-yl) methyl) piperazine-1-carboxylate (500 mg, 21%) as a Brown color viscous compound. LCMS: 293 [M+H]$^+$ Step-2: Synthesis of tert-butyl 4-((6-((5-fluoro-4-(8-fluoro-4-isopropyl-3,4-dihydro-2H-benzo[b][1,4] oxazin-6-yl)pyrimidin-2-yl)amino)pyridin-3-yl) methyl)piperazine-1-carboxylate To a solution of 6-(2-chloro-5-fluoropyrimidin-4-yl)-8-fluoro-4-isopropyl-3,4-dihydro-2H-benzo[b][1,4]oxazine (500 mg, 1.53 mmol, 1 equiv) in dioxane (10 mL), was added tert-butyl 4-((6-aminopyridin-3-yl)methyl)piperazine-1-carboxylate (494 mg, 1.69 mmol, 1.1 equiv) and cesium carbonate (748 mg, 2.29 mmol, 1.5 equiv). The reaction mixture was degassed with nitrogen gas for 30 min., followed by the addition of palladium acetate (7 mg, 0.03 mmol, 0.02 equiv) and BINAP (38 mg, 0.06 mmol, 0.04 equiv). The resultant reaction mixture was allowed to stir at 100° C. for overnight. Progress of the reaction was monitored by TLC and LCMS. After completion of the reaction, diluted with water (50 mL) and extracted with ethyl acetate (100 mL×2). Organic layer was washed with water (50 mL) and brine solution (50 mL). Organic layer was dried over anhydrous sodium sulphate and concentrated under reduced pressure to obtain tert-butyl 4-((6-((5-fluoro-4-(8-fluoro-4-isopropyl-3,4-dihydro-2H-benzo[b][1,4]oxazin-6-yl)pyrimidin-2-yl)amino)pyridin-3-yl)methyl)piperazine-1-carboxylate (700 mg, 78%) as a brown solid compound. LCMS: 582 [M+H]$^+$ Step-3: Synthesis of 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine A solution of tert-butyl 4-((6-((5-fluoro-4-(8-fluoro-4-isopropyl-3,4-dihydro-2H-benzo[b][1,4]oxazin-6-yl)pyrimidin-2-yl)amino)pyridin-3-yl)methyl)piperazine-1-carboxylate (700 mg, 1.2 mmol, 1 equiv) in 1.25 M HCl in ethanol (10 mL) was allowed to stir for 1 h at 50° C. Progress of the reaction was monitored by LCMS. After completion of the reaction, solvent was removed under reduced pressure to obtain crude compound, which was purified by making HCl salt to afford 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine (500 mg, 86%) as a yellow solid compound. LCMS: 482 [M+H]$^+$ Step-4: Synthesis of N-(5-((4-cyclopentylpiperazin-1-yl) methyl) pyridin-2-yl)-5-fluoro-4-(8-fluoro-4-isopropyl-3,4-dihydro-2H-benzo[b][1,4]oxazin-6-yl) pyrimidin-2-amine To a stirred solution of 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine (100 mg, 0.2 mmol, 1 equiv) in DCE (3 mL), was added cyclopentanone (52 mg, 0.61 mmol, 3 equiv), acetic acid (0.06 mL, 1.0 mmol, 5 equiv). The reaction mixture was allowed to stir at RT for 1 h. The reaction mixture was cooled to 0° C. NaCNBH$_3$ (38 mg, 0.61 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford N-(5-((4-cyclopentylpiperazin-1-yl)methyl)pyridin-2-yl)-5-fluoro-4-(8-fluoro-4-isopropyl-3,4-dihydro-2H-benzo[b][1,4]oxazin-6-yl)pyrimidin-2-amine (25 mg, 15%) as an off white color solid compound. LCMS: 550 [M+H]$^+$;

$^1$HNMR (400 MHz, DMSO-d6) δ 9.97 (s, 1H), 8.62 (d, J=3.9 Hz, 1H), 8.20-8.13 (m, 2H), 7.68-7.60 (m, 1H), 7.51 (s, 1H), 7.19 (d, J=11.6 Hz, 1H), 4.31 (t, J=4.2 Hz, 2H), 4.17 (p, J=6.8 Hz, 1H), 3.42 (s, 3H), 2.40 (dt, J=17.1, 7.8 Hz, 8H), 1.74 (dq, J=11.1, 6.1 Hz, 2H), 1.58 (dq, J=12.0, 6.2, 4.8 Hz, 2H), 1.48 (q, J=7.3, 5.3 Hz, 2H), 1.28 (dq, J=14.5, 8.1 Hz, 2H), 1.20 (d, J=6.5 Hz, 6H).

Example-128: Synthesis of 4-((5-fluoro-4-(8-fluoro-4-isopropyl-3,4-dihydro-2H-benzo[b][1,4]oxazin-6-yl)pyrimidin-2-yl)amino)benzenesulfonamide. (Compound 520)

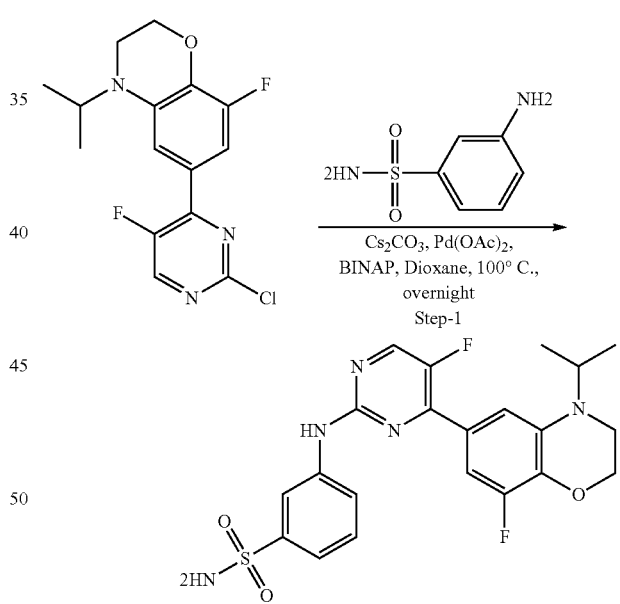

To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added 3-aminobenzenesulfonamide (57 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to afford 4-((5-fluoro-4-(8-fluoro-4-isopropyl-3,4-dihydro-2H-benzo[b][1,4]oxazin-6-yl)pyrimidin-2-yl)amino)benzenesulfonamide (50 mg, 35%) as a yellow color solid compound.

LCMS: 462 [M+H]$^+$; 1HNMR (400 MHz, DMSO-d6) δ 10.04 (s, 1H), 8.62 (d, J=3.9 Hz, 1H), 8.27 (t, J=1.9 Hz, 1H), 7.99 (d, J=7.9 Hz, 1H), 7.52-7.37 (m, 3H), 7.31 (s, 2H), 7.20 (d, J=11.5 Hz, 1H), 4.30 (t, J=4.3 Hz, 2H), 4.15 (h, J=6.5 Hz, 1H), 3.30 (d, J=4.5 Hz, 2H), 1.18 (d, J=6.5 Hz, 6H).

Example-129: Synthesis of 6-((5-fluoro-4-(8-fluoro-4-isopropyl-3,4-dihydro-2H-benzo[b][1,4]oxazin-6-yl)pyrimidin-2-yl)amino)nicotinamide. (Compound 521)

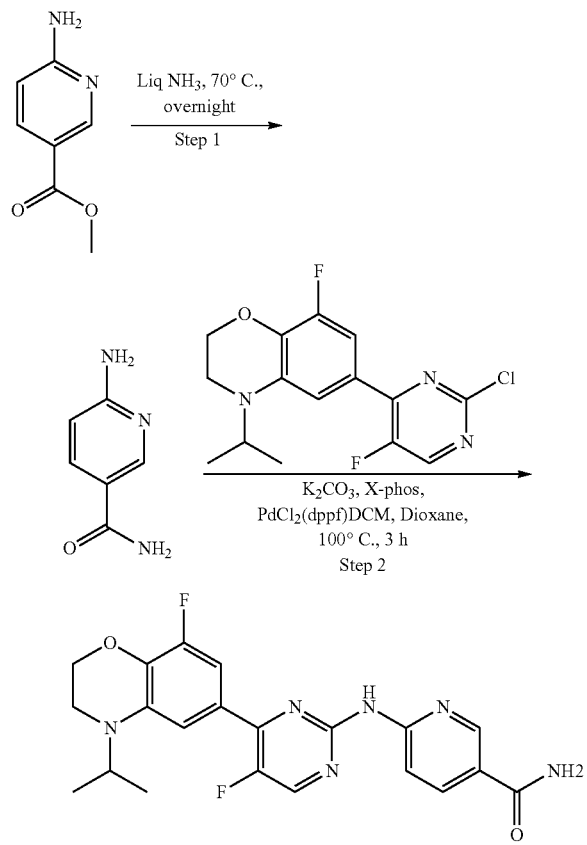 [SMILES: COC(=O)c1ccc(N)nc1 ; NC(=O)c1ccc(N)nc1 ; CC(C)N1CCOc2c(F)cc(-c3nc(Cl)ncc3F)cc21 ; CC(C)N1CCOc2c(F)cc(-c3nc(Nc4ccc(C(N)=O)cn4)ncc3F)cc21]

Step-1: Synthesis of 6-aminonicotinamide

A stirred solution of methyl 6-aminonicotinate (300 mg, 1.97 mmol, 1 equiv) in Liq. ammonia (5 mL), was allowed to stir at 70° C. for overnight. Progress of the reaction was monitored by TLC and LCMS. After completion of the reaction, the solvent was completely removed under reduced pressure to obtain 6-aminonicotinamide (250 mg, 93%) as a yellowish color solid compound. LCMS: 138 [M+H]$^+$ Step-2: Synthesis of 6-((5-fluoro-4-(8-fluoro-4-isopropyl-3,4-dihydro-2H-benzo[b][1,4]oxazin-6-yl)pyrimidin-2-yl)amino)nicotinamide To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (3 mL), was added 6-aminonicotinamide (45 mg, 0.33 mmol, 1.1 equiv) and potassium carbonate (104 mg, 0.75 mmol, 2.5 equiv). The reaction mixture was degassed with nitrogen gas for 30 min., followed by the addition of Pd (dppf) Cl2.DCM (12 mg, 0.015 mmol, 0.05 equiv) and X-Phos (14 mg, 0.03 mmol, 0.1 equiv). The resultant reaction mixture was allowed to stir at 100° C. for 3 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 6-((5-fluoro-4-(8-fluoro-4-isopropyl-3,4-dihydro-2H-benzo[b][1,4]oxazin-6-yl)pyrimidin-2-yl)amino)nicotinamide (5 mg, 4%) as a yellow color solid compound. LCMS: 427 [M+H]$^+$; $^1$HNMR (400 MHz, DMSO-d6) δ 10.39 (s, 1H), 8.80 (d, J=2.4 Hz, 1H), 8.68 (d, J=3.8 Hz, 1H), 8.28 (d, J=8.8 Hz, 1H), 8.18 (dd, J=8.8, 2.4 Hz, 1H), 8.00 (s, 1H), 7.49 (s, 1H), 7.37 (s, 1H), 7.20 (d, J=11.5 Hz, 1H), 4.31 (t, J=4.3 Hz, 2H), 4.17 (h, J=6.8 Hz, 1H), 3.35 (s, 2H), 1.20 (d, J=6.5 Hz, 6H).

Example-130: Synthesis of 5-fluoro-4-(8-fluoro-4-isopropyl-3,4-dihydro-2H-benzo[b][1,4]oxazin-6-yl)-N-(4-((4-methylpiperazin-1-yl)sulfonyl)phenyl)pyrimidin-2-amine. (Compound 522)

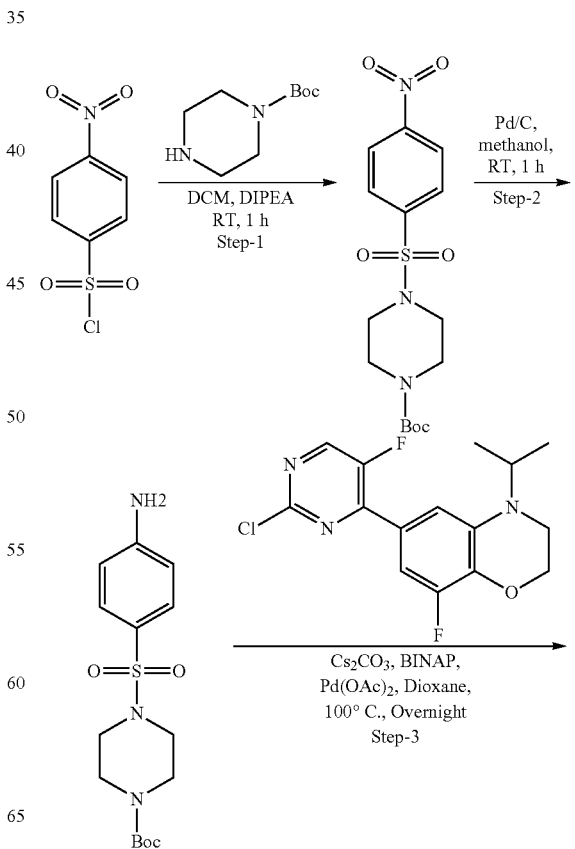

743
-continued

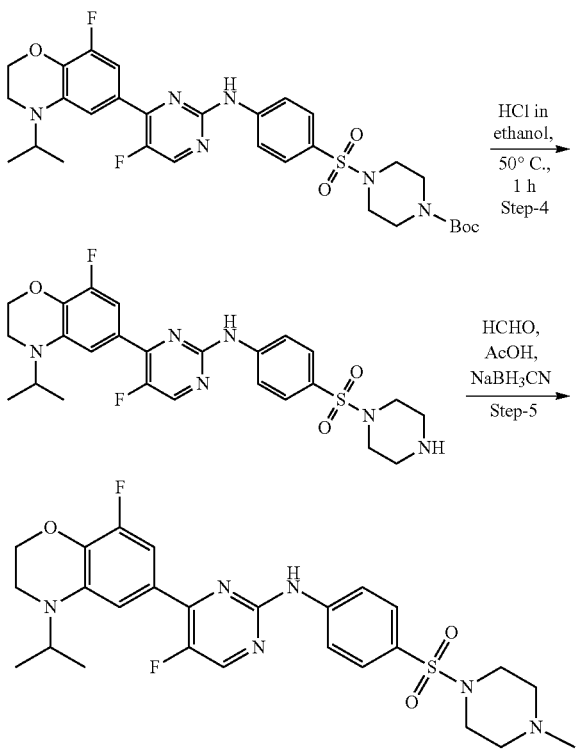

Step-1: Synthesis of tert-butyl 4-((4-nitrophenyl)sulfonyl) piperazine-1-carboxylate To a stirred solution of 4-nitrobenzenesulfonyl chloride (129 mg, 0.58 mmol, 1.3 equiv) in DCM (2 ml) was added DIPEA (0.1 mL, 0.59 mmol, 1.1 equiv), and tert-butyl piperazine-1-carboxylate (100 mg, 0.0.54 mmol, 1 equiv). The resultant reaction mixture was allowed to stir at RT for 1 h. Progress of the reaction was monitored by TLC and LCMS. After completion of the reaction, the mixture was diluted water (50 mL) and extracted with DCM (50 mL×2). Organic layer was washed with water (20 mL) and brine (20 mL). Organic layer was dried over anhydrous sodium sulphate and concentrated under reduced pressure to obtain tert-butyl piperazine-1-carboxylate. (70 mg, 88.75%) as a slightly yellow solid compound. LCMS: 272 [M+H]$^+$

Step-2: Synthesis of tert-butyl 4-((4-aminophenyl)sulfonyl) piperazine-1-carboxylate To a stirred solution of tert-butyl 4-((4-nitrophenyl) sulfonyl) piperazine-1-carboxylate (200 mg, 0.53 mmol, 1 equiv) in ethanol:Water (8+2 ml), was added Fe (filling), NH$_4$Cl (300 mg, 5.39 mmol, 10 equiv). The resulted reaction mixture was allowed to stir at 80° C. for 2 h. Progress of the reaction was monitored by TLC and LCMS. After completion of the reaction, the reaction mixture was passed through celide filter. Organic layer was washed with water (20), dried over anhydrous sodium sulphate and concentrated under reduced pressure to obtain tert-butyl 4-((4-aminophenyl) sulfonyl) piperazine-1-carboxylate (120 mg, 99.10%) as brown compound. LCMS: 242 [M+H]$^+$

744

Step-3: Synthesis of tert-butyl 4-((4-((5-fluoro-4-(8-fluoro-4-isopropyl-3,4-dihydro-2H-benzo[b][1,4]oxazin-6-yl)pyrimidin-2-yl)amino)phenyl)sulfonyl) piperazine-1-carboxylate To the solution of 6-(2-chloro-5-fluoropyrimidin-4-yl)-8-fluoro-4-isopropyl-3,4-dihydro-2H-benzo[b][1,4]oxazine (130 mg, 0.539 mmol, 1 equiv) was added dioxane (5 ml) and tert-butyl 4-((4-aminophenyl)sulfonyl)piperazine-1-carboxylate (175 mg, 0.539 mmol, 1 equiv), cesium carbonate (258 mg, 0.791 mmol, 1.5 equiv), resulted reaction mixture was degassed with nitrogen for 5 min thereafter was added Pd(Oac)$_2$, (20 mg, 0.053 mmol, 0.1 equiv), BINAP (80 mg, 0.122 mmol, 0.2 equiv), resulted reaction mixture was allowed to stir for 15 h at 100° C. Progress of the reaction was monitored by LCMS. After completion of the reaction, the reaction mixture was diluted with water (25 mL) and extracted with ethyl acetate (30 mL×3). Organic layer was washed with water (35 mL) and brine solution (15 mL). Organic layer was dried over anhydrous sodium sulphate and concentrated under reduced pressure to obtain crude, which was purified by combi-flash to obtain tert-butyl 4-((4-((5-fluoro-4-(8-fluoro-4-isopropyl-3,4-dihydro-2H-benzo[b][1,4]oxazin-6-yl)pyrimidin-2-yl)amino)phenyl) sulfonyl)piperazine-1-carboxylate (160 mg, 43.13%) as a light brown solid compound. LCMS: 531 [M+H]$^+$

Step-4: Synthesis of 5-fluoro-4-(8-fluoro-4-isopropyl-3,4-dihydro-2H-benzo[b][1,4]oxazin-6-yl)-N-(4-(piperazin-1-ylsulfonyl)phenyl)pyrimidin-2-amine To the solution tert-butyl 4-((4-((5-fluoro-4-(8-fluoro-4-isopropyl-3,4-dihydro-2H-benzo[b][1,4]oxazin-6-yl)pyrimidin-2-yl)amino)phenyl)sulfonyl)piperazine-1-carboxylate (150 mg, 0.52 mmol, 1 equiv) was taken in 1.25 M HCl in ethanol (5 mL) and the resultant reaction mixture was allowed to stir at 50° C. for 3 h. Progress of the reaction was monitored by LCMS. After completion of the reaction, solvent was removed under reduced pressure and the residue was dried under lyophilizer to get 5-fluoro-4-(8-fluoro-4-isopropyl-3,4-dihydro-2H-benzo[b][1,4]oxazin-6-yl)-N-(4-(piperazin-1-ylsulfonyl)phenyl)pyrimidin-2-amine (50 mg, 41.46%) as a brick red color solid compound. LCMS: 531 [M+H]$^+$

Step-5: Synthesis of 5-fluoro-4-(8-fluoro-4-isopropyl-3,4-dihydro-2H-benzo[b][1,4]oxazin-6-yl)-N-(4-((4-methylpiperazin-1-yl)sulfonyl)phenyl)pyrimidin-2-amine To a stirred solution of 5-fluoro-4-(8-fluoro-4-isopropyl-3,4-dihydro-2H-benzo[b][1,4]oxazin-6-yl)-N-(4-(piperazin-1-ylsulfonyl)phenyl)pyrimidin-2-amine (300 mg, 0.63 mmol, 1 equiv) in DCE (6 mL), was added Formaldehyde (40% in water) (0.33 mL, 0.96 mmol, 3 equiv), acetic acid (0.2 mL, 1.1 mmol, 5 equiv). The reaction mixture was allowed to stir at RT for 1 h. The reaction mixture was cooled to 0° C. NaCNBH$_3$ (60 mg, 0.91 mmol, 3 equiv) was added to above mixture and raise the temperature to RT. The reaction mixture was allowed to stir at RT for 4 h. Progress of the reaction was monitored by LCMS. After completion of the reaction, the reaction mixture was diluted with water (20 mL) and extracted with ethyl acetate (25 mL×2). Organic layer was washed with water (15 mL) and brine solution (20 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(4-((4-methylpiperazin-1-yl)sulfonyl)phenyl)pyrimidin-2-amine (10 mg, 98.22%) as a yellow color solid compound.

LCMS: 545 [M+H]+; 1HNMR (400 MHz, DMSO-d6) δ 10.30 (s, 1H), 8.67 (d, J=3.8 Hz, 1H), 8.44 (s, 1H), 8.02 (d, J=8.5 Hz, 2H), 7.64 (d, J=8.5 Hz, 2H), 7.44 (s, 1H), 7.19 (d, J=11.8 Hz, 1H), 4.31 (t, J=4.2 Hz, 2H), 4.16 (p, J=6.6 Hz, 1H), 3.32 (t, J=4.5 Hz, 3H), 3.14 (s, 2H), 2.94-2.83 (m, 4H), 2.35 (t, J=4.6 Hz, 6H), 2.13 (s, 3H), 1.19 (d, J=6.5 Hz, 6H).

Example-131: Synthesis of 4-(5-fluoro-4-(8-fluoro-4-isopropyl-3,4-dihydro-2H-benzo[b][1,4]oxazin-6-yl)pyrimidin-2-ylamino)-N-(2-methoxyethyl)benzenesulfonamide. (Compound 523)

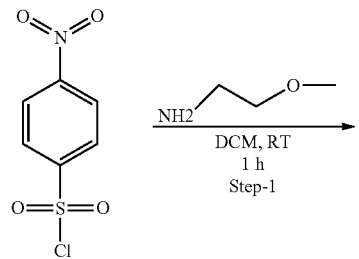

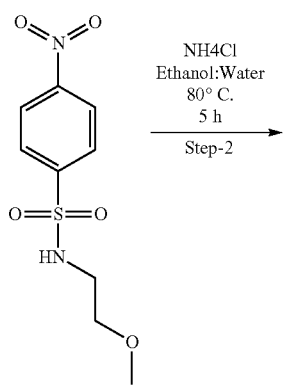

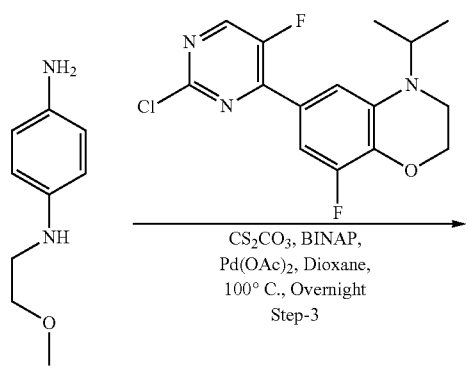

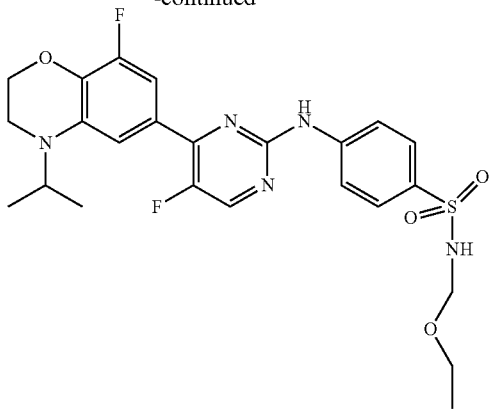

Step-1: Synthesis of N-(2-methoxyethyl)-4-nitro-benzenesulfonamide

A stirred solution of 4-nitrobenzenesulfonyl chloride (100 mg, 0.45 mmol, 1 equiv) in DCM (5 ml) was added DIPEA (0.2 mL, 0.59 mmol, 1.1 equiv), and 2-methoxyethanamine (100 mg, 0.54 mmol, 1 equiv). The resultant reaction mixture was allowed to stir at RT for 1 h. Progress of the reaction was monitored by TLC and LCMS. After completion of the reaction, the mixture was diluted water (20 mL) and extracted with DCM (15 mL×2). Organic layer was washed with water (20 mL) and brine (20 mL). Organic layer was dried over anhydrous sodium sulphate and concentrated under reduced pressure to obtain N-(2-methoxyethyl)-4-nitro-benzenesulfonamide (70 mg, 88.75%) as a slightly yellow solid compound. LCMS: 260 [M+H]+

Step-2: Synthesis of 4-amino-N-(2-methoxyethyl)benzenesulfonamide

To a stirred solution of N-(2-methoxyethyl)-4-nitro-benzenesulfonamide (200 mg, 0.76 mmol, 1 equiv) in ethanol:Water (8+2 ml), was added Fe (filling), NH4Cl (407 mg, 7.6 mmol, 10 equiv). The resulted reaction mixture was allowed to stir at 80° C. for 5 h. Progress of the reaction was monitored by TLC and LCMS. After completion of the reaction, the reaction mixture was passed through celide filter. Organic layer was washed with water (30), dried over anhydrous sodium sulphate and concentrated under reduced pressure to 4-amino-N-(2-methoxyethyl)benzenesulfonamide (129 mg, 99.10%) as brown compound. LCMS: 242 [M+H]+

Step-3: Synthesis of 4-(5-fluoro-4-(8-fluoro-4-isopropyl-3,4-dihydro-2H-benzo[b][1,4]oxazin-6-yl)pyrimidin-2-ylamino)-N-(2-methoxyethyl)benzenesulfonamide To the solution of 6-(2-chloro-5-fluoropyrimidin-4-yl)-8-fluoro-4-isopropyl-3,4-dihydro-2H-benzo[b][1,4]oxazine (130 mg, 0.53 mmol, 1 equiv) was added dioxane (5 ml), (2Z)—N4-(2-methoxyethyl)penta-2,4-diene-1,4-diamine (175 mg, 0.539 mmol, 1 equiv), cesium carbonate (258 mg, 0.791 mmol, 1.5 equiv), resulted reaction mixture was degassed with nitrogen for 5 min thereafter was added Pd(Oac)$_2$, (20 mg, 0.053 mmol, 0.1 equiv), BINAP (80 mg, 0.122 mmol, 0.2 equiv), resulted reaction mixture was allowed to stir for 15 h at 100° C. Progress of the reaction was monitored by LCMS. After completion of the reaction, the reaction mixture was diluted with water (30 mL) and extracted with ethyl acetate (30 mL×3). Organic layer was washed with water (35 mL) and brine solution (15 mL). Organic layer was dried over anhydrous sodium sulphate and concentrated under reduced pressure to obtain crude, which was purified by Reverse phase HPLC to 4-(5-fluoro-4-(8-fluoro-4-isopropyl-3,4-dihydro-2H-benzo[b][1,4]oxazin-6-yl)pyrimidin-2-ylamino)-N-(2-methoxyethyl)benzenesulfonamide (75 mg, 98.13%) as a yellow colour solid compound. LCMS: 520 [M+H]$^+$; $^1$HNMR (400 MHz, DMSO-d6) δ 10.19 (s, 1H), 8.65 (d, J=3.9 Hz, 1H), 7.94 (d, J=8.7 Hz, 2H), 7.70 (d, J=8.6 Hz, 2H), 7.54 (t, J=6.0 Hz, 1H), 7.44 (s, 1H), 7.22-7.14 (m, 1H), 4.31 (t, J=4.3 Hz, 2H), 4.15 (p, J=6.6 Hz, 1H), 3.29 (d, J=6.0 Hz, 2H), 3.17 (s, 3H), 2.88 (q, J=5.9 Hz, 2H), 1.20 (d, J=6.5 Hz, 7H).

Example-132: Synthesis of 5-fluoro-4-(8-fluoro-4-isopropyl-3,4-dihydro-2H-benzo[b][1,4]oxazin-6-yl)-N-(5-((4-(2-methoxyethyl)piperazin-1-yl)methyl)pyridin-2-yl)pyrimidin-2-amine. (Compound 524)

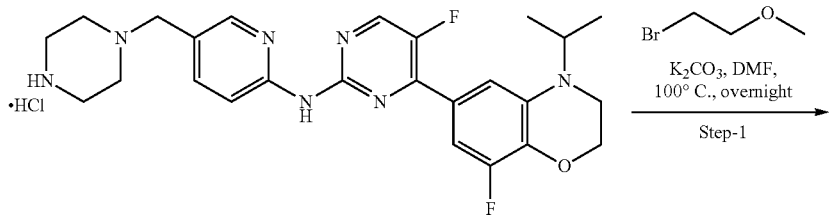

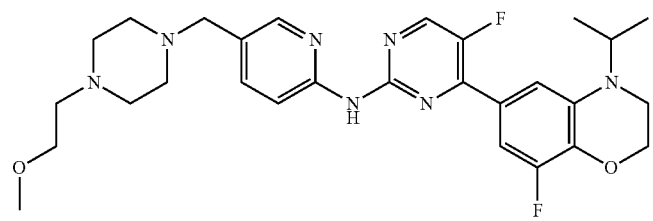

To a stirred solution of 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine (500 mg, 1.03 mmol, 1 equiv) in DMF (8 mL), was added K₂CO₃ (200 mg, 1.98 mmol, 2 equiv) and 1-bromo-2-methoxyethane (1000 mg, 1.58 mmol, 2 equiv). The resultant reaction mixture was allowed to stir at 100° C. for overnight. Progress of the reaction was monitored by LCMS. After completion of the reaction, diluted with water (50 mL), extracted with ethylacetate (30 mL×3):water (30 mL). resulted organic layer and dried under vacuum thereafter organic layer was purified by reverse phase chromatography to 5-fluoro-4-(8-fluoro-4-isopropyl-3,4-dihydro-2H-benzo[b][1,4]oxazin-6-yl)-N-(5-((4-(2-methoxyethyl)piperazin-1-yl)methyl)pyridin-2-yl)pyrimidin-2-amine (0.05 mg, 93.83%) as a yellow color solid compound. LCMS: 540 [M+H]⁺; ¹HNMR (400 MHz, DMSO-d6) δ 9.98 (s, 1H), 8.62 (d, J=4.0 Hz, 1H), 8.17 (d, J=8.6 Hz, 2H), 7.64 (dd, J=8.4, 2.5 Hz, 1H), 7.51 (s, 1H), 7.19 (d, J=11.7 Hz, 1H), 4.30 (t, J=4.3 Hz, 2H), 4.17 (p, J=6.6 Hz, 1H), 3.42 (dd, J=11.7, 5.9 Hz, 4H), 3.22 (s, 3H), 2.45-2.35 (m, 8H), 1.20 (d, J=6.5 Hz, 6H).

Example-133: Synthesis of N-(5-(4-aminopiperidin-1-yl) pyridin-2-yl)-5-fluoro-4-(8-fluoro-4-isopropyl-3,4-dihydro-2H-benzo[b][1,4]oxazin-6-yl)pyrimidin-2-amine. (Compound 788)

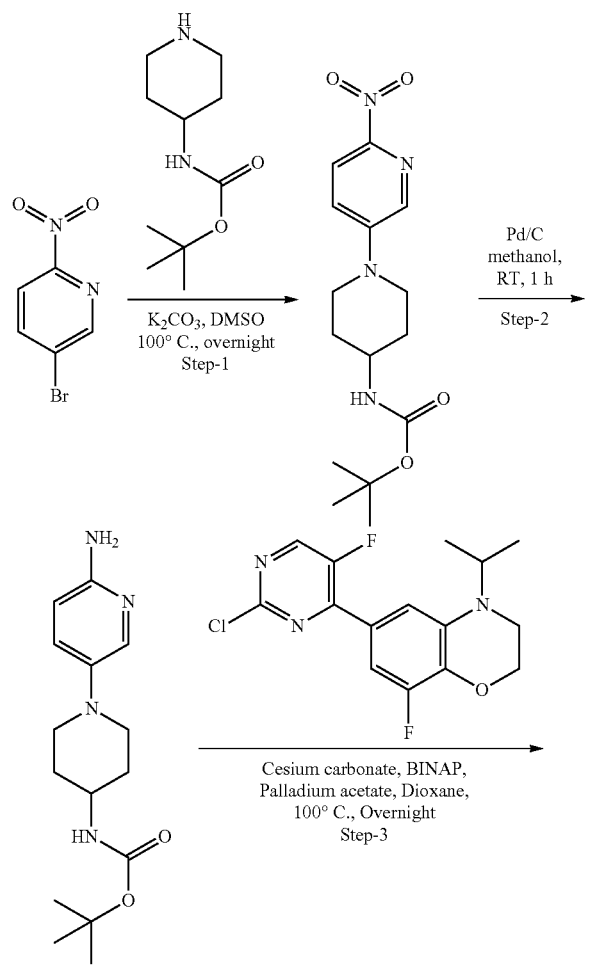

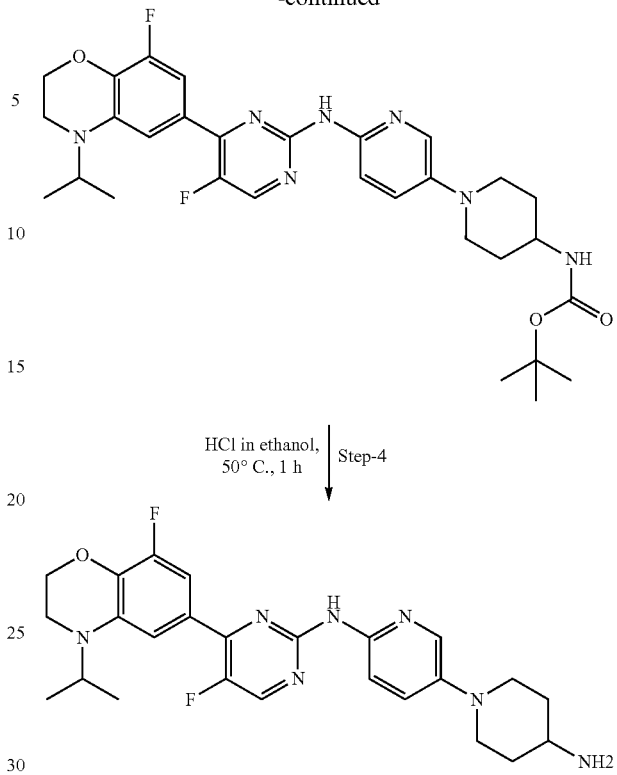

Step-1: Synthesis of tert-butyl (1-(6-nitropyridin-3-yl) piperidin-4-yl) carbamate To a stirred solution of 5-bromo-2-nitropyridine (300 mg, 1.48 mmol, 1 equiv) in DMSO (5 mL), was added K₂CO₃ (410 mg, 2.97 mmol, 2 equiv) and tert-butyl piperidin-4-ylcarbamate (594 mg, 2.97 mmol, 2 equiv). The resultant reaction mixture was allowed to stir at 100° C. for overnight. Progress of the reaction was monitored by LCMS. After completion of the reaction, diluted with water (50 mL), solid observed was filtered and dried under vacuum to obtain tert-butyl (1-(6-nitropyridin-3-yl)piperidin-4-yl)carbamate (400 mg, 83%) as a yellow color solid compound. LCMS: 323 [M+H]⁺

Step-2: Synthesis of tert-butyl (1-(6-aminopyridin-3-yl) piperidin-4-yl) carbamate To a stirred solution of tert-butyl (1-(6-nitropyridin-3-yl) piperidin-4-yl) carbamate (200 mg, 0.62 mmol, 1 equiv) in methanol (10 mL), was added Pd/C (20% w/w) (40 mg). The resultant reaction mixture was allowed to stir at RT for 1 h. Progress of the reaction was monitored by TLC and LCMS. After completion of the reaction, the mixture was passes through celite bed and the filtrate was concentrated under reduced pressure to obtain tert-butyl (1-(6-aminopyridin-3-yl) piperidin-4-yl) carbamate (150 mg, 82%) as a purple color solid compound.
LCMS: 293 [M+H]⁺

Step-3: Synthesis of tert-butyl (1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)carbamate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (5 mL), was added tert-butyl (1-(6-aminopyridin-3-yl)piperidin-4-yl)carbamate (96 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain tert-butyl (1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)carbamate (150 mg, 84%) as a brown color viscous compound. LCMS: 582 [M+H]$^+$ Step-4: Synthesis of N-(5-(4-aminopiperidin-1-yl)pyridin-2-yl)-5-fluoro-4-(8-fluoro-4-isopropyl-3,4-dihydro-2H-benzo[b][1,4]oxazin-6-yl)pyrimidin-2-amine tert-butyl (1-(6-((5-fluoro-4-(8-fluoro-4-isopropyl-3,4-dihydro-2H-benzo[b][1,4]oxazin-6-yl)pyrimidin-2-yl)amino)pyridin-3-yl)piperidin-4-yl)carbamate (150 mg, 0.26 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure to obtain crude, which was purified by reverse phase HPLC to obtain N-(5-(4-aminopiperidin-1-yl)pyridin-2-yl)-5-fluoro-4-(8-fluoro-4-isopropyl-3,4-dihydro-2H-benzo[b][1,4]oxazin-6-yl)pyrimidin-2-amine (60 mg, 48%) as a yellow color solid compound. LCMS: 482 [M+H]$^+$; $^1$HNMR: (DMSO-d$_6$,400 MHz): δ 9.68 (s, 1H), 8.56 (d, J=3.9 Hz, 1H), 7.84-8.05 (m, 2H), 7.46 (s, 1H), 7.39 (dd, J=8.8, 2.6 Hz, 1H), 7.17 (d, J=11.4 Hz, 1H), 4.30 (br. s., 2H), 4.02-4.18 (m, 1H), 3.63 (d, J=12.3 Hz, 2H), 3.30 (br. s., 2H), 2.98 (br. s., 1H), 2.74 (t, J=11.6 Hz, 2H), 1.90 (d, J=11.4 Hz, 2H), 1.53 (d, J=9.6 Hz, 2H), 1.19 ppm (d, J=6.1 Hz, 6H).

Example-134: Synthesis of 5-fluoro-4-(8-fluoro-4-isopropyl-3,4-dihydro-2H-benzo[b][, 4]oxazin-6-yl)-N-(5-((4-methylpiperazin-1-yl)methyl)pyridin-2-yl)pyrimidin-2-amine. (Compound 789)

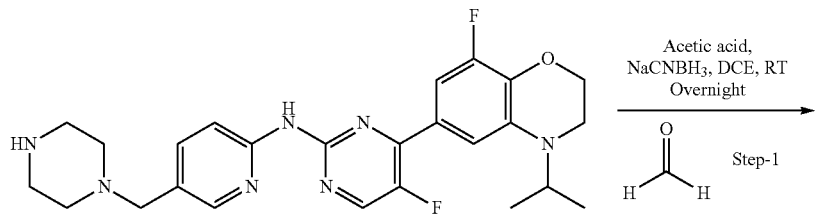

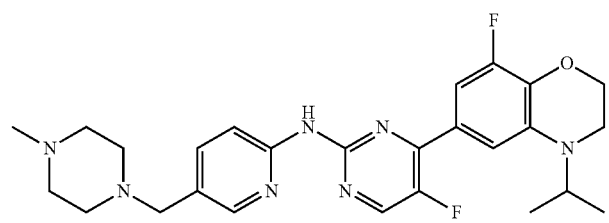

Step-1: Synthesis of 5-fluoro-4-(8-fluoro-4-isopropyl-3,4-dihydro-2H-benzo[b][1,4]oxazin-6-yl)-N-(5-((4-methylpiperazin-1-yl)methyl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(5-(piperazin-1-ylmethyl)pyridin-2-yl)pyrimidin-2-amine (100 mg, 0.2 mmol, 1 equiv) in DCE (3 mL), was added formaldehyde (40% in water) (0.03 mL, 0.61 mmol, 3 equiv), acetic acid (0.06 mL, 1.0 mmol, 5 equiv). The reaction mixture was allowed to stir at RT for 1 h. The reaction mixture was cooled to 0° C. NaCNBH$_3$ (38 mg, 0.61 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(5-((4-methylpiperazin-1-yl)methyl)pyridin-2-yl)pyrimidin-2-amine (10 mg, 10%) as an off white color solid compound.

LCMS: 496 [M+H]$^+$; $^1$HNMR (DMSO-d$_6$,400 MHz): δ 9.97 (s, 1H), 8.62 (d, J=3.9 Hz, 1H), 8.06-8.23 (m, 1H), 7.64 (d, J=10.5 Hz, 1H), 7.51 (s, 1H), 7.19 (d, J=11.8 Hz, 1H), 4.31 (br. s., 2H), 4.04-4.21 (m, 1H), 3.43 (s, 2H), 3.30 (t, J=4.2 Hz, 2H), 2.35 (d, J=18.9 Hz, 8H), 2.15 (s, 3H), 1.20 ppm (d, J=6.1 Hz, 6H).

Example-135: Synthesis of 2-fluoro-4-((5-fluoro-4-(8-fluoro-4-isopropyl-3,4-dihydro-2H-benzo[b][1,4]oxazin-6-yl)pyrimidin-2-yl)amino)benzamide. (Compound 790)

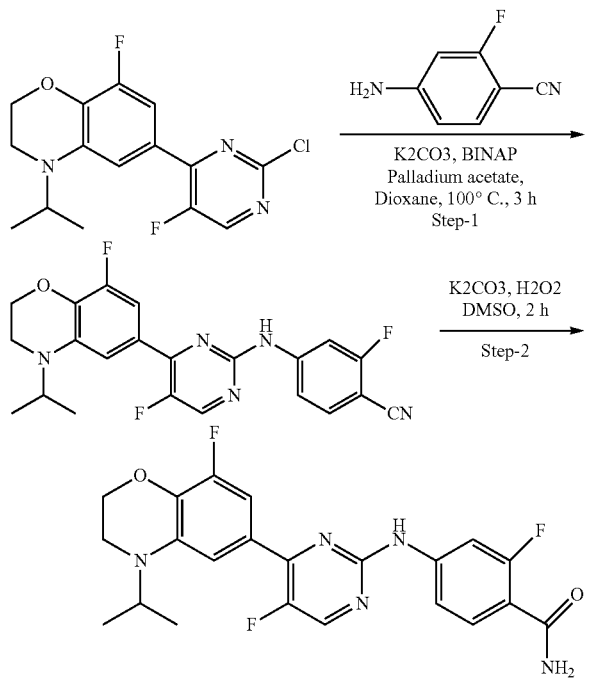

Step-1: Synthesis of 2-fluoro-4-((5-fluoro-4-(8-fluoro-4-isopropyl-3,4-dihydro-2H-benzo[b][1,4]oxazin-6-yl)pyrimidin-2-yl)amino)benzonitrile To a solution of 6-(2-chloro-5-fluoropyrimidin-4-yl)-8-fluoro-4-isopropyl-3,4-dihydro-2H-benzo[b][1,4]oxazine (500 mg, 1.53 mmol, 1 equiv) in dioxane (5 mL), was 4-amino-2-fluorobenzonitrile (280 mg, 1.69 mmol, 1.1 equiv) and cesium carbonate (745 mg, 2.29 mmol, 1.5 equiv). The reaction mixture was degassed with nitrogen gas for 30 min., followed by the addition of palladium acetate (35 mg, 0.153 mmol, 0.02 equiv) and BINAP (191 mg, 0.36 mmol, 0.2 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain 2-fluoro-4-((5-fluoro-4-(8-fluoro-4-isopropyl-3,4-dihydro-2H-benzo[b][1,4]oxazin-6-yl)pyrimidin-2-yl)amino)benzonitrile (400 mg, 84%) as a brown color viscous compound. LCMS: 426[M+H]$^+$

Step-2: Synthesis of 2-fluoro-4-((5-fluoro-4-(8-fluoro-4-isopropyl-3,4-dihydro-2H-benzo[b][1,4]oxazin-6-yl)pyrimidin-2-yl)amino)benzamide To a solution of 2-fluoro-4-((5-fluoro-4-(8-fluoro-4-isopropyl-3,4-dihydro-2H-benzo[b][1,4]oxazin-6-yl)pyrimidin-2-yl)amino)benzonitrile (200 mg, 0.46 mmol, 1 equiv) in DMSO (5 mL), was added K$_2$CO$_3$ (126 mg, 0.93 mmol, 2 equiv) and H$_2$O$_2$ (80 mg, 1.84 mmol, 4 equiv). The resultant reaction mixture was allowed to stir at RT for 2 h. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to and purified by reverse phase Chromatography to obtain 2-fluoro-4-((5-fluoro-4-(8-fluoro-4-isopropyl-3,4-dihydro-2H-benzo[b][1,4]oxazin-6-yl)pyrimidin-2-yl)amino)benzamide (5 mg, 99.48%) as a light yellow color solid compound. LCMS: 444 [M+H]$^+$; $^1$H NMR (400 MHz, DMSO-d$_6$) δ ppm 8.26 (d, J=7.91, 8.25 Hz, 1H) 8.10 (d, J=8.20 Hz, 1H) 7.81 (t, J=8.20 Hz, 1H) 7.5 (s, 1H) 7.42 (d, 1H) 8.20 (dd, 1H), 4.32 (d, 3H), 3.45 (s, 1H) 1.23 (s, 6H).

Example-136: Synthesis of 4-((5-fluoro-4-(8-fluoro-4-isopropyl-3,4-dihydro-2H-benzo[b][1,4]oxazin-6-yl)pyrimidin-2-yl)amino)-N-(piperidin-4-yl)benzenesulfonamide. (Compound 791)

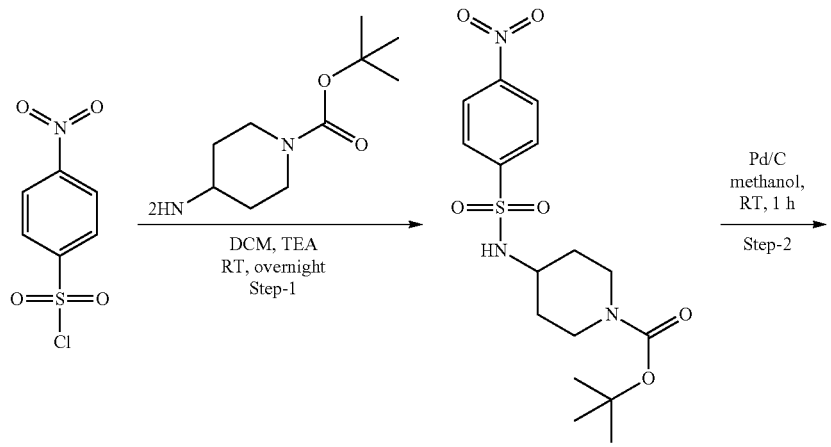

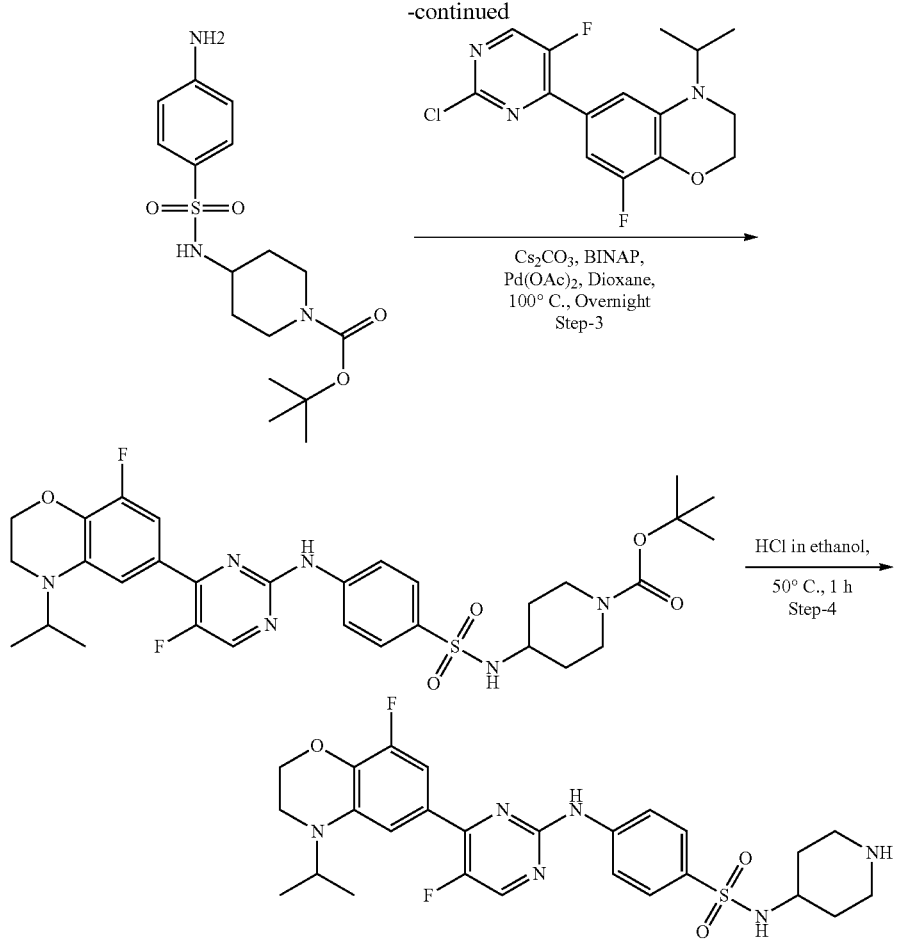

Step-1: Synthesis of tert-butyl 4-((4-nitrophenyl) sulfonyl) piperazine-1-carboxylate To a stirred solution of 4-nitrobenzenesulfonyl chloride (500 mg, 2.26 mmol, 1 equiv) in DCM (10 mL) was added TEA (0.5 mL, 3.39 mmol, 1.5 equiv), and tert-butyl piperazine-1-carboxylate (407 mg, 4.07 mmol, 1.8 equiv). The resultant reaction mixture was allowed to stir at RT for overnight. Progress of the reaction was monitored by TLC and LCMS. After completion of the reaction, the mixture was diluted water (50 mL) and extracted with DCM (50 mL×2). Organic layer was washed with water (50 mL) and brine (50 mL). Organic layer was dried over anhydrous sodium sulphate and concentrated under reduced pressure to obtain tert-butyl piperazine-1-carboxylate. (500 mg, 57%) as a light brown color solid compound.
LCMS: 386 [M+H]$^+$

Step-2: Synthesis of tert-butyl 4-((4-aminophenyl) sulfonyl) piperazine-1-carboxylate To a stirred solution of tert-butyl 4-((4-nitrophenyl) sulfonyl) piperazine-1-carboxylate (200 mg, 0.51 mmol, 1 equiv) in methanol (10 mL), was added Pd/C (20% w/w) (40 mg) under H$_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain tert-butyl 4-(6-aminopyridin-3-yl)-3-oxopiperazine-1-carboxylate (160 mg, 86%) as an off white color solid compound. LCMS: 356 [M+H]$^+$

Step-3: Synthesis of tert-butyl 4-((4-((5-fluoro-4-(8-fluoro-4-isopropyl-3,4-dihydro-2H-benzo[b][1,4] oxazin-6-yl)pyrimidin-2-yl)amino)phenyl)sulfonyl) piperazine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in Dioxane (10 mL), was added tert-butyl 4-(6-aminopyridin-3-yl)-3-oxopiperazine-1-carboxylate (117 mg, 0.33 mmol, 1.1 equiv) and cesium carbonate (147 mg, 0.47 mmol, 1.5 equiv). The reaction mixture was purged with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, the reaction mixture was diluted with water (30 mL) and extracted wit ethyl acetate (100 mL). Organic layer was washed with water (50 mL) and brine (50 mL). Organic layer was dried over anhydrous sodium sulphate and concentrated under reduced pressure to obtain tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate (150 mg, 76%) as a brown color viscous compound. LCMS: 645 [M+H]$^+$

Step-4: Synthesis of 4-((5-fluoro-4-(8-fluoro-4-isopropyl-3,4-dihydro-2H-benzo[b][1,4]oxazin-6-yl)pyrimidin-2-yl)amino)-N-(piperidin-4-yl)benzenesulfonamide tert-butyl 4-(6-((5-fluoro-4-(8-fluoro-4-isopropyl-3,4-dihydro-2H-benzo[b][1,4]oxazin-6-yl)pyrimidin-2-yl)amino)pyridin-3-yl)-3-oxopiperazine-1-carboxylate (150 mg, 0.23 mmol, 1 equiv) was taken in 1.25 M HCl in ethanol (5 mL) and the resultant reaction mixture was allowed to stir at 50° C. for 1 h. Progress of the reaction was monitored by LCMS. After completion of the reaction, solvent was removed under reduced pressure to obtain crude, which was purified by reverse phase HPLC to obtain 4-((5-fluoro-4-(8-fluoro-4-isopropyl-3,4-dihydro-2H-benzo[b][1,4]oxazin-6-yl)pyrimidin-2-yl)amino)-N-(piperidin-4-yl)benzenesulfonamide (2 mg, 2%) as a yellow color solid compound. LCMS: 545 [M+H]$^+$; $^1$HNMR (DMSO-d$_6$, 400 MHz): δ 10.21 (br. s., 1H), 8.65 (br. s., 1H), 7.94 (d, J=8.3 Hz, 2H), 7.71 (d, J=7.9 Hz, 2H), 7.60 (br. s., 1H), 7.44 (br. s., 1H), 7.18 (d, J=12.3 Hz, 1H), 4.31 (br. s., 2H), 4.16 (br. s., 1H), 3.39 (m, 2H), 3.17 (br. s., 1H), 2.99 (br. s., 2H), 2.92 (br. s., 2H), 2.09 (br. s., 1H), 1.54 (br. s., 2H), 1.36 (br. s., 2H), 1.20 ppm (d, J=6.1 Hz, 6H).

Example-137: Synthesis of 5-fluoro-N-(3-fluoro-4-((4-methylpiperazin-1-yl)methyl)phenyl)-4-(8-fluoro-4-isopropyl-3,4-dihydro-2H-benzo[b][1,4]oxazin-6-yl)pyrimidin-2-amine. (Compound 792)

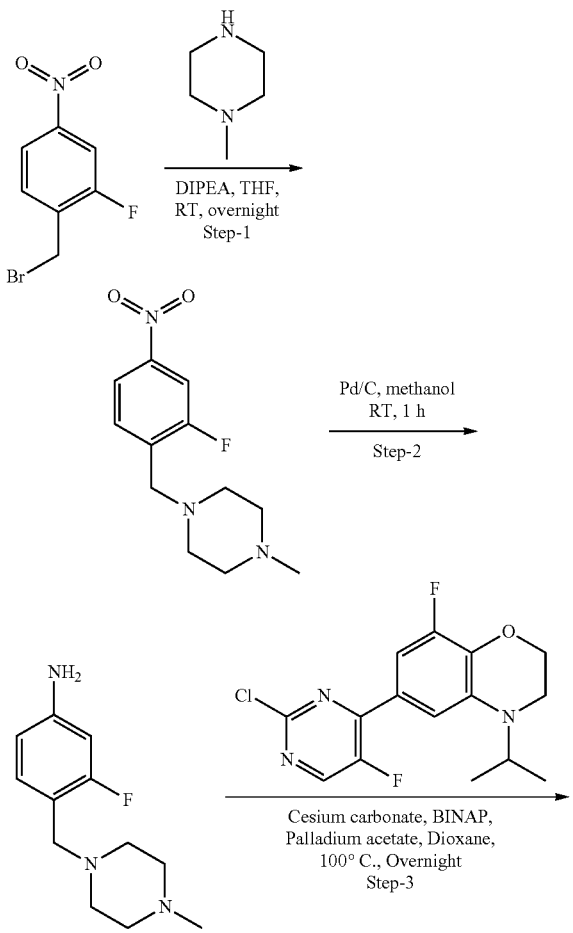

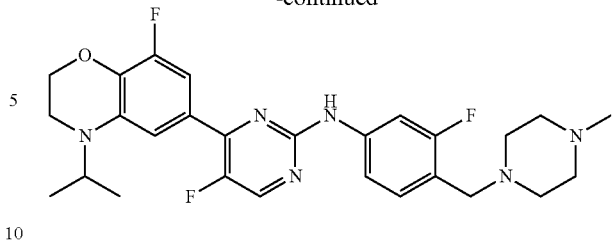

Step-1: Synthesis of 1-(2-fluoro-4-nitrobenzyl)-4-methylpiperazine

To a stirred solution of 1-(bromomethyl)-2-fluoro-4-nitrobenzene (300 mg, 1.29 mmol, 1 equiv) in THF (10 mL), was added 1-methylpiperazine (386 mg, 3.87 mmol, 3 equiv) and DIPEA (0.7 mL, 3.87 mmol, 3 equiv). The resultant reaction mixture was allowed to stir at RT for overnight. Progress of the reaction was monitored by LCMS and NMR. After completion of the reaction, diluted with water (30 mL), and extracted with ethyl acetate (100 mL). Organic layer was washed with water (50 mL) and brine solution (50 mL). Organic layer was dried over anhydrous sodium sulphate and concentrated under reduced pressure to obtain 1-(2-fluoro-4-nitrobenzyl)-4-methylpiperazine (300 mg, 92%) as a yellow viscous compound. LCMS: 254 [M+H]$^+$

Step-2: Synthesis of 3-fluoro-4-((4-methylpiperazin-1-yl)methyl)aniline

To a stirred solution of 1-(2-fluoro-4-nitrobenzyl)-4-methylpiperazine (300 mg, 1.18 mmol, 1 equiv) in methanol (10 mL), was added Pd/C (20% w/w) (60 mg) under H$_2$ atm. The resultant reaction mixture was allowed to stir at RT for 1 h. Progress of the reaction was monitored by LCMS. After completion of the reaction, the mixture was passes through celite bed and the filtrate was concentrated under reduced pressure to obtain 3-fluoro-4-((4-methylpiperazin-1-yl)methyl)aniline (200 mg, 75%) as an off white color solid compound. LCMS: 224 [M+H]$^+$

Step-3: Synthesis of 5-fluoro-N-(3-fluoro-4-((4-methylpiperazin-1-yl)methyl)phenyl)-4-(8-fluoro-4-isopropyl-3,4-dihydro-2H-benzo[b][1,4]oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 3-fluoro-4-((4-methylpiperazin-1-yl)methyl)aniline (74 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-N-(3-fluoro-4-((4-methylpiperazin-1-yl)methyl)

phenyl)-4-(8-fluoro-4-isopropyl-3,4-dihydro-2H-benzo[b][1,4]oxazin-6-yl)pyrimidin-2-amine (50 mg, 32%) as a yellow color solid compound.

LCMS: 513 [M+H]$^+$; $^1$HNMR (DMSO-d$_6$, 400 MHz): δ 9.93 (s, 1H), 8.61 (d, J=3.9 Hz, 1H), 7.77 (dd, J=12.9, 1.5 Hz, 1H), 7.37-7.52 (m, 2H), 7.22-7.29 (m, 1H), 7.17 (d, J=11.0 Hz, 1H), 4.30 (t, J=3.9 Hz, 2H), 4.17 (s, 1H), 3.44 (s, 2H), 3.13-3.39 (m, 2H), 2.38 (br. s., 4H), 2.33 (br. s., 4H), 2.15 (s, 3H), 1.18 ppm (d, J=6.6 Hz, 6H).

Example-138: Synthesis of 5-fluoro-4-(8-fluoro-4-isopropyl-3,4-dihydro-2H-benzo[b][1,4]oxazin-6-yl)-N-(5-(1-methylpiperidin-4-yl)-6-(trifluoromethyl)pyridin-2-yl)pyrimidin-2-amine. (Compound 841)

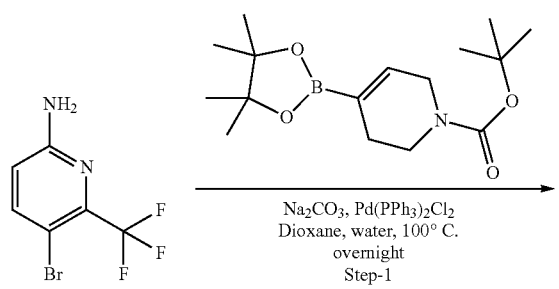

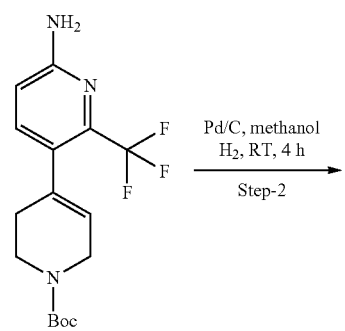

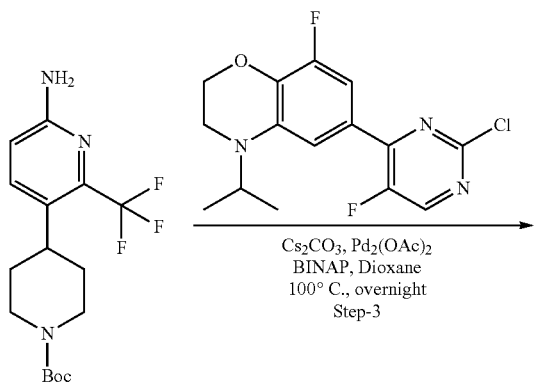

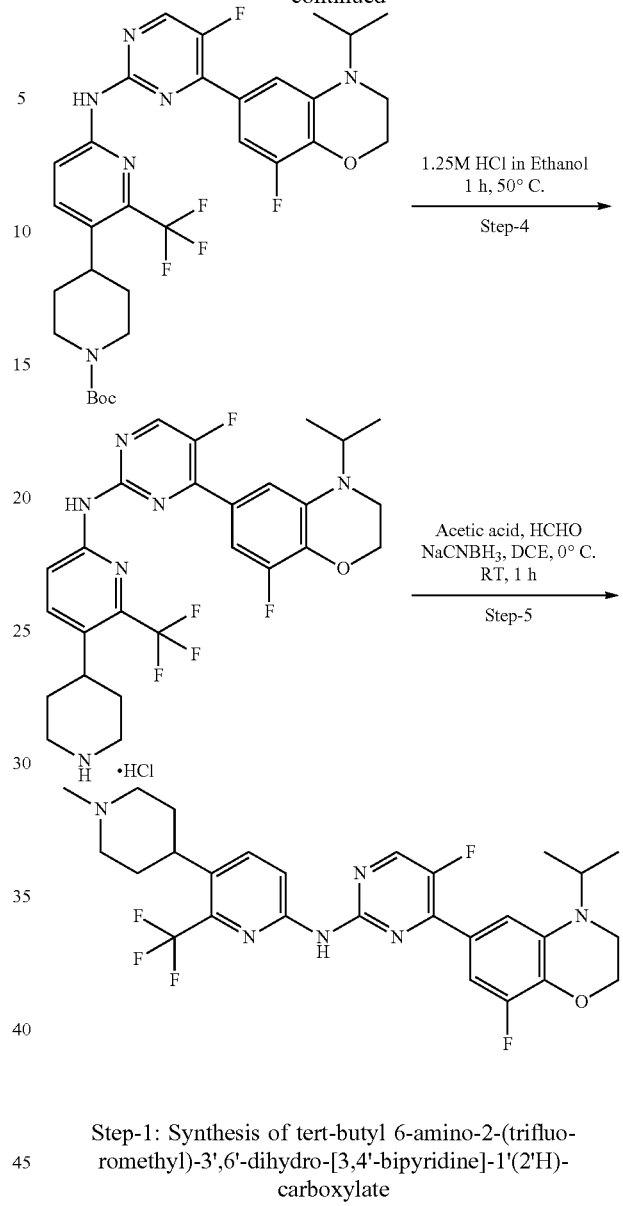

Step-1: Synthesis of tert-butyl 6-amino-2-(trifluoromethyl)-3',6'-dihydro-[3,4'-bipyridine]-1'(2'H)-carboxylate To a solution of 5-bromo-6-(trifluoromethyl)pyridin-2-amine (500 mg, 2.07 mmol, 1 equiv) in dioxane:water (10 mL:3 mL), was added tert-butyl 4-(4, 4, 5, 5-tetramethyl-1, 3, 2-dioxaborolan-2-yl)-3, 6-dihydropyridine-1(2H)-carboxylate (705 mg, 2.28 mmol, 1.1 equiv) and sodium carbonate (329 mg, 3.11 mmol, 1.5 equiv). The reaction mixture was degassed with nitrogen gas for 30 min., followed by the addition of Pd(PPh$_3$)$_2$Cl$_2$ (72 mg, 0.1 mmol, 0.05 equiv). The resultant reaction mixture was allowed to stir at 100° C. for 6 h. Progress of the reaction was monitored by TLC and LCMS. After completion of the reaction, reaction mixture was diluted with water (20 mL) and extracted with ethyl acetate (25 mL×2). Combined organic layer was washed with water (30 mL) and brine solution (30 mL). Organic layer was dried over anhydrous sodium sulphate and concentrated under reduced pressure to obtain crude, which was purified by normal phase combi flash by using 100-200 mesh silica gel column to afford tert-butyl 6-amino-2-(trifluoromethyl)-3',6'-dihydro-[3,4'- bipyridine]-1'(2'H)-carboxylate (450 mg, 63%) as an off white solid compound. LCMS: 343 [M+H]⁺

Step-2: Synthesis of tert-butyl 4-(6-amino-2-(trifluoromethyl)pyridin-3-yl)piperidine-1-carboxylate To a stirred solution of tert-butyl 6-amino-2-(trifluoromethyl)-3',6'-dihydro-[3,4'-bipyridine]-1'(2'H)-carboxylate (200 mg, 0.58 mmol, 1 equiv) in methanol (10 mL), was added Pd/C (10 wt. %) (40 mg) under $H_2$ atm. The resultant reaction mixture was allowed to stir at RT for 6 h. Progress of the reaction was monitored by LCMS. After completion of the reaction, the mixture was passes through celite bed and the filtrate was concentrated under reduced pressure to afford tert-butyl 4-(6-amino-2-(trifluoromethyl)pyridin-3-yl)piperidine-1-carboxylate (180 mg, 90%) as an off white solid compound. LCMS: 345 [M+H]⁺

Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)-2-(trifluoromethyl)pyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.45 mmol, 1 equiv) in dioxane (6 mL), was tert-butyl 4-(6-amino-2-(trifluoromethyl)pyridin-3-yl)piperidine-1-carboxylate (175 mg, 0.5 mmol, 1.1 equiv) and cesium carbonate (224 mg, 0.69 mmol, 1.5 equiv). The reaction mixture was degassed with nitrogen gas for 10 min., followed by the addition of palladium acetate (10 mg, 0.046 mmol, 0.1 equiv) and BINAP (57 mg, 0.092 mmol, 0.2 equiv). The resultant reaction mixture was allowed to stir at 100° C. for overnight. Progress of the reaction was monitored by TLC and LCMS. After completion of the reaction, diluted with water (10 mL) and extracted with ethyl acetate (15 mL). Organic layer was washed with water (10 mL) and brine solution (10 mL). Organic layer was dried over anhydrous sodium sulphate and concentrated under reduced pressure to obtain crude, which was purified by normal phase combi flash by using 100-200 mesh silica gel column to obtain tert-butyl 4-(6-((5-fluoro-4-(8-fluoro-4-isopropyl-3,4-dihydro-2H-benzo[b][1,4]oxazin-6-yl)pyrimidin-2-yl)amino)-2-(trifluoromethyl)pyridin-3-yl)piperidine-1-carboxylate (120 mg, 41%) as a yellow solid compound. LCMS: 635 [M+H]⁺

Step-4: Synthesis of 5-fluoro-4-(8-fluoro-4-isopropyl-3,4-dihydro-2H-benzo[b][1,4]oxazin-6-yl)-N-(5-(piperidin-4-yl)-6-(trifluoromethyl)pyridin-2-yl)pyrimidin-2-amine hydrochloride A solution of tert-butyl 4-(6-((5-fluoro-4-(8-fluoro-4-isopropyl-3,4-dihydro-2H-benzo[b][1,4]oxazin-6-yl)pyrimidin-2-yl) amino)-2-(trifluoromethyl)pyridin-3-yl)piperidine-1-carboxylate (120 mg, 0.2 mmol, 1 equiv) in 1.25 M HCl in ethanol (4 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(5-(piperidin-4-yl)-6-(trifluoromethyl)pyridin-2-yl)pyrimidin-2-amine hydrochloride (90 mg, 84%) as a yellow solid compound. LCMS: 535 [M+H]⁺

Step-5: Synthesis of 5-fluoro-4-(8-fluoro-4-isopropyl-3,4-dihydro-2H-benzo[b][1,4]oxazin-6-yl)-N-(5-(1-methylpiperidin-4-yl)-6-(trifluoromethyl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(5-(piperidin-4-yl)-6-(trifluoromethyl)pyridin-2-yl)pyrimidin-2-amine (100 mg, 0.19 mmol, 1 equiv) in DCE (5 mL), was added Formaldehyde (30% in water) (84 mg, 0.93 mmol, 5 equiv), acetic acid (57 mg, 0.93 mmol, 5 equiv). The reaction mixture was allowed to stir at RT for 1 h. The reaction mixture was cooled to 0° C. NaCNBH₃ (23 mg, 0.38 mmol, 2 equiv) was added to above mixture and raised the temperature to RT. The reaction mixture was allowed to stir at RT for 4 h. Progress of the reaction was monitored by LCMS. After completion of the reaction, the reaction mixture was diluted with water (20 mL) and extracted with ethyl acetate (20 mL×2). Organic layer was washed with water (20 mL) and brine solution (20 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(5-(1-methylpiperidin-4-yl)-6-(trifluoromethyl)pyridin-2-yl)pyrimidin-2-amine (15 mg, 14%) as a solid compound. LCMS: 549 [M+H]⁺; ¹HNMR (400 MHz, Methanol-d4) δ 8.61 (d, J=8.8 Hz, 1H), 8.47 (d, J=4.0 Hz, 1H), 7.94 (d, J=8.9 Hz, 1H), 7.53 (s, 1H), 7.30-7.22 (m, 1H), 4.33 (t, J=4.4 Hz, 1H), 4.24 (p, J=6.5 Hz, 1H), 3.23 (d, J=12.0 Hz, 3H), 3.04 (s, 2H), 2.52 (d, J=19.5 Hz, 5H), 2.16 (s, OH), 1.96-1.86 (m, 4H), 1.32-1.21 (m, 6H).

Example-139: Synthesis of N-(5-(4-((dimethylamino)methyl)piperidin-1-yl)pyridin-2-yl)-5-fluoro-4-(8-fluoro-4-isopropyl-3,4-dihydro-2H-benzo[b][1,4]oxazin-6-yl)pyrimidin-2-amine. (Compound 842)

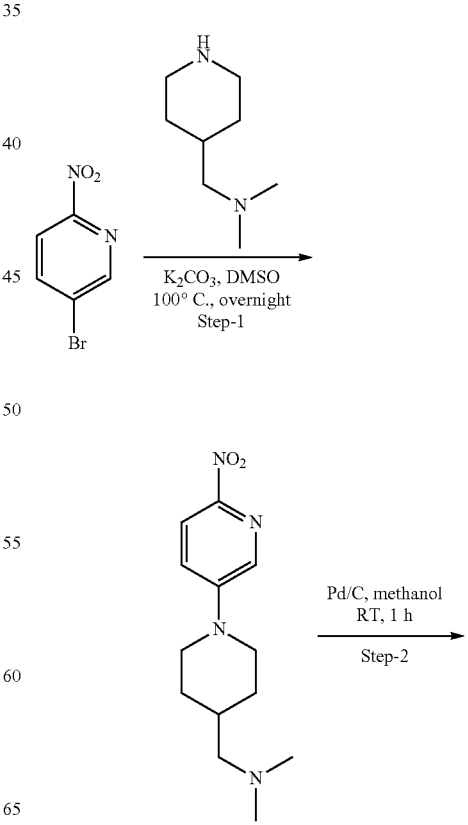

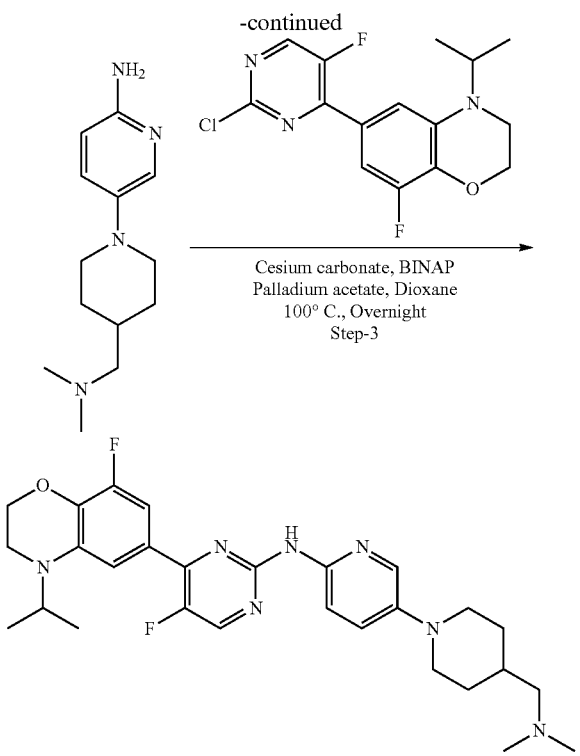

Step-1: Synthesis of N,N-dimethyl-1-(1-(6-nitropyridin-3-yl)piperidin-4-yl)methanamine To a stirred solution of 5-bromo-2-nitropyridine (500 mg, 2.46 mmol, 1 equiv) in DMSO (8 mL), was added N,N-dimethyl-1-(piperidin-4-yl)methanamine (635 mg, 2.95 mmol, 1.2 equiv) and K$_2$CO$_3$ (679 mg, 4.92 mmol, 2 equiv). The resultant reaction mixture was allowed to stir at 100° C. for overnight. Progress of the reaction was monitored by LCMS and NMR. After completion of the reaction, diluted with ice water (30 mL), solid observed was filtered and dried under vacuum to obtain N,N-dimethyl-1-(1-(6-nitropyridin-3-yl)piperidin-4-yl)methanamine (500 mg, 77%) as a yellow color solid compound. LCMS: 265 [M+H]$^+$ Step-2: Synthesis of 5-(4-((dimethyl amino) methyl) piperidin-1-yl) pyridin-2-amine To a stirred solution of N, N-dimethyl-1-(1-(6-nitropyridin-3-yl) piperidin-4-yl) methanamine (200 mg, 0.75 mmol, 1 equiv) in methanol (10 mL), was added Pd/C (20% w/w) (40 mg) under H$_2$ atm. The resultant reaction mixture was allowed to stir at RT for 1 h. Progress of the reaction was monitored by LCMS. After completion of the reaction, the mixture was passes through celite bed and the filtrate was concentrated under reduced pressure to obtain 5-(4-((dimethyl amino) methyl) piperidin-1-yl) pyridin-2-amine (150 mg, 85%) as an off white color solid compound. LCMS: 235 [M+H]$^+$ Step-3: Synthesis of N-(5-(4-((dimethylamino) methyl)piperidin-1-yl)pyridin-2-yl)-5-fluoro-4-(8-fluoro-4-isopropyl-3,4-dihydro-2H-benzo[b][1,4] oxazin-6-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 5-(4-((dimethyl amino)methyl)piperidin-1-yl)pyridin-2-amine (77 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain N-(5-(4-((dimethylamino)methyl)piperidin-1-yl)pyridin-2-yl)-5-fluoro-4-(8-fluoro-4-isopropyl-3,4-dihydro-2H-benzo[b][1,4]oxazin-6-yl)pyrimidin-2-amine (20 mg, 12%) as a yellow color solid compound. LCMS: 524 [M+H]$^+$; $^1$HNMR: (DMSO-d$_6$,400 MHz): δ 9.66 (s, 1H), 8.56 (d, J=3.9 Hz, 1H), 7.82-8.09 (m, 2H), 7.47 (br. s., 1H), 7.28-7.43 (m, 1H), 7.17 (d, J=12.3 Hz, 1H), 4.30 (br. s., 2H), 4.16 (d, J=6.6 Hz, 1H), 3.61 (d, J=12.3 Hz, 2H), 3.25 (br. s., 2H), 2.52-2.73 (m, 3H), 2.12 (s, 6H), 2.08 (d, J=7.9 Hz, 2H), 1.79 (d, J=10.5 Hz, 2H), 1.58 (br. s., 2H), 1.10-1.29 ppm (m, 6H).

Example-140: Synthesis of 5-fluoro-4-(8-fluoro-4-isopropyl-3,4-dihydro-2H-benzo[b][1,4]oxazin-6-yl)-N-(5-(4-methoxypiperidin-1-yl)pyridin-2-yl)pyrimidin-2-amine hydrochloride. (Compound 843)

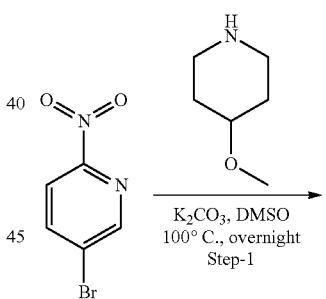

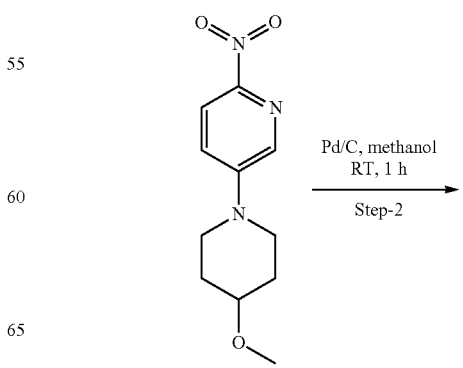

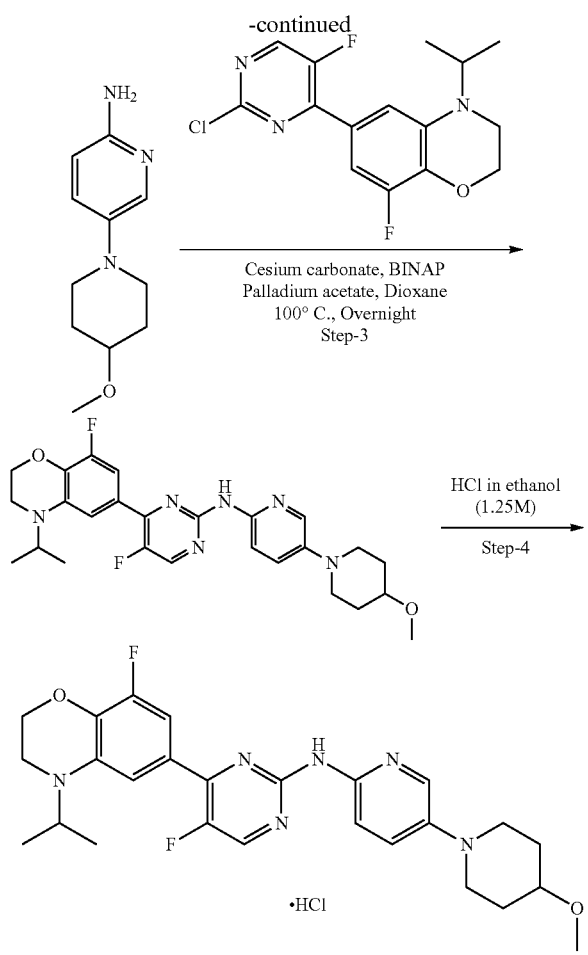

Step-1: Synthesis of 5-(4-methoxypiperidin-1-yl)-2-nitropyridine

To a stirred solution of 5-bromo-2-nitropyridine (500 mg, 2.46 mmol, 1 equiv) in DMSO (8 mL), was added 1-4-methoxypiperidine (567 mg, 4.92 mmol, 2 equiv) and $K_2CO_3$ (679 mg, 4.92 mmol, 2 equiv). The resultant reaction mixture was allowed to stir at 100° C. for overnight. Progress of the reaction was monitored by LCMS and NMR. After completion of the reaction, diluted with water (30 mL), solid observed was filtered and dried under vacuum to obtain 5-(4-methoxypiperidin-1-yl)-2-nitropyridine (500 mg, 86%) as a yellow color solid compound. LCMS: 238 $[M+H]^+$

Step-2: Synthesis of 5-(4-methoxypiperidin-1-yl)pyridin-2-amine

To a stirred solution of 5-(4-methoxypiperidin-1-yl)-2-nitropyridine (200 mg, 0.84 mmol, 1 equiv) in methanol (10 mL), was added Pd/C (20% w/w) (40 mg) under $H_2$ atm. The resultant reaction mixture was allowed to stir at RT for 1 h. Progress of the reaction was monitored by LCMS. After completion of the reaction, the mixture was passes through celite bed and the filtrate was concentrated under reduced pressure to obtain 5-(4-methoxypiperidin-1-yl)pyridin-2-amine (150 mg, 86%) as an off white color solid compound. LCMS: 208 $[M+H]^+$

Step-3: Synthesis of 5-fluoro-4-(8-fluoro-4-isopropyl-3,4-dihydro-2H-benzo[b][1,4]oxazin-6-yl)-N-(5-(4-methoxypiperidin-1-yl)pyridin-2-yl)pyrimidin-2-amine To a solution of 6-(2-chloro-5-fluoropyrimidin-4-yl)-8-fluoro-4-isopropyl-3,4-dihydro-2H-benzo[b][1,4]oxazine (100 mg, 0.3 mmol, 1 equiv) in dioxane (10 mL), was added 5-(4-methoxypiperidin-1-yl)pyridin-2-amine (69 mg, 0.33 mmol, 1.1 equiv) and cesium carbonate (147 mg, 0.47 mmol, 1.5 equiv). The reaction mixture was degassed with nitrogen gas for 30 min., followed by the addition of palladium acetate (2 mg, 0.006 mmol, 0.02 equiv) and BINAP (8 mg, 0.012 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by reverse phase HPLC to obtain 5-fluoro-4-(8-fluoro-4-isopropyl-3,4-dihydro-2H-benzo[b][1,4]oxazin-6-yl)-N-(5-(4-methoxypiperidin-1-yl)pyridin-2-yl)pyrimidin-2-amine (110 mg, 72%) as a yellow color solid compound. LCMS: 497 $[M+H]^+$

Step-4: Synthesis of 5-fluoro-4-(8-fluoro-4-isopropyl-3,4-dihydro-2H-benzo[b][1,4]oxazin-6-yl)-N(5-(4-methoxypiperidin-1-yl)pyridin-2-yl)pyrimidin-2-amine hydrochloride 5-fluoro-4-(8-fluoro-4-isopropyl-3,4-dihydro-2H-benzo[b][1,4]oxazin-6-yl)-N-(5-(4-methoxypiperidin-1-yl)pyridin-2-yl)pyrimidin-2-amine (30 mg, 0.06 mmol, 1 equiv) was taken in 1.25 M HCl in ethanol (5 mL) and the resultant reaction mixture was allowed to stir at RT for 1 h. Solvent was removed under reduced pressure and the residue was dried under lyophilizer to obtain 5-fluoro-4-(8-fluoro-4-isopropyl-3,4-dihydro-2H-benzo[b][1,4]oxazin-6-yl)-N-(5-(4-methoxypiperidin-1-yl)pyridin-2-yl)pyrimidin-2-amine hydrochloride (20 mg, 67%) as a brick red color solid compound. LCMS: 497 $[M+H]^+$; $^1$HNMR: (DMSO-$d_6$, 400 MHz, HCl salt): 611.66 (br. s., 1H), 8.77 (d, J=3.5 Hz, 1H), 8.11-8.30 (m, 1H), 7.94 (br. s., 1H), 7.72 (br. s., 1H), 7.39 (s, 1H), 7.20 (d, J=11.0 Hz, 1H), 4.24-4.38 (m, 2H), 4.14 (dt, J=13.2, 6.6 Hz, 1H), 3.50 (br. s., 3H), 3.32 (br. s., 2H), 3.28 (s, 3H), 3.07 (br. s., 2H), 1.97 (br. s., 2H), 1.60 (br. s., 2H), 1.18 ppm (d, J=6.6 Hz, 6H).

Example-141: Synthesis of 5-fluoro-4-(8-fluoro-4-isopropyl-3,4-dihydro-2H-benzo[b][1,4]oxazin-6-yl)-N-(6-methoxy-5-(1-methylpiperidin-4-yl)pyridin-2-yl)pyrimidin-2-amine. (Compound 844)

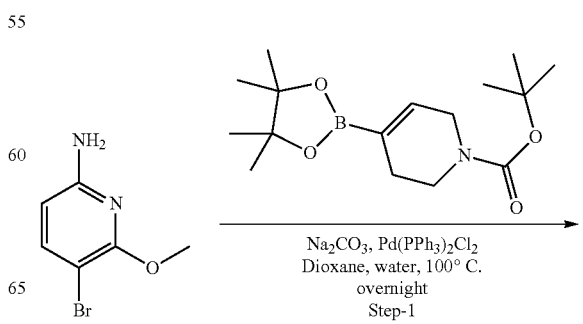

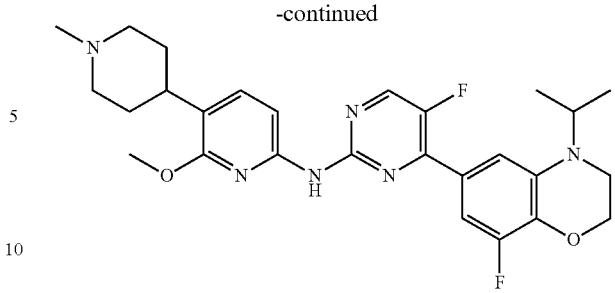
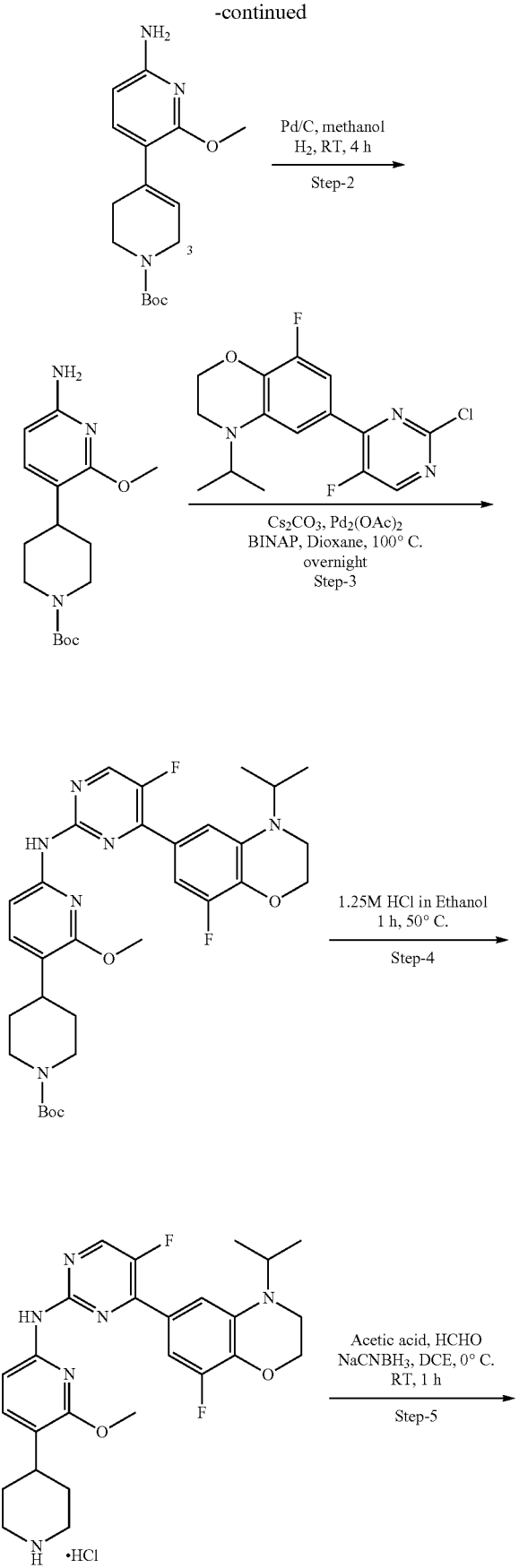

Step-1: Synthesis of tert-butyl 6-amino-2-methoxy-3',6'-dihydro-[3,4'-bipyridine]-1'(2'H)-carboxylate To a solution of 5-bromo-6-methoxypyridin-2-amine (200 mg, 0.98 mmol, 1 equiv) in dioxane:water (10 mL:3 mL), was added tert-butyl 4-(4, 4, 5, 5-tetramethyl-1, 3, 2-dioxaborolan-2-yl)-3, 6-dihydropyridine-1(2H)-carboxylate (334 mg, 1.08 mmol, 1.1 equiv) and sodium carbonate (158 mg, 1.47 mmol, 1.5 equiv). The reaction mixture was degassed with nitrogen gas for 30 min., followed by the addition of $Pd(PPh_3)_2Cl_2$ (34 mg, 0.049 mmol, 0.05 equiv). The resultant reaction mixture was allowed to stir at 100° C. for 6 h. Progress of the reaction was monitored by TLC and LCMS. After completion of the reaction, reaction mixture was diluted with water (20 mL) and extracted with ethyl acetate (25 mL×2). Combined organic layer was washed with water (30 mL) and brine solution (30 mL). Organic layer was dried over anhydrous sodium sulphate and concentrated under reduced pressure to obtain crude, which was purified by normal phase combi flash by using 100-200 mesh silica gel column to afford tert-butyl 6-amino-2-methoxy-3',6'-dihydro-[3,4'-bipyridine]-1'(2'H)-carboxylate (210 mg, 70%) as an off white solid compound. LCMS: 306 [M+H]$^+$ Step-2: Synthesis of tert-butyl 4-(6-amino-2-methoxypyridin-3-yl)piperidine-1-carboxylate To a stirred solution of tert-butyl 6-amino-2-methoxy-3',6'-dihydro-[3,4'-bipyridine]-1'(2'H)-carboxylate (300 mg, 0.98 mmol, 1 equiv) in methanol (10 mL), was added Pd/C (10 wt. %) (50 mg) under $H_2$ atm. The resultant reaction mixture was allowed to stir at RT for 6 h. Progress of the reaction was monitored by LCMS. After completion of the reaction, the mixture was passes through celite bed and the filtrate was concentrated under reduced pressure to afford tert-butyl 4-(6-amino-2-methoxypyridin-3-yl)piperidine-1-carboxylate (270 mg, 88%) as a transparent oil compound. LCMS: 308 [M+H]$^+$ Step-3: Synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)-2-methoxypyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (100 mg, 0.31 mmol, 1 equiv) in dioxane (3 mL), was added tert-butyl 4-(5-aminopyridin-2-yl) piperidine-1-carboxylate (104 mg, 0.33 mmol, 1.1 equiv) and cesium carbonate (151 mg, 0.46 mmol, 1.5 equiv). The reaction mixture was degassed with nitrogen gas for 10 min., followed by the addition of palladium acetate (7 mg, 0.03 mmol, 0.1 equiv) and BINAP (39 mg, 0.06 mmol, 0.2 equiv). The resultant reaction mixture was allowed to stir at 100° C. for overnight. Progress of the reaction was monitored by TLC and LCMS. After completion of the reaction, diluted with water (10 mL) and extracted with ethyl acetate (15 mL). Organic layer was washed with water (10 mL) and brine solution (10 mL). Organic layer was dried over anhydrous sodium sulphate and concentrated under reduced pressure to obtain crude, which was purified by normal phase combi flash to obtain tert-butyl 4-(6-((5-fluoro-4-(8-fluoro-4-isopropyl-3,4-dihydro-2H-benzo[b][1,4]oxazin-6-yl)pyrimidin-2-yl)amino)-2-methoxypyridin-3-yl)piperidine-1-carboxylate (90 mg, 49%) as a yellow solid compound. LCMS: 597 [M+H]+

Step-4: Synthesis of 5-fluoro-4-(8-fluoro-4-isopropyl-3,4-dihydro-2H-benzo[b][1,4]oxazin-6-yl)-N-(6-methoxy-5-(piperidin-4-yl)pyridin-2-yl)pyrimidin-2-amine hydrochloride A solution of tert-butyl 4-(6-((5-fluoro-4-(8-fluoro-4-isopropyl-3,4-dihydro-2H-benzo[b][1,4]oxazin-6-yl)pyrimidin-2-yl)amino)-2-methoxypyridin-3-yl)piperidine-1-carboxylate (120 mg, 0.2 mmol, 1 equiv) in 1.25 M HCl in ethanol (4 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(6-methoxy-5-(piperidin-4-yl)pyridin-2-yl)pyrimidin-2-amine hydrochloride (90 mg, 90%) as a yellow solid compound. LCMS: 497 [M+H]+

Step-5: Synthesis of 5-fluoro-4-(8-fluoro-4-isopropyl-3,4-dihydro-2H-benzo[b][1,4]oxazin-6-yl)-N-(6-methoxy-5-(1-methylpiperidin-4-yl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(6-methoxy-5-(piperidin-4-yl)pyridin-2-yl)pyrimidin-2-amine hydrochloride salt (200 mg, 0.4 mmol, 1 equiv) in DCE (5 mL), was added Formaldehyde (30% in water) (180 mg, 2 mmol, 5 equiv), acetic acid (120 mg, 2 mmol, 5 equiv). The reaction mixture was allowed to stir at RT for 1 h. The reaction mixture was cooled to 0° C. NaCNBH$_3$ (49 mg, 0.8 mmol, 2 equiv) was added to above mixture and raise the temperature to RT. The reaction mixture was allowed to stir at RT for 4 h. Progress of the reaction was monitored by LCMS. After completion of the reaction, the reaction mixture was diluted with water (20 mL) and extracted with ethyl acetate (20 mL×2). Organic layer was washed with water (20 mL) and brine solution (20 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(6-methoxy-5-(1-methylpiperidin-4-yl)pyridin-2-yl)pyrimidin-2-amine (6 mg, 15%) as a yellow color solid compound. LCMS: 511 [M+H]+; $^1$HNMR: (400 MHz, Methanol-d4) δ 8.43 (d, J=4.1 Hz, 1H), 7.92 (d, J=8.1 Hz, 1H), 7.53 (s, 1H), 7.50 (d, J=8.2 Hz, 1H), 7.26 (d, J=11.6 Hz, 1H), 4.33 (t, J=4.3 Hz, 2H), 4.24 (p, J=6.6 Hz, 1H), 3.96 (s, 3H), 3.58 (d, J=12.2 Hz, 2H), 3.36 (d, J=4.9 Hz, 2H), 3.20-3.02 (m, 3H), 2.91 (s, 3H), 2.11 (d, J=14.3 Hz, 2H), 2.00 (dd, J=17.6, 7.3 Hz, 2H), 1.27 (d, J=6.6 Hz, 6H).

Example-142: Synthesis of 6-((5-fluoro-4-(8-fluoro-4-isopropyl-3,4-dihydro-2H-benzo[b][1,4]oxazin-6-yl)pyrimidin-2-yl)amino)-3-(1-methylpiperidin-4-yl)picolinonitrile. (Compound 845)

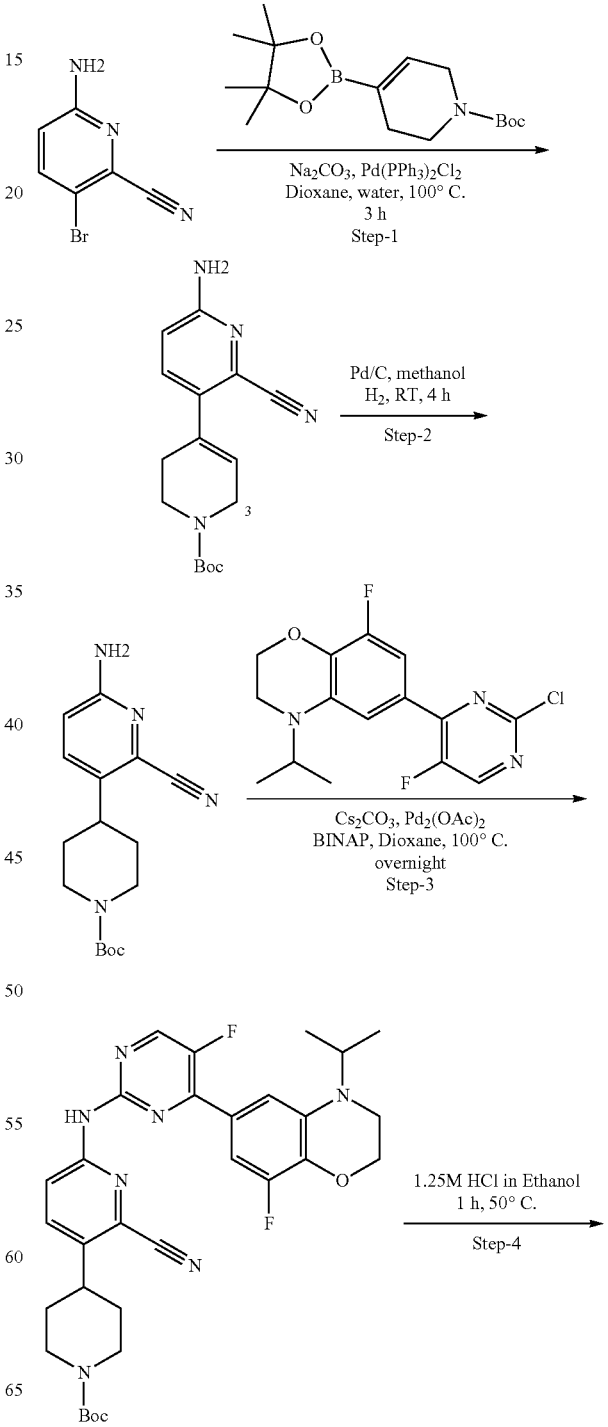

-continued

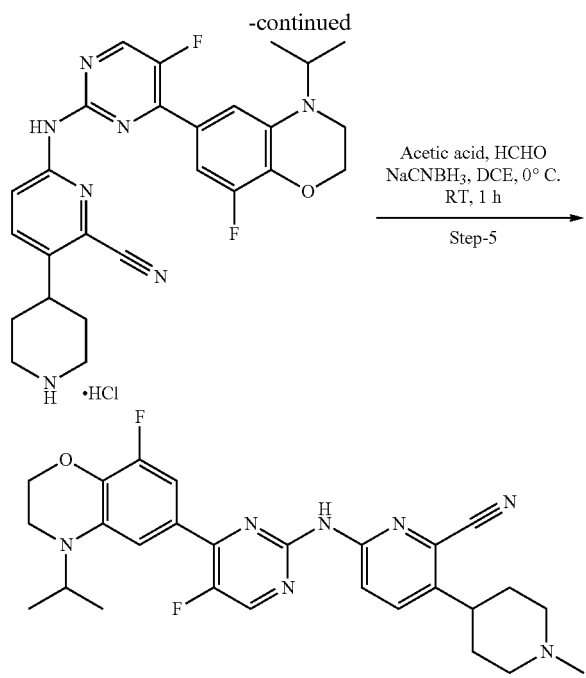

Step-1: Synthesis of tert-butyl 6-amino-2-cyano-3', 6'-dihydro-[3,4'-bipyridine]-1'(2'H)-carboxylate To a solution of 6-amino-3-bromopicolinonitrile (200 mg, 1.01 mmol, 1 equiv) in dioxane (4 mL), was added tert-butyl 4-(4,4,5,5-tetramethyl-1,3,2-dioxaborolan-2-yl)-3,6-dihydropyridine-1(2H)-carboxylate (376 mg, 1.2 mmol, 1 equiv) and a solution of sodium carbonate (318 mg, 3.03 mmol, 3 equiv). The reaction mixture was degassed with nitrogen gas for 15 min., followed by the addition of Pd (PPh$_3$)$_2$Cl$_2$ (36 mg, 0.05 mmol, 0.05 equiv). The resultant reaction mixture was allowed to stir at 100° C. for 3 h. Progress of the reaction was monitored by TLC and LCMS. After completion of the reaction, reaction mixture was diluted with water (30 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 6-amino-2-cyano-3',6'-dihydro-[3, 4'-bipyridine]-1'(2'H)-carboxylate (200 mg, 66%) as an off white color solid compound. LCMS: 301 [M+H]$^+$ Step-2: Synthesis of tert-butyl 4-(6-amino-2-cyano-pyridin-3-yl)piperidine-1-carboxylate To a stirred solution of tert-butyl 6-amino-2-cyano-3',6'-dihydro-[3,4'-bipyridine]-1'(2'H)-carboxylate (200 mg, 3.2 mmol, 1 equiv) in ethanol (10 mL), was added Pd/C (20% w/w) (40 mg) under H$_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain tert-butyl 4-(6-amino-2-cyanopyridin-3-yl) piperidine-1-carboxylate (180 mg, 90%) as a dark brown solid compound. LCMS: 303 [M+H]$^+$ Step-3: Synthesis of tert-butyl 4-(2-cyano-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.46 mmol, 1 equiv) in dioxane (10 mL), was added tert-butyl 4-(6-amino-2-cyanopyridin-3-yl)piperidine-1-carboxylate (151 mg, 0.50 mmol, 1.1 equiv) and cesium carbonate (225 mg, 0.69 mmol, 1.5 equiv). The reaction mixture was degassed with nitrogen gas for 30 min., followed by the addition of palladium acetate (2 mg, 0.009 mmol, 0.02 equiv) and BINAP (12 mg, 0.018 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain tert-butyl 4-(2-cyano-6-((5-fluoro-4-(8-fluoro-4-isopropyl-3,4-dihydro-2H-benzo[b][1, 4]oxazin-6-yl)pyrimidin-2-yl)amino)pyridin-3-yl)piperidine-1-carboxylate (200 mg, 74%) as a brown viscous compound. LCMS: 592 [M+H]$^+$ Step-4: Synthesis of 6-((5-fluoro-4-(8-fluoro-4-isopropyl-3,4-dihydro-2H-benzo[b][1,4]oxazin-6-yl) pyrimidin-2-yl)amino)-3-(piperidin-4-yl)picolinonitrile hydrochloride A solution of tert-butyl 4-(2-cyano-6-((5-fluoro-4-(8-fluoro-4-isopropyl-3,4-dihydro-2H-benzo[b][1,4]oxazin-6-yl)pyrimidin-2-yl) amino)pyridin-3-yl)piperidine-1-carboxylate (200 mg, 3.38 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain 6-((5-fluoro-4-(8-fluoro-4-isopropyl-3,4-dihydro-2H-benzo[b][1,4]oxazin-6-yl)pyrimidin-2-yl)amino)-3-(piperidin-4-yl)picolinonitrile hydrochloride (150 mg, 90%) as a yellow solid compound. LCMS: 492 [M+H]

Step-5: Synthesis of 6-((5-fluoro-4-(8-fluoro-4-isopropyl-3,4-dihydro-2H-benzo[b][1,4]oxazin-6-yl) pyrimidin-2-yl)amino)-3-(1-methylpiperidin-4-yl) picolinonitrile To a stirred solution of 6-((5-fluoro-4-(8-fluoro-4-isopropyl-3,4-dihydro-2H-benzo[b][1,4]oxazin-6-yl)pyrimidin-2-yl)amino)-3-(piperidin-4-yl)picolinonitrile hydrochloride salt (100 mg, 0.2 mmol, 1 equiv) in DCE (3 mL), was added Formaldehyde (40% in water) (0.02 mL, 0.6 mmol, 3 equiv), acetic acid (0.06 mL, 1.0 mmol, 5 equiv). The reaction mixture was allowed to stir at RT for 1 h. The reaction mixture was cooled to 0° C. NaCNBH$_3$ (39 mg, 0.6 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford 6-((5-fluoro-4-(8-fluoro-4-isopropyl-3,4-dihydro-2H-benzo[b][1,4]oxazin-6-yl)pyrimidin-2-yl)amino)-3-(1-methylpiperidin-4-yl)picolinonitrile (5 mg, 5%) as a yellow color solid compound. LCMS: 506 [M+H]$^+$; $^1$HNMR: (DMSO-d$_6$,400 MHz): δ 10.54 (s, 1H), 8.66 (d, J=3.9 Hz, 1H), 8.43 (d, J=8.8 Hz, 1H), 7.94 (d, J=9.2 Hz, 1H), 7.47 (s, 1H), 7.19 (d, J=11.4 Hz, 1H), 4.30 (d, J=3.9 Hz, 2H), 4.09-4.20 (m, 1H), 3.25 (br. s., 2H), 2.91 (d, J=11.0 Hz, 2H), 2.76 (br. s., 1H), 2.21 (s, 3H), 1.98 (d, J=11.4 Hz, 2H), 1.75 (br. s., 4H), 1.00-1.24 ppm (m, 6H).

Example-143: Synthesis of 5-fluoro-4-(8-fluoro-4-isopropyl-3,4-dihydro-2H-benzo[b][1,4]oxazin-6-yl)-N-(6-fluoro-5-(1-methylpiperidin-4-yl)pyridin-2-yl)pyrimidin-2-amine. (Compound 846)

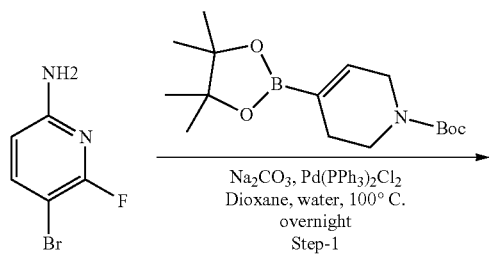

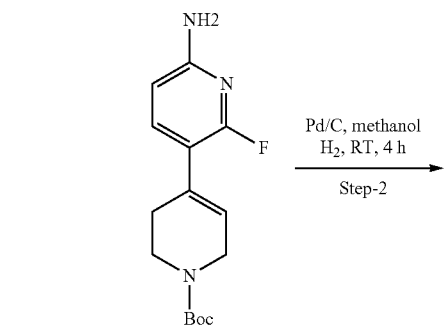

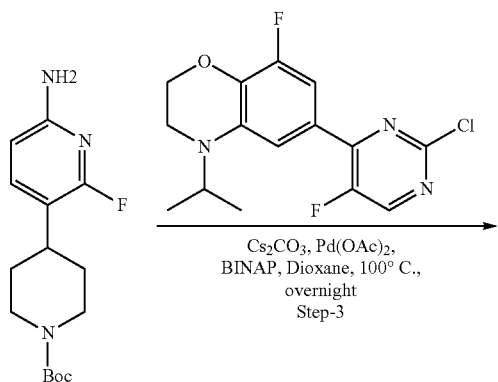

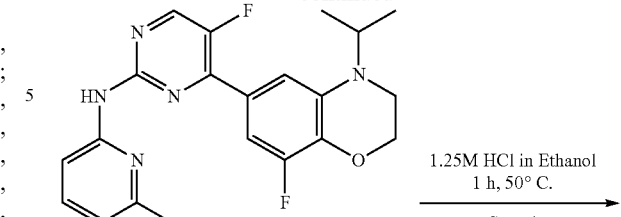

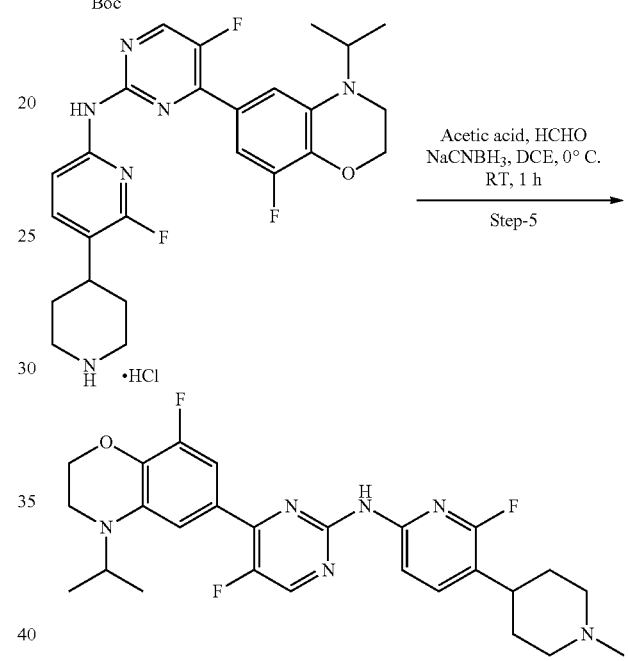

Step-1: Synthesis of tert-butyl 6-amino-2-fluoro-3',6'-dihydro-[3,4'-bipyridine]-1'(2'H)-carboxylate To a solution of 5-bromo-6-fluoropyridin-2-amine (500 mg, 2.1 mmol, 1 equiv) in dioxane:water (10 mL:3 mL), was added tert-butyl 4-(4, 4, 5, 5-tetramethyl-1, 3, 2-dioxaborolan-2-yl)-3, 6-dihydropyridine-1(2H)-carboxylate (714 mg, 2.31 mmol, 1.1 equiv) and sodium carbonate (333 mg, 3.15 mmol, 1.5 equiv). The reaction mixture was degassed with nitrogen gas for 30 min., followed by the addition of Pd(PPh$_3$)$_2$Cl$_2$ (74 mg, 0.11 mmol, 0.05 equiv). The resultant reaction mixture was allowed to stir at 100° C. for 6 h. Progress of the reaction was monitored by TLC and LCMS. After completion of the reaction, reaction mixture was diluted with water (20 mL) and extracted with ethyl acetate (25 mL×2). Combined organic layer was washed with water (30 mL) and brine solution (30 mL). Organic layer was dried over anhydrous sodium sulphate and concentrated under reduced pressure to obtain crude, which was purified by normal phase combi flash by using 100-200 mesh silica gel column to afford tert-butyl 6-amino-2-fluoro-3',6'-dihydro-[3,4'-bipyridine]-1'(2'H)-carboxylate (400 mg, 55%) as an off white solid compound. LCMS: 294 [M+H]$^+$

Step-2: Synthesis of tert-butyl 4-(6-amino-2-fluoro-pyridin-3-yl)piperidine-1-carboxylate To a stirred solution of tert-butyl 6-amino-2-fluoro-3',6'-dihydro-[3,4'-bipyridine]-1'(2'H)-carboxylate (400 mg, 1.53 mmol, 1 equiv) in methanol (15 mL), was added Pd/C (10 wt. %) (80 mg) under H₂ atm. The resultant reaction mixture was allowed to stir at RT for 6 h. Progress of the reaction was monitored by LCMS. After completion of the reaction, the mixture was passes through celite bed and the filtrate was concentrated under reduced pressure to afford tert-butyl 4-(6-amino-2-fluoropyridin-3-yl)piperidine-1-carboxylate (370 mg, 80%) as an off white solid compound. LCMS: 296 [M+H]⁺

Step-3: Synthesis of tert-butyl 4-(2-fluoro-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate To a solution of 6-(2-chloro-5-fluoropyrimidin-4-yl)-8-fluoro-4-isopropyl-3,4-dihydro-2H-benzo[b][1,4]oxazine (150 mg, 0.45 mmol, 1 equiv) in dioxane (10 mL), was added tert-butyl 4-(6-amino-2-fluoropyridin-3-yl)piperidine-1-carboxylate (147 mg, 0.5 mmol, 1.1 equiv) and cesium carbonate (224 mg, 0.69 mmol, 1.5 equiv). The reaction mixture was degassed with nitrogen gas for 10 min., followed by the addition of palladium acetate (10 mg, 0.046 mmol, 0.1 equiv) and BINAP (57 mg, 0.092 mmol, 0.2 equiv). The resultant reaction mixture was allowed to stir at 100° C. for overnight. Progress of the reaction was monitored by TLC and LCMS. After completion of the reaction, diluted with water (10 mL) and extracted with ethyl acetate (15 mL). Organic layer was washed with water (10 mL) and brine solution (10 mL). Organic layer was dried over anhydrous sodium sulphate and concentrated under reduced pressure to obtain crude, which was purified by normal phase combi flash by using 100-200 mesh silica gel column to obtain tert-butyl 4-(2-fluoro-6-((5-fluoro-4-(8-fluoro-4-isopropyl-3,4-dihydro-2H-benzo[b][1,4]oxazin-6-yl)pyrimidin-2-yl) amino)pyridin-3-yl)piperidine-1-carboxylate (120 mg, 44%) as a yellow solid compound. LCMS: 585 [M+H]⁺

Step-4: Synthesis of 5-fluoro-4-(8-fluoro-4-isopropyl-3,4-dihydro-2H-benzo[b][1,4]oxazin-6-yl)-N-(6-fluoro-5-(piperidin-4-yl)pyridin-2-yl)pyrimidin-2-amine hydrochloride A solution tert-butyl 4-(2-fluoro-6-((5-fluoro-4-(8-fluoro-4-isopropyl-3,4-dihydro-2H-benzo[b][1,4]oxazin-6-yl)pyrimidin-2-yl) amino)pyridin-3-yl)piperidine-1-carboxylate (120 mg, 0.2 mmol, 1 equiv) in 1.25 M HCl in ethanol (4 mL) was allowed to stir for 1 h at 50° C. Progress of the reaction was monitored by LCMS. After completion of the reaction, solvent was removed under reduced pressure to obtain 5-fluoro-4-(8-fluoro-4-isopropyl-3,4-dihydro-2H-benzo[b][1,4]oxazin-6-yl)-N-(6-fluoro-5-(piperidin-4-yl) pyridin-2-yl)pyrimidin-2-amine hydrochloride (90 mg, 84%) as a yellow solid compound. LCMS: 485 [M+H]⁺

Step-5: Synthesis of 5-fluoro-4-(8-fluoro-4-isopropyl-3,4-dihydro-2H-benzo[b][1,4]oxazin-6-yl)-N-(6-fluoro-5-(1-methylpiperidin-4-yl)pyridin-2-yl)pyrimidin-2-amine To a stirred solution of 5-fluoro-4-(8-fluoro-4-isopropyl-3,4-dihydro-2H-benzo[b][1,4]oxazin-6-yl)-N-(6-fluoro-5-(piperidin-4-yl)pyridin-2-yl)pyrimidin-2-amine (105 mg, 0.22 mmol, 1 equiv) in DCE (5 mL), was added Formaldehyde (30% in water) (97 mg, 1.08 mmol, 5 equiv), acetic acid (65 mg, 1.08 mmol, 5 equiv). The reaction mixture was allowed to stir at RT for 1 h. The reaction mixture was cooled to 0° C. NaCNBH₃ (27 mg, 0.44 mmol, 2 equiv) was added to above mixture and raised the temperature to RT. The reaction mixture was allowed to stir at RT for 4 h. Progress of the reaction was monitored by LCMS. After completion of the reaction, the reaction mixture was diluted with water (20 mL) and extracted with ethyl acetate (20 mL×2). Organic layer was washed with water (20 mL) and brine solution (20 mL). Organic layer was dried over anhydrous sodium sulphate and concentrated under reduced pressure to obtain crude, which was purified by reverse phase HPLC to afford 5-fluoro-4-(8-fluoro-4-isopropyl-3,4-dihydro-2H-benzo[b][1,4]oxazin-6-yl)-N-(6-fluoro-5-(1-methylpiperidin-4-yl)pyridin-2-yl)pyrimidin-2-amine (21 mg, 20%) as a solid compound. LCMS: 499 [M+H]⁺;

¹HNMR: (400 MHz, Methanol-d4) δ 8.45 (d, J=3.9 Hz, 1H), 8.22 (dd, J=8.2, 1.6 Hz, 1H), 7.74 (dd, J=10.0, 8.2 Hz, 1H), 7.50 (s, 1H), 7.25 (d, J=11.9 Hz, 1H), 4.33 (t, J=4.3 Hz, 2H), 4.22 (p, J=6.7 Hz, 1H), 3.53 (d, J=12.4 Hz, 2H), 3.35 (t, J=4.4 Hz, 2H), 3.12-2.99 (m, 3H), 2.85 (s, 3H), 2.15-1.97 (m, 4H), 1.26 (d, J=6.5 Hz, 6H).

Example-144: Synthesis of N-(6-cyclopropyl-5-(1-methylpiperidin-4-yl) pyridin-2-yl)-5-fluoro-4-(8-fluoro-4-isopropyl-3,4-dihydro-2H-benzo[b][1,4]oxazin-6-yl)pyrimidin-2-amine (Compound 847) and Example-145: Synthesis of 5-fluoro-4-(8-fluoro-4-isopropyl-3,4-dihydro-2H-benzo[b][1,4]oxazin-6-yl)-N-(5-(1-methylpiperidin-4-yl)-6-propylpyridin-2-yl)pyrimidin-2-amine (Compound 848)

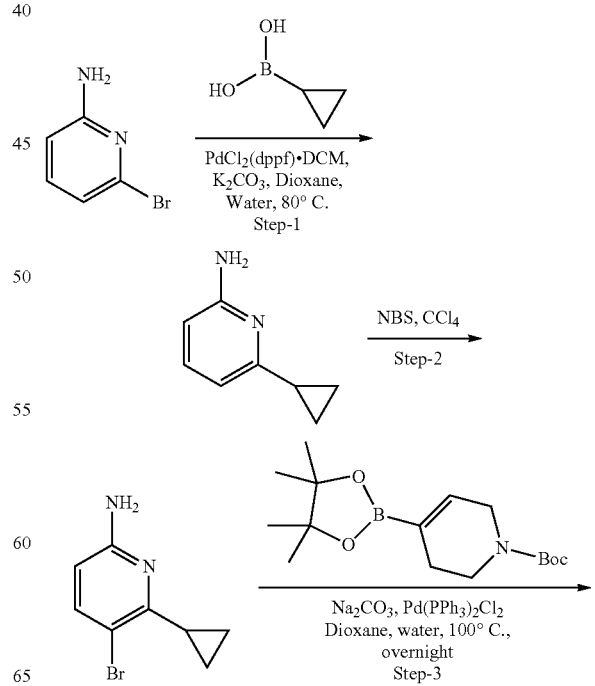

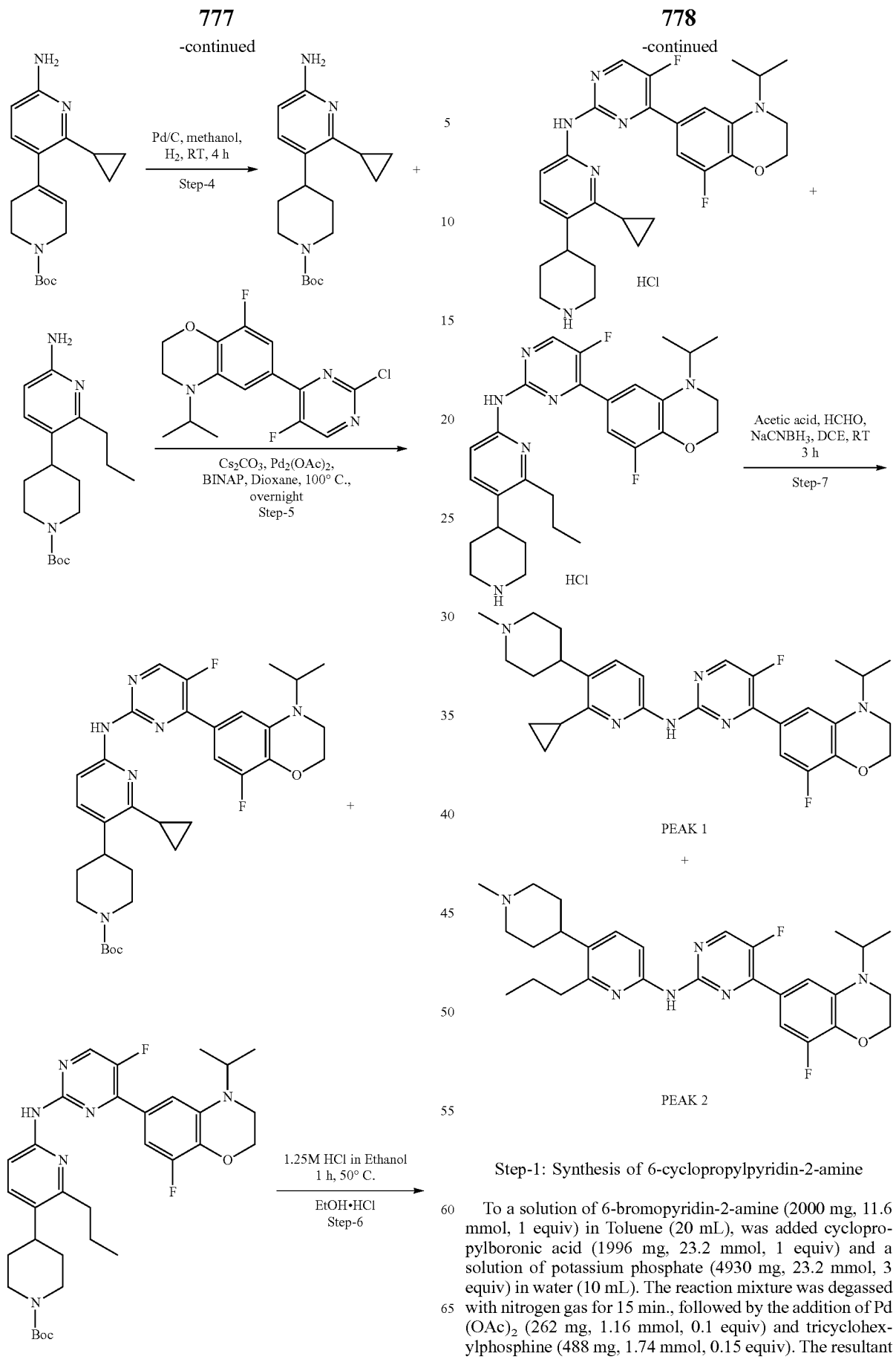

Step-1: Synthesis of 6-cyclopropylpyridin-2-amine

To a solution of 6-bromopyridin-2-amine (2000 mg, 11.6 mmol, 1 equiv) in Toluene (20 mL), was added cyclopropylboronic acid (1996 mg, 23.2 mmol, 1 equiv) and a solution of potassium phosphate (4930 mg, 23.2 mmol, 3 equiv) in water (10 mL). The reaction mixture was degassed with nitrogen gas for 15 min., followed by the addition of Pd(OAc)$_2$ (262 mg, 1.16 mmol, 0.1 equiv) and tricyclohexylphosphine (488 mg, 1.74 mmol, 0.15 equiv). The resultant reaction mixture was allowed to stir at 100° C. for overnight in a sealed tube. Progress of the reaction was monitored by TLC and LCMS. After completion of the reaction, reaction mixture was diluted with water (100 mL) and extracted with ethyl acetate (150 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain 6-cyclopropylpyridin-2-amine (1000 mg, 64%) as a yellow oil compound. LCMS: 135 [M+H]$^+$

Step-2: Synthesis of 5-bromo-6-cyclopropylpyridin-2-amine

To a stirred solution of 6-cyclopropylpyridin-2-amine (900 mg, 6.7 mmol, 1 equiv) in DMF (10 mL), was added NBS (1196 mg, 6.7 mmol, 1 equiv). The resultant reaction mixture was allowed to stir at RT for 1 h. Progress of the reaction was monitored by LCMS and TLC. After completion of the reaction, diluted with water (50 mL), and extracted with ethyl acetate (150 mL). Organic layer was washed with water (50 mL) and brine solution (50 mL). Organic layer was dried over anhydrous sodium sulphate and concentrated under reduced pressure to obtain crude, which was purified by normal phase combi flash to obtain 5-bromo-6-cyclopropylpyridin-2-amine (900 mg, 63%) as an off white solid compound. LCMS: 213 [M+H]$^+$

Step-3: Synthesis of tert-butyl 6-amino-2-cyclopropyl-3',6'-dihydro-[3,4'-bipyridine]-1'(2'H)-carboxylate To a solution of 5-bromo-6-cyclopropylpyridin-2-amine (800 mg, 3.77 mmol, 1 equiv) in dioxane (8 mL), was added tert-butyl 4-(4,4,5,5-tetramethyl-1,3,2-dioxaborolan-2-yl)-3,6-dihydropyridine-1(2H)-carboxylate (1399 mg, 4.5 mmol, 1.2 equiv) and a solution of sodium carbonate (1188 mg, 11.3 mmol, 3 equiv) I water (2 mL). The reaction mixture was degassed with nitrogen gas for 15 min., followed by the addition of Pd (PPh$_3$)$_2$Cl$_2$ (132 mg, 0.18 mmol, 0.05 equiv). The resultant reaction mixture was allowed to stir at 100° C. for overnight. Progress of the reaction was monitored by TLC and LCMS. After completion of the reaction, reaction mixture was diluted with water (30 mL) and extracted with ethyl acetate (100 mL×2). Organic layer was washed with water (100 mL) and brine solution (100 mL). Organic layer was dried over anhydrous sodium sulphate and concentrated under reduced pressure to obtain crude, which was purified by normal phase combi flash to obtain tert-butyl 6-amino-2-cyclopropyl-3',6'-dihydro-[3,4'-bipyridine]-1'(2'H)-carboxylate (800 mg, 67%) as an off white color solid compound. LCMS: 316 [M+H]$^+$

Step-4: Synthesis of tert-butyl 4-(6-amino-2-cyclopropylpyridin-3-yl)piperidine-1-carboxylate and synthesis of tert-butyl 4-(6-amino-2-propylpyridin-3-yl)piperidine-1-carboxylate To a stirred solution of tert-butyl 6-amino-2-cyclopropyl-3',6'-dihydro-[3,4'-bipyridine]-1'(2'H)-carboxylate (300 mg, 0.95 mmol, 1 equiv) in ethanol (10 mL), was added Pd/C (20% w/w) (60 mg) under H$_2$ atm. The resultant reaction mixture was allowed to stir at RT for 4 h. Progress of the reaction was monitored by LCMS. After completion of the reaction, the mixture was passes through celite bed and the filtrate was concentrated under reduced pressure to obtain a mixture of tert-butyl 4-(6-amino-2-cyclopropylpyridin-3-yl)piperidine-1-carboxylate and tert-butyl 4-(6-amino-2-propylpyridin-3-yl)piperidine-1-carboxylate (250 mg, 83%) as an off white solid compound. LCMS: 318 [M+H]$^+$, 320 [M+H]$^+$

Step-5: Synthesis of tert-butyl 4-(2-cyclopropyl-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate and synthesis of tert-butyl 4-(6-((5-fluoro-4-(8-fluoro-4-isopropyl-3,4-dihydro-2H-benzo[b][1,4]oxazin-6-yl)pyrimidin-2-yl)amino)-2-propylpyridin-3-yl)piperidine-1-carboxylate To the solution of mixture of tert-butyl 4-(6-amino-2-cyclopropylpyridin-3-yl) piperidine-1-carboxylate and tert-butyl 4-(6-amino-2-propylpyridin-3-yl)piperidine-1-carboxylate (150 mg, 0.46 mmol, 1 equiv) in dioxane (10 mL), was added a mixture of tert-butyl 4-(6-amino-2-cyclopropylpyridin-3-yl)piperidine-1-carboxylate and tert-butyl 4-(6-amino-2-propylpyridin-3-yl)piperidine-1-carboxylate (160 mg, 0.50 mmol, 1.1 equiv) and cesium carbonate (225 mg, 0.69 mmol, 1.5 equiv). The reaction mixture was degassed with nitrogen gas for 30 min., followed by the addition of palladium acetate (2 mg, 0.009 mmol, 0.02 equiv) and BINAP (12 mg, 0.018 mmol, 0.04 equiv). The resultant reaction mixture was allowed to stir at 100° C. for overnight. Progress of the reaction was monitored by TLC and LCMS. After completion of the reaction, diluted with water (30 mL) and extracted with ethyl acetate (100 mL). Organic layer was washed with water (50 mL) and brine solution (50 mL). Organic layer was dried over anhydrous sodium sulphate and concentrated under reduced pressure to obtain crude, which was purified by normal phase combi flash to obtain a mixture of tert-butyl 4-(2-cyclopropyl-6-((5-fluoro-4-(8-fluoro-4-isopropyl-3,4-dihydro-2H-benzo[b][1,4]oxazin-6-yl)pyrimidin-2-yl) amino)pyridin-3-yl)piperidine-1-carboxylate and tert-butyl 4-(6-((5-fluoro-4-(8-fluoro-4-isopropyl-3,4-dihydro-2H-benzo[b][1,4]oxazin-6-yl)pyrimidin-2-yl)amino)-2-propylpyridin-3-yl)piperidine-1-carboxylate (200 mg, 71%) as a brown viscous compound. LCMS: 607 [M+H]$^+$, 609 [M+H]$^+$

Step-6: Synthesis of N-(6-cyclopropyl-5-(piperidin-4-yl)pyridin-2-yl)-5-fluoro-4-(8-fluoro-4-isopropyl-3,4-dihydro-2H-benzo[b][1,4]oxazin-6-yl)pyrimidin-2-amine hydrochloride and synthesis of 5-fluoro-4-(8-fluoro-4-isopropyl-3,4-dihydro-2H-benzo[b][1,4]oxazin-6-yl)-N-(5-(piperidin-4-yl)-6-propylpyridin-2-yl)pyrimidin-2-amine hydrochloride A solution of a mixture of tert-butyl 4-(2-cyclopropyl-6-((5-fluoro-4-(8-fluoro-4-isopropyl-3,4-dihydro-2H-benzo[b][1,4]oxazin-6-yl)pyrimidin-2-yl)amino)pyridin-3-yl)piperidine-1-carboxylate and tert-butyl 4-(6-((5-fluoro-4-(8-fluoro-4-isopropyl-3,4-dihydro-2H-benzo[b][1,4]oxazin-6-yl)pyrimidin-2-yl)amino)-2-propylpyridin-3-yl)piperidine-1-carboxylate (200 mg, 0.33 mmol, 1 equiv) in 1.25 M HCl in ethanol (5 mL) was allowed to stir for 1 h at 50° C. Progress of the reaction was monitored by LCMS. After completion of the reaction, solvent was removed under reduced pressure to obtain a mixture of N-(6-cyclopropyl-5-(piperidin-4-yl)pyridin-2-yl)-5-fluoro-4-(8-fluoro-4-isopropyl-3,4-dihydro-2H-benzo[b][1,4]oxazin-6-yl)pyrimidin-2-amine hydrochloride and 5-fluoro-4-(8-fluoro-4-isopropyl-3,4-dihydro-2H-benzo[b][1,4]oxazin-6-yl)-N-(5-

(piperidin-4-yl)-6-propylpyridin-2-yl)pyrimidin-2-amine hydrochloride (140 mg, 84%) as a yellow solid compound. LCMS: 507 [M+H]⁺, 509 [M+H]⁺

Step-7: Synthesis of N-(6-cyclopropyl-5-(1-methylpiperidin-4-yl)pyridin-2-yl)-5-fluoro-4-(8-fluoro-4-isopropyl-3,4-dihydro-2H-benzo[b][1,4]oxazin-6-yl)pyrimidin-2-amine and synthesis of 5-fluoro-4-(8-fluoro-4-isopropyl-3,4-dihydro-2H-benzo[b][1,4]oxazin-6-yl)-N-(5-(1-methylpiperidin-4-yl)-6-propylpyridin-2-yl)pyrimidin-2-amine To the stirred solution of mixture of N-(6-cyclopropyl-5-(piperidin-4-yl)pyridin-2-yl)-5-fluoro-4-(8-fluoro-4-isopropyl-3,4-dihydro-2H-benzo[b][1,4]oxazin-6-yl)pyrimidin-2-amine and 5-fluoro-4-(8-fluoro-4-isopropyl-3,4-dihydro-2H-benzo[b][1,4]oxazin-6-yl)-N-(5-(piperidin-4-yl)-6-propylpyridin-2-yl)pyrimidin-2-amine (hydrodhloride salt) (100 mg, 0.197 mmol, 1 equiv) in DCE (3 mL), was added Formaldehyde (40% in water) (0.02 mL, 0.59 mmol, 3 equiv), acetic acid (0.06 mL, 1.0 mmol, 5 equiv). The reaction mixture was allowed to stir at RT for 1 h. The reaction mixture was cooled to 0° C. NaCNBH₃ (37 mg, 0.59 mmol, 3 equiv) was added to above mixture and raise the temperature to RT. The reaction mixture was allowed to stir at RT for 1 h. Progress of the reaction was monitored by LCMS. After completion of the reaction, the reaction mixture was diluted with water (25 mL) and extracted with ethyl acetate (50 mL×2). Organic layer was washed with water (50 mL) and brine solution (50 mL). Organic layer was dried over anhydrous sodium sulphate and concentrated under reduced pressure to obtain crude, which was purified by reverse phase HPLC to afford Peak1 as N-(6-cyclopropyl-5-(1-methylpiperidin-4-yl)pyridin-2-yl)-5-fluoro-4-(8-fluoro-4-isopropyl-3,4-dihydro-2H-benzo[b][1,4]oxazin-6-yl)pyrimidin-2-amine (15 mg, 14.5%) as a yellow colored solid compound and Peak2 as 5-fluoro-4-(8-fluoro-4-isopropyl-3,4-dihydro-2H-benzo[b][1,4]oxazin-6-yl)-N-(5-(1-methylpiperidin-4-yl)-6-propylpyridin-2-yl)pyrimidin-2-amine (15 mg, 14.5%) as a yellow colored solid compound.

PEAK-1: LCMS: 521 [M+H]⁺; ¹HNMR: (DMSO-d6, 400 MHz): δ 9.56 (br. s., 1H), 8.61 (d, J=4.4 Hz, 1H), 7.94 (d, J=8.3 Hz, 1H), 7.30-7.54 (m, 2H), 7.22 (d, J=4.4 Hz, 1H), 4.31 (br. s., 2H), 4.06-4.18 (m, 1H), 3.53 (d, J=12.3 Hz, 2H), 3.30 (br. s., 2H), 3.15 (d, J=12.3 Hz, 2H), 2.81 (s, 3H), 2.25 (br. s., 2H), 1.99-2.15 (m, 2H), 1.84-1.89 (m, 2H), 1.11-1.30 (m, 6H), 1.04 (br. s., 2H), 0.90 ppm (br. s., 2H).

PEAK-2: LCMS: 523 [M+H]⁺; ¹HNMR: (DMSO-d₆, 400 MHz): δ 9.73 (s, 1H), 8.60 (d, J=3.9 Hz, 1H), 8.02 (d, J=9.2 Hz, 1H), 7.41-7.61 (m, 2H), 7.20 (d, J=11.4 Hz, 1H), 4.30 (br. s., 2H), 4.03-4.27 (m, 1H), 3.30 (br. s., 2H), 3.13 (m, 3H), 2.55-2.73 (m, 5H), 1.74 (br. s., 4H), 1.45-1.69 (m, 4H), 1.08-1.29 (m, 6H), 0.97 ppm (t, J=7.2 Hz, 3H).

Compounds 40-46, 48-51, 53-177, 179-205, 207-435, 525-787 and 791-840 may be synthesized by the general synthetic schemes 1-7 or according to the experimental details as exemplified in Examples 1-145 using the appropriate starting materials and reagents.

Biological Examples

Example B1. In Vitro Kinase Inhibition $IC_{50}$ Determination $IC_{50}$ values of compounds against CDK4 and CDK6 were determined by luminescence using retinoblastoma as substrate. Kinase assays were performed in kinase buffer (#PV6135, Invitrogen, Life Technologies Grand Island, N.Y.) where total reaction volume was 30 μL/well in 96-well half area white plates (#3693, Costar). One microliter of 25× test compounds at specific concentrations (e.g., final concentration range: 0.1 nM-200 nM) were mixed with 10 μL of 2.5× kinase (5 nM, CDK4 #PR8064A and CDK6 #PR8422B, Invitrogen) solution and 14 μL of 4× mixed solution with retinoblastoma (1 μM, #12-439, EMD Millipore, Haywood, Calif.) and ATP (25 μM, #V7038, Promega, Madison, Wis.). The plates were covered and incubated for 2 h at room temperature. At the end of incubation, 25 μL of stop solution-ADP Glo reagent (#V7002, Promega) was added. After incubation for 45 min at room temperature, 50 μL of detection reagent (##V7002, Promega) was added. Readings were taken at 15 min and 45 min incubation after detection reagent was added in a Synergy Neo Plate reader (BioTek, Winooski) at single excitation of 340 nm and Dual emission at 495 nm and 520 nm respectively. The following equations were used in the CDK4 and CDK6 assay data analysis. Percent inhibition (100-% activity) was fitted to the "four-parameter logistic model" in XLfit for determination of $IC_{50}$ values.

Percent conversion of enzyme=100−{($RLU_{No\ Drug-No\ enzyme}$*100)/$RLU_{No\ drug+Enzyme}$}   Equation 1:

Percent conversion at each data point=100−{($RLU_{Average(Drug+enzyme)}$*100)/$RLU_{No\ drug+Enzyme}$}   Equation 2:

Percent Inhibition=100*(% $Conversion_{each\ data\ point}$/% $Conversion_{Enzyme}$)   Equation 3:

$IC_{50}$ values of compounds against CDK1 (cyclin B) were determined by Z'-LYTE™. These screening assays were performed at Invitrogen Life Technologies (Grand Island, N.Y.) on a low volume NBS, black 384-well plate (#4514, Corning). 0.1 μL of 100× test compound in 100% DMSO (at specific solutions) were mixed with 2.4 μL of Kinase Buffer (50 mM HEPES pH 7.5, 0.01% BRIJ-35, 10 mM MgCl₂, 1 mM EGTA), 5 μL of 2× Kinase (3.5-46.4 ng CDK1/cyclin B)/Peptide (2 μM Ser/Thr 18), and 2.5 μL of 4×ATP solution (34 μM). The plates were shaken for 30 seconds, and incubated for 60 minutes at room temperature. Development Reagent Solution (5 μL of 1:1024 dilution) was added to the plates followed with another 30-second plate shake, and the plates were further incubated at room temperature for one hour. The plates were read on fluorescence plate reader with Dual emission at 445 nm and 520 nm.

IC$_{50}$ values of compounds against CDK2 (cyclin A) were determined by Z'-LYTE™. These screening assays were performed at Invitrogen Life Technologies (Grand Island, N.Y.) on a low volume NBS, black 384-well plate (#4514, Corning). 0.1 μL of 100× test compound in 100% DMSO (at specific solutions) were mixed with 2.4 μL of Kinase Buffer (50 mM HEPES pH 7.5, 0.01% BRIJ-35, 10 mM MgCl$_2$, 1 mM EGTA), 5 μL of 2× Kinase (1.22-10.3 ng CDK2/cyclin A)/Peptide (2 μM Ser/Thr 12), and 2.5 μL of 4×ATP solution (31 μM). The plates were shaken for 30 seconds, and incubated for 60 minutes at room temperature. Development Reagent Solution (5 μL of 1:1024 dilution) was added to the plates followed with another 30-second plate shake and the plates were further incubated at room temperature for one hour. The plates were read on fluorescence plate reader with Dual emission at 445 nm and 520 nm.

IC$_{50}$ values of compounds against CDK5 (p25) were determined by Z'-LYTE™. These screening assays were performed at Invitrogen Life Technologies (Grand Island, N.Y.) on a low volume NBS, black 384-well plate (#4514, Corning). 0.1 μL of 100× test compound in 100% DMSO (at specific solutions) were mixed with 2.4 μL of Kinase Buffer (50 mM HEPES pH 7.5, 0.01% BRIJ-35, 10 mM MgCl$_2$, 1 mM EGTA), 5 μL of 2× Kinase (0.18-2 ng CDK5/p25)/Peptide (2 μM Ser/Thr 12), and 2.5 μL of 4×ATP solution (17 μM). The plates were shaken for 30 seconds, and incubated for 60 minutes at room temperature. Development Reagent Solution (5 μL of 1:4096 dilution) was added to the plates followed with another 30-second plate shake and the plates were further incubated at room temperature for one hour. The plates were read on fluorescence plate reader with Dual emission at 445 nm and 520 nm.

The following equations were used for Z'-LYTE™ Screening Assay Data Analysis. Percent inhibition (100-% activity) was fitted to the "four-parameter logistic model" in XLfit for determination of IC$_{50}$ values.

| | Equation |
|---|---|
| Correction for Background Fluorescence | $FI_{Sample} - FI_{TCFICtl}$ |
| Emission Ratio (using values corrected for background fluorescence) | $\dfrac{\text{Coumarin Emission (445 nm)}}{\text{Flourescein Emission (520 nm)}}$ |
| % Phosphorylation (% Phos) | $\left\{1 - \dfrac{(\text{Emission Ratio} \times F_{100\%}) - C_{100\%}}{(C_{0\%} - C_{100\%}) + [\text{Emission Ratio} \times (F_{100\%} - F_{0\%})]}\right\} * 100$ |
| % Inhibition | $\left\{1 - \dfrac{\% Phos_{Sample}}{\% Phos_{0\% InhibitionCtl}}\right\} * 100$ |
| Z' (using Emission Ratio values) | $1 - \dfrac{3 * Stdev_{0\% PhosCtl} + 3 * Stdev_{0\% Inhibition}}{Mean_{0\% PhosCtl} - Mean_{0\% Inhibition}}$ |
| Difference Between Data Points (single point only) | $\|\% Inhibition_{Point1} - \% Inhibition_{Point2}\|$ |
| Development Reaction Interference (DRI) (no ATP control) | $\dfrac{\text{Emission Ratio}_{DRICtl}}{\text{Emission Ratio}_{0\% PhosCtl}}$ |
| Test Compound Fluorescence Interference (TCFI) (check both Coumarin and Fluorescein emissions) | $\dfrac{FI_{TCFICtl}}{FI_{0\% InhibitorCtl}}$ |

FI = Fluorescence Intensity $C_{100\%}$ = Average Coumarin emission signal of the 100% Phos. Control $C_{0\%}$ = Average Coumarin emission signal of the 0% Phos. Control $F_{100\%}$ = Average Fluorescein emission signal of the 100% Phos. Control $F_{0\%}$ = Average Fluorescein emission signal of the 0% Phos. Control DRI = Development Reaction Interference TCFI = Test Compound Fluorescence Interference IC$_{50}$ values of compounds against CDK7 (cyclin H) were determined by Adapta™ Assay at Invitrogen Life Technologies (Grand Island, N.Y.) where total reaction volume was 10 µL/well in low volume, white 384-well plate (#4512, Corning). 0.100 µL of 100× test compound in 100% DMSO (at specific solutions) were mixed with 2.4 µL of HEPES (30 mM), 2.5 µL of 4×ATP solution (153 µM) and 5 µL of 2× Substrate/Kinase mixture (the 2×CDK7/cyclin H/MNAT1/CDK7/9tide mixture was prepared in 50 mM HEPES pH 7.5, 0.01% BRIJ-35, 10 mM MgCl$_2$, 1 mM EGTA). The final 10 µL Kinase Reaction consisted of 5-38.75 ng CDK7/cyclin H/MNAT1 and 200 µM CDK7/9tide in 32.5 mM HEPES pH 7.5, 0.005% BRIJ-35, 5 mM MgCl$_2$, 0.5 mM EGTA. The plates were shaken for 30 seconds, centrifuged for 1 min at 1000×g, and incubated for 60 minutes at room temperature. 5 µL of Detection Mix (prepared in TR-FRET Dilution Buffer; the Detection mix consists of EDTA (30 mM), Eu-anti-ADP antibody (6 nM) and ADP tracer, and contains the EC$_{60}$ concentration of tracer for 5-150 µM ATP) was added to the plates followed with another 30-second plate shake and centrifugation for 1 min at 1000×g, and the plates were further incubated at room temperature for one hour. The plates were read on fluorescence plate reader with Dual emission at 615 nm and 665 nm.

The following equations were used for Adapta™ Assay Data Analysis. The ATP/ADP standard curve was fit to model number 205 (sigmoidal dose-response model) in XLfit. The dose response curve was also curve fit to model number 205.

IC$_{50}$ values of compounds against CDK9 (cyclin K) were determined by LanthaScreen™ Eu Kinase Binding Assay at Invitrogen Life Technologies (Grand Island, N.Y.) where total reaction volume was 16 µL/well in low volume, white 384-well plate (#784207, Greiner). 0.16 µL of 100× test compound in 100% DMSO (at specific solutions) were mixed with 3.84 µL of Kinase Buffer (50 mM HEPES pH 7.5, 0.01% BRIJ-35, 10 mM MgCl$_2$, 1 mM EGTA), 8.0 µL of 2× Kinase (5 nM)/Antibody (Eu-anti-His, 2 nM) Mixture and 4.0 µL of 4× Tracer (Tracer 236, 100 nM). The plates were shaken for 30 seconds, and incubated for 60 minutes at room temperature. The plates were read on fluorescence plate reader with Dual emission at 615 nm and 665 nm.

IC$_{50}$ values of compounds against FMS kinase were determined by LanthaScreen™ Eu Kinase Binding Assay at Invitrogen (Life Technologies Grand Island, N.Y.) where total reaction volume was 10 µL in low-volume 384-well plates (#4511, Corning). Serially diluted compounds (3-fold) were incubated with kinase (1.25 nM) for 10 min, following which a mixture of ATP (10 µM) (#A1852, Sigma, St-Louis, Mo.) and fluorescent-PolyGT substrate (200 nM) (#PV3610, Invitrogen, Life Technologies Grand Island, N.Y.) was added and incubated in dark at room temperature for 1 h. After 1 h, 10 µL stop solution containing Terbium labeled antibody (4 nM) (#PV3529, Invitrogen, Life Technologies Grand Island, N.Y.) and EDTA (#E5134, Sigma,

| | Equation |
|---|---|
| Emission Ratio | $\dfrac{\text{AF647 Emission (665 nm)}}{\text{Europium Emission (615 nm)}}$ |
| % Conversion | $\left\{ \dfrac{EC_{50SC}}{\left( \dfrac{Top_{SC} - Bottom_{SC}}{\text{Emission Ratio}_{Sample} - Bottom_{SC}} \right) - 1 \wedge \left( \dfrac{1}{Hillslope_{SC}} \right)} \right\} * 100$ |
| % Inhibition | $\left\{ 1 - \dfrac{\% \text{ Conversion}_{Sample}}{\% \text{ Conversion}_{0\% InhibitionCtrl}} \right\} * 100$ |
| Difference Between Data Points (single point only) | $\lvert \% \text{ Inhibition}_{Point\ 1} - \% \text{ Inhibition}_{Point\ 2} \rvert$ |
| Test Compound Interference | For each emission wavelength, fluorescence intereference is flagged for a compound well that is more than 20% outside the range of the controls. |
| Z' (using Emission Ratio values) | $1 - \dfrac{3 * \text{Stdev}_{0\% ConvCtrl} + 3 * \text{Stdev}_{0\% Inhibition}}{\lvert \text{Mean}_{0\% ConvCtrl} - \text{Mean}_{0\% Inhibition} \rvert}$ |

*SC = Standard Curve

IC$_{50}$ values of compounds against CDK2 (cyclin E1) were determined by LanthaScreen™ Eu Kinase Binding Assay at Invitrogen Life Technologies (Grand Island, N.Y.)) where total reaction volume was 16 µL/well in low volume, white 384-well plate (#784207, Greiner). 0.16 µL of 100× test compound in 100% DMSO (at specific solutions) were mixed with 3.84 µL of Kinase Buffer (50 mM HEPES pH 7.5, 0.01% BRIJ-35, 10 mM MgCl$_2$, 1 mM EGTA), 8.0 µL of 2× Kinase (2.5 nM)/Antibody (Eu-anti-GST, 2 nM)

St-Louis, Mo.) (20 mM) in TR-FRET dilution buffer (#PV3574, Invitrogen, Life Technologies Grand Island, N.Y.) was added. Readings were taken in a Synergy Neo Plate reader (BioTek, Winooski) at single excitation of 340 nm and Dual emission at 495 nm and 520 nm respectively.

The following equations were used for LanthaScreen Eu Kinase Binding Assay Data Analysis. Percent inhibition (100-% activity) was fitted to the "four-parameter logistic model" in XLfit for determination of IC$_{50}$ values.

| Equation | |
|---|---|
| Emission Ratio (ER) | $\dfrac{\text{AF647 Emission (665 nm)}}{\text{Europium Emission (615 nm)}}$ |
| % Displacement | $\left\{\dfrac{ER_{0\%DispCtrl} - ER_{Sample}}{ER_{0\%DispCtrl} - ER_{100\%DispCtrl}}\right\} * 100$ |
| Difference Between Data Points (single point only) | $\lvert \%\,Displacement_{Point\,1} - \%\,Displacement_{Point\,2}\rvert$ |
| Test Compound Interference | For each emission wavelength, fluorescence interference is flagged for a compound well that is more than 20% outside the range of the controls. |
| Z' (using Emission Ratio values) | $1 - \dfrac{3*Stdev_{0\%DispCtrl} + 3*Stdev_{100\%DispCtrl}}{\lvert Mean_{0\%DispCtrl} - Mean_{100\%DispCtrl}\rvert}$ |

IC$_{50}$ values of compounds against the PI3Kδ kinase were performed by Reaction Biology Corporation. Briefly, this assay was conducted in buffer (Tris-HCl 40 mM (pH7.5), Orthovanadate 3 mM, MgCl$_2$ 20 mM, DTT 2 mM, CHAPS 0.05%, DMSO 1%). PI3Kδ kinase was added to the reaction solution and mixed gently. The test compounds in 100% DMSO (at specific solutions) were mixed with the kinase reaction mixture to achieve the final compounds at pre-defined concentrations (e.g., range—0.5 nM to 100 μM) by Acoustic technology (Echo550; nanoliter range). After incubating for 10 min at room temp, ATP was added into the reaction mixture to initiate the reaction followed by a 30-min incubation at 30° C. After quenching the reaction with ADP-Glo reagent, the plates were incubated for 40 min. The Detection Mixture was added, and the plate was incubated for an additional 30 min. At the end of incubation, luminescence was measured. For data analysis, the luminescence was converted into μM ADP production based on ADP standard curves. The nonlinear regression to obtain the standard curve and IC50 values were performed using Graphpad Prism software (La Jolla, Calif.).

IC$_{50}$ values of compounds disclosed herein against the kinases listed above are given in Table 2 below.

TABLE 2

| Compound No. | CDK4 IC$_{50}$ (nM) | CDK6 IC$_{50}$ (nM) | CDK1/B IC$_{50}$ (nM) | CDK2/A IC$_{50}$ (nM) | CDK2/E IC$_{50}$ (nM) | CDK5/p25 IC$_{50}$ (nM) | CDK7/H IC$_{50}$ (nM) | CDK9/K IC$_{50}$ (nM) | FMS IC$_{50}$ (nM) | PI3Kδ IC$_{50}$ (nM) |
|---|---|---|---|---|---|---|---|---|---|---|
| 1 | 0.2 | 0.2 | ND | ND | ND | ND | ND | ND | 1330 | 3360 |
| 2 | 6 | 6.9 | ND | ND | ND | ND | ND | ND | >5000 | ND |
| 3 | 3 | 5.7 | ND | ND | ND | ND | ND | ND | >5000 | ND |
| 4 | 0.7 | 0.1 | 130 | 12 | ND | ND | ND | ND | 566 | >5000 |
| 5 | ND | ND | ND | ND | ND | ND | ND | ND | >3630 | ND |
| 6 | ND | ND | ND | ND | ND | ND | ND | ND | 82 | ND |
| 8 | ND | ND | ND | ND | ND | ND | ND | ND | >5000 | ND |
| 9 | >183 | 173 | ND | ND | ND | ND | ND | ND | >5000 | ND |
| 10 | 4.5 | 2.5 | ND | ND | ND | ND | ND | ND | 570 | ND |
| 11 | 6 | 8 | ND | ND | ND | ND | ND | ND | 250 | ND |
| 12 | 12 | 2 | 3.9 | 0.7 | 7.2 | ND | ND | ND | 29 | 674 |
| 13 | 2 | 1.5 | ND | ND | ND | ND | ND | ND | 2 | ND |
| 14 | 3.5 | 2 | ND | ND | ND | ND | ND | ND | 49 | ND |
| 15 | 37 | 30 | ND | ND | ND | ND | ND | ND | 22 | ND |
| 16 | 1 | 1 | ND | ND | ND | ND | ND | ND | 2.5 | ND |
| 17 | 8 | 3.5 | ND | ND | ND | ND | ND | ND | 21 | ND |
| 18 | 10 | 15 | ND | ND | ND | ND | ND | ND | 19 | ND |
| 19 | 1 | 1 | ND | ND | ND | ND | ND | ND | 3 | ND |
| 20 | 95 | 187 | ND | ND | ND | ND | ND | ND | 17 | ND |
| 21 | 6 | 8 | ND | ND | ND | ND | ND | ND | 163 | ND |
| 22 | 2 | 2 | ND | ND | ND | ND | ND | ND | 6.5 | ND |
| 23 | 2 | 2 | ND | ND | ND | ND | ND | ND | 25 | 4885 |
| 24 | 9 | 5 | 5.8 | 4.6 | ND | 3.5 | 96 | 4 | 14 | >10000 |
| 25 | 6 | 4 | 6.7 | 3.4 | ND | 3.6 | 145 | 5 | 5 | 6100 |
| 26 | 10 | 134 | ND | ND | ND | ND | ND | ND | 61 | ND |
| 27 | 1 | 5 | ND | ND | ND | ND | ND | ND | 7.5 | ND |
| 28 | 1 | 11 | ND | ND | ND | ND | ND | ND | 123 | ND |
| 29 | 1 | 13 | ND | ND | ND | ND | ND | ND | 2.5 | ND |
| 30 | 1 | 13 | ND | ND | ND | ND | ND | ND | 79 | ND |
| 31 | 2.5 | 32 | ND | ND | ND | ND | ND | ND | 49 | ND |
| 32 | 12 | 21 | ND | ND | ND | ND | ND | ND | 177 | ND |
| 33 | 1.5 | 1.5 | 3 | 2 | ND | 1 | 54 | 2 | 48 | ND |
| 34 | 3 | 6 | ND | ND | ND | ND | ND | ND | 42 | ND |
| 35 | 2.5 | 3 | ND | ND | ND | ND | ND | ND | 58 | ND |
| 36 | 4 | 5 | ND | ND | ND | ND | ND | ND | 102 | ND |
| 37 | 6.5 | 3.5 | ND | ND | ND | ND | ND | ND | 18 | ND |
| 38 | 1.5 | 2 | 3 | 2 | ND | 2 | 163 | 2 | 40 | ND |
| 39 | 4 | 7.5 | ND | ND | ND | ND | ND | ND | 33 | ND |

TABLE 2-continued

| Compound No. | CDK4 IC$_{50}$ (nM) | CDK6 IC$_{50}$ (nM) | CDK1/B IC$_{50}$ (nM) | CDK2/A IC$_{50}$ (nM) | CDK2/E IC$_{50}$ (nM) | CDK5/p25 IC$_{50}$ (nM) | CDK7/H IC$_{50}$ (nM) | CDK9/K IC$_{50}$ (nM) | FMS IC$_{50}$ (nM) | PI3Kδ IC$_{50}$ (nM) |
|---|---|---|---|---|---|---|---|---|---|---|
| 47 | 3.5 | 4 | ND | ND | ND | ND | ND | ND | 2.5 | ND |
| 52 | 89 | 200 | ND | ND | ND | ND | ND | ND | 14 | ND |
| 178 | 48 | 98 | ND | ND | ND | ND | ND | ND | 5 | ND |
| 206 | 56 | 100 | ND | ND | ND | ND | ND | ND | 2.5 | ND |
| 436 | 1.5 | 2 | 82 | 8 | ND | 38 | 2360 | 73 | >5000 | ND |
| 437 | 4 | 5 | 9 | 3 | ND | 7.7 | 85 | 4 | 3 | ND |
| 438 | 41 | 74 | ND | ND | ND | ND | ND | ND | 5 | ND |
| 439 | 7.5 | 20 | ND | ND | ND | ND | ND | ND | 6 | ND |
| 440 | 2 | 2 | ND | ND | ND | ND | ND | ND | 24 | 34994 |
| 441 | 1 | 0.6 | ND | ND | ND | ND | ND | ND | 526 | >50000 |
| 442 | 2 | 1 | 73 | 7 | ND | 27 | 1160 | 41 | 353 | >50000 |
| 443 | 3 | 3 | ND | ND | ND | ND | ND | ND | 950 | >50000 |
| 444 | 1.6 | 3.4 | ND | ND | ND | ND | ND | ND | 67 | >50000 |
| 445 | 31 | 69 | ND | ND | ND | ND | ND | ND | 69 | >50000 |
| 446 | 3.9 | 8.8 | 679 | 68 | ND | ND | >10000 | 280 | 1115 | 21768 |
| 447 | 1.1 | 1.6 | 238 | 36 | ND | ND | >10000 | 243 | 1678 | >50000 |
| 448 | 3.2 | 8.8 | ND | ND | ND | ND | ND | ND | 8 | 8015 |
| 449 | 1.1 | 0.9 | ND | ND | ND | ND | ND | ND | 9.5 | 4485 |
| 450 | 0.5 | 0.3 | ND | ND | ND | ND | ND | ND | 214 | >50000 |
| 451 | 28 | 27 | ND | ND | ND | ND | ND | ND | 28 | >50000 |
| 452 | 20 | 45 | ND | ND | ND | ND | ND | ND | 8 | 589 |
| 453 | 12 | 30 | ND | ND | ND | ND | ND | ND | >5000 | >50000 |
| 454 | 18 | 83 | ND | ND | ND | ND | ND | ND | >5000 | >50000 |
| 455 | 4.5 | 3 | ND | ND | ND | ND | ND | ND | 1.5 | 13136 |
| 456 | 4 | 3.5 | <1 | <1 | ND | ND | ND | ND | 4 | 19499 |
| 457 | 3.5 | 7.5 | ND | ND | ND | ND | ND | ND | 68 | ND |
| 458 | 0.5 | 10 | ND | ND | ND | ND | ND | ND | 29 | ND |
| 460 | 13 | 18 | ND | ND | ND | ND | ND | ND | >5000 | ND |
| 461 | 3.5 | 9 | ND | ND | ND | ND | ND | ND | 17 | ND |
| 462 | 5.5 | 9 | ND | ND | ND | ND | ND | ND | 25 | ND |
| 463 | 1.5 | 3.5 | ND | ND | ND | ND | ND | ND | 17 | ND |
| 464 | 8.5 | 22 | ND | ND | ND | ND | ND | ND | 42 | ND |
| 465 | 37 | 123 | ND | ND | ND | ND | ND | ND | 66 | 397 |
| 466 | 4 | 10 | ND | ND | ND | ND | ND | ND | 35 | 1114 |
| 467 | 4 | 5 | ND | ND | ND | ND | ND | ND | 14 | 2427 |
| 468 | 8 | 8 | ND | ND | ND | ND | ND | ND | 36 | 3785 |
| 469 | >196 | 200 | ND | ND | ND | ND | ND | ND | 46 | >30000 |
| 470 | 2 | 19 | ND | ND | ND | ND | ND | ND | 142 | 3672 |
| 471 | 10 | 53 | ND | ND | ND | ND | ND | ND | 454 | 1994 |
| 472 | 2.5 | 5 | ND | ND | ND | ND | ND | ND | ND | 29072 |
| 473 | 54 | 105 | ND | ND | ND | ND | ND | ND | 7 | 3167 |
| 474 | 0.5 | 4.5 | ND | ND | ND | ND | ND | ND | 776 | 1164 |
| 476 | 4 | 25 | ND | ND | ND | ND | ND | ND | 174 | 703 |
| 477 | 3.5 | 4.5 | 158 | 25 | ND | ND | ND | ND | 752 | >50000 |
| 478 | 9 | 27 | 453 | 97 | ND | ND | ND | ND | 2215 | 33705 |
| 479 | 2.5 | 5 | 213 | 44 | ND | ND | ND | ND | 2597 | ND |
| 480 | 5.5 | 14 | ND | ND | ND | ND | ND | ND | 82 | 1159 |
| 481 | 1 | 4 | 69 | 24 | ND | ND | ND | ND | 426 | >20000 |
| 482 | 3 | 16 | 155 | 29 | ND | ND | ND | ND | 1751 | >50000 |
| 483 | 25 | 20 | 181 | 44 | ND | ND | ND | ND | >5000 | >50000 |
| 484 | 20 | 93 | ND | ND | ND | ND | ND | ND | >5000 | >50000 |
| 485 | 7.5 | 22 | ND | ND | ND | ND | ND | ND | 3248 | >50000 |
| 486 | 16 | 41 | ND | ND | ND | ND | ND | ND | >5000 | >50000 |
| 487 | 55 | 111.5 | ND | ND | ND | ND | ND | ND | >5000 | >50000 |
| 488 | 101 | 200 | ND | ND | ND | ND | ND | ND | >5000 | >50000 |
| 489 | 90 | 159 | ND | ND | ND | ND | ND | ND | >5000 | >50000 |
| 490 | 2 | 9.5 | ND | ND | ND | ND | ND | ND | 2117 | >50000 |
| 491 | 21 | 31 | ND | ND | ND | ND | ND | ND | 4586 | >50000 |
| 495 | 14 | 39 | 5 | 2 | ND | ND | ND | ND | ND | ND |
| 496 | >161 | >200 | ND | ND | ND | ND | ND | ND | ND | ND |
| 497 | 6 | 14 | 85 | 14 | ND | ND | ND | ND | ND | ND |
| 498 | 1 | 3 | 223 | 155 | ND | ND | ND | ND | ND | ND |
| 499 | 15 | 26 | 69 | 19 | ND | ND | ND | ND | ND | ND |
| 500 | 16 | 34 | ND | ND | ND | ND | ND | ND | ND | ND |
| 501 | 2 | 5 | ND | ND | ND | ND | ND | ND | ND | ND |
| 502 | 12 | 28 | 69 | 74 | ND | ND | ND | ND | ND | ND |
| 503 | 5 | 18 | ND | ND | ND | ND | ND | ND | ND | ND |
| 504 | 141 | >200 | ND | ND | ND | ND | ND | ND | ND | ND |
| 505 | 23 | 60 | ND | ND | ND | ND | ND | ND | ND | ND |
| 506 | 2 | 2 | ND | ND | ND | ND | ND | ND | ND | ND |
| 507 | 6 | 13 | 1.3 | 3.2 | ND | ND | ND | ND | ND | ND |
| 509 | 5 | 10 | 78 | 33 | ND | ND | ND | ND | ND | ND |
| 510 | 3 | 4 | ND | ND | ND | ND | ND | ND | ND | ND |
| 511 | ND | 16 | ND | ND | ND | ND | ND | ND | ND | ND |
| 512 | 1 | 2 | 2 | <1 | ND | ND | ND | ND | ND | ND |
| 513 | 2 | 8 | <1 | 3 | ND | ND | ND | ND | ND | ND |

TABLE 2-continued

| Compound No. | CDK4 IC$_{50}$ (nM) | CDK6 IC$_{50}$ (nM) | CDK1/B IC$_{50}$ (nM) | CDK2/A IC$_{50}$ (nM) | CDK2/E IC$_{50}$ (nM) | CDK5/p25 IC$_{50}$ (nM) | CDK7/H IC$_{50}$ (nM) | CDK9/K IC$_{50}$ (nM) | FMS IC$_{50}$ (nM) | PI3Kδ IC$_{50}$ (nM) |
|---|---|---|---|---|---|---|---|---|---|---|
| 515 | 145 | >200 | ND | ND | ND | ND | ND | ND | ND | ND |
| 516 | 1 | 4 | ND | ND | ND | ND | ND | ND | ND | ND |
| 517 | 1.5 | 4 | ND | ND | ND | ND | ND | ND | ND | ND |
| 518 | 4 | 28 | 1187 | 560 | ND | ND | ND | ND | ND | ND |
| 520 | 9 | 77 | <1 | <1 | ND | ND | ND | ND | ND | ND |
| 521 | 5.5 | 19.8 | ND | ND | ND | ND | ND | ND | ND | ND |
| 522 | 36 | 105 | ND | ND | ND | ND | ND | ND | ND | ND |
| 523 | 20 | 51 | 21 | 74 | ND | ND | ND | ND | ND | ND |
| 524 | 3.5 | 7.5 | ND | ND | ND | ND | ND | ND | ND | ND |
| 788 | 2 | 4 | ND | ND | ND | ND | ND | ND | ND | ND |
| 790 | ND | 3 | ND | ND | ND | ND | ND | ND | ND | ND |
| 791 | 9 | 41 | ND | ND | ND | ND | ND | ND | ND | ND |
| 792 | 4 | 4 | ND | ND | ND | ND | ND | ND | ND | ND |
| 843 | 65 | 24 | ND | ND | ND | ND | ND | ND | ND | ND |
| 844 | 31 | 35 | ND | ND | ND | ND | ND | ND | ND | ND |
| 845 | 23 | 29 | ND | ND | ND | ND | ND | ND | ND | ND |
| 846 | 3 | 4 | ND | ND | ND | ND | ND | ND | ND | ND |
| 847 | 44 | 107 | ND | ND | ND | ND | ND | ND | ND | ND |
| 848 | 44 | 110 | ND | ND | ND | ND | ND | ND | ND | ND |

ND: Not Determined

Example B2. Determination of Potency of Compounds in Cancer Cell Proliferation Assay as a Single Agent The effects of test compounds were studied in seven cell lines with various histotypes. The cancer cells (Table 3) were harvested during the logarithmic growth period and counted. Adjust cell concentrations to the appropriated number with respective medium and add 90 μL cell suspensions to 96-well plates. After cells were seeded, the plates were shaken gently to distribute cells evenly and incubated at 37° C., 5% CO$_2$ on day 1.

TABLE 3

Cell Culture Conditions

| No. | Cell Line | Histopathology | Rb Status | Medium |
|---|---|---|---|---|
| 1 | A549 | Lung adeno-carcinoma | Positive | DMEM + 10% FBS |
| 2 | HCT-116 | Colorectal carcinoma | Positive | McCoy's 5a + 10% FBS |
| 3 | MCF-7 | Breast adeno-carcinoma | Positive | MEM + 10% FBS |
| 4 | ZR-75-30 | Breast ductal carcinoma | Positive | RPMI-1640 + 10% FBS |
| 5 | Hs-578T | Breast epithelia carcinoma | Positive | RPMI-1640 + 10% FBS |
| 6 | BT-549 | Breast ductal carcinoma | Negative | RPMI1640 + 10% FBS |
| 7 | DU4475 | Breast carcinoma | Negative | RPMI1640 + 10% FBS |

Cells were treated with test compounds at 7 to 9 concentrations within a desired concentration range (e.g. 1.1 nM-10 μM) on day 2 by series diluting the test compound stock solution (10 mM in DMSO) with culture medium. Treatment duration was in the range of 24-168 hr, depending on the cell type. Cell viability was assessed by Cell Titer-Glo® as recommended by Promega (Cat. No.: G7572), or by Brdu ELISA assay or resazurin assay, as recommended by Sigma Aldrich (Cat. No.: 11647229001 and R$^{7017}$, respectively) post treatment.

Cell viability data were plotted using GraphPad Prism (version 5, GraphPad Software, Inc., San Diego, Calif.). In addition, a nonlinear regression model with a sigmoidal dose response and variable slope within GraphPad Prism was used to calculate the IC$_{50}$ value of individual test compounds. IC$_{50}$ values are given in Table 4. Additional compounds, treated for 24-168 hours, are shown in Table 5.

TABLE 4

| | IC$_{50}$ (nM) | | | | | | |
|---|---|---|---|---|---|---|---|
| | A549 | HCT116 | MCF-7 | ZR-75-30 | Hs-578T | BT-549 | DU4475 |
| | Treatment Duration (h) | | | | | | |
| Compound No. | 72 | 72 | 72 | 24 | 24 | 24 | 168 |
| 1 | 65 | 515 | 68 | 49 | 60 | 3200 | 575 |
| 12 | <13 | <13 | <10 | ND | ND | 230 | 40 |

ND: Not Determined

TABLE 5

| Compound No. | IC$_{50}$ (nM) | | | |
|---|---|---|---|---|
| | A549 | MCF-7 | BT-549 | DU4475 |
| 4 | ND | 110 | ND | ND |
| 6 | ND | 30 | ND | ND |
| 9 | ND | 3255 | ND | ND |
| 10 | ND | 280 | ND | ND |
| 11 | ND | 225 | ND | ND |
| 13 | ND | 3.8 | ND | ND |
| 14 | ND | 11 | ND | ND |
| 15 | ND | 114 | ND | ND |
| 16 | ND | 3.8 | ND | ND |
| 17 | ND | 15 | ND | ND |
| 18 | ND | <10 | ND | ND |
| 19 | ND | <10 | ND | ND |
| 20 | ND | 145 | ND | ND |
| 21 | ND | <10 | ND | ND |
| 22 | ND | <10 | ND | ND |
| 23 | ND | <10 | ND | ND |
| 24 | ND | <10 | <370 | 10 |
| 25 | ND | 25 | <1110 | 46 |
| 26 | ND | 163 | ND | ND |
| 27 | ND | 40 | ND | ND |
| 28 | ND | 150 | ND | ND |
| 29 | ND | 48 | ND | ND |
| 30 | ND | 233 | ND | ND |
| 31 | ND | 193 | ND | ND |
| 32 | ND | 130 | ND | ND |
| 33 | ND | <14 | ND | 40 |
| 34 | ND | 50 | ND | ND |
| 35 | ND | 20 | ND | ND |
| 36 | ND | 40 | ND | ND |
| 37 | ND | <14 | ND | ND |
| 38 | ND | 20 | ND | 45 |
| 39 | ND | 45 | ND | ND |
| 47 | ND | 20 | ND | ND |
| 52 | ND | 695 | ND | ND |
| 178 | ND | 210 | ND | ND |
| 206 | ND | 670 | ND | ND |
| 436 | 390 | 165 | ND | 383 |
| 437 | ND | 45 | ND | ND |
| 438 | ND | 200 | ND | ND |
| 439 | ND | 90 | ND | ND |
| 440 | ND | 30 | ND | ND |
| 441 | ND | 95 | ND | ND |
| 442 | 465 | 125 | ND | 503 |
| 443 | ND | 285 | ND | ND |
| 444 | ND | 1250 | ND | ND |
| 445 | ND | 120 | ND | ND |
| 446 | ND | 850 | ND | 385 |
| 447 | ND | 300 | ND | 230 |
| 448 | ND | 50 | ND | ND |
| 449 | ND | 50 | ND | ND |
| 450 | ND | 240 | ND | ND |
| 451 | ND | 30 | ND | ND |
| 452 | ND | 50 | ND | ND |
| 453 | ND | 695 | ND | ND |
| 454 | ND | 920 | ND | ND |
| 455 | ND | <4 | ND | ND |
| 456 | ND | <4 | ND | ND |
| 457 | ND | 55 | ND | 30 |
| 458 | ND | 30 | ND | 35 |
| 460 | ND | 595 | ND | ND |
| 461 | ND | 30 | ND | 50 |
| 462 | ND | 40 | ND | 65 |
| 463 | ND | 20 | ND | 25 |
| 464 | ND | 85 | ND | 80 |
| 465 | ND | 80 | ND | ND |
| 466 | ND | 105 | ND | ND |
| 467 | ND | 185 | ND | ND |
| 468 | ND | 95 | ND | ND |
| 469 | ND | 495 | ND | ND |
| 470 | ND | 100 | ND | 75 |
| 471 | ND | 45 | ND | 110 |
| 472 | ND | 30 | ND | 570 |
| 473 | ND | 30 | ND | 55 |
| 474 | ND | 300 | ND | 940 |
| 476 | ND | 65 | ND | 135 |
| 477 | ND | 280 | ND | 1100 |
| 478 | ND | 665 | ND | 1685 |
| 479 | ND | 240 | ND | ND |
| 480 | ND | 190 | ND | 435 |
| 481 | ND | 85 | ND | 345 |
| 482 | ND | 230 | ND | 540 |
| 483 | ND | 460 | ND | 665 |
| 484 | ND | 1345 | ND | 2485 |
| 485 | ND | 470 | ND | 555 |
| 486 | ND | 325 | ND | 1450 |
| 487 | ND | 615 | ND | 2170 |
| 488 | ND | 830 | ND | 2565 |
| 489 | ND | 1820 | ND | 4505 |
| 490 | ND | 80 | ND | 420 |
| 491 | ND | 465 | ND | 450 |
| 495 | ND | 110 | ND | 310 |
| 496 | ND | 1450 | ND | 3420 |
| 497 | ND | 40 | ND | 95 |
| 498 | ND | 170 | ND | 465 |
| 499 | ND | 175 | ND | 345 |
| 500 | ND | 625 | ND | 2495 |
| 501 | ND | 140 | ND | 1015 |
| 502 | ND | 435 | ND | 405 |
| 503 | ND | 240 | ND | 1260 |
| 504 | ND | 1940 | ND | 4150 |
| 505 | ND | 1037 | ND | 3440 |
| 506 | ND | 354 | ND | 1495 |
| 507 | ND | <5 | ND | 20 |
| 509 | ND | 1086 | ND | 1475 |
| 510 | ND | 293 | ND | 1970 |
| 511 | ND | 648 | ND | 3790 |
| 512 | ND | 6 | ND | 465 |
| 513 | ND | 17 | ND | 50 |
| 515 | ND | 2501 | ND | >10000 |
| 516 | ND | 155 | ND | 995 |
| 517 | ND | 108 | ND | 275 |
| 518 | ND | 1020 | ND | 1330 |
| 520 | ND | 13 | ND | <7 |
| 521 | ND | 3670 | ND | 7705 |
| 522 | ND | 345 | ND | 395 |
| 523 | ND | 55 | ND | 75 |
| 524 | ND | 332 | ND | ND |
| 788 | ND | 130 | ND | 920 |
| 790 | ND | 17 | ND | 20 |
| 791 | ND | 90 | ND | 205 |
| 792 | ND | 32 | ND | 75 |

ND: Not Determined

Effects of compound 24 on cell proliferation in additional cell lines (Table 6) were studied. Cells were harvested during the logarithmic growth period and counted. The cell concentrations were adjusted to the appropriate concentrations with their respective media, and 90 µl cell suspensions were added to 96-well plates. When cells were added, the plate was shaken gently to distribute cells evenly. The cells were incubated at 37° C., 5% CO2. The next day, cells were treated with the test compound. 3× serial dilutions of compound stock solutions were prepared with respective solvents. The stock solution was diluted with culture medium to make 10× working solutions. 10 µl (10×) drug solution was dispensed in each well (triplicates for each concentration). The plate was incubated for 72 hrs in a humidified incubator at 37° C. with 5% CO2. For plate reading, CTG solution was thawed and equilibrated to room temperature. 50 ul of CTG was added per well, the contents were mixed for 2 min on the plate shaker, and a 10 min incubation was done before recording the luminescence signal using an Envision plate reader (PerkinElmer).

TABLE 6

Inhibition of cancer cell proliferation by compound 24.

| | MOLM-13 | OCI-AML3 | SU-DHL-4 | U2932 | NCI-H929 | RPMI-8226 |
|---|---|---|---|---|---|---|
| Seeding Density (cells/well) | 6000 | 8000 | 10000 | 8000 | 10000 | 6000 |
| Compound 24 IC$_{50}$ (nM) | 20 | 36 | 42 | 29 | 44 | 65 |

Additional test compounds will be studied in the same and/or other cancer cell lines using similar proliferation methods with possible variables, such as cell seeding densities and/or incubation durations. The cell cycle phase distribution post treatment of test compounds will be studied using flow cytometer using DAPI staining. Cellular senescence will be evaluated after continuously treating cells for a long time (e.g., 14 days) followed by staining cells lines for Senescence associated-β-galactosidase (SAP3GAL).

Example B3. Determination of pRb Levels

Hypo-phosphorylation of the retinoblastoma protein (pRb) by cyclin D:Cdk4/6 complexes results in active pRb, which is a clinically relevant biomarker associated with CDK4 or CDK6 inhibition. As a confirmatory measure of functional activity of CDK4/6, the Ser780 phosphorylation state of RB1 was assessed. MCF-7 cells were plated at $2.5 \times 10^5$ to $3.0 \times 10^6$ cells/well in 6-well cell-culture plates and incubated at 37° C. for 24 h in MEM medium supplemented with 10% FBS. Cells were treated for 24 h with a medium containing test compound at various concentrations (e.g., 0.01, 0.1, 1 µM) or with DMSO (≤1%) in duplicate. After incubation period, the media was removed, and cells were rinsed once with ice-cold PBS and lysed with 0.2 mL of Cell Lysis Buffer containing 1 mM PMSF and Protease Inhibitor. Protein concentration was estimated following Bradford method. The lysis and the pRB measurements were performed following the manufacturer's ELISA kit protocols and buffers (Cell Signaling Technology, Cat. No.: 13016C). pRb inhibition of test compounds were calculated as percentage of vehicle control. Values are given in Table 7.

TABLE 7

| | pRb Inhibition % | | |
|---|---|---|---|
| Compound No. | 1 µM | 0.1 µM | 0.01 µM |
| 1 | 89 | 80 | 77 |
| 12 | 81 | 81 | −5 |

The effects of selected test compounds in additional cancer cell lines on clinically relevant biomarkers associated with CDK4 or CDK6 inhibition (e.g., pRB and thymidine kinase (TK)) is assessed using ELISA or Western Blotting methods with selective antibodies.

Example B4. Determination of Potency and Combination Effects of Compounds in Cancer Cell Proliferation Assays Using Combination Therapy Effects of test compounds on cell proliferation is studied in additional cancer cell lines, such as estrogen receptor over-expressing cancer cells, in the combination of another anti-cancer therapy (e.g., an aromatase inhibitor and/or a selective estrogen receptor degrader for breast cancer) using CTG, resazurin and/or Brdu assays. Cells seeded in a 96-well plate are treated with single agents to obtain a dose response curve for each agent. Cells are also treated with combinations of the drugs, based on a matrix generated by combining the two drugs at all different combinations of the doses used in the dose response curves. In place of a combination matrix method, a fixed drug ratio dilution method in which drugs are combined in a fixed ratio of 5 or more dilutions may also be used. The combined treatment effect, such as additive, synergistic, or antagonistic, is determined using the median-effect principle (Chou T C. Cancer Res 2010; 70:440-6.), with the combination index (CI) value indicating an additive effect (CI=1), synergism (CI<1), or antagonism (CI>1) in drug combinations.

Example B5. In Vivo Pharmacology Studies in Xenograft or Syngeneic Models

The anti-tumor activity of test compounds is studied against various human tumor xenograft or syngeneic models in mice for example, in breast cancer tumor models. For breast cancer tumor models, effects of test compounds on Rb-Positive or Rb-Negative tumors as a single agent or in combination with another anti-cancer therapy is determined by evaluating the difference of tumor volume between treatment group against the vehicle control group. The phosphorylation status of serine-780 on Rb is evaluated in tumor tissue and compared with antitumor response in Rb-Positive xenograft model(s). Additional pharmacodynamic end points (e.g., FoxM1, E2F1, c-Myc, and cyclin D1) are studied in tumor tissues collected at various time points post treatment. Induction of senescence is evaluated in tumor samples from various treatment groups by measuring SAP3GAL.

Example B6. In Vivo Pharmacology Study in MC-38 Mouse Model

The therapeutic efficacy of compound 24 in the treatment of the MC-38 murine colorectal cancer model was evaluated in combination with an anti mPD-1 antibody. Cultured MC-38 cells were harvested and re-suspended in base medium at a density of $1 \times 10^7$ cells/mL with viability greater than 90%. Female C57BL/6 mice were inoculated subcutaneously at the right flank with $1 \times 10^6$ cells in 0.1 mL base medium for tumor development. The treatments were started on day 5 after tumor inoculation when the tumor size reached 45-72 mm$^3$ (average tumor size 56 mm$^3$). The test article was administered to the mice according to the predetermined regimen as shown in the experimental design table (Table 8). Formulations were prepared as in Table 9 below.

TABLE 8

Groups and Treatments for Efficacy Study

| Group | n | Treatment | Dose (mg/kg) | Dosing Volume (mL/kg) | Dosing Route | Schedule |
|---|---|---|---|---|---|---|
| 1 | 10 | Vehicle control* | — | 10 | PO | QD × 21 days |
| 2 | 10 | anti mPD-1 | 10 | 10 | IP | BIW × 2 weeks |
| 3 | 5 | anti mPD-1 + compound 24 | 10 + 10 | 10 + 10 | IP + PO | BIW × 2 weeks + BIW × 2 weeks |
| 4 | 5 | compound 24 | 10 | 10 | PO | BIW × 2 weeks |

Vehicle was 0.5% HPMC Methocel K100 LV + 0.1% Polysorbate 80 (pH adjusted to 3.8 with citric acid for both compounds)

TABLE 9

Formulation Preparation

| Compounds | Package | Preparation | Conc. mg/mL | Storage |
|---|---|---|---|---|
| Vehicle | — | 1. Added 199.8 mL of water into a glass bottle. 2. Added 1 g of HPMC Methocel K100 LV into the glass bottle and stirred it. 3. Added 0.2 mL of Polysorbate 80 into the glass bottle and mixed thoroughly until a homogenous solution was obtained. 4. Adjusted PH to 3.8 with citric acid, kept the solution at 4° C. | — | 4° C. |
| compound 24 | 30.43 mg/vial | 1. Weighed 8.85 mg of compound 24 in clear, borosilicate glass vial; 2. Solubilized compound 24 in 8 mL of Vehicle solution; vortexed vigorously; 3. Adjusted PH to 3.8 with citric acid, kept the suspension at 4° C. and use within 7 days | 1 | 4° C. |
| Anti mPD-1 | 6.27 mg/mL | 1. Added 6.27 mL PBS into a 10 mL tube. 2. Added 1.19 mL stock solution into the tube and mixed thoroughly. | 1 | 4° C. |

Note:
Ensured that formulation was homogenous immediately before use by sonication and vigorous vortex.

Body Weight Change

Figure 2:
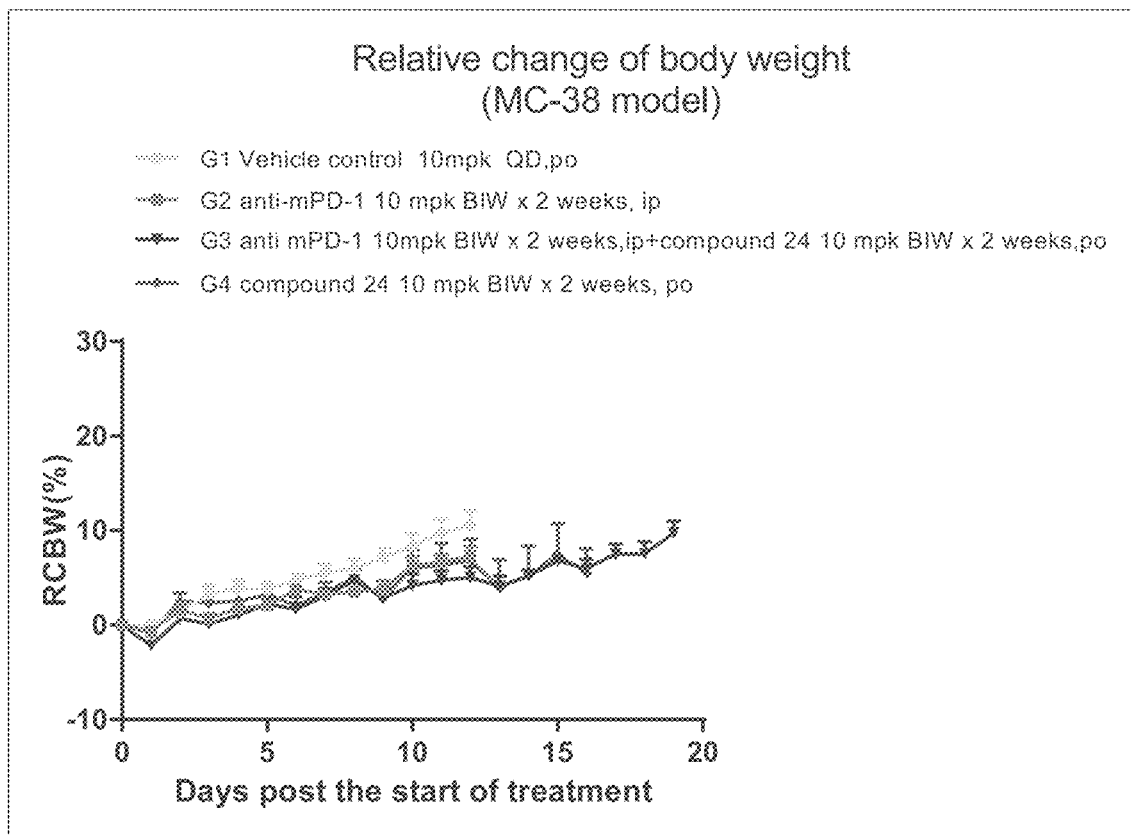
FIG. 2 shows the relative change of body weights (%) of the mice in the different groups of a pharmacological study of test compound in a MC-38 mouse model.

All treatments groups were well-tolerated. Mean (±SEM) body weight change and relative change (%) in female C57BL/6 mice bearing MC-38 tumors are shown in FIG. 1 and FIG. 2. In FIG. 1, data points represent group mean body weight. Error bars represent standard error of the mean (SEM). In FIG. 2, data points represent percent group mean change in body weight. Error bars represent standard error of the mean (SEM).

Tumor Measurements and Endpoints Tumor sizes were measured three times a week in two dimensions using a caliper, and the volume was expressed in mm$^3$ using the formula: V=0.5 a×b$^2$ where a and b are the long and short diameters of the tumor, respectively. The tumor sizes were then used for the calculations of both tumor growth inhibition (TGI) and T/C values.

TGI is calculated for each group using the formula listed below:

$$\text{TGI (\%)} = [1 - (TV_{Treatment\_DayN} - TV_{Treatment\_Day0}) / (TV_{Vehicle\_DayN} - TV_{Vehicle\_Day0})] \times 100\%$$

$TV_{Treatment\_DayN}$ is the average tumor volume of a treatment group on a given day, $TV_{Treatment\_Day0}$ is the average tumor volume of the treatment group on the first day of treatment, $TV_{Vehicle\_DayN}$ is the average tumor volume of the vehicle control group on a given day, and $TV_{Vehicle\_Day0}$ is the average tumor volume of the vehicle group on the first day of treatment.

The T/C value (in percent) is an indication of antitumor effectiveness and calculated as below:

$$T/C\ (\%) = RTV_{Treatment}/RTV_{Control} \times 100\%$$

($RTV_{Treatment}$: the mean RTV of the treatment group; $RTV_{Control}$: the mean RTV of the vehicle treated group).

$$RTV(\text{relative tumor volume}) = TV_{DayN}/TV_{Day0}.$$

$TV_{DayN}$ and $TV_{Day0}$ is the tumor volume on day N and Day 0 respectively. T/C (%)≤42% is considered as significant antitumor activity and <10% is considered as highly significant antitumor activity by the National Cancer Institute criteria.

Mean±SEM of tumor volume over time in female C57BL/6 mice bearing MC-38 tumors dosed with vehicle, anti-mPD-1, compound 24 and anti-mPD-1+compound 24 is shown in Table 10. Calculated tumor growth inhibition is shown in Table 11.

Figure 3A:
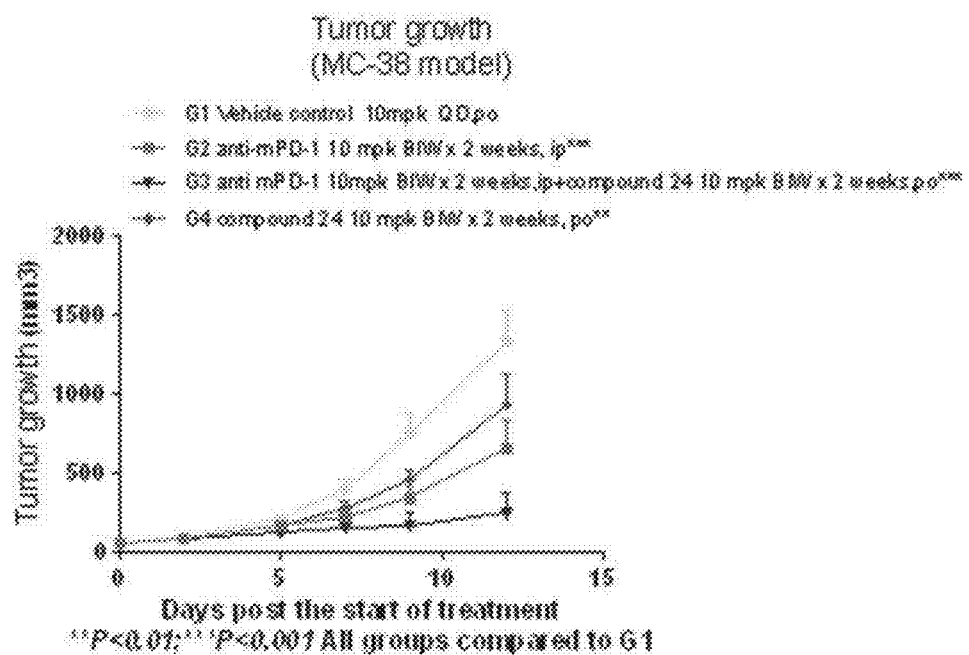
FIG. 3A and FIG. 3B show tumor growth curves of the mice in the different groups of a pharmacological study of test compound in a MC-38 mouse model.
Figure 3B:
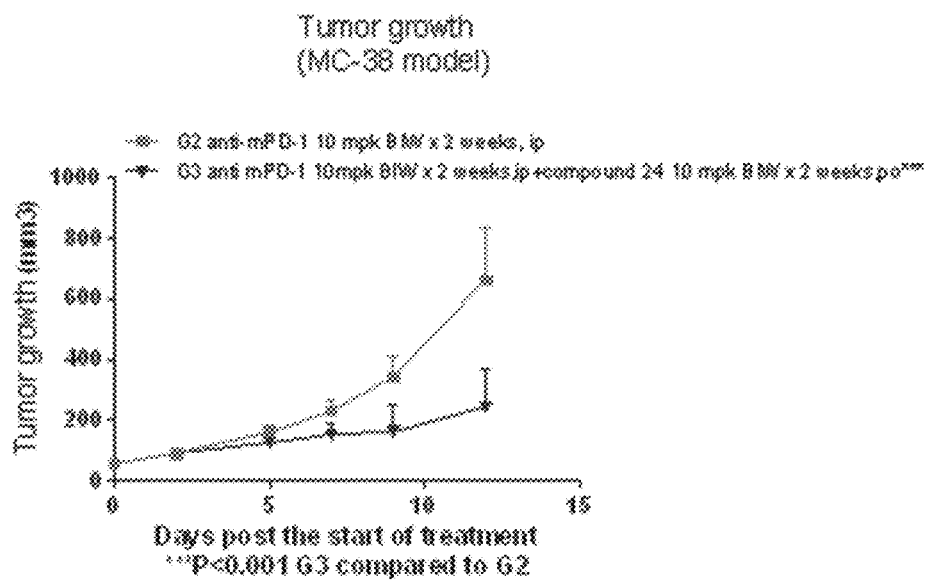
Figure 4A:
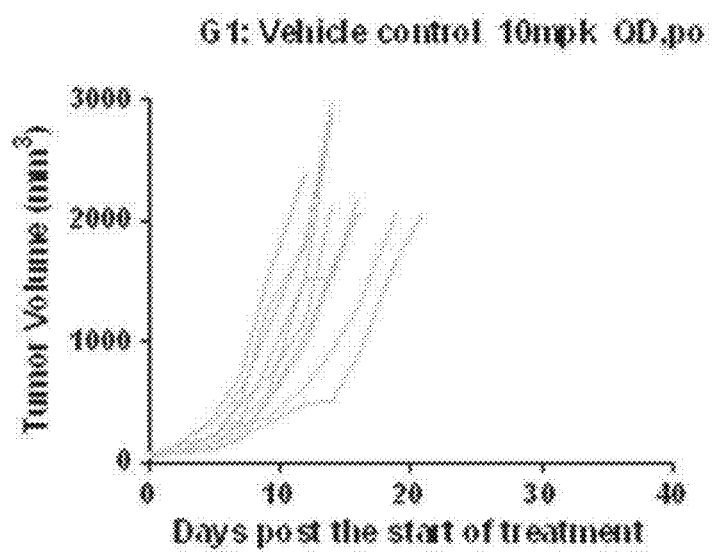
FIGS. 4A-4D show individual tumor growth curves of the mice in the different groups of a pharmacological study of test compound in a MC-38 mouse model.
Figure 4B:
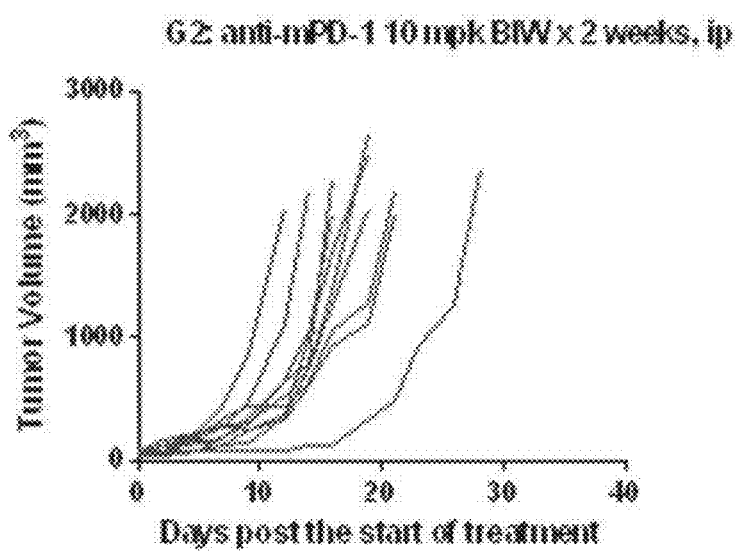
Figure 4C:
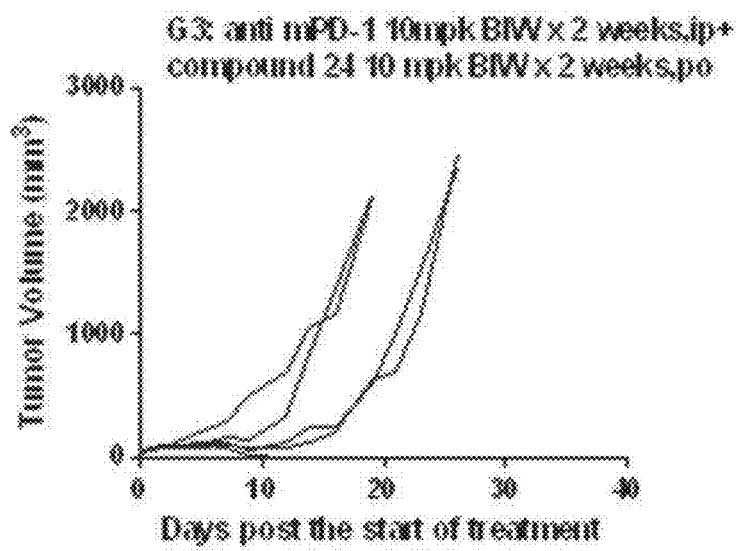
Figure 4D:
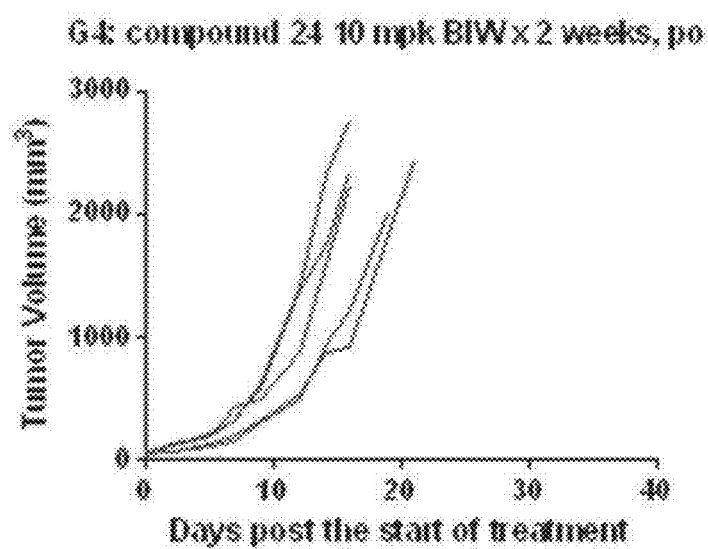
Figure 5:
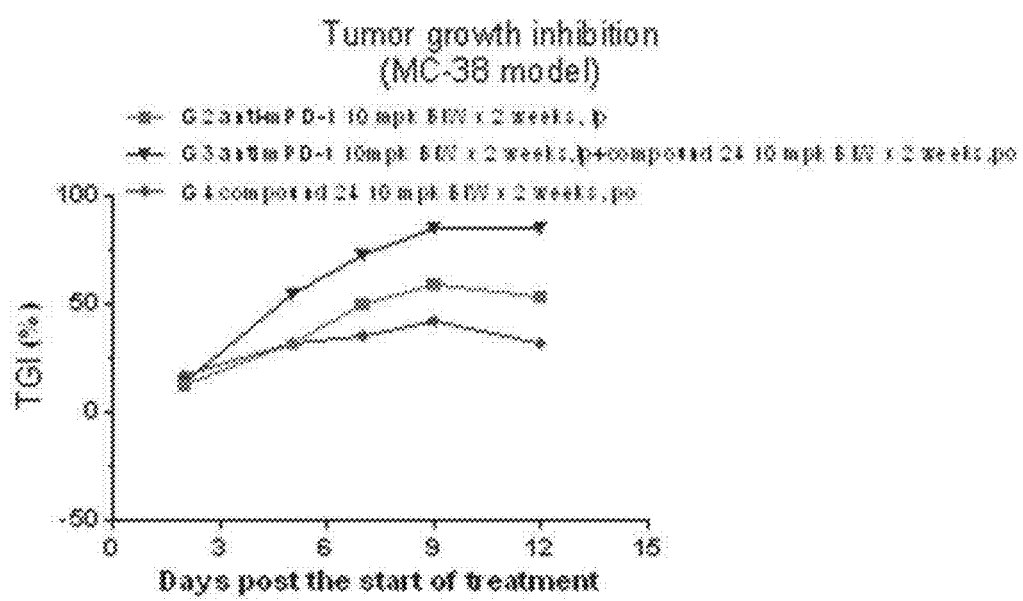
FIG. 5 shows tumor growth inhibition curves of the mice in the different groups of a pharmacological study of test compound in a MC-38 mouse model.

Tumor growth curves are shown in FIG. 3A and FIG. 3B. Data points represent group mean, error bars represent standard error of the mean (SEM). Individual tumor growth curves are shown in FIGS. 4A-4D. Tumor growth inhibition curves are shown in FIG. 5.

Survival Curves

Figure 6:
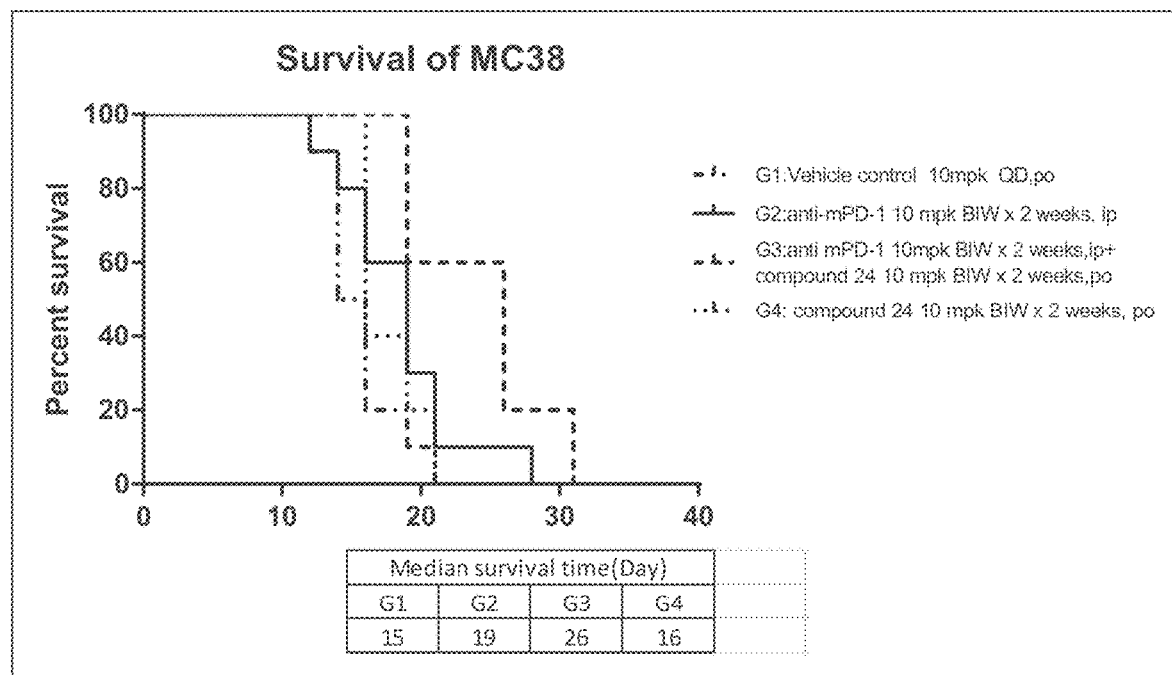
FIG. 6 shows time-to-end point Kaplan-Meier survival curves of the mice in the different groups of a pharmacological study of test compound in a MC-38 mouse model.

The time-to-end point Kaplan-Meier survival curves were plotted using Graphpad and presented in FIG. 6. Endpoint is defined as tumor volume reaching 2000 mm³.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:

1. A compound, or pharmaceutically acceptable a salt thereof, wherein the compound is selected from the group consisting of

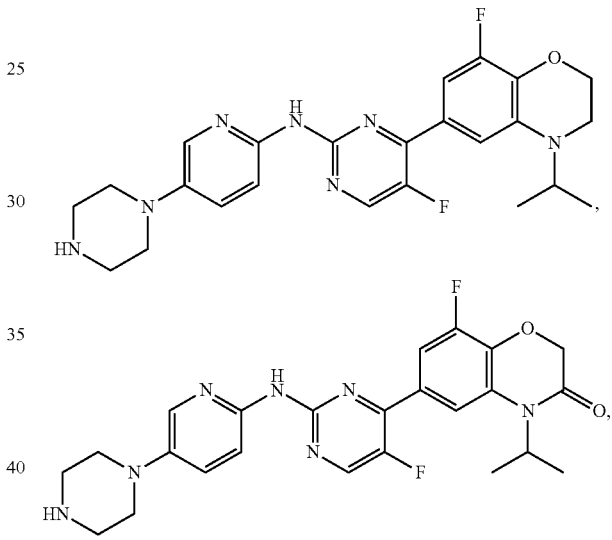

TABLE 10

Tumor Volume over Time

Tumor volume (mm³)[a]

| Days | Vehicle | Anti-mPD-1 10 mg/kg | Anti-mPD-1 10 mg/kg compound 24 10 mg/kg | compound 24 10 mg/kg |
|---|---|---|---|---|
| 0 | 57 ± 3 | 56 ± 3 | 56 ± 4 | 58 ± 4 |
| 2 | 94 ± 8 | 89 ± 12 | 88 ± 5 | 89 ± 13 |
| 5 | 213 ± 30 | 164 ± 20 | 127 ± 20 | 165 ± 20 |
| 7 | 400 ± 56 | 228 ± 35 | 152 ± 37 | 280 ± 47 |
| 9 | 754 ± 128 | 343 ± 70 | 164 ± 86 | 462 ± 62 |
| 12 | 1342 ± 187 | 659 ± 177 | 246 ± 126 | 929 ± 197 |
| 14 | | | 453 ± 208 | 1493 ± 267 |
| 16 | | | 597 ± 278 | 1892 ± 353 |
| 19 | | | 1094 ± 434 | |

Note:
[a]Mean ± SEM; For Group 1 and 2 n = 10, for group 3 and 4 n = 5

TABLE 11

Mean ± SEM Tumor Growth Inhibition
Calculation Based on TV Measurements at Day 12

| Treatment | Tumor Size (mm³)[a] at day 12 | RTV at day 12 | T/C (%) | TGI (%) | p value[b] | p value[c] |
|---|---|---|---|---|---|---|
| Vehicle | 1342 ± 187 | 23.62 ± 3.31 | — | — | — | |
| Anti-mPD-1 (10 mg/kg) | 659 ± 177 | 11.99 ± 3.44 | 50.76 | 53.06 | <0.001 | |
| Anti-mPD-1 (10 cmg/kg) + compound 24 10 mg/kg | 246 ± 126 | 4.74 ± 2.71 | 20.07 | 85.16 | <0.001 | <0.001 |
| compound 24 10 mg/kg | 929 ± 197 | 15.59 ± 2.41 | 66.00 | 32.19 | <0.01 | |

Note:
[a]Mean ± SEM.
[b]All groups compared to group 1
[c]Combination group compared to group 2

801
-continued
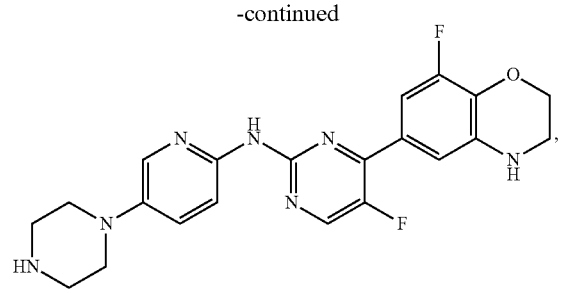
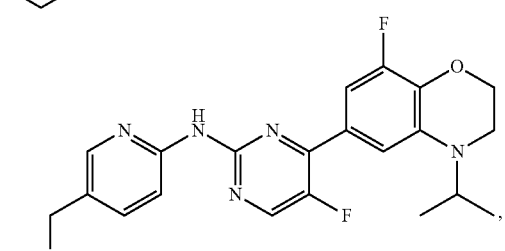
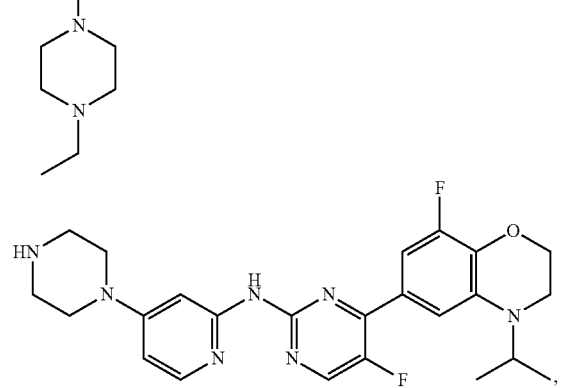
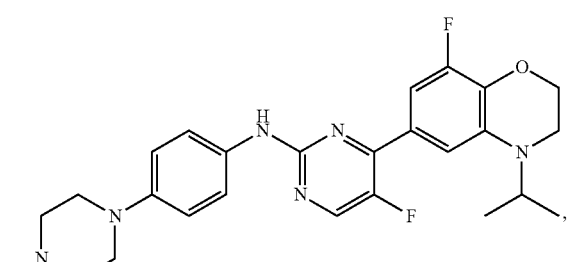
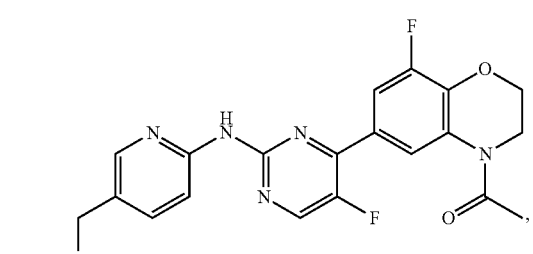
802
-continued -continued
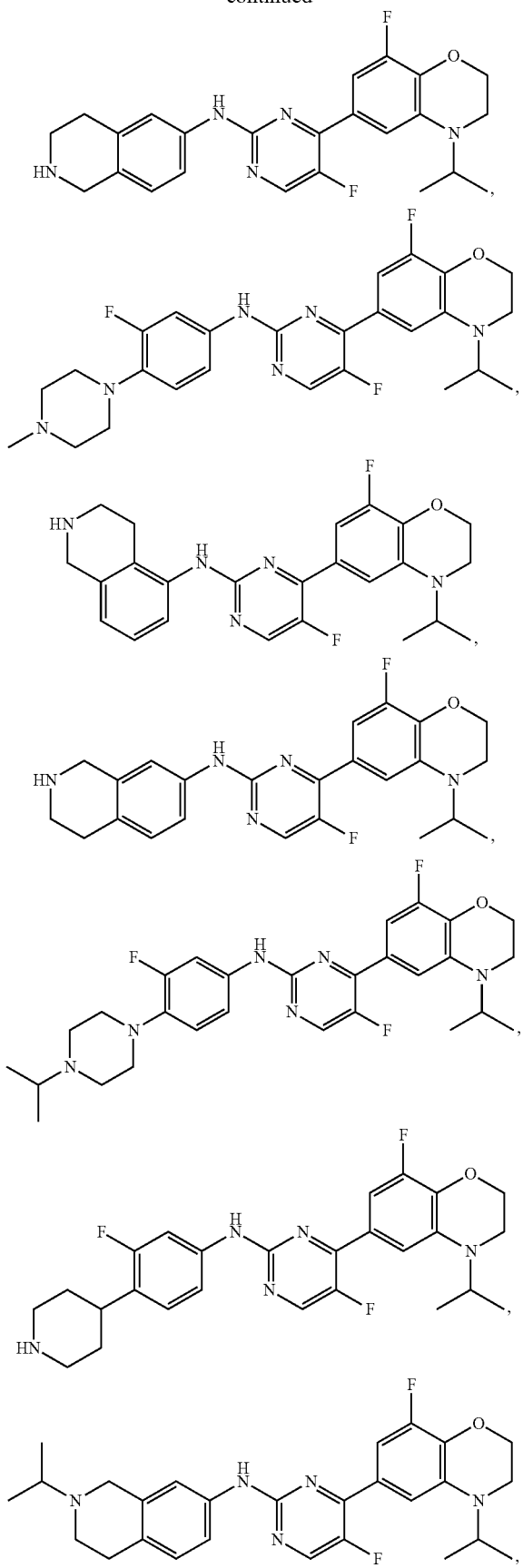
-continued
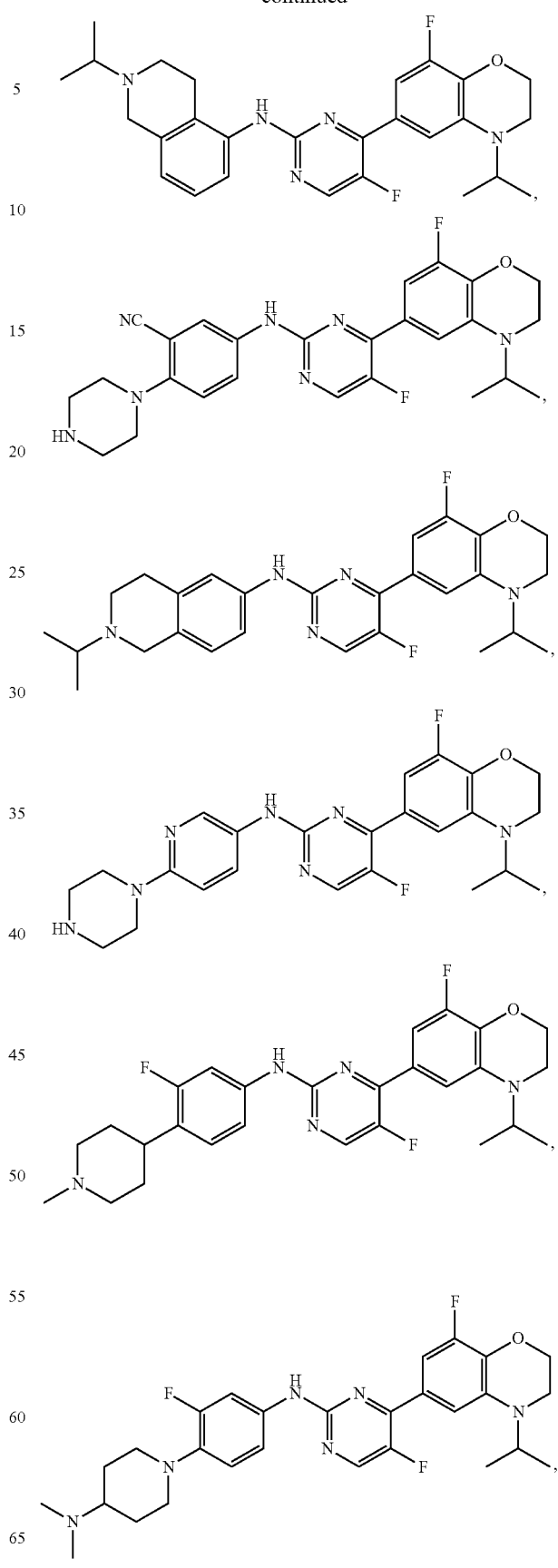

805
-continued
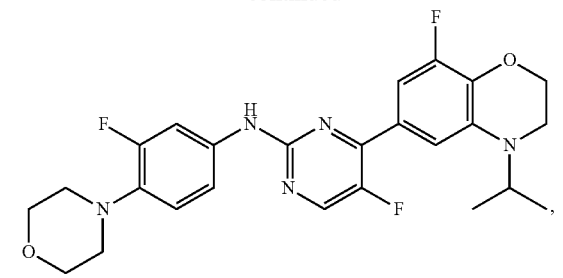
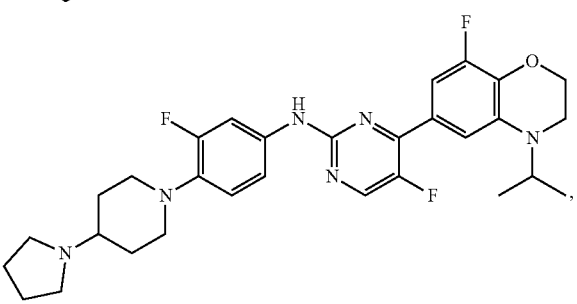
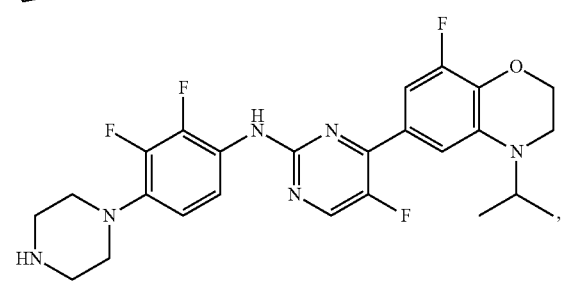
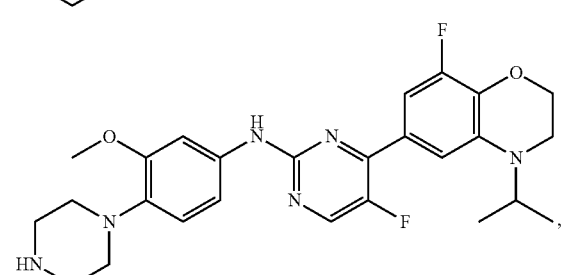
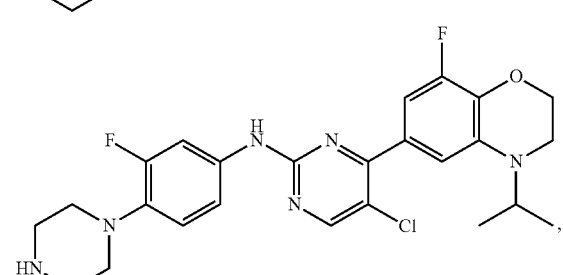
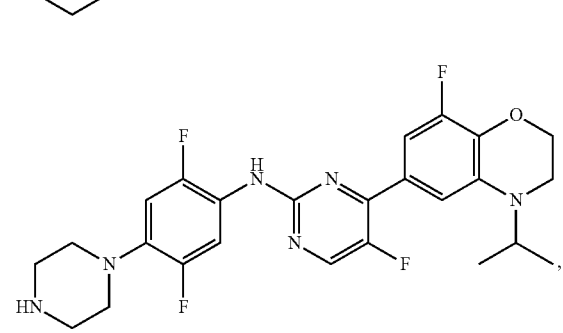
806
-continued
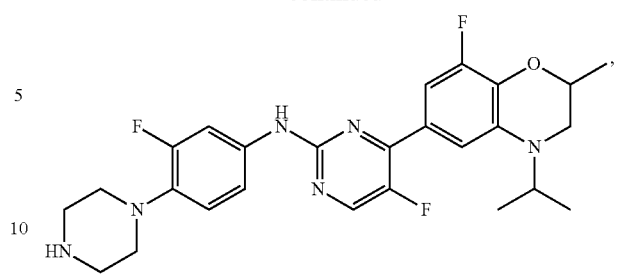
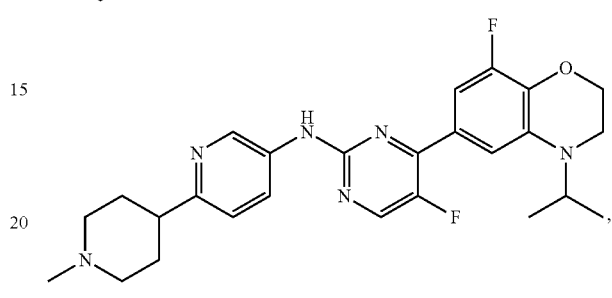
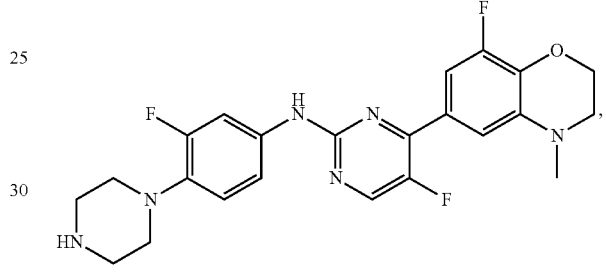
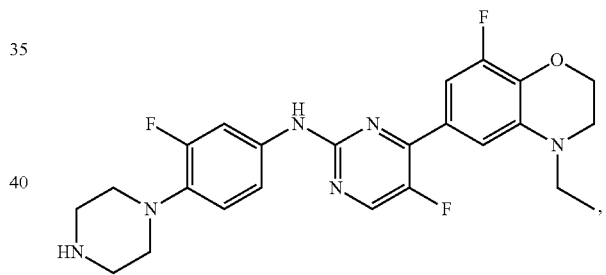
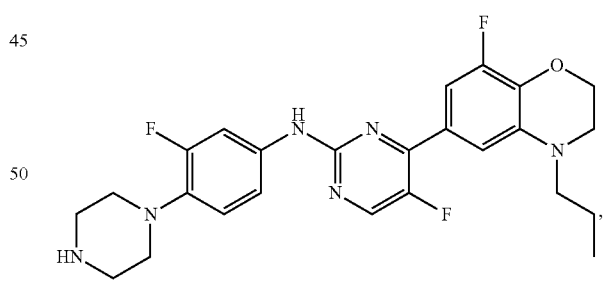
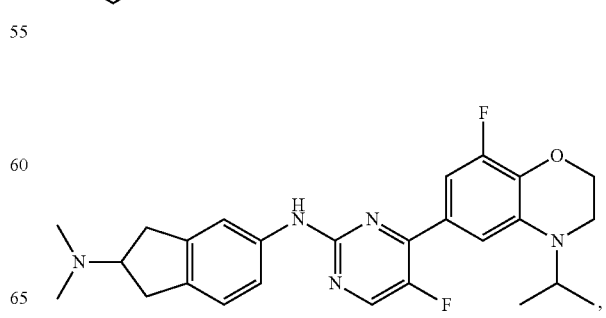

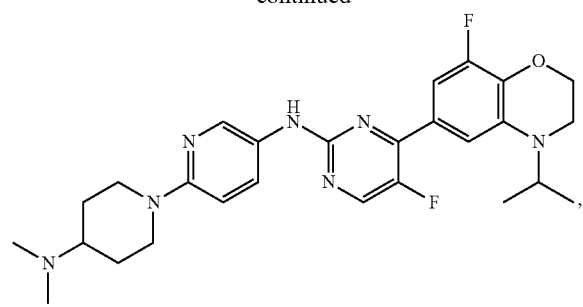
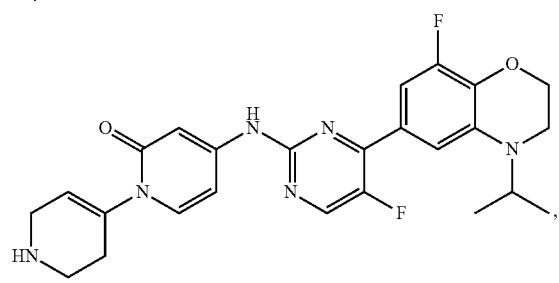
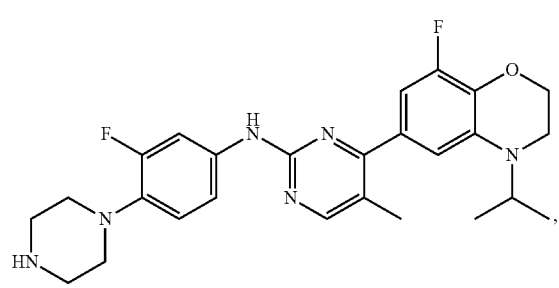
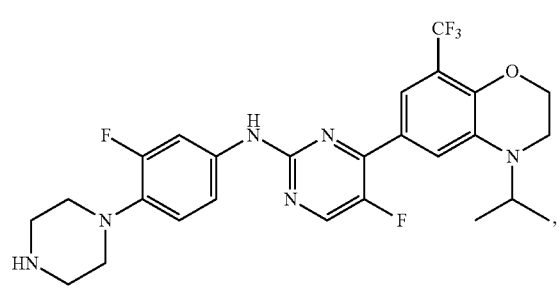
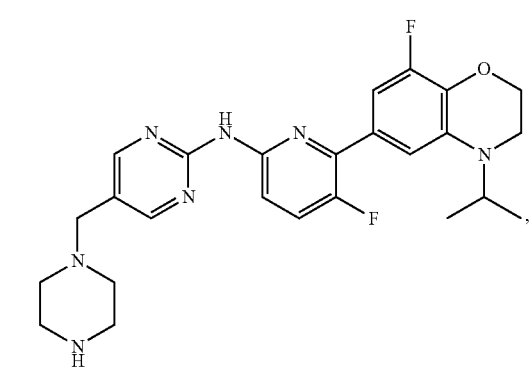
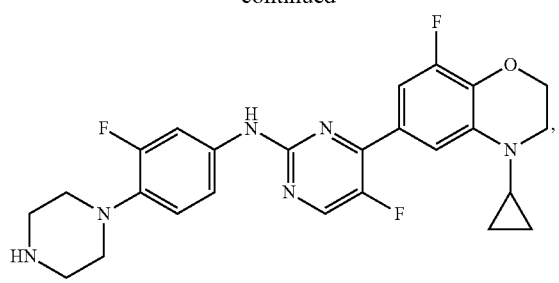
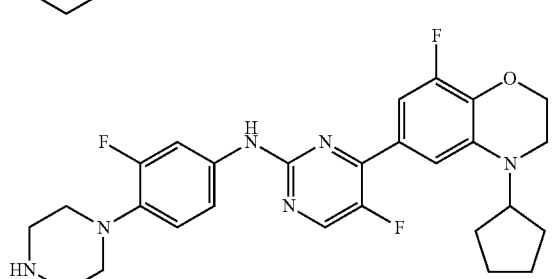
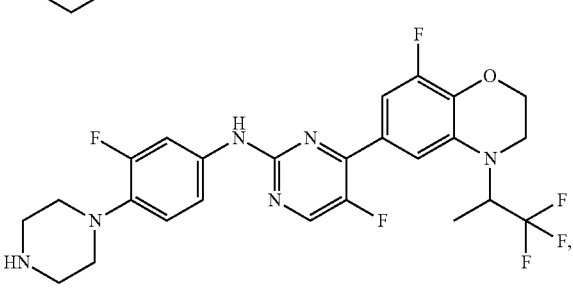
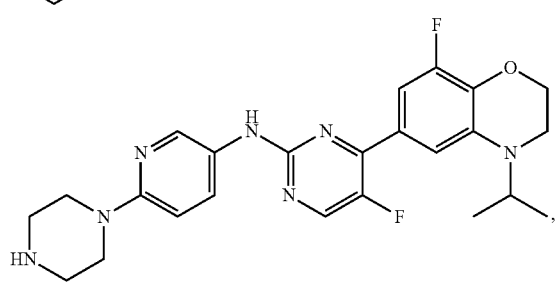
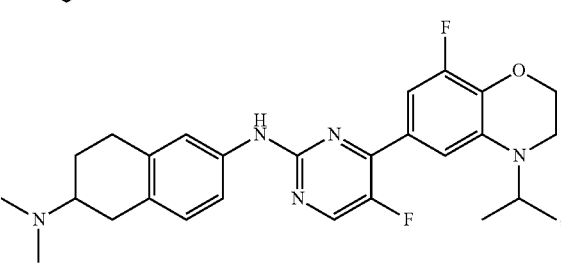
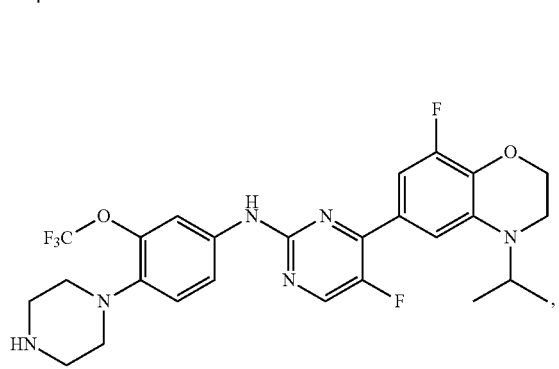

-continued
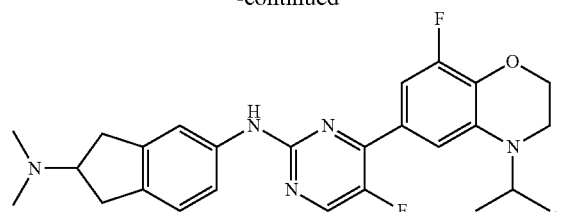
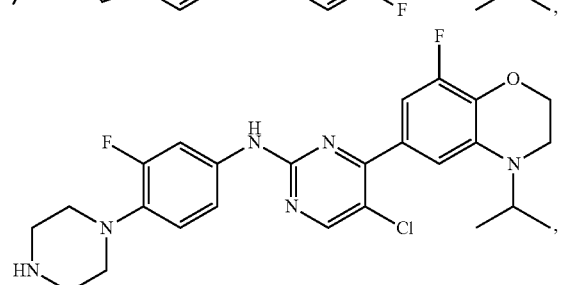
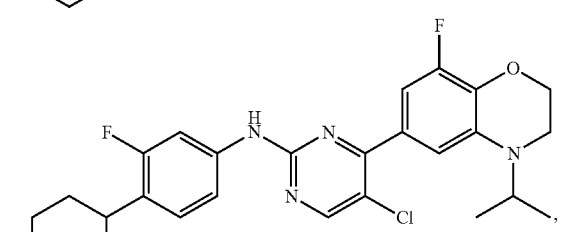
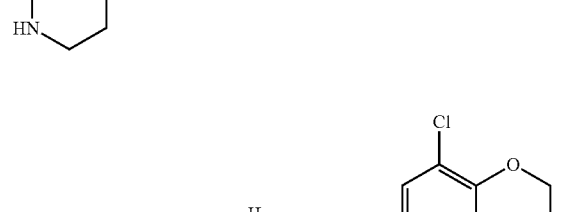
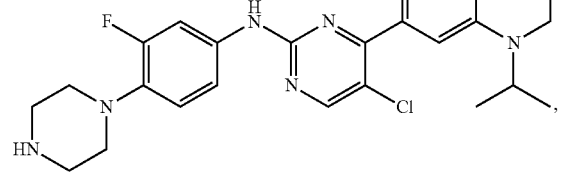
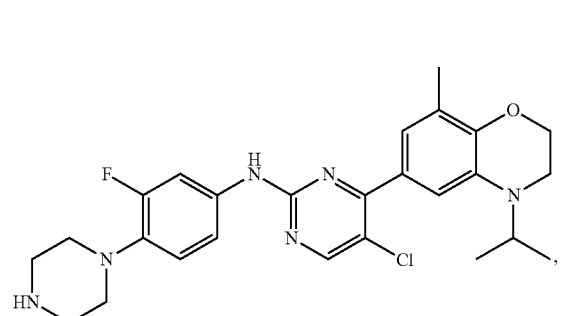
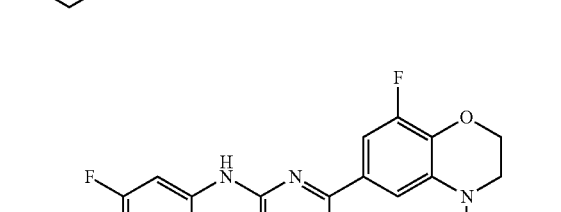
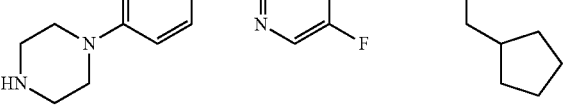
-continued
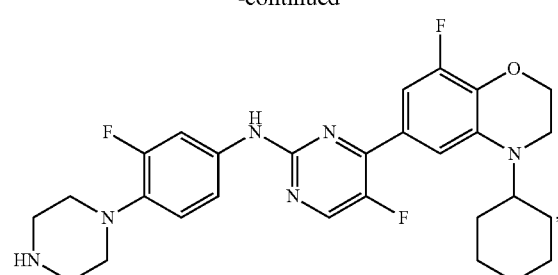
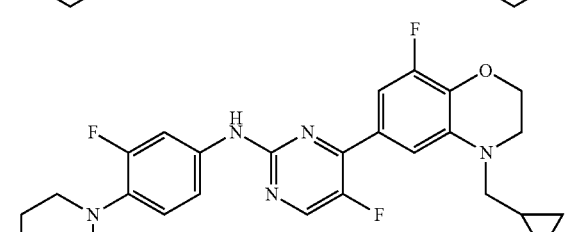
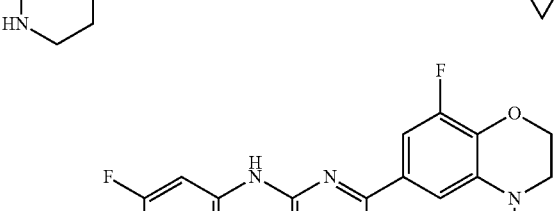
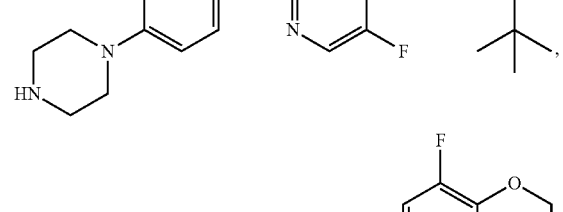
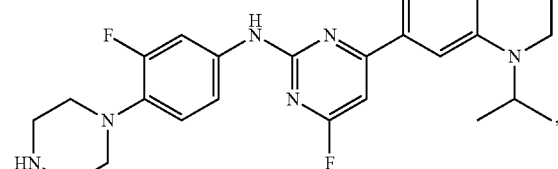
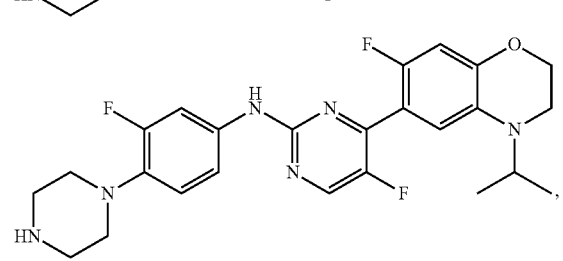
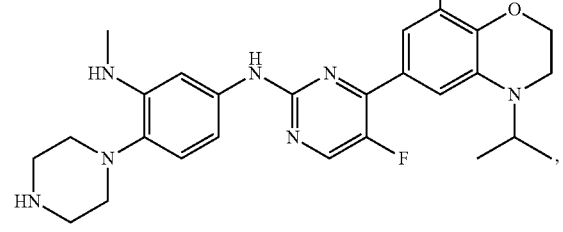

811
-continued
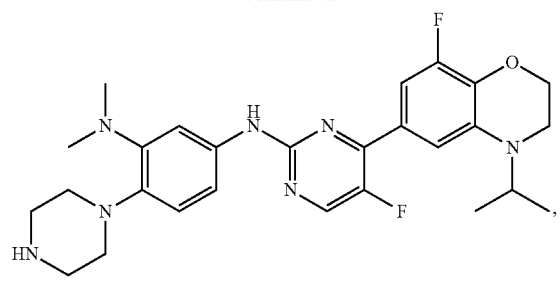
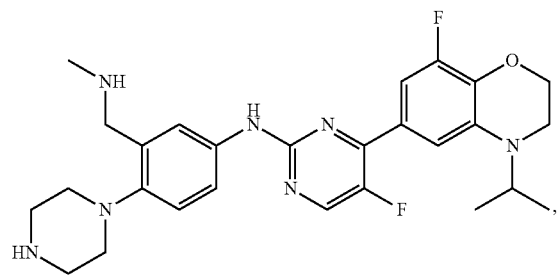
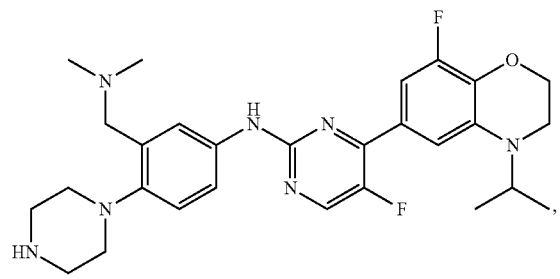
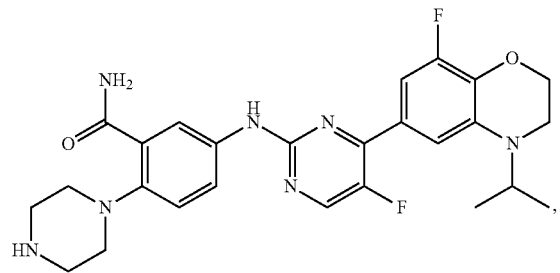
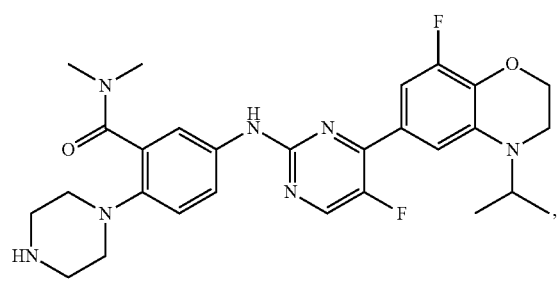
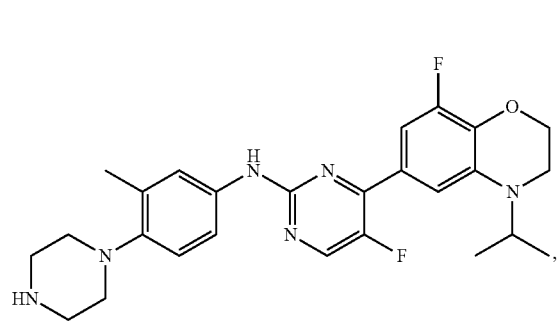 [SMILES: CC(C)N1CCOc2c(F)cc(-c3nc(Nc4ncc(N5CCNCC5)cn4)ccc3F)cc21]
812
-continued
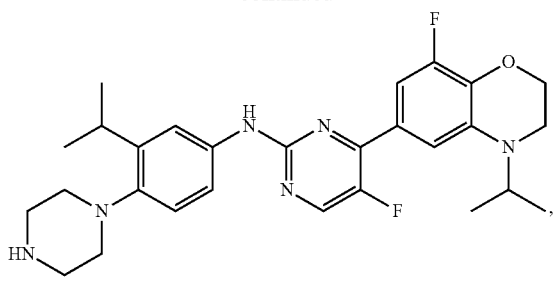
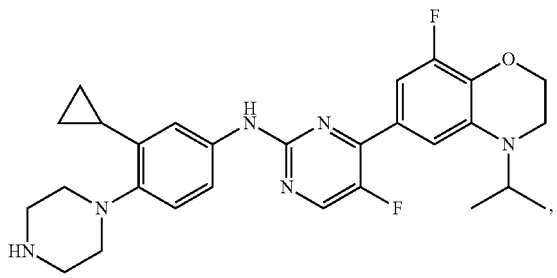
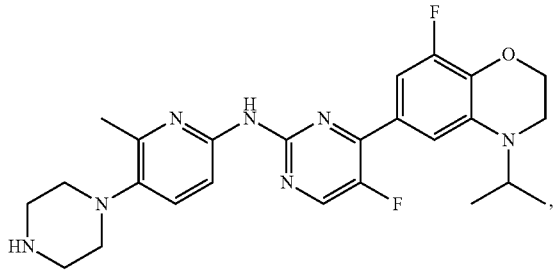
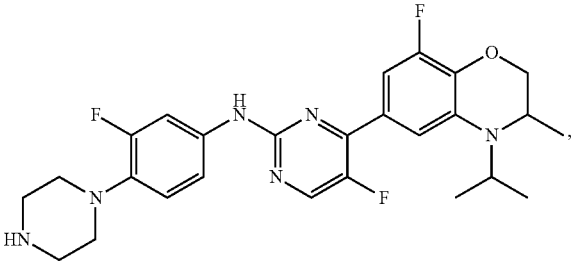
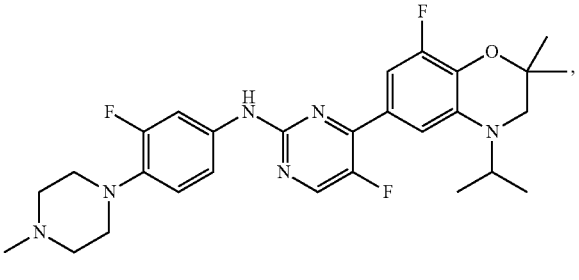
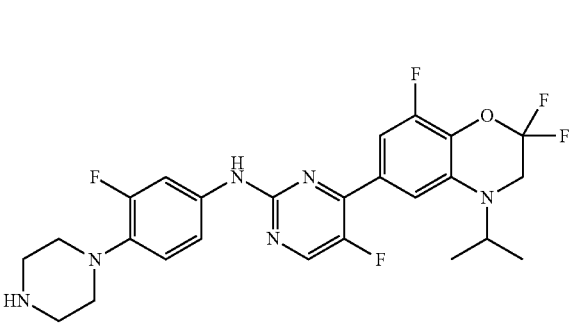

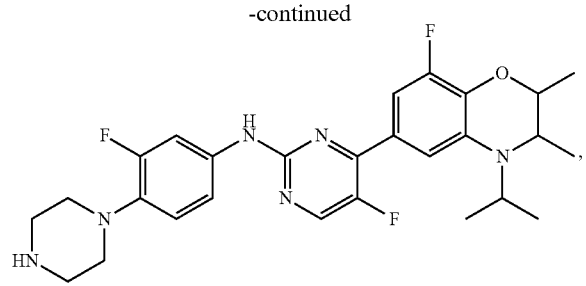
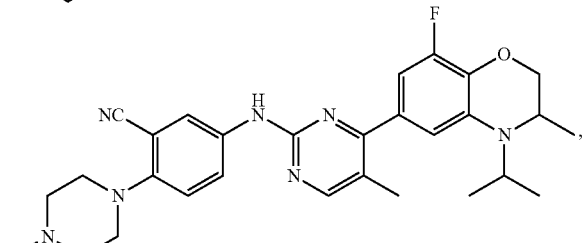
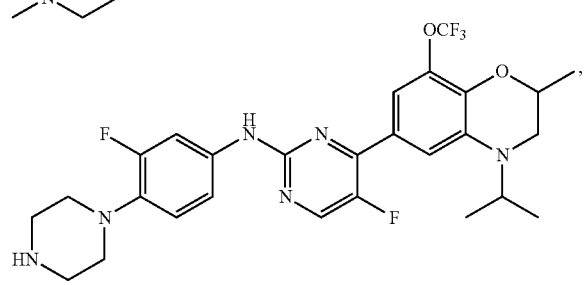
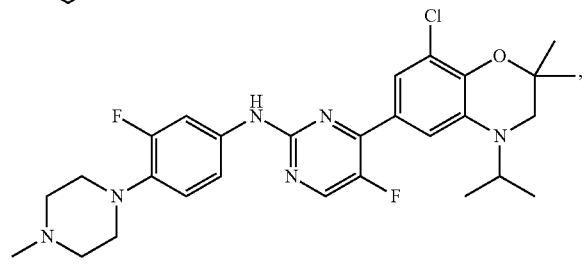
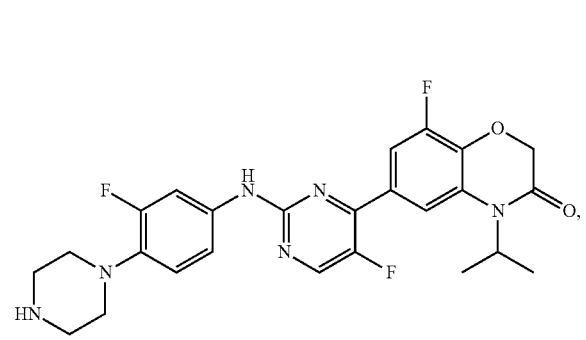
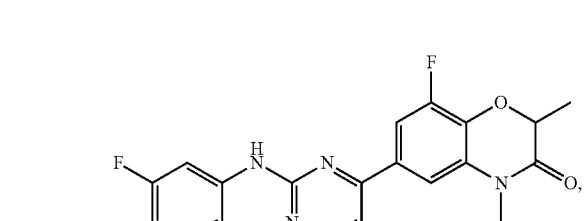
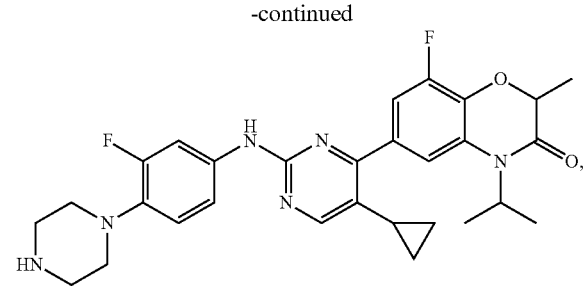
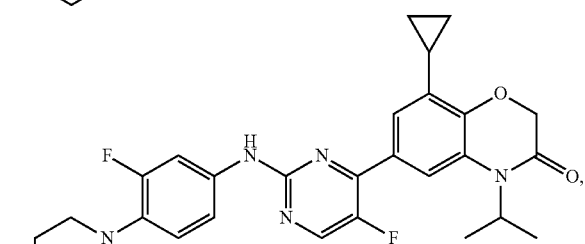
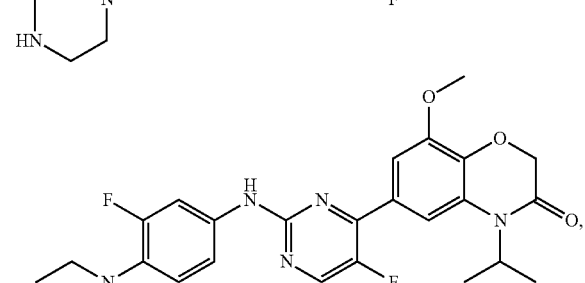
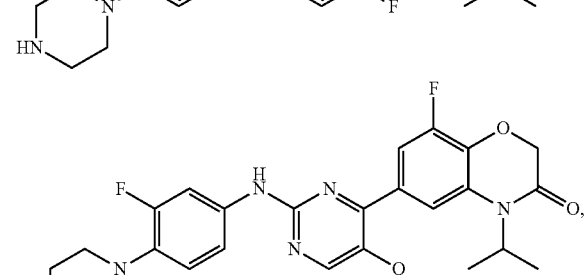
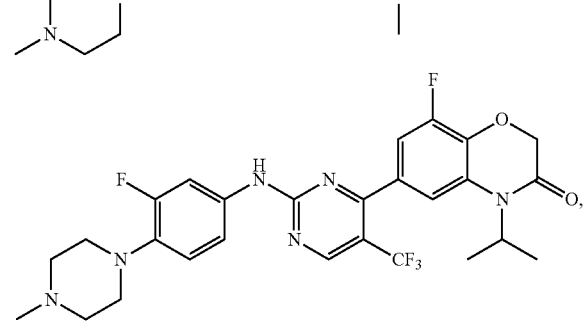
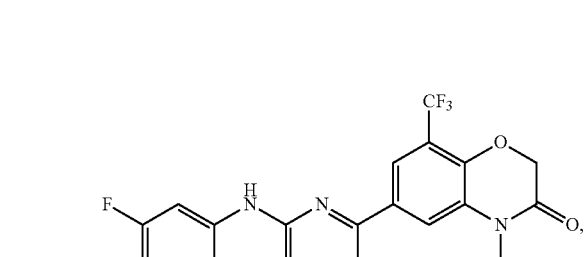

815
-continued
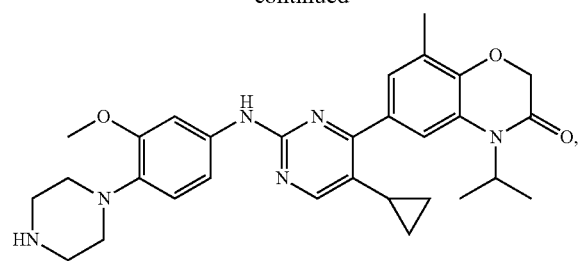
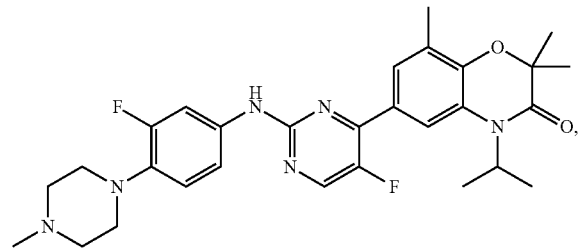
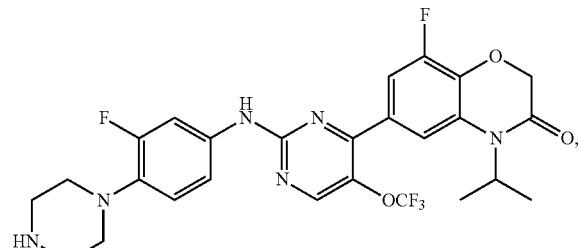
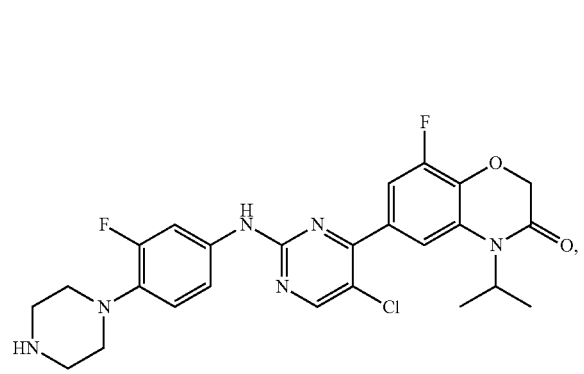
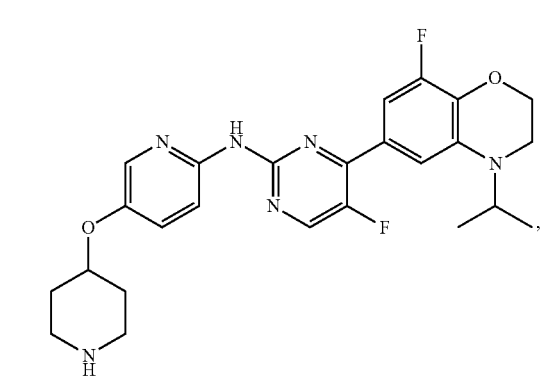
816
-continued
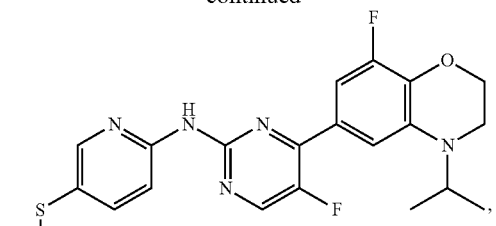
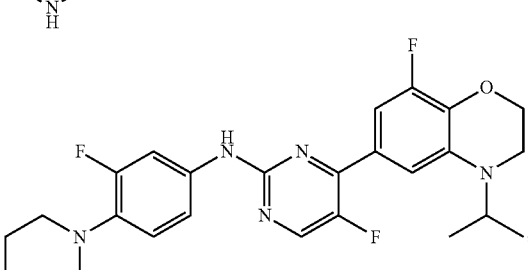
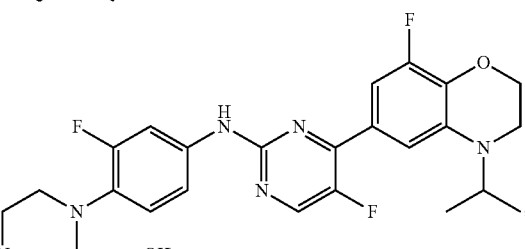
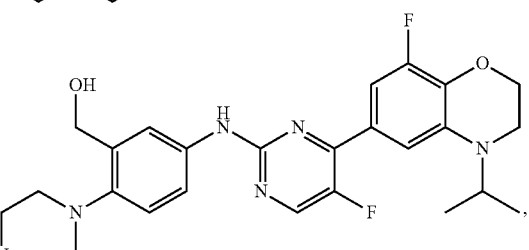
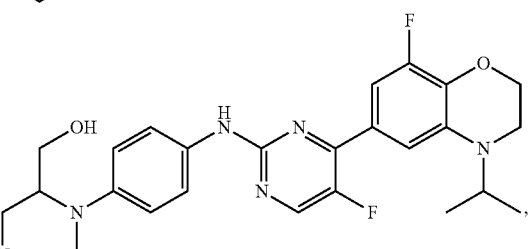
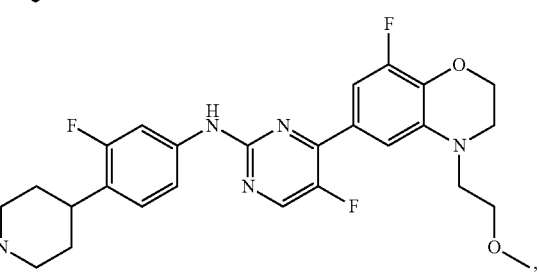

817
-continued
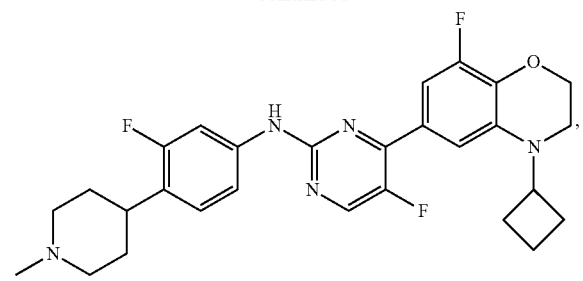
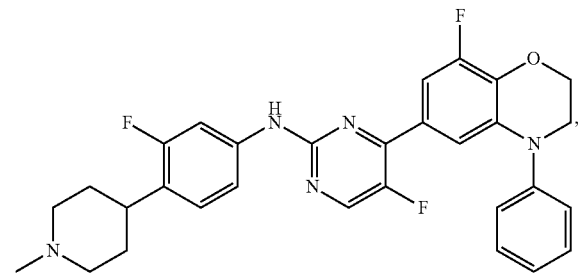
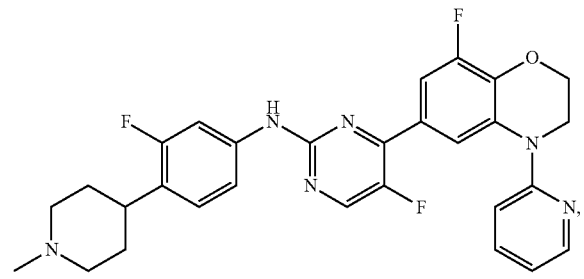
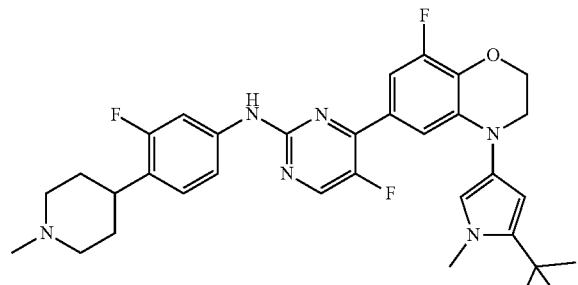
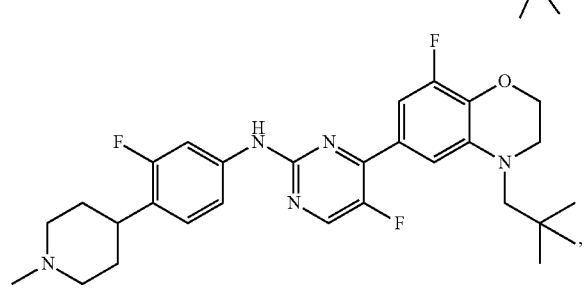
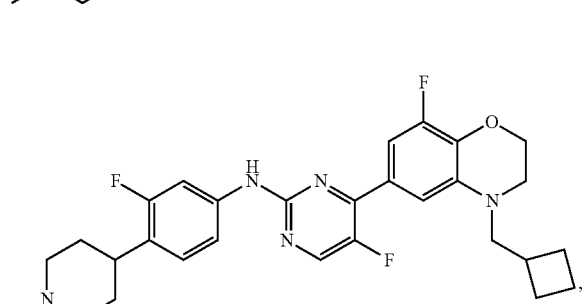
818
-continued
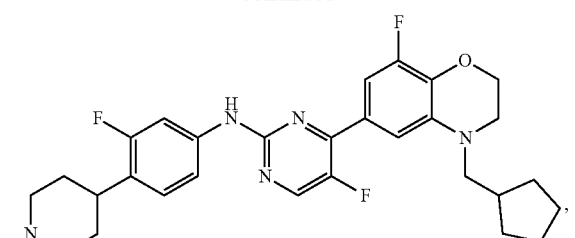
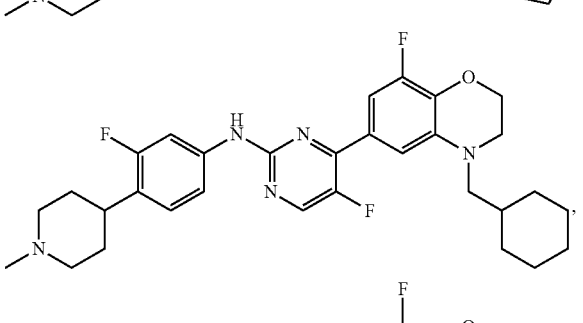
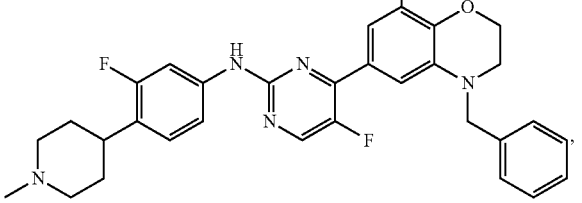
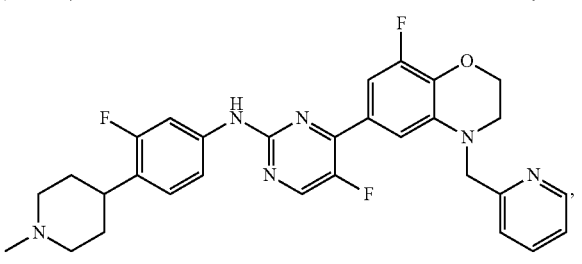
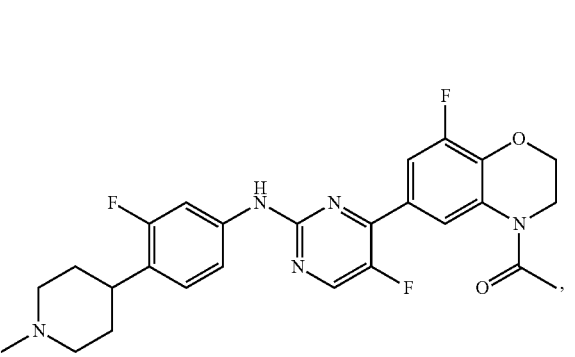
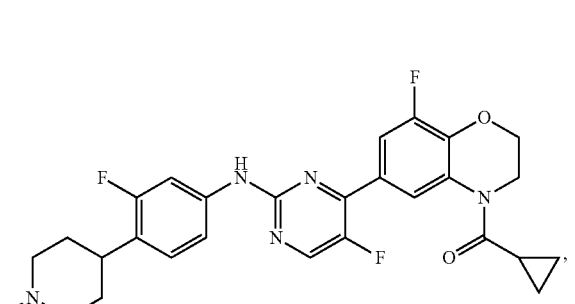

819
-continued
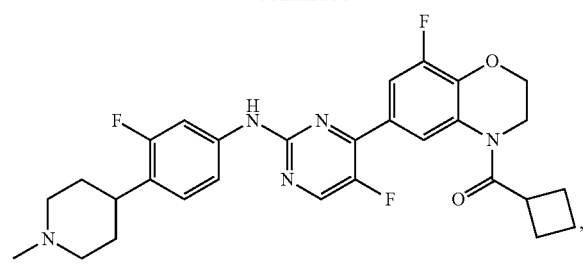
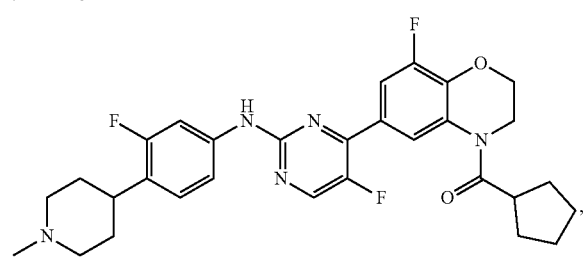
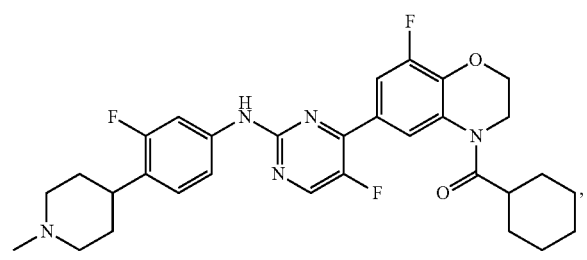
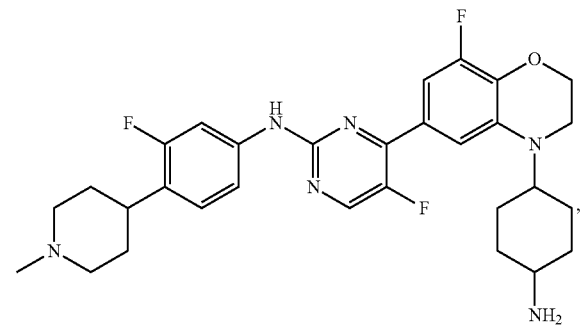
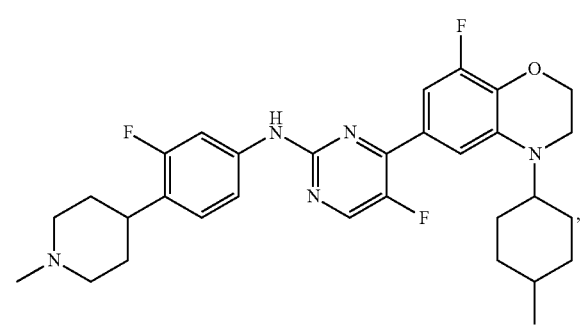
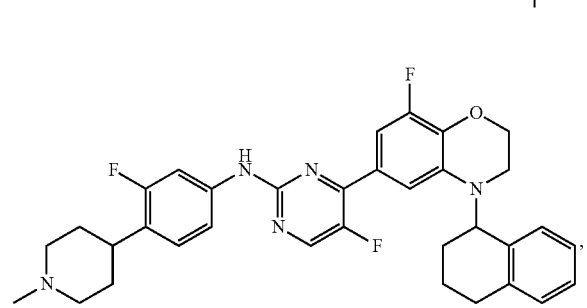
820
-continued
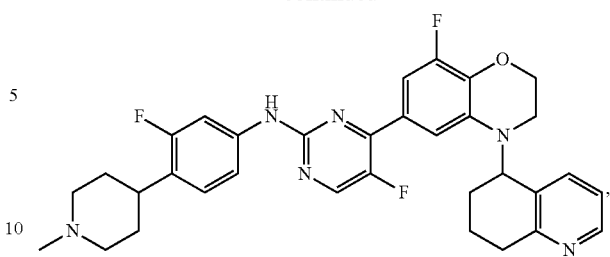
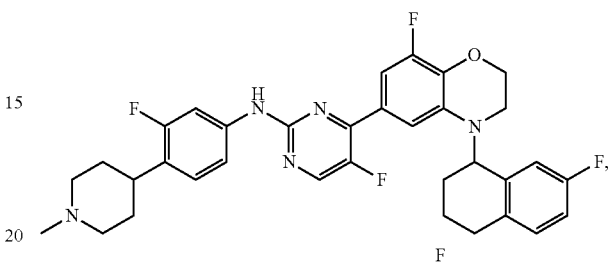
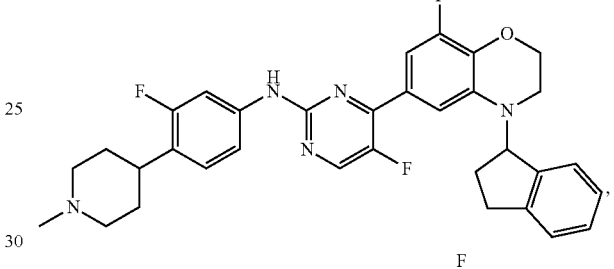
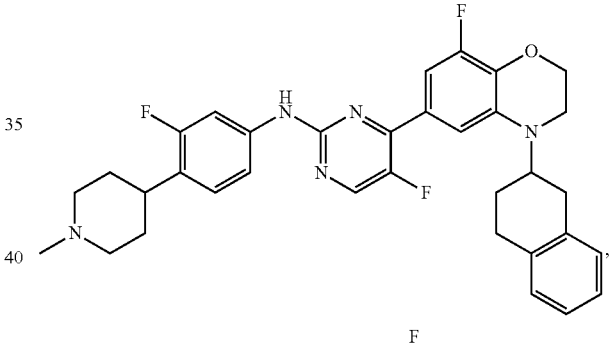
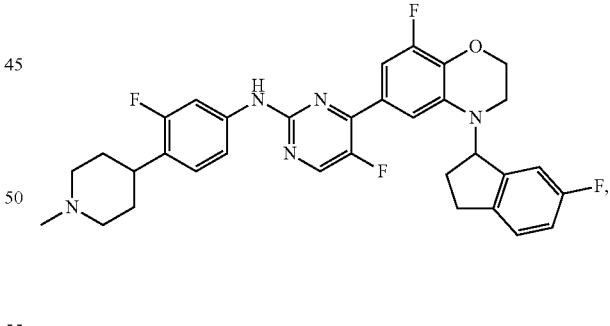
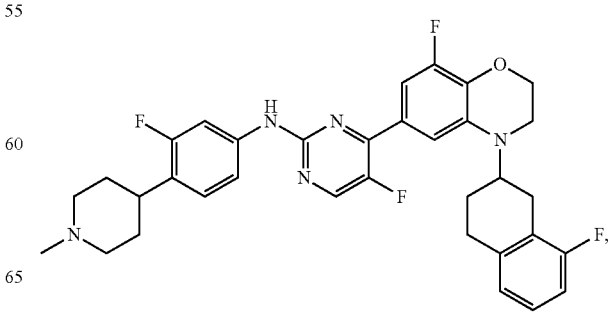

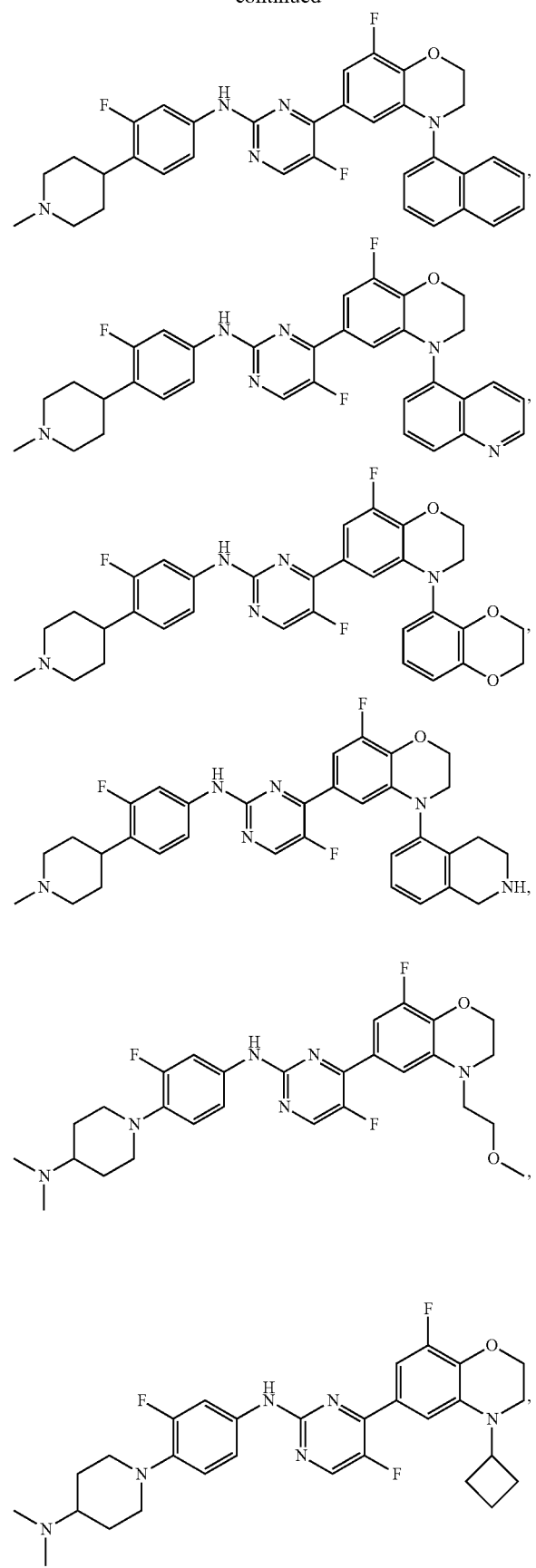
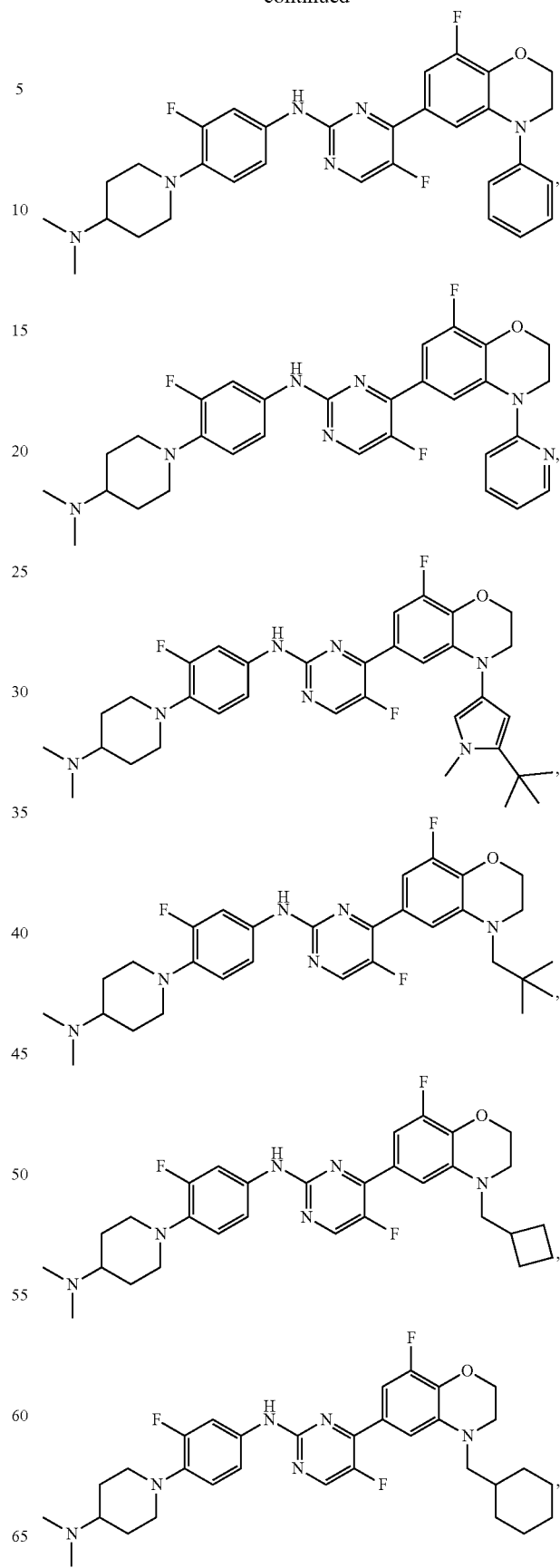

823
-continued
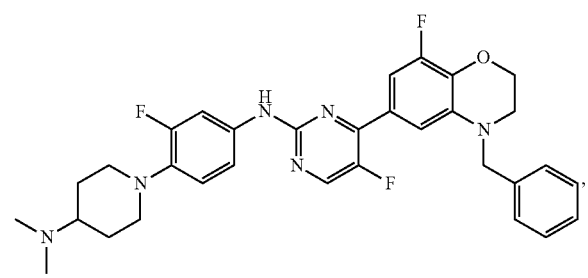
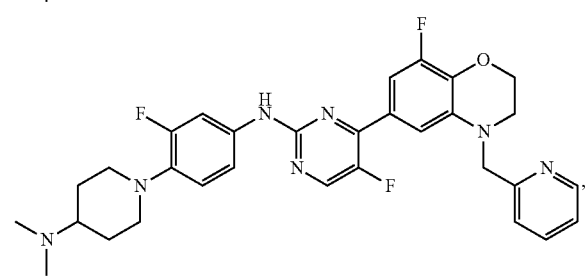
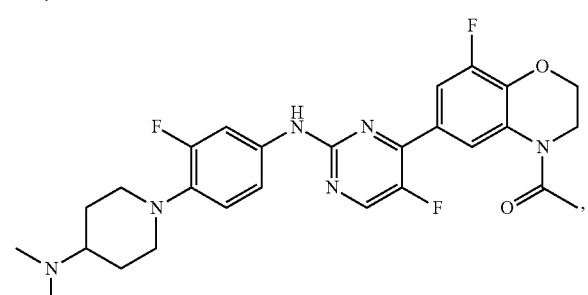
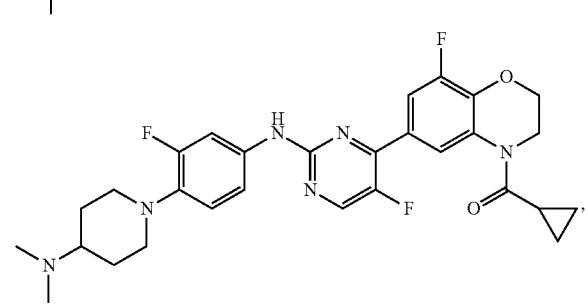
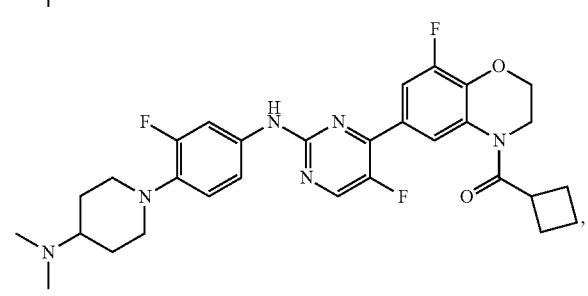
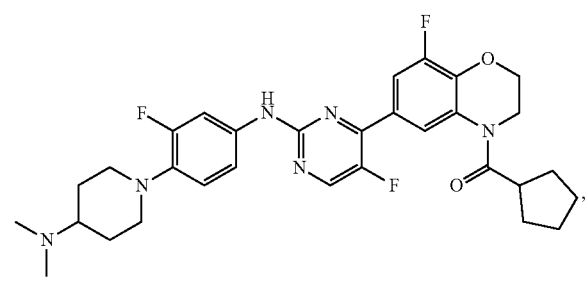
824
-continued
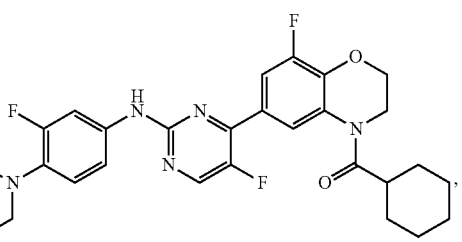
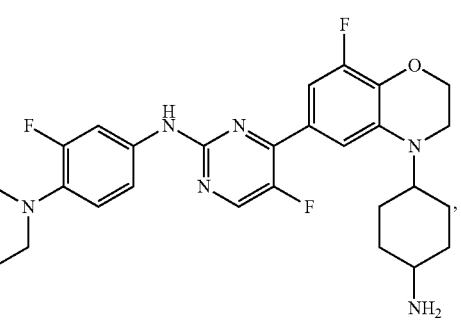
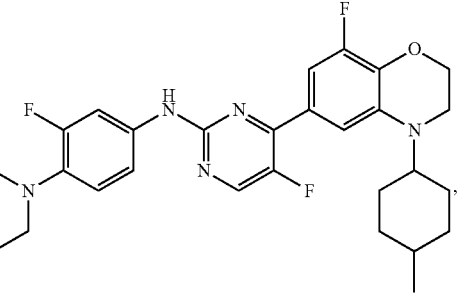
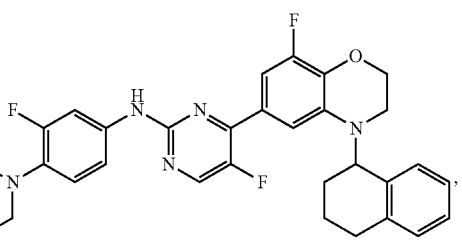
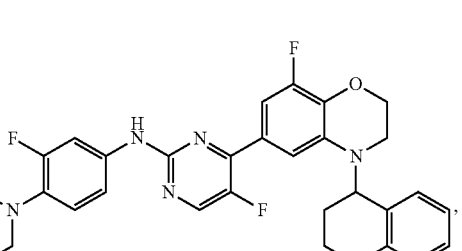
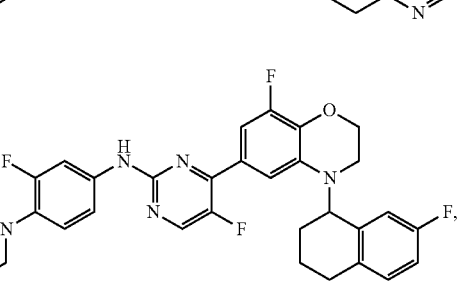

825
-continued
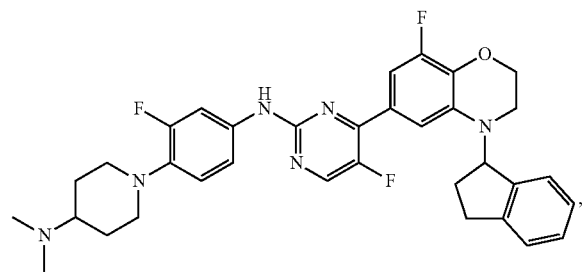
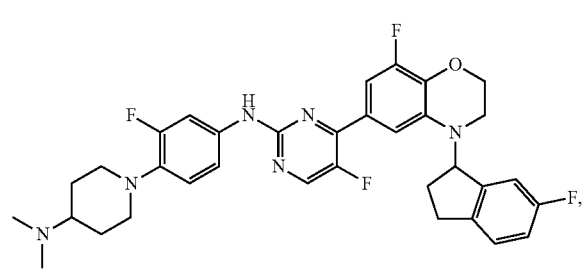
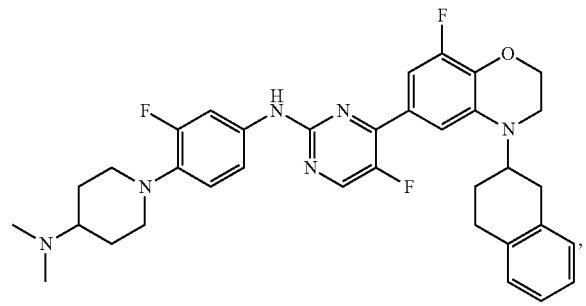
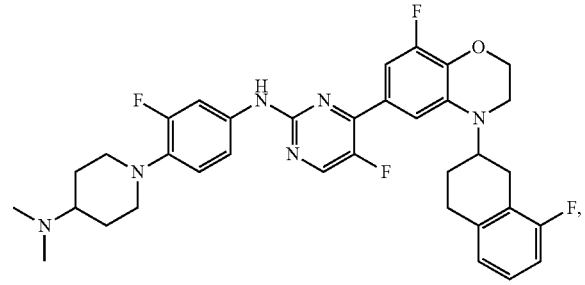
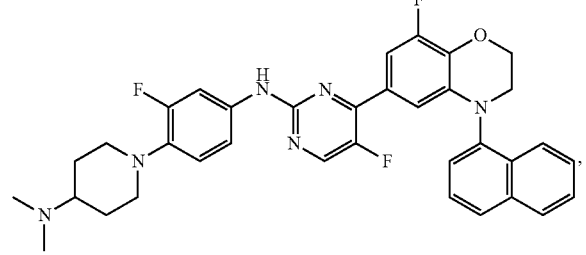
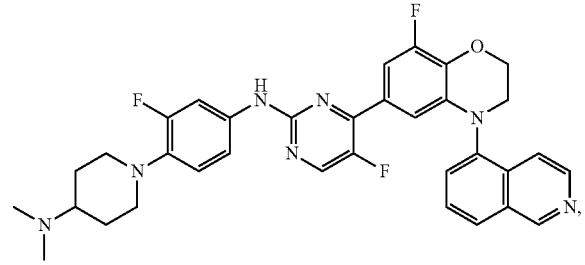
826
-continued
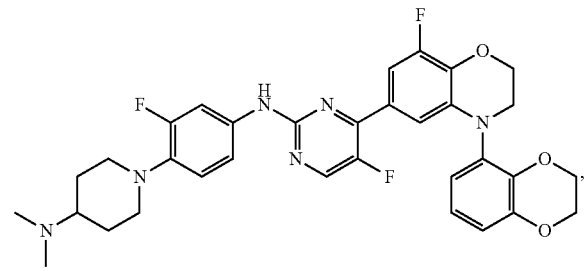
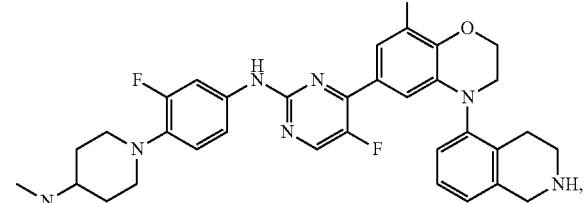
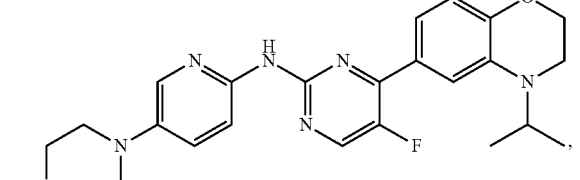
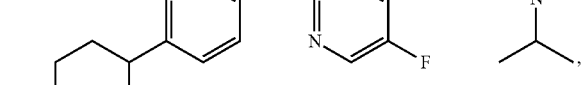
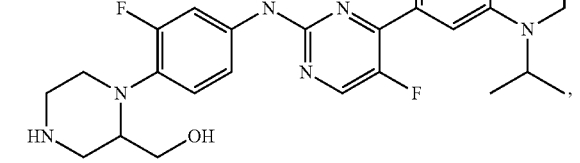
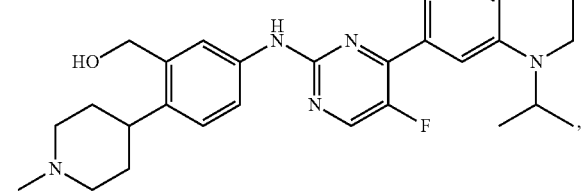

827
-continued
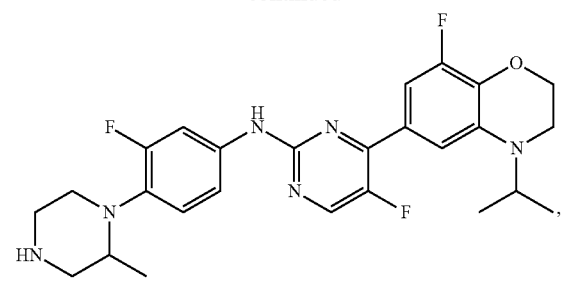
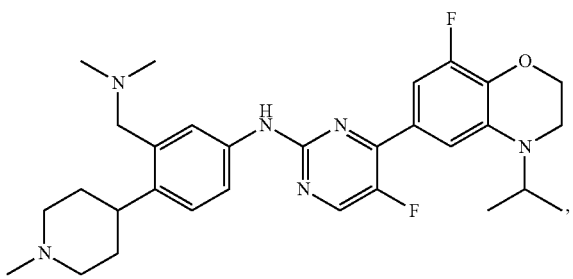
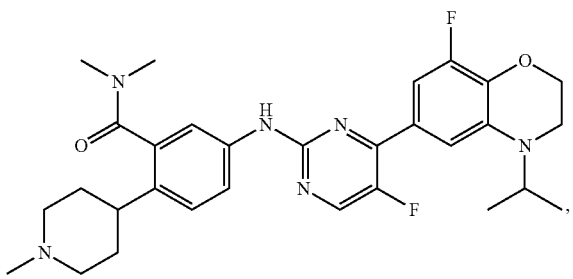
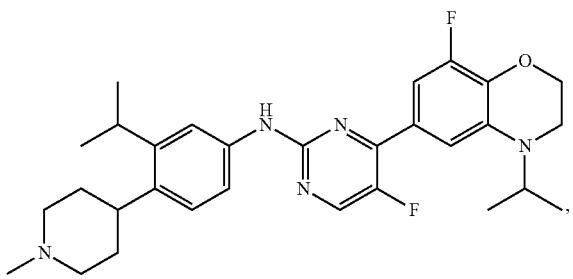
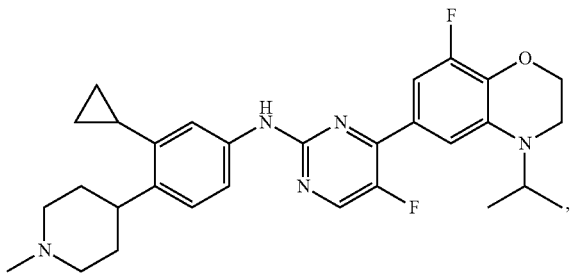
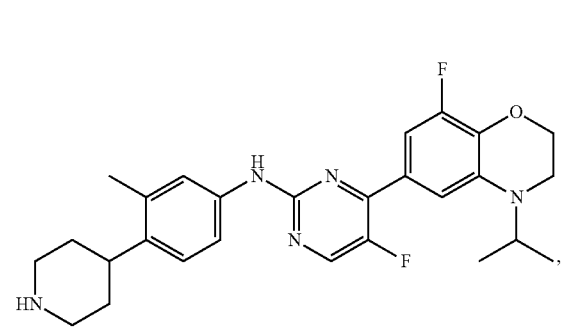
828
-continued
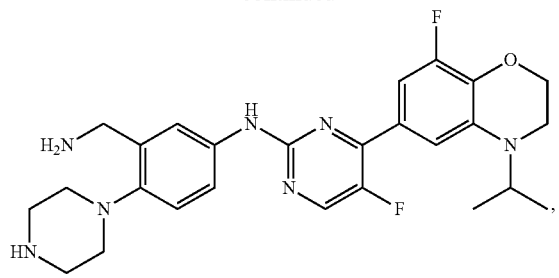
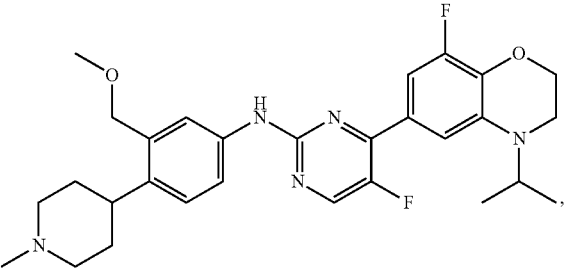
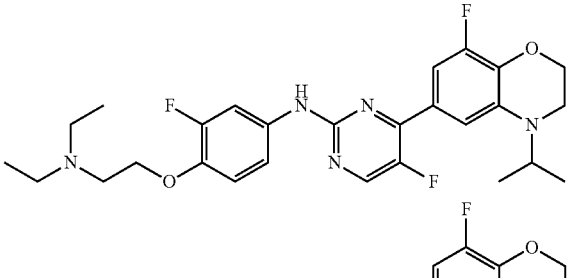
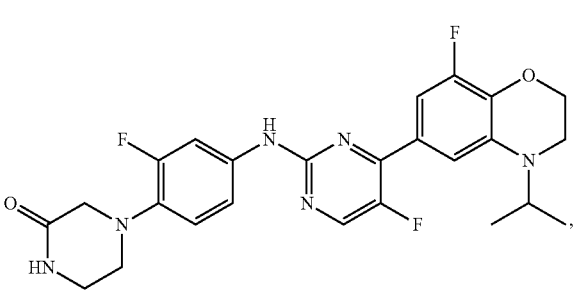

829
-continued
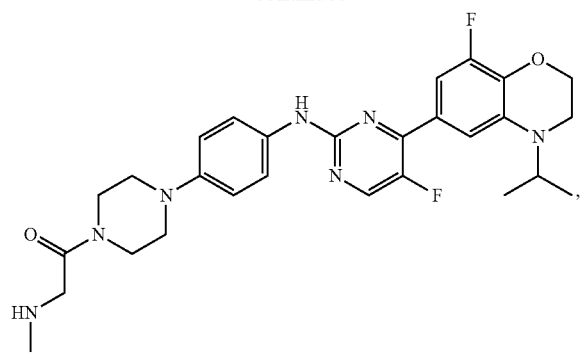
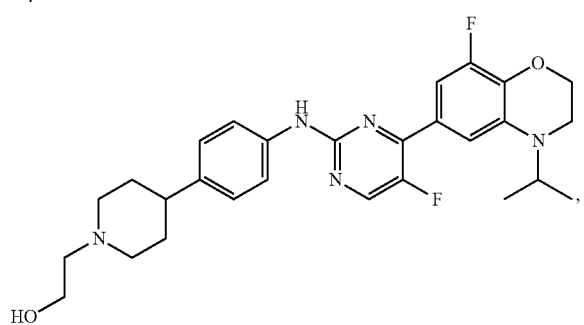
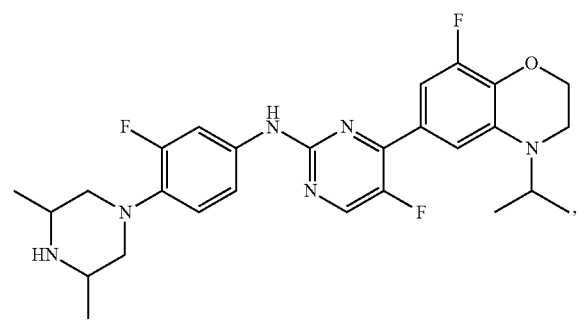
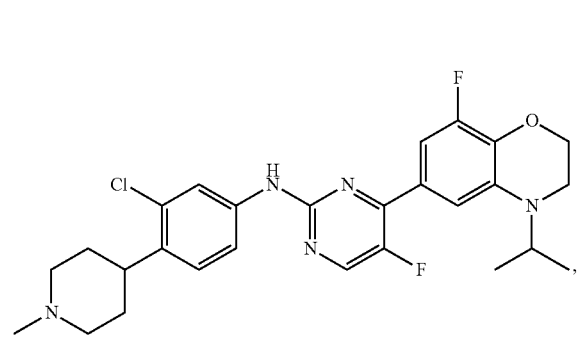 [SMILES: CC(C)N1CCOc2c(F)cc(-c3nc(Nc4ccc(C5CCN(C)CC5)c(F)c4)ncc3F)cc21]
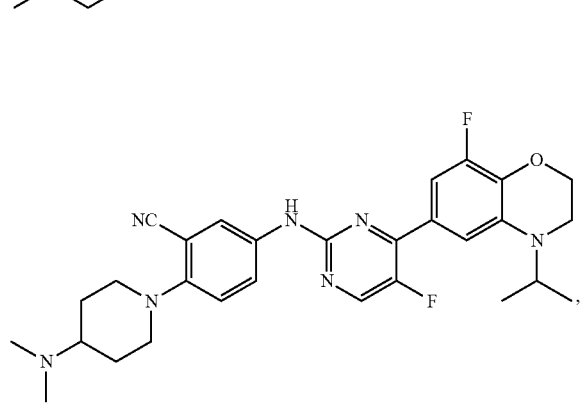
830
-continued
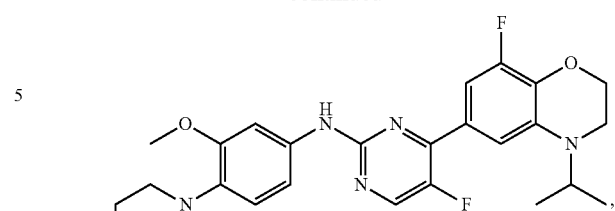
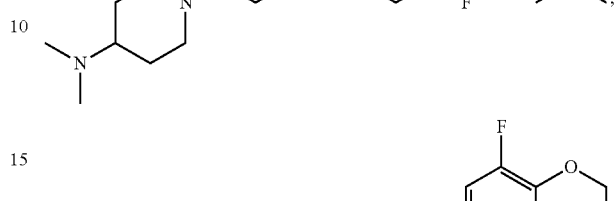
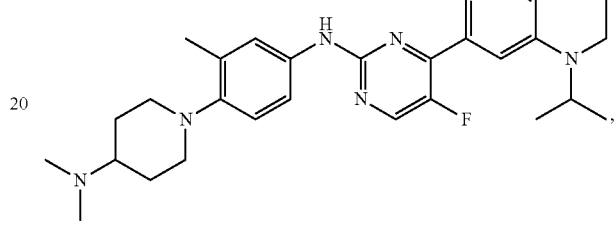
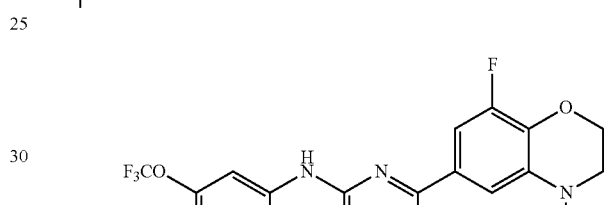
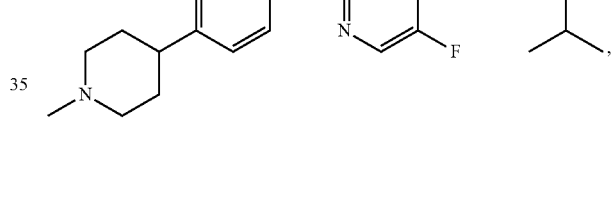
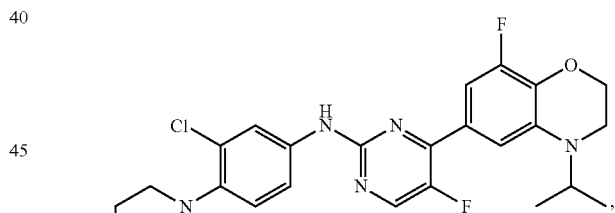

831
-continued
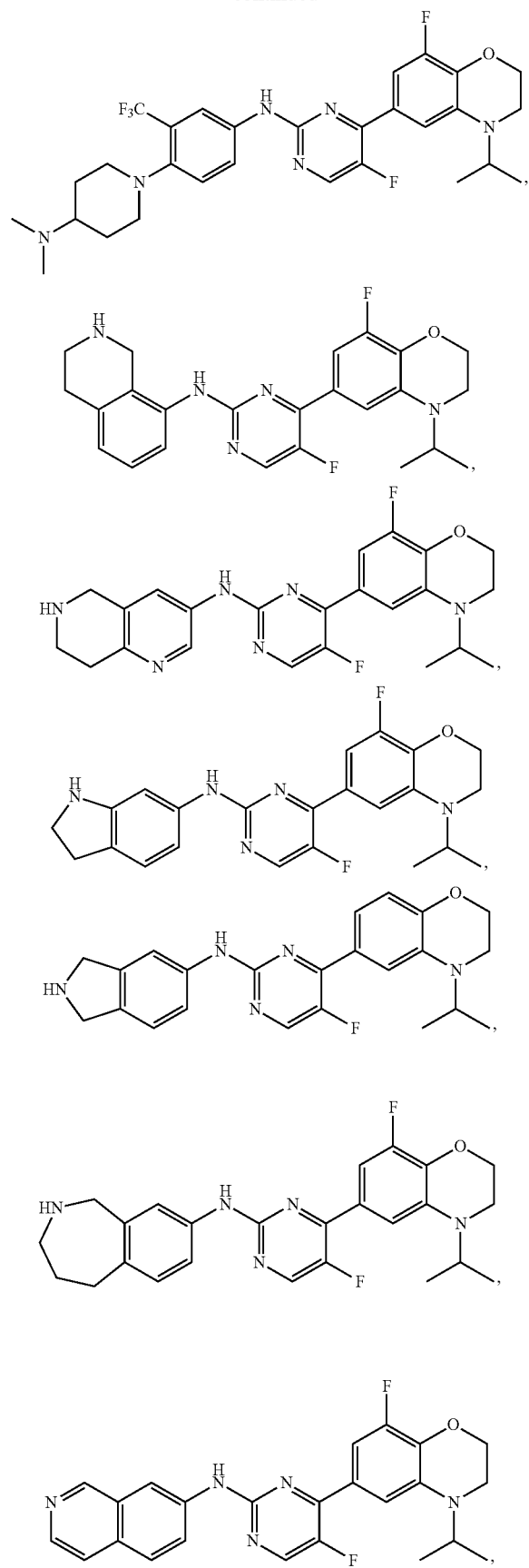
832
-continued
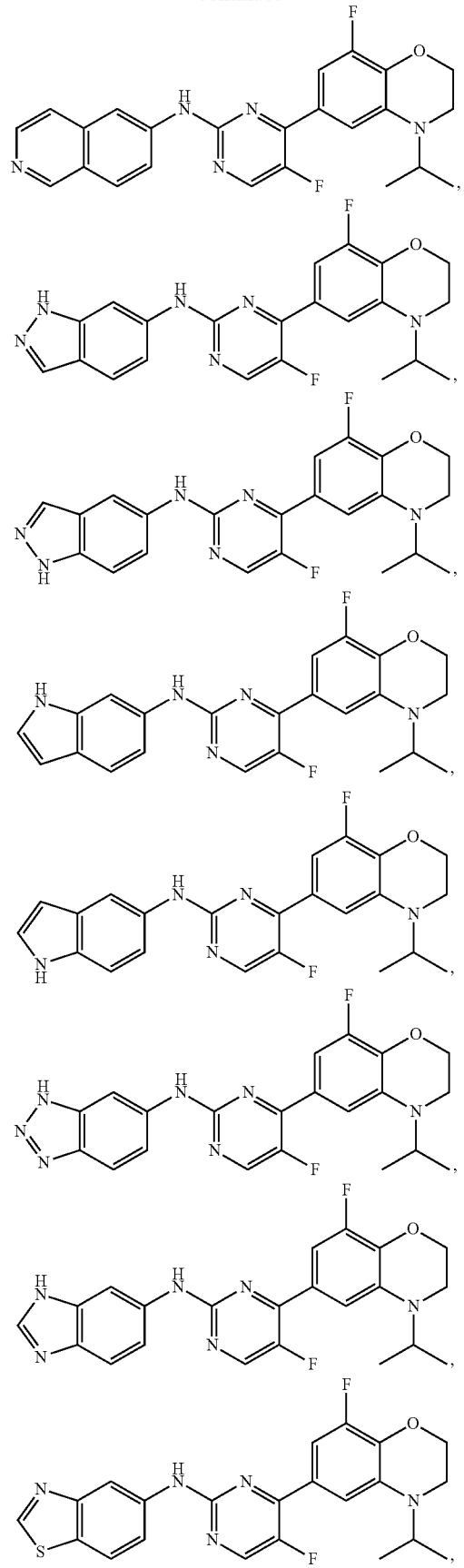

833
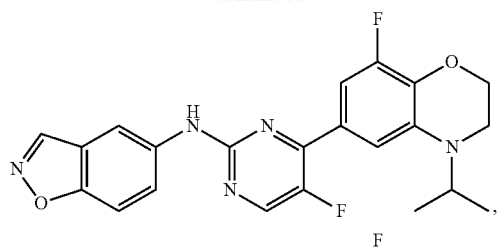
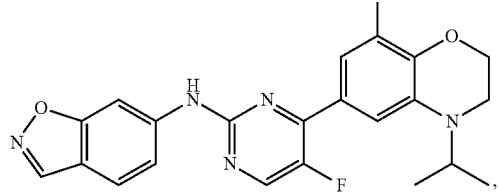
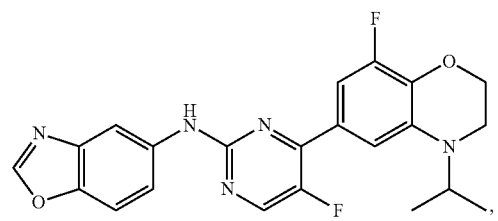
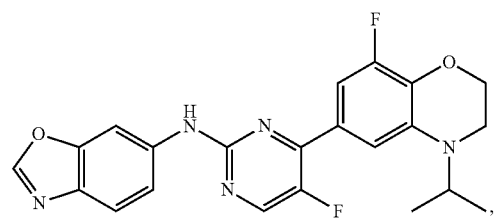
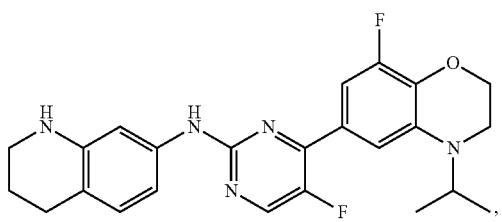
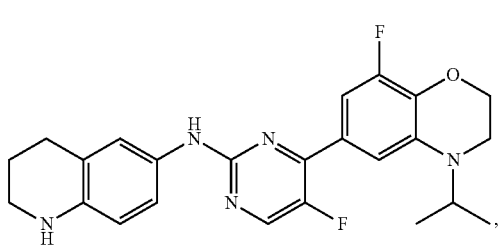
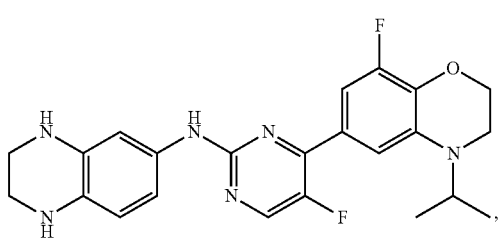
834
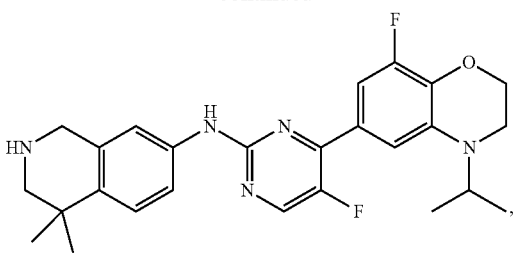
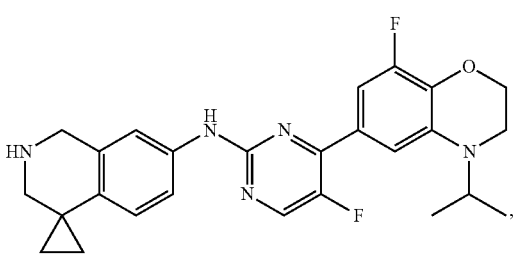
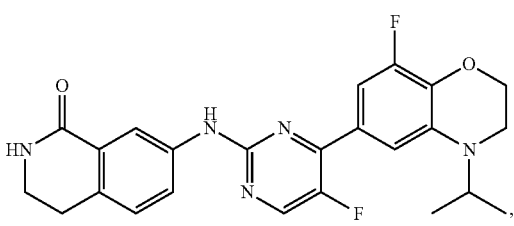
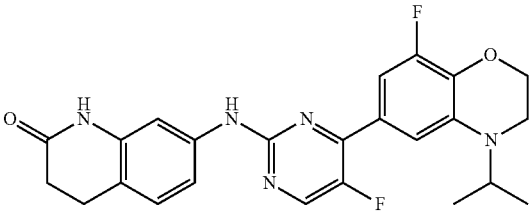
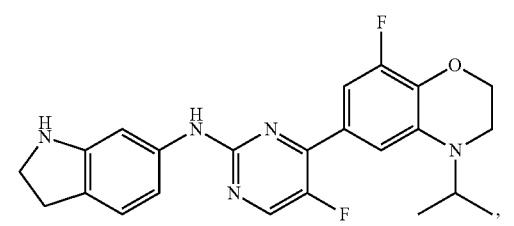
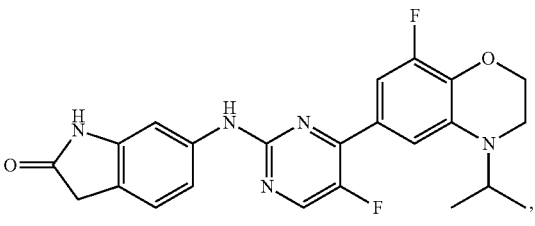

835
-continued
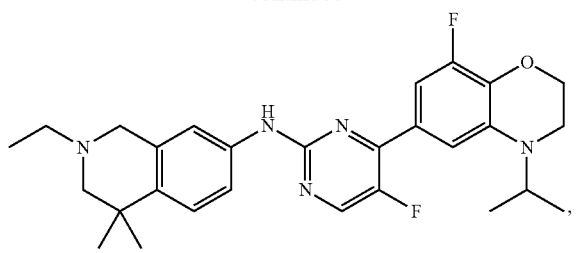
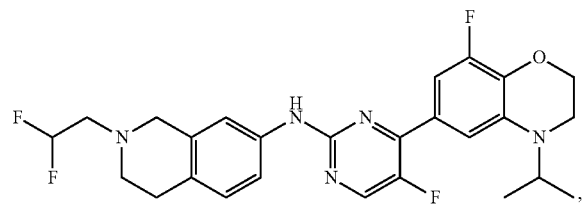
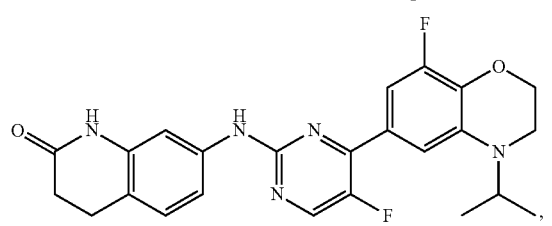
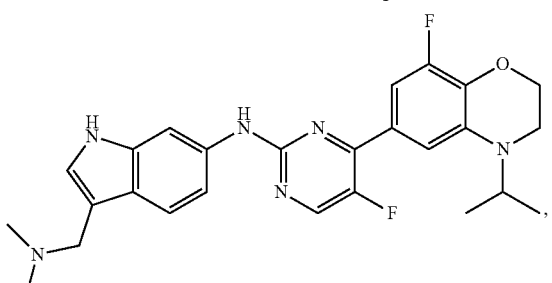
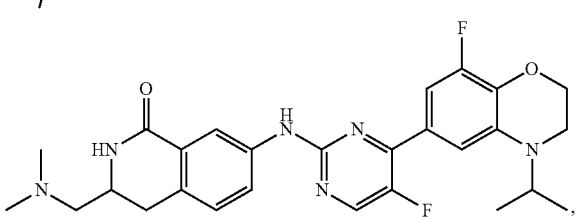
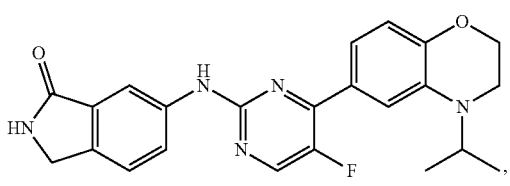
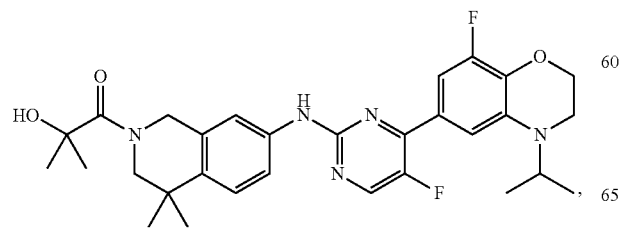
836
-continued
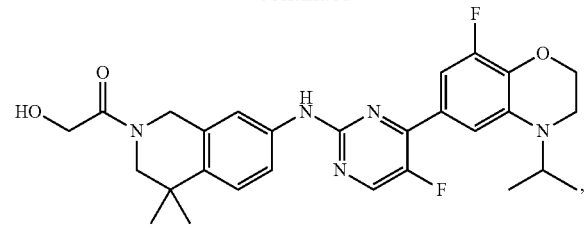
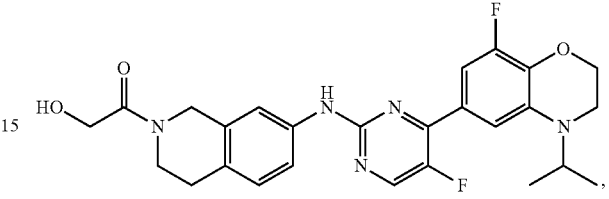
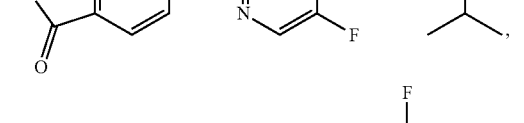
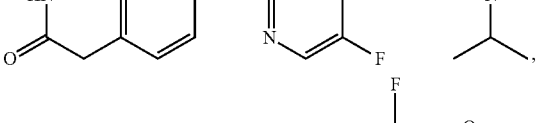
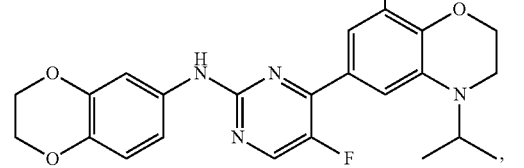
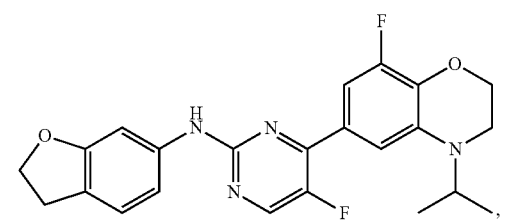

-continued
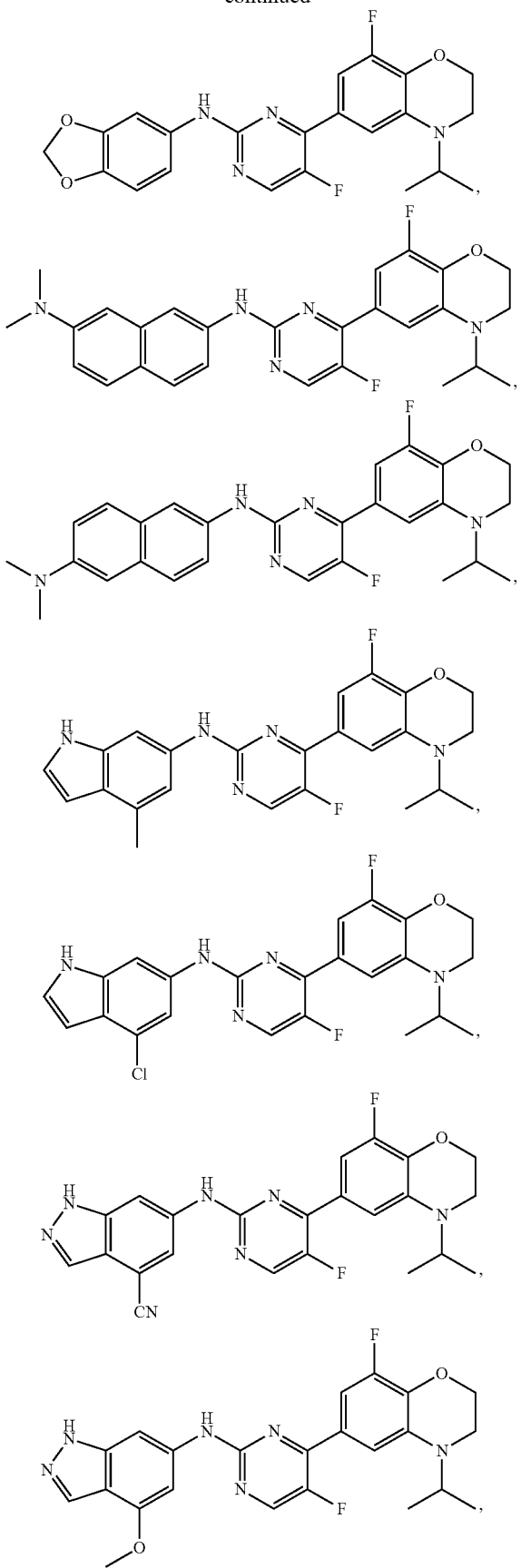
-continued
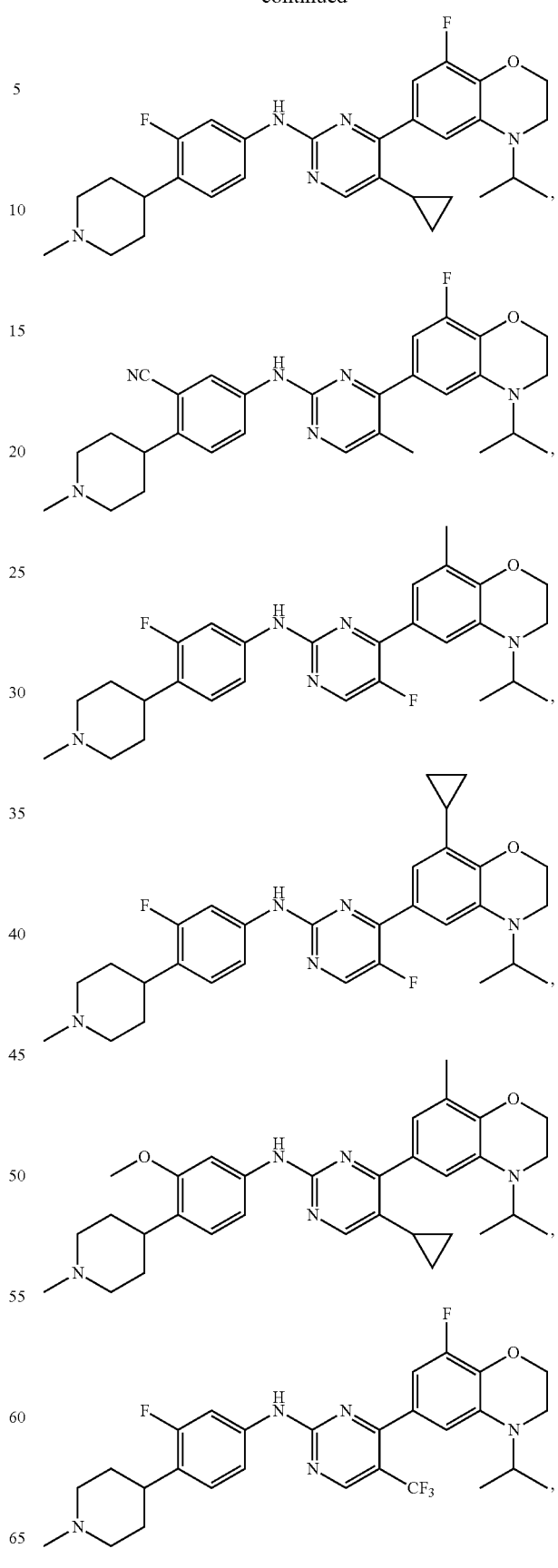

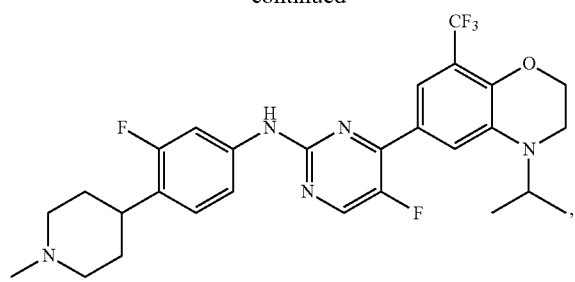
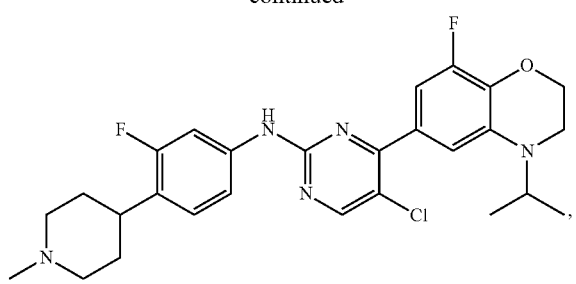
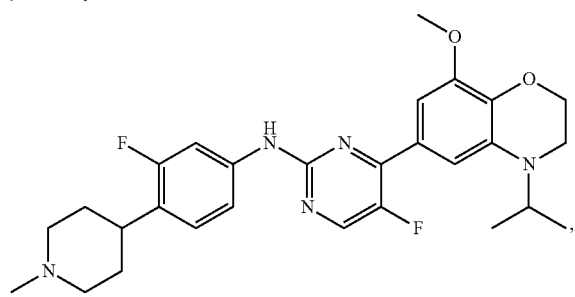
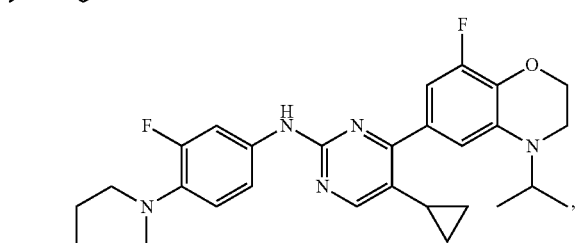
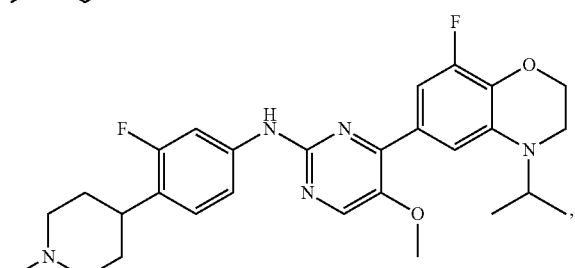
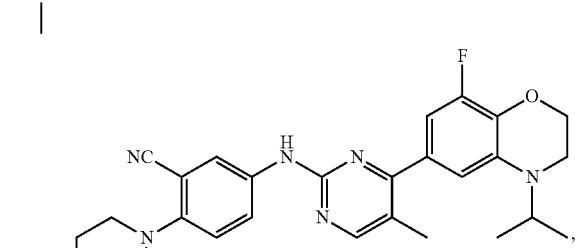
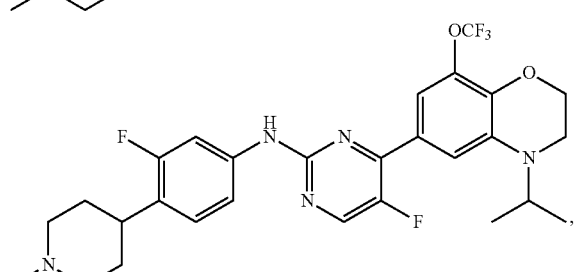
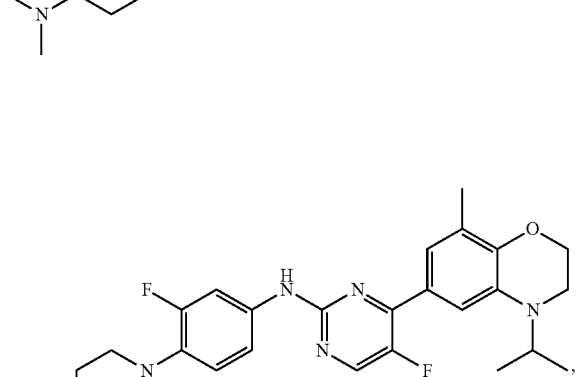
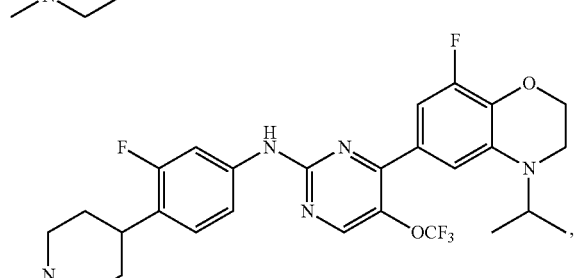
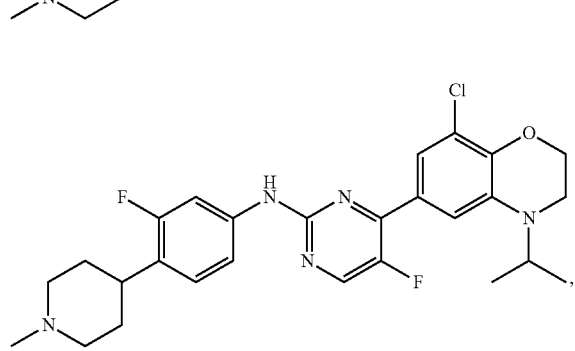
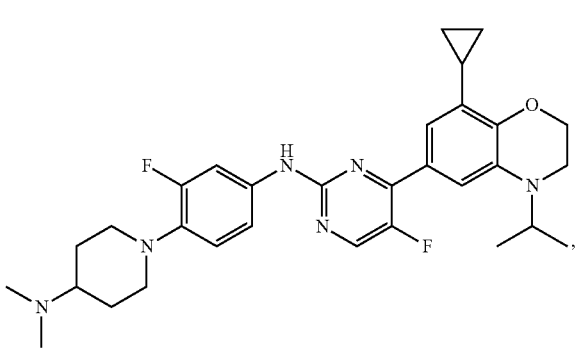

841
-continued
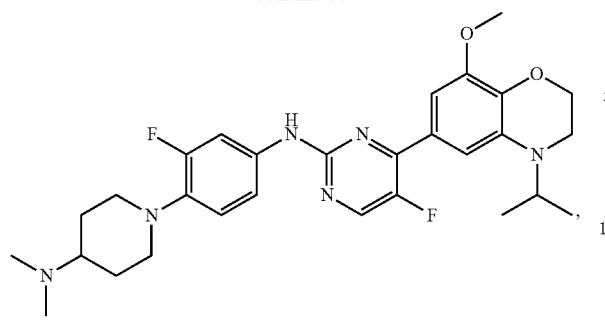
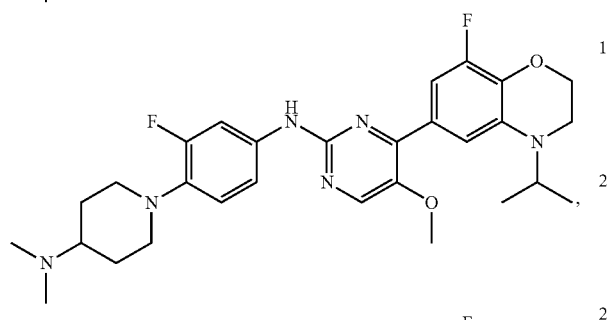
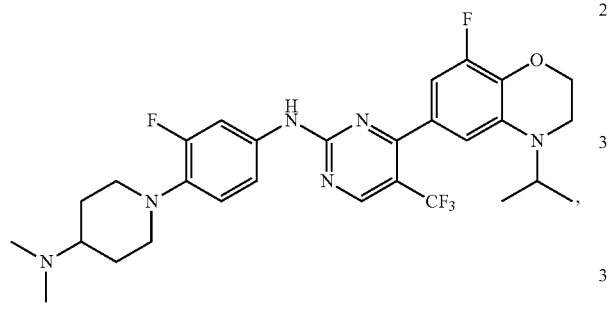
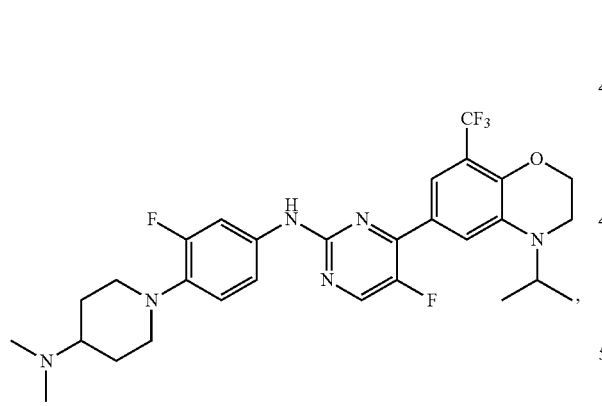
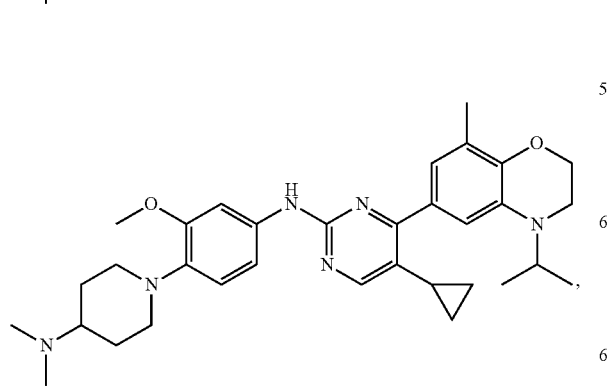
842
-continued
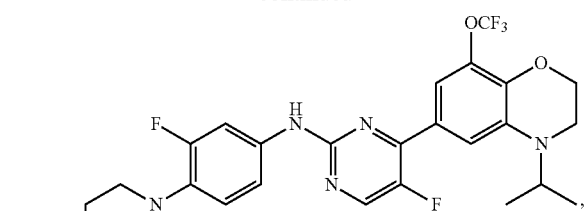
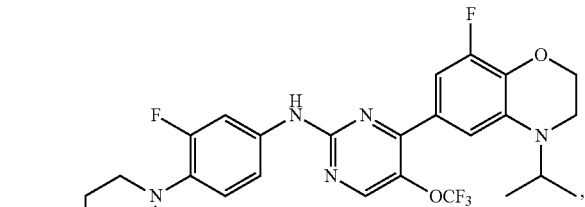
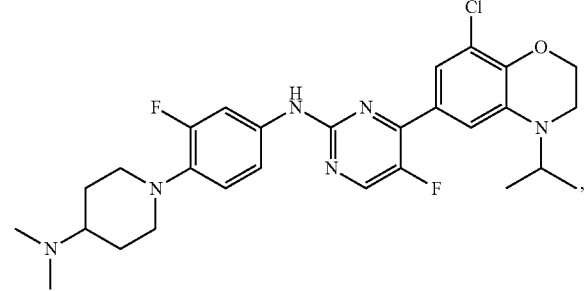
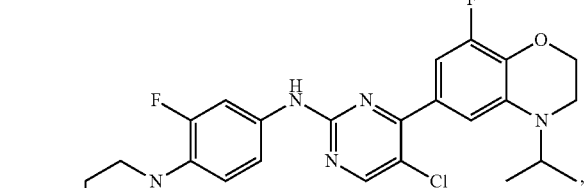
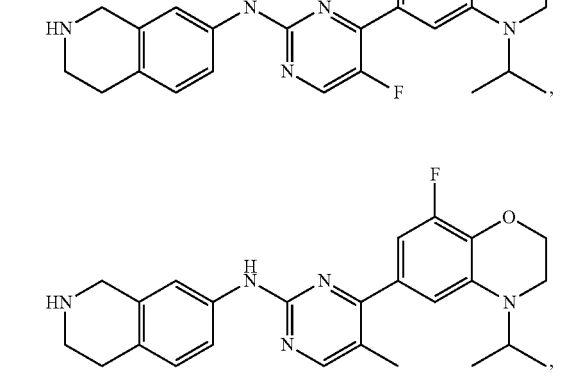

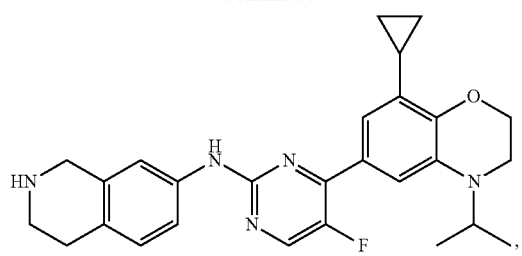
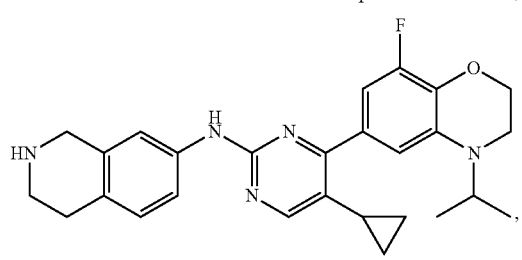
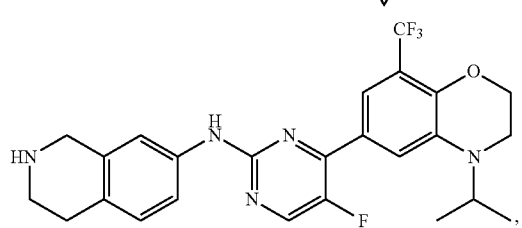
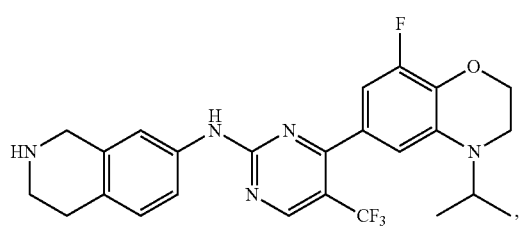
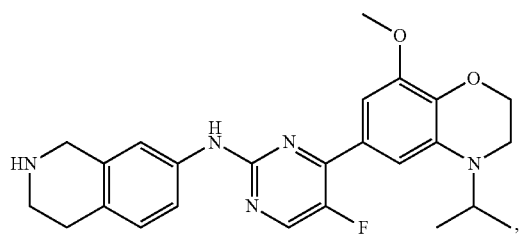
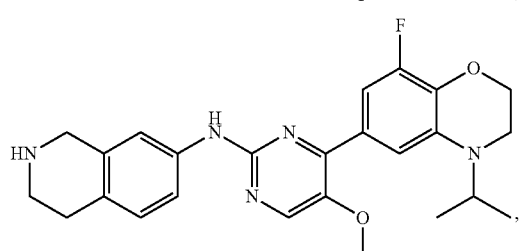
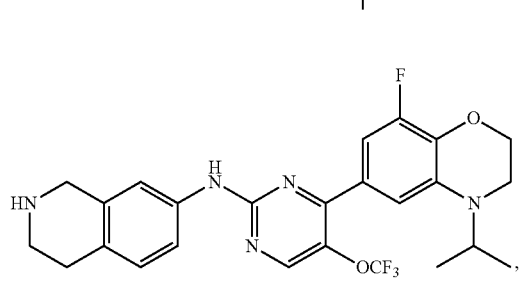
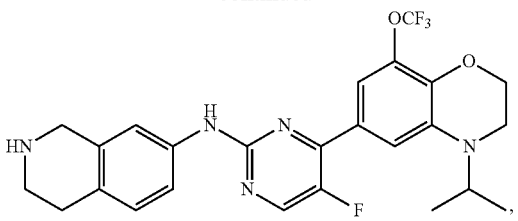
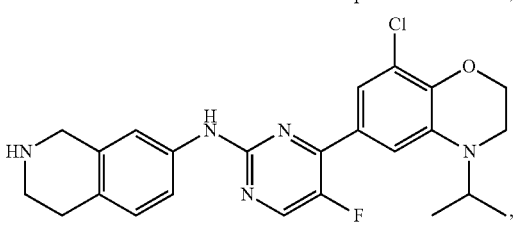
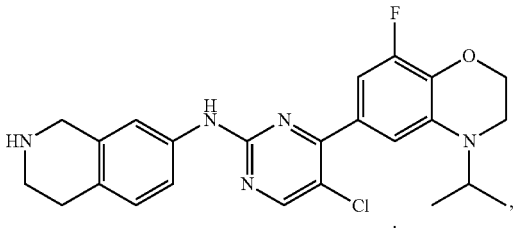
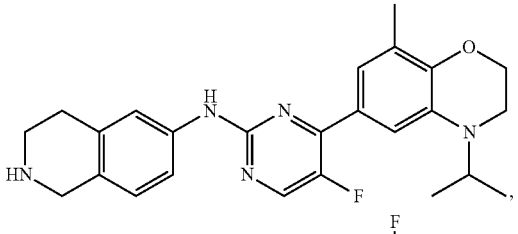
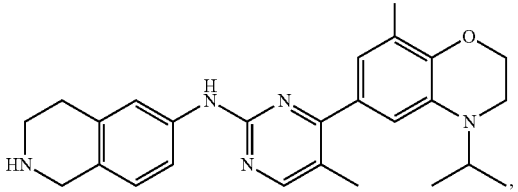
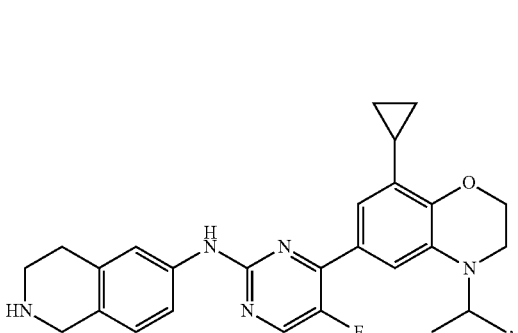
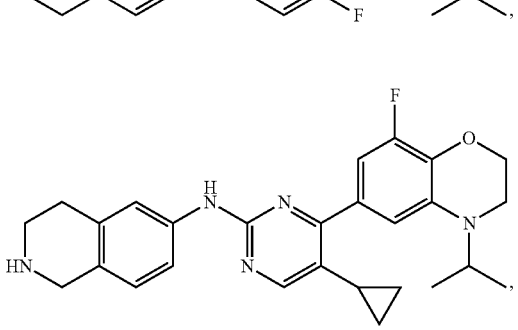

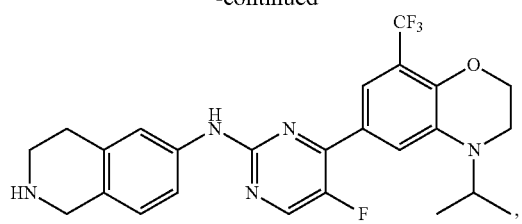
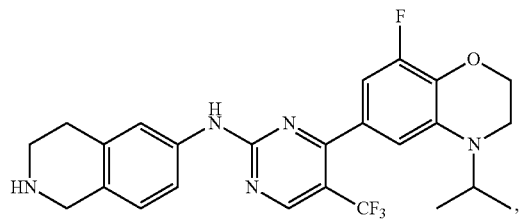
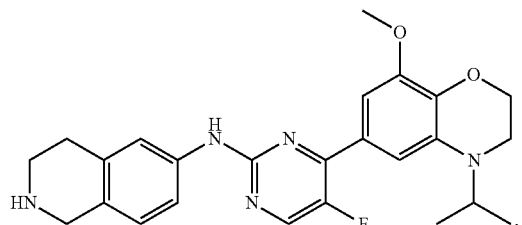
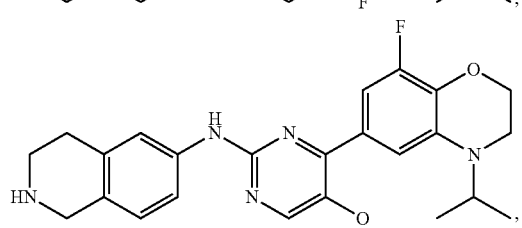
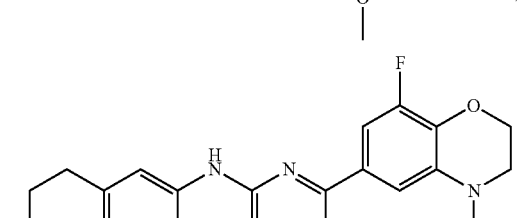
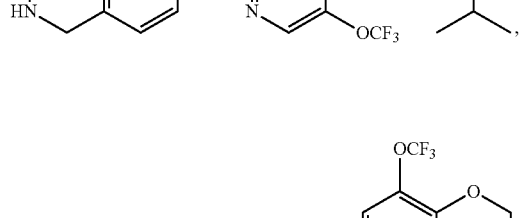
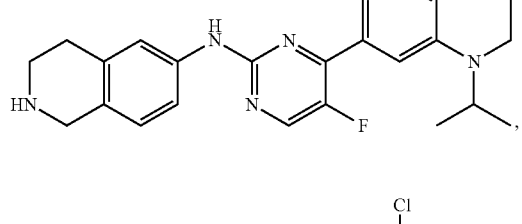
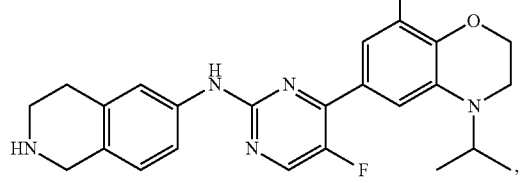
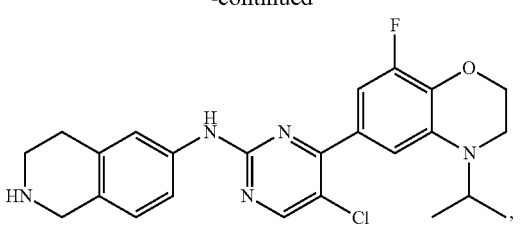
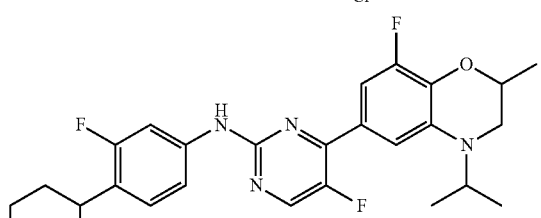
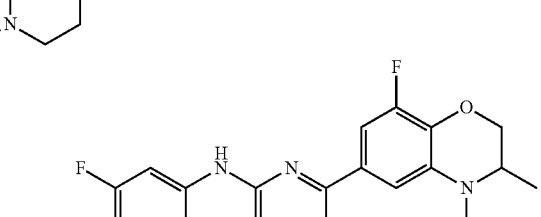
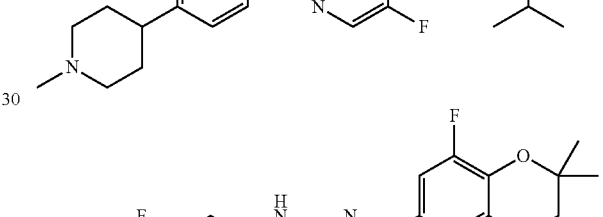
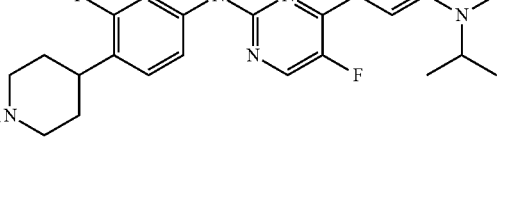
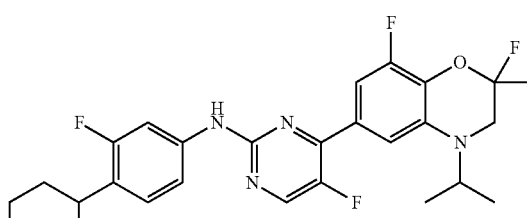
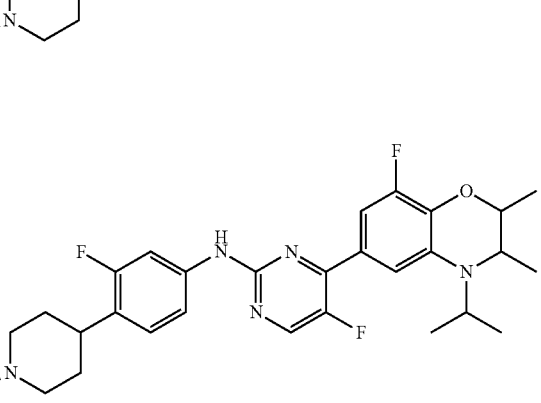

847
-continued
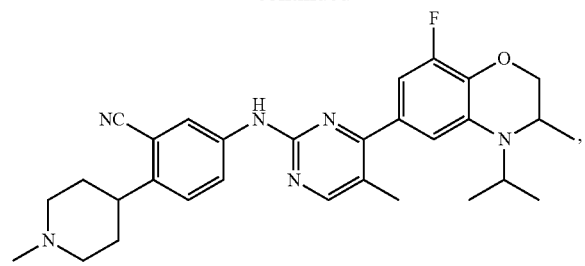
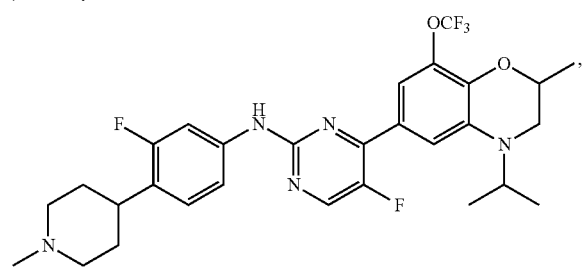
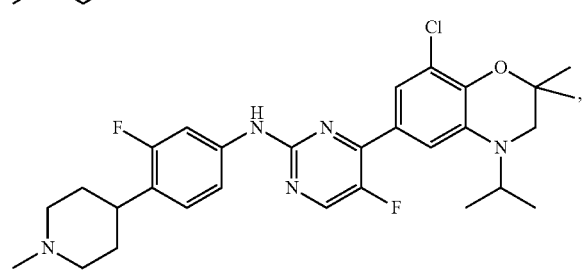
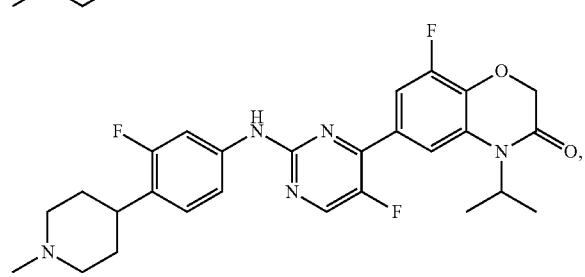
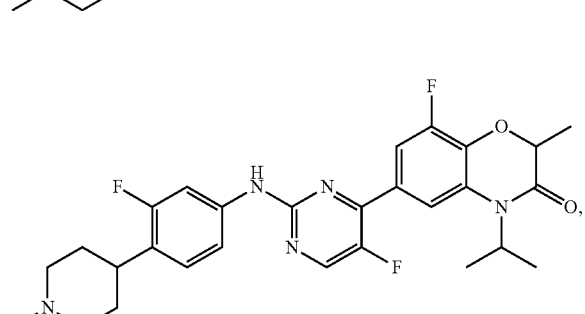
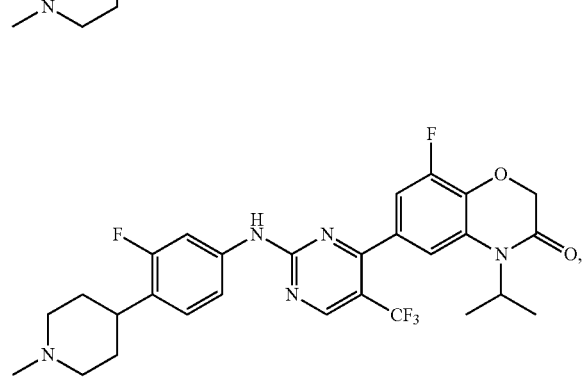
848
-continued
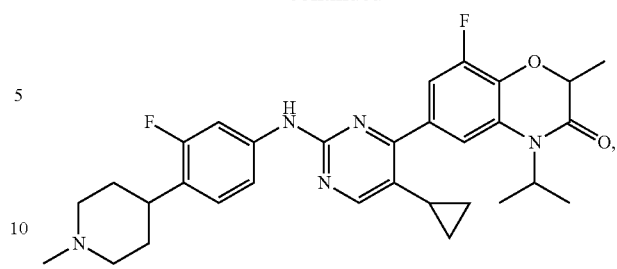
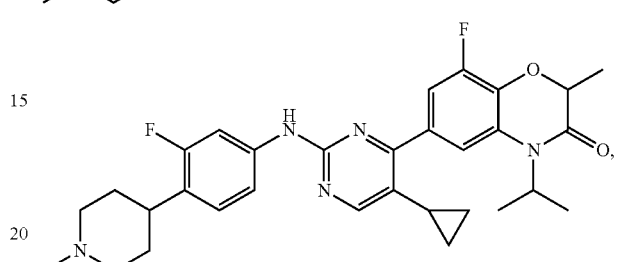
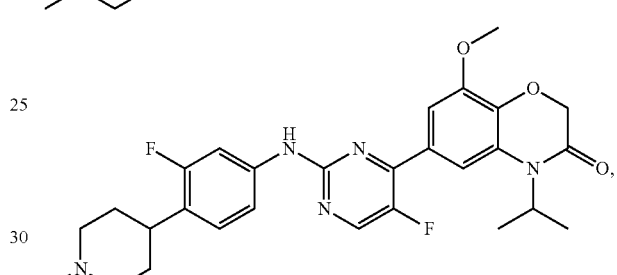
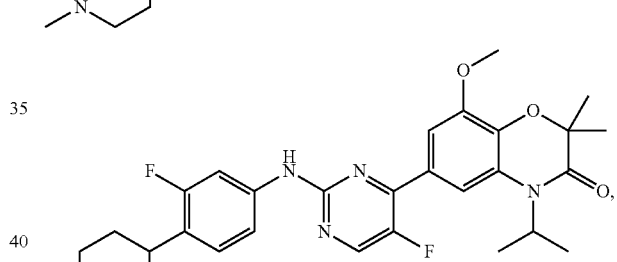
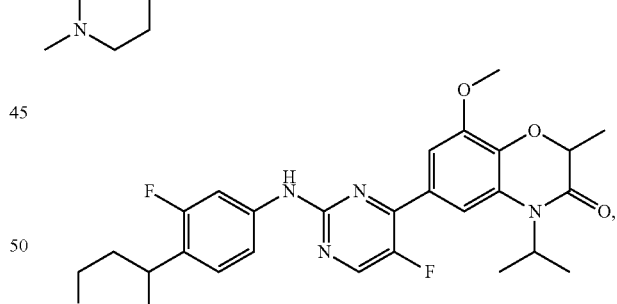
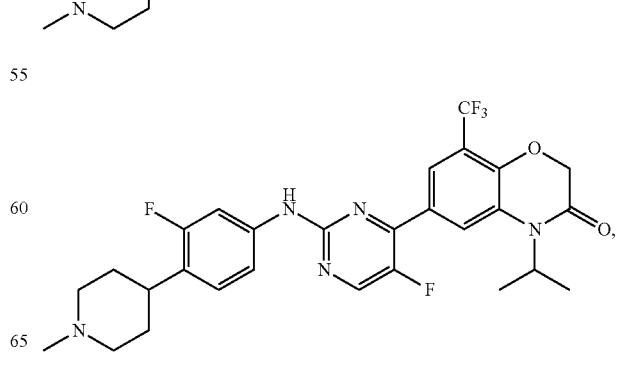

849
-continued
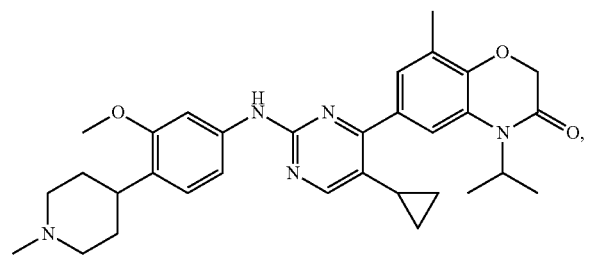
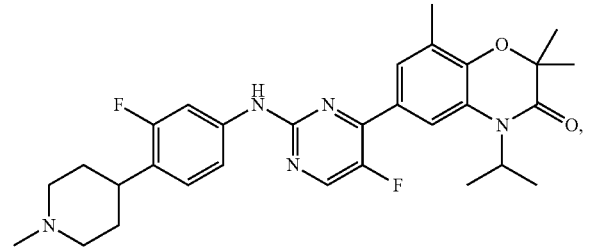
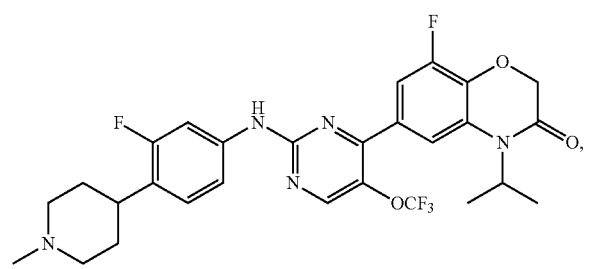
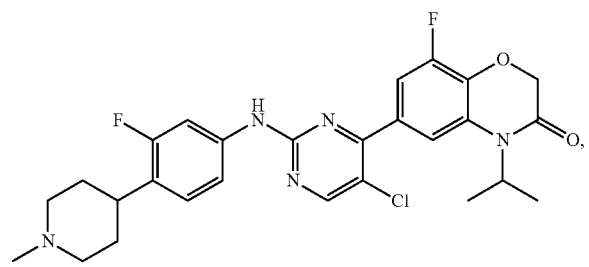
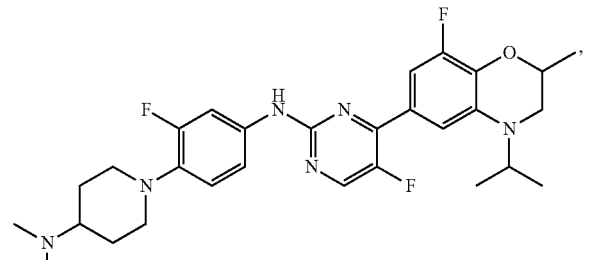
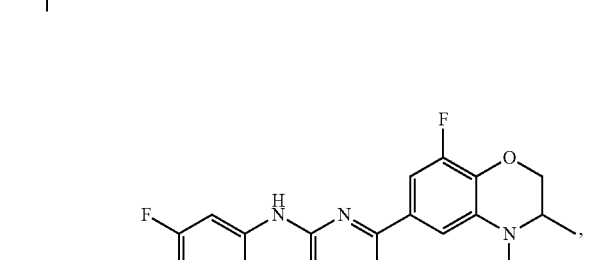
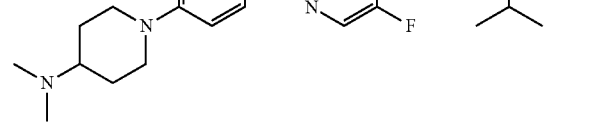
850
-continued
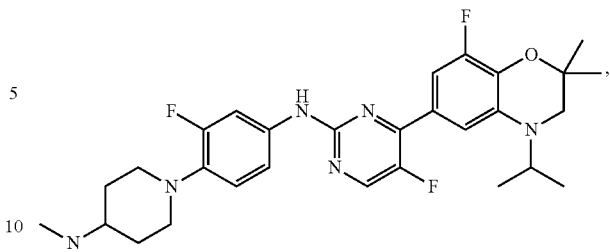
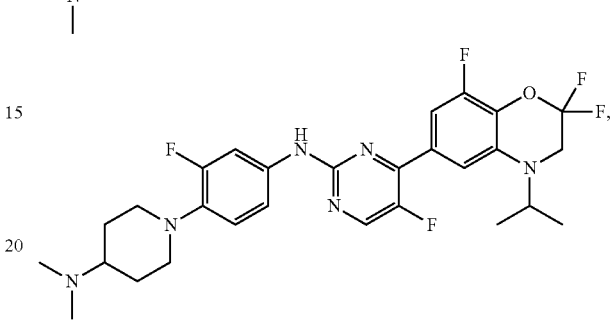
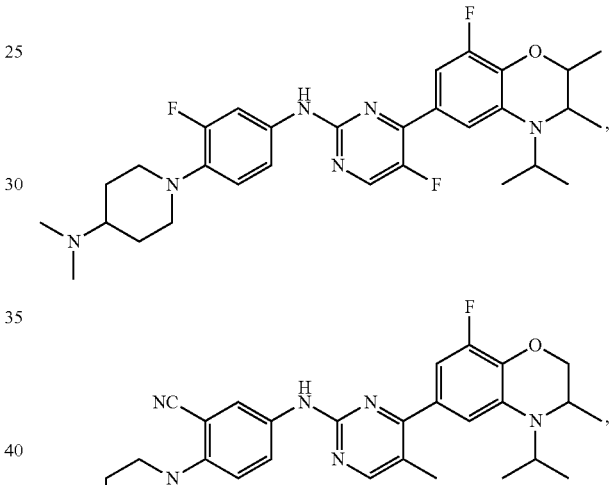
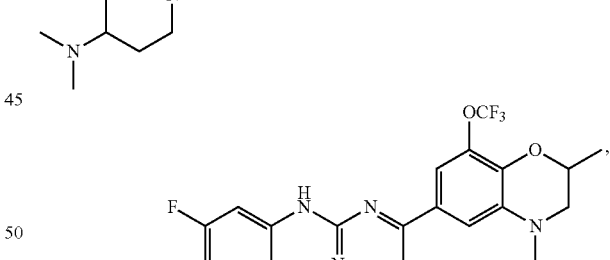
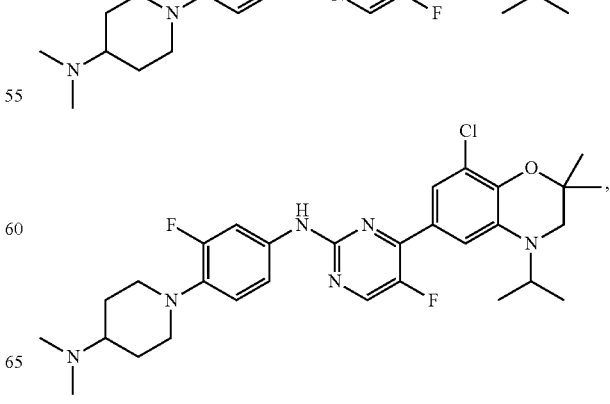

-continued
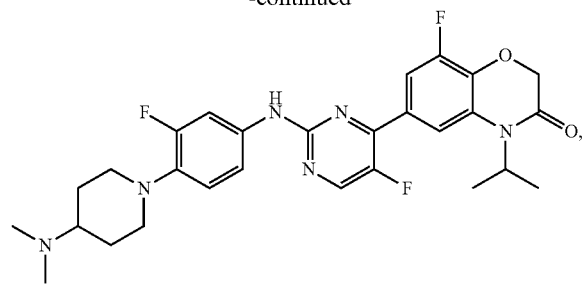
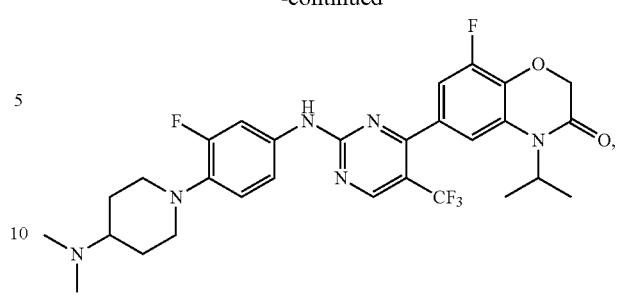
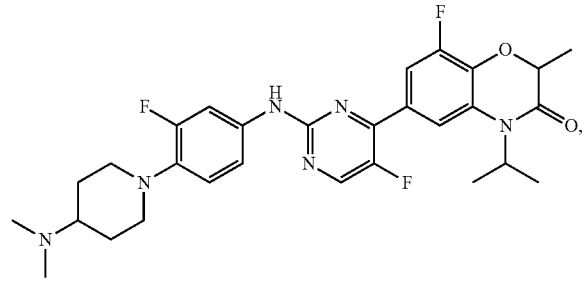
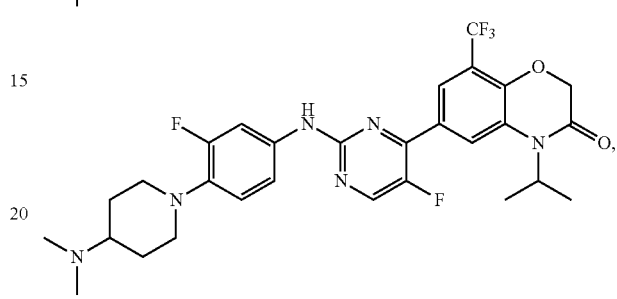
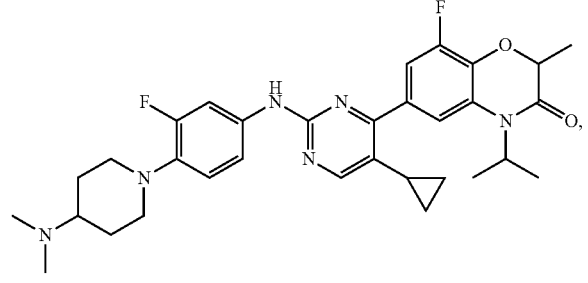
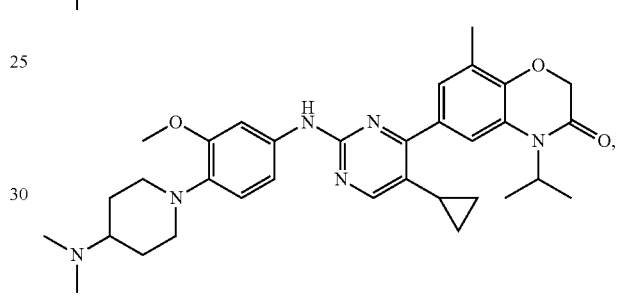
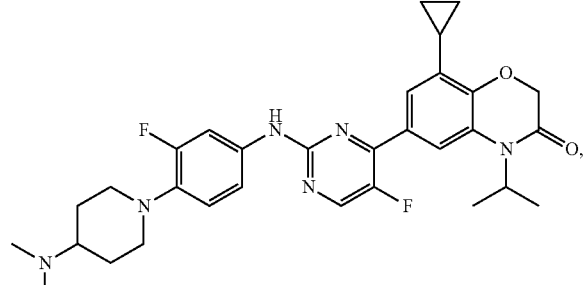
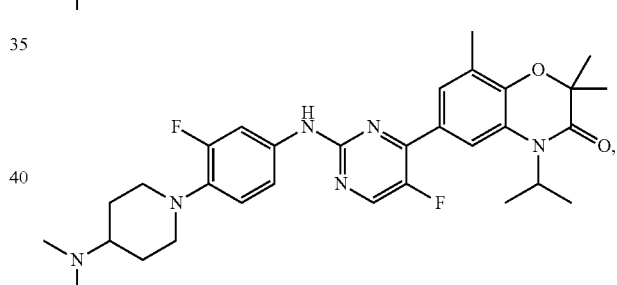
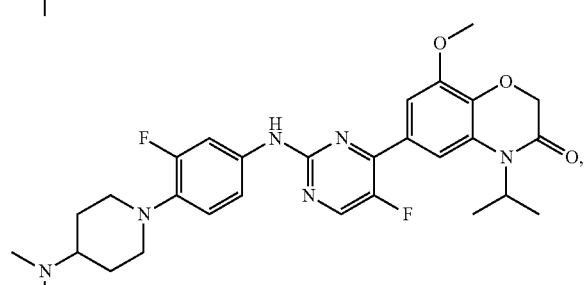
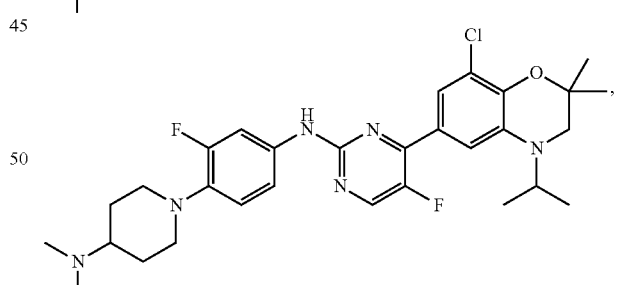
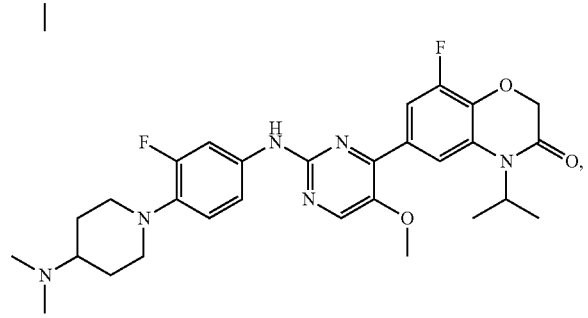
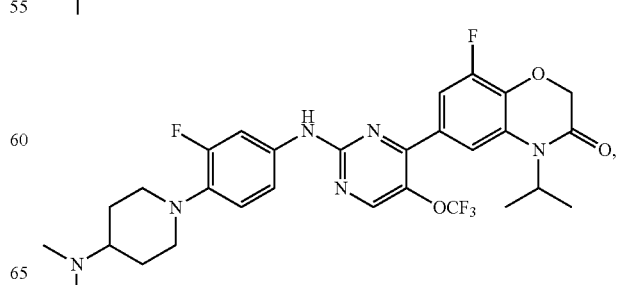

853
-continued
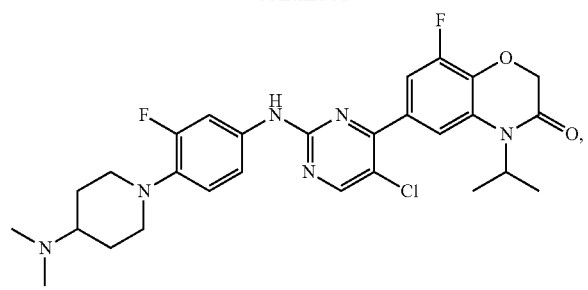
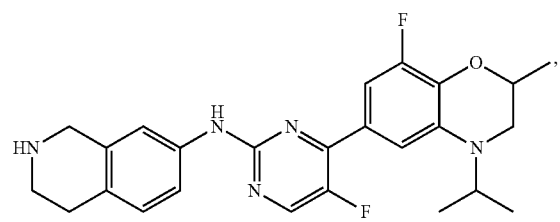
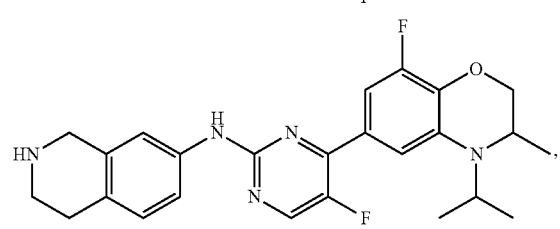
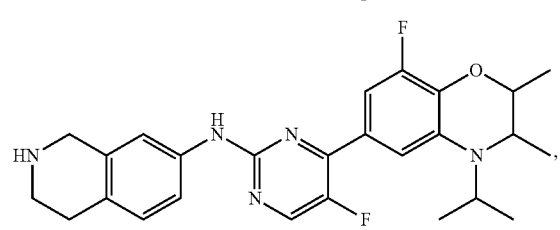
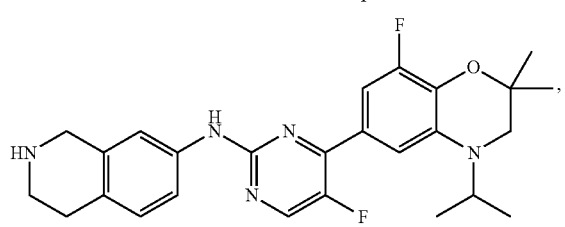
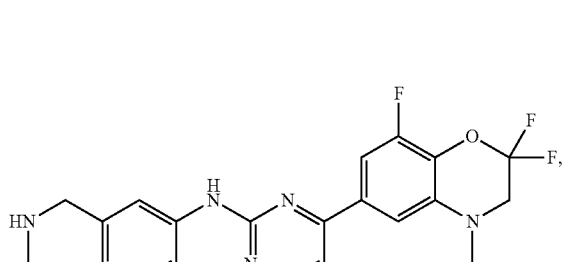
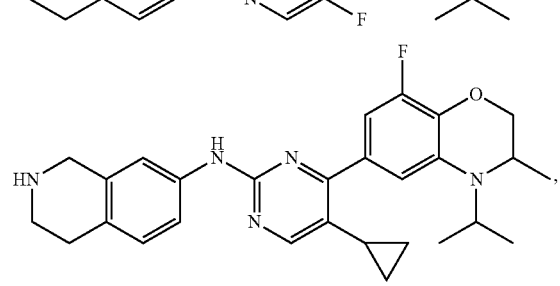
854
-continued
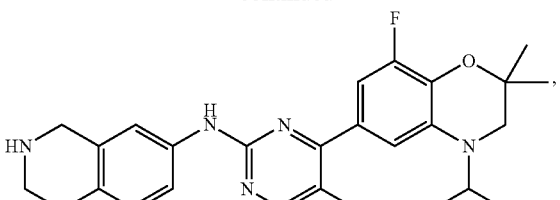
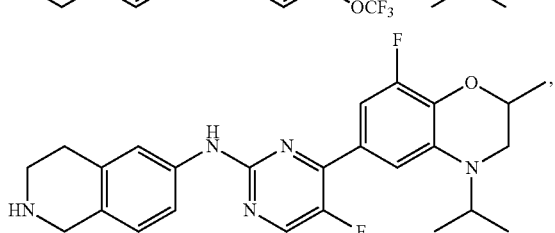
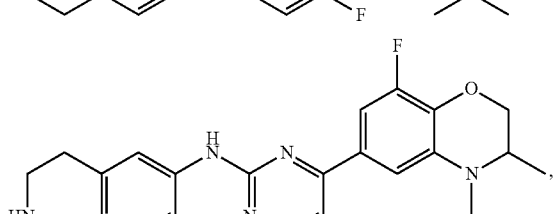
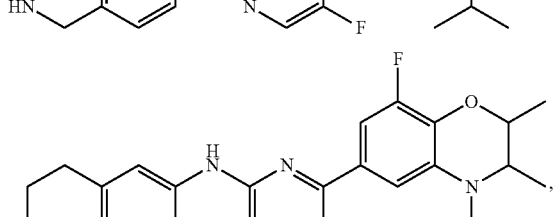
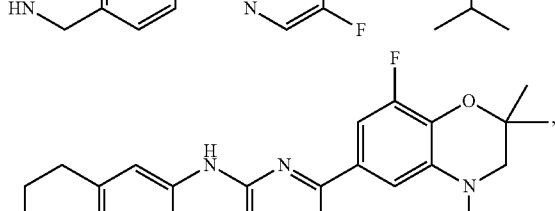
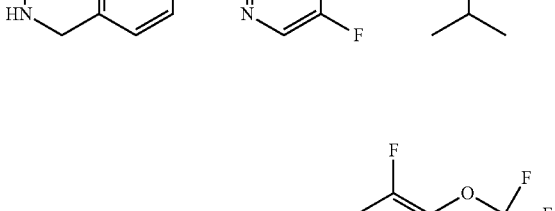
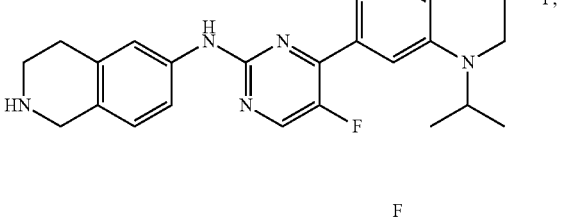
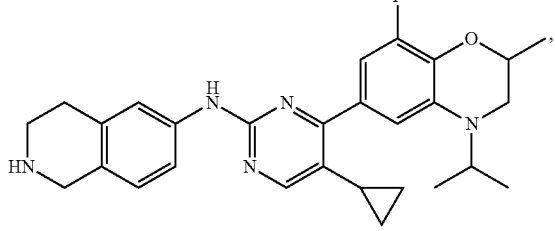

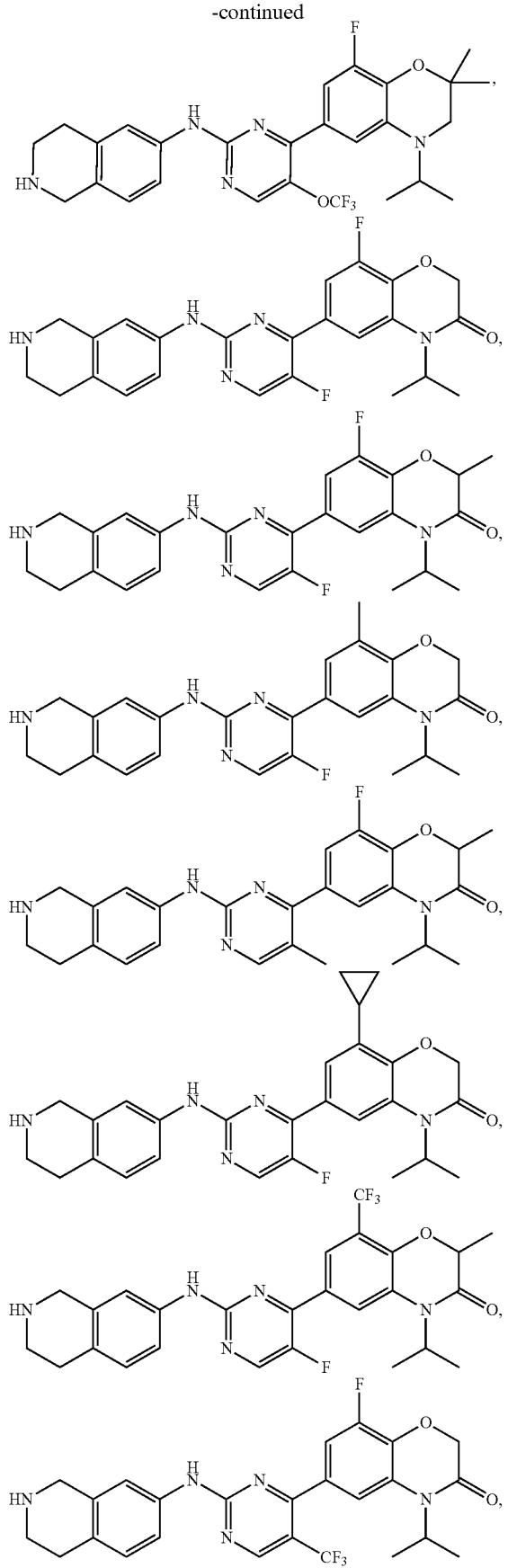
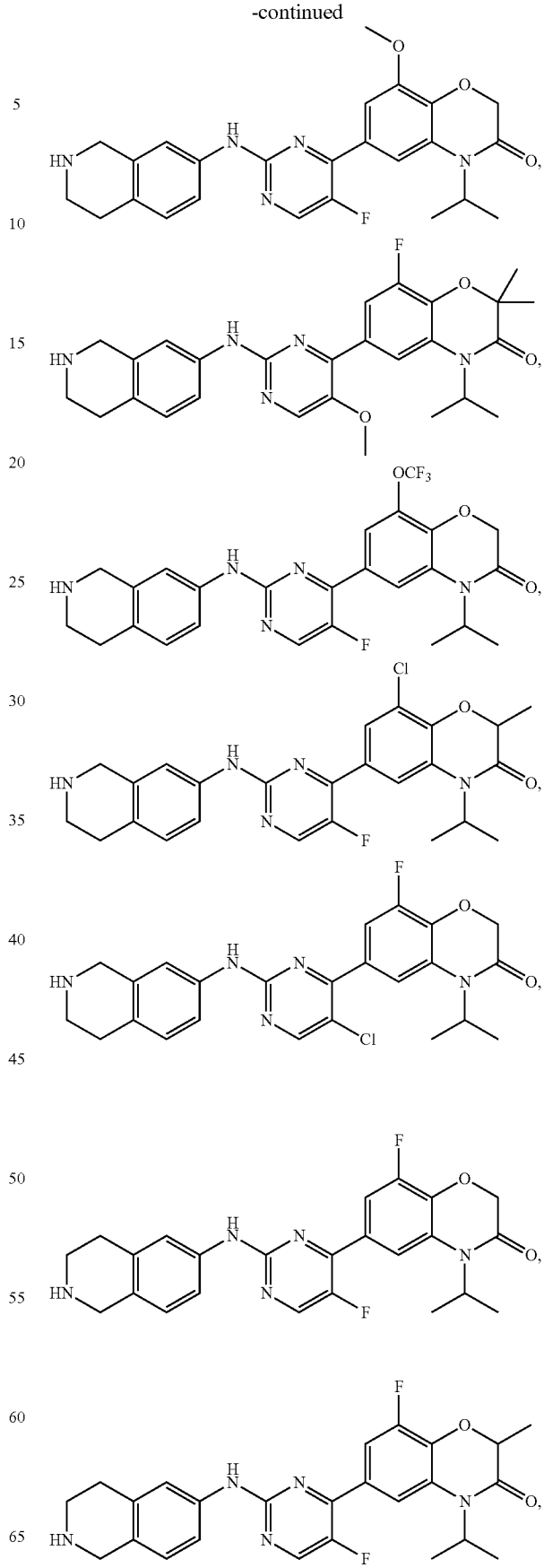

-continued
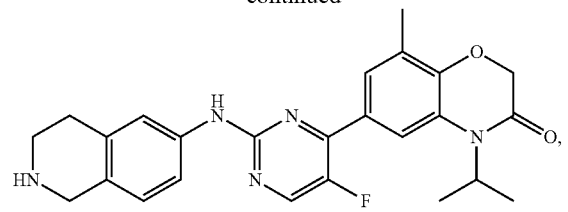
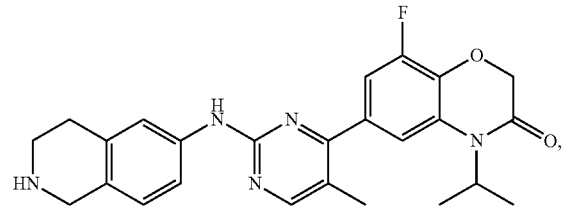
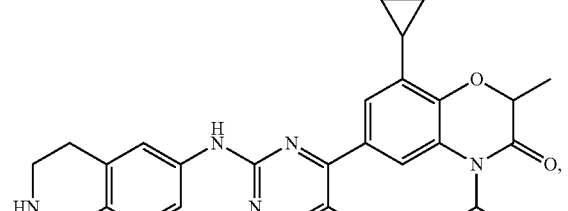
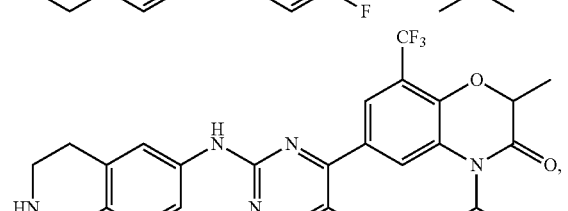
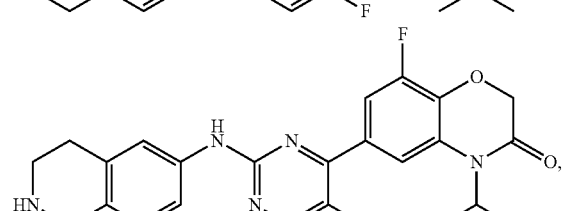
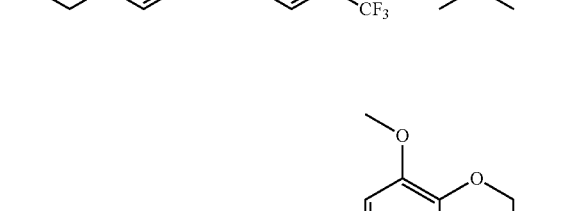
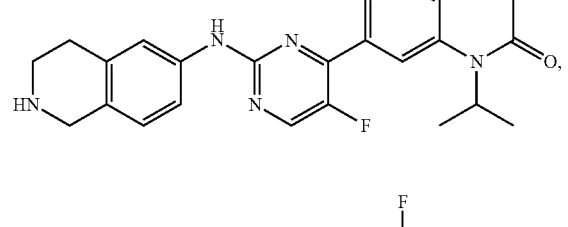
-continued
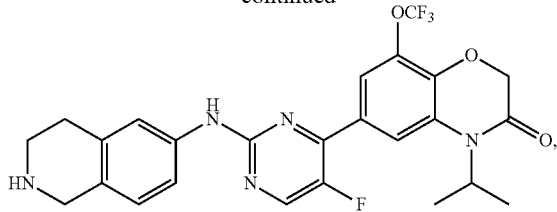
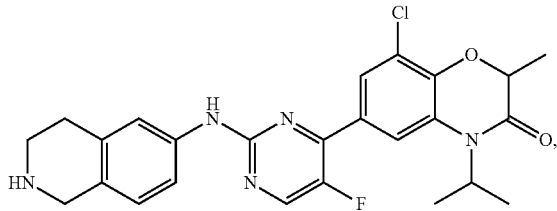
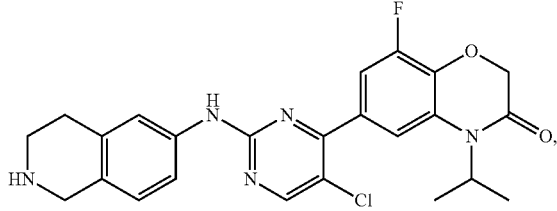
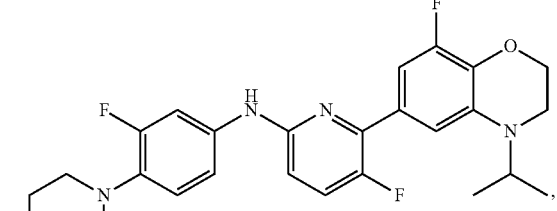
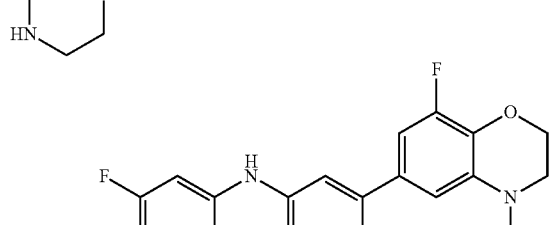
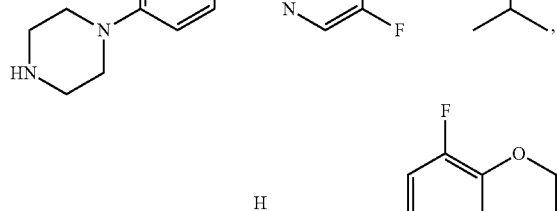
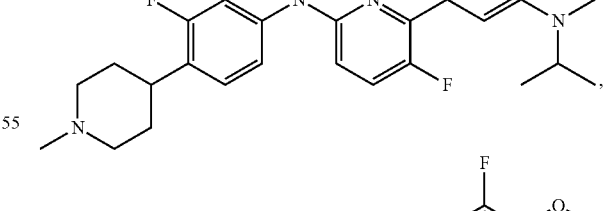
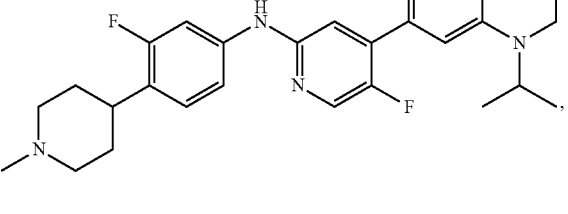

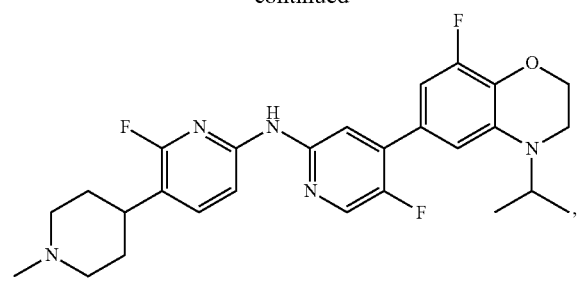
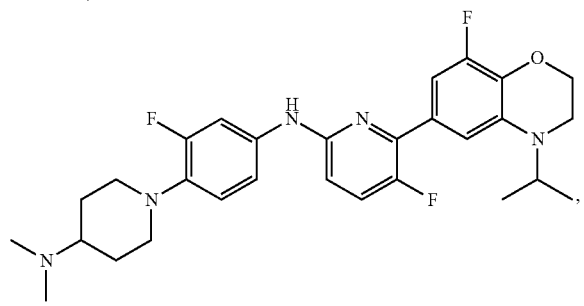
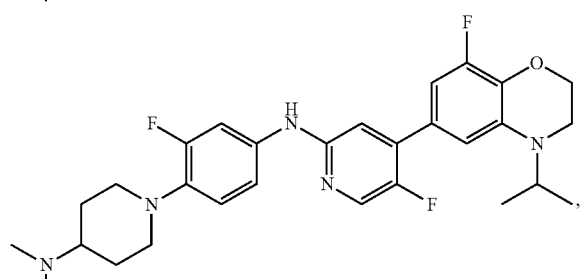
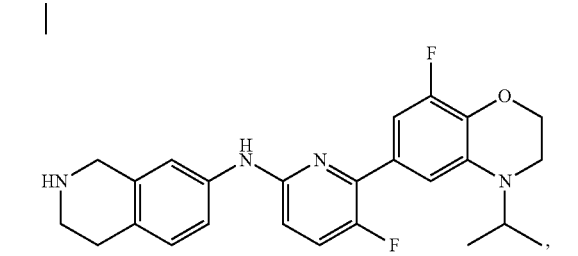
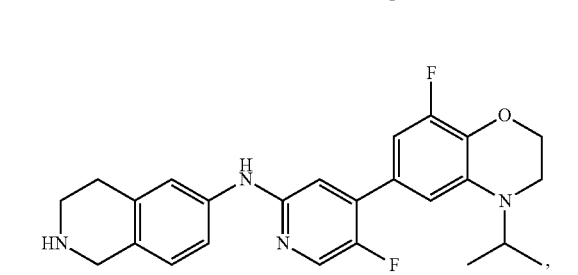
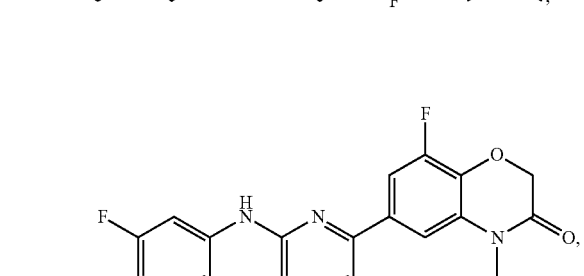
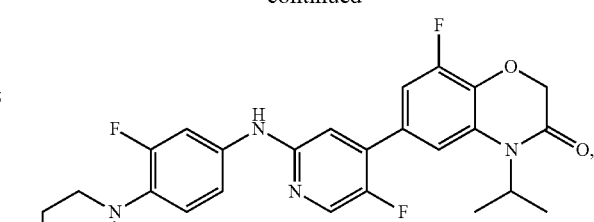
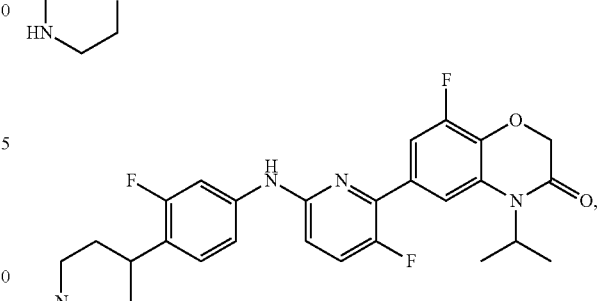
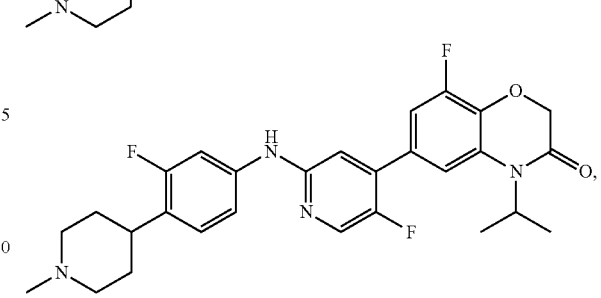
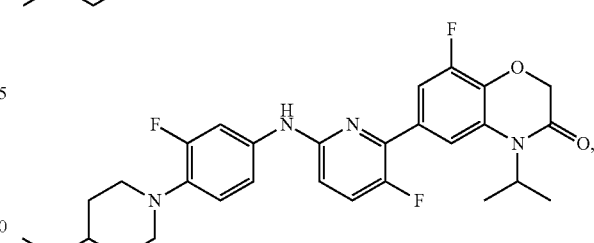
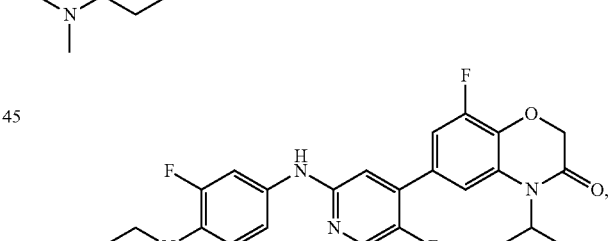
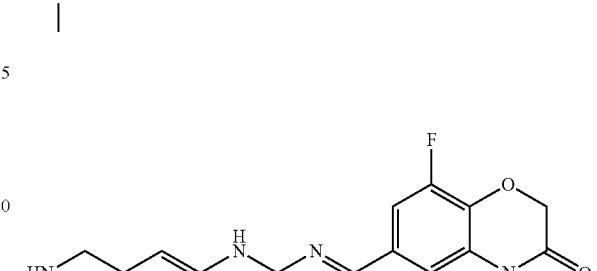

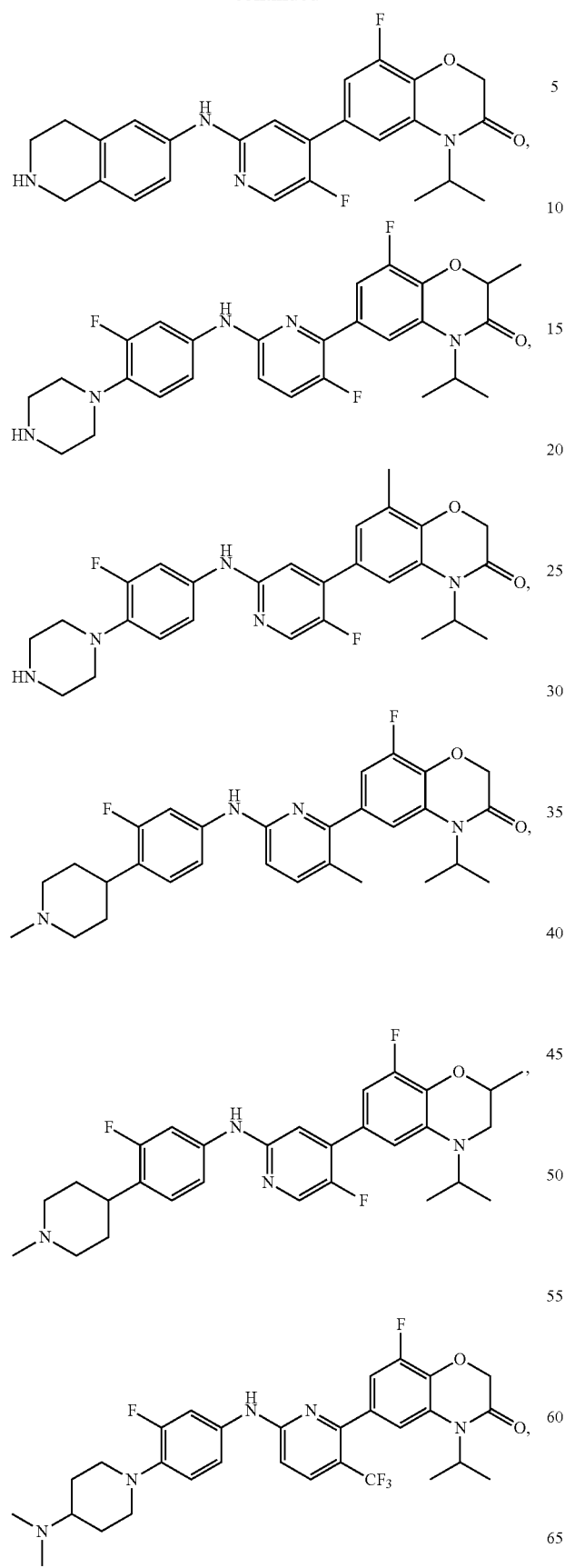
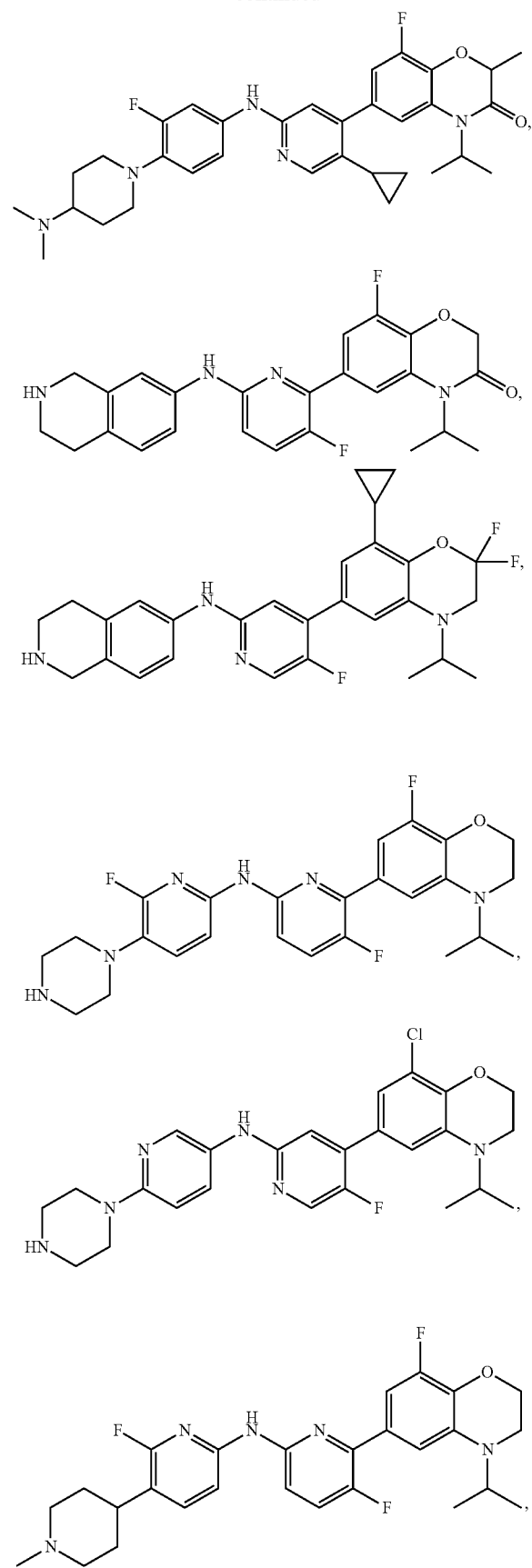

863
-continued
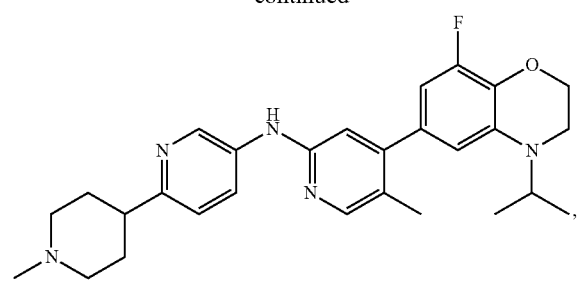
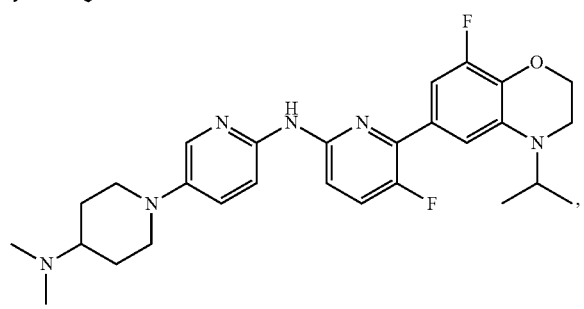
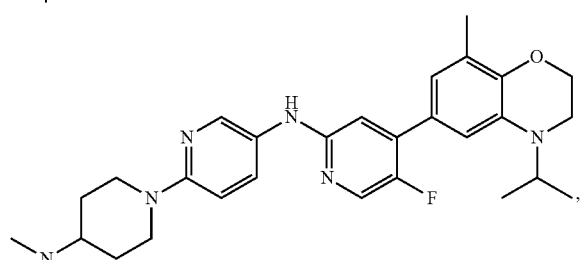
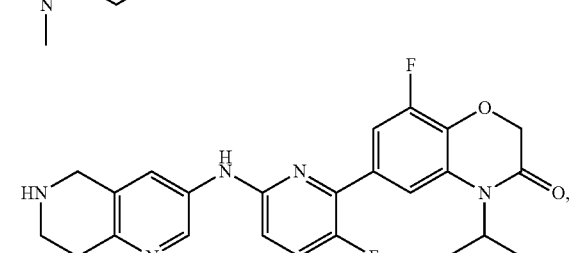
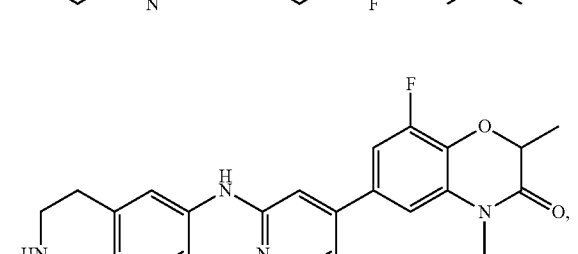
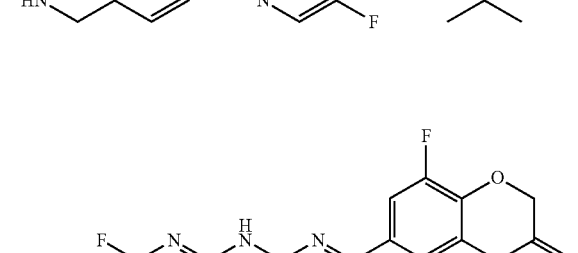
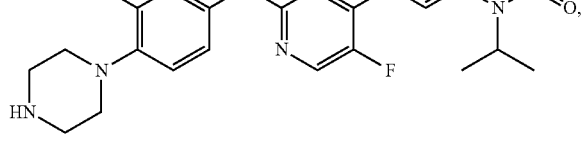
864
-continued
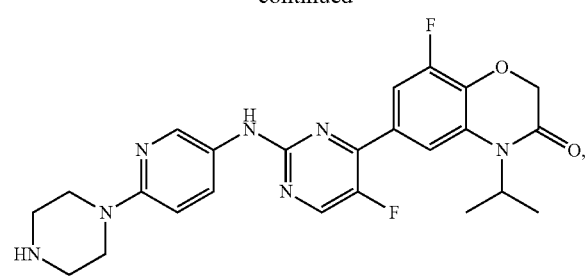
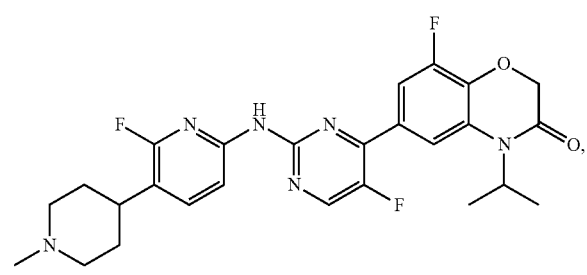
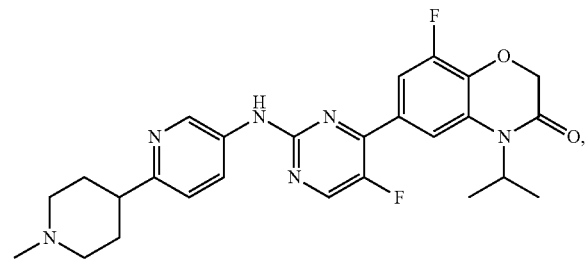
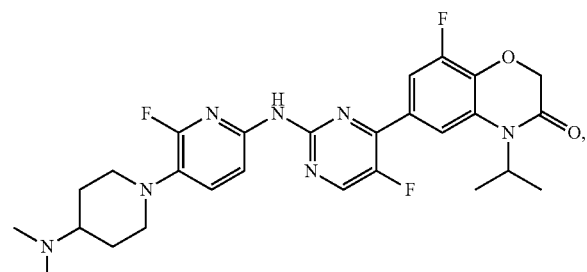
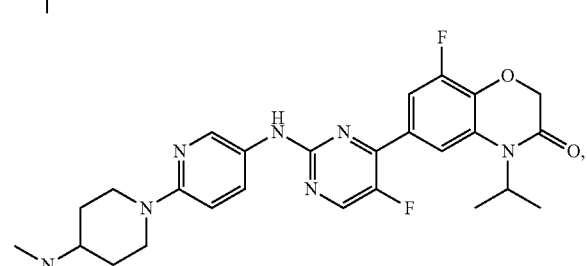
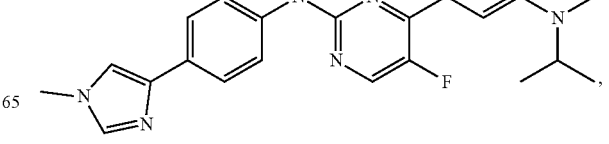

865
-continued
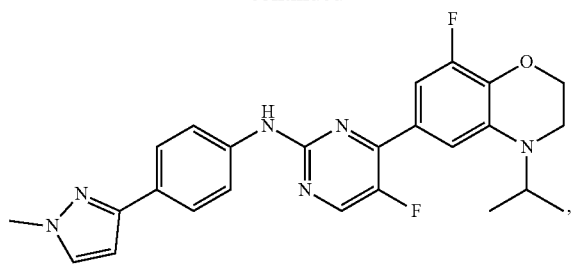
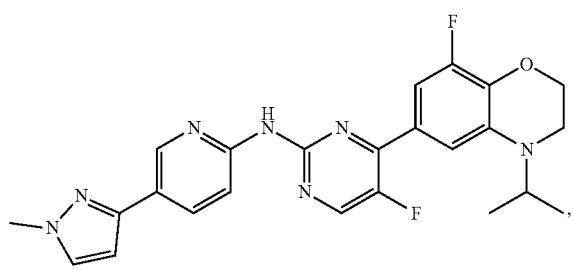
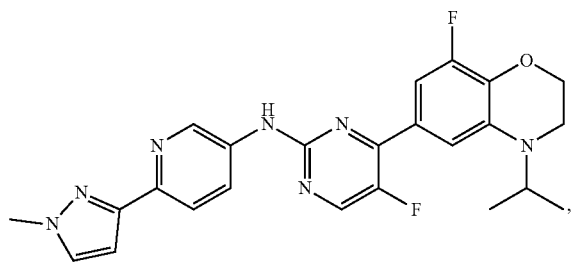
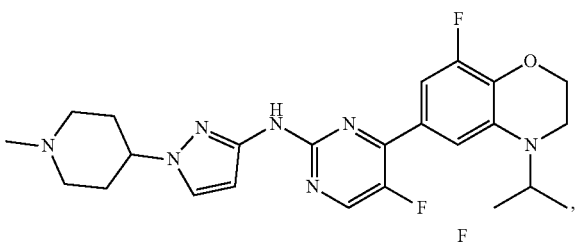
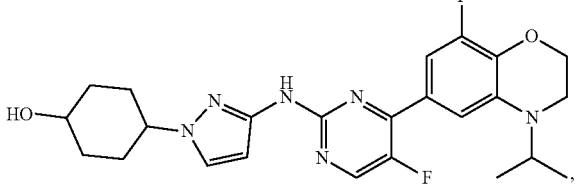
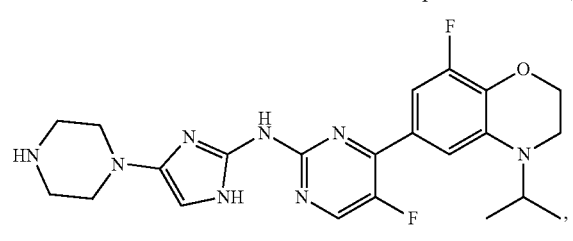
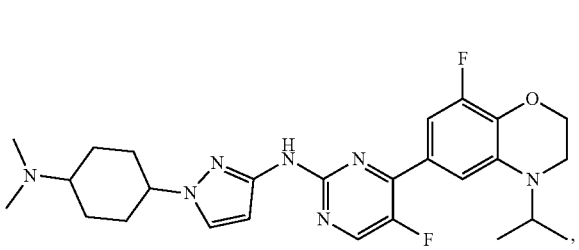
866
-continued
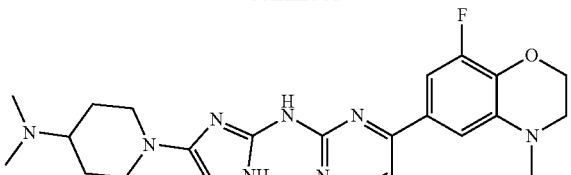
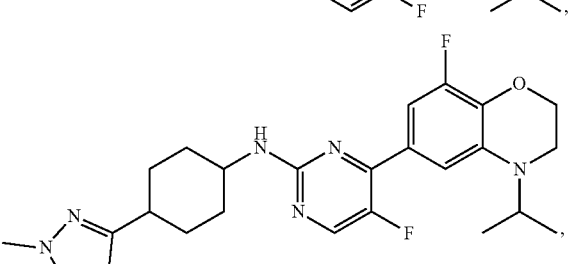
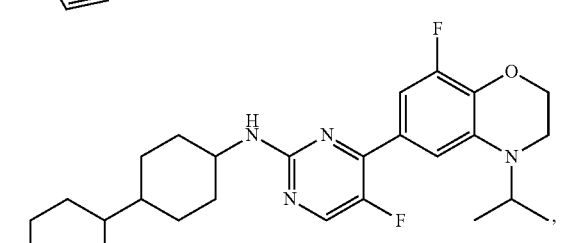
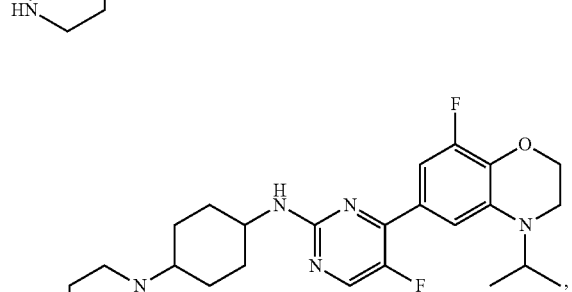
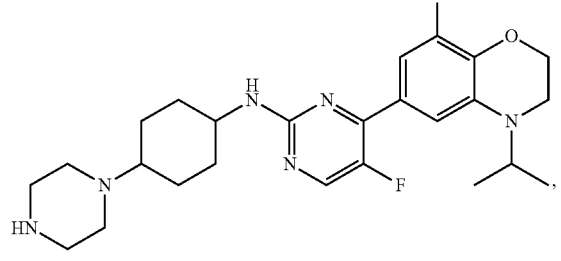
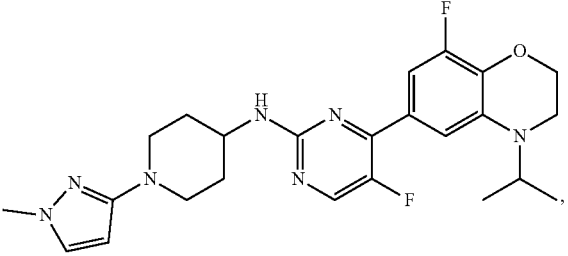

867
-continued
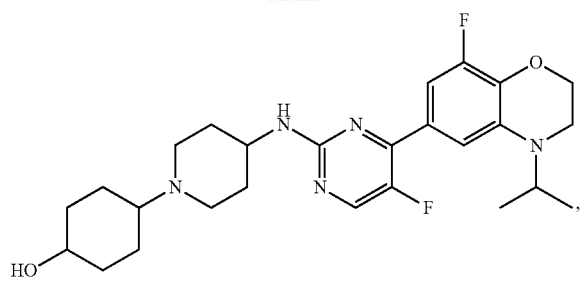
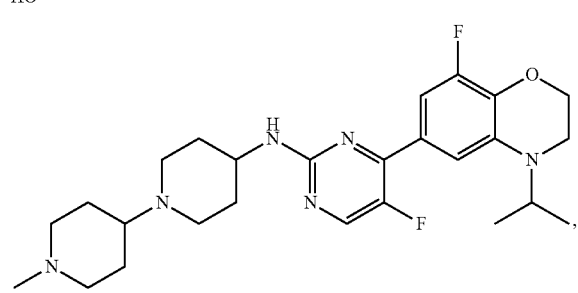
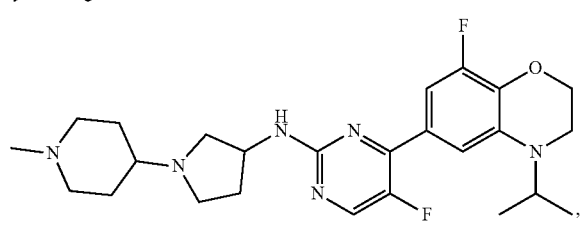
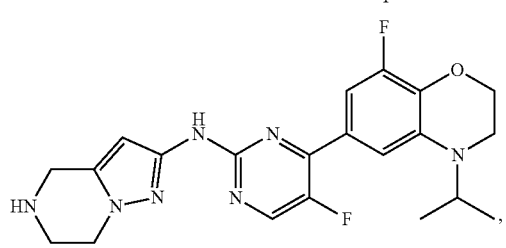
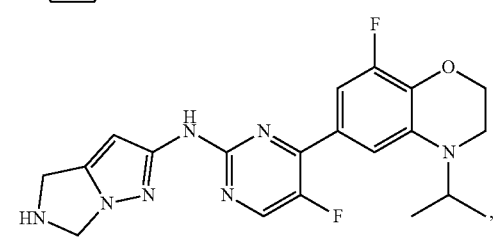
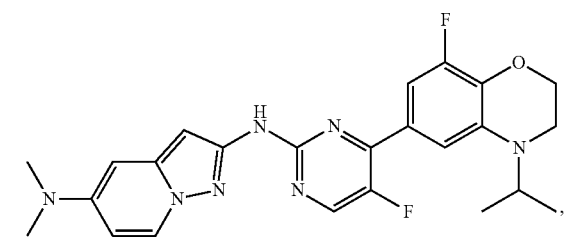
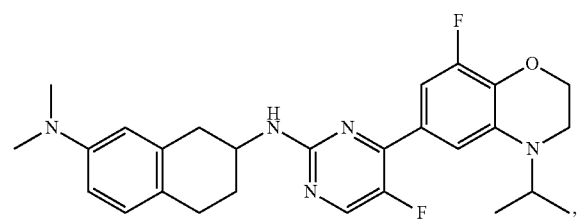
868
-continued
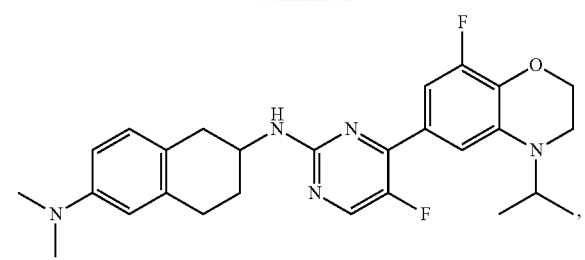
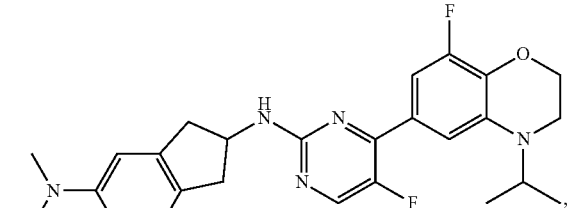
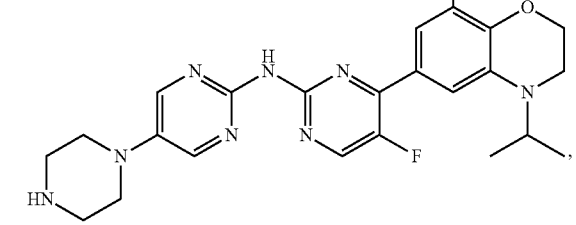
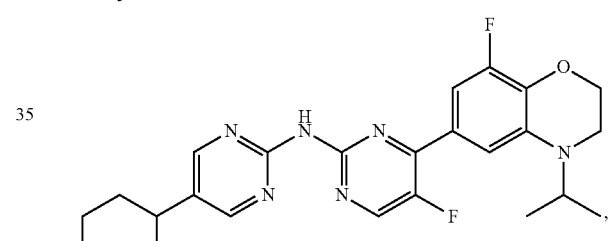
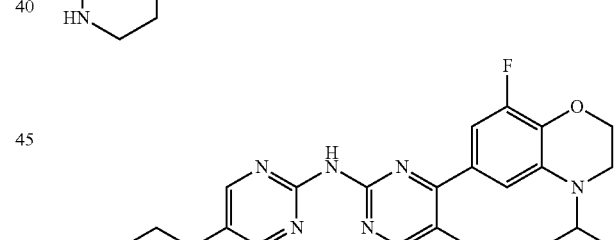
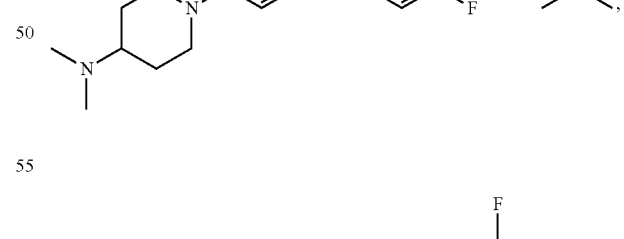
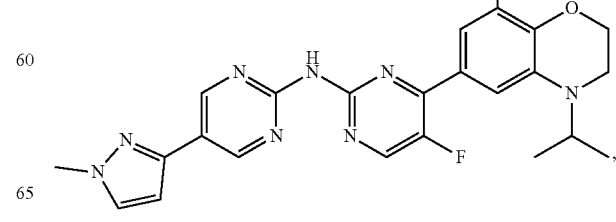

869
-continued
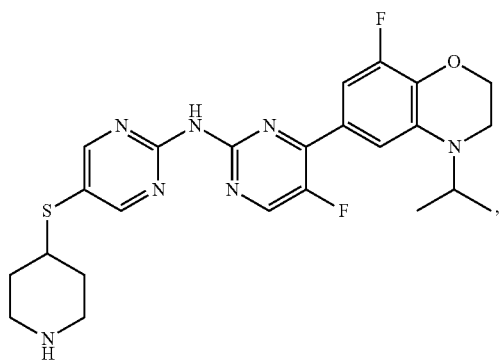
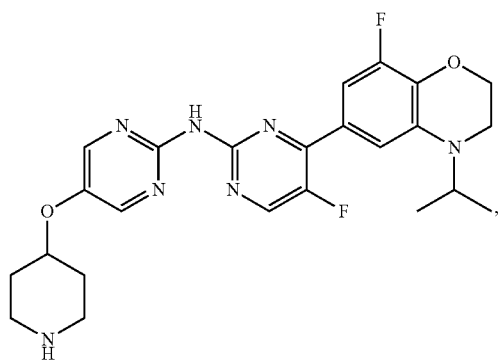
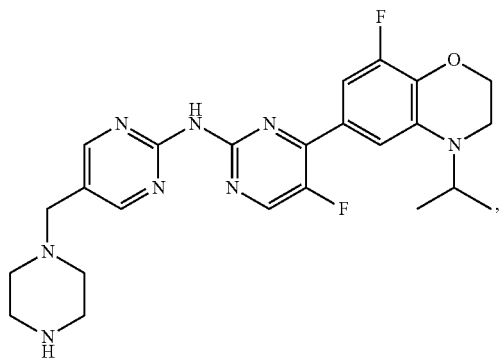
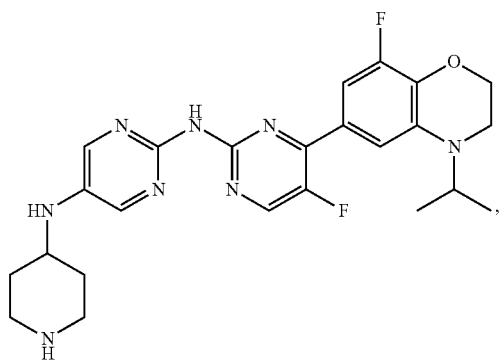
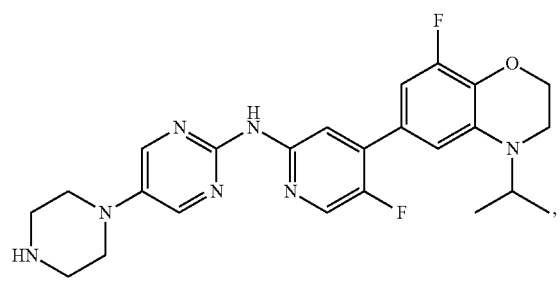
870
-continued
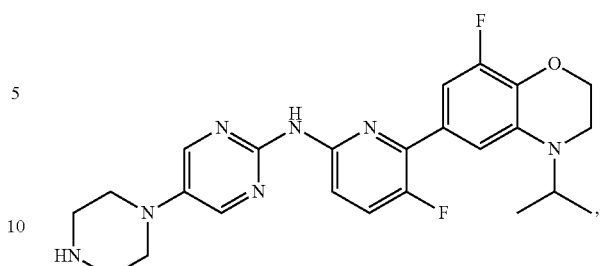
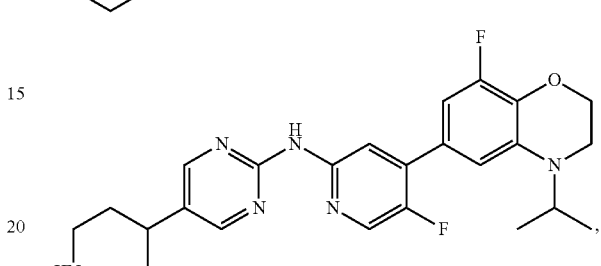
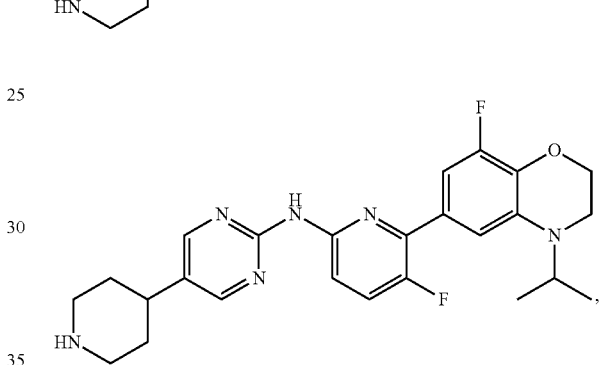
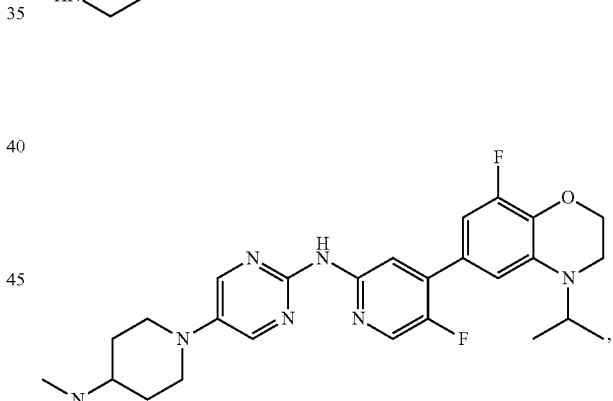

871
-continued
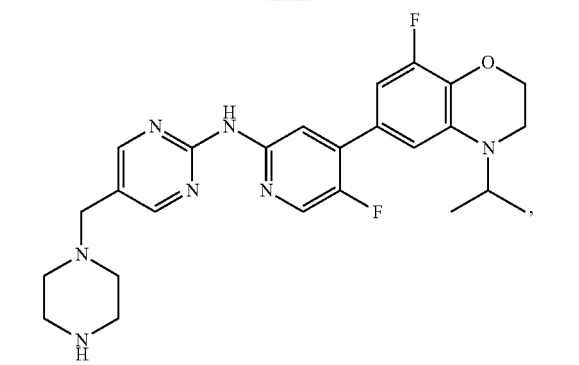
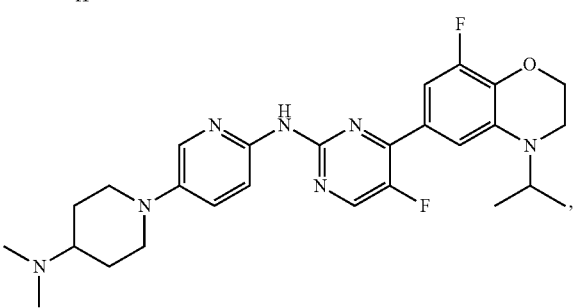
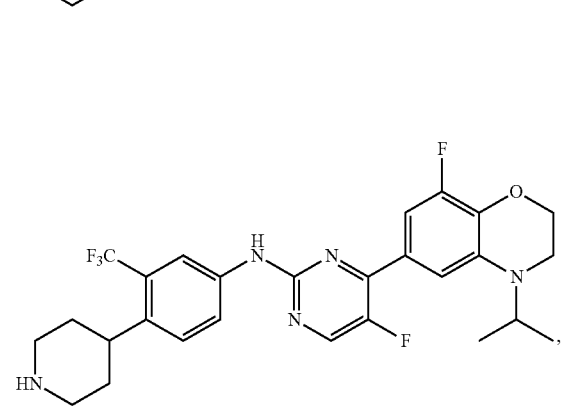
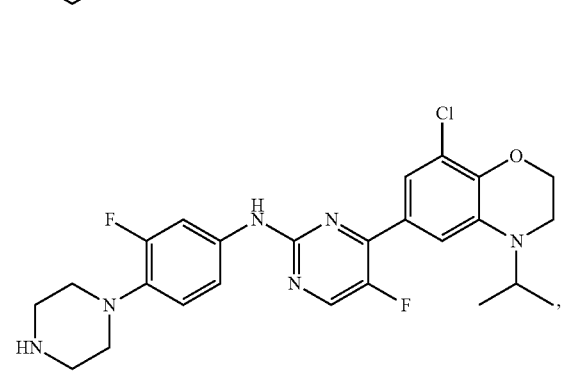
872
-continued
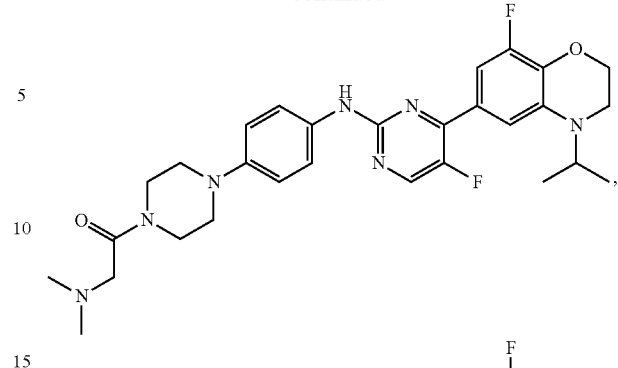
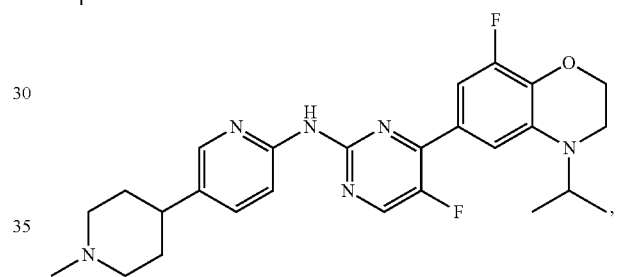
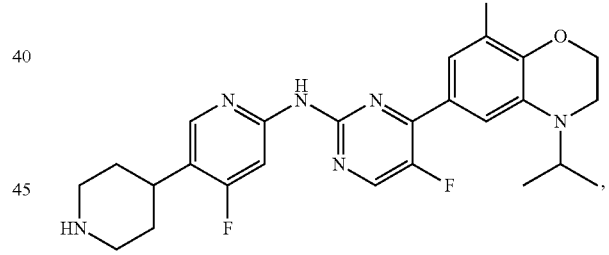
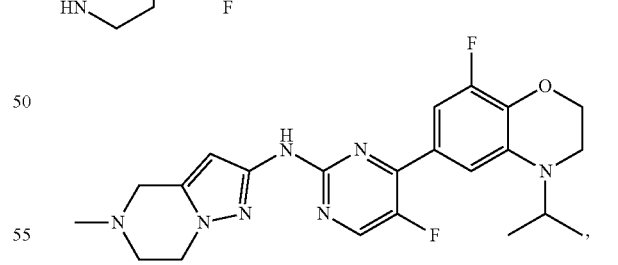
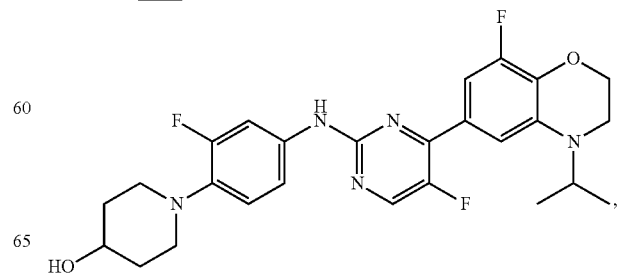

-continued
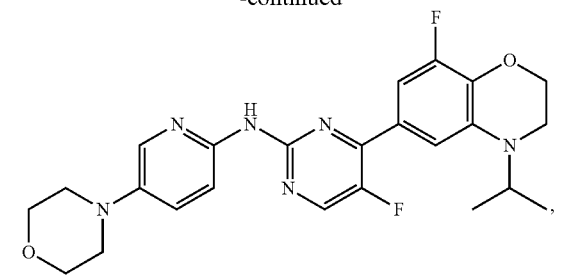
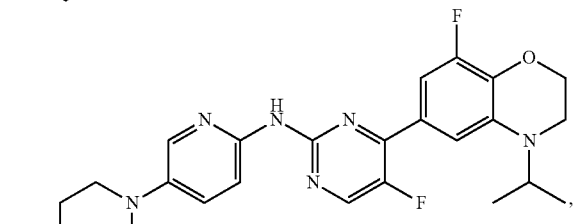
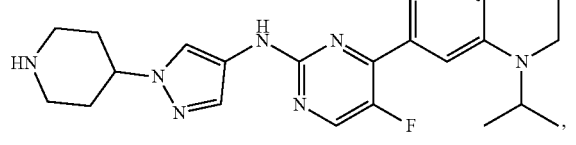
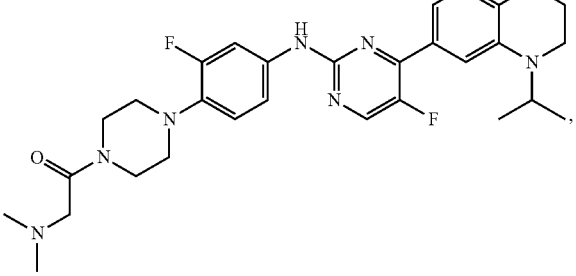
-continued
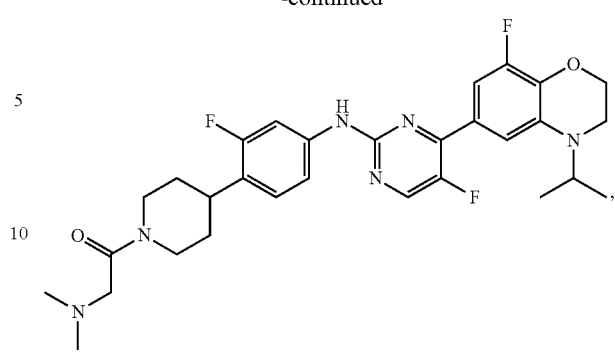
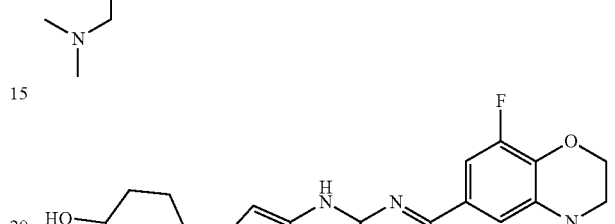
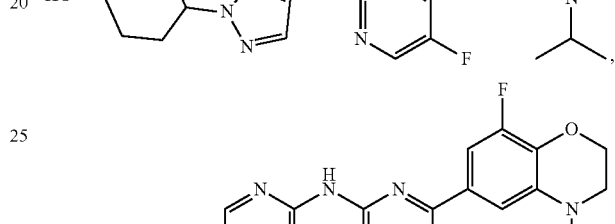
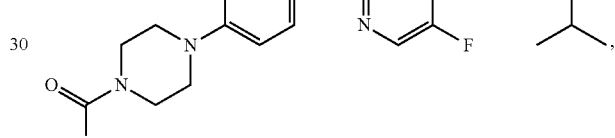
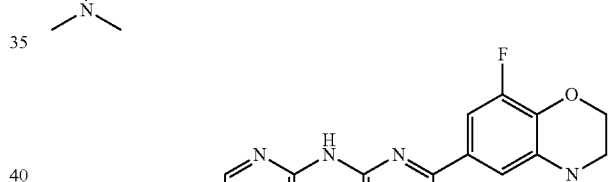
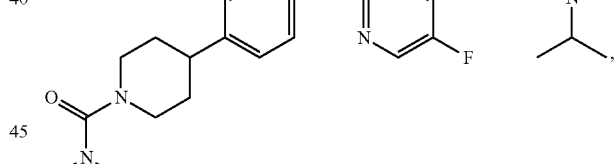
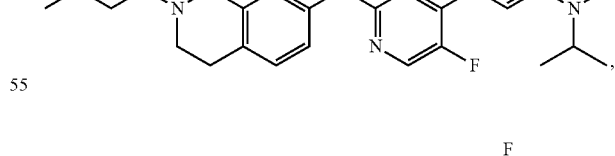
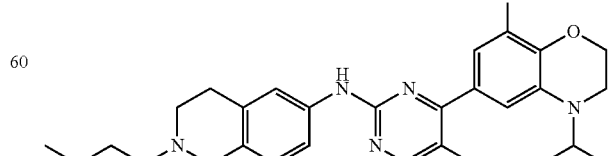

875
-continued
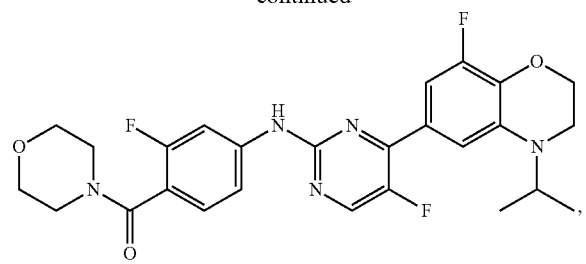
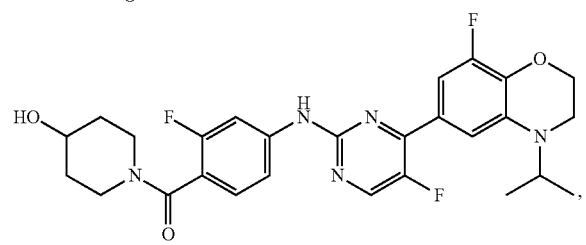
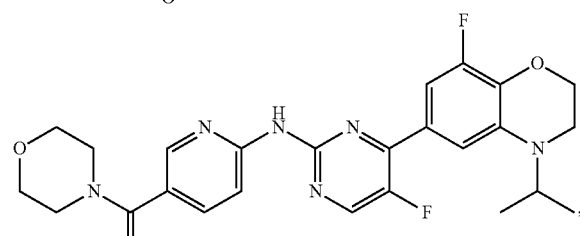
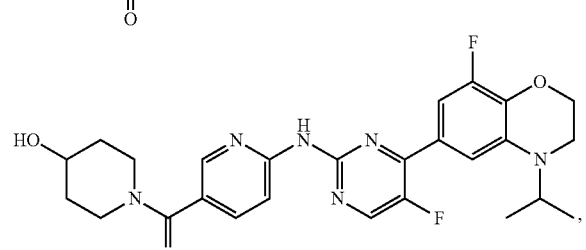
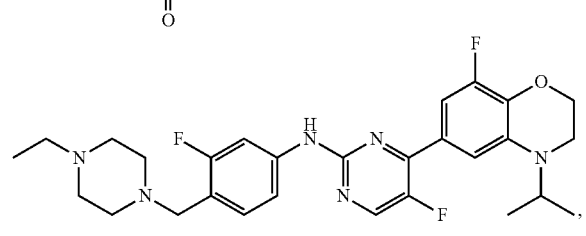
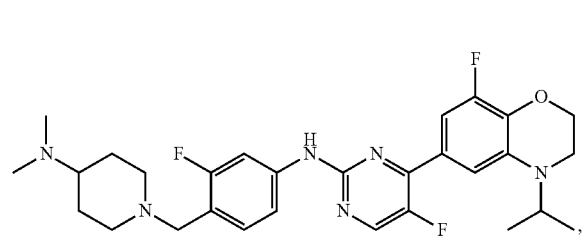
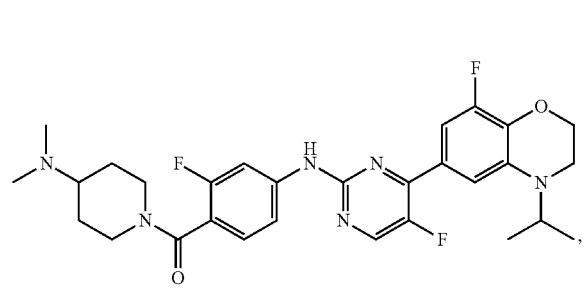
876
-continued
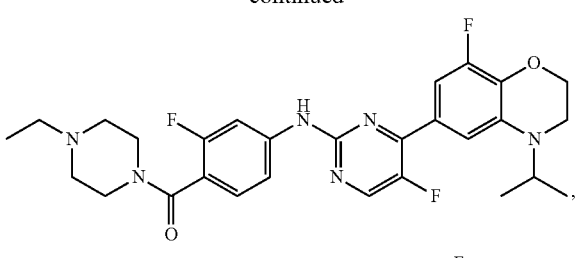
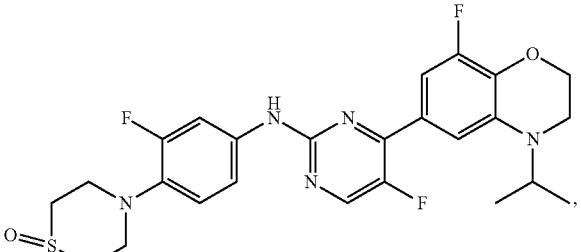
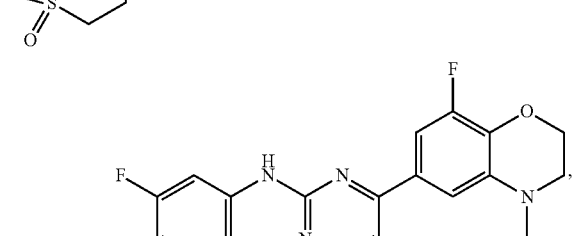
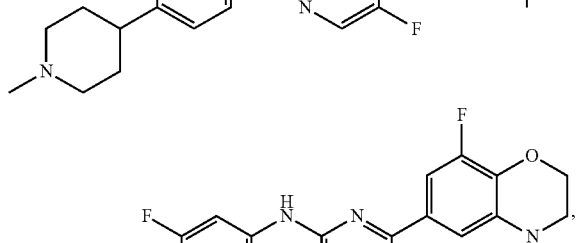
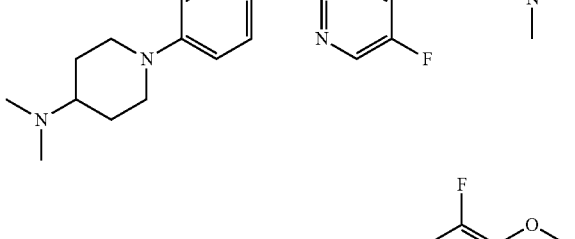
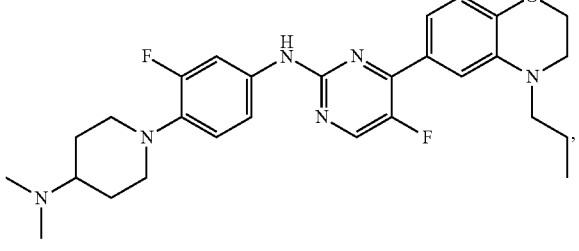
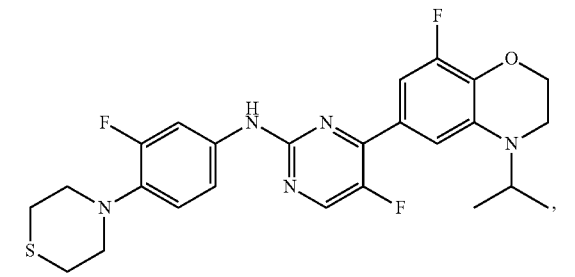

877
-continued
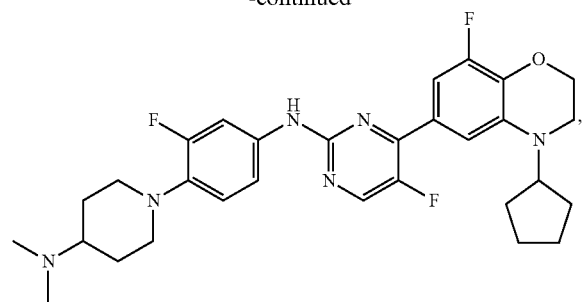
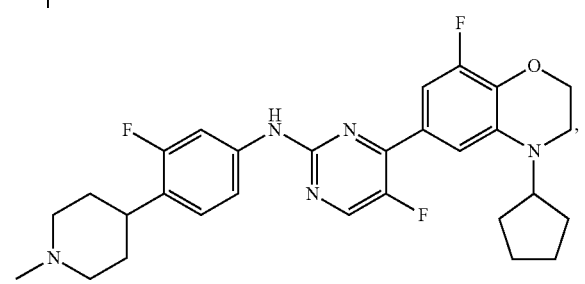
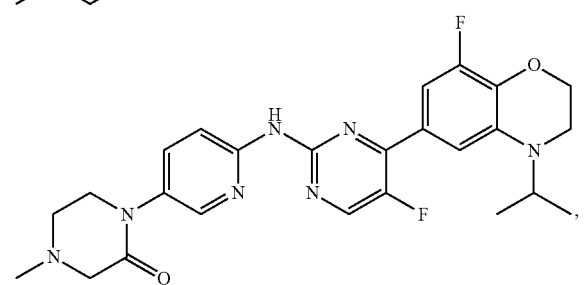
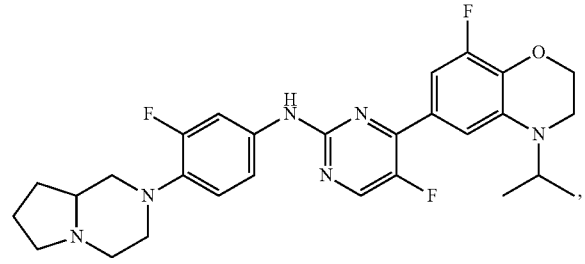
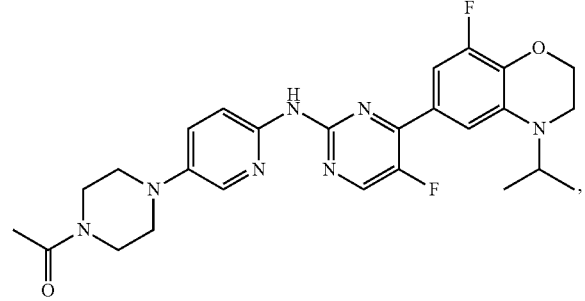
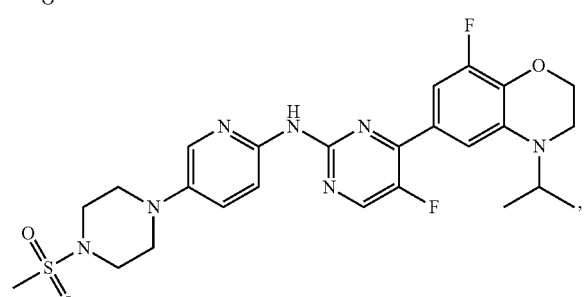
878
-continued
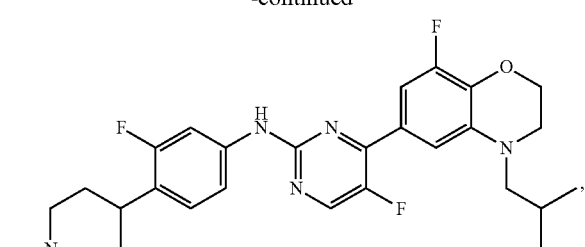
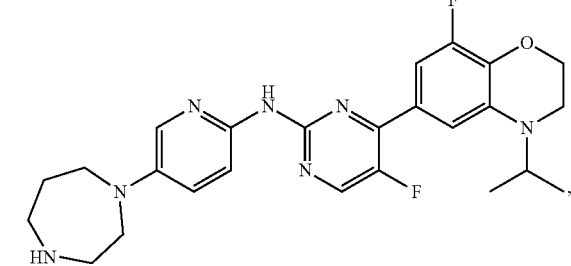
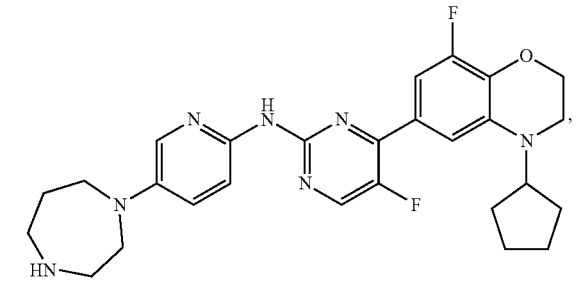
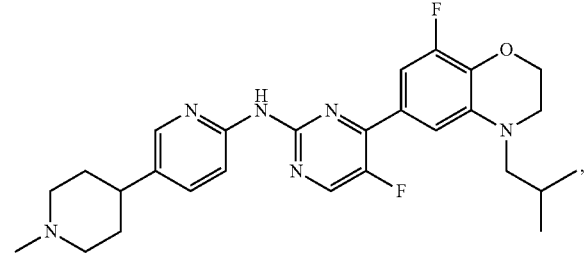
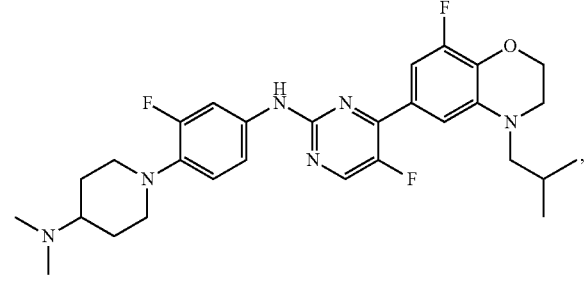
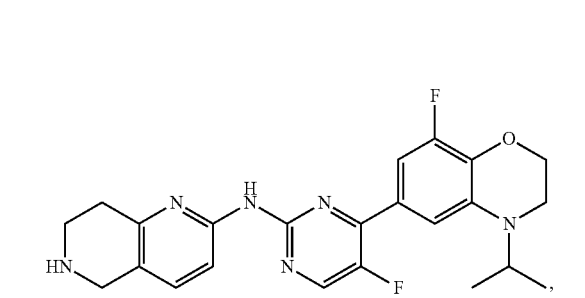

-continued
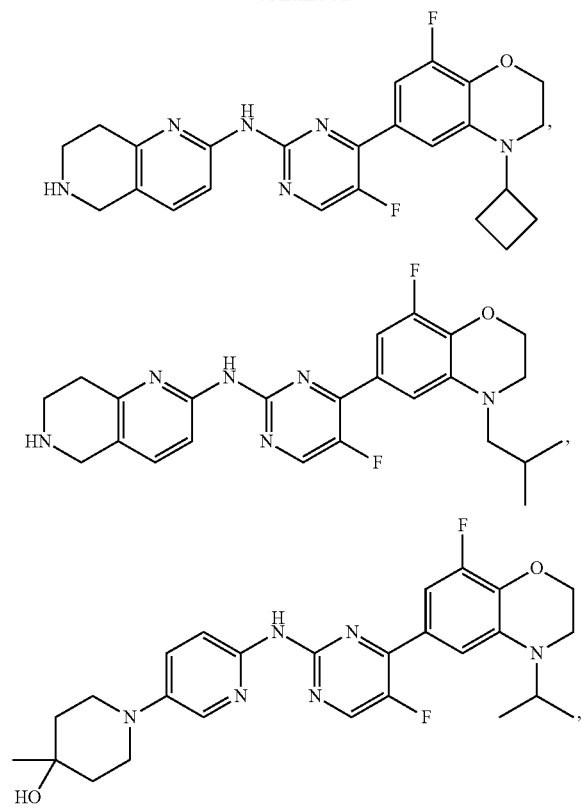
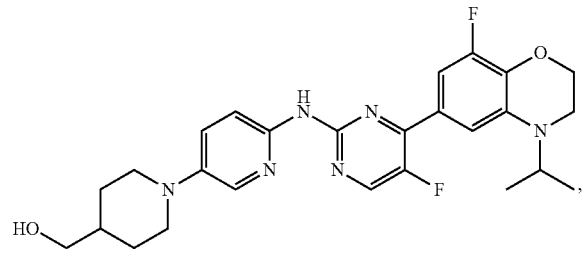
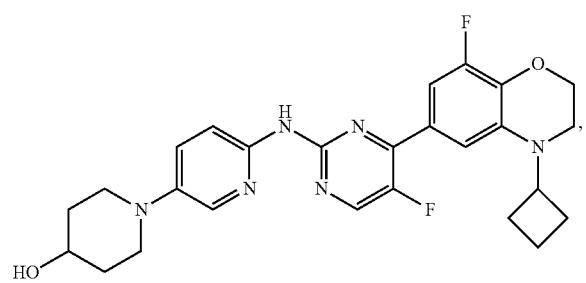
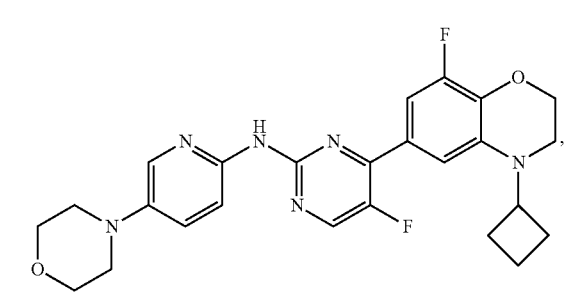
-continued
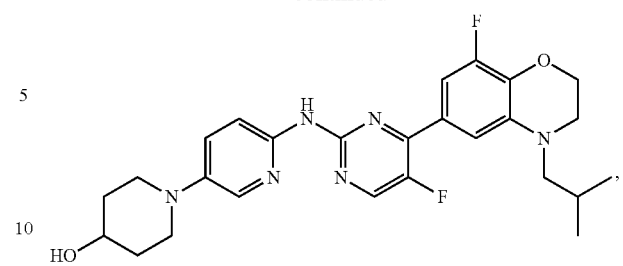
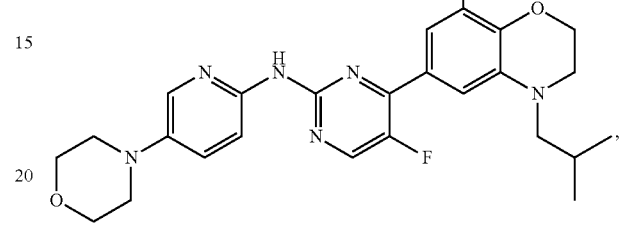
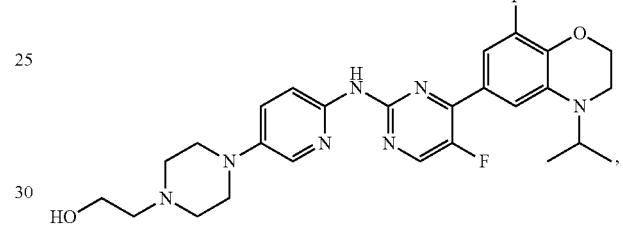
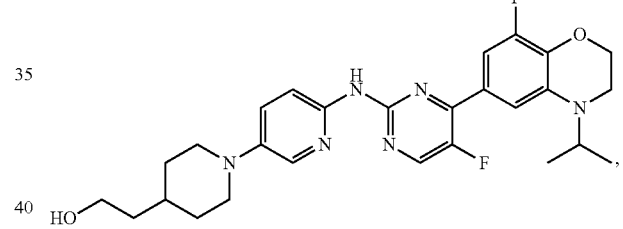
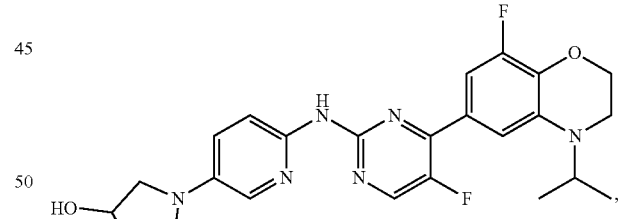
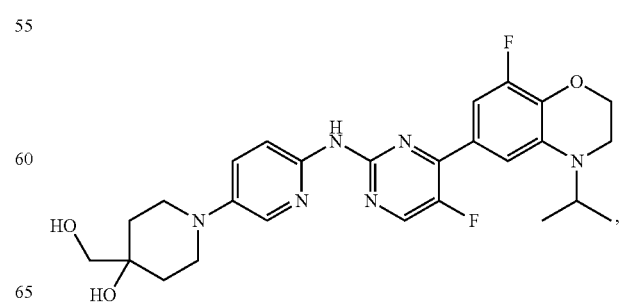

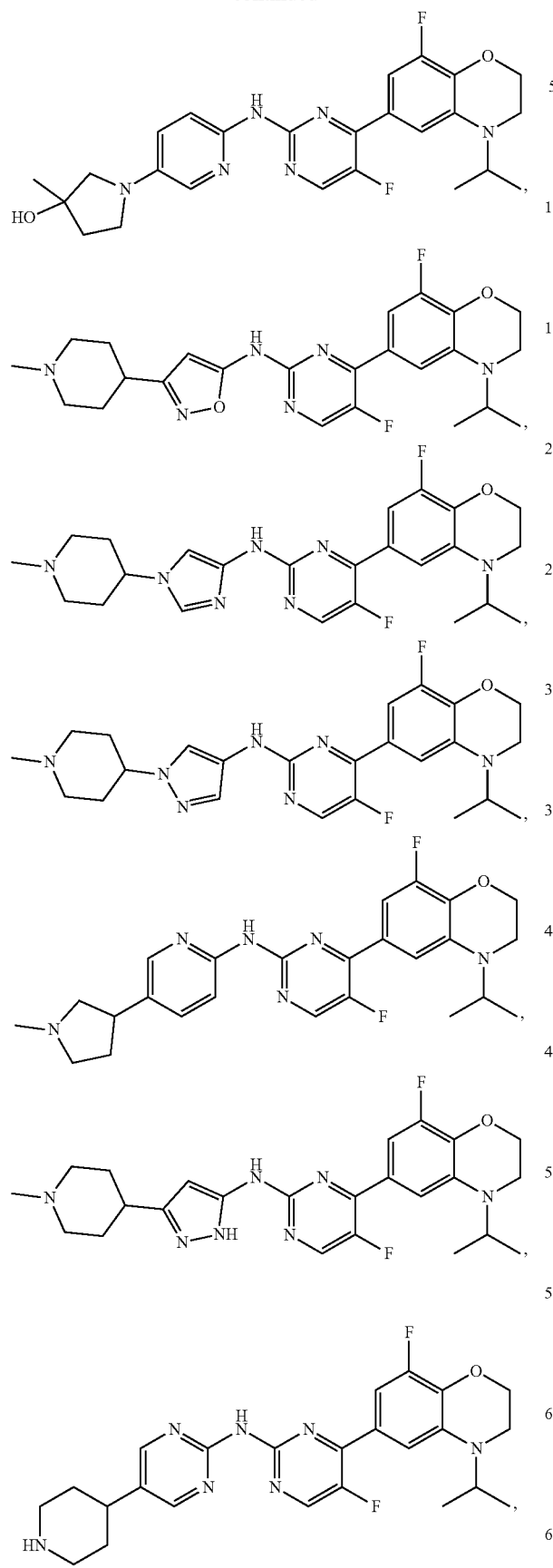
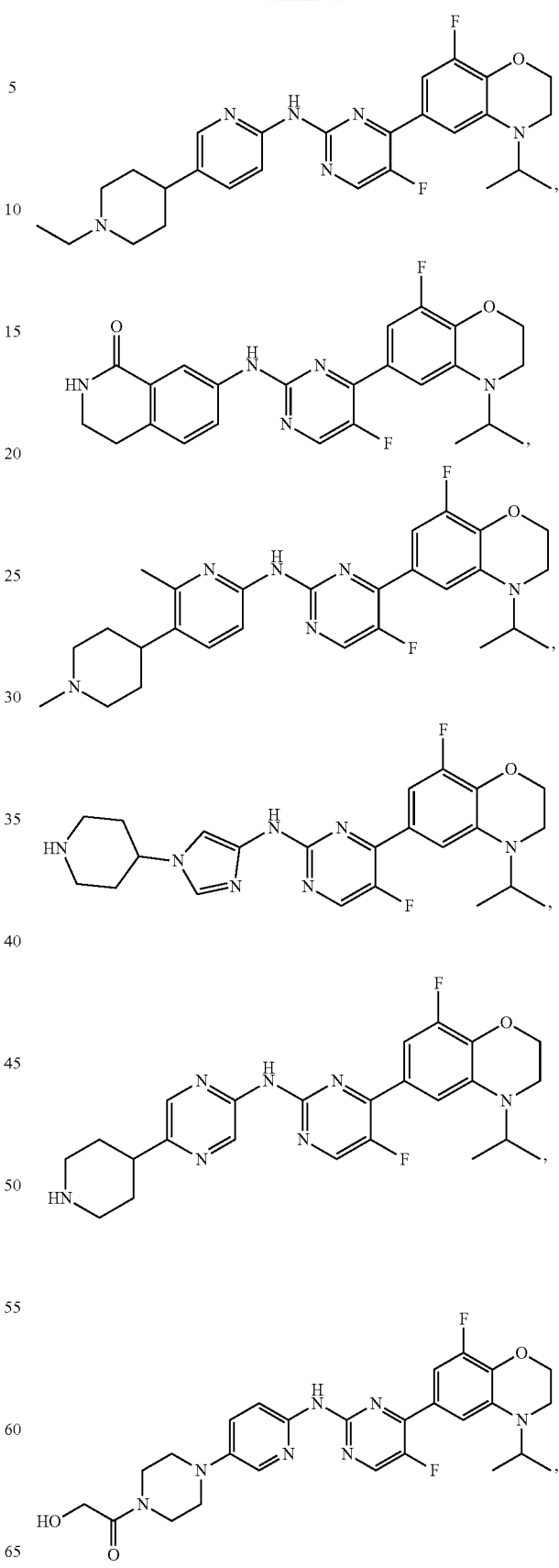

883
-continued
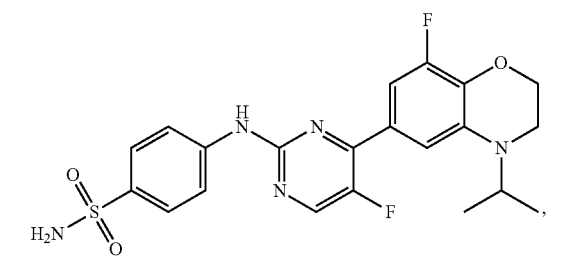
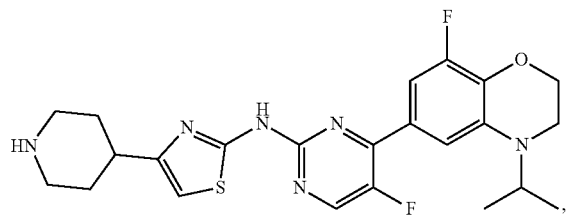
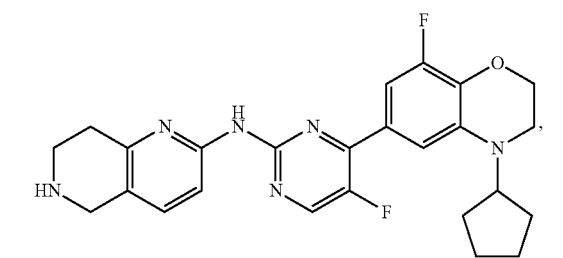
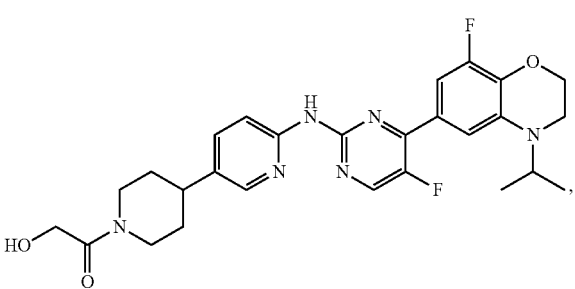
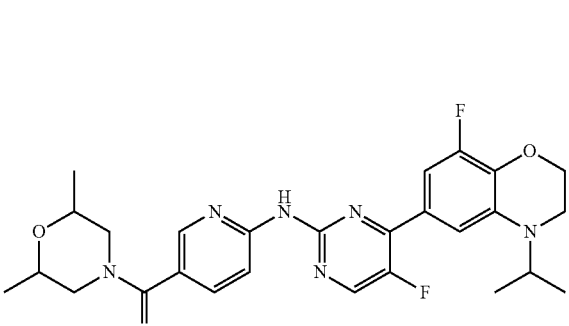
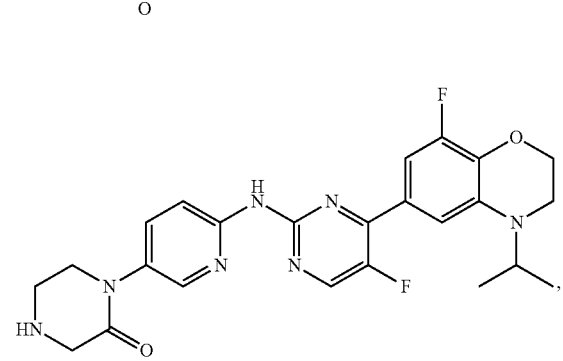
884
-continued
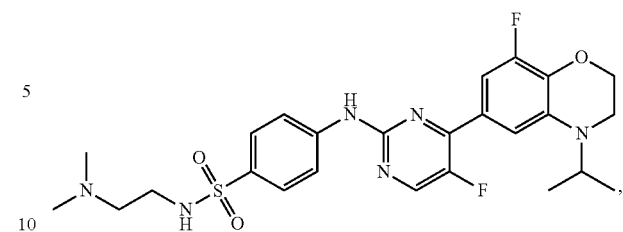
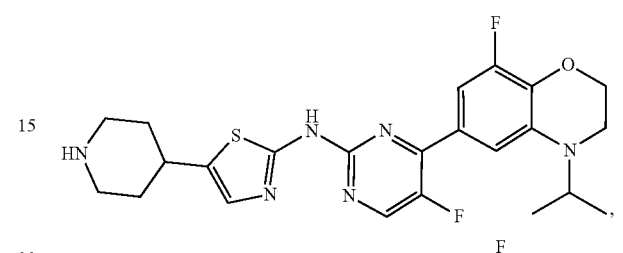
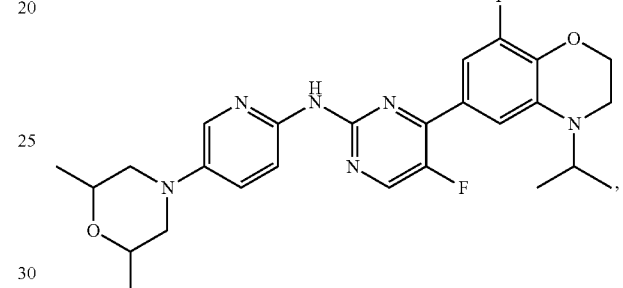
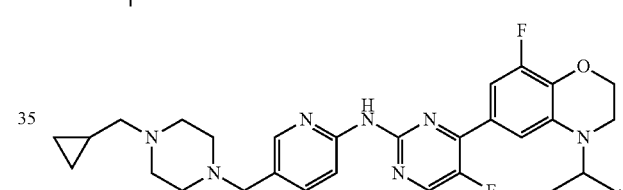
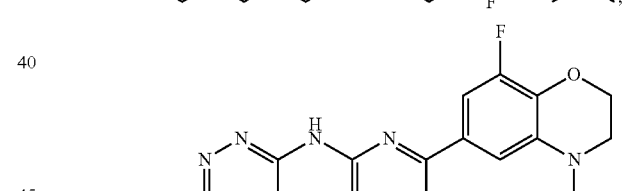
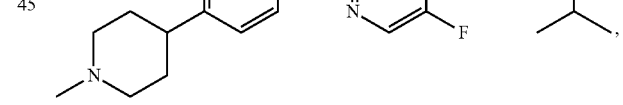
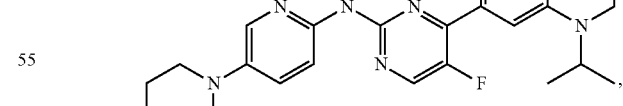
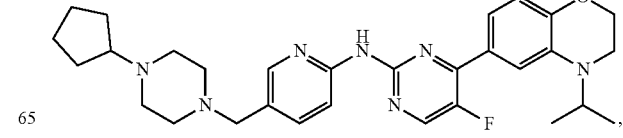

885
-continued
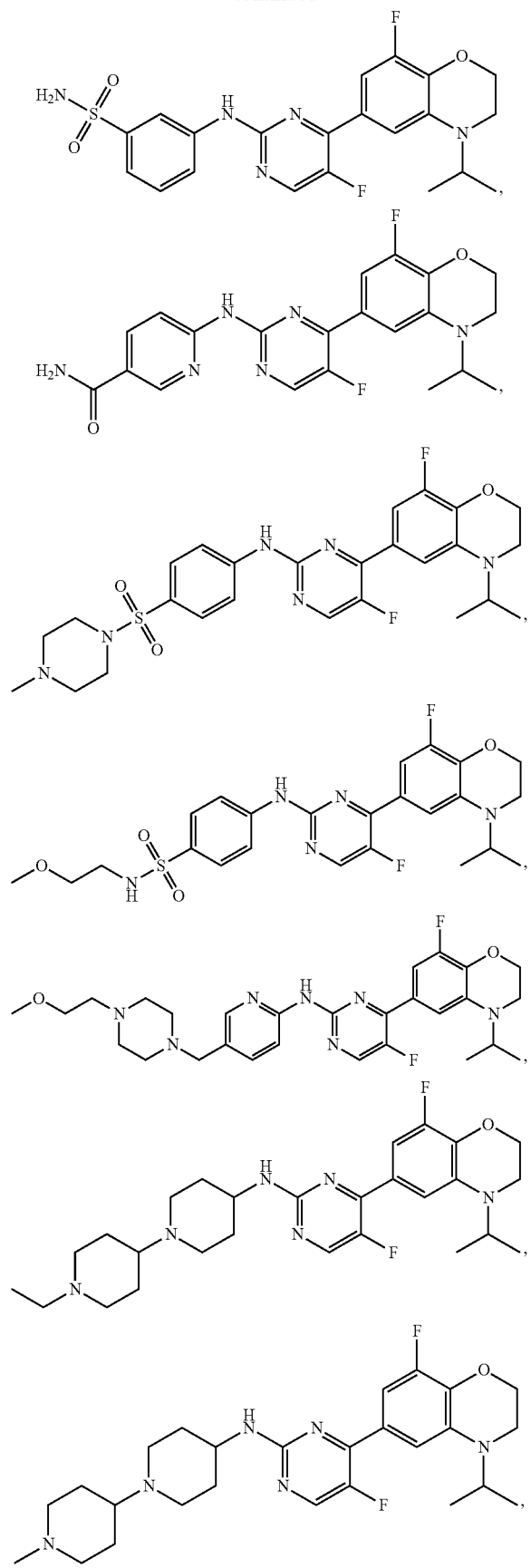
886
-continued
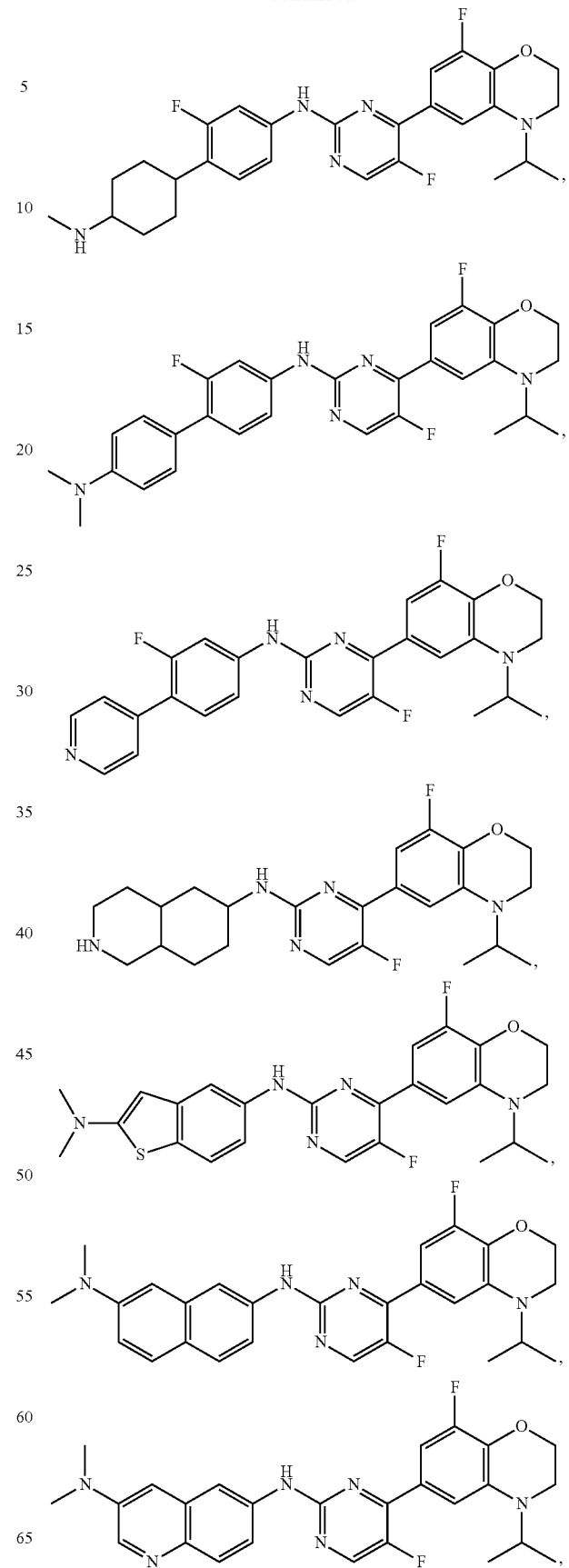

887
-continued
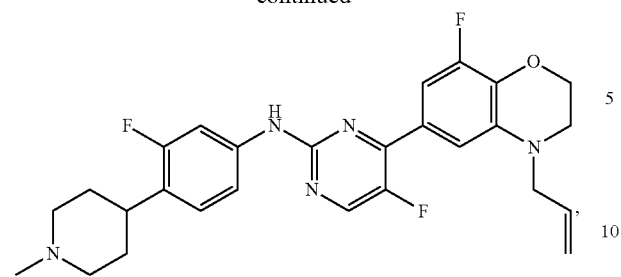
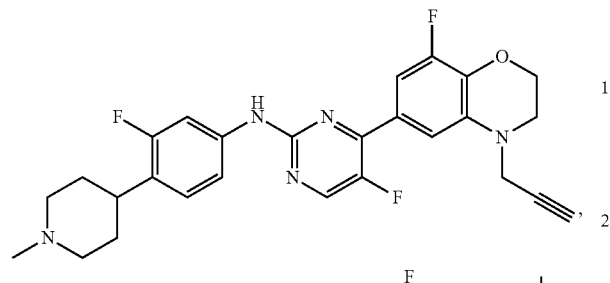
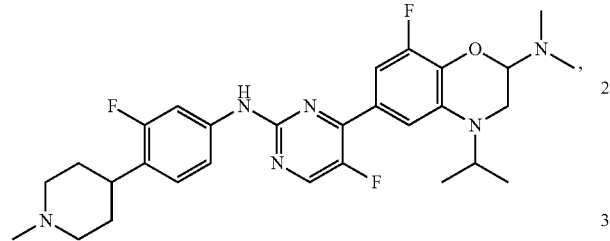
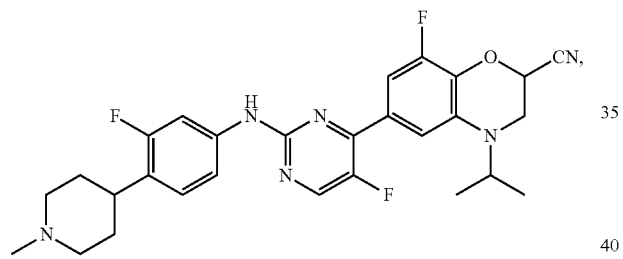
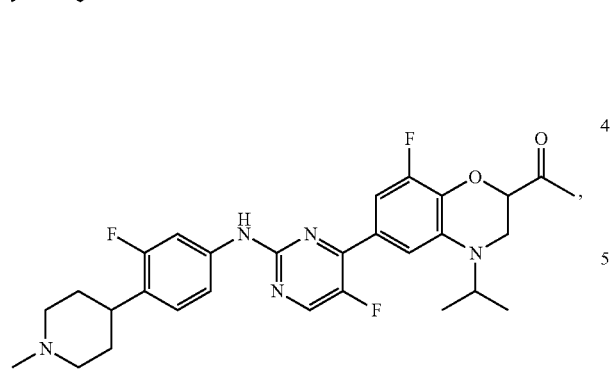
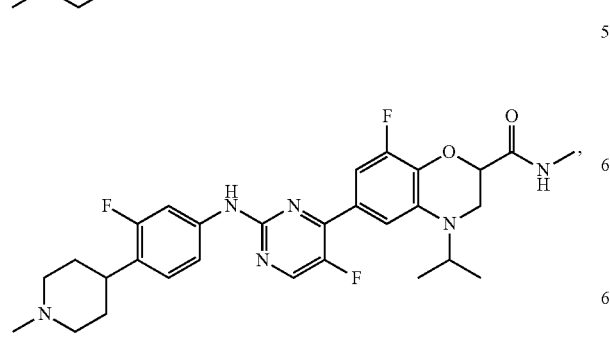
888
-continued
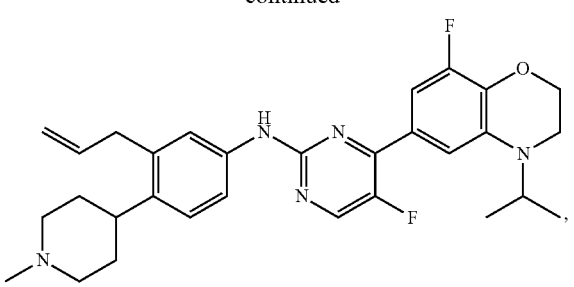
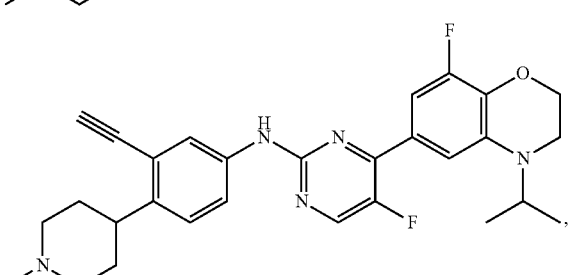
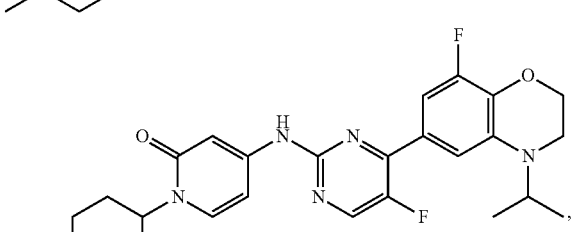
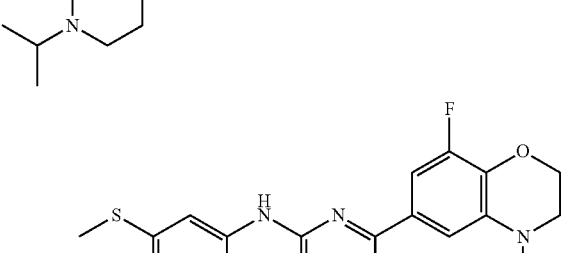
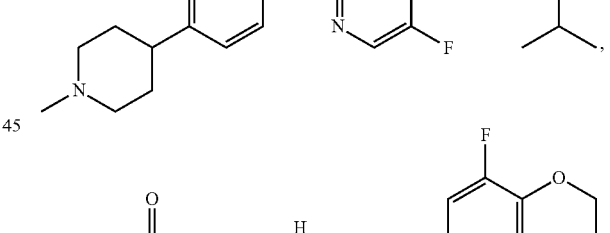
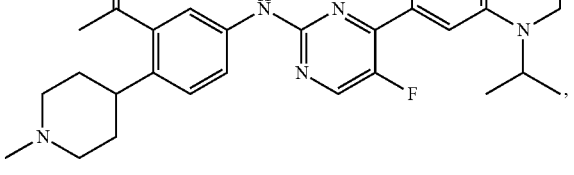
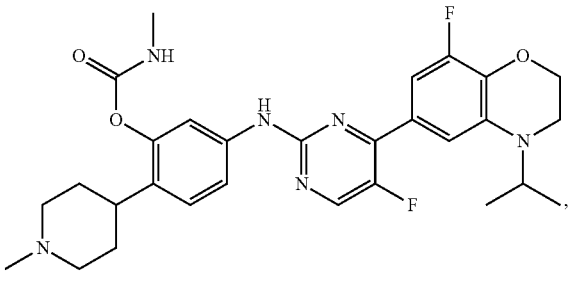

889
-continued
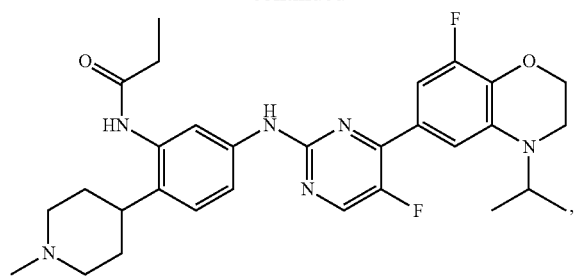
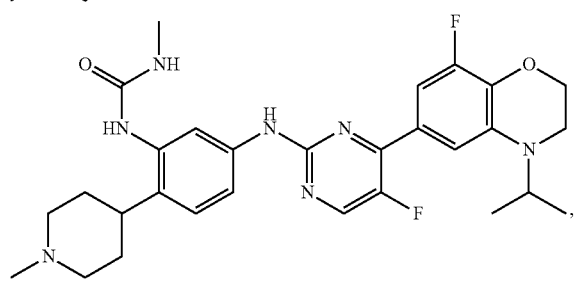
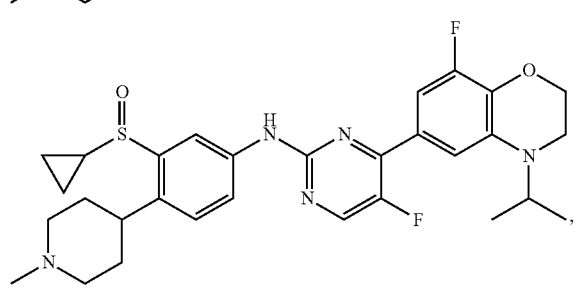
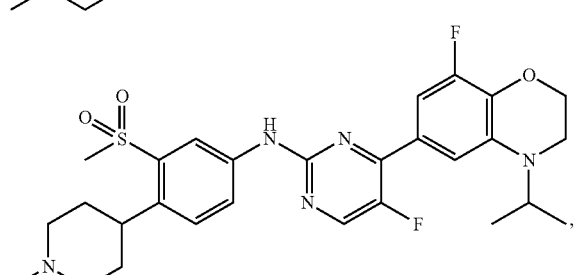
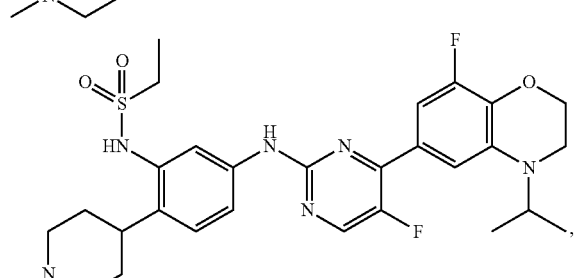
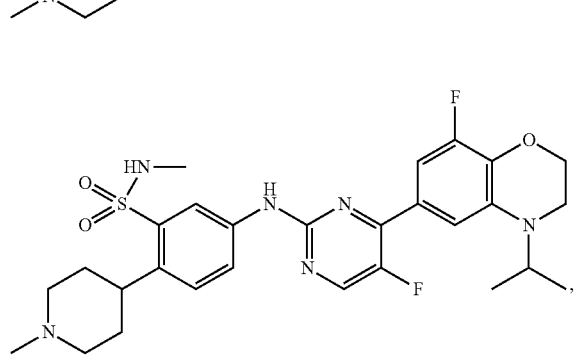
890
-continued
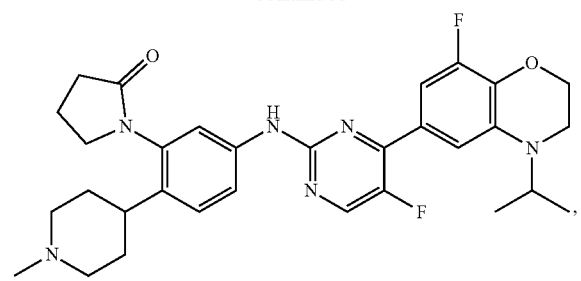
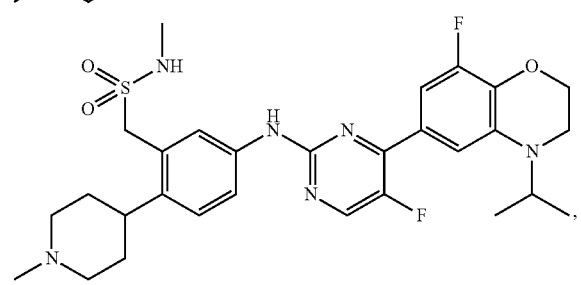
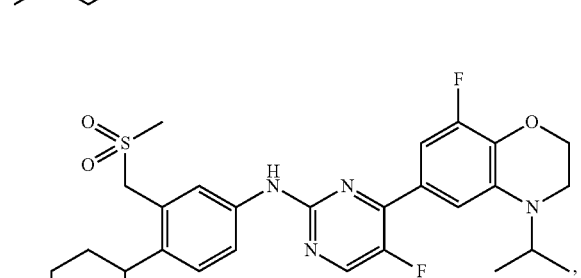
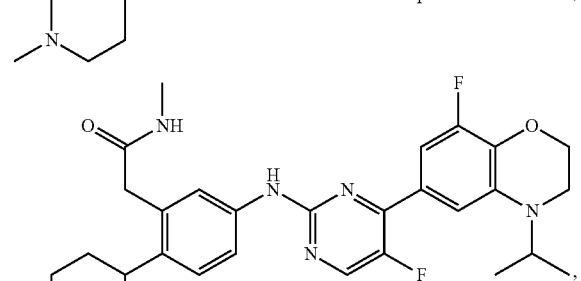
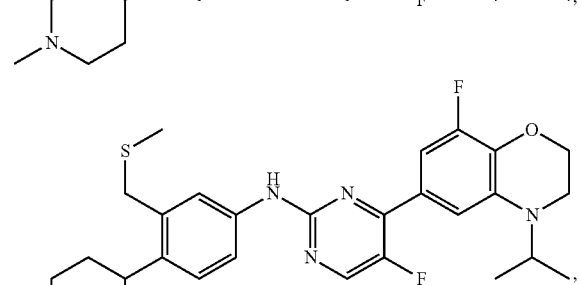
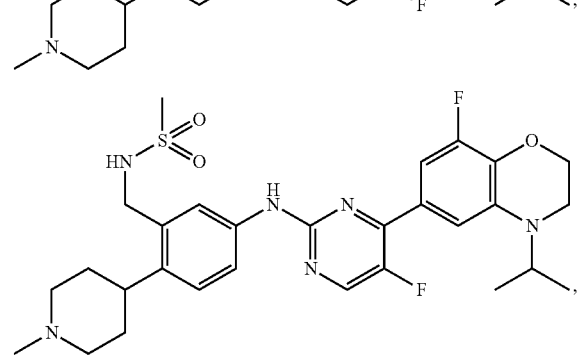

891
-continued
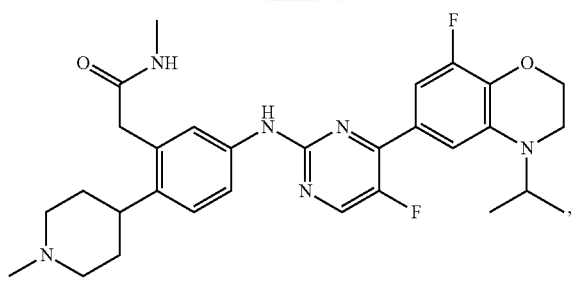
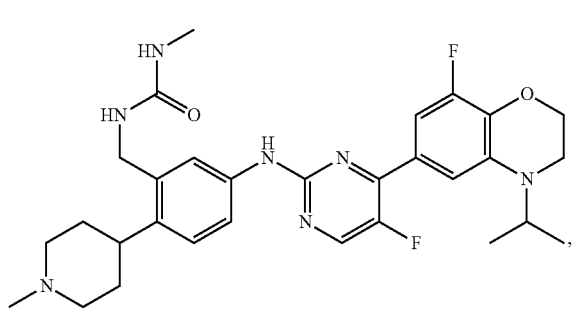
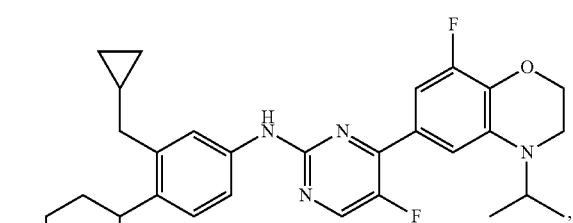
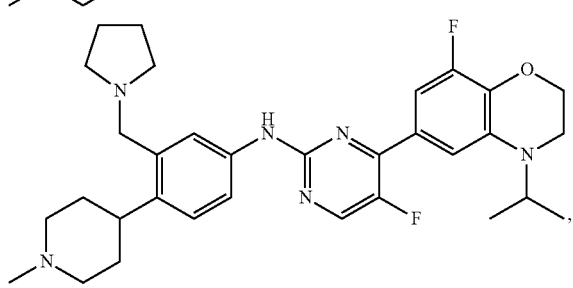
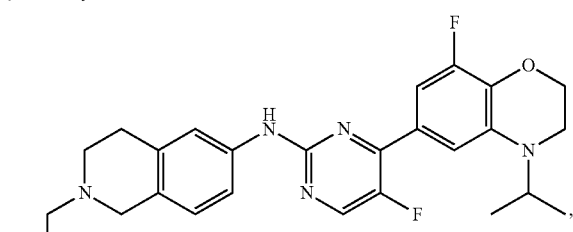
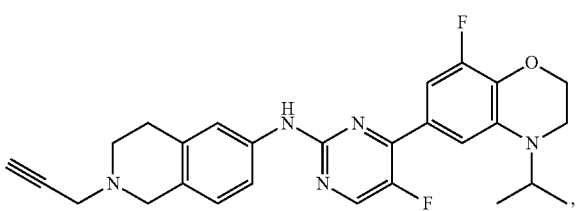
892
-continued
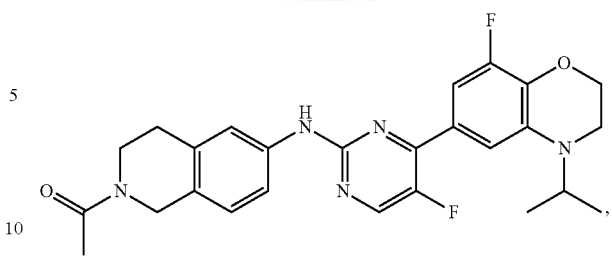
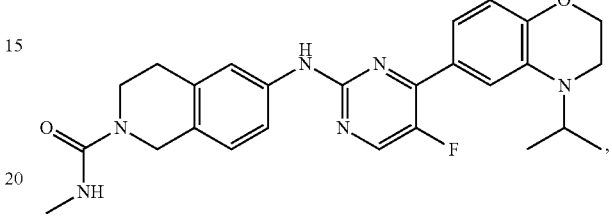
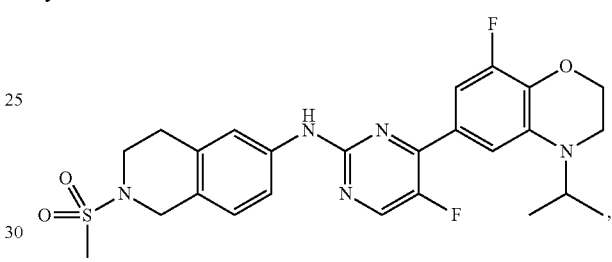
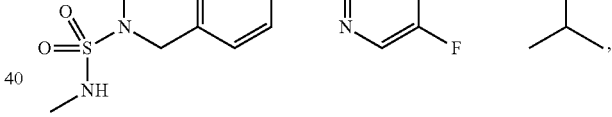
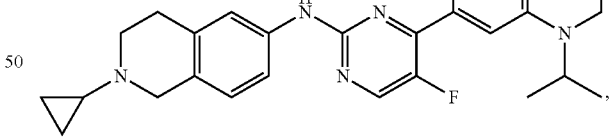
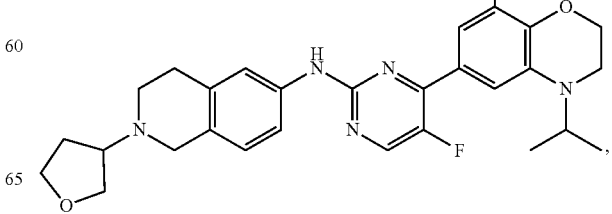

893
-continued
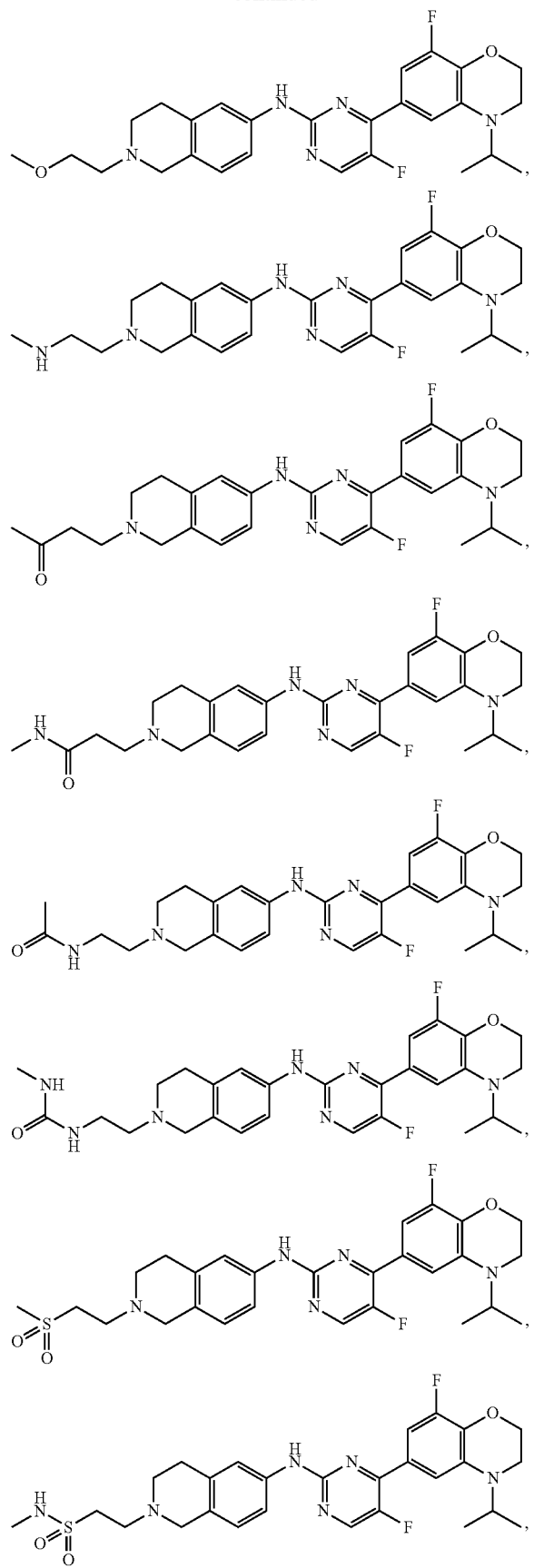
894
-continued
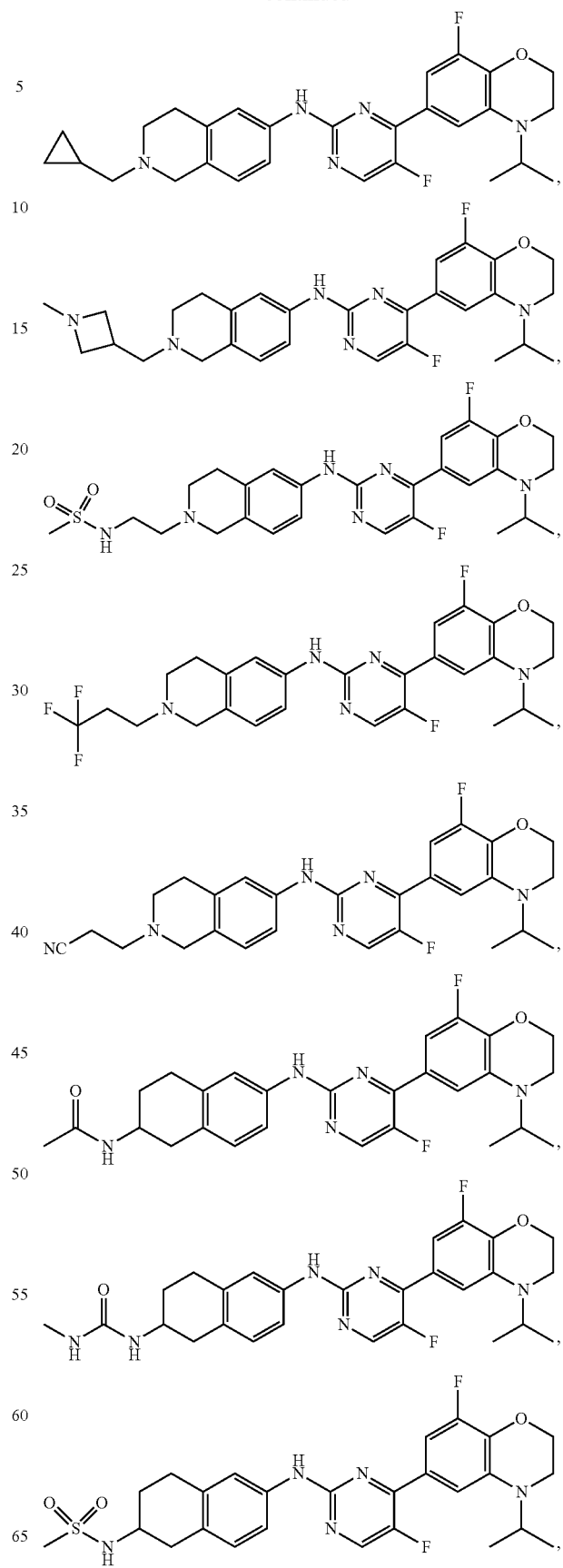

895
-continued
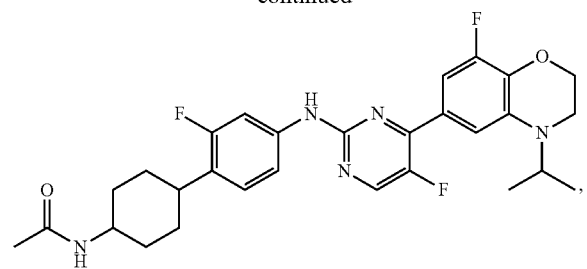
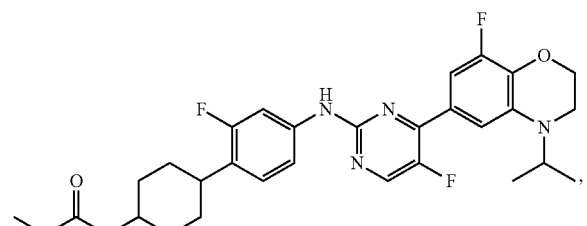
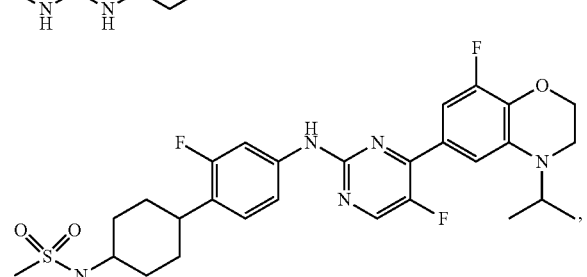
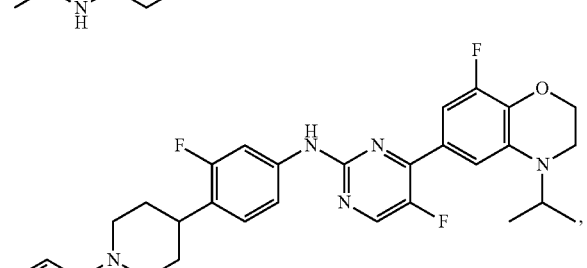
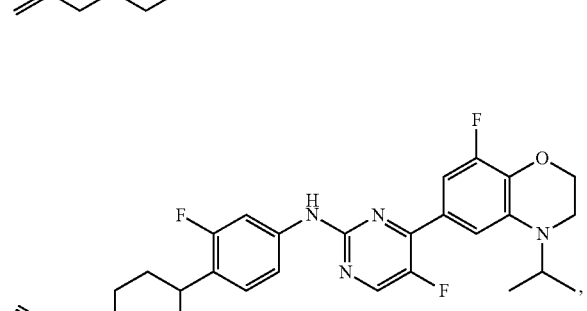
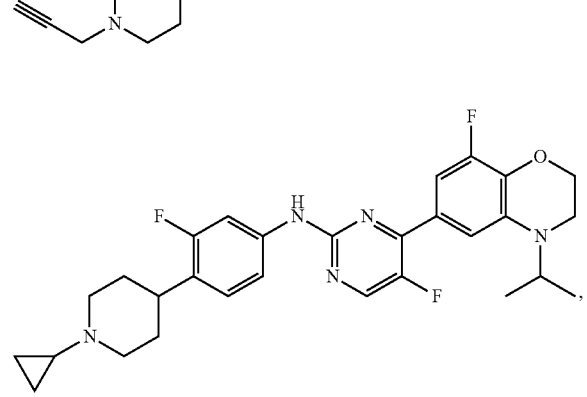
896
-continued
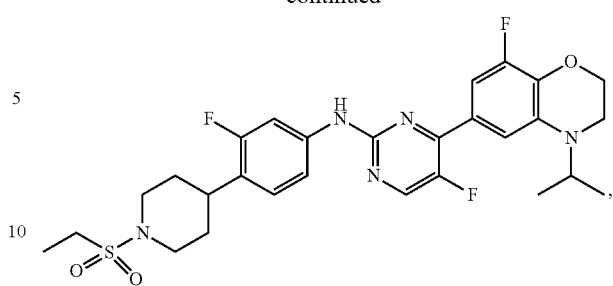
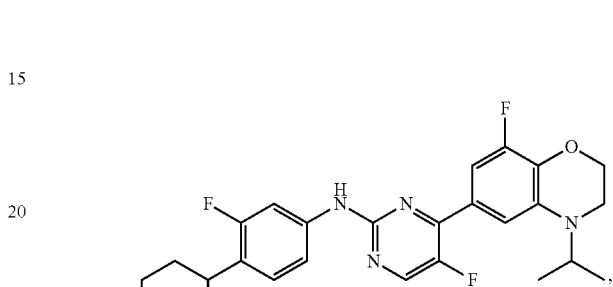
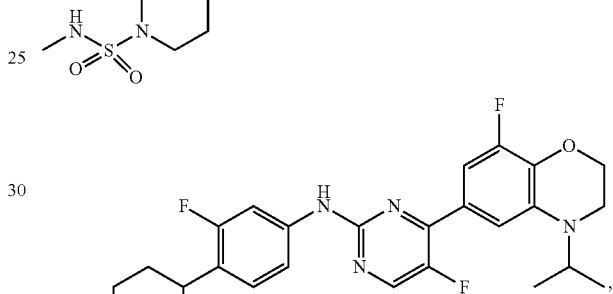
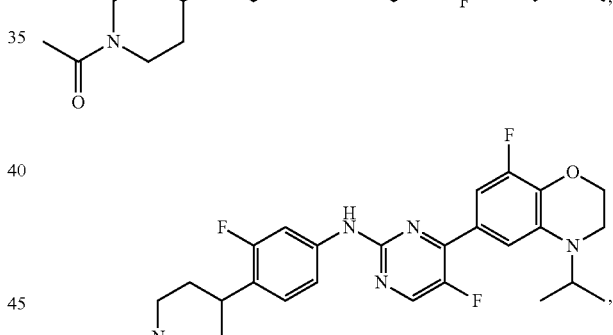
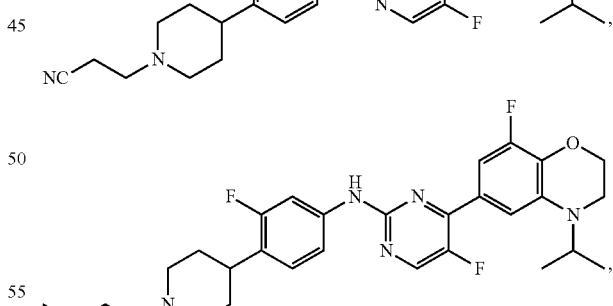
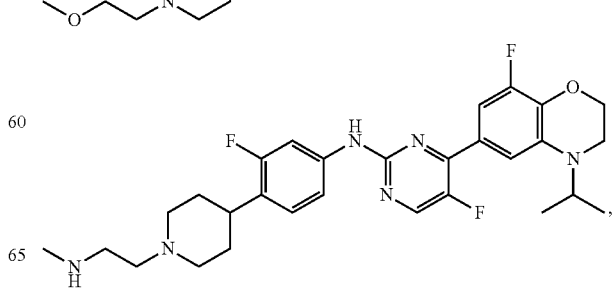

897
-continued
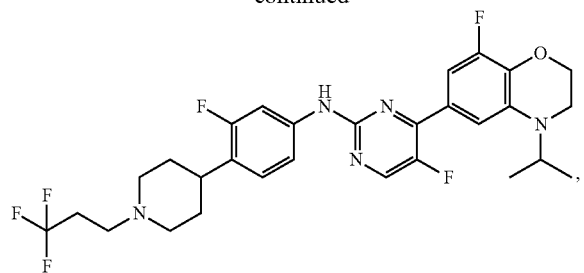
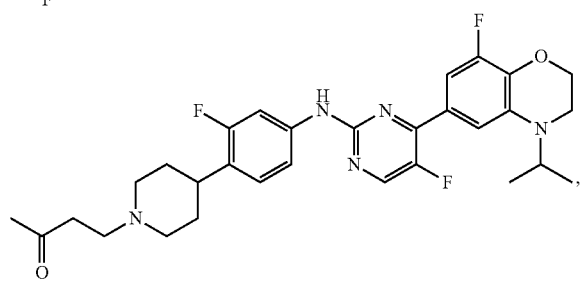
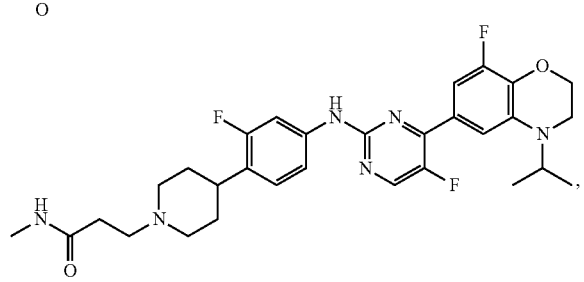
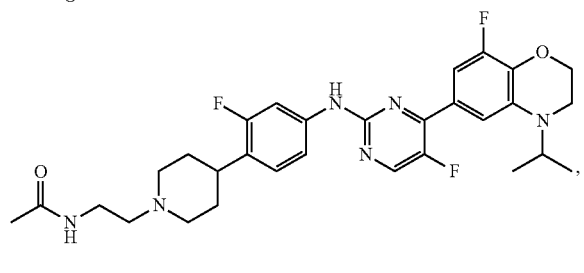
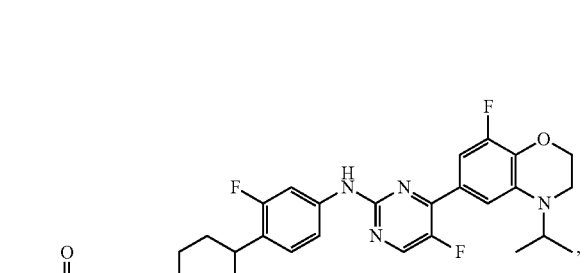
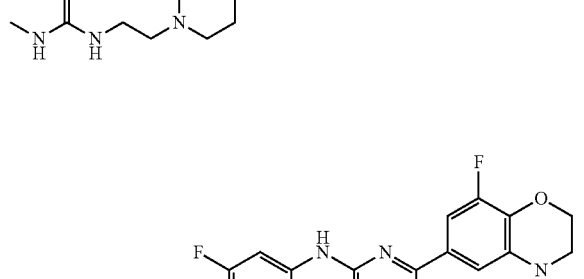
898
-continued
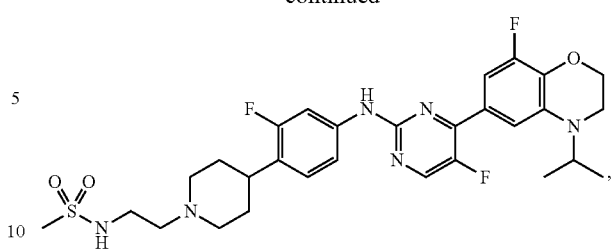
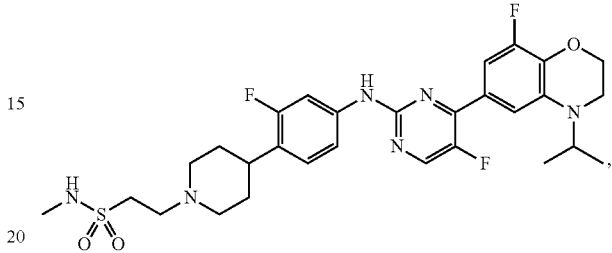
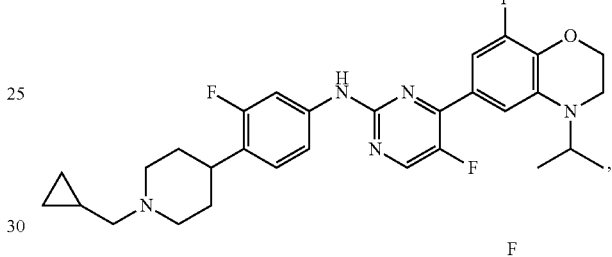
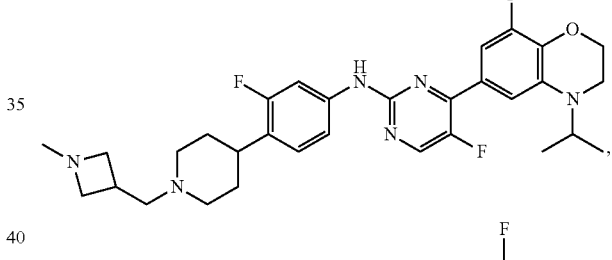
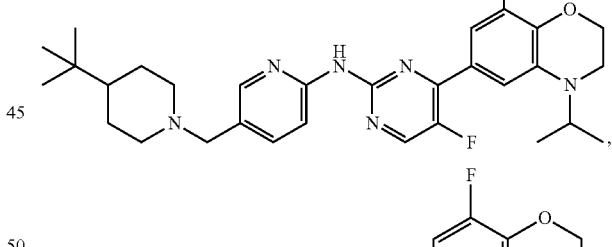
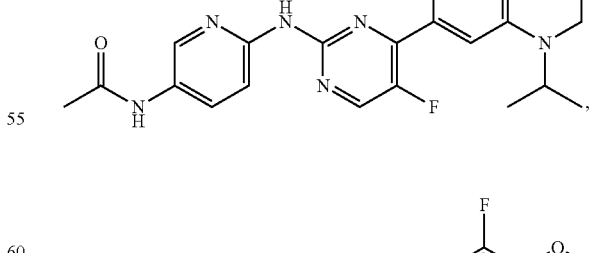
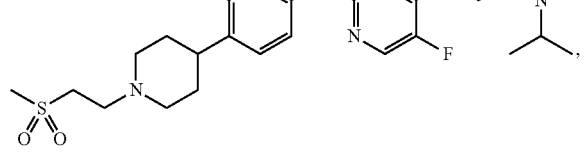
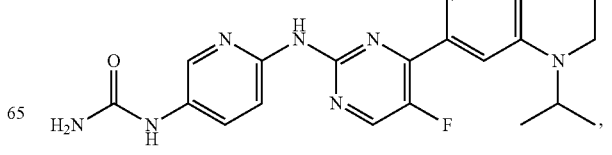

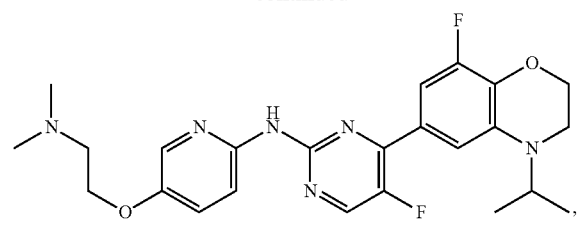
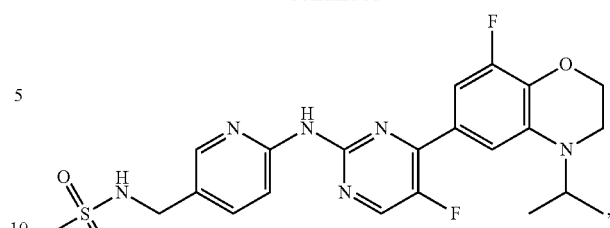
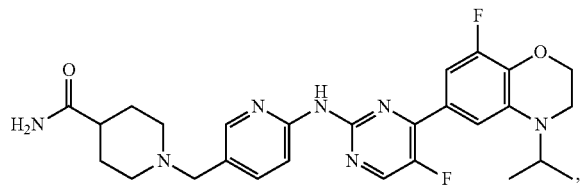
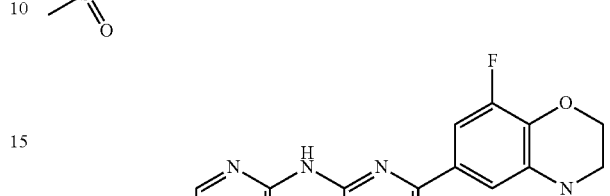
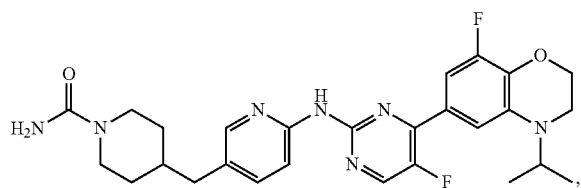
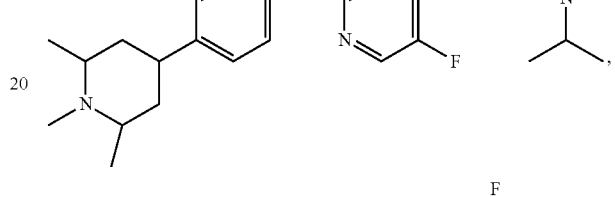
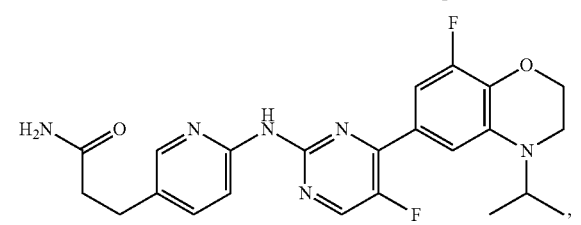
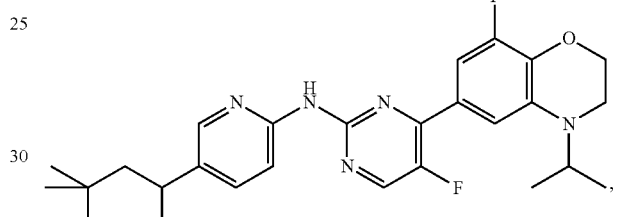
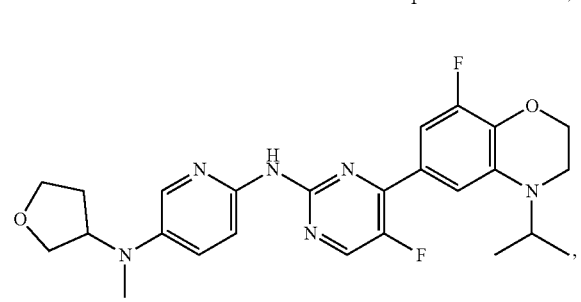
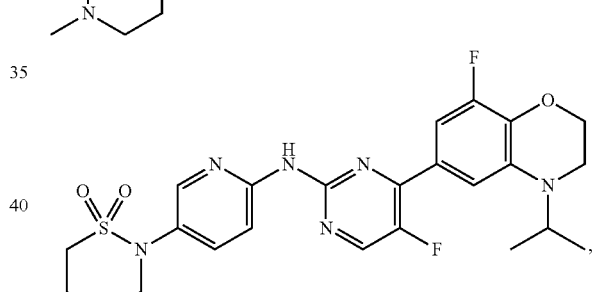
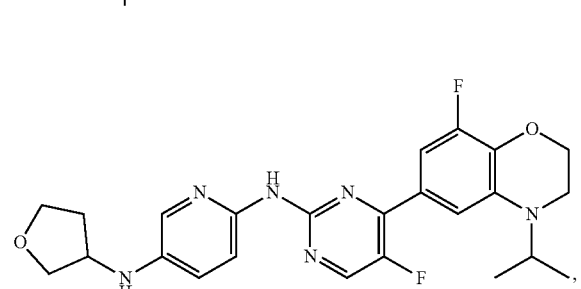
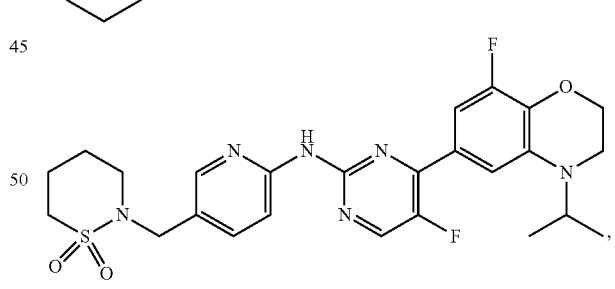
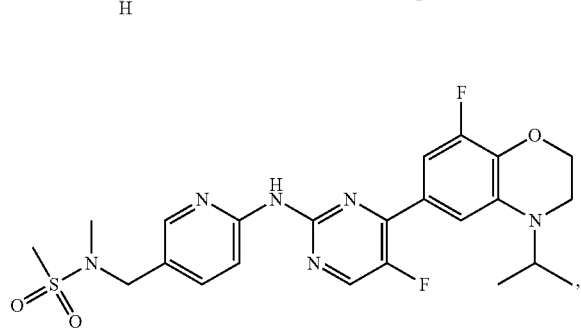
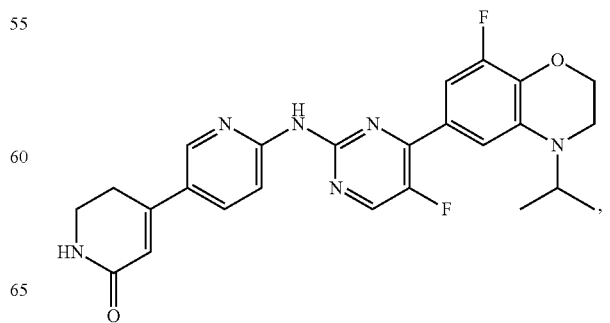

901
-continued
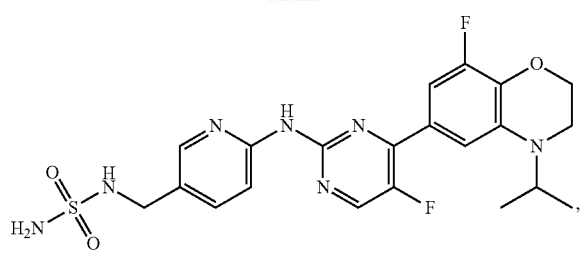
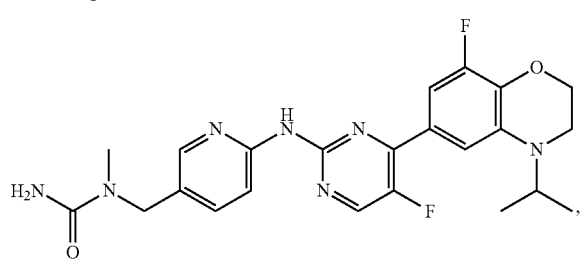
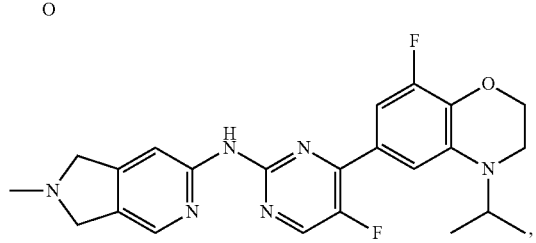
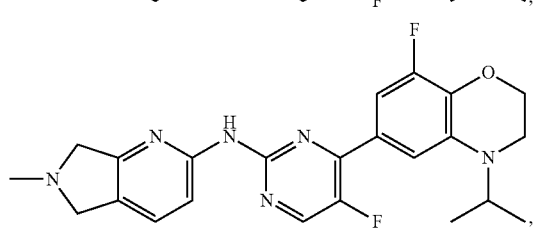
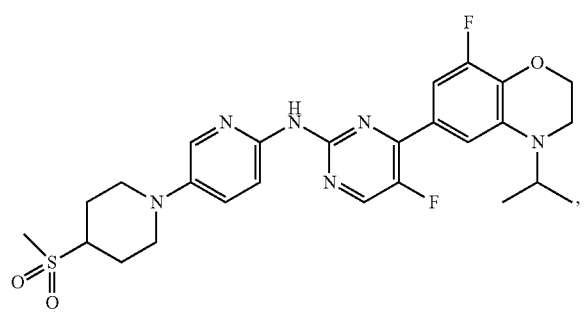
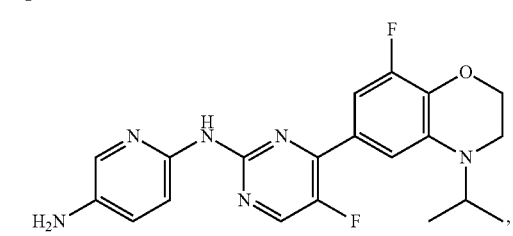
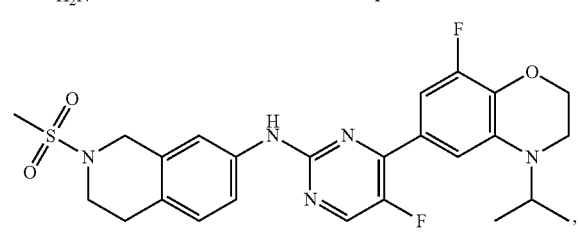
902
-continued
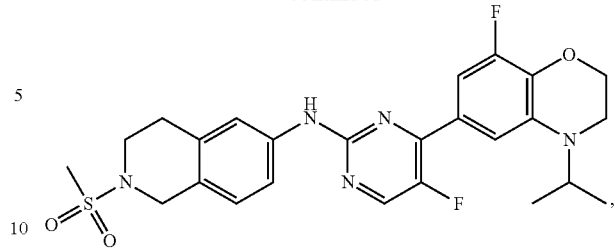
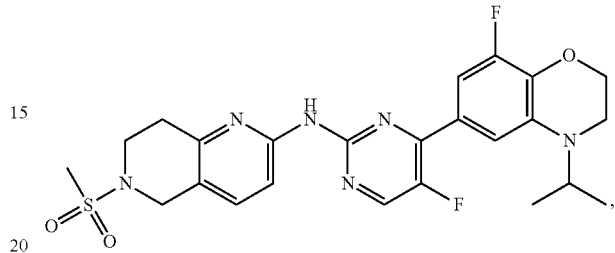
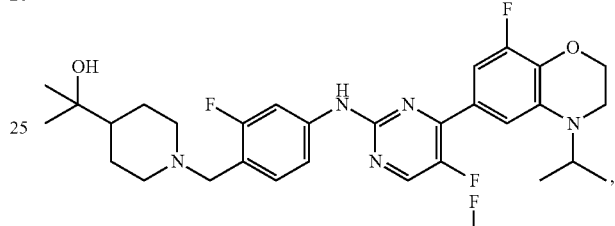
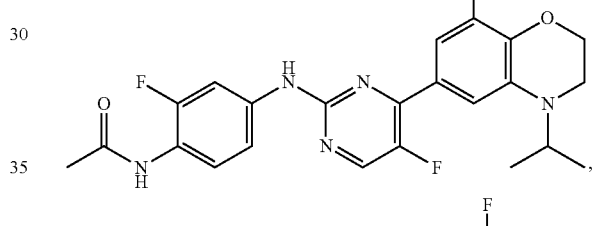
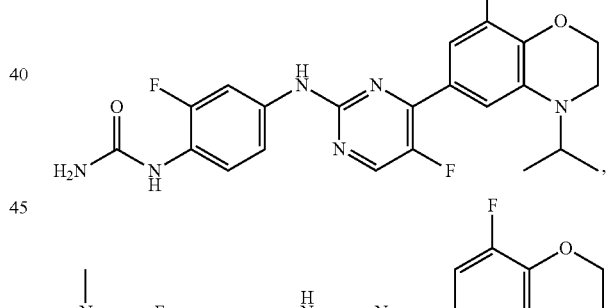
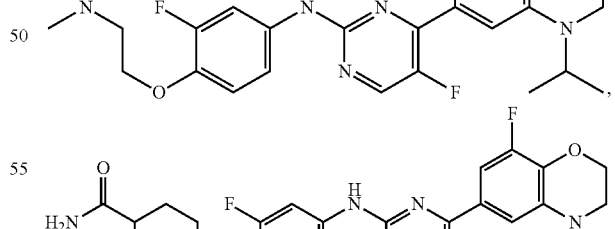
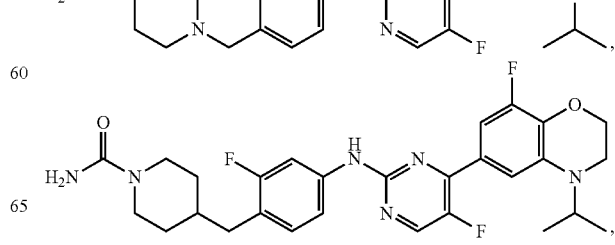

903
-continued
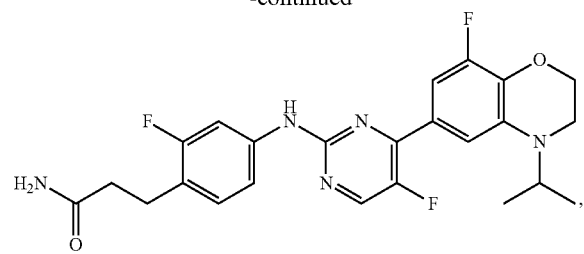
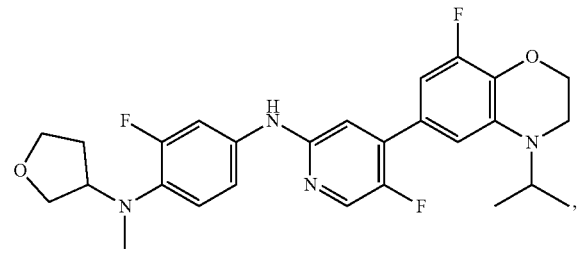
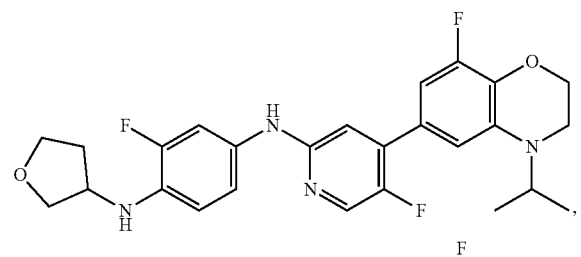
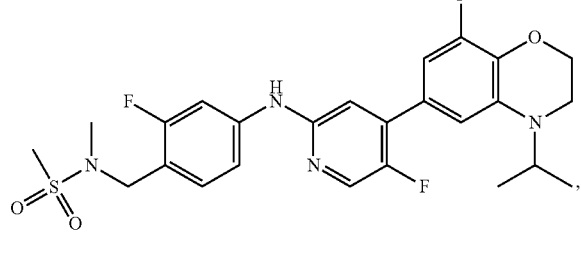
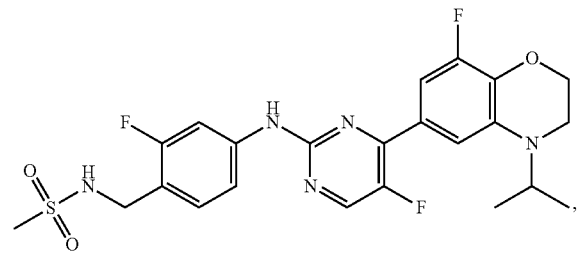
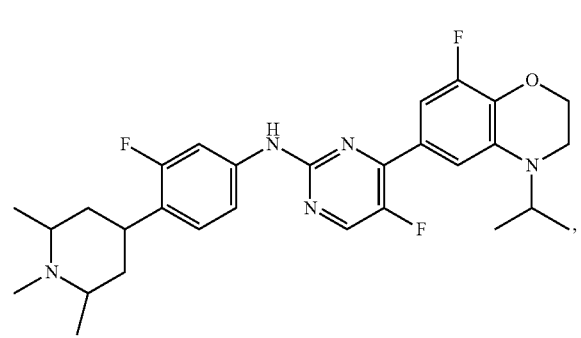
904
-continued
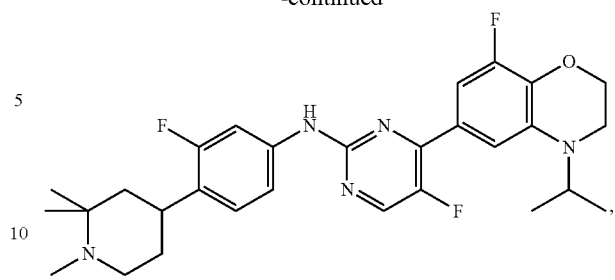
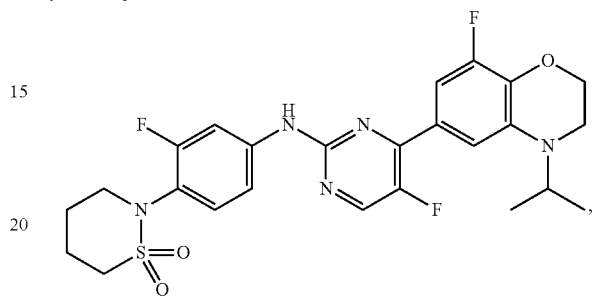
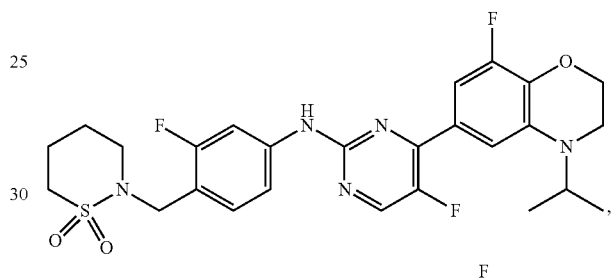
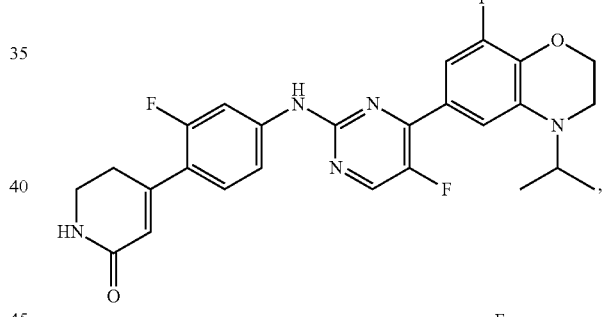
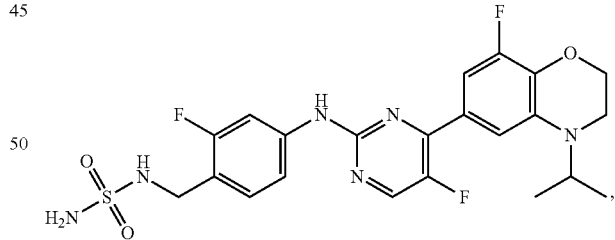
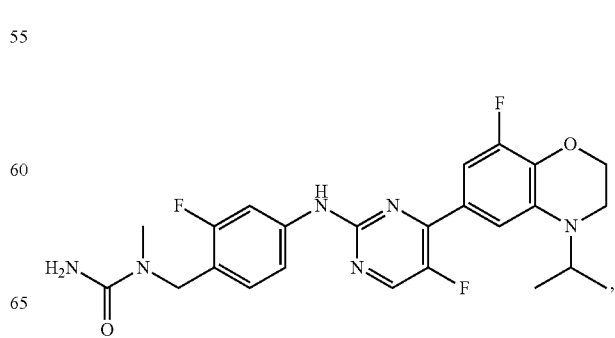

905
-continued
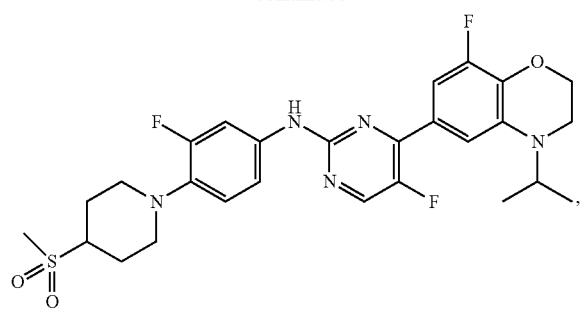
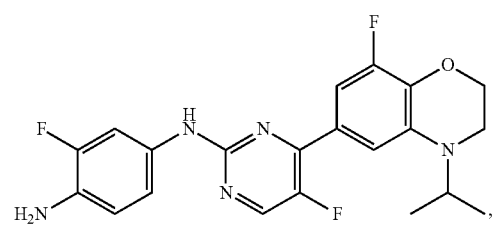
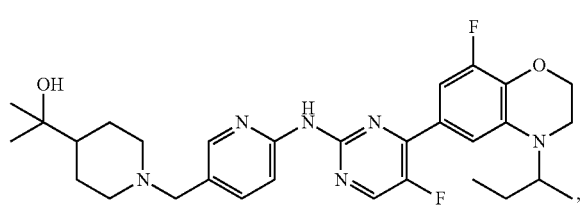
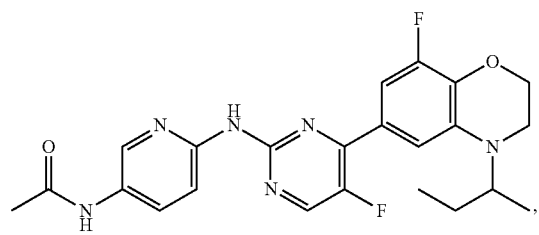
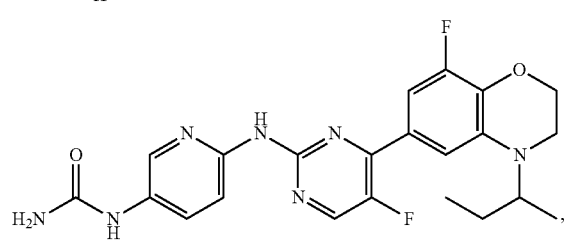
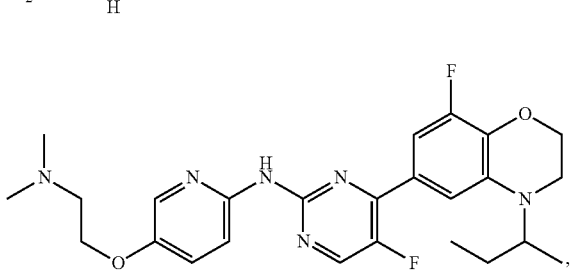
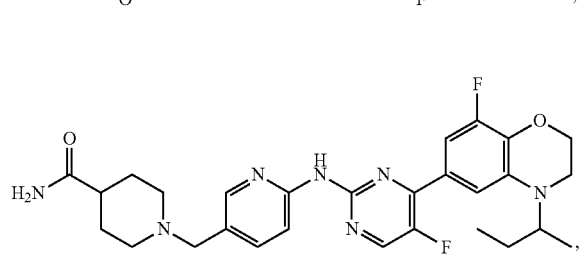
906
-continued
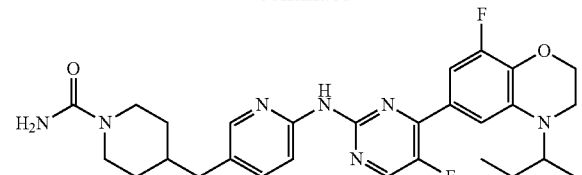
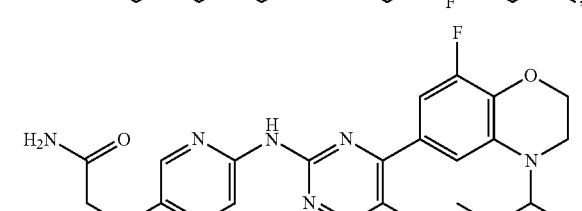
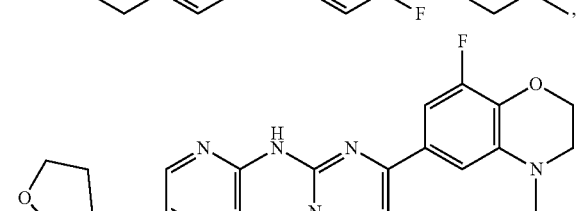
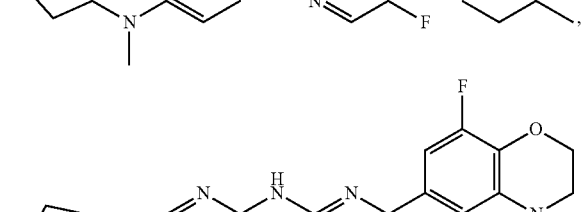
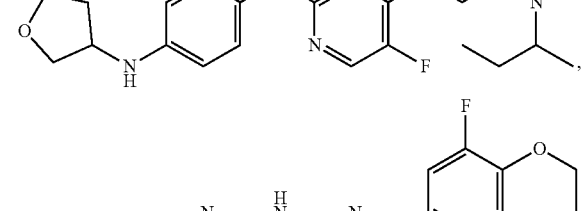
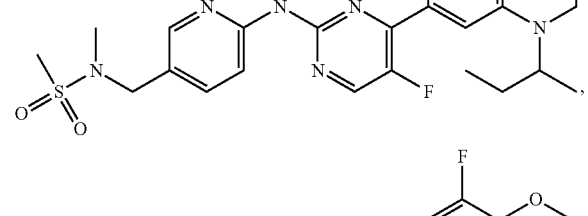
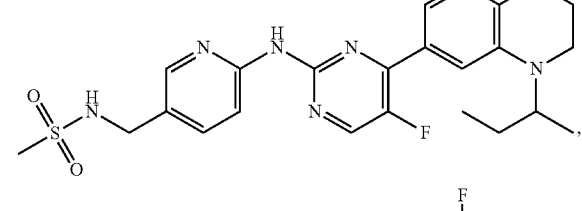
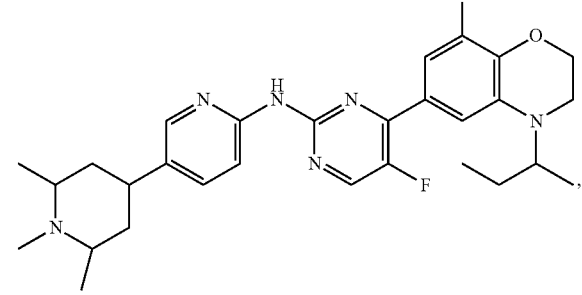

907
-continued
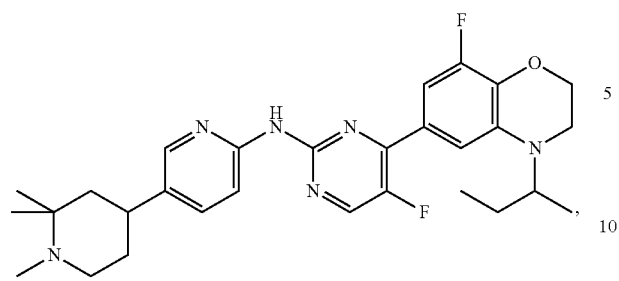
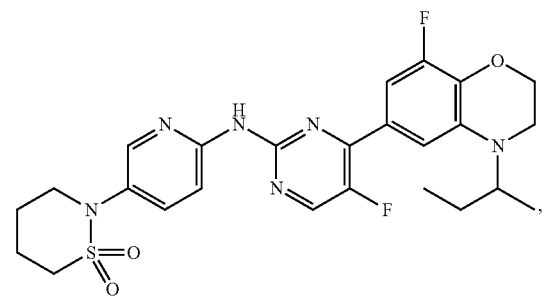
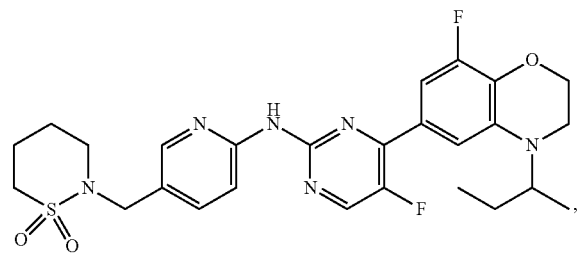
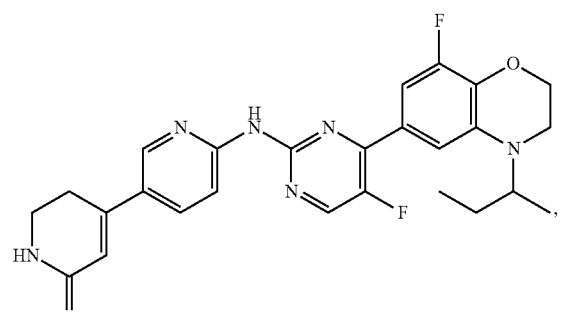
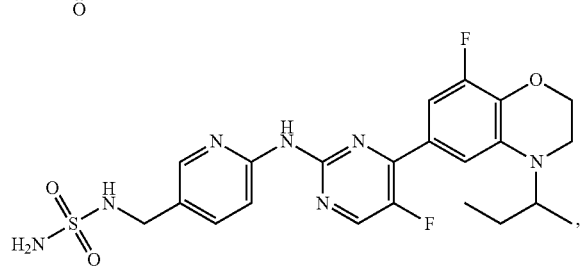
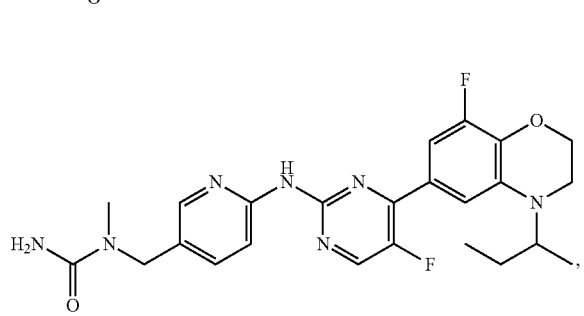
908
-continued
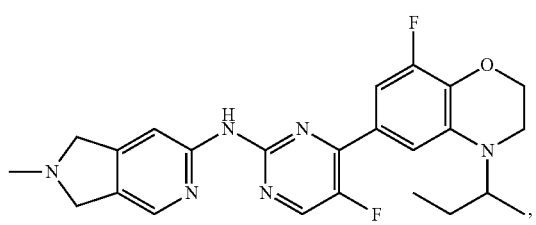
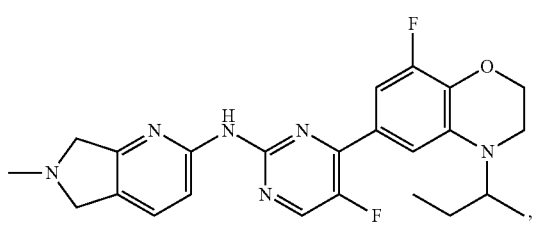
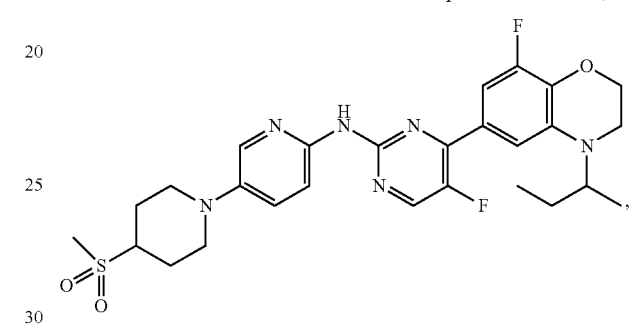
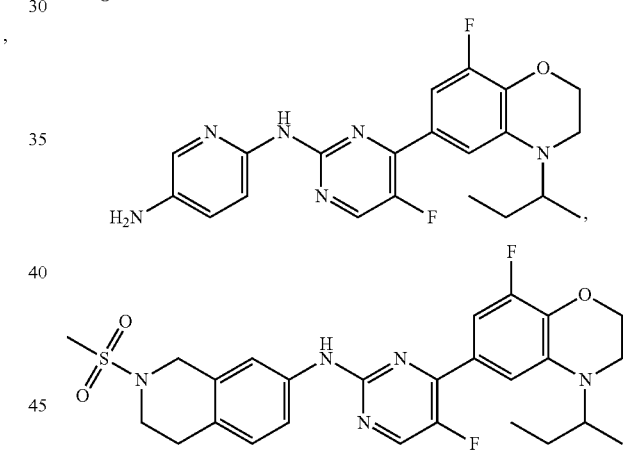
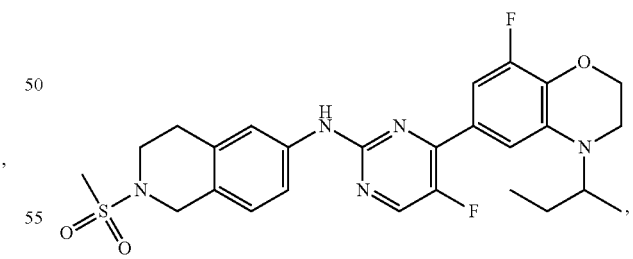
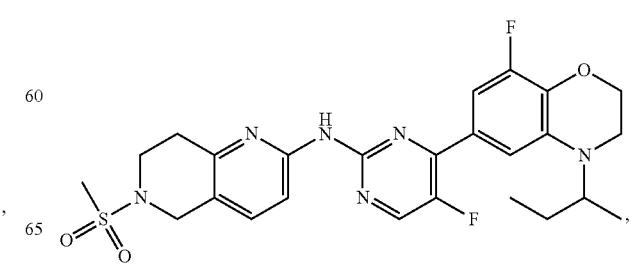

909
-continued
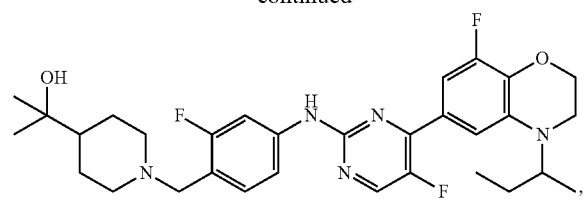
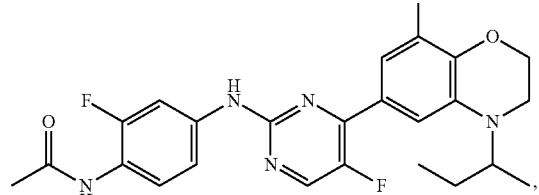
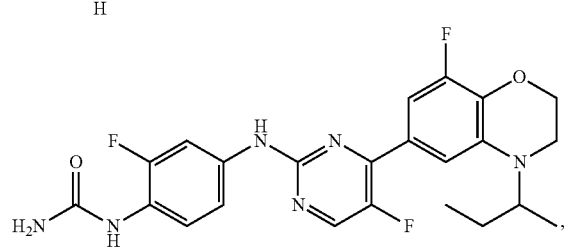
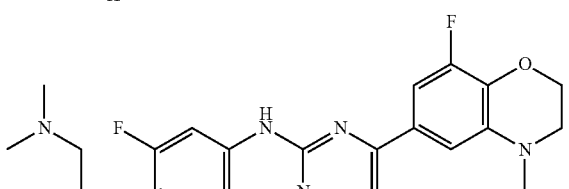
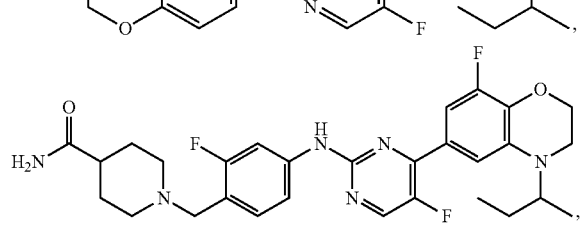
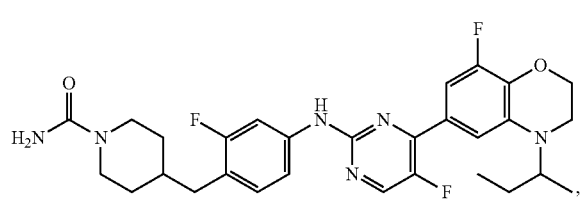
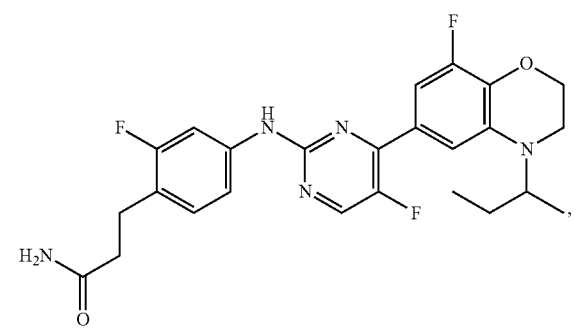
910
-continued
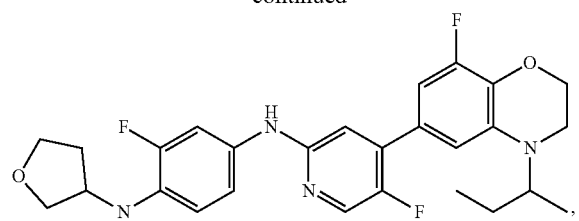
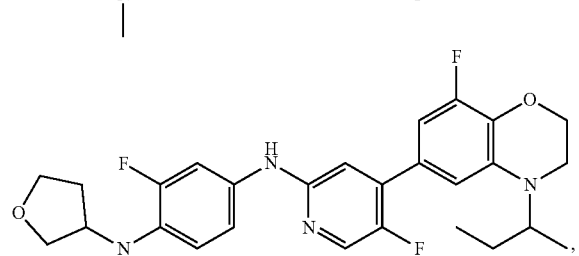
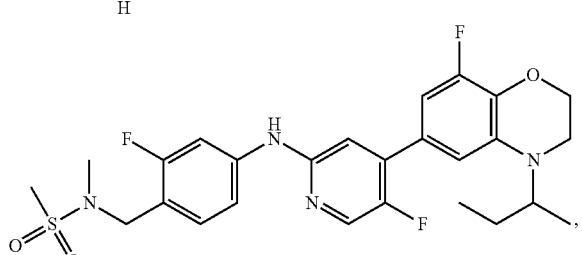
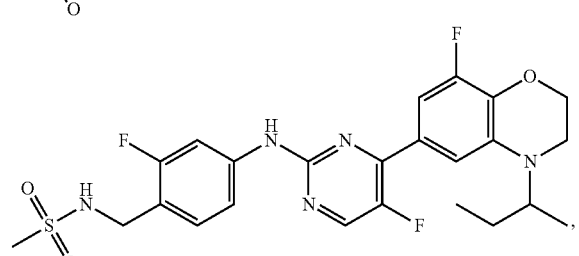
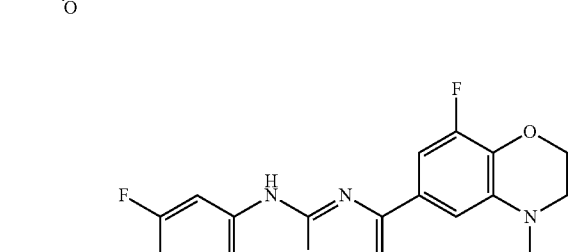
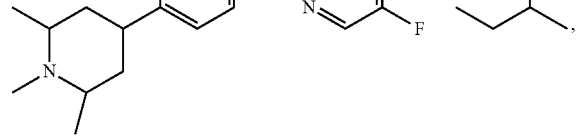
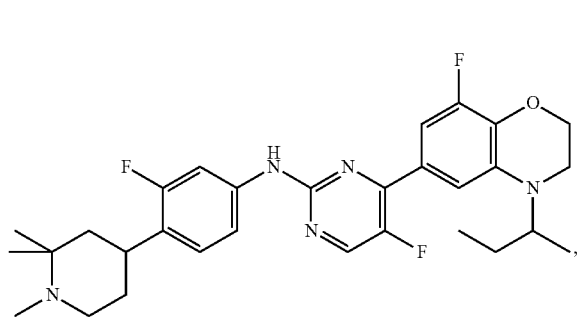

911
-continued
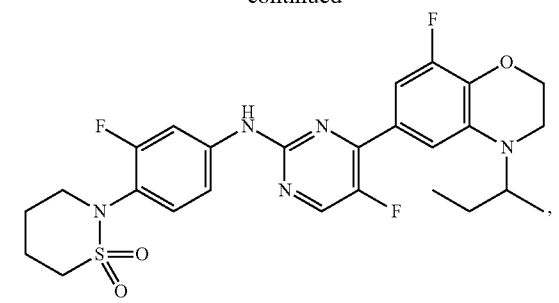
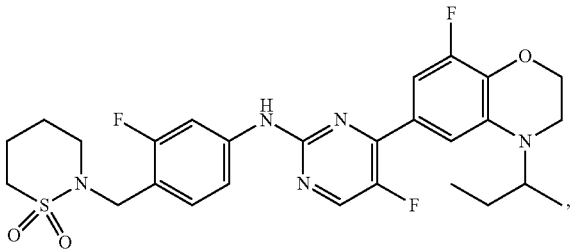
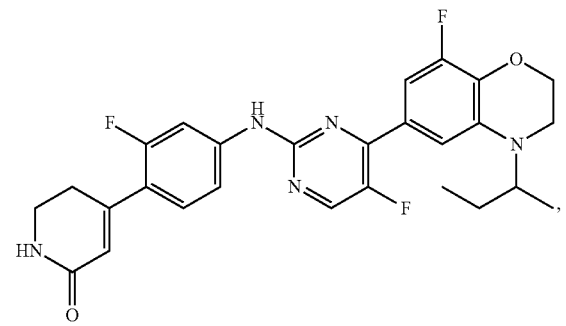
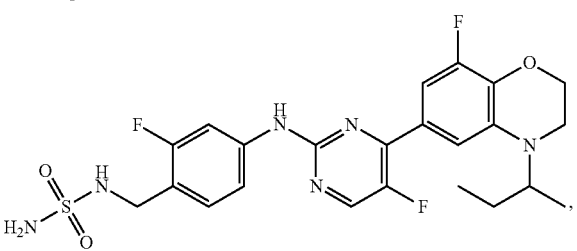
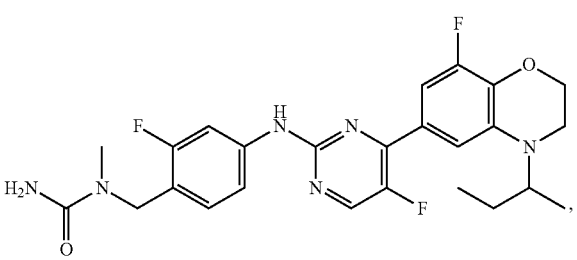
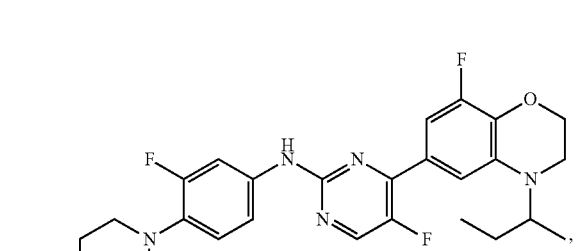
912
-continued
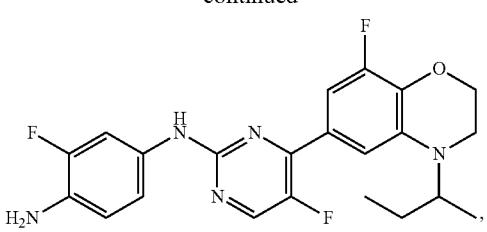
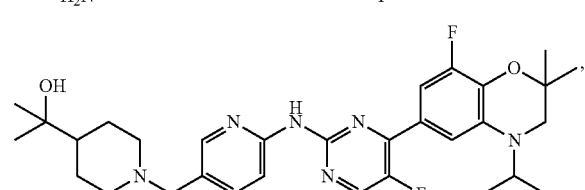
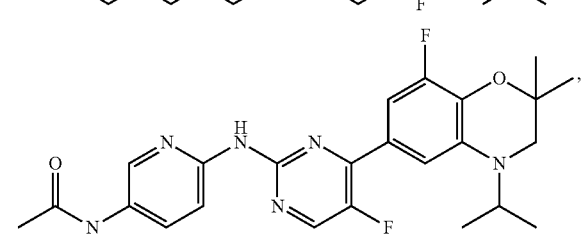
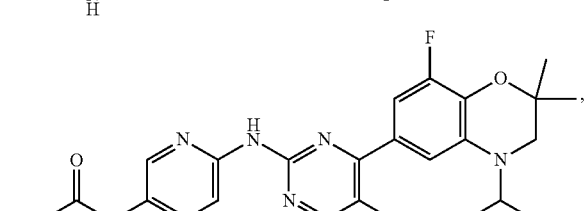
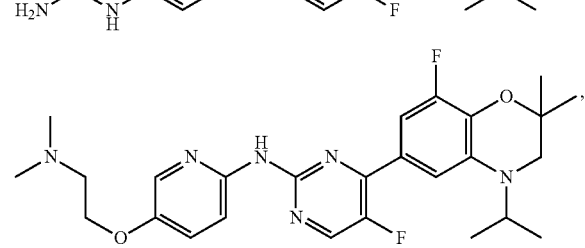
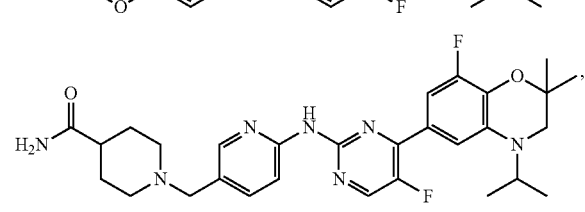
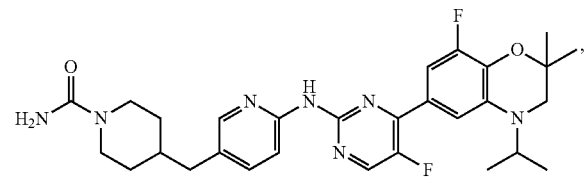
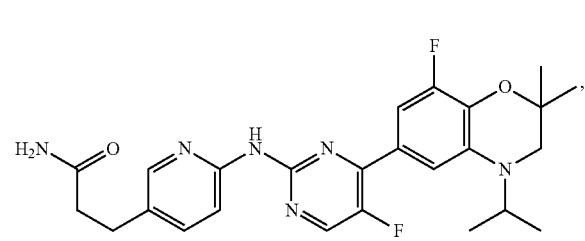

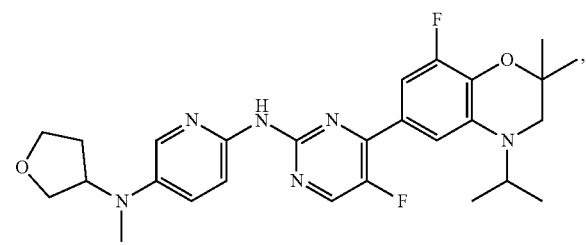
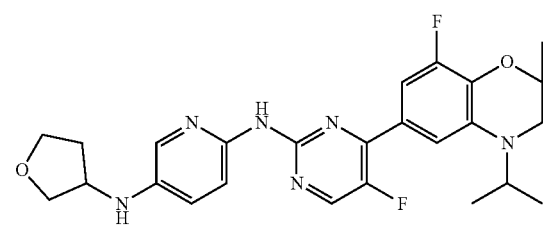
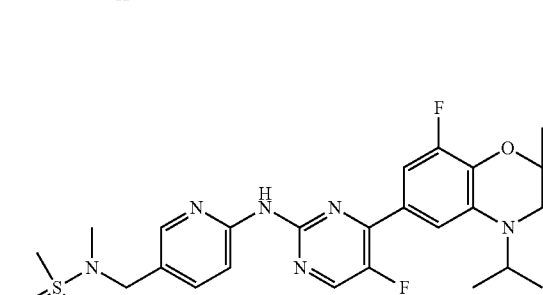
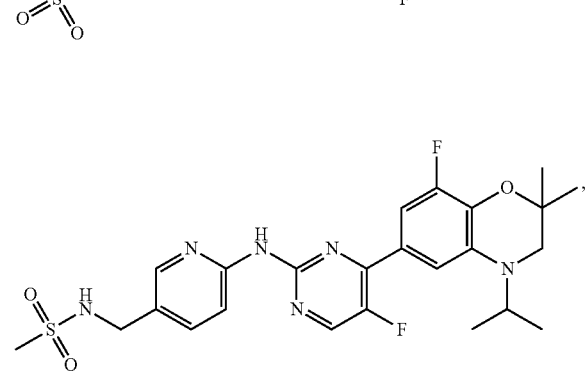
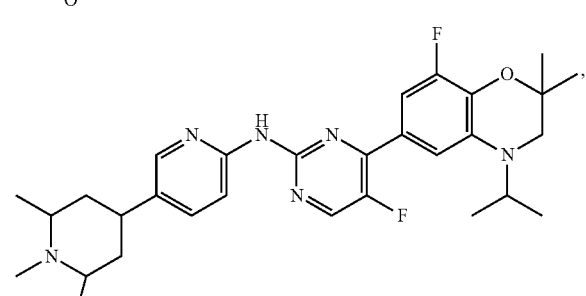
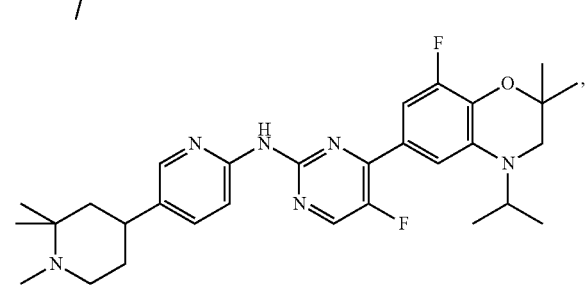
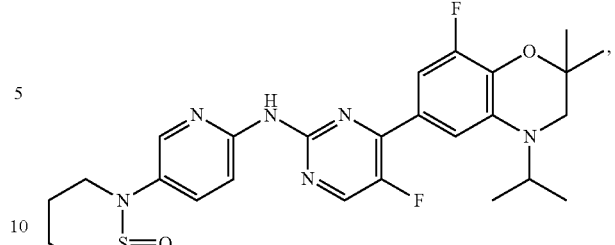
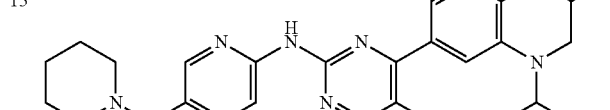
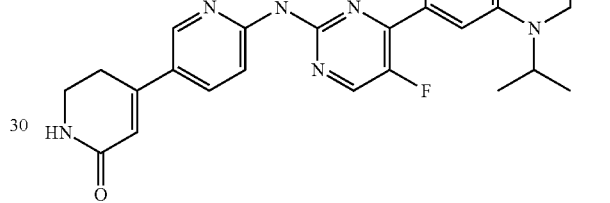
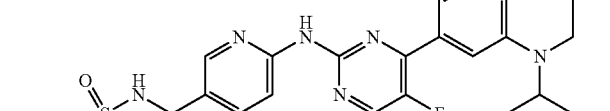
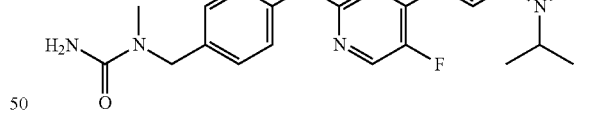
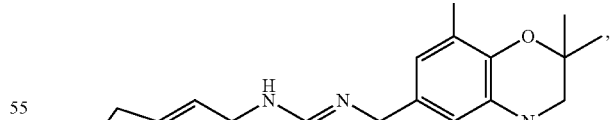
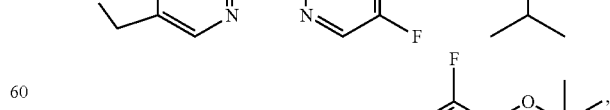
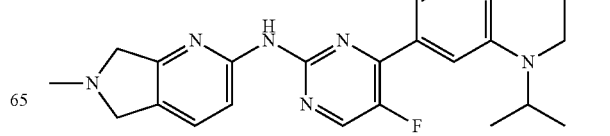

915
-continued
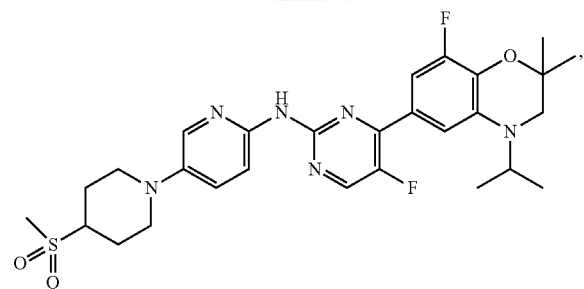
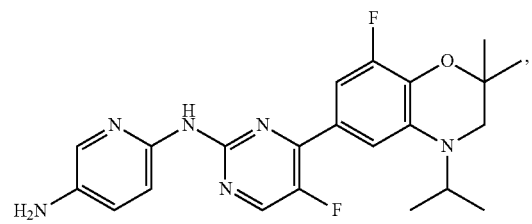
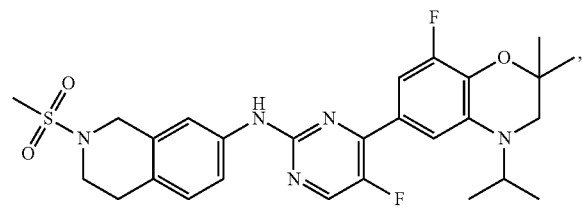
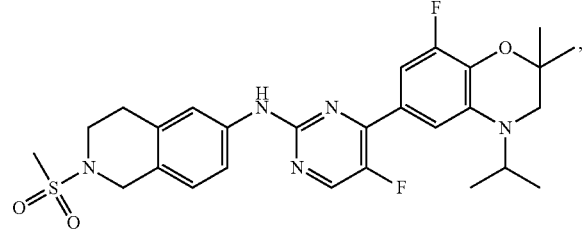
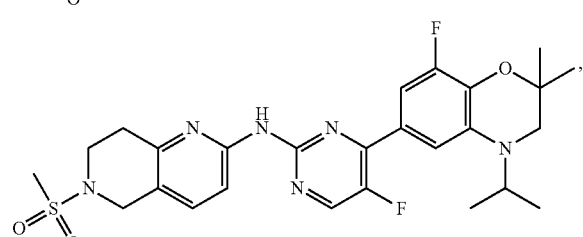
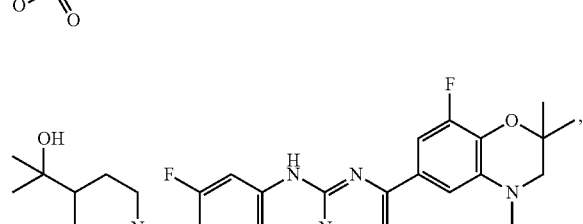
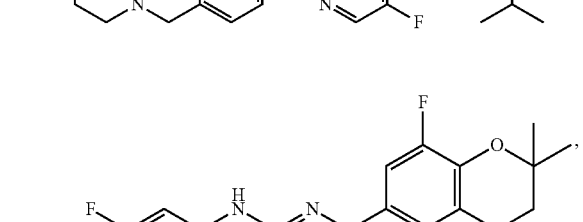
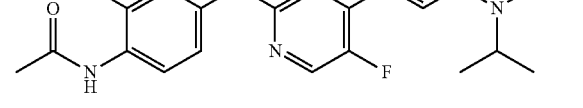
916
-continued
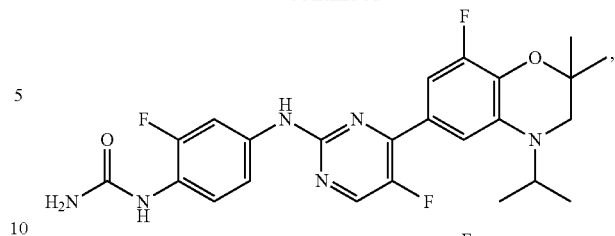
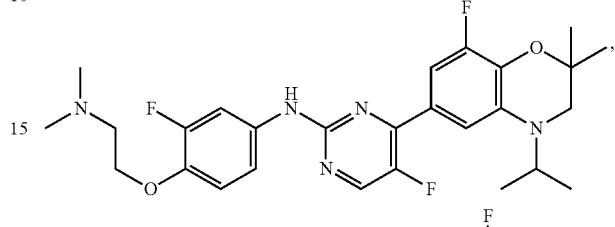
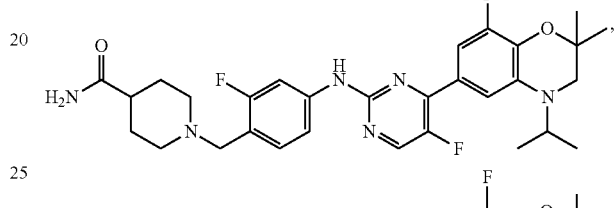
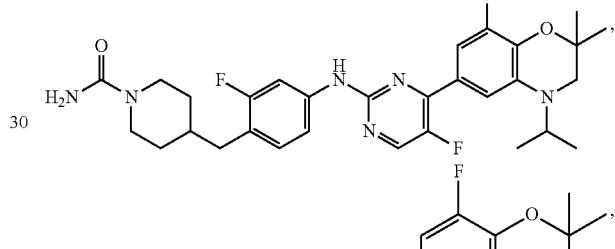
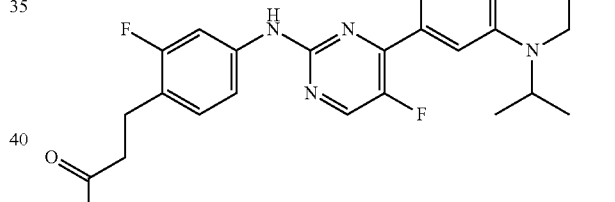
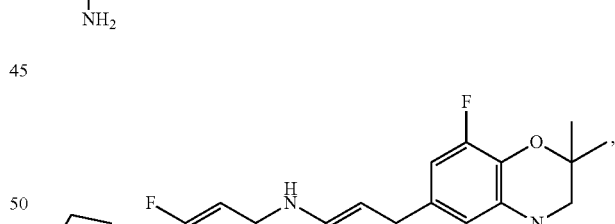
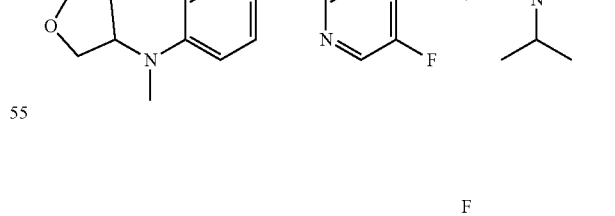
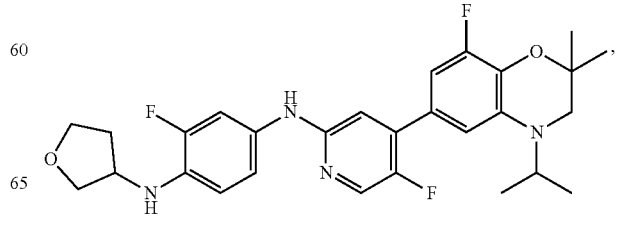

917
-continued
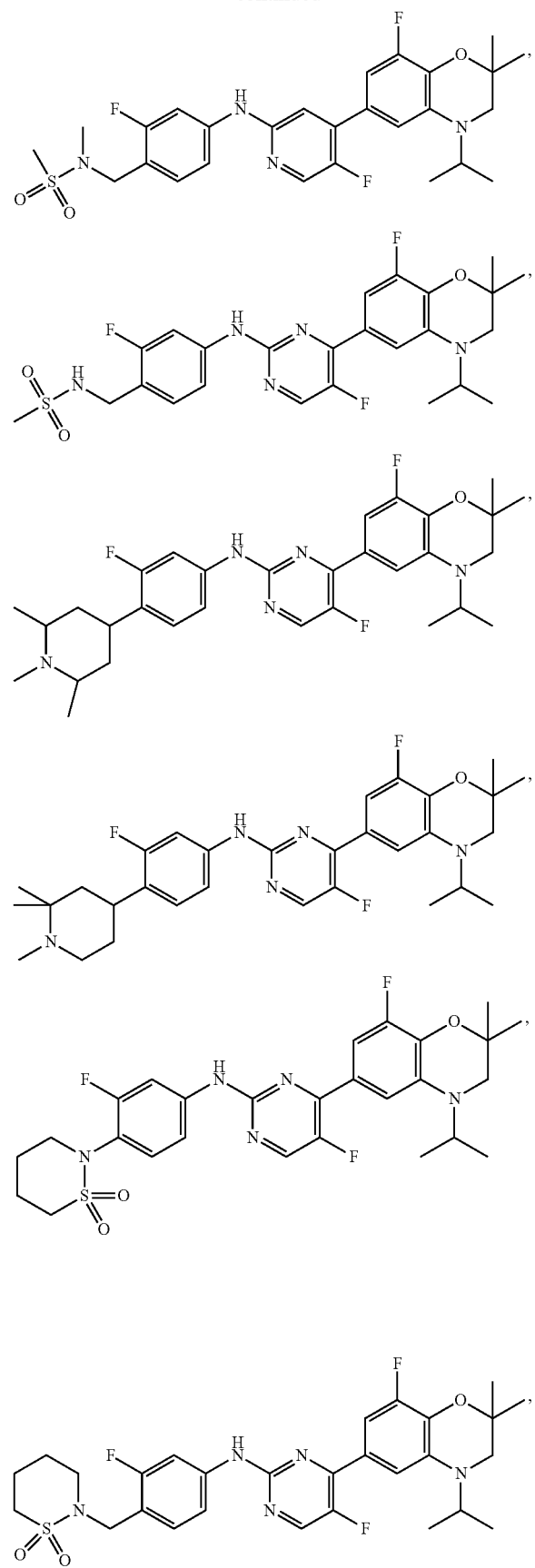
918
-continued
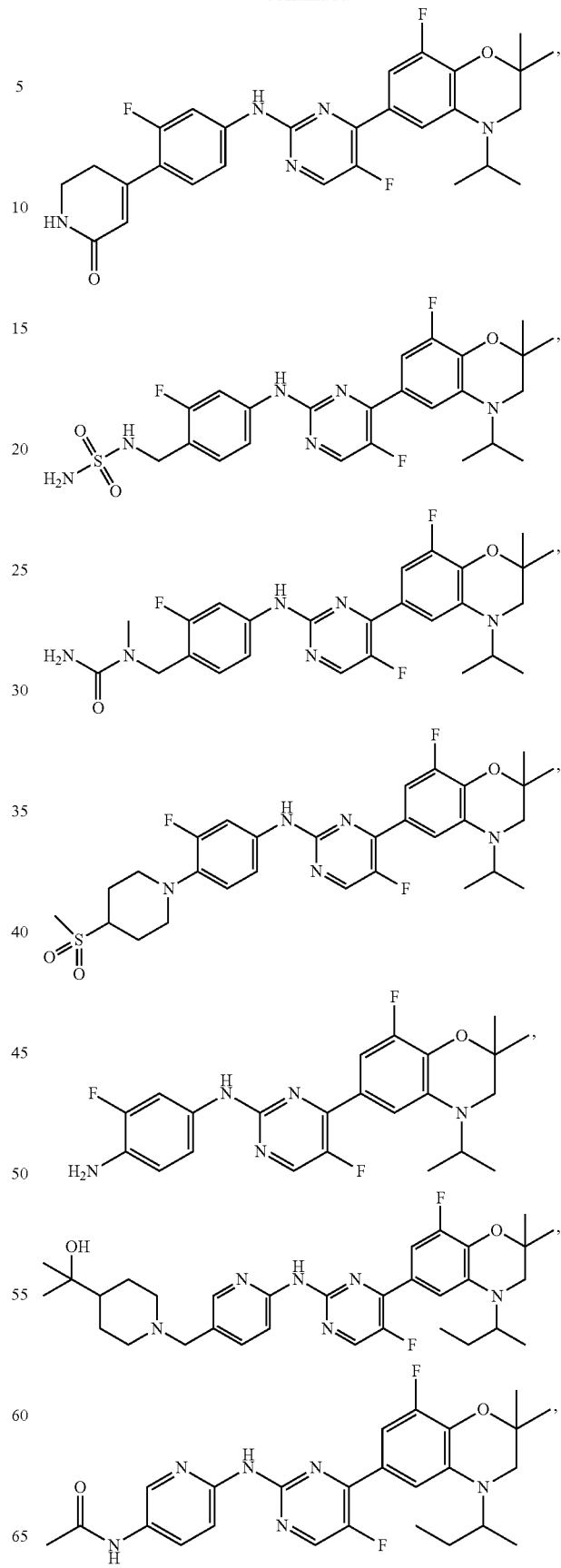

919
-continued
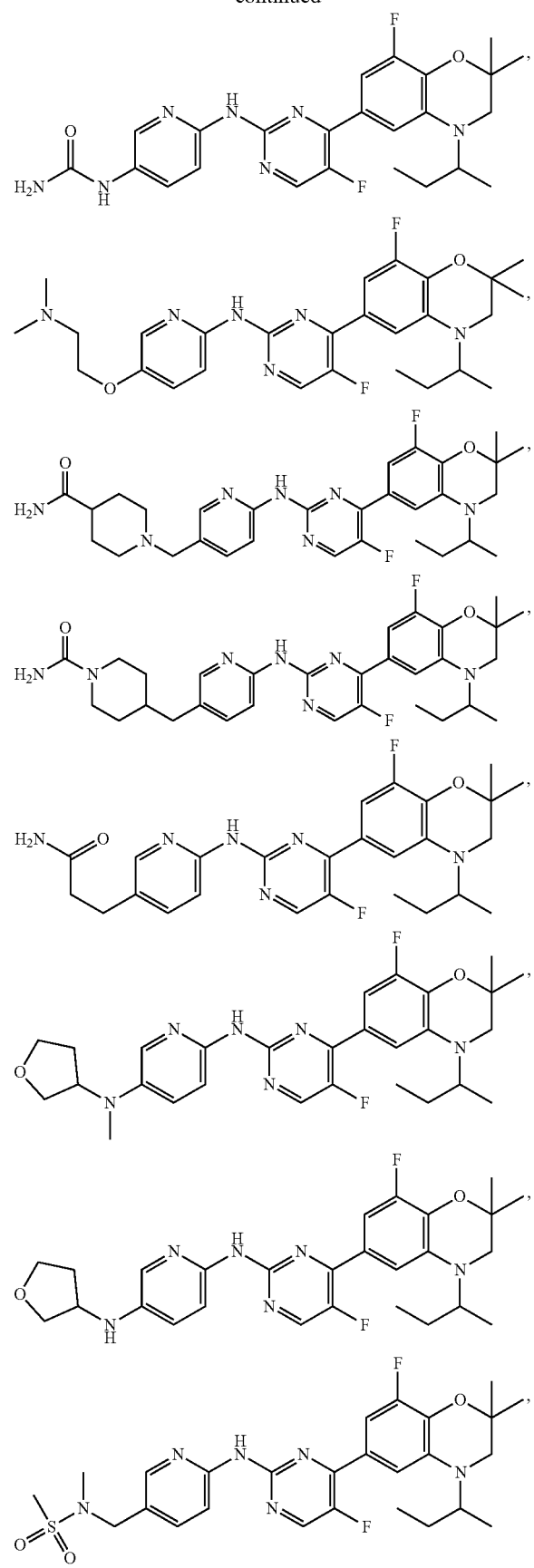
920
-continued
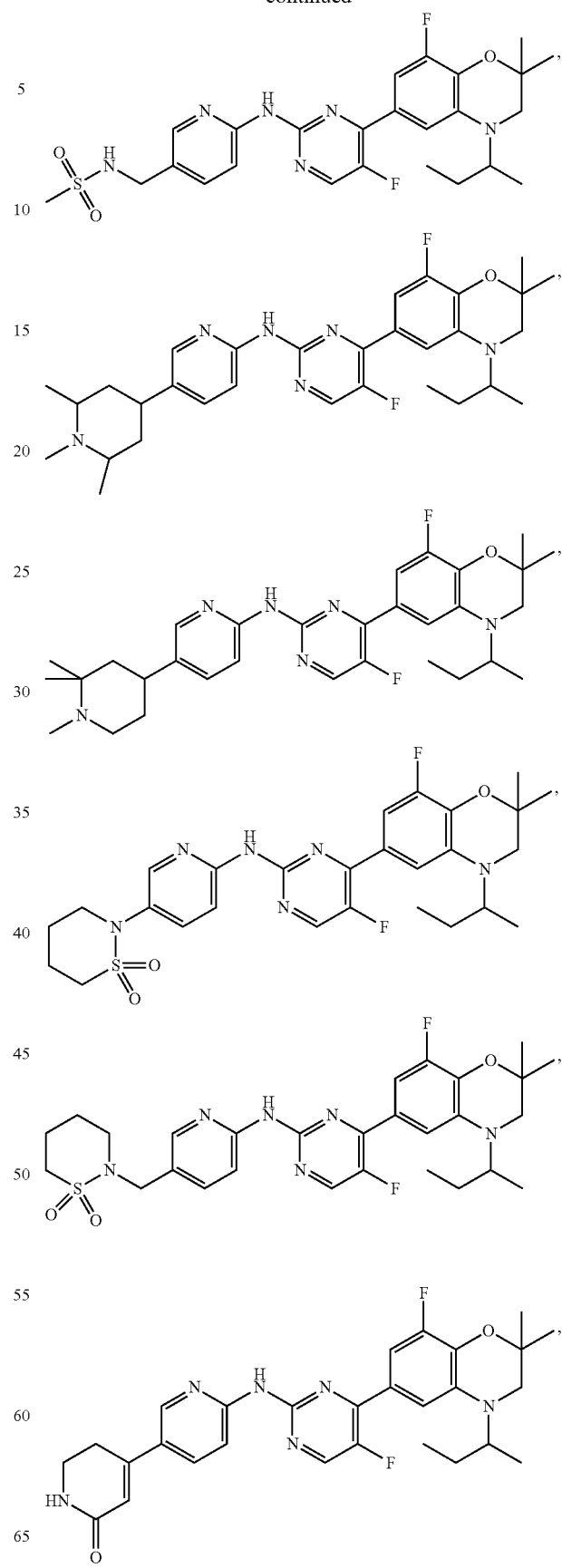

921
-continued
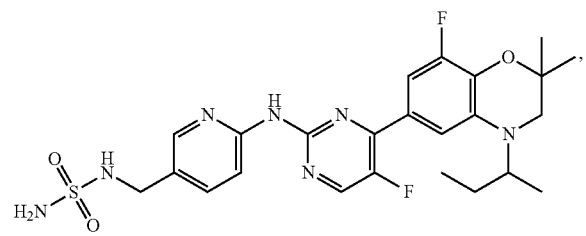
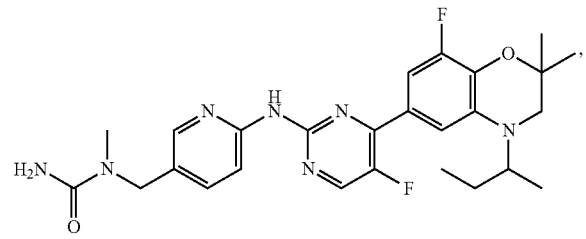
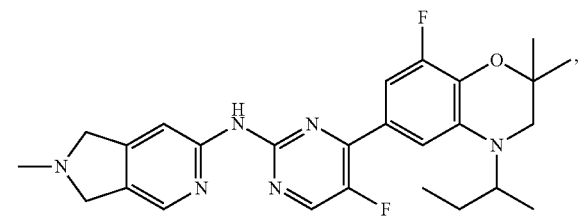
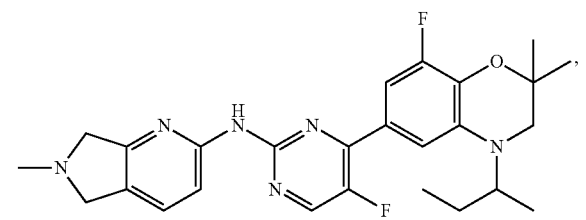
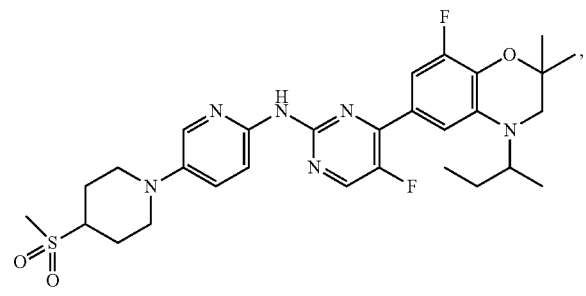
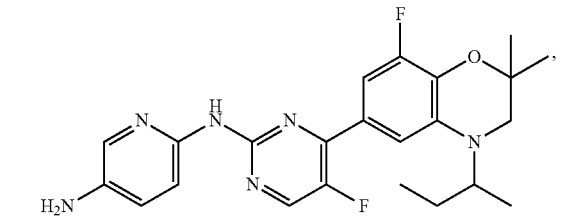
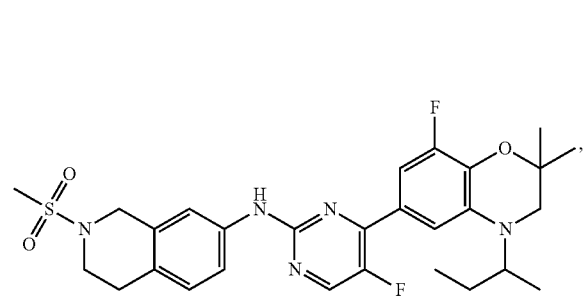
922
-continued
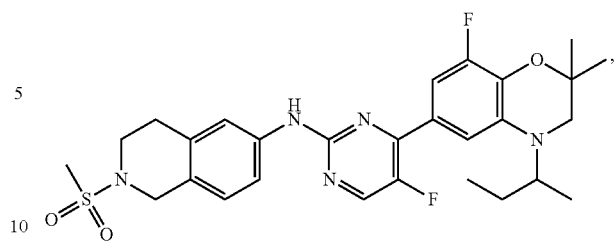
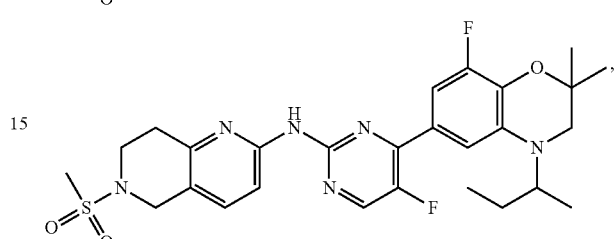
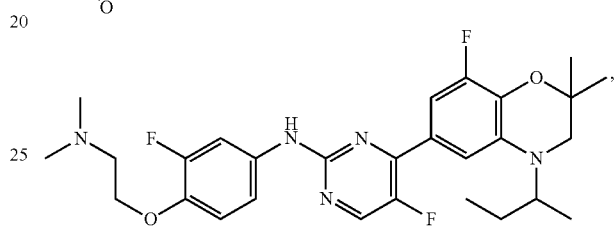
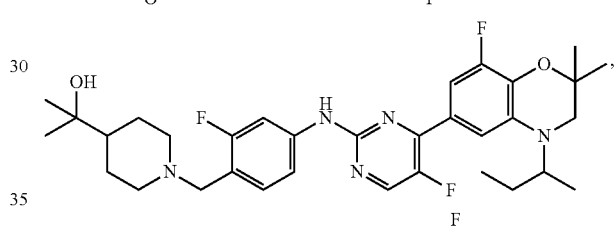
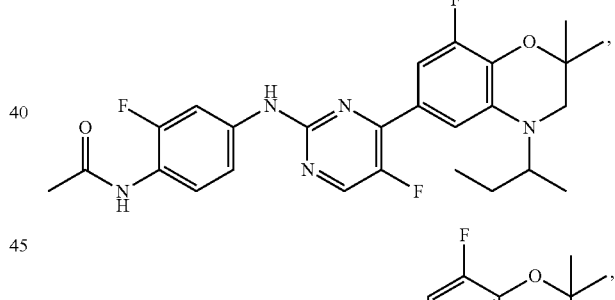
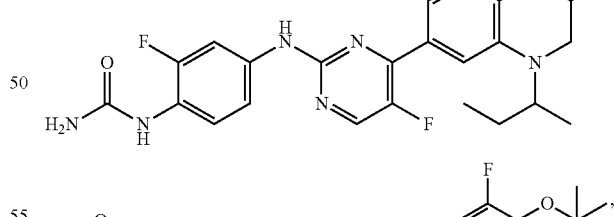
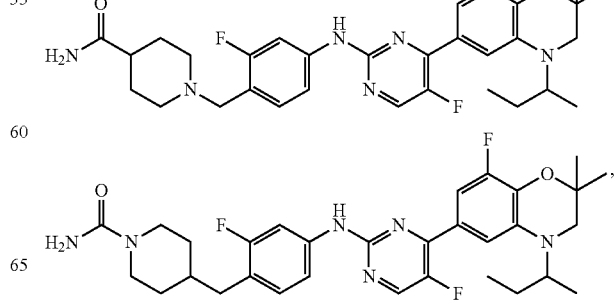

923
-continued
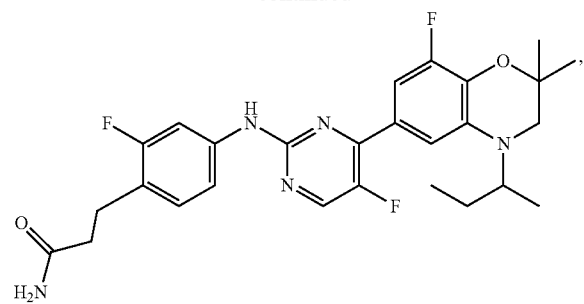
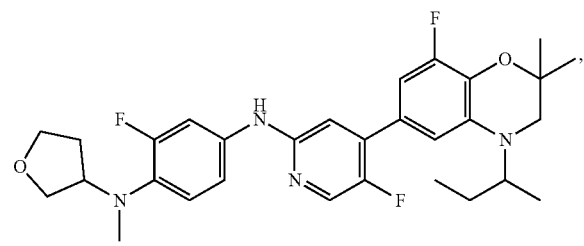
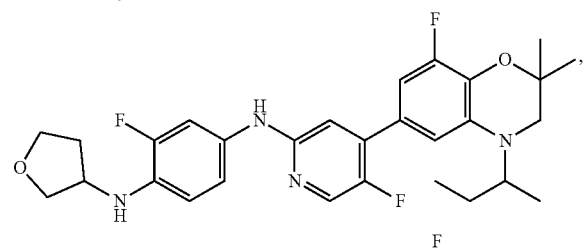
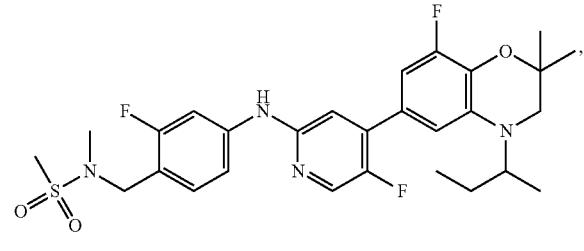
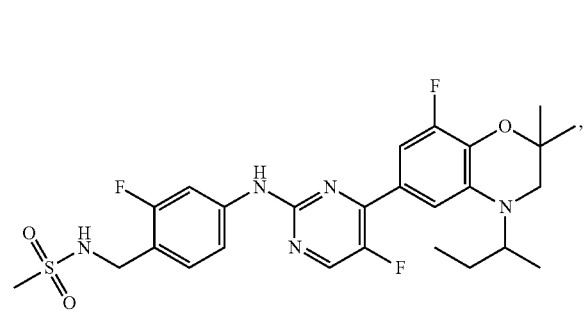
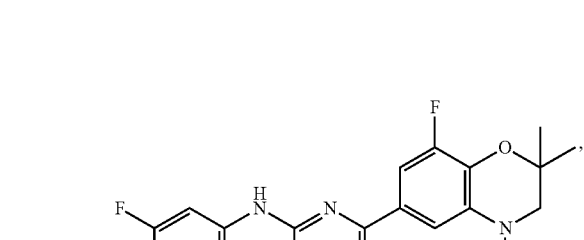
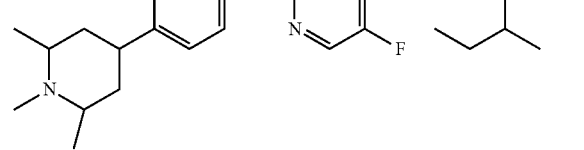
924
-continued
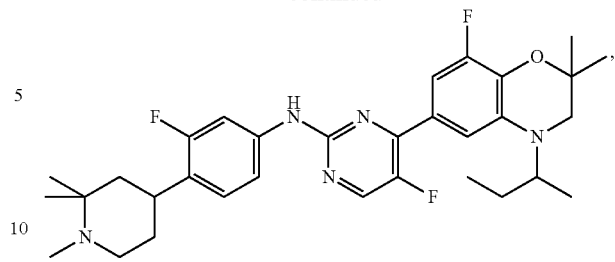
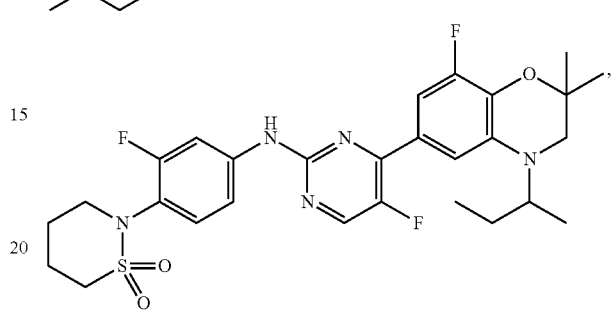
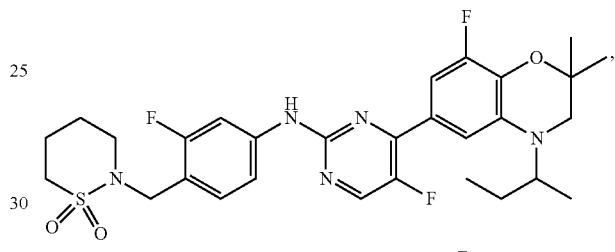
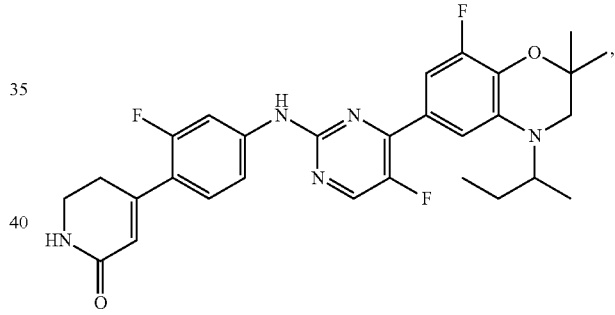
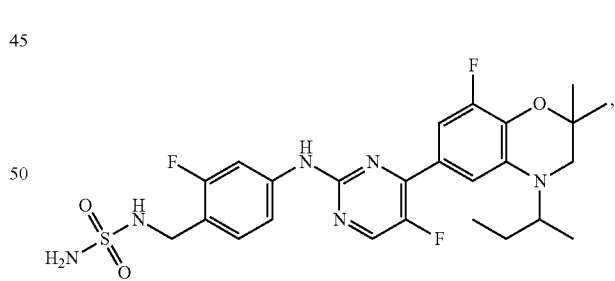
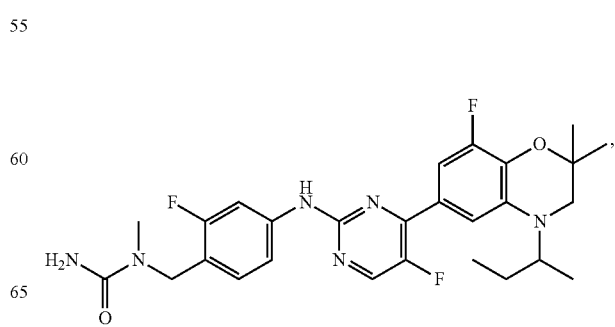

925
-continued
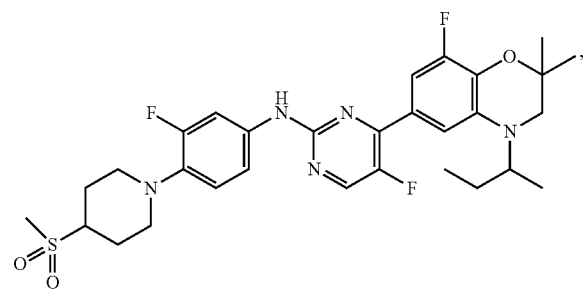
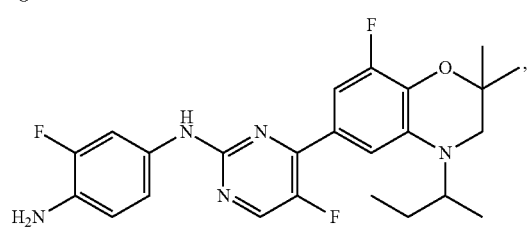
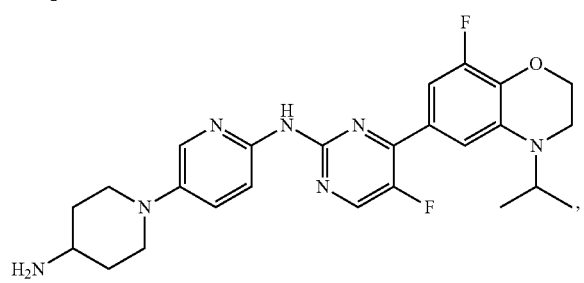
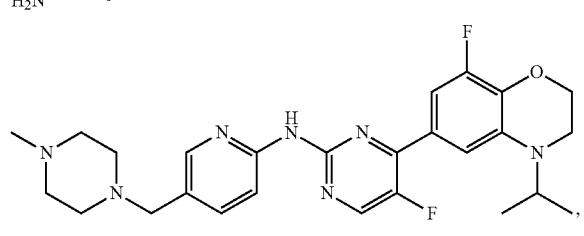
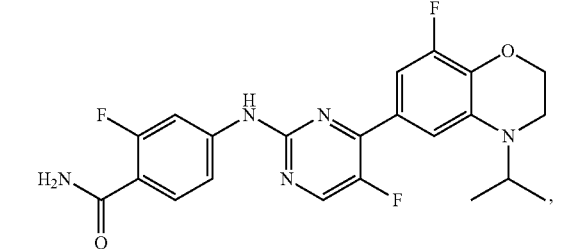
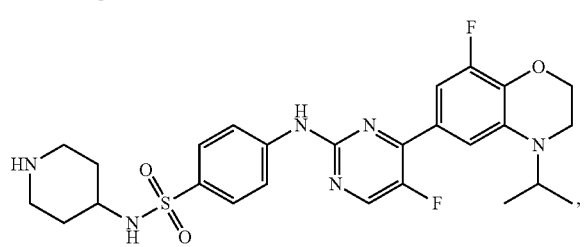
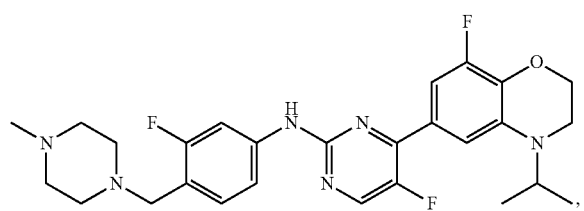
926
-continued
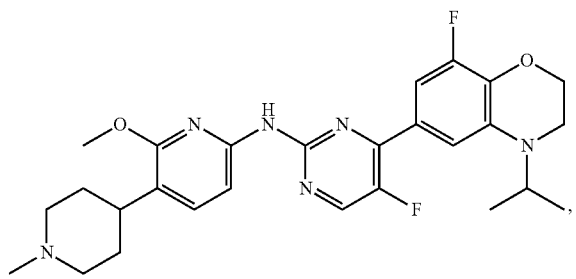
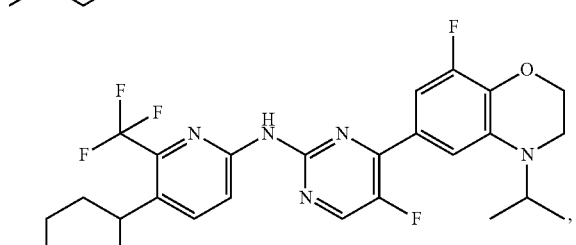
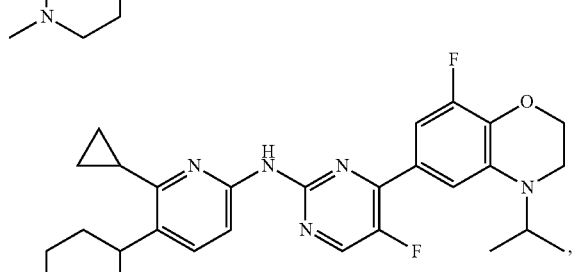
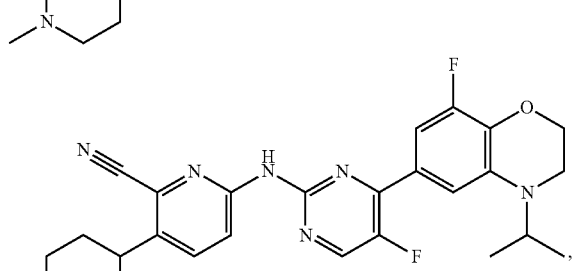
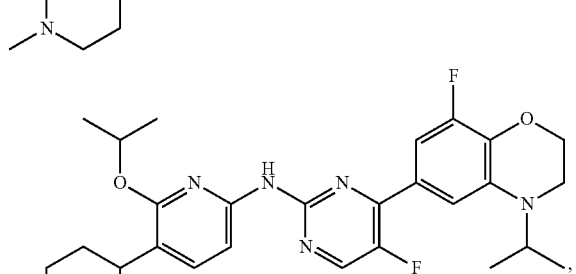
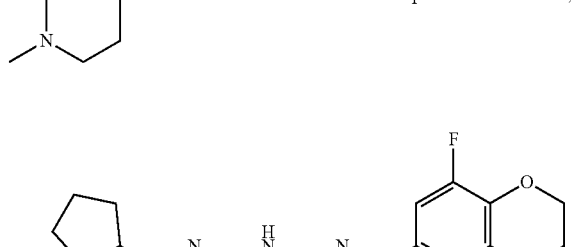
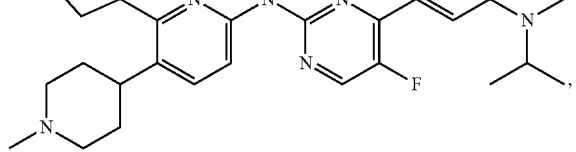

927
-continued
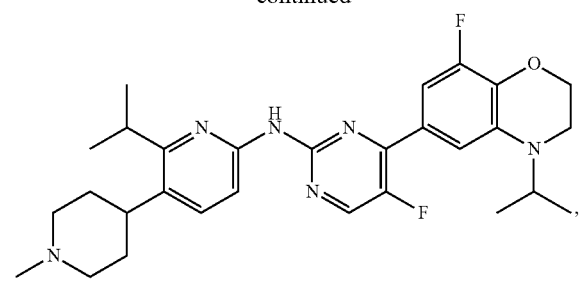
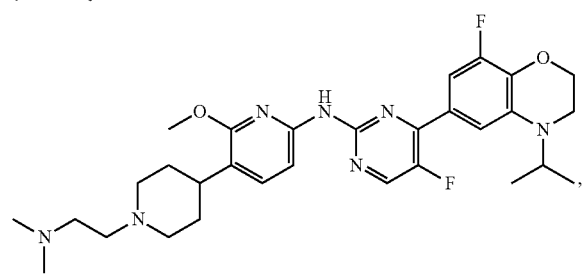
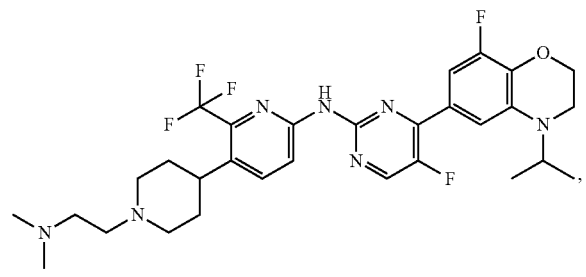
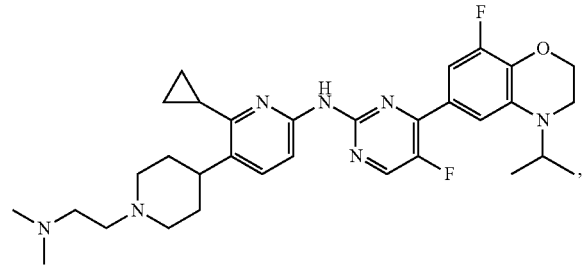
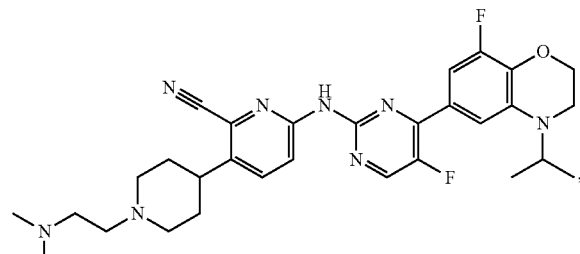
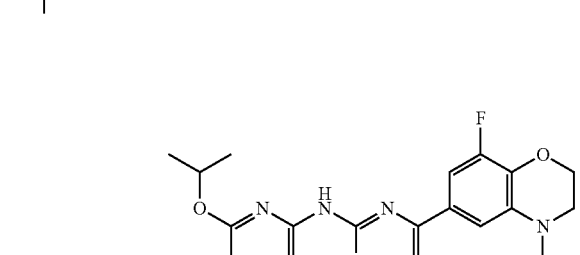
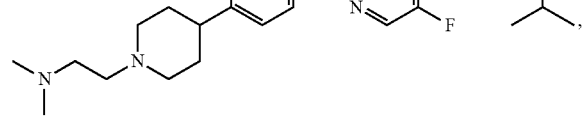
928
-continued
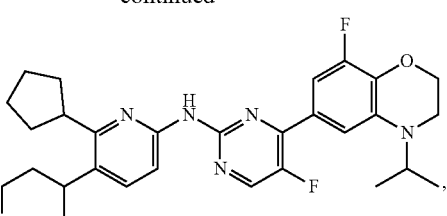
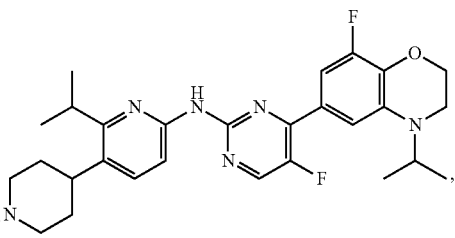
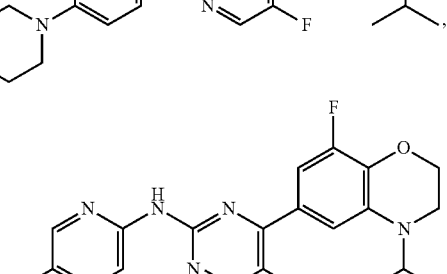
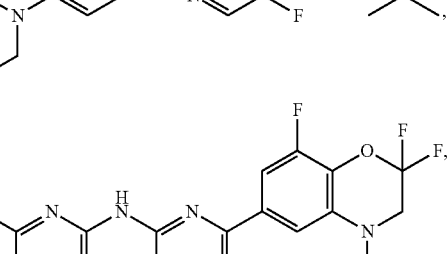
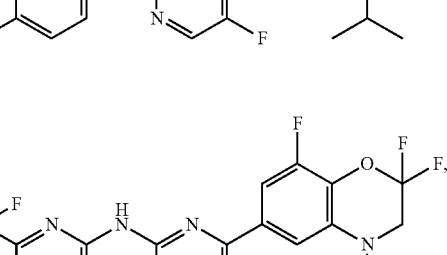
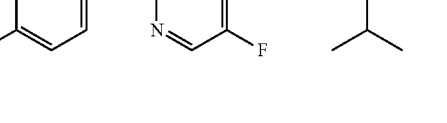

929
-continued
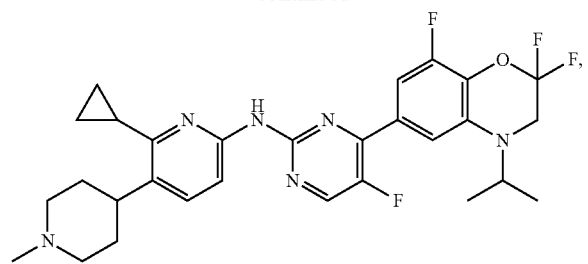
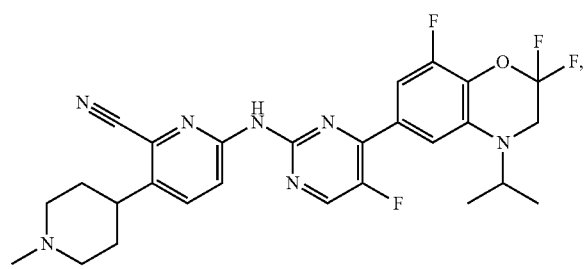
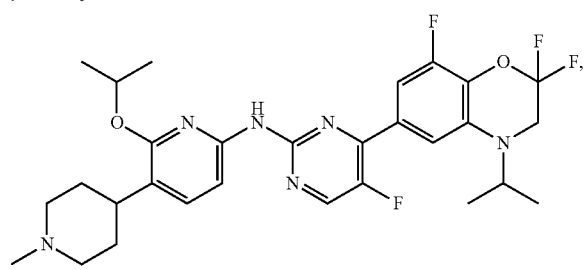
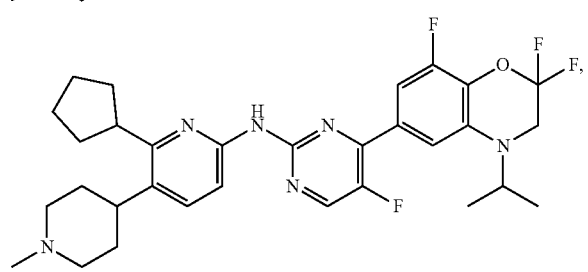
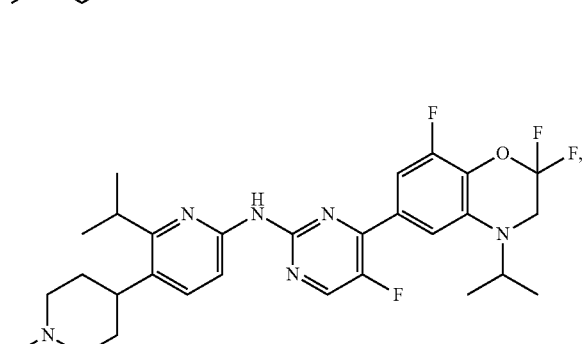
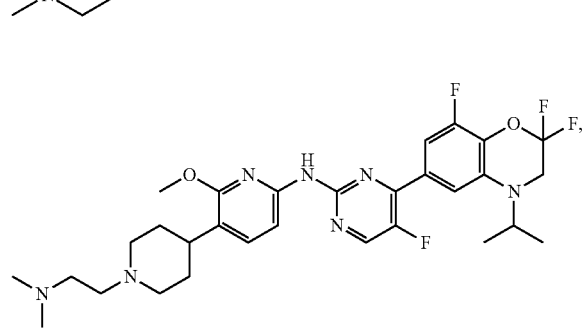
930
-continued
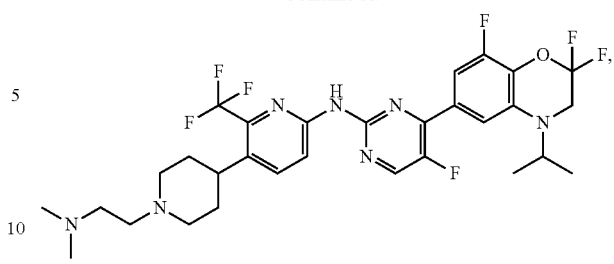
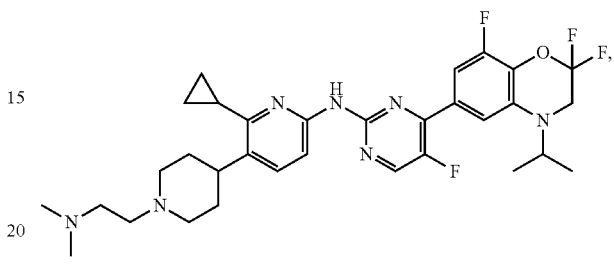
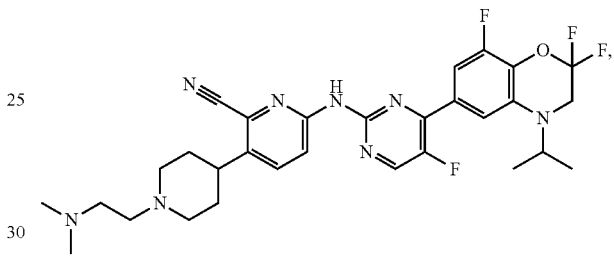
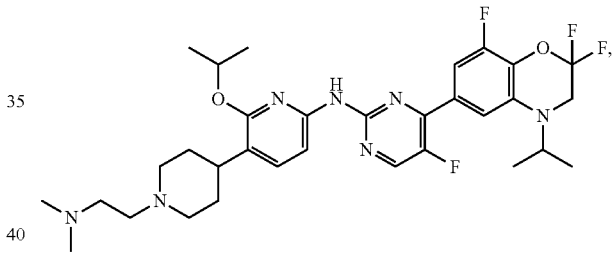
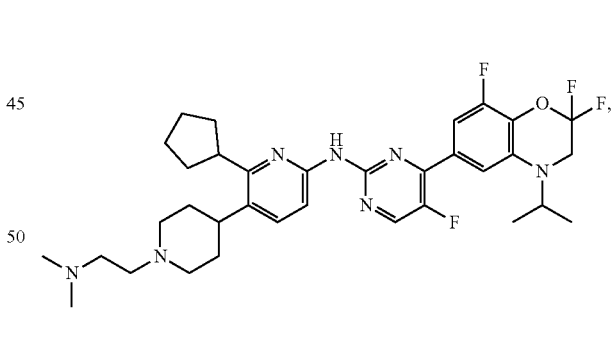
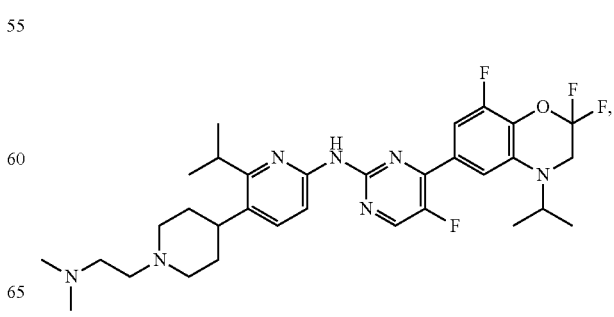

931
-continued
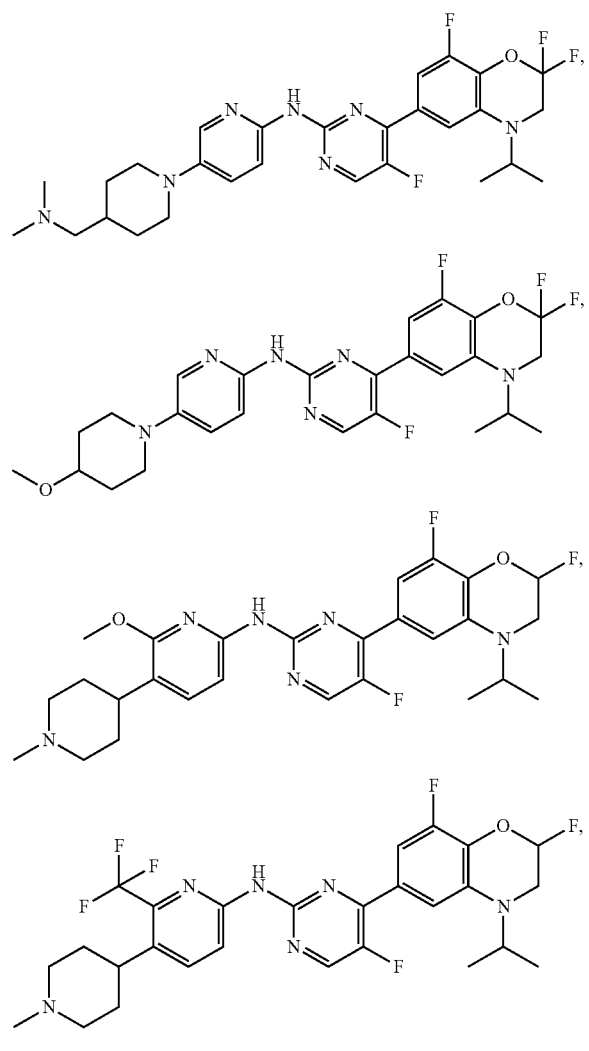
932
-continued
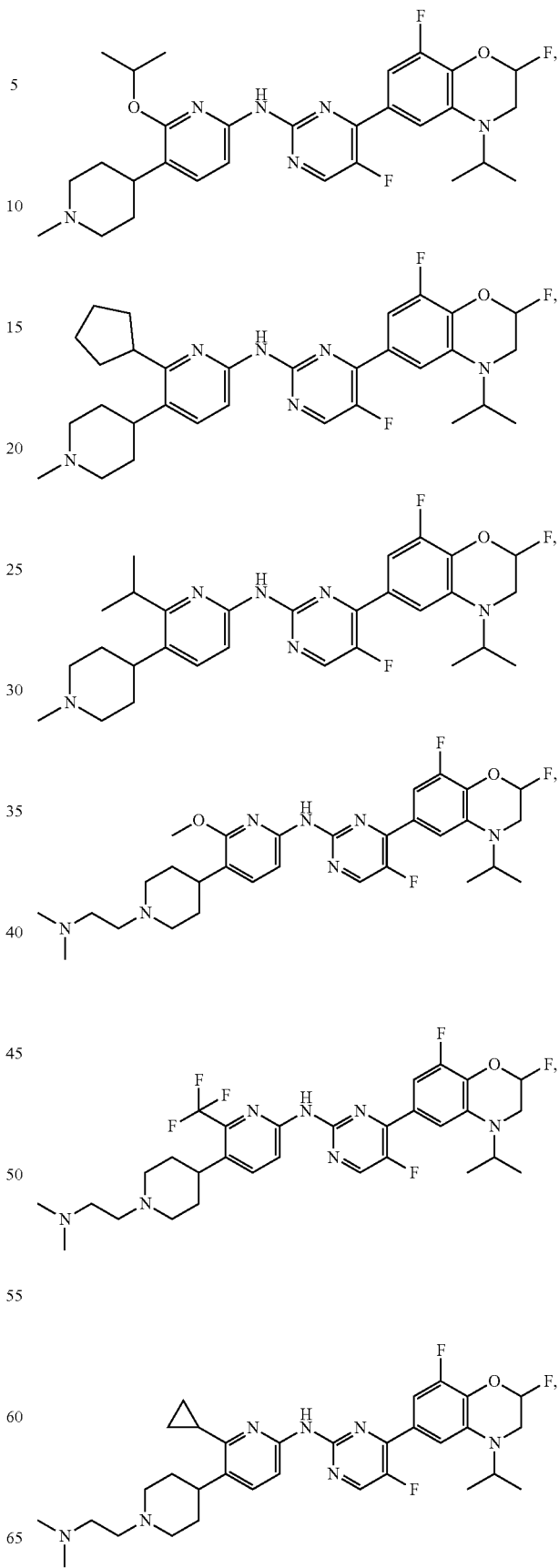

933
-continued
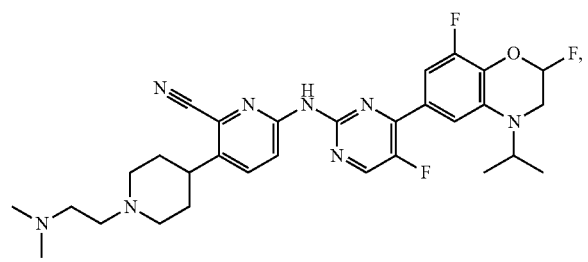
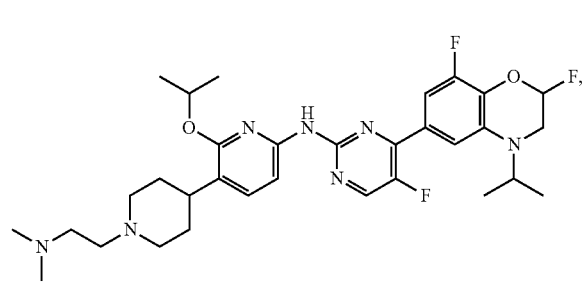
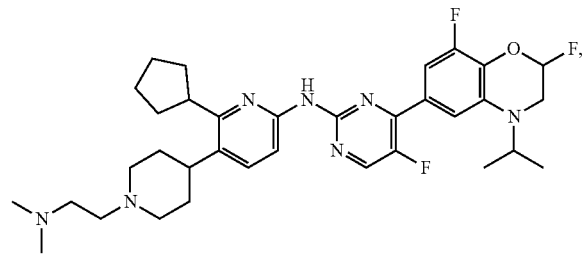
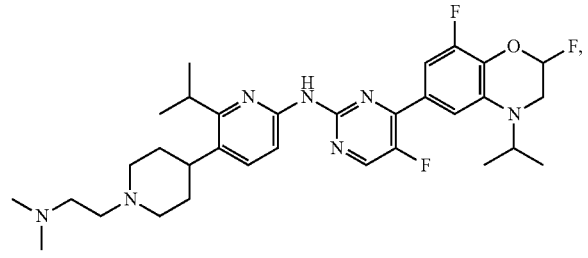
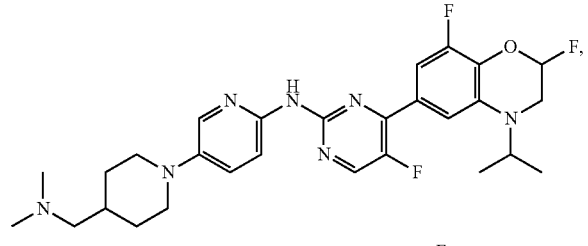
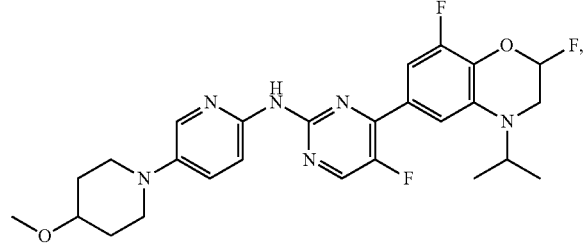
934
-continued
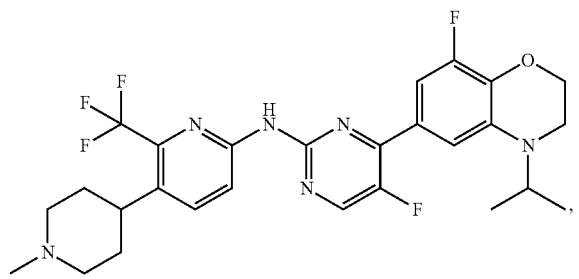
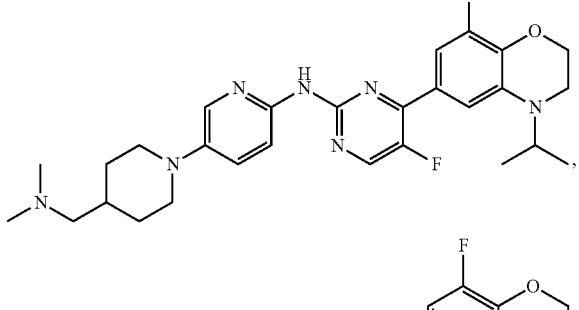
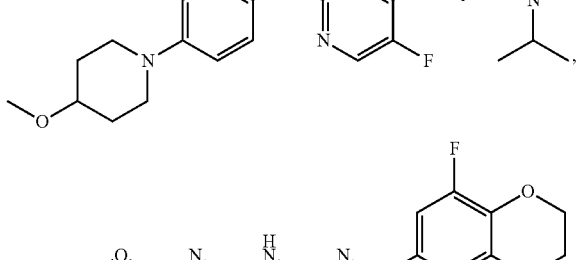
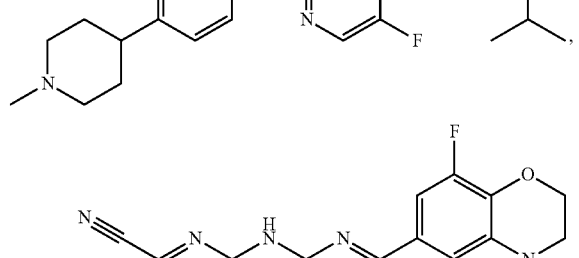
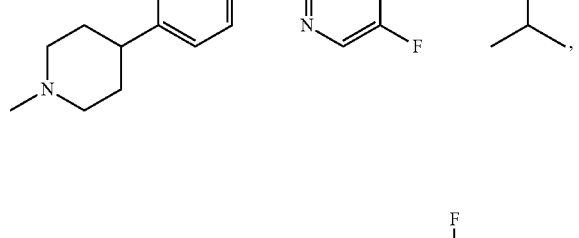
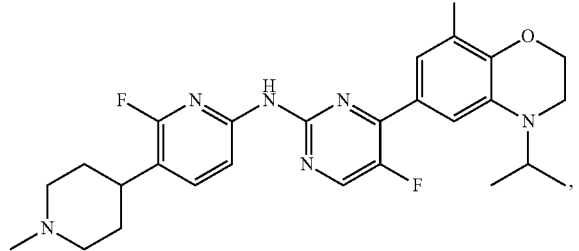

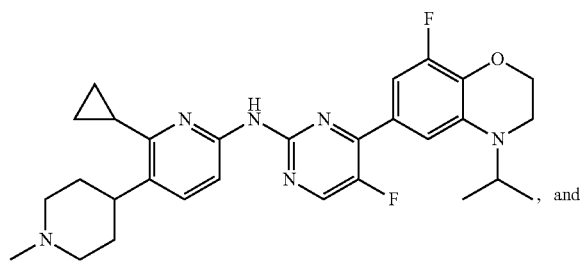
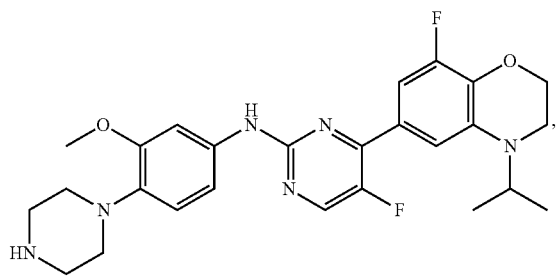 [SMILES: COc1cc(Nc2ncc(F)c(-c3cc(F)c4c(c3)N(C(C)C)CCO4)n2)ccc1N1CCNCC1]
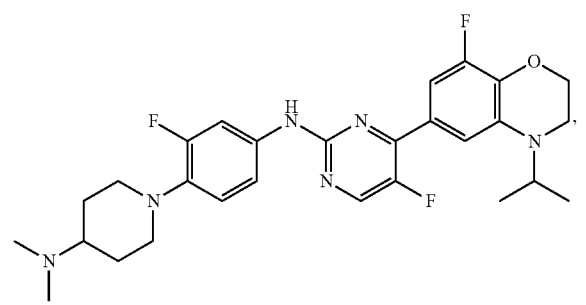
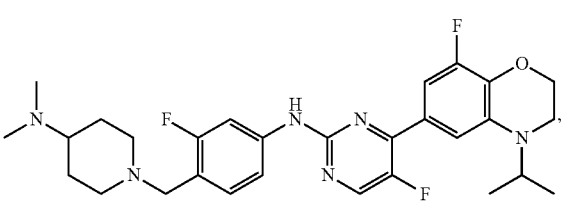 [SMILES: CC(C)N1CCOc2c(F)cc(-c3nc(Nc4ccc(CN5CCC(N(C)C)CC5)c(F)c4)ncc3F)cc21]
2. The compound of claim 1, or a pharmaceutically acceptable salt thereof, wherein the compound is selected from the group consisting of:
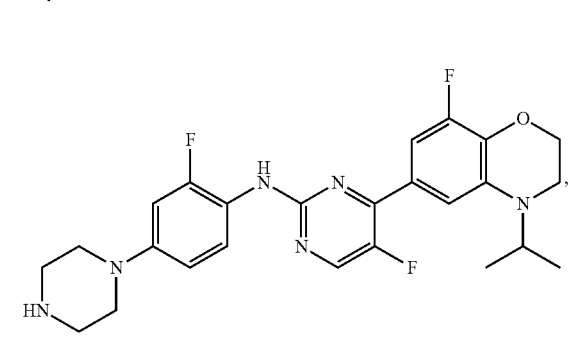
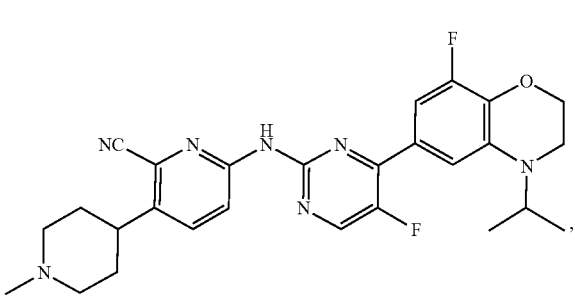
3. The compound of claim 1, or a pharmaceutically acceptable salt thereof, wherein the compound is selected from the group consisting of:
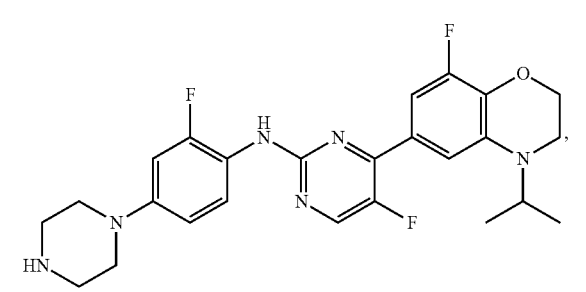
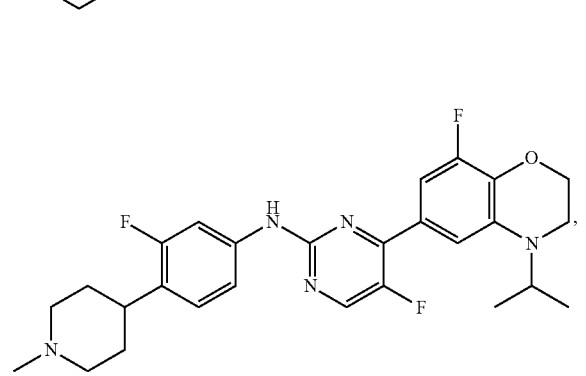
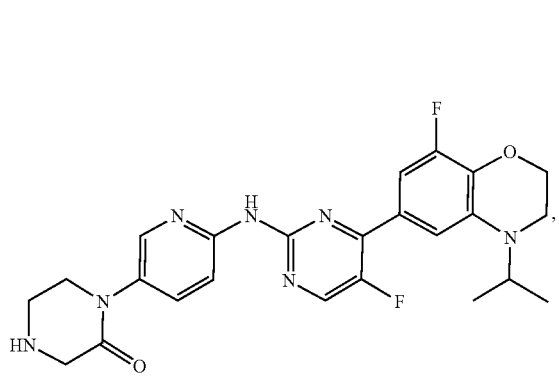

-continued
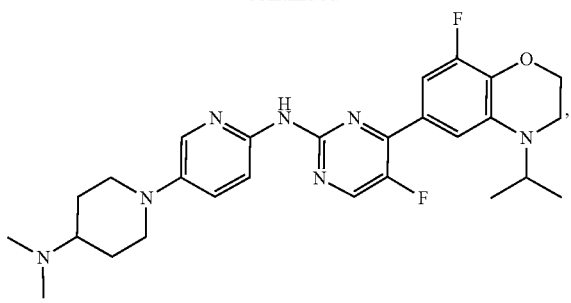
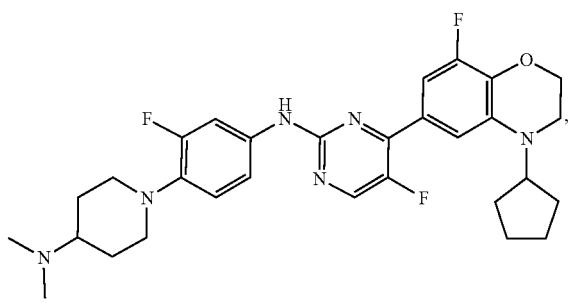
4. The compound of claim 1, or a pharmaceutically acceptable salt thereof, wherein the compound is selected from the group consisting of:
-continued
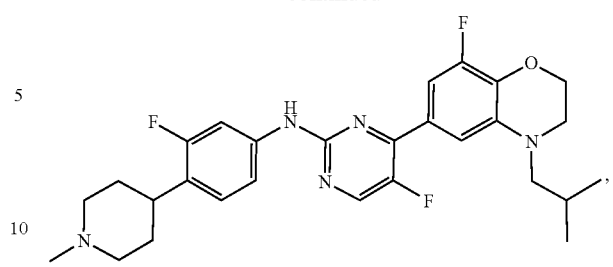
5. The compound of claim 1, or a pharmaceutically acceptable salt thereof, wherein the compound is selected from the group consisting of:
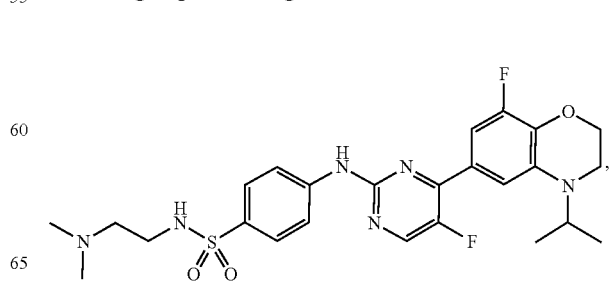

-continued

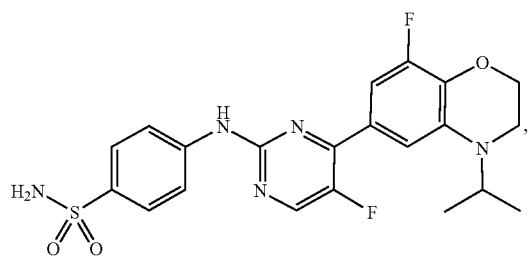

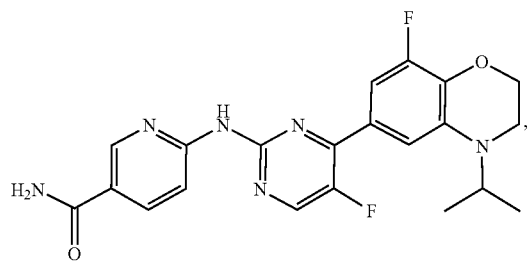

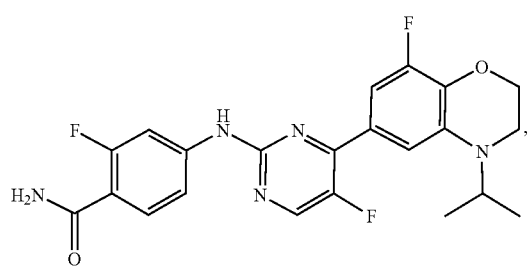

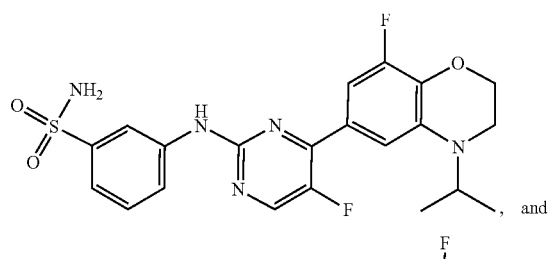

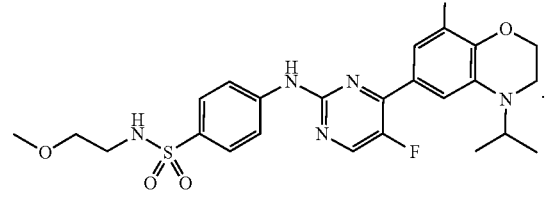, and

6. The compound of claim 1, or a pharmaceutically acceptable salt thereof, wherein the compound is

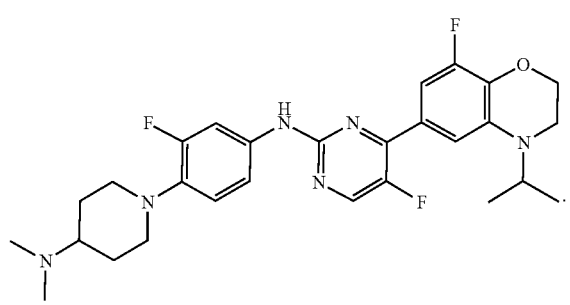

7. The compound of claim 1, or a pharmaceutically acceptable salt thereof, wherein the compound is

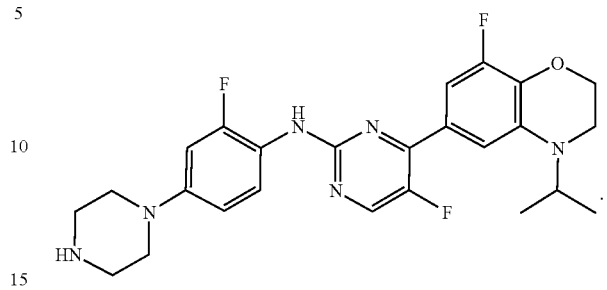

8. The compound of claim 1, or a pharmaceutically acceptable salt thereof, wherein the compound is

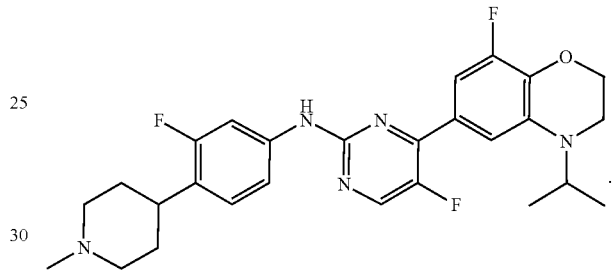

9. The compound of claim 1, or a pharmaceutically acceptable salt thereof, wherein the compound is

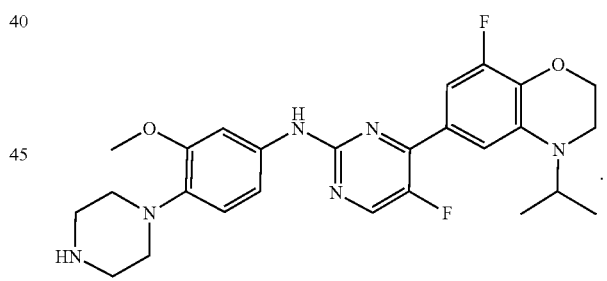

10. The compound of claim 1, or a pharmaceutically acceptable salt thereof, wherein the compound is

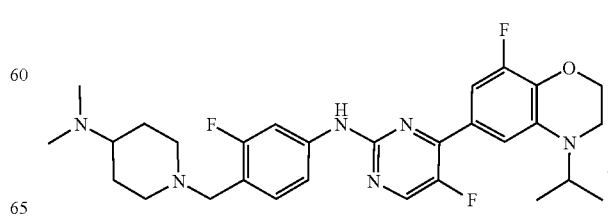

11. The compound of claim 1, or a pharmaceutically acceptable salt thereof, wherein the compound is

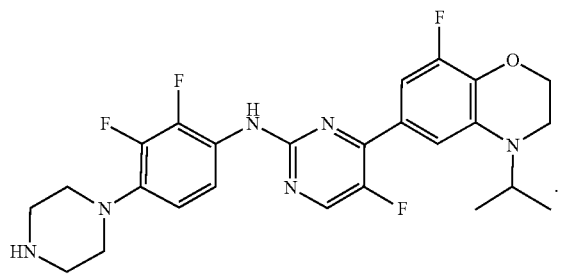 [SMILES: CC(C)N1CCOc2c(F)cc(-c3nc(Nc4ccc(N5CCNCC5)c(F)c4F)ncc3F)cc21]

12. The compound of claim 1, or a pharmaceutically acceptable salt thereof, wherein the compound is

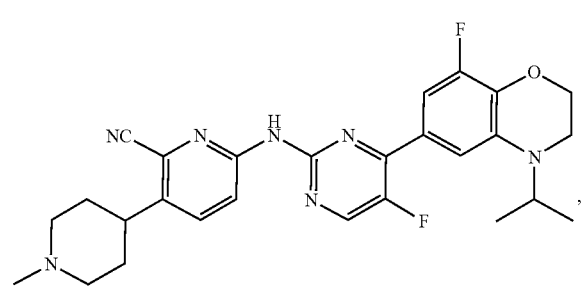 [SMILES: CC(C)N1CCOc2c(F)cc(-c3nc(Nc4ccc(C5CCN(C)CC5)c(C#N)n4)ncc3F)cc21]

13. The compound of claim 1, or a pharmaceutically acceptable salt thereof, wherein the compound is

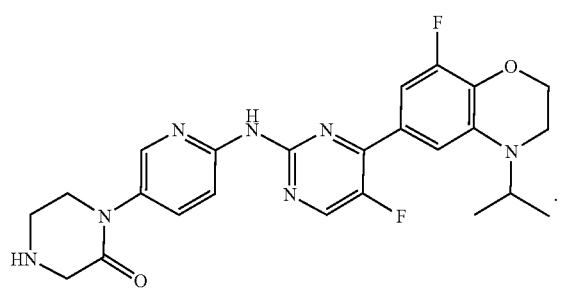 [SMILES: CC(C)N1CCOc2c(F)cc(-c3nc(Nc4ccc(N5CCNCC5=O)cn4)ncc3F)cc21]

14. The compound of claim 1, or a pharmaceutically acceptable salt thereof, wherein the compound is

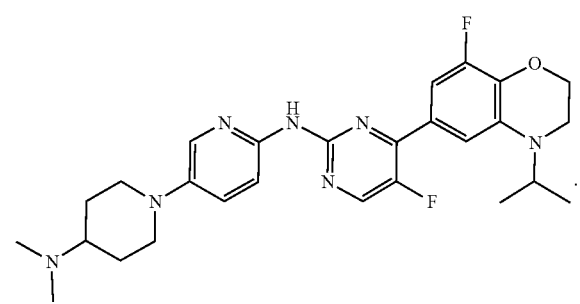 [SMILES: CC(C)N1CCOc2c(F)cc(-c3nc(Nc4ccc(N5CCC(N(C)C)CC5)cn4)ncc3F)cc21]

15. The compound of claim 1, or a pharmaceutically acceptable salt thereof, wherein the compound is

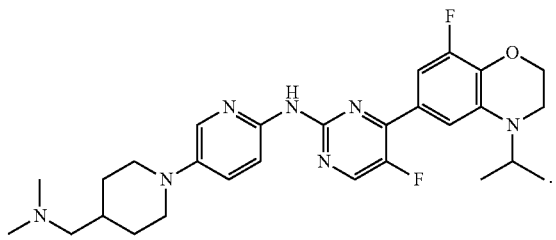 [SMILES: CC(C)N1CCOc2c(F)cc(-c3nc(Nc4ccc(N5CCC(CN(C)C)CC5)cn4)ncc3F)cc21]

16. The compound of claim 1, or a pharmaceutically acceptable salt thereof, wherein the compound is

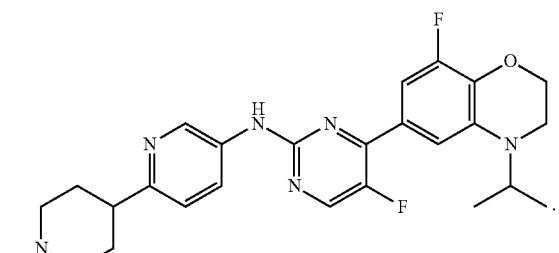

17. The compound of claim 1, or a pharmaceutically acceptable salt thereof, wherein the compound is

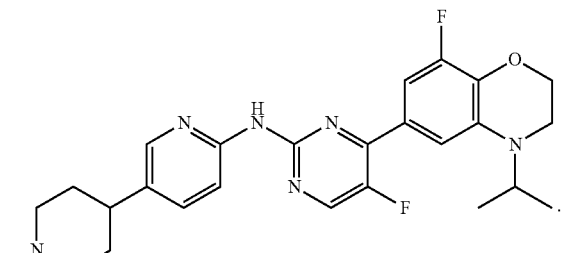

18. The compound of claim 1, or a pharmaceutically acceptable salt thereof, wherein the compound is

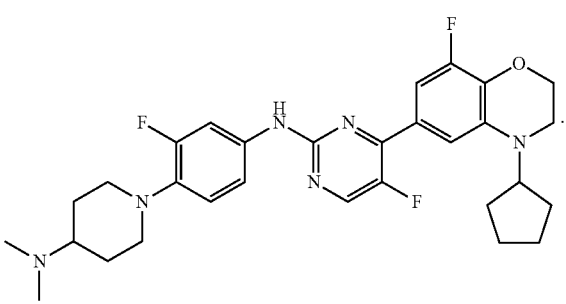 [SMILES: CN(C)C1CCN(c2ccc(Nc3ncc(F)c(-c4cc(F)c5c(c4)N(C4CCCC4)CCO5)n3)cc2F)CC1]

19. The compound of claim 1, or a pharmaceutically acceptable salt thereof, wherein the compound is

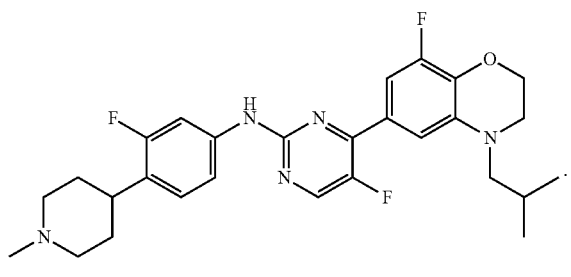 [SMILES: CC(C)CN1CCOc2c(F)cc(-c3nc(Nc4ccc(C5CCN(C)CC5)c(F)c4)ncc3F)cc21]

20. The compound of claim 1, or a pharmaceutically acceptable salt thereof, wherein the compound is

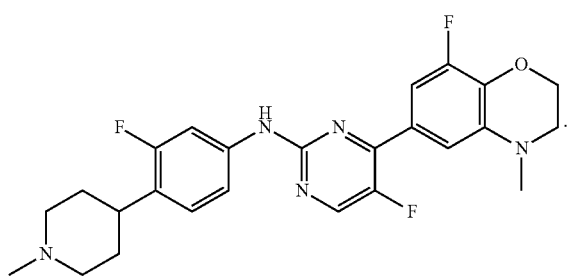 [SMILES: CN1CCC(c2ccc(Nc3ncc(F)c(-c4cc(F)c5c(c4)N(C)CCO5)n3)cc2F)CC1]

21. The compound of claim 1, or a pharmaceutically acceptable salt thereof, wherein the compound is

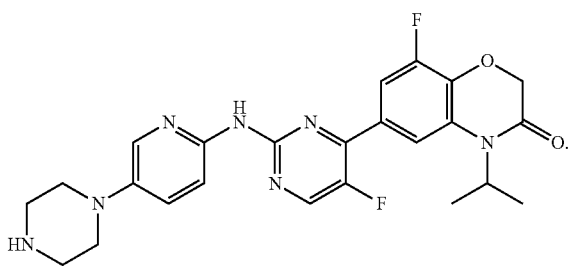 [SMILES: CC(C)N1C(=O)COc2c(F)cc(-c3nc(Nc4ccc(N5CCNCC5)cn4)ncc3F)cc21]

22. The compound of claim 1, or a pharmaceutically acceptable salt thereof, wherein the compound is

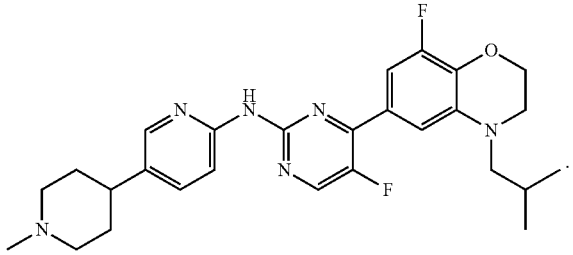 [SMILES: CC(C)CN1CCOc2c(F)cc(-c3nc(Nc4ccc(C5CCN(C)CC5)cn4)ncc3F)cc21]

23. The compound of claim 1, or a pharmaceutically acceptable salt thereof, wherein the compound is

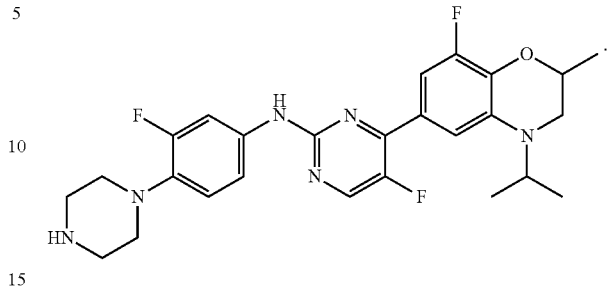

24. The compound of claim 1, or a pharmaceutically acceptable salt thereof, wherein the compound is

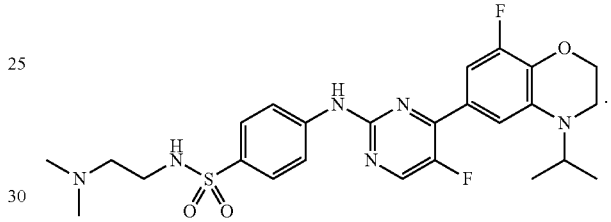

25. The compound of claim 1, or a pharmaceutically acceptable salt thereof, wherein the compound is

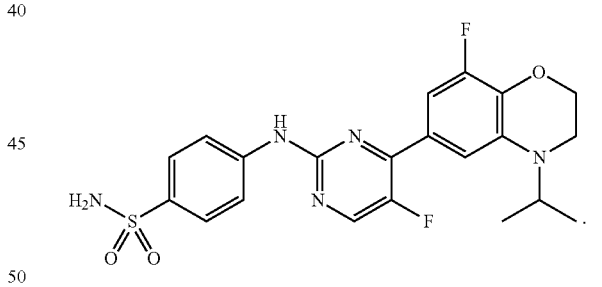

26. The compound of claim 1, or a pharmaceutically acceptable salt thereof, wherein the compound is

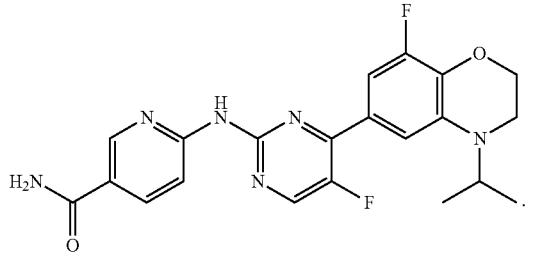 [SMILES: CC(C)N1CCOc2c(F)cc(-c3nc(Nc4ccc(C(N)=O)cn4)ncc3F)cc21]

27. The compound of claim 1, or a pharmaceutically acceptable salt thereof, wherein the compound is

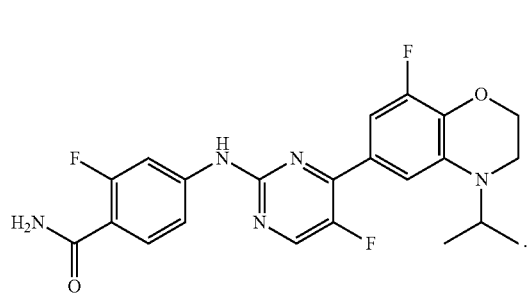 [SMILES: CC(C)N1CCOc2c(F)cc(-c3nc(Nc4ccc(C(N)=O)c(F)c4)ncc3F)cc21]

28. The compound of claim 1, or a pharmaceutically acceptable salt thereof, wherein the compound is

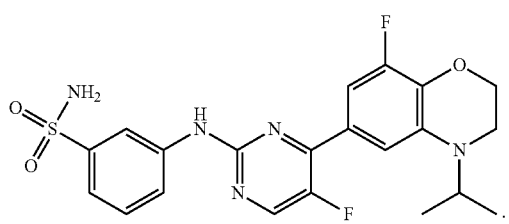 [SMILES: CC(C)N1CCOc2c(F)cc(-c3nc(Nc4cccc(S(N)(=O)=O)c4)ncc3F)cc21]

29. The compound of claim 1, or a pharmaceutically acceptable salt thereof, wherein the compound is

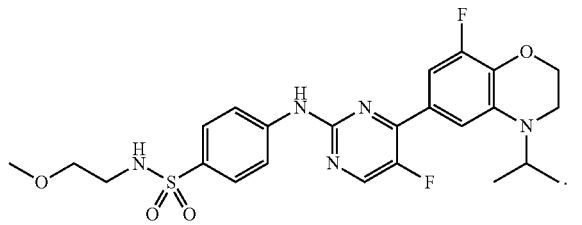

30. The compound of claim 6, wherein the compound is

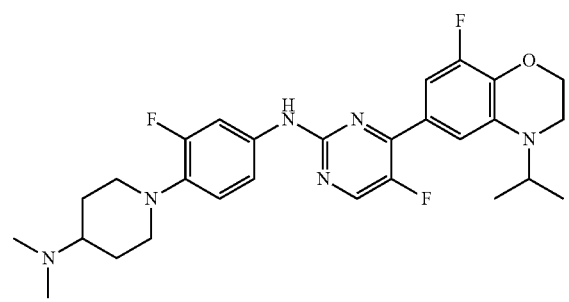

31. The compound of claim 7, wherein the compound is

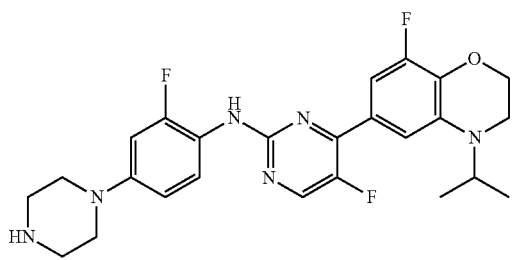

32. The compound of claim 8, wherein the compound is

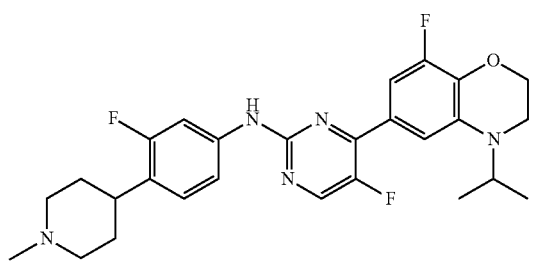

33. The compound of claim 9, wherein the compound is

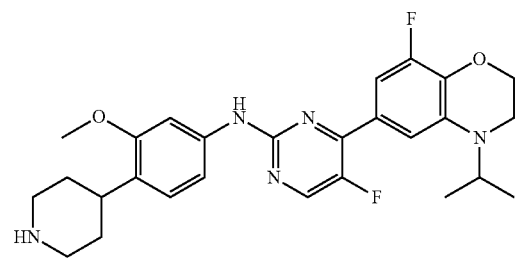

34. The compound of claim 10, wherein the compound is

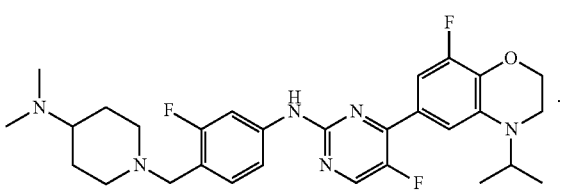 [SMILES: CC(C)N1CCOc2c(F)cc(-c3nc(Nc4ccc(CN5CCC(N(C)C)CC5)c(F)c4)ncc3F)cc21]

35. The compound of claim 11, wherein the compound is

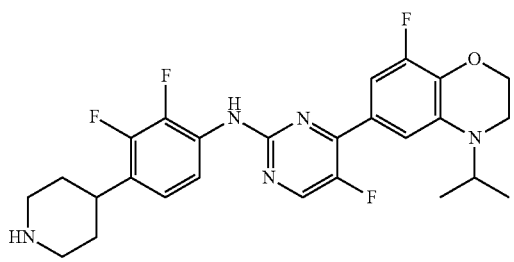

36. The compound of claim 12, wherein the compound is

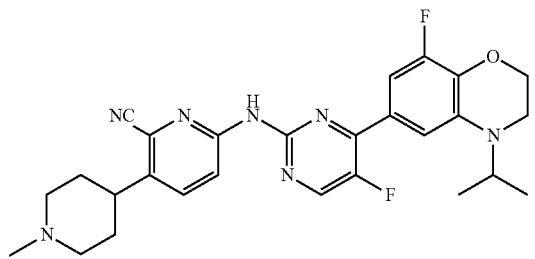

37. The compound of claim 13, wherein the compound is

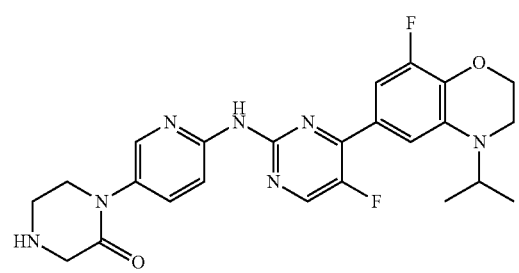

38. The compound of claim 19, wherein the compound is

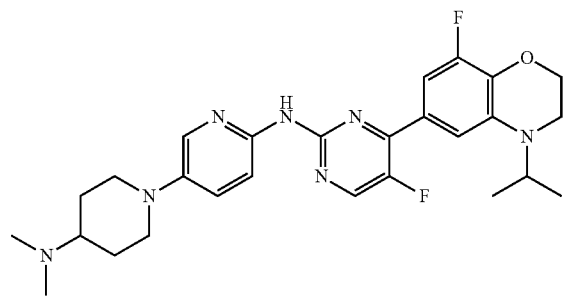

39. The compound of claim 15, wherein the compound is

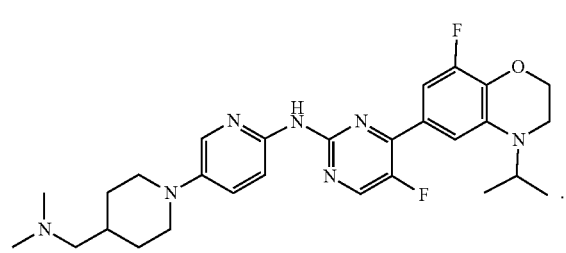 [SMILES: CC(C)N1CCOc2c(F)cc(-c3nc(Nc4ccc(N5CCC(CN(C)C)CC5)cn4)ncc3F)cc21]

40. The compound of claim 16, wherein the compound is

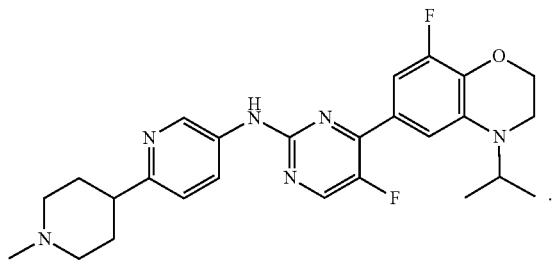 [SMILES: CC(C)N1CCOc2c(F)cc(-c3nc(Nc4ccc(C5CCN(C)CC5)nc4)ncc3F)cc21]

41. The compound of claim 17, wherein the compound is

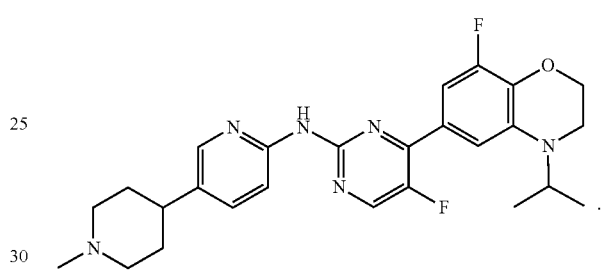

42. The compound of claim 18, wherein the compound is

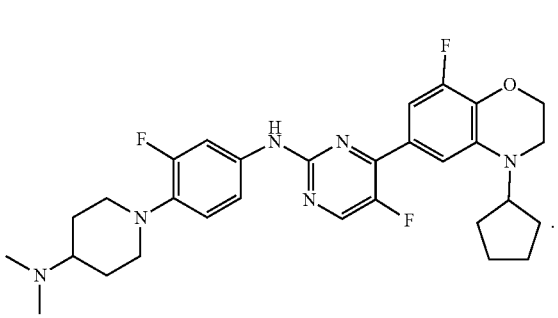 [SMILES: CN(C)C1CCN(c2ccc(Nc3ncc(F)c(-c4cc(F)c5c(c4)N(C4CCCC4)CCO5)n3)cc2F)CC1]

43. The compound of claim 19, wherein the compound is

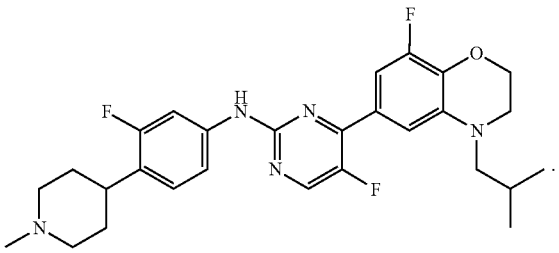 [SMILES: CC(C)CN1CCOc2c(F)cc(-c3nc(Nc4ccc(C5CCN(C)CC5)c(F)c4)ncc3F)cc21]

44. The compound of claim 20, wherein the compound is

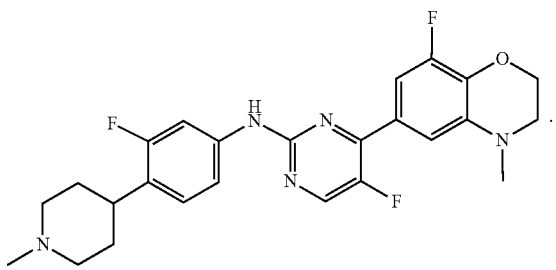 [SMILES: CN1CCC(c2ccc(Nc3ncc(F)c(-c4cc(F)c5c(c4)N(C)CCO5)n3)cc2F)CC1]

45. The compound of claim 21, wherein the compound is

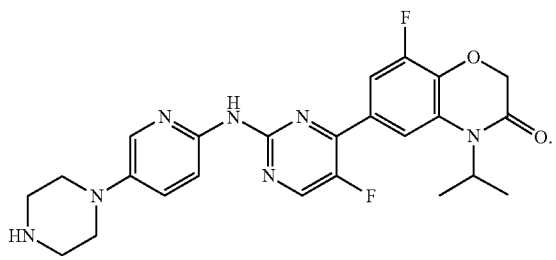 [SMILES: CC(C)N1C(=O)COc2c(F)cc(-c3nc(Nc4ccc(N5CCNCC5)cn4)ncc3F)cc21]

46. The compound of claim 22, wherein the compound is

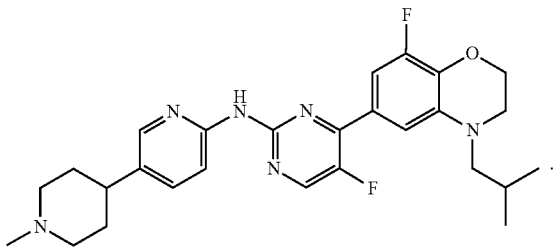 [SMILES: CC(C)CN1CCOc2c(F)cc(-c3nc(Nc4ccc(C5CCN(C)CC5)cn4)ncc3F)cc21]

47. The compound of claim 23, wherein the compound is

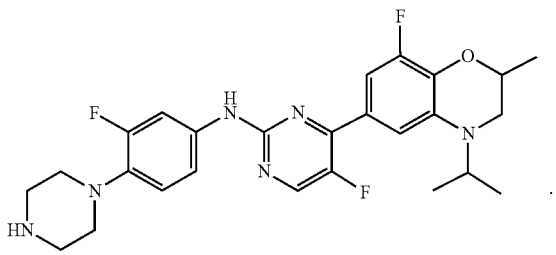 [SMILES: CC1CN(C(C)C)c2cc(-c3nc(Nc4ccc(N5CCNCC5)c(F)c4)ncc3F)cc(F)c2O1]

48. The compound of claim 24, wherein the compound is

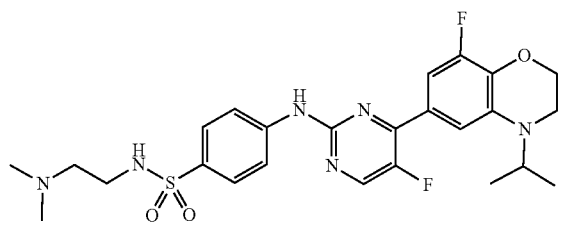

49. The compound of claim 25, wherein the compound is

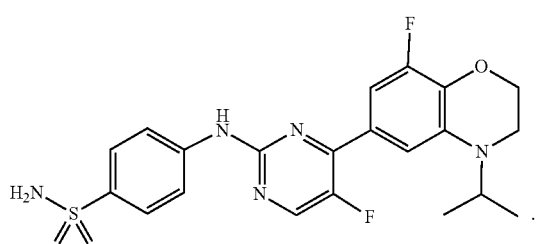

50. The compound of claim 26, wherein the compound is

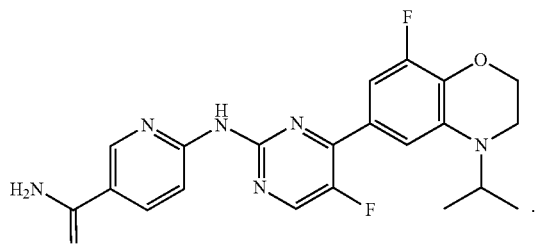

51. The compound of claim 27, wherein the compound is

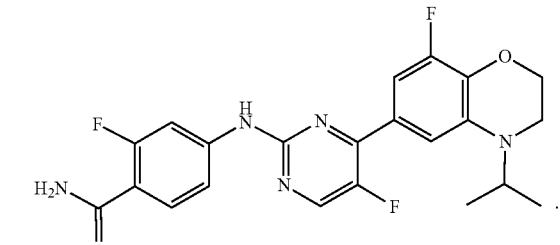

52. The compound of claim 28, wherein the compound is

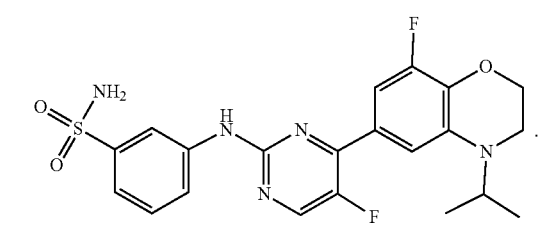 [SMILES: CC(C)N1CCOc2c(F)cc(-c3nc(Nc4cccc(S(N)(=O)=O)c4)ncc3F)cc21]

53. The compound of claim 29, wherein the compound is

[chemical structure]

54. A pharmaceutical composition comprising a compound of claim 1, or pharmaceutically acceptable salt thereof, and a pharmaceutically acceptable carrier.
55. A pharmaceutical composition comprising a compound of claim 2, or pharmaceutically acceptable salt thereof, and a pharmaceutically acceptable carrier.
56. A pharmaceutical composition comprising a compound of claim 3, or pharmaceutically acceptable salt thereof, and a pharmaceutically acceptable carrier.
57. A pharmaceutical composition comprising a compound of claim 4, or pharmaceutically acceptable salt thereof, and a pharmaceutically acceptable carrier.
58. A pharmaceutical composition comprising a compound of claim 5, or pharmaceutically acceptable salt thereof, and a pharmaceutically acceptable carrier.
59. A pharmaceutical composition comprising a compound of claim 6, or pharmaceutically acceptable salt thereof, and a pharmaceutically acceptable carrier.
60. A pharmaceutical composition comprising a compound of claim 7, or pharmaceutically acceptable salt thereof, and a pharmaceutically acceptable carrier.
61. A pharmaceutical composition comprising a compound of claim 8, or pharmaceutically acceptable salt thereof, and a pharmaceutically acceptable carrier.
62. A pharmaceutical composition comprising a compound of claim 9, or pharmaceutically acceptable salt thereof, and a pharmaceutically acceptable carrier.
63. A pharmaceutical composition comprising a compound of claim 10, or pharmaceutically acceptable salt thereof, and a pharmaceutically acceptable carrier.
64. A pharmaceutical composition comprising a compound of claim 11, or pharmaceutically acceptable salt thereof, and a pharmaceutically acceptable carrier.
65. A pharmaceutical composition comprising a compound of claim 12, or pharmaceutically acceptable salt thereof, and a pharmaceutically acceptable carrier.
66. A pharmaceutical composition comprising a compound of claim 13, or pharmaceutically acceptable salt thereof, and a pharmaceutically acceptable carrier.
67. A pharmaceutical composition comprising a compound of claim 14, or pharmaceutically acceptable salt thereof, and a pharmaceutically acceptable carrier.
68. A pharmaceutical composition comprising a compound of claim 15, or pharmaceutically acceptable salt thereof, and a pharmaceutically acceptable carrier.
69. A pharmaceutical composition comprising a compound of claim 16, or pharmaceutically acceptable salt thereof, and a pharmaceutically acceptable carrier.
70. A pharmaceutical composition comprising a compound of claim 17, or pharmaceutically acceptable salt thereof, and a pharmaceutically acceptable carrier.
71. A pharmaceutical composition comprising a compound of claim 18, or pharmaceutically acceptable salt thereof, and a pharmaceutically acceptable carrier.
72. A pharmaceutical composition comprising a compound of claim 19, or pharmaceutically acceptable salt thereof, and a pharmaceutically acceptable carrier.
73. A pharmaceutical composition comprising a compound of claim 20, or pharmaceutically acceptable salt thereof, and a pharmaceutically acceptable carrier.
74. A pharmaceutical composition comprising a compound of claim 21, or pharmaceutically acceptable salt thereof, and a pharmaceutically acceptable carrier.
75. A pharmaceutical composition comprising a compound of claim 22, or pharmaceutically acceptable salt thereof, and a pharmaceutically acceptable carrier.
76. A pharmaceutical composition comprising a compound of claim 23, or pharmaceutically acceptable salt thereof, and a pharmaceutically acceptable carrier.
77. A pharmaceutical composition comprising a compound of claim 24, or pharmaceutically acceptable salt thereof, and a pharmaceutically acceptable carrier.
78. A pharmaceutical composition comprising a compound of claim 25, or pharmaceutically acceptable salt thereof, and a pharmaceutically acceptable carrier.
79. A pharmaceutical composition comprising a compound of claim 26, or pharmaceutically acceptable salt thereof, and a pharmaceutically acceptable carrier.
80. A pharmaceutical composition comprising a compound of claim 27, or pharmaceutically acceptable salt thereof, and a pharmaceutically acceptable carrier.
81. A pharmaceutical composition comprising a compound of claim 28, or pharmaceutically acceptable salt thereof, and a pharmaceutically acceptable carrier.
82. A pharmaceutical composition comprising a compound of claim 29, or pharmaceutically acceptable salt thereof, and a pharmaceutically acceptable carrier.
83. A pharmaceutical composition comprising a compound of claim 30 and a pharmaceutically acceptable carrier.
84. A pharmaceutical composition comprising a compound of claim 31 and a pharmaceutically acceptable carrier.
85. A pharmaceutical composition comprising a compound of claim 32 and a pharmaceutically acceptable carrier.
86. A pharmaceutical composition comprising a compound of claim 33 and a pharmaceutically acceptable carrier.
87. A pharmaceutical composition comprising a compound of claim 34 and a pharmaceutically acceptable carrier.
88. A pharmaceutical composition comprising a compound of claim 35 and a pharmaceutically acceptable carrier.
89. A pharmaceutical composition comprising a compound of claim 36 and a pharmaceutically acceptable carrier.
90. A pharmaceutical composition comprising a compound of claim 37 and a pharmaceutically acceptable carrier.
91. A pharmaceutical composition comprising a compound of claim 38 and a pharmaceutically acceptable carrier.
92. A pharmaceutical composition comprising a compound of claim 39 and a pharmaceutically acceptable carrier.
93. A pharmaceutical composition comprising a compound of claim 40 and a pharmaceutically acceptable carrier.
94. A pharmaceutical composition comprising a compound of claim 41 and a pharmaceutically acceptable carrier.
95. A pharmaceutical composition comprising a compound of claim 42 and a pharmaceutically acceptable carrier.
96. A pharmaceutical composition comprising a compound of claim 43 and a pharmaceutically acceptable carrier.
97. A pharmaceutical composition comprising a compound of claim 44 and a pharmaceutically acceptable carrier.
98. A pharmaceutical composition comprising a compound of claim 45 and a pharmaceutically acceptable carrier.
99. A pharmaceutical composition comprising a compound of claim 46 and a pharmaceutically acceptable carrier.

100. A pharmaceutical composition comprising a compound of claim 47 and a pharmaceutically acceptable carrier.

101. A pharmaceutical composition comprising a compound of claim 48 and a pharmaceutically acceptable carrier.

102. A pharmaceutical composition comprising a compound of claim 49 and a pharmaceutically acceptable carrier.

103. A pharmaceutical composition comprising a compound of claim 50 and a pharmaceutically acceptable carrier.

104. A pharmaceutical composition comprising a compound of claim 51 and a pharmaceutically acceptable carrier.

105. A pharmaceutical composition comprising a compound of claim 52 and a pharmaceutically acceptable carrier.

106. A pharmaceutical composition comprising a compound of claim 53 and a pharmaceutically acceptable carrier.

* * * * *